(12) United States Patent
Velaparthi et al.

(10) Patent No.: US 10,954,238 B1
(45) Date of Patent: *Mar. 23, 2021

(54) SUBSTITUTED NAPHTHYRIDINONE COMPOUNDS USEFUL AS T CELL ACTIVATORS

(71) Applicant: BRISTOL-MYERS SQUIBB COMPANY, Princeton, NJ (US)

(72) Inventors: Upender Velaparthi, Princeton Junction, NJ (US); Louis S. Chupak, Old Saybrook, CT (US); Chetan Padmakar Darne, Ewing, NJ (US); Min Ding, Stow, MA (US); Robert G. Gentles, Killingworth, CT (US); Yazhong Huang, Wallingford, CT (US); Manjunatha Narayana Rao Kamble, Bangalore (IN); Scott W. Martin, Middletown, CT (US); Raju Mannoori, Bangalore (IN); Ivar M. McDonald, Woodstock, CT (US); Richard E. Olson, Cambridge, MA (US); Hasibur Rahaman, Bangalore (IN); Prasada Rao Jalagam, Bangalore (IN); Saumya Roy, Bangalore (IN); Gopikishan Tonukunuru, Bangalore (IN); Sivasudar Velaiah, Hosur (IN); Jayakumar Sankara Warrier, Bangalore (IN); Xiaofan Zheng, Cheshire, CT (US); John S. Tokarski, Princeton, NJ (US); Bireshwar Dasgupta, Doylestown, PA (US); Kotha Rathnakar Reddy, Warangal West (IN); Thiruvenkadam Raja, Hosur (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/843,024

(22) Filed: Apr. 8, 2020

Related U.S. Application Data

(63) Continuation of application No. 16/452,679, filed on Jun. 26, 2019, now Pat. No. 10,669,272.

(60) Provisional application No. 62/840,459, filed on Apr. 30, 2019, provisional application No. 62/690,439, filed on Jun. 27, 2018.

(51) Int. Cl.
| C07D 403/04 | (2006.01) |
| C07D 487/04 | (2006.01) |
| A61K 31/196 | (2006.01) |
| C07D 471/04 | (2006.01) |

(52) U.S. Cl.
CPC ................ *C07D 471/04* (2013.01)

(58) Field of Classification Search
CPC ... C07D 403/04; C07D 487/04; A61K 31/496
See application file for complete search history.

(56) References Cited

U.S. PATENT DOCUMENTS

| 4,324,893 | A  | 4/1982  | Scotese et al. |
| 7,084,141 | B2 | 8/2006  | Gaeta et al. |
| 7,173,036 | B2 | 2/2007  | Sircar et al. |
| 7,220,856 | B2 | 5/2007  | Dunning et al. |
| 7,279,481 | B2 | 10/2007 | Falchi et al. |
| 7,381,401 | B2 | 6/2008  | Gajewski |
| 9,050,334 | B2 | 6/2015  | Gaweco et al. |
| 9,133,164 | B2 | 9/2015  | Gaweco et al. |

(Continued)

FOREIGN PATENT DOCUMENTS

| WO | WO2004056824 A2 | 7/2004 |
| WO | WO2004074218 A2 | 9/2004 |

(Continued)

OTHER PUBLICATIONS

Avila-Flores, A. et al., "Predominant Contribution of DGKζ over DGKα in the Control of PKC/DPK-1 Regulated Functions in T Cells", Immunology and Cell Biology (2017) 95: 549-563.

(Continued)

*Primary Examiner* — Bruck Kifle
(74) *Attorney, Agent, or Firm* — Gary Greenblatt

(57) ABSTRACT

Disclosed are compounds of Formula (I):

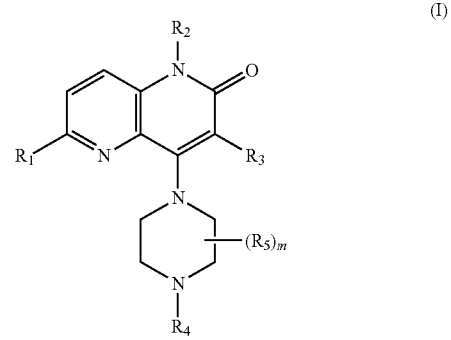

or a salt thereof, wherein: $R_1$, $R_2$, $R_3$, $R_4$, $R_5$, and m are defined herein. Also disclosed are methods of using such compounds to inhibit the activity of one or both of diacylglycerol kinase alpha (DGKα) and diacylglycerol kinase zeta (DGKζ), and pharmaceutical compositions comprising such compounds. These compounds are useful in the treatment of viral infections and proliferative disorders, such as cancer.

11 Claims, No Drawings

Specification includes a Sequence Listing.

(56) References Cited

U.S. PATENT DOCUMENTS

| | | | |
|---|---|---|---|
| 2005/0124604 A1 | 6/2005 | Sircar et al. |
| 2005/0266510 A1 | 12/2005 | Gajewski |
| 2008/0139551 A1 | 6/2008 | Sircar et al. |
| 2011/0281908 A1 | 11/2011 | Sun et al. |
| 2015/0224142 A1 | 8/2015 | Albelda et al. |
| 2018/0334454 A1 | 11/2018 | Lanman et al. |

FOREIGN PATENT DOCUMENTS

| | | | |
|---|---|---|---|
| WO | WO2004087880 A2 | 10/2004 |
| WO | WO2005009967 A2 | 2/2005 |
| WO | WO2005021546 A1 | 3/2005 |
| WO | WO2007109251 A2 | 9/2007 |
| WO | WO2007132948 A1 | 11/2007 |
| WO | WO2007136125 A1 | 11/2007 |
| WO | WO2010042489 A2 | 4/2010 |
| WO | WO2010088408 A2 | 8/2010 |
| WO | WO2012009649 A1 | 1/2012 |
| WO | WO2012142498 A2 | 10/2012 |
| WO | WO2013118071 A1 | 8/2013 |
| WO | WO2016164675 A1 | 10/2016 |
| WO | WO2017106607 A1 | 6/2017 |
| WO | WO2017177037 A1 | 10/2017 |
| WO | WO2018119183 A2 | 6/2018 |
| WO | WO2018134685 A2 | 7/2018 |
| WO | WO2019005883 A1 | 1/2019 |

OTHER PUBLICATIONS

Barraza et al., "Discovery of Anthranilamides as a Novel Class of Inhyibitors of Neurotropic Alphavirus Replication", Bioorg. Med. Chem 23 (2015) 1569-1567.

Boroda et al., "Dual Activites of Ritanserin and R59022 as DGKα inhibitors and Serotonin Receptor Antagonists" Biochemical Pharmacology 123 (2017) 29-39.

Chen et al., "Diacylglycerol Kinases in T Cell Tolerance and Effector Function", Frontiers in Cell and Development Biology 2016 4, 130.

Dagia et al., "A fluorinated Analog of ISO-1 blocks the Recognition and Biological Function of MIF and is Orally Efficacious in a Murine Model of Colitis" Eur. J. Pharmacology 607 (2009) 201-212.

Database Registry Chemical Abstracts Service: Database RN 2249638-34-2 (Entered STN Nov. 19, 2018).

Facciabene, et al. "T-Regulartory Cells: Key Players in Tumor Immune Escape and Angiogenesis" Cancer Res. 72(9) 2162-2171 (2012).

Franks et al., "The Ligand Binding Landscape of Diacylglycerol Kinases" Cell Chem Bio 24, 879-880 (2017).

Ganesan et al., "Comprehensive in vitro Characterization of PD-L1 Small Molecule Inhibitors", Scientirfic Reports 9, Article No. 12392 (2019).

International Search Report for PCT Application PCT/US2019/039135, dated Aug. 29, 2019, entered Nov. 19, 2018.

Jing et al., "T Cells Deficient in Diacylglycerol Kinase are Resistance to PD-1 Inhibition and Help Create Persistent Host Immunity to Leukemia" Cancer Res 77(20) 5676-5686 (2017).

Krishna et al., "Regulation of Lipid Signaling by Diacylglycerol Kinases During T Cell Development and Function" Front Immunolog. (2013) 4: Article 178.

LiuLiu et al., "A Novel Diacylglycerol Kinase α-Selectve Inhibitor CU-3. Induces Cancer Cell Apoptosis and Enhances Immune Response" J. Lipid Res. 57, 368-379 (2016).

McCloud et al., "Deconstructing Lipid Kinase Inhibitors by Chemical Proteomics" Biochem. 2018, 57, 231-236.

McLean et al., "Fragment Screening of Inhibitors for MIF Tautomerase Reveals a Cryptic Surface Binding Site" Bio. Med. Chem. Lett. 20 (2010) 1621-1624.

Mellman et al. "Cancer Immunotherapy Comes of Age" Nature 480 480-489 (2011).

Merida et al., "Redundant and Specialized Roles for Diacylglycerol Kinases α and ζ in the Control of T cell Functions" Science Signaling 8 (374), re6 (2015).

Merida I., Arranz-Nicolás J., et al., "Diacylglycerol Kinase Malfunction in Human Disease and the Search for Specific Inhibitors", Handbook of Experimental Pharmacology, Springer, Berlin, Heidelberg (2019), First Online: Jun. 22, 2019.

Mizoguchi et al., "Alterations in Signal Transduction Molecules in T Lumphocytes from Tumor-Bearing Mice" (1992) Science 258:1795-98.

Noessner, "DGK-α: A Checkpoint in Cancer-Mediated Immune-Inhibition and Target for Immunotherapy" Front Cell Dev Bio 2017 5, Article 16.

Olenchock et al., "Disruption of the Diacylglycerol Metabolism Impairs the Induction of T cell Anergy", Nature Immunology 7(11) 1174-1181 (2006).

Prinz et al., "High DGK-α and Disabled MAPK Pathways Cause Dysfunction of Human Tumor-Infiltrating CD8+ T Cells that Is Reversible by Pharmacologic Intervention", J Immunology 188(12) 5990-6000 (2012).

Purow, B. "Molecular Pathways: Targeting Diacylglycerol Kinase Aplha in Cancer" Clin. Cancer Res. 21(22) 5008-5012 (2015).

Riese et al., "Decreased Diacylglycerol Metabolism Enhances ERK Activation and Augments DC8+ T Cell Functional Responses", J Bio Chem 286(7) 5254-5265 (2011).

Riese et al., "Diacylglycerol Kinases (DGKs): Novel Targets for Improving T Cell Activity in Cancer" Frontiers Cell Dev Bio (2016) 4, Article 108.

Santilli et al., "2-Oxo-1,8-naphthyridine-3-carboxylic Acid Derivaties with Potent Gastric Antisecretory Properties" J. Med. Chem. 1987, 30, 2270-2277.

Sjoblom et al. "The Consensus Coding Sequences of Human Breast and Colorectal Cancers" Science 314 268-274 (2006).

Topalian et al., "Targetomg the PD-1/B7-H1(PD-L1) Pathway to Activate Anti-tumor Immunity", Curr. Opin. Immunol. 2012, 24:207-212.

Velnati et al., "Identification of a Novel DGKα Inhibitor for XLP-1 Therapy by Virtual Screening", Eur J Med Chem 164 (2019) 378-390.

Wesley et al., "Diacylglycerol Kinase ζ (DGKζ) and Casitas b-Lineage Proto-Oncogene b-Deficient Mice Have Similar Functional Outcomes in T Cells but DGK ζ-Deficient Mice have Increased T Cell Activatin and Tumor Clearance" ImmunoHorizons 2018 2 94) 107-118.

Zha Y. et al., "T Cell Anergy is Reversed by Active Ras and is Regulated by Diacylglycerol Kinase-α" Nature Immunology, (2006) 7(11) 1166-1173; Erratum 7(12) 1343.

SUBSTITUTED NAPHTHYRIDINONE COMPOUNDS USEFUL AS T CELL ACTIVATORS

CROSS REFERENCE TO RELATED APPLICATIONS

This application is a continuation application, which claims the benefit of U.S. patent application Ser. No. 16/452,679 filed Jun. 26, 2019, which claims the benefit of U.S. Provisional Application Ser. No. 62/840,459, filed Apr. 30, 2019 and U.S. Provisional Application Ser. No. 62/690,439, filed Jun. 27, 2018, each incorporated herein in its entirety.

DESCRIPTION

The present invention generally relates to substituted naphthyridinone compounds that activate T cells, promote T cell proliferation, and/or exhibit antitumor activity. Provided herein are substituted naphthyridinone compounds, compositions comprising such compounds, and methods of their use. The invention further pertains to pharmaceutical compositions comprising at least one compound according to the invention that are useful for the treatment of proliferative disorders, such as cancer, and viral infections.

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities. However, although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively subvert anti-tumor immunity. These mechanisms include dysfunctional T-cell signaling (Mizoguchi et al., (1992) *Science* 258:1795-98), suppressive regulatory cells (Facciabene et al., (2012) *Cancer Res.* 72:2162-71), and the co-opting of endogenous "immune checkpoints", which serve to down-modulate the intensity of adaptive immune responses and protect normal tissues from collateral damage, by tumors to evade immune destruction (Topalian et al., (2012) *Curr. Opin. Immunol.* 24:1-6; Mellman et al. (2011) *Nature* 480:480-489).

Diacylglycerol kinases (DGKs) are lipid kinases that mediate the conversion of diacylglycerol to phosphatidic acid thereby terminating T cell functions propagated through the TCR signaling pathway. Thus, DGKs serve as intracellular checkpoints and inhibition of DGKs are expected to enhance T cell signaling pathways and T cell activation. Supporting evidence include knock-out mouse models of either DGKα or DGKζ which show a hyper-responsive T cell phenotype and improved anti-tumor immune activity (Riese M. J. et al., *Journal of Biological Chemistry*, (2011) 7: 5254-5265; Zha Y et al., *Nature Immunology*, (2006) 12:1343; Olenchock B. A. et al., (2006) 11: 1174-81). Furthermore tumor infiltrating lymphocytes isolated from human renal cell carcinoma patients were observed to overexpress DGKα which resulted in inhibited T cell function (Prinz, P. U. et al., *J Immunology* (2012) 12:5990-6000). Thus, DGKα and DGKζ are viewed as targets for cancer immunotherapy (Riese M. J. et al., *Front Cell Dev Biol.* (2016) 4: 108; Chen, S. S. et al., *Front Cell Dev Biol.* (2016) 4: 130; Avila-Flores, A. et al., *Immunology and Cell Biology* (2017) 95: 549-563; Noessner, E., *Front Cell Dev Biol.* (2017) 5: 16; Krishna, S., et al., *Front Immunology* (2013) 4:178; Jing, W. et al., *Cancer Research* (2017) 77: 5676-5686.

There remains a need for compounds useful as inhibitors of one or both of DGKα and DGKζ. Additionally, there remains a need for compounds useful as inhibitors of one of both of DGKα and DGKζ that have selectivity over other diacylglycerol kinases, protein kinases, and/or other lipid kinases.

Accordingly, an agent that is safe and effective in restoring T cell activation, lowering antigen threshold, enhancing antitumor functionality, and/or overcoming the suppressive effects of one or more endogenous immune checkpoints, such as PD-1, LAG-3 and TGFβ, would be an important addition for the treatment of patients with proliferative disorders, such as cancer, as well as viral infections.

Applicants have found compounds that have activity as inhibitors of one or both of DGKα and DGKζ. Further, applicants have found compounds that have activity as inhibitors of one or both of DGKα and DGKζ and have selectivity over other diacylglycerol kinases, protein kinases, and/or other lipid kinases. These compounds are provided to be useful as pharmaceuticals with desirable stability, bioavailability, therapeutic index, and toxicity values that are important to their drugability.

SUMMARY OF THE INVENTION

The present invention provides substituted naphthyridinone compounds of Formula (I), which are useful as inhibitors of DGKα, DGKζ, or both DGKα and DGKζ, including salts and prodrugs thereof.

The present invention also provides pharmaceutical compositions comprising a compound of Formula (I) and/or a pharmaceutically acceptable salt thereof; and a pharmaceutically acceptable carrier.

The present invention also provides a method of treating a disease or disorder associated with the activity of DGKα, DGKζ, or both DGKα and DGKζ, the method comprising administering to a mammalian patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament for the treatment of proliferative disorders, such as cancer and viral infections.

The compounds of Formula (I) and compositions comprising the compounds of Formula (I) may be used in treating, preventing, or curing viral infections and various proliferative disorders, such as cancer. Pharmaceutical compositions comprising these compounds are useful in treating, preventing, or slowing the progression of diseases or disorders in a variety of therapeutic areas, such as viral infections and cancer.

These and other features of the invention will be set forth in expanded form as the disclosure continues.

DETAILED DESCRIPTION

The first aspect of the present invention provides at least one compound of Formula (I):

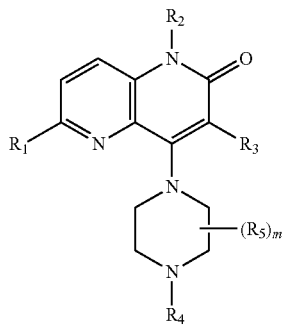

or a salt thereof, wherein:
$R_1$ is H, F, Cl, Br, —CN, $C_{1-3}$ alkyl substituted with zero to 4 $R_{1a}$, $C_{3-4}$ cycloalkyl substituted with zero to 4 $R_{1a}$, $C_{1-3}$ alkoxy substituted with zero to 4 $R_{1a}$, —$NR_aR_a$, —$S(O)_n$ $R_e$, or —$P(O)R_eR_e$;
each $R_{1a}$ is independently F, Cl, —CN, —OH, —$OCH_3$, or —$NR_aR_a$;
each $R_a$ is independently H or $C_{1-3}$ alkyl;
each $R_e$ is independently $C_{3-4}$ cycloalkyl or $C_{1-3}$ alkyl substituted with zero to 4 $R_{1a}$;
$R_2$ is H, $C_{1-3}$ alkyl substituted with zero to 4 $R_{2a}$, or $C_{3-4}$ cycloalkyl substituted with zero to 4 $R_{2a}$;
each $R_{2a}$ is independently F, Cl, —CN, —OH, —O($C_{1-2}$ alkyl), $C_{3-4}$ cycloalkyl, $C_{3-4}$ alkenyl, or $C_{3-4}$ alkynyl;
$R_3$ is H, F, Cl, Br, —CN, $C_{1-3}$ alkyl, $C_{1-2}$ fluoroalkyl, $C_{3-4}$ cycloalkyl, $C_{3-4}$ fluorocycloalkyl, or —$NO_2$;
$R_4$ is —$CH_2R_{4a}$, —$CH_2CH_2R_{4a}$, —$CH_2CHR_{4a}R_{4d}$, —$CHR_{4a}R_{4b}$, or —$CR_{4a}R_{4b}R_{4c}$;
$R_{4a}$ and $R_{4b}$ are independently:
(i) $C_{1-6}$ alkyl substituted with zero to 4 substituents independently selected from F, Cl, —CN, —OH, —$OCH_3$, —$SCH_3$, $C_{1-3}$ fluoroalkoxy, —$NR_aR_a$, —$S(O)_2R_e$, or —$NR_aS(O)_2R_e$;
(ii) $C_{3-6}$ cycloalkyl, heterocyclyl, phenyl, or heteroaryl, each substituted with zero to 4 substituents independently selected from F, Cl, Br, —CN, —OH, $C_{1-6}$ alkyl, $C_{1-3}$ fluoroalkyl, $C_{1-4}$ hydroxy alkyl, —$(CH_2)_{1-2}O(C_{1-3}$ alkyl), $C_{1-4}$ alkoxy, —O($C_{1-4}$ hydroxy alkyl), —O($CH)_{1-3}O(C_{1-3}$ alkyl), $C_{1-3}$ fluoroalkoxy, —$O(CH)_{1-3}$ $NR_cR_c$, —$OCH_2CH=CH_2$, —$OCH_2C\equiv CH$, —$C(O)$ ($C_{1-4}$ alkyl), —$C(O)OH$, —$C(O)O(C_{1-4}$ alkyl), —$NR_c$ $R_c$, —$NR_aS(O)_2(C_{1-3}$ alkyl), —$NR_aC(O)(C_{1-3}$ alkyl), —$NR_aC(O)O(C_{1-4}$ alkyl), —$P(O)(C_{1-3}$ alkyl)$_2$, —$S(O)_2$ ($C_{1-3}$ alkyl), —$O(CH_2)_{1-2}(C_{3-6}$ cycloalkyl), —$O(CH_2)_{1-2}$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, and $R_d$; or
(iii) $C_{1-4}$ alkyl substituted with one cyclic group selected from $C_{3-6}$ cycloalkyl, heterocyclyl, aryl, and heteroaryl, said cyclic group substituted with zero to 3 substituents independently selected from F, Cl, Br, —OH, —ON, $C_{1-6}$ alkyl, $C_{1-3}$ fluoroalkyl, $C_{1-3}$ alkoxy, $C_{1-3}$ fluoroalkoxy, —$OCH_2CH=CH_2$, —$OCH_2C\equiv CH$, —$NR_cR_c$, —$NR_aS(O)_2(C_{1-3}$ alkyl), —$NR_aC(O)(C_{1-3}$ alkyl), —$NR_aC(O)O(C_{1-4}$ alkyl), and $C_{3-6}$ cycloalkyl;
or $R_{4a}$ and $R_{4b}$ together with the carbon atom to which they are attached form a $C_{3-6}$ cycloalkyl or a 3- to 6-membered heterocyclyl, each substituted with zero to 3 $R_f$;
each $R_f$ is independently F, Cl, Br, —OH, —ON, =O, $C_{1-6}$ alkyl, $C_{1-3}$ fluoroalkyl, $C_{1-3}$ alkoxy, $C_{1-3}$ fluoroalkoxy, —$OCH_2CH=CH_2$, —$OCH_2C\equiv CH$, —$NR_cR_c$, or a cyclic group selected from $C_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —ON, $C_{1-6}$ alkyl, $C_{1-3}$ fluoroalkyl, $C_{1-3}$ alkoxy, $C_{1-3}$ fluoroalkoxy, and —$NR_cR_c$;
$R_{4c}$ is $C_{1-6}$ alkyl or $C_{3-6}$ cycloalkyl, each substituted with zero to 4 substituents independently selected from F, Cl, —OH, $C_{1-2}$ alkoxy, $C_{1-2}$ fluoroalkoxy, and —CN;
$R_{4d}$ is —$OCH_3$;
each $R_c$ is independently H or $C_{1-2}$ alkyl;
$R_d$ is phenyl substituted with zero to 1 substituent selected from F, Cl, —CN, —$CH_3$, and —$OCH_3$;
each $R_5$ is independently —CN, $C_{1-6}$ alkyl substituted with zero to 4 $R_g$, $C_{2-4}$ alkenyl substituted with zero to 4 $R_g$, $C_{2-4}$ alkynyl substituted with zero to 4 $R_g$, $C_{3-4}$ cycloalkyl substituted with zero to 4 $R_g$, phenyl substituted with zero to 4 $R_g$, oxadiazolyl substituted with zero to 4 $R_g$, pyridinyl substituted with zero to 4 $R_g$, —$(CH_2)_{1-2}$(heterocyclyl substituted with zero to 4 $R_g$), —$(CH_2)_{1-2}NR_cC$ $(O)(C_{1-4}$ alkyl), —$(CH_2)_{1-2}NR_cC(O)O(C_{1-4}$ alkyl), —$(CH_2)_{1-2}NR_cS(O)_2(C_{1-4}$ alkyl), —$C(O)(C_{1-4}$ alkyl), —$C(O)OH$, —$C(O)O(C_{1-4}$ alkyl), —$C(O)O(C_{3-4}$ cycloalkyl), —$C(O)NRaRa$, or —$C(O)NR_a(C_{3-4}$ cycloalkyl);
each $R_g$ is independently F, Cl, —CN, —OH, $C_{1-3}$ alkoxy, $C_{1-3}$ fluoroalkoxy, —$O(CH_2)_{1-2}O(C_{1-2}$ alkyl), or —$NR_cR_c$;
m is 1, 2, or 3; and
n is zero, 1, or 2.

The second aspect of the present invention provides at least one compound of Formula (I) or a salt thereof, wherein:
$R_1$ is H, F, Cl, Br, —CN, $C_{1-3}$ alkyl substituted with zero to 4 $R_{1a}$, $C_{3-4}$ cycloalkyl substituted with zero to 4 $R_{1a}$, $C_{1-3}$ alkoxy substituted with zero to 4 $R_{1a}$, —$NR_aR_a$, —$S(O)_n$ $R_e$, or —$P(O)R_eR_e$;
each $R_{1a}$ is independently F, Cl, —CN, —OH, —$OCH_3$, or —$NR_aR_a$;
each $R_a$ is independently H or $C_{1-3}$ alkyl;
each $R_e$ is independently $C_{3-4}$ cycloalkyl or $C_{1-3}$ alkyl substituted with zero to 4 $R_{1a}$; $R_2$ is H, $C_{1-3}$ alkyl substituted with zero to 4 $R_{2a}$, or $C_{3-4}$ cycloalkyl substituted with zero to 4 $R_{2a}$;
each $R_{2a}$ is independently F, Cl, —CN, —OH, —O($C_{1-2}$ alkyl), $C_{3-4}$ cycloalkyl, $C_{3-4}$ alkenyl, or $C_{3-4}$ alkynyl;
$R_3$ is H, F, Cl, Br, —CN, $C_{1-3}$ alkyl, $C_{1-2}$ fluoroalkyl, $C_{3-4}$ cycloalkyl, $C_{3-4}$ fluorocycloalkyl, or —$NO_2$;
$R_4$ is —$CH_2R_{4a}$, —$CH_2CH_2R_{4a}$, —$CH_2CHR_{4a}R_{4d}$, —$CHR_{4a}R_{4b}$, or —$CR_{4a}R_{4b}R_{4c}$;
$R_{4a}$ and $R_{4b}$ are independently:
(i) $C_{1-6}$ alkyl substituted with zero to 4 substituents independently selected from F, Cl, —CN, —OH, —$OCH_3$, $C_{1-3}$ fluoroalkoxy and —$NR_aR_a$;
(ii) $C_{3-6}$ cycloalkyl, heterocyclyl, phenyl, or heteroaryl, each substituted with zero to 4 substituents independently selected from F, Cl, Br, —CN, —OH, $C_{1-6}$ alkyl, $C_{1-3}$ fluoroalkyl, —$CH_2OH$, $C_{1-3}$ alkoxy, $C_{1-3}$ fluoroalkoxy, —$OCH_2CH=CH_2$, —$OCH_2C\equiv CH$, —$C(O)(C_{1-3}$ alkyl), —$C(O)OH$, —$C(O)O(C_{1-3}$ alkyl), —$NR_cR_c$, —$NR_aS(O)_2(C_{1-3}$ alkyl), —$NR_aC(O)(C_{1-3}$ alkyl), —$NR_aC(O)O(C_{1-4}$ alkyl), —$S(O)_2(C_{1-3}$ alkyl), cyclopropyl, cyanocyclopropyl, (tert-butoxycarbonyl)azetidinyl, tetrahydropyranyl, morpholinyl, methylpiperidinyl, and $R_a$; or (iii) $C_{1-4}$ alkyl substituted with one cyclic group selected from $C_{3-6}$ cycloalkyl, heterocyclyl, aryl, and heteroaryl, said cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —$OCH_2CH=CH_2$, —$OCH_2C\equiv CH$, —$NR_cR_c$, —$NR_aS(O)_2(C_{1-3}$ alkyl), —$NR_aC(O)(C_{1-3}$ alkyl), and —$NR_aC(O)O(C_{1-4}$ alkyl);

or $R_{4a}$ and $R_{4b}$ together with the carbon atom to which they are attached form a $C_{3-6}$ cycloalkyl or a 3- to 6-membered heterocyclyl, each substituted with zero to 3 $R_f$;

each $R_f$ is independently F, Cl, Br, —OH, —CN, $C_{1-6}$ alkyl, $C_{1-3}$ fluoroalkyl, $C_{1-3}$ alkoxy, $C_{1-3}$ fluoroalkoxy, —$OCH_2CH=CH_2$, —$OCH_2C\equiv CH$, —$NR_cR_c$, or a cyclic group selected from $C_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, and —$NR_cR_c$;

$R_{4c}$ is $C_{1-6}$ alkyl or $C_{3-6}$ cycloalkyl, each substituted with zero to 4 substituents independently selected from F, Cl, —OH, $C_{1-2}$ alkoxy, $C_{1-2}$ fluoroalkoxy, and —CN;

$R_{4d}$ is —$OCH_3$;

each $R_c$ is independently H or $C_{1-2}$ alkyl;

$R_d$ is phenyl substituted with zero to 1 substituent selected from F, Cl, —$CH_3$, and —$OCH_3$;

each $R_5$ is independently —CN, $C_{1-6}$ alkyl substituted with zero to 4 $R_g$, $C_{2-4}$ alkenyl substituted with zero to 4 $R_g$, $C_{2-4}$ alkynyl substituted with zero to 4 $R_g$, $C_{3-4}$ cycloalkyl substituted with zero to 4 $R_g$, phenyl substituted with zero to 4 $R_g$, pyridinyl substituted with zero to 4 $R_g$, —$C(O)(C_{1-4}$ alkyl), —$C(O)OH$, —$C(O)O(C_{1-4}$ alkyl), —$C(O)O(C_{3-4}$ cycloalkyl), —$C(O)NR_aR_a$, —$C(O)NHNHC(O)CH_3$, or —$C(O)NR_a(C_{3-4}$ cycloalkyl);

each $R_g$ is independently F, Cl, —CN, —OH, $C_{1-3}$ alkoxy, or $C_{1-3}$ fluoroalkoxy;

m is 1, 2, or 3; and n is zero, 1, or 2.

The third aspect of the present invention provides at least one compound of Formula (I) or a salt thereof, wherein:

$R_1$ is H, F, Cl, Br, —CN, $C_{1-3}$ alkyl substituted with zero to 4 $R_{1a}$, $C_{3-4}$ cycloalkyl substituted with zero to 4 $R_{1a}$, $C_{1-3}$ alkoxy substituted with zero to 4 $R_{1a}$, —$NR_aR_a$, $S(O)_nR_e$, or —$P(O)R_eR_e$;

each $R_{1a}$ is independently F, Cl, —CN, —OH, —$OCH_3$, or —$NR_aR_a$;

each $R_a$ is independently H or $C_{1-3}$ alkyl;

each $R_e$ is independently $C_{3-4}$ cycloalkyl or $C_{1-3}$ alkyl substituted with zero to 4 $R_{1a}$; $R_2$ is H, $C_{1-3}$ alkyl substituted with zero to 4 $R_{2a}$, or $C_{3-4}$ cycloalkyl substituted with zero to 4 $R_{2a}$;

each $R_{2a}$ is independently F, Cl, —CN, —OH, —$O(C_{1-2}$ alkyl), $C_{3-4}$ cycloalkyl, $C_{3-4}$ alkenyl, or $C_{3-4}$ alkynyl;

$R_3$ is H, F, Cl, Br, —CN, $C_{1-2}$ alkyl, —$CF_3$, $C_{3-4}$ cycloalkyl, $C_{3-4}$ fluorocycloalkyl, or —$NO_2$;

$R_4$ is —$CH_2R_{4a}$, —$CHR_{4a}R_{4b}$, or —$CR_{4a}R_{4b}R_{4c}$;

$R_{4a}$ and $R_{4b}$ are independently:

(i) $C_{1-6}$ alkyl substituted with zero to 4 substituents independently selected from F, Cl, —CN, —OH, —$OCH_3$, $C_{1-3}$ fluoroalkoxy and —$NR_aR_a$;

(ii) $C_{3-6}$ cycloalkyl, heterocyclyl, aryl, or heteroaryl, each substituted with zero to 4 substituents independently selected from F, Cl, Br, —OH, —CN, $C_{1-6}$ alkyl, $C_{1-3}$ fluoroalkyl, —$CH_2OH$, $C_{1-3}$ alkoxy, $C_{1-3}$ fluoroalkoxy, —$OCH_2CH=CH_2$, —$OCH_2C\equiv CH$, —$NR_cR_c$, —$NR_aS(O)_2(C_{1-3}$ alkyl), —$NR_aC(O)(C_{1-3}$ alkyl), —$NR_aC(O)O(C_{1-4}$ alkyl), and $R_a$; or (iii) $C_{1-4}$ alkyl substituted with one cyclic group selected from $C_{3-6}$ cycloalkyl, heterocyclyl, aryl, and heteroaryl, said cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —$OCH_2CH=CH_2$, —$OCH_2C\equiv CH$, —$NR_cR_c$, —$NR_aS(O)_2(C_{1-3}$ alkyl), —$NR_aC(O)(C_{1-3}$ alkyl), and —$NR_aC(O)O(C_{1-4}$ alkyl);

or $R_{4a}$ and $R_{4b}$ together with the carbon atom to which they are attached form a $C_{3-6}$ cycloalkyl or a 3- to 6-membered heterocyclyl, each substituted with zero to 3 $R_f$;

each $R_f$ is independently F, Cl, Br, —OH, —CN, $C_{1-6}$ alkyl, $C_{1-3}$ fluoroalkyl, $C_{1-3}$ alkoxy, $C_{1-3}$ fluoroalkoxy, —$OCH_2CH=CH_2$, —$OCH_2C\equiv CH$, —$NR_cR_c$, or a cyclic group selected from $C_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, and —$NR_cR_c$;

$R_{4c}$ is $C_{1-6}$ alkyl or $C_{3-6}$ cycloalkyl, each substituted with zero to 4 substituents independently selected from F, Cl, —OH, $C_{1-2}$ alkoxy, $C_{1-2}$ fluoroalkoxy, and —CN;

each $R_c$ is independently H or $C_{1-2}$ alkyl;

$R_d$ is phenyl substituted with zero to 1 substituent selected from F, Cl, —$CH_3$, and —$OCH_3$;

each $R_5$ is independently —CN, $C_{1-6}$ alkyl substituted with zero to 4 $R_g$, $C_{2-4}$ alkenyl substituted with zero to 4 $R_g$, $C_{2-4}$ alkynyl substituted with zero to 4 $R_g$, $C_{3-4}$ cycloalkyl substituted with zero to 4 $R_g$, phenyl substituted with zero to 4 $R_g$, pyridinyl substituted with zero to 4 $R_g$, —$C(O)OH$, —$C(O)O(C_{1-4}$ alkyl), —$C(O)O(C_{3-4}$ cycloalkyl), —$C(O)NR_aR_a$, —$C(O)NHNHC(O)CH_3$, or —$C(O)NR_a(C_{3-4}$ cycloalkyl);

each $R_g$ is independently F, Cl, —CN, —OH, $C_{1-3}$ alkoxy, or $C_{1-3}$ fluoroalkoxy;

m is 1, 2, or 3; and n is zero, 1, or 2.

In one embodiment, a compound of Formula (I) or a salt thereof is provided wherein: $R_1$ is H, F, Cl, Br, —CN, $C_{1-3}$ alkyl substituted with zero to 4 $R_{1a}$, cyclopropyl substituted with zero to 3 $R_{1a}$, $C_{1-3}$ alkoxy substituted with zero to 3 $R_{1a}$, —$NR_aR_a$, —$S(O)_nCH_3$, or —$P(O)(CH_3)_2$; each $R_{1a}$ is independently F, Cl, or —CN; each $R_a$ is independently H or $C_{1-3}$ alkyl; $R_2$ is H or $C_{1-2}$ alkyl substituted with zero to 2 $R_{2a}$; each $R_{2a}$ is independently F, Cl, —CN, —OH, —$O(C_{1-2}$ alkyl), cyclopropyl, $C_{3-4}$ alkenyl, or $C_{3-4}$ alkynyl; $R_3$ is H, F, Cl, Br, —CN, $C_{1-2}$ alkyl, —$CF_3$, cyclopropyl, or —$NO_2$; $R_{4a}$ and $R_{4b}$ are independently: (i) $C_{1-4}$ alkyl substituted with zero to 4 substituents independently selected from F, Cl, —CN, —OH, —$OCH_3$, —$SCH_3$, $C_{1-3}$ fluoroalkoxy, and —$NR_aR_a$; (ii) $C_{3-6}$ cycloalkyl, heterocyclyl, phenyl, or heteroaryl, each substituted with zero to 4 substituents independently selected from F, Cl, —CN, —OH, $C_{1-6}$ alkyl, $C_{1-3}$ fluoroalkyl, —$CH_2OH$, —$(CH_2)_{1-2}O(C_{1-2}$ alkyl), $C_{1-4}$ alkoxy, —$O(C_{1-4}$ hydroxy alkyl), —$O(CH)_{1-2}O(C_{1-2}$ alkyl), $C_{1-3}$ fluoroalkoxy, —$O(CH)_{1-2}NR_cR_c$, —OCH$_2$CH═CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-2}$ alkyl)$_2$, —S(O)$_2$(C$_{1-3}$ alkyl), —O(CH$_2$)$_{1-2}$(C$_{3-4}$ cycloalkyl), —O(CH$_2$)$_{1-2}$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, and R$_a$; or (iii) C$_{1-3}$ alkyl substituted with one cyclic group selected from C$_{3-6}$ cycloalkyl, heterocyclyl, phenyl, and heteroaryl, said cyclic group substituted with zero to 3 substituents independently selected from F, Cl, Br, —OH, —CN, C$_{1-3}$ alkyl, C$_{1-2}$ fluoroalkyl, C$_{1-3}$ alkoxy, C$_{1-2}$ fluoroalkoxy, —OCH$_2$CH═CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and C$_{3-4}$ cycloalkyl; or R$_{4a}$ and R$_{4b}$ together with the carbon atom to which they are attached, form a C$_{3-6}$ cycloalkyl or a 3- to 6-membered heterocyclyl, each substituted with zero to 3 R$_f$; each R$_f$ is independently F, Cl, Br, —OH, —CN, ═O, C$_{1-4}$ alkyl, C$_{1-2}$ fluoroalkyl, C$_{1-3}$ alkoxy, C$_{1-2}$ fluoroalkoxy, —OCH$_2$CH═CH$_2$, —OCH$_2$C≡CH, —NR$_c$R$_c$, or a cyclic group selected from C$_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, C$_{1-4}$ alkyl, C$_{1-2}$ fluoroalkyl, C$_{1-3}$ alkoxy, C$_{1-2}$ fluoroalkoxy, and —NR$_c$R$_c$; R$_{4c}$ is C$_{1-4}$ alkyl or C$_{3-6}$ cycloalkyl, each substituted with zero to 4 substituents independently selected from F, Cl, —OH, C$_{1-2}$ alkoxy, C$_{1-2}$ fluoroalkoxy, and —CN; and each R$_5$ is independently —CN, C$_{1-5}$ alkyl substituted with zero to 4 R$_g$, C$_{2-3}$ alkenyl substituted with zero to 4 R$_g$, C$_{2-3}$ alkynyl substituted with zero to 4 R$_g$, C$_{3-4}$ cycloalkyl substituted with zero to 4 R$_g$, phenyl substituted with zero to 3 R$_g$, oxadiazolyl substituted with zero to 3 R$_g$, pyridinyl substituted with zero to 3 R$_g$, —(CH$_2$)$_{1-2}$(heterocyclyl substituted with zero to 4 R$_g$), —(CH$_2$)$_{1-2}$NR$_c$C(O)(C$_{1-4}$ alkyl), —(CH$_2$)$_{1-2}$NR$_c$C(O)O(C$_{1-4}$ alkyl), —(CH$_2$)$_{1-2}$NR$_c$S(O)$_2$(C$_{1-4}$ alkyl), —C(O)(C$_{1-4}$ alkyl), —C(O)OH, —C(O)O(C$_{1-4}$ alkyl), —C(O)O(C$_{3-4}$ cycloalkyl), —C(O)NR$_a$R$_a$, or —C(O)NR$_a$(C$_{3-4}$ cycloalkyl).

In one embodiment, a compound of Formula (I) or a salt thereof is provided wherein: R$_1$ is H, F, Cl, Br, —CN, C$_{1-3}$ alkyl substituted with zero to 4 R$_{1a}$, cyclopropyl substituted with zero to 3 R$_{1a}$, C$_{1-3}$ alkoxy substituted with zero to 3 R$_{1a}$, —NR$_a$R$_a$, —S(O)$_n$CH$_3$, or —P(O)(CH$_3$)$_2$; each R$_{1a}$ is independently F, Cl, or —CN; each R$_a$ is independently H or C$_{1-3}$ alkyl; each R$_e$ is independently C$_{3-4}$ cycloalkyl or C$_{1-2}$ alkyl substituted with zero to 4 R$_{1a}$; R$_2$ is H or C$_{1-2}$ alkyl substituted with zero to 2 R$_{2a}$; each R$_{2a}$ is independently F, Cl, —CN, —OH, —O(C$_{1-2}$ alkyl), cyclopropyl, C$_{3-4}$ alkenyl, or C$_{3-4}$ alkynyl; R$_3$ is H, F, Cl, Br, —CN, C$_{1-2}$ alkyl, —CF$_3$, cyclopropyl, or —NO$_2$; R$_{4a}$ and R$_{4b}$ are independently: (i) C$_{1-4}$ alkyl substituted with zero to 4 substituents independently selected from F, Cl, —CN, —OH, —OCH$_3$, C$_{1-3}$ fluoroalkoxy, C$_{3-6}$ cycloalkyl, and —NR$_a$R$_a$; (ii) C$_{3-6}$ cycloalkyl, heterocyclyl, phenyl, or heteroaryl, each substituted with zero to 4 substituents independently selected from F, Cl, Br, —OH, —CN, C$_{1-6}$ alkyl, C$_{1-3}$ fluoroalkyl, —CH$_2$OH, C$_{1-3}$ alkoxy, C$_{1-3}$ fluoroalkoxy, —OCH$_2$CH═CH$_2$, —OCH$_2$C≡CH, —C(O)(C$_{1-3}$ alkyl), —C(O)OH, —C(O)O(C$_{1-3}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —S(O)$_2$(C$_{1-3}$ alkyl), cyclopropyl, cyanocyclopropyl, (tert-butoxycarbonyl)azetidinyl, tetrahydropyranyl, morpholinyl, methylpiperidinyl, and R$_a$; or (iii) C$_{1-3}$ alkyl substituted with one cyclic group selected from C$_{3-6}$ cycloalkyl, heterocyclyl, phenyl, and heteroaryl, said cyclic group substituted with zero to 3 substituents independently selected from F, Cl, Br, —OH, —CN, C$_{1-3}$ alkyl, C$_{1-2}$ fluoroalkyl, C$_{1-3}$ alkoxy, C$_{1-2}$ fluoroalkoxy, —OCH$_2$CH═CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), and —NR$_a$C(O)O(C$_{1-4}$ alkyl); or R$_{4a}$ and R$_{4b}$ together with the carbon atom to which they are attached, form a C$_{3-6}$ cycloalkyl or a 3- to 6-membered heterocyclyl, each substituted with zero to 3 R$_f$; each R$_f$ is independently F, Cl, Br, —OH, —CN, C$_{1-4}$ alkyl, C$_{1-2}$ fluoroalkyl, C$_{1-3}$ alkoxy, C$_{1-2}$ fluoroalkoxy, —OCH$_2$CH═CH$_2$, —OCH$_2$C≡CH, —NR$_c$R$_c$, or a cyclic group selected from C$_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, C$_{1-4}$ alkyl, C$_{1-2}$ fluoroalkyl, C$_{1-3}$ alkoxy, C$_{1-2}$ fluoroalkoxy, and —NR$_c$R$_c$; R$_{4c}$ is C$_{1-4}$ alkyl or C$_{3-6}$ cycloalkyl, each substituted with zero to 4 substituents independently selected from F, Cl, —OH, C$_{1-2}$ alkoxy, C$_{1-2}$ fluoroalkoxy, and —CN; each R$_5$ is independently —CN, C$_{1-5}$ alkyl substituted with zero to 4 R$_g$, C$_{2-3}$ alkenyl substituted with zero to 4 R$_g$, C$_{2-3}$ alkynyl substituted with zero to 4 R$_g$, C$_{3-4}$ cycloalkyl substituted with zero to 4 R$_g$, phenyl substituted with zero to 3 R$_g$, oxadiazolyl substituted with zero to 3 R$_g$, pyridinyl substituted with zero to 3 R$_g$, —C(O)OH, —C(O)O(C$_{1-4}$ alkyl), —C(O)O(C$_{3-4}$ cycloalkyl), —C(O)NR$_a$R$_a$, or —C(O)NR$_a$(C$_{3-4}$ cycloalkyl); each R$_g$ is independently F, Cl, —CN, —OH, C$_{1-3}$ alkoxy, or C$_{1-3}$ fluoroalkoxy; m is 1, 2, or 3; and n is zero, 1, or 2.

In one embodiment, a compound of Formula (I) or a salt thereof is provided wherein: R$_1$ is H, Cl, Br, —CN, or —OCH$_3$; R$_2$ is —CH$_3$; R$_3$ is H, F, Cl, Br, —CN, —CH$_3$, cyclopropyl, or —NO$_2$; R$_4$ is —CH$_2$R$_{4a}$, —CH$_2$CH$_2$R$_{4a}$, —CH$_2$CHR$_{4a}$R$_{4d}$, or —CHR$_{4a}$R$_{4b}$; R$_{4a}$ is phenyl, pyridinyl, pyrimidinyl, pyrazinyl, pyridazinyl, pyrazolyl, imidazolyl, isoxazolyl, isothiazolyl, oxazolyl, oxadiazolyl, tetrazolyl, thiadiazolyl, thiazolyl, triazolyl, thiophenyl, tetrahydropyranyl, dihydrobenzo[b][1,4]dioxinyl, dihydrobenzo[b][1,4]dioxepinyl, dihydrobenzofuranyl, benzo[d]isoxazolyl, benzoxazinyl, benzoxazinonyl, indazolyl, indolyl, benzo[d][1,3]dioxolyl, pyrazolo[1,5-a]pyridinyl, dioxidotetrahydrothiopyranyl, quinolinyl, or naphthyridinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —CH$_2$OH, —CH$_2$OCH$_3$, —OCH$_3$, —OCH$_2$CH$_3$, —OCH(CH$_3$)$_2$, —OC(CH$_3$)$_3$, —OCH$_2$C(CH$_3$)$_2$OH, —OCH$_2$CH$_2$OCH$_3$, —OCHF$_2$, —OCF$_3$, —OCH$_2$CH$_2$N(CH$_3$)$_2$, —C(O)CH$_3$, —C(O)C(CH$_3$)$_3$, —C(O)OH, —C(O)OCH$_3$, —C(O)OC(CH$_3$)$_3$, —N(CH$_3$)$_2$, —P(O)(CH$_3$)$_2$, —S(O)$_2$CH$_3$, —OCH$_2$(cyclopropyl), —OCH$_2$CH$_2$(cyclopropyl), —OCH$_2$CH$_2$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, phenyl, fluorophenyl, cyanophenyl, thiophenyl, fluorophenyl, and methylpiperidinyl; R$_{4b}$ is: (i) —CH$_3$, —CH$_2$CH$_3$, —CH$_2$CH$_2$CH$_3$, —C(CH$_3$)$_3$, —CH$_2$F, —CF$_3$, —CH$_2$OH, —C(CH$_3$)$_2$OH, —CH$_2$OCH$_3$, —CH$_2$OCHF$_2$, —CF$_2$CH$_2$OH, —CF$_2$CH$_2$OCH$_3$, —CH$_2$SCH$_3$, cyclopropyl, —CH$_2$(cyclohexyl), or —CH$_2$(cyclopropyl-oxadiazolyl); or (ii) phenyl, pyridinyl, pyrimidinyl, pyrazinyl, pyridazinyl, pyrazolyl, imidazolyl, isoxazolyl, isothiazolyl, oxazolyl, oxadiazolyl, tetrazolyl, thiadiazolyl, thiazolyl, triazolyl, thiophenyl, tetrahydropyranyl, dihydrobenzo[b][1,4]dioxinyl, dihydrobenzo[b][1,4]dioxepinyl, dihydrobenzofuranyl, benzo[d]isoxazolyl, benzoxazinyl, benzoxazinonyl, indazolyl, indolyl, benzo[d][1,3]dioxolyl, pyrazolo[1,5-a]pyridinyl, dioxidotetrahydrothiopyranyl, quinolinyl, or naphthyridinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —CH$_2$OH, —CH$_2$OCH$_3$, —OCH$_3$, —OCH$_2$CH$_3$, —OCH(CH$_3$)$_2$, —OC(CH$_3$)$_3$, —OCH$_2$C(CH$_3$)$_2$OH, —OCH$_2$CH$_2$OCH$_3$, —OCHF$_2$, —OCF$_3$, —OCH$_2$CH$_2$N(CH$_3$)$_2$, —C(O)CH$_3$, —C(O)C(CH$_3$)$_3$, —C(O)OH, —C(O)OCH$_3$, —C(O)OC(CH$_3$)$_3$, —N(CH$_3$)$_2$, —P(O)(CH$_3$)$_2$, —S(O)$_2$CH$_3$, —OCH$_2$(cyclopropyl), —OCH$_2$CH$_2$(cyclopropyl), —OCH$_2$CH$_2$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, phenyl, fluorophenyl, cyanophenyl, thiophenyl, fluorophenyl, and methylpiperidinyl; or R$_{4a}$ and R$_{4b}$ together with the carbon atom to which they are attached form oxotetrahydrofuranyl or cyclopropyl substituted with fluorophenyl; each R$_5$ is independently —CN, —CH$_3$, —CH$_2$CH$_3$, —CH(CH$_3$)$_2$, —CH$_2$F, —C(CH$_3$)$_2$F, —CF(CH$_3$)CH(CH$_3$)$_2$, —CH$_2$CN, —CH$_2$OH, —C(CH$_3$)$_2$OH, —C(CH$_3$)(OH)CH(CH$_3$)$_2$, —CH$_2$OCH$_3$, —CH$_2$OCH$_2$CH$_3$, —CH$_2$OCHF$_2$, —CH$_2$OCH$_2$CH$_2$OCH$_3$, —CH$_2$N(CH$_3$)$_2$, —CH$_2$NHC(O)CH$_3$, —CH$_2$NHC(O)OCH$_3$, —CH$_2$NHS(O)$_2$CH$_3$, —C(O)C(CH$_3$)$_2$, —CH$_2$(hydroxyazetidinyl), —CH$_2$(morpholinyl), —CH$_2$(methylpiperazinyl), —C(O)OH, —C(O)OCH$_3$, —C(O)OC(CH$_3$)$_2$, —C(O)NH$_2$, —C(O)NH(cyclopropyl), —C(O)O(cyclopropyl), cyclopropyl, phenyl, methyloxadiazolyl, or methylpyridinyl; and m is 1 or 2.

In one embodiment, a compound of Formula (I) or a salt thereof is provided wherein: R$_1$ is H, Br, —CN, or —OCH$_3$; R$_2$ is —CH$_3$; R$_3$ is H, F, Cl, Br, —CN, —CH$_3$, cyclopropyl, or —NO$_2$; R$_4$ is —CH$_2$R$_{4a}$, —CH$_2$CH$_2$R$_{4a}$, —CH$_2$CHR$_{4a}$R$_{4d}$, or —CHR$_{4a}$R$_{4b}$; R$_{4a}$ is phenyl, pyridinyl, pyrimidinyl, pyrazinyl, pyrazolyl, imidazolyl, isoxazolyl, isothiazolyl, oxazolyl, oxadiazolyl, tetrazolyl, thiadiazolyl, thiazolyl, triazolyl, tetrahydropyranyl, dihydrobenzo[b][1,4]dioxinyl, dihydrobenzo[b][1,4]dioxepinyl, dihydrobenzofuranyl, benzoxazinyl, benzoxazinonyl, indazolyl, indolyl, benzo[d][1,3]dioxolyl, pyrazolo[1,5-a]pyridinyl, quinolinyl, or naphthyridinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —OCH$_3$, —OCH$_2$CH$_3$, —OCH(CH$_3$)$_2$, —OCHF$_2$, —OCF$_3$, —C(O)CH$_3$, —C(O)OH, —C(O)OCH$_3$, —C(O)OC(CH$_3$)$_3$, —N(CH$_3$)$_2$, —S(O)$_2$CH$_3$, cyclopropyl, cyanocyclopropyl, (tert-butoxycarbonyl)azetidinyl, tetrahydropyranyl, morpholinyl, phenyl, fluorophenyl, and methylpiperidinyl; R$_{4b}$ is: (i) —CH$_3$, —CH$_2$CH$_3$, —CH$_2$CH$_2$CH$_3$, —C(CH$_3$)$_3$, —CH$_2$F, —CF$_3$, —CH$_2$OH, —CH$_2$OCH$_3$, —CH$_2$OCHF$_2$, —CH$_2$(cyclohexyl), or cyclopropyl; or (ii) phenyl, pyridinyl, pyrimidinyl, pyrazinyl, pyrazolyl, imidazolyl, isoxazolyl, isothiazolyl, oxazolyl, oxadiazolyl, tetrazolyl, thiadiazolyl, thiazolyl, triazolyl, tetrahydropyranyl, dihydrobenzo[b][1,4]dioxinyl, dihydrobenzo[b][1,4]dioxepinyl, dihydrobenzofuranyl, benzoxazinyl, benzoxazinonyl, indazolyl, indolyl, benzo[d][1,3]dioxolyl, pyrazolo[1,5-a]pyridinyl, quinolinyl, or naphthyridinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —OCH$_3$, —OCH$_2$CH$_3$, —OCH(CH$_3$)$_2$, —OCHF$_2$, —OCF$_3$, —C(O)CH$_3$, —C(O)OH, —C(O)OCH$_3$, —C(O)OC(CH$_3$)$_3$, —N(CH$_3$)$_2$, —S(O)$_2$CH$_3$, cyclopropyl, cyanocyclopropyl, (tert-butoxycarbonyl)azetidinyl, tetrahydropyranyl, morpholinyl, phenyl, fluorophenyl, and methylpiperidinyl; R$_{4d}$ is —OCH$_3$; each R$_5$ is independently —CN, —CH$_3$, —CH$_2$CH$_3$, —CH(CH$_3$)$_2$, —CHC(CH$_3$)$_2$, —CH$_2$F, —C(CH$_3$)$_2$F, —CF(CH$_3$)CH(CH$_3$)$_2$, —CH$_2$OH, —C(CH$_3$)$_2$OH, —C(CH$_3$)(OH)CH(CH$_3$)$_2$, —CH$_2$OCH$_3$, —C(O)C(CH$_3$)$_2$, —C(O)OH, —C(O)OCH$_3$, —C(O)OC(CH$_3$)$_2$, —C(O)NH$_2$, —C(O)NH(cyclopropyl), —C(O)O(cyclopropyl), cyclopropyl, phenyl, methyloxadiazolyl, or methylpyridinyl; and m is 1 or 2.

In one embodiment, a compound of Formula (I) or a salt thereof is provided wherein: R$_1$ is H, Br, —CN, or —OCH$_3$; R$_2$ is —CH$_3$; R$_3$ is H, F, Cl, Br, —CN, —CH$_3$, cyclopropyl, or —NO$_2$; R$_4$ is —CH$_2$R$_{4a}$ or —CHR$_{4a}$R$_{4b}$; R$_{4a}$ is phenyl or pyridinyl, each substituted with zero to 3 substituents independently selected from F, Cl, —CN, —OH, —CH$_3$, —CH$_2$CH$_3$, —CH(CH$_3$)$_2$, —CHF$_2$, —CF$_3$, —CH$_2$OH, —OCH$_3$, —OCH$_2$CH$_3$, —OCH(CH$_3$)$_2$, and —OCF$_3$; R$_{4b}$ is —CH$_3$, —C(CH$_3$)$_3$, or phenyl substituted with zero to 1 substituent selected from F, Cl, —CH$_3$, and —CH$_2$OH; each $R_5$ is independently —CN, —$CH_3$, —$CH_2CH_3$, —CH($CH_3$)$_2$, —CHC($CH_3$)$_2$, —$CH_2$F, —C($CH_3$)$_2$F, —CF($CH_3$)CH($CH_3$)$_2$, —$CH_2$OH, —C($CH_3$)$_2$OH, —C($CH_3$)(OH)CH($CH_3$)$_2$, —$CH_2OCH_3$, —C(O)C($CH_3$)$_2$, —C(O)OH, —C(O)$OCH_3$, —C(O)OC($CH_3$)$_3$, —C(O)$NH_2$, —C(O)NH(cyclopropyl), —C(O)O(cyclopropyl), cyclopropyl, phenyl, methyloxadiazolyl, or methylpyridinyl; and m is 1 or 2. Included in this embodiment are compounds in which each $R_5$ is independently —$CH_3$, —$CH_2CH_3$, —CH($CH_3$)$_2$, —CHC($CH_3$)$_2$, —$CH_2$F, —C($CH_3$)$_2$F, —CF($CH_3$)CH($CH_3$)$_2$, —$CH_2$OH, —C($CH_3$)$_2$OH, —C($CH_3$)(OH)CH($CH_3$)$_2$, —$CH_2OCH_3$, —C(O)C($CH_3$)$_2$, —C(O)$OCH_3$, —C(O)OC($CH_3$)$_3$, —C(O)O(cyclopropyl), cyclopropyl, phenyl, methyloxadiazolyl, or methylpyridinyl.

In one embodiment, a compound of Formula (I) or a salt thereof is provided wherein $R_4$ is —$CH_2R_{4a}$, —$CD_2R_{4a}$, or —$CH_2CH_2R_{4a}$. Included in this embodiment are compounds in which $R_4$ is —$CH_2R_{4a}$ or —$CD_2R_{4a}$. Also included in this embodiment are compounds in which $R_{4a}$ is phenyl, pyridinyl, tetrahydropyranyl, benzoxazinyl, benzo[d][1,3]dioxolyl, benzoxazinonyl, indazolyl, indolyl, or quinolinyl, each substituted with zero to 3 substituents independently selected from F, Cl, Br, —CN, —OH, —$CH_3$, —$CH_2CH_3$, —CH($CH_3$)$_2$, —C($CH_3$)$_3$, —$CHF_2$, —$CF_3$, —$OCH_3$, —$OCH_2CH_3$, —OCH($CH_3$)$_2$, —$OCHF_2$, —$OCF_3$, —C(O)$CH_3$, —C(O)OC($CH_3$)$_3$, —N($CH_3$)$_2$, cyanocyclopropyl, and phenyl.

In one embodiment, a compound of Formula (I) or a salt thereof is provided wherein $R_4$ is —$CHR_{4a}R_{4b}$, —$CDR_{4a}R_{4b}$, or —$CH_2CHR_{4a}R_{4d}$. Included in this embodiment are compounds in which $R_4$ is —$CHR_{4a}R_{4b}$ or —$CDR_{4a}R_{4b}$. Also included in this embodiment are compounds in which $R_{4a}$ is phenyl, pyridinyl, dihydrobenzofuranyl, benzodioxolyl, isoxazolyl, naphthyridinyl, quinolinyl, or thiazolyl, each substituted with zero to 3 substituents independently selected from F, Cl, Br, —CN, —OH, —$CH_3$, —$CF_3$, —$OCH_3$, —$OCHF_2$, —$OCF_3$, —C(O)OH, —C(O)$OCH_3$, and cyclopropyl; $R_{4b}$ is —$CH_3$, —$CH_2CH_3$, —$CH_2CH_2CH_3$, —C($CH_3$)$_3$, —$CH_2$F, —$CF_3$, —$CH_2$OH, —C($CH_3$)$_2$OH, —$CH_2OCH_3$, —$CH_2OCHF_2$, —$CF_2CH_2$OH, —$CF_2CH_2OCH_3$, —$CH_2SCH_3$, cyclopropyl, —$CH_2$(cyclohexyl), or —$CH_2$(cyclopropyl-oxadiazolyl); and $R_{4d}$ is —$OCH_3$.

In one embodiment, a compound of Formula (I) or a salt thereof is provided wherein $R_4$ is —$CHR_{4a}R_{4b}$ or —$CHR_{4b}CH_2R_{4a}$. Included in this embodiment are compounds in which $R_4$ is —$CHR_{4a}R_{4b}$. Also included in this embodiment are compounds in which $R_{4a}$ and $R_{4b}$ are independently phenyl, pyridinyl, pyrimidinyl, pyrazinyl, pyridazinyl, pyrazolyl, imidazolyl, isoxazolyl, isothiazolyl, oxazolyl, oxadiazolyl, tetrazolyl, thiadiazolyl, thiazolyl, triazolyl, thiophenyl, tetrahydropyranyl, dihydrobenzo[b][1,4]dioxinyl, dihydrobenzo[b][1,4]dioxepinyl, dihydrobenzofuranyl, benzo[d]isoxazolyl, benzoxazinyl, benzoxazinonyl, indazolyl, indolyl, benzo[d][1,3]dioxolyl, pyrazolo[1,5-a]pyridinyl, dioxidotetrahydrothiopyranyl, quinolinyl, or naphthyridinyl, each substituted with zero to 3 substituents independently selected from F, Cl, Br, —CN, —OH, —$CH_3$, —$CH_2CH_3$, —CH($CH_3$)$_2$, —C($CH_3$)$_3$, —$CHF_2$, —$CF_3$, —$CH_2$OH, —$CH_2OCH_3$, —$OCH_3$, —$OCH_2CH_3$, —OCH($CH_3$)$_2$, —OC($CH_3$)$_3$, —$OCH_2$C($CH_3$)$_2$OH, —$OCH_2CH_2OCH_3$, —$OCHF_2$, —$OCF_3$, —$OCH_2CH_2$N($CH_3$)$_2$, —C(O)$CH_3$, —C(O)C($CH_3$)$_3$, —C(O)OH, —C(O)$OCH_3$, —C(O)OC($CH_3$)$_3$, —N($CH_3$)$_2$, —P(O)($CH_3$)$_2$, —S(O)$_2CH_3$, —$OCH_2$(cyclopropyl), —$OCH_2CH_2$(cyclopropyl), —$OCH_2CH_2$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, phenyl, fluorophenyl, cyanophenyl, thiophenyl, fluorophenyl, and methylpiperidinyl.

In one embodiment, a compound of Formula (I) or a salt thereof is provided wherein $R_4$ is —$CH_2R_{4a}$, —$CD_2R_{4a}$, —$CHR_{4a}R_{4b}$, or —$CDR_{4a}R_{4b}$. Included in this embodiment are compounds in which $R_4$ is —$CH_2R_{4a}$, or —$CHR_{4a}R_{4b}$. Also included in this embodiment are compounds in which $R_4$ is —$CH_2R_{4a}$, —$CD_2R_{4a}$, —$CHR_{4a}R_{4b}$, or —$CDR_{4a}R_{4b}$.

In one embodiment, a compound of Formula (I) or a salt thereof is provided wherein $R_4$ is —$CHR_{4a}R_{4b}$: $R_{4a}$ is phenyl or pyridinyl, each substituted with zero to 2 substituents independently selected from F, Cl, Br, —CN, —$CH_3$, and —$OCF_3$; and $R_{4b}$ is phenyl, pyridinyl, pyrimidinyl, pyrazinyl, pyridazinyl, pyrazolyl, imidazolyl, isoxazolyl, isothiazolyl, oxazolyl, oxadiazolyl, tetrazolyl, thiadiazolyl, thiazolyl, triazolyl, thiophenyl, tetrahydropyranyl, dihydrobenzo[b][1,4]dioxinyl, dihydrobenzo[b][1,4]dioxepinyl, dihydrobenzofuranyl, benzo[d]isoxazolyl, benzoxazinyl, benzoxazinonyl, indazolyl, indolyl, benzo[d][1,3]dioxolyl, pyrazolo[1,5-a]pyridinyl, dioxidotetrahydrothiopyranyl, quinolinyl, or naphthyridinyl, each substituted with zero to 3 substituents independently selected from F, Cl, Br, —CN, —OH, —$CH_3$, —$CH_2CH_3$, —CH($CH_3$)$_2$, —C($CH_3$)$_3$, —$CHF_2$, —$CF_3$, —$CH_2$OH, —$CH_2OCH_3$, —$OCH_3$, —$OCH_2CH_3$, —OCH($CH_3$)$_2$, —OC($CH_3$)$_3$, —$OCH_2$C($CH_3$)$_2$OH, —$OCH_2CH_2OCH_3$, —$OCHF_2$, —$OCF_3$, —$OCH_2CH_2$N($CH_3$)$_2$, —C(O)$CH_3$, —C(O)C($CH_3$)$_3$, —C(O)OH, —C(O)$OCH_3$, —C(O)OC($CH_3$)$_3$, —N($CH_3$)$_2$, —P(O)($CH_3$)$_2$, —S(O)$_2CH_3$, —$OCH_2$(cyclopropyl), —$OCH_2CH_2$(cyclopropyl), —$OCH_2CH_2$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, phenyl, fluorophenyl, cyanophenyl, thiophenyl, fluorophenyl, and methylpiperidinyl.

In one embodiment, a compound of Formula (I) or a salt thereof is provided having the structure of Formula (II):

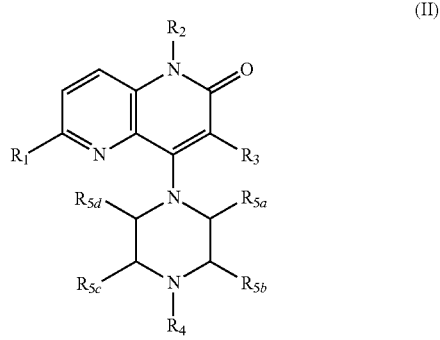

(II)

wherein one, two, or three of $R_{5a}$, $R_{5b}$, $R_{5c}$, and $R_{5d}$ are each $R_5$ and the remainder of $R_{5a}$, $R_{5b}$, $R_{5c}$, and $R_{5d}$ are each hydrogen. Included in this embodiment are compounds in which each $R_5$ is independently —CN, —$CH_3$, —$CH_2CH_3$, —CH($CH_3$)$_2$, —CHC($CH_3$)$_2$, —$CH_2$F, —C($CH_3$)$_2$F, —CF($CH_3$)CH($CH_3$)$_2$, —$CH_2$OH, —C($CH_3$)$_2$OH, —C($CH_3$)(OH)CH($CH_3$)$_2$, —$CH_2OCH_3$, —C(O)C($CH_3$)$_2$, —C(O)OH, —C(O)$OCH_3$, —C(O)OC($CH_3$)$_2$, —C(O)$NH_2$, —C(O)NH(cyclopropyl), —C(O)O(cyclopropyl), cyclopropyl, phenyl, methyloxadiazolyl, or methylpyridinyl.

In one embodiment, a compound of Formula (I) or a salt thereof is provided having the structure of Formula (II):

13

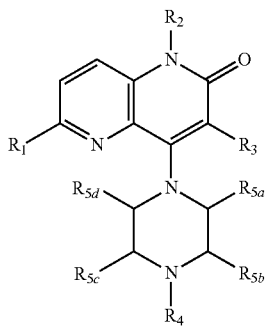

(II)

wherein
(i) R$_{5a}$ is —CN, —CH$_3$, —CH$_2$CH$_3$, —CH(CH$_3$)$_2$, —CH$_2$F, —CH$_2$OH, —C(O)OH, —C(O)OCH$_3$, —C(O)NH$_2$, cyclopropyl, —C(O)NH(cyclopropyl), or phenyl, and R$_{5b}$, R$_{5c}$, and R$_{5d}$ are each H;
(ii) R$_{5a}$ is cyclopropyl, R$_{5b}$ is H, R$_{5c}$ is cyclopropyl, and R$_{5d}$ is H;
(iii) R$_{5b}$ is —CN, —CH$_3$, —CH$_2$CH$_3$, —CH(CH$_3$)$_2$, —CH$_2$F, —C(CH$_3$)$_2$F, —CF(CH$_3$)CH(CH$_3$)$_2$, —CH$_2$OH, —C(CH$_3$)$_2$OH, —CH$_2$OCH$_3$, —C(O)OH, —C(O)OCH$_3$, —C(O)C(CH$_3$)$_2$, —C(O)OCH$_3$, —C(O)OC(CH$_3$)$_2$, —C(O)NH$_2$, —C(CH$_3$)(OH)CH(CH$_3$)$_2$, —C(O)NH(cyclopropyl), —C(O)O(cyclopropyl), or methyloxadiazolyl, and R$_{5a}$, R$_{5c}$, and R$_{5d}$ are each H;
(iv) R$_{5b}$ is —CH$_3$ or methyl-pyridinyl, R$_{5c}$ is —CH$_3$, and R$_{5a}$ and R$_{5d}$ are each H;
(v) R$_{5a}$ is —CH$_3$, —CH$_2$CH$_3$, —CH(CH$_3$)$_2$, —CH$_2$OH, or —CH$_2$OCH$_3$, R$_{5c}$ is —CH$_3$, and R$_{5b}$ and R$_{5d}$ are each H; or
(vi) R$_{5a}$ is —CH$_3$, R$_{5b}$ is —CH$_3$ or —CH$_2$OCF$_2$, and R$_{5c}$ and R$_{5d}$ are each H;
(vii) R$_{5a}$ is —CH$_3$, R$_{5C}$ is —CH$_2$CH$_3$, —CH$_2$CN, —CH$_2$OH, —CH$_2$OCH$_3$, —CH$_2$OCH$_2$CH$_3$, —CH$_2$OCH$_2$CH$_2$OH$_3$, —CH$_2$N(CH$_3$)$_2$, —CH$_2$NHC(O)CH$_3$, —CH$_2$NHC(O)OCH$_3$, —CH$_2$NHS(O)$_2$CH$_3$, —CH$_2$(morpholinyl), —CH$_2$(hydroxyazetidinyl), or —CH$_2$(methylpiperazinyl), and R$_{5b}$ and R$_{5d}$ are each H; or
(viii) R$_{5a}$ is —CH$_2$CH$_3$, R$_{5c}$ is —CH$_2$CH$_3$ or —CH$_2$OCH$_3$, and R$_{5b}$ and R$_{5d}$ are each H; and R$_1$, R$_2$, R$_3$, and R$_4$ are defined in the first aspect, the second aspect, or the third aspect. Included in this embodiment are compounds in which R$_1$ is C$_1$, —CN, or —OCH$_3$; R$_2$ is —CH$_3$; and R$_3$ is H, F, Cl, or —CN.

In one embodiment, a compound of Formula (I) or a salt thereof is provided having the structure of Formula (II):

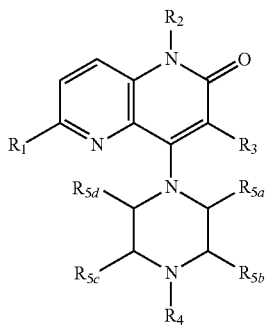

(II)

wherein:
(i) R$_{5a}$ is —CN, —CH$_2$CH$_3$, —CH(CH$_3$)$_2$, —CH$_2$F, —CH$_2$OH, —C(O)OH, —C(O)OCH$_3$, —C(O)NH$_2$, cyclopropyl, —C(O)NH(cyclopropyl), or phenyl, and R$_{5b}$, R$_{5c}$, and R$_{5d}$ are each H;
(ii) R$_{5a}$ is cyclopropyl, R$_{5b}$ is H, R$_{5c}$ is cyclopropyl, and R$_{5d}$ is H;
(iii) R$_{5b}$ is —CN, —CH$_3$, —CH$_2$CH$_3$, —CH(CH$_3$)$_2$, —CH$_2$F, —C(CH$_3$)$_2$F, —CF(CH$_3$)CH(CH$_3$)$_2$, —CH$_2$OH, —C(CH$_3$)$_2$OH, —CH$_2$OCH$_3$, —C(O)CH$_3$, —C(O)OH, —C(O)OCH$_3$, —C(O)OC(CH$_3$)$_2$, —C(O)NH$_2$, —C(CH$_3$)(OH)CH(CH$_3$)$_2$, —C(O)NH(cyclopropyl), —C(O)O(cyclopropyl), or methyloxadiazolyl, and R$_{5a}$, R$_{5c}$, and R$_{5d}$ are each H;
(iv) R$_{5b}$ is —CH$_3$, R$_{5c}$ is —CH$_3$, and R$_{5a}$ and R$_{5d}$ are each H;
(v) R$_{5a}$ is —CH$_3$, —CH$_2$CH$_3$, or —CH(CH$_3$)$_2$, R$_{5c}$ is —CH$_3$, and R$_{5b}$ and R$_{5d}$ are each H; (v) R$_{5a}$ is —CH$_3$, R$_{5c}$ is —CH$_2$OH, and R$_{5b}$ and R$_{5d}$ are each H;
(vii) R$_{5a}$ is —CH$_3$ or —CH$_2$CH$_3$, R$_{5c}$ is —CH$_2$CH$_3$ or —CH$_2$OCH$_3$ and R$_{5b}$ and R$_{5d}$ are each H; or
(viii) R$_{5a}$ is —CH$_3$, R$_{5b}$ is —CH$_3$, and R$_{5c}$ and R$_{5d}$ are each H;

and R$_1$, R$_2$, R$_3$, and R$_4$ are defined in the first aspect, the second aspect, or the third aspect.

In one embodiment, a compound of Formula (I) or a salt thereof is provided having the structure of Formula (II) wherein:
(i) R$_{5a}$ is —CN, —CH$_2$CH$_3$, —CH(CH$_3$)$_2$, —CH$_2$F, —CH$_2$OH, —C(O)OH, —C(O)OCH$_3$, —C(O)NH$_2$, cyclopropyl, —C(O)NH(cyclopropyl), or phenyl, and R$_{5b}$, R$_{5c}$, and R$_{5d}$ are each H;
(ii) R$_{5a}$ is cyclopropyl, R$_{5b}$ is H, R$_{5c}$ is cyclopropyl, and R$_{5d}$ is H;
(iii) R$_{5b}$ is —CN, —CH$_3$, —CH$_2$CH$_3$, —CH(CH$_3$)$_2$, —CH$_2$F, —C(CH$_3$)$_2$F, —CF(CH$_3$)CH(CH$_3$)$_2$, —CH$_2$OH, —C(CH$_3$)$_2$OH, —CH$_2$OCH$_3$, —C(O)OH, —C(O)OCH$_3$, —C(O)OC(CH$_3$)$_2$, —C(O)NH$_2$, —C(CH$_3$)(OH)CH(CH$_3$)$_2$, —C(O)NH(cyclopropyl), —C(O)O(cyclopropyl), or methyloxadiazolyl, and R$_{5a}$, R$_{5c}$, and R$_{5d}$ are each H;
(iv) R$_{5b}$ is —CH$_3$ or methyl-pyridinyl, R$_{5c}$ is —CH$_3$, and R$_{5a}$ and R$_{5d}$ are each H;
(v) R$_{5a}$ is —CH$_3$ or —CH(CH$_3$)$_2$, R$_{5c}$ is —CH$_3$, and R$_{5b}$ and R$_{5d}$ are each H; or
(vi) R$_{5a}$ is —CH$_3$, R$_{5b}$ is —CH$_3$, and R$_{5c}$ and R$_{5d}$ are each H;

and R$_1$, R$_2$, R$_3$, and R$_4$ are defined in the first aspect, the second aspect, or the third aspect. Included in this embodiment are compounds in which:
(i) R$_{5a}$ is —CH$_2$CH$_3$, —CH(CH$_3$)$_2$, —CH$_2$F, —CH$_2$OH, —C(O)OCH$_3$, cyclopropyl, or phenyl, and R$_{5b}$, R$_{5c}$, and R$_{5d}$ are each H;
(ii) R$_{5a}$ is cyclopropyl, R$_{5b}$ is H, R$_{5c}$ is cyclopropyl, and R$_{5d}$ is H;
(iii) R$_{5b}$ is —CN, —CH$_3$, —CH$_2$CH$_3$, —CH(CH$_3$)$_2$, —CH$_2$F, —C(CH$_3$)$_2$F, —CF(CH$_3$)CH(CH$_3$)$_2$, —CH$_2$OH, —C(CH$_3$)$_2$OH, —CH$_2$OCH$_3$, —C(O)OCH$_3$, —C(O)OC(CH$_3$)$_2$, —C(CH$_3$)(OH)CH(CH$_3$)$_2$, —C(O)O(cyclopropyl), or methyloxadiazolyl, and R$_{5a}$, R$_{5c}$, and R$_{5d}$ are each H;
(iv) R$_{5b}$ is —CH$_3$ or methyl-pyridinyl, R$_{5c}$ is —CH$_3$, and R$_{5a}$ and R$_{5d}$ are each H;
(v) R$_{5a}$ is —CH$_3$ or —CH(CH$_3$)$_2$, R$_{5c}$ is —CH$_3$, and R$_{5b}$ and R$_{5d}$ are each H; or
(vi) R$_{5a}$ is —CH$_3$, R$_{5b}$ is —CH$_3$, and R$_{5c}$ and R$_{5d}$ are each H.

In one embodiment, a compound of Formula (I) or a salt thereof is provided having the structure of Formula (II) wherein $R_{5a}$ is —CH$_3$, $R_{5c}$ is —CH$_3$, and $R_{5b}$ and $R_{5d}$ are each H; and $R_1$, $R_2$, $R_3$, and $R_4$ are defined in the first aspect, the second aspect, or the third aspect.

In one embodiment, a compound of Formula (I) or a salt thereof is provided having the structure of Formula (II) wherein $R_{5a}$ is —CH$_2$CH$_3$, $R_{5c}$ is —CH$_2$CH$_3$, and $R_{5b}$ and $R_{5d}$ are each H; and $R_1$, $R_2$, $R_3$, and $R_4$ are defined in the first aspect, the second aspect, or the third aspect.

In one embodiment, a compound of Formula (I) or a salt thereof is provided having the structure of Formula (II) wherein $R_{5b}$ is —CH$_3$, $R_{5c}$ is —CH$_2$CH$_3$, and $R_{5b}$ and $R_{5d}$ are each H; and $R_1$, $R_2$, $R_3$, and $R_4$ are defined in the first aspect, the second aspect, or the third aspect.

In one embodiment, a compound of Formula (I) or a salt thereof is provided having the structure of Formula (II) wherein $R_{5b}$ is —CH$_2$CH$_3$, $R_{5c}$ is —CH$_3$, and $R_{5b}$ and $R_{5d}$ are each H; and $R_1$, $R_2$, $R_3$, and $R_4$ are defined in the first aspect, the second aspect, or the third aspect.

In one embodiment, a compound of Formula (I) or a salt thereof is provided having the structure of Formula (II) wherein $R_{5a}$ is —CH$_3$, and $R_{5b}$, $R_{5c}$, and $R_{5d}$ are each H; and $R_1$, $R_2$, $R_3$, and $R_4$ are defined in the first aspect, the second aspect, or the third aspect.

In one embodiment, a compound of Formula (I) or a salt thereof is provided wherein: $R_1$ is H, F, Cl, Br, —CN, $C_{1-3}$ alkyl substituted with zero to 4 $R_{1a}$, cyclopropyl substituted with zero to 3 $R_{1a}$, $C_{1-3}$ alkoxy substituted with zero to 3 $R_{1a}$, —NR$_a$R$_a$, —S(O)$_n$CH$_3$, or —P(O)(CH$_3$)$_2$; and $R_{1a}$, $R_a$, $R_2$, $R_3$, $R_4$, $R_5$, m, and n are defined in the first aspect, the second aspect, or the third aspect. Included in this embodiment are compounds in which $R_1$ is H, F, Cl, Br, —CN, $C_{1-3}$ alkyl substituted with zero to 4 $R_{1a}$, cyclopropyl substituted with zero to 3 $R_{1a}$, $C_{1-3}$ alkoxy substituted with zero to 3 $R_{1a}$, or —NR$_a$R$_3$. Also included in this embodiment are compounds in which $R_1$ is H, F, Cl, Br, —CN, —CH$_3$, cyclopropyl, or —NR$_a$R$_a$; and each $R_{1a}$ is independently H or —CH$_3$. Additionally, included in this embodiment are compounds in which $R_1$ is H, Br, —CN, or —OCH$_3$.

In one embodiment, a compound of Formula (I) or a salt thereof is provided wherein: $R_2$ is H, $C_{1-3}$ alkyl substituted with zero to 3 $R_{2a}$, or $C_{3-4}$ cycloalkyl substituted with zero to 3 $R_{2a}$; and $R_1$, $R_{2a}$, $R_3$, $R_4$, $R_5$ and m are defined in the first aspect, the second aspect, or the third aspect. Included in this embodiment are compounds in which $R_2$ is H, $C_{1-2}$ alkyl substituted with zero to 2 $R_{2a}$, or cyclopropyl substituted with zero to 2 $R_{2a}$. Also included in this embodiment are compounds in which $R_2$ is H or $C_{1-2}$ alkyl substituted with zero to 2 $R_{2a}$. Additionally, included in this embodiment are compounds in which $R_2$ is —CH$_3$.

In one embodiment, a compound of Formula (I) or a salt thereof is provided wherein: $R_3$ is H, F, Cl, Br, —CN, $C_{1-3}$ alkyl, $C_{1-2}$ fluoroalkyl, $C_{3-4}$ cycloalkyl, or —NO$_2$; and $R_1$, $R_2$, $R_4$, $R_5$ and m are defined in the first aspect, the second aspect, or the third aspect. Included in this embodiment are compounds in which $R_3$ is H, F, Cl, Br, —CN, $C_{1-2}$ alkyl, —CF$_3$, cyclopropyl, or —NO$_2$. Also included in this embodiment are compounds in which $R_3$ is H, F, Cl, Br, —CN, —CH$_3$, cyclopropyl, or —NO$_2$. Additionally, included in this embodiment are compounds in which $R_3$ is H, F, Cl, or —CN.

In one embodiment, a compound of Formula (I) or a salt thereof is provided wherein: $R_4$ is —CH$_2$R$_{4a}$, —CHR$_{4a}$R$_{4b}$, or —CR$_{4a}$R$_{4b}$R$_{4c}$; $R_{4a}$ and $R_{4b}$ are independently: (i) $C_{1-4}$ alkyl substituted with zero to 4 substituents independently selected from F, Cl, —CN, —OH, —OCH$_3$, $C_{1-3}$ fluoro-alkoxy, and —NR$_a$R$_a$; (ii) $C_{3-6}$ cycloalkyl, heterocyclyl, phenyl, or heteroaryl, each substituted with zero to 4 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH═CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and R$_d$; or (iii) $C_{1-3}$ alkyl substituted with one cyclic group selected from $C_{3-6}$ cycloalkyl, heterocyclyl, phenyl, and heteroaryl, said cyclic group substituted with zero to 3 substituents independently selected from F, Cl, Br, —OH, —CN, $C_{1-3}$ alkyl, $C_{1-2}$ fluoroalkyl, $C_{1-3}$ alkoxy, $C_{1-2}$ fluoroalkoxy, —OCH$_2$CH═CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), and —NR$_a$C(O)O(C$_{1-4}$ alkyl); or $R_{4a}$ and $R_{4b}$ together with the carbon atom to which they are attached, form a $C_{3-6}$ cycloalkyl or a 3- to 6-membered heterocyclyl, each substituted with zero to 3 $R_f$; and $R_1$, $R_2$, $R_3$, $R_5$, $R_a$, $R_c$, $R_d$, $R_f$, and m are defined in the first aspect, the second aspect, or the third aspect. Included in this embodiment are compounds in which $R_{4a}$ is phenyl or heteroaryl, each substituted with zero to 3 substituents independently selected from F, Cl, —CN, —OH, —CH$_3$, —CH$_2$CH$_3$, —CH(CH$_3$)$_2$, —CHF$_2$, —CF$_3$, —CH$_2$OH, —OCH$_3$, —OCH$_2$CH$_3$, —OCH(CH$_3$)$_2$, and —OCF$_3$; and $R_{4b}$ is $C_{1-3}$ alkyl, or phenyl substituted with zero to 1 substituent selected from F, Cl, —CH$_3$, and —CH$_2$OH.

In one embodiment, a compound of Formula (I) or a salt thereof is provided wherein: $R_{4a}$ and $R_{4b}$ are independently: (i) $C_{1-6}$ alkyl substituted with zero to 4 substituents independently selected from F, Cl, —CN, —OH, —OCH$_3$, $C_{1-3}$ fluoroalkoxy and —NR$_a$R$_a$; (ii) $C_{3-6}$ cycloalkyl, 5- to 14-membered heterocyclyl, 5- to 10-membered aryl, or 5- to 10-membered heteroaryl, each substituted with zero to 4 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH═CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and R$_d$; or (iii) $C_{1-4}$ alkyl substituted with one cyclic group selected from $C_{3-6}$ cycloalkyl, 5- to 14-membered heterocyclyl, 5- to 10-membered aryl, or 5- to 10-membered heteroaryl, said cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —OCH$_2$CH═CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), and —NR$_a$C(O)O(C$_{1-4}$ alkyl); or $R_{4a}$ and $R_{4b}$ together with the carbon atom to which they are attached form a $C_{3-6}$ cycloalkyl or a 3- to 6-membered heterocyclyl, each substituted with zero to 3 $R_f$; and $R_1$, $R_2$, $R_3$, $R_5$, $R_a$, $R_c$, $R_d$, $R_f$, and m are defined in the first aspect, the second aspect, or the third aspect. Included in this embodiment are compounds in which $R_{4a}$ and $R_{4b}$ are independently: (i) $C_{1-6}$ alkyl substituted with zero to 4 substituents independently selected from F, Cl, —CN, —OH, —OCH$_3$, $C_{1-3}$ fluoroalkoxy and —NR$_a$R$_a$; (ii) $C_{3-6}$ cycloalkyl, 5- to 6-membered heterocyclyl, phenyl, naphthalenyl, 5- to 6-membered heteroaryl, each substituted with zero to 4 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH═CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and R$_a$; or (iii) $C_{1-4}$ alkyl substituted with one cyclic group selected from $C_{3-6}$ cycloalkyl, 5- to 6-membered heterocyclyl, 5- to 10-membered aryl, or 5- to 6-membered heteroaryl, said cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —OCH$_2$CH═CH$_2$, —OCH$_2$C≡CH, —NR$_c$R$_c$, —NR$_a$S(O)$_2$ ($C_{1-3}$ alkyl), —NR$_a$C(O)($C_{1-3}$ alkyl), and —NR$_a$C(O)O ($C_{1-4}$ alkyl); or R$_{4a}$ and R$_{4b}$ together with the carbon atom to which they are attached form a $C_{3-6}$ cycloalkyl or a 3- to 6-membered heterocyclyl, each substituted with zero to 3 R$_f$.

In one embodiment, a compound of Formula (I) or a salt thereof is provided wherein: R$_4$ is —CH$_2$R$_{4a}$ or —CHR$_{4a}$R$_{4b}$; and R$_1$, R$_2$, R$_3$, R$_{4a}$, R$_{4b}$, R$_5$, and m are defined in the first aspect, the second aspect, or the third aspect. Included in this embodiment are compounds in which R$_{4a}$ and R$_{4b}$ are independently: (i) $C_{1-4}$ alkyl substituted with zero to 4 substituents independently selected from F, Cl, —CN, —OH, —OCH$_3$, $C_{1-3}$ fluoroalkoxy, and —NR$_a$R$_a$; (ii) $C_{3-6}$ cycloalkyl, heterocyclyl, phenyl, or heteroaryl, each substituted with zero to 4 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH═CH$_2$, —OCH$_2$C≡CH, —NR$_c$R$_c$, —NR$_a$S(O)$_2$ ($C_{1-3}$ alkyl), —NR$_a$C(O)($C_{1-3}$ alkyl), —NR$_a$C(O)O($C_{1-4}$ alkyl), and R$_a$; or (iii) $C_{1-3}$ alkyl substituted with one cyclic group selected from $C_{3-6}$ cycloalkyl, heterocyclyl, phenyl, and heteroaryl, said cyclic group substituted with zero to 3 substituents independently selected from F, Cl, Br, —OH, —CN, $C_{1-3}$ alkyl, $C_{1-2}$ fluoroalkyl, $C_{1-3}$ alkoxy, $C_{1-2}$ fluoroalkoxy, —OCH$_2$CH═CH$_2$, —OCH$_2$C≡CH, —NR$_c$R$_c$, —NR$_a$S(O)$_2$($C_{1-3}$ alkyl), —NR$_a$C(O)($C_{1-3}$ alkyl), and —NR$_a$C(O)O($C_{1-4}$ alkyl); and R$_a$, R$_c$, and R$_d$ are defined in the first aspect, the second aspect, or the third aspect. Included in this embodiment are compounds in which R$_{4a}$ and R$_{4b}$ are independently: (i) $C_{1-6}$ alkyl substituted with zero to 4 substituents independently selected from F, Cl, —CN, —OH, —OCH$_3$, $C_{1-3}$ fluoroalkoxy and —NR$_a$R$_a$; (ii) $C_{3-6}$ cycloalkyl, 5- to 6-membered heterocyclyl, phenyl, naphthalenyl, 5- to 6-membered heteroaryl, each substituted with zero to 4 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH═CH$_2$, —OCH$_2$C≡CH, —NR$_c$R$_c$, and R$_a$; or (iii) $C_{1-4}$ alkyl substituted with one cyclic group selected from $C_{3-6}$ cycloalkyl, 5- to 6-membered heterocyclyl, 5- to 10-membered aryl, or 5- to 6-membered heteroaryl, said cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —OCH$_2$CH═CH$_2$, —OCH$_2$C≡CH, and —NR$_c$R$_c$; and R$_a$, R$_c$, and R$_d$ are defined in the first aspect, the second aspect, or the third aspect. Also included in this embodiment are compounds in which R$_{4a}$ is phenyl or pyridinyl, each substituted with zero to 3 substituents independently selected from F, Cl, —CN, —OH, —CH$_3$, —CH$_2$CH$_3$, —CH(CH$_3$)$_2$, —CHF$_2$, —CF$_3$, —CH$_2$OH, —OCH$_3$, —OCH$_2$CH$_3$, —OCH(CH$_3$)$_2$, and —OCF$_3$; and R$_{4b}$ is —CH$_3$, —C(CH$_3$)$_3$, or phenyl substituted with zero to 1 substituent selected from F, Cl, —CH$_3$, and —CH$_2$OH.

In one embodiment, a compound of Formula (I) or a salt thereof is provided wherein: R$_4$ is —CH$_2$R$_{4a}$; and R$_1$, R$_2$, R$_3$, R$_{4a}$, R$_5$, and m are defined in the first aspect, the second aspect, or the third aspect. Included in this embodiment are compounds in which R$_{4a}$ is: (i) $C_{1-4}$ alkyl substituted with zero to 4 substituents independently selected from F, Cl, —CN, —OH, —OCH$_3$, $C_{1-3}$ fluoroalkoxy, and —NR$_a$R$_a$; (ii) $C_{3-6}$ cycloalkyl, heterocyclyl, phenyl, or heteroaryl, each substituted with zero to 4 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —OCH$_2$CH═CH$_2$, —OCH$_2$C≡CH, —NR$_c$R$_c$, and R$_a$; or (iii) $C_{1-3}$ alkyl substituted with one cyclic group selected from $C_{3-6}$ cycloalkyl, heterocyclyl, phenyl, and heteroaryl, said cyclic group substituted with zero to 3 substituents independently selected from F, Cl, Br, —OH, —CN, $C_{1-3}$ alkyl, $C_{1-2}$ fluoroalkyl, $C_{1-3}$ alkoxy, $C_{1-2}$ fluoroalkoxy, —OCH$_2$CH═CH$_2$, —OCH$_2$C≡CH, and —NR$_c$R$_c$; and R$_a$, R$_c$, and R$_d$ are defined in the first aspect, the second aspect, or the third aspect. Also included in this embodiment are compounds in which R$_{4a}$ is phenyl or pyridinyl, each substituted with zero to 3 substituents independently selected from F, Cl, —CN, —OH, —CH$_3$, —CH$_2$CH$_3$, —CH(CH$_3$)$_2$, —CHF$_2$, —CF$_3$, —CH$_2$OH, —OCH$_3$, —OCH$_2$CH$_3$, —OCH(CH$_3$)$_2$, and —OCF$_3$.

In one embodiment, a compound of Formula (I) or a salt thereof is provided wherein: R$_4$ is —CH$_2$R$_{4a}$, —CD$_2$R$_{4a}$, or —CH$_2$CH$_2$R$_{4a}$; and R$_1$, R$_2$, R$_3$, R$_{4a}$, R$_5$, and m are defined in the first aspect, the second aspect, or the third aspect. Included in this embodiment are compounds in which R$_4$ is —CH$_2$R$_{4a}$ or —CD$_2$R$_{4a}$. Also, included in this embodiment are compounds in which R$_{4a}$ is phenyl, pyridinyl, tetrahydropyranyl, benzoxazinyl, benzo[d][1,3]dioxolyl, benzoxazinonyl, indazolyl, indolyl, or quinolinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —OCH$_3$, —OCH$_2$CH$_3$, —OCH(CH$_3$)$_2$, —OCHF$_2$, —OCF$_3$, —C(O)CH$_3$, —C(O) OC(CH$_3$)$_3$, —N(CH$_3$)$_2$, cyanocyclopropyl, and phenyl.

In one embodiment, a compound of Formula (I) or a salt thereof is provided wherein: R$_4$ is —CHR$_{4a}$R$_{4b}$; and R$_1$, R$_2$, R$_3$, R$_{4a}$, R$_{4b}$, R$_5$, and m are defined in the first aspect, the second aspect, or the third aspect. Included in this embodiment are compounds in which R$_{4a}$ and R$_{4b}$ are independently (i) $C_{1-4}$ alkyl substituted with zero to 4 substituents independently selected from F, Cl, —CN, —OH, —OCH$_3$, $C_{1-3}$ fluoroalkoxy, and —NR$_a$R$_a$; (ii) $C_{3-6}$ cycloalkyl, heterocyclyl, phenyl, or heteroaryl, each substituted with zero to 4 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH═CH$_2$, —OCH$_2$C≡CH, —NR$_c$R$_c$, and R$_a$; or (iii) $C_{1-3}$ alkyl substituted with one cyclic group selected from $C_{3-6}$ cycloalkyl, heterocyclyl, phenyl, and heteroaryl, said cyclic group substituted with zero to 3 substituents independently selected from F, Cl, Br, —OH, —CN, $C_{1-3}$ alkyl, $C_{1-2}$ fluoroalkyl, $C_{1-3}$ alkoxy, $C_{1-2}$ fluoroalkoxy, —OCH$_2$CH═CH$_2$, —OCH$_2$C≡CH, and —NR$_c$R$_c$; and R$_a$, R$_c$, and R$_d$ are defined in the first aspect, the second aspect, or the third aspect. Also included in this embodiment are compounds in which R$_{4a}$ is phenyl or pyridinyl, each substituted with zero to 3 substituents independently selected from F, Cl, —CN, —OH, —CH$_3$, —CH$_2$CH$_3$, —CH(CH$_3$)$_2$, —CHF$_2$, —CF$_3$, —CH$_2$OH, —OCH$_3$, —OCH$_2$CH$_3$, —OCH(CH$_3$)$_2$, and —OCF$_3$; and R$_{4b}$ is $C_{1-3}$ alkyl, or phenyl substituted with zero to 1 substituent selected from F, Cl, —CH$_3$, and —CH$_2$OH. Additionally, included in this embodiment are compounds in which R$_{4a}$ is phenyl or pyridinyl, each substituted with zero to 3 substituents independently selected from F, Cl, —CN, —OH, —CH$_3$, —CH$_2$CH$_3$, —CH(CH$_3$)$_2$, —CHF$_2$, —CF$_3$, —CH$_2$OH, —OCH$_3$, —OCH$_2$CH$_3$, —OCH(CH$_3$)$_2$, and —OCF$_3$; and R$_{4b}$ is —CH$_3$ or —C(CH$_3$)$_3$.

In one embodiment, a compound of Formula (I) or a salt thereof is provided wherein: R$_4$ is —CHR$_{4a}$R$_{4b}$; R$_{4a}$ is: (i) $C_{1-4}$ alkyl substituted with zero to 4 substituents independently selected from F, Cl, —CN, —OH, —OCH$_3$, $C_{1-3}$ fluoroalkoxy, and —NR$_a$R$_a$; (ii) $C_{3-6}$ cycloalkyl, heterocyclyl, phenyl, or heteroaryl, each substituted with zero to 4 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH=CH$_2$, —OCH$_2$C≡CH, —NR$_c$R$_c$, and R$_a$; or (iii) $C_{1-3}$ alkyl substituted with one cyclic group selected from $C_{3-6}$ cycloalkyl, heterocyclyl, phenyl, and heteroaryl, said cyclic group substituted with zero to 3 substituents independently selected from F, Cl, Br, —OH, —CN, $C_{1-3}$ alkyl, $C_{1-2}$ fluoroalkyl, $C_{1-3}$ alkoxy, $C_{1-2}$ fluoroalkoxy, —OCH$_2$CH=CH$_2$, —OCH$_2$C≡CH, and —NR$_c$R$_c$; R$_{4b}$ is $C_{1-4}$ alkyl substituted with zero to 4 substituents independently selected from F, Cl, —CN, —OH, —OCH$_3$, $C_{1-3}$ fluoroalkoxy, and —NR$_a$R$_a$; and R$_1$, R$_2$, R$_3$, R$_5$, R$_a$, R$_c$, R$_d$, and m are defined in the first aspect, the second aspect, or the third aspect. Included in this embodiment are compounds in which R$_{4a}$ is (i) $C_{3-6}$ cycloalkyl, 5- to 14-membered heterocyclyl, 5- to 10-membered aryl, or 5- to 10-membered heteroaryl, each substituted with zero to 3 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH=CH$_2$, —OCH$_2$C≡CH, —NR$_c$R$_c$, and R$_a$; or (ii) $C_{1-4}$ alkyl substituted with one cyclic group selected from $C_{3-6}$ cycloalkyl, 5- to 14-membered heterocyclyl, 5- to 10-membered aryl, or 5- to 10-membered heteroaryl, said cyclic group substituted with zero to 4 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —OCH$_2$CH=CH$_2$, —OCH$_2$C≡CH, —NR$_c$R$_c$, —NR$_a$S(O)$_2$($C_{1-3}$ alkyl), —NR$_a$C(O)($C_{1-3}$ alkyl), and —NR$_a$C(O)O($C_{1-4}$ alkyl). Also included in this embodiment are compounds in which R$_{4a}$ is $C_{3-6}$ cycloalkyl, 5- to 14-membered heterocyclyl, 5- to 10-membered aryl, or 5- to 10-membered heteroaryl, each substituted with zero to 3 substituents independently selected from F, Cl, Br, —OH, —CN, $C_{1-6}$ alkyl, $C_{1-3}$ fluoroalkyl, —CH$_2$OH, $C_{1-3}$ alkoxy, $C_{1-3}$ fluoroalkoxy, —OCH$_2$CH=CH$_2$, —OCH$_2$C≡CH, —NR$_c$R$_c$, —NR$_a$S(O)$_2$($C_{1-3}$ alkyl), —NR$_a$C(O)($C_{1-3}$ alkyl), —NR$_a$C(O)O($C_{1-4}$ alkyl), and R$_d$. Additionally, included in this embodiment are compounds in which R$_{4a}$ is phenyl or pyridinyl, each substituted with zero to 3 substituents independently selected from F, Cl, —CN, —OH, —CH$_3$, —CH$_2$CH$_3$, —CH(CH$_3$)$_2$, —CHF$_2$, —CF$_3$, —CH$_2$OH, —OCH$_3$, —OCH$_2$CH$_3$, —OCH(CH$_3$)$_2$, and —OCF$_3$.

In one embodiment, a compound of Formula (I) or a salt thereof is provided wherein: R$_4$ is —CHR$_{4a}$R$_{4b}$, —CDR$_{4a}$R$_{4b}$, or —CH$_2$CHR$_{4a}$R$_{4d}$; R$_{4a}$ is phenyl, pyridinyl, dihydrobenzofuranyl, benzodioxolyl, isoxazolyl, naphthyridinyl, quinolinyl, or thiazolyl, each substituted with zero to 3 substituents independently selected from F, Cl, Br, —CN, —OH, —CH$_3$, —CF$_3$, —OCH$_3$, —OCHF$_2$, —OCF$_3$, —C(O)OH, —C(O)OCH$_3$, and cyclopropyl; R$_{4b}$ is —CH$_3$, —CH$_2$CH$_3$, —CH$_2$CH$_2$CH$_3$, —C(CH$_3$)$_3$, —CH$_2$F, —CF$_3$, —CH$_2$OH, —CH$_2$OCH$_3$, —CH$_2$OCHF$_2$, —CH$_2$(cyclohexyl), or cyclopropyl; R$_{4d}$ is —OCH$_3$; and R$_1$, R$_2$, R$_3$, R$_5$, and m are defined in the first aspect, the second aspect, or the third aspect.

In one embodiment, a compound of Formula (I) or a salt thereof is provided wherein: R$_4$ is —CHR$_{4a}$R$_{4b}$ or —CDR$_{4a}$R$_{4b}$; R$_{4a}$ is phenyl, pyridinyl, dihydrobenzofuranyl, benzodioxolyl, isoxazolyl, naphthyridinyl, quinolinyl, or thiazolyl, each substituted with zero to 3 substituents independently selected from F, Cl, Br, —CN, —OH, —CH$_3$, —CF$_3$, —OCH$_3$, —OCHF$_2$, —OCF$_3$, —C(O)OH, —C(O)OCH$_3$, and cyclopropyl; R$_{4b}$ is —CH$_3$, —CH$_2$CH$_3$, —CH$_2$CH$_2$CH$_3$, —C(CH$_3$)$_3$, —CH$_2$F, —CF$_3$, —CH$_2$OH, —CH$_2$OCH$_3$, —CH$_2$OCHF$_2$, —CH$_2$(cyclohexyl), or cyclopropyl; and R$_1$, R$_2$, R$_3$, R$_5$, and m are defined in the first aspect, the second aspect, or the third aspect.

In one embodiment, a compound of Formula (I) or a salt thereof is provided wherein: R$_4$ is —CH$_2$R$_{4a}$, —CD$_2$R$_{4a}$, or —CH$_2$CH$_2$R$_{4a}$, —CHR$_{4a}$R$_{4b}$, —CDR$_{4a}$R$_{4b}$, or —CH$_2$CHR$_{4a}$R$_{4d}$; R$_{4a}$ is phenyl, pyridinyl, tetrahydropyranyl, benzoxazinyl, benzo[d][1,3]dioxolyl, dihydrobenzofuranyl, benzodioxolyl, benzoxazinonyl, indazolyl, indolyl, isoxazolyl, thiazolyl, quinolinyl, or naphthyridinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —OCH$_3$, —OCH$_2$CH$_3$, —OCH(CH$_3$)$_2$, —OCHF$_2$, —OCF$_3$, —C(O)CH$_3$, —C(O)OH, —C(O)OCH$_3$, —C(O)OC(CH$_3$)$_3$, —N(CH$_3$)$_2$, cyclopropyl, cyanocyclopropyl, and phenyl; R$_{4b}$ is —CH$_3$, —CH$_2$CH$_3$, —CH$_2$CH$_2$CH$_3$, —C(CH$_3$)$_3$, —CH$_2$F, —CF$_3$, —CH$_2$OH, —CH$_2$OCH$_3$, —CH$_2$OCHF$_2$, —CH$_2$(cyclohexyl), or cyclopropyl; R$_{4d}$ is —OCH$_3$; and R$_1$, R$_2$, R$_3$, R$_5$, and m are defined in the first aspect, the second aspect, or the third aspect. Included in this embodiment are compounds in which R$_4$ is —CH$_2$R$_{4a}$, —CD$_2$R$_{4a}$, or —CH$_2$CH$_2$R$_{4a}$, —CHR$_{4a}$R$_{4b}$, or —CDR$_{4a}$R$_{4b}$. Also included in this embodiment are compounds in which R$_4$ is —CH$_2$R$_{4a}$, —CH$_2$CH$_2$R$_{4a}$, or —CHR$_{4a}$R$_{4b}$.

In one embodiment, a compound of Formula (I) or a salt thereof is provided wherein: R$_4$ is —CHR$_{4a}$R$_{4b}$; R$_{4a}$ and R$_{4b}$ are independently phenyl, pyridinyl, pyrimidinyl, pyrazinyl, pyrazolyl, imidazolyl, isoxazolyl, isothiazolyl, oxazolyl, oxadiazolyl, tetrazolyl, thiadiazolyl, thiazolyl, triazolyl, dihydrobenzo[b][1,4]dioxinyl, dihydrobenzo[b][1,4]dioxepinyl, dihydrobenzofuranyl, benzo[d][1,3]dioxolyl, or pyrazolo[1,5-a]pyridinyl, each substituted with zero to 3 substituents independently selected from F, Cl, Br, —CN, —CH$_3$, —CH$_2$CH$_3$, —CH(CH$_3$)$_2$, —C(CH$_3$)$_3$, —CHF$_2$, —OCH$_3$, —OCH$_2$CH$_3$, —OCH(CH$_3$)$_2$, —OCF$_3$, —CF$_3$, —S(O)$_2$CH$_3$, cyclopropyl, (tert-butoxycarbonyl)azetidinyl, tetrahydropyranyl, morpholinyl, fluorophenyl, and methylpiperidinyl; and R$_1$, R$_2$, R$_3$, R$_5$, and m are defined in the first aspect, the second aspect, or the third aspect.

In one embodiment, a compound of Formula (I) or a salt thereof is provided wherein: R$_4$ is —CHR$_{4a}$R$_{4b}$; R$_{4a}$ is phenyl or pyridinyl, each substituted with zero to 2 substituents independently selected from F, Cl, Br, —CN, —CH$_3$, and —OCF$_3$; R$_{4b}$ is phenyl, pyridinyl, pyrimidinyl, pyridazinyl, pyrazinyl, imidazolyl, isothiazolyl, isoxazolyl, oxadiazolyl, oxazolyl, pyrazolyl, tetrazolyl, thiazolyl, thiadiazolyl, triazolyl, tetrahydropyranyl, pyrazolo[1,5-a]pyridinyl, benzodioxolyl, dihydrobenzofuranyl, benzo[d][1,3]dioxolyl, or dihydrobenzo[b][1,4]dioxepinyl, each substituted with zero to 3 substituents independently selected from F, Cl, —CN, —CH$_3$, —CH$_2$CH$_3$, —CH(CH$_3$)$_2$, —C(CH$_3$)$_3$, —CHF$_2$, —CF$_3$, —OCH$_3$, —OCH$_2$CH$_3$, —OCH(CH$_3$)$_2$, —OCF$_3$, —S(O)$_2$CH$_3$, cyclopropyl, (tert-butoxycarbonyl)azetidinyl, tetrahydropyranyl, morpholinyl, and methylpiperidinyl; and R$_1$, R$_2$, R$_3$, R$_5$, and m are defined in the first aspect, the second aspect, or the third aspect.

In one embodiment, a compound of Formula (I) or a salt thereof is provided wherein: R$_4$ is —CHR$_{4a}$R$_{4b}$; R$_{4a}$ and R$_{4b}$ together with the carbon atom to which they are attached, form a $C_{3-6}$ cycloalkyl or a 3- to 6-membered heterocyclyl, each substituted with zero to 3 R$_f$; and R$_1$, R$_2$, R$_3$, R$_5$, R$_f$, and m are defined in the first aspect, the second aspect, or the third aspect. Included in this embodiment are compounds in which R$_{4a}$ and R$_{4b}$ together with the carbon atom to which they are attached, form a $C_{3-6}$ cycloalkyl substituted with zero to 3 R$_f$. Also included in this embodiment are compounds in which R$_{4a}$ and R$_{4b}$ together with the carbon atom to which they are attached, form a 3- to 6-membered heterocyclyl substituted with zero to 3 R$_f$.

In one embodiment, a compound of Formula (I) or a salt thereof is provided wherein R₄ is:
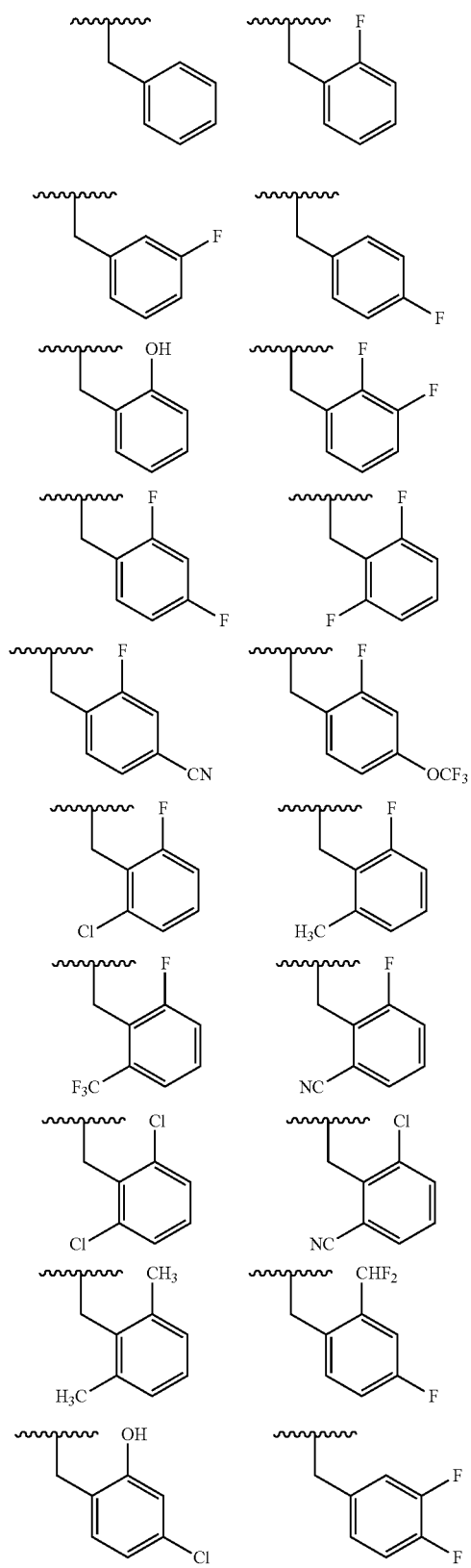
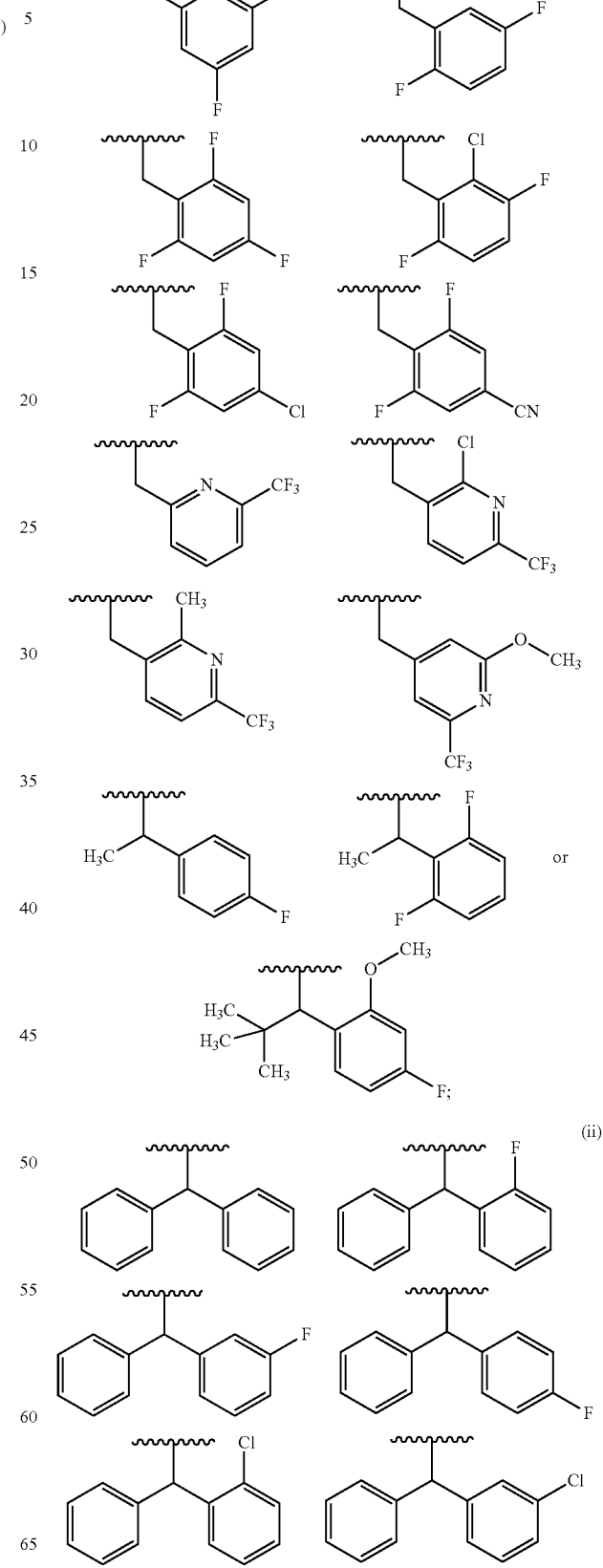

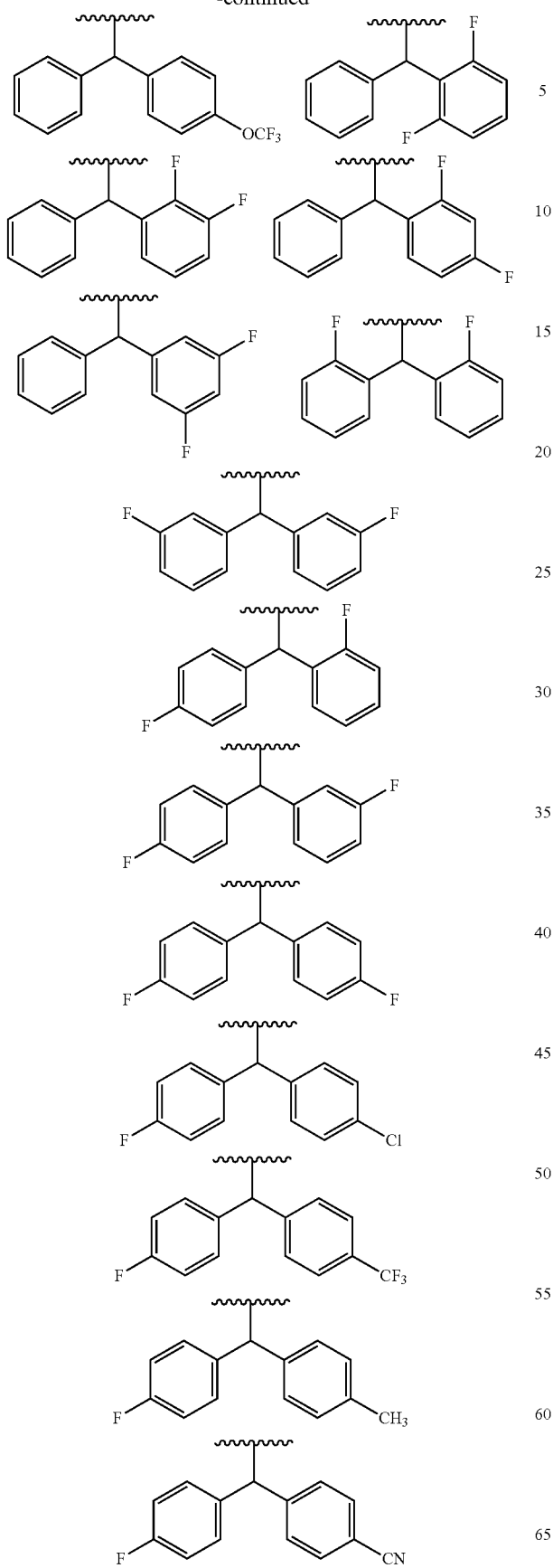
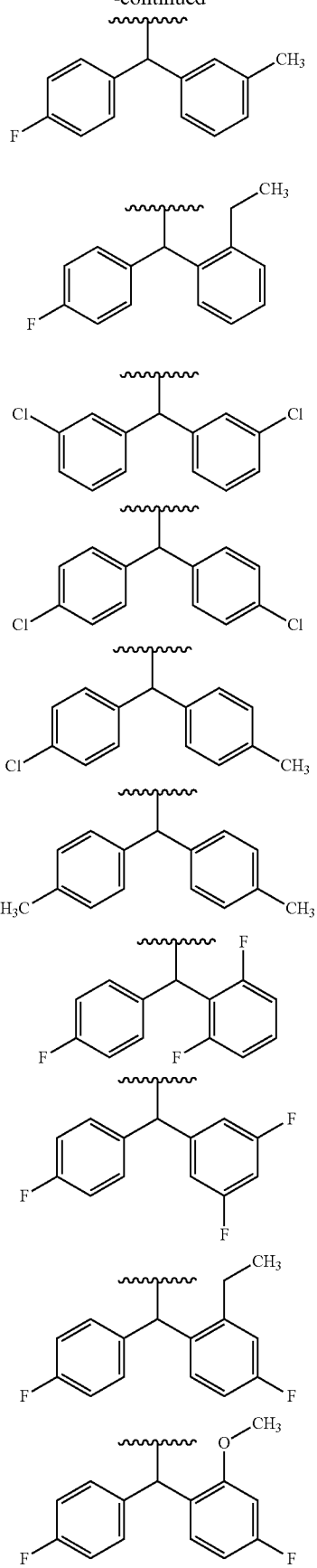

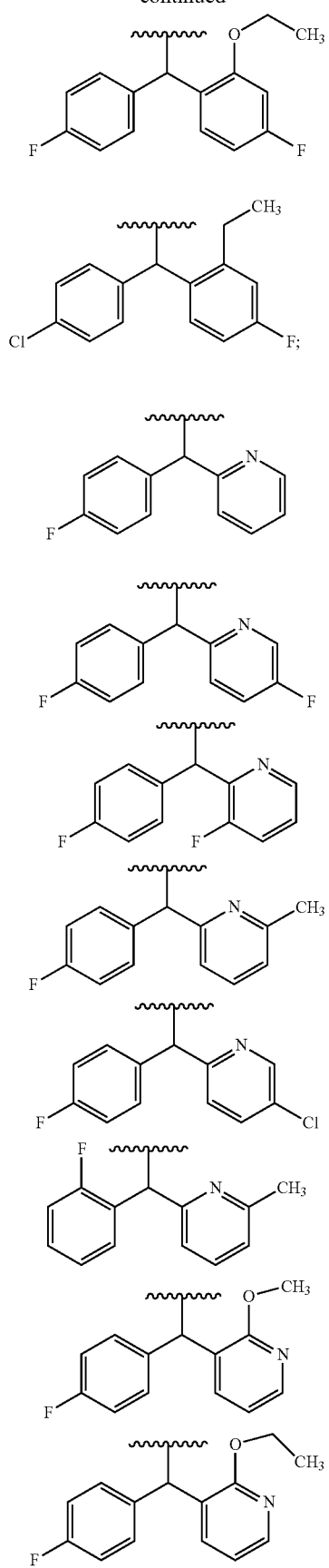
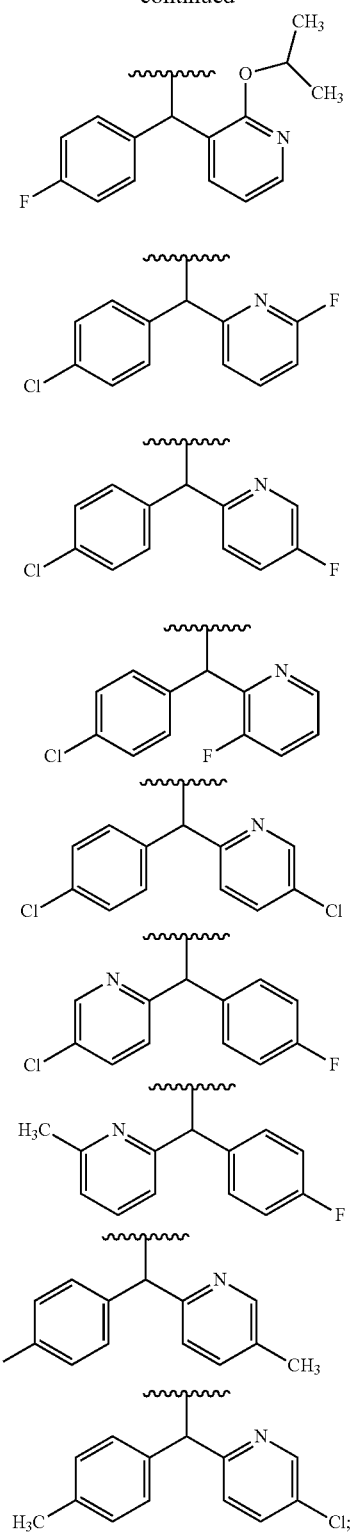
and $R_1$, $R_2$, $R_3$, $R_5$ and m are defined in the first aspect, the second aspect, or the third aspect. Included in this embodiment are compounds in which $R_1$ is H, Br, —CN, or —OCH$_3$; $R_2$ is —CH$_3$; and $R_3$ is H, F, Cl, or —CN.
In one embodiment, a compound of Formula (I) or a salt thereof is provided wherein $R_4$ is:

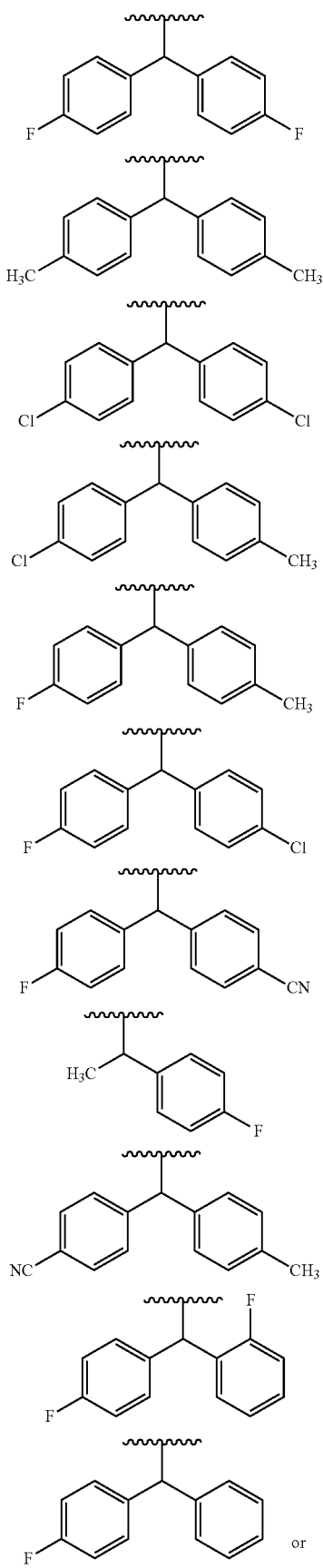

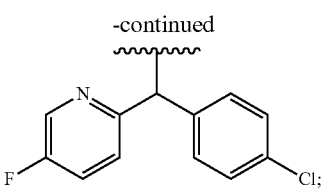

and $R_1$, $R_2$, $R_3$, $R_5$, and m are defined in the first aspect, the second aspect, or the third aspect. Included in this embodiment are compounds in which $R_1$ is H, Br, —CN, or —OCH$_3$; $R_2$ is —CH$_3$; and $R_3$ is H, F, Cl, or —CN. Also included in this embodiment are compounds in which $R_1$ is —CN; $R_2$ is —CH$_3$; and $R_3$ is H, F, or —CN.

In one embodiment, a compound of Formula (I) or a salt thereof is provided wherein said compound has the structure of Formula (III):

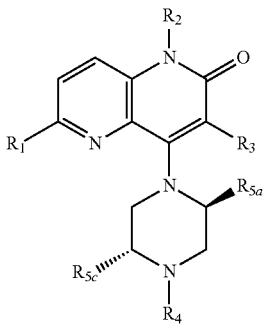

wherein $R_1$ is —CN; $R_2$ is —CH$_3$; $R_3$ is H, F, or —CN; $R_{5a}$ and $R_{5c}$ are independently H, —CH$_3$, or —CH$_2$CH$_3$, wherein at least one of $R_{5a}$ and $R_{5c}$ is —CH$_3$ or —CH$_2$CH$_3$; and $R_4$ is:

(i)

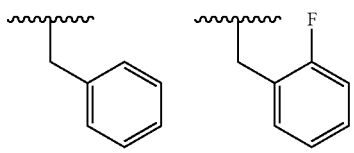

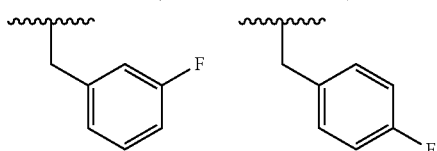

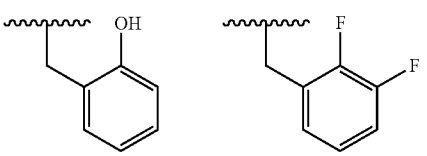

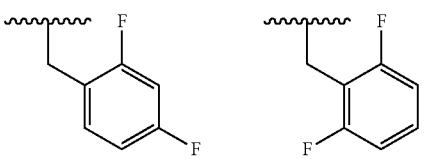

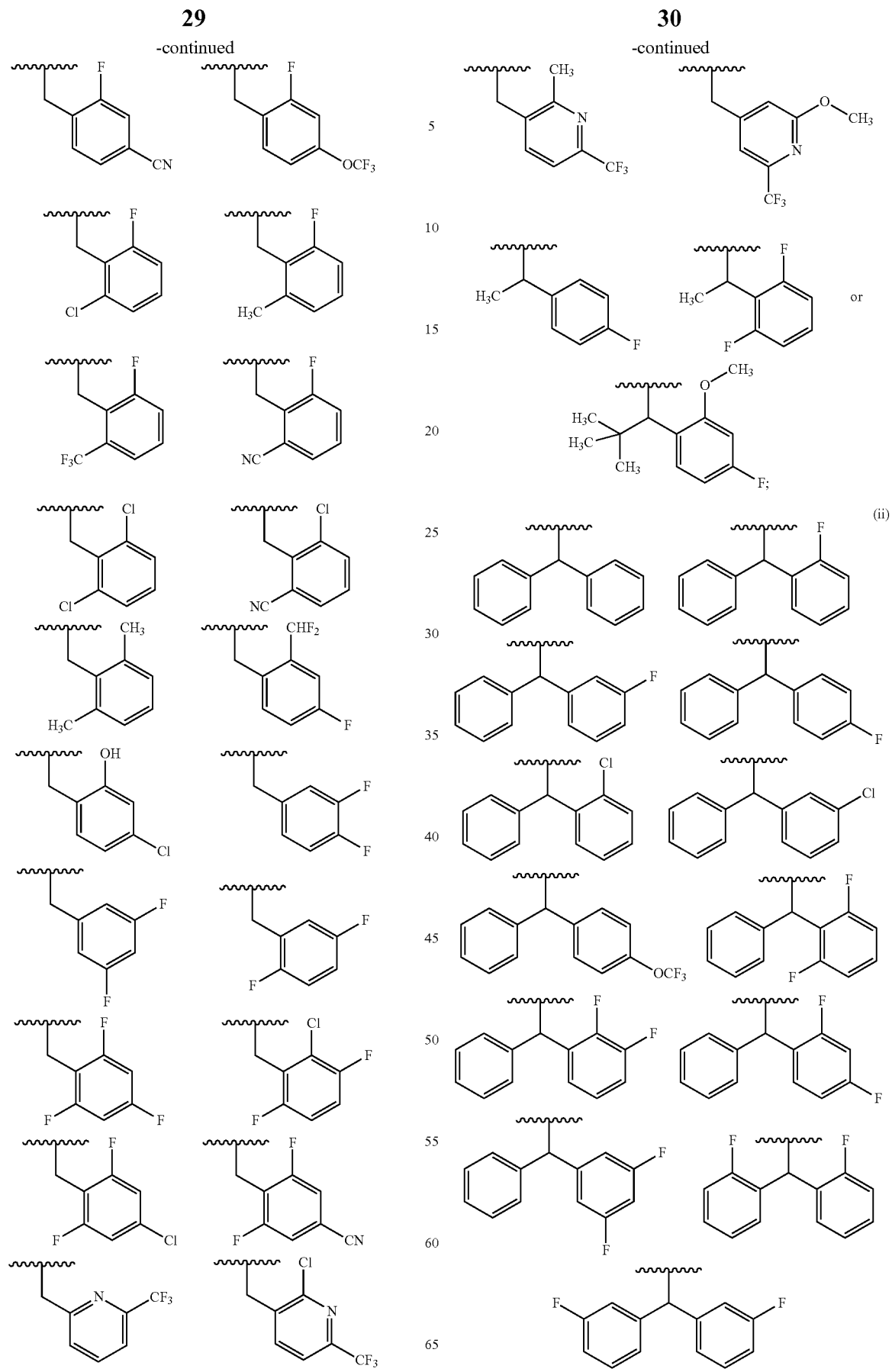

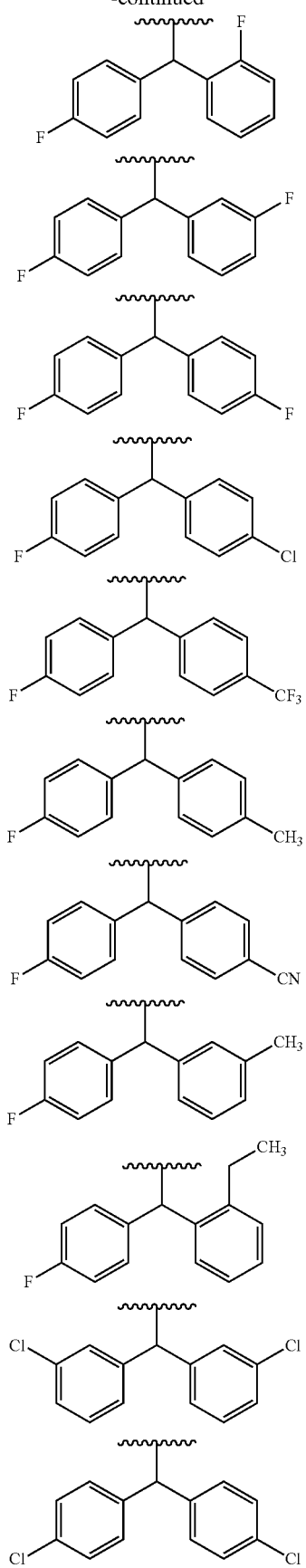
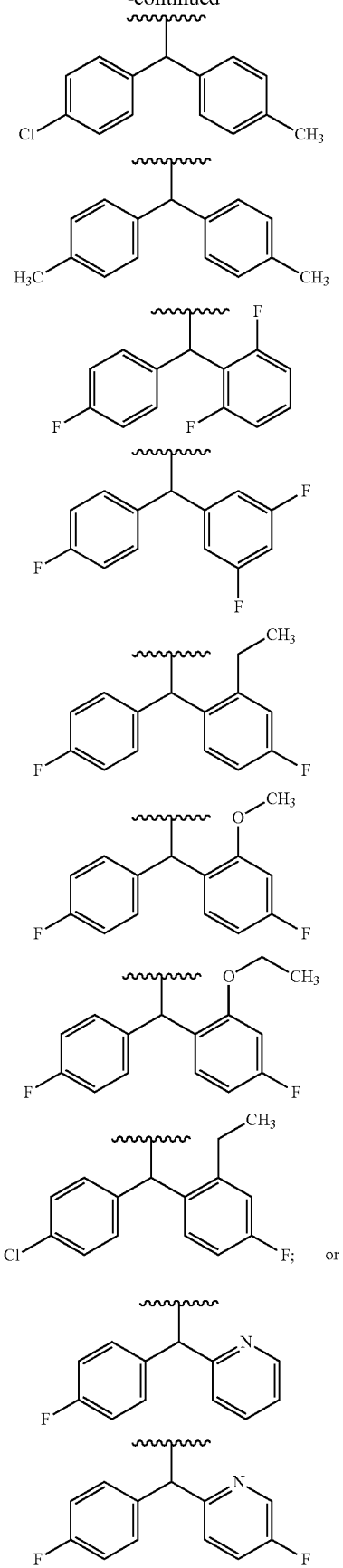

-continued
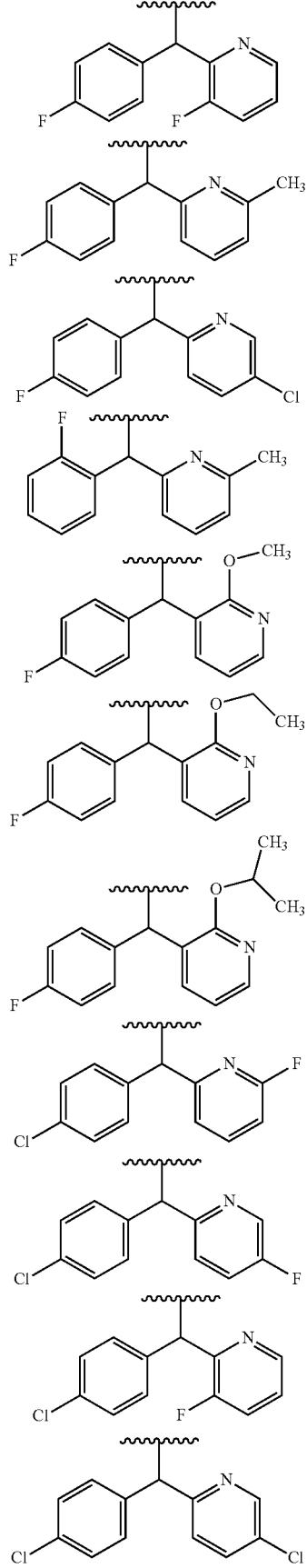
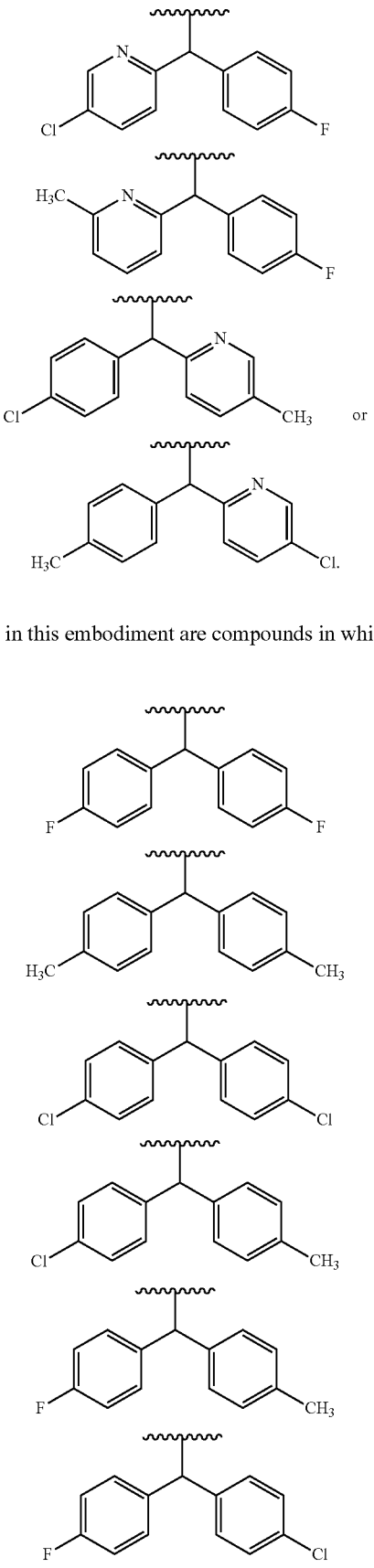
Included in this embodiment are compounds in which $R_4$ is:

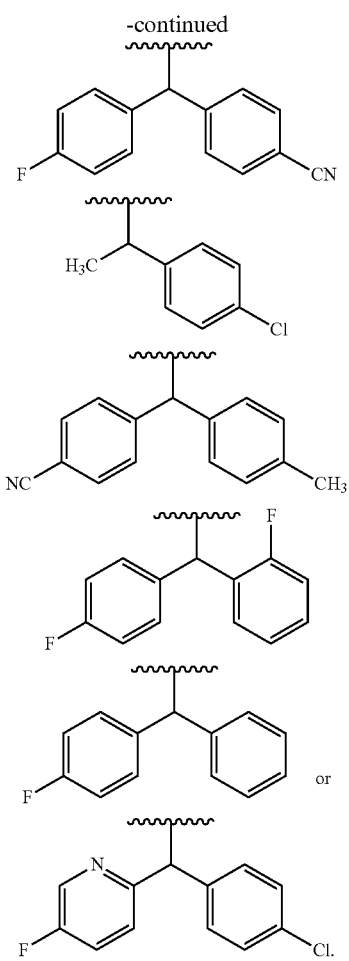
In one embodiment, a compound of Formula (I) or a salt thereof is provided wherein said compound is:
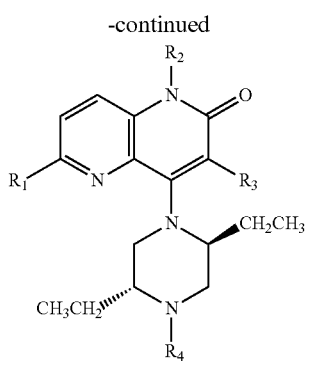
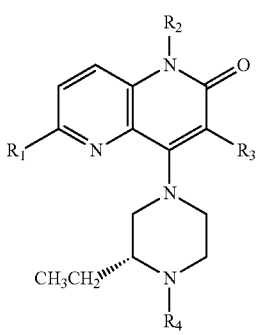
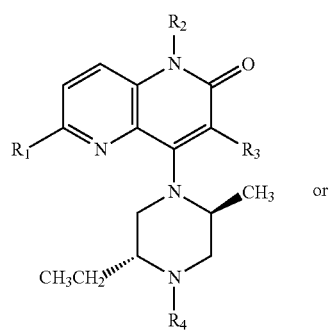
or
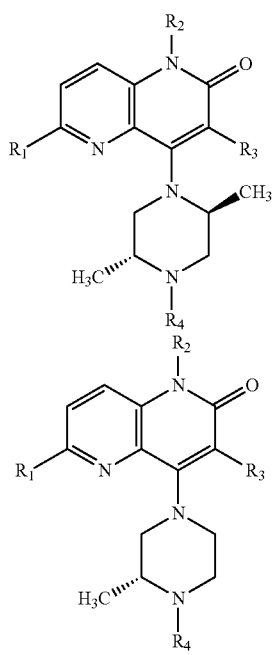
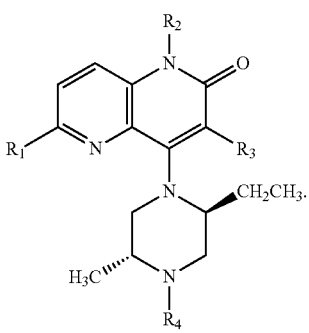
In one embodiment, a compound of Formula (I) or a salt thereof is provided wherein said compound has the structure of Formula (III):

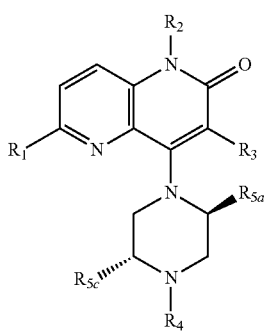

(III)

and $R_1$, $R_2$, $R_3$, and $R_4$ are defined in the first aspect, the second aspect, or the third aspect. Included in this embodiment are compounds in which $R_1$ is H, F, Cl, Br, —CN, $C_{1-3}$ alkyl substituted with zero to 4 $R_{1a}$, cyclopropyl substituted with zero to 3 $R_{1a}$, $C_{1-3}$ alkoxy substituted with zero to 3 $R_{1a}$, —$NR_aR_a$, —$S(O)_nCH_3$, or —$P(O)(CH_3)_2$; each $R_{1a}$ is independently F, Cl, or —CN; each 1% is independently H or $C_{1-3}$ alkyl; $R_2$ is H or $C_{1-2}$ alkyl substituted with zero to 2 $R_{2a}$; each $R_{2a}$ is independently F, Cl, —CN, —OH, —O($C_{1-2}$ alkyl), cyclopropyl, $C_{3-4}$ alkenyl, or $C_{3-4}$ alkynyl; $R_3$ is H, F, Cl, Br, —CN, $C_{1-2}$ alkyl, —$CF_3$, cyclopropyl, or —$NO_2$; $R_4$ is —$CH_2R_{4a}$, —$CHR_{4a}R_{4b}$, or —$CR_{4a}R_{4b}R_{4c}$; $R_{4a}$ and $R_{4b}$ are independently: (i) $C_{1-4}$ alkyl substituted with zero to 4 substituents independently selected from F, Cl, —CN, —OH, —$OCH_3$, $C_{1-3}$ fluoroalkoxy, and —$NR_aR_a$; (ii) $C_{3-6}$ cycloalkyl, heterocyclyl, phenyl, or heteroaryl, each substituted with zero to 4 substituents independently selected from F, Cl, Br, —OH, —CN, $C_{1-6}$ alkyl, $C_{1-3}$ fluoroalkyl, —$CH_2OH$, $C_{1-3}$ alkoxy, $C_{1-3}$ fluoroalkoxy, —$OCH_2CH=CH_2$, —$OCH_2C\equiv CH$, —$NR_cR_c$, —$NR_aS(O)_2$($C_{1-3}$ alkyl), —$NR_aC(O)(C_{1-3}$ alkyl), —$NR_aC(O)O(C_{1-4}$ alkyl), and $R_a$; or (iii) $C_{1-3}$ alkyl substituted with one cyclic group selected from $C_{3-6}$ cycloalkyl, heterocyclyl, phenyl, and heteroaryl, said cyclic group substituted with zero to 3 substituents independently selected from F, Cl, Br, —OH, —CN, $C_{1-3}$ alkyl, $C_{1-2}$ fluoroalkyl, $C_{1-3}$ alkoxy, $C_{1-2}$ fluoroalkoxy, —$OCH_2CH=CH_2$, —$OCH_2C\equiv CH$, —$NR_cR_c$, —$NR_aS(O)_2(C_{1-3}$ alkyl), —$NR_aC(O)(C_{1-3}$ alkyl), and —$NR_aC(O)O(C_{1-4}$ alkyl); or $R_{4a}$ and $R_{4b}$ together with the carbon atom to which they are attached, form a $C_{3-6}$ cycloalkyl or a 3- to 6-membered heterocyclyl, each substituted with zero to 3 $R_f$; each $R_f$ is independently F, Cl, Br, —OH, —CN, $C_{1-4}$ alkyl, $C_{1-32}$ fluoroalkyl, $C_{1-3}$ alkoxy, $C_{1-2}$ fluoroalkoxy, —$OCH_2CH=CH_2$, —$OCH_2C\equiv CH$, —$NR_cR_c$, or a cyclic group selected from $C_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, $C_{1-4}$ alkyl, $C_{1-2}$ fluoroalkyl, $C_{1-3}$ alkoxy, $C_{1-2}$ fluoroalkoxy, and —$NR_cR_c$; $R_{4c}$ is $C_{1-4}$ alkyl or $C_{3-6}$ cycloalkyl, each substituted with zero to 4 substituents independently selected from F, Cl, —OH, $C_{1-2}$ alkoxy, $C_{1-2}$ fluoroalkoxy, and —CN; each $R_c$ is independently H or $C_{1-2}$ alkyl; $R_d$ is phenyl substituted with zero to 1 substituent selected from F, Cl, —$CH_3$, and —$OCH_3$; and n is zero, 1, or 2.

In one embodiment, a compound of Formula (I) or a salt thereof is provided wherein $R_4$ is —$C(CH_3)R_{4a}$; and $R_1$, $R_2$, $R_3$, $R_{4a}$, $R_5$, and m are defined in the first aspect, the second aspect, or the third aspect. Included in this embodiment are compounds in which $R_{4a}$ is phenyl or pyridinyl, each substituted with zero to 3 substituents independently selected from F, Cl, —CN, —$CH_3$, —$CF_3$, —$OCH_3$, —$OCHF_2$, and —$OCF_3$. Also included in this embodiment are compounds in which $R_{4a}$ is phenyl or pyridinyl, each substituted with zero to 3 substituents independently selected from F, Cl, —CN, —$CH_3$, —$CF_3$, —$OCH_3$, —$OCHF_2$, and —$OCF_3$; $R_1$ is —CN; $R_2$ is —$CH_3$; and $R_3$ is hydrogen or —CN. Additionally, included in this embodiment are compounds in which $R_{4a}$ is phenyl or pyridinyl, each substituted with zero to 3 substituents independently selected from F, Cl, —CN, —$CH_3$, —$CF_3$, —$OCH_3$, —$OCHF_2$, and —$OCF_3$. Also included in this embodiment are compounds in which $R_{4a}$ is phenyl substituted with 1 to 2 substituents independently selected from F, Cl, —CN, —$CH_3$, —$CF_3$, —$OCH_3$, —$OCHF_2$, and —$OCF_3$; $R_1$ is —CN; $R_2$ is —$CH_3$; $R_3$ is hydrogen or —CN; m is 1 or 2; and each $R_5$ is independently —CN, —$CH_3$, or —$CH_2CH_3$.

In one embodiment, a compound of Formula (I) or a salt thereof is provided wherein $R_4$ is —$C(CH_3)R_{4a}$; $R_{4a}$ is phenyl substituted with 1 to 2 substituents independently selected from F, Cl, —CN, —$CH_3$, —$CF_3$, —$OCH_3$, —$OCHF_2$, and —$OCF_3$; and $R_1$, $R_2$, $R_3$, $R_5$, and m are defined in the first aspect, the second aspect, or the third aspect. Included in this embodiment are compounds in which $R_{4a}$ is phenyl substituted with 1 to 2 substituents independently selected from F, —$CF_3$, —$OCHF_2$, and —$OCF_3$. Also included in this embodiment are compounds in which $R_{4a}$ is phenyl substituted with —$CF_3$, —$OCHF_2$, and —$OCF_3$; $R_1$ is —CN; $R_2$ is —$CH_3$; and $R_3$ is hydrogen or —CN. Additionally, included in this embodiment are compounds in which $R_{4a}$ is phenyl substituted with —$CF_3$, —$OCHF_2$, and —$OCF_3$; $R_1$ is —CN; $R_2$ is —$CH_3$; $R_3$ is hydrogen or —CN; m is 1 or 2; and each $R_5$ is independently —CN, —$CH_3$, or —$CH_2CH_3$.

In one embodiment, a compound of Formula (I) or a salt thereof is provided wherein said compound has the structure of Formula (IV):

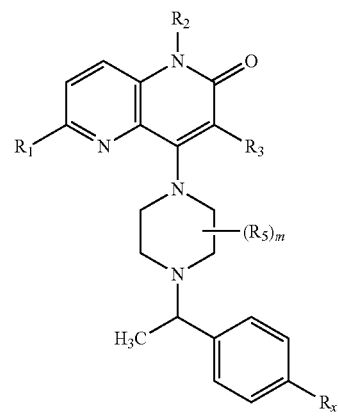

(IV)

wherein $R_x$ is —$CF_3$, —$OCHF_2$, or —$OCF_3$; and $R_1$, $R_2$, $R_3$, $R_5$, and m are defined in the first aspect, the second aspect, or the third aspect. Included in this embodiment are compounds in which $R_1$ is —CN; $R_2$ is —$CH_3$; $R_3$ is hydrogen or —CN; m is 1 or 2; and each $R_5$ is independently —$CH_3$ or —$CH_2CH_3$.

In one embodiment, a compound of Formula (I) or a salt thereof is provided wherein said compound has the structure of Formula (IVA):

(IVA)

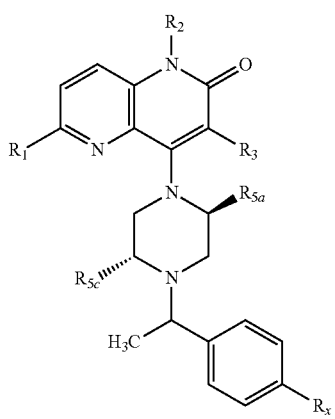

wherein R$_x$ is —CF$_3$, —OCHF$_2$, or —OCF$_3$; and R$_1$, R$_2$, R$_3$, R$_{5a}$, and R$_{5c}$ are defined in the first aspect, the second aspect, or the third aspect. Included in this embodiment are compounds in which R$_1$ is —CN; R$_2$ is —CH$_3$; R$_3$ is hydrogen or —CN; and R$_{5a}$ and R$_{5c}$ are independently —CH$_3$ or —CH$_2$CH$_3$. Also included in this embodiment are compounds in which R$_x$ is —CF$_3$ or —OCF$_3$. Additionally, included in this embodiment are compounds in which R$_{5a}$ is —CH$_3$ and R$_{5c}$ is —CH$_3$; or R$_{5a}$ is —CH$_2$CH$_3$ and R$_{5c}$ is —CH$_2$CH$_3$.

In one embodiment, a compound of Formula (I) or a salt thereof is provided wherein said compound is: 8-(4-(bis(4-fluorophenyl)methyl)-3-(hydroxymethyl) piperazin-1-yl)-5-methyl-6-oxo-5,6-dihydro-1,5-naphthyridine-2-carbonitrile (1-2); 8-((2S,5R)-4-(bis(4-fluorophenyl)methyl)-2,5-dimethylpiperazin-1-yl)-5-methyl-6-oxo-5,6-dihydro-1,5-naphthyridine-2-carbonitrile (3); 8-((2R,5S)-4-(bis(4-fluorophenyl)methyl)-2,5-dimethylpiperazin-1-yl)-5-methyl-6-oxo-5,6-dihydro-1,5-naphthyridine-2-carbonitrile (4); 4-((2R,5S)-4-(bis(4-fluorophenyl)methyl)-2,5-dimethylpiperazin-1-yl)-6-bromo-1-methyl-2-oxo-1,2-dihydro-1,5-naphthyridine-3-carbonitrile (5); 8-((2R,5S)-4-(bis(4-fluorophenyl)methyl)-2,5-dimethylpiperazin-1-yl)-5-methyl-6-oxo-5,6-dihydro-1,5-naphthyridine-2,7-dicarbonitrile (6); 4-((2R,5S)-4-(bis(4-fluorophenyl)methyl)-2,5-dimethylpiperazin-1-yl)-6-bromo-1-methyl-2-oxo-1,2-dihydro-1,5-naphthyridine-3-carbonitrile (7); 8-(4-(bis(4-fluorophenyl)methyl)-3-(fluoromethyl)piperazin-1-yl)-5-methyl-6-oxo-5,6-dihydro-1,5-naphthyridine-2-carbonitrile (8); 4-(4-(bis(4-fluorophenyl)methyl)-3-(fluoromethyl)piperazin-1-yl)-6-bromo-1-methyl-2-oxo-1,2-dihydro-1,5-naphthyridine-3-carbonitrile (9); (S)-8-(4-(bis(4-fluorophenyl)methyl)-3-isopropylpiperazin-1-yl)-5-methyl-6-oxo-5,6-dihydro-1,5-naphthyridine-2-carbonitrile (10); (S)-4-(4-(bis(4-fluorophenyl)methyl)-3-isopropylpiperazin-1-yl)-6-bromo-1-methyl-2-oxo-1,2-dihydro-1,5-naphthyridine-3-carbonitrile (11); (S)-8-(4-(bis(4-fluorophenyl)methyl)-3-isopropylpiperazin-1-yl)-5-methyl-6-oxo-5,6-dihydro-1,5-naphthyridine-2,7-dicarbonitrile (12); (S)-4-(4-(bis(4-fluorophenyl)methyl)-3-isopropylpiperazin-1-yl)-6-bromo-1-methyl-2-oxo-1,2-dihydro-1,5-naphthyridine-3-carbonitrile (13); 4-(4-(bis(4-fluorophenyl)methyl)-3-(hydroxymethyl)piperazin-1-yl)-6-bromo-1-methyl-2-oxo-1,2-dihydro-1,5-naphthyridine-3-carbonitrile (14); 4-(4-(bis(4-fluorophenyl)methyl)-3-(hydroxymethyl)piperazin-1-yl)-6-bromo-1-methyl-2-oxo-1,2-dihydro-1,5-naphthyridine-3-carbonitrile (15-16); 4-(4-(bis(4-fluorophenyl)methyl)-3-(hydroxymethyl)piperazin-1-yl)-6-bromo-1-methyl-2-oxo-1,2-dihydro-1,5-naphthyridine-3-carbonitrile (17); 8-((2S,5R)-4-(bis(4-fluorophenyl)methyl)-2,5-dimethylpiperazin-1-yl)-7-chloro-5-methyl-6-oxo-5,6-dihydro-1,5-naphthyridine-2-carbonitrile (18); 8-((2S,5R)-4-(bis(4-fluorophenyl)methyl)-2,5-dimethylpiperazin-1-yl)-7-bromo-5-methyl-6-oxo-5,6-dihydro-1,5-naphthyridine-2-carbonitrile (19); 8-((2S,5R)-4-(bis(4-fluorophenyl)methyl)-2,5-dimethylpiperazin-1-yl)-7-cyclopropyl-5-methyl-6-oxo-5,6-dihydro-1,5-naphthyridine-2-carbonitrile (20); 8-((2S,5R)-4-(bis(4-fluorophenyl)methyl)-2,5-dimethylpiperazin-1-yl)-7-bromo-5-methyl-6-oxo-5,6-dihydro-1,5-naphthyridine-2-carbonitrile (21); 8-((2S,5R)-4-(bis(4-fluorophenyl)methyl)-2,5-dimethylpiperazin-1-yl)-5,7-dimethyl-6-oxo-5,6-dihydro-1,5-naphthyridine-2-carbonitrile (22); 8-(4-(bis(4-fluorophenyl)methyl)-2-cyclopropylpiperazin-1-yl)-5-methyl-6-oxo-5,6-dihydro-1,5-naphthyridine-2-carbonitrile (23-24); 8-((2S,5R)-4-(bis(4-chlorophenyl)methyl)-2,5-dimethylpiperazin-1-yl)-5-methyl-6-oxo-5,6-dihydro-1,5-naphthyridine-2-carbonitrile (25); 8-((2S,5R)-4-(bis(4-chlorophenyl)methyl)-2,5-dimethylpiperazin-1-yl)-7-chloro-5-methyl-6-oxo-5,6-dihydro-1,5-naphthyridine-2-carbonitrile (26); methyl 1-(bis(4-fluorophenyl)methyl)-4-(6-cyano-1-methyl-2-oxo-1,2-dihydro-1,5-naphthyridin-4-yl)piperazine-2-carboxylate (27); (R)-8-(4-(bis(4-fluorophenyl)methyl)-3-methylpiperazin-1-yl)-5-methyl-6-oxo-5,6-dihydro-1,5-naphthyridine-2-carbonitrile (28); (R)-8-(4-(bis(4-fluorophenyl)methyl)-3-methylpiperazin-1-yl)-7-chloro-5-methyl-6-oxo-5,6-dihydro-1,5-naphthyridine-2-carbonitrile (29); (R)-8-(4-(bis(4-fluorophenyl)methyl)-3-methylpiperazin-1-yl)-7-fluoro-5-methyl-6-oxo-5,6-dihydro-1,5-naphthyridine-2-carbonitrile (30); (R)-4-(4-(bis(4-fluorophenyl)methyl)-3-methylpiperazin-1-yl)-6-bromo-1-methyl-2-oxo-1,2-dihydro-1,5-naphthyridine-3-carbonitrile (31); (R)-8-(4-(bis(4-fluorophenyl)methyl)-3-methylpiperazin-1-yl)-5-methyl-6-oxo-5,6-dihydro-1,5-naphthyridine-2,7-dicarbonitrile (32); (R)-8-(4-(bis(4-chlorophenyl)methyl)-3-methylpiperazin-1-yl)-5-methyl-6-oxo-5,6-dihydro-1,5-naphthyridine-2-carbonitrile (33); (R)-8-(4-(bis(4-chlorophenyl)methyl)-3-methylpiperazin-1-yl)-7-fluoro-5-methyl-6-oxo-5,6-dihydro-1,5-naphthyridine-2-carbonitrile (34); (S)-8-(4-(bis(4-fluorophenyl)methyl)-3-methylpiperazin-1-yl)-5-methyl-6-oxo-5,6-dihydro-1,5-naphthyridine-2-carbonitrile (35); (S)-8-(4-(bis(4-fluorophenyl)methyl)-3-methylpiperazin-1-yl)-7-chloro-5-methyl-6-oxo-5,6-dihydro-1,5-naphthyridine-2-carbonitrile (36); (S)-4-(4-(bis(4-fluorophenyl)methyl)-3-methylpiperazin-1-yl)-6-bromo-1-methyl-2-oxo-1,2-dihydro-1,5-naphthyridine-3-carbonitrile (37); (S)-8-(4-(bis(4-fluorophenyl)methyl)-3-methylpiperazin-1-yl)-5-methyl-6-oxo-5,6-dihydro-1,5-naphthyridine-2,7-dicarbonitrile (38); methyl 1-(bis(4-fluorophenyl)methyl)-4-(6-cyano-1-methyl-2-oxo-1,2-dihydro-1,5-naphthyridin-4-yl)piperazine-2-carboxylate (39-40); 1-(bis(4-fluorophenyl)methyl)-4-(6-cyano-1-methyl-2-oxo-1,2-dihydro-1,5-naphthyridin-4-yl)piperazine-2-carboxamide (41-42); 8-(4-(bis(4-fluorophenyl)methyl)-3-cyanopiperazin-1-yl)-5-methyl-6-oxo-5,6-dihydro-1,5-naphthyridine-2-carbonitrile (43); 8-(4-(bis(4-fluorophenyl)methyl)-3-cyanopiperazin-1-yl)-5-methyl-6-oxo-5,6-dihydro-1,5-naphthyridine-2-carbonitrile (44-45); 1-(bis(4-fluorophenyl)methyl)-4-(6-cyano-1-methyl-2-oxo-1,2-dihydro-1,5-naphthyridin-4-yl)-N-cyclopropylpiperazine-2-carboxamide (46-48); methyl 1-(bis(4-fluorophenyl)methyl)-4-(6-bromo-3-cyano-1-methyl-2-oxo-1,2-dihydro-1,5-naphthyridin-4-yl)piperazine-2-carboxylate (49); methyl 1-(bis(4-fluorophenyl)methyl)-4-(3,6-dicyano-1-methyl-2-oxo-1,2-dihydro-1,5-naphthyridin-4-yl)piperazine-2-carboxylate (50-51); 1-(bis(4-fluorophenyl)methyl)-4-(6-bromo-3-cyano-1-methyl-2-oxo-1,2-dihydro-1,5-naphthyridin-4-yl)piperazine-2-carboxylic acid (52); 1-(bis (4-fluorophenyl)methyl)-4-(3,6-dicyano-1-methyl-2-oxo-1, 2-dihydro-1,5-naphthyridin-4-yl)piperazine-2-carboxylic acid (53-54); 1-(bis(4-fluorophenyl)methyl)-4-(6-cyano-1-methyl-2-oxo-1,2-dihydro-1,5-naphthyridin-4-yl)piperazine-2-carboxylic acid (55); 1-(bis(4-fluorophenyl)methyl)-4-(6-bromo-3-cyano-1-methyl-2-oxo-1,2-dihydro-1,5-naphthyridin-4-yl)piperazine-2-carboxamide (56); 1-(bis(4-fluorophenyl)methyl)-4-(3,6-dicyano-1-methyl-2-oxo-1,2-dihydro-1,5-naphthyridin-4-yl)piperazine-2-carboxamide (57-58); 1-(bis(4-fluorophenyl)methyl)-4-(6-bromo-3-cyano-1-methyl-2-oxo-1,2-dihydro-1,5-naphthyridin-4-yl)-N-cyclopropylpiperazine-2-carboxamide (59); 1-(bis(4-fluorophenyl)methyl)-N-cyclopropyl-4-(3,6-dicyano-1-methyl-2-oxo-1,2-dihydro-1,5-naphthyridin-4-yl) piperazine-2-carboxamide (60-61); isopropyl 1-(bis(4-fluorophenyl)methyl)-4-(6-cyano-1-methyl-2-oxo-1,2-dihydro-1,5-naphthyridin-4-yl)piperazine-2-carboxylate (62-63); isopropyl 1-(bis(4-fluorophenyl)methyl)-4-(3,6-dicyano-1-methyl-2-oxo-1,2-dihydro-1,5-naphthyridin-4-yl) piperazine-2-carboxylate (64-65); methyl (S)-1-(bis(4-fluorophenyl)methyl)-4-(6-cyano-1-methyl-2-oxo-1,2-dihydro-1,5-naphthyridin-4-yl)piperazine-2-carboxylate (66); methyl 4-(6-cyano-1-methyl-2-oxo-1,2-dihydro-1,5-naphthyridin-4-yl)-1-((4-fluoro-2-methoxyphenyl)(4-fluorophenyl)methyl)piperazine-2-carboxylate (67-68); methyl 4-(6-cyano-1-methyl-2-oxo-1,2-dihydro-1,5-naphthyridin-4-yl)-1-((4-fluoro-2-methoxyphenyl)(4-fluorophenyl)methyl) piperazine-2-carboxylate (69-70); methyl 4-(6-cyano-1-methyl-2-oxo-1,2-dihydro-1,5-naphthyridin-4-yl)-1-((4-fluoro-2-methoxyphenyl)(4-fluorophenyl)methyl) piperazine-2-carboxylate (71-72); methyl 1-(bis(4-fluorophenyl)methyl)-4-(6-cyano-1-methyl-3-nitro-2-oxo-1,2-dihydro-1,5-naphthyridin-4-yl)piperazine-2-carboxylate (73); methyl 1-(bis(4-fluorophenyl)methyl)-4-(6-cyano-3-fluoro-1-methyl-2-oxo-1,2-dihydro-1,5-naphthyridin-4-yl) piperazine-2-carboxylate (74-75); methyl 1-(bis(4-fluorophenyl)methyl)-4-(3-chloro-6-cyano-1-methyl-2-oxo-1,2-dihydro-1,5-naphthyridin-4-yl)piperazine-2-carboxylate (76-77); 8-(4-(bis(4-fluorophenyl)methyl)-3-(2-hydroxypropan-2-yl)piperazin-1-yl)-5-methyl-6-oxo-5,6-dihydro-1, 5-naphthyridine-2-carbonitrile (78-79); 8-(4-(bis(4-fluorophenyl)methyl)-3-(2-fluoropropan-2-yl)piperazin-1-yl)-5-methyl-6-oxo-5,6-dihydro-1,5-naphthyridine-2-carbonitrile (80-81); 8-(4-(bis(4-fluorophenyl)methyl)-3-methyl-5-(2-methylpyridin-4-yl)piperazin-1-yl)-5-methyl-6-oxo-5,6-dihydro-1,5-naphthyridine-2-carbonitrile (84); 8-(4-(bis(4-fluorophenyl)methyl)-3-isobutyrylpiperazin-1-yl)-5-methyl-6-oxo-5,6-dihydro-1,5-naphthyridine-2-carbonitrile (86-87); 8-(4-(bis(4-fluorophenyl)methyl)-3-(2-hydroxy-3-methylbutan-2-yl)piperazin-1-yl)-5-methyl-6-oxo-5,6-dihydro-1,5-naphthyridine-2-carbonitrile (88-89); 8-(4-(bis(4-fluorophenyl)methyl)-3-(2-fluoro-3-methylbutan-2-yl) piperazin-1-yl)-5-methyl-6-oxo-5,6-dihydro-1,5-naphthyridine-2-carbonitrile, TFA (90-91); 8-(4-(bis(4-fluorophenyl)methyl)-3-(methoxymethyl)piperazin-1-yl)-5-methyl-6-oxo-5,6-dihydro-1,5-naphthyridine-2-carbonitrile (92-93); methyl 1-(bis(4-chlorophenyl)methyl)-4-(6-cyano-3-fluoro-1-methyl-2-oxo-1,2-dihydro-1,5-naphthyridin-4-yl)piperazine-2-carboxylate (94-95); methyl 1-(bis(4-chlorophenyl)methyl)-4-(6-cyano-1-methyl-2-oxo-1,2-dihydro-1,5-naphthyridin-4-yl)piperazine-2-carboxylate (96-97); (R)-8-(4-(bis(4-fluorophenyl)methyl)-3-methylpiperazin-1-yl)-7-bromo-5-methyl-6-oxo-5,6-dihydro-1,5-naphthyridine-2-carbonitrile (98); (R)-8-(4-(bis(4-fluorophenyl) methyl)-3-methylpiperazin-1-yl)-5,7-dimethyl-6-oxo-5,6-dihydro-1,5-naphthyridine-2-carbonitrile (99); 8-(4-(bis(4-fluorophenyl)methyl)-3-(hydroxymethyl)piperazin-1-yl)-7-chloro-5-methyl-6-oxo-5,6-dihydro-1,5-naphthyridine-2-carbonitrile (100-101); (R)-4-(4-(bis(4-chlorophenyl) methyl)-3-methylpiperazin-1-yl)-6-bromo-1-methyl-2-oxo-1,2-dihydro-1,5-naphthyridine-3-carbonitrile (102); (R)-8-(4-(bis(4-chlorophenyl)methyl)-3-methylpiperazin-1-yl)-5-methyl-6-oxo-5,6-dihydro-1,5-naphthyridine-2,7-dicarbonitrile (103); (R)-8-(4-(bis(4-chlorophenyl)methyl)-3-methylpiperazin-1-yl)-5-methyl-6-oxo-5,6-dihydro-1,5-naphthyridine-2-carbonitrile, dimethylformamide (104); (R)-8-(4-(bis(4-chlorophenyl)methyl)-3-methylpiperazin-1-yl)-7-chloro-5-methyl-6-oxo-5,6-dihydro-1,5-naphthyridine-2-carbonitrile, dimethylformamide (105); cyclopropyl 1-(bis(4-fluorophenyl)methyl)-4-(6-cyano-1-methyl-2-oxo-1,2-dihydro-1,5-naphthyridin-4-yl)piperazine-2-carboxylate (106-107); 8-((2S,5R)-4-((4-fluoro-2-methoxyphenyl)(4-fluorophenyl)methyl)-2,5-dimethylpiperazin-1-yl)-5-methyl-6-oxo-5,6-dihydro-1,5-naphthyridine-2-carbonitrile (108-109); 6-bromo-4-((2S,5R)-4-((4-fluoro-2-methoxyphenyl)(4-fluorophenyl)methyl)-2,5-dimethylpiperazin-1-yl)-1-methyl-2-oxo-1,2-dihydro-1,5-naphthyridine-3-carbonitrile (110); 8-((2S,5R)-4-((4-fluoro-2-methoxyphenyl)(4-fluorophenyl)methyl)-2,5-dimethylpiperazin-1-yl)-5-methyl-6-oxo-5,6-dihydro-1,5-naphthyridine-2,7-dicarbonitrile (111-112); methyl 4-(bis(4-fluorophenyl) methyl)-1-(6-bromo-3-cyano-1-methyl-2-oxo-1,2-dihydro-1,5-naphthyridin-4-yl)piperazine-2-carboxylate (113); methyl 4-(bis(4-fluorophenyl)methyl)-1-(3,6-dicyano-1-methyl-2-oxo-1,2-dihydro-1,5-naphthyridin-4-yl)piperazine-2-carboxylate (114); methyl 4-(bis(4-fluorophenyl) methyl)-1-(6-bromo-3-cyano-1-methyl-2-oxo-1,2-dihydro-1,5-naphthyridin-4-yl)piperazine-2-carboxylate (115); methyl 4-(bis(4-fluorophenyl)methyl)-1-(3,6-dicyano-1-methyl-2-oxo-1,2-dihydro-1,5-naphthyridin-4-yl)piperazine-2-carboxylate (116-117); 4-(4-(bis(4-fluorophenyl) methyl)-2-(hydroxymethyl)piperazin-1-yl)-6-bromo-1-methyl-2-oxo-1,2-dihydro-1,5-naphthyridine-3-carbonitrile (118); 8-((2R,5S)-4-((4-fluoro-2-methoxyphenyl)(4-fluorophenyl)methyl)-2,5-dimethylpiperazin-1-yl)-5-methyl-6-oxo-5,6-dihydro-1,5-naphthyridine-2-carbonitrile (119); 8-((2R,5S)-4-((4-fluoro-2-methoxyphenyl)(4-fluorophenyl) methyl)-2,5-dimethylpiperazin-1-yl)-5-methyl-7-nitro-6-oxo-5,6-dihydro-1,5-naphthyridine-2-carbonitrile (120); 8-((2S,5R)-4-((4-fluoro-2-methoxyphenyl)(4-fluorophenyl) methyl)-2,5-dimethylpiperazin-1-yl)-5-methyl-7-nitro-6-oxo-5,6-dihydro-1,5-naphthyridine-2-carbonitrile (121-122); 8-(4-(bis(4-fluorophenyl)methyl)-2,3-dimethylpiperazin-1-yl)-5-methyl-6-oxo-5,6-dihydro-1,5-naphthyridine-2-carbonitrile (123-124); 8-((2S,5S)-4-(bis (4-fluorophenyl)methyl)-2-isopropyl-5-methylpiperazin-1-yl)-5-methyl-6-oxo-5,6-dihydro-1,5-naphthyridine-2-carbonitrile (125); 8-(4-(bis(4-fluorophenyl)methyl)-3-(5-methyl-1,3,4-oxadiazol-2-yl)piperazin-1-yl)-5-methyl-6-oxo-5,6-dihydro-1,5-naphthyridine-2-carbonitrile (126); (S)-8-(4-(bis(4-fluorophenyl) methyl)-2-ethylpiperazin-1-yl)-5-methyl-6-oxo-5,6-dihydro-1,5-naphthyridine-2-carbonitrile (127); (S)-8-(4-(bis(4-fluorophenyl)methyl)-3-ethylpiperazin-1-yl)-5-methyl-6-oxo-5,6-dihydro-1,5-naphthyridine-2-carbonitrile (128); 8-((2S)-4-((4-fluoro-2-methoxyphenyl)(4-fluorophenyl)methyl)-2-methylpiperazin-1-yl)-5-methyl-6-oxo-5,6-dihydro-1,5-naphthyridine-2-carbonitrile (129-130); 8-((2R,5R)-4-(bis (4-fluorophenyl) methyl)-2,5-dimethylpiperazin-1-yl)-5-methyl-6-oxo-5,6-dihydro-1,5-naphthyridine-2-carbonitrile (131); 8-((2R,5R)-4-(bis(4-fluorophenyl)methyl)-2,5-dimethylpiperazin-1-yl)-7-chloro-5-methyl-6-oxo-5,6-dihydro-1,5-naphthyridine-2-carbonitrile (132); 8-((2S,5S)-4-(bis(4-fluorophenyl)methyl)-2,5-dimethylpiperazin-1-yl)-5-methyl-6-oxo-5,6-dihydro-1,5-naphthyridine-2-carbonitrile (133); (S)-8-(4-(bis(4-fluorophenyl)methyl)-2-methylpiperazin-1-yl)-5-methyl-6-oxo-5,6-dihydro-1,5-naphthyridine-2-carbonitrile (134); (R)-8-(4-(bis(4-fluorophenyl)methyl)-2-methylpiperazin-1-yl)-5-methyl-6-oxo-5,6-dihydro-1,5-naphthyridine-2-carbonitrile (135); methyl 4-(bis(4-fluorophenyl) methyl)-1-(6-cyano-1-methyl-2-oxo-1,2-dihydro-1,5-naphthyridin-4-yl)piperazine-2-carboxylate (136-137); 4-(bis(4-fluorophenyl)methyl)-1-(6-cyano-1-methyl-2-oxo-1,2-dihydro-1,5-naphthyridin-4-yl)piperazine-2-carboxylic acid (138); 4-(bis(4-fluorophenyl)methyl)-1-(6-cyano-1-methyl-2-oxo-1,2-dihydro-1,5-naphthyridin-4-yl)-N-cyclopropylpiperazine-2-carboxamide (139-140); 4-(bis(4-fluorophenyl)methyl)-1-(6-cyano-1-methyl-2-oxo-1,2-dihydro-1,5-naphthyridin-4-yl)piperazine-2-carboxamide (141-142); 8-(4-(bis(4-fluorophenyl)methyl)-2-cyanopiperazin-1-yl)-5-methyl-6-oxo-5,6-dihydro-1,5-naphthyridine-2-carbonitrile (143-144); 8-(4-(bis(4-fluorophenyl)methyl)-2-cyanopiperazin-1-yl)-5-methyl-6-oxo-5,6-dihydro-1,5-naphthyridine-2-carbonitrile (145); 8-(4-(bis(4-fluorophenyl)methyl)-2-(hydroxymethyl)piperazin-1-yl)-5-methyl-6-oxo-5,6-dihydro-1,5-naphthyridine-2-carbonitrile (146-148); 8-(4-(bis(4-fluorophenyl)methyl)-2-(fluoromethyl)piperazin-1-yl)-5-methyl-6-oxo-5,6-dihydro-1,5-naphthyridine-2-carbonitrile (149-151); 8-(4-(bis(4-fluorophenyl)methyl)-2,5-dicyclopropylpiperazin-1-yl)-5-methyl-6-oxo-5,6-dihydro-1,5-naphthyridine-2-carbonitrile (152-153); 8-(4-(bis(4-fluorophenyl)methyl)-2-phenylpiperazin-1-yl)-5-methyl-6-oxo-5,6-dihydro-1,5-naphthyridine-2-carbonitrile (154-156); 8-((2S,5R)-4-(bis(4-fluorophenyl)methyl)-2,5-dimethylpiperazin-1-yl)-7-fluoro-5-methyl-6-oxo-5,6-dihydro-1,5-naphthyridine-2-carbonitrile (157); 4-((2S,5R)-4-(bis(4-fluorophenyl)methyl)-2,5-dimethylpiperazin-1-yl)-6-bromo-1-methyl-2-oxo-1,2-dihydro-1,5-naphthyridine-3-carbonitrile (158); 8-((2S,5R)-4-(bis(4-fluorophenyl)methyl)-2,5-dimethylpiperazin-1-yl)-5-methyl-6-oxo-5,6-dihydro-1,5-naphthyridine-2,7-dicarbonitrile (159); 4-((2S,5R)-4-(bis(4-fluorophenyl)methyl)-2,5-dimethylpiperazin-1-yl)-1-methyl-2-oxo-1,2-dihydro-1,5-naphthyridine-3-carbonitrile (160); 8-((2S,5R)-4-(bis(4-fluorophenyl)methyl)-2,5-dimethylpiperazin-1-yl)-5-methyl-7-nitro-6-oxo-5,6-dihydro-1,5-naphthyridine-2-carbonitrile (161); methyl 4-(bis(4-fluorophenyl)methyl)-1-(3-bromo-6-cyano-1-methyl-2-oxo-1,2-dihydro-1,5-naphthyridin-4-yl)piperazine-2-carboxylate (162); 8-(4-(bis(4-fluorophenyl)methyl)-3,5-dimethylpiperazin-1-yl)-5-methyl-6-oxo-5,6-dihydro-1,5-naphthyridine-2-carbonitrile (163); (R)-8-(4-(bis(4-chlorophenyl)methyl)-3-isopropylpiperazin-1-yl)-5-methyl-6-oxo-5,6-dihydro-1,5-naphthyridine-2-carbonitrile (167); (R)-8-(4-(bis(4-fluorophenyl)methyl)-3-isopropylpiperazin-1-yl)-5-methyl-6-oxo-5,6-dihydro-1,5-naphthyridine-2-carbonitrile (168); (R)-8-(4-(bis(4-fluorophenyl)methyl)-3-isopropylpiperazin-1-yl)-5-methyl-6-oxo-5,6-dihydro-1,5-naphthyridine-2,7-dicarbonitrile (169); (R)-8-(4-(bis(4-fluorophenyl)methyl)-2-ethylpiperazin-1-yl)-5-methyl-6-oxo-5,6-dihydro-1,5-naphthyridine-2-carbonitrile (170); 8-(4-(bis(4-fluorophenyl)methyl)-3,3-dimethylpiperazin-1-yl)-5-methyl-6-oxo-5,6-dihydro-1,5-naphthyridine-2-carbonitrile (171); (R)-8-(4-(bis(4-fluorophenyl)methyl)-3-ethylpiperazin-1-yl)-5-methyl-6-oxo-5,6-dihydro-1,5-naphthyridine-2-carbonitrile (172); (R)-8-(4-(bis(4-fluorophenyl)methyl)-3-ethylpiperazin-1-yl)-5-methyl-6-oxo-5,6-dihydro-1,5-naphthyridine-2,7-dicarbonitrile (173); (R)-8-(4-(bis(4-fluorophenyl)methyl)-3-ethylpiperazin-1-yl)-7-fluoro-5-methyl-6-oxo-5,6-dihydro-1,5-naphthyridine-2-carbonitrile (174); (R)-8-(4-(bis(4-fluorophenyl) methyl)-3-ethylpiperazin-1-yl)-7-chloro-5-methyl-6-oxo-5,6-dihydro-1,5-naphthyridine-2-carbonitrile (175); (R)-8-(4-(bis(4-chlorophenyl)methyl)-3-ethylpiperazin-1-yl)-5-methyl-6-oxo-5,6-dihydro-1,5-naphthyridine-2-carbonitrile (176); (R)-8-(4-(bis(4-chlorophenyl)methyl)-3-ethylpiperazin-1-yl)-7-chloro-5-methyl-6-oxo-5,6-dihydro-1,5-naphthyridine-2-carbonitrile (177); (R)-8-(4-(bis(4-chlorophenyl)methyl)-3-ethylpiperazin-1-yl)-7-fluoro-5-methyl-6-oxo-5,6-dihydro-1,5-naphthyridine-2-carbonitrile (178); (R)-8-(4-(bis(4-chlorophenyl)methyl)-3-ethylpiperazin-1-yl)-5-methyl-6-oxo-5,6-dihydro-1,5-naphthyridine-2,7-dicarbonitrile (179); (R)-8-(4-(bis(4-chlorophenyl)methyl)-3-ethylpiperazin-1-yl)-5-methyl-6-oxo-5,6-dihydro-1,5-naphthyridine-2-carbonitrile (180); (R)-8-(4-(bis(4-fluorophenyl)methyl)-2-isopropylpiperazin-1-yl)-5-methyl-6-oxo-5,6-dihydro-1,5-naphthyridine-2-carbonitrile (181); 8-[(2S,5R)-4-[(4-fluorophenyl)(phenyl)methyl]-2,5-dimethylpiperazin-1-yl]-5-methyl-6-oxo-5,6-dihydro-1,5-naphthyridine-2-carbonitrile (182); 8-[(2S,5R)-4-[(4-fluorophenyl)(phenyl)methyl]-2,5-dimethylpiperazin-1-yl]-5-methyl-6-oxo-5,6-dihydro-1,5-naphthyridine-2-carbonitrile (183-184); 8-[(2S,5R)-4-[1-(4-fluoro-2-methoxyphenyl)-2,2-dimethylpropyl]-2,5-dimethylpiperazin-1-yl]-5-methyl-6-oxo-5,6-dihydro-1,5-naphthyridine-2-carbonitrile (185-186); 8-[(2S,5R)-4-[(4-fluorophenyl)(3-fluoropyridin-2-yl)methyl]-2,5-dimethylpiperazin-1-yl]-5-methyl-6-oxo-5,6-dihydro-1,5-naphthyridine-2-carbonitrile (187); 8-[(2S,5R)-4-[(4-fluorophenyl)(3-fluoropyridin-2-yl)methyl]-2,5-dimethylpiperazin-1-yl]-5-methyl-6-oxo-5,6-dihydro-1,5-naphthyridine-2-carbonitrile (188); 8-[(2S,5R)-4-[(4-chlorophenyl)(3-fluoropyridin-2-yl)methyl]-2,5-dimethylpiperazin-1-yl]-5-methyl-6-oxo-5,6-dihydro-1,5-naphthyridine-2-carbonitrile (189-190); 8-[(2S,5R)-4-[(4-chlorophenyl)(5-fluoropyridin-2-yl)methyl]-2,5-dimethylpiperazin-1-yl]-5-methyl-6-oxo-5,6-dihydro-1,5-naphthyridine-2-carbonitrile (191-192); 8-[(2S,5R)-4-[(4-fluorophenyl)(5-fluoropyridin-2-yl)methyl]-2,5-dimethylpiperazin-1-yl]-5-methyl-6-oxo-5,6-dihydro-1,5-naphthyridine-2-carbonitrile (193-194); 8-[(2S,5R)-4-[(4-chlorophenyl)(6-fluoropyridin-2-yl)methyl]-2,5-dimethylpiperazin-1-yl]-5-methyl-6-oxo-5,6-dihydro-1,5-naphthyridine-2-carbonitrile (197-198); 8-[(2S,5R)-4-[(4-fluorophenyl)(pyridin-2-yl)methyl]-2,5-dimethylpiperazin-1-yl]-5-methyl-6-oxo-5,6-dihydro-1,5-naphthyridine-2-carbonitrile (197-198); 8-[(2S,5R)-4-[(5-chloropyridin-2-yl)(4-methylphenyl)methyl]-2,5-dimethylpiperazin-1-yl]-5-methyl-6-oxo-5,6-dihydro-1,5-naphthyridine-2-carbonitrile (201-202); 8-[(2S,5R)-4-[(4-chlorophenyl)(5-chloropyridin-2-yl)methyl]-2,5-dimethylpiperazin-1-yl]-5-methyl-6-oxo-5,6-dihydro-1,5-naphthyridine-2-carbonitrile (201-202); 8-[(2S,5R)-4-[(4-fluorophenyl)(6-methylpyridin-2-yl) methyl]-2,5-dimethylpiperazin-1-yl]-5-methyl-6-oxo-5,6-dihydro-1,5-naphthyridine-2-carbonitrile (203-204); 8-[(2S,5R)-4-[(2-ethoxypyridin-3-yl)(4-fluorophenyl)methyl]-2,5-dimethylpiperazin-1-yl]-5-methyl-6-oxo-5,6-dihydro-1,5-naphthyridine-2-carbonitrile (205-206); 8-[(2S,5R)-4-[(4-fluorophenyl)[2-(propan-2-yloxy)pyridin-3-yl]methyl]-2,5-dimethylpiperazin-1-yl]-5-methyl-6-oxo-5,6-dihydro-1,5-naphthyridine-2-carbonitrile (207-208); 8-[(2S,5R)-4-[(4-fluorophenyl)(2-methoxypyridin-3-yl)methyl]-2,5-dimethylpiperazin-1-yl]-5-methyl-6-oxo-5,6-dihydro-1,5-naphthyridine-2-carbonitrile (209-210); 8-[(2S,5R)-4-[(5-chloropyridin-2-yl)(4-fluorophenyl)methyl]-2,5-dimethylpiperazin-1-yl]-5-methyl-6-oxo-5,6-dihydro-1,5- naphthyridine-2-carbonitrile (211-212); 8-[(2S,5R)-4-[(4-chlorophenyl)(5-methylpyridin-2-yl)methyl]-2,5-dimethylpiperazin-1-yl]-5-methyl-6-oxo-5,6-dihydro-1,5-naphthyridine-2-carbonitrile (213-214); 8-[(2S,5R)-4-[(3-fluorophenyl)(5-methylpyridin-2-yl)methyl]-2,5-dimethylpiperazin-1-yl]-5-methyl-6-oxo-5,6-dihydro-1,5-naphthyridine-2-carbonitrile (215-216); 7-chloro-8-[(2S,5R)-4-[(4-fluorophenyl)(phenyl)methyl]-2,5-dimethylpiperazin-1-yl]-5-methyl-6-oxo-5,6-dihydro-1,5-naphthyridine-2-carbonitrile (217-218); 3-chloro-4-{4-[(4-fluorophenyl)(phenyl)methyl]piperazin-1-yl}-6-methoxy-1-methyl-1,2-dihydro-1,5-naphthyridin-2-one (219-220); 8-[(2S,5R)-2,5-dimethyl-4-{phenyl[4-(trifluoromethoxy)phenyl]methyl}piperazin-1-yl]-5-methyl-6-oxo-5,6-dihydro-1,5-naphthyridine-2-carbonitrile (221-222); 8-[(2S,5R)-4-[(4-fluorophenyl)(3-methylphenyl)methyl]-2,5-dimethylpiperazin-1-yl]-5-methyl-6-oxo-5,6-dihydro-1,5-naphthyridine-2-carbonitrile (223-224); 8-[(2S,5R)-4-[(4-chlorophenyl)(2-ethyl-4-fluorophenyl)methyl]-2,5-dimethylpiperazin-1-yl]-5-methyl-6-oxo-5,6-dihydro-1,5-naphthyridine-2-carbonitrile (225-226); 8-[(2S,5R)-4-[(2-ethyl-4-fluorophenyl)(4-fluorophenyl)methyl]-2,5-dimethylpiperazin-1-yl]-5-methyl-6-oxo-5,6-dihydro-1,5-naphthyridine-2-carbonitrile (227-228); 8-[(2S,5R)-4-[(2-ethoxy-4-fluorophenyl)(4-fluorophenyl)methyl]-2,5-dimethylpiperazin-1-yl]-5-methyl-6-oxo-5,6-dihydro-1,5-naphthyridine-2-carbonitrile (229-230); 4-[(2S,5R)-4-[(4-chlorophenyl)(2-ethyl-4-fluorophenyl)methyl]-2,5-dimethylpiperazin-1-yl]-6-methoxy-1-methyl-1,2-dihydro-1,5-naphthyridin-2-one (231-232); 4-[(2S,5R)-4-[(2-ethyl-4-fluorophenyl)(4-fluorophenyl)methyl]-2,5-dimethylpiperazin-1-yl]-6-methoxy-1-methyl-1,2-dihydro-1,5-naphthyridin-2-one (233-234); 4-[(2S,5R)-4-[(2-ethylphenyl)(4-fluorophenyl)methyl]-2,5-dimethylpiperazin-1-yl]-6-methoxy-1-methyl-1,2-dihydro-1,5-naphthyridin-2-one (235-236); 8-[(2S,5R)-4-(diphenylmethyl)-2,5-dimethylpiperazin-1-yl]-5-methyl-6-oxo-5,6-dihydro-1,5-naphthyridine-2-carbonitrile (237); 4-[(2S,5R)-4-[(4-fluorophenyl)(phenyl)methyl]-2,5-dimethylpiperazin-1-yl]-6-methoxy-1-methyl-1,2-dihydro-1,5-naphthyridin-2-one (238-239); 4-[(2S,5R)-4-[(4-chlorophenyl)(4-fluorophenyl)methyl]-2,5-dimethylpiperazin-1-yl]-6-methoxy-1-methyl-1,2-dihydro-1,5-naphthyridin-2-one (240); 4-[(2S,5R)-4-[bis(4-fluorophenyl)methyl]-2,5-dimethylpiperazin-1-yl]-6-methoxy-1-methyl-1,2-dihydro-1,5-naphthyridin-2-one (241); 8-[(2S,5R)-4-{[2-(difluoromethyl)-4-fluorophenyl]methyl}-2,5-dimethylpiperazin-1-yl]-5-methyl-6-oxo-5,6-dihydro-1,5-naphthyridine-2-carbonitrile (242); 8-[(2S,5R)-4-{[2-fluoro-4-(trifluoromethoxy)phenyl]methyl}-2,5-dimethylpiperazin-1-yl]-5-methyl-6-oxo-5,6-dihydro-1,5-naphthyridine-2-carbonitrile (243); 8-[(2S,5R)-4-[(4-chloro-2-hydroxyphenyl)methyl]-2,5-dimethylpiperazin-1-yl]-5-methyl-6-oxo-5,6-dihydro-1,5-naphthyridine-2-carbonitrile (244); 8-[(2S,5R)-4-[(2-hydroxyphenyl)methyl]-2,5-dimethylpiperazin-1-yl]-5-methyl-6-oxo-5,6-dihydro-1,5-naphthyridine-2-carbonitrile (245); 8-[(2S,5R)-2,5-dimethyl-4-[(2,4,6-trifluorophenyl)methyl]piperazin-1-yl]-5-methyl-6-oxo-5,6-dihydro-1,5-naphthyridine-2-carbonitrile (246); 8-[(2S,5R)-4-[(4-chlorophenyl)(4-methylphenyl)methyl]-2,5-dimethylpiperazin-1-yl]-5-methyl-6-oxo-5,6-dihydro-1,5-naphthyridine-2-carbonitrile (247); 8-[(2S,5R)-4-[(3-fluorophenyl)(4-fluorophenyl)methyl]-2,5-dimethylpiperazin-1-yl]-5-methyl-6-oxo-5,6-dihydro-1,5-naphthyridine-2-carbonitrile (248); 8-[(2S,5R)-4-[(3-fluorophenyl)(4-fluorophenyl)methyl]-2,5-dimethylpiperazin-1-yl]-5-methyl-6-oxo-5,6-dihydro-1,5-naphthyridine-2-carbonitrile (249); 8-[(2S,5R)-4-[(4-chlorophenyl)(4-methylphenyl)methyl]-2,5-dimethylpiperazin-1-yl]-5-methyl-6-oxo-5,6-dihydro-1,5-naphthyridine-2-carbonitrile (250); 8-[(2S,5R)-4-[(4-fluorophenyl)(4-methylphenyl)methyl]-2,5-dimethylpiperazin-1-yl]-5-methyl-6-oxo-5,6-dihydro-1,5-naphthyridine-2-carbonitrile (251); 8-[(2S,5R)-4-[(4-fluorophenyl)(4-methylphenyl)methyl]-2,5-dimethylpiperazin-1-yl]-5-methyl-6-oxo-5,6-dihydro-1,5-naphthyridine-2-carbonitrile (252); 8-[(2S,5R)-4-[(4-cyano-2-fluorophenyl)methyl]-2,5-dimethylpiperazin-1-yl]-5-methyl-6-oxo-5,6-dihydro-1,5-naphthyridine-2-carbonitrile (253); 8-[(2S,5R)-4-{[2-fluoro-6-(trifluoromethyl)phenyl]methyl}-2,5-dimethylpiperazin-1-yl]-5-methyl-6-oxo-5,6-dihydro-1,5-naphthyridine-2-carbonitrile (254); 8-[(2S,5R)-4-[(2-fluoro-6-methylphenyl)methyl]-2,5-dimethylpiperazin-1-yl]-5-methyl-6-oxo-5,6-dihydro-1,5-naphthyridine-2-carbonitrile (255); 8-[(2S,5R)-4-[1-(2,6-difluorophenyl)ethyl]-2,5-dimethylpiperazin-1-yl]-5-methyl-6-oxo-5,6-dihydro-1,5-naphthyridine-2-carbonitrile (256); 8-[(2S,5R)-4-[bis(3-chlorophenyl)methyl]-2,5-dimethylpiperazin-1-yl]-5-methyl-6-oxo-5,6-dihydro-1,5-naphthyridine-2-carbonitrile (257); 8-[(2S,5R)-4-[bis(2-fluorophenyl)methyl]-2,5-dimethylpiperazin-1-yl]-5-methyl-6-oxo-5,6-dihydro-1,5-naphthyridine-2-carbonitrile (258); 8-[(2S,5R)-4-[(2-chlorophenyl)(phenyl)methyl]-2,5-dimethylpiperazin-1-yl]-5-methyl-6-oxo-5,6-dihydro-1,5-naphthyridine-2-carbonitrile (259); 8-[(2S,5R)-4-[(2-chloro-6-cyanophenyl)methyl]-2,5-dimethylpiperazin-1-yl]-5-methyl-6-oxo-5,6-dihydro-1,5-naphthyridine-2-carbonitrile (260); 8-[(2S,5R)-4-[(2-chloro-6-fluorophenyl)methyl]-2,5-dimethylpiperazin-1-yl]-5-methyl-6-oxo-5,6-dihydro-1,5-naphthyridine-2-carbonitrile (261); 8-[(2S,5R)-4-[(2,5-difluorophenyl)methyl]-2,5-dimethylpiperazin-1-yl]-5-methyl-6-oxo-5,6-dihydro-1,5-naphthyridine-2-carbonitrile (262); 8-[(2S,5R)-4-[(2,6-dichlorophenyl)methyl]-2,5-dimethylpiperazin-1-yl]-5-methyl-6-oxo-5,6-dihydro-1,5-naphthyridine-2-carbonitrile (263); 8-[(2S,5R)-4-benzyl-2,5-dimethylpiperazin-1-yl]-5-methyl-6-oxo-5,6-dihydro-1,5-naphthyridine-2-carbonitrile (264); 8-[(2S,5R)-4-[(2,6-dimethylphenyl)methyl]-2,5-dimethylpiperazin-1-yl]-5-methyl-6-oxo-5,6-dihydro-1,5-naphthyridine-2-carbonitrile (265); 8-[(2S,5R)-4-[(2-chloro-3,6-difluorophenyl)methyl]-2,5-dimethylpiperazin-1-yl]-5-methyl-6-oxo-5,6-dihydro-1,5-naphthyridine-2-carbonitrile (266); 8-[(2S,5R)-4-[(4-cyano-2,6-difluorophenyl)methyl]-2,5-dimethylpiperazin-1-yl]-5-methyl-6-oxo-5,6-dihydro-1,5-naphthyridine-2-carbonitrile (267); 8-[(2S,5R)-4-[(4-chloro-2,6-difluorophenyl)methyl]-2,5-dimethylpiperazin-1-yl]-5-methyl-6-oxo-5,6-dihydro-1,5-naphthyridine-2-carbonitrile (268); 8-[(2S,5R)-4-[(2-cyano-6-fluorophenyl)methyl]-2,5-dimethylpiperazin-1-yl]-5-methyl-6-oxo-5,6-dihydro-1,5-naphthyridine-2-carbonitrile (269); 8-[(2S,5R)-4-[bis(3-fluorophenyl)methyl]-2,5-dimethylpiperazin-1-yl]-5-methyl-6-oxo-5,6-dihydro-1,5-naphthyridine-2-carbonitrile (270); 8-[(2S,5R)-4-[(2,6-difluorophenyl)methyl]-2,5-dimethylpiperazin-1-yl]-5-methyl-6-oxo-5,6-dihydro-1,5-naphthyridine-2-carbonitrile (271); 8-[(2S,5R)-4-[(2,6-difluorophenyl)(phenyl)methyl]-2,5-dimethylpiperazin-1-yl]-5-methyl-6-oxo-5,6-dihydro-1,5-naphthyridine-2-carbonitrile (272); 8-[(2S,5R)-4-[(2,6-difluorophenyl)(phenyl)methyl]-2,5-dimethylpiperazin-1-yl]-5-methyl-6-oxo-5,6-dihydro-1,5-naphthyridine-2-carbonitrile, TFA (273); 8-[(2S,5R)-4-[(2,6-difluorophenyl)(4-fluorophenyl)methyl]-2,5-dimethylpiperazin-1-yl]-5-methyl-6-oxo-5,6-dihydro-1,5-naphthyridine-2-carbonitrile (274); 8-[(2S,5R)-4-[(2,6-difluorophenyl)(4-fluorophenyl)methyl]-2,5-dimethylpiperazin-1-yl]-5-methyl-6-oxo-5,6-dihydro-1,5- naphthyridine-2-carbonitrile (275); 8-[(2S,5R)-4-[(2,3-difluorophenyl)(phenyl)methyl]-2,5-dimethylpiperazin-1-yl]-5-methyl-6-oxo-5,6-dihydro-1,5-naphthyridine-2-carbonitrile (276); 8-[(2S,5R)-4-[(2,4-difluorophenyl)methyl]-2,5-dimethylpiperazin-1-yl]-5-methyl-6-oxo-5,6-dihydro-1,5-naphthyridine-2-carbonitrile (277); 8-[(2S,5R)-2,5-dimethyl-4-{[6-(trifluoromethyl)pyridin-2-yl]methyl}piperazin-1-yl]-5-methyl-6-oxo-5,6-dihydro-1,5-naphthyridine-2-carbonitrile (278); 8-[(2S,5R)-2,5-dimethyl-4-{[2-methyl-6-(trifluoromethyl)pyridin-3-yl]methyl}piperazin-1-yl]-5-methyl-6-oxo-5,6-dihydro-1,5-naphthyridine-2-carbonitrile (279); 8-[(2S,5R)-4-{[2-methoxy-6-(trifluoromethyl)pyridin-4-yl]methyl}-2,5-dimethylpiperazin-1-yl]-5-methyl-6-oxo-5,6-dihydro-1,5-naphthyridine-2-carbonitrile (280); 8-[(2S,5R)-4-{[2-chloro-6-(trifluoromethyl)pyridin-3-yl]methyl}-2,5-dimethylpiperazin-1-yl]-5-methyl-6-oxo-5,6-dihydro-1,5-naphthyridine-2-carbonitrile (281); 8-[(2S,5R)-4-[(3-chlorophenyl)(phenyl)methyl]-2,5-dimethylpiperazin-1-yl]-5-methyl-6-oxo-5,6-dihydro-1,5-naphthyridine-2-carbonitrile (282); 8-[(2S,5R)-4-[(2,4-difluorophenyl)(phenyl)methyl]-2,5-dimethylpiperazin-1-yl]-5-methyl-6-oxo-5,6-dihydro-1,5-naphthyridine-2-carbonitrile (283); 8-[(2S,5R)-4-[(2-fluorophenyl)(4-fluorophenyl)methyl]-2,5-dimethylpiperazin-1-yl]-5-methyl-6-oxo-5,6-dihydro-1,5-naphthyridine-2-carbonitrile (284); 8-[(2S,5R)-4-[(2-fluorophenyl)(phenyl)methyl]-2,5-dimethylpiperazin-1-yl]-5-methyl-6-oxo-5,6-dihydro-1,5-naphthyridine-2-carbonitrile (285); 8-[(2S,5R)-4-[(2,3-difluorophenyl)methyl]-2,5-dimethylpiperazin-1-yl]-5-methyl-6-oxo-5,6-dihydro-1,5-naphthyridine-2-carbonitrile (286); 8-[(2S,5R)-4-[(2-fluorophenyl)methyl]-2,5-dimethylpiperazin-1-yl]-5-methyl-6-oxo-5,6-dihydro-1,5-naphthyridine-2-carbonitrile (287); 8-[(2S,5R)-4-[(3,5-difluorophenyl)(phenyl)methyl]-2,5-dimethylpiperazin-1-yl]-5-methyl-6-oxo-5,6-dihydro-1,5-naphthyridine-2-carbonitrile (288); 8-[(2S,5R)-4-[(3,5-difluorophenyl)(4-fluorophenyl)methyl]-2,5-dimethylpiperazin-1-yl]-5-methyl-6-oxo-5,6-dihydro-1,5-naphthyridine-2-carbonitrile (289); 8-[(2S,5R)-4-[(3,5-difluorophenyl)methyl]-2,5-dimethylpiperazin-1-yl]-5-methyl-6-oxo-5,6-dihydro-1,5-naphthyridine-2-carbonitrile (290); 8-[(2S,5R)-4-[(3,4-difluorophenyl)methyl]-2,5-dimethylpiperazin-1-yl]-5-methyl-6-oxo-5,6-dihydro-1,5-naphthyridine-2-carbonitrile (291); 8-[(2S,5R)-4-[(3-fluorophenyl)methyl]-2,5-dimethylpiperazin-1-yl]-5-methyl-6-oxo-5,6-dihydro-1,5-naphthyridine-2-carbonitrile (292); 8-[(2S,5R)-4-[(3-fluorophenyl)(4-fluorophenyl)methyl]-2,5-dimethylpiperazin-1-yl]-5-methyl-6-oxo-5,6-dihydro-1,5-naphthyridine-2-carbonitrile (293); 8-[(2S,5R)-4-[(4-fluorophenyl)[4-(trifluoromethyl)phenyl]methyl]-2,5-dimethylpiperazin-1-yl]-5-methyl-6-oxo-5,6-dihydro-1,5-naphthyridine-2-carbonitrile (294); 8-[(2S,5R)-4-[(4-fluorophenyl)(4-methylphenyl)methyl]-2,5-dimethylpiperazin-1-yl]-5-methyl-6-oxo-5,6-dihydro-1,5-naphthyridine-2-carbonitrile (295); 8-[(2S,5R)-4-[(3-fluorophenyl)(phenyl)methyl]-2,5-dimethylpiperazin-1-yl]-5-methyl-6-oxo-5,6-dihydro-1,5-naphthyridine-2-carbonitrile (296); 8-[(2S,5R)-4-[(4-fluorophenyl)methyl]-2,5-dimethylpiperazin-1-yl]-5-methyl-6-oxo-5,6-dihydro-1,5-naphthyridine-2-carbonitrile (297); 8-((2S,5R)-4-((4-chlorophenyl)(4-cyanophenyl)methyl)-2,5-dimethylpiperazin-1-yl)-5-methyl-6-oxo-5,6-dihydro-1,5-naphthyridine-2-carbonitrile (298); 8-[(2S,5R)-4-[(4-chlorophenyl)(4-methylphenyl)methyl]-2,5-dimethylpiperazin-1-yl]-5-methyl-6-oxo-5,6-dihydro-1,5-naphthyridine-2-carbonitrile (299); 8-[(2S,5R)-4-[(4-chlorophenyl)(4-fluorophenyl)methyl]-2,5-dimethylpiperazin-1-yl]-5-methyl-6-oxo-5,6-dihydro-1,5-naphthyridine-2-carbonitrile (300); 8-[(2S,5R)-4-[bis(4-methylphenyl)methyl]-2,5-dimethylpiperazin-1-yl]-5-methyl-6-oxo-5,6-dihydro-1,5-naphthyridine-2-carbonitrile (301); 8-((2S,5R)-4-((4-chlorophenyl)(4-fluorophenyl)methyl)-2,5-dimethylpiperazin-1-yl)-5-methyl-6-oxo-5,6-dihydro-1,5-naphthyridine-2-carbonitrile (302); 8-((2S,5R)-4-((4-chlorophenyl)(4-fluorophenyl)methyl)-2,5-dimethylpiperazin-1-yl)-5-methyl-6-oxo-5,6-dihydro-1,5-naphthyridine-2-carbonitrile (303); 8-((2S,5R)-4-((2-fluorophenyl)(4-fluorophenyl)methyl)-2,5-dimethylpiperazin-1-yl)-5-methyl-6-oxo-5,6-dihydro-1,5-naphthyridine-2-carbonitrile (304); 8-((2S,5R)-4-((2-fluorophenyl)(4-fluorophenyl)methyl)-2,5-dimethylpiperazin-1-yl)-5-methyl-6-oxo-5,6-dihydro-1,5-naphthyridine-2-carbonitrile (305); 8-((2S,5R)-4-((4-cyanophenyl)(4-fluorophenyl)methyl)-2,5-dimethylpiperazin-1-yl)-5-methyl-6-oxo-5,6-dihydro-1,5-naphthyridine-2-carbonitrile (306); 8-((2S,5R)-4-((4-cyanophenyl)(4-fluorophenyl)methyl)-2,5-dimethylpiperazin-1-yl)-5-methyl-6-oxo-5,6-dihydro-1,5-naphthyridine-2-carbonitrile (307); 8-((2S,5R)-4-(1-(4-fluorophenyl)ethyl)-2,5-dimethylpiperazin-1-yl)-5-methyl-6-oxo-5,6-dihydro-1,5-naphthyridine-2-carbonitrile (308-309); 8-((2S,5R)-4-((4-cyanophenyl)(p-tolyl)methyl)-2,5-dimethylpiperazin-1-yl)-5-methyl-6-oxo-5,6-dihydro-1,5-naphthyridine-2-carbonitrile, TFA salt (310-311); 8-((3R)-4-((4-fluorophenyl)(pyrimidin-4-yl)methyl)-3-methylpiperazin-1-yl)-5-methyl-6-oxo-5,6-dihydro-1,5-naphthyridine-2,7-dicarbonitrile (312-313); 8-((3R)-4-((4-chlorophenyl)(2-methylpyrimidin-5-yl)methyl)-3-methylpiperazin-1-yl)-5-methyl-6-oxo-5,6-dihydro-1,5-naphthyridine-2,7-dicarbonitrile (314); 8-((3R)-4-((4-fluorophenyl)(2-methylpyrimidin-4-yl)methyl)-3-methylpiperazin-1-yl)-5-methyl-6-oxo-5,6-dihydro-1,5-naphthyridine-2,7-dicarbonitrile (315-316); 8-((3R)-4-((4-fluorophenyl)(pyrimidin-5-yl)methyl)-3-methylpiperazin-1-yl)-5-methyl-6-oxo-5,6-dihydro-1,5-naphthyridine-2,7-dicarbonitrile (317-318); 8-((3R)-4-((4-chlorophenyl)(pyrimidin-4-yl)methyl)-3-methylpiperazin-1-yl)-5-methyl-6-oxo-5,6-dihydro-1,5-naphthyridine-2,7-dicarbonitrile (319-320); 8-((3R)-4-((2-(tert-butyl)pyrimidin-4-yl)(4-fluorophenyl)methyl)-3-methylpiperazin-1-yl)-5-methyl-6-oxo-5,6-dihydro-1,5-naphthyridine-2,7-dicarbonitrile (321); 8-((2S,5R)-4-((4-cyanophenyl)(p-tolyl)methyl)-2,5-dimethylpiperazin-1-yl)-7-fluoro-5-methyl-6-oxo-5,6-dihydro-1,5-naphthyridine-2-carbonitrile (322); 8-((2S,5R)-4-((4-chlorophenyl)(4-(trifluoromethoxy)phenyl)methyl)-2,5-dimethylpiperazin-1-yl)-7-fluoro-5-methyl-6-oxo-5,6-dihydro-1,5-naphthyridine-2-carbonitrile (323-324); 7-fluoro-8-((2S,5R)-4-((4-fluorophenyl)(4-(trifluoromethyl)phenyl)methyl)-2,5-dimethylpiperazin-1-yl)-5-methyl-6-oxo-5,6-dihydro-1,5-naphthyridine-2-carbonitrile (325-326); 8-((2S,5R)-4-((4-cyanophenyl)(4-fluorophenyl)methyl)-2,5-dimethylpiperazin-1-yl)-7-fluoro-5-methyl-6-oxo-5,6-dihydro-1,5-naphthyridine-2-carbonitrile (327-328); 8-((2S,5R)-4-((2,6-difluorophenyl)(4-fluorophenyl)methyl)-2,5-dimethylpiperazin-1-yl)-7-fluoro-5-methyl-6-oxo-5,6-dihydro-1,5-naphthyridine-2-carbonitrile (329 and 336); 7-fluoro-8-((2S,5R)-4-((3-fluorophenyl)(4-fluorophenyl)methyl)-2,5-dimethylpiperazin-1-yl)-5-methyl-6-oxo-5,6-dihydro-1,5-naphthyridine-2-carbonitrile (330-331); 7-fluoro-8-((2S,5R)-4-((4-fluorophenyl)(p-tolyl)methyl)-2,5-dimethylpiperazin-1-yl)-5-methyl-6-oxo-5,6-dihydro-1,5-naphthyridine-2-carbonitrile (332); 7-fluoro-8-((2S,5R)-4-((2-fluorophenyl)(4-fluorophenyl)methyl)-2,5-dimethylpiperazin-1-yl)-5-methyl-6-oxo-5,6-dihydro-1,5- naphthyridine-2-carbonitrile (333-334); 7-fluoro-8-((2S,5R)-4-((4-fluorophenyl)(p-tolyl)methyl)-2,5-dimethylpiperazin-1-yl)-5-methyl-6-oxo-5,6-dihydro-1,5-naphthyridine-2-carbonitrile (335); 8-((2S,5R)-4-(1-(2,4-difluorophenyl)propyl)-2,5-dimethylpiperazin-1-yl)-5-methyl-6-oxo-5,6-dihydro-1,5-naphthyridine-2-carbonitrile (337-339); 8-[(2S,5R)-5-ethyl-2-methyl-4-[(pyridin-2-yl)[4-(trifluoromethoxy)phenyl]methyl]piperazin-1-yl]-5-methyl-6-oxo-5,6-dihydro-1,5-naphthyridine-2-carbonitrile (340-341); 8-((2S,5R)-5-ethyl-2-methyl-4-(pyridin-2-yl(4-(trifluoromethoxy)phenyl)methyl)piperazin-1-yl)-5-methyl-6-oxo-5,6-dihydro-1,5-naphthyridine-2-carbonitrile (342-343); 8-((2S,5R)-4-(1-(3,4-difluorophenyl)propyl)-2,5-dimethylpiperazin-1-yl)-5-methyl-6-oxo-5,6-dihydro-1,5-naphthyridine-2-carbonitrile (344); 8-((2R,5S)-2,5-dimethyl-4-(1-(4-(trifluoromethyl)phenyl)ethyl)piperazin-1-yl)-5-methyl-6-oxo-5,6-dihydro-1,5-naphthyridine-2-carbonitrile (345-346); 8-((2S,5R)-4-(1-(2,4-difluorophenyl)propyl)-2,5-dimethylpiperazin-1-yl)-5-methyl-6-oxo-5,6-dihydro-1,5-naphthyridine-2-carbonitrile (347-349); 8-((2S,5R)-4-((5-ethylpyridin-2-yl)(3-fluorophenyl)methyl)-2,5-dimethylpiperazin-1-yl)-5-methyl-6-oxo-5,6-dihydro-1,5-naphthyridine-2-carbonitrile (350-351); 8-((2S,5R)-4-(2-methoxy-4-(trifluoromethoxy)benzyl)-2,5-dimethylpiperazin-1-yl)-5-methyl-6-oxo-5,6-dihydro-1,5-naphthyridine-2-carbonitrile (352); 8-((2S,5R)-4-(1-(5-chloro-2,3-dihydrobenzofuran-7-yl)propyl)-2,5-dimethylpiperazin-1-yl)-5-methyl-6-oxo-5,6-dihydro-1,5-naphthyridine-2-carbonitrile (353 and 356-357); 8-((2S,5R)-4-((5-ethylpyridin-2-yl)(3-fluorophenyl) methyl)-2,5-dimethylpiperazin-1-yl)-5-methyl-6-oxo-5,6-dihydro-1,5-naphthyridine-2-carbonitrile (354); 8-((2S,5R)-4-((3-chlorophenyl)(5-ethylpyridin-2-yl)methyl)-2,5-dimethylpiperazin-1-yl)-5-methyl-6-oxo-5,6-dihydro-1,5-naphthyridine-2-carbonitrile (354-355); 8-((2S,5R)-4-((4-fluorophenyl)(tetrahydro-2H-pyran-2-yl)methyl)-2,5-dimethylpiperazin-1-yl)-5-methyl-6-oxo-5,6-dihydro-1,5-naphthyridine-2-carbonitrile (358-359); 8-((2S,5R)-4-((4-cyanophenyl)(5-methylpyridin-2-yl)methyl)-2,5-dimethylpiperazin-1-yl)-5-methyl-6-oxo-5,6-dihydro-1,5-naphthyridine-2-carbonitrile (360-361); 8-((2S,5R)-4-((4-chlorophenyl)(4-methylpyridin-2-yl)methyl)-2,5-dimethylpiperazin-1-yl)-5-methyl-6-oxo-5,6-dihydro-1,5-naphthyridine-2-carbonitrile (362 and 364); 8-((2S,5R)-4-((4-chlorophenyl)(5-methylpyridin-2-yl)methyl)-2,5-dimethylpiperazin-1-yl)-5-methyl-6-oxo-5,6-dihydro-1,5-naphthyridine-2-carbonitrile (363-365); 8-((2S,5R)-4-((3,4-difluorophenyl)(pyridin-2-yl)methyl)-2,5-dimethylpiperazin-1-yl)-5-methyl-6-oxo-5,6-dihydro-1,5-naphthyridine-2-carbonitrile (366); 8-((2S,5R)-4-((6-fluoropyridin-2-yl)(4-(trifluoromethoxy)phenyl)methyl)-2,5-dimethylpiperazin-1-yl)-5-methyl-6-oxo-5,6-dihydro-1,5-naphthyridine-2-carbonitrile (367-368); 8-((2S,5R)-4-((3-chlorophenyl)(5-methylpyridin-2-yl)methyl)-2,5-dimethylpiperazin-1-yl)-5-methyl-6-oxo-5,6-dihydro-1,5-naphthyridine-2-carbonitrile (369); 8-((2S,5R)-4-((3-fluorophenyl)(5-(trifluoromethyl)pyridin-2-yl)methyl)-2,5-dimethylpiperazin-1-yl)-5-methyl-6-oxo-5,6-dihydro-1,5-naphthyridine-2-carbonitrile (370-371); 8-((2S,5R)-4-((3-chlorophenyl)(5-methylpyridin-2-yl)methyl)-2,5-dimethylpiperazin-1-yl)-5-methyl-6-oxo-5,6-dihydro-1,5-naphthyridine-2-carbonitrile (372); 8-((2S,5R)-4-((3-chloro-4-methylphenyl)(5-methylpyridin-2-yl)methyl)-2,5-dimethylpiperazin-1-yl)-5-methyl-6-oxo-5,6-dihydro-1,5-naphthyridine-2-carbonitrile (373 and 380); 8-((2S,5R)-4-((3-fluorophenyl)(pyridin-2-yl)methyl)-2,5-dimethylpiperazin-1-yl)-5-methyl-6-oxo-5,6-dihydro-1,5-naphthyridine-2-carbonitrile (374 and 379); 8-((2S,5R)-4-((3,4-difluorophenyl)(pyridin-2-yl)methyl)-2,5-dimethylpiperazin-1-yl)-5-methyl-6-oxo-5,6-dihydro-1,5-naphthyridine-2-carbonitrile (375-376); 8-((2S,5R)-2,5-dimethyl-4-(pyridin-2-yl(4-(trifluoromethoxy)phenyl) methyl) piperazin-1-yl)-5-methyl-6-oxo-5,6-dihydro-1,5-naphthyridine-2-carbonitrile (377-378); 8-((2S,5R)-4-((4-chlorophenyl)(pyridin-2-yl)methyl)-2,5-dimethylpiperazin-1-yl)-5-methyl-6-oxo-5,6-dihydro-1,5-naphthyridine-2-carbonitrile (381 and 382); 8-((2S,5R)-4-((4-fluorophenyl)(pyridazin-3-yl)methyl)-2,5-dimethylpiperazin-1-yl)-5-methyl-6-oxo-5,6-dihydro-1,5-naphthyridine-2-carbonitrile (383-384); 8-((2S,5R)-4-((4-chlorophenyl) (2-methylpyrimidin-5-yl)methyl)-2,5-dimethylpiperazin-1-yl)-5-methyl-6-oxo-5,6-dihydro-1,5-naphthyridine-2-carbonitrile (385); 8-((2S,5R)-4-((4-fluorophenyl)(5-fluoropyridin-3-yl)methyl)-2,5-dimethylpiperazin-1-yl)-5-methyl-6-oxo-5,6-dihydro-1,5-naphthyridine-2-carbonitrile (386); 8-((2S,5R)-4-((4-fluorophenyl)(tetrahydro-2H-pyran-4-yl)methyl)-2,5-dimethylpiperazin-1-yl)-5-methyl-6-oxo-5,6-dihydro-1,5-naphthyridine-2-carbonitrile (387-388); 8-((2S,5R)-4-((4-fluorophenyl)(2-methylpyrimidin-4-yl) methyl)-2,5-dimethylpiperazin-1-yl)-5-methyl-6-oxo-5,6-dihydro-1,5-naphthyridine-2-carbonitrile (389); 8-((2S,5R)-4-((3-fluorophenyl)(6-methylpyridin-3-yl)methyl)-2,5-dimethylpiperazin-1-yl)-5-methyl-6-oxo-5,6-dihydro-1,5-naphthyridine-2-carbonitrile (390); 8-((2S,5R)-4-((5-fluoropyridin-3-yl)(p-tolyl)methyl)-2,5-dimethylpiperazin-1-yl)-5-methyl-6-oxo-5,6-dihydro-1,5-naphthyridine-2-carbonitrile (391); 8-((2S,5R)-4-((4-fluorophenyl)(pyrimidin-4-yl)methyl)-2,5-dimethylpiperazin-1-yl)-5-methyl-6-oxo-5,6-dihydro-1,5-naphthyridine-2-carbonitrile (392); 8-((2S,5R)-4-((4-fluorophenyl) (pyrimidin-5-yl)methyl)-2,5-dimethylpiperazin-1-yl)-5-methyl-6-oxo-5,6-dihydro-1,5-naphthyridine-2-carbonitrile (393-394); 8-((2S,5R)-4-((3-fluorophenyl)(6-methylpyridin-3-yl)methyl)-2,5-dimethylpiperazin-1-yl)-5-methyl-6-oxo-5,6-dihydro-1,5-naphthyridine-2-carbonitrile (395); 8-((2S,5R)-4-((4-chlorophenyl)(pyrimidin-4-yl)methyl)-2,5-dimethylpiperazin-1-yl)-5-methyl-6-oxo-5,6-dihydro-1,5-naphthyridine-2-carbonitrile (396-397); 8-((2S,5R)-4-((3-chlorophenyl)(5-methylpyridin-2-yl)methyl)-2,5-dimethylpiperazin-1-yl)-5-methyl-6-oxo-5,6-dihydro-1,5-naphthyridine-2-carbonitrile (398); 8-((2S,5R)-4-((3-chloro-4-methylphenyl)(5-methylpyridin-2-yl)methyl)-2,5-dimethylpiperazin-1-yl)-5-methyl-6-oxo-5,6-dihydro-1,5-naphthyridine-2-carbonitrile (399); 8-((2S,5R)-4-((4-fluorophenyl)(5-fluoropyridin-3-yl)methyl)-2,5-dimethylpiperazin-1-yl)-5-methyl-6-oxo-5,6-dihydro-1,5-naphthyridine-2-carbonitrile (400); 8-((2S,5R)-4-((4-fluorophenyl)(2-methylpyrimidin-4-yl)methyl)-2,5-dimethylpiperazin-1-yl)-5-methyl-6-oxo-5,6-dihydro-1,5-naphthyridine-2-carbonitrile (401); 8-((2S,5R)-4-((4-fluorophenyl)(pyrimidin-4-yl)methyl)-2,5-dimethylpiperazin-1-yl)-5-methyl-6-oxo-5,6-dihydro-1,5-naphthyridine-2-carbonitrile (402); 8-((2S,5R)-4-((4-chlorophenyl)(pyridin-2-yl)methyl)-2,5-dimethylpiperazin-1-yl)-5-methyl-6-oxo-5,6-dihydro-1,5-naphthyridine-2-carbonitrile (403); 8-((2S,5R)-4-((3-fluorophenyl)(pyridin-2-yl)methyl)-2,5-dimethylpiperazin-1-yl)-5-methyl-6-oxo-5,6-dihydro-1,5-naphthyridine-2-carbonitrile (404); 8-((2S,5R)-2,5-dimethyl-4-(pyridin-2-yl(4-(trifluoromethoxy)phenyl)methyl)piperazin-1-yl)-5-methyl-6-oxo-5,6-dihydro-1,5-naphthyridine-2-carbonitrile (405); 8-((2S,5R)-4-((4-fluorophenyl)(2-methylpyrimidin-5-yl)methyl)-2,5-dimethylpiperazin-1-yl)-5-methyl-6-oxo-5,6-dihydro-1,5-naphthyridine-2-carbonitrile (406); 8-((2S,5R)-4-(bis(5- fluoropyridin-2-yl)methyl)-2,5-dimethylpiperazin-1-yl)-5-methyl-6-oxo-5,6-dihydro-1,5-naphthyridine-2-carbonitrile (407); 8-((2S,5R)-4-((2-(tert-butyl)pyrimidin-4-yl)(4-fluorophenyl)methyl)-2,5-dimethylpiperazin-1-yl)-5-methyl-6-oxo-5,6-dihydro-1,5-naphthyridine-2-carbonitrile (408-409); 8-((2S,5R)-4-((4-fluorophenyl)(2-methylpyrimidin-5-yl)methyl)-2,5-dimethylpiperazin-1-yl)-5-methyl-6-oxo-5,6-dihydro-1,5-naphthyridine-2-carbonitrile (410); 8-((2S,5R)-4-(1-(3,4-difluorophenyl)propyl)-2,5-dimethylpiperazin-1-yl)-5-methyl-6-oxo-5,6-dihydro-1,5-naphthyridine-2-carbonitrile (411); 8-((2S,5R)-4-(1-(2-fluoro-4-(trifluoromethyl)phenyl)ethyl)-2,5-dimethylpiperazin-1-yl)-5-methyl-6-oxo-5,6-dihydro-1,5-naphthyridine-2-carbonitrile (412); 8-((3R)-4-((4-chlorophenyl)(2-methylpyrimidin-5-yl)methyl)-3-methylpiperazin-1-yl)-5-methyl-6-oxo-5,6-dihydro-1,5-naphthyridine-2,7-dicarbonitrile (413-414); 8-((2S,5R)-4-((4-fluorophenyl)(5-fluoropyridin-3-yl)methyl)-2,5-dimethylpiperazin-1-yl)-5-methyl-6-oxo-5,6-dihydro-1,5-naphthyridine-2-carbonitrile (415); 8-((2S,5R)-4-((5-fluoropyridin-3-yl)(p-tolyl)methyl)-2,5-dimethylpiperazin-1-yl)-5-methyl-6-oxo-5,6-dihydro-1,5-naphthyridine-2-carbonitrile (416); 8-((2S,5R)-4-((3-fluorophenyl)(6-methylpyridin-3-yl)methyl)-2,5-dimethylpiperazin-1-yl)-5-methyl-6-oxo-5,6-dihydro-1,5-naphthyridine-2-carbonitrile (417); 8-((2S,5R)-5-ethyl-4-((4-fluorophenyl)(2-methylpyrimidin-4-yl)methyl)-2-methylpiperazin-1-yl)-5-methyl-6-oxo-5,6-dihydro-1,5-naphthyridine-2-carbonitrile (418-419); 8-((2S,5R)-5-ethyl-4-(1-(2-fluoro-4-(trifluoromethoxy)phenyl)propyl)-2-methylpiperazin-1-yl)-5-methyl-6-oxo-5,6-dihydro-1,5-naphthyridine-2-carbonitrile (420-421); 8-((2S,5R)-4-((4-chlorophenyl)(pyridin-2-yl)methyl)-5-ethyl-2-methylpiperazin-1-yl)-5-methyl-6-oxo-5,6-dihydro-1,5-naphthyridine-2-carbonitrile (422-423); 7-fluoro-8-((2S,5R)-4-(1-(4-fluorophenyl)ethyl-1-d)-2,5-dimethylpiperazin-1-yl)-5-methyl-6-oxo-5,6-dihydro-1,5-naphthyridine-2-carbonitrile and 7-fluoro-8-((2S,5R)-4-(1-(4-fluorophenyl)ethyl-1-d)-2,5-dimethylpiperazin-1-yl)-5-methyl-6-oxo-5,6-dihydro-1,5-naphthyridine-2-carbonitrile (424-425); 7-fluoro-8-((2S,5R)-4-(1-(4-fluorophenyl)ethyl-1-d)-2,5-dimethylpiperazin-1-yl)-5-methyl-6-oxo-5,6-dihydro-1,5-naphthyridine-2-carbonitrile (426-427); 8-((2S,5R)-4-(1-(4-fluorophenyl)ethyl-1-d)-2,5-dimethylpiperazin-1-yl)-5-methyl-6-oxo-5,6-dihydro-1,5-naphthyridine-2-carbonitrile (428-429); 8-((2S,5R)-2,5-dimethyl-4-((2,4,6-trifluorophenyl)methyl-d2)piperazin-1-yl)-5-methyl-6-oxo-5,6-dihydro-1,5-naphthyridine-2-carbonitrile (430); 8-((2S,5R)-4-(1-(2-fluoro-4-(trifluoromethyl)phenyl) ethyl)-2,5-dimethylpiperazin-1-yl)-5-methyl-6-oxo-5,6-dihydro-1,5-naphthyridine-2-carbonitrile (431); 8-((2S,5R)-2,5-dimethyl-4-(1-(2,4,6-trifluorophenyl)ethyl)piperazin-1-yl)-5-methyl-6-oxo-5,6-dihydro-1,5-naphthyridine-2-carbonitrile (432); 8-((2S,5R)-4-(1-(2-chloro-4-fluoro-3-methylphenyl)ethyl)-2,5-dimethylpiperazin-1-yl)-5-methyl-6-oxo-5,6-dihydro-1,5-naphthyridine-2-carbonitrile (433); 8-((2S,5R)-4-(1-(2-fluoro-4-(trifluoromethyl)phenyl)ethyl)-2,5-dimethylpiperazin-1-yl)-5-methyl-6-oxo-5,6-dihydro-1,5-naphthyridine-2-carbonitrile (434); 8-((2S,5R)-2,5-dimethyl-4-(1-(4-(trifluoromethoxy)phenyl)ethyl)piperazin-1-yl)-5-methyl-6-oxo-5,6-dihydro-1,5-naphthyridine-2-carbonitrile (435-436); 8-((2S,5R)-4-(1-(2-fluoro-4-(trifluoromethoxy) phenyl)ethyl)-2,5-dimethylpiperazin-1-yl)-5-methyl-6-oxo-5,6-dihydro-1,5-naphthyridine-2-carbonitrile (437, 439, and 442); 8-((2S,5R)-4-(1-(2-fluoro-4-(trifluoromethoxy)phenyl)propyl)-2,5-dimethylpiperazin-1-yl)-5-methyl-6-oxo-5,6-dihydro-1,5-naphthyridine-2-carbonitrile (438 and 440-441); 8-((2S,5R)-4-((4-chlorophenyl)(6-methylpyridin-2-yl)methyl)-2,5-dimethylpiperazin-1-yl)-5-methyl-6-oxo-5,6-dihydro-1,5-naphthyridine-2-carbonitrile (443); 8-((2S,5R)-4-((5-fluoropyridin-2-yl)(p-tolyl)methyl)-2,5-dimethylpiperazin-1-yl)-5-methyl-6-oxo-5,6-dihydro-1,5-naphthyridine-2-carbonitrile (444); 8-((2S,5R)-4-((3,4-dihydro-2H-benzo[b][1,4]dioxepin-6-yl)(3-fluorophenyl)methyl)-2,5-dimethylpiperazin-1-yl)-5-methyl-6-oxo-5,6-dihydro-1,5-naphthyridine-2-carbonitrile (445); 8-((2S,5R)-4-((4-chlorophenyl)(4-fluoropyridin-2-yl)methyl)-2,5-dimethylpiperazin-1-yl)-5-methyl-6-oxo-5,6-dihydro-1,5-naphthyridine-2-carbonitrile (446); 8-((2S,5R)-4-((4-chlorophenyl)(2,3-dihydrobenzo[b][1,4]dioxin-5-yl) methyl)-2,5-dimethylpiperazin-1-yl)-5-methyl-6-oxo-5,6-dihydro-1,5-naphthyridine-2-carbonitrile (447); 8-((2S,5R)-4-((4-chlorophenyl)(4-methylpyridin-2-yl)methyl)-2,5-dimethylpiperazin-1-yl)-5-methyl-6-oxo-5,6-dihydro-1,5-naphthyridine-2-carbonitrile (448); 8-((2S,5R)-4-((4-fluorophenyl)(5-methylpyridin-2-yl)methyl)-2,5-dimethylpiperazin-1-yl)-5-methyl-6-oxo-5,6-dihydro-1,5-naphthyridine-2-carbonitrile (449); 8-((2S,5R)-2,5-dimethyl-4-((6-methylpyridin-2-yl)(p-tolyl)methyl) piperazin-1-yl)-5-methyl-6-oxo-5,6-dihydro-1,5-naphthyridine-2-carbonitrile (450); 8-((2S,5R)-4-((3,4-dihydro-2H-benzo[b][1,4]dioxepin-6-yl)(5-methylpyridin-2-yl)methyl)-2,5-dimethylpiperazin-1-yl)-5-methyl-6-oxo-5,6-dihydro-1,5-naphthyridine-2-carbonitrile (451); 8-((2S,5R)-4-((4-cyanophenyl)(5-methylpyridin-2-yl)methyl)-2,5-dimethylpiperazin-1-yl)-5-methyl-6-oxo-5,6-dihydro-1,5-naphthyridine-2-carbonitrile (452-453); 8-((2S,5R)-2,5-dimethyl-4-((5-methylpyridin-2-yl)(p-tolyl)methyl)piperazin-1-yl)-5-methyl-6-oxo-5,6-dihydro-1,5-naphthyridine-2-carbonitrile (454, 457); 8-((2S,5R)-4-((4-fluorophenyl)(4-methylpyridin-2-yl)methyl)-2,5-dimethylpiperazin-1-yl)-5-methyl-6-oxo-5,6-dihydro-1,5-naphthyridine-2-carbonitrile (455-456); 8-((2S,5R)-4-((4-chlorophenyl)(4-fluoro-2,2-dimethyl-2,3-dihydrobenzofuran-7-yl)methyl)-2,5-dimethylpiperazin-1-yl)-5-methyl-6-oxo-5,6-dihydro-1,5-naphthyridine-2-carbonitrile (458-459); 8-((2S,5R)-2,5-dimethyl-4-((4-methylpyridin-2-yl)(p-tolyl)methyl)piperazin-1-yl)-5-methyl-6-oxo-5,6-dihydro-1,5-naphthyridine-2-carbonitrile (460-461); 8-((2S,5R)-4-((5-fluoropyridin-2-yl)(4-(trifluoromethoxy)phenyl)methyl)-2,5-dimethylpiperazin-1-yl)-5-methyl-6-oxo-5,6-dihydro-1,5-naphthyridine-2-carbonitrile (462, 466, 468); 8-((2S,5R)-4-((4-cyanophenyl)(5-fluoropyridin-2-yl)methyl)-2,5-dimethylpiperazin-1-yl)-5-methyl-6-oxo-5,6-dihydro-1,5-naphthyridine-2-carbonitrile (463-464); 8-((2S,5R)-4-((2,2-dimethyl-2,3-dihydrobenzofuran-7-yl)(5-fluoropyridin-2-yl)methyl)-2,5-dimethylpiperazin-1-yl)-5-methyl-6-oxo-5,6-dihydro-1,5-naphthyridine-2-carbonitrile (465, 467); 8-((2S,5R)-4-((3,4-dihydro-2H-benzo[b][1,4]dioxepin-6-yl)(5-methylpyridin-2-yl) methyl)-2,5-dimethylpiperazin-1-yl)-5-methyl-6-oxo-5,6-dihydro-1,5-naphthyridine-2-carbonitrile (469); 8-((2S,5R)-4-((3-fluorophenyl)(6-methylpyridin-2-yl)methyl)-2,5-dimethylpiperazin-1-yl)-5-methyl-6-oxo-5,6-dihydro-1,5-naphthyridine-2-carbonitrile (470); 8-((2S,5R)-4-((4-fluorophenyl)(6-fluoropyridin-2-yl)methyl)-2,5-dimethylpiperazin-1-yl)-5-methyl-6-oxo-5,6-dihydro-1,5-naphthyridine-2-carbonitrile (471); 8-((2S,5R)-4-((4-fluorophenyl)(4-fluoropyridin-2-yl)methyl)-2,5-dimethylpiperazin-1-yl)-5-methyl-6-oxo-5,6-dihydro-1,5-naphthyridine-2-carbonitrile (472-474); 8-((2S,5R)-2,5-dimethyl-4-((1-methyl-1H-indazol-4-yl)methyl)piperazin-1-yl)-5-methyl-6-oxo-5,6-dihydro-1,5-naphthyridine-2- carbonitrile (475); 8-((2S,5R)-4-((6-fluoropyridin-2-yl)(p-tolyl)methyl)-2,5-dimethylpiperazin-1-yl)-5-methyl-6-oxo-5,6-dihydro-1,5-naphthyridine-2-carbonitrile (476, 478-479); 8-((2S,5R)-4-(cyclopropyl(2-fluoro-4-(trifluoromethoxy)phenyl)methyl)-2,5-dimethylpiperazin-1-yl)-5-methyl-6-oxo-5,6-dihydro-1,5-naphthyridine-2-carbonitrile (480-481); 8-((2S,5R)-5-ethyl-4-(1-(4-methoxyphenyl)ethyl)-2-methylpiperazin-1-yl)-5-methyl-6-oxo-5,6-dihydro-1,5-naphthyridine-2-carbonitrile (482-483); 8-((2S,5R)-4-((4-fluorophenyl)(4-methylpyridin-2-yl)methyl)-2,5-dimethylpiperazin-1-yl)-5-methyl-6-oxo-5,6-dihydro-1,5-naphthyridine-2-carbonitrile (484); 8-((2S,5R)-2,5-dimethyl-4-((4-methylpyridin-2-yl)(p-tolyl)methyl)piperazin-1-yl)-5-methyl-6-oxo-5,6-dihydro-1,5-naphthyridine-2-carbonitrile (485); 8-((2S,5R)-4-(1-(2-chloro-4,5-difluorophenyl)ethyl)-2,5-dimethylpiperazin-1-yl)-5-methyl-6-oxo-5,6-dihydro-1,5-naphthyridine-2-carbonitrile (486); 8-((2S,5R)-4-(1-(2-chloro-4-fluoro-3-methylphenyl)ethyl)-2,5-dimethylpiperazin-1-yl)-5-methyl-6-oxo-5,6-dihydro-1,5-naphthyridine-2-carbonitrile (487); 8-((2S,5R)-2,5-dimethyl-4-(1-(2,4,6-trifluorophenyl)ethyl)piperazin-1-yl)-5-methyl-6-oxo-5,6-dihydro-1,5-naphthyridine-2-carbonitrile (488-489, 555); 8-[(2S,5R)-4-[2-fluoro-1-(4-fluorophenyl)ethyl]-2,5-dimethylpiperazin-1-yl]-5-methyl-6-oxo-5,6-dihydro-1,5-naphthyridine-2-carbonitrile (556); 8-((2S,5R)-4-(1-(4-fluorophenyl)-2-hydroxyethyl)-2,5-dimethylpiperazin-1-yl)-5-methyl-6-oxo-5,6-dihydro-1,5-naphthyridine-2-carbonitrile (557-558); 8-((2S,5R)-4-(1-(4-fluorophenyl)-2-methoxyethyl)-2,5-dimethylpiperazin-1-yl)-5-methyl-6-oxo-5,6-dihydro-1,5-naphthyridine-2-carbonitrile (559-560); 8-((2S,5R)-4-(2-(4-fluorophenyl)-2-methoxyethyl)-2,5-dimethylpiperazin-1-yl)-5-methyl-6-oxo-5,6-dihydro-1,5-naphthyridine-2-carbonitrile (561); 8-((2S,5R)-4-(4-(1-cyanocyclopropyl)benzyl)-2,5-dimethylpiperazin-1-yl)-5-methyl-6-oxo-5,6-dihydro-1,5-naphthyridine-2-carbonitrile (567); 8-((2S,5R)-4-((1-ethyl-1H-benzo[d]imidazol-7-yl)methyl)-2,5-dimethylpiperazin-1-yl)-5-methyl-6-oxo-5,6-dihydro-1,5-naphthyridine-2-carbonitrile (568-569); 7-(difluoromethyl)-8-((2S,5R)-4-(2-fluoro-4-(trifluoromethoxy)benzyl)-2,5-dimethylpiperazin-1-yl)-5-methyl-6-oxo-5,6-dihydro-1,5-naphthyridine-2-carbonitrile (570); 8-((2S,5R)-4-(3-(dimethylamino)benzyl)-2,5-dimethylpiperazin-1-yl)-5-methyl-6-oxo-5,6-dihydro-1,5-naphthyridine-2-carbonitrile (573); 8-((2S,5R)-4-(1-(4-fluorophenyl)propyl-1-d)-2,5-dimethylpiperazin-1-yl)-5-methyl-6-oxo-5,6-dihydro-1,5-naphthyridine-2-carbonitrile (574-575); 8-((2S,5R)-4-(2-cyano-4-(trifluoromethoxy) benzyl)-2,5-dimethylpiperazin-1-yl)-5-methyl-6-oxo-5,6-dihydro-1,5-naphthyridine-2-carbonitrile (581); 8-((2S,5R)-2,5-dimethyl-4-(2,2,2-trifluoro-1-(4-fluorophenyl)ethyl) piperazin-1-yl)-5-methyl-6-oxo-5,6-dihydro-1,5-naphthyridine-2-carbonitrile (582-583); 8-((2S,5R)-4-(3-cyano-4-(trifluoromethoxy)benzyl)-2,5-dimethylpiperazin-1-yl)-5-methyl-6-oxo-5,6-dihydro-1,5-naphthyridine-2-carbonitrile (584); 8-((2S,5R)-4-(4-fluoro-3-(trifluoromethoxy)benzyl)-2,5-dimethylpiperazin-1-yl)-5-methyl-6-oxo-5,6-dihydro-1,5-naphthyridine-2-carbonitrile (585); 8-((2S,5R)-2,5-dimethyl-4-(3-(trifluoromethoxy)benzyl)piperazin-1-yl)-5-methyl-6-oxo-5,6-dihydro-1,5-naphthyridine-2-carbonitrile (586); 8-((2S,5R)-4-(4-(tert-butyl)benzyl)-2,5-dimethylpiperazin-1-yl)-5-methyl-6-oxo-5,6-dihydro-1,5-naphthyridine-2-carbonitrile (587); 8-((2S,5R)-4-(4-(difluoromethoxy)benzyl)-2,5-dimethylpiperazin-1-yl)-5-methyl-6-oxo-5,6-dihydro-1,5-naphthyridine-2-carbonitrile (588); 8-((2S,5R)-4-((2,2-difluorobenzo[d][1,3]dioxol-5-yl)methyl)-2,5-dimethylpiperazin-1-yl)-5-methyl-6-oxo-5,6-dihydro-1,5-naphthyridine-2-carbonitrile (589); 8-((2S,5R)-4-(4-(difluoromethoxy)-2-fluorobenzyl)-2,5-dimethylpiperazin-1-yl)-5-methyl-6-oxo-5,6-dihydro-1,5-naphthyridine-2-carbonitrile (590); 8-((2S,5R)-4-(2-fluoro-4-(trifluoromethoxy)benzyl)-2,5-dimethylpiperazin-1-yl)-5-methyl-6-oxo-5,6-dihydro-1,5-naphthyridine-2-carbonitrile (591); 8-((2S,5R)-4-(1-(2,6-difluoro-4-hydroxyphenyl)-2,2,2-trifluoroethyl)-2,5-dimethylpiperazin-1-yl)-5-methyl-6-oxo-5,6-dihydro-1,5-naphthyridine-2-carbonitrile (592); 8-((2S,5R)-4-(2-bromo-4-(trifluoromethoxy)benzyl)-2,5-dimethylpiperazin-1-yl)-5-methyl-6-oxo-5,6-dihydro-1,5-naphthyridine-2-carbonitrile (593); 8-((2S,5R)-4-(3-isopropoxybenzyl)-2,5-dimethylpiperazin-1-yl)-5-methyl-6-oxo-5,6-dihydro-1,5-naphthyridine-2-carbonitrile (594); 8-((2S,5R)-4-(2-isopropoxybenzyl)-2,5-dimethylpiperazin-1-yl)-5-methyl-6-oxo-5,6-dihydro-1,5-naphthyridine-2-carbonitrile (595); 8-((2S,5R)-4-((1-ethyl-3-fluoro-1H-indol-4-yl)methyl)-2,5-dimethylpiperazin-1-yl)-5-methyl-6-oxo-5,6-dihydro-1,5-naphthyridine-2-carbonitrile (596); 8-((2S,5R)-4-(4-fluoro-2-isopropoxybenzyl)-2,5-dimethylpiperazin-1-yl)-5-methyl-6-oxo-5,6-dihydro-1,5-naphthyridine-2-carbonitrile (598); 8-((2S,5R)-4-(3-ethoxybenzyl)-2,5-dimethylpiperazin-1-yl)-5-methyl-6-oxo-5,6-dihydro-1,5-naphthyridine-2-carbonitrile (599); 8-((2S,5R)-4-(2-methoxy-5-(trifluoromethoxy)benzyl)-2,5-dimethylpiperazin-1-yl)-5-methyl-6-oxo-5,6-dihydro-1,5-naphthyridine-2-carbonitrile (601); 8-((2S,5R)-4-(4-isopropylbenzyl)-2,5-dimethylpiperazin-1-yl)-5-methyl-6-oxo-5,6-dihydro-1,5-naphthyridine-2-carbonitrile (602); 8-((2S,5R)-4-(4-chlorobenzyl)-2,5-dimethylpiperazin-1-yl)-5-methyl-6-oxo-5,6-dihydro-1,5-naphthyridine-2-carbonitrile (603); 8-((2S,5R)-2,5-dimethyl-4-((1-methyl-1H-indol-4-yl)methyl)piperazin-1-yl)-5-methyl-6-oxo-5,6-dihydro-1,5-naphthyridine-2-carbonitrile (606); 8-((2S,5R)-4-(2-chloro-4-(trifluoromethoxy)benzyl)-2,5-dimethylpiperazin-1-yl)-5-methyl-6-oxo-5,6-dihydro-1,5-naphthyridine-2-carbonitrile (607); 8-((2S,5R)-2,5-dimethyl-4-(2-methyl-4-(trifluoromethoxy)benzyl)piperazin-1-yl)-5-methyl-6-oxo-5,6-dihydro-1,5-naphthyridine-2-carbonitrile (608); 8-((2S,5R)-2,5-dimethyl-4-(4-(trifluoromethoxy)benzyl)piperazin-1-yl)-5-methyl-6-oxo-5,6-dihydro-1,5-naphthyridine-2-carbonitrile (609); 8-((2S,5R)-4-(3-fluoro-4-(trifluoromethoxy)benzyl)-2,5-dimethylpiperazin-1-yl)-5-methyl-6-oxo-5,6-dihydro-1,5-naphthyridine-2-carbonitrile (610); 8-((2S,5R)-4-(3-chloro-4-(trifluoromethoxy)benzyl)-2,5-dimethylpiperazin-1-yl)-5-methyl-6-oxo-5,6-dihydro-1,5-naphthyridine-2-carbonitrile (611); 8-((2S,5R)-2,5-dimethyl-4-((tetrahydro-2H-pyran-4-yl)methyl)piperazin-1-yl)-5-methyl-6-oxo-5,6-dihydro-1,5-naphthyridine-2-carbonitrile (623); 8-((2S,5R)-4-(2-fluoro-4-(trifluoromethoxy)benzyl)-2,5-dimethylpiperazin-1-yl)-5-methyl-6-oxo-5,6-dihydro-1,5-naphthyridine-2-carbonitrile (624); 8-((2S,5R)-2,5-dimethyl-4-(2,2,2-trifluoro-1-(2-fluoro-4-hydroxyphenyl)ethyl)piperazin-1-yl)-5-methyl-6-oxo-5,6-dihydro-1,5-naphthyridine-2-carbonitrile (625); 8-((2S,5R)-2,5-dimethyl-4-(2,2,2-trifluoro-1-(4-hydroxyphenyl)ethyl)piperazin-1-yl)-5-methyl-6-oxo-5,6-dihydro-1,5-naphthyridine-2-carbonitrile (626); 8-((2S,5R)-4-(1-(2,6-difluoro-4-hydroxyphenyl)-2,2,2-trifluoroethyl)-2,5-dimethylpiperazin-1-yl)-5-methyl-6-oxo-5,6-dihydro-1,5-naphthyridine-2-carbonitrile (627-628); 8-((2S,5R)-4-(3-bromo-4-(trifluoromethoxy)benzyl)-2,5-dimethylpiperazin-1-yl)-5-methyl-6-oxo-5,6-dihydro-1,5-naphthyridine-2-carbonitrile (629); tert-butyl 8-{[(2R,5S)-4-(6-cyano-1-methyl-2-oxo-1,2-dihydro-1,5-naphthyridin-4-yl)-2,5-dimethylpiperazin-1-yl]methyl}-3,4-dihydro-2H-1,4-benzoxazine-4-carboxylate (630); 8-[(2S,5R)-4-[(4-acetyl-3,4-dihydro-2H-1,4-benzoxazin-8-yl)methyl]-2,5- dimethylpiperazin-1-yl]-5-methyl-6-oxo-5,6-dihydro-1,5-naphthyridine-2-carbonitrile (631); 8-[(2S,5R)-2,5-dimethyl-4-(2-phenylethyl)piperazin-1-yl]-5-methyl-6-oxo-5,6-dihydro-1,5-naphthyridine-2-carbonitrile (632); 8-[(2S,5R)-2,5-dimethyl-4-[2-(4-methylphenyl)ethyl]piperazin-1-yl]-5-methyl-6-oxo-5,6-dihydro-1,5-naphthyridine-2-carbonitrile (633); 8-[(2S,5R)-4-[(3,4-dihydro-2H-1,4-benzoxazin-8-yl)methyl]-2,5-dimethylpiperazin-1-yl]-5-methyl-6-oxo-5,6-dihydro-1,5-naphthyridine-2-carbonitrile (634); 8-[(2S,5R)-2,5-dimethyl-4-[(4-methyl-3-oxo-3,4-dihydro-2H-1,4-benzoxazin-5-yl)methyl]piperazin-1-yl]-5-methyl-6-oxo-5,6-dihydro-1,5-naphthyridine-2-carbonitrile (635); 8-[(2S,5R)-2,5-dimethyl-4-{1-[6-(trifluoromethyl)pyridin-2-yl]ethyl}piperazin-1-yl]-5-methyl-6-oxo-5,6-dihydro-1,5-naphthyridine-2-carbonitrile (636-637); 8-[(2S,5R)-2,5-dimethyl-4-[1-(quinolin-5-yl)ethyl]piperazin-1-yl]-5-methyl-6-oxo-5,6-dihydro-1,5-naphthyridine-2-carbonitrile (638-639); 8-[(2S,5R)-4-[1-(5-fluoropyridin-2-yl)ethyl]-2,5-dimethylpiperazin-1-yl]-5-methyl-6-oxo-5,6-dihydro-1,5-naphthyridine-2-carbonitrile (640-641); 8-[(2S,5R)-2,5-dimethyl-4-{1-[5-(trifluoromethyl)pyridin-2-yl]ethyl}piperazin-1-yl]-5-methyl-6-oxo-5,6-dihydro-1,5-naphthyridine-2-carbonitrile (642-643); 8-[(2S,5R)-4-[1-(5-methoxypyridin-2-yl)ethyl]-2,5-dimethylpiperazin-1-yl]-5-methyl-6-oxo-5,6-dihydro-1,5-naphthyridine-2-carbonitrile (644-645); 8-[(2S,5R)-4-[1-(4-cyclopropyl-1,3-thiazol-2-yl)ethyl]-2,5-dimethylpiperazin-1-yl]-5-methyl-6-oxo-5,6-dihydro-1,5-naphthyridine-2-carbonitrile (646-647); 8-[(2S,5R)-2,5-dimethyl-4-[1-(5-methyl-1,2-oxazol-3-yl)ethyl]piperazin-1-yl]-5-methyl-6-oxo-5,6-dihydro-1,5-naphthyridine-2-carbonitrile (648-649); 8-[(2S,5R)-2,5-dimethyl-4-[1-(quinoxalin-6-yl)ethyl]piperazin-1-yl]-5-methyl-6-oxo-5,6-dihydro-1,5-naphthyridine-2-carbonitrile (650-651); 8-[(2S,5R)-4-{1-[4-(difluoromethoxy)phenyl]ethyl}-2,5-dimethylpiperazin-1-yl]-5-methyl-6-oxo-5,6-dihydro-1,5-naphthyridine-2-carbonitrile (652-653); 8-[(2S,5R)-4-[1-(2,2-difluoro-2H-1,3-benzodioxol-5-yl)ethyl]-2,5-dimethylpiperazin-1-yl]-5-methyl-6-oxo-5,6-dihydro-1,5-naphthyridine-2-carbonitrile (654-655); 8-[(2S,5R)-4-[(4-chlorophenyl)(2,2-difluoro-2H-1,3-benzodioxol-5-yl)methyl]-2,5-dimethylpiperazin-1-yl]-5-methyl-6-oxo-5,6-dihydro-1,5-naphthyridine-2-carbonitrile (656-657); 8-[(2S,5R)-4-[(4-fluorophenyl)(4-methoxyphenyl)methyl]-2,5-dimethylpiperazin-1-yl]-5-methyl-6-oxo-5,6-dihydro-1,5-naphthyridine-2-carbonitrile (658-659); 8-[(2S,5R)-4-[(4-fluorophenyl)(3-methoxyphenyl)methyl]-2,5-dimethylpiperazin-1-yl]-5-methyl-6-oxo-5,6-dihydro-1,5-naphthyridine-2-carbonitrile (660-661); 8-[(2S,5R)-4-[(4-fluorophenyl) [4-(morpholin-4-yl)phenyl]methyl]-2,5-dimethylpiperazin-1-yl]-5-methyl-6-oxo-5,6-dihydro-1,5-naphthyridine-2-carbonitrile (662-663); 8-[(2S,5R)-4-[(4-fluorophenyl)[2-(morpholin-4-yl)phenyl]methyl]-2,5-dimethylpiperazin-1-yl]-5-methyl-6-oxo-5,6-dihydro-1,5-naphthyridine-2-carbonitrile (664-665); 8-[(2S,5R)-4-{[4-(difluoromethyl) phenyl](4-fluorophenyl)methyl}-2,5-dimethylpiperazin-1-yl]-5-methyl-6-oxo-5,6-dihydro-1,5-naphthyridine-2-carbonitrile (666-667); 8-[(2S,5R)-4-[(2,2-difluoro-2H-1,3-benzodioxol-4-yl)(4-fluorophenyl)methyl]-2,5-dimethylpiperazin-1-yl]-5-methyl-6-oxo-5,6-dihydro-1,5-naphthyridine-2-carbonitrile (668-669); 8-[(2S,5R)-4-[(4-chlorophenyl) (phenyl)methyl]-2,5-dimethylpiperazin-1-yl]-5-methyl-6-oxo-5,6-dihydro-1,5-naphthyridine-2-carbonitrile (670-671); 8-[(2S,5R)-4-[(4-fluorophenyl)[3-(morpholin-4-yl)phenyl]methyl]-2,5-dimethylpiperazin-1-yl]-5-methyl-6-oxo-5,6-dihydro-1,5-naphthyridine-2-carbonitrile (672-673); 8-[(2S,5R)-4-[(4-fluorophenyl)(pyrazin-2-yl) methyl]-2,5-dimethylpiperazin-1-yl]-5-methyl-6-oxo-5,6-dihydro-1,5-naphthyridine-2-carbonitrile (674-675); 8-[(2S,5R)-4-[(4-fluorophenyl)(pyrimidin-2-yl)methyl]-2,5-dimethylpiperazin-1-yl]-5-methyl-6-oxo-5,6-dihydro-1,5-naphthyridine-2-carbonitrile (676-677); 8-[(2S,5R)-4-[(4-fluorophenyl)[6-(trifluoromethyl)pyridin-2-yl]methyl]-2,5-dimethylpiperazin-1-yl]-5-methyl-6-oxo-5,6-dihydro-1,5-naphthyridine-2-carbonitrile (678-679); 8-[(2S,5R)-4-[(4-fluorophenyl)[5-(trifluoromethyl)pyridin-2-yl]methyl]-2,5-dimethylpiperazin-1-yl]-5-methyl-6-oxo-5,6-dihydro-1,5-naphthyridine-2-carbonitrile (680-681); 8-[(2S,5R)-4-[(2,4-difluorophenyl)(pyridin-2-yl)methyl]-2,5-dimethylpiperazin-1-yl]-5-methyl-6-oxo-5,6-dihydro-1,5-naphthyridine-2-carbonitrile (682-683); 8-[(2S,5R)-4-[(2,4-difluorophenyl)(5-fluoropyridin-2-yl)methyl]-2,5-dimethylpiperazin-1-yl]-5-methyl-6-oxo-5,6-dihydro-1,5-naphthyridine-2-carbonitrile (684-685); 8-[(2S,5R)-4-[(3-fluorophenyl)(5-methoxypyridin-2-yl)methyl]-2,5-dimethylpiperazin-1-yl]-5-methyl-6-oxo-5,6-dihydro-1,5-naphthyridine-2-carbonitrile (686-687); 8-[(2S,5R)-4-[(4-fluorophenyl)(3-methanesulfonylphenyl)methyl]-2,5-dimethylpiperazin-1-yl]-5-methyl-6-oxo-5,6-dihydro-1,5-naphthyridine-2-carbonitrile (688-689); 8-[(2S,5R)-4-[(3-fluorophenyl)[5-(propan-2-yloxy)pyridin-2-yl]methyl]-2,5-dimethylpiperazin-1-yl]-5-methyl-6-oxo-5,6-dihydro-1,5-naphthyridine-2-carbonitrile (690-691); 8-[(2S,5R)-4-[(4-fluorophenyl)(2,4,6-trifluorophenyl)methyl]-2,5-dimethylpiperazin-1-yl]-5-methyl-6-oxo-5,6-dihydro-1,5-naphthyridine-2-carbonitrile (692-693); 8-[(2S,5R)-4-[(4-fluorophenyl)({pyrazolo[1,5-a]pyridin-7-yl})methyl]-2,5-dimethylpiperazin-1-yl]-5-methyl-6-oxo-5,6-dihydro-1,5-naphthyridine-2-carbonitrile (694-695); 8-[(2S,5R)-4-{[6-(difluoromethyl)pyridin-2-yl](4-fluorophenyl)methyl}-2,5-dimethylpiperazin-1-yl]-5-methyl-6-oxo-5,6-dihydro-1,5-naphthyridine-2-carbonitrile (696-697); 8-[(2S,5R)-4-[(4-fluorophenyl)({pyrazolo[1,5-a]pyridin-3-yl})methyl]-2,5-dimethylpiperazin-1-yl]-5-methyl-6-oxo-5,6-dihydro-1,5-naphthyridine-2-carbonitrile (698-699); 8-((2S,5R)-4-((4-cyclopropylthiazol-2-yl)(4-fluorophenyl)methyl)-2,5-dimethylpiperazin-1-yl)-5-methyl-6-oxo-5,6-dihydro-1,5-naphthyridine-2-carbonitrile (700-701); 8-[(2S,5R)-4-[(4-fluorophenyl)(1-methyl-1H-pyrazol-4-yl)methyl]-2,5-dimethylpiperazin-1-yl]-5-methyl-6-oxo-5,6-dihydro-1,5-naphthyridine-2-carbonitrile (702-703); 8-[(2S,5R)-4-[(4-fluorophenyl)(1-methyl-1H-imidazol-5-yl)methyl]-2,5-dimethylpiperazin-1-yl]-5-methyl-6-oxo-5,6-dihydro-1,5-naphthyridine-2-carbonitrile (704-705); 8-[(2S,5R)-4-[(4-fluorophenyl)(1,2-oxazol-3-yl)methyl]-2,5-dimethylpiperazin-1-yl]-5-methyl-6-oxo-5,6-dihydro-1,5-naphthyridine-2-carbonitrile (706-707); 8-[(2S,5R)-4-[(4-fluorophenyl)(1-methyl-1H-imidazol-4-yl)methyl]-2,5-dimethylpiperazin-1-yl]-5-methyl-6-oxo-5,6-dihydro-1,5-naphthyridine-2-carbonitrile (708); 8-[(2S,5R)-4-[(4-fluorophenyl)(1,3-oxazol-4-yl)methyl]-2,5-dimethylpiperazin-1-yl]-5-methyl-6-oxo-5,6-dihydro-1,5-naphthyridine-2-carbonitrile (709-710); 8-[(2S,5R)-4-[(4-fluorophenyl)(1,3-thiazol-2-yl)methyl]-2,5-dimethylpiperazin-1-yl]-5-methyl-6-oxo-5,6-dihydro-1,5-naphthyridine-2-carbonitrile (711-712); 8-[(2S,5R)-4-[(4-fluorophenyl)(1-methyl-1H-imidazol-2-yl)methyl]-2,5-dimethylpiperazin-1-yl]-5-methyl-6-oxo-5,6-dihydro-1,5-naphthyridine-2-carbonitrile (713-714); 8-[(2S,5R)-4-[(4-fluorophenyl)(1,2-thiazol-4-yl)methyl]-2,5-dimethylpiperazin-1-yl]-5-methyl-6-oxo-5,6-dihydro-1,5-naphthyridine-2-carbonitrile (715-716); 8-[(2S,5R)-4-[(4-fluorophenyl)(1,3-oxazol-2-yl)methyl]-2,5-dimethylpiperazin-1-yl]-5-methyl-6-oxo-5,6-dihydro-1,5-naphthyridine-2-carbonitrile (717-718); 8-[(2S,5R)-4-[(4- fluorophenyl)(1,2-thiazol-5-yl)methyl]-2,5-dimethylpiperazin-1-yl]-5-methyl-6-oxo-5,6-dihydro-1,5-naphthyridine-2-carbonitrile (719-720); 8-[(2S,5R)-4-[(4-fluorophenyl)(1,3-thiazol-4-yl)methyl]-2,5-dimethylpiperazin-1-yl]-5-methyl-6-oxo-5,6-dihydro-1,5-naphthyridine-2-carbonitrile (721-722); 8-[(2S,5R)-4-[(2-cyclopropyl-1,3-thiazol-4-yl)(4-fluorophenyl)methyl]-2,5-dimethylpiperazin-1-yl]-5-methyl-6-oxo-5,6-dihydro-1,5-naphthyridine-2-carbonitrile (723-724); 8-[(2S,5R)-4-[(1-cyclopropyl-1H-pyrazol-4-yl)(4-fluorophenyl)methyl]-2,5-dimethylpiperazin-1-yl]-5-methyl-6-oxo-5,6-dihydro-1,5-naphthyridine-2-carbonitrile (725-726); 8-[(2S,5R)-4-[(2-cyclopropyl-1,3-thiazol-5-yl)(4-fluorophenyl)methyl]-2,5-dimethylpiperazin-1-yl]-5-methyl-6-oxo-5,6-dihydro-1,5-naphthyridine-2-carbonitrile (727-728); 8-((2S,5R)-4-((5-cyclopropylisoxazol-3-yl)(4-fluorophenyl)methyl)-2,5-dimethylpiperazin-1-yl)-5-methyl-6-oxo-5,6-dihydro-1,5-naphthyridine-2-carbonitrile (729-730); 8-((2S,5R)-4-((5-(tert-butyl)isoxazol-3-yl)(4-fluorophenyl)methyl)-2,5-dimethylpiperazin-1-yl)-5-methyl-6-oxo-5,6-dihydro-1,5-naphthyridine-2-carbonitrile (731-732); 8-((2S,5R)-4-((4-fluorophenyl)(5-methylisoxazol-3-yl)methyl)-2,5-dimethylpiperazin-1-yl)-5-methyl-6-oxo-5,6-dihydro-1,5-naphthyridine-2-carbonitrile (733-734); 8-((2S,5R)-4-((3-cyclopropyl-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile (735-736); 8-[(2S,5R)-4-[(3-tert-butyl-1,2,4-oxadiazol-5-yl)(4-fluorophenyl)methyl]-2,5-dimethylpiperazin-1-yl]-5-methyl-6-oxo-5,6-dihydro-1,5-naphthyridine-2-carbonitrile (737-738); 8-[(2S,5R)-4-[(4-fluorophenyl)[3-(oxan-4-yl)-1,2,4-oxadiazol-5-yl]methyl]-2,5-dimethylpiperazin-1-yl]-5-methyl-6-oxo-5,6-dihydro-1,5-naphthyridine-2-carbonitrile (739-740); 8-[(2S,5R)-4-[(4-fluorophenyl)[3-(4-fluorophenyl)-1,2,4-oxadiazol-5-yl]methyl]-2,5-dimethylpiperazin-1-yl]-5-methyl-6-oxo-5,6-dihydro-1,5-naphthyridine-2-carbonitrile (741-742); 8-[(2S,5R)-4-{[3-(difluoromethyl)-1,2,4-oxadiazol-5-yl](4-fluorophenyl)methyl}-2,5-dimethylpiperazin-1-yl]-5-methyl-6-oxo-5,6-dihydro-1,5-naphthyridine-2-carbonitrile (743-744); 8-[(2S,5R)-4-[(4-fluorophenyl)(3-methyl-1,2,4-oxadiazol-5-yl)methyl]-2,5-dimethylpiperazin-1-yl]-5-methyl-6-oxo-5,6-dihydro-1,5-naphthyridine-2-carbonitrile (745-746); 8-[(2S,5R)-4-[(4-fluorophenyl)[3-(propan-2-yl)-1,2,4-oxadiazol-5-yl]methyl]-2,5-dimethylpiperazin-1-yl]-5-methyl-6-oxo-5,6-dihydro-1,5-naphthyridine-2-carbonitrile (747-748); 8-[(2S,5R)-4-[(4-fluorophenyl)[3-(morpholin-4-yl)-1,2,4-oxadiazol-5-yl]methyl]-2,5-dimethylpiperazin-1-yl]-5-methyl-6-oxo-5,6-dihydro-1,5-naphthyridine-2-carbonitrile (749-750); 8-[(2S,5R)-4-[(4-fluorophenyl)[3-(1-methylpiperidin-4-yl)-1,2,4-oxadiazol-5-yl]methyl]-2,5-dimethylpiperazin-1-yl]-5-methyl-6-oxo-5,6-dihydro-1,5-naphthyridine-2-carbonitrile (751-752); 8-[(2S,5R)-4-[(3-ethyl-1,2,4-oxadiazol-5-yl)(4-fluorophenyl) methyl]-2,5-dimethylpiperazin-1-yl]-5-methyl-6-oxo-5,6-dihydro-1,5-naphthyridine-2-carbonitrile (753-754); 8-[(2S,5R)-4-[(4-fluorophenyl)(1,2,4-oxadiazol-5-yl)methyl]-2,5-dimethylpiperazin-1-yl]-5-methyl-6-oxo-5,6-dihydro-1,5-naphthyridine-2-carbonitrile (755); tert-butyl 3-(5-{[(2R,5S)-4-(6-cyano-1-methyl-2-oxo-1,2-dihydro-1,5-naphthyridin-4-yl)-2,5-dimethylpiperazin-1-yl](4-fluorophenyl)methyl}-1,2,4-oxadiazol-3-yl)azetidine-1-carboxylate (756-757); 8-[(2S,5R)-4-[(3-cyclopropyl-1,2,4-oxadiazol-5-yl)[4-(trifluoromethoxy)phenyl]methyl]-2,5-dimethylpiperazin-1-yl]-5-methyl-6-oxo-5,6-dihydro-1,5-naphthyridine-2-carbonitrile (758-759); 8-[(2S,5R)-4-[(4-bromophenyl)(3-cyclopropyl-1,2,4-oxadiazol-5-yl)methyl]-2,5-dimethylpiperazin-1-yl]-5-methyl-6-oxo-5,6-dihydro-1,5-naphthyridine-2-carbonitrile (760-761); 8-((2S,5R)-4-((5-cyclopropyl-1,3,4-oxadiazol-2-yl)(4-fluorophenyl)methyl)-2,5-dimethylpiperazin-1-yl)-5-methyl-6-oxo-5,6-dihydro-1,5-naphthyridine-2-carbonitrile (762-763); 8-((2S,5R)-4-((5-(tert-butyl)-1,2,4-oxadiazol-3-yl)(4-fluorophenyl)methyl)-2,5-dimethylpiperazin-1-yl)-5-methyl-6-oxo-5,6-dihydro-1,5-naphthyridine-2-carbonitrile (764-765); 8-((2S,5R)-4-((5-cyclopropyl-4H-1,2,4-triazol-3-yl)(4-fluorophenyl)methyl)-2,5-dimethylpiperazin-1-yl)-5-methyl-6-oxo-5,6-dihydro-1,5-naphthyridine-2-carbonitrile (766-767); 8-((2S,5R)-4-((3-cyclopropyl-1-methyl-1H-1,2,4-triazol-5-yl)(4-fluorophenyl)methyl)-2,5-dimethylpiperazin-1-yl)-5-methyl-6-oxo-5,6-dihydro-1,5-naphthyridine-2-carbonitrile (768-769); 8-((2S,5R)-4-((1-(tert-butyl)-1H-tetrazol-5-yl)(4-fluorophenyl)methyl)-2,5-dimethylpiperazin-1-yl)-5-methyl-6-oxo-5,6-dihydro-1,5-naphthyridine-2-carbonitrile (770-771); 8-((2S,5R)-4-((4-fluorophenyl)(5-isopropyl-1,3,4-thiadiazol-2-yl)methyl)-2,5-dimethylpiperazin-1-yl)-5-methyl-6-oxo-5,6-dihydro-1,5-naphthyridine-2-carbonitrile (772-773); 8-((2S,5R)-4-((5-cyclopropyl-1,3,4-thiadiazol-2-yl)(4-fluorophenyl)methyl)-2,5-dimethylpiperazin-1-yl)-5-methyl-6-oxo-5,6-dihydro-1,5-naphthyridine-2-carbonitrile (774-775); 8-((2S,5R)-4-((4-cyclopropyloxazol-2-yl)(4-fluorophenyl) methyl)-2,5-dimethylpiperazin-1-yl)-5-methyl-6-oxo-5,6-dihydro-1,5-naphthyridine-2-carbonitrile (776-777); 8-[(2S,5R)-4-[(4-tert-butyl-1,3-oxazol-2-yl)(4-fluorophenyl) methyl]-2,5-dimethylpiperazin-1-yl]-5-methyl-6-oxo-5,6-dihydro-1,5-naphthyridine-2-carbonitrile (778-779); 8-((2S,5R)-4-(1-(2,6-difluorophenyl)ethyl)-2,5-dimethylpiperazin-1-yl)-5-methyl-6-oxo-5,6-dihydro-1,5-naphthyridine-2,7-dicarbonitrile (780-781); 8-[(2S,5R)-4-[1-(4-fluorophenyl)ethyl]-2,5-dimethylpiperazin-1-yl]-5-methyl-6-oxo-5,6-dihydro-1,5-naphthyridine-2,7-dicarbonitrile (782-783); 8-[(2S,5R)-2,5-dimethyl-4-[1-(4-methylphenyl)ethyl]piperazin-1-yl]-5-methyl-6-oxo-5,6-dihydro-1,5-naphthyridine-2,7-dicarbonitrile (784-785); 4-{1-[(2R,5S)-4-(3,6-dicyano-1-methyl-2-oxo-1,2-dihydro-1,5-naphthyridin-4-yl)-2,5-dimethylpiperazin-1-yl]ethyl}benzoic acid (786-787); 8-[(2S,5R)-2,5-dimethyl-4-{1-[4-(trifluoromethyl)phenyl]ethyl}piperazin-1-yl]-5-methyl-6-oxo-5,6-dihydro-1,5-naphthyridine-2,7-dicarbonitrile (788); 8-[(2S,5R)-4-[1-(4-bromophenyl)ethyl]-2,5-dimethylpiperazin-1-yl]-5-methyl-6-oxo-5,6-dihydro-1,5-naphthyridine-2,7-dicarbonitrile (789-790); 8-[(2S,5R)-4-[1-(4-chlorophenyl)ethyl]-2,5-dimethylpiperazin-1-yl]-5-methyl-6-oxo-5,6-dihydro-1,5-naphthyridine-2,7-dicarbonitrile (791-792); methyl 4-{1-[(2R,5S)-4-(3,6-dicyano-1-methyl-2-oxo-1,2-dihydro-1,5-naphthyridin-4-yl)-2,5-dimethylpiperazin-1-yl]ethyl}benzoate (793-794); methyl 3-{1-[(2R,5S)-4-(3,6-dicyano-1-methyl-2-oxo-1,2-dihydro-1,5-naphthyridin-4-yl)-2,5-dimethylpiperazin-1-yl]ethyl}benzoate (795-796); 8-[(2S,5R)-4-[1-(2-fluorophenyl)ethyl]-2,5-dimethylpiperazin-1-yl]-5-methyl-6-oxo-5,6-dihydro-1,5-naphthyridine-2,7-dicarbonitrile (797-798); 8-[(2S,5R)-4-[1-(5-methoxypyridin-2-yl)ethyl]-2,5-dimethylpiperazin-1-yl]-5-methyl-6-oxo-5,6-dihydro-1,5-naphthyridine-2,7-dicarbonitrile (799-800); 8-[(2S,5R)-2,5-dimethyl-4-{1-[4-(trifluoromethoxy)phenyl]ethyl}piperazin-1-yl]-5-methyl-6-oxo-5,6-dihydro-1,5-naphthyridine-2,7-dicarbonitrile (801-802); 8-[(2S,5R)-2,5-dimethyl-4-[1-(5-methyl-1,2-oxazol-3-yl)ethyl]piperazin-1-yl]-5-methyl-6-oxo-5,6-dihydro-1,5-naphthyridine-2,7-dicarbonitrile (803-804); 8-[(2S,5R)-4-[bis(4-chlorophenyl)methyl]-2,5-dimethylpiperazin-1-yl]-5-methyl-6-oxo-5,6-dihydro-1,5-naphthyridine-2,7-dicarbonitrile (805); 8-[(2S,5R)-4-[bis(4-methylphenyl)methyl]-2,5-dimethylpiperazin-1-yl]-5-methyl-6-oxo-5,6-dihydro-1,5-naphthyridine-2,7- dicarbonitrile (806); 8-[(2S,5R)-4-[(4-fluorophenyl)(phenyl)methyl]-2,5-dimethylpiperazin-1-yl]-5-methyl-6-oxo-5,6-dihydro-1,5-naphthyridine-2,7-dicarbonitrile (807-808); 8-[(2S,5R)-4-[(2-ethylphenyl)(4-fluorophenyl)methyl]-2,5-dimethylpiperazin-1-yl]-5-methyl-6-oxo-5,6-dihydro-1,5-naphthyridine-2,7-dicarbonitrile (809-810); 8-[(2S,5R)-4-[(4-ethylphenyl)(4-fluorophenyl)methyl]-2,5-dimethylpiperazin-1-yl]-5-methyl-6-oxo-5,6-dihydro-1,5-naphthyridine-2,7-dicarbonitrile (811-812); 8-[(2S,5R)-4-[(3,5-difluorophenyl)(phenyl)methyl]-2,5-dimethylpiperazin-1-yl]-5-methyl-6-oxo-5,6-dihydro-1,5-naphthyridine-2,7-dicarbonitrile (813-814); 8-[(2S,5R)-4-[(4-fluorophenyl) (6-methylpyridin-2-yl)methyl]-2,5-dimethylpiperazin-1-yl]-5-methyl-6-oxo-5,6-dihydro-1,5-naphthyridine-2,7-dicarbonitrile (815-816); 8-[(2S,5R)-4-[(4-fluorophenyl)(4-methylphenyl)methyl]-2,5-dimethylpiperazin-1-yl]-5-methyl-6-oxo-5,6-dihydro-1,5-naphthyridine-2,7-dicarbonitrile (817-818); 8-[(2S,5R)-4-[(4-chlorophenyl)(3-fluoropyridin-2-yl)methyl]-2,5-dimethylpiperazin-1-yl]-5-methyl-6-oxo-5,6-dihydro-1,5-naphthyridine-2,7-dicarbonitrile (819 and 822); 8-[(2S,5R)-4-[(4-fluorophenyl)(3-fluoropyridin-2-yl)methyl]-2,5-dimethylpiperazin-1-yl]-5-methyl-6-oxo-5,6-dihydro-1,5-naphthyridine-2,7-dicarbonitrile (820-821); 8-[(2S,5R)-4-[(4-cyanophenyl)(4-fluorophenyl)methyl]-2,5-dimethylpiperazin-1-yl]-5-methyl-6-oxo-5,6-dihydro-1,5-naphthyridine-2,7-dicarbonitrile (823-824); 8-[(2S,5R)-4-[(4-chlorophenyl)(4-methylphenyl)methyl]-2,5-dimethylpiperazin-1-yl]-5-methyl-6-oxo-5,6-dihydro-1,5-naphthyridine-2,7-dicarbonitrile (825-826); 8-[(2S,5R)-4-[(4-fluorophenyl)(5-fluoropyridin-2-yl)methyl]-2,5-dimethylpiperazin-1-yl]-5-methyl-6-oxo-5,6-dihydro-1,5-naphthyridine-2,7-dicarbonitrile (827-828); 8-[(2S,5R)-4-[(4-chlorophenyl)(5-fluoropyridin-2-yl)methyl]-2,5-dimethylpiperazin-1-yl]-5-methyl-6-oxo-5,6-dihydro-1,5-naphthyridine-2,7-dicarbonitrile (829-830); 8-[(2S,5R)-4-[(2-chloro-4-fluorophenyl)(5-methylpyridin-2-yl)methyl]-2,5-dimethylpiperazin-1-yl]-5-methyl-6-oxo-5,6-dihydro-1,5-naphthyridine-2,7-dicarbonitrile (831-832); 8-[(2S,5R)-4-[(5-fluoropyridin-2-yl)(4-methylphenyl)methyl]-2,5-dimethylpiperazin-1-yl]-5-methyl-6-oxo-5,6-dihydro-1,5-naphthyridine-2,7-dicarbonitrile (833); 8-[(2S,5R)-4-[(4-chlorophenyl)(phenyl)methyl]-2,5-dimethylpiperazin-1-yl]-5-methyl-6-oxo-5,6-dihydro-1,5-naphthyridine-2,7-dicarbonitrile (834-835); 8-[(2S,5R)-4-[(4-fluorophenyl)[5-(trifluoromethyl)pyridin-2-yl]methyl]-2,5-dimethylpiperazin-1-yl]-5-methyl-6-oxo-5,6-dihydro-1,5-naphthyridine-2,7-dicarbonitrile (836-837); 8-[(2S,5R)-4-[(4-fluorophenyl)(4-methoxyphenyl)methyl]-2,5-dimethylpiperazin-1-yl]-5-methyl-6-oxo-5,6-dihydro-1,5-naphthyridine-2,7-dicarbonitrile (838-839); 8-[(2S,5R)-4-[(3-fluorophenyl)[5-(trifluoromethyl)pyridin-2-yl]methyl]-2,5-dimethylpiperazin-1-yl]-5-methyl-6-oxo-5,6-dihydro-1,5-naphthyridine-2,7-dicarbonitrile (840-841); 8-[(2S,5R)-4-[(4-fluorophenyl)(pyridin-2-yl)methyl]-2,5-dimethylpiperazin-1-yl]-5-methyl-6-oxo-5,6-dihydro-1,5-naphthyridine-2,7-dicarbonitrile (842-843); 8-[(2S,5R)-4-[(4-fluorophenyl)[6-(trifluoromethyl)pyridin-2-yl]methyl]-2,5-dimethylpiperazin-1-yl]-5-methyl-6-oxo-5,6-dihydro-1,5-naphthyridine-2,7-dicarbonitrile (844-845); 8-[(2S,5R)-4-[(4-fluorophenyl)(1-methyl-1H-pyrazol-4-yl)methyl]-2,5-dimethylpiperazin-1-yl]-5-methyl-6-oxo-5,6-dihydro-1,5-naphthyridine-2,7-dicarbonitrile (846-847); 8-[(2S,5R)-4-[(4-fluorophenyl)(1-methyl-1H-imidazol-5-yl)methyl]-2,5-dimethylpiperazin-1-yl]-5-methyl-6-oxo-5,6-dihydro-1,5-naphthyridine-2,7-dicarbonitrile (848-849); 8-[(2S,5R)-4-[(4-fluorophenyl)(1,2-oxazol-3-yl)methyl]-2,5-dimethylpiperazin-1-yl]-5-methyl-6-oxo-5,6-dihydro-1,5-naphthyridine-2,7-dicarbonitrile (850-851); 8-[(2S,5R)-4-[(4-fluorophenyl)(1-methyl-1H-imidazol-4-yl)methyl]-2,5-dimethylpiperazin-1-yl]-5-methyl-6-oxo-5,6-dihydro-1,5-naphthyridine-2,7-dicarbonitrile (852-853); 8-[(2S,5R)-4-[(4-fluorophenyl)(1,2-thiazol-5-yl)methyl]-2,5-dimethylpiperazin-1-yl]-5-methyl-6-oxo-5,6-dihydro-1,5-naphthyridine-2,7-dicarbonitrile (854-855); 8-[(2S,5R)-4-[(4-fluorophenyl)(1,3-thiazol-4-yl)methyl]-2,5-dimethylpiperazin-1-yl]-5-methyl-6-oxo-5,6-dihydro-1,5-naphthyridine-2,7-dicarbonitrile (856-857); 8-[(2S,5R)-4-[(2-cyclopropyl-1,3-thiazol-4-yl)(4-fluorophenyl)methyl]-2,5-dimethylpiperazin-1-yl]-5-methyl-6-oxo-5,6-dihydro-1,5-naphthyridine-2,7-dicarbonitrile (858-859); 8-[(2S,5R)-4-[(3-cyclopropyl-1,2,4-oxadiazol-5-yl)(4-fluorophenyl)methyl]-2,5-dimethylpiperazin-1-yl]-5-methyl-6-oxo-5,6-dihydro-1,5-naphthyridine-2,7-dicarbonitrile (860-861); 8-[(2S,5R)-4-[(3-tert-butyl-1,2,4-oxadiazol-5-yl)(4-fluorophenyl)methyl]-2,5-dimethylpiperazin-1-yl]-5-methyl-6-oxo-5,6-dihydro-1,5-naphthyridine-2,7-dicarbonitrile (862-863); 8-[(2S,5R)-4-[(4-fluorophenyl)(5-methyl-1,2-oxazol-3-yl)methyl]-2,5-dimethylpiperazin-1-yl]-5-methyl-6-oxo-5,6-dihydro-1,5-naphthyridine-2,7-dicarbonitrile (864-865); 8-[(2S,5R)-4-[(5-tert-butyl-1,2-oxazol-3-yl) (4-fluorophenyl)methyl]-2,5-dimethylpiperazin-1-yl]-5-methyl-6-oxo-5,6-dihydro-1,5-naphthyridine-2,7-dicarbonitrile (866-867); 8-[(2S,5R)-4-[(5-cyclopropyl-1,2-oxazol-3-yl)(4-fluorophenyl)methyl]-2,5-dimethylpiperazin-1-yl]-5-methyl-6-oxo-5,6-dihydro-1,5-naphthyridine-2,7-dicarbonitrile (868-869); 8-[(3R)-4-[bis(4-methylphenyl)methyl]-3-methylpiperazin-1-yl]-5-methyl-6-oxo-5,6-dihydro-1,5-naphthyridine-2,7-dicarbonitrile (870); 8-[(3R)-4-[(4-cyanophenyl)(4-fluorophenyl)methyl]-3-methylpiperazin-1-yl]-5-methyl-6-oxo-5,6-dihydro-1,5-naphthyridine-2,7-dicarbonitrile (871); 8-[(3R)-4-[(4-chlorophenyl)(4-cyanophenyl)methyl]-3-methylpiperazin-1-yl]-5-methyl-6-oxo-5,6-dihydro-1,5-naphthyridine-2,7-dicarbonitrile (872-873); 8-[(3R)-4-[(3,5-difluorophenyl) (phenyl)methyl]-3-methylpiperazin-1-yl]-5-methyl-6-oxo-5,6-dihydro-1,5-naphthyridine-2,7-dicarbonitrile (874-875); 8-[(3R)-4-[(2-ethylphenyl)(4-fluorophenyl)methyl]-3-methylpiperazin-1-yl]-5-methyl-6-oxo-5,6-dihydro-1,5-naphthyridine-2,7-dicarbonitrile (876-877); 8-[(3R)-4-[(4-fluorophenyl)(phenyl)methyl]-3-methylpiperazin-1-yl]-5-methyl-6-oxo-5,6-dihydro-1,5-naphthyridine-2,7-dicarbonitrile (878-879); 8-[(3R)-4-[(3-fluorophenyl)(4-fluorophenyl)methyl]-3-methylpiperazin-1-yl]-5-methyl-6-oxo-5,6-dihydro-1,5-naphthyridine-2,7-dicarbonitrile (880-881); 8-[(3R)-4-[(2-fluorophenyl)(4-fluorophenyl)methyl]-3-methylpiperazin-1-yl]-5-methyl-6-oxo-5,6-dihydro-1,5-naphthyridine-2,7-dicarbonitrile (882-883); 8-[(3R)-4-[(4-ethylphenyl)(4-fluorophenyl) methyl]-3-methylpiperazin-1-yl]-5-methyl-6-oxo-5,6-dihydro-1,5-naphthyridine-2,7-dicarbonitrile (884-885); 8-[(3R)-4-[(4-chlorophenyl)(phenyl)methyl]-3-methylpiperazin-1-yl]-5-methyl-6-oxo-5,6-dihydro-1,5-naphthyridine-2,7-dicarbonitrile (886-887); 8-[(3R)-4-[(4-fluorophenyl)(4-methylphenyl)methyl]-3-methylpiperazin-1-yl]-5-methyl-6-oxo-5,6-dihydro-1,5-naphthyridine-2,7-dicarbonitrile (888-889); 8-[(3R)-4-[(3-fluoropyridin-2-yl)(4-methylphenyl)methyl]-3-methylpiperazin-1-yl]-5-methyl-6-oxo-5,6-dihydro-1,5-naphthyridine-2,7-dicarbonitrile (890 and 892); 8-[(3R)-4-[(4-fluorophenyl)(3-fluoropyridin-2-yl)methyl]-3-methylpiperazin-1-yl]-5-methyl-6-oxo-5,6-dihydro-1,5-naphthyridine-2,7-dicarbonitrile (891 and 893); 8-[(3R)-4-[(4-fluorophenyl) (2-methoxypyridin-3-yl)methyl]-3-methylpiperazin-1-yl]-5-methyl-6-oxo-5,6-dihydro-1,5-naphthyridine-2,7-dicarbonitrile (894-895); 8-[(3R)-4-[(4- fluorophenyl)[5-(trifluoromethyl)pyridin-2-yl]methyl]-3-methylpiperazin-1-yl]-5-methyl-6-oxo-5,6-dihydro-1,5-naphthyridine-2,7-dicarbonitrile (896-897); 8-[(3R)-4-[(5-fluoropyridin-2-yl)(4-methylphenyl)methyl]-3-methylpiperazin-1-yl]-5-methyl-6-oxo-5,6-dihydro-1,5-naphthyridine-2,7-dicarbonitrile (898-899); 8-[(3R)-4-[(4-chlorophenyl)(5-fluoropyridin-2-yl)methyl]-3-methylpiperazin-1-yl]-5-methyl-6-oxo-5,6-dihydro-1,5-naphthyridine-2,7-dicarbonitrile (900-901); 8-[(3R)-4-[(4-fluorophenyl)(5-fluoropyridin-2-yl)methyl]-3-methylpiperazin-1-yl]-5-methyl-6-oxo-5,6-dihydro-1,5-naphthyridine-2,7-dicarbonitrile (902-903); 8-[(3R)-4-[(4-fluorophenyl)(5-methylpyridin-2-yl)methyl]-3-methylpiperazin-1-yl]-5-methyl-6-oxo-5,6-dihydro-1,5-naphthyridine-2,7-dicarbonitrile (904); 8-[(3R)-4-[(4-fluorophenyl)(6-methylpyridin-2-yl)methyl]-3-methylpiperazin-1-yl]-5-methyl-6-oxo-5,6-dihydro-1,5-naphthyridine-2,7-dicarbonitrile (905-906); 8-[(3R)-4-[(4-chlorophenyl)(4-methylphenyl)methyl]-3-methylpiperazin-1-yl]-5-methyl-6-oxo-5,6-dihydro-1,5-naphthyridine-2,7-dicarbonitrile (907); 8-[(3R)-4-[(5-cyanopyridin-2-yl)(4-fluorophenyl)methyl]-3-methylpiperazin-1-yl]-5-methyl-6-oxo-5,6-dihydro-1,5-naphthyridine-2,7-dicarbonitrile (908); 8-[(3R)-4-[(4-chlorophenyl)(3-fluoropyridin-2-yl)methyl]-3-methylpiperazin-1-yl]-5-methyl-6-oxo-5,6-dihydro-1,5-naphthyridine-2,7-dicarbonitrile (909); 8-[(3R)-4-[(4-fluorophenyl)[4-(trifluoromethyl)phenyl]methyl]-3-methylpiperazin-1-yl]-5-methyl-6-oxo-5,6-dihydro-1,5-naphthyridine-2,7-dicarbonitrile (910); 8-[(3R)-4-[(3-fluorophenyl)(5-fluoropyridin-2-yl)methyl]-3-methylpiperazin-1-yl]-5-methyl-6-oxo-5,6-dihydro-1,5-naphthyridine-2,7-dicarbonitrile (911); 8-[(3R)-4-[(3-fluorophenyl)(5-methylpyridin-2-yl)methyl]-3-methylpiperazin-1-yl]-5-methyl-6-oxo-5,6-dihydro-1,5-naphthyridine-2,7-dicarbonitrile (912); 8-[(3R)-4-[(4-chlorophenyl)(3-fluoropyridin-2-yl)methyl]-3-methylpiperazin-1-yl]-5-methyl-6-oxo-5,6-dihydro-1,5-naphthyridine-2,7-dicarbonitrile (913); 8-[(3R)-4-[(4-fluorophenyl)[4-(trifluoromethyl) phenyl]methyl]-3-methylpiperazin-1-yl]-5-methyl-6-oxo-5,6-dihydro-1,5-naphthyridine-2,7-dicarbonitrile (914); 8-[(3R)-4-[(4-fluorophenyl)(5-methylpyridin-2-yl)methyl]-3-methylpiperazin-1-yl]-5-methyl-6-oxo-5,6-dihydro-1,5-naphthyridine-2,7-dicarbonitrile (915); 8-[(3R)-4-[(4-fluorophenyl)(3-methylphenyl)methyl]-3-methylpiperazin-1-yl]-5-methyl-6-oxo-5,6-dihydro-1,5-naphthyridine-2,7-dicarbonitrile (916-917); 8-[(3R)-4-[(4-fluorophenyl)(pyridin-2-yl)methyl]-3-methylpiperazin-1-yl]-5-methyl-6-oxo-5,6-dihydro-1,5-naphthyridine-2,7-dicarbonitrile (918-919); 8-[(3R)-4-[(4-cyanophenyl)(4-fluorophenyl)methyl]-3-methylpiperazin-1-yl]-5-methyl-6-oxo-5,6-dihydro-1,5-naphthyridine-2,7-dicarbonitrile (920); 8-[(3R)-4-[(4-fluorophenyl)[6-(trifluoromethyl) pyridin-2-yl]methyl]-3-methylpiperazin-1-yl]-5-methyl-6-oxo-5,6-dihydro-1,5-naphthyridine-2,7-dicarbonitrile (921-922); 8-[(3R)-4-[(3-fluorophenyl)(5-methylpyridin-2-yl)methyl]-3-methylpiperazin-1-yl]-5-methyl-6-oxo-5,6-dihydro-1,5-naphthyridine-2,7-dicarbonitrile (923); 8-[(3R)-4-[(5-cyanopyridin-2-yl)(4-fluorophenyl)methyl]-3-methylpiperazin-1-yl]-5-methyl-6-oxo-5,6-dihydro-1,5-naphthyridine-2,7-dicarbonitrile (924); 8-[(3R)-4-[(3-fluorophenyl)(5-fluoropyridin-2-yl)methyl]-3-methylpiperazin-1-yl]-5-methyl-6-oxo-5,6-dihydro-1,5-naphthyridine-2,7-dicarbonitrile (925); 8-[(3R)-4-[(3-chlorophenyl)(5-fluoropyridin-2-yl)methyl]-3-methylpiperazin-1-yl]-5-methyl-6-oxo-5,6-dihydro-1,5-naphthyridine-2,7-dicarbonitrile (926-927); 8-[(3R)-4-[(3-chlorophenyl)(5-methylpyridin-2-yl)methyl]-3-methylpiperazin-1-yl]-5-methyl-6-oxo-5,6-dihydro-1,5-naphthyridine-2,7-dicarbonitrile (928-929); 8-[(3R)-4-[(4-chlorophenyl)(5-chloropyridin-2-yl)methyl]-3-methylpiperazin-1-yl]-5-methyl-6-oxo-5,6-dihydro-1,5-naphthyridine-2,7-dicarbonitrile (930-931); 8-[(3R)-4-[(5-chloropyridin-2-yl)(4-fluorophenyl)methyl]-3-methylpiperazin-1-yl]-5-methyl-6-oxo-5,6-dihydro-1,5-naphthyridine-2,7-dicarbonitrile (932-933); 8-[(3R)-4-[(2,2-dimethyl-2,3-dihydro-1-benzofuran-7-yl)(4-fluorophenyl) methyl]-3-methylpiperazin-1-yl]-5-methyl-6-oxo-5,6-dihydro-1,5-naphthyridine-2,7-dicarbonitrile (934-935); 8-[(3R)-4-[(5-chloropyridin-2-yl)(4-methylphenyl)methyl]-3-methylpiperazin-1-yl]-5-methyl-6-oxo-5,6-dihydro-1,5-naphthyridine-2,7-dicarbonitrile (936-937); 8-[(3R)-4-[(2-chloro-4-fluorophenyl)(5-methylpyridin-2-yl)methyl]-3-methylpiperazin-1-yl]-5-methyl-6-oxo-5,6-dihydro-1,5-naphthyridine-2,7-dicarbonitrile (938); 8-[(3R)-4-[(2,2-difluoro-2H-1,3-benzodioxol-4-yl)(4-fluorophenyl) methyl]-3-methylpiperazin-1-yl]-5-methyl-6-oxo-5,6-dihydro-1,5-naphthyridine-2,7-dicarbonitrile (939-940); 8-[(3R)-4-[(4-chlorophenyl)(2,2-difluoro-2H-1,3-benzodioxol-5-yl)methyl]-3-methylpiperazin-1-yl]-5-methyl-6-oxo-5,6-dihydro-1,5-naphthyridine-2,7-dicarbonitrile (941-942); 8-[(3R)-4-[(4-fluorophenyl)(pyrazin-2-yl)methyl]-3-methylpiperazin-1-yl]-5-methyl-6-oxo-5,6-dihydro-1,5-naphthyridine-2,7-dicarbonitrile (943); 8-[(3R)-4-[(4-chlorophenyl)(4-methylphenyl)methyl]-3-methylpiperazin-1-yl]-5-methyl-6-oxo-5,6-dihydro-1,5-naphthyridine-2,7-dicarbonitrile (944-945); 8-[(3R)-4-[(2,4-difluorophenyl)(4-fluorophenyl)methyl]-3-methylpiperazin-1-yl]-5-methyl-6-oxo-5,6-dihydro-1,5-naphthyridine-2,7-dicarbonitrile (946-947); 8-[(3R)-4-[(3-fluorophenyl)[5-(trifluoromethyl) pyridin-2-yl]methyl]-3-methylpiperazin-1-yl]-5-methyl-6-oxo-5,6-dihydro-1,5-naphthyridine-2,7-dicarbonitrile (948-949); 8-[(3R)-4-[1-(2,6-difluorophenyl)ethyl]-3-methylpiperazin-1-yl]-5-methyl-6-oxo-5,6-dihydro-1,5-naphthyridine-2,7-dicarbonitrile (950-951); 5-methyl-8-[(3R)-3-methyl-4-[1-(4-methylphenyl)ethyl]piperazin-1-yl]-6-oxo-5,6-dihydro-1,5-naphthyridine-2,7-dicarbonitrile (952-953); 8-[(3R)-4-[1-(4-cyanophenyl)ethyl]-3-methylpiperazin-1-yl]-5-methyl-6-oxo-5,6-dihydro-1,5-naphthyridine-2,7-dicarbonitrile (954-955); 8-[(3R)-4-[1-(3,4-difluorophenyl)ethyl]-3-methylpiperazin-1-yl]-5-methyl-6-oxo-5,6-dihydro-1,5-naphthyridine-2,7-dicarbonitrile (956); 8-[(3R)-4-[1-(4-fluorophenyl)ethyl]-3-methylpiperazin-1-yl]-5-methyl-6-oxo-5,6-dihydro-1,5-naphthyridine-2,7-dicarbonitrile (957 and 959); 5-methyl-8-[(3R)-3-methyl-4-{1-[4-(trifluoromethoxy)phenyl]ethyl}piperazin-1-yl]-6-oxo-5,6-dihydro-1,5-naphthyridine-2,7-dicarbonitrile (958 and 962); 5-methyl-8-[(3R)-3-methyl-4-{1-[4-(trifluoromethyl)phenyl]ethyl}piperazin-1-yl]-6-oxo-5,6-dihydro-1,5-naphthyridine-2,7-dicarbonitrile (960-961); 5-methyl-8-[(3R)-3-methyl-4-[1-(pyridin-2-yl)ethyl]piperazin-1-yl]-6-oxo-5,6-dihydro-1,5-naphthyridine-2,7-dicarbonitrile (963 and 965); 5-methyl-8-[(3R)-3-methyl-4-[1-(6-methylpyridin-2-yl)ethyl]piperazin-1-yl]-6-oxo-5,6-dihydro-1,5-naphthyridine-2,7-dicarbonitrile (964); 5-methyl-8-[(3R)-3-methyl-4-{1-[2-(trifluoromethyl)phenyl]ethyl}piperazin-1-yl]-6-oxo-5,6-dihydro-1,5-naphthyridine-2,7-dicarbonitrile (966 and 968); 5-methyl-8-[(3R)-3-methyl-4-[1-(6-methylpyridin-2-yl)ethyl]piperazin-1-yl]-6-oxo-5,6-dihydro-1,5-naphthyridine-2,7-dicarbonitrile (967); 8-[(3R)-4-[1-(2,4-difluorophenyl)ethyl]-3-methylpiperazin-1-yl]-5-methyl-6-oxo-5,6-dihydro-1,5-naphthyridine-2,7-dicarbonitrile (969-970); 5-methyl-8-[(3R)-3-methyl-4-{1-[3-(trifluoromethyl)phenyl]ethyl}piperazin-1-yl]-6-oxo-5,6-dihydro-1,5- naphthyridine-2,7-dicarbonitrile (971-972); 4-{1-[(2R)-4-(3,6-dicyano-1-methyl-2-oxo-1,2-dihydro-1,5-naphthyridin-4-yl)-2-methylpiperazin-1-yl]ethyl}benzoic acid (973-974); 8-[(3R)-4-[1-(4-bromophenyl)ethyl]-3-methylpiperazin-1-yl]-5-methyl-6-oxo-5,6-dihydro-1,5-naphthyridine-2,7-dicarbonitrile (974-975); 8-[(3R)-4-[1-(2,5-dimethylphenyl)ethyl]-3-methylpiperazin-1-yl]-5-methyl-6-oxo-5,6-dihydro-1,5-naphthyridine-2,7-dicarbonitrile (976-977); 8-[(3R)-4-[1-(4-chlorophenyl) ethyl]-3-methylpiperazin-1-yl]-5-methyl-6-oxo-5,6-dihydro-1,5-naphthyridine-2,7-dicarbonitrile (978-979); methyl 4-{1-[(2R)-4-(3,6-dicyano-1-methyl-2-oxo-1,2-dihydro-1,5-naphthyridin-4-yl)-2-methylpiperazin-1-yl]ethyl}benzoate (980-981); methyl 3-{1-[(2R)-4-(3,6-dicyano-1-methyl-2-oxo-1,2-dihydro-1,5-naphthyridin-4-yl)-2-methylpiperazin-1-yl]ethyl}benzoate (982-983); 8-[(3R)-4-[(2-chloro-6-fluorophenyl) methyl]-3-methylpiperazin-1-yl]-5-methyl-6-oxo-5,6-dihydro-1,5-naphthyridine-2,7-dicarbonitrile (984); 8-[(3R)-4-[(2,4-difluorophenyl)methyl]-3-methylpiperazin-1-yl]-5-methyl-6-oxo-5,6-dihydro-1,5-naphthyridine-2,7-dicarbonitrile (985); 5-methyl-8-[(3R)-3-methyl-4-[(2,4,6-trifluorophenyl)methyl]piperazin-1-yl]-6-oxo-5,6-dihydro-1,5-naphthyridine-2,7-dicarbonitrile (986); 8-[(3R)-4-[(3,4-difluorophenyl)methyl]-3-methylpiperazin-1-yl]-5-methyl-6-oxo-5,6-dihydro-1,5-naphthyridine-2,7-dicarbonitrile (987); 5-methyl-8-[(3R)-3-methyl-4-[(6-methylpyridin-2-yl)methyl]piperazin-1-yl]-6-oxo-5,6-dihydro-1,5-naphthyridine-2,7-dicarbonitrile (988); 8-[(3R)-4-[(6-cyanopyridin-2-yl)methyl]-3-methylpiperazin-1-yl]-5-methyl-6-oxo-5,6-dihydro-1,5-naphthyridine-2,7-dicarbonitrile (989); 5-methyl-8-[(3R)-3-methyl-4-[(pyridin-2-yl)methyl]piperazin-1-yl]-6-oxo-5,6-dihydro-1,5-naphthyridine-2,7-dicarbonitrile (990); 5-methyl-8-[(3R)-3-methyl-4-{[6-(trifluoromethyl)pyridin-2-yl]methyl}piperazin-1-yl]-6-oxo-5,6-dihydro-1,5-naphthyridine-2,7-dicarbonitrile (991); 5-methyl-8-[(3R)-3-methyl-4-[(quinolin-2-yl) methyl]piperazin-1-yl]-6-oxo-5,6-dihydro-1,5-naphthyridine-2,7-dicarbonitrile (992); 8-[(3R)-4-[(2-chloro-4-fluorophenyl) methyl]-3-methylpiperazin-1-yl]-5-methyl-6-oxo-5,6-dihydro-1,5-naphthyridine-2,7-dicarbonitrile (993); 8-[(3R)-4-({[1,1'-biphenyl]-4-yl}methyl)-3-methylpiperazin-1-yl]-5-methyl-6-oxo-5,6-dihydro-1,5-naphthyridine-2,7-dicarbonitrile (994); 8-[(3R)-4-[(4-fluoro-3-methylphenyl)methyl]-3-methylpiperazin-1-yl]-5-methyl-6-oxo-5,6-dihydro-1,5-naphthyridine-2,7-dicarbonitrile (995); 8-[(3R)-4-[(3,4-dichlorophenyl)methyl]-3-methylpiperazin-1-yl]-5-methyl-6-oxo-5,6-dihydro-1,5-naphthyridine-2,7-dicarbonitrile (996); 8-[(3R)-4-[(2-chlorophenyl)methyl]-3-methylpiperazin-1-yl]-5-methyl-6-oxo-5,6-dihydro-1,5-naphthyridine-2,7-dicarbonitrile (997); 5-methyl-8-[(3R)-3-methyl-4-[(pyridin-3-yl)methyl]piperazin-1-yl]-6-oxo-5,6-dihydro-1,5-naphthyridine-2,7-dicarbonitrile (998); 5-methyl-8-[(3R)-3-methyl-4-{[2-(trifluoromethoxy)phenyl]methyl}piperazin-1-yl]-6-oxo-5,6-dihydro-1,5-naphthyridine-2,7-dicarbonitrile (999); 8-[(3R)-4-[(3,5-dimethylphenyl)methyl]-3-methylpiperazin-1-yl]-5-methyl-6-oxo-5,6-dihydro-1,5-naphthyridine-2,7-dicarbonitrile (1000); 8-[(3R)-4-[(5-fluoro-2-methylphenyl)methyl]-3-methylpiperazin-1-yl]-5-methyl-6-oxo-5,6-dihydro-1,5-naphthyridine-2,7-dicarbonitrile (1001); 8-[(3R)-4-[(3-fluoro-4-methylphenyl) methyl]-3-methylpiperazin-1-yl]-5-methyl-6-oxo-5,6-dihydro-1,5-naphthyridine-2,7-dicarbonitrile (1002); 5-methyl-8-[(3R)-3-methyl-4-{[3-(trifluoromethyl)phenyl]methyl}piperazin-1-yl]-6-oxo-5,6-dihydro-1,5-naphthyridine-2,7-dicarbonitrile (1003); 8-[(3R)-4-({[1,1'-biphenyl]-3-yl}methyl)-3-methylpiperazin-1-yl]-5-methyl-6-oxo-5,6-dihydro-1,5-naphthyridine-2,7-dicarbonitrile (1004); 8-[(3R)-4-[(3-fluorophenyl)methyl]-3-methylpiperazin-1-yl]-5-methyl-6-oxo-5,6-dihydro-1,5-naphthyridine-2,7-dicarbonitrile (1005); 8-[(3R)-4-[(2-fluoro-5-methylphenyl)methyl]-3-methylpiperazin-1-yl]-5-methyl-6-oxo-5,6-dihydro-1,5-naphthyridine-2,7-dicarbonitrile (1006); 5-methyl-8-[(3R)-3-methyl-4-[(4-methylphenyl)methyl]piperazin-1-yl]-6-oxo-5,6-dihydro-1,5-naphthyridine-2,7-dicarbonitrile (1007); 5-methyl-8-[(3R)-3-methyl-4-{[3-(trifluoromethoxy)phenyl]methyl}piperazin-1-yl]-6-oxo-5,6-dihydro-1,5-naphthyridine-2,7-dicarbonitrile (1008); 8-[(3R)-4-[(2-cyanophenyl)methyl]-3-methylpiperazin-1-yl]-5-methyl-6-oxo-5,6-dihydro-1,5-naphthyridine-2,7-dicarbonitrile (1009); 8-[(3R)-4-[(3-fluoro-2-methylphenyl)methyl]-3-methylpiperazin-1-yl]-5-methyl-6-oxo-5,6-dihydro-1,5-naphthyridine-2,7-dicarbonitrile (1010); 8-[(3R)-4-[(4-chlorophenyl)methyl]-3-methylpiperazin-1-yl]-5-methyl-6-oxo-5,6-dihydro-1,5-naphthyridine-2,7-dicarbonitrile (1011); 5-methyl-8-[(3R)-3-methyl-4-[(3-methylphenyl)methyl]piperazin-1-yl]-6-oxo-5,6-dihydro-1,5-naphthyridine-2,7-dicarbonitrile (1012); 8-[(3R)-4-[(4-tert-butylphenyl)methyl]-3-methylpiperazin-1-yl]-5-methyl-6-oxo-5,6-dihydro-1,5-naphthyridine-2,7-dicarbonitrile (1013); 5-methyl-8-[(3R)-3-methyl-4-{[2-(trifluoromethyl)phenyl]methyl}piperazin-1-yl]-6-oxo-5,6-dihydro-1,5-naphthyridine-2,7-dicarbonitrile (1014); 8-[(3R)-4-[(4-chloro-3-fluorophenyl)methyl]-3-methylpiperazin-1-yl]-5-methyl-6-oxo-5,6-dihydro-1,5-naphthyridine-2,7-dicarbonitrile (1015); 8-[(3R)-4-[(4-fluorophenyl)(1-methyl-1H-pyrazol-4-yl)methyl]-3-methylpiperazin-1-yl]-5-methyl-6-oxo-5,6-dihydro-1,5-naphthyridine-2,7-dicarbonitrile (1016-1017); 8-[(3R)-4-[(4-fluorophenyl)(1-methyl-1H-imidazol-5-yl)methyl]-3-methylpiperazin-1-yl]-5-methyl-6-oxo-5,6-dihydro-1,5-naphthyridine-2,7-dicarbonitrile (1018-1019); 8-[(3R)-4-[(4-fluorophenyl)(1,3-oxazol-4-yl)methyl]-3-methylpiperazin-1-yl]-5-methyl-6-oxo-5,6-dihydro-1,5-naphthyridine-2,7-dicarbonitrile (1022-1023); 8-[(3R)-4-[(4-fluorophenyl)(1,3-thiazol-2-yl)methyl]-3-methylpiperazin-1-yl]-5-methyl-6-oxo-5,6-dihydro-1,5-naphthyridine-2,7-dicarbonitrile (1024-1025); 8-[(3R)-4-[(4-fluorophenyl)(1-methyl-1H-imidazol-4-yl)methyl]-3-methylpiperazin-1-yl]-5-methyl-6-oxo-5,6-dihydro-1,5-naphthyridine-2,7-dicarbonitrile (1026-1027); 8-[(3R)-4-[(4-fluorophenyl)(1,2-thiazol-4-yl)methyl]-3-methylpiperazin-1-yl]-5-methyl-6-oxo-5,6-dihydro-1,5-naphthyridine-2,7-dicarbonitrile (1028); 8-[(3R)-4-[(3-cyclopropyl-1,2,4-oxadiazol-5-yl)(4-fluorophenyl)methyl]-3-methylpiperazin-1-yl]-5-methyl-6-oxo-5,6-dihydro-1,5-naphthyridine-2,7-dicarbonitrile (1029-1030); 8-[(2S,5R)-4-[(4-chlorophenyl)(4-fluorophenyl)methyl]-2,5-diethylpiperazin-1-yl]-5-methyl-6-oxo-5,6-dihydro-1,5-naphthyridine-2-carbonitrile (1031); 8-[(2S,5R)-4-[bis(4-chlorophenyl) methyl]-2,5-diethylpiperazin-1-yl]-5-methyl-6-oxo-5,6-dihydro-1,5-naphthyridine-2-carbonitrile (1032); 8-[(2S,5R)-4-[(4-chlorophenyl)(5-fluoropyridin-2-yl) methyl]-2,5-diethylpiperazin-1-yl]-5-methyl-6-oxo-5,6-dihydro-1,5-naphthyridine-2-carbonitrile (1033-1034); 8-[(2S,5R)-4-[(4-cyanophenyl)(4-fluorophenyl)methyl]-2,5-diethylpiperazin-1-yl]-5-methyl-6-oxo-5,6-dihydro-1,5-naphthyridine-2-carbonitrile (1035-1036); 8-[(2S,5R)-2,5-diethyl-4-[(4-fluorophenyl)(3-fluoropyridin-2-yl)methyl]piperazin-1-yl]-5-methyl-6-oxo-5,6-dihydro-1,5-naphthyridine-2-carbonitrile (1037-1038); 8-[(2S,5R)-2,5-diethyl-4-[(4-fluorophenyl)[5-(trifluoromethyl)pyridin-2-yl]methyl]piperazin-1-yl]-5-methyl-6-oxo-5,6-dihydro-1,5-naphthyridine-2-carbonitrile (1039-1040); 8-[(2S,5R)-2,5-diethyl-4-[(3-fluorophenyl)(5-fluoropyridin-2-yl)methyl] piperazin-1-yl]-5-methyl-6-oxo-5,6-dihydro-1,5- naphthyridine-2-carbonitrile (1041-1042); 8-[(2S,5R)-2,5-diethyl-4-[(4-fluorophenyl)(pyridin-2-yl)methyl]piperazin-1-yl]-5-methyl-6-oxo-5,6-dihydro-1,5-naphthyridine-2-carbonitrile (1043-1044); 8-[(2S,5R)-2,5-diethyl-4-[(4-fluorophenyl)[6-(trifluoromethyl)pyridin-2-yl]methyl]piperazin-1-yl]-5-methyl-6-oxo-5,6-dihydro-1,5-naphthyridine-2-carbonitrile (1045-1046); 8-[(2S,5R)-2,5-diethyl-4-[(3-fluorophenyl)(5-methoxypyridin-2-yl)methyl]piperazin-1-yl]-5-methyl-6-oxo-5,6-dihydro-1,5-naphthyridine-2-carbonitrile (1047-1048); 8-[(2S,5R)-2,5-diethyl-4-[1-(4-fluorophenyl)ethyl]piperazin-1-yl]-5-methyl-6-oxo-5,6-dihydro-1,5-naphthyridine-2-carbonitrile (1049-1050); 8-[(2S,5R)-2,5-diethyl-4-{1-[4-(trifluoromethyl)phenyl]ethyl}piperazin-1-yl]-5-methyl-6-oxo-5,6-dihydro-1,5-naphthyridine-2-carbonitrile (1051-1052); 8-[(2S,5R)-2,5-diethyl-4-{1-[4-(trifluoromethoxy)phenyl]ethyl}piperazin-1-yl]-5-methyl-6-oxo-5,6-dihydro-1,5-naphthyridine-2-carbonitrile (1053-1054); 8-[(2S,5R)-4-[1-(2,4-difluorophenyl)ethyl]-2,5-diethylpiperazin-1-yl]-5-methyl-6-oxo-5,6-dihydro-1,5-naphthyridine-2-carbonitrile (1055-1056); 8-[(2S,5R)-2,5-diethyl-4-{1-[2-fluoro-4-(trifluoromethoxy)phenyl]propyl}piperazin-1-yl]-5-methyl-6-oxo-5,6-dihydro-1,5-naphthyridine-2-carbonitrile (1057-1058); 8-[(2S,5R)-2,5-diethyl-4-{1-[4-(trifluoromethoxy)phenyl]propyl}piperazin-1-yl]-5-methyl-6-oxo-5,6-dihydro-1,5-naphthyridine-2-carbonitrile (1059-1060); 8-[(2S,5R)-2,5-diethyl-4-[(4-fluorophenyl)methyl]piperazin-1-yl]-5-methyl-6-oxo-5,6-dihydro-1,5-naphthyridine-2-carbonitrile (1061); 8-[(2S,5R)-4-[(2,4-difluorophenyl)methyl]-2,5-diethylpiperazin-1-yl]-5-methyl-6-oxo-5,6-dihydro-1,5-naphthyridine-2-carbonitrile (1062); 8-[(2S,5R)-4-[(2,2-difluoro-2H-1,3-benzodioxol-5-yl)methyl]-2,5-diethylpiperazin-1-yl]-5-methyl-6-oxo-5,6-dihydro-1,5-naphthyridine-2-carbonitrile (1063); 8-[(2S,5R)-4-[(3-cyclopropyl-1,2,4-oxadiazol-5-yl)(4-fluorophenyl)methyl]-2,5-diethylpiperazin-1-yl]-5-methyl-6-oxo-5,6-dihydro-1,5-naphthyridine-2-carbonitrile (1064-1065); 8-[(2S,5R)-4-[(4-cyclopropyl-1,3-thiazol-2-yl)(4-fluorophenyl)methyl]-2,5-diethylpiperazin-1-yl]-5-methyl-6-oxo-5,6-dihydro-1,5-naphthyridine-2-carbonitrile (1066-1067); 8-[(2S,5R)-2,5-diethyl-4-[(4-fluorophenyl)(1,3-oxazol-4-yl)methyl]piperazin-1-yl]-5-methyl-6-oxo-5,6-dihydro-1,5-naphthyridine-2-carbonitrile (1068-1069); 8-[(2S,5R)-2,5-diethyl-4-[(4-fluorophenyl)(1,3-thiazol-4-yl)methyl]piperazin-1-yl]-5-methyl-6-oxo-5,6-dihydro-1,5-naphthyridine-2-carbonitrile (1070-1071); 8-[(2S,5R)-2,5-diethyl-4-[(4-fluorophenyl)(1,2-oxazol-3-yl)methyl]piperazin-1-yl]-5-methyl-6-oxo-5,6-dihydro-1,5-naphthyridine-2-carbonitrile (1072-1073); 8-[(2S,5R)-4-[(5-cyclopropyl-1,2-oxazol-3-yl)(4-fluorophenyl)methyl]-2,5-diethylpiperazin-1-yl]-5-methyl-6-oxo-5,6-dihydro-1,5-naphthyridine-2-carbonitrile (1074-1075); 8-[(2S,5R)-4-benzyl-5-ethyl-2-methylpiperazin-1-yl]-5-methyl-6-oxo-5,6-dihydro-1,5-naphthyridine-2-carbonitrile (1076); 8-[(2S,5R)-4-[(2,4-difluorophenyl)methyl]-5-ethyl-2-methylpiperazin-1-yl]-5-methyl-6-oxo-5,6-dihydro-1,5-naphthyridine-2-carbonitrile (1077); 8-[(2S,5R)-4-[(2-chloro-4-fluorophenyl)methyl]-5-ethyl-2-methylpiperazin-1-yl]-5-methyl-6-oxo-5,6-dihydro-1,5-naphthyridine-2-carbonitrile (1078); 8-[(2S,5R)-5-ethyl-4-[(4-fluorophenyl)methyl]-2-methylpiperazin-1-yl]-5-methyl-6-oxo-5,6-dihydro-1,5-naphthyridine-2-carbonitrile (1079); 8-[(2S,5R)-5-ethyl-2-methyl-4-[(2,4,6-trifluorophenyl)methyl]piperazin-1-yl]-5-methyl-6-oxo-5,6-dihydro-1,5-naphthyridine-2-carbonitrile (1080); 8-[(2S,5R)-5-ethyl-4-{[2-methoxy-4-(trifluoromethoxy)phenyl]methyl}-2-methylpiperazin-1-yl]-5-methyl-6-oxo-5,6-dihydro-1,5-naphthyridine-2-carbonitrile (1081); 8-[(2S,5R)-4-[(2,2-difluoro-2H-1,3-benzodioxol-5-yl)methyl]-5-ethyl-2-methylpiperazin-1-yl]-5-methyl-6-oxo-5,6-dihydro-1,5-naphthyridine-2-carbonitrile (1082); 8-[(2S,5R)-5-ethyl-4-[1-(4-fluorophenyl)ethyl]-2-methylpiperazin-1-yl]-5-methyl-6-oxo-5,6-dihydro-1,5-naphthyridine-2-carbonitrile (1083-1084); 8-[(2S,5R)-5-ethyl-4-{1-[2-fluoro-4-(trifluoromethyl)phenyl]ethyl}-2-methylpiperazin-1-yl]-5-methyl-6-oxo-5,6-dihydro-1,5-naphthyridine-2-carbonitrile (1085-1086); 8-[(2S,5R)-4-[1-(2,4-difluorophenyl)ethyl]-5-ethyl-2-methylpiperazin-1-yl]-5-methyl-6-oxo-5,6-dihydro-1,5-naphthyridine-2-carbonitrile (1087-1088); 8-[(2S,5R)-5-ethyl-2-methyl-4-[1-(2,4,6-trifluorophenyl)ethyl]piperazin-1-yl]-5-methyl-6-oxo-5,6-dihydro-1,5-naphthyridine-2-carbonitrile (1089-1090); 8-[(2S,5R)-4-[1-(3,4-difluorophenyl)ethyl]-5-ethyl-2-methylpiperazin-1-yl]-5-methyl-6-oxo-5,6-dihydro-1,5-naphthyridine-2-carbonitrile (1091-1092); 8-[(2S,5R)-5-ethyl-2-methyl-4-{1-[4-(trifluoromethyl)phenyl]ethyl}piperazin-1-yl]-5-methyl-6-oxo-5,6-dihydro-1,5-naphthyridine-2-carbonitrile (1093-1094); 8-[(2S,5R)-5-ethyl-4-{1-[2-fluoro-4-(trifluoromethoxy)phenyl]ethyl}-2-methylpiperazin-1-yl]-5-methyl-6-oxo-5,6-dihydro-1,5-naphthyridine-2-carbonitrile (1095-1096); 8-[(2S,5R)-4-[bis(4-fluorophenyl)methyl]-5-ethyl-2-methylpiperazin-1-yl]-5-methyl-6-oxo-5,6-dihydro-1,5-naphthyridine-2-carbonitrile (1097); 8-[(2S,5R)-4-[bis(4-methylphenyl)methyl]-5-ethyl-2-methylpiperazin-1-yl]-5-methyl-6-oxo-5,6-dihydro-1,5-naphthyridine-2-carbonitrile (1098); 8-[(2S,5R)-4-[bis(4-chlorophenyl)methyl]-5-ethyl-2-methylpiperazin-1-yl]-5-methyl-6-oxo-5,6-dihydro-1,5-naphthyridine-2-carbonitrile (1099); 8-[(2S,5R)-4-[(4-chlorophenyl)(4-fluorophenyl)methyl]-5-ethyl-2-methylpiperazin-1-yl]-5-methyl-6-oxo-5,6-dihydro-1,5-naphthyridine-2-carbonitrile (1100-1101); 8-[(2S,5R)-4-[(4-cyanophenyl)(4-fluorophenyl)methyl]-5-ethyl-2-methylpiperazin-1-yl]-5-methyl-6-oxo-5,6-dihydro-1,5-naphthyridine-2-carbonitrile (1102-1103); 8-[(2S,5R)-5-ethyl-4-[(4-fluorophenyl)(3-fluoropyridin-2-yl)methyl]-2-methylpiperazin-1-yl]-5-methyl-6-oxo-5,6-dihydro-1,5-naphthyridine-2-carbonitrile (1104-1105); 8-[(2S,5R)-5-ethyl-4-[(4-fluorophenyl)[5-(trifluoromethyl)pyridin-2-yl]methyl]-2-methylpiperazin-1-yl]-5-methyl-6-oxo-5,6-dihydro-1,5-naphthyridine-2-carbonitrile (1106-1107); 8-[(2S,5R)-5-ethyl-4-[(3-fluorophenyl)(5-fluoropyridin-2-yl)methyl]-2-methylpiperazin-1-yl]-5-methyl-6-oxo-5,6-dihydro-1,5-naphthyridine-2-carbonitrile (1108-1109); 8-[(2S,5R)-4-[(4-chlorophenyl)(5-fluoropyridin-2-yl)methyl]-5-ethyl-2-methylpiperazin-1-yl]-5-methyl-6-oxo-5,6-dihydro-1,5-naphthyridine-2-carbonitrile (1110-1111); 8-[(2S,5R)-5-ethyl-4-[(4-fluorophenyl)[6-(trifluoromethyl)pyridin-2-yl]methyl]-2-methylpiperazin-1-yl]-5-methyl-6-oxo-5,6-dihydro-1,5-naphthyridine-2-carbonitrile (1112-1113); 8-[(2S,5R)-5-ethyl-4-[(4-fluorophenyl)(1,2-oxazol-3-yl)methyl]-2-methylpiperazin-1-yl]-5-methyl-6-oxo-5,6-dihydro-1,5-naphthyridine-2-carbonitrile (1114-1115); 8-[(2S,5R)-4-[(3-cyclopropyl-1,2,4-oxadiazol-5-yl)(4-fluorophenyl)methyl]-5-ethyl-2-methylpiperazin-1-yl]-5-methyl-6-oxo-5,6-dihydro-1,5-naphthyridine-2-carbonitrile (1116-1117); 8-[(2S,5R)-4-[bis(4-fluorophenyl)methyl]-2-ethyl-5-methylpiperazin-1-yl]-5-methyl-6-oxo-5,6-dihydro-1,5-naphthyridine-2-carbonitrile (1118); 8-[(2S,5R)-4-[bis(4-methylphenyl)methyl]-2-ethyl-5-methylpiperazin-1-yl]-5-methyl-6-oxo-5,6-dihydro-1,5-naphthyridine-2-carbonitrile (1119); 8-[(2S,5R)-4-[bis(4-chlorophenyl)methyl]-2-ethyl-5-methylpiperazin-1-yl]-5-methyl-6-oxo-5,6-dihydro-1,5-naphthyridine-2-carbonitrile (1120); 8-[(2S,5R)-4-[(4-chlorophenyl)(4-methylphenyl)methyl]-2-ethyl- 5-methylpiperazin-1-yl]-5-methyl-6-oxo-5,6-dihydro-1,5-naphthyridine-2-carbonitrile (1121-1122); 8-[(2S,5R)-4-[(4-cyanophenyl)(4-fluorophenyl)methyl]-2-ethyl-5-methylpiperazin-1-yl]-5-methyl-6-oxo-5,6-dihydro-1,5-naphthyridine-2-carbonitrile (1123-1124); 8-[(2S,5R)-2-ethyl-4-[(3-fluorophenyl)(5-methylpyridin-2-yl)methyl]-5-methylpiperazin-1-yl]-5-methyl-6-oxo-5,6-dihydro-1,5-naphthyridine-2-carbonitrile (1125-1126); 8-[(2S,5R)-4-[(4-chlorophenyl)(4-fluorophenyl)methyl]-2-ethyl-5-methylpiperazin-1-yl]-5-methyl-6-oxo-5,6-dihydro-1,5-naphthyridine-2-carbonitrile (1127-1128); 8-[(2S,5R)-4-[(4-chlorophenyl)(5-fluoropyridin-2-yl)methyl]-2-ethyl-5-methylpiperazin-1-yl]-5-methyl-6-oxo-5,6-dihydro-1,5-naphthyridine-2-carbonitrile (1129-1130); 8-[(2S,5R)-2-ethyl-4-[(4-fluorophenyl)[5-(trifluoromethyl)pyridin-2-yl]methyl]-5-methylpiperazin-1-yl]-5-methyl-6-oxo-5,6-dihydro-1,5-naphthyridine-2-carbonitrile (1131-1132); 8-[(2S,5R)-2-ethyl-4-[(4-fluorophenyl)[6-(trifluoromethyl)pyridin-2-yl]methyl]-5-methylpiperazin-1-yl]-5-methyl-6-oxo-5,6-dihydro-1,5-naphthyridine-2-carbonitrile (1133-1134); 8-[(2S,5R)-2-ethyl-4-[1-(4-fluorophenyl)ethyl]-5-methylpiperazin-1-yl]-5-methyl-6-oxo-5,6-dihydro-1,5-naphthyridine-2-carbonitrile (1135-1136); 8-[(2S,5R)-4-[1-(2,4-difluorophenyl)ethyl]-2-ethyl-5-methylpiperazin-1-yl]-5-methyl-6-oxo-5,6-dihydro-1,5-naphthyridine-2-carbonitrile (1137-1138); 8-[(2S,5R)-4-[1-(3,4-difluorophenyl)ethyl]-2-ethyl-5-methylpiperazin-1-yl]-5-methyl-6-oxo-5,6-dihydro-1,5-naphthyridine-2-carbonitrile (1139-1140); 8-[(2S,5R)-2-ethyl-5-methyl-4-{1-[4-(trifluoromethoxy)phenyl]ethyl}piperazin-1-yl]-5-methyl-6-oxo-5,6-dihydro-1,5-naphthyridine-2-carbonitrile (1141-1142); 8-[(2S,5R)-2-ethyl-5-methyl-4-{1-[4-(trifluoromethyl)phenyl]ethyl}piperazin-1-yl]-5-methyl-6-oxo-5,6-dihydro-1,5-naphthyridine-2-carbonitrile (1143-1144); 8-[(2S,5R)-4-{1-[4-(difluoromethoxy)phenyl]ethyl}-2-ethyl-5-methylpiperazin-1-yl]-5-methyl-6-oxo-5,6-dihydro-1,5-naphthyridine-2-carbonitrile (1145); 8-[(2S,5R)-2-ethyl-5-methyl-4-{1-[4-(trifluoromethoxy)phenyl]propyl}piperazin-1-yl]-5-methyl-6-oxo-5,6-dihydro-1,5-naphthyridine-2-carbonitrile (1146-1147); 8-[(2S,5R)-2-ethyl-5-methyl-4-[(2,4,6-trifluorophenyl)methyl]piperazin-1-yl]-5-methyl-6-oxo-5,6-dihydro-1,5-naphthyridine-2-carbonitrile (1148); 8-[(2S,5R)-2-ethyl-5-methyl-4-[(3,4,5-trifluorophenyl)methyl]piperazin-1-yl]-5-methyl-6-oxo-5,6-dihydro-1,5-naphthyridine-2-carbonitrile (1149); 8-(4-(bis(4-fluorophenyl)methyl)-3-(hydroxymethyl)piperazin-1-yl)-5-methyl-6-oxo-5,6-dihydro-1,5-naphthyridine-2-carbonitrile (1150); 8-[(2S,5S)-4-[bis(4-fluorophenyl)methyl]-5-(hydroxymethyl)-2-methylpiperazin-1-yl]-5-methyl-6-oxo-5,6-dihydro-1,5-naphthyridine-2-carbonitrile (1151); 8-[(2S,5S)-4-[bis(4-chlorophenyl)methyl]-5-(hydroxymethyl)-2-methylpiperazin-1-yl]-5-methyl-6-oxo-5,6-dihydro-1,5-naphthyridine-2-carbonitrile (1152); 8-[(2S,5S)-4-[(3-fluorophenyl)(5-methylpyridin-2-yl)methyl]-5-(hydroxymethyl)-2-methylpiperazin-1-yl]-5-methyl-6-oxo-5,6-dihydro-1,5-naphthyridine-2-carbonitrile (1153-1154); 8-((2S,5S)-4-(bis(4-fluorophenyl)methyl)-5-(methoxymethyl)-2-methylpiperazin-1-yl)-5-methyl-6-oxo-5,6-dihydro-1,5-naphthyridine-2-carbonitrile (1155); 8-[(2S,5S)-4-[bis(4-methylphenyl)methyl]-5-(methoxymethyl)-2-methylpiperazin-1-yl]-5-methyl-6-oxo-5,6-dihydro-1,5-naphthyridine-2-carbonitrile (1156); 8-((2S,5S)-4-((4-cyanophenyl)(4-fluorophenyl) methyl)-5-(methoxymethyl)-2-methylpiperazin-1-yl)-5-methyl-6-oxo-5,6-dihydro-1,5-naphthyridine-2-carbonitrile (1157-1158); 8-((2S,5S)-4-(1-(4-fluorophenyl)ethyl)-5-(methoxymethyl)-2-methylpiperazin-1-yl)-5-methyl-6-oxo-5,6-dihydro-1,5-naphthyridine-2-carbonitrile (1159-1160); 8-[(2S,5S)-5-(methoxymethyl)-2-methyl-4-[(3,4,5-trifluorophenyl)methyl]piperazin-1-yl]-5-methyl-6-oxo-5,6-dihydro-1,5-naphthyridine-2-carbonitrile (1161); 8-[(2S,5S)-5-(methoxymethyl)-2-methyl-4-{1-[4-(trifluoromethoxy)phenyl]ethyl}piperazin-1-yl]-5-methyl-6-oxo-5,6-dihydro-1,5-naphthyridine-2-carbonitrile (1162-1163); 8-((2S,5S)-4-(bis(4-fluorophenyl)methyl)-5-(ethoxymethyl)-2-methylpiperazin-1-yl)-5-methyl-6-oxo-5,6-dihydro-1,5-naphthyridine-2-carbonitrile (1164); N-(((2R,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)acetamide (1165); methyl (((2R,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)carbamate (1166); 8-((2S,5R)-4-(bis(4-fluorophenyl)methyl)-2-methyl-5-(morpholinomethyl)piperazin-1-yl)-5-methyl-6-oxo-5,6-dihydro-1,5-naphthyridine-2-carbonitrile (1167); 8-[(2S,5R)-4-[bis(4-fluorophenyl)methyl]-5-[(3-hydroxyazetidin-1-yl)methyl]-2-methylpiperazin-1-yl]-5-methyl-6-oxo-5,6-dihydro-1,5-naphthyridine-2-carbonitrile (1168); 8-[(2S,5R)-4-[bis(4-fluorophenyl)methyl]-5-[(dimethylamino)methyl]-2-methylpiperazin-1-yl]-5-methyl-6-oxo-5,6-dihydro-1,5-naphthyridine-2-carbonitrile (1169); 8-((2S,5S)-4-((4-cyanophenyl) (4-fluorophenyl) methyl)-2-ethyl-5-(methoxymethyl) piperazin-1-yl)-5-methyl-6-oxo-5,6-dihydro-1,5-naphthyridine-2-carbonitrile (1170-1171); 8-((2R,5R)-4-(bis(4-fluorophenyl) methyl)-5-(hydroxymethyl)-2-methylpiperazin-1-yl)-5-methyl-6-oxo-5,6-dihydro-1,5-naphthyridine-2-carbonitrile (1172); 8-[(2R,5R)-4-[bis(4-methylphenyl)methyl]-5-(hydroxymethyl)-2-methylpiperazin-1-yl]-5-methyl-6-oxo-5,6-dihydro-1,5-naphthyridine-2-carbonitrile (1173); 8-[(2R,5R)-4-[(4-chlorophenyl)(4-fluorophenyl)methyl]-5-(hydroxymethyl)-2-methylpiperazin-1-yl]-5-methyl-6-oxo-5,6-dihydro-1,5-naphthyridine-2-carbonitrile (1174-1175); 8-[(2R,5R)-4-[(4-cyanophenyl)(4-fluorophenyl)methyl]-5-(hydroxymethyl)-2-methylpiperazin-1-yl]-5-methyl-6-oxo-5,6-dihydro-1,5-naphthyridine-2-carbonitrile (1176-1177); 8-[(2R,5R)-4-[1-(4-fluorophenyl) ethyl]-5-(hydroxymethyl)-2-methylpiperazin-1-yl]-5-methyl-6-oxo-5,6-dihydro-1,5-naphthyridine-2-carbonitrile (1178-1179); 8-[(2R,5R)-5-(hydroxymethyl)-2-methyl-4-{1-[4-(trifluoromethoxy)phenyl]ethyl}piperazin-1-yl]-5-methyl-6-oxo-5,6-dihydro-1,5-naphthyridine-2-carbonitrile (1180-1181); 8-[(2R,5R)-5-(hydroxymethyl)-2-methyl-4-[(2,4,6-trifluorophenyl)methyl]piperazin-1-yl]-5-methyl-6-oxo-5,6-dihydro-1,5-naphthyridine-2-carbonitrile (1182); 8-((2R,5R)-4-(bis(4-fluorophenyl) methyl)-5-(methoxymethyl)-2-methylpiperazin-1-yl)-5-methyl-6-oxo-5,6-dihydro-1,5-naphthyridine-2-carbonitrile (1183); 8-(4-(2-chloro-4-fluorobenzyl)-3-((difluoromethoxy) methyl)piperazin-1-yl)-5-methyl-6-oxo-5,6-dihydro-1,5-naphthyridine-2-carbonitrile (1184-1185); 8-{4-[bis(4-fluorophenyl)methyl]-3-[(difluoromethoxy)methyl]piperazin-1-yl}-5-methyl-6-oxo-5,6-dihydro-1,5-naphthyridine-2-carbonitrile (1186-1187); 8-((2S,5R)-4-(2-(difluoromethoxy)-1-(4-fluorophenyl)ethyl)-2,5-dimethylpiperazin-1-yl)-5-methyl-6-oxo-5,6-dihydro-1,5-naphthyridine-2-carbonitrile (1188-1189); 8-[(2S,5R)-4-{cyclopropyl[4-(trifluoromethoxy)phenyl]methyl}-5-ethyl-2-methylpiperazin-1-yl]-5-methyl-6-oxo-5,6-dihydro-1,5-naphthyridine-2-carbonitrile (1190); 4-[(2S,5R)-2,5-dimethyl-4-{1-[4-(trifluoromethoxy)phenyl]ethyl}piperazin-1-yl]-1,6-dimethyl-2-oxo-1,2-dihydro-1,5-naphthyridine-3-carbonitrile (1191-1192); 8-[(2S,5R)-5-ethyl-2-methyl-4-(1-phenylbutyl)piperazin-1-yl]-5-methyl- 6-oxo-5,6-dihydro-1,5-naphthyridine-2-carbonitrile (1193-1194); 8-[(2S,5R)-4-{2-cyclohexyl-1-[4-(trifluoromethoxy)phenyl]ethyl}-5-ethyl-2-methylpiperazin-1-yl]-5-methyl-6-oxo-5,6-dihydro-1,5-naphthyridine-2-carbonitrile (1195-1196); 8-[(2S,5R)-4-{[2,4-bis(trifluoromethyl)phenyl]methyl}-5-ethyl-2-methylpiperazin-1-yl]-5-methyl-6-oxo-5,6-dihydro-1,5-naphthyridine-2-carbonitrile (1197); 8-[(2S,5R)-5-ethyl-2-methyl-4-{1-[4-(trifluoromethoxy)phenyl]propyl}piperazin-1-yl]-5-methyl-6-oxo-5,6-dihydro-1,5-naphthyridine-2-carbonitrile (1198-1199); 8-((2S,5R)-4-(1-(4-cyclopropyl-2-fluorophenyl)ethyl)-2,5-dimethylpiperazin-1-yl)-5-methyl-6-oxo-5,6-dihydro-1,5-naphthyridine-2-carbonitrile (1200-1201); 8-((2S,5R)-4-(1-(2-fluoro-5-(trifluoromethoxy)phenyl)ethyl)-2,5-dimethylpiperazin-1-yl)-5-methyl-6-oxo-5,6-dihydro-1,5-naphthyridine-2-carbonitrile (1202-1203); 8-((2S,5R)-4-(1-(3-fluoro-4-(trifluoromethoxy)phenyl)ethyl)-2,5-dimethylpiperazin-1-yl)-5-methyl-6-oxo-5,6-dihydro-1,5-naphthyridine-2-carbonitrile (1204-1205); 8-((2S,5R)-4-(1-(2-fluoro-5-(trifluoromethoxy)phenyl)propyl)-2,5-dimethylpiperazin-1-yl)-5-methyl-6-oxo-5,6-dihydro-1,5-naphthyridine-2-carbonitrile (1206-1207); 8-((2S,5R)-4-(1-(2-fluoro-3-(trifluoromethoxy)phenyl)ethyl)-2,5-dimethylpiperazin-1-yl)-5-methyl-6-oxo-5,6-dihydro-1,5-naphthyridine-2-carbonitrile (1208-1209); 8-((2S,5R)-4-(1-(3-fluoro-5-(trifluoromethoxy)phenyl)ethyl)-2,5-dimethylpiperazin-1-yl)-5-methyl-6-oxo-5,6-dihydro-1,5-naphthyridine-2-carbonitrile (1210-1211); 8-((2S,5R)-2,5-dimethyl-4-(1-(2-(trifluoromethoxy)phenyl)ethyl)piperazin-1-yl)-5-methyl-6-oxo-5,6-dihydro-1,5-naphthyridine-2-carbonitrile (1212-1213); 8-((2S,5R)-4-(1-(4-cyclopropylphenyl)ethyl)-2,5-dimethylpiperazin-1-yl)-5-methyl-6-oxo-5,6-dihydro-1,5-naphthyridine-2-carbonitrile (1214-1215); 8-((2S,5R)-4-(1-(2,2-difluorobenzo[d][1,3]dioxol-4-yl)ethyl)-2,5-dimethylpiperazin-1-yl)-5-methyl-6-oxo-5,6-dihydro-1,5-naphthyridine-2-carbonitrile (1216-1217); 8-((2S,5R)-4-(1-(4-cyclopropyl-2-fluorophenyl)propyl)-2,5-dimethylpiperazin-1-yl)-5-methyl-6-oxo-5,6-dihydro-1,5-naphthyridine-2-carbonitrile (1218-1219); 8-((2S,5R)-4-(1-(4-cyclopropylphenyl) propyl)-2,5-dimethylpiperazin-1-yl)-5-methyl-6-oxo-5,6-dihydro-1,5-naphthyridine-2-carbonitrile (1220-1221); 8-((2S,5R)-4-(1-(6-(difluoromethyl)pyridin-2-yl)ethyl)-2,5-dimethylpiperazin-1-yl)-5-methyl-6-oxo-5,6-dihydro-1,5-naphthyridine-2-carbonitrile (1222-1223); 8-((2S,5R)-4-(1-(5-(difluoromethoxy)pyridin-2-yl)ethyl)-2,5-dimethylpiperazin-1-yl)-5-methyl-6-oxo-5,6-dihydro-1,5-naphthyridine-2-carbonitrile (1224-1225); 8-((2S,5R)-4-(1-(4-cyano-2-fluorophenyl)ethyl)-2,5-dimethylpiperazin-1-yl)-5-methyl-6-oxo-5,6-dihydro-1,5-naphthyridine-2-carbonitrile (1226-1227); 8-((2S,5R)-4-(1-(5-(difluoromethoxy)-2-fluorophenyl)ethyl)-2,5-dimethylpiperazin-1-yl)-5-methyl-6-oxo-5,6-dihydro-1,5-naphthyridine-2-carbonitrile (1228-1229); 8-((2S,5R)-4-(1-(4-chloro-2-fluorophenyl)ethyl)-2,5-dimethylpiperazin-1-yl)-5-methyl-6-oxo-5,6-dihydro-1,5-naphthyridine-2-carbonitrile (1230); 8-((2S,5R)-4-(1-(4-fluoro-3-methoxyphenyl)ethyl)-2,5-dimethylpiperazin-1-yl)-5-methyl-6-oxo-5,6-dihydro-1,5-naphthyridine-2-carbonitrile (1231-1232); 8-((2S,5R)-4-(1-(4-isopropylphenyl)ethyl)-2,5-dimethylpiperazin-1-yl)-5-methyl-6-oxo-5,6-dihydro-1,5-naphthyridine-2-carbonitrile (1233-1234); 8-((2S,5R)-2,5-dimethyl-4-(3,4,5-trifluorobenzyl)piperazin-1-yl)-5-methyl-6-oxo-5,6-dihydro-1,5-naphthyridine-2-carbonitrile (1235); 8-((2S,5R)-4-(1-(4-fluoro-2-methoxyphenyl)ethyl)-2,5-dimethylpiperazin-1-yl)-5-methyl-6-oxo-5,6-dihydro-1,5-naphthyridine-2-carbonitrile (1236-1237); 8-((2S,5R)-4-(1-(4-(1H-1,2,4-triazol-1-yl) phenyl)ethyl)-2,5-dimethylpiperazin-1-yl)-5-methyl-6-oxo-5,6-dihydro-1,5-naphthyridine-2-carbonitrile (1238-1239); 8-((2S,5R)-2,5-dimethyl-4-(1-(3,4,5-trifluorophenyl)ethyl)piperazin-1-yl)-5-methyl-6-oxo-5,6-dihydro-1,5-naphthyridine-2-carbonitrile (1240-1241); 8-((2S,5R)-4-(1-(2,6-difluoro-4-methoxyphenyl)ethyl)-2,5-dimethylpiperazin-1-yl)-5-methyl-6-oxo-5,6-dihydro-1,5-naphthyridine-2-carbonitrile (1242-1243); 8-((2S,5R)-4-(1-(2,5-difluoro-4-methoxyphenyl)ethyl)-2,5-dimethylpiperazin-1-yl)-5-methyl-6-oxo-5,6-dihydro-1,5-naphthyridine-2-carbonitrile (1244-1245); 8-((2S,5R)-4-(1-(2-fluoro-4,5-dimethoxyphenyl)ethyl)-2,5-dimethylpiperazin-1-yl)-5-methyl-6-oxo-5,6-dihydro-1,5-naphthyridine-2-carbonitrile (1246-1247); 8-((2S,5R)-4-(1-(4-methoxy-3-(trifluoromethyl)phenyl)ethyl)-2,5-dimethylpiperazin-1-yl)-5-methyl-6-oxo-5,6-dihydro-1,5-naphthyridine-2-carbonitrile (1248-1249); 8-((2S,5R)-4-(1-(4-(1-cyanocyclopropyl)-2-fluorophenyl)ethyl)-2,5-dimethylpiperazin-1-yl)-5-methyl-6-oxo-5,6-dihydro-1,5-naphthyridine-2-carbonitrile (1250-1251); 8-((2S,5R)-4-(1-(4-(1-cyanocyclopropyl)phenyl)ethyl)-2,5-dimethylpiperazin-1-yl)-5-methyl-6-oxo-5,6-dihydro-1,5-naphthyridine-2-carbonitrile (1253-1254); 8-((2S,5R)-4-(1-(4-fluoro-3-methylphenyl)ethyl)-2,5-dimethylpiperazin-1-yl)-5-methyl-6-oxo-5,6-dihydro-1,5-naphthyridine-2-carbonitrile (1255); 8-((2S,5R)-4-(1-(3-chloro-4-fluorophenyl)ethyl)-2,5-dimethylpiperazin-1-yl)-5-methyl-6-oxo-5,6-dihydro-1,5-naphthyridine-2-carbonitrile (1256-1257); 8-((2S,5R)-4-(1-(2,3-dihydrobenzo[b][1,4]dioxin-6-yl)ethyl)-2,5-dimethylpiperazin-1-yl)-5-methyl-6-oxo-5,6-dihydro-1,5-naphthyridine-2-carbonitrile (1258-1259); 8-((2S,5R)-2,5-dimethyl-4-(1-(2-methylbenzo[d]oxazol-4-yl)ethyl)piperazin-1-yl)-5-methyl-6-oxo-5,6-dihydro-1,5-naphthyridine-2-carbonitrile (1260-1261); 8-((2S,5R)-4-(1-(3-cyano-4-fluorophenyl) ethyl)-2,5-dimethylpiperazin-1-yl)-5-methyl-6-oxo-5,6-dihydro-1,5-naphthyridine-2-carbonitrile (1262); 8-((2S,5R)-2,5-dimethyl-4-(1-(2-methylbenzo[d]thiazol-6-yl)ethyl) piperazin-1-yl)-5-methyl-6-oxo-5,6-dihydro-1,5-naphthyridine-2-carbonitrile (1263-1264); 8-((2S,5R)-4-(1-(4-(methoxymethyl)phenyl)ethyl)-2,5-dimethylpiperazin-1-yl)-5-methyl-6-oxo-5,6-dihydro-1,5-naphthyridine-2-carbonitrile (1265-1266); 8-((2S,5R)-2,5-dimethyl-4-(1-(3-(trifluoromethoxy)phenyl)ethyl)piperazin-1-yl)-5-methyl-6-oxo-5,6-dihydro-1,5-naphthyridine-2-carbonitrile (1267-1268); 8-((2S,5R)-4-(1-(3-fluoro-4-(trifluoromethoxy)phenyl)ethyl)-2,5-dimethylpiperazin-1-yl)-5-methyl-6-oxo-5,6-dihydro-1,5-naphthyridine-2-carbonitrile (1269-1270); 8-((2S,5R)-4-(1-(3-(difluoromethoxy)phenyl)ethyl)-2,5-dimethylpiperazin-1-yl)-5-methyl-6-oxo-5,6-dihydro-1,5-naphthyridine-2-carbonitrile (1271-1272); 8-((2S,5R)-2,5-dimethyl-4-(1-(2-(trifluoromethyl)thiazol-4-yl)ethyl)piperazin-1-yl)-5-methyl-6-oxo-5,6-dihydro-1,5-naphthyridine-2-carbonitrile (1273-1274); 8-((2S,5R)-4-(4-ethoxy-2,6-difluorobenzyl)-2,5-dimethylpiperazin-1-yl)-5-methyl-6-oxo-5,6-dihydro-1,5-naphthyridine-2-carbonitrile (1275-1276); 8-((2S,5R)-4-(2-methoxy-1-(5-(trifluoromethyl)pyridin-2-yl) ethyl)-2,5-dimethylpiperazin-1-yl)-5-methyl-6-oxo-5,6-dihydro-1,5-naphthyridine-2-carbonitrile (1277-1278); 8-((2S,5R)-4-(2-hydroxy-1-(5-(trifluoromethyl)pyridin-2-yl) ethyl)-2,5-dimethylpiperazin-1-yl)-5-methyl-6-oxo-5,6-dihydro-1,5-naphthyridine-2-carbonitrile (1279-1280); 8-((2S,5R)-4-(1-(5-cyclopropylisoxazol-3-yl)ethyl)-2,5-dimethylpiperazin-1-yl)-5-methyl-6-oxo-5,6-dihydro-1,5-naphthyridine-2-carbonitrile (1281-1282); 8-((2S,5R)-4-(1-(5-(tert-butyl)isoxazol-3-yl)ethyl)-2,5-dimethylpiperazin-1-yl)-5-methyl-6-oxo-5,6-dihydro-1,5-naphthyridine-2-carbonitrile (1283-

1284); 8-((2S,5R)-4-((4-chlorophenyl)(3-cyclopropyl-1,2,4-oxadiazol-5-yl)methyl)-2,5-dimethylpiperazin-1-yl)-5-methyl-6-oxo-5,6-dihydro-1,5-naphthyridine-2-carbonitrile (1285-1286); 8-((2S,5R)-4-((2-(dimethylphosphoryl)phenyl)(4-fluorophenyl)methyl)-2,5-dimethylpiperazin-1-yl)-5-methyl-6-oxo-5,6-dihydro-1,5-naphthyridine-2-carbonitrile (1287-1288); 8-((2S,5R)-4-(4-(dimethylphosphoryl)benzyl)-2,5-dimethylpiperazin-1-yl)-5-methyl-6-oxo-5,6-dihydro-1,5-naphthyridine-2-carbonitrile (1289); 8-((2S,5R)-4-(1-(4-(dimethylphosphoryl)phenyl)ethyl)-2,5-dimethylpiperazin-1-yl)-5-methyl-6-oxo-5,6-dihydro-1,5-naphthyridine-2-carbonitrile (1290-1291); 8-((2S,5R)-4-((4-(dimethylphosphoryl)phenyl)(4-fluorophenyl)methyl)-2,5-dimethylpiperazin-1-yl)-5-methyl-6-oxo-5,6-dihydro-1,5-naphthyridine-2-carbonitrile (1292-1293); 8-((2S,5R)-4-(1-(4-(dimethylphosphoryl)phenyl)ethyl)-2,5-dimethylpiperazin-1-yl)-5-methyl-6-oxo-5,6-dihydro-1,5-naphthyridine-2,7-dicarbonitrile (1294-1295); 8-((2S,5R)-4-((3-(1-acetylazetidin-3-yl)-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile (1296-1297); 8-((2S,5R)-4-((4-fluorophenyl)(3-(1-methylazetidin-3-yl)-1,2,4-oxadiazol-5-yl)methyl)-2,5-dimethylpiperazin-1-yl)-5-methyl-6-oxo-5,6-dihydro-1,5-naphthyridine-2-carbonitrile (1298-1299); 8-((2S,5R)-4-((1,1-dioxidotetrahydro-2H-thiopyran-4-yl)(4-fluorophenyl)methyl)-2,5-dimethylpiperazin-1-yl)-5-methyl-6-oxo-5,6-dihydro-1,5-naphthyridine-2-carbonitrile (1300-1301); 8-((2S,5R)-4-(1-(4-methoxy-3-(2-methoxyethoxy)phenyl)ethyl)-2,5-dimethylpiperazin-1-yl)-5-methyl-6-oxo-5,6-dihydro-1,5-naphthyridine-2-carbonitrile (1302-1303); 8-((2S,5R)-4-(1-(4-methoxy-3-(2-morpholinoethoxy)phenyl)ethyl)-2,5-dimethylpiperazin-1-yl)-5-methyl-6-oxo-5,6-dihydro-1,5-naphthyridine-2-carbonitrile (1304-1305); 8-((2S,5R)-4-(1-(3-cyclopropyl-1,2,4-oxadiazol-5-yl)ethyl)-2,5-dimethylpiperazin-1-yl)-5-methyl-6-oxo-5,6-dihydro-1,5-naphthyridine-2,7-dicarbonitrile (1306-1307); 8-((2S,5R)-4-(1-(4-fluorophenyl)-2-hydroxy-2-methylpropyl)-2,5-dimethylpiperazin-1-yl)-5-methyl-6-oxo-5,6-dihydro-1,5-naphthyridine-2-carbonitrile (1308-1309); 8-((2S,5R)-4-(2,2-difluoro-1-(4-fluorophenyl)-3-hydroxypropyl)-2,5-dimethylpiperazin-1-yl)-5-methyl-6-oxo-5,6-dihydro-1,5-naphthyridine-2-carbonitrile (1310-1311); 8-((2S,5R)-4-(2,2-difluoro-1-(4-fluorophenyl)-3-methoxypropyl)-2,5-dimethylpiperazin-1-yl)-5-methyl-6-oxo-5,6-dihydro-1,5-naphthyridine-2-carbonitrile (1312-1313); 8-((2S,5R)-4-(1-(4-fluoro-2-(methoxymethyl)phenyl)ethyl)-2,5-dimethylpiperazin-1-yl)-5-methyl-6-oxo-5,6-dihydro-1,5-naphthyridine-2-carbonitrile (1314-1315); 8-((2S,5R)-4-(1-(4-fluoro-3-(methoxymethyl)phenyl)ethyl)-2,5-dimethylpiperazin-1-yl)-5-methyl-6-oxo-5,6-dihydro-1,5-naphthyridine-2-carbonitrile (1316-1317); 8-((2S,5R)-4-(1-(4-fluorophenyl)-2-(methylthio)ethyl)-2,5-dimethylpiperazin-1-yl)-5-methyl-6-oxo-5,6-dihydro-1,5-naphthyridine-2-carbonitrile (1318-1319); 8-((2S,5R)-4-(1-(4-cyano-3-(2-methoxyethoxy)phenyl)ethyl)-2,5-dimethylpiperazin-1-yl)-5-methyl-6-oxo-5,6-dihydro-1,5-naphthyridine-2-carbonitrile (1320-1321); 8-((2S,5R)-4-(1-(4-cyano-3-(2-(dimethylamino)ethoxy)phenyl)ethyl)-2,5-dimethylpiperazin-1-yl)-5-methyl-6-oxo-5,6-dihydro-1,5-naphthyridine-2-carbonitrile (1322-1323); 8-((2S,5R)-4-(1-(6-isopropoxypyridin-3-yl)ethyl)-2,5-dimethylpiperazin-1-yl)-5-methyl-6-oxo-5,6-dihydro-1,5-naphthyridine-2-carbonitrile (1324-1325); 8-((2S,5R)-4-(2-(3-cyclopropyl-1,2,4-oxadiazol-5-yl)-1-(4-fluorophenyl)ethyl)-2,5-dimethylpiperazin-1-yl)-5-methyl-6-oxo-5,6-dihydro-1,5-naphthyridine-2-carbonitrile (1326-1327); 8-((2S,5R)-5-ethyl-2-methyl-4-(1-(4-(trifluoromethoxy)phenyl)ethyl)piperazin-1-yl)-7-fluoro-5-methyl-6-oxo-5,6-dihydro-1,5-naphthyridine-2-carbonitrile (1328-1329); 8-((2S,5R)-4-(4-(difluoromethoxy)benzyl)-5-ethyl-2-methylpiperazin-1-yl)-5-methyl-6-oxo-5,6-dihydro-1,5-naphthyridine-2-carbonitrile (1330); 8-((2S,5R)-4-(4-chloro-2-fluorobenzyl)-5-ethyl-2-methylpiperazin-1-yl)-5-methyl-6-oxo-5,6-dihydro-1,5-naphthyridine-2-carbonitrile (1331); 8-((2S,5R)-5-ethyl-4-(3-fluoro-4-(trifluoromethoxy)benzyl)-2-methylpiperazin-1-yl)-5-methyl-6-oxo-5,6-dihydro-1,5-naphthyridine-2-carbonitrile (1332); 8-((2S,5R)-4-((4-fluorophenyl)(2-(trifluoromethyl)thiazol-4-yl)methyl)-2,5-dimethylpiperazin-1-yl)-5-methyl-6-oxo-5,6-dihydro-1,5-naphthyridine-2-carbonitrile (1333-1334); 8-((2S,5R)-4-(bis(4-(hydroxymethyl)phenyl)methyl)-2,5-dimethylpiperazin-1-yl)-5-methyl-6-oxo-5,6-dihydro-1,5-naphthyridine-2-carbonitrile (1335); 8-((2S,5R)-4-((4-cyanophenyl)(4-fluorophenyl)methyl)-2,5-dimethylpiperazin-1-yl)-6-oxo-5,6-dihydro-1,5-naphthyridine-2-carbonitrile (1336-1337); 8-((2S,5R)-4-((4-cyclopropylthiazol-2-yl)(4-fluorophenyl)methyl)-5-ethyl-2-methylpiperazin-1-yl)-5-methyl-6-oxo-5,6-dihydro-1,5-naphthyridine-2-carbonitrile (1338-1339); 8-((2S,5R)-4-(1-(4-cyclopropyl-2-fluorophenyl)ethyl)-5-ethyl-2-methylpiperazin-1-yl)-5-methyl-6-oxo-5,6-dihydro-1,5-naphthyridine-2-carbonitrile (1340-1341); 8-((2S,5R)-4-(4-(difluoromethoxy)benzyl)-5-ethyl-2-methylpiperazin-1-yl)-5-methyl-6-oxo-5,6-dihydro-1,5-naphthyridine-2-carbonitrile (1342); 8-((2S,5R)-4-(1-(4-(difluoromethoxy)phenyl)ethyl)-5-ethyl-2-methylpiperazin-1-yl)-5-methyl-6-oxo-5,6-dihydro-1,5-naphthyridine-2-carbonitrile (1343-1344); 8-((2S,5R)-4-(1-(4-cyanophenyl)ethyl)-5-ethyl-2-methylpiperazin-1-yl)-5-methyl-6-oxo-5,6-dihydro-1,5-naphthyridine-2-carbonitrile (1345-1346); 8-((2S,5R)-5-ethyl-4-(2-fluoro-4-(trifluoromethoxy)benzyl)-2-methylpiperazin-1-yl)-5-methyl-6-oxo-5,6-dihydro-1,5-naphthyridine-2-carbonitrile (1347); 8-((2S,5R)-5-ethyl-4-(1-(4-isopropoxyphenyl)ethyl)-2-methylpiperazin-1-yl)-5-methyl-6-oxo-5,6-dihydro-1,5-naphthyridine-2-carbonitrile (1348-1349); 8-((2S,5R)-5-ethyl-4-(1-(4-methoxyphenyl)ethyl)-2-methylpiperazin-1-yl)-5-methyl-6-oxo-5,6-dihydro-1,5-naphthyridine-2-carbonitrile (1350-1351); 8-((2S,5R)-4-(1-(4-chloro-2-fluorophenyl)ethyl)-5-ethyl-2-methylpiperazin-1-yl)-5-methyl-6-oxo-5,6-dihydro-1,5-naphthyridine-2-carbonitrile (1352-1353); 8-((2S,5R)-2,5-diethyl-4-(3,4,5-trifluorobenzyl)piperazin-1-yl)-5-methyl-6-oxo-5,6-dihydro-1,5-naphthyridine-2-carbonitrile (1354); 8-((2S,5R)-4-(1-(4-cyclopropylphenyl)ethyl)-2,5-diethylpiperazin-1-yl)-5-methyl-6-oxo-5,6-dihydro-1,5-naphthyridine-2-carbonitrile (1355-1356); 8-((2S,5R)-4-(1-(4-cyclopropyl-2-fluorophenyl)ethyl)-2,5-diethylpiperazin-1-yl)-5-methyl-6-oxo-5,6-dihydro-1,5-naphthyridine-2-carbonitrile (1357-1358); 8-((2S,5R)-4-(1-(4-cyclopropyl-2-fluorophenyl)propyl)-2,5-diethylpiperazin-1-yl)-5-methyl-6-oxo-5,6-dihydro-1,5-naphthyridine-2-carbonitrile (1359-1360); 8-((2S,5R)-2,5-diethyl-4-((4-fluorophenyl)(2-(trifluoromethyl)thiazol-4-yl)methyl)piperazin-1-yl)-5-methyl-6-oxo-5,6-dihydro-1,5-naphthyridine-2-carbonitrile (1361-1362); 8-((2S,5R)-2,5-diethyl-4-(4-(trifluoromethoxy)benzyl)piperazin-1-yl)-5-methyl-6-oxo-5,6-dihydro-1,5-naphthyridine-2-carbonitrile (1363); 8-((2S,5R)-2,5-diethyl-4-(1-(2-fluoro-4-(trifluoromethyl)phenyl)ethyl)piperazin-1-yl)-5-methyl-6-oxo-5,6-dihydro-1,5-naphthyridine-2-carbonitrile (1364-1365); 8-((2S,5R)-2,5-diethyl-4-(1-(4-methoxyphenyl)ethyl)piperazin-1-yl)-5-methyl-6-oxo-5,6-dihydro-1,5-naphthyridine-2-carbonitrile (1366-1367); 8-((2S,5R)-4-(1-(2,2-difluorobenzo[d][1,3]dioxol-5-yl)ethyl)-2,5-diethylpiperazin-1-yl)-5-methyl-6- oxo-5,6-dihydro-1,5-naphthyridine-2-carbonitrile (1368-1369); 8-((2S,5R)-2,5-diethyl-4-(2-fluoro-4-(trifluoromethoxy)benzyl)piperazin-1-yl)-5-methyl-6-oxo-5,6-dihydro-1,5-naphthyridine-2-carbonitrile (1370); 8-((2S,5R)-2,5-diethyl-4-(1-(2-fluoro-4-trifluoromethoxy) phenyl)ethyl)piperazin-1-yl)-5-methyl-6-oxo-5,6-dihydro-1,5-naphthyridine-2-carbonitrile (1371-1372); 8-((2S,5R)-4-(1-(4-(difluoromethoxy)phenyl) ethyl)-2,5-diethylpiperazin-1-yl)-5-methyl-6-oxo-5,6-dihydro-1,5-naphthyridine-2-carbonitrile (1373-1374); 8-((2S,5R)-4-(1-(4-(difluoromethoxy)phenyl)ethyl)-2,5-dimethylpiperazin-1-yl)-5-methyl-6-oxo-5,6-dihydro-1,5-naphthyridine-2,7-dicarbonitrile (1375-1376); 8-((2S,5R)-2-ethyl-4-(1-(2-fluoro-4-(trifluoromethoxy)phenyl)propyl)-5-methylpiperazin-1-yl)-5-methyl-6-oxo-5,6-dihydro-1,5-naphthyridine-2-carbonitrile (1377-1378); 8-((2S,5R)-4-(1-(4-(difluoromethoxy)phenyl)ethyl)-2-ethyl-5-methylpiperazin-1-yl)-5-methyl-6-oxo-5,6-dihydro-1,5-naphthyridine-2-carbonitrile (1379); 8-((2S,5R)-2-ethyl-4-(1-(2-fluoro-5-(trifluoromethoxy)phenyl)propyl)-5-methylpiperazin-1-yl)-5-methyl-6-oxo-5,6-dihydro-1,5-naphthyridine-2-carbonitrile (1380-1381); 8-((2S,5R)-2-ethyl-5-methyl-4-(1-(3,4,5-trifluorophenyl)ethyl)piperazin-1-yl)-5-methyl-6-oxo-5,6-dihydro-1,5-naphthyridine-2-carbonitrile (1382-1383); 8-((2S,5R)-2-ethyl-4-(1-(3-fluoro-5-(trifluoromethoxy)phenyl)ethyl)-5-methylpiperazin-1-yl)-5-methyl-6-oxo-5,6-dihydro-1,5-naphthyridine-2-carbonitrile (1384-1385); 8-((2S,5S)-5-(hydroxymethyl)-2-methyl-4-(1-(4-(trifluoromethoxy) phenyl)ethyl)piperazin-1-yl)-5-methyl-6-oxo-5,6-dihydro-1,5-naphthyridine-2-carbonitrile (1386-1387); 8-((2S,5S)-4-((4-fluorophenyl)(5-(trifluoromethyl)pyridin-2-yl)methyl)-5-(hydroxymethyl)-2-methylpiperazin-1-yl)-5-methyl-6-oxo-5,6-dihydro-1,5-naphthyridine-2-carbonitrile (1388-1389); 8-((2S,5S)-4-((2,2-difluorobenzo[d][1,3]dioxol-5-yl)methyl)-5-(hydroxymethyl)-2-methylpiperazin-1-yl)-5-methyl-6-oxo-5,6-dihydro-1,5-naphthyridine-2-carbonitrile (1390); 8-((2S,5S)-4-((4-fluorophenyl)(isoxazol-3-yl)methyl)-5-(hydroxymethyl)-2-methylpiperazin-1-yl)-5-methyl-6-oxo-5,6-dihydro-1,5-naphthyridine-2-carbonitrile (1391-1392); 8-((2S,5S)-4-((3-cyclopropyl-1,2,4-oxadiazol-5-yl)(4-fluorophenyl)methyl)-5-(methoxymethyl)-2-methylpiperazin-1-yl)-5-methyl-6-oxo-5,6-dihydro-1,5-naphthyridine-2-carbonitrile (1393-1394); 8-((2S,5S)-4-((4-cyclopropylthiazol-2-yl)(4-fluorophenyl)methyl)-5-(methoxymethyl)-2-methylpiperazin-1-yl)-5-methyl-6-oxo-5,6-dihydro-1,5-naphthyridine-2-carbonitrile (1395-1396); 8-((2S,5S)-5-(ethoxymethyl)-2-methyl-4-(1-(4-(trifluoromethoxy)phenyl)ethyl)piperazin-1-yl)-5-methyl-6-oxo-5,6-dihydro-1,5-naphthyridine-2-carbonitrile (1397-1398); 8-((2S,5S)-4-((4-fluorophenyl)(isoxazol-3-yl)methyl)-5-(methoxymethyl)-2-methylpiperazin-1-yl)-5-methyl-6-oxo-5,6-dihydro-1,5-naphthyridine-2-carbonitrile (1399-1400); 8-((2S,5S)-4-((4-fluorophenyl)(5-(trifluoromethyl)pyridin-2-yl)methyl)-5-(methoxymethyl)-2-methylpiperazin-1-yl)-5-methyl-6-oxo-5,6-dihydro-1,5-naphthyridine-2-carbonitrile (1401-1402); 8-((2S,5S)-5-(ethoxymethyl)-4-((4-fluorophenyl)(5-(trifluoromethyl)pyridin-2-yl)methyl)-2-methylpiperazin-1-yl)-5-methyl-6-oxo-5,6-dihydro-1,5-naphthyridine-2-carbonitrile (1403-1404); 8-((2S,5S)-5-((2-methoxyethoxy)methyl)-2-methyl-4-(1-(4-(trifluoromethoxy)phenyl) ethyl)piperazin-1-yl)-5-methyl-6-oxo-5,6-dihydro-1,5-naphthyridine-2-carbonitrile (1405-1406); 8-((2S,5S)-4-((2,2-difluorobenzo[d][1,3]dioxol-5-yl)methyl)-2-ethyl-5-(methoxymethyl)piperazin-1-yl)-5-methyl-6-oxo-5,6-dihydro-1,5-naphthyridine-2-carbonitrile (1407); 8-((2S,5S)-2-ethyl-5-(methoxymethyl)-4-(1-(4-(trifluoromethoxy)phenyl)ethyl)piperazin-1-yl)-5-methyl-6-oxo-5,6-dihydro-1,5-naphthyridine-2-carbonitrile (1408-1409); N-(((2S,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)methanesulfonamide (1410); 8-((2S,5R)-5-(cyanomethyl)-2-methyl-4-(1-(4-(trifluoromethoxy)phenyl)ethyl)piperazin-1-yl)-5-methyl-6-oxo-5,6-dihydro-1,5-naphthyridine-2-carbonitrile (1411-1412); 8-((2S,5R)-5-((dimethylamino) methyl)-2-methyl-4-(1-(4-(trifluoromethoxy)phenyl)ethyl) piperazin-1-yl)-5-methyl-6-oxo-5,6-dihydro-1,5-naphthyridine-2-carbonitrile (1413-1414); 5-methyl-8-((2S,5R)-2-methyl-5-(morpholinomethyl)-4-(1-(4-(trifluoromethoxy)phenyl)ethyl)piperazin-1-yl)-6-oxo-5,6-dihydro-1,5-naphthyridine-2-carbonitrile (1415-1416); 5-methyl-8-((2S,5R)-2-methyl-5-((4-methylpiperazin-1-yl)methyl)-4-(1-(4-(trifluoromethoxy) phenyl)ethyl) piperazin-1-yl)-6-oxo-5,6-dihydro-1,5-naphthyridine-2-carbonitrile (1417-1418); 8-((2R,5R)-2-(hydroxymethyl)-5-methyl-4-(1-(4-(trifluoromethoxy) phenyl)ethyl) piperazin-1-yl)-5-methyl-6-oxo-5,6-dihydro-1,5-naphthyridine-2-carbonitrile (1419-1420); 8-((2R,5R)-4-(bis(4-fluorophenyl)methyl)-2-(methoxymethyl)-5-methylpiperazin-1-yl)-5-methyl-6-oxo-5,6-dihydro-1,5-naphthyridine-2-carbonitrile (1421); 8-((2S,5R)-4-((4-cyanothiophen-2-yl)methyl)-2,5-dimethylpiperazin-1-yl)-5-methyl-6-oxo-5,6-dihydro-1,5-naphthyridine-2-carbonitrile (1422); 8-((2S,5R)-4-((1-cyclopropyl-1H-tetrazol-5-yl)methyl)-2,5-dimethylpiperazin-1-yl)-5-methyl-6-oxo-5,6-dihydro-1,5-naphthyridine-2-carbonitrile (1423); 8-((2S,5R)-2,5-dimethyl-4-((5-methylisoxazol-3-yl)methyl)piperazin-1-yl)-5-methyl-6-oxo-5,6-dihydro-1,5-naphthyridine-2-carbonitrile (1424); 8-((2S,5R)-2,5-dimethyl-4-((3-phenylisoxazol-5-yl)methyl)piperazin-1-yl)-5-methyl-6-oxo-5,6-dihydro-1,5-naphthyridine-2-carbonitrile (1425); 8-((2S,5R)-4-((3,5-dimethylisoxazol-4-yl)methyl)-2,5-dimethylpiperazin-1-yl)-5-methyl-6-oxo-5,6-dihydro-1,5-naphthyridine-2-carbonitrile (1426); 8-((2S,5R)-4-((3-(2-cyanophenyl)isoxazol-5-yl) methyl)-2,5-dimethylpiperazin-1-yl)-5-methyl-6-oxo-5,6-dihydro-1,5-naphthyridine-2-carbonitrile (1427); 8-((2S,5R)-4-(isoxazol-4-ylmethyl)-2,5-dimethylpiperazin-1-yl)-5-methyl-6-oxo-5,6-dihydro-1,5-naphthyridine-2-carbonitrile (1428); 8-((2S,5R)-4-((2-(3-fluorophenyl)-5-methyloxazol-4-yl)methyl)-2,5-dimethylpiperazin-1-yl)-5-methyl-6-oxo-5,6-dihydro-1,5-naphthyridine-2-carbonitrile (1429-1430); 8-((2S,5R)-2,5-dimethyl-4-((5-methylisoxazol-4-yl)methyl) piperazin-1-yl)-5-methyl-6-oxo-5,6-dihydro-1,5-naphthyridine-2-carbonitrile (1431); 8-((2S,5R)-4-((5-isopropyl-1,2,4-oxadiazol-3-yl) methyl)-2,5-dimethylpiperazin-1-yl)-5-methyl-6-oxo-5,6-dihydro-1,5-naphthyridine-2-carbonitrile (1432); 8-((2S,5R)-4-(benzo[d]isoxazol-3-ylmethyl)-2,5-dimethylpiperazin-1-yl)-5-methyl-6-oxo-5,6-dihydro-1,5-naphthyridine-2-carbonitrile (1433); 8-((2S,5R)-2,5-dimethyl-4-((2-(thiophen-2-yl)oxazol-4-yl)methyl)piperazin-1-yl)-5-methyl-6-oxo-5,6-dihydro-1,5-naphthyridine-2-carbonitrile (1434); 8-((2S,5R)-2,5-dimethyl-4-((1-methyl-1H-1,2,3-triazol-4-yl)methyl)piperazin-1-yl)-5-methyl-6-oxo-5,6-dihydro-1,5-naphthyridine-2-carbonitrile (1435); 8-((2S,5R)-2,5-dimethyl-4-((5-(trifluoromethyl)-1,3,4-oxadiazol-2-yl)methyl)piperazin-1-yl)-5-methyl-6-oxo-5,6-dihydro-1,5-naphthyridine-2-carbonitrile (1436); 8-((2S,5R)-2,5-dimethyl-4-(1-(5-methyl-1,3,4-oxadiazol-2-yl)ethyl) piperazin-1-yl)-5-methyl-6-oxo-5,6-dihydro-1,5-naphthyridine-2-carbonitrile (1437-1438); 8-((2S,5R)-4-(1-(4-(cyclopropylmethoxy)phenyl)propyl)-2,5-dimethylpiperazin-1-yl)-5-methyl-6-oxo-5,6-dihydro-1,5-naphthyridine-2-carbonitrile (1439-1440); 8-((2S,5R)-4-(1-

(4-(tert-butoxy)phenyl)ethyl)-2,5-dimethylpiperazin-1-yl)-5-methyl-6-oxo-5,6-dihydro-1,5-naphthyridine-2-carbonitrile (1441-1442); 8-((2S,5R)-4-(1-(4-(tert-butoxy)phenyl)propyl)-2,5-dimethylpiperazin-1-yl)-5-methyl-6-oxo-5,6-dihydro-1,5-naphthyridine-2-carbonitrile (1443-1444); 8-((2S,5R)-4-(1-(4-(2-cyclopropylethoxy)phenyl)propyl)-2,5-dimethylpiperazin-1-yl)-5-methyl-6-oxo-5,6-dihydro-1,5-naphthyridine-2-carbonitrile (1445-1446); 8-((2S,5R)-5-ethyl-4-(1-(4-isopropoxyphenyl)propyl)-2-methylpiperazin-1-yl)-5-methyl-6-oxo-5,6-dihydro-1,5-naphthyridine-2-carbonitrile (1447-1448); 8-((2S,5R)-4-(1-(4-isopropoxyphenyl)propyl)-2,5-dimethylpiperazin-1-yl)-5-methyl-6-oxo-5,6-dihydro-1,5-naphthyridine-2-carbonitrile (1449-1450); 8-((2S,5R)-4-(1-(4-(cyclopropylmethoxy)phenyl)propyl)-5-ethyl-2-methylpiperazin-1-yl)-5-methyl-6-oxo-5,6-dihydro-1,5-naphthyridine-2-carbonitrile (1451); 8-((2S,5R)-4-(1-(4-(2-hydroxy-2-methylpropoxy)phenyl)propyl)-2,5-dimethylpiperazin-1-yl)-5-methyl-6-oxo-5,6-dihydro-1,5-naphthyridine-2-carbonitrile (1452); 8-((2S,5R)-4-(1-(4-(2-cyclopropylethoxy)phenyl)propyl)-5-ethyl-2-methylpiperazin-1-yl)-5-methyl-6-oxo-5,6-dihydro-1,5-naphthyridine-2-carbonitrile (1453); or 8-((2S,5R)-4-(1-(4-fluorophenyl)cyclopropyl)-2,5-dimethylpiperazin-1-yl)-5-methyl-6-oxo-5,6-dihydro-1,5-naphthyridine-2-carbonitrile (1454).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group ═O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "C$_{1-4}$ fluoroalkyl" is intended to include C$_1$, C$_2$, C$_3$, and C$_4$ alkyl groups substituted with one or more fluorine atoms. Representative examples of fluoroalkyl groups include, but are not limited to, —CF$_3$ and —CH$_2$CF$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and C$_{1-4}$ hydroxy alkyl.

The term "alkenyl" refers to a straight or branched chain hydrocarbon radical containing from 2 to 12 carbon atoms and at least one carbon-carbon double bond. Exemplary such groups include ethenyl or allyl. For example, "C$_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "C$_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" as used herein is intended to include a cycloalkyl group substituted with one or more fluorine atoms.

The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The terms "carbocyclo", "carbocyclic" or "carbocyclyl" may be used interchangeably and refer to cyclic groups having at least one saturated or partially saturated non-aromatic ring wherein all atoms of all rings are carbon. The carbocyclyl ring may be unsubstituted or may contain one or more substituents as valence allows. Thus, the term includes nonaromatic rings such as for example, cycloalkyl, cycloalkenyl, and cycloalkynyl rings. Exemplary bicyclic carbocyclyl groups include, indanyl, indenyl, dihydronaphthalenyl, tetrahydronaphthenyl, hexahydronaphthalenyl, octahydronaphthalenyl, decahydronaphthalenyl, bicycloheptanyl, bicyclooctanyl, and bicyclononanyl.

The term "aryl" as used herein, refers to a group of atoms derived from a molecule containing aromatic ring(s) by removing one hydrogen that is bonded to the aromatic ring(s). Representative examples of aryl groups include, but are not limited to, phenyl and naphthyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having at least one saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or tribaloacetic acid, for example, trifluoroacetic acid), adipates, alginates, ascorbates, aspartates, benzoates, benzenesulfonates, hi sulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, pi crates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethyl amine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor of DGKα and/or DGKζ, or effective to treat or prevent viral infections and proliferative disorders, such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol poly ethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The compounds of Formula (I) are useful for the treatment of cancer.

In another embodiment, the present invention provides a combined preparation of a compound of Formula (I), and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with DGK target inhibition in T cells.

In another aspect, the invention provides a method of treating a patient suffering from or susceptible to a medical condition that is associated with DGK target inhibition in T cells. A number of medical conditions can be treated. The method comprises administering to the patient a therapeutically effective amount of a composition comprising a compound of Formula (I) and/or a pharmaceutically acceptable salt thereof, a stereoisomer thereof or a tautomer thereof. For example, the compounds described herein may be used to treat or prevent viral infections and proliferative diseases such as cancer.

The compounds for Formula (I) and pharmaceutical compositions comprising at least one compound of Formula (I) are useful in treating or preventing any disease or conditions that are associated with DGK target inhibition in T cells. These include viral and other infections (e.g., skin infections, GI infection, urinary tract infections, genito-urinary infections, systemic infections), and proliferative diseases (e.g., cancer). The compounds of Formula (I) and pharmaceutical compositions comprising in at least one compound of Formula (I) may be administered to animals, preferably mammals (e.g., domesticated animals, cats, dogs, mice, rats), and more preferably humans. Any method of administration may be used to deliver the compound or pharmaceutical composition to the patient. In certain embodiments, the compound of Formula (I) or pharmaceutical composition comprising at least compound of Formula (I) is administered orally. In other embodiments, the Formula (I) or pharmaceutical composition comprising at least compound of Formula (I) is administered parenterally.

The compounds of Formula (I) can inhibit activity of the diacylglycerol kinase alpha and zeta (DGKα/ζ). For example, the compounds of Formula (I) can be used to inhibit activity of DGKα and DGKζ in a cell or in an individual in need of modulation of DGKα and DGKζ by administering an inhibiting amount of a compound of Formula (I) or a salt thereof.

The present invention further provides methods of treating diseases associated with activity or expression, including abnormal activity and/or overexpression, of DGKα and DGKζ in an individual (e.g., patient) by administering to the individual in need of such treatment a therapeutically effective amount or dose of a compound of Formula (I) or a pharmaceutical composition thereof. Example diseases can include any disease, disorder or condition that is directly or indirectly linked to expression or activity of DGKα and DGKζ enzyme, such as over expression or abnormal activity. A DGKα and DGKζ-associated disease can also include any disease, disorder or condition that can be prevented, ameliorated, or cured by modulating DGKα and DGKζ enzyme activity. Examples of DGKα and DGKζ associated diseases include cancer and viral infections such as HIV infection, hepatitis B, and hepatitis C.

In one aspect, the compound(s) of Formula (I) are sequentially administered prior to administration of the immuno-oncology agent. In another aspect, compound(s) of Formula (I) are administered concurrently with the immuno-oncology agent. In yet another aspect, compound(s) of Formula (I) are sequentially administered after administration of the immuno-oncology agent.

In another aspect, compounds of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD 137), 4-1BBL, ICOS, ICOS-L, OX40, OX40L, GITR, GITRL, CD70, CD27, CD40, DR3 and CD28H.

Other agents that can be combined with compounds of Formula (I) for the treatment of cancer include antagonists of inhibitory receptors on NK cells or agonists of activating receptors on NK cells. For example, compounds of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WG2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO 11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, BMS-986205, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the DGKα and DGKζ enzyme with a compound of Formula (I) includes the administration of a compound of the present invention to an individual or patient, such as a human, having DGKα and DGKζ, as well as, for example, introducing a compound of Formula (I) into a sample containing a cellular or purified preparation containing DGKα and DGKζ enzyme.

The term "DGKα and DGKζ inhibitor" refers to an agent capable of inhibiting the activity of diacylglycerol kinase alpha and/or diacylglycerol kinase zeta (DGKα and DGKζ) in T cells resulting in T cell stimulation. The DGKα and DGKζ inhibitor may be a reversible or irreversible DGKα and DGKζ inhibitor. "A reversible DGKα and DGKζ inhibitor" is a compound that reversibly inhibits DGKα and DGKζ enzyme activity either at the catalytic site or at a non-catalytic site and "an irreversible DGKα and DGKζ inhibitor" is a compound that irreversibly destroys DGKα and DGKζ enzyme activity by forming a covalent bond with the enzyme.

Types of cancers that may be treated with the compound of Formula (I) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of Formula (I) for treatment of DGKα and DGKζ associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of Formula (I) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds of Formula (I) may also be combined with immunotherapy drugs, including cytokines such as interferon alpha, interleukin 2, and tumor necrosis factor (TNF) in the treatment of melanoma.

Compounds of Formula (I) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of Formula (I), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 38.9° C. to 40° C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epipodophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., Clin. Cancer Res., 1:1311-1318 (1995)], and Abgenix: ABX-EGF); (iii) her-2/neu receptor inhibitors such as farnesyl transferase inhibitors (FTI) such as, for example, L-744,832 (Kohl et al., Nat. Med, 1(8):792-797 (1995)); (iv) inhibitors of Akt family kinases or the Akt pathway, such as, for example, rapamycin (see, for example, Sekulic et al., Cancer Res., 60:3504-3513 (2000)); (v) cell cycle kinase inhibitors such as, for example, flavopiridol and UCN-O1 (see, for example, Sausville, Curr. Med Chem. Anti-Canc. Agents, 3:47-56 (2003)); and (vi) phosphatidyl inositol kinase inhibitors such as, for example, LY294002 (see, for example, Vlahos et al., J. Biol. Chem., 269:5241-5248 (1994)). Alternatively, at least one STI and at least one compound of Formula (I) may be in separate pharmaceutical compositions. In a specific embodiment of the present invention, at least one compound of Formula (I) and at least one STI may be administered to the patient concurrently or sequentially. In other words, at least one compound of Formula (I) may be administered first, at least one STI may be administered first, or at least one compound of Formula (I) and at least one STI may be administered at the same time. Additionally, when more than one compound of Formula (I) and/or STI is used, the compounds may be administered in any order.

The present invention further provides a pharmaceutical composition for the treatment of a chronic viral infection in a patient comprising at least one compound of Formula (I), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present invention, at least one compound of Formula (I) and at least one chemotherapeutic agent are administered to the patient concurrently or sequentially. In other words, at least one compound of Formula (I) may be administered first, at least one chemotherapeutic agent may be administered first, or at least one compound of Formula (I) and the at least one STI may be administered at the same time. Additionally, when more than one compound of Formula (I) and/or chemotherapeutic agent is used, the compounds may be administered in any order. Similarly, any antiviral agent or STI may also be administered at any point in comparison to the administration of the compound of Formula (I).

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

Suitable antiviral agents contemplated for use in combination with the compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir; BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-S-(1-methylethyl)-6-(phenylmethyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir; DMP-450; BMS-2322623; ABT-378; and AG-1549. Other antiviral agents include hydroxyurea, ribavirin, IL-2, IE-12, pentafuside and Yissum Project No. 11607.

The present invention also includes pharmaceutical kits useful, for example, in the treatment or prevention of DGKα and DGKζ-associated diseases or disorders, and other diseases referred to herein which include one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The invention also provides pharmaceutically acceptable compositions which comprise a therapeutically effective amount of one or more of the compounds of Formula (I), formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms; and not injurious to the patient.

The term "pharmaceutical composition" means a composition comprising a compound of the invention in combination with at least one additional pharmaceutically acceptable carrier.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. L gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the therapeutic effect and gradually increase the dosage until the effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1 or I1, Int. 2 or I2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety. $^1$H NMR data collected in deuterated dimethyl sulfoxide used water suppression in the data processing. The reported spectra are uncorrected for the effects of water suppression. Protons adjacent to the water suppression frequency of 3.35 ppm exhibit diminished signal intensity.

ABBREVIATIONS

Ac acetyl
ACN acetonitrile
AcOH acetic acid
$Ac_2O$ acetic anhydride
anhyd. anhydrous
aq. aqueous
Bn benzyl
BOC tert-butoxy carbonyl
BOP benzotriazol-1-yloxytris-(dimethylamino)-phosphonium hexafluorophosphate
Bu butyl
CV Column Volumes
DAST diethylaminosulfur trifluoride
DCM dichloromethane
DEA diethylamine
DIEA or DIPEA diisopropylethylamine
DMA N,N-dimethylacetamide
DMAP 4-dimethylaminopyridine
DMF dimethylformamide
DMSO dimethyl sulfoxide
dppf 1,1'-bis(diphenylphosphino)ferrocene
Et ethyl
EtOAc ethyl acetate
$Et_2O$ diethyl ether
EtOH ethanol
$Et_3N$ triethyl amine
h, hours or hrs hour(s)
HATU (1-[bis(dimethylamino)methylene]-1H-1,2,3-triazolo[4,5-b]pyridinium 3-oxid hexafluorophosphate)
HCl hydrochloric acid
HPLC high pressure liquid chromatography
KHMDS potassium bis(trimethylsilyl)amide
KOAc potassium acetate
LAH lithium aluminum hydride
EC liquid chromatography
LCMS liquid chromatography-mass spectrometry
M molar
mM millimolar
Me methyl
MeI methyl iodide
MeOH methanol
Mesyl-Cl methanesulfonyl chloride
MHz megahertz
mins minute(s)
$M^{+1}$ $(M+H)^+$
MS mass spectrometry
n or N normal
MBS A-bromosuccinimide
NCS N-chlorosuccinimide
$NH_4OAC$ ammonium acetate
nM nanomolar
NMP A-methyl pyrrolidinone
$Pd_2(dba)_3$ tris-(dibenzylideneacetone)dipalladium
$PdCl_2(dppf)$ [1,1'-bis(diphenylphosphino)ferrocene]dichloropalladium(II)
$Pd(PPh_3)_4$ tetrakis(triphenylphosphine)palladium
pet ether petroleum ether
Ph phenyl
$POCl_3$ phosphorous oxychloride
rt or Ret time retention time
sat. saturated Selectfluor® 1-chloromethyl-4-fluoro-1,4-diazoniabicyclo[2.2.2]octane bis(tetrafluoroborate)
t-BuOH tertiary butanol
TBAI tetrabutylammonium iodide
TEA triethylamine
TFA trifluoroacetic acid
TFAA trifluoroacetic anhydride
THF tetrahydrofuran
TEC thin layer chromatography
TMS-OTf trimethylsilyl triflate
Xantphos 4,5-bis(diphenylphosphino)-9,9 dimethylxanthene Intermediate 1

1-(tert-butyl) 3-methyl 4-(bis(4-fluorophenyl)methyl)piperazine-1,3-dicarboxylate

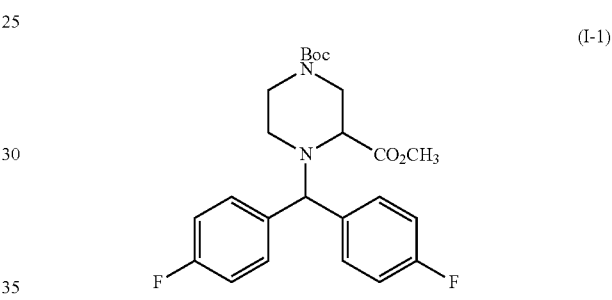

(I-1)

To a solution of 4,4'-(chloromethylene)bis(fluorobenzene) (1.5 g, 6.29 mmol) in acetonitrile (15 mL) was added 1-(tert-butyl) 3-methyl piperazine-1,3-dicarboxylate (1.842 g, 7.54 mmol), followed by DIPEA (3.29 mL, 18.86 mmol). The reaction mixture was stirred at 85° C. overnight. The reaction mixture was concentrated under reduced pressure to remove the volatiles and the residue was dissolved in ethyl acetate (150 mL) and washed with water. The aqueous layer was back-extracted with ethyl acetate (100 mL×2). The combined organic layer was washed with brine, dried over $Na_2SO_4$, filtered and the filtrate was concentrated under reduced pressure to give the crude product. The crude residue was purified via silica gel chromatography on ISCO® (5-10% EtOAc/petroleum ether; 40 g column) to afford the 1-(tert-butyl) 3-methyl 4-(bis(4-fluorophenyl)methyl)piperazine-1,3-dicarboxylate (2.15 g, 4.82 mmol, 77% yield). LCMS: m/z=447.4 (M+H); rt 2.16 min. (LCMS Method: Column: Waters Acquity UPLC BEH C18 (2.1×50 mm) 1.7 μm, Mobile phase A: 10 mM ammonium acetate: acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Intermediate 2 tert-butyl 4-(bis(4-fluorophenyl)methyl)-3-(hydroxymethyl)piperazine-1-carboxylate

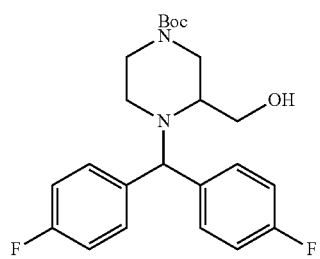

(I-2)

To a solution of 1-(tert-butyl) 3-methyl 4-(bis(4-fluorophenyl)methyl)piperazine-1,3-dicarboxylate (1.0 g, 2.24 mmol) in ethanol (20 mL) at room temperature were added NaBH$_4$ (0.85 g, 22.4 mmol) and calcium chloride (1.24 g, 11.2 mmol). The reaction mixture was stirred at room temperature for 24 h. The reaction mixture was filtered through a celite pad and the filtrate was concentrated under reduced pressure to give the crude product. The crude product was purified by silica gel column chromatography using 24 g flash column, eluting with 50-80% EtOAc in petroleum ether. The fractions were concentrated under reduced pressure to yield tert-butyl 4-(bis(4-fluorophenyl)methyl)-3-(hydroxymethyl)piperazine-1-carboxylate (535 mg, 57.1% yield). LCMS: m/z=419.2 (M+H); rt 3.304 min. (LCMS Method: Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 4

(1-(bis(4-fluorophenyl)methyl)piperazin-2-yl)methanol, HCl

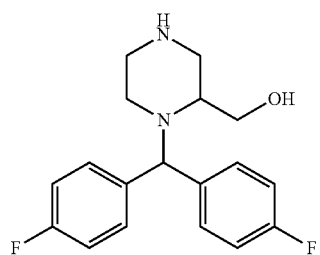

(I-4)

To a solution of tert-butyl 4-(bis(4-fluorophenyl)methyl)-3-(hydroxymethyl) piperazine-1-carboxylate (50 mg, 0.12 mmol) in DCM (1 mL) was added HCl (0.3 mL, 1.2 mmol, 4 M in dioxane) and the reaction mixture was stirred for 3 h. The reaction mixture was evaporated under reduced pressure and the crude product was triturated with hexane. The solid was filtered through sintered funnel, dried under vacuum to yield the HCl salt of (1-(bis(4-fluorophenyl)methyl)piperazin-2-yl)methanol (41 mg, 96% yield). LCMS: m/z=319.2 (M+H); rt 2.28 min. (LCMS Method: Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Examples 1 and 2

8-(4-(bis(4-fluorophenyl)methyl)-3-(hydroxymethyl)piperazin-1-yl)-5-methyl-6-oxo-5,6-dihydro-1,5-naphthyridine-2-carbonitrile

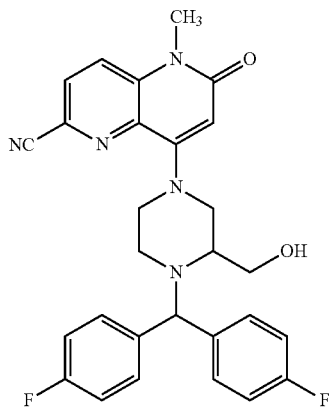

(I-2)

To a stirred solution of 6-cyano-1-methyl-2-oxo-1,2-dihydro-1,5-naphthyridin-4-yl trifluoromethanesulfonate (Intermediate 32) (100 mg, 0.300 mmol) in acetonitrile (3 mL) were added DIPEA (0.157 mL, 0.900 mmol) and (1-(bis(4-fluorophenyl)methyl) piperazin-2-yl) methanol (143 mg, 0.450 mmol). The reaction mixture was stirred at 85° C. overnight. The solvent was removed under reduced pressure and the residue was dissolved in ethyl acetate (100 mL). The organic layer was washed with brine, dried over Na$_2$SO$_4$ and concentrated under reduced pressure to yield the crude product, which was purified by preparative chiral HPLC (HPLC Method: Column: Sunfire C18, 150×19 mm ID, 5 µm; Mobile Phase A: 10 mM ammonium acetate in water; Mobile Phase B: acetonitrile; Gradient: 0-100% B over 18 minutes, then a 5 minute hold at 100% B; Flow: 17 mL/min) to yield peak-1 (Enantiomer 1) and peak-2 (Enantiomer 2). Fraction-1 (peak-1) was concentrated under reduced pressure and the residue was diluted with (EtOH/H$_2$O, 1:5) and lyophilized to yield Example 1 (2.7 mg, 1.7% yield); LCMS: m/z=502.2 (M+H); rt 1.977 min; (LCMS method: Column: XBridge BEH XP C18 (50×2.1 mm), 2.5p; Mobile phase A: 95% water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$): δ ppm 8.15 (d, J=8.8 Hz, 1H), 8.07 (d, J=8.8 Hz, 1H), 7.53 (dd, J=8.7, 5.7 Hz, 4H), 7.15 (q, J=8.8 Hz, 4H), 6.11 (s, 1H), 5.24 (s, 1H), 4.40 (br. s., 2H), 3.88 (d, J=11.0 Hz, 1H), 3.83-3.70 (m, 3H), 3.53 (s, 3H), 3.34 (br. s., 1H), 3.23 (br. s., 1H), 2.89-2.79 (m, 2H). Fraction-2 (peak-2) was concentrated under reduced pressure and the residue was diluted with (EtOH/H$_2$O, 1:5) and lyophilized to yield Example 2 (3.4 mg, 2.2% yield); LCMS: m/z=502.2 (M+H); rt 1.978 min; (LCMS Method: Column: XBridge BEH XP C18 (50×2.1 mm), 2.5 µm; Mobile phase A: 95% water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%). ¹H NMR (400 MHz, DMSO-$d_6$): δ ppm 8.7, 5.7 Hz, 4H), 7.15 (q, J=8.8 Hz, 4H), 6.11 (s, 1H), 5.24 (s, 1H), 4.40 (t, J=5.1 Hz, 1H), 3.89 (d, J=9.8 Hz, 1H), 3.81-3.67 (m, 3H), 3.53 (s, 3H), 3.35 (d, J=2.4 Hz, 1H), 3.26-3.19 (m, 1H), 2.91-2.80 (m, 3H).

Intermediate 5 tert-butyl (2S,5R)-4-(bis(4-fluorophenyl)methyl)-2,5-dimethylpiperazine-1-carboxylate

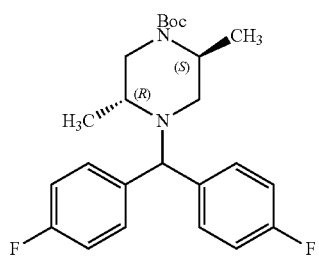

(I-5)

To a solution of 4,4'-(chloromethylene)bis(fluorobenzene) (3.76 g, 15.75 mmol) in acetonitrile (15 mL) was added tert-butyl (2S,5R)-2,5-dimethylpiperazine-1-carboxylate (2.25 g, 10.50 mmol), followed by DIPEA (5.50 mL, 31.5 mmol). The reaction mixture was stirred at 85° C. overnight. The reaction mixture was concentrated under reduced pressure to remove volatiles, the residue was dissolved in ethyl acetate (150 mL), and washed with water. The aqueous layer was back-extracted with ethyl acetate (100 mL×2). The combined organic layer was washed with brine, dried over $Na_2SO_4$ and concentrated under reduced pressure to give the crude product, which was purified by silica gel chromatography on ISCO® (5-10% EtOAc/petroleum ether; 80 g column) to afford tert-butyl (2S,5R)-4-(bis(4-fluorophenyl)methyl)-2,5-dimethylpiperazine-1-carboxylate (3.55 g, 81% yield). LCMS: m/z=417.4 (M+H); rt 1.561 min. (LCMS Condition: Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 6

(2R,5S)-1-(bis(4-fluorophenyl)methyl)-2,5-dimethylpiperazine hydrochloride

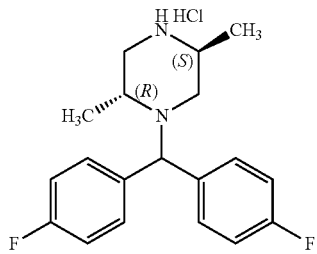

(I-6)

To a solution of tert-butyl (2S,5R)-4-(bis(4-fluorophenyl)methyl)-2,5-dimethylpiperazine-1-carboxylate (600 mg, 1.441 mmol) in DCM (10 mL) was added 4 M HCl (1.801 mL, 7.20 mmol) in dioxane. The reaction mixture was stirred at room temperature for 3 h. The reaction mixture was evaporated under reduced pressure and the crude material was triturated with hexane. The solid was filtered through a sintered funnel, dried under vacuum to yield the HCl salt of (2R,5S)-1-(bis(4-fluorophenyl) methyl)-2,5-dimethylpiperazine (437 mg, 86% yield). LCMS: m/z=317.4 (M+H); rt 1.53 min. (LCMS Condition: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Example 3

8-(2S,5R)-4-(bis(4-fluorophenyl)methyl)-2,5-dimethylpiperazin-1-yl)-5-methyl-6-oxo-5,6-dihydro-1,5-naphthyridine-2-carbonitrile

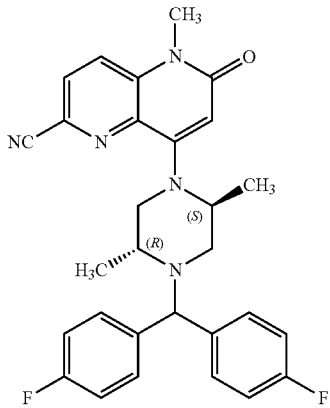

(3)

To a stirred solution of 6-cyano-1-methyl-2-oxo-1,2-dihydro-1,5-naphthyridin-d-yl trifluoromethanesulfonate (40 mg, 0.12 mmol) in acetonitrile (5 mL) were added DIPEA (0.063 mL, 0.360 mmol) and (2R,5S)-1-(bis(4-fluorophenyl)methyl)-2,5-dimethylpiperazine (57.0 mg, 0.18 mmol).

The reaction mixture was stirred at 80° C. overnight. The solvent was removed under reduced pressure and the residue was dissolved in ethyl acetate (15 mL). The organic layer was washed with brine, dried over Na$_2$SO$_4$ and concentrated under reduced pressure to yield the crude product, which was purified by preparative HPLC. (HPLC Method: Column: DAD 1: Bridge Phenyl (250 mm×4.6 mm) 5 μm, DAD-2: Inersil ODS (250 MM×4.6 MM) 5 μm, Flow: 2 mL/min; Mobile phase A: 10 mM ammonium acetate in water pH: 4.5, Mobile phase B: methanol:acetonitrile: 50:50, Gradient=60-100% B over 15 minute, then a 5 minute hold at 100% B; Temperature: 50° C.; Flow rate: 0.7 mL/min; Detection: UV at 220 nm. Fractions containing the product were combined and dried via centrifugal evaporation to afford 8-((2S,5R)-4-(bis(4-fluorophenyl)methyl)-2,5-dimethylpiperazin-1-yl)-5-methyl-6-oxo-5,6-dihydro-1,5-naphthyridine-2-carbonitrile (7.6 mg, 12.2% yield); LCMS: m/z, 500.3 (M+H); rt 2.47 min. (LCMS Method: Column: XBridge BEH XP C18 (50×2.1) mm, 2.5 μm; Mobile phase A: 95% Water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.14 (d, J=8.8 Hz, 1H), 8.06 (d, J=9.0 Hz, 1H), 7.67-7.49 (m, 4H), 7.24-7.04 (m, 4H), 6.00 (s, 1H), 4.70 (s, 1H), 4.58 (hr. s., 1H), 3.54-3.66 (m, 2H), 3.51 (s, 3H), 3.15-3.02 (m, 1H), 2.86 (dd, J=11.6, 3.5 Hz, 1H), 2.38-2.24 (m, 1H), 1.30 (d, J=6.4 Hz, 3H), 1.06 (d, J=6.4 Hz, 3H).

Intermediate 7 tert-butyl (2R,5S)-4-(bis(4-fluorophenyl)methyl)-2,5-dimethylpiperazine-1-carboxylate

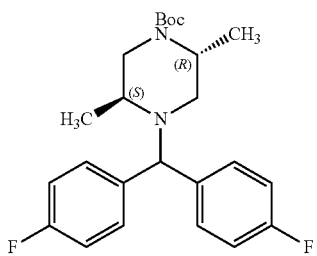

(I-7)

To a solution of bis(4-fluorophenyl)methyl trifluoromethanesulfonate (500 mg, 1.419 mmol) in acetonitrile (6 mL) was added tert-butyl (2R,5S)-2,5-dimethylpiperazine-1-carboxylate (365 mg, 1.703 mmol), followed by DIPEA (0.744 mL, 4.26 mmol). The reaction mixture was stirred at 85° C. overnight. The reaction mixture was concentrated under reduced pressure to remove volatiles, the residue was dissolved in ethyl acetate and washed with water. The aqueous layer was back-extracted with ethyl acetate (50 mL×2). The combined organic layer was washed with brine, dried over Na$_2$SO$_4$ and concentrated under reduced pressure. The crude residue was purified by silica gel chromatography on ISCO® (5-10% EtOAc/pet ether; 12 g column) to afford tert-butyl (2R,5S)-4-(bis(4-fluorophenyl)methyl)-2,5-dimethylpiperazine-1-carboxylate (195 mg, 33.0% yield); LCMS: m/z=417.2 (M+H); rt 4.125 min. (LCMS Condition: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 8

(2S,5R)-1-(bis(4-fluorophenyl)methyl)-2,5-dimethylpiperazine, HCl

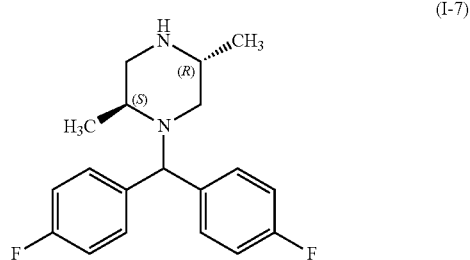

(I-7)

To a solution of tert-butyl (2R,5S)-4-(bis(4-fluorophenyl)methyl)-2,5-dimethylpiperazine-1-carboxylate (190 mg, 0.456 mmol) in DCM (10 mL) was added 4 M HCl (0.570 mL, 2.281 mmol) solution in dioxane. The reaction mixture was stirred for 3 h. The reaction mixture was evaporated under reduced pressure and the crude product was triturated with hexane. The solid was filtered through sintered funnel and dried under vacuum to yield the HCl salt of (2S,5R)-1-(bis(4-fluorophenyl)methyl)-2,5-dimethylpiperazine (142 mg, 88% yield); LCMS: m/z=317.4 (M+H); rt 1.33 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Example 4

8-((2R,5S)-4-(bis(4-fluorophenyl)methyl)-2,5-dimethylpiperazin-1-yl)-5-methyl-6-oxo-5,6-dihydro-1,5-naphthyridine-2-carbonitrile

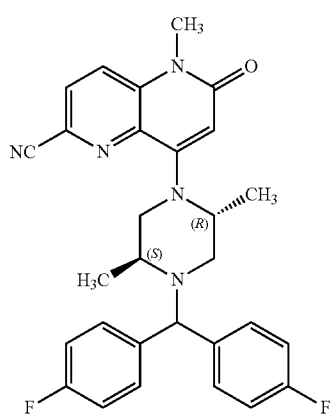

(4)

To a stirred solution of 6-cyano-1-methyl-2-oxo-1,2-dihydro-1,5-naphthyridin-d-yl trifluoromethanesulfonate (45.3 mg, 0.136 mmol) in acetonitrile (5 mL) were added DIPEA (0.06 mL, 0.34 mmol) and HCl salt of (2S,5R)-1-(bis(4-fluorophenyl)methyl)-2,5-dimethylpiperazine (40 mg, 0.113 mmol). The reaction mixture was stirred at 85° C. overnight. The solvent was removed under reduced pressure and the residue was dissolved in ethyl acetate (15 mL). The organic layer was washed with brine, dried over $Na_2SO_4$ and concentrated under reduced pressure. The crude material was purified via preparative HPLC. (HPLC Method: column: DAD 1: Bridge Phenyl (250 mm×4.6 mm) 5 μm; DAD-2: Inersil ODS (250 mm×4.6 mm) 5 μm; Flow: 2 mL/min; Mobile phase A: 10 mM ammonium acetate in water pH:4.5; Mobile phase B: methanol:acetonitrile: 50:50; Gradient=70-100% B over 15 minute, then a 5 minute hold at 100% B; Temperature: 50° C.; Detection: UV at 220 nm). Fractions containing the product were combined and dried via centrifugal evaporation to afford 8-((2R,5S)-4-(bis(4-fluorophenyl)methyl)-2,5-dimethylpiperazin-1-yl)-5-methyl-6-oxo-5,6-dihydro-1,5-naphthyridine-2-carbonitrile (8.6 mg, 15.19% yield); LCMS: m/z=500.3 (M+H); rt 2.398 min. (LCMS Method: Column: XBridge BEH XP C18 (50×2.1 mm), 2.5 μm; Mobile phase A: 95% Water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100). $^1$H NMR (400 MHz, DMSO-$d_6$) δ ppm 8.14 (d, J=8.8 Hz, 1H), 8.06 (d, J=8.8 Hz, 1H), 7.69-7.49 (m, 4H), 7.15 (q, J=8.8 Hz, 4H), 6.00 (s, 1H), 4.70 (s, 1H), 4.59 (br. s., 1H), 3.69 (d, J=12.7 Hz, 1H), 3.60-3.45 (m, 4H), 3.07 (d, J=7.1 Hz, 1H), 2.86 (dd, 7=11.9, 3.5 Hz, 1H), 2.33 (d, 7=11.2 Hz, 1H), 1.30 (d, 7=6.6 Hz, 3H), 1.06 (d, 7=6.6 Hz, 3H).

Example 5

4-((2R,5S)-4-(bis(4-fluorophenyl)methyl)-2,5-dimethylpiperazin-1-yl)-6-bromo-1-methyl-2-oxo-1,2-dihydro-1,5-naphthyridine-3-carbonitrile

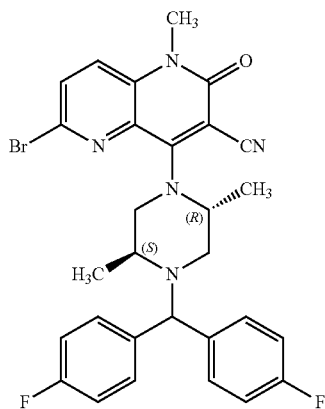

(5)

To a stirred solution of 6-bromo-3-cyano-1-methyl-2-oxo-1,2-dihydro-1,5-naphthyridin-4-yl trifluoromethanesulfonate (80 mg, 0.194 mmol) in acetonitrile (5 mL) were added DIPEA (0.102 mL, 0.582 mmol) and HCl salt of (2S,5R)-1-(bis(4-fluorophenyl)methyl)-2,5-dimethylpiperazine (75 mg, 0.214 mmol). The reaction mixture was stirred at 85° C. overnight. The solvent was removed under reduced pressure and the residue was dissolved in ethyl acetate (15 mL). The organic layer was washed with brine, dried over $Na_2SO_4$ and concentrated under reduced pressure. The crude residue purified by silica gel column chromatography using 24 g flash column, eluting with 50-80% EtOAc in petroleum ether. The fractions were concentrated under reduced pressure to yield 4-((2R,5S)-4-(bis(4-fluorophenyl)methyl)-2,5-dimethylpiperazin-1-yl)-6-bromo-1-methyl-2-oxo-1,2-dihydro-1,5-naphthyridine-3-carbonitrile (95 mg, 85% yield); LCMS: m/z=578.2 (M+H); rt 3.916 min.

Example 6

8-((2R,5S)-4-(bis(4-fluorophenyl)methyl)-2,5-dimethylpiperazin-1-yl)-5-methyl-6-oxo 5,6-dihydro-1,5-naphthyridine-2,7-dicarbonitrile

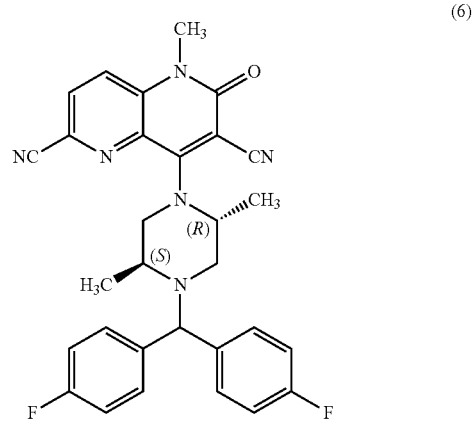

(6)

To a solution of 4-((2R,5S)-4-(bis(4-fluorophenyl)methyl)-2,5-dimethylpiperazin-1-yl)-6-bromo-1-methyl-2-oxo-1,2-dihydro-1,5-naphthyridine-3-carbonitrile (80 mg, 0.138 mmol) in NMP (3 mL) was added zinc (1.81 mg, 0.028 mmol), dppf (4.60 mg, 8.30 μmol), and zinc cyanide (32.5 mg, 0.277 mmol). The reaction mixture was degassed with $N_2$ followed by the addition of $Pd_2(dba)_3$ (12.66 mg, 0.014 mmol). The reaction mixture was heated to 80° C. for 3 h. The reaction mixture was diluted with water and extracted twice with ethyl acetate (20 mL). The combined organic layer was dried over $Na_2SO_4$ and evaporated to dryness under reduced pressure. The crude material was purified via preparative HPLC using the following conditions: Column: Sunfire C18, 19×150 mm, 5 μm particles; Mobile Phase A: 10 mM ammonium acetate; Mobile Phase B: acetonitrile; Gradient: 40-100% B over 20 minutes, then a 5 minute hold at 100% B; Flow: 19 mL/min. Fractions containing the product were combined and dried via centrifugal evaporation to afford 8-((2R,5S)-4-(bis(4-fluorophenyl)methyl)-2,5-dimethylpiperazin-1-yl)-5-methyl-6-oxo-5,6-dihydro-1,5-naphthyridine-2,7-dicarbonitrile (4.1 mg, 5.48% yield); LCMS: m/z=525.3 (M+H); rt 2.256 min. $^1$H NMR (400 MHz, DMSO-$d_6$) δ ppm 8.26 (d, J=8.8 Hz, 1H), 8.16 (d, J=9.0 Hz, 1H), 7.62 (dd, J=11.0, 8.6 Hz, 2H), 7.63 (dd, J=10.9, 8.7 Hz, 2H), 7.25-7.06 (m, 4H), 4.74 (s, 2H), 4.24 (d, J=10.5 Hz, 1H), 3.60-3.47 (m, 3H), 3.42 (d, J=12.0 Hz, 1H), 3.15-3.08 (m, 1H), 3.03 (br. s., 1H), 2.40 (d, J=11.5 Hz, 1H), 1.44 (d, J=6.6 Hz, 3H), 0.91 (d, J=6.4 Hz, 3H) ppm.

Intermediate 9 tert-butyl 4-(bis(4-fluorophenyl)methyl)-3-(fluoromethyl)piperazine-1-carboxylate

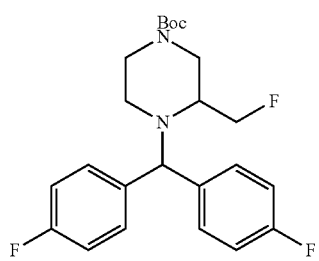

(I-9)

To a solution of tert-butyl 4-(bis(4-fluorophenyl)methyl)-3-(hydroxymethyl) piperazine-1-carboxylate (150 mg, 0.358 mmol) in DCM (5 mL) at 0° C. was added DAST (0.095 mL, 0.717 mmol) diluted with 2 mL DCM dropwise. The reaction mixture was warmed to room temperature and stirred for 5 h. The reaction mixture was diluted with DCM (20 mL) and washed with saturated aqueous NaHCO$_3$. The organic layer was dried over Na$_2$SO$_4$ and concentrated under reduced pressure to yield tert-butyl 4-(bis(4-fluorophenyl)methyl)-3-(fluoromethyl)piperazine-1-carboxylate; LCMS: m/z=421.2 (M+H); rt 4.114 min (LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 10

1-(bis(4-fluorophenyl)methyl)-2-(fluoromethyl)piperazine, HCl

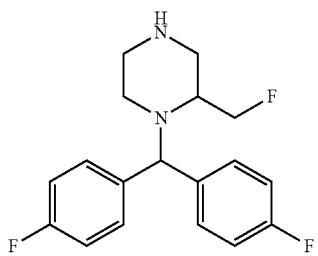

(I-10)

To a solution of tert-butyl 4-(bis(4-fluorophenyl)methyl)-3-(fluoromethyl) piperazine-1-carboxylate (180 mg, 0.428 mmol) in DCM (10 mL) was added HCl (2.14 mL, 4.28 mmol) as a 4 M solution in dioxane. The reaction mixture was stirred for 3 h, evaporated under reduced pressure and the crude material was triturated with hexane. The solid was filtered through sintered funnel, dried under vacuum to yield 1-(bis(4-fluorophenyl)methyl)-2-(fluoromethyl)piperazine, HCl (115 mg, 75% yield); LCMS: m/z=321.2 (M+H); rt 2.698 min (LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Example 8

8-(bis(4-fluorophenyl)methyl)-3-(fluoromethyl)piperazin-1-yl)-5-methyl-6-oxo-5,6-dihydro-1,5-naphthyridine-2-carbonitrile

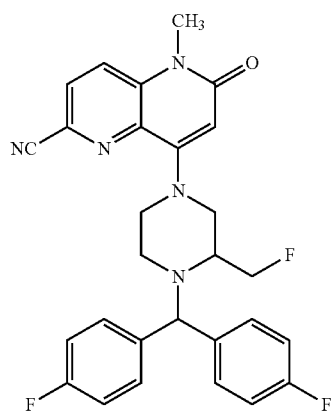

(8)

To a stirred solution of 6-cyano-1-methyl-2-oxo-1,2-dihydro-1,5-naphthyridin-d-yl trifluoromethanesulfonate (39.2 mg, 0.118 mmol) in acetonitrile (5 mL) were added DIPEA (0.044 mL, 0.252 mmol) and HCl salt of 1-(bis(4-fluorophenyl)methyl)-2-(fluoromethyl)piperazine (30 mg, 0.084 mmol). The reaction mixture was stirred at 85° C. overnight. The solvent was removed under reduced pressure and the residue was dissolved in ethyl acetate (15 mL). The organic layer was washed with brine, dried over Na$_2$SO$_4$ and concentrated under reduced pressure. The crude material was purified via preparative HPLC with the following conditions: Column: Sunfire C18, 19×150 mm, 5 μm particles; Mobile Phase A: 10 mM ammonium acetate pH-4.5 with acetic acid; Mobile Phase B: methanol:acetonitrile (1:1); Gradient: 50-100% B over 20 minutes, then a 5 minute hold at 100% B; Flow: 17 mL/min. Fractions containing the product were combined and dried via centrifugal evaporation to yield 8-(4-(bis(4-fluorophenyl) methyl)-3-(fluoromethyl)piperazin-1-yl)-5-methyl-6-oxo-5,6-dihydro-1,5-naphthyridine-2-carbonitrile (6.8 mg, 15.2% yield); LCMS: m/z=504.3 (M+H); rt 2.16 min (LCMS Method: Column: XBridge BEH XP C18 (50×2.1) mm, 2.5 μm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); $^1$H NMR (400 MHz, DMSO-d$_6$) δ ppm 8.17 (d, J=8.8 Hz, 1H), 8.07 (d, J=9.0 Hz, 1H), 7.55-7.33 (m, 4H), 7.21-7.05 (m, 4H), 6.08 (s, 1H), 5.06 (br. s., 1H), 4.94 (br. s., 1H), 4.89 (s, 1H), 4.43-4.31 (m, 1H), 4.28-4.20 (m, 1H), 3.77-3.62 (m, 2H), 3.54 (s, 3H), 2.26-2.91 (m, 4H).

Example 9

4-(4-(bis(4-fluorophenyl)methyl)-3-(fluoromethyl)piperazin-1-yl)-6-bromo-1-methyl-2-oxo-1,2-dihydro-1,5-naphthyridine-3-carbonitrile

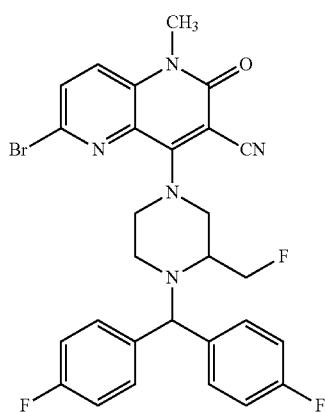

(9)

To a stirred solution of 6-bromo-3-cyano-1-methyl-2-oxo-1,2-dihydro-1,5-naphthyridin-4-yl trifluoromethanesulfonate (20 mg, 0.05 mmol) in acetonitrile (1 mL) were added DIPEA (0.025 mL, 0.146 mmol) and HCl salt of 1-(bis(4-fluorophenyl) methyl)-2-(fluoromethyl)piperazine (26.0 mg, 0.07 mmol). The reaction mixture was stirred at 85° C. for 12 h. The solvent was removed under reduced pressure and the residue was dissolved in ethyl acetate (10 mL). The organic layer was washed with brine, dried over $Na_2SO_4$ and concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0 minute hold at 15% B, 15-50% B over 25 minutes, then a 5 minute hold at 100% B; Flow Rate: 15 mL/min; Column Temperature: 25° C. Fractions containing the product were combined and dried via centrifugal evaporation to yield 4-(4-(bis(4-fluorophenyl)methyl)-3-(fluoromethyl)piperazin-1-yl)-6-bromo-1-methyl-2-oxo-1,2-dihydro-1,5-naphthyridine-3-carbonitrile (6.7 mg, 22.5% yield); LCMS: m/z=582.2 (M+H); rt 2.171 min (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$) δ ppm 7.96 (d, J=9.0 Hz, 1H), 7.90 (d, J=8.8 Hz, 1H), 7.59 (br. s., 4H), 7.24-7.04 (m, 4H), 5.31 (br. s., 1H), 4.20 (d, J=13.7 Hz, 1H), 4.09 (d, J=11.0 Hz, 1H), 3.64 (br. s., 2H), 3.52 (s, 3H), 3.26 (br. s., 1H), 3.18 (s, 2H), 2.88 (br. s., 1H), 2.61 (br. s., 1H).

Intermediate 11 tert-butyl (S)-4-(bis(4-fluorophenyl)methyl)-3-isopropylpiperazine-1-carboxylate

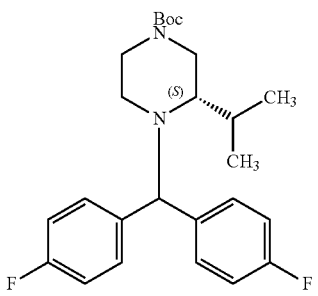

(I-11)

To a solution of 4,4'-(chloromethylene)bis(fluorobenzene) (0.784 g, 3.28 mmol) in acetonitrile (10 mL) was added tert-butyl (S)-3-isopropylpiperazine-1-carboxylate (0.5 g, 2.19 mmol), followed by DIPEA (1.147 mL, 6.57 mmol). The reaction mixture was stirred at 85° C. overnight. The reaction mixture was concentrated under reduced pressure to remove volatiles and the residue was dissolved in ethyl acetate and washed with water. The aqueous layer was back-extracted with ethyl acetate (20 mL×2). The combined organic layer was washed with brine, dried over $Na_2SO_4$ and concentrated under reduced pressure. The crude residue was purified by silica gel chromatography on ISCO® (5-10% EtOAc/petroleum ether; 24 g column) to afford the tert-butyl (S)-4-(bis(4-fluorophenyl)methyl)-3-isopropylpiperazine-1-carboxylate (425 mg, 45.1% yield); LCMS: m/z=431.2 (M+H); rt 2.215 min (LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 12

(S)-1-(bis(4-fluorophenyl)methyl)-2-isopropylpiperazine, HCl

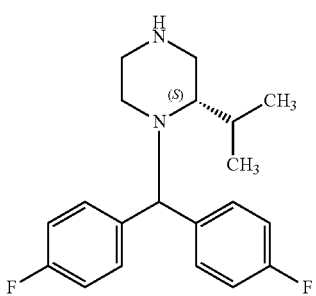

(I-12)

To a solution of tert-butyl (S)-4-(bis(4-fluorophenyl)methyl)-3-isopropylpiperazine-1-carboxylate (250 mg, 0.581 mmol) in DCM (1 mL) was added HCl (0.176 mL, 5.81 mmol) as a 4 M solution in dioxane. The reaction mixture was stirred for 3 h. The reaction mixture was evaporated under reduced pressure and the crude product was triturated with hexane. The solid was filtered through sintered funnel, dried under vacuum to yield the HCl salt of ((S)-1-(bis(4-fluorophenyl)methyl)-2-isopropylpiperazine. LCMS: m/z=331.4 (M+H); rt 1.54 min (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Example 10

(S)-8-(4-(bis(4-fluorophenyl)methyl)-3-isopropylpiperazin-1-yl)-5-methyl-6-oxo-5,6-dihydro-1,5-naphthyridine-2-carbonitrile

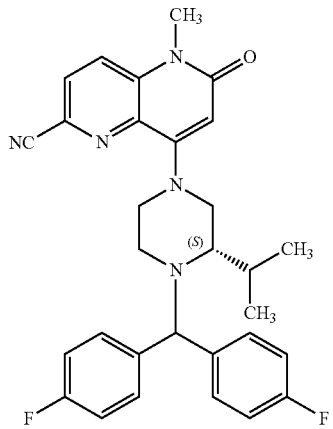

(3)

To a stirred solution of 6-cyano-1-methyl-2-oxo-1,2-dihydro-1,5-naphthyridin-4-yl trifluoromethanesulfonate (50 mg, 0.15 mmol) in acetonitrile (3 mL) were added DIPEA (0.079 mL, 0.450 mmol) and the HCl salt of (S)-1-(bis(4-fluorophenyl)methyl)-2-isopropylpiperazine (83 mg, 0.225 mmol). The reaction mixture was stirred at 85° C. overnight. The solvent was removed under reduced pressure and the residue was dissolved in ethyl acetate (15 mL). The organic layer was washed with brine, dried over $Na_2SO_4$ and concentrated under reduced pressure. The crude material was purified via preparative HPLC (HPLC Method: Column: Sunfire C18, 150×4.6 mm, 5 µm; Mobile Phase A: 0.05% TFA in water; Mobile Phase B: acetonitrile; Gradient: 0-100% B over 20 minutes, then a 5 minute hold at 100% B; Flow: 1 mL/min). Fractions containing the product were combined and dried via centrifugal evaporation to yield (S)-8-(4-(bis(4-fluorophenyl)methyl)-3-isopropylpiperazin-1-yl)-5-methyl-6-oxo-5,6-dihydro-1,5-naphthyridine-2-carbonitrile (48.2 mg, 61.9% yield); LCMS: m/z=514.3 (M+H); rt 2.521 min (LCMS Method: Column: XBridge BEH XP C18 (50×2.1 mm), 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100). $^1$H NMR (400 MHz, DMSO-$d_6$) δ ppm 8.16 (d, J=8.8 Hz, 1H), 8.08 (d, J=8.8 Hz, 1H), 7.58-7.42 (m, 4H), 7.26-7.03 (m, 4H), 6.12 (s, 1H), 5.50 (s, 1H), 3.82 (dd, J=12.7, 3.7 Hz, 1H), 3.62-3.47 (m, 4H), 3.36 (hr. s., 1H), 3.15-3.01 (m, 2H), 2.61-2.53 (m, 1H), 2.30-2.21 (m, 1H), 1.08 (d, J=6.6 Hz, 3H), 0.94 (d, J=6.6 Hz, 3H). One proton merged with DMSO-$d_6$.

Example 11

(S)-4-(4-(bis(4-fluorophenyl)methyl)-3-isopropylpiperazin-1-yl)-6-bromo-1-methyl-2-oxo-1,2-dihydro-1,5-naphthyridine-3-carbonitrile

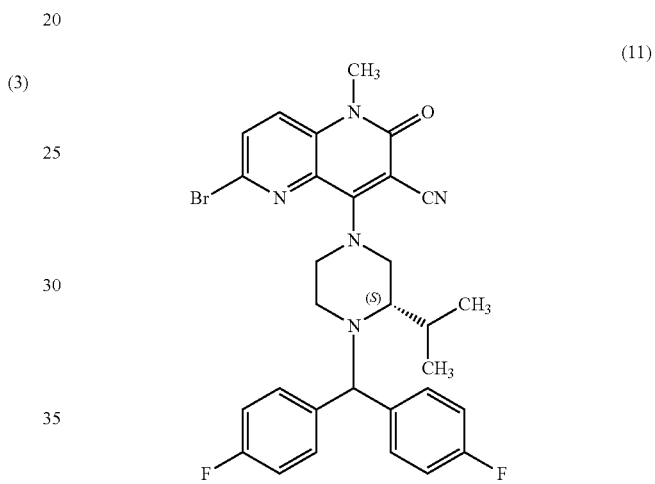

(11)

To a stirred solution of 6-bromo-3-cyano-1-methyl-2-oxo-1,2-dihydro-1,5-naphthyridin-4-yl trifluoromethanesulfonate (99 mg, 0.24 mmol) in acetonitrile (5 mL) were added DIPEA (0.114 mL, 0.654 mmol) and HCl salt of (S)-1-(bis(4-fluorophenyl) methyl)-2-isopropylpiperazine (80 mg, 0.22 mmol). The reaction mixture was stirred at 85° C. overnight. The solvent was removed under reduced pressure and the residue was dissolved in ethyl acetate (15 mL). The organic layer was washed with brine, dried over $Na_2SO_4$ and concentrated under reduced pressure. The crude residue was purified by silica gel column chromatography using 24 g flash column, eluting with 50-80% EtOAc in petroleum ether. The fractions were concentrated under reduced pressure to yield (S)-4-(4-(bis(4-fluorophenyl) methyl)-3-isopropylpiperazin-1-yl)-6-bromo-1-methyl-2-oxo-1,2-dihydro-1,5-naphthyridine-3-carbonitrile (79 mg, 0.133 mmol, 61.1% yield); LCMS: m/z=594.2 (M+H); rt 1.45 min (LCMS Method: Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Example 12

(S)-8-(4-(bis(4-fluorophenyl)methyl)-3-isopropylpiperazin-1-yl)-5-methyl-6-oxo-5,6-dihydro-1,5-naphthyridine-2,7-carbonitrile

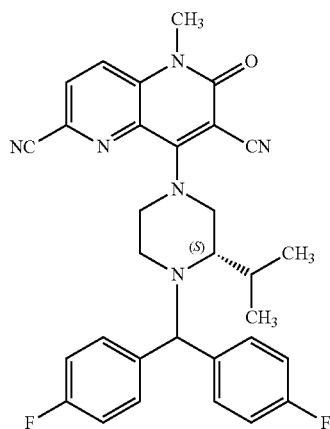

(12)

To a solution of (S)-4-(4-(bis(4-fluorophenyl)methyl)-3-isopropylpiperazin-1-yl)-6-bromo-1-methyl-2-oxo-1,2-dihydro-1,5-naphthyridine-3-carbonitrile (70 mg, 0.118 mmol) in NMP (5 mL) were added zinc (1.55 mg, 0.024 mmol), dppf (3.93 mg, 7.09 μmol) and zinc cyanide (27.7 mg, 0.236 mmol). The reaction mixture was degassed under $N_2$ and $Pd_2(dba)_3$ (10.82 mg, 0.012 mmol) was added. The reaction mixture was heated at 80° C. for 3 h. The reaction mixture was diluted with water and extracted twice with ethyl acetate (20 mL). The combined organic layer dried over $Na_2SO_4$ and evaporated to dryness under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 40% B, 40-73% B over 22 minutes, then a 5 minute hold at 100% B; Flow Rate: 15 mL/min; Column Temperature: 25° C. Fractions containing the product were combined and dried via centrifugal evaporation to yield (S)-8-(4-(bis(4-fluorophenyl)methyl)-3-isopropylpiperazin-1-yl)-5-methyl-6-oxo-5,6-dihydro-1,5-naphthyridine-2,7-dicarbonitrile (8.5 mg, 12.4% yield); LCMS: m/z=539.3 (M+H); rt 2.307 min (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.25 (d, J=9.0 Hz, 1H), 8.15 (d, J=9.0 Hz, 1H), 7.59-7.41 (m, 4H), 7.16 (td, J=8.9, 7.2 Hz, 4H), 5.56 (s, 1H), 4.26 (dd, J=13.3, 3.3 Hz, 1H), 3.91 (d, J=12.7 Hz, 1H), 3.80-3.67 (m, 2H), 3.53 (s, 3H), 3.41-3.32 (m, 1H), 2.60-2.53 (m, 1H), 2.48 (d, J=3.7 Hz, 1H), 2.26 (dd, J=14.4, 7.1 Hz, 1H), 1.06 (d, J=6.8 Hz, 3H), 0.71 (d, J=6.6 Hz, 3H).

Examples 15 and 16

4-(4-(bis(4-fluorophenyl)methyl)-3-(hydroxymethyl)piperazin-1-yl)-6-bromo-1-methyl-2-oxo-1,2-dihydro-1,5-naphthyridine-3-carbonitrile

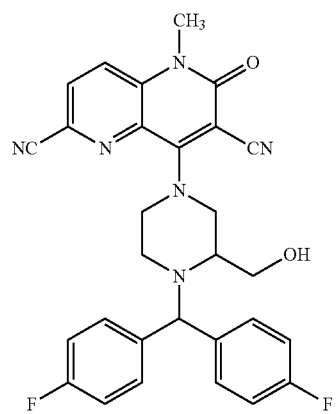

(15-16)

To a solution of 4-(4-(bis(4-fluorophenyl)methyl)-3-(hydroxymethyl)piperazin-1-yl)-6-bromo-1-methyl-2-oxo-1,2-dihydro-1,5-naphthyridine-3-carbonitrile (80 mg, 0.138 mmol) in NMP (5 mL) were added zinc (1.802 mg, 0.028 mmol), dppf (4.58 mg, 8.27 μmol) and zinc cyanide (32.4 mg, 0.276 mmol). The reaction mixture degassed under $N_2$ and $Pd_2(dba)_3$ (12.62 mg, 0.014 mmol) was added. The reaction mixture was heated to 80° C. for 3 h. The reaction mass diluted with water and extracted twice with ethyl acetate (20 mL). The combined organic layer dried over $Na_2SO_4$ and evaporated to dryness under reduced pressure. The crude material was purified via preparative HPLC. Fractions containing the product were combined and dried via centrifugal evaporation to yield 8-(4-(bis(4-fluorophenyl)methyl)-3-(hydroxymethyl)piperazin-1-yl)-5-methyl-6-oxo-5,6-dihydro-1,5-naphthyridine-2,7-dicarbonitrile (55 mg, 76% yield) as a racemic mixture. The racemic mixture was separated by chiral separation to enantiomers 1 and 2. Chiral separation (HPLC Method: Column: DAD-1: CELLULOSE-2 (250×4.6 mm), 5 micron; DAD-2 CELLULOSE-4 (250×4.6 mm), 5 μm; Mobile Phase: 0.1% DEA in methanol; Flow: 2 mL/min): Enantiomer 1 (Example 15, 5.4 mg, 9.8% yield); LCMS: m/z=527.2 (M+H); rt 1.888 min (HPLC Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$): δ ppm 8.26 (d, J=9.0 Hz, 1H), 8.16 (d, J=8.8 Hz, 1H), 7.58 (dd, J=8.1, 5.9 Hz, 4H), 7.27-7.04 (m, 4H), 5.24 (s, 1H), 4.43 (br. s., 1H), 4.21 (d, J=14.2 Hz, 1H), 4.12 (d, J=12.7 Hz, 1H), 3.89 (dd, J=13.0, 3.4 Hz, 1H), 3.69-3.45 (m, 6H), 3.12 (t, J=10.3 Hz, 1H), 2.84 (d, J=3.4 Hz, 1H), 2.66-2.56 (m, 1H). Enantiomer 2 (Peak −2) (Example 16, 4.1 mg, 7.36% yield); LCMS: m/z=527.2 (M+H); rt 1.888 min (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$): δ ppm 8.26 (d, J=8.8 Hz, 1H), 8.16 (d, J=8.8 Hz, 1H), 7.58 (dd, J=8.1, 5.9 Hz, 4H), 7.33-7.04 (m, 4H), 5.24 (s, 1H), 4.43 (t, J=5.1 Hz, 1H), 4.21 (d, J=14.2 Hz, 1H), 4.12 (d, J=12.7 Hz, 1H), 3.89 (dd, J=12.6, 3.1 Hz, 1H), 3.69-3.49 (m, 5H), 3.12 (t, J=10.4 Hz, 1H), 2.84 (d, J=4.2 Hz, 1H), 2.66-2.55 (m, 2H).

Example 17

4-(4-(bis(4-fluorophenyl)methyl)-3-(hydroxymethyl) piperazin-1-yl)-6-bromo-1-methyl-2-oxo-1,2-dihydro-1,5-naphthyridine-3-carbonitrile

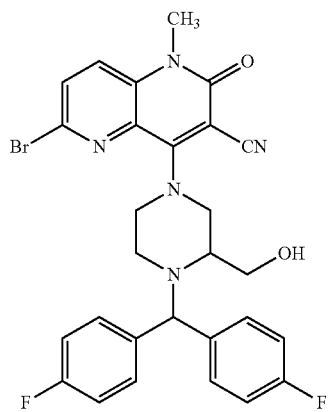

(17)

To a stirred solution of 6-bromo-3-cyano-1-methyl-2-oxo-1,2-dihydro-1,5-naphthyridin-4-yl trifluoromethanesulfonate (20 mg, 0.049 mmol) in acetonitrile (1 mL) were added DIPEA (0.025 mL, 0.146 mmol) and HCl salt of (1-(bis(4-fluorophenyl) methyl)piperazin-2-yl)methanol (20.6 mg, 0.058 mmol). The reaction mixture was stirred at 85° C. for 12 h. The solvent was removed under reduced pressure and the residue was dissolved in ethyl acetate (10 mL). The organic layer was washed with brine, dried over Na$_2$SO$_4$ and concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 0.1% TFA; Mobile Phase B: 95:5 acetonitrile:water with 0.1% trifluoroacetic acid; Gradient: a 0 minute hold at 15% B, 15-60% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 4-(4-(bis(4-fluorophenyl)methyl)-3-(hydroxymethyl) piperazin-1-yl)-6-bromo-1-methyl-2-oxo-1,2-dihydro-1,5-naphthyridine-3-carbonitrile (3.3 mg, 11.7% yield); LCMS: m/z=582.2 (M+H); rt 2.394 min (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%); $^1$H NMR (400 MHz, DMSO-d$_6$): δ ppm 7.98 (d, J=9.0 Hz, 1H), 7.92 (d, J=8.8 Hz, 1H), 7.50 (td, J=9.1, 5.5 Hz, 4H), 7.26-7.03 (m, 4H), 5.30 (d, J=3.9 Hz, 1H), 5.18 (d, J=5.1 Hz, 1H), 4.92 (s, 1H), 4.45-4.36 (m, 1H), 4.21 (dd, J=15.2, 8.8 Hz, 1H), 3.88-4.18 (m, 2H), 3.54 (s, 3H), 3.00-3.10 (m, 1H), 2.87-2.99 (m, 2H), 2.68-2.71 (m, 1H).

Example 18

8-((2S,5R)-4-(bis(4-fluorophenyl)methyl)-2,5-dimethylpiperazin-1-yl)-7-chloro-5-methyl-6-oxo-5,6-dihydro-1,5-naphthyridine-2-carbonitrile

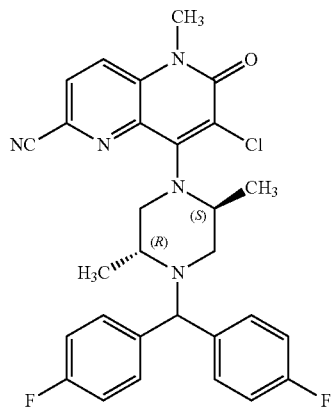

(18)

To a stirred solution of 8-((2S,5R)-4-(bis(4-fluorophenyl) methyl)-2,5-dimethylpiperazin-1-yl)-5-methyl-6-oxo-5,6-dihydro-1,5-naphthyridine-2-carbonitrile (50 mg, 0.1 mmol) in DCM (3 mL) was added NCS (26.7 mg, 0.2 mmol). The reaction mixture was stirred at room temperature overnight. The solvent was removed under reduced pressure and the residue was dissolved in ethyl acetate (20 mL). The organic layer was washed with, saturated aqueous NaHCO$_3$, brine, dried over Na$_2$SO$_4$ and concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 40% B, 40-79% B over 15 minutes, then a 5 minute hold at 100% B; Flow Rate: 15 mL/min; Column Temperature: 25° C. Fractions containing the product were combined and dried via centrifugal evaporation to yield 8-((2S,5R)-4-(bis(4-fluorophenyl)methyl)-2, 5-dimethylpiperazin-1-yl)-7-chloro-5-methyl-6-oxo-5,6-dihydro-1,5-naphthyridine-2-carbonitrile (39.6 mg, 72.6% yield); LCMS: m/z=534.2 (M+H); rt 2.554 min (LCMS Method: Column: XB ridge BEH XP C18 (50×2.1) mm, 2.5 μm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); $^1$H NMR (400 MHz, DMSO-d$_6$): δ ppm 8.25-8.10 (m, 2H), 7.59 (dd, J=7.6, 5.6 Hz, 4H), 7.15 (td, J=8.8, 4.6 Hz, 4H), 4.77 (s, 1H), 4.19 (d, J=9.8 Hz, 1H), 4.12 (br. s., 1H), 3.64 (s, 3H), 3.12 (dd, J=11.2, 3.7 Hz, 1H), 2.99-2.83 (m, 2H), 2.28 (d, J=9.0 Hz, 1H), 1.30 (d, J=6.6 Hz, 3H), 0.97 (d, J=6.1 Hz, 3H).

Example 19

8-((2S,5R)-4-(bis(4-fluorophenyl)methyl)-2,5-dimethylpiperazin-1-yl)-7-bromo-5-methyl-6-oxo-5,6-dihydro-1,5-naphthyridine-2-carbonitrile (19)

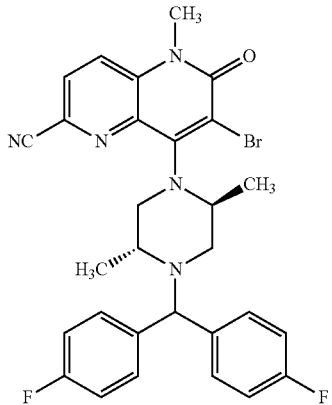

To a stirred solution of 8-((2S,5R)-4-(bis(4-fluorophenyl)methyl)-2,5-dimethylpiperazin-1-yl)-5-methyl-6-oxo-5,6-dihydro-1,5-naphthyridine-2-carbonitrile (300 mg, 0.601 mmol) in DMF (8 mL) was added NBS (160 mg, 0.901 mmol). The reaction mixture was stirred at room temperature for 2 h. The solvent was removed under reduced pressure and the residue was dissolved in ethyl acetate (50 mL). The organic layer was washed with brine, dried over $Na_2SO_4$ and concentrated under reduced pressure. The crude residue was purified via silica gel chromatography on ISCO® (40-80% EtOAc/Petroleum ether; 80 g column) to afford 8-((2S,5R)-4-(bis(4-fluorophenyl) methyl)-2,5-dimethylpiperazin-1-yl)-7-bromo-5-methyl-6-oxo-5,6-dihydro-1,5-naphthyridine-2-carbonitrile (305 mg, 88% yield); LCMS: m/z=580.2 (M+H); rt 1.297 min (LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98); Gradient=20-100% B over 4 minutes, then a 0.6 minute hold at 100% B; Temperature: 27° C.; Flow rate: 1.0 mL/min; Detection: UV at 220 nm).

Example 20

8-((2S,5R)-4-(bis(4-fluorophenyl)methyl)-2,5-dimethylpiperazin-1-yl)-7-cyclopropyl-5-methyl-6-oxo-5,6-dihydro-1,5-naphthyridine-2-carbonitrile (20)

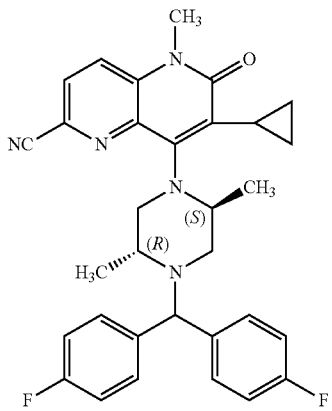

To a solution of 8-((2S,5R)-4-(bis(4-fluorophenyl)methyl)-2,5-dimethylpiperazin-1-yl)-7-bromo-5-methyl-6-oxo-5,6-dihydro-1,5-naphthyridine-2-carbonitrile (50 mg, 0.086 mmol) in dioxane (5 mL) were added $Na_2CO_3$ (27.5 mg, 0.259 mmol) and cyclopropylboronic acid (14.85 mg, 0.173 mmol). The reaction mixture was degassed under $N_2$ and $PdCl_2$(dppf) (6.32 mg, 8.64 μmol) was added. The reaction mixture was heated at 100° C. for 16 h. The volatiles were removed from the reaction mixture. The residue was dissolved in ethyl acetate and washed with water. The aqueous layer was back extracted with ethyl acetate. The combined organic layer was washed with brine, dried over $Na_2SO_4$ and concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-85% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 8-((2S,5R)-4-(bis(4-fluorophenyl)methyl)-2,5-dimethylpiperazin-1-yl)-7-cyclopropyl-5-methyl-6-oxo-5,6-dihydro-1,5-naphthyridine-2-carbonitrile (7.7 mg, 16.5% yield); LCMS: m/z=540.3 (M+H); rt 2.730 min (LCMS Method: Column: XBridge BEH XP C18 (50×2.1) mm, 2.5 μm; Mobile phase A: 95% Water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$): δ ppm 8.16-7.98 (m, 2H), 7.60-7.37 (m, 4H), 7.29-7.06 (m, 4H), 4.98 (s, 1H), 4.20 (br. s., 1H), 3.81 (br. s., 1H), 3.53 (s, 3H), 3.20-3.12 (m, 1H), 3.08-2.97 (m, 1H), 2.74 (br. s., 1H), 2.18-2.03 (m, 2H), 1.43 (d, J=5.6 Hz, 1H), 1.10 (d, J=6.6 Hz, 3H), 1.02 (d, J=6.1 Hz, 4H), 0.92-0.79 (m, 1H), 0.71 (dd, J=6.1, 2.9 Hz, 1H).

Example 22

8-((2S,5R)-4-(bis(4-fluorophenyl)methyl)-2,5-dimethylpiperazin-1-yl)-5,7-dimethyl-6-oxo-5,6-dihydro-1,5-naphthyridine-2-carbonitrile (22)

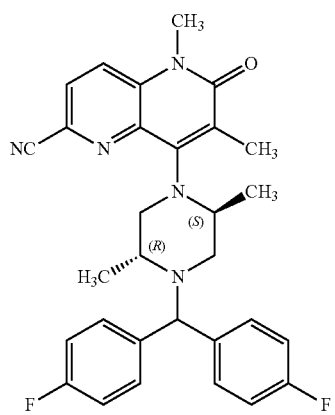

To a solution of 8-((2S,5R)-4-(bis(4-fluorophenyl)methyl)-2,5-dimethylpiperazin-1-yl)-7-bromo-5-methyl-6- oxo-5,6-dihydro-1,5-naphthyridine-2-carbonitrile (50 mg, 0.086 mmol) in dioxane (4 mL) were added K$_2$CO$_3$ (35.8 mg, 0.259 mmol) and methyl boronic acid (7.76 mg, 0.130 mmol). The reaction mixture was degassed with N$_2$ for 10 min and PdCl$_2$(dppf) (6.32 mg, 8.64 µmol) was added. The reaction mixture was heated to 110° C. for 12 h. The volatiles were removed from the reaction mixture. The residue was dissolved in ethyl acetate (50 mL) and washed with water. The aqueous layer was back extracted with ethyl acetate (20 mL×2). The combined organic layer was washed with brine, dried over Na$_2$SO$_4$ and concentrated under reduced pressure to yield crude product which was purified by preparative HPLC purification (Method: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 42% B, 42-82% B over 25 minutes, then a 5 minute hold at 100% B; Flow Rate: 15 m/min; Column Temperature: 25° C. Fractions containing the product were combined and dried via centrifugal evaporation to yield 8-((2S,5R)-4-(bis(4-fluorophenyl)methyl)-2,5-dimethylpiperazin-1-yl)-5,7-dimethyl-6-oxo-5,6-dihydro-1,5-naphthyridine-2-carbonitrile (11.0 mg, 24.8%). LCMS: m/z=514.3 (M+H); rt 2.647 min. (LCMS Method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.20-8.02 (m, 2H), 7.67-7.40 (m, 4H), 7.26-7.02 (m, 4H), 4.98 (s, 1H), 3.99 (br. s., 1H), 3.73 (br. s., 1H), 3.61 (s, 3H), 3.12-2.86 (m, 2H), 2.75 (d, J=7.6 Hz, 1H), 2.21-2.00 (m, 4H), 1.17-0.92 (m, 6H).

Intermediate 12

2-cyclopropylpyrazine

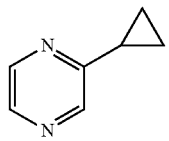

(I-12)

To a solution of 2-chloropyrazine (500 mg, 4.37 mmol) in toluene (20 mL)/water (2 mL) were added Cs$_2$CO$_3$ (4267 mg, 13.10 mmol) and cyclopropylboronic acid (750 mg, 8.73 mmol). The reaction mixture was degassed with N$_2$ for 10 min and PdCl$_2$(dppf) (319 mg, 0.437 mmol) was added. The reaction mixture was heated to 110° C. for 12 h. The volatiles were removed from the reaction mixture. The residue was dissolved in ethyl acetate and washed with water. The aqueous layer was back extracted with ethyl acetate. The combined organic layer was washed with brine, dried over Na$_2$SO$_4$ and concentrated under reduced pressure. The crude compound was purified by Combi (24 g Silica gel column, eluted with 30-50% ethyl acetate/petroleum ether) to yield 2-cyclopropylpyrazine (259 mg, 2.156 mmol, 49.4% yield); LCMS: m/z=121.4 (M+H); rt 0.81 min (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Intermediate 13

2-cyclopropylpiperazine, 2 HCl

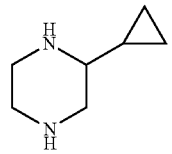

(I-13)

To a solution of 2-cyclopropylpyrazine (255 mg, 2.122 mmol) in AcOH (10 mL) was added platinum (IV) oxide (24.10 mg, 0.106 mmol). The solution was stirred at a H$_2$ atmosphere (Balloon) for 3 h. The reaction mixture was filtered trough celite pad, washed with acetic acid and DCM. The filtrate was concentrated under reduced pressure. The solid was washed with HCl in dioxane under reduced pressure to yield the diHCl salt of 2-cyclopropylpiperazine (385 mg, 91% yield); LCMS: m/z=127.2 (M+H); rt 0.361 min (LCMS Method: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 14

1-(bis(4-fluorophenyl)methyl)-3-cyclopropylpiperazine

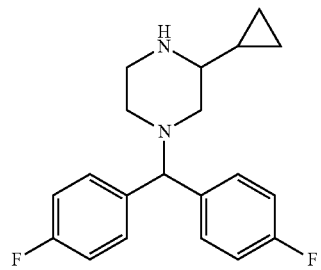

(I-14)

To a solution of 4,4'-(chloromethylene)bis(fluorobenzene) (0.528 g, 2.213 mmol) in acetonitrile (10 mL) was added HCl salt of 2-cyclopropylpiperazine (0.3 g, 1.844 mmol), followed by DIPEA (1.611 mL, 9.22 mmol). The reaction mixture was stirred at 85° C. overnight. The reaction mixture was concentrated under reduced pressure to remove volatiles and dissolved in ethyl acetate and washed with water. The aqueous layer was back extracted with ethyl acetate (10 mL×2). The combined organic layer was washed with brine, dried over Na$_2$SO$_4$ and concentrated under reduced pressure. The crude residue was purified via silica gel chromatography on ISCO® (5-10% methanol/CHCl$_3$; 24 g column) to afford 1-(bis(4-fluorophenyl)methyl)-3-cyclopropylpiperazine (123 mg, 0.375 mmol, 20.31% yield); LCMS: m/z=329.2 (M+H); rt 3.645 min (LCMS Method: Column:

Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Examples 23 and 24

8-(4-(bis(4-fluorophenyl)methyl)-2-cyclopropylpiperazin-1-yl)-5-methyl-6-oxo-5,6-dihydro-1,5-naphthyridine-2-carbonitrile

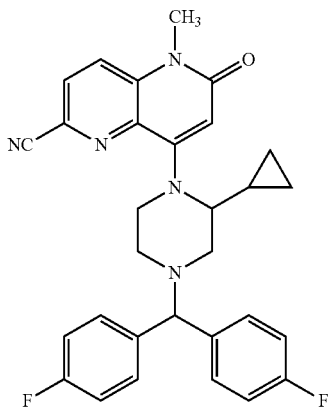

(23-24)

To a stirred solution of 6-cyano-1-methyl-2-oxo-1,2-dihydro-1,5-naphthyridin-d-yl trifluoromethanesulfonate (82 mg, 0.247 mmol) in acetonitrile (7 mL) were added DIPEA (0.108 mL, 0.617 mmol) and the HCl salt of 1-(bis(4-fluorophenyl)methyl)-3-cyclopropylpiperazine (75 mg, 0.206 mmol). The reaction mixture was stirred at 85° C. overnight. The solvent was removed under reduced pressure and the residue was dissolved in ethyl acetate (50 mL). The organic layer was washed with brine, dried over Na$_2$SO$_4$ and concentrated under reduced pressure (enantiomeric mixture). Individual enantiomers were separated using chiral HPLC. Chiral separation (HPLC Method: column: Cellulose-C4 (250*21 mm) 5 μm; Mobile phase: 0.1% DEA in methanol; Detection: UV at 254 nm. Flow rate: 20 mL/min) of enantiomeric mixture gave individual enantiomers. Fractions containing the product were combined and dried via centrifugal evaporation to yield individual enantiomers.

Enantiomer 1 (Example 23, 5.0 mg, 4.71% yield); LCMS: m/z=512.2 (M+H); rt 2.362 min (LCMS Method: column: Cellulose-C$_4$ (250*21 mm) 5 μm; Mobile phase: 0.1% DEA in methanol; Detection: UV at 254 nm. Flow rate: 20 mL/min); $^1$H NMR (400 MHz, DMSO-d$_6$) δ ppm 8.14 (d, J=8.8 Hz, 1H), 8.07 (d, J=8.8 Hz, 1H), 7.54 (dd, J=8.8, 5.6 Hz, 4H), 7.23-7.10 (m, 4H), 6.10 (s, 1H), 4.47 (s, 1H), 4.18 (d, J=10.0 Hz, 1H), 3.66-3.57 (m, 1H), 3.54 (s, 3H), 3.22 (d, J=13.0 Hz, 1H), 2.93-2.82 (m, 2H), 2.37-2.32 (m, 1H), 2.22-2.14 (m, 1H), 1.87 (br. s., 1H), 0.41 (dd, J=8.9, 4.5 Hz, 1H), 0.30 (dd, J=7.7, 4.0 Hz, 1H), -0.11 (dd, J=9.3, 4.9 Hz, 1H), -0.41 (dd, J=9.3, 4.2 Hz, 1H).

Enantiomer 2: (Example 24, 4.4 mg, 4.1% yield); LCMS: m/z=512.2 (M+H); rt 2.362 min (LCMS Method: column: Cellulose-C$_4$ (250*21 mm) 5 μm; Mobile phase: 0.1% DEA in methanol; Detection: UV at 254 nm. Flow rate: 20 mL/min); $^1$H NMR (400 MHz, DMSO-d$_6$) δ ppm 8.14 (d, J=9.0 Hz, 1H), 8.07 (d, J=8.8 Hz, 1H), 7.54 (dd, 0.7=8.7, 5.5 Hz, 4H), 7.22-7.12 (m, 4H), 6.10 (s, 1H), 4.47 (s, 1H), 4.18 (d, 0.7=9.8 Hz, 1H), 3.61 (dd, 0.7=11.9, 9.2 Hz, 1H), 3.54 (s, 3H), 3.22 (d, 0.7=12.2 Hz, 1H), 2.93-2.80 (m, 2H), 2.37-2.32 (m, 1H), 2.23-2.12 (m, 1H), 1.87 (d, J=4.9 Hz, 1H), 0.46-0.37 (m, 1H), 0.34-0.26 (m, 1H), -0.11 (dd, 0.7=9.3, 4.4 Hz, 1H), -0.41 (dd, 0.7=9.2, 4.3 Hz, 1H).

Intermediate 15 tert-butyl (2S,5R)-4-(bis(chlorphenyl)methyl)-2,5-dimethylpiperazine-1-carboxylate

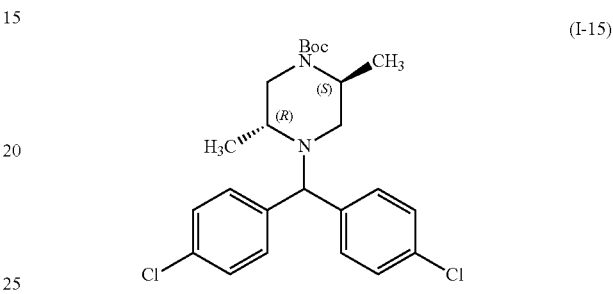

(I-15)

To a solution of 4,4'-(bromomethylene)bis(chlorobenzene) (0.147 g, 0.467 mmol) in acetonitrile (2 mL) was added tert-butyl (2S,5R)-2,5-dimethylpiperazine-1-carboxylate (0.05 g, 0.233 mmol), followed by DIPEA (0.122 mL, 0.700 mmol). The reaction mixture was stirred at 82° C. overnight. The reaction mixture was concentrated under reduced pressure to remove volatiles, and dissolved in ethyl acetate and washed with water. The aqueous layer was back extracted with ethyl acetate (50 mL×2). The combined organic layer was washed with brine, dried over Na$_2$SO$_4$ and concentrated under reduced pressure. The crude residue was purified via silica gel chromatography on ISCO® (5-10% EtOAc/petroleum ether; 12 g column) to afford tert-butyl (2S,5R)-4-(bis(4-chlorophenyl)methyl)-2,5-dimethylpiperazine-1-carboxylate (90 mg, 86% yield); LCMS: m/z=451.2 (M+H); rt 2.532 min (Column: Kinetex XB-C18 (3×75 mm) 2.6 μm; Mobile phase A: 10 mM ammonium formate: acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 16

(2R,5S)-1-(bis(4-chlorophenyl)methyl)-2,5-dimethylpiperazine, HCl

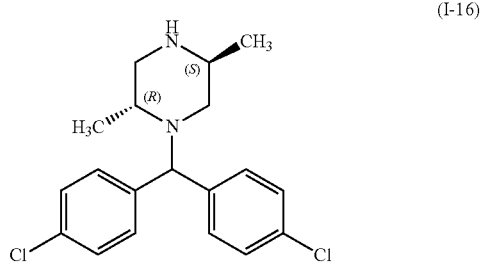

(I-16)

To a solution of tert-butyl (2S,5R)-4-(bis(4-chlorophenyl)methyl)-2,5-dimethylpiperazine-1-carboxylate (0.3 g, 0.668 mmol) in DCM (10 mL) was added HCl (0.834 mL, 3.34 mmol) in 4 M dioxane. The reaction mixture was stirred for 3 h. The reaction mixture was evaporated under reduced pressure and the crude material was triturated with hexane. The solid was filtered through a sintered funnel and dried under vacuum to yield HCl salt of (2R,5S)-1-(bis(4-chlorophenyl)methyl)-2,5-dimethylpiperazine (Crude=286 mg). LCMS: m/z=349.0 (M+H); rt 1.73 min (Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Example 25

8-((2S,5R)-4-(bis(4-chlorophenyl)methyl)-2,5-dimethylpiperazin-1-yl)-5-methyl-6-oxo-5,6-dihydro-1,5-naphthyridine-2-carbonitrile

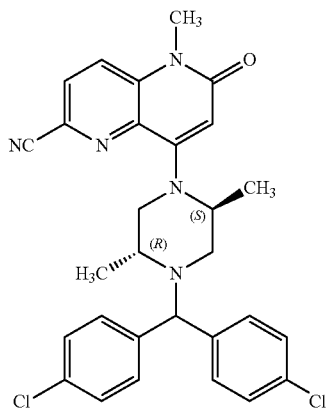

(25)

To a stirred solution of 6-cyano-1-methyl-2-oxo-1,2-dihydro-1,5-naphthyridin-d-yl trifluoromethanesulfonate (0.065 g, 0.194 mmol) in acetonitrile (2 mL) were added DIPEA (0.068 mL, 0.39 mmol) and HCl salt of (2R,5S)-1-(bis(4-chlorophenyl)methyl)-2,5-dimethylpiperazine (0.05 g, 0.13 mmol). The reaction mixture was stirred at 85° C. overnight. The solvent was removed under reduced pressure and the residue was dissolved in ethyl acetate (20 mL). The organic layer was washed with brine, dried over $Na_2SO_4$ and concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 41% B, 41-82% B over 25 minutes, then a 5 minute hold at 100% B; Flow Rate: 15 mL/min; Column Temperature: 25° C. Fractions containing the product were combined and dried via centrifugal evaporation to yield 8-((2S,5R)-4-(bis(4-chlorophenyl)methyl)-2,5-dimethylpiperazin-1-yl)-5-methyl-6-oxo-5,6-dihydro-1,5-naphthyridine-2-carbonitrile (7.3 mg, 10.6% yield); LCMS: m/z=532.1 (M+H); rt 2.636 min (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$) δ ppm 8.14 (d, J=8.8 Hz, 1H), 8.06 (d, J=9.0 Hz, 1H), 7.57 (d, J=8.3 Hz, 2H), 7.60 (d, J=8.6 Hz, 2H), 7.38 (t, J=8.4 Hz, 4H), 6.00 (s, 1H), 4.71 (s, 1H), 4.60 (br. s., 1H), 3.68 (d, J=11.7 Hz, 1H), 3.61-3.45 (m, 4H), 3.06 (br. s., 1H), 2.92-2.83 (m, 1H), 2.34-2.29 (m, 1H), 1.30 (d, J=6.6 Hz, 3H), 1.06 (d, J=6.6 Hz, 3H).

Example 26

8-((2S,5R)-4-(bis(4-chlorophenyl)methyl)-2,5-dimethylpiperazin-1-yl)-7-chloro-5-methyl-6-oxo-5,6-dihydro-1,5-naphthyridine-2-carbonitrile

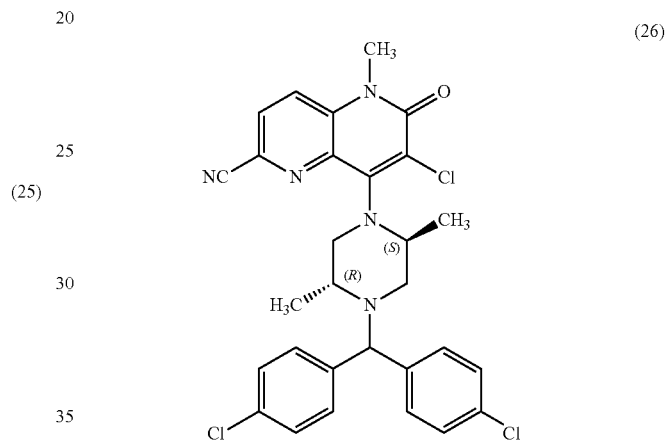

(26)

To a stirred solution of 8-((2S,5R)-4-(bis(4-chlorophenyl)methyl)-2,5-dimethylpiperazin-1-yl)-5-methyl-6-oxo-5,6-dihydro-1,5-naphthyridine-2-carbonitrile (40 mg, 0.075 mmol) in DCM (3 mL) was added NCS (20.06 mg, 0.150 mmol). The reaction mixture was stirred at room temperature overnight. The crude LCMS showed formation of the product. The solvent was removed under reduced pressure and the residue was dissolved in ethyl acetate (20 mL). The organic layer was washed with brine, dried over $Na_2SO_4$ and concentrated under reduced pressure to yield crude product, which was which was purified by preparative HPLC for purification. (HPLC Method: Column: Waters XBridge C18, 150 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 10% B, 10-45% B over 25 minutes, then a 5 minute hold at 100% B; Flow Rate: 15 mL/min; Column Temperature: 25° C. Fractions containing the product were combined and dried via centrifugal evaporation to yield 8-((2S,5R)-4-(bis(4-chlorophenyl)methyl)-2,5-dimethylpiperazin-1-yl)-7-chloro-5-methyl-6-oxo-5,6-dihydro-1,5-naphthyridine-2-carbonitrile (25.2 mg, 52%).); LCMS: m/z=566.2 (M+H); rt 2.873 min. (LCMS Method: Column: XB ridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$) δ ppm 8.27-8.07 (m, 2H), 7.59 (d, J=8.6 Hz, 4H), 7.38 (dd, J=8.4, 5.3 Hz, 4H), 4.78 (s, 1H), 4.19 (d, J=9.8 Hz, 1H), 4.11 (br. s., 1H), 3.64 (s, 3H), 3.22-3.05 (m, 1H), 2.98-2.78 (m, 2H), 2.27 (d, J=93 Hz, 1H), 1.30 (d, J=6.6 Hz, 3H), 0.97 (d, J=6.1 Hz, 3H).

Intermediate 17

Ethyl 3-aminopicolinate

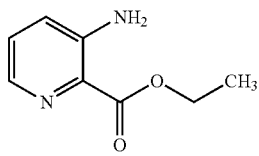

(I-17)

To a stirred suspension of 3-aminopicolinic acid (150 g, 1086 mmol) in ethanol (1500 mL) at 0-5° C. was added H$_2$SO$_4$ (463 mL, 8688 mmol) through a 1 L addition funnel over 60 min. After completion of the addition, the reaction mixture turned to a clear brown solution which was refluxed at 90° C. for 24 h. The reaction mixture was cooled to room temperature and poured onto ice pellets in a 10 L beaker with overhead stirring, basified using NH$_4$OH solution (~2 L required) to pH ~9, and stirred at room temperature for 60 min. Solid material was observed in the beaker which was filtered through Buchner funnel, washed with water (1 L) and dried under line vacuum to yield 60 g of product as an off-yellow solid. The mother liquor contained product which was extracted out thrice using DCM (3×1000 mL), the combined organic layer washed with brine solution (1×1.5 L) and then dried over Na$_2$SO$_4$ and concentrated to yield ethyl 3-aminopicolinate (116 g, 691 mmol, 63.6% yield) including first 60 g of compound. LCMS: m/z=167.2 (M+H); RT 0.783 min; Method: Column-KINETEX-XB-C, 18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 18

Ethyl 3-acetamidopicolinate

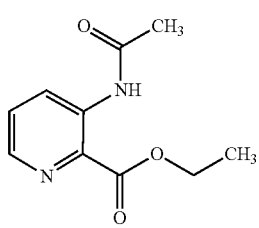

(I-18)

To a stirred solution of ethyl 3-aminopicolinate (115 g, 692 mmol) in THF (1000 mL) was added Ac$_2$O (588 mL, 6228 mmol) at room temperature. The reaction mixture was heated to 60° C. under nitrogen atmosphere for ~7-8 h. The reaction mixture was cooled to room temperature and the volatiles were evaporated at water bath temperature (~50° C.) under line vacuum, followed by acetic acid under high vacuum at 50° C. to yield an off-white solid. The solid was triturated with petroleum ether (500 mL), stirred for 30 min at room temperature, then filtered through a Buchner funnel and washed with petroleum ether (500 mL) upon filtration, dried under vacuum at room temperature for 3 h to yield ethyl 3-acetamidopicolinate (139 g, 641 mmol, 93% yield) as an off-white solid; LCMS: m/z=209.3 (M+H); rt 0.76 min; LC-MS Method: Column-KINETEX-XB-C18 (75×3 mm-2.6 µm); Mobile phase A: 10 mM ammonium formate in water: acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 19

Ethyl 3-(N-methylacetamido)picolinate

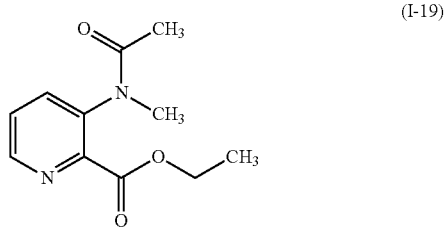 [SMILES: CCOC(=O)c1ncccc1N(C)C(C)=O]

(I-19)

To a stirred light brown suspension of ethyl 3-acetamidopicolinate (75 g, 360 mmol) and cesium carbonate (176 g, 540 mmol) in DMF (750 mL) was added methyl iodide (36.0 mL, 576 mmol) at room temperature (slight exotherm observed). The resulting partial brown mixture was stirred at room temperature for ~8 h. The reaction was quenched with water (1500 mL) [slight exotherm observed] and extracted with DCM (3×1000 mL). The separated organic layer washed with water (2×1000 mL) and the aqueous layer was re-extracted with DCM (2×500 mL). The combined organic solutions were washed with brine (2×1000 mL), dried over Na$_2$SO$_4$ and concentrated at 50° C., and then dried under vacuum at ~60° C. to yield a brown color solution (contains some DMF). The material was dried under high vacuum to remove DMF at 58° C. for 25 min to yield a brown solid which was dissolved in petroleum ether (1000 mL), stirred for 30 min at room temperature, filtered through a Buchner funnel, washed with petroleum ether (500 mL) upon filtration, dried under line vacuum for 8 h to yield ethyl 3-(N-methylacetamido)picolinate (70 g, 302 mmol, 84% yield) as a brown solid; LCMS: m/z=223.2 (M+H); rt 0.641 min; LC-MS Method: Column-KINETEX-XB-C, 18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 20

2-(ethoxycarbonyl-3-(N-methylacetamido)pyridine 1-oxide

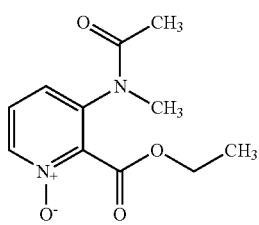
(I-20)

To a stirred brown clear solution of ethyl 3-(N-methylacetamido)picolinate (70 g, 315 mmol) in DCM (700 mL) at 0-5° C. was added urea hydrogen peroxide (44.4 g, 472 mmol), followed by trifluoroacetic anhydride (66.7 mL, 472 mmol) slowly over 40 min through a 100 mL addition funnel. The reaction mixture solidified during the trifluoroacetic anhydride addition. After completion of the addition, the reaction mixture was stirred at room temperature for ~2 h. The reaction was quenched with 10% NaHCO$_3$ solution (700 mL). The reaction mixture was extracted with DCM (3×500 mL). The combined organic layer was washed with brine solution (2×500 mL), dried over Na$_2$SO$_4$ and concentrated to yield 2-(ethoxycarbonyl)-3-(N-methylacetamido)pyridine 1-oxide (70 g, 285 mmol, 90% yield) as a light yellow solid; LCMS: m/z=239.0 (M+H); rt 0.482 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 21

Ethyl 6-cyano-3-(N-methylacetamido)picolinate

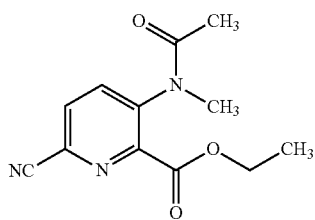
(I-21)

To a stirred pale yellow solution of ethyl 3-(N-methylacetamido)-1-(1-oxidanyl)-114-pyridine-2-carboxylate (50 g, 210 mmol) in DCM (500 mL) at room temperature was added trimethylsilyl cyanide (39.4 mL, 294 mmol). The reaction mixture was stirred for 10 min and cooled the mixture to −10° C. Next, benzoyl chloride (34.1 mL, 294 mmol) was added through a 50 mL addition funnel over 15 min followed by TEA (41.0 mL, 294 mmol) through a 50 mL addition funnel slowly over 20 min. An exothermic reaction was observed during TEA addition. The reaction mixture turned to a turbid mixture (TEA salt) which was stirred for 2.5 h at the same temperature. The reaction was quenched with 10% NaHCO$_3$ solution (500 mL) and extracted with DCM (3×300 mL). The combined organic solution was washed with brine (2×250 mL) then dried over Na$_2$SO$_4$ and concentrated to yield a light yellow crude material. The crude material was purified through normal phase RediSep silica column on ISCO® using EA/petroleum ether as eluent. The product was isolated by 65-70% EA/petroleum ether, fractions were concentrated to afford ethyl 6-cyano-3-(N-methylacetamido)picolinate (43 g, 83% yield) as a light brown liquid; LCMS: m/z=248.0 (M+H); rt 1.255 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 22

8-Hydroxy-5-methyl-6-oxo-5,6-dihydro-1,5-naphthyridine-2-carbonitrile

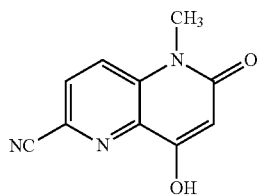
(I-22)

To a stirred solution of ethyl 6-cyano-3-(N-methylacetamido)picolinate (0.9 g, 3.64 mmol) in tetrahydrofuran (10 mL) was added KHMDS (4.80 mL, 4.37 mmol) at −78° C. over 10 min. The reaction mixture was stirred for 15 min. The reaction mixture was slowly warmed to room temperature over 30 min and then stirred for another 90 min. The reaction mixture was cooled to 0° C. The reaction was quenched with saturated sodium bicarbonate solution (70 mL). The mixture was diluted with ethyl acetate (2×100 mL). The aqueous layer was collected and acidified with 1.5 N HCL to adjust the pH to ~3.0. The mixture was stirred for 15 min to form a solid mass, which was filtered through a Buchner funnel to yield 8-hydroxy-5-methyl-6-oxo-5,6-dihydro-1,5-naphthyridine-2-carbonitrile 550 mg, 75% yield) as a brown solid. LCMS: m/z=202.0 (M+H); rt 0.361 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 23

8-Chloro-5-methyl-6-oxo-5,6-dihydro-1,5-naphthyridine-2-carbonitrile

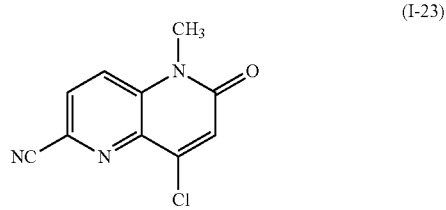

(I-23)

To a stirred solution of 8-hydroxy-5-methyl-6-oxo-5,6-dihydro-1,5-naphthyridine-2-carbonitrile (0.55 g, 2.73 mmol) in acetonitrile (10 mL) was added POCl$_3$ (1.53 mL, 16.4 mmol). The reaction mixture was heated up to 85° C. over 5 min and was stirred for 16 h. The reaction mixture was concentrated under reduced pressure to yield crude material. The reaction mixture was cooled to 0° C. The reaction was quenched with saturated sodium bicarbonate solution (50 mL). The reaction was diluted with DCM (3×100 mL). The combined organic layer was dried over anhydrous sodium sulfate, filtered, and evaporated under reduced pressure to yield 8-chloro-5-methyl-6-oxo-5,6-dihydro-1,5-naphthyridine-2-carbonitrile (0.25 g, 29.1% yield) as a brown solid. LCMS: m/z=220.2 (M+H); rt 1.528 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 24

1-(tert-Butyl) 3-methyl 4-(bis(4-fluorophenyl)methyl)piperazine-1,3-dicarboxylate

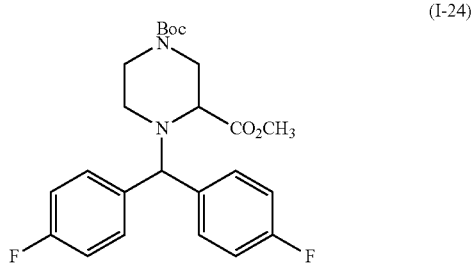 [SMILES: COC(=O)C1CN(C(=O)OC(C)(C)C)CCN1C(c1ccc(F)cc1)c1ccc(F)cc1]

(I-24)

To a stirred solution of 1-(tert-butyl) 3-methyl piperazine-1,3-dicarboxylate (0.6 g, 2.46 mmol) in acetonitrile (8 mL) were added DIPEA (1.29 mL, 7.37 mmol) and 4,4'-(chloromethylene)bis(fluorobenzene) (0.703 g, 2.95 mmol). The reaction mixture was heated up to 85° C. over 10 min and was stirred for 36 h. The reaction mixture was concentrated under high vacuum to yield a brown gum. The crude compound was purified by ISCO® using a 24 g silica gel column; 8%-12% ethylacetate/petroleum ether to yield 1-(tert-butyl) 3-methyl 4-(bis(4-fluorophenyl)methyl)piperazine-1,3-dicarboxylate (140 mg, 0.285 mmol, 11.62% yield) as a brown solid. LCMS: m/z 447.2 (M+H); rt 4.147 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 25

Methyl 1-(bis(4-fluorophenyl)methyl)piperazine-2-carboxylate, HCl

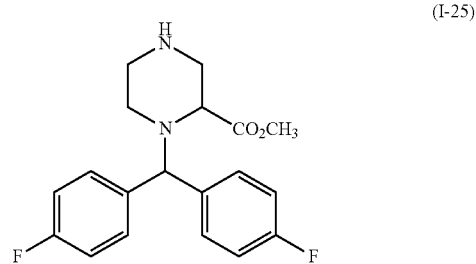 [SMILES: COC(=O)C1CNCCN1C(c1ccc(F)cc1)c1ccc(F)cc1]

(I-25)

A stirred solution of 1-(tert-butyl) 3-methyl 4-(bis(4-fluorophenyl)methyl) piperazine-1,3-dicarboxylate (70 mg, 0.157 mmol) in HCl in dioxane (1.0 mL, 4.00 mmol) was stirred at room temperature for 2 h. The reaction mixture was concentrated under high vacuum to yield a HCl salt of methyl 1-(bis(4-fluorophenyl)methyl) piperazine-2-carboxylate (49 mg, 53.4% yield) as a brown solid. LCMS: m/z=347.3 (M+H); rt 1.46 min. LC-MS Method: Column AQUITY UPLC BEH C18 (3.0×50 mm) 1.7 μm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.2 minute hold at 100% B, flow rate 0.7 mL/min.

Example 27

Methyl 1-(bis(4-fluorophenyl)methyl)-4-(6-cyano-1-methyl-2-oxo-1,2-dihydro-1,5-naphthyridin-4-yl)piperazine-2-carboxylate

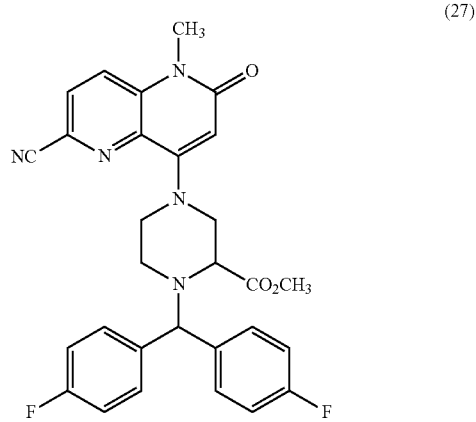 [SMILES: COC(=O)C1CN(c2cc(=O)n(C)c3ccc(C#N)nc23)CCN1C(c1ccc(F)cc1)c1ccc(F)cc1]

(27)

To a stirred solution of 8-chloro-5-methyl-6-oxo-5,6-dihydro-1,5-naphthyridine-2-carbonitrile (22.90 mg, 0.104 mmol) in DMA (1 mL) and t-butanol (4 mL) was added the TFA salt of methyl 1-(bis(4-fluorophenyl)methyl)piperazine-2-carboxylate (40 mg, 0.087 mmol) and cesium carbonate (85 mg, 0.261 mmol) under a nitrogen atmosphere, followed by the addition of chloro(2-dicyclohexylphosphino-2',6'-diisopropoxy-1,1'-biphenyl)[2-(2'-amino-1,1'-biphenyl)] palladium(II) (3.37 mg, 4.34 µmol). The reaction vessel was immersed in an oil bath at 70° C. The bath temperature was raised to 90° C. over 2 min and the reaction mixture was stirred for 16 h. The reaction mixture was filtered through a celite bed and was concentrated under high vacuum to yield a brown gum. The crude material was purified via preparative HPLC with the following conditions: Column: Sunfire C18, 19×150 mm, 5 µm particles; Mobile Phase A: 10 mM ammonium acetate pH 4.5 with acetic acid; Mobile Phase B: acetonitrile; Gradient: 30-100% B over 15 minutes, then a 5 minute hold at 100% B; Flow: 17 mL/min. Fractions containing the product were combined and dried via centrifugal evaporation to yield methyl 1-(bis(4-fluorophenyl)methyl)-4-(6-cyano-1-methyl-2-oxo-1,2-dihydro-1,5-naphthyridin-4-yl)piperazine-2-carboxylate (3.5 mg, 6.23 µmol, 7.17% yield). LCMS: m/z=530.2 (M+H); rt 2.20 min. LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.16 (d, J=8.8 Hz, 1H), 8.08 (d, J=9.0 Hz, 1H), 7.57 (dd, J=8.8, 5.6 Hz, 2H), 7.42-7.28 (m, 2H), 7.22-7.08 (m, 4H), 6.14 (s, 1H), 5.17 (s, 1H), 4.78 (d, J=12.2 Hz, 1H), 3.64 (d, J=12.0 Hz, 1H), 3.59 (s, 3H), 3.54 (s, 3H), 3.45-3.35 (m, 2H), 3.15 (dd, J=12.5, 3.9 Hz, 1H), 3.04 (td, J=11.7, 2.9 Hz, 1H), 2.71-2.63 (m, 1H).

Intermediate 26 tert-Butyl (R)-4-(bis(4-fluorophenyl)methyl)-3-methylpiperazine-1-carboxylate

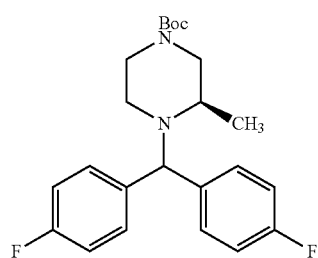

(I-26)

To a stirred solution of tert-butyl (R)-3-methylpiperazine-1-carboxylate (1.0 g, 4.99 mmol) in acetonitrile (10 mL) were added DIPEA (2.62 mL, 14.98 mmol) and 4,4'-(chloromethylene) bis(fluorobenzene) (1.4 g, 6 mmol). The reaction mixture was heated up to 85° C. over 10 min and was stirred for 16 h. The reaction mixture was concentrated under high vacuum to yield a brown gum. The crude compound was purified by ISCO® (using 24 g silica gel column; using 8-12% ethylacetate/petroleum ether) to yield tert-butyl (R)-4-(bis(4-fluorophenyl)methyl)-3-methylpiperazine-1-carboxylate (1.45 g, 72.2% yield) as a brown solid. LCMS: m/z=403.2 (M+H); rt 1.127 min; LC-MS Method: Column-KINETEX-XB-C18 (75×3 mm-2.6 µm); Mobile phase A: 10 mM ammonium formate in water: acetonitrile (98:2); Mobile phase B: 10 mM ammonium formate in water:acetonitrile (2:98); Gradient: 80% B over 0.5 minutes, flow rate 1.0 mL/min, then a 2.5 minute hold at 98% B flow rate 1.0 mL/min; then Gradient: 98% B over 1 minute, flow rate 1.0 mL/min.

Intermediate 27

(R)-1-(bis(4-fluorophenyl)methyl)-2-methylpiperazine, TFA

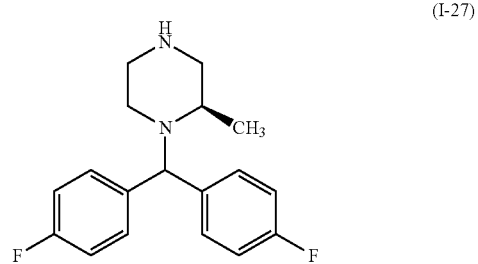 [SMILES: C[C@@H]1CNCCN1C(c1ccc(F)cc1)c1ccc(F)cc1]

(I-27)

To a stirred solution of tert-butyl (R)-4-(bis(4-fluorophenyl)methyl)-3-methylpiperazine-1-carboxylate (0.45 g, 1.118 mmol) in DCM (8 mL) was added TFA (0.431 mL, 5.59 mmol). The reaction mixture was stirred at room temperature for 16 h. The reaction mixture was concentrated under high vacuum to yield a brown gum. The residue was triturated with DCM and petroleum ether and was stirred for 15 min to yield a brown solid which was filtered through a Buchner funnel to yield a TFA salt of (R)-1-(bis(4-fluorophenyl)methyl)-2-methylpiperazine (320 mg, 56.4% yield) as a brown solid. LCMS: m/z=303.2 (M+H); rt 2.409 min; LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Example 28

(R)-8-(4-(bis(4-fluorophenyl)methyl)-3-methylpiperazin-1-yl)-5-methyl-6-oxo-5,6-dihydro-1,5-naphthyridine-2-carbonitrile

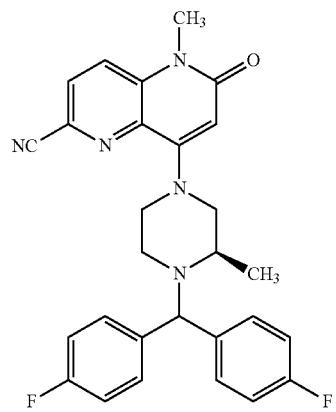

(28)

To a stirred solution of 8-chloro-5-methyl-6-oxo-5,6-dihydro-1,5-naphthyridine-2-carbonitrile (40 mg, 0.182 mmol) and cesium carbonate (178 mg, 0.546 mmol) in DMA (1 mL) and t-butanol (4 mL) was added the TFA salt of (R)-1-(bis(4-fluorophenyl)methyl)-2-methylpiperazine (76 mg, 0.182 mmol) under a nitrogen atmosphere, followed by the addition of chloro(2-dicyclohexylphosphino-2',6'-diisopropoxy-1,1'-biphenyl)[2-(2'-amino-1,1'-biphenyl)]palladium(II) (7.07 mg, 9.11 µmol). The reaction vessel was immersed in an oil bath at 70° C. The bath temperature was raised to 90° C. over 2 min and the reaction mixture was stirred for 16 h. The reaction mixture was filtered through celite bed and concentrated under high vacuum to yield a brown gum. The crude material was purified via preparative HPLC with the following conditions: Column: Sunfire C18, 19×150 mm, 5 µm particles; Mobile Phase A: 10 mM ammonium acetate pH 4.5 with acetic acid; Mobile Phase B: acetonitrile; Gradient: 30-100% B over 15 minutes, then a 5 minute hold at 100% B; Flow: 17 mL/min. Fractions containing the product were combined and dried via centrifugal evaporation to yield (R)-8-(4-(bis(4-fluorophenyl)methyl)-3-methylpiperazin-1-yl)-5-methyl-6-oxo-5,6-dihydro-1,5-naphthyridine-2-carbonitrile (6.0 mg, 6.5% yield). LCMS: m/z=486.2 (M+H); rt 2.33 min. LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.12-8.16 (m, 1H), 8.05-8.08 (m, 1H), 7.50-7.57 (m, 4H), 7.12-7.18 (m, 4H), 6.08 (s, 1H), 4.85 (s, 1H), 3.97-4.10 (m, 1H), 3.52-3.59 (m, 4H), 3.08-3.20 (m, 2H), 2.95-3.02 (m, 1H), 2.69-2.74 (m, 1H), 2.44-2.48 (m, 1H), 1.18 (d, J=6.4 Hz, 3H).

Example 29

(R)-8-(4-(bis(4-fluorophenyl)methyl)-3-methylpiperazin-1-yl)-7-chloro-5-methyl-6-oxo-5,6-dihydro-1,5-naphthyridine-2-carbonitrile

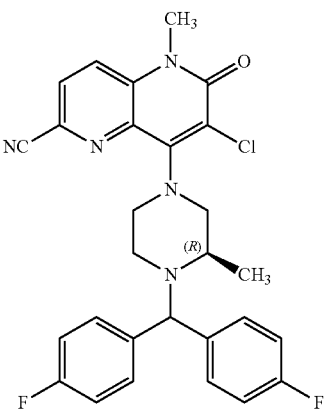

(29)

To a stirred solution of (R)-8-(4-(bis(4-fluorophenyl)methyl)-3-methylpiperazin-1-yl)-5-methyl-6-oxo-5,6-dihydro-1,5-naphthyridine-2-carbonitrile (40 mg, 0.082 mmol) in DCM (5 mL) was added NCS (22.00 mg, 0.165 mmol). The reaction mixture was stirred at room temperature for 16 h. The reaction was quenched with water (5 mL). The reaction mixture was diluted with ethyl acetate (3×10 mL). The combined organic layer was dried over anhydrous sodium sulfate, filtered and evaporated under reduced pressure to yield a brown oil. The crude material was purified via preparative HPLC with the following conditions: Column: Sunfire C18, 19×150 mm, 5 µm particles; Mobile Phase A: 10 mM ammonium acetate pH-4.5 with acetic acid; Mobile Phase B: acetonitrile; Gradient: 30-100% B over 15 minutes, then a 5 minute hold at 100% B; Flow: 17 mL/min. Fractions containing the product were combined and dried via centrifugal evaporation to yield (R)-8-(4-(bis(4-fluorophenyl)methyl)-3-methylpiperazin-1-yl)-7-chloro-5-methyl-6-oxo-5,6-dihydro-1,5-naphthyridine-2-carbonitrile (18.0 mg, 42.0% yield); LCMS: m/z=520.2 (M+H); rt 2.475 min. LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.17 (q, J=8.8 Hz, 2H), 7.55 (dd, J=10.5, 8.6 Hz, 2H), 7.57 (dd, J=10.4, 8.7 Hz, 2H), 7.15 (td, J=8.8, 1.7 Hz, 4H), 4.86 (s, 1H), 3.85 (dd, J=12.0, 2.7 Hz, 1H), 3.74-3.53 (m, 4H), 3.47-3.33 (m, 2H), 2.93 (t, J=9.5 Hz, 2H), 2.44 (d, J=11.5 Hz, 1H), 1.04 (d, J=6.6 Hz, 3H).

Example 30

(R)-8-(4-(bis(4-fluorophenyl)methyl)-3-methylpiperazin-1-yl)-7-fluoro-5-methyl-6-oxo-5,6-dihydro-1,5-naphthyridine-2-carbonitrile

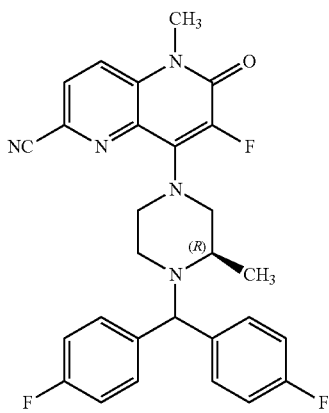

(30)

To a stirred solution of (R)-8-(4-(bis(4-fluorophenyl)methyl)-3-methylpiperazin-1-yl)-5-methyl-6-oxo-5,6-dihydro-1,5-naphthyridine-2-carbonitrile (40 mg, 0.082 mmol) in acetonitrile (6 mL) at 0° C. was added 1-chloromethyl-4-fluoro-1 4-diazoniabicyclo 2.2.2 octane bis(tetrafluoroborate) (37.9 mg, 0.107 mmol) in THF\H$_2$O (0.5\0.5 mL) dropwise at 0° C. The reaction mixture was stirred for 1.5 h. The reaction mixture was slowly warmed to room temperature and was stirred for another 1.5 h. The reaction mixture was concentrated under reduced pressure to yield a brown oil. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: 0 minute hold at 10% B, 10-40% B over 25 minutes, then a 5 minute hold at 100% B; Flow Rate: 15 mL/min; Column Temperature: 25° C. Fractions containing the product were combined and dried via centrifugal evaporation to yield (R)-8-(4-(bis(4-fluorophenyl)methyl)-3-methylpiperazin-1-yl)-7-fluoro-5-methyl-6-oxo-5,6-dihydro-1,5-naphthyridine-2-carbonitrile (2.2 mg, 5.3% yield); LCMS: m/z=504.2 (M+H); rt 2.385 min. LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.11-8.19 (m, 2H), 7.50-7.59 (m, 4H), 7.11-7.20 (m, 4H), 4.86 (s, 1H), 3.49-3.65 (m, 6H), 3.43 (br d, J=2.0 Hz, 1H), 2.91-2.98 (m, 1H), 2.72-2.79 (m, 1H), 2.41-2.47 (m, 1H), 1.15 (d, J=6.4 Hz, 3H).

Intermediate 28

6-Bromo-3-cyano-1-methyl-2-oxo-1,2-dihydro-1,5-naphthyridin-4-yl trifluoromethanesulfonate

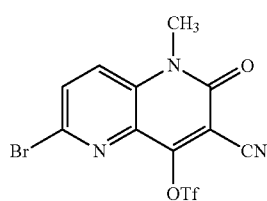

(I-28)

To a stirred solution of 6-bromo-1-methyl-2,4-dioxo-1,2,3,4-tetrahydro-1,5-naphthyridine-3-carbonitrile (0.6 g, 2.14 mmol) in DCM (8 mL) were added TEA (0.896 mL, 6.43 mmol) and DMAP (0.026 g, 0.214 mmol) at 0° C., followed by the addition of trifluoromethanesulfonic anhydride (0.724 mL, 4.28 mmol). The reaction mixture was slowly warmed to room temperature and was stirred for 3 h. The reaction was quenched with water (50 mL). The reaction mixture was diluted with DCM (3×100 mL). The combined organic layer was dried over anhydrous sodium sulfate, filtered and evaporated under reduced pressure to yield a brown solid. The crude compound was triturated with DCM and hexane (1:4) to yield 6-bromo-3-cyano-1-methyl-2-oxo-1,2-dihydro-1,5-naphthyridin-4-yl trifluoromethanesulfonate (700 mg, 79% yield) as a brown solid; LCMS: m/z=414.1 (M+H); rt 0.65 min. LC-MS Method: Column-AQUITY UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Example 31

(R)-4-(4-(bis(4-fluorophenyl)methyl)-3-methylpiperazin-1-yl)-6-bromo-1-methyl-2-oxo-1,2-dihydro-1,5-naphthyridine-3-carbonitrile

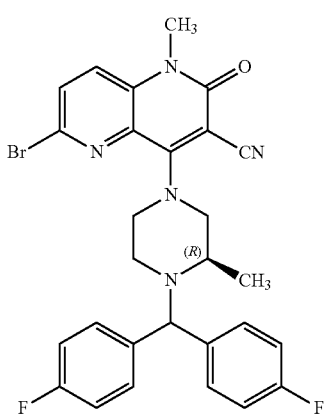

(31)

To a stirred solution of 6-bromo-3-cyano-1-methyl-2-oxo-1,2-dihydro-1,5-naphthyridin-4-yl trifluoromethanesulfonate (100 mg, 0.243 mmol) in acetonitrile (8 mL) were added DIPEA (0.127 mL, 0.728 mmol) and HCl salt of (R)-1-(bis(4-fluorophenyl) methyl)-2-methylpiperazine (82 mg, 0.243 mmol). The reaction mixture was heated up to 85° C. over 5 min and was stirred for 1 h. The reaction mixture was concentrated under high vacuum to yield a brown gum. The crude compound was purified by ISCO® using 12 g silica gel column; 60-67% ethyl acetate/petroleum ether to yield (R)-4-(4-(bis(4-fluorophenyl)methyl)-3-methylpiperazin-1-yl)-6-bromo-1-methyl-2-oxo-1,2-dihydro-1,5-naphthyridine-3-carbonitrile (90 mg, 42.7% yield) as a brown gum; LCMS: m/z=566.0 (M+2H); rt 2.23 min. LC-MS Method: Column-AQUITY UPLC BEH C18 (3.0×50 mm) 1.7 µm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.2 minute hold at 100% B, flow rate 0.7 mL/min.

Example 32

(R)-8-(4-(bis(4-fluorophenyl)methyl)-3-methylpiperazin-1-yl)-5-methyl-6-oxo-5,6-dihydro-1,5-naphthyridine-2,7-dicarbonitrile

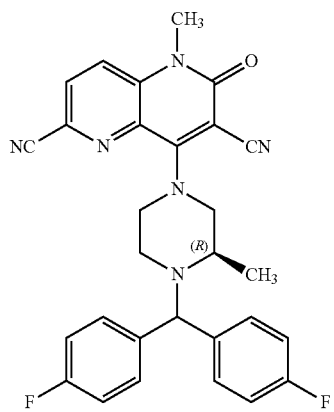

(32)

To a stirred solution of (R)-4-(4-(bis(4-fluorophenyl) methyl)-3-methylpiperazin-1-yl)-6-bromo-1-methyl-2-oxo-1,2-dihydro-1,5-naphthyridine-3-carbonitrile (90 mg, 0.159 mmol) in NMP (5 mL) were added zinc (2.085 mg, 0.032 mmol) and zinc cyanide (37.4 mg, 0.319 mmol) under nitrogen. The nitrogen purging was continued for 3 min and dppf (5.30 mg, 9.57 µmol) and Pd$_2$(dba)$_3$ (14.6 mg, 0.016 mmol) were added. The reaction mixture was heated up to 80° C. over 5 min and was stirred for 4 h. The reaction mixture was filtered through celite bed and was concentrated under high vacuum to yield a brown gum. The crude material was purified via preparative HPLC. HPLC Method: Column-SUNFIRE C18 (150 mm×19 mm ID, 5 µm); Mobile phase A: 10 mM Ammonium acetate in water; Mobile phase B: acetonitrile; Gradient: 40-60% B over 3.0 minutes, flow rate 17 mL/min, then a 17 minute hold at 60-100% B flow rate 17 mL/min. Fractions containing the product were combined and concentrated under high vacuum. Then sample was diluted with (EtOH\H$_2$O, 1:3) and was lyophilized overnight to yield (R)-8-(4-(bis(4-fluorophenyl)methyl)-3-methylpiperazin-1-yl)-5-methyl-6-oxo-5,6-dihydro-1,5-naphthyridine-2,7-dicarbonitrile (50 mg, 61.4% yield) as pale yellow solid. LCMS: m/z=511.2 (M+H); rt 3.520 min. LC-MS Method: Column-KINETEX-XB-C18 (75×3 mm-2.6µ); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min. $^1$H NMR (400 MHz, DMSO-d$_6$) δ ppm 8.26 (d, J=8.8 Hz, 1H), 8.15 (d, J=9.0 Hz, 1H), 7.56 (dd, J=11.9, 8.7 Hz, 2H), 7.57 (dd, J=11.7, 8.8 Hz, 2H), 7.16 (t, J=8.9 Hz, 4H), 4.90 (s, 1H), 4.10 (d, J=13.0 Hz, 1H), 4.01 (d, J=12.5 Hz, 1H), 3.86 (dd, J=12.2, 2.9 Hz, 1H), 3.66-3.55 (m, 1H), 3.53 (s, 3H), 3.08-2.97 (m, 1H), 2.97-2.90 (m, 1H), 2.90 (s, 1H), 1.03 (d, J=6.6 Hz, 3H).

Intermediate 29

4,4'-(bromomethylene)bis(chlorobenzene)

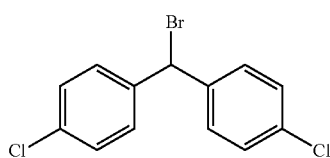

(I-29)

To a stirred solution of bis(4-chlorophenyl)methanol (0.75 g, 2.96 mmol) in DCM (10 mL) was added BBr$_3$ in DCM (3.6 mL, 3.60 mmol) dropwise at 0° C. The reaction mixture was stirred for 1 h. The reaction was quenched with water (50 mL) and was diluted with ethyl acetate (3×100 mL). The combined organic layer was dried over anhydrous sodium sulfate, filtered and evaporated under reduced pressure to yield 4,4'-(bromomethylene)bis(chlorobenzene) (700 mg, 74.8% yield) as a brown solid. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 40-100% B over 25 minutes, flow rate 1.0 mL/min, then a 5 minute hold at 100% B flow rate 1.5 mL/min; then Gradient: 100% B over 2 minutes, flow rate 1.5 mL/min; Gradient: 100% B over 4 minutes, flow rate 1.5 mL/min.

Intermediate 30 tert-butyl (R)-4-(bis(4-chlorophenyl)methyl)-3-methylpiperazine-1-carboxylate

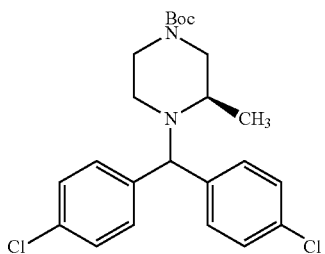

(I-30)

To a stirred solution of tert-butyl (R)-3-methylpiperazine-1-carboxylate (100 mg, 0.5 mmol) in acetonitrile (6 mL) was added DIPEA (0.262 mL, 1.5 mmol) and 4,4'-(bromomethylene)bis(chlorobenzene) (237 mg, 0.75 mmol). The reaction mixture was heated up to 85° C. over 10 min and was stirred for 16 h. The reaction mixture was concentrated under high vacuum to yield a brown gum. The crude compound was purified by ISCO® (using 24 g silica gel column; using 8-12% ethylacetate/petroleum ether) to yield tert-butyl (R)-4-(bis(4-chlorophenyl)methyl)-3-methylpiperazine-1-carboxylate (180 mg, 83% yield) as a brown gum; LCMS: m/z=437.2 (M+H); rt 1.945 min. LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 80% B over 0.5 minutes, flow rate 1.0 mL/min, 80-98% B over 2.5 minutes, flow rate 1.0 mL/min, then a 1.0 minute hold at 98% B flow rate 1.0 mL/min.

Intermediate 31

(R)-1-(bis(4-chlorophenyl)methyl)-2-methylpiperazine, HCl

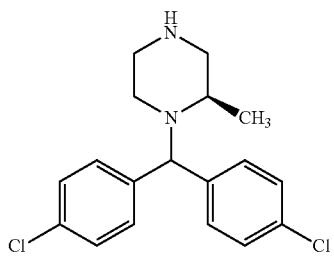

(I-31)

To a stirred solution of tert-butyl (R)-4-(bis(4-chlorophenyl)methyl)-3-methylpiperazine-1-carboxylate (130 mg, 0.3 mmol) in HCl in dioxane (5.0 mL, 165 mmol). The reaction mixture was stirred at room temperature for 1 h. The reaction mixture was concentrated under high vacuum to yield HCl salt of (R)-1-(bis(4-chlorophenyl)methyl)-2-methylpiperazine (105 mg, 95% yield) as a brown solid; LCMS: m/z=337.0 (M+H); rt 2.457 min. LC-MS Method: Column-KINETEX-XB-C18 (75×3 mm-2.6 μm); Mobile phase A: 0.1% TFA in Milli-Q water; Mobile phase B: 0.1% TFA in acetonitrile; Gradient: 20-100% B over 4.0 minutes, flow rate 1.0 mL/min, then a 0.6 minute hold at 100% B flow rate 1.5 mL/min, 100-20% B over 0.1 minutes, flow rate 1.5 mL/min.

Intermediate 32

6-Cyano-1-methyl-2-oxo-1,2-dihydro-1,5-naphthyridin-4-yl trifluoromethanesulfonate

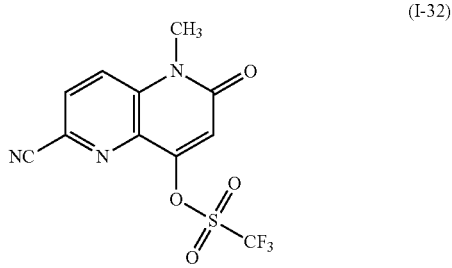 [SMILES: Cn1c(=O)cc(OS(=O)(=O)C(F)(F)F)c2nc(C#N)ccc21]

(I-32)

To a mixture of 8-hydroxy-5-methyl-6-oxo-5,6-dihydro-1,5-naphthyridine-2-carbonitrile (0.3 g, 1.49 mmol), DMAP (0.018 g, 0.15 mmol) and TEA (0.312 mL, 2.24 mmol) in DCM (30 mL) was added dropwise trifluoromethanesulfonic anhydride (0.269 mL, 1.640 mmol) in DCM (3 mL) at 0° C. The reaction mixture was stirred for 3 h. The reaction mixture was diluted with DCM, washed with water, the organic layer was dried over Na$_2$SO$_4$, filtered and evaporated under reduced pressure to yield 6-cyano-1-methyl-2-oxo-1,2-dihydro-1,5-naphthyridin-4-yl trifluoromethanesulfonate (0.45 g, 81% yield) as a pale yellow solid; LCMS: m/z=334.2 (M+H); rt 1.40 min. LC-MS Method: Column-AQUITY UPLC BEH C18 (3.0×50 mm) 1.7 μm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.2 minute hold at 100% B, flow rate 0.7 mL/min.

Example 34

(R)-8-(4-(bis(4-chlorophenyl)methyl)-3-methylpiperazin-1-yl)-7-fluoro-5-methyl-6-oxo-5,6-dihydro-1,5-naphthyridine-2-carbonitrile

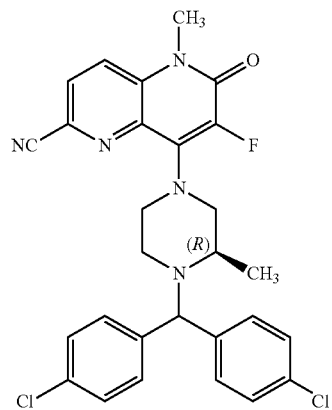

(34)

To a stirred solution of (R)-8-(4-(bis(4-chlorophenyl)methyl)-3-methylpiperazin-1-yl)-5-methyl-6-oxo-5,6-dihydro-1,5-naphthyridine-2-carbonitrile (45 mg, 0.087 mmol) in acetonitrile (6 mL) at 0° C. was added 1-chloromethyl-4-fluoro-1 4-diazoniabicyclo 2.2.2 octane bis(tetrafluoroborate) (40.0 mg, 0.113 mmol) in THF/H₂O (0.5/0.5 mL) drop wise. The reaction mixture was stirred for 1.5 h. The reaction mixture was slowly warmed to room temperature and was stirred for another 1.5 h. The reaction mixture was concentrated under reduced pressure to yield a brown oil. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 10 minute hold at 10% B, 10-40% B over 25 minutes, then a 5 minute hold at 100% B; Flow Rate: 15 mL/min; Column Temperature: 25° C. Fractions containing the product were combined and dried via centrifugal evaporation to yield (R)-8-(4-(bis(4-chlorophenyl)methyl)-3-methylpiperazin-1-yl)-7-fluoro-5-methyl-6-oxo-5,6-dihydro-1,5-naphthyridine-2-carbonitrile (1 mg, 2.2% yield). LCMS: m/z 536.2 (M+H); rt 2.69 min. LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 8.21-8.09 (m, 2H), 7.52 (d, J=8.6 Hz, 2H), 7.56 (d, J=8.3 Hz, 2H), 7.39 (dd, J=8.6, 2.2 Hz, 4H), 4.87 (s, 1H), 3.67-3.54 (m, 4H), 3.52 (d, J=12.5 Hz, 2H), 2.92 (d, J=14.4 Hz, 2H), 2.78 (d, J=10.8 Hz, 1H), 1.15 (d, J=6.4 Hz, 3H). One proton merged with residual solvent peak.

Intermediate 33 tert-butyl (S)-4-(bis(4-fluorophenyl)methyl)-3-methylpiperazine-1-carboxylate

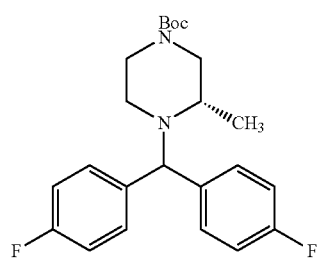

(I-33)

To a stirred solution of tert-butyl (S)-3-methylpiperazine-1-carboxylate (2.0 g, 10 mmol) in acetonitrile (20 mL) were added DIPEA (5.23 mL, 30 mmol) and 4,4'-(chloromethylene)bis(fluorobenzene) (3.57 g, 15 mmol). The reaction mixture was heated up to 50° C. over 3 min and stirred for 16 h. The reaction mixture was concentrated under high vacuum to yield crude product, which was purified by ISCO® (using 40 g silica gel column; using 8-12% ethyl acetate/petroleum ether) to yield tert-butyl (S)-4-(bis(4-fluorophenyl)methyl)-3-methylpiperazine-1-carboxylate (1.0 g, 24.9% yield) as a brown solid; LCMS: m/z=403.3 (M+H); rt 3.01 min; LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 34

(S)-1-(bis(4-fluorophenyl)methyl)-2-methylpiperazine

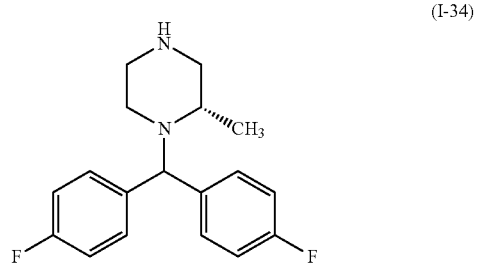 [SMILES: C[C@H]1CNCCN1C(c1ccc(F)cc1)c1ccc(F)cc1]

(I-34)

To a stirred solution of tert-butyl (S)-4-(bis(4-fluorophenyl)methyl)-3-methylpiperazine-1-carboxylate (1.0 g, 2.485 mmol) in HCl in dioxane (3.0 mL, 12.00 mmol). The reaction mixture was stirred at room temperature for 2 h. The reaction mixture was concentrated under high vacuum to yield a HCl salt of (S)-1-(bis(4-fluorophenyl)methyl)-2-methylpiperazine (0.7 g, 86% yield) as a brown solid; LCMS: m/z=303.2 (M+H); rt 1.834 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Example 35

(S)-8-(4-(bis(4-fluorophenyl)methyl)-3-methylpiperazin-1-yl)-5-methyl-6-oxo-5,6-dihydro-1,5-naphthyridine-2-carbonitrile

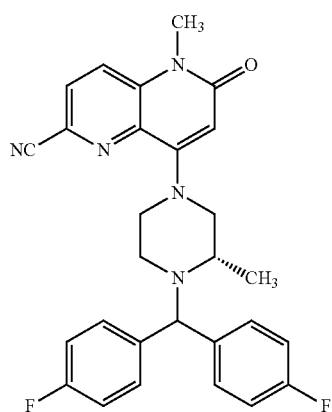

(35)

To a stirred solution of 6-cyano-1-methyl-2-oxo-1,2-dihydro-1,5-naphthyridin-4-yl trifluoromethanesulfonate (70 mg, 0.210 mmol) in acetonitrile (8 mL) were added DIPEA (0.110 mL, 0.630 mmol) and HCl salt of (S)-1-(bis(4-fluorophenyl)methyl)-2-methylpiperazine (71.2 mg, 0.21 mmol). The reaction mixture was heated up to 85° C. over 5 min and was stirred for 2 h. The reaction mixture was filtered and was concentrated under high vacuum to yield a brown gum. The crude material was purified via preparative HPLC with the following conditions: Column: Sunfire C18, 19×150 mm, 5 µm particles; Mobile Phase A: 10 mM ammonium acetate; Mobile Phase B: acetonitrile; Gradient: 30-100% B over 20 minutes, then a 5 minute hold at 100% B; Flow: 17 mL/min. Fractions containing the product were combined and dried via centrifugal evaporation to afford (S)-8-(4-(bis(4-fluorophenyl)methyl)-3-methylpiperazin-1-yl)-5-methyl-6-oxo-5,6-dihydro-1,5-naphthyridine-2-carbonitrile (25 mg, 24.2% yield); LCMS: m/z=486.3 (M+H); rt 2.218 min. LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.14 (d, J=8.8 Hz, 1H), 8.06 (d, J=8.8 Hz, 1H), 7.63-7.42 (m, 4H), 7.24-7.04 (m, 4H), 6.07 (s, 1H), 4.85 (s, 1H), 4.02 (d, J=11.7 Hz, 1H), 3.65-3.44 (m, 4H), 3.23-3.04 (m, 2H), 3.04-2.93 (m, 1H), 2.79-2.64 (m, 2H), 1.17 (d, J=6.4 Hz, 3H).

Example 36

(S)-8-(4-(bis(4-fluorophenyl)methyl)-3-methylpiperazin-1-yl)-7-chloro-5-methyl-6-oxo-5,6-dihydro-1,5-naphthyridine-2-carbonitrile

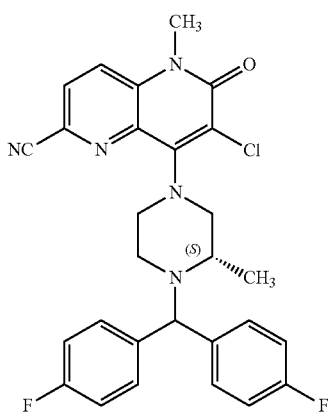

(36)

To a stirred solution of (S)-8-(4-(bis(4-fluorophenyl) methyl)-3-methylpiperazin-yl)-5-methyl-6-oxo-5,6-dihydro-1,5-naphthyridine-2-carbonitrile (30 mg, 0.062 mmol) in DCM (4 mL) was added NCS (16.50 mg, 0.124 mmol). The reaction mixture was stirred at room temperature for 16 h. The reaction was quenched with water (5 mL). The reaction mixture was diluted with ethyl acetate (3×10 mL). The combined organic layer was dried over anhydrous sodium sulfate, filtered and evaporated under reduced pressure to yield a brown oil. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 34% B, 34-75% B over 25 minutes, then a 5 minute hold at 100% B; Flow Rate: 15 mL/min; Column Temperature: 25° C. Fractions containing the product were combined and dried via centrifugal evaporation to yield (S)-8-(4-(bis(4-fluorophenyl)methyl)-3-methylpiperazin-1-yl)-7-chloro-5-methyl-6-oxo-5,6-dihydro-1,5-naphthyridine-2-carbonitrile (21 mg, 64.8% yield); LCMS: m/z=520.2 (M+H); rt 2.937 min. LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.17 (q, J=8.8 Hz, 2H), 7.55 (dd, J=10.5, 8.8 Hz, 2H), 7.57 (dd, J=10.5, 8.8 Hz, 2H), 7.15 (td, J=8.8, 1.5 Hz, 4H), 4.86 (s, 1H), 3.85 (dd, J=12.0, 2.7 Hz, 1H), 3.71-3.55 (m, 4H), 3.47-3.32 (m, 2H), 3.03-2.82 (m, 2H), 2.44 (d, J=11.5 Hz, 1H), 1.04 (d, J=6.6 Hz, 3H).

Example 37

(S)-4-(4-(bis(4-fluorophenyl)methyl)-3-methylpiperazin-1-yl)-6-bromo-1-methyl-2-oxo-1,2-dihydro-1,5-naphthyridine-3-carbonitrile

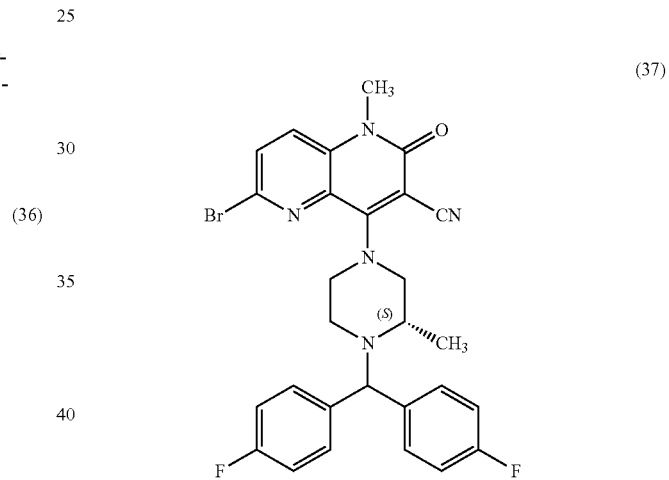

(37)

To a stirred solution of 6-bromo-3-cyano-1-methyl-2-oxo-1,2-dihydro-1,5-naphthyridin-4-yl trifluoromethanesulfonate (100 mg, 0.243 mmol) in acetonitrile (8 mL) were added DIPEA (0.127 mL, 0.728 mmol) and TFA salt of (S)-1-(bis(4-fluorophenyl) methyl)-2-methylpiperazine (101 mg, 0.243 mmol). The reaction mixture was heated up to 85° C. over 5 min and was stirred for 2 h. The reaction mixture was concentrated under high vacuum to yield a brown gum. The crude compound was purified by ISCO® (using 12 g silica gel column; using 12-15% ethyl acetate/petroleum ether) to yield (S)-4-(4-(bis(4-fluorophenyl)methyl)-3-methylpiperazin-1-yl)-6-bromo-1-methyl-2-oxo-1,2-dihydro-1,5-naphthyridine-3-carbonitrile (100 mg, 67.9% yield) as a brown solid; LCMS: m/z=564.0 (M+H); rt 3.958 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Example 38

(S)-8-(4-(bis(4-fluorophenyl)methyl)-3-methylpiperazin-1-yl)-5-methyl-6-oxo-5,6-dihydro-1,5-naphthyridine-2,7-dicarbonitrile

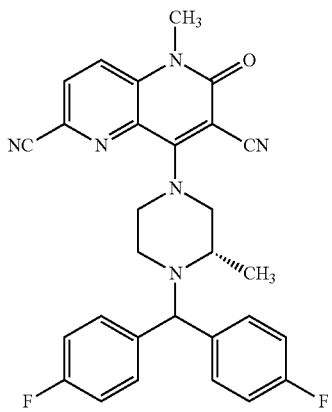

(38)

To a stirred solution of (S)-4-(4-(bis(4-fluorophenyl)methyl)-3-methylpiperazin-1-yl)-6-bromo-1-methyl-2-oxo-1,2-dihydro-1,5-naphthyridine-3-carbonitrile (80 mg, 0.142 mmol) in NMP (5 mL) were added zinc (1.853 mg, 0.028 mmol) and zinc cyanide (33.3 mg, 0.283 mmol) under nitrogen. The nitrogen purging was continued for 3 min., dppf (4.71 mg, 8.50 μmol) and Pd$_2$(dba)$_3$ (12.98 mg, 0.014 mmol) were added, and purging was continued for another 3 min. The reaction mixture was heated up to 80° C. over 5 min and was stirred for 1 h. The reaction mixture was concentrated under reduced pressure to yield a brown oil. The crude material was purified via preparative HPLC Method: Column-Sunfire C18 (150×4.6 mm) 5 μm; Mobile phase A: 10 mM ammonium acetate plain in water; Mobile phase B: acetonitrile; Gradient: 30-60% B over 2.0 minutes, flow rate 20 mL/min, then a 18 minute hold at 60-100% B flow rate 20 mL/min. Fractions containing the product were combined and dried via centrifugal evaporation to yield (S)-8-(4-(bis(4-fluorophenyl)methyl)-3-methylpiperazin-1-yl)-5-methyl-6-oxo-5,6-dihydro-1,5-naphthyridine-2,7-dicarbonitrile (20 mg, 27.1% yield); LCMS: m/z=511.2 (M+H); rt 2.158 min. LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.25 (d, J=8.8 Hz, 1H), 8.15 (d, J=8.8 Hz, 1H), 7.56 (dd, J=11.9, 3.1 Hz, 2H), 7.56 (dd, J=14.2, 12.0 Hz, 2H), 7.16 (t, J=8.9 Hz, 4H), 4.91 (s, 1H), 4.10 (d, J=13.2 Hz, 1H), 4.01 (d, J=12.2 Hz, 1H), 3.90-3.80 (m, 1H), 3.68-3.55 (m, 1H), 3.53 (s, 3H), 3.09-2.97 (m, 1H), 2.92 (t, J=10.0 Hz, 1H), 2.57-2.52 (m, 1H), 1.04 (d, J=6.4 Hz, 3H).

Examples 39 and 40

Methyl 1-(bis(4-fluorophenyl)methyl)-4-(6-cyano-1-methyl-2-oxo-1,2-dihydro-1,5-naphthyridin-4-yl)piperazine-2-carboxylate

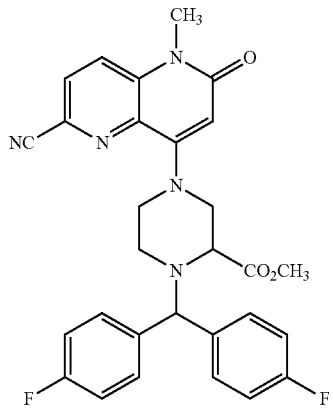

(39-40)

To a stirred solution of 6-cyano-1-methyl-2-oxo-1,2-dihydro-1,5-naphthyridin-4-yl trifluoromethanesulfonate (130 mg, 0.39 mmol) in acetonitrile (8 mL) were added DIPEA (0.204 mL, 1.17 mmol) and HCl salt of methyl 1-(bis(4-fluorophenyl)methyl) piperazine-2-carboxylate (149 mg, 0.390 mmol). The reaction mixture was heated up to 85° C. over 5 min and was stirred for 1 h at the same temperature. The reaction mixture was concentrated under reduced pressure to yield a brown gum. The crude compound was purified by ISCO® (24 g silica gel column; using 60-64% ethylacetate/petroleum ether) to yield methyl 1-(bis(4-fluorophenyl)methyl)-4-(6-cyano-1-methyl-2-oxo-1,2-dihydro-1,5-naphthyridin-4-yl)piperazine-2-carboxylate (racemate) as a brown solid. Enantiomers were separated using chiral HPLC. Chiral separation Method: Column-DAD-1: (R, R) Whelk-01 (250×4.6 mm), 5 μm; DAD-2: CHIRALPAK AD-H (250×4.6 mm), 5; Method: 4.0_50_120; Co-Solvent: 0.2% ammonia in methanol.

Example 39: Enantiomer 1: (14.2 mg, 35.1% yield); LCMS: m/z=530.2 (M+H); rt 2.210 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.15 (d, J=8.8 Hz, 1H), 8.08 (d, J=9.0 Hz, 1H), 7.64-7.50 (m, 2H), 7.43-7.29 (m, 2H), 7.23-7.05 (m, 4H), 6.14 (s, 1H), 5.17 (s, 1H), 4.78 (d, J=12.5 Hz, 1H), 3.64 (d, J=11.0 Hz, 1H), 3.60 (s, 3H), 3.54 (s, 3H), 3.46-3.34 (m, 2H), 3.15 (dd, J=12.3, 4.0 Hz, 1H), 3.04 (td, J=11.9, 3.3 Hz, 1H), 2.71-2.62 (m, 1H).

Example 40: Enantiomer 2; (15.4 mg, 38.1% yield); LCMS: m/z=530.2 (M+H); rt 2.210 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.15 (d, J=9.0 Hz, 1H), 8.08 (d, J=8.8 Hz, 1H), 7.57 (dd, J=8.8, 5.6 Hz, 2H), 7.43-7.32 (m, 2H), 7.25-7.05 (m, 4H), 6.14 (s, 1H), 5.17 (s, 1H), 4.78 (d, J=12.5 Hz, 1H), 3.64 (d, J=10.5 Hz, 1H), 3.60 (s, 3H), 3.54 (s, 3H), 3.45-3.36 (m, 2H), 3.15 (dd, J=12.6, 4.0 Hz, 1H), 3.09-2.99 (m, 1H), 2.71-2.63 (m, 1H).

Intermediate 35

1-(Bis(4-fluorophenyl)methyl)-4-(tert-butoxycarbonyl)piperazine-2-carboxylic acid

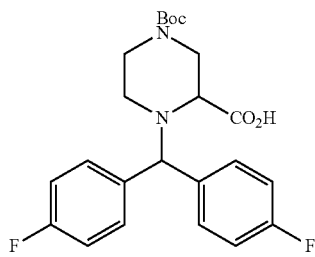

(I-35)

To a stirred solution of 1-(tert-butyl) 3-methyl 4-(bis(4-fluorophenyl)methyl) piperazine-1,3-dicarboxylate (750 mg, 1.680 mmol) in tetrahydrofuran (6 mL) and water (3 mL) was added LiOH (201 mg, 8.40 mmol). The reaction mixture was heated up to 60° C. over 5 min and was stirred for 36 h. The reaction mixture was concentrated under reduced pressure, then acidified with 1.5 N HCl to adjust the pH to ~6. The reaction was quenched with water (50 mL). The reaction mixture was diluted with DCM (3×100 mL). The combined organic layer was dried over anhydrous sodium sulfate, filtered and evaporated under reduced pressure to yield 1-(bis(4-fluorophenyl)methyl)-4-(tert-butoxycarbonyl)piperazine-2-carboxylic acid (520 mg, 44.4% yield) as a brown oil. LCMS: m/z=431.5 (M−H); rt 1.45 min. LC-MS Method: Column-AQUITY UPLC BEH C18 (3.0×50 mm) 1.7 μm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.2 minute hold at 100% B, flow rate 0.7 mL/min.

Intermediate 36 tert-Butyl 4-(bis(4-fluorophenyl)methyl)-3-carbamoylpiperazine-1-carboxylate

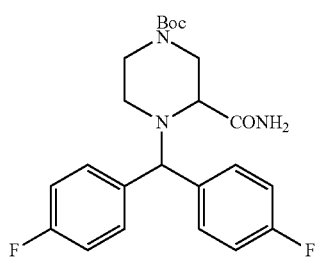

(I-36)

To a stirred solution of 1-(bis(4-fluorophenyl)methyl)-4-(tert-butoxycarbonyl) piperazine-2-carboxylic acid (0.25 g, 0.58 mmol) in DMF (5 mL) were added DIPEA (0.303 mL, 1.73 mmol) and HATU (0.33 g, 0.87 mmol). The reaction mixture was stirred for 5 min and ammonium chloride (0.046 g, 0.87 mmol) was added. The reaction mixture was stirred at room temperature for 3 h. The reaction was quenched with water (50 mL) and was diluted with ethyl acetate (3×100 mL). The combined organic layer was dried over anhydrous sodium sulfate, filtered and evaporated under reduced pressure to yield tert-butyl 4-(bis(4-fluorophenyl)methyl)-3-carbamoylpiperazine-1-carboxylate (280 mg, 43.8% yield) as a brown gum. LCMS: m/z=432.4 (M+H); rt 1.78 min. LC-MS Method: Column-AQUITY UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Intermediate 37

1-(Bis(4-fluorophenyl)methyl)piperazine-2-carboxamide, HCl

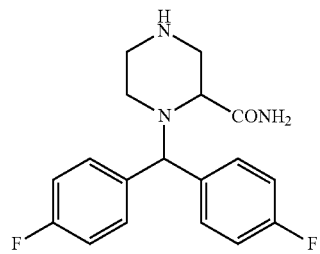

(I-37)

A solution of tert-butyl 4-(bis(4-fluorophenyl)methyl)-3-carbamoylpiperazine-1-carboxylate (200 mg, 0.464 mmol) in HCl in dioxane (1.0 mL, 4.00 mmol) was stirred at room temperature for 1 h. The reaction mixture was concentrated under high vacuum to yield HCl salt of 1-(bis(4-fluorophenyl)methyl)piperazine-2-carboxamide (200 mg, 64.5% yield) as a brown solid. LCMS: m/z=332.3 (M+H); rt 1.06 min. LC-MS Method: Column-AQUITY UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Examples 41 and 42

1-(bis(4-fluorophenyl)methyl)-4-(6-cyano-1-methyl-2-oxo-1,2-dihydro-1,5-naphthyridin-4-yl)piperazine-2-carboxamide

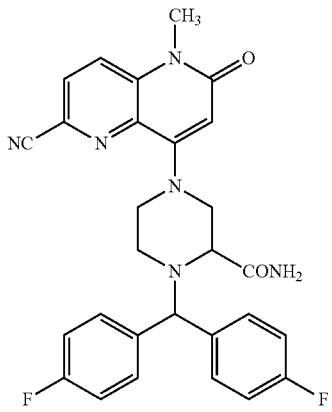

(41-42)

To a stirred solution of 6-cyano-1-methyl-2-oxo-1,2-dihydro-1,5-naphthyridin-4-yl trifluoromethanesulfonate (80 mg, 0.24 mmol) in acetonitrile (9 mL) were added DIPEA (0.13 mL, 0.72 mmol) and HCl salt of 1-(bis(4-fluorophenyl)methyl)piperazine-2-carboxamide (88 mg, 0.24 mmol). The reaction mixture was heated up to 85° C. over 5 min and was stirred for 1 h. The reaction mixture was concentrated under reduced pressure to yield a brown gum. The crude material was purified via preparative HPLC with the following conditions: Column: Sunfire C18, 19×150 mm, 5 μm particles; Mobile Phase A: 10 mM ammonium acetate pH-4.5 with acetic acid; Mobile Phase B: acetonitrile; Gradient: 20-100% B over 16 minutes, then a 5 minute hold at 100% B; Flow: 17 mL/min. Fractions containing the product were combined and dried via centrifugal evaporation to yield product as enantiomeric mixture. Enantiomers were separated using chiral HPLC. Chiral separation method: Column: Lux Cellulose-4 (250×4.6) mm, 5.0 μm; Isocratic Mode, Co-Solvent: 0.2% NH$_4$OH in methanol+acetonitrile (1:1); Co-Solvent percentage: 50%, Column Temperature: 30° C.; Back Pressure: 100 bars; Total Flow rate: 4 g/min. of enantiomeric mixture afforded Enantiomer 1 and Enantiomer 2.

Example 41: Enantiomer 1 (3.6 mg, 2.9% yield); LCMS: m/z=515.2 (M+H); rt 1.788 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.47 (s, 1H), 8.13-8.17 (m, 1H), 8.04-8.08 (m, 1H), 7.63-7.76 (m, 1H), 7.54-7.63 (m, 4H), 7.15 (m, J=8.8, 8.8, 3.9 Hz, 4H), 6.04 (s, 1H), 5.33 (s, 1H), 4.18 (br d, J=9.5 Hz, 1H), 3.72-3.81 (m, 1H), 3.62-3.70 (m, 1H), 3.52 (s, 3H), 3.20-3.27 (m, 2H), 3.15-3.18 (m, 1H), 2.54-2.57 (m, 1H).

Example 42: Enantiomer 2: (4.1 mg, 3.3% yield); LCMS: m/z=515.2 (M+H); rt 1.788 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.47 (s, 1H), 8.13-8.16 (m, 1H), 8.04-8.08 (m, 1H), 7.70-7.75 (m, 1H), 7.54-7.64 (m, 4H), 7.13-7.19 (m, 4H), 6.04 (s, 1H), 5.33 (s, 1H), 4.15-4.22 (m, 1H), 3.73-3.80 (m, 1H), 3.62-3.70 (m, 1H), 3.52 (s, 3H), 3.35-3.40 (m, 1H), 3.14-3.29 (m, 3H).

Example 43

8-(4-(bis(4-fluorophenyl)methyl)-3-cyanopiperazin-1-yl)-5-methyl-6-oxo-5,6-dihydro-1,5-naphthyridine-2-carbonitrile

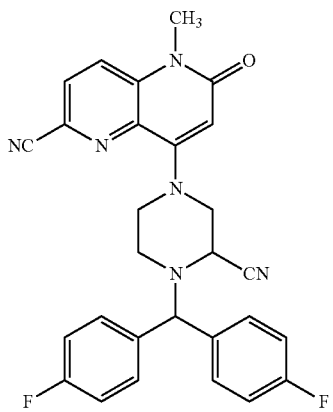

(43)

To a stirred solution of 1-(bis(4-fluorophenyl)methyl)-4-(6-cyano-1-methyl-2-oxo-1,2-dihydro-1,5-naphthyridin-4-yl)piperazine-2-carboxamide (0.02 g, 0.039 mmol) in DCM (5 mL) was added TEA (0.022 mL, 0.155 mmol) at 0° C., followed by the addition of TFAA (10.98 μL, 0.078 mmol). The reaction mixture was warmed to room temperature and was stirred for 1 h. The reaction mixture was concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 30% B, 30-75% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 8-(4-(bis(4-fluorophenyl)methyl)-3-cyanopiperazin-1-yl)-5-methyl-6-oxo-5,6-dihydro-1,5-naphthyridine-2-carbonitrile (5.2 mg, 25.9% yield); LCMS: m/z=497.2 (M+H); rt 2.056 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.18 (d, J=8.8 Hz, 1H), 8.11 (d, J=9.0 Hz, 1H), 7.63 (dd, J=8.6, 5.4 Hz, 2H), 7.55 (dd, J=8.9, 5.5 Hz, 2H), 7.29-7.11 (m, 4H), 6.17 (s, 1H), 4.69-4.57 (m, 2H), 4.01 (s, 1H), 3.81 (d, J=10.3 Hz, 1H), 3.60-3.49 (m, 3H), 3.11 (dd, J=13.1, 2.8 Hz, 1H), 3.07-2.98 (m, 1H), 2.83 (d, J=11.7 Hz, 1H), 2.57-2.53 (m, 1H).

Examples 44 and 45

8-(4-(bis(4-fluorophenyl)methyl)-3-cyanopiperazin-1-yl)-5-methyl-6-oxo-5,6-dihydro-1,5-naphthyridine-2-carbonitrile

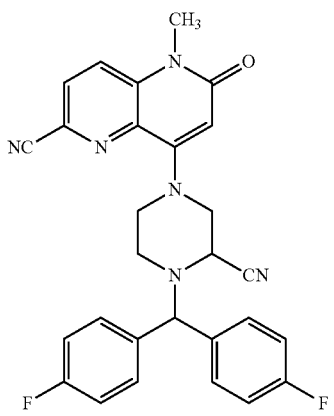

(44-45)

Example 43 was separated into two enantiomers using chiral HPLC. Chiral separation method: Method: Column-Lux-cellulose C4 (250×21.2) mm, 5 micron; M. Phase A: M. Phase B: 0.1% DEA in acetonitrile:methanol (10:90); Flow: 21 mL/min; Gradient: 0-100% B over 20 minutes.

Example 44: Enantiomer 1: (7.5 mg, 9.6% yield); LCMS: m/z=497.3 (M+H); rt 1.977 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.15-8.20 (m, 1H), 8.06-8.15 (m, 1H), 7.60-7.65 (m, 2H), 7.53-7.57 (m, 2H), 7.20 (td, J=8.9, 6.7 Hz, 4H), 6.16 (s, 1H), 4.60-4.68 (m, 2H), 3.99-4.02 (m, 1H), 3.78-3.87 (m, 1H), 3.55 (s, 3H), 3.09-3.15 (m, 1H), 2.99-3.07 (m, 1H), 2.80-2.86 (m, 1H), 2.54-2.58 (m, 1H).

Example 45: Enantiomer 2: (7.5 mg, 9.6% yield); LCMS: m/z=497.3 (M+H); rt 1.977 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.16-8.20 (m, 1H), 8.09-8.13 (m, 1H), 7.60-7.65 (m, 2H), 7.52-7.57 (m, 2H), 7.16-7.24 (m, 4H), 6.16 (s, 1H), 4.60-4.66 (m, 2H), 3.99-4.02 (m, 1H), 3.79-3.86 (m, 1H), 3.55 (s, 3H), 3.09-3.14 (m, 1H), 2.98-3.07 (m, 1H), 2.82 (s, 1H), 2.54-2.58 (m, 1H).

Intermediate 38 tert-Butyl 4-(bis(4-fluorophenyl)methyl)-3-(cyclopropylcarbamoyl)piperazine-1-carboxylate

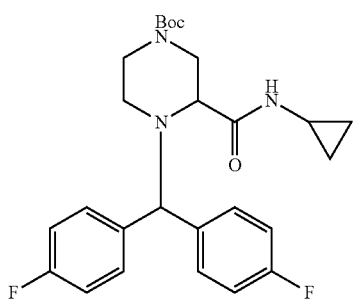

(I-38)

To a stirred solution of 1-(bis(4-fluorophenyl)methyl)-4-(tert-butoxycarbonyl) piperazine-2-carboxylic acid (0.15 g, 0.347 mmol) in DMF (5 mL) were added DIPEA (0.182 mL, 1.041 mmol) and HATU (0.198 g, 0.520 mmol). The reaction mixture was stirred for 5 min and cyclopropanamine (0.020 g, 0.347 mmol) was added. The reaction mixture was stirred at room temperature for 3 h. The reaction was quenched with water (50 mL) and was extracted with ethyl acetate (3×100 mL). The combined organic layer was dried over anhydrous sodium sulfate, filtered and evaporated under reduced pressure to yield tert-butyl 4-(bis(4-fluorophenyl)methyl)-3-(cyclopropylcarbamoyl)piperazine-1-carboxylate (200 mg, 51.4% yield) as a brown gum. LCMS: m/z=472.5 (M+H); rt 1.91 min. LC-MS Method: Column-AQUITY UPLC BEH C18 (3.0×50 mm) 1.7 µm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.2 minute hold at 100% B, flow rate 0.7 mL/min.

Intermediate 39

1-(Bis(4-fluorophenyl)methyl)-N-cyclopropylpiperazine-2-carboxamide, HCl

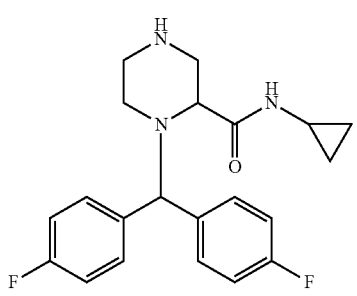

(I-39)

To a stirred solution of tert-butyl 4-(bis(4-fluorophenyl)methyl)-3-(cyclopropylcarbamoyl)piperazine-1-carboxylate (0.11 g, 0.233 mmol) in HCl in dioxane (1.5 mL, 49.4 mmol). The reaction mixture was stirred at room temperature for 1h. The reaction mixture was concentrated under high vacuum to yield 1-(bis(4-fluorophenyl) methyl)-N-cyclopropylpiperazine-2-carboxamide, HCl (0.11 g, 79% yield) as a brown solid. LCMS: m/z=372.2 (M+H); rt 2.276 min. LC-MS Method: Column-KINETEX-XB-C18 (75×3 mm-2.6 µm); Mobile phase A: 10 mM ammonium formate in water: acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Examples 46 to 48

1-(bis(4-fluorophenyl)methyl)-4-(6-cyano-1-methyl-2-oxo-1,2-dihydro-1,5-naphthyridin-4-yl)-N-cyclopropylpiperazine-2-carboxamide

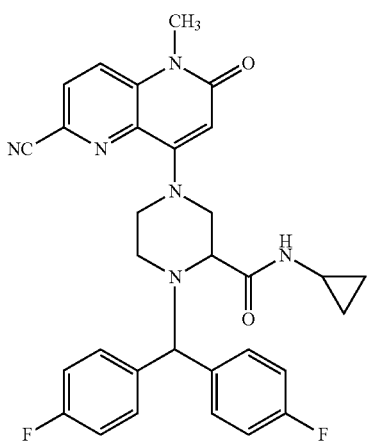

(46-48)

To a stirred solution of 6-cyano-1-methyl-2-oxo-1,2-dihydro-1,5-naphthyridin-4-yl trifluoromethanesulfonate (80 mg, 0.240 mmol) in acetonitrile (9 mL) were added DIPEA (0.126 mL, 0.72 mmol) and HCl salt of 1-(bis(4-fluorophenyl)methyl)-N-cyclopropylpiperazine-2-carboxamide (144 mg, 0.24 mmol). The reaction mixture was heated up to 85° C. over 5 min and was stirred for 1 h. The reaction mixture was concentrated under reduced pressure to yield a brown gum. A sample of the crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 5 minute hold at 20% B, 20-55% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield racemic 1-(bis(4-fluorophenyl)methyl)-4-(6-cyano-1-methyl-2-oxo-1,2-dihydro-1,5-naphthyridin-4-yl)-N-cyclopropylpiperazine-2-carboxamide (Example 46), followed by chiral separation afford enantiomers 1 and 2. Chiral separation method: Method: Column-DAD-1 Cellulose-2 (250×4.6) mm, 5 micron; DAD-2 Cellulose-4 (250×4.6) mm, 5 micron; M. Phase: 0.1% DEA in acetonitrile:IPA (70:30); Flow rate: 2.0 mL/min.

Example 47: Enantiomer 1: (12.9 mg, 9.5% yield); LCMS: m/z=555.3 (M+H); rt 1.979 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.16 (d, J=8.8 Hz, 1H), 8.04-8.09 (m, 1H), 7.98 (d, J=3.7 Hz, 1H), 7.55 (dd, J=8.6, 5.6 Hz, 2H), 7.46 (dd, J=8.6, 5.6 Hz, 2H), 7.11-7.18 (m, 4H), 6.03 (s, 1H), 5.21 (s, 1H), 4.22-4.35 (m, 1H), 3.67-3.75 (m, 1H), 3.59-3.65 (m, 1H), 3.52 (s, 3H), 3.33-3.39 (m, 1H), 3.22-3.30 (m, 1H), 3.13-3.16 (m, 1H), 2.52-2.54 (m, 1H), 2.45-2.48 (m, 1H), 0.48-0.61 (m, 2H), 0.18-0.35 (m, 2H).

Example 48: Enantiomer 2: (12.9 mg, 9.64% yield); LCMS: m/z=555.3 (M+H); rt 1.980 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.16 (d, J=8.8 Hz, 1H), 8.07 (d, J=9.0 Hz, 1H), 7.98 (d, J=3.7 Hz, 1H), 7.55 (dd, J=8.4, 5.7 Hz, 2H), 7.46 (dd, J=8.8, 5.6 Hz, 2H), 7.15 (td, J=8.8, 2.0 Hz, 4H), 6.03 (s, 1H), 5.21 (s, 1H), 4.39-4.23 (m, 1H), 3.78 (dt, J=12.2, 6.0 Hz, 1H), 3.68 (br. s., 1H), 3.62 (dd, J=13.1, 3.5 Hz, 1H), 3.53 (s, 3H), 3.38 (br. s., 1H), 3.30-3.22 (m, 1H), 3.15 (t, J=3.8 Hz, 1H), 2.47 (br. s., 1H), 0.61-0.44 (m, 2H), 0.35-0.17 (m, 2H).

Example 49

Methyl 1-(bis(4-fluorophenyl)methyl)-4-(6-bromo-3-cyano-1-methyl-2-oxo-1,2-dihydro-1,5-naphthyridin-4-yl)piperazine-2-carboxylate

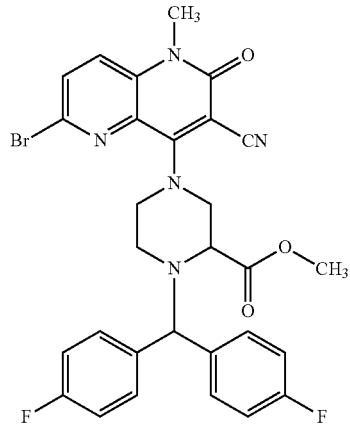

(49)

To a stirred solution of 6-bromo-3-cyano-1-methyl-2-oxo-1,2-dihydro-1,5-naphthyridin-4-yl trifluoromethanesulfonate (120 mg, 0.291 mmol) in acetonitrile (8 mL) were added DIPEA (0.153 mL, 0.873 mmol) and HCl salt of methyl 1-(bis(4-fluorophenyl)methyl)piperazine-2-carboxylate (111 mg, 0.291 mmol). The reaction mixture was heated up to 85° C. over 5 min and was stirred for 1 h. The reaction mixture was concentrated under high vacuum to yield a brown gum. The crude compound was purified by ISCO® (using 12 g silica gel column; using 12-15% ethyl acetate/petroleum ether) to yield methyl 1-(bis(4-fluorophenyl)methyl)-4-(6-bromo-3-cyano-1-methyl-2-oxo-1,2-dihydro-1,5-naphthyridin-4-yl)piperazine-2-carboxylate (120 mg, 0.197 mmol, 67.7% yield) as a brown solid. LCMS:

m/z=608.1 (M+H); rt 2.37 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 7.95 (d, J=9.0 Hz, 1H), 7.89 (d, J=9.0 Hz, 1H), 7.60 (dd, J=8.8, 5.6 Hz, 2H), 7.46 (dd, J=8.6, 5.6 Hz, 2H), 7.16 (q, J=8.9 Hz, 4H), 5.23 (s, 1H), 4.44 (d, J=12.7 Hz, 1H), 4.20 (d, J=12.0 Hz, 1H), 3.64-3.48 (m, 6H), 3.46 (s, 3H), 3.37 (br. s., 1H), 2.73-2.63 (m, 1H).

Examples 50 to 51 methyl 1-(bis(4-fluorophenyl)methyl)-4-(3,6-dicyano-1-methyl-2-oxo-1,2-dihydro-1,5-naphthyridin-4-yl)piperazine-2-carboxylate

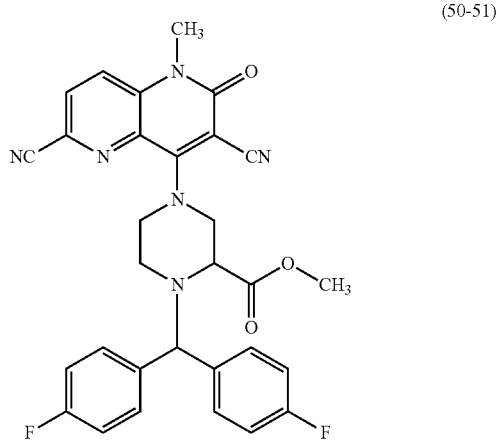 [SMILES: COC(=O)C1CN(c2c(C#N)c(=O)n(C)c3ccc(C#N)nc23)CCN1C(c1ccc(F)cc1)c1ccc(F)cc1]

(50-51)

To a stirred solution of methyl 1-(bis(4-fluorophenyl)methyl)-4-(6-bromo-3-cyano-1-methyl-2-oxo-1,2-dihydro-1,5-naphthyridin-4-yl)piperazine-2-carboxylate (100 mg, 0.164 mmol) in NMP (3 mL) were added zinc (2.149 mg, 0.033 mmol) and zinc cyanide (38.6 mg, 0.329 mmol) under nitrogen. The nitrogen purging was continued for 3 min, dppf (5.47 mg, 9.86 μmol) and Pd₂(dba)₃ (15.05 mg, 0.016 mmol) were added, and purging was continued for another 3 min. The reaction mixture was heated up to 80° C. over 5 min and was stirred for 1 h. The reaction was quenched with saturated ammonium chloride solution (5 mL). The reaction mixture was extracted with ethyl acetate (3×10 mL). The combined organic layer was dried over anhydrous sodium sulfate, filtered and evaporated under reduced pressure to yield a brown oil. The crude material was purified via preparative HPLC (Method) Method: Column-Lux-cellulose C4 (250×21.2) mm, 5 micron; M. phase A: M. Phase B: 0.1% DEA in acetonitrile:methanol (70:30); Flow: 21 mL/min; Gradient: 0-100% B over 20 minutes. Fractions containing the product were combined and dried via centrifugal evaporation to yield product as an enantiomeric mixture. Enantiomers were separated using chiral HPLC. Chiral separation method: Column-X-Bridge Phenyl (250 mm×19 mm ID, 5 μm); Mobile phase A: Buffer: 10 mM ammonium acetate in water pH-4.5; Mobile phase B: acetonitrile; Gradient: 50-80% B over 20 minutes, flow rate 17 mL/min.

Example 50: Enantiomer 1: (6.4 mg, 0.011 mmol, 6.9% yield); LCMS: m/z 555.2 (M+H); rt 2.179 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 8.26 (d, J=8.8 Hz, 1H), 8.16 (d, J=8.8 Hz, 1H), 7.61 (dd, J=8.8, 5.6 Hz, 2H), 7.47 (dd, J=8.8, 5.6 Hz, 2H), 7.26-7.04 (m, 4H), 5.21 (s, 1H), 4.53 (d, J=13.0 Hz, 1H), 4.18 (d, J=11.2 Hz, 1H), 3.97 (dd, J=13.3, 3.5 Hz, 1H), 3.72-3.52 (m, 5H), 3.48 (s, 3H), 3.38-3.32 (m, 1H), 2.69 (d, J=12.5 Hz, 1H).

Example 51: Enantiomer 2: (7.4 mg, 8.0% yield); LCMS: m/z=555.2 (M+H); rt 2.179 min; LC-MS Method: Column-X Bridge BEH XP C18 (50×2.1 mm 2.5; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 8.26 (d, J=9.0 Hz, 1H), 8.16 (d, J=9.0 Hz, 1H), 7.61 (dd, J=8.7, 5.5 Hz, 2H), 7.47 (dd, J=8.7, 5.7 Hz, 2H), 7.16 (q, J=9.0 Hz, 4H), 5.21 (s, 1H), 4.53 (d, J=13.2 Hz, 1H), 4.18 (d, J=12.0 Hz, 1H), 3.97 (dd, J=13.1, 3.8 Hz, 1H), 3.66-3.50 (m, 5H), 3.48 (s, 3H), 3.37-3.32 (m, 1H), 2.69 (d, J=12.0 Hz, 1H).

Intermediate 40

1-(bis(4-fluorophenyl)methyl)piperazine-2-carboxylic acid, HCl

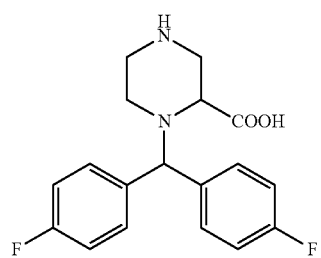

(I-40)

A stirred solution of 1-(bis(4-fluorophenyl)methyl)-4-(tert-butoxycarbonyl) piperazine-2-carboxylic acid (190 mg, 0.439 mmol) in HCl in dioxane (1.0 mL, 4.00 mmol) was stirred at room temperature for 1 h. The reaction mixture was concentrated under high vacuum to yield HCl salt of 1-(bis(4-fluorophenyl)methyl)piperazine-2-carboxylic acid (145 mg, 80.0% yield) as a brown solid. LCMS: m/z=333.2 (M+H); rt 2.99 min. LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Example 52

1-(bis(4-fluorophenyl)methyl)-4-(6-bromo-3-cyano-1-methyl-2-oxo-1,2-dihydro-1,5-naphthyridin-4-yl)piperazine-2-carboxylic acid

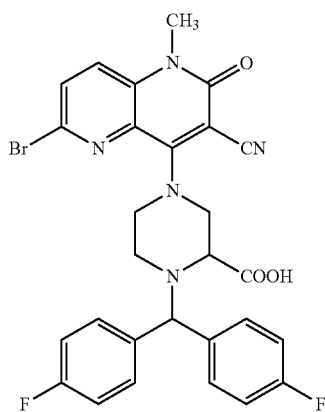

(52)

To a stirred solution of 6-bromo-3-cyano-1-methyl-2-oxo-1,2-dihydro-1,5-naphthyridin-4-yl trifluoromethanesulfonate (180 mg, 0.437 mmol) in acetonitrile (8 mL) were added DIPEA (0.229 mL, 1.310 mmol) and HCl salt of 1-(bis(4-fluorophenyl) methyl)piperazine-2-carboxylic acid (161 mg, 0.437 mmol). The reaction mixture was heated up to 85° C. over 5 min and was stirred for 1 h. The reaction mixture was concentrated under high vacuum to yield a brown gum. The crude compound was purified by ISCO® (using 12 g silica gel column; using 62-65% ethyl acetate/petroleum ether) to yield 1-(bis(4-fluorophenyl)methyl)-4-(6-bromo-3-cyano-1-methyl-2-oxo-1,2-dihydro-1,5-naphthyridin-4-yl)piperazine-2-carboxylic acid (150 mg, 48.5% yield). LCMS: m/z=594.1 (M+H); rt 1.73 min; LC-MS Method: Column-KINETEX-XB-C18 (75×3 mm-2.6 μm); Mobile phase A: 10 mM ammonium formate in water: acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min. $^1$H NMR (400 MHz, DMSO-$d_6$) δ ppm 12.47-12.69 (m, 1H), 7.94-7.96 (m, 1H), 7.86-7.93 (m, 1H), 7.58-7.66 (m, 2H), 7.43-7.49 (m, 2H), 7.16 (s, 4H), 5.39 (s, 1H), 4.41-4.55 (m, 1H), 4.27-4.37 (m, 1H), 3.87-3.99 (m, 1H), 3.40-3.54 (m, 6H), 2.63-2.69 (m, 1H).

Examples 53-54

1-(bis(4-fluorophenyl)methyl)-4-(3,6-di cyano-1-methyl-2-oxo-1,2-dihydro-1,5-naphthyridin-4-yl)piperazine-2-carboxylic acid

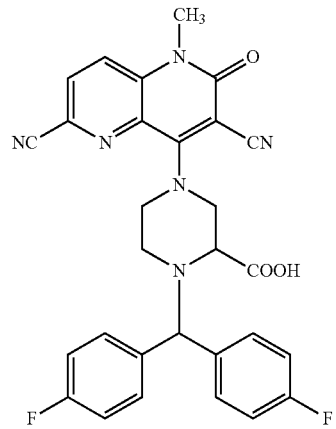

(53-54)

To a stirred solution of 1-(bis(4-fluorophenyl)methyl)-4-(6-bromo-3-cyano-1-methyl-2-oxo-1,2-dihydro-1,5-naphthyridin-4-yl)piperazine-2-carboxylic acid (80 mg, 0.135 mmol) in NMP (5 mL) were added zinc (1.760 mg, 0.027 mmol) and zinc cyanide (31.6 mg, 0.269 mmol) under nitrogen. The nitrogen purging was continued for 3 min., dppf (4.48 mg, 8.08 μmol) and Pd$_2$(dba)$_3$ (12.32 mg, 0.013 mmol) were added, and purging was continued for another 3 min. The reaction mixture was heated up to 80° C. over 5 min and was stirred for 1 h. The reaction was quenched saturated ammonium chloride solution (5 mL) and was extracted with ethyl acetate (3×10 mL). The combined organic layer was dried over anhydrous sodium sulfate, filtered and evaporated under reduced pressure to yield a brown oil. The crude material was purified via preparative HPLC: Method: Column-Sunfire C18 (250×4.6 mm) 5 μm; Mobile phase A: 10 mM ammonium acetate; Mobile phase B: acetonitrile; Gradient: 40% B over 2.0 minutes, flow rate 1 mL/min, 40-80% B over 13 minutes, 80-100% B over 15 minutes, then a 1 minute hold at 100% B flow rate 1 mL/min. Fractions containing the product were combined and dried via centrifugal evaporation to yield product as Enantiomeric mixture. The enantiomers were separated using chiral HPLC. Chiral separation method: Method: Column-DAD-1 Cellulose-2 (250×4.6) mm, 5 micron; DAD-2 Cellulose-4 (250×4.6) mm, 5 micron; M. Phase: 0.1% DEA in acetonitrile:IPA (90:10); Flow rate: 2.0 mL/min.

Example 53: Enantiomer 1: (6.8 mg, 9.0% yield); LCMS: m/z=541.3 (M+H); rt 1.760 min; LC-MS: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.08 (d, J=8.8 Hz, 1H), 8.03 (d, J=8.8 Hz, 1H), 7.60 (dd, J=8.7, 5.5 Hz, 2H), 7.52-7.38 (m, 2H), 7.12-6.96 (m, 4H), 5.51 (s, 1H), 4.68 (d, J=13.7 Hz, 1H), 4.45 (d, J=11.0 Hz, 1H), 4.07 (d, J=11.2 Hz, 1H), 3.76-3.56 (m, 5H), 3.42 (br. s., 1H), 2.76 (d, J=12.0 Hz, 1H).

Example 54: Enantiomer 2: (11.2 mg, 14.78% yield); LCMS: m/z=541.2 (M+H); rt 1.759 min; LC-MS: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.10 (d, J=8.8 Hz, 1H), 8.05 (d, J=8.8 Hz, 1H), 7.60 (dd, J=8.7, 5.5 Hz, 2H), 7.49 (dd, J=8.4, 5.5 Hz, 2H), 7.07 (q, J=8.8 Hz, 4H), 5.43 (s, 1H), 4.69 (d, J=12.7 Hz, 1H), 4.44 (d, J=12.5 Hz, 1H), 4.07 (d, J=10.5 Hz, 1H), 3.76 (d, J=6.6 Hz, 1H), 3.72-3.61 (m, 3H), 3.57 (t, J=9.7 Hz, 2H), 3.25 (d, J=7.6 Hz, 1H).

Example 55

1-(bis(4-fluorophenyl)methyl)-4-(6-cyano-1-methyl-2-oxo-1,2-dihydro-1,5-naphthyridin-4-yl)piperazine-2-carboxylic acid

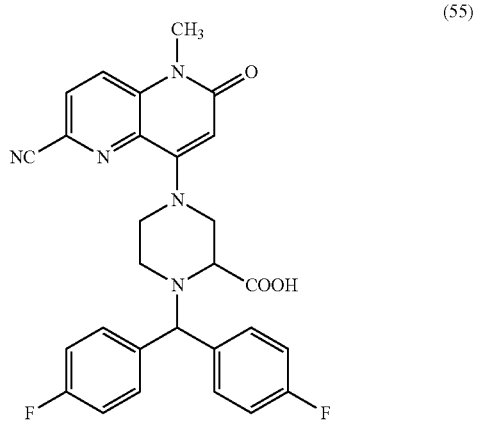

(55)

To a stirred solution of methyl 1-(bis(4-fluorophenyl)methyl)-4-(6-cyano-1-methyl-2-oxo-1,2-dihydro-1,5-naphthyridin-4-yl)piperazine-2-carboxylate (200 mg, 0.378 mmol) in DMF (8 mL) was added lithium chloride (160 mg, 3.78 mmol). The reaction mixture was heated up to 150° C. over 10 min on a microwave and was stirred for 1.5 h. The reaction mixture was filtered through a celite bed and was concentrated under high vacuum to yield a brown gum (180 mg, 92% yield). The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 10% B, 10-40% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 1-(bis(4-fluorophenyl)methyl)-4-(6-cyano-1-methyl-2-oxo-1,2-dihydro-1,5-naph-thyridin-4-yl)piperazine-2-carboxylic acid (7.1 mg, 34.8% yield); LCMS: m/z=516.2 (M+H); rt 1.616 min; LC-MS: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 12.43 (br. s., 1H), 8.15 (d, J=8.8 Hz, 1H), 8.07 (d, J=8.8 Hz, 1H), 7.57 (dd, J=8.7, 5.5 Hz, 2H), 7.40 (dd, J=8.8, 5.6 Hz, 2H), 7.24-7.03 (m, 4H), 6.13 (s, 1H), 5.33 (s, 1H), 4.48 (d, J=9.5 Hz, 1H), 4.02 (d, J=13.4 Hz, 1H), 3.53 (s, 3H), 3.42-3.33 (m, 3H), 3.11-2.99 (m, 1H), 2.60-2.54 (m, 1H).

Example 56

1-(bis(4-fluorophenyl)methyl)-4-(6-bromo-3-cyano-1-methyl-2-oxo-1,2-dihydro-1,5-naphthyridin-4-yl)piperazine-2-carboxamide

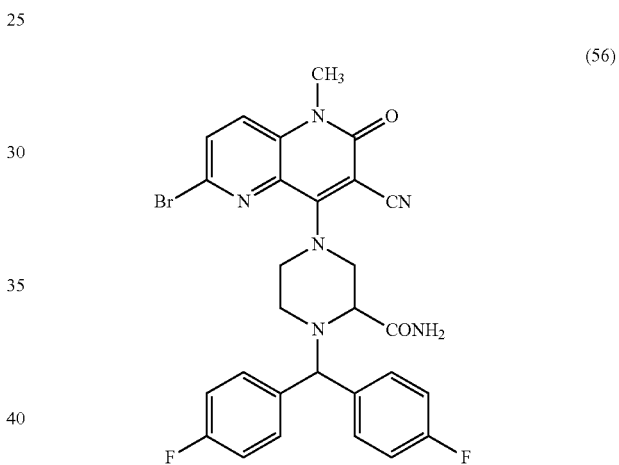

(56)

To a stirred solution of 6-bromo-3-cyano-1-methyl-2-oxo-1,2-dihydro-1,5-naphthyridin-4-yl trifluoromethanesulfonate (150 mg, 0.364 mmol) in acetonitrile (8 mL) were added DIPEA (0.191 mL, 1.092 mmol) and HCl salt of 1-(bis(4-fluorophenyl) methyl)piperazine-2-carboxamide (134 mg, 0.364 mmol). The reaction mixture was heated up to 85° C. over 5 min and stirred for 1 h. The reaction was quenched with water (50 mL) and was extracted with ethyl acetate (3×100 mL). The combined organic layer was dried over anhydrous sodium sulfate, filtered and evaporated under reduced pressure to yield 1-(bis(4-fluorophenyl)methyl)-4-(6-bromo-3-cyano-1-methyl-2-oxo-1,2-dihydro-1,5-naphthyridin-4-yl)piperazine-2-carboxamide (170 mg, 26% yield) as a brown gum. LCMS: m/z=595.3 (M+H); rt 1.69 min. LC-MS Method: Column-AQUITY UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Examples 57 to 58

1-(bis (4-fluorophenyl)methyl)-4-(3,6-dicyano-1-methyl-2-oxo-1,2-dihydro-1,5-naphthyridin-4-yl)piperazine-2-carboxamide

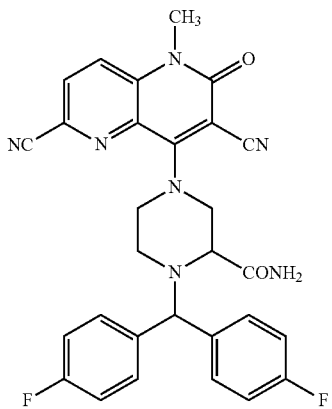

(57-58)

To a stirred solution of 1-(bis(4-fluorophenyl)methyl)-4-(6-bromo-3-cyano-1-methyl-2-oxo-1,2-dihydro-1,5-naphthyridin-4-yl)piperazine-2-carboxamide (80 mg, 0.135 mmol) in NMP (5 mL) were added zinc (1.763 mg, 0.027 mmol) and zinc cyanide (31.7 mg, 0.270 mmol) under nitrogen. The nitrogen purging was continued for 3 min and dppf (4.48 mg, 8.09 μmol) and $Pd_2$ $(dba)_3$ (12.34 mg, 0.013 mmol) were added. Purging was continued for another 3 min. The reaction mixture was heated up to 80° C. over 5 min and was stirred for 1 h. The reaction was quenched saturated ammonium chloride solution (5 mL). The mixture was extracted with ethyl acetate (3×10 mL). The combined organic layer was dried over anhydrous sodium sulfate, filtered and evaporated under reduced pressure to yield a brown oil. The crude material was purified to yield product as enantiomeric mixture via preparative HPLC (Method) Column: Inersil ODS (250 mm×20 mm ID, 5 μm); Mobile phase A=Buffer: 0.1% TFA in $H_2O$; Mobile phase B=acetonitrile; Flow rate: 17 mL/min; Gradient: 20-40% B over 2 minutes, 40-80% B over 13 minutes, 80-100% B over 1 minute. Enantiomers were separated using chiral HPLC. Chiral separation method: Method: Column-DAD-1 Cellulose-2 (250×4.6) mm, 5 micron; DAD-2 Cellulose-4 (250×4.6) mm, 5 micron; M. Phase: 0.1% DEA in acetonitrile:IPA (70:30); Flow rate: 2.0 mL/min.

Example 57: Enantiomer 1: (1.0 mg, 1.4% yield); LCMS: m/z=540.3 (M+H); rt 1.707 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.24-8.27 (m, 1H), 8.15 (d, J=9.0 Hz, 1H), 7.85 (s, 1H), 7.66-7.77 (m, 4H), 7.28 (s, 1H), 7.13-7.20 (m, 4H), 5.51 (s, 1H), 4.36-4.44 (m, 1H), 4.06-4.16 (m, 2H), 3.65-3.73 (m, 1H), 3.49-3.58 (m, 4H), 3.21-3.25 (m, 1H), 2.69-2.75 (m, 1H).

Example 58: Enantiomer 2: (1.2 mg, 1.7% yield); LCMS: m/z=540.3 (M+H); rt 1.707 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.24-8.28 (m, 1H), 8.15 (d, J=9.0 Hz, 1H), 7.84-7.87 (m, 1H), 7.66-7.77 (m, 4H), 7.27-7.30 (m, 1H), 7.13-7.19 (m, 4H), 5.51 (s, 1H), 4.36-4.42 (m, 1H), 4.05-4.16 (m, 2H), 3.64-3.72 (m, 1H), 3.49-3.57 (m, 4H), 3.21-3.24 (m, 1H), 2.70-2.75 (m, 1H).

Intermediate 41

1-(bis(4-(fluorophenyl)methyl)-N-cyclopropylpiperazine-2-carboxamide, HCl

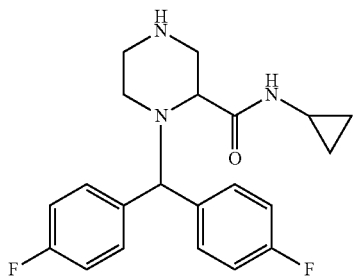

(I-41)

A stirred solution of tert-butyl 4-(bis(4-fluorophenyl)methyl)-3-(cyclopropylcarbamoyl)piperazine-1-carboxylate (140 mg, 0.297 mmol) in HCl in dioxane (1.5 mL, 49.4 mmol) was stirred at room temperature for 1 h. The reaction mixture was concentrated under high vacuum to yield HCl salt of 1-(bis(4-fluorophenyl) methyl)-N-cyclopropylpiperazine-2-carboxamide (100 mg, 83% yield) as a brown solid. LCMS: m/z=372.4 (M+H); rt 1.21 min. LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 0.1% TFA; Solvent B: 5% water:95% acetonitrile; 0.1% TFA).

Example 59

1-(bis(4-fluorophenyl)methyl)-4-(6-bromo-3-cyano-1-methyl-2-oxo-1,2-dihydro-1,5-naphthyridin-4-yl)-N-cyclopropylpiperazine-2-carboxamide

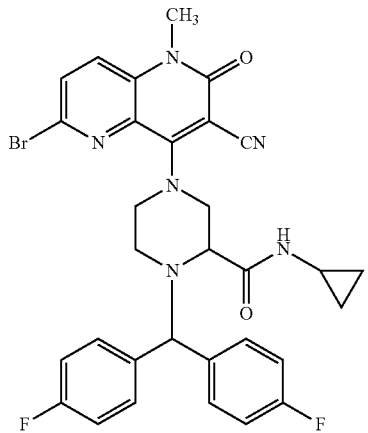

(59)

To a stirred solution of 6-bromo-3-cyano-1-methyl-2-oxo-1,2-dihydro-1,5-naphthyridin-4-yl trifluoromethanesulfonate (150 mg, 0.364 mmol) in acetonitrile (8 mL) were added DIPEA (0.191 mL, 1.092 mmol) and HCl salt of 1-(bis(4-fluorophenyl) methyl)-N-cyclopropylpiperazine-2-carboxamide (148 mg, 0.364 mmol). The reaction mixture was heated up to 85° C. over 5 min and was stirred for 1 h. The reaction mixture was concentrated under reduced pressure to yield a brown gum. The crude compound was purified by ISCO® (using 12 g silica gel column; using 60-64% ethylacetate/petroleum ether) to yield 1-(bis(4-fluorophenyl)methyl)-4-(6-bromo-3-cyano-1-methyl-2-oxo-1,2-dihydro-1,5-naphthyridin-4-yl)-N-cyclopropylpiperazine-2-carboxamide (80 mg, 21.9% yield) as a brown solid. LCMS: m/z=635.3 (M+H); rt 1.88 min. LC-MS: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Examples 60 to 61

1-(bis(4-fluorophenyl)methyl)-N-cyclopropyl-4-(3,6-dicyano-1-methyl-2-oxo-1,2-dihydro-1,5-naphthyridin-4-yl)piperazine-2-carboxamide

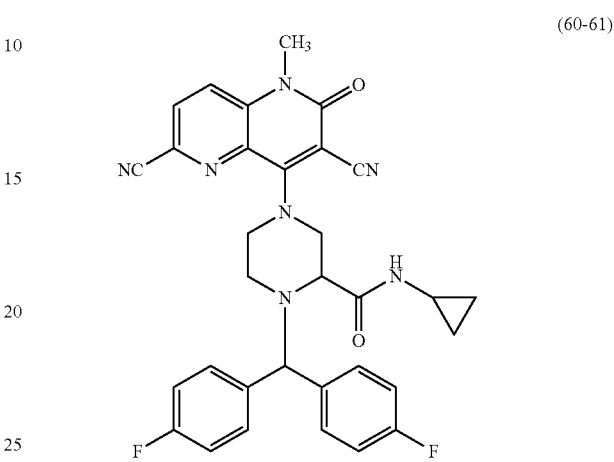

(60-61)

To a stirred solution of 1-(bis(4-fluorophenyl)methyl)-4-(6-bromo-3-cyano-1-methyl-2-oxo-1,2-dihydro-1,5-naphthyridin-4-yl)-N-cyclopropylpiperazine-2-carboxamide (80 mg, 0.126 mmol) in NMP (5 mL) were added zinc (1.651 mg, 0.025 mmol) and zinc cyanide (29.7 mg, 0.253 mmol) under nitrogen. The nitrogen purging was continued for 3 min and dppf (4.20 mg, 7.58 µmol) and $Pd_2(dba)_3$ (11.56 mg, 0.013 mmol) were added. Purging was continued for another 3 min. The reaction mixture was heated up to 80° C. over 5 min and was stirred for 1 h. The reaction was quenched with saturated ammonium chloride solution (5 mL). The reaction mixture was extracted with ethyl acetate (3×10 mL). The combined organic layer was dried over anhydrous sodium sulfate, filtered and evaporated under reduced pressure to yield a brown oil. The crude material was purified via preparative HPLC. Method: Column-Sunfire C18 (150×19 mm) 5 µm; Mobile phase A: 10 mM ammonium acetate in water; Mobile phase B: acetonitrile; Gradient: 50-68% B over 19 minutes, flow rate 17 mL/min. Enantiomers were separated using chiral HPLC. Chiral separation method: Method: Column-DAD-1 Cellulose-2 (250×4.6) mm, 5 micron; DAD-2 Cellulose-4 (250×4.6) mm, 5 µm; M. Phase: 0.1% DEA in acetonitrile; Flow rate: 2.0 mL/min.

Example 60: Enantiomer 1: (4 mg, 5.46% yield); LCMS: m/z=580.3 (M+H); rt 1.894 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.26 (d, J=9.0 Hz, 1H), 8.22-8.02 (m, 2H), 7.68 (dd, J=11.7, 8.6 Hz, 2H), 7.70 (dd, J=11.6, 8.7 Hz, 2H), 7.28-7.05 (m, 4H), 5.42 (s, 1H), 4.36 (d, J=12.7 Hz, 1H), 4.16 (dd, J=13.2, 3.7 Hz, 1H), 4.05 (d, J=13.9 Hz, 1H), 3.67 (t, J=10.8 Hz, 1H), 3.54 (s, 3H), 3.45 (t, J=10.4 Hz, 1H), 3.23 (br. s., 1H), 2.68-2.61 (m, 1H), 2.49-2.44 (m, 1H), 0.67-0.48 (m, 2H), 0.47-0.37 (m, 1H), 0.36-0.27 (m, 1H).

Example 61: Enantiomer 2: (4 mg, 5.5% yield); LCMS: m/z=580.3 (M+H); rt 1.894 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 8.26 (d, J=8.8 Hz, 1H), 8.20-8.03 (m, 2H), 7.68 (dd, J=11.6, 8.4 Hz, 2H), 7.70 (dd, J=11.6, 8.7 Hz, 2H), 7.16 (td, J=8.8, 1.5 Hz, 4H), 5.42 (s, 1H), 4.36 (d, J=11.5 Hz, 1H), 4.16 (dd, J=13.2, 3.4 Hz, 1H), 4.05 (d, J=13.9 Hz, 1H), 3.67 (t, J=10.6 Hz, 1H), 3.54 (s, 3H), 3.45 (t, J=10.4 Hz, 1H), 3.23 (br. s., 1H), 2.71-2.61 (m, 1H), 2.48-2.42 (m, 1H), 0.65-0.49 (m, 2H), 0.47-0.40 (m, 1H), 0.36-0.23 (m, 1H).

Intermediate 42

1-(tert-Butyl) 3-isopropyl 4-(bis(4-fluorophenyl)methyl)piperazine-1,3-dicarboxylate

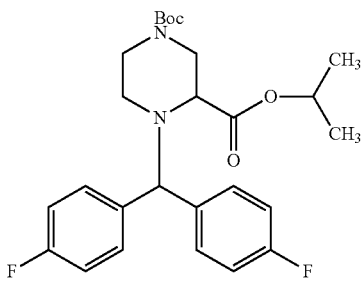

(I-42)

To a stirred solution of 1-(bis(4-fluorophenyl)methyl)-4-(tert-butoxycarbonyl) piperazine-2-carboxylic acid (250 mg, 0.578 mmol) in DMF (8 mL) were added K₂CO₃ (80 mg, 0.578 mmol) and 2-iodopropane (0.347 mL, 3.47 mmol). The reaction mixture was stirred at room temperature for 16 h. The reaction was quenched with water (50 mL). The mixture was extracted with ethyl acetate (3×100 mL). The combined organic layer was dried over anhydrous sodium sulfate, filtered and evaporated under reduced pressure to yield (270 mg, 84% yield) as a brown oil. LCMS: m/z=475.5 (M+H); rt 1.60 min. LC-MS Method: Column-AQUITY UPLC BEH C18 (3.0×50 mm) 1.7 µm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Intermediate 43

Isopropyl 1-(bis(4-fluorophenyl)methyl)piperazine-2-carboxylate, HCl

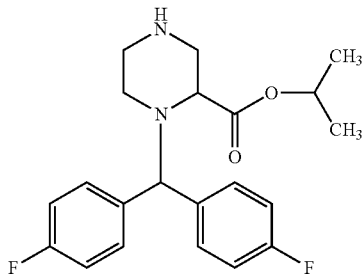

(I-43)

A stirred solution of 1-(tert-butyl) 3-isopropyl 4-(bis(4-fluorophenyl)methyl) piperazine-1,3-dicarboxylate (270 mg, 0.569 mmol) in HCl in dioxane (1.5 mL, 6.00 mmol) was stirred at room temperature for 1 h. The reaction mixture was concentrated under high vacuum to yield HCl salt of isopropyl 1-(bis(4-fluorophenyl)methyl) piperazine-2-carboxylate (230 mg, 90% yield) as a brown solid. LCMS: m/z=375.2 (M+H); rt 1.606 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Examples 62 to 63

Isopropyl 1-(bis(4-fluorophenyl)methyl)-4-(6-cyano-1-methyl-2-oxo-1,2-dihydro-1,5-naphthyridin-4-yl)piperazine-2-carboxylate

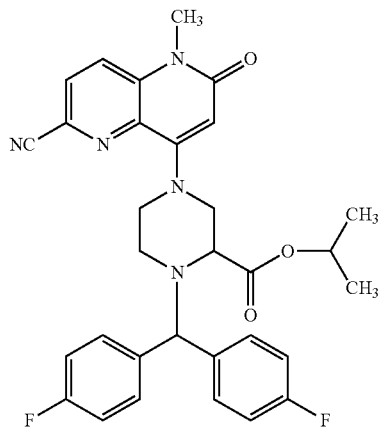

(62-63)

To a stirred solution of 6-cyano-1-methyl-2-oxo-1,2-dihydro-1,5-naphthyridin-4-yl trifluoromethanesulfonate (100 mg, 0.300 mmol) in acetonitrile (8 mL) were added DIPEA (0.157 mL, 0.900 mmol) and HCl salt of isopropyl 1-(bis(4-fluorophenyl)methyl) piperazine-2-carboxylate (123 mg, 0.300 mmol). The reaction mixture was heated up to 85° C. over 5 min and was stirred for 1 h. The reaction mixture was filtered and was concentrated under high vacuum to yield a brown gum. The crude material was purified via preparative HPLC. Method: Column-SUNFIRE C18 (150 mm×19 mm ID, 5 μm); Mobile phase A: 10 mM ammonium acetate in water; Mobile phase B: acetonitrile; Gradient: 40-60% B over 3.0 minutes, flow rate 17 mL/min, then a 17 minute hold at 60-100% B flow rate 17 mL/min. To afford the product as enantiomeric mixture. Enantiomers were separated using chiral HPLC. Chiral separation: Method: Column-DAD-1 Cellulose-2 (250×4.6) mm, 5 micron; DAD-2 Cellulose-4 (250×4.6) mm, 5 micron; M. Phase: 0.1% DEA in methanol; Flow rate: 2.0 mL/min.

Example 62: Enantiomer 1: (17.5 mg, 10.0% yield); LCMS: m/z=558.3 (M+H); rt 2.156 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.16 (d, J=8.8 Hz, 1H), 8.07 (d, J=8.8 Hz, 1H), 7.57 (dd, J=8.8, 5.4 Hz, 2H), 7.43-7.30 (m, 2H), 7.23-7.06 (m, 4H), 6.12 (s, 1H), 5.20 (s, 1H), 4.74 (dt, J=12.5, 6.3 Hz, 1H), 4.65 (d, J=13.2 Hz, 1H), 4.01 (d, J=10.3 Hz, 1H), 3.58-3.50 (m, 3H), 3.47 (dd, J=13.1, 3.8 Hz, 1H), 3.38-3.33 (m, 2H), 3.19-3.09 (m, 1H), 2.66-2.54 (m, 1H), 1.12-0.95 (m, 3H), 0.93-0.85 (m, 3H).

Example 63: Enantiomer 2: (20.7 mg, 11.4% yield); LCMS: m/z=558.3 (M+H); rt 2.157 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.27 (d, J=8.8 Hz, 1H), 8.17 (d, J=9.0 Hz, 1H), 7.59-7.66 (m, 2H), 7.45-7.50 (m, 2H), 7.12-7.21 (m, 4H), 5.32 (s, 1H), 4.72-4.80 (m, 1H), 4.46-4.54 (m, 1H), 4.25-4.37 (m, 1H), 3.94-4.02 (m, 1H), 3.47-3.57 (m, 5H), 2.66-2.73 (m, 2H), 1.03 (d, J=6.4 Hz, 3H), 0.95 (d, J=6.4 Hz, 3H).

Examples 64 to 65

Isopropyl 1-(bis(4-fluorophenyl)methyl)-4-(3,6-dicyano-1-methyl-2-oxo-1,2-dihydro-1,5-naphthyridin-4-yl)piperazine-2-carboxylate

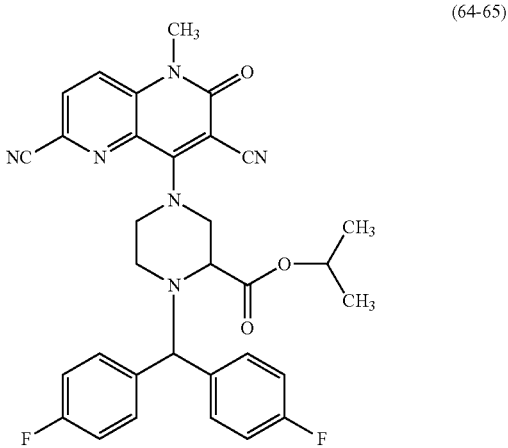 [SMILES: CC(C)OC(=O)C1CN(c2c(C#N)c(=O)n(C)c3ccc(C#N)nc23)CCN1C(c1ccc(F)cc1)c1ccc(F)cc1]

(64-65)

To a stirred solution of 3,6-dicyano-1-methyl-2-oxo-1,2-dihydro-1,5-naphthyridin-4-yl trifluoromethanesulfonate (40 mg, 0.112 mmol) in acetonitrile (6 mL) were added DIPEA (0.059 mL, 0.335 mmol) and isopropyl HCl salt of 1-(bis(4-fluorophenyl)methyl)piperazine-2-carboxylate (45.9 mg, 0.112 mmol). The reaction mixture was heated up to 85° C. over 5 min and stirred for 1 h. The reaction mixture was filtered and concentrated under high vacuum to yield a brown gum. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 18% B, 18-67% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield the product as an enantiomeric mixture. Enantiomers were separated using chiral HPLC. Chiral separation: Method: Column-DAD-1 Cellulose-2 (250×4.6) mm, 5 micron; DAD-2 Cellulose-4 (250×4.6) mm, 5 micron; M. Phase: 0.1% DEA in acetonitrile:IPA (70:30); Flow rate: 2.0 mL/min.

Example 64: Enantiomer 1: (5.6 mg, 8.6% yield); LCMS: m/z=583.3 (M+H); rt 2.21 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.27 (d, J=8.8 Hz, 1H), 8.17 (d, J=9.0 Hz, 1H), 7.62 (dd, J=8.8, 5.6 Hz, 2H), 7.54-7.39 (m, 2H), 7.16 (q, J=9.0 Hz, 4H), 5.32 (s, 1H), 4.76 (quin, J=6.2 Hz, 1H), 4.50 (d, J=13.2 Hz, 1H), 4.37-4.21 (m, 1H), 3.98 (dd, =13.1, 3.3 Hz, 1H), 3.65-3.44 (m, 4H), 3.37 (br. s., 1H), 2.81-2.62 (m, 2H), 1.03 (d, J=6.4 Hz, 3H), 0.95 (d, J=6.4 Hz, 3H).

Example 65: Enantiomer 2: (5.2 mg, 8.0% yield); LCMS: m/z=583.3 (M+H); rt 2.21 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.27 (d, J=8.8 Hz, 1H), 8.17 (d, J=9.0 Hz, 1H), 7.62 (dd, J=8.8, 5.6 Hz, 2H), 7.54-7.40 (m, 2H), 7.16 (q, J=9.0 Hz, 4H), 5.32 (s, 1H), 4.76 (dt, J=12.5, 6.2 Hz, 1H), 4.50 (d, J=13.2 Hz, 1H), 4.35-4.24 (m, 1H), 3.98 (dd, J=13.2, 3.4 Hz, 1H), 3.63-3.45 (m, 5H), 2.77-2.63 (m, 2H), 1.03 (d, J=6.4 Hz, 3H), 0.95 (d, J=6.4 Hz, 3H).

Intermediate 44

1-(tert-butyl) 2-methyl (S)-4-(6-cyano-1-methyl-2-oxo-1,2-dihydro-1,5-naphthyridin-4-yl)piperazine-1,2-dicarboxylate

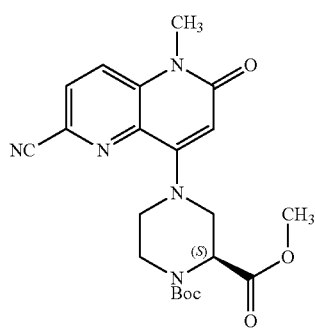

(I-44)

To a stirred solution of 6-cyano-1-methyl-2-oxo-1,2-dihydro-1,5-naphthyridin-4-yl trifluoromethanesulfonate (220 mg, 0.660 mmol) in acetonitrile (6 mL) was added DIPEA (0.346 mL, 1.981 mmol) and 1-(tert-butyl) 2-methyl (S)-piperazine-1,2-dicarboxylate (161 mg, 0.660 mmol). The reaction mixture was heated up to 85° C. over 5 min and was stirred for 3 h. The reaction mixture was concentrated under high vacuum to yield a brown gum. The crude compound was purified by ISCO® (using 12 g silica gel column; using 68-73% ethylacetate/petroleum ether) to yield 1-(tert-butyl) 2-methyl (S)-4-(6-cyano-1-methyl-2-oxo-1,2-dihydro-1,5-naphthyridin-4-yl)piperazine-1,2-dicarboxylate (230 mg, 80% yield) as a brown gum. LCMS: m/z=428.2 (M+H); rt 2.367 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 45 methyl (S)-4-(6-cyano-1-methyl-2-oxo-1,2-dihydro-1,5-naphthyridin-4-yl)piperazine-2-carboxylate, TFA

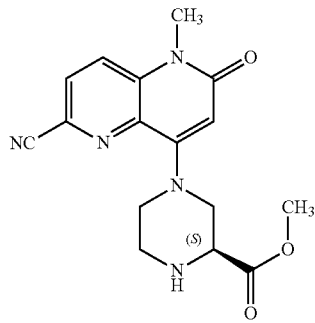

(I-45)

To a stirred solution of 1-(tert-butyl) 2-methyl (S)-4-(6-cyano-1-methyl-2-oxo-1,2-dihydro-1,5-naphthyridin-4-yl)piperazine-1,2-dicarboxylate (230 mg, 0.538 mmol) in DCM (5 mL) was added TFA (0.415 mL, 5.38 mmol). The reaction mixture was stirred at room temperature for 2 h. The reaction mixture was concentrated under high vacuum to yield TFA salt of methyl (S)-4-(6-cyano-1-methyl-2-oxo-1,2-dihydro-1,5-naphthyridin-4-yl)piperazine-2-carboxylate (230 mg, 80% yield) as a brown gum. LCMS: m/z 328.2 (M+H); rt 0.751 min. LC-MS Method: Column-KINETEX-XB-C18 (75×3 mm-2.6 µm); Mobile phase A: 0.1% TFA in Milli-Q water; Mobile phase B: 0.1% TFA in acetonitrile; Gradient: 20-100% B over 4.0 minutes, flow rate 1.0 mL/min, then a 0.6 minute hold at 100% B flow rate 1.5 mL/min, 100-20% B over 0.1 minutes, flow rate 1.5 mL/min.

Example 66

Methyl (S)-1-(bis(4-fluorophenyl)methyl)-4-(6-cyano-1-methyl-2-oxo-1,2-dihydro-1,5-naphthyridin-4-yl)piperazine-2-carboxylate

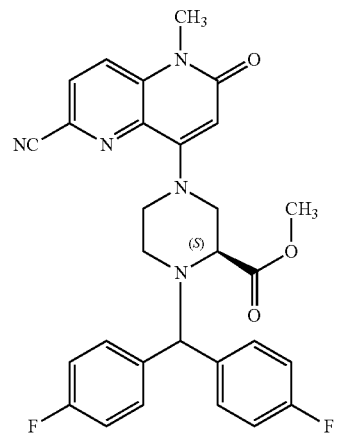

(66)

To a stirred solution of TFA salt of methyl (S)-4-(6-cyano-1-methyl-2-oxo-1,2-dihydro-1,5-naphthyridin-4-yl)piperazine-2-carboxylate (60 mg, 0.136 mmol) in acetonitrile (6 mL) were added DIPEA (0.024 mL, 0.136 mmol) and 4,4'-(chloromethylene)bis(fluorobenzene) (32.4 mg, 0.136 mmol). The reaction mixture was heated up to 80° C. over 3 min and was stirred for 16 h. The reaction mixture was filtered and concentrated under high vacuum to yield a brown gum. The crude material was purified via preparative HPLC with the following conditions: Column: Inersil ODS, 21×250 mm, 5 µm particles; Mobile Phase A: 10 mM ammonium acetate pH-4.5 with acetic acid; Mobile Phase B: methanol:acetonitrile (1:1); Gradient: 70-100% B over 25 minutes, then a 5 minute hold at 100% B; Flow: 18 mL/min. Fractions containing the product were combined and dried via centrifugal evaporation to yield methyl (S)-1-(bis(4-fluorophenyl)methyl)-4-(6-cyano-1-methyl-2-oxo-1,2-dihydro-1,5-naphthyridin-4-yl) piperazine-2-carboxylate (9.6 mg, 13.15% yield); LCMS: m/z=530.2 (M+H); rt 2.1 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.16 (d, J=9.0 Hz, 1H), 8.08 (d, J=9.0 Hz, 1H), 7.57 (dd, J=8.6, 5.6 Hz, 2H), 7.43-7.30 (m, 2H), 7.24-7.04 (m, 4H), 6.14 (s, 1H), 5.17 (s, 1H), 4.78 (d, J=12.5 Hz, 1H), 3.64 (d, J=10.3 Hz, 1H), 3.60 (s, 3H), 3.54 (s, 3H), 3.46-3.34 (m, 2H), 3.20-3.12 (m, 1H), 3.09-2.99 (m, 1H), 2.68-2.61 (m, 1H).

Examples 67-68

Methyl 4-(6-cyano-1-methyl-2-oxo-1,2-dihydro-1,5-naphthyridin-4-yl)-1-((4-fluoro-2-methoxyphenyl)(4-fluorophenyl)methyl)piperazine-2-carboxylate

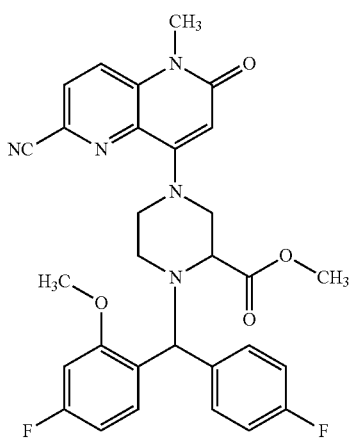

(67-68)

To a stirred solution of methyl 4-(6-cyano-1-methyl-2-oxo-1,2-dihydro-1,5-naphthyridin-4-yl)piperazine-2-carboxylate (150 mg, 0.458 mmol) in acetonitrile (8 mL) were added DIPEA (0.240 mL, 1.375 mmol) and 1-(chloro(4-fluorophenyl)methyl)-4-fluoro-2-methoxybenzene (123 mg, 0.458 mmol). The reaction mixture was heated up to 85° C. over 5 min and was stirred for 3 h. The reaction mixture was filtered and was concentrated under high vacuum to yield a brown gum. The crude material was purified via preparative HPLC: Method: Column-SUNFIRE C18 (150 mm×19 mm ID, 5 μm); Mobile phase A: 10 mM ammonium acetate in water; Mobile phase B: acetonitrile; Gradient: 40-60% B over 3.0 minutes, flow rate 17 mL/min, then a 17 minute hold at 60-100% B flow rate 17 mL/min. Isomer-A (Diastereomer mixture): Example 67; and Isomer-B (Diastereomer mixture): Example 68. Enantiomers were separated using chiral HPLC.

Examples 69 to 70

Methyl 4-(6-cyano-1-methyl-2-oxo-1,2-dihydro-1,5-naphthyridin-4-yl)-1-((4-fluoro-2-methoxyphenyl)(4-fluorophenyl)methyl)piperazine-2-carboxylate

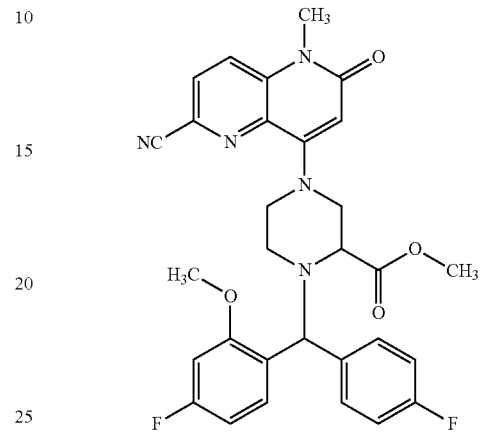

(69-70)

Enantiomers were separated using chiral HPLC. Chiral separation method for Isomer-A (Diastereomer mixture): Example 67: Method: Column-Cellulose C5 (250×4.6) mm, 5 micron; M. Phase A: 0.1% DEA in methanol; Flow rate: 1.0 mL/min. Isomer-1 (Homochiral): Example 69: (4.2 mg, 34.1% yield); LCMS: m/z=560.2 (M+H); rt 2.091 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.15 (d, J=8.8 Hz, 1H), 8.08 (d, J=9.0 Hz, 1H), 7.55-7.34 (m, 3H), 7.15 (t, J=8.9 Hz, 2H), 6.88 (dd, J=11.4, 2.6 Hz, 1H), 6.77 (td, J=8.4, 2.4 Hz, 1H), 6.13 (s, 1H), 5.52 (s, 1H), 4.67 (d, J=12.2 Hz, 1H), 3.85-3.71 (m, 3H), 3.60 (s, 4H), 3.56-3.47 (m, 4H), 3.40-3.35 (m, 1H), 3.23 (dd, J=12.5, 3.9 Hz, 1H), 3.14-3.04 (m, 1H), 2.59-2.53 (m, 1H). Isomer-2 (Homochiral): Example 70: (1.8 mg, 15.0% yield); LCMS: m/z=560.2 (M+H); rt 2.091 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.15 (d, J=8.8 Hz, 1H), 8.08 (d, J=9.0 Hz, 1H), 7.55-7.36 (m, 3H), 7.15 (t, J=8.9 Hz, 2H), 6.88 (dd, J=11.5, 2.4 Hz, 1H), 6.77 (td, J=8.4, 2.4 Hz, 1H), 6.13 (s, 1H), 5.52 (s, 1H), 4.67 (d, J=12.7 Hz, 1H), 3.78 (s, 3H), 3.60 (s, 4H), 3.56-3.48 (m, 4H), 3.43-3.33 (m, 1H), 3.23 (dd, J=12.5, 3.9 Hz, 1H), 3.14-3.03 (m, 1H), 2.55 (d, J=11.7 Hz, 1H).

Examples 71 to 72

Methyl 4-(6-cyano-1-methyl-2-oxo-1,2-dihydro-1,5-naphthyridin-4-yl)-1-((4-fluoro-2-methoxyphenyl)(4-fluorophenyl)methyl)piperazine-2-carboxylate

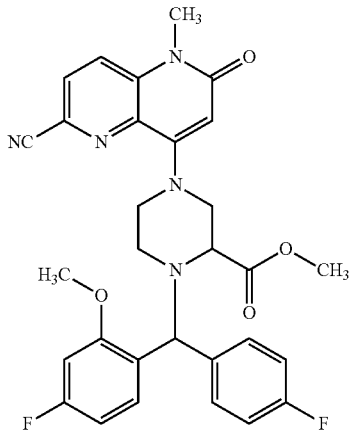

(71-72)

Chiral separation method: Column: Chiralcel ODH (250× 4.6) mm; 5 µm; Isocratic Mode, Co-Solvent: 0.2% NH₄OH in methanol and acetonitrile (1:1); Co-Solvent percentage: 30%, Column Temperature: 30° C.; Back Pressure: 100 bars; Total Flow: 4 g/min. Chiral separation of Isomer-B (Diastereomer mixture) Example 68. Isomer-1 (Homochiral): Example 71: (4.9 mg, 37.8% yield); LCMS: m/z=560.2 (M+H); rt 2.11 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 8.15 (d, J=9.0 Hz, 1H), 8.08 (d, J=9.0 Hz, 1H), 7.78 (t, J=7.8 Hz, 1H), 7.37-7.19 (m, 2H), 7.19-7.02 (m, 2H), 6.92-6.76 (m, 2H), 6.21-6.06 (m, 1H), 5.55-5.37 (m, 1H), 4.81 (d, J=12.5 Hz, 1H), 3.85-3.70 (m, 4H), 3.60 (s, 4H), 3.58-3.44 (m, 4H), 3.44-3.36 (m, 1H), 3.11-3.00 (m, 1H), 2.76-2.67 (m, 1H). Isomer-2 (Homochiral): Example 72: (4.7 mg, 36.2% yield); LCMS: m/z=560.3 (M+H); rt 2.11 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 8.13-8.18 (m, 1H), 8.06-8.10 (m, 1H), 7.79 (t, J=7.8 Hz, 1H), 7.23-7.29 (m, 2H), 7.08-7.15 (m, 2H), 6.81-6.88 (m, 2H), 6.14 (s, 1H), 5.47 (s, 1H), 4.79-4.84 (m, 1H), 3.76 (s, 3H), 3.59-3.65 (m, 1H), 3.58 (s, 3H), 3.53 (s, 3H), 3.35-3.45 (m, 1H), 2.96-3.12 (m, 2H), 2.69-2.73 (m, 1H), 2.52-2.54 (m, 1H).

Intermediate 46

8-Hydroxy-5-methyl-7-nitro-6-oxo-5,6-dihydro-1,5-naphthyridine-2-carbonitrile

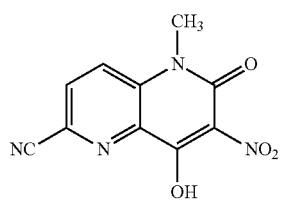

(I-46)

To a stirred solution of 8-hydroxy-5-methyl-6-oxo-5,6-dihydro-1,5-naphthyridine-2-carbonitrile (1 g, 4.97 mmol) in acetic acid (10 mL) was added nitric acid (0.666 mL, 14.91 mmol). The mixture was heated to 80° C. for 1 h. The reaction mixture was cooled to room temperature and diluted with water, stirred for 10 min and the resulting solid was filtered to yield 8-hydroxy-5-methyl-7-nitro-6-oxo-5,6-dihydro-1,5-naphthyridine-2-carbonitrile (0.805 g, 65.1% yield) as pale yellow solid; LCMS: m/z=247.2 (M+H); rt 1.190 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 47

6-Cyano-1-methyl-3-nitro-2-oxo-1,2-dihydro-1,5-naphthyridine-4-yl trifluoromethanesulfonate

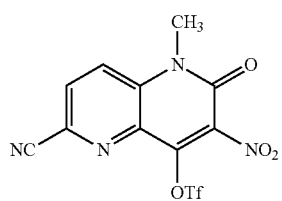

(I-47)

To a suspension of 8-hydroxy-5-methyl-7-nitro-6-oxo-5,6-dihydro-1,5-naphthyridine-2-carbonitrile (0.25 g, 1.016 mmol) in dry DCM (10 mL) was added TEA (0.212 mL, 1.523 mmol) followed by trifluoromethanesulfonic anhydride (0.183 mL, 1.117 mmol) under nitrogen atmosphere at 0° C. The reaction mixture was stirred for 3 h. The reaction mixture was diluted with DCM, washed with water, the organic layer was dried over Na₂SO₄, filtered and evaporated under reduced pressure to yield 6-cyano-1-methyl-3-nitro-2-oxo-1,2-dihydro-1,5-naphthyridin-4-yl trifluoromethanesulfonate (0.25 g, 48.8% yield) as a light brown solid; LCMS: m/z=379.2 (M+H); rt 1.66 min. LC-MS Method: Column-AQUITY UPLC BEH C18 (3.0×50 mm) 1.7 µm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Example 73

Methyl 1-(bis(4-fluorophenyl)methyl)-4-(6-cyano-1-methyl-3-nitro-2-oxo-1,2-dihydro-1,5-naphthyridin-4-yl)piperazine-2-carboxylate

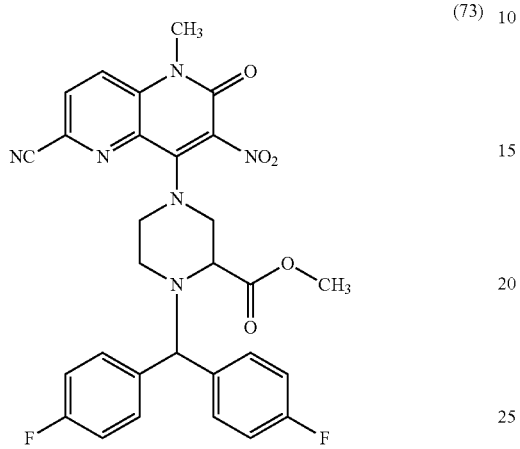

(73)

To a stirred solution of 6-cyano-1-methyl-3-nitro-2-oxo-1,2-dihydro-1,5-naphthyridin-4-yl trifluoromethanesulfonate (80 mg, 0.212 mmol) in acetonitrile (6 mL) were added DIPEA (0.111 mL, 0.635 mmol) and HCl salt of methyl 1-(bis(4-fluorophenyl)methyl)piperazine-2-carboxylate (81 mg, 0.212 mmol). The reaction mixture was heated up to 85° C. over 5 min and was stirred for 1 h. The reaction mixture was filtered and was concentrated under high vacuum to yield a brown gum. The crude material was purified via preparative HPLC with the following conditions: Column: Sunfire C18, 19×150 mm, 5 μm particles; Mobile Phase A: 10 mM ammonium acetate pH-4.5 with acetic acid; Mobile Phase B: methanol:acetonitrile (1:1); Gradient: 60-80% over 15 minutes, then a 5 minute hold at 100% B; Flow: 17 mL/min. Fractions containing the product were combined and dried via centrifugal evaporation to yield the product as an enantiomeric mixture. Enantiomers were separated using chiral HPLC. Chiral separation method: Column: Chiralcel ODH (250×4.6) mm; 5 μm; Isocratic Mode, Co-Solvent: 0.2% NH$_4$OH in methanol and acetonitrile (1:1); Co-Solvent percentage: 25%, Column Temperature: 30° C.; Back Pressure: 100 bars; Total Flow: 3 g/min. Example 73: Enantiomer 1: (3.0 mg, 2.4% yield); LCMS: m/z=575.2 (M+H); rt 2.206 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.29 (d, J=8.8 Hz, 1H), 8.22 (d, J=9.0 Hz, 1H), 7.59 (dd, J=8.6, 5.9 Hz, 2H), 7.42 (dd, J=8.7, 5.5 Hz, 2H), 7.24-7.06 (m, 4H), 5.25 (s, 1H), 3.79 (d, J=10.3 Hz, 2H), 3.65-3.55 (m, 4H), 3.53 (s, 4H), 3.28 (br. s., 3H).

Examples 74 to 75

Methyl 1-(bis(4-fluorophenyl)methyl)-4-(6-cyano-3-fluoro-1-methyl-2-oxo-1,2-dihydro-1,5-naphthyridin-4-yl)piperazine-2-carboxylate

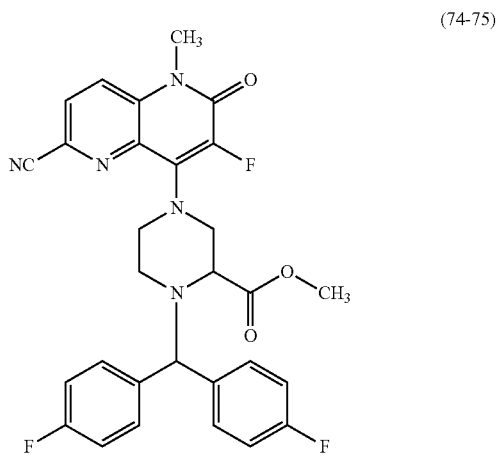 [SMILES: COC(=O)C1CN(c2c(F)c(=O)n(C)c3ccc(C#N)nc23)CCN1C(c1ccc(F)cc1)c1ccc(F)cc1]

(74-75)

To a stirred solution of methyl 1-(bis(4-fluorophenyl)methyl)-4-(6-cyano-1-methyl-2-oxo-1,2-dihydro-1,5-naphthyridin-4-yl)piperazine-2-carboxylate (90 mg, 0.170 mmol) in acetonitrile (6 mL) at 0° C. was added 1-chloromethyl-4-fluoro-1 4-diazoniabicyclo 2.2.2 octane bis(tetrafluoroborate) (78 mg, 0.221 mmol) in THF\H$_2$O (0.5\0.5 mL) drop wise. The reaction mixture was stirred at 0° C. for 1.5 h. The reaction mixture was slowly warmed to room temperature and stirred for another 1.5 h. The reaction mixture was concentrated under reduced pressure to yield a brown oil. The crude material was purified via preparative HPLC (Method) Column: Sun fire OBD (250×30 ID) 5 μm; Mobile Phase A: 10 mM Ammonium Acetate in Milli Q water; Mobile Phase B: acetonitrile; Flow rate: 25 mL/min; Gradient: 60-100% B over 20 minutes. Fractions containing the product were combined and dried via centrifugal evaporation to yield the product as an enantiomeric mixture. Enantiomers were separated using chiral HPLC. Chiral separation method: Column-Cellulose C4 (250×21) mm, 5 micron; M. Phase A: M. Phase B: 100% methanol; Flow rate: 20 mL/min.

Example 74: Enantiomer 1: (2.7 mg, 2.9% yield); LCMS: m/z=548.2 (M+H); rt 2.15 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.25-7.99 (m, 2H), 7.59 (dd, J=8.7, 5.7 Hz, 2H), 7.40 (dd, J=8.7, 5.7 Hz, 2H), 7.26-7.04 (m, 4H), 5.19 (s, 1H), 4.07 (d, J=13.9 Hz, 1H), 3.71-3.57 (m, 5H), 3.55 (s, 3H), 3.49-3.38 (m, 2H), 3.35 (br. s., 1H), 2.59 (d, J=11.2 Hz, 1H).

Example 75: Enantiomer 2: (4.0 mg, 7.25 4.27% yield); LCMS: m/z=548.2 (M+H); rt 2.15 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 8.28-8.09 (m, 2H), 7.59 (dd, J=8.6, 5.6 Hz, 2H), 7.40 (dd, J=8.7, 5.5 Hz, 2H), 7.24-7.03 (m, 4H), 5.19 (s, 1H), 4.07 (d, J=12.2 Hz, 1H), 3.70-3.57 (m, 5H), 3.55 (s, 3H), 3.50-3.37 (m, 2H), 3.37-3.32 (m, 1H), 2.59 (d, J=11.2 Hz, 1H).

Examples 76 to 77 methyl 1-(bis(4-fluorophenyl)methyl)-4-(3-chloro-6-cyano-1-methyl-2-oxo-1,2-dihydro-1,5-naphthyridin-4-yl)piperazine-2-carboxylate

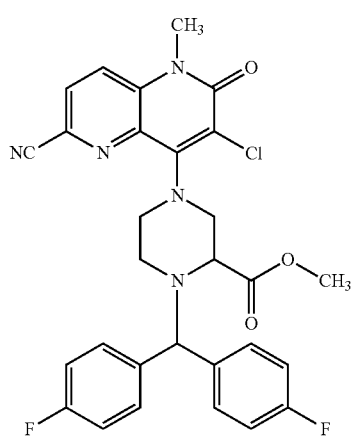

(76-77)

To a stirred solution of methyl 1-(bis(4-fluorophenyl)methyl)-4-(6-cyano-1-methyl-2-oxo-1,2-dihydro-1,5-naphthyridin-4-yl)piperazine-2-carboxylate (120 mg, 0.227 mmol) in DCM (8 mL) was added NCS (60.5 mg, 0.453 mmol). The reaction mixture was stirred at room temperature for 16 h. The reaction was quenched with water (5 mL). The reaction mixture was extracted with ethyl acetate (3×10 mL). The combined organic layer was dried over anhydrous sodium sulfate, filtered and evaporated under reduced pressure to yield a brown oil. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 0 minute hold at 50% B, 50-72% B over 15 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield the product as an enantiomeric mixture. Enantiomers were separated using chiral HPLC. Chiral separation method: Method: Column-Lux-cellulose C2 (250×21.2) mm, 5 micron; M. Phase: 0.1% Ammonium Hydroxide in acetonitrile:methanol (70:30); Flow rate: 20 mL/min.

Example 76: Enantiomer 1: (20.3 mg, 15.9% yield); LCMS: m/z=564.2 (M+H); rt 2.35 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ ppm 8.28-8.10 (m, 2H), 7.61 (dd, J=8.7, 5.5 Hz, 2H), 7.51-7.34 (m, 2H), 7.23-7.06 (m, 4H), 5.33 (s, 1H), 3.95 (dd, J=12.7, 3.4 Hz, 1H), 3.79 (d, J=12.7 Hz, 1H), 3.64 (s, 3H), 3.56-3.41 (m, 6H), 3.41-3.33 (m, 1H), 2.59 (d, J=11.2 Hz, 1H).

Example 77: Enantiomer 2: (17.5 mg, 0.031 mmol, 13.69% yield); LCMS: m/z 564.2 (M+H); rt 2.35 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). ¹H NMR (400 MHz, DMSO-d₆) δ 8.28-8.09 (m, 2H), 7.61 (dd, J=8.7, 5.5 Hz, 2H), 7.49-7.38 (m, 2H), 7.24-7.05 (m, 4H), 5.33 (s, 1H), 3.95 (dd, J=12.7, 3.4 Hz, 1H), 3.79 (d, J=12.2 Hz, 1H), 3.64 (s, 3H), 3.55-3.41 (m, 6H), 3.41-3.33 (m, 1H), 2.59 (d, J=10.5 Hz, 1H).

Intermediate 48 tert-butyl 4-(bis(4-fluorophenyl)methyl)-3-(2-hydroxypropan-2-yl)piperazine-1-carboxylate

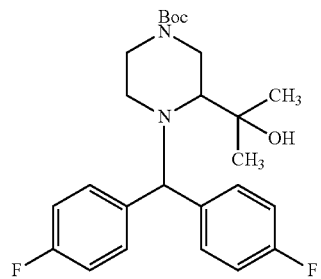

(I-48)

To a stirred solution of 1-(tert-butyl) 3-methyl 4-(bis(4-fluorophenyl)methyl) piperazine-1,3-dicarboxylate (0.3 g, 0.672 mmol) in tetrahydrofuran (5 mL) at 0° C. was added methyl magnesium chloride in THF (1.120 mL, 3.36 mmol) drop wise under nitrogen over 3 min. The reaction mixture was slowly warmed to room temperature and was stirred for 3 h. The reaction was quenched with saturated ammonium chloride solution (50 mL). The reaction mixture was extracted with ethyl acetate (3×100 mL). The combined organic layer was dried over anhydrous sodium sulfate, filtered and evaporated under reduced pressure to yield tert-butyl 4-(bis(4-fluorophenyl)methyl)-3-(2-hydroxypropan-2-yl)piperazine-1-carboxylate (290 mg, 92% yield) as a brown oil. LCMS: m/z=447.3 (M+H); rt 3.58 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 49

2-(1-(bis(4-fluorophenyl)methyl)piperazin-2-yl)propan-2-ol, HCl

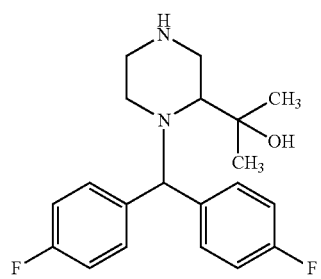

(I-49)

tert-butyl 4-(bis(4-fluorophenyl)methyl)-3-(2-hydroxypropan-2-yl)piperazine-1-carboxylate (240 mg, 0.537 mmol) in HCl in dioxane (3.0 mL, 99 mmol). The reaction mixture was stirred at room temperature for 1 h. The reaction mixture was concentrated under high vacuum to yield HCl salt of 2-(1-(bis(4-fluorophenyl)methyl)piperazin-2-yl) propan-2-ol (180 mg, 65.6% yield) as a brown solid. LCMS: m/z=347.3 (M+H); rt 1.26 min. LC-MS Method: Column-AQUITY UPLC BEH C18 (3.0×50 mm) 1.7 μm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.2 minute hold at 100% B, flow rate 0.7 mL/min.

Examples 78 to 79

8-(4-(bis(4-fluorophenyl)methyl)-3-(2-hydroxypropan-2-yl)piperazin-1-yl)-5-methyl-6-oxo-5,6-dihydro-1,5-naphthyridine-2-carbonitrile

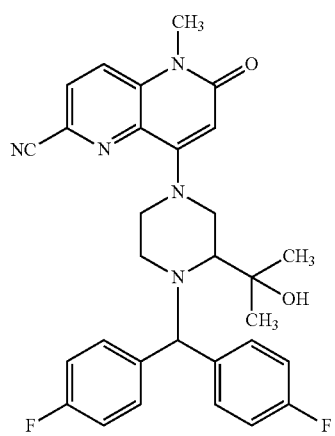

(78-79)

To a stirred solution of 6-cyano-1-methyl-2-oxo-1,2-dihydro-1,5-naphthyridin-4-yl trifluoromethanesulfonate (100 mg, 0.300 mmol) in acetonitrile (8 mL) were added DIPEA (0.157 mL, 0.900 mmol) and HCl salt of 2-(1-(bis(4-fluorophenyl)methyl) piperazin-2-yl)propan-2-ol (115 mg, 0.300 mmol). The reaction mixture was heated up to 85° C. over 5 min and was stirred for 2 h. The reaction mixture was concentrated under reduced pressure to yield a brown oil. The crude material was purified via preparative HPLC (Method) Method: Column-SUNFRE C18 (150 mm×19 mm ID, 5 μm); Mobile phase A: 10 mM ammonium acetate in water; Mobile phase B: acetonitrile; Gradient: 40% B over 2.0 minutes, 40-60% B over 1.0 minute, 60-100% B over 17 minutes, flow rate 17 mL/min. Fractions containing the product were combined and dried via centrifugal evaporation to yield the product as an enantiomeric mixture. Enantiomers were separated using chiral HPLC. Chiral separation method: Method: Column-Cellulose C4 (250×21) mm, 5 micron; M. Phase A: M. Phase B: 0.1% DEA in acetonitrile: methanol (70:30); Flow rate: 20 mL/min.

Example 78: Enantiomer 1: (34 mg, 20.1% yield); LCMS: m/z=530.3 (M+H); rt 1.961 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.18 (d, J=8.8 Hz, 1H), 8.09 (d, J=9.0 Hz, 1H), 7.48 (dd, J=8.6, 5.6 Hz, 2H), 7.43-7.31 (m, 2H), 7.17-7.01 (m, 4H), 5.94 (s, 1H), 5.49 (s, 1H), 3.93-3.87 (m, 1H), 3.68 (dd, J=13.4, 6.4 Hz, 1H), 3.61-3.51 (m, 3H), 3.48-3.33 (m, 1H), 3.28-3.19 (m, 1H), 3.18-3.11 (m, 1H), 2.78 (q, J=7.3 Hz, 3H), 1.18-1.05 (m, 6H).

Example 79: Enantiomer 2: (34 mg, 20.7% yield); LCMS: m/z=530.3 (M+H); rt 1.961 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.18 (d, J=8.8 Hz, 1H), 8.09 (d, J=8.8 Hz, 1H), 7.48 (dd, J=8.8, 5.6 Hz, 2H), 7.37 (dd, J=8.6, 5.6 Hz, 2H), 7.20-6.98 (m, 4H), 5.94 (s, 1H), 5.49 (s, 1H), 3.89 (dd, J=13.3, 5.0 Hz, 1H), 3.68 (dd, J=13.3, 6.2 Hz, 1H), 3.60-3.50 (m, 3H), 3.48-3.31 (m, 1H), 3.29-3.19 (m, 1H), 3.15 (d, J=12.0 Hz, 1H), 2.75 (q, J=7.1 Hz, 3H), 1.17-1.01 (m, 6H).

Examples 80 to 81

8-(4-(bis(4-fluorophenyl)methyl)-3-(2-fluoropropan-2-yl)piperazin-1-yl)-5-methyl-6-oxo-5,6-dihydro-1,5-naphthyridine-2-carbonitrile

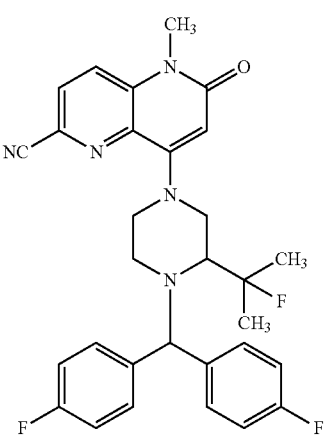

(80-81)

To a stirred solution of 8-(4-(bis(4-fluorophenyl)methyl)-3-(2-hydroxypropan-2-yl)piperazin-1-yl)-5-methyl-6-oxo-5,6-dihydro-1,5-naphthyridine-2-carbonitrile (0.1 g, 0.189 mmol) in DCM (5 mL) at 0° C. was added DAST (0.050 mL, 0.378 mmol). The reaction mixture was slowly warmed to room temperature and was stirred for 2 h. The reaction mixture was quenched with water (20 mL) and was extracted with ethyl acetate (3×50 mL). The combined organic layer was dried over anhydrous sodium sulfate, filtered and evaporated under reduced pressure to yield a brown oil. The crude material was purified via preparative HPLC (Method) Method: Column-Sun fire C18 (150×20 mm) 5 µm; Mobile phase A: 10 mM ammonium acetate in water; Mobile phase B: acetonitrile; Gradient: 60-100% B over 16 minutes, 100-60% B over 1 minute, flow rate 20 mL/min. Fractions containing the product were combined and dried via centrifugal evaporation to yield to yield the product as an enantiomeric mixture. Enantiomers were separated using chiral HPLC. Chiral separation method: Column: Chiralcel ODH (250×4.6) mm; 5 µm; Isocratic Mode, Co-Solvent: 0.2% NH$_4$OH in methanol+acetonitrile (1:1); Co-Solvent percentage: 25%, Column Temperature: 30° C.; Back Pressure: 100 bars; Total Flow: 3 g/min.

Example 80: Enantiomer 1: (7 mg, 6.8% yield); LCMS: m/z=532.2 (M+H); rt 2.292 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.18 (d, J=8.8 Hz, 1H), 8.09 (d, J=9.0 Hz, 1H), 7.47 (dd, J=8.8, 5.6 Hz, 2H), 7.34 (dd, J=8.6, 5.6 Hz, 2H), 7.11 (td, J=8.9, 6.7 Hz, 4H), 5.91 (s, 1H), 5.36 (s, 1H), 4.06 (dd, J=13.3, 5.7 Hz, 1H), 3.75 (dd, J=13.4, 6.8 Hz, 1H), 3.55 (s, 3H), 3.27 (d, J=10.8 Hz, 2H), 3.23-3.09 (m, 2H), 2.77 (d, J=12.0 Hz, 1H), 1.45 (s, 2H), 1.40 (s, 1H), 1.37 (s, 1H), 1.31 (s, 2H).

Example 81: Enantiomer 2: (9 mg, 9.0% yield); LCMS: m/z=532.3 (M+H); rt 2.292 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.18 (d, J=9.0 Hz, 1H), 8.09 (d, J=9.0 Hz, 1H), 7.47 (dd, J=8.6, 5.6 Hz, 2H), 7.34 (dd, J=8.6, 5.6 Hz, 2H), 7.11 (td, J=8.8, 6.6 Hz, 4H), 5.91 (s, 1H), 5.36 (s, 1H), 4.06 (dd, J=13.1, 5.0 Hz, 1H), 3.75 (dd, J=13.2, 7.1 Hz, 1H), 3.55 (s, 3H), 3.30-3.11 (m, 4H), 2.77 (d, J=13.4 Hz, 1H), 1.45 (s, 2H), 1.40 (s, 1H), 1.37 (s, 1H), 1.31 (s, 2H).

Intermediate 54

5-methyl-8-(3-methyl-5-(2-methylpyridin-4-yl)piperazin-1-yl)-6-oxo-5,6-dihydro-1,5-naphthyridine-2-carbonitrile

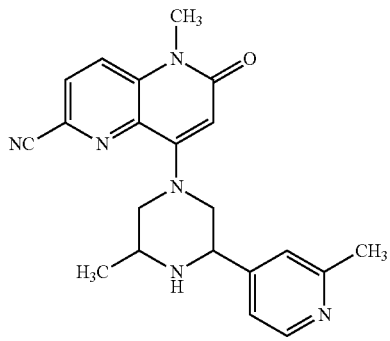

(I-54)

To a stirred solution of 6-cyano-1-methyl-2-oxo-1,2-dihydro-1,5-naphthyridin-4-yl trifluoromethanesulfonate (120 mg, 0.360 mmol) in acetonitrile (8 mL) were added DIPEA (0.189 mL, 1.080 mmol) and 2-methyl-6-(2-methylpyridin-4-yl)piperazine (103 mg, 0.540 mmol). The reaction mixture was heated up to 85° C. over 5 min and was stirred for 1 h. The reaction mixture was concentrated under high vacuum to yield 5-methyl-8-(3-methyl-5-(2-methylpyridin-4-yl)piperazin-1-yl)-6-oxo-5,6-dihydro-1,5-naphthyridine-2-carbonitrile (100 mg, 74.2% yield) as a brown gum; LCMS: m/z=375.2 (M+H); rt 1.473 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Example 84

8-(4-(bis(4-fluorophenyl)methyl)-3-methyl-5-(2-methylpyridin-4-yl)piperazin-1-yl)-5-methyl-6-oxo-5,6-dihydro-1,5-naphthyridine-2-carbonitrile

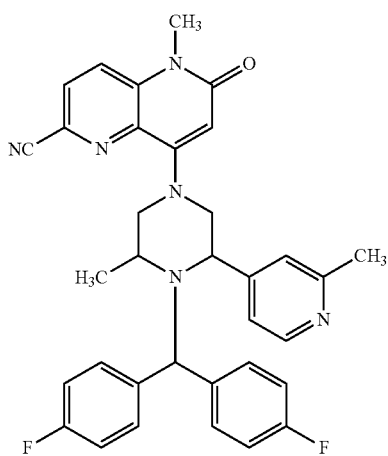

(84)

To a stirred solution of 5-methyl-8-(3-methyl-5-(2-methylpyridin-4-yl)piperazin-1-yl)-6-oxo-5,6-dihydro-1,5-naphthyridine-2-carbonitrile (60 mg, 0.160 mmol) in acetonitrile (6 mL) were added sodium tert-butoxide (77 mg, 0.801 mmol) and 4,4'-(chloromethylene)bis(fluorobenzene) (57.4 mg, 0.240 mmol). The reaction mixture was heated up to 85° C. and was stirred for 16 h. The reaction mixture was filtered and was concentrated under high vacuum to yield a brown gum. The crude material was purified via preparative HPLC (Method) Method: Column-X-Bridge Phenyl (250 mm×19 mm ID, 5 μm); Mobile phase A: Buffer: Buffer: 10 mm Ammonium bicarbonate in water pH-9.5; Mobile phase B: acetonitrile:methanol (1:1); gradient: 70-85% B over 11 minutes, flow rate 17 mL/min. Fractions containing the product were combined and dried via centrifugal evaporation to yield 8-(4-(bis(4-fluorophenyl)methyl)-3-methyl-5-(2-methylpyridin-4-yl)piperazin-1-yl)-5-methyl-6-oxo-5,6-dihydro-1,5-naphthyridine-2-carbonitrile (8.2 mg, 8.9% yield); LCMS: m/z=577.3 (M+H); rt 2.132 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.32 (d, J=4.9 Hz, 1H), 8.16 (d, J=9.0 Hz, 1H), 8.11 (d, J=9.0 Hz, 1H), 7.39-7.25 (m, 2H), 7.25-7.02 (m, 7H), 6.99 (br. s., 2H), 6.33 (br. s., 1H), 4.00 (br. s., 1H), 3.51 (s, 3H), 3.20 (d, J=11.7 Hz, 1H), 3.08 (br. s., 1H), 2.96 (d, J=9.8 Hz, 2H), 2.83 (br. s., 1H), 2.40 (s, 3H), 1.09-0.90 (m, 3H).

Intermediate 57 tert-butyl 4-(bis(4-fluorophenyl)methyl)-3-isobutyrylpiperazine-1-carboxylate

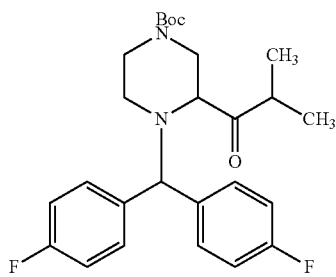

(I-57)

To a stirred solution of 1-(tert-butyl) 3-methyl 4-(bis(4-fluorophenyl)methyl) piperazine-1,3-dicarboxylate (0.4 g, 0.896 mmol) in tetrahydrofuran (6 mL) at 0° C. was added isopropyl magnesium chloride in THF (2.240 mL, 4.48 mmol) drop wise under nitrogen over 3 min. The reaction mixture was slowly warmed to room temperature and was stirred for 3 h. The reaction was quenched with saturated ammonium chloride solution (50 mL). The mixture was extracted with ethyl acetate (3×100 mL). The combined organic layer was dried over anhydrous sodium sulfate, filtered and evaporated under reduced pressure to yield tert-butyl 4-(bis(4-fluorophenyl)methyl)-3-isobutyrylpiperazine-1-carboxylate (400 mg, 97% yield) as a brown oil. LCMS: m/z 459.2 (M+H); rt 4.25 min. LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 58

1-(1-(bis(4-fluorophenyl)methyl)piperazin-2-yl)-2-methylpropan-1-one

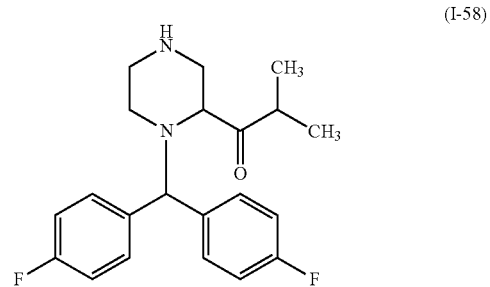 [SMILES: CC(C)C(=O)C1CNCCN1C(c1ccc(F)cc1)c1ccc(F)cc1]

(I-58)

To a stirred solution of tert-butyl 4-(bis(4-fluorophenyl)methy)-3-isobutyrylpiperazine-1-carboxylate (80 mg, 0.174 mmol) in HCl in dioxane (26.5 μL, 0.872 mmol). The reaction mixture was stirred at room temperature for 1 h. The reaction mixture was concentrated under high vacuum to yield HCl salt of 1-(1-(bis(4-fluorophenyl)methyl)piperazin-2-yl)-2-methylpropan-1-one (71 mg, 78% yield) as a brown solid. LCMS: m/z=359.2 (M+H); rt 2.373 min. LC-MS Method: Column-KINETEX-XB-C18 (75×3 mm-2.6 μm); Mobile phase A: 0.1% TFA in Milli-Q water; Mobile phase B: 0.1% TFA in acetonitrile; Gradient: 20-100% B over 4.0 minutes, flow rate 1.0 mL/min, then a 0.6 minute hold at 100% B flow rate 1.5 mL/min, 100-20% B over 0.1 minutes, flow rate 1.5 mL/min.

Examples 86 to 87

8-(4-(bis(4-fluorophenyl)methyl)-3-isobutyrylpiperazin-1-yl)-5-methyl-6-oxo-5,6-dihydro-1,5-naphthyridine-2-carbonitrile

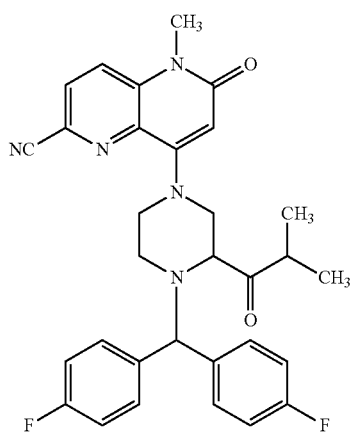

(86-87)

To a stirred solution of 6-cyano-1-methyl-2-oxo-1,2-dihydro-1,5-naphthyridin-4-yl trifluoromethanesulfonate (60 mg, 0.18 mmol) in acetonitrile (5 mL) were added DIPEA (0.094 mL, 0.540 mmol) and HCl salt of 1-(1-(bis(4-fluorophenyl)methyl) piperazin-2-yl)-2-methylpropan-1-one (71.1 mg, 0.18 mmol). The reaction mixture was heated up to 85° C. over 5 min and was stirred for 1 h. The reaction mixture was concentrated under reduced pressure to yield a brown oil. The crude material was purified via preparative HPLC (Method) Method: Column-X-Bridge Phenyl (250 mm×19 mm ID, 5 μm); Mobile phase A: Buffer: Buffer: 10 mm ammonium bicarbonate in water pH-9.5; Mobile phase B: acetonitrile; Gradient: 50-75% B over 12 minutes, flow rate 17 mL/min. Fractions containing the product were combined and dried via centrifugal evaporation to yield the product as an enantiomeric mixture. Enantiomers were separated using chiral HPLC. Chiral separation method: Method: Column-Cellulose C4 (250×21) mm, 5 micron; M. Phase A: M. Phase B: 0.1% DEA in methanol; Flow rate: 20 mL/min.

Example 86: Enantiomer 1: (3.2 mg, 3.2% yield); LCMS: m/z=542.3 (M+H); rt 2.31 min; LC-MS Method: Column-X: Bridge BEH XP C18 (50×2.1 mm 2.5; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.18 (d, J=8.8 Hz, 1H), 8.10 (d, J=8.8 Hz, 1H), 7.57 (dd, J=8.7, 5.7 Hz, 2H), 7.37 (dd, J=8.7, 5.5 Hz, 2H), 7.15 (q, J=8.6 Hz, 4H), 6.16 (s, 1H), 5.26 (s, 1H), 5.01 (d, J=12.2 Hz, 1H), 3.77 (br. s., 1H), 3.63-3.51 (m, 4H), 3.48 (t, J=12.0 Hz, 1H), 3.24 (dd, J=13.1, 4.3 Hz, 1H), 3.17-3.08 (m, 1H), 3.05-2.96 (m, 1H), 2.62 (d, J=12.2 Hz, 1H), 0.85 (d, J=6.4 Hz, 3H), 0.55 (d, J=7.1 Hz, 3H).

Example 87: Enantiomer 2: (3.4 mg, 3.4% yield); LCMS: m/z=542.2 (M+H); rt 2.31 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.18 (d, J=8.8 Hz, 1H), 8.10 (d, J=9.0 Hz, 1H), 7.57 (dd, J=8.7, 5.5 Hz, 2H), 7.37 (dd, J=8.8, 5.6 Hz, 2H), 7.15 (q, J=8.6 Hz, 4H), 6.16 (s, 1H), 5.26 (s, 1H), 5.01 (d, J=13.0 Hz, 1H), 3.77 (br. s., 1H), 3.63-3.51 (m, 4H), 3.48 (t, J=11.5 Hz, 1H), 3.24 (dd, J=13.1, 4.3 Hz, 1H), 3.17-3.10 (m, 1H), 3.06-2.97 (m, 1H), 2.62 (d, J=11.5 Hz, 1H), 0.85 (d, J=6.4 Hz, 3H), 0.55 (d, J=7.1 Hz, 3H).

Intermediate 59 tert-butyl 4-(bis(4-fluorophenyl)methyl)-3-(2-hydroxy-3-methylbutan-2-yl)piperazine-1-carboxylate

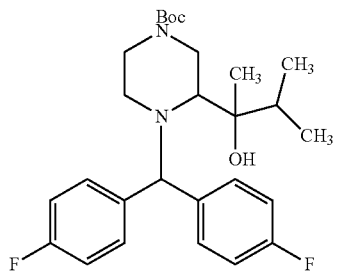 [SMILES: CC(C)C(C)(O)C1CN(C(=O)OC(C)(C)C)CCN1C(c1ccc(F)cc1)c1ccc(F)cc1]

To a stirred solution of tert-butyl 4-(bis(4-fluorophenyl)methyl)-3-isobutyrylpiperazine-1-carboxylate (320 mg, 0.698 mmol) in tetrahydrofuran (5 mL) at 0° C. was added methyl magnesium chloride in THF (1.163 mL, 3.49 mmol) drop wise under nitrogen over 3 min. The reaction mixture was slowly warmed to room temperature and was stirred for 3 h. The reaction was quenched with saturated ammonium chloride solution (50 mL). The mixture was extracted with ethyl acetate (3×100 mL). The combined organic layer was dried over anhydrous sodium sulfate, filtered and evaporated under reduced pressure to yield tert-butyl 4-(bis(4-fluorophenyl)methyl)-3-(2-hydroxy-3-methylbutan-2-yl)piperazine-1-carboxylate (230 mg, 36.1% yield) as a brown oil. LCMS: m/z=475.5 (M+H); rt 1.32 min. LC-MS Method: Column-AQUITY UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Intermediate 60

2-(1-(bis(4-fluorophenyl)methyl)piperazin-2-yl)-3-methylbutan-2-ol, HCl

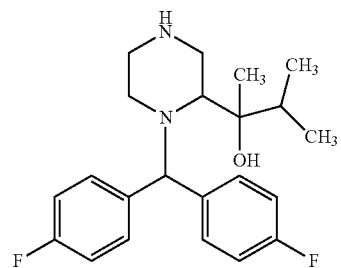

A solution of tert-butyl 4-(bis(4-fluorophenyl)methyl)-3-(2-hydroxy-3-methylbutan-2-yl) piperazine-1-carboxylate (230 mg, 0.485 mmol) in HCl in dioxane (3.0 mL, 99 mmol) was stirred at room temperature for 1 h. The reaction mixture was concentrated under high vacuum to yield HCl salt of 2-(1-(bis(4-fluorophenyl)methyl) piperazin-2-yl)-3-methylbutan-2-ol (200 mg, 50.2% yield) as a brown solid. LCMS: m/z 375.2 (M+H); rt 2.574 min. LC-MS Method: Column-KINETEX-XB-C18 (75×3 mm-2.6 μm); Mobile phase A: 0.1% TFA in Milli-Q water; Mobile phase B: 0.1% TFA in acetonitrile; Gradient: 20-100% B over 4.0 minutes, flow rate 1.0 mL/min, then a 0.6 minute hold at 100% B flow rate 1.5 mL/min, 100-20% B over 0.1 minutes, flow rate 1.5 mL/min.

Examples 88 to 89

8-(4-(bis(4-fluorophenyl)methyl)-3-(2-hydroxy-3-methylbutan-2-yl)piperazin-1-yl)-5-methyl-6-oxo-5,6-dihydro-1,5-naphthyridine-2-carbonitrile

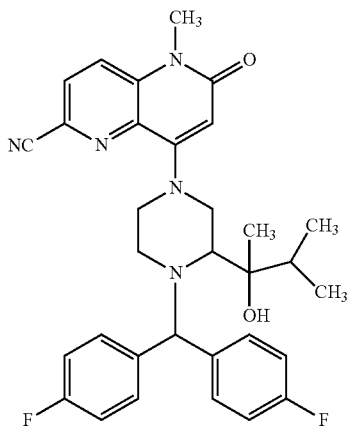

(88-89)

To a stirred solution of 6-cyano-1-methyl-2-oxo-1,2-dihydro-1,5-naphthyridin-4-yl trifluoromethanesulfonate (80 mg, 0.240 mmol) in acetonitrile (5 mL) were added DIPEA (0.126 mL, 0.720 mmol) and 2-(1-(bis(4-fluorophenyl)methyl)piperazin-2-yl)-3-methylbutan-2-ol, HCl (99 mg, 0.240 mmol). The reaction mixture was heated up to 85° C. over 5 min and stirred for 1 h. The reaction mixture was concentrated under reduced pressure to yield a brown oil. The crude material was purified via preparative HPLC (Method) Method: Column-sun fire C18 (150 mm×19 mm ID, 5 µm); Mobile phase A: 0.1% TFA in water; Mobile phase B: acetonitrile; Gradient: 20% B over 2.0 minutes, 20-60% B over 13 minutes, flow rate 20 mL/min. Fractions containing the product were combined and dried via centrifugal evaporation to yield the product as a diastereomeric mixture. Diastereomer 1 (Racemate/Major) and Diastereomer 2 (Racemate/Minor); Enantiomers were separated using chiral HPLC. Chiral separation method: Method: Column-Lux-cellulose C4 (250×21.2) mm, 5 micron; M. Phase A: M. Phase B: 0.1% DEA in methanol; Flow rate: 20 mL/min.

Example 88: Diastereomer 1, Enantiomer 1: (9.3 mg, 6.7% yield); LCMS: m/z 558.3 (M+H); rt 2.21 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.20 (d, J=8.8 Hz, 1H), 8.11 (d, J=8.8 Hz, 1H), 7.48 (dd, J=8.7, 5.5 Hz, 2H), 7.35 (dd, J=8.6, 5.6 Hz, 2H), 7.07 (td, J=8.8, 5.4 Hz, 4H), 5.87 (s, 1H), 5.42 (s, 1H), 4.14-4.05 (m, 2H), 3.61-3.46 (m, 5H), 3.30-3.25 (m, 1H), 3.11 (br. s., 2H), 2.90 (s, 1H), 2.74 (s, 1H), 1.02 (s, 3H), 0.82 (d, J=6.8 Hz, 3H), 0.52 (d, J=6.6 Hz, 3H).

Example 89: Diastereomer 1, Enantiomer 2: (5.6 mg, 4.0% yield); LCMS: m/z 558.2 (M+H); rt 2.195 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.15-8.21 (m, 1H), 8.08-8.13 (m, 1H), 7.45-7.52 (m, 2H), 7.32-7.39 (m, 2H), 7.02-7.12 (m, 4H), 5.87 (s, 1H), 5.42 (s, 1H), 4.08 (br d, J=4.9 Hz, 1H), 3.50-3.61 (m, 5H), 3.26-3.29 (m, 1H), 3.07-3.13 (m, 2H), 2.79-2.86 (m, 1H), 2.52-2.55 (m, 1H), 1.92-2.00 (m, 1H), 1.02 (s, 3H), 0.82 (d, J=6.6 Hz, 3H), 0.52 (d, J=6.6 Hz, 3H).

Examples 90 and 91

8-(4-(bis(4-fluorophenyl)methyl)-3-(2-fluoro-3-methylbutan-2-yl)piperazin-1-yl)-5-methyl-6-oxo-5,6-dihydro-1,5-naphthyridine-2-carbonitrile, TFA

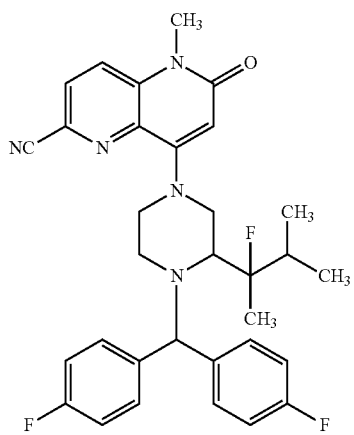

(90-91)

To a stirred solution of 8-(4-(bis(4-fluorophenyl)methyl)-3-(2-hydroxy-3-methylbutan-2-yl)piperazin-1-yl)-5-methyl-6-oxo-5,6-dihydro-1,5-naphthyridine-2-carbonitrile (80 mg, 0.143 mmol) in DCM (5 mL) at 0° C. was added DAST (0.038 mL, 0.287 mmol). The reaction mixture was slowly warmed to room temperature and was stirred for 2 h. The reaction mixtures was quenched with water (20 mL) and was extracted with ethyl acetate (3×50 mL). The combined organic layer was dried over anhydrous sodium sulfate, filtered and evaporated under reduced pressure to yield a brown oil. The crude material was purified via preparative HPLC (Method) Method: Column-SUNFIRE C18 (150 mm×19 mm ID, 5 µm); Mobile phase A: 10 mM ammonium acetate in water; Mobile phase B: acetonitrile; Gradient: 70-85.33% B over 9.5 minutes, flow rate 17 mL/min. Fractions containing the product were combined and dried via centrifugal evaporation to yield a diastereomeric mixture: Diastereomer 1 (Racemate/Major) and Diastereomer 2 (Racemate/Minor); Enantiomers were separated using chiral HPLC. Chiral separation method: Method: Column-DAD-1 Cellulose-2 (250×4.6) mm, 5 micron; DAD-2 Cellulose-4 (250×4.6) mm, 5 micron; M. Phase: 0.1% DEA in acetonitrile:IPA (70:30); Flow rate: 2.0 mL/min.

Example 90: Diastereomer 1, Enantiomer 1 (homochiral): (3.1 mg, 3.2% yield); LCMS: m/z=560.3 (M+H); rt 2.506 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.21 (d, J=8.8 Hz, 1H), 8.12 (d, J=8.8 Hz, 1H), 7.57 (dd, J=8.4, 5.5 Hz, 2H), 7.33 (dd, J=8.7, 5.5 Hz, 2H), 7.22-6.99 (m, 4H), 5.95 (s, 1H), 5.30 (s, 1H), 4.23 (dd, J=13.4, 6.6 Hz, 1H), 3.76 (dd, J=13.3, 7.2 Hz, 1H), 3.57 (s, 3H), 3.47-3.39 (m, 1H), 3.29 (br. s., 1H), 3.26-3.15 (m, 3H), 2.90 (t, J=6.6 Hz, 1H), 1.33-1.12 (m, 3H), 0.83 (d, J=6.6 Hz, 3H), 0.55 (d, J=7.1 Hz, 3H).

Example 91: Diastereomer 1, Enantiomer 2 (homochiral): (2.1 mg, 2.2% yield); LCMS: m/z=560.3 (M+H); rt 2.506 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.21 (d, J=8.8 Hz, 1H), 8.12 (d, J=8.8 Hz, 1H), 7.57 (dd, J=8.6, 5.6 Hz, 2H), 7.33 (dd, J=8.6, 5.6 Hz, 2H), 7.15 (t, J=8.9 Hz, 2H), 7.08 (t, J=8.9 Hz, 2H), 5.95 (s, 1H), 5.30 (s, 1H), 4.23 (dd, J=13.3, 6.7 Hz, 1H), 3.76 (dd, J=13.3, 7.5 Hz, 1H), 3.57 (s, 3H), 3.47-3.39 (m, 1H), 3.29 (br. s., 1H), 3.24-3.15 (m, 3H), 2.95-2.87 (m, 1H), 1.35-1.18 (m, 3H), 0.83 (d, J=6.6 Hz, 3H), 0.55 (d, J=7.1 Hz, 3H).

Intermediate 61 tert-butyl 4-(bis(4-fluorophenyl)methyl)-3-(hydroxymethyl)piperazine-1-carboxylate

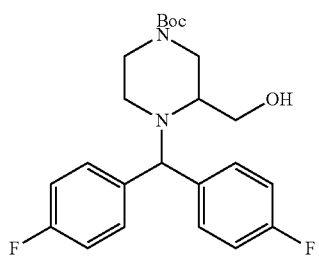

(I-61)

To a stirred solution of 1-(tert-butyl) 3-methyl 4-(bis(4-fluorophenyl)methyl) piperazine-1,3-dicarboxylate (1.5 g, 3.36 mmol) in ethanol (15 mL) at 0° C. were added NaBH$_4$ (0.635 g, 16.80 mmol) and calcium chloride (1.864 g, 16.80 mmol). The reaction mixture was slowly warmed to room temperature and was stirred for 24 h. The reaction mixture was concentrated under reduced pressure and DCM (200 mL) was added. The reaction mixture was filtered through celite bed. The reaction was quenched with water (100 mL). The mixture was extracted with DCM (3×100 mL). The combined organic layer was dried over anhydrous sodium sulfate, filtered and evaporated under reduced pressure to yield a brown oil. The crude compound was purified by ISCO® (using 24 g silica gel column; using 13%-17% ethylacetate/petroleum ether) to yield tert-butyl 4-(bis(4-fluorophenyl)methyl)-3-(hydroxymethyl)piperazine-1-carboxylate (0.8 g, 56.3% yield) as a brown solid. LCMS: m/z=419.2 (M+H); rt 3.39 min. LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 62 tert-butyl 4-(bis(4-fluorophenyl)methyl)-3-(methoxymethyl)piperazine-1-carboxylate

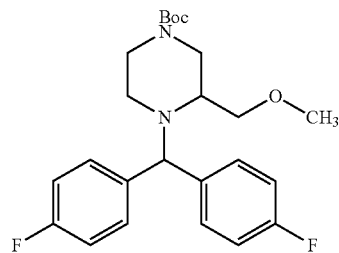

(I-62)

To a stirred solution of tert-butyl 4-(bis(4-fluorophenyl)methyl)-3-(hydroxymethyl)piperazine-1-carboxylate (150 mg, 0.358 mmol) in DMF (8 mL) at 0° C. was added NaH (43.0 mg, 1.075 mmol). The reaction mixture was stirred for 10 min at 0° C., followed by the addition of methyl iodide (0.034 mL, 0.538 mmol). The reaction mixture was warmed to room temperature and was stirred for 3 h. The reaction was quenched with water (50 mL). The mixture was extracted with ethyl acetate (3×100 mL). The combined organic layer was dried over anhydrous sodium sulfate, filtered and evaporated under reduced pressure to yield tert-butyl 4-(bis(4-fluorophenyl)methyl)-3-(methoxymethyl)piperazine-1-carboxylate (0.15 g, 97% yield) as a brown gum. LCMS: m/z=433.5 (M+H); rt 2.31 min. LC-MS Method: Column-AQUITY UPLC BEH C18 (3.0×50 mm) 1.7 μm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.2 minute hold at 100% B, flow rate 0.7 mL/min.

Intermediate 63

1-(bis(4-fluorophenyl)methyl)-2-(methoxymethyl)piperazine, HCl

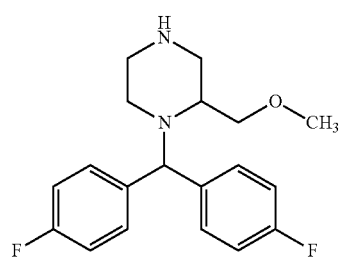

(I-63)

A stirred solution of tert-butyl 4-(bis(4-fluorophenyl)methyl)-3-(methoxymethyl)piperazine-1-carboxylate (0.1 g, 0.231 mmol) in HCl in dioxane (3.0 mL, 99 mmol) was stirred at room temperature for 1 h. The reaction mixture was concentrated under high vacuum to yield HCl salt of 1-(bis(4-fluorophenyl) methyl)-2-(methoxymethyl)piperazine (85 mg, 100% yield) as a brown solid. LCMS: m/z=333.2 (M+H); rt 2.16 min. LC-MS Method: Column-KINETEX-XB-C18 (75×3 mm-2.6 μm); Mobile phase A: 0.1% TFA in Milli-Q water; Mobile phase B: 0.1% TFA in acetonitrile; Gradient: 20-100% B over 4.0 minutes, flow rate 1.0 mL/min, then a 0.6 minute hold at 100% B flow rate 1.5 mL/min, 100-20% B over 0.1 minutes, flow rate 1.5 mL/min.

Examples 92 to 93

8-(4-(bis(4-fluorophenyl)methyl)-3-(methoxymethyl)piperazin-1-yl)-5-methyl-6-oxo-5,6-dihydro-1,5-naphthyridine-2-carbonitrile

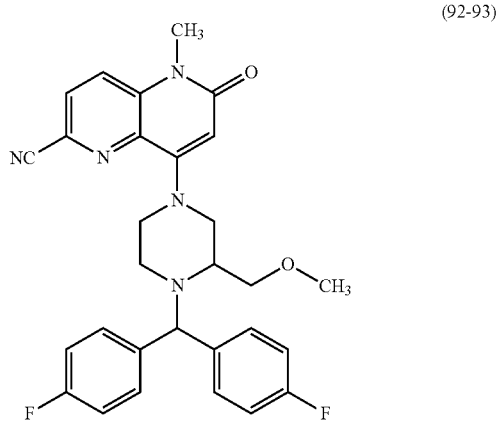 [SMILES: COCC1CN(c2cc(=O)n(C)c3ccc(C#N)nc23)CCN1C(c1ccc(F)cc1)c1ccc(F)cc1]

(92-93)

To a stirred solution of 6-cyano-1-methyl-2-oxo-1,2-dihydro-1,5-naphthyridin-4-yl trifluoromethanesulfonate (100 mg, 0.300 mmol) in acetonitrile (6 mL) were added DIPEA (0.157 mL, 0.900 mmol) and HCl salt of 1-(bis(4-fluorophenyl)methyl)-2-(methoxymethyl)piperazine (111 mg, 0.300 mmol). The reaction mixture was heated up to 85° C. over 5 min and was stirred for 2 h. The reaction mixture was concentrated under reduced pressure to yield a brown oil. The crude material was purified via preparative HPLC with the following conditions: Column: Waters XBridge C18, 150 mm×19 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0 minute hold at 18% B, 18-50% B over 20 minutes, then a 5 minute hold at 100% B; Flow Rate: 15 mL/min; Column Temperature: 25° C. Fractions containing the product were combined and dried via centrifugal evaporation to yield the product as an enantiomeric mixture. Enantiomers were separated using chiral HPLC. Chiral separation method: Method: Column-Cellulose C4 (250×21) mm, 5 micron; M. Phase A: M. Phase B: 0.1% DEA in acetonitrile; Flow rate: 20 mL/min. The enantiomeric mixture gave Enantiomer 1 and Enantiomer 2.

Example 92: Enantiomer 1: (24.9 mg, 16.03% yield); LCMS: m/z=516.2 (M+H); rt 2.21 min; LC-MS Method: Column-X Bridge BEH XP C18 (50×2.1 mm 2.5 m; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.15 (d, J=8.8 Hz, 1H), 8.07 (d, J=8.8 Hz, 1H), 7.62-7.41 (m, 4H), 7.15 (td, J=8.9, 2.3 Hz, 4H), 6.11 (s, 1H), 5.14 (s, 1H), 4.13 (d, J=11.2 Hz, 1H), 3.77 (d, J=6.6 Hz, 2H), 3.62 (d, J=11.7 Hz, 1H), 3.54 (s, 3H), 3.25-3.08 (m, 5H), 2.96 (br. s., 1H), 2.80-2.71 (m, 1H), 2.55 (br. s., 1H).

Example 93: Enantiomer 2: (27.7 mg, 0.053 mmol, 17.74% yield); LCMS: m/z 516.2 (M+H); rt 2.21 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.15 (d, J=8.8 Hz, 1H), 8.07 (d, J=8.8 Hz, 1H), 7.53 (dt, J=8.7, 5.4 Hz, 4H), 7.15 (td, J=8.9, 2.3 Hz, 4H), 6.11 (s, 1H), 5.14 (s, 1H), 4.13 (d, J=12.0 Hz, 1H), 3.77 (d, J=6.4 Hz, 2H), 3.62 (d, J=13.0 Hz, 1H), 3.54 (s, 3H), 3.22-3.09 (m, 5H), 2.96 (br.s, 1H), 2.81-2.70 (m, 1H), 2.57-2.53 (m, 1H).

Intermediate 65

1-(tert-butyl) 3-methyl 4-(bis(4-chlorophenyl)methyl)piperazine-1,3-dicarboxylate

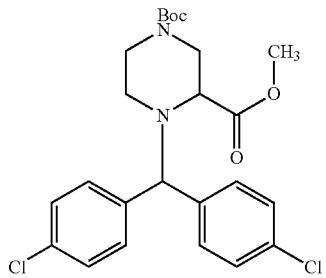

(I-66)

To a stirred solution of 1-(tert-butyl) 3-methyl piperazine-1,3-dicarboxylate (250 mg, 1.023 mmol) in acetonitrile (8 mL) were added DIPEA (0.536 mL, 3.07 mmol) and 4,4'-(bromomethylene)bis(chlorobenzene) (485 mg, 1.535 mmol). The reaction mixture was heated up to 85° C. over 10 min and was stirred for 16 h. The reaction mixture was concentrated under high vacuum to yield a brown gum. The crude compound was purified by ISCO® (using 24 g silica gel column; using 8%-12% ethyl acetate/petroleum ether) to yield 1-(tert-butyl) 3-methyl 4-(bis(4-chlorophenyl)methyl) piperazine-1,3-dicarboxylate (280 mg, 57.1% yield) as a brown gum. LCMS: m/z 481.2 (M+2H); rt 1.803 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 80% B over 0.5 minute, 80-98% B over 2.5 minutes, flow rate 1.0 mL/min, then a 1 minute hold at 98% B flow rate 1.0 mL/min.

Intermediate 66 methyl 1-(bis(4-chlorophenyl)methyl)piperazine-2-carboxylate, HCl

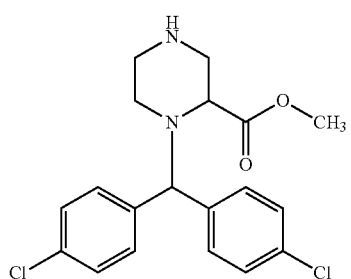

(94-95)

A solution of 1-(tert-butyl) 3-methyl 4-(bis(4-chlorophenyl)methyl) piperazine-1,3-dicarboxylate (400 mg, 0.834 mmol) in HCl in dioxane (5.0 mL, 165 mmol) was stirred at room temperature for 1 h. The reaction mixture was concentrated under high vacuum to yield HCl salt of methyl 1-(bis(4-chlorophenyl)methyl)piperazine-2-carboxylate (320 mg, 86% yield) as a brown solid. LCMS: m/z=379.2 (M+H); rt 2.44 min. LC-MS Method: Column-KINETEX-XB-C18 (75×3 mm-2.6 μm); Mobile phase A: 0.1% TFA in Milli-Q water; Mobile phase B: 0.1% TFA in acetonitrile; Gradient: 20-100% B over 4.0 minutes, flow rate 1.0 mL/min, then a 0.6 minute hold at 100% B flow rate 1.5 mL/min, 100-20% B over 0.1 minutes, flow rate 1.5 mL/min.

Examples 94 to 95 methyl 1-(bis(4-chlorophenyl)methyl)-4-(6-cyano-3-fluoro-1-methyl-2-oxo-1,2-dihydro-1,5-naphthyridin-4-yl)piperazine-2-carboxylate

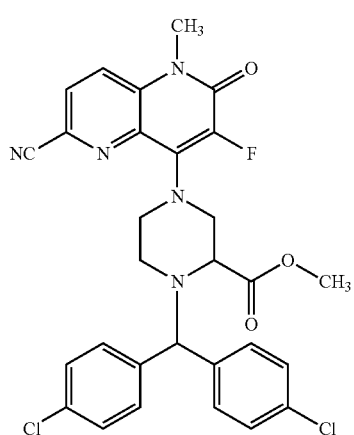

(94-95)

To a stirred solution of methyl 1-(bis(4-chlorophenyl) methyl)-4-(6-cyano-1-methyl-2-oxo-1,2-dihydro-1,5-naphthyridin-4-yl)piperazine-2-carboxylate (80 mg, 0.142 mmol) in acetonitrile (6 mL) at 0° C. was added 1-chloromethyl-4-fluoro-1 4-diazoniabicyclo 2.2.2 octane bis(tetrafluoroborate) (65.5 mg, 0.185 mmol) in THF\H$_2$O (0.5\0.5 mL) drop wise at 0° C. The reaction mixture was stirred for 1.5 h. The reaction mixture was slowly warmed to room temperature and stirred for another 3 h. The reaction mixture was concentrated under reduced pressure to yield a brown oil. The crude material was purified via preparative HPLC (Method) Method: Column-SUNFIRE C18 (150 mm×19 mm ID, 5 μm); Mobile phase A: 10 mM Ammonium acetate in water; Mobile phase B: acetonitrile; Gradient: 50-86% B over 15 minutes, flow rate 17 mL/min. Fractions containing the product were combined and dried via centrifugal evaporation to yield product as an enantiomeric mixture. Enantiomers were separated using chiral HPLC. Chiral separation method: Method: Column-Lux-cellulose C2 (250×21.2) mm, 5 micron; M. Phase: 0.1% Ammonium Hydroxide in acetonitrile:methanol (70:30); Flow rate: 20 mL/min.

Example 94: Enantiomer 1: (1.5 mg, 1.9% yield); LCMS: m/z=580.1 (M+H); rt 2.52 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.23-8.07 (m, 2H), 7.58 (d, J=8.3 Hz, 2H), 7.49-7.30 (m, 6H), 5.19 (s, 1H), 4.07 (d, J=12.7 Hz, 1H), 3.70-3.57 (m, 4H), 3.55 (s, 3H), 3.50-3.39 (m, 2H), 2.59 (d, J=11.7 Hz, 2H), 2.11 (s, 1H).

Example 95: Enantiomer 2: (1.5 mg, 1.9% yield); LCMS: m/z=580.1 (M+H); rt 2.52 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.23-8.09 (m, 2H), 7.58 (d, J=8.6 Hz, 2H), 7.49-7.32 (m, 6H), 5.19 (s, 1H), 4.07 (d, J=11.2 Hz, 1H), 3.72-3.56 (m, 5H), 3.54 (s, 3H), 3.49-3.39 (m, 2H), 2.59 (d, J=11.0 Hz, 1H), 2.11 (s, 1H).

Examples 96 to 97 methyl 1-(bis(4-chlorophenyl)methyl)-4-(6-cyano-1-methyl-2-oxo-1,2-dihydro-1,5-naphthyridin-4-yl)piperazine-2-carboxylate

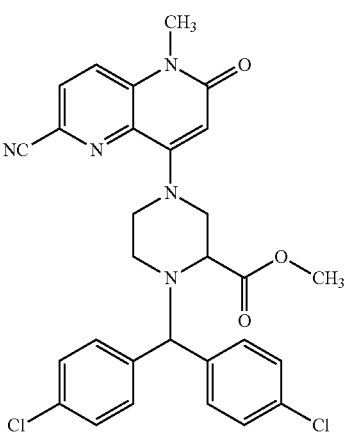

(96-97)

To a stirred solution of 6-cyano-1-methyl-2-oxo-1,2-dihydro-1,5-naphthyridin-4-yl trifluoromethanesulfonate (85 mg, 0.255 mmol) in acetonitrile (8 mL) were added DIPEA (0.134 mL, 0.765 mmol) and HCl salt of methyl 1-(bis(4-chlorophenyl)methyl) piperazine-2-carboxylate (106 mg, 0.255 mmol). The reaction mixture was heated up to 85° C. over 5 min and was stirred for 2 h. The reaction mixture was concentrated under reduced pressure to yield a brown oil. The crude material was purified via preparative HPLC (Method) Method: Column-Sun fire C18 (250×4.6 mm) 3.5 µm; Mobile phase A: 10 mM ammonium acetate in water; Mobile phase B: acetonitrile; Gradient: 40% B over 2 minutes, 40-60% B over 1 minute, 60-100% B over 17 minute, flow rate: 1 mL/min. Fractions containing the product were combined and dried via centrifugal evaporation to yield product as an enantiomeric mixture. Enantiomers were separated using chiral HPLC. Chiral separation method: Column: Chiral Pak IG (250×4.6) mm; 5µ; Co-Solvent: 0.2% NH$_4$OH in methanol+acetonitrile (1:1); Co-Solvent percentage: 40%, Column Temperature: 30° C.; Back Pressure: 100 bars; Total Flow: 4 g/min.

Example 96: Enantiomer 1: (3 mg, 2.1% yield); LCMS: m/z=562.2 (M+H); rt 2.49 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.16 (d, J=8.8 Hz, 1H), 8.09 (d, J=9.0 Hz, 1H), 7.56 (d, J=8.6 Hz, 2H), 7.47-7.29 (m, 6H), 6.14 (s, 1H), 5.17 (s, 1H), 4.79 (d, J=12.5 Hz, 1H), 3.65 (d, J=13.9 Hz, 1H), 3.60 (s, 3H), 3.54 (s, 3H), 3.47-3.35 (m, 2H), 3.16 (dd, J=12.5, 3.9 Hz, 1H), 3.10-2.99 (m, 1H), 2.65 (d, J=14.4 Hz, 1H).

Example 97: Enantiomer 2: (4 mg, 2.8% yield); LCMS: m/z=562.2 (M+H); rt 2.49 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.16 (d, J=8.8 Hz, 1H), 8.09 (d, J=9.0 Hz, 1H), 7.56 (d, J=8.6 Hz, 2H), 7.46-7.30 (m, 6H), 6.15 (s, 1H), 5.17 (s, 1H), 4.79 (d, J=12.2 Hz, 1H), 3.65 (d, J=9.8 Hz, 1H), 3.60 (s, 3H), 3.56-3.47 (m, 3H), 3.46-3.36 (m, 2H), 3.16 (dd, J=12.3, 3.5 Hz, 1H), 3.09-2.99 (m, 1H), 2.65 (d, J=13.9 Hz, 1H).

Example 98

(R)-8-(4-(bis(4-fluorophenyl)methyl)-3-methylpiperazin-1-yl)-7-bromo-5-methyl-6-oxo-5,6-dihydro-1,5-naphthyridine-2-carbonitrile

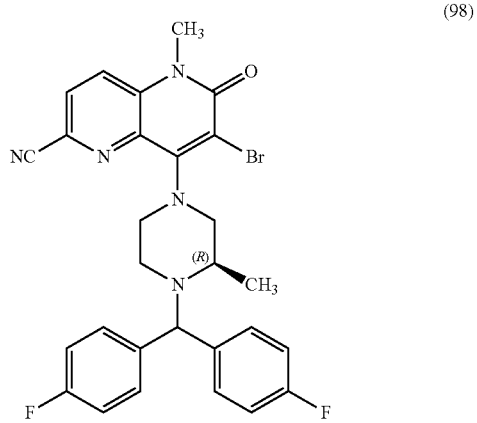

(98)

To a stirred solution of (R)-8-(4-(bis(4-fluorophenyl)methyl)-3-methylpiperazin-1-yl)-5-methyl-6-oxo-5,6-dihydro-1,5-naphthyridine-2-carbonitrile (220 mg, 0.453 mmol) in DMF (8 mL) was added NBS (121 mg, 0.680 mmol). The reaction mixture was stirred at room temperature for 1 h. The reaction mixture was concentrated under high vacuum to yield a brown gum. The crude compound was purified by ISCO® (using 12 g silica gel column; using 56%-60% ethyl acetate/petroleum ether) to yield (R)-8-(4-(bis(4-fluorophenyl)methyl)-3-methylpiperazin-1-yl)-7-bromo-5-methyl-6-oxo-5,6-dihydro-1,5-naphthyridine-2-carbonitrile (150 mg, 58.7% yield) as a brown solid. LCMS: m/z 564.2 (M+H); rt 4.045 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Example 99

(R)-8-(4-(bis(4-fluorophenyl)methyl)-3-methylpiperazin-1-yl)-5,7-dimethyl-6-oxo-5,6-dihydro-1,5-naphthyridine-2-carbonitrile

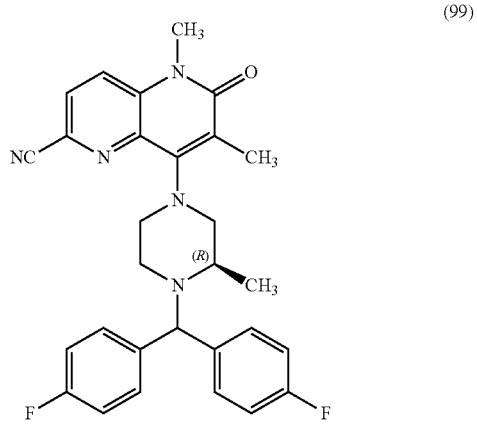

(99)

To a stirred solution of (R)-8-(4-(bis(4-fluorophenyl)methyl)-3-methylpiperazin-1-yl)-7-bromo-5-methyl-6-oxo-5,6-dihydro-1,5-naphthyridine-2-carbonitrile (70 mg, 0.124 mmol) in dioxane (5 mL) were added methylboronic acid (11.14 mg, 0.186 mmol) and K$_2$CO$_3$ (51.4 mg, 0.372 mmol) under nitrogen. The nitrogen purging was continued for 3 min and PdCl$_2$(dppf) (9.07 mg, 0.012 mmol) was added. Purging was continued for another 3 min. The reaction mixture was heated up to 85° C. over 5 min and was stirred for 16 h. The reaction mixture was filtered through cartridge and was concentrated under high vacuum to yield a brown gum. The crude material was purified via preparative HPLC (Method) Method: Column-Sun fire C18 (150×19 mm) 5 μm; Mobile phase A: 10 mM ammonium acetate in water; Mobile phase B: acetonitrile; Gradient: 50-68% B over 19 minutes, flow rate 17 mL/min. Fractions containing the product were combined and dried via centrifugal evaporation to yield (R)-8-(4-(bis(4-fluorophenyl)methyl)-3-methylpiperazin-1-yl)-5,7-dimethyl-6-oxo-5,6-dihydro-1,5-naphthyridine-2-carbonitrile (17.9 mg, 28.9% yield). LCMS: m/z=500.3 (M+H); rt 1.73 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 0.1% TFA; Solvent B: 5% water:95% acetonitrile; 0.1% TFA). $^1$H NMR (400 MHz, DMSO-d$_6$) δ ppm 8.19-7.98 (m, 2H), 7.54 (dd, J=10.5, 8.8 Hz, 2H), 7.56 (dd, =10.5, 8.8 Hz, 2H), 7.15 (td, J=8.9, 4.0 Hz, 4H), 4.87 (s, 1H), 3.84 (d, J=9.3 Hz, 1H), 3.59 (s, 3H), 3.47-3.33 (m, 2H), 3.07 (d, J=11.7 Hz, 1H), 2.97-2.74 (m, 2H), 2.40 (d, J=11.5 Hz, 1H), 2.16 (s, 3H), 1.06 (d, J=6.4 Hz, 3H).

Examples 100 to 101

8-(4-(bis (4-fluorophenyl)methyl)-3-(hydroxymethyl)piperazin-1-yl)-7-chloro-5-methyl-6-oxo-5,6-dihydro-1,5-naphthyridine-2-carbonitrile

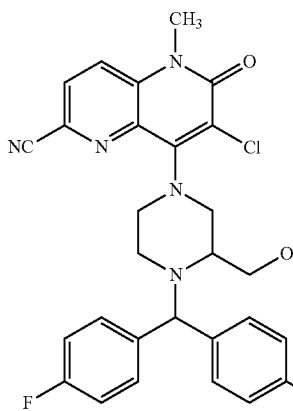

(100-101)

To a stirred solution of 8-(4-(bis(4-fluorophenyl) methyl)-3-(hydroxymethyl) piperazin-1-yl)-5-methyl-6-oxo-5,6-dihydro-1,5-naphthyridine-2-carbonitrile (90 mg, 0.179 mmol) in DCM (6 mL) was added NCS (47.9 mg, 0.359 mmol). The reaction mixture was stirred at room temperature for 4 h. The reaction was quenched with water (5 mL). The reaction mixture was extracted with ethyl acetate (3×10 mL). The combined organic layer was dried over anhydrous sodium sulfate, filtered and evaporated under reduced pressure to yield a brown oil. The crude material was purified via preparative LC-MS. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 10% B, 10-40% B over 25 minutes, then a 5 minute hold at 100% B; Flow Rate: 15 mL/min; Column Temperature: 25° C. Fractions containing the product were combined and dried via centrifugal evaporation to yield product as an enantiomeric mixture. Enantiomers were separated using chiral HPLC. Chiral separation method: Method: Column-Cellulose C5 (250×30) mm, 5 micron; M. Phase A: 0.1% ammonia in methanol; Flow rate: 30 mL/min.

Example 100: Enantiomer 1: (9.8 mg, 10.2% yield); LCMS: m/z=536.2 (M+H); rt 2.33 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.18 (q, J=8.8 Hz, 2H), 7.66-7.49 (m, 4H), 7.15 (td, J=8.9, 3.5 Hz, 4H), 5.20 (s, 1H), 4.25 (br. s., 1H), 3.80 (d, J=10.0 Hz, 2H), 3.73-3.60 (m, 5H), 3.57 (d, J=12.2 Hz, 1H), 3.42-3.36 (m, 1H), 3.11-3.03 (m, 1H), 2.74 (s, 1H), 2.48 (br. s., 1H).

Example 101: Enantiomer 2: (6.5 mg, 6.8% yield); LCMS: m/z=536.2 (M+H); rt 2.33 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.18 (q, J=8.8 Hz, 2H), 7.67-7.46 (m, 4H), 7.15 (td, J=8.9, 3.4 Hz, 4H), 5.20 (s, 1H), 4.24 (t, J=5.3 Hz, 1H), 3.86-3.74 (m, 2H), 3.73-3.60 (m, 5H), 3.57 (d, J=12.2 Hz, 1H), 3.42-3.35 (m, 1H), 3.07 (t, J=10.1 Hz, 1H), 2.74 (br. s., 1H), 2.48 (br. s., 1H).

Intermediate 67 tert-butyl (R)-4-(bis(4-chlorophenyl)methyl)-3-methylpiperazine-1-carboxylate

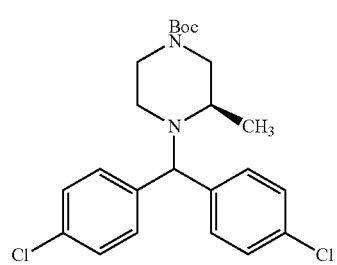

(I-67)

To a stirred solution of tert-butyl (R)-3-methylpiperazine-1-carboxylate (500 mg, 2.496 mmol) in acetonitrile (6 mL) were added DIPEA (1.308 mL, 7.49 mmol) and 4,4'-(bromomethylene)bis(chlorobenzene) (1183 mg, 3.74 mmol). The reaction mixture was heated up to 85° C. over 10 min and was stirred for 16 h. The reaction mixture was concentrated under high vacuum to yield a brown gum. The crude compound was purified by ISCO® (using 24 g silica gel column; using 8%-12% ethyl acetate/petroleum ether) to yield tert-butyl (R)-4-(bis(4-chlorophenyl)methyl)-3-methylpiperazine-1-carboxylate (180 mg, 83% yield) as a brown gum. LCMS: m/z 437.2 (M+H); rt 2.24 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 80% B over 0.5 minute, 80-98% B over 2.5 minutes, flow rate 1.0 mL/min, then a 1 minute hold at 98% B flow rate 1.0 mL/min.

Intermediate 68

(R)-1-(bis(4-chlorophenyl)methyl)-2-methylpiperazine

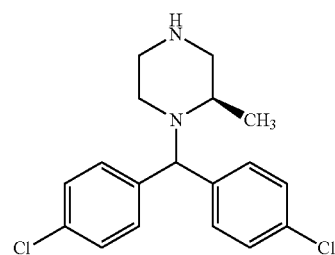

(I-68)

A solution of tert-butyl (R)-4-(bis(4-chlorophenyl)methyl)-3-methylpiperazine-1-carboxylate (170 mg, 0.390 mmol) in HCl in dioxane (3.0 mL, 99 mmol) was stirred at room temperature for 1 h. The reaction mixture was concentrated under high vacuum to yield HCl salt of (110 mg, 84% yield) as a brown solid. LCMS: m/z=336.2 (M+H); rt 2.39 min. LC-MS Method: Column-KINETEX-XB-C18 (75×3 mm-2.6 µm); Mobile phase A: 0.1% TFA in Milli-Q water; Mobile phase B: 0.1% TFA in acetonitrile; Gradient: 20-100% B over 4.0 minutes, flow rate 1.0 mL/min, then a 0.6 minute hold at 100% B flow rate 1.5 mL/min, 100-20% B over 0.1 minutes, flow rate 1.5 mL/min.

Example 102

(R)-4-(4-(bis(4-chlorophenyl)methyl)-3-methylpiperazin-1-yl)-6-bromo-1-methyl-2-oxo-1,2-dihydro-1,5-naphthyridine-3-carbonitrile

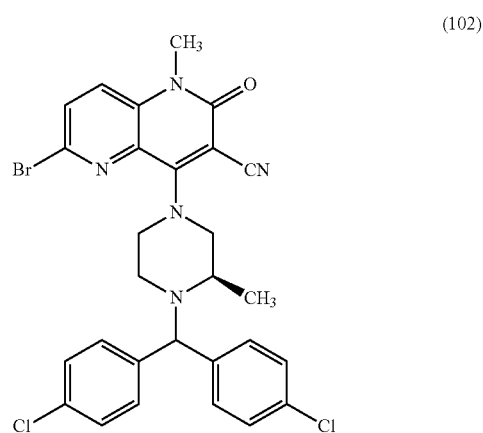 [SMILES: C[C@@H]1CN(c2c(C#N)c(=O)n(C)c3ccc(Br)nc23)CCN1C(c1ccc(Cl)cc1)c1ccc(Cl)cc1]

(102)

To a stirred solution of 6-bromo-3-cyano-1-methyl-2-oxo-1,2-dihydro-1,5-naphthyridin-4-yl trifluoromethanesulfonate (100 mg, 0.243 mmol) in acetonitrile (8 mL) were added DIPEA (0.127 mL, 0.728 mmol) and HCl salt of (R)-1-(bis(4-chlorophenyl) methyl)-2-methylpiperazine, HCl (90 mg, 0.243 mmol). The reaction mixture was heated up to 85° C. over 5 min and was stirred for 3 h. The reaction mixture was concentrated under high vacuum to yield a brown gum. The crude compound was purified by ISCO® (using 12 g silica gel column; using 58%-62% ethyl acetate/petroleum ether) to yield (R)-4-(4-(bis(4-chlorophenyl) methyl)-3-methylpiperazin-1-yl)-6-bromo-1-methyl-2-oxo-1,2-dihydro-1,5-naphthyridine-3-carbonitrile (110 mg, 50.8% yield) as a brown solid. LCMS: m/z=598.0 (M+H); rt 4.41 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Example 103

(R)-8-(4-(bis(4-chlorophenyl)methyl)-3-methylpiperazin-1-yl)-5-methyl-6-oxo-5,6-dihydro-1,5-naphthyridine-2,7-dicarbonitrile

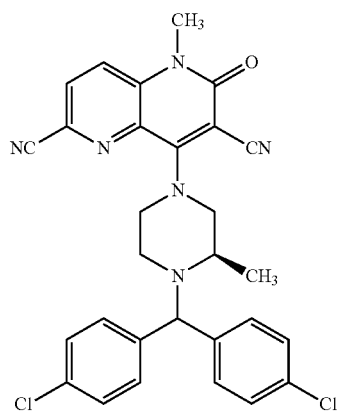

(103)

To a stirred solution of (R)-4-(4-(bis(4-chlorophenyl)methyl)-3-methylpiperazin-1-yl)-6-bromo-1-methyl-2-oxo-1,2-dihydro-1,5-naphthyridine-3-carbonitrile (80 mg, 0.134 mmol) in NMP (5 mL) were added zinc (1.751 mg, 0.027 mmol) and zinc cyanide (31.5 mg, 0.268 mmol) under nitrogen. The nitrogen purging was continued for 3 min. Next, dppf (4.45 mg, 8.04 µmol) and Pd$_2$(dba)$_3$ (12.26 mg, 0.013 mmol) were added and purging was continued for another 3 min. The reaction mixture was heated up to 80° C. over 5 min and was stirred for 4 h. The reaction was quenched saturated ammonium chloride solution (5 mL). The reaction mixture was extracted with ethyl acetate (3×10 mL). The combined organic layer was dried over anhydrous sodium sulfate, filtered and evaporated under reduced pressure to yield a brown oil. The crude material was purified via preparative HPLC (Method) DAD 1: Bridge phenyl (250 mm×4.6 mm) 5 µm; DAD-2: Inersil ODS (250 mm×4.6 mm) 5 µm; MPA: 10 mM ammonium acetate in water pH: 4.5; MPB: acetonitrile; Gradient: 30-60% B over 2 minutes, 60-100% B over 14 minutes, then a 4 minute hold at 100% B; 100-20% B over 1 minute; Flow rate: 2 mL/min. Fractions containing the product were combined and dried via centrifugal evaporation to yield (R)-8-(4-(bis(4-chlorophenyl)methyl)-3-methylpiperazin-1-yl)-5-methyl-6-oxo-5,6-dihydro-1,5-naphthyridine-2,7-dicarbonitrile (35.0 mg, 47.6% yield); LCMS: m/z 543.2 (M+H); rt 2.729 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.25 (d, J=8.8 Hz, 1H), 8.15 (d, J=9.0 Hz, 1H), 7.54 (d, J=8.6 Hz, 2H), 7.57 (d, J=8.6 Hz, 2H), 7.39 (d, J=8.6 Hz, 4H), 4.92 (s, 1H), 4.10 (d, J=13.7 Hz, 1H), 4.00 (d, J=12.2 Hz, 1H), 3.87 (dd, J=12.8, 2.8 Hz, 1H), 3.60 (t, J=10.3 Hz, 1H), 3.53 (s, 3H), 3.09-2.97 (m, 1H), 2.96-2.86 (m, 1H), 1.04 (d, J=6.4 Hz, 3H). One proton peak merged with residual solvent peak.

Example 104

(R)-8-(4-(bis(4-chlorophenyl)methyl)-3-methylpiperazin-1-yl)-5-methyl-6-oxo-5,6-dihydro-1,5-naphthyridine-2-carbonitrile, dimethylformamide

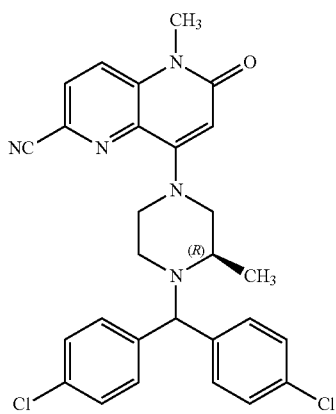

(104)

To a stirred solution of 6-cyano-1-methyl-2-oxo-1,2-dihydro-1,5-naphthyridin-4-yl trifluoromethanesulfonate (60 mg, 0.180 mmol) in acetonitrile (6 mL) were added DIPEA (0.094 mL, 0.540 mmol) and (R)-1-(bis(4-chlorophenyl)methyl)-2-methylpiperazine, HCl (66.9 mg, 0.180 mmol). The reaction mixture was heated up to 85° C. over 5 min and was stirred for 2 h. The reaction mixture was concentrated under reduced pressure to yield a brown oil. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 12% B, 12-60% B over 25 minutes, then a 5 minute hold at 100% B; Flow Rate: 15 mL/min; Column Temperature: 25° C. Fractions containing the product were combined and dried via centrifugal evaporation to yield (R)-8-(4-(bis(4-chlorophenyl) methyl)-3-methylpiperazin-1-yl)-5-methyl-6-oxo-5,6-dihydro-1,5-naphthyridine-2-carbonitrile, dimethylformamide (15.4 mg, 14.5% yield); LCMS: m/z 518.2 (M+H); rt 2.585 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.15 (d, J=8.8 Hz, 1H), 8.07 (d, J=8.8 Hz, 1H), 7.51 (d, J=8.6 Hz, 2H), 7.54 (d, J=8.6 Hz, 2H), 7.39 (dd, J=8.6, 3.7 Hz, 4H), 6.08 (s, 1H), 4.86 (s, 1H), 4.02 (d, J=10.5 Hz, 1H), 3.63-3.47 (m, 4H), 3.21-3.05 (m, 2H), 2.98 (d, J=6.4 Hz, 1H), 2.90 (s, 1H), 2.46 (br. s., 1H), 1.18 (d, J=6.4 Hz, 3H).

Example 105

(R)-8-(4-(bis(4-chlorophenyl)methyl)-3-methylpiperazin-1-yl)-7-chloro-5-methyl-6-oxo-5,6-dihydro-1,5-naphthyridine-2-carbonitrile, dimethylformamide

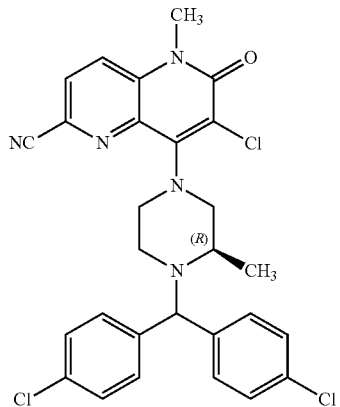

(105)

To a stirred solution of (R)-8-(4-(bis(4-chlorophenyl)methyl)-3-methylpiperazin-1-yl)-5-methyl-6-oxo-5,6-dihydro-1,5-naphthyridine-2-carbonitrile (45 mg, 0.087 mmol) in DCM (5 mL) was added NCS (23.18 mg, 0.174 mmol). The reaction mixture was stirred at room temperature for 16 h. The reaction mixture was quenched with water (5 mL) and was extracted with ethyl acetate (3×10 mL). The combined organic layer was dried over anhydrous sodium sulfate, filtered and evaporated under reduced pressure to yield a brown oil. The crude material was purified via preparative LC-MS (Method). The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 10% B, 10-40% B over 25 minutes, then a 5 minute hold at 100% B; Flow Rate: 15 mL/min; Column Temperature: 25° C. Fractions containing the product were combined and dried via centrifugal evaporation to yield (R)-8-(4-(bis (4-chlorophenyl)methyl)-3-methylpiperazin-1-yl)-7-chloro-5-methyl-6-oxo-5,6-dihydro-1,5-naphthyridine-2-carbonitrile, dimethylformamide (5.2 mg, 9.6% yield); LCMS: m/z=552.2 (M+H); rt 2.779 min; LC-MS Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.17 (q, J=8.8 Hz, 2H), 7.54 (d, J=8.6 Hz, 2H), 7.57 (d, J=8.6 Hz, 2H), 7.39 (dd, J=8.6, 1.2 Hz, 4H), 4.87 (s, 1H), 3.90-3.81 (m, 1H), 3.72-3.53 (m, 4H), 3.45-3.32 (m, 2H), 3.00-2.85 (m, 1H), 2.44 (d, J=11.7 Hz, 1H), 2.13-2.02 (m, 1H), 1.12-0.94 (m, 3H).

Intermediate 69

1-(tert-butyl) 3-cyclopropyl 4-(bis(4-fluorophenyl)methyl)piperazine-1,3-dicarboxylate

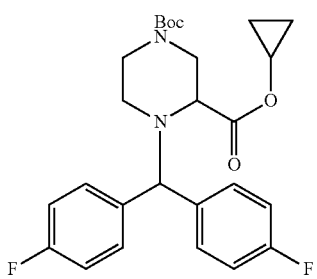

(I-69)

To a stirred solution of 1-(bis(4-fluorophenyl)methyl)-4-(tert-butoxycarbonyl) piperazine-2-carboxylic acid (350 mg, 0.809 mmol) in DCM (8 mL) were added DCC (501 mg, 2.428 mmol) and DMAP (99 mg, 0.809 mmol) followed by the addition of cyclopropanol (94 mg, 1.619 mmol). The reaction mixture was stirred at room temperature for 16 h. The reaction was quenched with water (50 mL). The reaction mixture was extracted with ethyl acetate (3×100 mL). The combined organic layer was dried over anhydrous sodium sulphate, filtered and evaporated under reduced pressure to yield a brown oil. The crude compound was purified by ISCO® (using 24 g silica gel column; using 11%-15% ethyl acetate/petroleum ether) to yield a brown gum (50 mg, 13.1% yield). LCMS: m/z=473.2 (M+H); rt 4.201 min. LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water: acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 70 cyclopropyl 1-(bis(4-fluorophenyl)methyl)piperazine-2-carboxylate, HCl

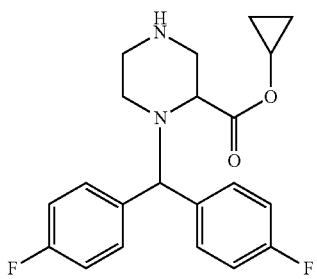

(I-70)

A stirred solution of 1-(tert-butyl) 3-cyclopropyl 4-(bis (4-fluorophenyl)methyl) piperazine-1,3-dicarboxylate (50 mg, 0.106 mmol) in HCl in dioxane (16.07 μL, 0.529 mmol) was stirred at room temperature for 2 h. The reaction mixture was concentrated under high vacuum to yield cyclopropyl 1-(bis(4-fluorophenyl)methyl)piperazine-2-carboxylate, HCl as a brown solid (46 mg, 61.7% yield); LCMS: m/z=373.2 (M+H); rt 2.329 min.

Examples 106 and 107 cyclopropyl 1-(bis(4-fluorophenyl)methyl)-4-(6-cyano-1-methyl-2-oxo-1,2-dihydro-1,5-naphthyridin-4-yl)piperazine-2-carboxylate

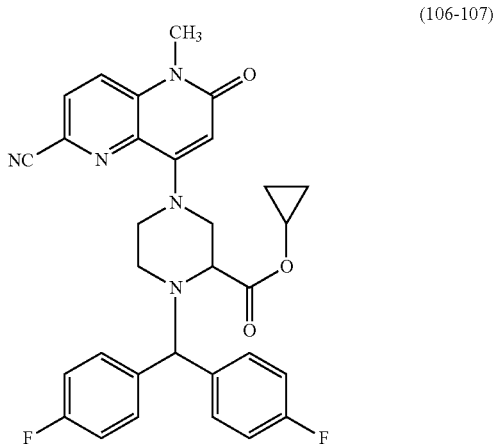 [SMILES: Cn1c(=O)cc(N2CCN(C(c3ccc(F)cc3)c3ccc(F)cc3)C(C(=O)OC3CC3)C2)c2nc(C#N)ccc21]

(106-107)

To a stirred solution of 6-cyano-1-methyl-2-oxo-1,2-dihydro-1,5-naphthyridin-4-yl trifluoromethanesulfonate (50 mg, 0.150 mmol) in acetonitrile (5 mL) were added DIPEA (0.079 mL, 0.450 mmol) and cyclopropyl 1-(bis(4-fluorophenyl)methyl) piperazine-2-carboxylate, HCl (61.3 mg, 0.150 mmol). The reaction mixture was heated up to 85° C. over 5 min and was stirred for 1 h. The reaction mixture was concentrated under reduced pressure to yield a brown oil. The crude material was purified via preparative HPLC Method: Column-SUNFIRE C18 (150 mm×19 mm ID, 5 µm); Mobile phase A: 10 mM Ammonium acetate in water; Mobile phase B: acetonitrile; Gradient: 40% B over 2.0 minutes, 40-60% B over 1.0 minute, 60-100% B over 17 minutes, flow rate 17 mL/min. Fractions containing the product were combined and dried via centrifugal evaporation to yield product as an enantiomeric mixture. Enantiomers were separated using chiral HPLC. Chiral separation method: Column: Chiralcel ODH (250×4.6) mm; 5 µm; Isocratic Mode, Co-Solvent: 0.2% NH$_4$OH in methanol+acetonitrile (1:1); Co-Solvent percentage: 30%, Column Temperature: 30° C.; Back Pressure: 100 bars; Total Flow: 4 g/min.

Example 106: Enantiomer 1: (10.7 mg, 12.3% yield); LCMS: m/z=556.3 (M+H); rt 2.27 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.14-8.19 (m, 1H), 8.07-8.11 (m, 1H), 7.55-7.60 (m, 2H), 7.35-7.40 (m, 2H), 7.12-7.19 (m, 4H), 6.13 (s, 1H), 5.17 (s, 1H), 4.57-4.68 (m, 1H), 3.84-3.99 (m, 2H), 3.54 (s, 3H), 3.33-3.38 (m, 2H), 3.01-3.14 (m, 1H), 2.57-2.64 (m, 1H), 2.52-2.54 (m, 1H), 0.50-0.67 (m, 2H), 0.26-0.37 (m, 2H).

Example 107: Enantiomer 2: (5.0 mg, 5.7% yield); LCMS: m/z=556.3 (M+H); rt 2.27 min; LC-MS Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-d$_6$) δ ppm 8.17 (d, J=8.8 Hz, 1H), 8.06-8.12 (m, 1H), 7.57 (dd, J=8.7, 5.5 Hz, 2H), 7.38 (dd, J=8.6, 5.6 Hz, 2H), 7.13-7.20 (m, 4H), 6.13 (s, 1H), 5.17 (s, 1H), 4.58-4.65 (m, 1H), 3.84-3.97 (m, 2H), 3.54 (s, 3H), 3.33-3.38 (m, 3H), 3.03-3.14 (m, 1H), 2.57-2.64 (m, 1H).

Intermediate 71

(4-Fluoro-2-methoxyphenyl)(4-fluorophenyl)methanol

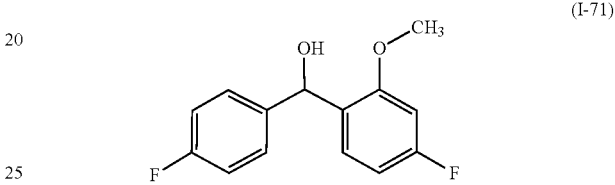

(I-71)

To a solution of 4-fluoro-2-methoxybenzaldehyde (5 g, 32.4 mmol) in tetrahydrofuran (10 mL) was added (4-fluorophenyl)magnesium bromide (64.9 mL, 64.9 mmol) at 0° C. The reaction mixture was stirred at room temperature for 16 h. The reaction was quenched with saturated NH$_4$Cl solution. The mixture was extracted twice with ethyl acetate (50 mL). The organic layer was separated, dried over Na$_2$SO$_4$ and evaporated to dryness to yield (4-fluoro-2-methoxyphenyl) (4-fluorophenyl)methanol (4.5 g, 41.0% yield) as an off-white solid. LC-MS Method: Column: AQUITY UPLC BEH C18 (3.0×50 mm) 1.7 µm, Mobile phase A: 10 mM ammonium acetate:acetonitrile (95:5) Mobile phase B: 10 mM ammonium acetate:acetonitrile (5:95), Flow: 0.7 mL/min. $^1$H NMR (400 MHz, Methanol-d4): δ 7.92 (d, J=12.00 Hz, 1H), 7.76 (d, J=12.00 Hz, 1H), 7.21-7.27 (m, 2H), 6.85-6.94 (m, 3H), 5.84 (s, 1H), 3.78 (s, 3H).

Intermediate 72

1-(Chloro(4-fluorophenyl)methyl)-4-fluoro-2-methoxybenzene

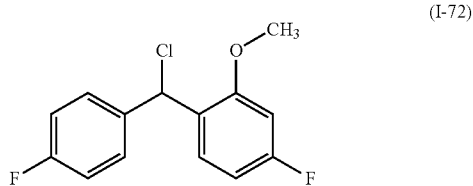 [SMILES: COc1cc(F)ccc1C(Cl)c1ccc(F)cc1]

(I-72)

To a solution of (4-fluoro-2-methoxyphenyl)(4-fluorophenyl)methanol (200 mg, 0.799 mmol) in dichloromethane (40 mL) was added thionyl chloride (0.175 mL, 2.398 mmol). The reaction mixture was heated to 45° C. for 3 h. The reaction mixture was evaporated to dryness under high vacuum to yield 1-(chloro(4-fluorophenyl)methyl)-4-fluoro-2-methoxybenzene (170 mg, 69.7% yield) as a brown liquid.

Method: Column: AQUITY UPLC BEH C18 (3.0×50 mm) 1.7 μm, Mobile phase A: 10 mM ammonium acetate:acetonitrile (95:5) M. phase B: 10 mM ammonium acetate:acetonitrile (5:95), Flow: 0.7 mL/min.

Intermediate 73 tert-Butyl (2S,5R)-4-((4-fluoro-2-methoxyphenyl)(4-fluorophenyl)methyl)-2,5-dimethylpiperazine-1-carboxylate

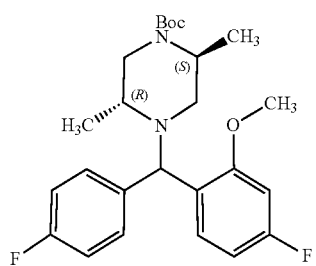

(I-73)

To a solution of 1-(chloro(4-fluorophenyl)methyl)-4-fluoro-2-methoxybenzene (200 mg, 0.744 mmol) in acetonitrile (5 mL) were added tert-butyl (2S,5R)-2,5-dimethylpiperazine-1-carboxylate (239 mg, 1.117 mmol) and DIPEA (0.390 mL, 2.233 mmol). The reaction mixture was heated to 80° C. for 4 h. The reaction mixture was diluted with water and extracted twice with ethyl acetate (20 mL). The organic layer was separated and dried over Na₂SO₄ and evaporated to dryness to yield tert-butyl (2S,5R)-4-((4-fluoro-2-methoxyphenyl)(4-fluorophenyl)methyl)-2,5-dimethylpiperazine-1-carboxylate (160 mg, 39.5% yield) as an off-white solid; LCMS: m/z=447.4 (M+H); rt 1.75 and 1.76 min (Diastereomer mixture). Method: Column: AQUITY UPLC BEH C18 (3.0×50 mm) 1.7 μm, Mobile phase A: 10 mM ammonium acetate:acetonitrile (95:5) M. phase B: 10 mM ammonium acetate:acetonitrile (5:95), Flow: 0.7 mL/min.

Intermediate 74

(2R, 5S)-1-((4-fluoro-2-methoxyphenyl)(4-fluorophenyl)methyl)-2,5-dimethylpiperazine

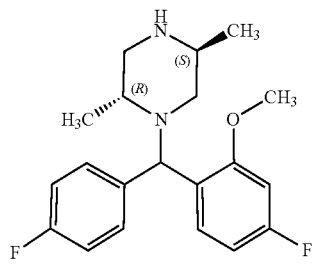

(I-74)

To a solution of tert-butyl (2S,5R)-4-((4-fluoro-2-methoxyphenyl)(4-fluorophenyl)methyl)-2,5-dimethylpiperazine-1-carboxylate (200 mg, 0.448 mmol) in 1,4-dioxane (5 mL) was added HCl in dioxane (1.120 mL, 4.48 mmol). The reaction mixture was stirred at room temperature for 16 h and then evaporated to dryness. The solid was washed with diethyl ether to yield (2R,5S)-1-((4-fluoro-2-methoxyphenyl)(4-fluorophenyl)methyl)-2,5-dimethylpiperazine, HCl (190 mg, 82% yield) as an off-white solid; LCMS: m/z=347.4 (M+H); rt 1.48 and 1.56 min (Diastereomer mixture). Method: Column: AQUITY UPLC BEH C18 (3.0×50 mm) 1.7 μm, Mobile phase A: 10 mM ammonium acetate:acetonitrile (95:5) M. phase B: 10 mM ammonium acetate:acetonitrile (5:95), Flow: 0.7 mL/min.

Examples 108 and 109

8-((2S,5R)-4-((4-fluoro-2-methoxyphenyl)(4-fluorophenyl)methyl)-2,5-dimethylpiperazin-1-yl)-5-methyl-6-oxo-5,6-dihydro-1,5-naphthyridine-2-carbonitrile

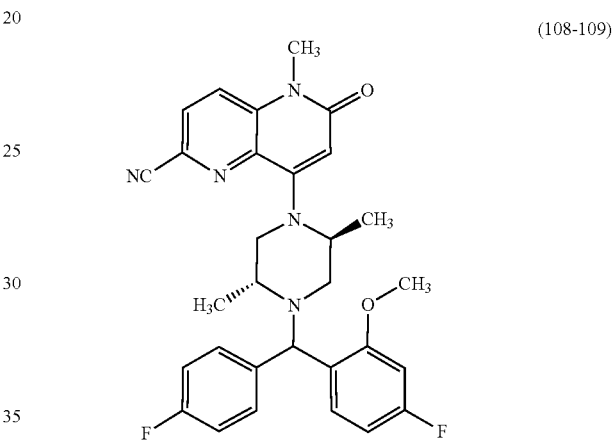

(108-109)

To a solution of (2R,5S)-1-((4-fluoro-2-methoxyphenyl)(4-fluorophenyl)methyl)-2,5-dimethylpiperazine, HCl (100 mg, 0.261 mmol) in acetonitrile (5 mL) were added DIPEA (0.137 mL, 0.784 mmol) and 6-cyano-1-methyl-2-oxo-1,2-dihydro-1,5-naphthyridin-4-yl trifluoromethanesulfonate (104 mg, 0.313 mmol). The reaction mass was heated to 80° C. for 16 h and evaporated to dryness. The crude material was purified via preparative HPLC with the following conditions: Column: Xbridge phenyl, 21×250 mm, 5 μm particles; Mobile Phase A: 10 mM ammonium bicarbonate pH-9.5; Mobile Phase B: acetonitrile; Gradient: 60-100% B over 14 minutes, then a 5 minute hold at 100% B; Flow: 18 mL/min. Fractions containing the product were combined and dried via centrifugal evaporation to yield the product as a diastereomeric mixture. Enantiomers were separated using chiral HPLC. Chiral separation (Prep HPLC Method: Column: C2/160 (250×20 mm, 5 micron; M. Phase A: acetonitrile; M. Phase B: 0.1% DEA in acetonitrile; Flow rate: 20 mL/min.) of diastereomeric mixture gave Diastereomer 1 (homochiral); rt 12.690 min, and Diastereomer 2 (homochiral); rt 14.178 min.

Example 108: Diastereomer 1: (6.3 mg, 4.4% yield); LCMS: m/z=530.3 (M+H); rt 1.508 min; Method: XBridge BEH XP C18 (50×2.1) mm, 2.5 μm, Mobile phase A: 95% water:5% acetonitrile; 0.1% TFA, Mobile phase B: 5% water:95% acetonitrile; 0.1% TFA, Flow: 1.1 mL/min. ¹H NMR (400 MHz, DMSO-d₆) δ ppm 8.13 (d, J=9.0 Hz, 1H), 8.05 (d, J=8.5 Hz, 1H), 7.73 (t, J=7.8 Hz, 1H), 7.51 (dd, J=8.5, 5.5 Hz, 2H), 7.13 (t, J=8.8 Hz, 2H), 6.90-6.66 (m, 2H), 5.99 (s, 1H), 4.98 (s, 1H), 4.57 (br. s., 1H), 3.80 (s, 3H), 3.71 (d, J=12.0 Hz, 1H), 3.58-3.42 (m, 4H), 3.01 (d, J=6.5 Hz, 1H), 2.82 (dd, J=11.5, 3.5 Hz, 1H), 2.39 (d, J=11.0 Hz, 1H), 1.45-1.20 (m, 3H), 1.04 (d, J=6.5 Hz, 3H).

Example 109: Diastereomer 2: (3.7 mg, 2.5% yield); LCMS: m/z=530.3 (M+H); rt 1.568 min; Method: XBridge BEH XP C18 (50×2.1) mm, 2.5, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.14 (d, J=8.8 Hz, 1H), 8.06 (d, J=9.0 Hz, 1H), 7.71-7.61 (m, 1H), 7.49 (dd, J=8.6, 5.6 Hz, 2H), 7.12 (t, J=8.8 Hz, 2H), 6.89 (dd, J=11.6, 2.6 Hz, 1H), 6.81 (td, J=8.6, 2.4 Hz, 1H), 6.00 (s, 1H), 5.06 (s, 1H), 4.56 (br. s., 1H), 3.86 (s, 3H), 3.72 (d, J=12.7 Hz, 1H), 3.60-3.46 (m, 4H), 3.16 (br. s., 1H), 2.82 (dd, J=12.1, 3.5 Hz, 1H), 2.30 (d, J=12.2 Hz, 1H), 1.29 (d, J=6.6 Hz, 3H), 1.02 (d, J=6.6 Hz, 3H).

Example 110

6-Bromo-4-((2S,5R)-4-((4-fluoro-2-methoxyphenyl)(4-fluorophenyl)methyl)-2,5-dimethylpiperazin-1-yl)-1-methyl-2-oxo-1,2-dihydro-1,5-naphthyridine-3-carbonitrile

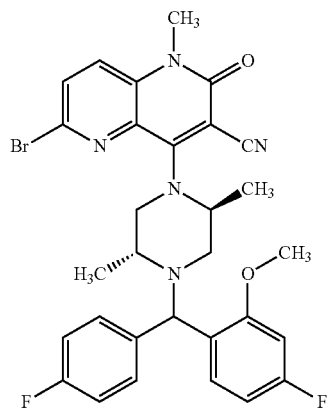

(110)

To a solution of (2R,5S)-1-((4-fluoro-2-methoxyphenyl)(4-fluorophenyl)methyl)-2,5-dimethylpiperazine, HCl (150 mg, 0.392 mmol) in acetonitrile (5 mL) were added DIPEA (0.205 mL, 1.175 mmol) and 6-bromo-3-cyano-1-methyl-2-oxo-1,2-dihydro-1,5-naphthyridin-4-yl trifluoromethanesulfonate (194 mg, 0.470 mmol). The reaction mixture was heated to 80° C. for 16 h. The reaction mixture was diluted with water and extracted twice with ethyl acetate (20 mL). The organic layer was separated, dried over $Na_2SO_4$ and evaporated to dryness. The crude was purified by ISCO® (Column: 40 g RediSep silica, Solvent run: 0-50% EtOAc in petroleum ether). The product was eluted at 35% EtOAc in petroleum ether to afford 6-bromo-4-((2S,5R)-4-((4-fluoro-2-methoxyphenyl)(4-fluorophenyl)methyl)-2,5-dimethylpiperazin-1-yl)-1-methyl-2-oxo-1,2-dihydro-1,5-naphthyridine-3-carbonitrile (110 mg, 33.7% yield); LCMS: m/z=610.4 (M+H); rt 1.35 and 1.39 min. Method: Column: AQUITY UPLC BEH C18 (3.0×50 mm) 1.7 μm, Mobile phase A: 10 mM ammonium acetate:acetonitrile (95:5) M. phase B: 10 mM ammonium acetate:acetonitrile (5:95), Flow: 0.7 mL/min.

Examples 111 and 112

8-((2S,5R)-4-((4-fluoro-2-methoxyphenyl)(4-fluorophenyl)methyl)-2,5-dimethylpiperazin-1-yl)-5-methyl-6-oxo-5,6-dihydro-1,5-naphthyridine-2,7-dicarbonitrile

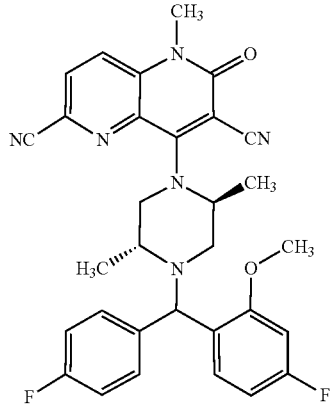

(111-112)

To a solution of 6-bromo-4-((2S,5R)-4-((4-fluoro-2-methoxyphenyl)(4-fluorophenyl)methyl)-2,5-dimethylpiperazin-1-yl)-1-methyl-2-oxo-1,2-dihydro-1,5-naphthyridine-3-carbonitrile (120 mg, 0.197 mmol) in NMP (1 mL) were added zinc (2.58 mg, 0.039 mmol), dppf (6.56 mg, 0.012 mmol) and zinc cyanide (46.3 mg, 0.394 mmol). The reaction mixture was degasified under $N_2$ and $Pd_2(dba)_3$ (18.06 mg, 0.020 mmol) was added under $N_2$. The reaction mass was irradiated under microwave to 80° C. for 2 h. The reaction mixture was evaporated to dryness and purified by preparative HPLC. Method: (Mobile Phase A: 10 mM ammonium acetate in water, Mobile Phase B: acetonitrile, Column: Sunfire C18, 21.2×150 mm, 5 μm, Flow: 20 mL/min) (Diastereomeric mixture). Enantiomers were separated using chiral HPLC. Chiral separation (Column: Cellulose-C4 (250×21 mm) 5 micron, Mobile Phase A: acetonitrile, Mobile Phase B: methanol Flow: 20 mL/min) of Diastereomeric mixture gave Diastereomer 1 (homochiral); rt 17.824 min, and Diastereomer 2 (homochiral); rt 20.415 min. Fractions containing the product were combined and dried via centrifugal evaporation to yield Example 111 and Example 112.

Example 111: Diastereomer 1: (1.5 mg, 1.3% yield); LCMS: m/z=555.3 (M+H); rt 1.644 min; Method: XBridge BEH XP C18 (50×2.1) mm, 2.5 μm, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.25 (d, J=9.0 Hz, 1H), 8.15 (d, J=8.5 Hz, 1H), 7.84-7.69 (m, 1H), 7.54 (dd, J=8.5, 6.0 Hz, 2H), 7.13 (t, J=8.8 Hz, 2H), 6.89-6.64 (m, 2H), 5.00 (s, 1H), 4.75 (br. s., 1H), 4.22 (dd, J=12.8, 3.3 Hz, 1H), 3.81 (s, 3H), 3.61-3.48 (m, 3H), 3.46-3.35 (m, 1H), 3.08 (dd, J=11.5, 3.5 Hz, 1H), 2.98 (d, J=6.0 Hz, 1H), 2.44 (br. s., 1H), 1.44 (d, J=6.5 Hz, 3H), 0.88 (d, J=6.0 Hz, 3H).

Example 112: Diastereomer 2: (5.6 mg, 5.1% yield); LCMS: m/z=555.3 (M+H); rt 1.768 min; Method: XBridge BEH XP C18 (50×2.1) mm, 2.5 μm, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.25 (d, J=9.0 Hz, 1H), 8.15 (d, J=8.5 Hz, 1H), 7.81-7.68 (m, 1H), 7.52 (dd, J=8.5, 5.5 Hz, 2H), 7.12 (t, J=8.8 Hz, 2H), 6.94-6.73 (m, 2H), 5.05 (s, 1H), 4.75 (br. s., 1H), 4.22 (dd, J=12.5, 3.0 Hz, 1H), 3.84 (s, 3H), 3.64-3.48 (m, 3H), 3.42 (d, J=11.5 Hz, 1H), 3.14-3.00 (m, 2H), 2.37 (d, J=11.5 Hz, 1H), 1.42 (d, J=6.5 Hz, 3H), 0.85 (d, J=6.5 Hz, 3H).

Intermediate 75 methyl 4-(bis(4-fluorophenyl)methyl)piperazine-2-carboxylate, HCl

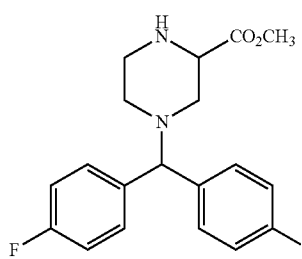

(I-75)

To a solution of 1-(tert-butyl) 2-methyl 4-(bis(4-fluorophenyl)methyl)piperazine-1,2-dicarboxylate (3 g, 6.72 mmol) in 1,4-dioxane (10 mL) was added HCl in 1,4-dioxane (16.80 mL, 67.2 mmol). The reaction mixture was stirred at room temperature for 16 h and evaporated to dryness. The crude material was washed with diethyl ether to yield methyl 4-(bis(4-fluorophenyl)methyl)piperazine-2-carboxylate, HCl (2.5 g, 70% yield) as an off-white solid; LCMS: m/z=347.4 (M+H); rt 1.61 min. Method: Column: AQUITY UPLC BEH C18 (3.0×50 mm) 1.7 µm, Mobile phase A: 10 mM ammonium acetate:acetonitrile (95:5) M. phase B: 10 mM ammonium acetate:acetonitrile (5:95), Flow: 0.7 mL/min.

Example 114

Methyl 4-(bis(4-fluorophenyl)methyl)-1-(3,6-dicyano-1-methyl-2-oxo-1,2-dihydro-1,5-naphthyridin-4-yl)piperazine-2-carboxylate

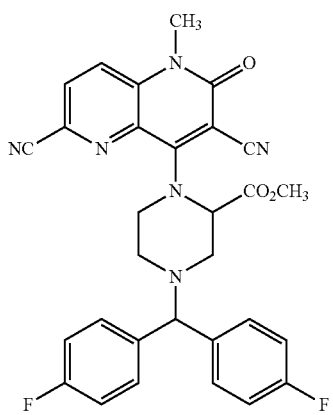

(114)

To a solution of methyl 4-(bis(4-fluorophenyl)methyl)-1-(6-bromo-3-cyano-1-methyl-2-oxo-1,2-dihydro-1,5-naphthyridin-4-yl)piperazine-2-carboxylate (70 mg, 0.115 mmol) in NMP (1 mL) were added zinc (1.504 mg, 0.023 mmol), dppf (3.83 mg, 6.90 µmol), and zinc cyanide (27.0 mg, 0.230 mmol). The reaction mixture was degasified under $N_2$ and $Pd_2(dba)_3$ (10.54 mg, 0.012 mmol) was added under $N_2$. The reaction mass was irradiated under microwave to 80° C. for 2 h. The reaction mixture was diluted with water and extracted twice with ethyl acetate (20 mL). The organic layer was separated, dried over $Na_2SO_4$ and evaporated to dryness. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 35% B, 35-60% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield methyl 4-(bis(4-fluorophenyl)methyl)-1-(3,6-dicyano-1-methyl-2-oxo-1,2-dihydro-1,5-naphthyridin-4-yl)piperazine-2-carboxylate (3.5 mg, 5.4% yield); LCMS: m/z=555.2 (M+H); rt 2.162 min. Method: XBridge BEH XP C18 (50×2.1) mm, 2.5 µm, Mobile phase A: 95% water:5% acetonitrile; 10 mM ammonium acetate, Mobile phase B: 5% water:95% acetonitrile; 10 mM ammonium acetate, Flow: 1.1 mL/min. $^1$H NMR (400 MHz, DMSO-$d_6$) δ ppm 8.25 (d, J=9.0 Hz, 1H), 8.17 (d, J=9.0 Hz, 1H), 7.56-7.38 (m, 4H), 7.18 (q, J=8.8 Hz, 4H), 5.36 (br. s., 1H), 4.51 (s, 1H), 4.16-4.05 (m, 1H), 3.94 (d, J=12.0 Hz, 1H), 3.82 (s, 3H), 3.55 (s, 3H), 3.26 (d, J=12.0 Hz, 1H), 2.84 (d, J=9.5 Hz, 1H), 2.40 (dd, J=11.9, 3.8 Hz, 1H), 2.31-2.23 (m, 1H).

Example 115

Methyl 4-(bis(4-fluorophenyl)methyl)-1-(6-bromo-3-cyano-1-methyl-2-oxo-1,2-dihydro-1,5-naphthyridin-4-yl)piperazine-2-carboxylate

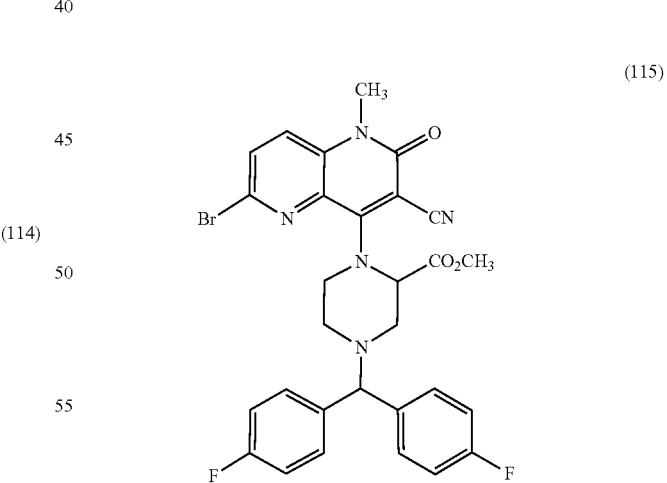

(115)

To a solution of methyl 4-(bis(4-fluorophenyl)methyl) piperazine-2-carboxylate, HCl (111 mg, 0.291 mmol) in acetonitrile (5 mL) was added DIPEA (0.085 mL, 0.485 mmol). The reaction mixture was heated at 80° C. for 30 minutes. Next, 6-bromo-3-cyano-1-methyl-2-oxo-1,2-dihydro-1,5-naphthyridin-4-yl trifluoromethanesulfonate (100 mg, 0.243 mmol) was added and heating was continued for 16 h. The reaction mixture was evaporated to dryness. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-55% B over 20 minutes, then a 5 minute hold at 100% B; Flow Rate: 15 mL/min; Column Temperature: 25° C. Fractions containing the product were combined and dried via centrifugal evaporation to afford methyl 4-(bis(4-fluorophenyl) methyl)-1-(6-bromo-3-cyano-1-methyl-2-oxo-1,2-dihydro-1,5-naphthyridin-4-yl) piperazine-2-carboxylate (4.6 mg, 3.1% yield); LCMS: m/z=610.2 (M+H); rt 2.344 min. Method: XBridge BEH XP C18 (50×2.1) mm, 2.5 µm, Mobile phase A: 95% water:5% acetonitrile; 10 mM ammonium acetate, Mobile phase B: 5% water:95% acetonitrile; 10 mM ammonium acetate, Flow: 1.1 mL/min. $^1$H NMR (400 MHz, DMSO-d6) δ ppm 7.95 (d, J=9.0 Hz, 1H), 7.88 (d, J=8.8 Hz, 1H), 7.51-7.39 (m, 4H), 7.17 (q, J=9.0 Hz, 4H), 5.40 (br. s., 1H), 4.50 (s, 1H), 4.08 (br. s., 1H), 3.89 (d, J=12.2 Hz, 1H), 3.81 (s, 3H), 3.53 (s, 3H), 3.25 (br. s., 1H), 2.82 (d, J=8.8 Hz, 1H), 2.41 (d, J=7.8 Hz, 1H), 2.24 (d, J=10.0 Hz, 1H).

Examples 116 and 117

Methyl 4-(bis(4-fluorophenyl)methyl)-1-(3,6-dicyano-1-methyl-2-oxo-1,2-dihydro-1,5-naphthyridin-4-yl)piperazine-2-carboxylate

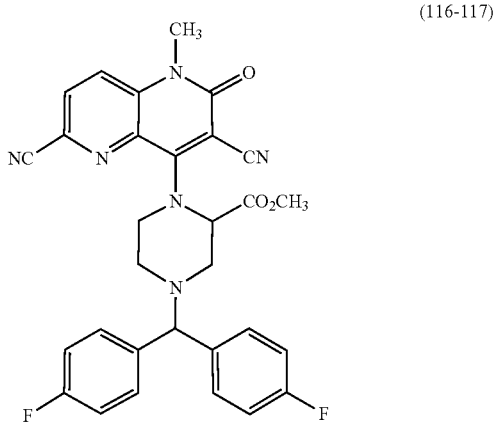 [SMILES: COC(=O)C1CN(C(c2ccc(F)cc2)c2ccc(F)cc2)CCN1c1c(C#N)c(=O)n(C)c2ccc(C#N)nc12]

(116-117)

To a solution of methyl 4-(bis(4-fluorophenyl)methyl)-1-(6-bromo-3-cyano-1-methyl-2-oxo-1,2-dihydro-1,5-naphthyridin-4-yl)piperazine-2-carboxylate (60 mg, 0.099 mmol) in NMP (1 mL) were added zinc (1.289 mg, 0.020 mmol), dppf (3.28 mg, 5.92 µmol) and zinc cyanide (23.16 mg, 0.197 mmol). The reaction mixture was degasified under N$_2$ and Pd$_2$(dba)$_3$ (9.03 mg, 9.86 µmol) was added under N$_2$. The reaction mass was irradiated under microwave to 80° C. for 2 h. The reaction mass was diluted with water and extracted twice with ethyl acetate (20 mL). The organic layer was separated, dried over Na$_2$SO$_4$ and evaporated to dryness. The crude material was purified via preparative HPLC (Column: X-Bridge Phenyl (250 mm×19 mm ID, 5 µm). Mobile phase A=10 mm ammonium acetate pH 4.5 Mobile phase B=acetonitrile, Flow 17 mL/min). Fractions containing the product were combined and evaporated to dryness to yield methyl 4-(bis(4-fluorophenyl) methyl)-1-(3,6-dicyano-1-methyl-2-oxo-1,2-dihydro-1,5-naphthyridin-4-yl)piperazine-2-carboxylate (40 mg, 69.5% yield; Enantiomeric mixture). Enantiomers were separated using chiral HPLC. Chiral separation (Column: Lux Cellulose-2 (250×4.6) mm; 5 µm, 0.2% NH$_4$OH in methanol+ acetonitrile (1:1) of Enantiomeric mixture yield Enantiomer 1; rt 5.52 min, and Enantiomer 2; rt 6.46 min.

Example 116: Enantiomer 1: (6.7 mg, 10.4% yield); LCMS: m/z=555.2 (M+H); rt 3.229 min; Method: Column-Kinetex XB-C18 (75×3 mm-2.6 µm), Mobile phase A: 10 mM NH$_4$COOH in water:acetonitrile (98:2), Mobile phase B: 10 mM NH$_4$COOH in water:acetonitrile (2:98). $^1$H NMR (400 MHz, DMSO-d$_6$) δ 8.29-8.21 (m, 1H), 8.20-8.11 (m, 1H), 7.46 (br. s., 4H), 7.18 (q, J=8.9 Hz, 4H), 5.36 (br. s., 1H), 4.51 (s, 1H), 4.24-4.01 (m, 1H), 3.82 (s, 3H), 3.55 (s, 3H), 2.90-2.77 (m, 1H), 2.07 (s, 4H).

Example 117: Enantiomer 2: (8.1 mg, 12.5% yield); LCMS: m/z=555.2 (M+H); rt 3.229 min; Method: Column-Kinetex XB-C18 (75×3 mm-2.6 µm), Mobile phase A: 10 mM NH$_4$COOH in water:acetonitrile (98:2), Mobile phase B: 10 mM NH$_4$COOH in water:acetonitrile (2:98). $^1$H NMR (400 MHz, DMSO-d$_6$) δ 8.30-8.20 (m, 1H), 8.19-8.10 (m, 1H), 7.53-7.38 (m, 4H), 7.18 (q, J=9.0 Hz, 4H), 5.36 (br. s., 1H), 4.51 (s, 1H), 4.19-4.05 (m, 1H), 3.86 (s, 3H), 3.56 (s, 3H), 2.84 (d, J=10.0 Hz, 1H), 2.41 (dd, J=3.8, 11.8 Hz, 1H), 2.31-2.21 (m, 1H), 2.03 (s, 2H).

Intermediate 77 tert-butyl 4-(bis(4-fluorophenyl)methyl)-2-(hydroxymethyl)piperazine-1-carboxylate

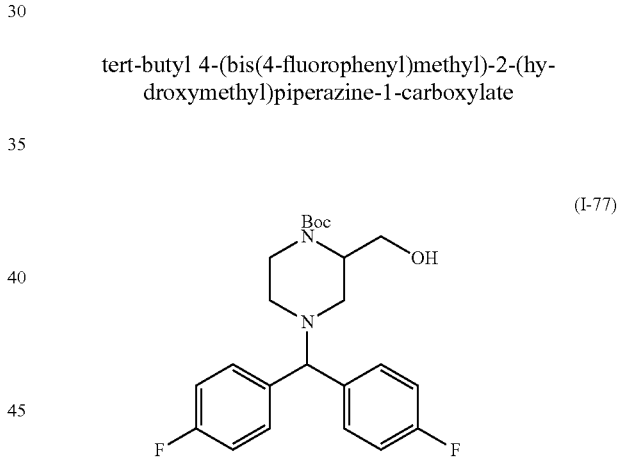

(I-77)

To a solution of 1-(tert-butyl) 2-methyl 4-(bis(4-fluorophenyl)methyl)piperazine-1,2-dicarboxylate (2.3 g, 5.15 mmol) in ethanol (25 mL) was added calcium chloride (2.86 g, 25.8 mmol) at room temperature. The reaction mixture was cooled to 0° C. and sodium borohydride (1.559 g, 41.2 mmol) was added. The reaction mass was stirred at room temperature for 16 h. The reaction mixture was evaporated to dryness. Water was added to the reaction mass. The reaction mass was extracted twice with ethyl acetate (50 mL). The organic layer was separated, dried over Na$_2$SO$_4$ and evaporated to dryness to yield tert-butyl 4-(bis(4-fluorophenyl)methyl)-2-(hydroxymethyl)piperazine-1-carboxylate (1.9 g, 70.5% yield) as an off-white solid; LCMS: m/z=419.4 (M+H); rt 2.05 min. Method: Column: AQUITY UPLC BEH C18 (3.0×50 mm) 1.7 µm, Mobile phase A: 10 mM ammonium acetate:acetonitrile (95:5) M. phase B: 10 mM ammonium acetate:acetonitrile (5:95), Flow: 0.7 mL/min.

Intermediate 78

(4-(bis(4-fluorophenyl)methyl)piperazin-2-yl)methanol

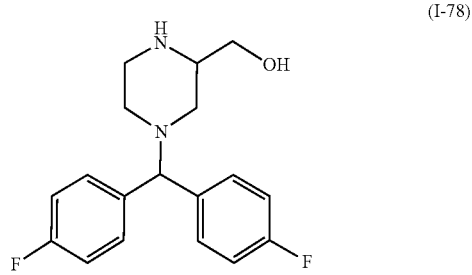 [SMILES: OCC1CN(C(c2ccc(F)cc2)c2ccc(F)cc2)CCN1]

(I-78)

To a solution of tert-butyl 4-(bis(4-fluorophenyl)methyl)-2-(hydroxymethyl) piperazine-1-carboxylate (70 mg, 0.167 mmol) in 1,4-dioxane (4 mL) was added HCl in dioxane (0.051 mL, 1.673 mmol). The reaction mixture was stirred at room temperature for 16 h. The reaction mixture was evaporated to dryness and washed with diethyl ether (10 mL) to yield (4-(bis(4-fluorophenyl)methyl)piperazin-2-yl)methanol, HCl (50 mg, 94% yield) as an off-white solid; LCMS: m/z=319.4 (M+H); rt 1.19 min. Method: Column: AQUITY UPLC BEH C18 (3.0×50 mm) 1.7 µm, Mobile phase A: 10 mM ammonium acetate:acetonitrile (95:5) M. phase B: 10 mM ammonium acetate:acetonitrile (5:95), Flow: 0.7 mL/min.

Example 118

4-(4-(bis(4-fluorophenyl)methyl)-2-(hydroxymethyl)piperazin-1-yl)-6-bromo-1-methyl-2-oxo-1,2-dihydro-1,5-naphthyridine-3-carbonitrile

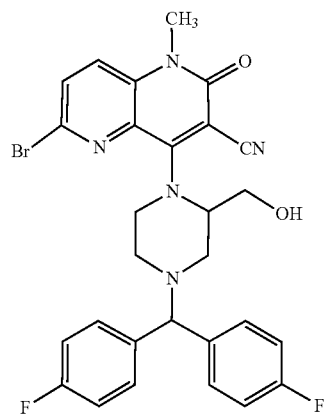

(118)

To a solution of (4-(bis(4-fluorophenyl)methyl)piperazin-2-yl) methanol, HCl (103 mg, 0.291 mmol) in acetonitrile (5 mL) was added DIPEA (0.085 mL, 0.485 mmol). The reaction mixture was heated at 80° C. for 30 minutes. Next, 6-bromo-3-cyano-1-methyl-2-oxo-1,2-dihydro-1,5-naphthyridin-4-yl trifluoromethanesulfonate (100 mg, 0.243 mmol) was added and heating of the reaction mass continued for 16 h. The reaction mass was evaporated to dryness. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 30% B, 30-65% B over 20 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 4-(4-(bis(4-fluorophenyl)methyl)-2-(hydroxymethyl)piperazin-1-yl)-6-bromo-1-methyl-2-oxo-1,2-dihydro-1,5-naphthyridine-3-carbonitrile (2.2 mg, 1.5% yield); LCMS: m/z=580.2 (M+H); rt 2.217 min. Method: XBridge BEH XP C18 (50×2.1) mm, 2.5 µm, Mobile phase A: 95% water:5% acetonitrile; 10 mM ammonium acetate, Mobile phase B: 5% water:95% acetonitrile; 10 mM ammonium acetate, Flow: 1.1 mL/min. $^1$H NMR (400 MHz, DMSO-d$_6$) δ ppm 7.93-7.97 (m, 1H), 7.86-7.90 (m, 1H), 7.48-7.56 (m, 4H), 7.13-7.20 (m, 4H), 4.80-4.92 (m, 1H), 4.59-4.69 (m, 1H), 4.43 (s, 1H), 3.97-4.13 (m, 2H), 3.61-3.68 (m, 1H), 3.49-3.55 (m, 4H), 2.80-2.91 (m, 2H), 2.43-2.46 (m, 1H), 2.01-2.10 (m, 1H).

Example 119

8-((2R,5S)-4-((4-fluoro-2-methoxyphenyl)(4-fluorophenyl)methyl)-2,5-dimethylpiperazin-1-yl)-5-methyl-6-oxo-5,6-dihydro-1,5-naphthyridine-2-carbonitrile

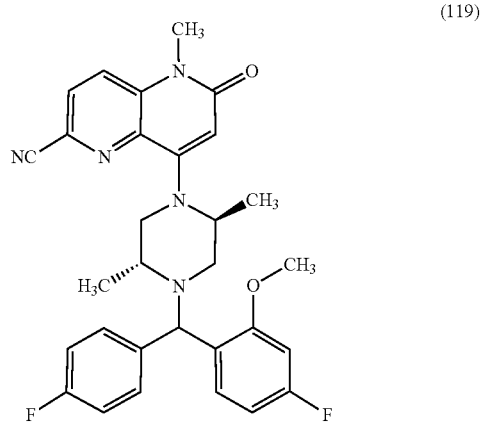 [SMILES: COc1cc(F)ccc1C(c1ccc(F)cc1)N1C[C@H](C)N(c2cc(=O)n(C)c3ccc(C#N)nc23)C[C@H]1C]

(119)

To a solution of (2S,5R)-1-((4-fluoro-2-methoxyphenyl)(4-fluorophenyl)methyl)-2,5-dimethylpiperazine, HCl (100 mg, 0.261 mmol) in acetonitrile (5 mL) were added DIPEA (0.137 mL, 0.784 mmol) and 6-cyano-1-methyl-2-oxo-1,2-dihydro-1,5-naphthyridin-4-yl trifluoromethanesulfonate (104 mg, 0.313 mmol). The reaction mass was heated to 80° C. for 16 h and evaporated to dryness. The crude material was purified via preparative HPLC (Column: Xbridge Phenyl (250 mm×19 mm ID, 5 µm). Mobile phase A=10 mM ammonium bicarbonate pH 9.5 in H$_2$O, Mobile phase B=acetonitrile, Flow 19 mL/min). Fractions containing the product were combined and dried via centrifugal evaporation to yield the product as diastereomeric mixture. Enantiomers were separated using chiral HPLC. Chiral separation (Chiralpak IG (250×4.6) mm; 5, 10 mM Ammonium Acetate in ethanol) of diastereomeric mixture gave Diastereomer 1 (homochiral); rt 6.8 min, and Diastereomer 2 (homochiral); rt 7.52 min.

Example 119: Diastereomer 1: (8.0 mg, 5.7% yield); LCMS: m/z=530.3 (M+H); rt 1.573 min; Method: XBridge BEH XP C18 (50×2.1) mm, 2.5 μm, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.15 (d, J=8.5 Hz, 1H), 8.04-8.09 (m, 1H), 7.71-7.78 (m, 1H), 7.52 (dd, J=8.8, 5.8 Hz, 2H), 7.14 (t, J=8.8 Hz, 2H), 6.78-6.85 (m, 2H), 6.00 (s, 1H), 4.99 (s, 1H), 4.53-4.64 (m, 1H), 3.80 (s, 3H), 3.67-3.74 (m, 1H), 3.50-3.56 (m, 4H), 2.98-3.06 (m, 1H), 2.79-2.87 (m, 1H), 2.37-2.43 (m, 1H), 1.31 (d, J=6.5 Hz, 3H), 1.04 (d, J=6.5 Hz, 3H).

Example 120

8-((2R,5S)-4-((4-fluoro-2-methoxyphenyl)(4-fluorophenyl)methyl)-2,5-dimethylpiperazin-1-yl)-5-methyl-7-nitro-6-oxo-5,6-dihydro-1,5-naphthyridine-2-carbonitrile

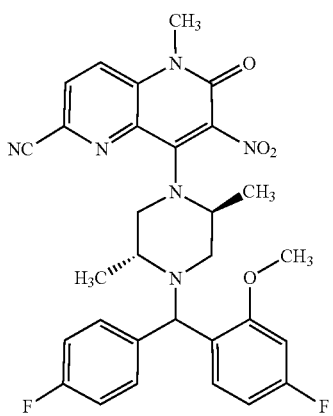

(120)

To a solution of (2S,5R)-1-((4-fluoro-2-methoxyphenyl)(4-fluorophenyl)methyl)-2,5-dimethylpiperazine, HCl (40 mg, 0.104 mmol) in acetonitrile (5 mL) were added DIPEA (0.055 mL, 0.313 mmol) and 6-cyano-1-methyl-3-nitro-2-oxo-1,2-dihydro-1,5-naphthyridin-4-yl trifluoromethanesulfonate (47.4 mg, 0.125 mmol). The reaction mass was heated to 80° C. for 16 h and evaporated to dryness. The crude material was purified via preparative HPLC (Column: DAD-1: Cellulose-2 (250×4.6 mm), 5 micron DAD-2: CELLULOSE-4 (250×4.6 mm), 5 μm, MOBILE PHASE: 0.1% DEA in methanol FLOW: 2.0 mL\min). Fractions containing the product were combined and evaporated to dryness to yield 8-((2R,5S)-4-((4-fluoro-2-methoxyphenyl)(4-fluorophenyl)methyl)-2,5-dimethylpiperazin-1-yl)-5-methyl-7-nitro-6-oxo-5,6-dihydro-1,5-naphthyridine-2-carbonitrile (15.4 mg, 25.7% yield); LCMS: m/z=575.3 (M+H); rt 1.661 and 1.776 min; Method: XBridge BEH XP C18 (50×2.1) mm, 2.5 μm, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.28 (d, J=8.8 Hz, 1H), 8.21 (d, J=9.0 Hz, 1H), 7.78-7.59 (m, 1H), 7.51 (ddd, J=8.7, 5.6, 3.1 Hz, 2H), 7.12 (td, J=8.9, 2.4 Hz, 2H), 6.91-6.72 (m, 2H), 5.09 (s, 1H), 4.65 (br. s., 1H), 3.83 (d, J=9.0 Hz, 3H), 3.75 (d, J=10.5 Hz, 1H), 3.58 (s, 3H), 3.15-2.98 (m, 2H), 2.64 (t, J=12.3 Hz, 1H), 2.30 (d, J=11.7 Hz, 1H), 1.36 (dd, J=13.6, 6.7 Hz, 3H), 0.90 (t, J=6.6 Hz, 3H).

Examples 121 and 122

8-((2S,5R)-4-((4-fluoro-2-methoxyphenyl)(4-fluorophenyl)methyl)-2,5-dimethylpiperazin-1-yl)-5-methyl-7-nitro-6-oxo-5,6-dihydro-1,5-naphthyridine-2-carbonitrile

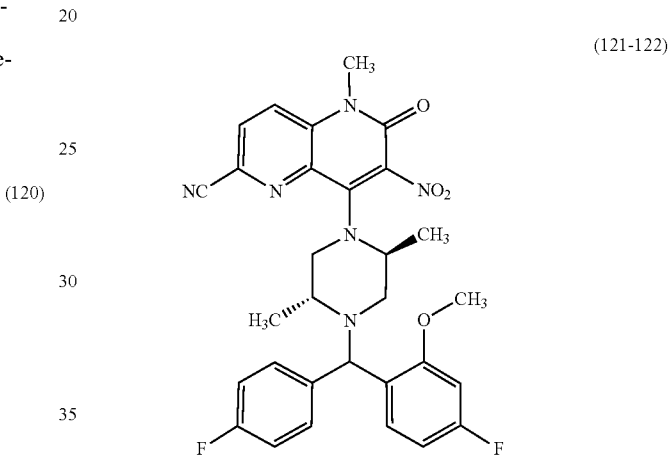

(121-122)

To a solution of (2R,5S)-1-((4-fluoro-2-methoxyphenyl)(4-fluorophenyl)methyl)-2,5-dimethylpiperazine, HCl (40 mg, 0.104 mmol) in acetonitrile (5 mL) were added DIPEA (0.055 mL, 0.313 mmol) and 6-cyano-1-methyl-3-nitro-2-oxo-1,2-dihydro-1,5-naphthyridin-4-yl trifluoromethanesulfonate (47.4 mg, 0.125 mmol). The reaction mass was heated to 80° C. for 16 h and evaporated to dryness. The crude material was purified via preparative HPLC with the following conditions: Column: Sunfire C18, 19×150 mm, 5 μm particles; Mobile Phase A: 10 mM ammonium acetate pH-4.5 with acetic acid; Mobile Phase B: acetonitrile; Gradient: 60-100% B over 20 minutes, then a 5 minute hold at 100% B; Flow: 19 mL/min. Fractions containing the product were combined and dried via centrifugal evaporation to yield the diastereomeric mixture. Enantiomers were separated using chiral HPLC. Chiral separation (Column: DAD-1 CELLULOSE-2 (250×4.6 mm), 5 micron, DAD-2 CELLULOSE-4 (250×4.6 mm), 5 micron, Mobile Phase: 0.1% DEA in (acetonitrile:methanol)::70:30 FLOW:2.0 mL\min) of diastereomeric mixture gave Diastereomer 1 (homochiral); rt 5.217 min, and Diastereomer 2 (homochiral); rt 5.642 min.

Example 121: Diastereomer 1: (1.2 mg, 2.0% yield); LCMS: m/z=575.3 (M+H); rt 1.662 min; Method: XBridge BEH XP C18 (50×2.1) mm, 2.5 µm, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.28 (d, J=9.0 Hz, 1H), 8.21 (d, J=8.8 Hz, 1H), 7.72 (dd, J=8.6, 7.1 Hz, 1H), 7.58-7.45 (m, 2H), 7.11 (t, J=8.9 Hz, 2H), 6.89-6.73 (m, 2H), 5.01 (s, 1H), 4.65 (br. s., 1H), 3.82 (s, 3H), 3.75 (dd, J=11.9, 2.8 Hz, 1H), 3.58 (s, 3H), 3.09 (dd, J=11.7, 3.9 Hz, 1H), 2.91 (d, J=6.6 Hz, 1H), 2.62 (d, J=11.5 Hz, 1H), 2.39 (d, J=11.0 Hz, 1H), 1.37 (d, J=6.8 Hz, 3H), 0.91 (d, J=6.4 Hz, 3H).

Example 122: Diastereomer 2: (3.6 mg, 6.0% yield); LCMS: m/z=575.3 (M+H); rt 1.774 min; Method: XBridge BEH XP C18 (50×2.1) mm, 2.5 µm, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.29 (d, J=9.0 Hz, 1H), 8.21 (d, J=9.0 Hz, 1H), 7.66 (dd, J=8.6, 7.1 Hz, 1H), 7.51 (dd, J=8.8, 5.6 Hz, 2H), 7.12 (t, J=8.9 Hz, 2H), 6.87 (dd, J=11.5, 2.4 Hz, 1H), 6.79 (td, J=8.4, 2.7 Hz, 1H), 5.09 (s, 1H), 4.65 (br. s., 1H), 3.84 (s, 3H), 3.74 (dd, J=12.1, 3.3 Hz, 1H), 3.59 (s, 3H), 3.10-2.98 (m, 2H), 2.69-2.61 (m, 1H), 2.29 (d, J=13.0 Hz, 1H), 1.34 (d, J=6.6 Hz, 3H), 0.89 (d, J=6.6 Hz, 3H).

Intermediate 79

1-(bis(4-fluorophenyl)methyl)-2,3-dimethylpiperazine

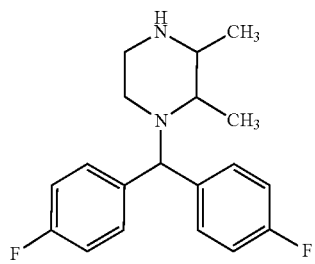

(I-79)

To a solution of 4,4'-(chloromethylene)bis(fluorobenzene) (200 mg, 0.838 mmol) in acetonitrile (5 mL) were added 2,3-dimethylpiperazine (115 mg, 1.006 mmol) and DIPEA (0.439 mL, 2.51 mmol). The reaction mass was heated to 80° C. for 4 h. The reaction mass was diluted with water and extracted twice with ethyl acetate (20 mL). The organic layer was separated, dried over $Na_2SO_4$ and evaporated to dryness (250 mg, 59.4% yield); LCMS: m/z=317.4 (M+H); rt 1.41 min. Method: Column: AQUITY UPLC BEH C18 (3.0×50 mm) 1.7 µm, Mobile phase A: 10 mM ammonium acetate:acetonitrile (95:5) Mobile phase B: 10 mM ammonium acetate:acetonitrile (5:95), Flow: 0.7 mL/min.

Examples 123 and 124

8-(4-(bis(4-fluorophenyl)methyl)-2,3-dimethylpiperazin-1-yl)-5-methyl-6-oxo-5,6-dihydro-1,5-naphthyridine-2-carbonitrile

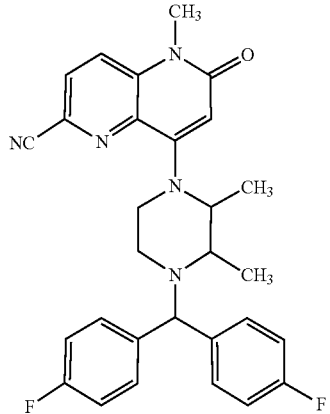

(123-124)

To a solution of 1-(bis(4-fluorophenyl)methyl)-2,3-dimethylpiperazine (200 mg, 0.567 mmol) in acetonitrile (10 mL) were added DIPEA (0.297 mL, 1.700 mmol) and 6-cyano-1-methyl-2-oxo-1,2-dihydro-1,5-naphthyridin-4-yl trifluoromethanesulfonate (227 mg, 0.680 mmol). The reaction mass was heated to 80° C. for 16 h and evaporated to dryness. The crude material was purified via preparative HPLC (Column-Kinetex XB-C18 (75×3 mm-2.6 µm) Mobile phase A: 10 mM ammonium formate in water:acetonitrile (98:2), Mobile phase B: 10 mM ammonium formate in water:acetonitrile (2:98). Fractions containing the product were combined and evaporated to dryness to yield a diastereomeric mixture. Enantiomers were separated using chiral HPLC. Chiral separation (Column: DAD-1: CELLULOSE-2 (250×4.6 mm), 5 micron, DAD-2: CELLULOSE-4 (250×4.6 mm), 5 micron, Mobile Phase: 0.1% DEA in (acetonitrile:methanol) 90:10 FLOW: 2.0 mL\min) of diastereomeric mixture gave Diastereomer 1 (homochiral); rt 6.754 min, and Diastereomer 2 (homochiral); rt 8.197 min.

Example 123: Diastereomer 1: (3.5 mg, 1.2% yield); LCMS: m/z=500.3 (M+H); rt 1.831 min; Method: XBridge BEH XP C18 (50×2.1) mm, 2.5 µm, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.14 (d, J=8.8 Hz, 1H), 8.04-8.10 (m, 1H), 7.59-7.65 (m, 2H), 7.52-7.57 (m, 2H), 7.12-7.18 (m, 4H), 6.03 (s, 1H), 4.70-4.78 (m, 2H), 3.53 (s, 3H), 3.35-3.45 (m, 1H), 3.19-3.26 (m, 1H), 2.80-2.87 (m, 1H), 2.63-2.72 (m, 1H), 2.54-2.57 (m, 1H), 1.28 (d, J=6.8 Hz, 3H), 1.19 (d, J=6.6 Hz, 3H).

Example 124: Diastereomer 2: (3.5 mg, 1.2% yield); LCMS: m/z=500.3 (M+H); rt 1.830 min; Method: XBridge BEH XP C18 (50×2.1) mm, 2.5 µm, Mobile phase A: 95% water:5% acetonitrile; 0.1% TFA, Mobile phase B: 5% water:95% acetonitrile; 0.1% TFA, Flow: 1.1 mL/min. $^1$H NMR (400 MHz, DMSO-$d_6$) δ ppm 8.14 (d, J=8.6 Hz, 1H), 8.06 (d, J=8.8 Hz, 1H), 7.62 (dd, J=8.7, 5.7 Hz, 2H), 7.55 (dd, J=8.6, 5.6 Hz, 2H), 7.15 (td, J=8.7, 6.5 Hz, 4H), 6.03 (s, 1H), 4.80-4.67 (m, 2H), 3.53 (s, 3H), 3.43-3.34 (m, 1H), 3.24-3.17 (m, 1H), 2.83 (d, J=5.1 Hz, 1H), 2.71-2.65 (m, 1H), 2.55 (br. s., 1H), 1.28 (d, J=6.6 Hz, 3H), 1.19 (d, J=6.4 Hz, 3H).

Intermediate 80

L-valyl-L-alanine

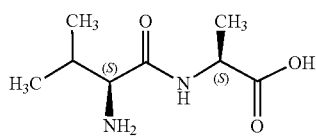
(I-80)

To a solution of ((benzyloxy)carbonyl)-L-valyl-L-alanine (1 g, 3.10 mmol) in methanol (20 mL) was added Pd—C (0.330 g, 0.310 mmol) under N$_2$. The reaction mixture was stirred under hydrogen pressure for 16 h. The reaction mixture was filtered through a celite bed. The bed was washed with methanol (40 mL). The clear filtrate was collected and evaporated to dryness to yield L-valyl-L-alanine (3.5 mg, 1.2% yield) as a white solid. LCMS: m/z=189.2 (M+H); rt 0.17 min; Column-Kinetex XB-C18 (75×3 mm-2.6 µm), Mobile phase A: 10 mM ammonium formate in water:acetonitrile (98:2), Mobile phase B: 10 mM ammonium formate in water:acetonitrile (2:98).

Intermediate 81

(3S,6S)-3-isopropyl-6-methylpiperazine-2,5-dione

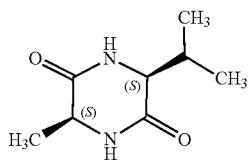
(I-81)

L-valyl-L-alanine (260 mg, 1.381 mmol) was taken in a 5 mL vial and heated to 200° C. for 30 minutes. The solid collected on the side walls of the vial to yield the (3S,6S)-3-isopropyl-6-methylpiperazine-2,5-dione (235 mg, 99% yield) as an off-white solid. LCMS: m/z=171.2 (M+H); rt 0.22 min; Column-Kinetex XB-C18 (75×3 mm-2.6 m), Mobile phase A: 10 mM ammonium formate in water:acetonitrile (98:2), Mobile phase B: 10 mM ammonium formate in water:acetonitrile (2:98).

Intermediate 82

(2S,5S)-2-isopropyl-5-methylpiperazine

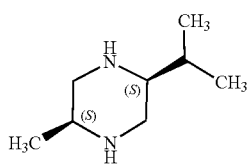
(I-82)

To a solution of (3S,6S)-3-isopropyl-6-methylpiperazine-2,5-dione (250 mg, 1.469 mmol) in tetrahydrofuran (5 mL) was added borane tetrahydrofuran complex (5.88 mL, 5.88 mmol) at 0° C. The reaction mass was heated to 70° C. for 16 h. The reaction was quenched with methanol. The reaction mass was stirred for 30 min. and evaporated to dryness to yield (2S,5S)-2-isopropyl-5-methylpiperazine (220 mg, 96% yield) as a colorless liquid; LCMS: m/z=143.2 (M+H); rt 0.45 min; Column-Kinetex XB-C18 (75×3 mm-2.6 µm), Mobile phase A: 10 mM ammonium formate in water:acetonitrile (98:2), Mobile phase B: 10 mM ammonium formate in water:acetonitrile (2:98).

Intermediate 83

(2S,5S)-1-(bis(4-fluorophenyl)methyl)-5-isopropyl-2-methylpiperazine

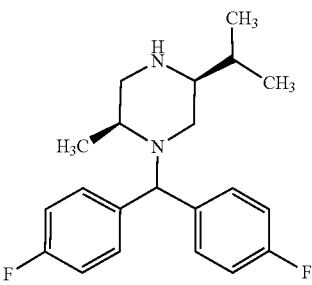
(I-83)

To a solution of (2S,5S)-2-isopropyl-5-methylpiperazine (100 mg, 0.703 mmol), 4,4'-(chloromethylene)bis(fluorobenzene) (0.131 mL, 0.703 mmol) in acetonitrile (2 mL) was added DIPEA (0.246 mL, 1.406 mmol). The reaction mixture was heated to 80° C. for 2 h. The reaction mixture was diluted with water and extracted twice with ethyl acetate (20 mL). The organic layer was separated, dried over Na$_2$SO$_4$ and evaporated to dryness. The crude material was purified by ISCO® (Column: 24 g RediSep silica, Solvent run: 0-20% methanol in chloroform). The product was eluted at 5% methanol in chloroform to afford (2S,5S)-1-(bis(4-fluorophenyl)methyl)-5-isopropyl-2-methylpiperazine (80 mg, 21.47% yield) as a brown liquid; LCMS: m/z=345.2 (M+H); rt 1.60 min; Column-Luna 3.0 C18(2) 100 Å LC column (20×4.0 mm) Mercury MS TM, Mobile phase A: 10 mM ammonium formate in water:acetonitrile (98:2), Mobile phase B: 10 mM ammonium formate in water:acetonitrile (2:98).

Example 125

8-((2S,5S)-4-(bis(4-fluorophenyl)methyl)-2-isopropyl-5-methylpiperazin-1-yl)-5-methyl-6-oxo-5,6-dihydro-1,5-naphthyridine-2-carbonitrile

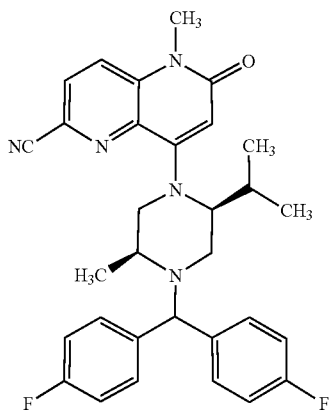

(125)

To a solution of (2S,5S)-1-(bis(4-fluorophenyl)methyl)-5-isopropyl-2-methylpiperazine (27 mg, 0.078 mmol), 6-cyano-1-methyl-2-oxo-1,2-dihydro-1,5-naphthyridin-4-yl trifluoromethanesulfonate (20.90 mg, 0.063 mmol) in acetonitrile (2 mL) was added DIPEA (0.041 mL, 0.235 mmol). The reaction mixture was heated to 80° C. for 2 h and evaporated to dryness. The crude material was purified via preparative HPLC (Column: X-Bridge Phenyl (250 mm×19 mm ID, 5 μm), Mobile phase A: Buffer: 10 mM ammonium acetate in water pH-4.5, Mobile phase B: acetonitrile, Flow: 17 mL/min). Fractions containing the product were combined and evaporated to dryness to yield 8-((2S,5S)-4-(bis(4-fluorophenyl)methyl)-2-isopropyl-5-methylpiperazin-1-yl)-5-methyl-6-oxo-5,6-dihydro-1,5-naphthyridine-2-carbonitrile (1 mg, 2.4% yield); LCMS: m/z=528.3 (M+H); rt 2.517 min. Method: XBridge BEH XP C18 (50×2.1) mm, 2.5 μm, Mobile phase A: 95% water:5% acetonitrile; 10 mM ammonium acetate, Mobile phase B: 5% water:95% acetonitrile; 10 mM ammonium acetate, Flow: 1.1 mL/min. $^1$H NMR (400 MHz, DMSO-$d_6$) δ ppm 8.16 (d, J=9.0 Hz, 1H), 8.08 (d, J=9.0 Hz, 1H), 7.40 (dd, J=8.8, 5.8 Hz, 2H), 7.30 (dd, J=8.5, 5.5 Hz, 2H), 7.22-6.97 (m, 4H), 6.02 (s, 1H), 5.32 (s, 1H), 4.16 (br. s., 1H), 3.89 (br. s., 1H), 3.60-3.50 (m, 3H), 3.21 (dd, J=13.3, 9.8 Hz, 1H), 2.72 (dd, J=13.3, 6.8 Hz, 1H), 2.42-2.35 (m, 1H), 1.24 (s, 1H), 1.19-1.06 (m, 3H), 1.03-0.86 (m, 6H). One proton peak merged with residual solvent peak.

Intermediate 84 tert-butyl 3-(2-acetylhydrazine-1-carbonyl)-4-(bis(4-fluorophenyl)methyl)piperazine-1-carboxylate

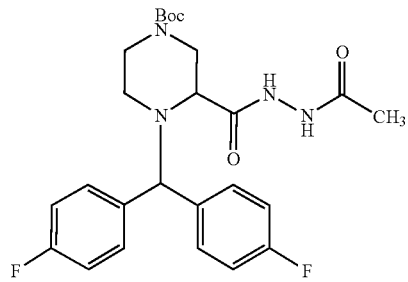

(I-84)

To a solution of 1-(bis(4-fluorophenyl)methyl)-4-(tert-butoxycarbonyl)piperazine-2-carboxylic acid (450 mg, 1.041 mmol) in DMF (2 mL) were added HATU (791 mg, 2.081 mmol) and DIPEA (0.363 mL, 2.081 mmol). The reaction mixture was stirred for 10 minutes, acetohydrazide (116 mg, 1.561 mmol) was added, and stirring was continued for 16 h. Cold water was added to the reaction mixture, and the solids were separated, filtered and washed with water. The solids were washed with diethylether (20 mL) and evaporated under high vacuum to yield tert-butyl 3-(2-acetylhydrazine-1-carbonyl)-4-(bis(4-fluorophenyl)methyl)piperazine-1-carboxylate (300 mg, 49.6% yield); LCMS: m/z=489.2 (M+H); rt 2.782 min; Method: Column-Kinetex XB-C18 (75×3 mm-2.6 μm), Mobile phase A: 10 mM ammonium formate in water:acetonitrile (98:2); Mobile phase B: 10 mM ammonium formate in water:acetonitrile (2:98).

Intermediate 85 tert-butyl 4-(bis(4-fluorophenyl)methyl)-3-(5-methyl-1,3,4-oxadiazol-2-yl)piperazine-1-carboxylate

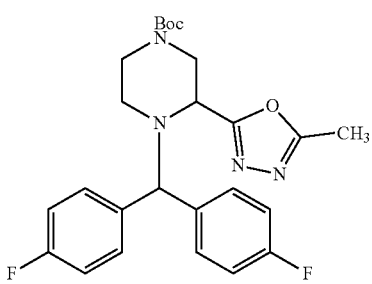

(I-85)

To a solution of tert-butyl 3-(2-acetylhydrazine-1-carbonyl)-4-(bis(4-fluorophenyl)methyl)piperazine-1-carboxylate (350 mg, 0.716 mmol) in tetrahydrofuran (2 mL) was added Burgess reagent (512 mg, 2.149 mmol). The reaction mixture was heated to 80° C. for 16 h. LCMS showed 24% starting material and 37% product. Another lot of Burgess reagent (512 mg, 2.149 mmol) was added and heating was continued for another 16 h. The reaction mass was heated to dryness. The crude material was purified by ISCO® (Column: 40 g RediSep silica, Solvent run: 0-50% EtOAc in petroleum ether). The product was eluted at 45% EtOAc in petroleum ether to afford tert-butyl 4-(bis(4-fluorophenyl)methyl)-3-(5-methyl-1,3,4-oxadiazol-2-yl)piperazine-1-carboxylate (250 mg, 70.5% yield); LCMS: m/z=471.2 (M+H); rt 2.084 min; Column-Luna 3.0 C18(2) 100 Å LC column (20×4.0 mm) Mercury MS TM, Mobile phase A: 0.1% TFA in Milli-Q water, Mobile phase B: 0.1% TFA in acetonitrile.

Intermediate 86

2-(1-(bis(4-fluorophenyl)methyl)piperazin-2-yl)-5-methyl-1,2,4-oxadiazole

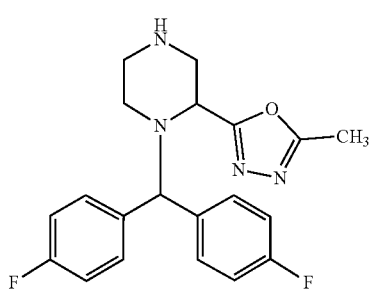

(I-86)

To a solution of tert-butyl 4-(bis(4-fluorophenyl)methyl)-3-(5-methyl-1,3,4-oxadiazol-2-yl)piperazine-1-carboxylate (230 mg, 0.489 mmol) in dichloromethane (5 mL) was added TFA (0.377 mL, 4.89 mmol). The reaction mixture was stirred at room temperature for 16 h. and evaporated to dryness. Method: AQUITY UPLC BEH C18 (3.0×50 mm) 1.7 μm, Mobile phase A: 10 mM ammonium acetate:acetonitrile (95:5) Mobile phase B: 10 mM ammonium acetate:acetonitrile (5:95), Flow: 0.7 mL/min.

Example 126

8-(4-(bis(4-fluorophenyl)methyl)-3-(5-methyl-1,3,4-oxadiazol-2-yl)piperazin-1-yl)-5-methyl-6-oxo-5,6-dihydro-1,5-naphthyridine-2-carbonitrile

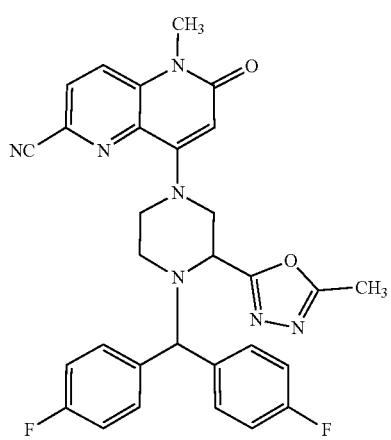

(126)

To a solution of 2-(1-(bis(4-fluorophenyl)methyl)piperazin-2-yl)-5-methyl-1,3,4-oxadiazole (50 mg, 0.135 mmol) and 6-cyano-1-methyl-2-oxo-1,2-dihydro-1,5-naphthyridin-4-yl trifluoromethanesulfonate (36.0 mg, 0.108 mmol) in acetonitrile (4 mL) was added DIPEA (0.071 mL, 0.405 mmol). The reaction mixture was heated to 80° C. for 2 h. and evaporated to dryness. The crude material was purified via preparative HPLC (Column: Xbridge Phenyl (250 mm×19 mm ID, 5 μm) Mobile phase A=10 mM ammonium acetate in water Mobile phase B: acetonitrile:MeOH Flow 17 mL/min). Fractions containing the product were combined and evaporated to dryness to yield 8-(4-(bis(4-fluorophenyl)methyl)-3-(5-methyl-1,3,4-oxadiazol-2-yl)piperazin-1-yl)-5-methyl-6-oxo-5,6-dihydro-1,5-naphthyridine-2-carbonitrile (7.1 mg, 9.14% yield); LCMS: m/z 554.3 (M+H); rt 2.178 min. Method: XBridge BEH XP C18 (50×2.1) mm, 2.5 μm, Mobile phase A: 95% water:5% acetonitrile: 0.1% TFA, Mobile phase B: 5% water:95% acetonitrile; 0.1% TFA, Flow: 1.1 mL/min. $^1$H NMR (400 MHz, METHANOL-d4) δ ppm 8.08-8.14 (m, 1H), 8.06 (s, 1H), 7.54-7.59 (m, 2H), 7.25-7.29 (m, 2H), 7.09-7.19 (m, 4H), 6.12 (s, 1H), 5.01 (s, 1H), 4.71-4.77 (m, 1H), 4.14-4.18 (m, 1H), 3.61-3.68 (m, 1H), 3.51 (s, 3H), 3.34-3.39 (m, 2H), 3.15-3.23 (m, 1H), 2.69-2.75 (m, 1H), 2.43 (s, 3H).

Intermediate 87 tert-butyl (S)-4-(6-cyano-1-methyl-2-oxo-1,2-dihydro-1,5-naphthyridin-4-yl)-3-ethylpiperazine-1-carboxylate

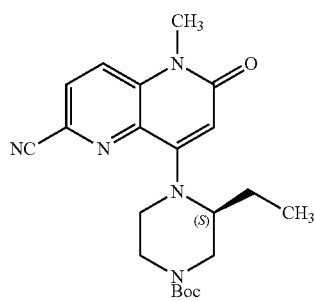

(I-87)

To a solution of tert-butyl (S)-3-ethylpiperazine-1-carboxylate (150 mg, 0.700 mmol), 6-cyano-1-methyl-2-oxo-1,2-dihydro-1,5-naphthyridin-4-yl trifluoromethanesulfonate (187 mg, 0.560 mmol) in acetonitrile (2 mL) was added DIPEA (0.244 mL, 1.400 mmol). The reaction mixture was heated to 80° C. for 2 h. The reaction mixture was diluted with water and extracted twice with ethyl acetate (20 mL). The organic layer was separated, dried over Na$_2$SO$_4$ and evaporated to dryness. The crude material was purified by ISCO® (Column: 24 g RediSep silica, Solvent run: 0-50% EtOAc in petroleum ether). The product was eluted at 30% EtOAc in petroleum ether to afford tert-butyl (S)-4-(6-cyano-1-methyl-2-oxo-1,2-dihydro-1,5-naphthyridin-4-yl)-3-ethylpiperazine-1-carboxylate (55 mg, 0.082 mmol, 11.66% yield); LCMS: m/z=398.4 (M+H); rt 1.63 min. Method: AQUITY UPLC BEH C18 (3.0×50 mm) 1.7 μm, Mobile phase A: 10 mM ammonium acetate:acetonitrile (95:5) Mobile phase B: 10 mM ammonium acetate:acetonitrile (5:95), Flow: 0.7 mL/min.

Intermediate 88

(S)-8-(2-ethylpiperazin-1-yl)-5-methyl-6-oxo-5,6-dihydro-1,5-naphthyridine-2-carbonitrile

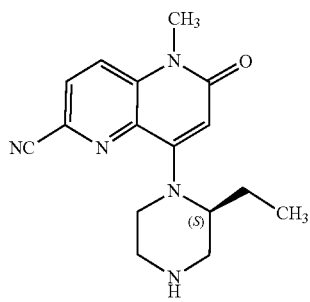

(I-88)

To a solution of tert-butyl (S)-4-(6-cyano-1-methyl-2-oxo-1,2-dihydro-1,5-naphthyridin-4-yl)-3-ethylpiperazine-1-carboxylate (50 mg, 0.126 mmol) in dichloromethane (5 mL) was added TFA (0.097 mL, 1.258 mmol) at room temperature. The reaction mixture was stirred at room temperature for 2 h. and evaporated to dryness. The semi-solid was washed with diethyl ether to yield (S)-8-(2-ethylpiperazin-1-yl)-5-methyl-6-oxo-5,6-dihydro-1,5-naphthyridine-2-carbonitrile, TFA (38 mg, 68% yield) as a solid; LCMS: m/z=298.4 (M+H); rt 0.65 min. Method: AQUITY UPLC BEH C18 (3.0×50 mm) 1.7 µm, Mobile phase A: 10 mM ammonium acetate:acetonitrile (95:5) Mobile phase B: 10 mM ammonium acetate:acetonitrile (5:95), Flow: 0.7 mL/min.

Example 127

(S)-8-(4-(bis(4-fluorophenyl)methyl)-2-ethylpiperazin-1-yl)-5-methyl-6-oxo-5,6-dihydro-1,5-naphthyridine-2-carbonitrile

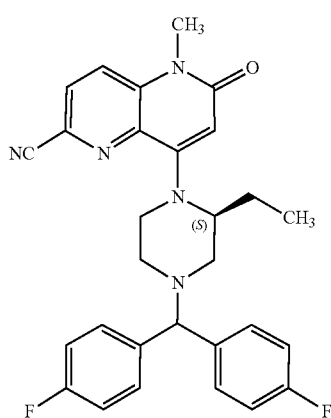

(127)

To a solution of (S)-1-(bis(4-fluorophenyl)methyl)-2-ethylpiperazine (75 mg, 0.213 mmol) TFA salt and 6-cyano-1-methyl-2-oxo-1,2-dihydro-1,5-naphthyridin-4-yl trifluoromethanesulfonate (56.7 mg, 0.170 mmol) in acetonitrile (2 mL) was added DIPEA (0.074 mL, 0.425 mmol). The reaction mixture was heated to 80° C. for 2 h. and evaporated to dryness. The crude material was purified via preparative HPLC (Column: SUNFIRE C18 (150 mm×19 mm ID, 5 µm). Mobile phase A=Buffer: 10 mM ammonium acetate in water Mobile phase B=acetonitrile Flow: 17 mL/min). Fractions containing the product were combined and evaporated to dryness to yield (S)-8-(4-(bis(4-fluorophenyl)methyl)-3-ethylpiperazin-1-yl)-5-methyl-6-oxo-5,6-dihydro-1,5-naphthyridine-2-carbonitrile (5 mg, 3.3% yield); LCMS: m/z=500.3 (M+H); rt 2.92 min; Method: XBridge BEH XP C18 (50×2.1) mm, 2.5 µm, Mobile phase A: 95% water:5% acetonitrile; 10 mM ammonium acetate, Mobile phase B: 5% water:95% acetonitrile; 10 mM ammonium acetate, Flow: 1.1 mL/min. $^1$H NMR (400 MHz, DMSO-d6) δ ppm 8.12-8.16 (m, 1H), 8.05-8.08 (m, 1H), 7.44-7.59 (m, 4H), 7.11-7.23 (m, 4H), 6.03 (s, 1H), 4.57-4.70 (m, 1H), 4.40 (s, 1H), 3.53 (s, 3H), 3.34-3.49 (m, 2H), 2.70-2.82 (m, 2H), 2.25 (dd, J=11.5, 2.9 Hz, 1H), 1.99-2.18 (m, 2H), 1.62-1.77 (m, 1H), 0.67 (t, J=7.5 Hz, 3H).

Intermediate 89 tert-butyl (S)-4-(bis(4-fluorophenyl)methyl)-3-ethylpiperazine-1-carboxylate

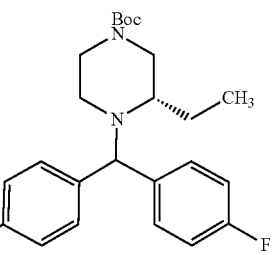

(I-89)

To a solution of tert-butyl (S)-3-ethylpiperazine-1-carboxylate (150 mg, 0.700 mmol) and 4,4'-(chloromethylene)bis(fluorobenzene) (0.131 mL, 0.700 mmol) in acetonitrile (2 mL) was added DIPEA (0.244 mL, 1.400 mmol). The reaction mixture was heated to 80° C. for 2 h. and diluted with water. The mixture was extracted twice with ethyl acetate (20 mL). The organic layer was separated, dried over Na$_2$SO$_4$ and evaporated to dryness. The crude was purified by ISCO® (Column: 24 g RediSep silica, Solvent run: 0-50% EtOAc in petroleum ether). The product was eluted at 30% EtOAc in petroleum ether to afford tert-butyl (S)-4-(bis(4-fluorophenyl)methyl)-3-ethylpiperazine-1-carboxylate (50 mg, 8.8% yield); LCMS: m/z=417.4 (M+H); rt 2.39 min. Method: AQUITY UPLC BEH C18 (3.0×50 mm) 1.7 µm, Mobile phase A: 10 mM ammonium acetate:acetonitrile (95:5) Mobile phase B: 10 mM ammonium acetate:acetonitrile (5:95), Flow: 0.7 mL/min.

Intermediate 90

(S)-1-(bis(4-fluorophenyl)methyl)-2-ethylpiperazine

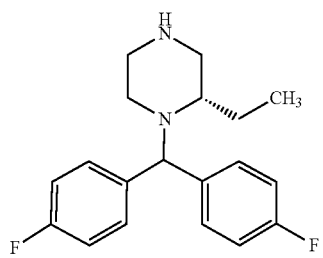

(I-90)

To a solution of tert-butyl (S)-4-(bis(4-fluorophenyl)methyl)-3-ethylpiperazine-1-carboxylate (50 mg, 0.120 mmol) in 1,4-dioxane (5 mL) was added HCl in dioxane (0.036 mL, 1.200 mmol) at room temperature. The reaction mixture was stirred at room temperature for 2 h. and evaporated to dryness. The semi-solid obtained was washed with diethyl ether to yield (S)-1-(bis(4-fluorophenyl)methyl)-2-ethylpiperazine, HCl (35 mg, 32.3% yield) as a solid; LCMS: m/z=317.4 (M+H); rt 1.50 min. Method: AQUITY UPLC BEH C18 (3.0×50 mm) 1.7 μm, Mobile phase A: 10 mM ammonium acetate:acetonitrile (95:5) Mobile phase B: 10 mM ammonium acetate:acetonitrile (5:95), Flow: 0.7 mL/min.

Example 128

(S)-8-(4-(bis(4-fluorophenyl)methyl)-3-ethylpiperazin-1-yl)-5-methyl-6-oxo-5,6-dihydro-1,5-naphthyridine-2-carbonitrile

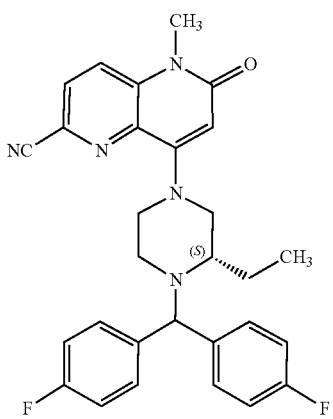

(128)

To a solution of (S)-1-(bis(4-fluorophenyl)methyl)-2-ethylpiperazine, HCl (75 mg, 0.213 mmol) and 6-cyano-1-methyl-2-oxo-1,2-dihydro-1,5-naphthyridin-4-yl trifluoromethanesulfonate (56.7 mg, 0.170 mmol) in acetonitrile (2 mL) was added DIPEA (0.074 mL, 0.425 mmol). The reaction mixture was heated to 80° C. for 2 h. and evaporated to dryness. The crude material was purified via preparative HPLC (Column: SUNFIRE C18 (150 mm×19 mm ID, 5 μm) Mobile phase A: Buffer: 10 mM ammonium acetate in water Mobile phase B: acetonitrile Flow: 17 mL/min). Fractions containing the product were combined and evaporated to dryness to yield (S)-8-(4-(bis(4-fluorophenyl)methyl)-3-ethylpiperazin-1-yl)-5-methyl-6-oxo-5,6-dihydro-1,5-naphthyridine-2-carbonitrile (39 mg, 36.4% yield); LCMS: m/z=500.3 (M+H); rt 2.92 min; Method: XBridge BEH XP C18 (50×2.1) mm, 2.5 μm, Mobile phase A: 95% water:5% acetonitrile; 10 mM ammonium acetate, Mobile phase B: 5% water:95% acetonitrile; 10 mM ammonium acetate, Flow: 1.1 mL/min. $^1$H NMR (400 MHz, DMSO-$d_6$) δ ppm 8.14 (d, J=8.8 Hz, 1H), 8.07 (d, J=8.8 Hz, 1H), 7.56 (dd, J=8.4, 5.7 Hz, 2H), 7.51 (dd, J=8.6, 5.6 Hz, 2H), 7.15 (t, J=8.6 Hz, 4H), 6.11 (s, 1H), 4.98 (s, 1H), 4.23 (d, J=12.0 Hz, 1H), 3.53 (s, 3H), 3.40 (d, J=11.5 Hz, 1H), 3.12-3.02 (m, 2H), 2.99 (d, J=10.8 Hz, 1H), 2.76-2.64 (m, 1H), 2.00-1.86 (m, 1H), 1.76-1.60 (m, 1H), 0.77 (t, J=7.3 Hz, 3H). One proton peak merged with residual solvent peak.

Intermediate 91 tert-butyl (S)-4-(6-cyano-1-methyl-2-oxo-1,2-dihydro-1,5-naphthyridin-4-yl)-3-methylpiperazine-1-carboxylate

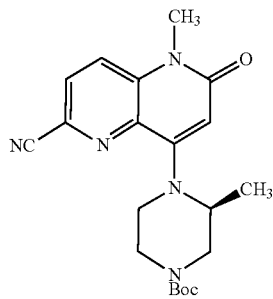

(I-91)

To a solution of tert-butyl (S)-3-methylpiperazine-1-carboxylate (361 mg, 1.800 mmol) in acetonitrile (5 mL) at room temperature was added DIPEA (0.786 mL, 4.50 mmol). The reaction mixture was heated to 85° C. for 15 mins. and 6-cyano-1-methyl-2-oxo-1,2-dihydro-1,5-naphthyridin-4-yl trifluoromethanesulfonate (500 mg, 1.500 mmol) was added. The reaction mixture was heated to 85° C. overnight. The reaction mixture was concentrated under reduced pressure. The residue was dissolved in ethyl acetate (100 mL), and the organic layer was washed with water, brine and dried over sodium sulfate. The solvent was evaporated under reduced pressure. The crude residue was purified by silica gel column chromatography using 24 g flash column, eluting with 30% EtOAc in petroleum ether. The fractions were concentrated under reduced pressure to yield the tert-butyl (S)-4-(6-cyano-1-methyl-2-oxo-1,2-dihydro-1,5-naphthyridin-4-yl)-3-methylpiperazine-1-carboxylate (200 mg, 31.6% yield); LCMS: m/z=384.4 (M+H); rt 1.49 min; LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 μm Flow: 0.7 mL/min.

Intermediate 92

(S)-5-methyl-8-(2-methylpiperazin-1-yl)-6-oxo-5,6-dihydro-1,5-napthyridine-2-carbonitrile, TFA

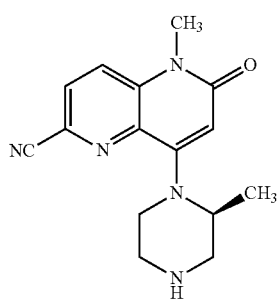

(I-92)

To a solution of tert-butyl (S)-4-(6-cyano-1-methyl-2-oxo-1,2-dihydro-1,5-naphthyridin-4-yl)-3-methylpiperazine-1-carboxylate (120 mg, 0.313 mmol) in DCM (5 mL) at 0° C. was added TFA (0.241 mL, 3.13 mmol). The reaction mixture was stirred at room temperature for 2 h. The reaction mixture was concentrated under reduced pressure. The residue was washed with a mixture of petroleum ether:diethyl ether (1:1) and dried under high vacuum to yield (S)-5-methyl-8-(2-methylpiperazin-1-yl)-6-oxo-5,6-dihydro-1,5-naphthyridine-2-carbonitrile, TFA (130 mg, 91% yield); LCMS: m/z=284.2 (M+H); rt 0.46 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 μm Flow: 0.7 mL/min.

Examples 129 and 130

8-((2S)-4-((4-fluoro-2-methoxyphenyl)(4-fluorophenyl)methyl-2-methylpiperazin-1-yl)-5-methyl-6-oxo-5,6-dihydro-1,5-naphthyridine-2-carbonitrile

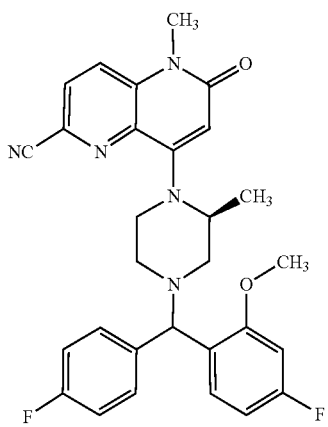

(129-130)

To a solution of (S)-5-methyl-8-(2-methylpiperazin-1-yl)-6-oxo-5,6-dihydro-1,5-naphthyridine-2-carbonitrile TFA salt (70 mg, 0.176 mmol) in acetonitrile (2 mL) at room temperature was added DIPEA (0.092 mL, 0.528 mmol). The reaction mixture was heated to 85° C. for 15 mins and 1-(chloro(4-fluorophenyl)methyl)-4-fluoro-2-methoxybenzene (47.3 mg, 0.176 mmol) was added. The reaction mixture was stirred at 85° C. overnight. The reaction mixture was concentrated under reduced pressure. The residue was dissolved in EtOAc and washed with water, brine and dried over sodium sulfate. The solvent was evaporated under reduced pressure to afford a diastereomeric mixture. Enantiomers were separated using chiral HPLC. Chiral separation (Inj. Vol.: 10 Instrument Method: 3 gr-15%-100 bar Co-Solvent: 0.2% NH$_4$OH in methanol+acetonitrile (1:1) Column: Chiralcel OJH (250×4.6) mm. Separation of the diastereomeric mixture gave Diastereomer 1 (homochiral) and Diastereomer 2 (homochiral). Fractions containing the products were combined and dried via centrifugal evaporation.

Example 129: Diastereomer 1: (3 mg, 3.3% yield); LCMS: m/z=516.2 (M+H); rt 2.242 min; LCMS Method A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 μm. $^1$H NMR (400 MHz, DMSO-d$_6$) δ ppm 8.15 (d, J=8.8 Hz, 1H), 8.07 (d, J=9.0 Hz, 1H), 7.66 (dd, J=8.6, 7.1 Hz, 1H), 7.42 (dd, J=8.8, 5.6 Hz, 2H), 7.12 (t, J=8.9 Hz, 2H), 6.93-6.75 (m, 2H), 6.04 (s, 1H), 4.87 (br. s., 1H), 4.72 (s, 1H), 3.81 (s, 3H), 3.53 (s, 3H), 3.46-3.37 (m, 1H), 3.34 (br. s., 1H), 2.88 (d, J=9.8 Hz, 1H), 2.61-2.52 (m, 1H), 2.35 (dd, J=11.7, 3.4 Hz, 1H), 2.18-2.03 (m, 1H), 1.24-1.09 (m, 3H). F Example 130: Diastereomer 2: (4.5 mg, 4.81% yield); LCMS: m/z=516.3 (M+H); rt 1.329 min; LCMS Method A: 95% water:5% acetonitrile; 10 mM ammonium acetate B: 5% water:95% acetonitrile; 10 mM ammonium acetate Flow: 1.1 mL/min Temp: 50° C.; Column: XBridge BEH XP C18 (50×2.1) mm, 2.5 μm. $^1$H NMR (400 MHz, DMSO-d$_6$) δ ppm 8.15 (d, J=8.8 Hz, 1H), 8.07 (d, J=8.8 Hz, 1H), 7.66-7.57 (m, 1H), 7.45 (dd, J=8.7, 5.5 Hz, 2H), 7.19-7.03 (m, 2H), 6.96 (s, 1H), 6.88-6.75 (m, 2H), 6.04 (s, 1H), 4.89 (br. s., 1H), 4.70 (s, 1H), 3.87-3.72 (m, 3H), 3.53 (s, 3H), 3.41-3.34 (m, 2H), 2.94 (dd, J=12.7, 6.8 Hz, 1H), 2.79-2.67 (m, 1H), 2.55 (s, 1H), 2.36-2.27 (m, 1H), 2.14 (t, J=11.1 Hz, 1H), 1.34-1.08 (m, 4H).

Intermediate 93 tert-butyl (2R,5R)-4-(bis(4-fluorophenyl)methyl)-2,5-dimethylpiperazine-1-carboxylate

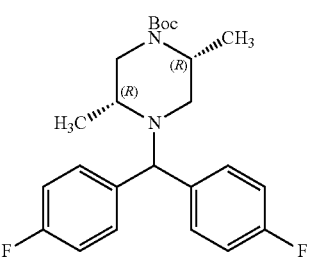

(I-93)

To a solution of 4,4'-(chloromethylene)bis(fluorobenzene) (130 mg, 0.545 mmol) in acetonitrile (20 mL) at room temperature were added tert-butyl (2R,5R)-2,5-dimethylpiperazine-1-carboxylate (128 mg, 0.599 mmol) and DIPEA (0.285 mL, 1.634 mmol). The reaction mixture was heated to 80° C. overnight. The reaction mixture was concentrated under reduced pressure, the residue was dissolved in DCM and washed with water, brine and dried over sodium sulfate and concentrated under reduced pressure. The crude residue was purified by silica gel column chromatography using 24 g flash column, eluting with 30% EtOAc in petroleum ether. The fractions were concentrated under reduced pressure to yield tert-butyl (2R,5R)-4-(bis(4-fluorophenyl)methyl)-2,5-dimethylpiperazine-1-carboxylate (150 mg, 58.2% yield); LCMS: m/z=417.4 (M+H); rt 1.72 min. LCMS Method: M. phase A: 10 mM ammonium acetate:acetonitrile (95:5) Mobile phase B: 10 mM ammonium acetate:acetonitrile (5:95) Method: % B: 0 min-20:2 min-100:2.3 min-100 Flow: 0.7 mL/min Column: AQUITY UPLC BEH C18 (3.0×50 mm) 1.7 μm.

Intermediate 94

(2R,5R)-1-(bis(4-fluorophenyl)methyl)-2,5-dimethylpiperazine, HCl

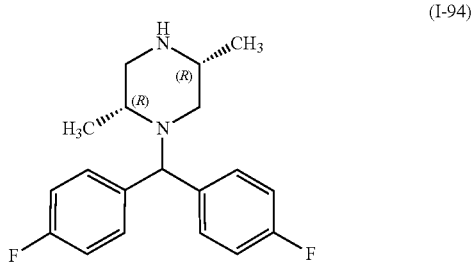

(I-94)

To a solution of tert-butyl (2R,5R)-4-(bis(4-fluorophenyl)methyl)-2,5-dimethylpiperazine-1-carboxylate (120 mg, 0.288 mmol) in dioxane (5 mL) at 0° C. was added HCl in dioxane (0.088 mL, 2.88 mmol). The reaction mixture was stirred at room temperature for 2 h. The reaction mixture was concentrated under reduced pressure and the residue was washed with 1:1 diethyl ether: petroleum ether and dried under high vacuum to yield (2R,5R)-1-(bis(4-fluorophenyl) methyl)-2,5-dimethylpiperazine, HCl (100 mg, 58.4% yield); LCMS: m/z=317.4 (M+H); rt 1.38 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 μm, Flow: 0.7 mL/min.

Example 131

8-((2R,5R)-4-(bis(4-fluorophenyl)methyl)-2,5-dimethylpiperazin-1-yl)-5-methyl-6-oxo-5,6-dihydro-1,5-naphthyridine-2-carbonitrile

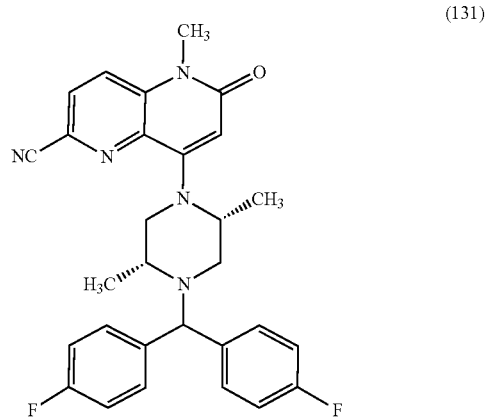

(131)

To a solution of 6-cyano-1-methyl-2-oxo-1,2-dihydro-1,5-naphthyridin-4-yl trifluoromethanesulfonate (100 mg, 0.300 mmol) in acetonitrile (5 mL) at room temperature were added (2R,5R)-1-(bis(4-fluorophenyl)methyl)-2,5-dimethylpiperazine, HCl (116 mg, 0.330 mmol) and DIPEA (0.157 mL, 0.900 mmol). The reaction mixture was stirred at 80° C. overnight. The reaction mixture was concentrated under reduced pressure. The residue was dissolved in DCM and washed with water, brine and dried over sodium sulfate and concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 30% B, 30-72% B over 25 minutes, then a 5 minute hold at 100% B; Flow Rate: 15 mL/min; Column Temperature: 25° C. Fractions containing the product were combined and dried via centrifugal evaporation to yield 8-((2R,5R)-4-(bis(4-fluorophenyl)methyl)-2,5-dimethylpiperazin-1-yl)-5-methyl-6-oxo-5,6-dihydro-1,5-naphthyridine-2-carbonitrile (16.2 mg, 10.4% yield); LCMS: m/z 500.2 (M+H); rt 2.303 min; LCMS Method: A: 95% water: 5% acetonitrile; 10 mM ammonium acetate B: 5% water: 95% acetonitrile; 10 mM ammonium acetate; Flow: 1.1 mL/min; Temp: 50° C. Column: XBridge BEH XP C18 (50×2.1) mm, 2.5 μm. $^1$H NMR (400 MHz, DMSO-$d_6$) δ ppm 8.14 (d, J=8.8 Hz, 1H), 8.06 (d, J=9.0 Hz, 1H), 7.42 (dd, J=8.6, 5.6 Hz, 2H), 7.35 (dd, J=8.7, 5.7 Hz, 2H), 7.25-7.07 (m, 4H), 6.07 (s, 1H), 5.30 (s, 1H), 4.50 (br. s., 1H), 3.53 (s, 3H), 3.36 (d, J=12.0 Hz, 1H), 3.28-3.20 (m, 1H), 2.67-2.55 (m, 2H), 2.37 (dd, J=12.2, 3.9 Hz, 1H), 1.34-1.23 (m, 3H), 1.19 (d, J=6.4 Hz, 3H).

Example 132

8-((2R,5R)-4-(bis(4-fluorophenyl)methyl)-2,5-dimethylpiperazin-1-yl)-7-chloro-5-methyl-6-oxo-5,6-dihydro-1,5-naphthyridine-2-carbonitrile

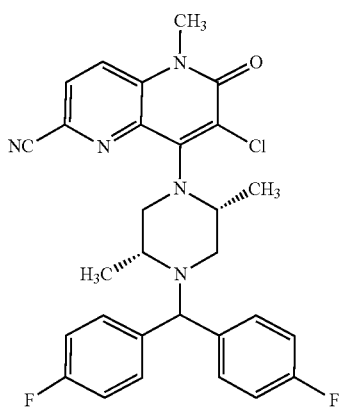

(132)

To a solution of 8-((2R,5R)-4-(bis(4-fluorophenyl) methyl)-2,5-dimethylpiperazin-1-yl)-5-methyl-6-oxo-5,6-dihydro-1,5-naphthyridine-2-carbonitrile (30 mg, 0.060 mmol) in dichloromethane (2 mL) at room temperature was added NCS (16.04 mg, 0.120 mmol). The reaction mixture was stirred at room temperature overnight. The reaction was quenched with 10% NaHCO$_3$ solution. The reaction mixture was extracted with DCM and washed with water, brine, and dried over sodium sulfate and concentrated under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 50% B, 50-77% B over 15 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 8-((2R,5R)-4-(bis(4-fluorophenyl)methyl)-2,5-dimethylpiperazin-1-yl)-7-chloro-5-methyl-6-oxo-5,6-dihydro-1,5-naphthyridine-2-carbonitrile (7.6 mg, 23.7% yield); LCMS: m/z=534.3 (M+H); rt 1.534 min. LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 µm. $^1$H NMR (400 MHz, DMSO-d$_6$) δ ppm 8.23 (s, 2H), 7.64-7.45 (m, 4H), 7.24-7.07 (m, 4H), 4.88 (s, 1H), 4.16 (br. s., 1H), 3.83-3.56 (m, 4H), 3.01-2.83 (m, 2H), 2.48 (br. s., 1H), 2.45-2.36 (m, 1H), 1.24 (d, J=6.1 Hz, 3H), 0.76 (d, J=6.4 Hz, 3H).

Intermediate 95 tert-butyl (2S,5S)-4-(bis(4-fluorophenyl)methyl)-2,5-dimethylpiperazine-1-carboxylate

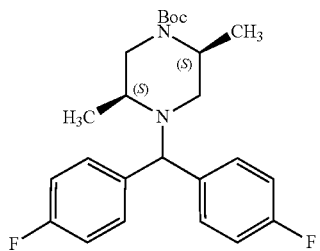

(I-95)

To a solution of 4,4'-(chloromethylene)bis(fluorobenzene) (200 mg, 0.838 mmol) in acetonitrile (20 mL) at room temperature were added tert-butyl (2S,5S)-2,5-dimethylpiperazine-1-carboxylate (198 mg, 0.922 mmol) and DIPEA (0.439 mL, 2.51 mmol). The reaction mixture was heated to 85° C. overnight and concentrated under reduced pressure to yield residue. The residue was dissolved in DCM (100 mL) and washed with water (20 mL), brine (20 mL) and dried over sodium sulfate and concentrated under reduced pressure. The crude residue was purified by silica gel column chromatography using 24 g flash column, eluting with 30% EtOAc in petroleum ether. The fractions were concentrated under reduced pressure to yield tert-butyl (2S,5S)-4-(bis(4-fluorophenyl)methyl)-2,5-dimethylpiperazine-1-carboxylate (200 mg, 51.8% yield); LCMS: m/z=417.4 (M+H); rt 1.74 min. LCMS Method: Mobile phase A: Buffer: acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 µm, Flow: 0.7 mL/min.

Intermediate 96

(2S,5S)-1-(bis(4-fluorophenyl)methyl)-2,5-dimethylpiperazine

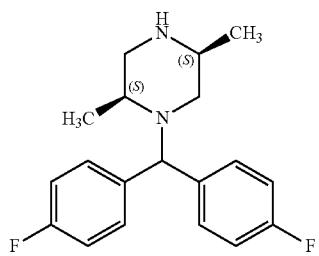

(I-96)

To a solution of tert-butyl (2S,5S)-4-(bis(4-fluorophenyl)methyl)-2,5-dimethylpiperazine-1-carboxylate (120 mg, 0.288 mmol) in dioxane (5 mL) at 0° C. was added HCl in dioxane (0.088 mL, 2.88 mmol). The reaction mixture was stirred at room temperature for 2 h. and concentrated under reduced pressure. The residue was washed with diethyl ether:petroleum ether (1:1) and dried under high vacuum to yield (2S,5S)-1-(bis(4-fluorophenyl)methyl)-2,5-dimethylpiperazine, HCl (90 mg, 61.3% yield); LCMS: m/z=317.4

(M+H); rt 1.30 min. LCMS Method: Mobile phase A: Buffer: acetonitrile (95:5) Mobile phase B: Buffer:acetonitrile (5:95) Method: % B: 0 min-20%:1.1 min-90%: 1.7 min-90% Column: AQUITY UPLC BEH C18 (3.0×50 mm) 1.7 µm, Flow: 0.7 mL/min.

Example 133

8-((2S,5S)-4-(bis(4-fluorophenyl)methyl)-2,5-dimethylpiperazin-1-yl)-5-methyl-6-oxo-5,6-dihydro-1,5-naphthyridine-2-carbonitrile

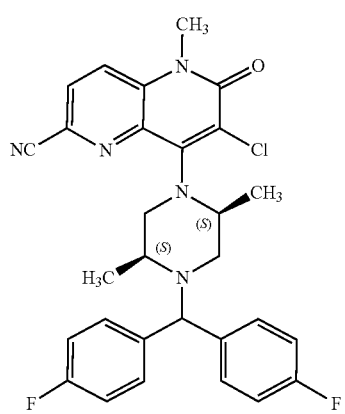

(133)

To a solution of 6-cyano-1-methyl-2-oxo-1,2-dihydro-1,5-naphthyridin-4-yl trifluoromethanesulfonate (70 mg, 0.210 mmol) in acetonitrile (5 mL) at room temperature were added (2S,5S)-1-(bis(4-fluorophenyl)methyl)-2,5-dimethylpiperazine, HCl (82 mg, 0.231 mmol) and DIPEA (0.110 mL, 0.630 mmol). The reaction mixture was stirred at 80° C. overnight. The reaction mixture was concentrated under reduced pressure. The residue was dissolved in DCM, washed with water, brine and dried over sodium sulfate, and concentrated under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-55% B over 25 minutes, then a 5 minute hold at 100% B; Flow Rate: 15 mL/min; Column Temperature: 25° C. Fractions containing the product were combined and dried via centrifugal evaporation to yield 8-((2S,5S)-4-(bis(4-fluorophenyl)methyl)-2,5-dimethylpiperazin-1-yl)-5-methyl-6-oxo-5,6-dihydro-1,5-naphthyridine-2-carbonitrile (8.7 mg, 7.8% yield); LCMS: m/z 500.2 (M+H); rt 2.296 min. LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 µm. $^1$H NMR (400 MHz, DMSO-$d_6$) δ ppm 8.14 (d, J=8.8 Hz, 1H), 8.06 (d, J=8.8 Hz, 1H), 7.50-7.29 (m, 4H), 7.27-7.02 (m, 4H), 6.07 (s, 1H), 5.30 (s, 1H), 4.50 (br. s., 1H), 3.53 (s, 3H), 3.42-3.34 (m, 1H), 3.29-3.21 (m, 1H), 2.67-2.54 (m, 2H), 2.36 (dd, J=11.5, 7.6 Hz, 1H), 1.34-1.22 (m, 3H), 1.19 (d, J=6.4 Hz, 3H).

Intermediate 94 tert-butyl (S)-4-(6-cyano-1-methyl-2-oxo-1,2-dihydro-1,5-naphthyridin-4-yl)-3-methylpiperazine-1-carboxylate

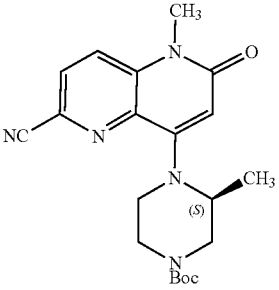

(I-97)

To a solution of tert-butyl (S)-3-methylpiperazine-1-carboxylate (361 mg, 1.800 mmol) in acetonitrile (5 mL) at room temperature was added DIPEA (0.786 mL, 4.50 mmol). The reaction mixture was heated to 85° C. for 15 min. and 6-cyano-1-methyl-2-oxo-1,2-dihydro-1,5-naphthyridin-4-yl trifluoromethanesulfonate (500 mg, 1.500 mmol) was added. The reaction mixture was heated to 85° C. overnight. The reaction mixture was concentrated under reduced pressure and the residue was dissolved in ethyl acetate (100 mL). The organic layer was washed with water, brine and dried over sodium sulfate. The solvent was evaporated under reduced pressure. The crude residue was purified by silica gel column chromatography using 24 g flash column, eluting with 30% EtOAc in petroleum ether. The fractions were concentrated under reduced pressure to yield tert-butyl (S)-4-(6-cyano-1-methyl-2-oxo-1,2-dihydro-1,5-naphthyridin-4-yl)-3-methylpiperazine-1-carboxylate (200 mg, 31.6% yield); LCMS: m/z=384.4 (M+H); rt 1.49 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 µm, Flow: 0.7 mL/min.

Intermediate 98

(S)-5-methyl-8-(2-methylpiperazin-1-yl)-6-oxo-5,6-dihydro-1,5-naphthyridine-2-carbonitrile, TFA

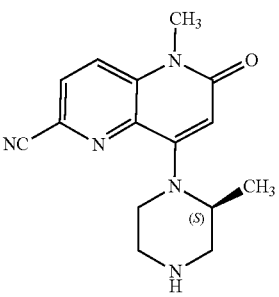

(I-98)

To a solution of tert-butyl (S)-4-(6-cyano-1-methyl-2-oxo-1,2-dihydro-1,5-naphthyridin-4-yl)-3-methylpiperazine-1-carboxylate (120 mg, 0.313 mmol) in DCM (5 mL)

at 0° C. was added TFA (0.241 mL, 3.13 mmol). The reaction mixture was stirred at room temperature for 2 h. The reaction mixture was concentrated under reduced pressure. The residue was washed with a mixture of petroleum ether:diethyl ether (1:1) and dried under high vacuum to yield (S)-5-methyl-8-(2-methylpiperazin-1-yl)-6-oxo-5,6-dihydro-1,5-naphthyridine-2-carbonitrile, TFA (130 mg, 91% yield); LCMS: m/z=284.2 (M+H); rt 0.46 min. LCMS Method: Mobile phase A: 10 mM NH₄OAc:acetonitrile (95:5) Mobile phase B: 10 mM NH₄OAc:acetonitrile (5:95) Method: % B: 0 min-20%:1.1 min-90%:1.7 min-90% Column: AQUITY UPLC BEH C18 (3.0×50 mm) 1.7 µm, Flow: 0.7 mL/min.

Example 134

(S)-8-(4-(bis(4-fluorophenyl)methyl)-2-methylpiperazin-1-yl)-5-methyl-6-oxo-5,6-dihydro-1,5-naphthyridine-2-carbonitrile

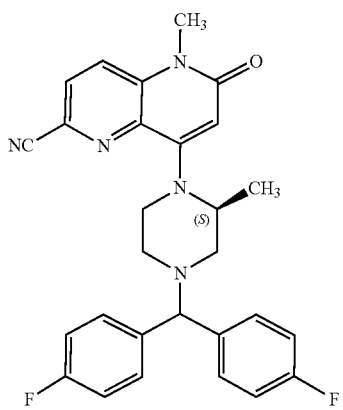

(134)

To a solution of (S)-5-methyl-8-(2-methylpiperazin-1-yl)-6-oxo-5,6-dihydro-1,5-naphthyridine-2-carbonitrile, TFA (40 mg, 0.101 mmol) in acetonitrile (2 mL) at room temperature was added DIPEA (0.053 mL, 0.302 mmol). The reaction mixture was heated at 85° C. for 15 mins and 4,4'-(chloromethylene)bis(fluorobenzene) (24.02 mg, 0.101 mmol) was added. The reaction mixture was stirred at 85° C. overnight. The solvent was evaporated under reduced pressure. The residue was dissolved in DCM and washed with water and brine, dried over sodium sulfate, and concentrated under reduced pressure. The crude material was purified via preparative HPLC using the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-55% B over 25 minutes, then a 5 minute hold at 100% B; Flow Rate: 15 mL/min; Column Temperature: 25° C. Fractions containing the product were combined and dried via centrifugal evaporation to yield (S)-8-(4-(bis(4-fluorophenyl)methyl)-2-methylpiperazin-1-yl)-5-methyl-6-oxo-5,6-dihydro-1,5-naphthyridine-2-carbonitrile (7.7 mg, 15.0% yield); LCMS: m/z=486.3 (M+H); rt 2.22 min. LCMS Method: A: 95% water:5% acetonitrile; 10 mM ammonium acetate B: 5% water:95% acetonitrile; 10 mM ammonium acetate; Flow: 1.1 mL/min Temp: 50° C. Column: XBridge BEH XP C18 (50×2.1 mm), 2.5 µm. ¹H NMR (400 MHz, DMSO-d₆) δ ppm 8.13-8.19 (m, 1H), 8.06-8.10 (m, 1H), 7.43-7.57 (m, 4H), 7.11-7.20 (m, 4H), 6.04 (s, 1H), 4.82-4.92 (m, 1H), 4.43 (s, 1H), 3.53 (s, 3H), 3.35-3.47 (m, 2H), 2.74-2.84 (m, 1H), 2.60-2.70 (m, 1H), 2.31-2.42 (m, 1H), 2.10-2.21 (m, 1H), 1.21 (d, J=6.6 Hz, 3H).

Intermediate 99 tert-butyl (R)-4-(6-cyano-1-methyl-2-oxo-1,2-dihydro-1,5-naphthyridin-4-yl)-3-methylpiperazine-1-carboxylate

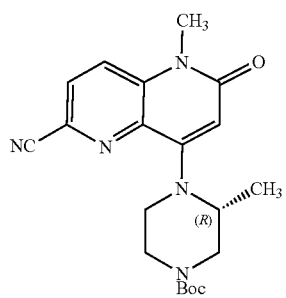

(I-99)

To a solution of tert-butyl (R)-3-methylpiperazine-1-carboxylate (144 mg, 0.720 mmol) in acetonitrile (5 mL) at room temperature was added DIPEA (0.314 mL, 1.800 mmol). The reaction mixture was heated to 85° C. for 15 mins. and 6-cyano-1-methyl-2-oxo-1,2-dihydro-1,5-naphthyridin-4-yl trifluoromethanesulfonate (200 mg, 0.600 mmol) was added. The reaction mixture was heated to 85° C. overnight and concentrated under reduced pressure. The residue was dissolved in DCM, washed with water and brine, and dried over sodium sulfate. The solvent was evaporated under reduced pressure to yield tert-butyl (R)-4-(6-cyano-1-methyl-2-oxo-1,2-dihydro-1,5-naphthyridin-4-yl)-3-methylpiperazine-1-carboxylate (200 mg, 33.0% yield); LCMS: m/z=384.4 (M+H); rt 1.50 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 µm, Flow: 0.7 mL/min.

Intermediate 100

(R)-5-methyl-8-(2-methylpiperazin-1-yl)-6-oxo-5,6-dihydro-1,5-naphthyridine-2-carbonitrile, TFA

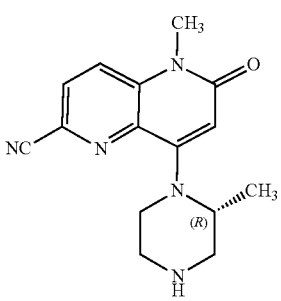

(I-100)

To a solution of tert-butyl (R)-4-(6-cyano-1-methyl-2-oxo-1,2-dihydro-1,5-naphthyridin-4-yl)-3-methylpiperazine-1-carboxylate (120 mg, 0.313 mmol) in DCM (5 mL) at 0° C. was added TFA (0.241 mL, 3.13 mmol). The reaction mixture was stirred at room temperature for 2 h. The reaction mixture was concentrated under reduced pressure. The residue was washed mixture of petroleum ether: EtOAc (1:1) and dried under high vacuum to yield (R)-5-methyl-8-(2-methylpiperazin-1-yl)-6-oxo-5,6-dihydro-1,5-naphthyridine-2-carbonitrile, TFA (130 mg, 91% yield); LCMS: m/z=284.4 (M+H); rt 0.46 min. LCMS Method: Mobile phase A: Buffer:acetonitrile (95:5); Mobile phase B: Buffer:acetonitrile (5:95) Method: % B: 0 min-20%:1.1 min-90%:1.7 min-90% Column: AQUITY UPLC BEH C18 (3.0×50 mm) 1.7 µm, Flow: 0.7 mL/min.

Example 135

(R)-8-(4-(bis(4-fluorophenyl)methyl)-2-methylpiperazin-1-yl)-5-methyl-6-oxo-5,6-dihydro-1,5-naphthyridine-2-carbonitrile

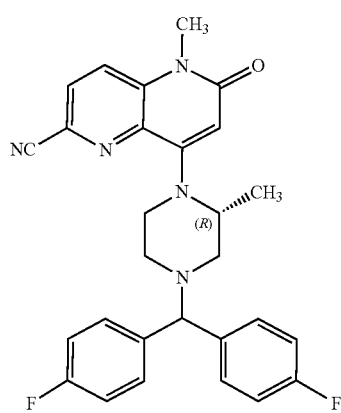

(135)

To a solution (R)-5-methyl-8-(2-methylpiperazin-1-yl)-6-oxo-5,6-dihydro-1,5-naphthyridine-2-carbonitrile, TFA (100 mg, 0.252 mmol) in acetonitrile (5 mL) at room temperature was added DIPEA (0.132 mL, 0.755 mmol). The reaction mixture was heated to 85° C. for 15 mins. and 4,4'-(chloromethylene)bis(fluorobenzene) (60.1 mg, 0.252 mmol) was added. The reaction mixture was stirred at 85° C. overnight and concentrated under reduced pressure. The residue was dissolved in DCM and washed with water and brine, dried over sodium sulfate, and concentrated under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 3 minute hold at 30% B, 30-70% B over 25 minutes, then a 5 minute hold at 100% B; Flow Rate: 15 mL/min; Column Temperature: 25° C. Fractions containing the product were combined and dried via centrifugal evaporation to yield (R)-8-(4-(bis(4-fluorophenyl)methyl)-2-methylpiperazin-1-yl)-5-methyl-6-oxo-5,6-dihydro-1,5-naphthyridine-2-carbonitrile (17.7 mg, 14.3% yield); LCMS: m/z=486.3 (M+H); rt 2.223 min. LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 µm. $^1$H NMR (400 MHz, DMSO-$d_6$) δ ppm 8.15 (d, J=8.8 Hz, 1H), 8.07 (d, J=9.0 Hz, 1H), 7.61-7.41 (m, 4H), 7.27-7.05 (m, 4H), 6.04 (s, 1H), 4.87 (br. s., 1H), 4.43 (s, 1H), 3.53 (s, 3H), 3.45-3.34 (m, 2H), 2.79 (d, J=9.3 Hz, 1H), 2.71-2.61 (m, 1H), 2.40-2.30 (m, 1H), 2.20-2.12 (m, 1H), 1.32-1.13 (m, 3H).

Intermediate 101

1-(tert-butyl) 2-methyl 4-(bis(4-fluorophenyl)methyl)piperazine-1,2-dicarboxylate

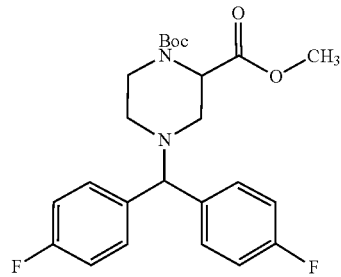

(I-101)

To a solution of 4,4'-(chloromethylene)bis(fluorobenzene) (4 g, 16.76 mmol) in acetonitrile (20 mL) at room temperature was added 1-(tert-butyl) 2-methyl piperazine-1,2-dicarboxylate (8.19 g, 33.5 mmol), DIPEA (5.85 mL, 33.5 mmol). The reaction mixture was heated to 80° C. overnight. The reaction mixture was concentrated under reduced pressure. The residue was dissolved in DCM, washed with water and brine, dried over sodium sulfate, and concentrated under reduced pressure. The crude residue was purified by silica gel column chromatography using 24 g flash column, eluting with 30% EtOAc in petroleum ether. The fractions were concentrated under reduced pressure to yield 1-(tert-butyl) 2-methyl 4-(bis(4-fluorophenyl)methyl)piperazine-1,2-dicarboxylate (5 g, 26.4% yield); LCMS: m/z=447.6 (M+H); rt 2.22 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 µm, Flow: 0.7 mL/min.

Intermediate 102

Methyl 4-(bis(4-fluorophenyl)methyl)piperazine-2-carboxylate, HCl

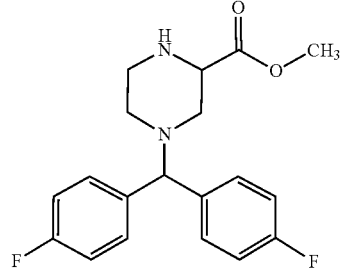

(I-102)

To a solution of 1-(tert-butyl) 2-methyl 4-(bis(4-fluorophenyl)methyl)piperazine-1,2-dicarboxylate (1 g, 2.240 mmol) in dioxane (5 mL) at room temperature was added HCl in 1,4-dioxane (5.60 mL, 22.40 mmol). The reaction mixture was stirred at room temperature for 3 h. The reaction mixture was concentrated under reduced pressure and washed in mixture of petroleum ether:diethyl ether (1:1) and dried under high vacuum to yield methyl 4-(bis(4-fluorophenyl)methyl)piperazine-2-carboxylate, HCl (900 mg, 94% yield); LCMS: m/z=347.2 (M+H); rt 2.67 min. LCMS Method: Column-Kinetex XB-C18 (75×3 mm-2.6 μm) Mphase A: 10 mM ammonium formate in water:acetonitrile (98:2) Mphase B: 10 mM ammonium formate in water acetonitrile (2:98).

Examples 136 to 137

Methyl 4-(bis(4-fluorophenyl)methyl)-1-(6-cyano-1-methyl-2-oxo-1,2-dihydro-1,5-naphthyridin-4-yl)piperazine-2-carboxylate

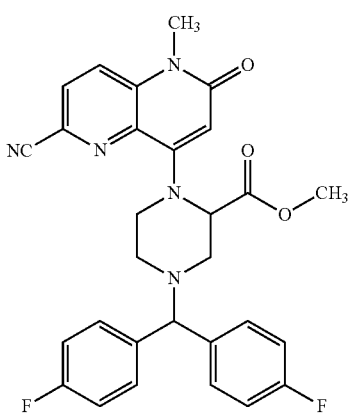

(136-137)

To a solution of 6-cyano-1-methyl-2-oxo-1,2-dihydro-1,5-naphthyridin-4-yl trifluoromethanesulfonate (200 mg, 0.600 mmol) in acetonitrile (5 mL) at room temperature were added methyl 4-(bis(4-fluorophenyl)methyl)piperazine-2-carboxylate, HCl (230 mg, 0.600 mmol) and DIPEA (0.314 mL, 1.800 mmol). The reaction mixture was stirred at 80° C. overnight. The reaction was quenched with water. The reaction mixture was extracted with DCM (2×100 mL), the combined organic layer was washed with water and brine, and dried over sodium sulfate. The solvent was evaporated under reduced pressure. The crude product was purified by silica gel column chromatography using 24 g flash column and 100% EtOAc in petroleum ether. The fractions were concentrated under reduced pressure to yield an enantiomeric mixture. Enantiomers were separated using chiral HPLC. Chiral separation: (Column: Lux C5 (250× 30×5) PRHP112F250-0001 Mobile Phase A-Crude Purity:- Mobile Phase B-0.1% DEA in methanol:acetonitrile (70:30) Solubility: DMSO:methanol Flow: 35 gradient ISO) of enantiomeric mixture afforded Example 136 (Enantiomer 1) and Example 137 (Enantiomer 2). Fractions containing the products were combined and dried via centrifugal evaporation.

Example 136: Enantiomer 1: (8.9 mg, 2.8% yield); LCMS: m/z=530.2 (M+H); rt 2.18 min; LCMS Method: A: 95% water:5% acetonitrile; 10 mM ammonium acetate, B: 5% water:95% acetonitrile; 10 mM ammonium acetate Flow: 1.1 mL/min Temp: 50° C. Column: XBridge BEH XP C18 (50×2.1) mm, 2.5 μm. $^1$H NMR (400 MHz, DMSO-d$_6$) δ ppm 8.15 (d, J=8.8 Hz, 1H), 8.08 (d, J=8.8 Hz, 1H), 7.54-7.34 (m, 4H), 7.30-7.06 (m, 4H), 6.14 (s, 1H), 5.80 (br. s., 1H), 4.47 (s, 1H), 3.69 (s, 3H), 3.60-3.38 (m, 5H), 3.28 (d, J=11.7 Hz, 1H), 2.80 (d, J=9.5 Hz, 1H), 2.54 (d, J=6.6 Hz, 1H), 2.45 (dd, J=11.4, 3.3 Hz, 1H), 2.24-2.11 (m, 1H).

Example 137: Enantiomer 2: (8.4 mg, 2.6% yield); LCMS: m/z=530.3 (M+H); rt 2.183 min. LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 μm. $^1$H NMR (400 MHz, DMSO-d$_6$) δ ppm 8.14 (d, J=8.8 Hz, 1H), 8.07 (d, J=8.8 Hz, 1H), 7.54-7.37 (m, 4H), 7.29-7.07 (m, 4H), 6.14 (s, 1H), 5.80 (br. s., 1H), 4.46 (s, 1H), 3.69 (s, 3H), 3.60-3.40 (m, 5H), 3.28 (d, J=11.5 Hz, 1H), 2.80 (d, J=10.3 Hz, 1H), 2.45 (dd, J=11.5, 3.4 Hz, 1H), 2.20 (td, J=11.1, 4.5 Hz, 1H).

Example 138

4-(bis(4-fluorophenyl)methyl)-1-(6-cyano-1-methyl-2-oxo-1,2-dihydro-1,5-naphthyridin-4-yl)piperazine-2-carboxylic acid

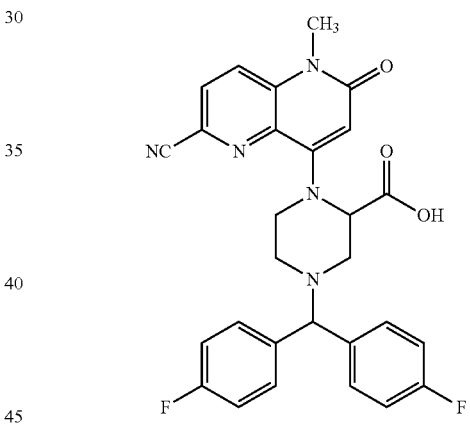

(138)

To a solution of methyl 4-(bis(4-fluorophenyl)methyl)-1-(6-cyano-1-methyl-2-oxo-1,2-dihydro-1,5-naphthyridin-4-yl)piperazine-2-carboxylate (60 mg, 0.113 mmol) in DMF (2 mL) at room temperature was added lithium chloride (48.0 mg, 1.133 mmol). The reaction mixture was maintained at 150° C. for 30 mins. The reaction mixture was filtered though syringe filter and the filtrate was concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 2 minute hold at 12% B, 12-42% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 4-(bis(4-fluorophenyl)methyl)-1-(6-cyano-1-methyl-2-oxo-1,2-dihydro-1,5-naphthyridin-4-yl)piperazine-2-carboxylic acid (8.9 mg, 14.2% yield); LCMS: m/z=516.2 (M+H); rt 1.702 min. LCMS Method: A: 95% water:5% acetonitrile; 10 mM ammonium acetate B: 5% water:95% acetonitrile; 10 mM ammonium acetate; Flow: 1.1 mL/min Temp: 50° C. Column: XBridge BEH XP C18 (50×2.1) mm, 2.5 μm. $^1$H NMR (400 MHz, METHANOL-d4) δ 8.08 (dd, J=8.9, 4.3 Hz, 1H), 7.99 (dd, J=9.0, 5.1 Hz, 1H), 7.62-7.36 (m, 4H), 7.13-6.94 (m, 4H), 6.22 (s, 1H), 5.89 (br. s., 1H), 4.40 (s, 1H), 3.79-3.68 (m, 1H), 3.59-3.45 (m, 2H), 2.96 (d, J=11.0 Hz, 1H), 2.52 (dd, J=11.5, 3.7 Hz, 1H), 2.38-2.26 (m, 1H).

Intermediate 103

4-(bis(4-fluorophenyl)methyl)-1-(tert-butoxycarbonyl)piperazine-2-carboxylic acid

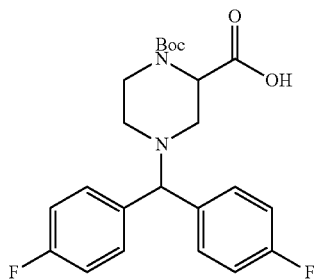

(I-103)

To a solution of 1-(tert-butyl) 2-methyl 4-(bis(4-fluorophenyl)methyl)piperazine-1,2-dicarboxylate (1.8 g, 4.03 mmol) in THF (10 mL) and water (5 mL) was added LiGH (0.483 g, 20.16 mmol). The reaction mixture was stirred at room temperature overnight. The volatiles were removed from the reaction mixture under reduced pressure. The residue was dissolved in water and the aqueous layer was washed with diethyl ether (2×50 mL). The aqueous layer was acidified with 1.5 N HCl and extracted with EtOAc (2×100 mL). The combine organic layer was washed with water and brine, and dried over sodium sulfate. The solvent was concentrated under reduced pressure to yield 4-(bis(4-fluorophenyl)methyl)-1-(tert-butoxycarbonyl)piperazine-2-carboxylic acid (1.5 g, 61.1% yield); LCMS: m/z=433.4 (M+H); rt 1.39 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 μm, Flow: 0.7 mL/min.

Intermediate 104 tert-butyl 4-(bis(4-fluorophenyl)methyl)-2-(cyclopropylcarbamoyl)piperazine-1-carboxylate

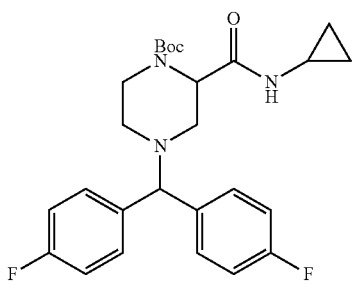

(I-104)

To a solution of 4-(bis(4-fluorophenyl)methyl)-1-(tert-butoxycarbonyl)piperazine-2-carboxylic acid (500 mg, 1.156 mmol) in DMF (2 mL) at room temperature were added HATU (528 mg, 1.387 mmol), DIPEA (0.606 mL, 3.47 mmol) and cyclopropanamine (0.160 mL, 2.312 mmol). The reaction mixture was stirred at room temperature for 4 h. The reaction was quenched with water. The reaction mixture was extracted with ethyl acetate (2×100 mL), the combined organic layer was washed with water and brine, and dried over sodium sulfate. The solvent was evaporated under reduced pressure. The crude product was purified by silica gel column chromatography using 24 g flash column and 40% EtOAc in petroleum ether. The fractions were concentrated under reduced pressure to yield tert-butyl 4-(bis(4-fluorophenyl)methyl)-2-(cyclopropylcarbamoyl) piperazine-1-carboxylate (450 mg, 79% yield); LCMS: m/z=472.2 (M+H); rt 3.434 min. LCMS Method: Column-Kinetex XB-C18 (75×3 mm-2.6 μm). Mphase A: 10 mM ammonium formate in water:acetonitrile (98:2) Mphase B: 10 mM ammonium formate in water:acetonitrile (2:98).

Intermediate 105

4-(bis(4-fluorophenyl)methyl)-N-cyclopropylpiperazine-2-carboxamide, HCl

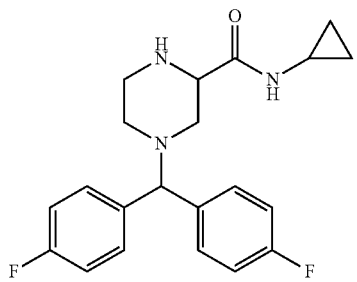

(I-105)

To a solution of tert-butyl 4-(bis(4-fluorophenyl)methyl)-2-(cyclopropylcarbamoyl)piperazine-1-carboxylate (350 mg, 0.742 mmol) in dioxane (5 mL) at room temperature was added HCl in 1,4-dioxane (5 mL, 20.00 mmol). The reaction mixture was stirred at room temperature overnight and concentrated under reduced pressure. The residue was washed with mixture of petroleum ether: Di ethyl ether (1:1) and dried under high vacuum to yield 4-(bis(4-fluorophenyl) methyl)-N-cyclopropylpiperazine-2-carboxamide, HCl (300 mg, 50.5% yield); LCMS: m/z=372.5 (M+H); rt 1.46 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 μm, Flow: 0.7 mL/min.

247

Examples 139 to 140

4-(bis(4-fluorophenyl)methyl)-1-(6-cyano-1-methyl-2-oxo-1,2-dihydro-1,5-naphthyridin-4-yl)-N-cyclopropylpiperazine-2-carboxamide

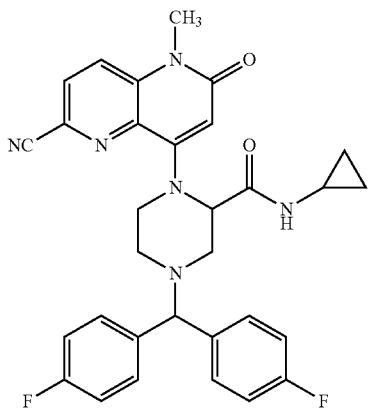

(139-140)

To a solution of 4-(bis(4-fluorophenyl)methyl)-N-cyclopropylpiperazine-2-carboxamide, HCl (98 mg, 0.240 mmol) in acetonitrile (5 mL) at room temperature was added DIPEA (0.126 mL, 0.720 mmol). The reaction mixture was heated to 85° C. for 15 mins. and 6-cyano-1-methyl-2-oxo-1,2-dihydro-1,5-naphthyridin-4-yl trifluoromethanesulfonate (80 mg, 0.240 mmol) was added. The reaction mixture was heated to 85° C. overnight and concentrated under reduced pressure. The residue was dissolved in DCM (100 mL), the organic layer was washed with water and brine, and dried over sodium sulfate. The solvent was evaporated under reduced pressure. The crude product was purified by silica gel column chromatography using 24 g flash column and 100% EtOAc in petroleum ether. The fractions were concentrated under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-60% B over 25 minutes, then a 5 minute hold at 100% B; Flow Rate: 15 mL/min; Column Temperature: 25° C. Fractions containing the product were combined and dried via centrifugal evaporation to yield 4-(bis(4-fluorophenyl)methyl)-1-(6-cyano-1-methyl-2-oxo-1,2-dihydro-1,5-naphthyridin-4-yl)-N-cyclopropylpiperazine-2-carboxamide. Enantiomers were separated using chiral HPLC. Chiral separation: Column: C2/160 (250×20) mm, 5 micron M. Phase A: M. Phase B: 0.1% DEA in methanol. Flow: 20 mL/min Time (min)/% B: 0/100, 15/100. Fractions containing the products were combined and dried via centrifugal evaporation.

Example 139: Enantiomer 1: (6.4 mg, 4.6% yield); LCMS: m/z=555.3 (M+H); rt 2.001 min; LCMS Method: A:

248

95% water:5% acetonitrile; 10 mM ammonium acetate B: 5% water:95% acetonitrile; 10 mM ammonium acetate. Flow: 1.1 mL/min Temp: 50° C. Column: XBridge BEH XP C18 (50×2.1) mm, 2.5 μm. $^1$H NMR (400 MHz, DMSO-d6) δ ppm 8.14 (d, J=8.8 Hz, 1H), 8.04-8.10 (m, 1H), 7.76-7.80 (m, 1H), 7.41-7.48 (m, 4H), 7.10-7.19 (m, 4H), 6.07 (s, 1H), 5.33 (br s, 1H), 4.40 (s, 1H), 3.77-3.87 (m, 1H), 3.53 (s, 3H), 3.44-3.50 (m, 1H), 3.17-3.24 (m, 1H), 2.71-2.78 (m, 1H), 2.58-2.65 (m, 1H), 2.33 (s, 1H), 2.13-2.22 (m, 1H), 0.54-0.75 (m, 2H), 0.29-0.48 (m, 2H).

Example 140: Enantiomer 2: (5.6 mg, 4.1% yield); LCMS: m/z=555.3 (M+H); rt 2.001 min; LCMS Method: A: 95% water:5% acetonitrile; 10 mM ammonium acetate B: 5% water:95% acetonitrile; 10 mM ammonium acetate; Flow: 1.1 mL/min Temp: 50° C.; Column: XBridge BEH XP C18 (50×2.1) mm, 2.5 μm. $^1$H NMR (400 MHz, DMSO-$d_6$) δ ppm 8.14 (d, J=8.8 Hz, 1H), 8.03-8.11 (m, 1H), 7.78 (d, J=3.9 Hz, 1H), 7.40-7.47 (m, 4H), 7.09-7.19 (m, 4H), 6.07 (s, 1H), 5.31-5.37 (m, 1H), 4.40 (s, 1H), 3.77-3.87 (m, 1H), 3.53 (s, 3H), 3.44-3.50 (m, 1H), 3.17-3.23 (m, 1H), 2.72-2.78 (m, 1H), 2.59-2.66 (m, 1H), 2.34 (br d, J=1.7 Hz, 1H), 2.14-2.23 (m, 1H), 0.64-0.73 (m, 1H), 0.54-0.63 (m, 1H), 0.40-0.49 (m, 1H), 0.29-0.38 (m, 1H).

Intermediate 106 tert-butyl 4-(bis(4-fluorophenyl)methyl)-2-carbamoylpiperazine-1-carboxylate

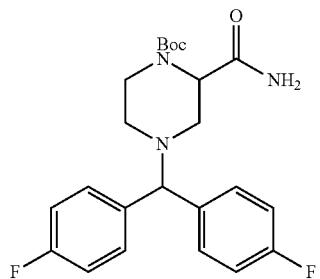

(I-106)

To a solution of 4-(bis(4-fluorophenyl)methyl)-1-(tert-butoxycarbonyl)piperazine-2-carboxylic acid (500 mg, 1.156 mmol) in DMF (2 mL) at room temperature were added HATU (879 mg, 2.312 mmol), DIPEA (0.606 mL, 3.47 mmol) and ammonium chloride (124 mg, 2.312 mmol). The reaction mixture was stirred at room temperature for 4 h. The reaction was quenched with water. The reaction mixture was extracted with ethyl acetate (2×100 mL). The combined organic layer was washed with water and brine, and dried over sodium sulfate. The solvent was evaporated under reduced pressure. The crude product was purified by silica gel column chromatography using 24 g flash column and 30% EtOAc in petroleum ether. The fractions were concentrated under reduced pressure to afford tert-butyl 4-(bis(4-fluorophenyl)methyl)-2-carbamoylpiperazine-1-carboxylate (400 mg, 52.1% yield); LCMS: m/z=432.4 (M+H); rt 1.81 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 μm, Flow: 0.7 mL/min.

Intermediate 107

4-(bis(4-fluorophenyl)methyl)piperazine-2-carboxamide

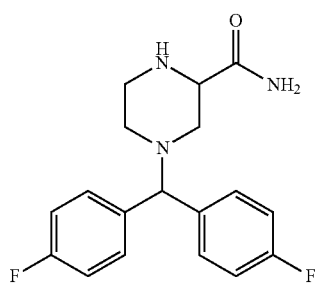

(I-107)

To a solution of tert-butyl 4-(bis(4-fluorophenyl)methyl)-2-carbamoylpiperazine-1-carboxylate (100 mg, 0.232 mmol) in dioxane (5 mL) at room temperature was added HCl in 1,4-dioxane (0.579 mL, 2.318 mmol). The reaction mixture was stirred at room temperature for 3 h. and concentrated under reduced pressure. The residue was washed with mixture of petroleum ether: diethyl ether (1:1) and dried under high vacuum to yield 4-(bis(4-fluorophenyl) methyl)piperazine-2-carboxamide, HCl (75 mg, 45.9% yield); LCMS: m/z=332.3 (M+H); rt 1.25 min. LCMS Method: Mobile phase A: Buffer:acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 µm, Flow: 0.7 mL/min.

Examples 141 and 142

4-(bis(4-fluorophenyl)methyl)-1-(6-cyano-1-methyl-2-oxo-1,2-dihydro-1,5-naphthyridin-4-yl)piperazine-2-carboxamide residue was dissolved in DCM, washed with water and brine, dried over sodium sulfate, and concentrated under reduced pressure to yield an enantiomeric mixture. Enantiomers were separated using chiral HPLC. Chiral separation method: Column: DAD-1 CELLULOSE-2 (250×4.6 mm), 5 µm, DAD-2 CELLULOSE-4 (250×4.6 mm), 5 micron Mobile Phase: 0.1% DEA in acetonitrile:methanol:70:30 Flow: 2.0 mL\min of enantiomeric mixture afforded Example 141 (Enantiomer 1) and Example 142 (Enantiomer 2). Fractions containing the product were combined and dried via centrifugal evaporation.

Example 141: Enantiomer 1: (5.9 mg, 1.9% yield); LCMS: m/z=515.2 (M+H); rt 1.846 min; LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 µm. $^1$H NMR (400 MHz, DMSO-$d_6$) δ ppm 8.14 (d, J=8.8 Hz, 1H), 8.07 (d, J=8.8 Hz, 1H), 7.57-7.34 (m, 4H), 7.28-7.06 (m, 5H), 6.99 (br. s., 1H), 6.08 (s, 1H), 5.33 (br. s., 1H), 4.45 (s, 1H), 3.86-3.69 (m, 1H), 3.62-3.41 (m, 4H), 3.28 (br. s., 1H), 2.75 (d, J=10.0 Hz, 1H), 2.38 (dd, J=11.9, 3.8 Hz, 1H), 2.26-2.11 (m, 1H).

Example 142: Enantiomer 2: (6.4 mg, 2.1% yield); LCMS: m/z=515.2 (M+H); rt 1.846 min; LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 µm. H NMR (400 MHz, DMSO-d6) δ ppm 8.14 (d, J=8.8 Hz, 1H), 8.07 (d, J=8.8 Hz, 1H), 7.61-7.38 (m, 4H), 7.31-7.05 (m, 5H), 6.99 (br. s., 1H), 6.08 (s, 1H), 5.33 (br. s., 1H), 4.45 (s, 1H), 3.85-3.71 (m, 1H), 3.61-3.42 (m, 4H), 3.28 (br. s., 1H), 2.75 (d, J=10.3 Hz, 1H), 2.38 (dd, J=11.7, 3.9 Hz, 1H), 2.25-2.11 (m, 1H).

Examples 143 and 144

8-(4-(bis(4-fluorophenyl)methyl)-2-cyanopiperazin-1-yl)-5-methyl-6-oxo-5,6-dihydro-1,5-naphthyridine-2-carbonitrile

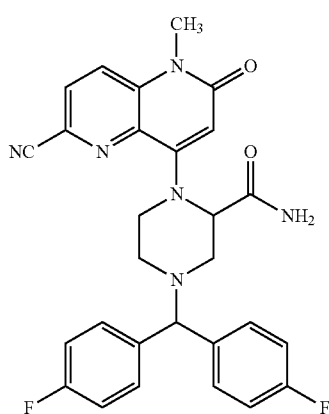

(141-142)

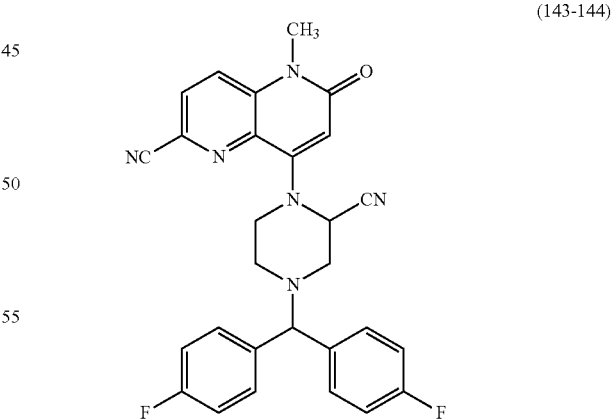

(143-144)

To a solution of 6-cyano-1-methyl-2-oxo-1,2-dihydro-1,5-naphthyridin-4-yl trifluoromethanesulfonate (200 mg, 0.600 mmol) in acetonitrile (5 mL) at room temperature was added 4-(bis(4-fluorophenyl)methyl)piperazine-2-carboxamide, HCl (221 mg, 0.600 mmol) and DIPEA (0.314 mL, 1.800 mmol). The reaction mixture was stirred at 80° C. overnight and concentrated under reduced pressure. The To a solution of 4-(bis(4-fluorophenyl)methyl)-1-(6-cyano-1-methyl-2-oxo-1,2-dihydro-1,5-naphthyridin-4-yl) piperazine-2-carboxamide (200 mg, 0.389 mmol) in DCM (5 mL) at 0° C. were added TEA (0.217 mL, 1.555 mmol) and trifluoroacetic anhydride (0.110 mL, 0.777 mmol). The reaction mixture was stirred at room temperature for 1 h. The reaction was quenched with 10% NaHCO$_3$ solution. The reaction mixture was extracted with DCM and the organic layer was washed with water and brine, dried over sodium sulfate, and concentrated under reduced pressure to yield an enantiomeric mixture. Enantiomers were separated using chiral HPLC. Chiral separation method: MPB: 0.1% DEA acetonitrile, Column: Cellulose-C5 (30*250 mm), 5 μm Gradient:-Time: 0.00 20.00% of B Conc.: 100 100 Flow: 30 mL/min. Fractions containing the product were combined and dried via centrifugal evaporation.

Example 143: Enantiomer 1: (2.4 mg, 1.2% yield); LCMS: m/z=497.2 (M+H); rt 2.096 min. A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 μm. $^1$H NMR (400 MHz, DMSO-$d_6$) δ ppm 8.22 (d, J=8.8 Hz, 1H), 8.16 (d, J=9.0 Hz, 1H), 7.52 (dt, J=8.6, 5.5 Hz, 4H), 7.30-7.10 (m, 4H), 6.35 (s, 1H), 5.89 (br. s., 1H), 4.67 (s, 1H), 3.58 (s, 3H), 3.48 (d, J=12.5 Hz, 1H), 3.29-3.22 (m, 1H), 3.10 (d, J=11.7 Hz, 1H) 2.90-2.86 (m, 1H), 2.28 (t, J=11.4 Hz, 1H) (one proton merged with DMSO-$d_6$ residual peak).

Example 144: Enantiomer 2: (2 mg, 1.0% yield); LCMS: m/z=497.2 (M+H); rt 2.097 min. LCMS Method: A: 95% water:5% acetonitrile; 10 mM ammonium acetate B: 5% water:95% acetonitrile; 10 mM ammonium acetate Flow: 1.1 mL/min. Temp: 50° C. Column: XBridge BEH XP C18 (50×2.1) mm, 2.5 μm. $^1$H NMR (400 MHz, DMSO-$d_6$) δ ppm 8.21 (d, J=8.8 Hz, 1H), 8.16 (d, J=8.8 Hz, 1H), 7.62-7.41 (m, 4H), 7.21 (td, J=8.9, 2.3 Hz, 4H), 6.35 (s, 1H), 5.89 (br. s., 1H), 4.67 (s, 1H), 3.58 (s, 3H), 3.47 (d, J=11.5 Hz, 1H), 3.29-3.21 (m, 1H), 3.10 (d, J=11.7 Hz, 1H), 2.93-2.82 (m, 1H), 2.32-2.21 (m, 1H).

Example 145

8-(4-(bis(4-fluorophenyl)methyl)-2-cyanopiperazin-1-yl)-5-methyl-6-oxo-5,6-dihydro-1,5-naphthyridine-2-carbonitrile

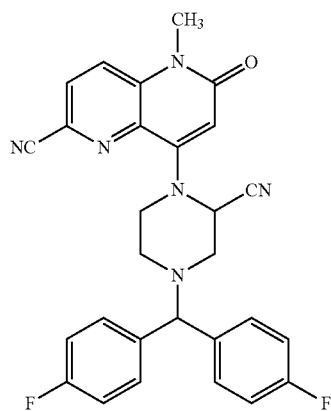

(145)

To a solution of 4-(bis(4-fluorophenyl)methyl)-1-(6-cyano-1-methyl-2-oxo-1,2-dihydro-1,5-naphthyridin-4-yl) piperazine-2-carboxamide (30 mg, 0.058 mmol) in DCM (5 mL) at 0° C. were added TEA (0.033 mL, 0.233 mmol) and trifluoroacetic anhydride (0.016 mL, 0.117 mmol). The reaction mixture was stirred at room temperature for 1 h. The reaction was quenched with 10% NaHCO$_3$ solution. The reaction mixture was extracted with DCM. The organic layer was washed with water and brine, dried over sodium sulfate, and concentrated under reduced pressure. The crude material was purified via preparative HPLC with the following conditions: Column: Sunfire C18, 21×150 mm, 5 μm particles; Mobile Phase A: 10 mM ammonium acetate pH-4.5 with acetic acid; Mobile Phase B: acetonitrile; Gradient: 50-70% B over 9 minutes, then a 5 minute hold at 100% B; Flow: 20 mL/min. Fractions containing the product were combined and dried via centrifugal evaporation to yield the 8-(4-(bis(4-fluorophenyl)methyl)-2-cyanopiperazin-1-yl)-5-methyl-6-oxo-5,6-dihydro-1,5-naphthyridine-2-carbonitrile (2.5 mg, 8.4% yield); LCMS: m/z=497.2 (M+H); rt 2.02 min. LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 μm. $^1$H NMR (400 MHz, DMSO-$d_6$) δ ppm 8.21 (d, J=8.8 Hz, 1H), 8.16 (d, J=9.0 Hz, 1H), 7.52 (dt, J=8.7, 5.6 Hz, 4H), 7.32-7.12 (m, 4H), 6.35 (s, 1H), 5.89 (br. s., 1H), 4.67 (s, 1H), 3.58 (s, 3H), 3.47 (d, J=12.0 Hz, 1H), 3.26 (br. s., 1H), 3.10 (d, J=12.5 Hz, 1H), 2.87 (d, J=13.4 Hz, 1H), 2.28 (t, J=10.4 Hz, 1H). One proton peak was obscured with moisture peak.

Examples 146 to 148

8-(4-(bis(4-fluorophenyl)methyl)-2-(hydroxymethyl) piperazin-1-yl)-5-methyl-6-oxo-5,6-dihydro-1,5-naphthyridine-2-carbonitrile

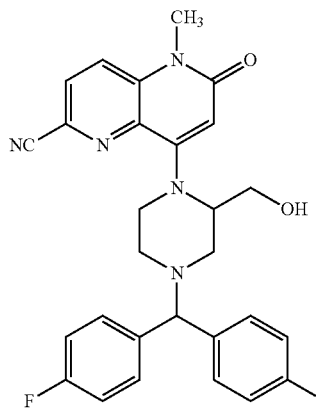

(146-148)

To a solution of 6-cyano-1-methyl-2-oxo-1,2-dihydro-1,5-naphthyridin-4-yl trifluoromethanesulfonate (650 mg, 1.951 mmol) in acetonitrile (5 mL) at room temperature were added (4-(bis(4-fluorophenyl)methyl)piperazin-2-yl) methanol, HCl (692 mg, 1.951 mmol) and DIPEA (1.022 mL, 5.85 mmol). The reaction mixture was stirred at 85° C. overnight and concentrated under reduced pressure. The residue was dissolved in EtOAc, washed with water and brine, dried over sodium sulfate, and concentrated under reduced pressure. The crude compound was purified by ISCO® (using 24 g silica gel column; using 20%-40% ethyl acetate/petroleum ether). The fractions were concentrated under reduced pressure to an enantiomeric mixture. The compound was further purified by preparative HPLC with the following conditions: Column: Sunfire C18, 19×150 mm, 5 μm particles; Mobile Phase A: 10 mM ammonium acetate pH-4.5 with acetic acid; Mobile Phase B: methanol: acetonitrile (1:1); Gradient: 60-100% B over 20 minutes, then a 5 minute hold at 100% B; Flow: 17 mL/min. Fractions containing the product were combined and dried via centrifugal evaporation.

Example 146: Racemate: Chiral separation Column: Cellulose C2 (250*21 mm) 5 micron Mobile Phase A: 0.1% DEA in acetonitrile:IPA (90:10) Mobile Phase B: Flow: 20 mL/min of enantiomeric mixture gave Enantiomer 1 and Enantiomer 2.

Example 147: Enantiomer 1: (7.5 mg, 0.7% yield); LCMS: m/z=502.3 (M+H); rt 1.525 min; LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 µm. $^1$H NMR (400 MHz, DMSO-d6) δ ppm 8.13-8.17 (m, 1H), 8.04-8.07 (m, 1H), 7.46-7.51 (m, 4H), 7.12-7.19 (m, 4H), 6.02 (s, 1H), 4.90-4.99 (m, 1H), 4.41 (s, 1H), 3.80-3.87 (m, 1H), 3.65-3.70 (m, 1H), 3.53 (s, 3H), 3.35-3.44 (m, 2H), 3.27-3.33 (m, 1H), 2.86-2.95 (m, 1H), 2.27-2.32 (m, 1H), 2.05-2.18 (m, 1H).

Example 148: Enantiomer 2: (5.7 mg, 0.5% yield); LCMS: m/z=502.3 (M+H); rt 1.522 min; LCMS Method: A: 95% water:5% acetonitrile; 10 mM ammonium acetate B: 5% water:95% acetonitrile; 10 mM ammonium acetate Flow: 1.1 mL/min; Temp: 50° C. Column: XBridge BEH XP C18 (50×2.1) mm, 2.5 µm. $^1$H NMR (400 MHz, DMSO-d6) δ ppm 8.12-8.16 (m, 1H), 8.04-8.07 (m, 1H), 7.46-7.51 (m, 4H), 7.12-7.18 (m, 4H), 6.02 (s, 1H), 4.91-5.01 (m, 1H), 4.41 (s, 1H), 3.82-3.86 (m, 1H), 3.65-3.70 (m, 1H), 3.53 (s, 3H), 2.87-2.94 (m, 1H), 2.81-2.84 (m, 1H), 2.27-2.32 (m, 1H), 2.10-2.18 (m, 1H), (2 proton peaks obscured with moisture peak).

Examples 149 to 151

8-(4-(bis(4-fluorophenyl)methyl)-2-(fluoromethyl)piperazin-1-yl)-5-methyl-6-oxo-5,6-dihydro-1,5-naphthyridine-2-carbonitrile

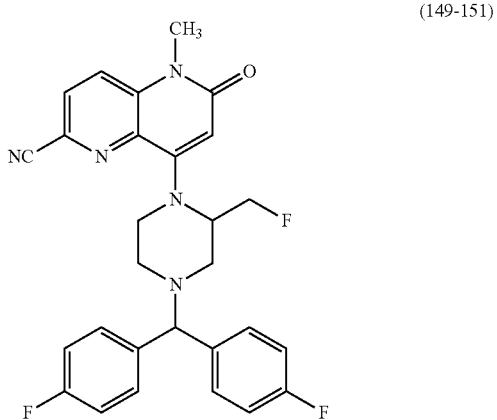 [SMILES: Cn1c(=O)cc(N2CCN(C(c3ccc(F)cc3)c3ccc(F)cc3)CC2CF)c2nc(C#N)ccc21]

(149-151)

To a solution of 8-(4-(bis(4-fluorophenyl)methyl)-2-(hydroxymethyl)piperazin-1-yl)-5-methyl-6-oxo-5,6-dihydro-1,5-naphthyridine-2-carbonitrile (140 mg, 0.279 mmol) in DCM (5 mL) at 0° C. was added DAST (0.037 mL, 0.279 mmol). The reaction mixture was stirred at room temperature for 30 mins. The reaction was quenched with NaHCO$_3$ solution. The reaction mixture was extracted with ethyl acetate (2×100 mL). The combined organic layer was washed with water and brine, and dried over sodium sulfate. The solvent was evaporated under reduced pressure to yield an enantiomeric mixture (Example 149). The crude product was purified by preparative HPLC (Prep LCMS method: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 5 minute hold at 30% B, 30-66% B over 20 minutes, then a 5 minute hold at 100% B; Flow Rate: 15 mL/min; Column Temperature: 25° C. Fraction collection was triggered by MS signals. Fractions containing the product were combined and dried via centrifugal evaporation.

Example 149: Racemate: Chiral separation Column: Lux-cellulose C4 (250×21.2) mm, 5 micron M. Phase A: M. Phase B: methanol Flow: 20 mL/min isocratic of enantiomeric mixture afford Enantiomer 1 and Enantiomer 2.

Example 150: Enantiomer 1: (2 mg, 1.4% yield); LCMS: m/z=504.2 (M+H); rt 2.20 min; LCMS Method: A: 95% water:5% acetonitrile; 10 mM ammonium acetate B: 5% water:95% acetonitrile; 10 mM ammonium acetate Flow: 1.1 mL/min Temp: 50° C. Column: XBridge BEH XP C18 (50×2.1) mm, 2.5 µm. H NMR (400 MHz, DMSO-d$_6$) δ ppm 8.16 (d, J=8.8 Hz, 1H), 8.05-8.12 (m, 1H), 7.44-7.55 (m, 4H), 7.12-7.20 (m, 4H), 6.10 (s, 1H), 5.28-5.39 (m, 1H), 4.93-5.14 (m, 1H), 4.55-4.74 (m, 1H), 4.43 (s, 1H), 3.48-3.55 (m, 4H), 3.24-3.29 (m, 1H), 2.82-2.89 (m, 2H), 2.36-2.42 (m, 1H), 2.13-2.21 (m, 1H)

Example 151: Enantiomer 2: (2 mg, 1.4% yield); LCMS: m/z=504.2 (M+H); rt 2.207 min; LCMS Method: A: 95% water:5% acetonitrile; 10 mM ammonium acetate B: 5% water:95% acetonitrile; 10 mM ammonium acetate; Flow: 1.1 mL/min; Temp: 50° C. Column: XBridge BEH XP C18 (50×2.1) mm, 2.5 µm $^1$H NMR (400 MHz, DMSO-d$_6$) δ ppm 8.16 (d, J=8.8 Hz, 1H), 8.06-8.11 (m, 1H), 7.45-7.56 (m, 4H), 7.13-7.20 (m, 4H), 6.10 (s, 1H), 5.28-5.38 (m, 1H), 4.93-5.13 (m, 1H), 4.56-4.74 (m, 1H), 4.43 (s, 1H), 3.48-3.56 (m, 4H), 3.25-3.29 (m, 1H), 2.81-2.88 (m, 2H), 2.36-2.43 (m, 1H), 2.12-2.23 (m, 1H).

Intermediate 108

2,5-dicyclopropylpiperazine, Diacetate Salt

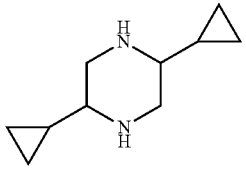

(I-108)

To a solution of 2,5-dicyclopropylpyrazine (100 mg, 0.624 mmol) in acetic acid (5 mL) at room temperature was added platinum(IV) oxide (35 mg, 0.154 mmol). The reaction vessel was evacuated and a hydrogen balloon was applied. The reaction mixture was stirred at room temperature under a hydrogen atmosphere for 5 h. The hydrogen balloon was removed and the reaction mixture was filtered through a celite bed. The filtrate was concentrated under reduced pressure to yield residue. The residue was washed with 1:1 diethyl ether: petroleum ether and dried under high vacuum to yield the 2,5-dicyclopropylpiperazine, diacetic acid salt (130 mg, 52.2% yield); LCMS: m/z 167.4 (M+H); rt 0.45 min. LCMS Method: Mobile phase A: Buffer:

acetonitrile (95:5) Mobile phase B: Buffer:acetonitrile (5:95) Method: % B: 0 min-20%:1.1 min-90%:1.7 min-90% Column: AQUITY UPLC BEH C18 (3.0×50 mm) 1.7 μm, Flow: 0.7 mL/min.

Intermediate 109

1-(bis(4-fluorophenyl)methyl)-2,5-dicyclopropylpiperazine

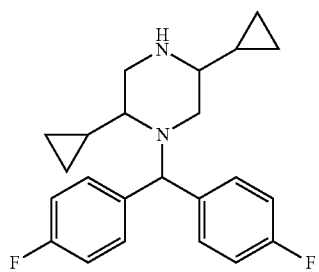

(I-109)

To a solution of 4,4'-(chloromethylene)bis(fluorobenzene) (60 mg, 0.251 mmol) in acetonitrile (20 mL) at room temperature were added 2,5-dicyclopropylpiperazine (41.8 mg, 0.251 mmol) and DIPEA (0.132 mL, 0.754 mmol). The reaction mixture was heated to 80° C. overnight. The crude reaction mixture was concentrated under reduced pressure. The residue was dissolved in DCM and washed with water and brine, dried over sodium sulfate, and concentrated under reduced pressure. The crude product was purified by silica gel column chromatography using 24 g flash column and 5% methanol in CHCl₃. The fractions were concentrated under reduced pressure to yield 1-(bis(4-fluorophenyl)methyl)-2,5-dicyclopropylpiperazine (40 mg, 16.0% yield); LCMS: m/z 369.4 (M+H); rt 1.65 and 1.71 min. LCMS Method: Mobile phase A: Buffer:acetonitrile (95:5) Mobile phase B: Buffer:acetonitrile (5:95) Method: % B: 0 min-20%:1.1 min-90%: 1.7 min-90% Column: AQUITY UPLC BEH C18 (3.0×50 mm) 1.7 μm, Flow: 0.7 mL/min.

Examples 152 and 153

8-(4-(bis(4-fluorophenyl)methyl)-2,5-dicyclopropylpiperazin-1-yl)-5-methyl-6-oxo-5,6-dihydro-1,5-naphthyridine-2-carbonitrile

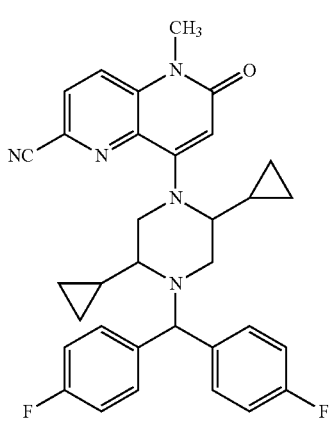

(152-153)

To a solution of 1-(bis(4-fluorophenyl)methyl)-2,5-dicyclopropylpiperazine (65 mg, 0.176 mmol) in acetonitrile (2 mL) at room temperature was added DIPEA (0.092 mL, 0.529 mmol). The reaction mixture was stirred at 85° C. for 10 mins and 6-cyano-1-methyl-2-oxo-1,2-dihydro-1,5-naphthyridin-4-yl trifluoromethanesulfonate (58.8 mg, 0.176 mmol) was added. The reaction mixture was heated to 85° C. overnight. The reaction mixture was concentrated under reduced pressure. The residue was dissolved in DCM, washed with water and brine, dried over sodium sulfate, and concentrated under reduced pressure. Chiral separation Column: Cellulose-C4 (250*21 mm) 5 μm; Mobile Phase A: Mobile Phase B: methanol Flow: 20 mL/min of isomeric mixture gave Isomer 1 and Isomer 2.

Example 152: Isomer 1: (0.6 mg, 0.6% yield); LCMS: m/z=552.3 (M+H); rt 1.81 min. LCMS Method: A: 95% water:5% acetonitrile; 10 mM ammonium acetate B: 5% water:95% acetonitrile; 10 mM ammonium acetate. Flow: 1.1 mL/min Temp: 50° C. Column: XBridge BEH XP C18 (50×2.1) mm, 2.5 μm. ¹H NMR (400 MHz, DMSO-d₆) δ ppm 8.11-8.15 (m, 1H), 8.03-8.09 (m, 1H), 7.45-7.52 (m, 2H), 7.28-7.34 (m, 2H), 7.12-7.24 (m, 4H), 6.07 (s, 1H), 5.84 (s, 1H), 3.91-3.97 (m, 1H), 3.51-3.58 (m, 4H), 2.79-2.84 (m, 1H), 2.35-2.38 (m, 1H), 1.99-2.06 (m, 1H), 1.78-1.88 (m, 1H), 0.98-1.11 (m, 1H), 0.83-0.89 (m, 1H), 0.67-0.74 (m, 1H), 0.52-0.61 (m, 1H), 0.41-0.48 (m, 2H), 0.32-0.41 (m, 1H), 0.23-0.31 (m, 1H), −0.08-0.02 (m, 1H), −0.28-0.15 (m, 1H).

Example 153: Isomer 2: (0.5 mg, 1.0% yield); LCMS: m/z=552.3 (M+H); rt 2.55 min. LCMS Method: A: 95% water:5% acetonitrile; 10 mM ammonium acetate B: 5% water:95% acetonitrile; 10 mM ammonium acetate; Flow: 1.1 mL/min; Temp: 50° C. Column: XBridge BEH XP C18 (50×2.1) mm, 2.5 μm. ¹H NMR (400 MHz, DMSO-d₆) δ ppm 8.18-8.09 (m, 1H), 8.09-7.99 (m, 1H), 7.48 (dd, J=8.0, 5.5 Hz, 2H), 7.30 (dd, J=8.5, 5.5 Hz, 2H), 7.26-6.98 (m, 4H), 6.07 (s, 1H), 5.84 (s, 1H), 3.92 (br.s., 1H), 3.59-3.49 (m, 3H), 3.42 (d, J=1.0 Hz, 2H), 2.82 (d, J=9.0 Hz, 1H), 2.36 (br. s., 1H), 2.03 (d, J=9.0 Hz, 1H), 1.83 (br. s., 2H), 0.86 (d, J=8.0 Hz, 1H), 0.70 (br. s., 1H), 0.55 (d, J=5.0 Hz, 1H), 0.43 (br. s., 1H), 0.37 (br. s., 1H), 0.28 (d, J=5.5 Hz, 1H), −0.04 (d, J=4.5 Hz, 1H), −0.22 (br. s., 1H).

Intermediate 111 tert-butyl 4-(bis(4-fluorophenyl)methyl)-2-phenylpiperazine-1-carboxylate

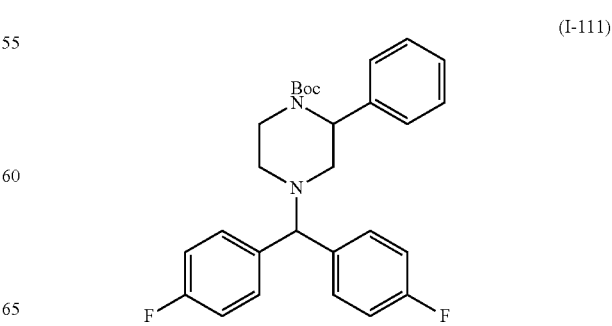

(I-111)

To a solution of 4,4'-(chloromethylene)bis(fluorobenzene) (75 mg, 0.314 mmol) in acetonitrile (20 mL) at room temperature were added tert-butyl 2-phenylpiperazine-1-carboxylate (91 mg, 0.346 mmol) and DIPEA (0.165 mL, 0.943 mmol) The reaction mixture was heated to 80° C. overnight and concentrated under reduced pressure. The residue was dissolved in DCM, washed with water and brine, dried over sodium sulfate, and concentrated under reduced pressure. The crude residue was purified by silica gel column chromatography using 24 g flash column, eluting with 30% EtOAc in petroleum ether. The fractions were concentrated under reduced pressure to yield the product tert-butyl 4-(bis(4-fluorophenyl)methyl)-2-phenylpiperazine-1-carboxylate (100 mg, 65.2% yield); LCMS: m/z=465.5 (M+H); rt 1.63 min. LCMS Method: M. phase A: 10 mM ammonium acetate:acetonitrile (95:5) Mobile phase B: 10 mM ammonium acetate:acetonitrile (5:95) Method: % B: 0 min-20:2 min-100:2.3 min-100 Flow: 0.7 mL/min Column: AQUITY UPLC BEH C18 (3.0×50 mm) 1.7 µm.

Intermediate 112

1-(bis(4-fluorophenyl)methyl)-3-phenylpiperazine, HCl

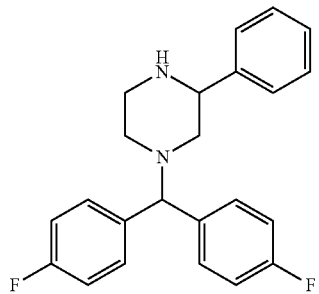

(I-112)

To a solution of tert-butyl 4-(bis(4-fluorophenyl)methyl)-2-phenylpiperazine-1-carboxylate (80 mg, 0.172 mmol) in dioxane (5 mL) at 0° C. was added HCl in dioxane (0.052 mL, 1.722 mmol). The reaction mixture was stirred at room temperature for 2 h. and concentrated under reduced pressure. The residue was washed with petroleum ether:diethyl ether (1:1) and dried under high vacuum to yield 1-(bis(4-fluorophenyl)methyl)-3-phenylpiperazine, HCl (60 mg, 58.8% yield); LCMS: m/z 365.4 (M+H); rt 0.80 min. LCMS Method: M. phase A: 10 mM ammonium acetate:acetonitrile (95:5); Mobile phase B: 10 mM ammonium acetate:acetonitrile (5:95) Method: % B: 0 min-20:2 min-100:2.3 min-100; Flow: 0.7 mL/min Column: AQUITY UPLC BEH C18 (3.0×50 mm) 1.7 µm.

Examples 154 to 156

8-(4-(bis(4-fluorophenyl)methyl)-2-phenylpiperazin-1-yl)-5-methyl-6-oxo-5,6-dihydro-1,5-naphthyridine-2-carbonitrile

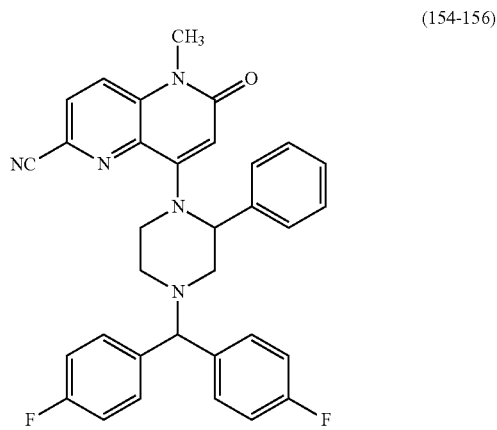 [SMILES: Cn1c(=O)cc(N2CCN(C(c3ccc(F)cc3)c3ccc(F)cc3)CC2c2ccccc2)c2nc(C#N)ccc21]

(154-156)

To a solution of 1-(bis(4-fluorophenyl)methyl)-3-phenylpiperazine, HCl (80 mg, 0.200 mmol) in acetonitrile (2 mL) at room temperature was added DIPEA (0.105 mL, 0.599 mmol). The reaction mixture was stirred at 85° C. for 10 mins and 6-cyano-1-methyl-2-oxo-1,2-dihydro-1,5-naphthyridin-4-yl trifluoromethanesulfonate (66.5 mg, 0.200 mmol) was added. The reaction mixture was heated to 85° C. overnight and concentrated under reduced pressure. The residue was dissolved in DCM, and the organic layer was washed with water (50 mL) and brine (50 mL), dried over $Na_2SO_4$, and concentrated under reduced pressure to afford Example 154 (Racemate). Enantiomers were separated using chiral HPLC. Chiral separation Method: Column/dimensions: Lux Amylose-2 (250×4.6) mm, 5 µm; % $CO_2$: 85%; % Cosolvent: 15% of 0.2% DEA in ethanol; Total Flow: 4.0 g/min; Back Pressure: 100 bar; Temperature: 30° C.; UV: 225 nm.

Example 155: Enantiomer 1: (6.4 mg, 5.86% yield); LCMS: m/z=548.2 (M+H); rt 2.405 min. LCMS Method: A: 95% water:5% acetonitrile; 10 mM ammonium acetate B: 5% water:95% acetonitrile; 10 mM ammonium acetate; Flow: 1.1 mL/min; Temp: 50° C. Column: XBridge BEH XP C18 (50×2.1) mm, 2.5 µm. H NMR (400 MHz, DMSO-d6) δ ppm 8.14-8.20 (m, 1H), 8.05-8.09 (m, 1H), 7.41-7.51 (m, 4H), 7.31-7.34 (m, 2H), 7.24-7.29 (m, 2H), 7.10-7.21 (m, 5H), 6.00 (s, 1H), 5.28-5.38 (m, 1H), 4.50 (s, 1H), 3.78-3.88 (m, 1H), 3.48 (s, 3H), 3.25 (br d, J=16.4 Hz, 1H), 2.61-2.77 (m, 3H), 2.52-2.58 (m, 1H).

Example 156: Enantiomer 2: (5.5 mg, 4.93% yield); LCMS: m/z=548.2 (M+H); rt 2.404 min. LCMS Method: A: 95% water:5% acetonitrile; 10 mM ammonium acetate B: 5% water:95% acetonitrile; 10 mM ammonium acetate; Flow: 1.1 mL/min; Temp: 50° C.; Column: XBridge BEH XP C18 (50×2.1) mm, 2.5 µm$^1$H NMR (400 MHz, DMSO-d6) δ ppm 8.15-8.18 (m, 1H), 8.07 (d, J=8.8 Hz, 1H), 7.41-7.50 (m, 4H), 7.31-7.34 (m, 2H), 7.24-7.29 (m, 2H), 7.10-7.21 (m, 5H), 6.00 (s, 1H), 5.27-5.38 (m, 1H), 4.50 (s, 1H), 3.76-3.89 (m, 1H), 3.48 (s, 3H), 3.21-3.28 (m, 1H), 2.66-2.76 (m, 3H), (1H obscured with solvent residual peak).

Example 157

8-((2S,5R)-4-(bis(4-fluorophenyl)methyl)-2,5-dimethylpiperazin-1-yl)-7-fluoro-5-methyl-6-oxo-5,6-dihydro-1,5-naphthyridine-2-carbonitrile

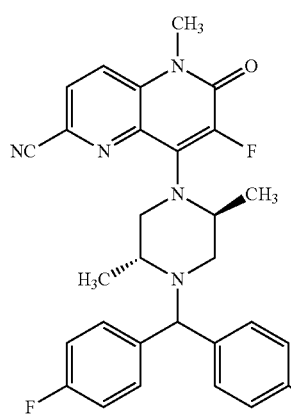

(157)

To a solution of 8-((2S,5R)-4-(bis(4-fluorophenyl)methyl)-2,5-dimethylpiperazin-1-yl)-5-methyl-6-oxo-5,6-dihydro-1,5-naphthyridine-2-carbonitrile (50 mg, 0.055 mmol) in acetonitrile (1 mL) was added Selectfluor (19.50 mg, 0.055 mmol) dissolved in water (0.15 mL) and THF (0.15 mL) at ° C. The reaction mixture was placed under nitrogen and stirred at 0° C., warmed to room temperature over 1.5 h, and then stirred for 3 h. The solvent was removed under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 31% B, 31-75% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 8-((2S,5R)-4-(bis(4-fluorophenyl)methyl)-2,5-dimethylpiperazin-1-yl)-7-fluoro-5-methyl-6-oxo-5,6-dihydro-1,5-naphthyridine-2-carbonitrile (3.6 mg, 12.6% yield); LCMS: m/z=518.3 (M+H); rt 2.391 min; Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.26-8.03 (m, 2H), 7.67-7.50 (m, 4H), 7.15 (td, J=8.8, 6.4 Hz, 4H), 4.77 (s, 1H), 4.20 (d, J=6.6 Hz, 1H), 4.01 (d, J=12.2 Hz, 1H), 3.61 (s, 3H), 3.07-2.91 (m, 2H), 2.90 (s, 1H), 2.29 (d, J=9.8 Hz, 1H), 1.30 (d, J=6.6 Hz, 3H), 1.00 (d, J=6.4 Hz, 3H).

Example 158

4-((2S,5R)-4-(bis(4-fluorophenyl)methyl)-2,5-dimethylpiperazin-1-yl)-6-bromo-1-methyl-2-oxo-1,2-dihydro-1,5-naphthyridine-3-carbonitrile

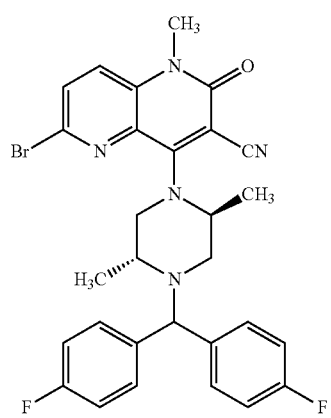

(158)

To a stirred solution of 6-bromo-3-cyano-1-methyl-2-oxo-1,2-dihydro-1,5-naphthyridin-4-yl trifluoromethanesulfonate (0.1 g, 0.243 mmol) and (2R,5S)-1-(bis(4-fluorophenyl)methyl)-2,5-dimethylpiperazine, HCl (0.077 g, 0.243 mmol) in acetonitrile (10 mL) was added DIPEA (0.127 mL, 0.728 mmol). The reaction mixture was heated to 85° C. for 2 h. The solvent was removed under reduced pressure. The crude compound was purified by Combi (24 g column silica, eluted with 0-5% methanol/DCM) to afford 4-((2S,5R)-4-(bis(4-fluorophenyl)methyl)-2,5-dimethylpiperazin-1-yl)-6-bromo-1-methyl-2-oxo-1,2-dihydro-1,5-naphthyridine-3-carbonitrile (65 mg, 38.7% yield) as a semi-solid; LCMS: m/z=580.2 (M+H); rt 2.30 min. Method: Column-AQUITY UPLC BEH C18 (3.0×50 mm) 1.7 µm; Mobile phase A: Buffer:acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Example 159

8-((2S,5R)-4-(bis(4-fluorophenyl)methyl)-2,5-dimethylpiperazin-1-yl)-5-methyl-6-oxo-5,6-dihydro-1,5-naphthyridine-2,7-dicarbonitrile

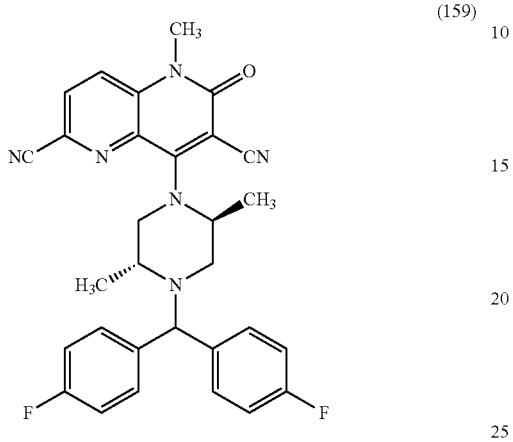

(159)

A stirred solution of 4-((2S,5R)-4-(bis(4-fluorophenyl)methyl)-2,5-dimethylpiperazin-1-yl)-6-bromo-1-methyl-2-oxo-1,2-dihydro-1,5-naphthyridine-3-carbonitrile (50 mg, 0.086 mmol), dppf (2.88 mg, 5.19 μmol), zinc (1.130 mg, 0.017 mmol) and zinc cyanide (20.30 mg, 0.173 mmol) in NMP (1 mL) was degassed for 1 min under a nitrogen atmosphere. Next, $Pd_2(dba)_3$ (7.92 mg, 8.64 μmol) was added and the reaction mixture was heated to 80° C. for 2 h. The reaction mixture was diluted with ethyl acetate washed with water, the organic layer was dried over anhydrous $Na_2SO_4$, filtered and evaporated under reduced pressure. The crude material was purified via preparative HPLC with the following conditions: Column: Waters XBridge C18, 150 mm×19 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 2 minute hold at 12% B, 12-57% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 8-((2S,5R)-4-(bis(4-fluorophenyl)methyl)-2,5-dimethylpiperazin-1-yl)-5-methyl-6-oxo-5,6-dihydro-1,5-naphthyridine-2,7-dicarbonitrile (8.9 mg, 19.6% yield); LCMS: m/z=525.3 (M+H); rt 2.361 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1H$ NMR (400 MHz, DMSO-$d_6$) δ ppm 8.26 (d, J=8.8 Hz, 1H), 8.16 (d, J=9.0 Hz, 1H), 7.62 (dd, J=10.9, 5.3 Hz, 2H), 7.64 (dd, J=10.9, 5.5 Hz, 2H), 7.26-7.07 (m, 4H), 4.74 (s, 2H), 4.27-4.18 (m, 1H), 3.54 (s, 3H), 3.42 (d, J=11.2 Hz, 1H), 3.17-3.08 (m, 1H), 3.03 (br. s., 1H), 2.41 (d, J=12.0 Hz, 1H), 1.44 (d, J=6.6 Hz, 3H), 0.94-0.86 (m, 3H).

Example 160

4-((2S,5R)-4-(bis(4-fluorophenyl)methyl)-2,5-dimethylpiperazin-1-yl)-1-methyl-2-oxo-1,2-dihydro-1,5-naphthyridine-3-carbonitrile

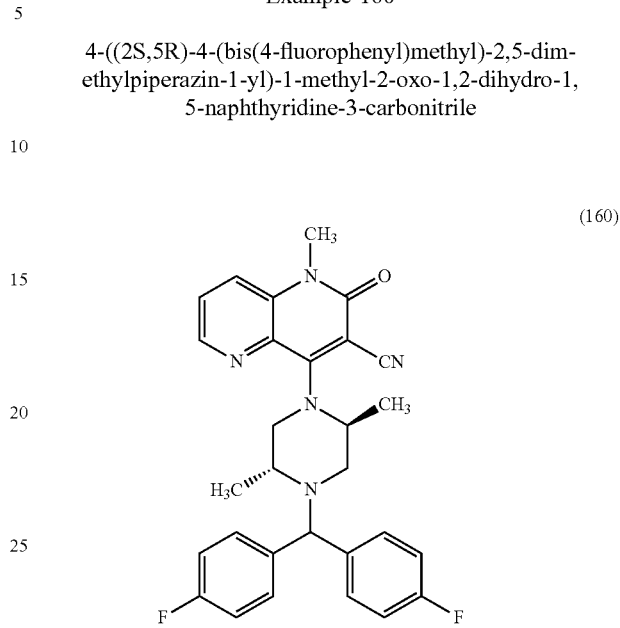

(160)

To a stirred solution of 4-((2S,5R)-4-(bis(4-fluorophenyl)methyl)-2,5-dimethylpiperazin-1-yl)-6-bromo-1-methyl-2-oxo-1,2-dihydro-1,5-naphthyridine-3-carbonitrile (50 mg, 0.086 mmol) in ethyl acetate (2 mL) was added 10% Pd—C (60 mg, 0.056 mmol). The reaction mixture was stirred at room temperature for 16 h under a hydrogen atmosphere. The reaction mixture was filtered through a celite pad, washed with ethyl acetate, and the filtrate was evaporated under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 20% B, 20-75% B over 25 minutes, then a 5 minute hold at 100% B; Flow Rate: 15 mL/min; Column Temperature: 25° C. Fractions containing the product were combined and dried via centrifugal evaporation to yield 4-((2S,5R)-4-(bis(4-fluorophenyl)methyl)-2,5-dimethylpiperazin-1-yl)-1-methyl-2-oxo-1,2-dihydro-1,5-naphthyridine-3-carbonitrile (18.9 mg, 43.8% yield); LCMS: m/z=500.3 (M+H); rt 2.5763 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1H$ NMR (400 MHz, DMSO-$d_6$) δ ppm 8.53 (d, J=3.2 Hz, 1H), 8.00 (d, J=7.6 Hz, 1H), 7.70 (dd, J=8.6, 4.4 Hz, 1H), 7.67-7.44 (m, 4H), 7.15 (td, J=8.8, 2.9 Hz, 4H), 4.90 (br. s., 1H), 4.71 (s, 1H), 4.26 (d, J=9.3 Hz, 1H), 3.53 (s, 3H), 3.39 (d, J=13.2 Hz, 1H), 3.14 (d, J=8.3 Hz, 1H), 3.02 (d, J=6.4 Hz, 1H), 2.35 (d, J=11.7 Hz, 1H), 1.41 (d, J=6.6 Hz, 3H), 0.89 (d, J=6.4 Hz, 3H).

Example 161

8-((2S,5R)-4-(bis(4-fluorophenyl)methyl)-2,5-dimethylpiperazin-1-yl)-5-methyl-7-nitro-6-oxo-5,6-dihydro-1,5-naphthyridine-2-carbonitrile

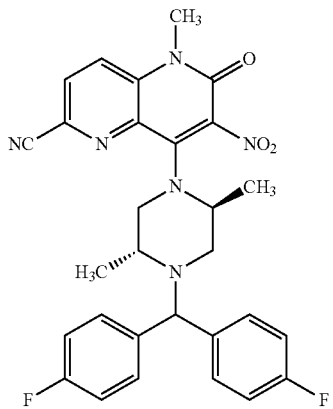

(161)

To a stirred solution of (2R,5S)-1-(bis(4-fluorophenyl)methyl)-2,5-dimethylpiperazine, HCl (78 mg, 0.222 mmol) in dry acetonitrile (3 mL) was added DIPEA (0.032 mL, 0.185 mmol), followed by 6-cyano-1-methyl-3-nitro-2-oxo-1,2-dihydro-1,5-naphthyridin-4-yl trifluoromethanesulfonate (70 mg, 0.185 mmol). The reaction mixture was heated at 85° C. for 2 h. The reaction mixture was cooled to room temperature and the solvent was removed under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 20% B, 20-75% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 8-((2S,5R)-4-(bis(4-fluorophenyl)methyl)-2,5-dimethylpiperazin-1-yl)-5-methyl-7-nitro-6-oxo-5,6-dihydro-1,5-naphthyridine-2-carbonitrile (82.8 mg, 80% yield); LCMS: m/z=545.2 (M+H); rt 2.383 min. Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate). $^1$H NMR (400 MHz, DMSO-$d_6$) δ ppm 8.29 (d, J=8.8 Hz, 1H), 8.21 (d, J=9.0 Hz, 1H), 7.59 (ddd, J=8.8, 5.4, 3.4 Hz, 4H), 7.13 (td, J=8.8, 1.7 Hz, 4H), 4.76 (s, 1H), 4.65 (d, J=5.9 Hz, 1H), 3.75 (dd, J=12.0, 2.9 Hz, 1H), 3.59 (s, 3H), 3.11 (dd, J=11.4, 3.5 Hz, 1H), 3.02-2.91 (m, 1H), 2.64 (d, J=11.5 Hz, 1H), 2.37-2.29 (m, 1H), 1.36 (d, J=6.6 Hz, 3H), 0.94 (d, J=6.6 Hz, 3H).

Intermediate 113

7-bromo-8-hydroxy-5-methyl-6-oxo-5,6-dihydro-1,5-naphthyridine-2-carbonitrile

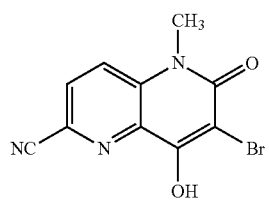

(I-113)

To a stirred solution of 8-hydroxy-5-methyl-6-oxo-5,6-dihydro-1,5-naphthyridine-2-carbonitrile (1000 mg, 4.97 mmol) in dry DMF (10 mL) was added NBS (973 mg, 5.47 mmol). The reaction mixture was stirred at room temperature for 3 h. The solvent was removed under reduced pressure to yield residue. The residue was dissolved in water and stirred for 10 min. The solid material was filtered and washed with petroleum ether to yield 7-bromo-8-hydroxy-5-methyl-6-oxo-5,6-dihydro-1,5-naphthyridine-2-carbonitrile (0.8 g, 56.9% yield) as an off-white solid; LCMS: m/z=282 (M+H); rt 1.599 min. Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then gradient: 100-20% B over 0.1 minutes, flow rate 1.5 mL/min.

Intermediate 114

3-bromo-6-cyano-1-methyl-2-oxo-1,2-dihydro-1,5-naphthyridin-4-yl trifluoromethanesulfonate

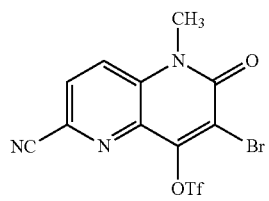

(I-114)

To a stirred solution of 7-bromo-8-hydroxy-5-methyl-6-oxo-5,6-dihydro-1,5-naphthyridine-2-carbonitrile (0.175 g, 0.625 mmol) and TEA (0.131 mL, 0.937 mmol) in dry DCM (10 mL) was added trifluoromethanesulfonic anhydride (0.137 mL, 0.812 mmol) at 0° C. The reaction mixture was stirred at room temperature for 3 h. The reaction mixture was diluted with DCM and washed with water, followed by brine wash, the organic layer was dried over anhydrous $Na_2SO_4$, filtered and evaporated under reduced pressure to yield 3-bromo-6-cyano-1-methyl-2-oxo-1,2-dihydro-1,5-naphthyridin-4-yl trifluoromethanesulfonate (190 mg, 53.9% yield) as a pale yellow solid; LCMS: m/z=414 (M+H); rt 1.61 min. Method: Column-AQUITY UPLC BEH C18 (3.0×50 mm) 1.7 µm; Mobile phase A: Buffer: acetonitrile (95:5); Mobile phase B: Buffer: acetonitrile (5:95), Buffer:

Example 162

Methyl 4-(bis(4-fluorophenyl)methyl)-1-(3-bromo-6-cyano-1-methyl-2-oxo-1,2-dihydro-1,5-naphthyridin-4-yl)piperazine-2-carboxylate

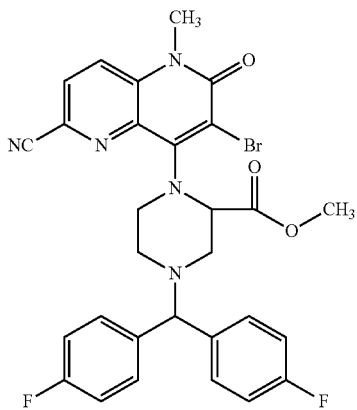

(162)

A solution of methyl 4-(bis(4-fluorophenyl)methyl)piperazine-2-carboxylate, HCl (134 mg, 0.349 mmol) and DIPEA (0.127 mL, 0.728 mmol) in acetonitrile (2 mL) was stirred at room temperature for 5 min. Next, 3-bromo-6-cyano-1-methyl-2-oxo-1,2-dihydro-1,5-naphthyridin-4-yl trifluoromethanesulfonate (120 mg, 0.291 mmol) was added and the reaction mixture was heated to 85° C. for 3 h. The reaction mixture was evaporated under reduced pressure. The crude material was purified via preparative HPLC with the following conditions: Column: Sunfire C18, 19×150 mm, 5 µm particles; Mobile Phase A: 10 mM ammonium acetate; Mobile Phase B: acetonitrile; Gradient: 50-80% B over 16 minutes, then a 5 minute hold at 100% B; Flow: 17 mL/min. Fractions containing the product were combined and dried via centrifugal evaporation to yield methyl 4-(bis (4-fluorophenyl)methyl)-1-(3-bromo-6-cyano-1-methyl-2-oxo-1,2-dihydro-1,5-naphthyridin-4-yl)piperazine-2-carboxylate (5.4 mg, 3.01% yield); LCMS: m/z 610.1 (M+H); rt 2.330 min. Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-$d_6$) δ ppm 8.17-8.21 (m, 1H), 8.11-8.16 (m, 1H), 7.42-7.51 (m, 4H), 7.13-7.21 (m, 5H), 4.78-4.83 (m, 1H), 4.48 (s, 1H), 4.04-4.14 (m, 1H), 3.74 (s, 3H), 3.64 (s, 3H), 3.52-3.59 (m, 1H), 3.08-3.15 (m, 1H), 2.69-2.75 (m, 1H), 2.53-2.55 (m, 1H), 2.35-2.41 (m, 1H).

Intermediate 115

8-(3,5-dimethylpiperazin-1-yl)-5-methyl-6-oxo-5,6-dihydro-1,5-naphthyridine-2-carbonitrile

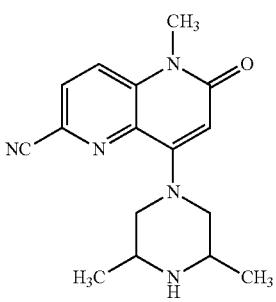

(I-115)

To a stirred solution of 6-cyano-1-methyl-2-oxo-1,2-dihydro-1,5-naphthyridin-4-yl trifluoromethanesulfonate (300 mg, 0.900 mmol) and 2,6-dimethylpiperazine (103 mg, 0.900 mmol) in acetonitrile (10 mL) was added DIPEA (0.472 mL, 2.70 mmol). The reaction mixture was heated to 85° C. for 16 h. The solvent was removed under reduced pressure to yield 8-(3,5-dimethylpiperazin-1-yl)-5-methyl-6-oxo-5,6-dihydro-1,5-naphthyridine-2-carbonitrile (0.22 g, 74.0% yield) as light brown solid. LCMS: m/z 298.4 (M+H); rt 0.62 min. Method: Column-AQUITY UPLC BEH C18 (3.0×50 mm) 1.7 µm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Example 163

8-(4-(bis(4-fluorophenyl)methyl)-3,5-dimethylpiperazin-1-yl)-5-methyl-6-oxo-5,6-dihydro-1,5-naphthyridine-2-carbonitrile

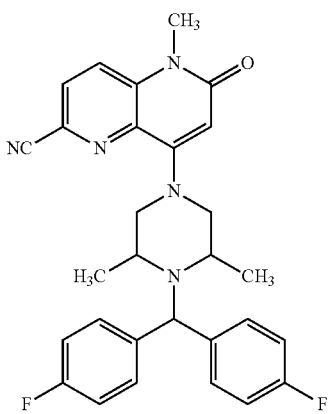

(163)

To a stirred solution of 8-(3,5-dimethylpiperazin-1-yl)-5-methyl-6-oxo-5,6-dihydro-1,5-naphthyridine-2-carbonitrile (101 mg, 0.341 mmol) and bis(4-fluorophenyl)methyl trifluoromethanesulfonate (150 mg, 0.426 mmol) in acetonitrile (5 mL) was added DIPEA (0.223 mL, 1.277 mmol). The reaction mixture was heated to 85° C. for 16 h. The solvent was removed under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-55% B over 25 minutes, then a 5 minute hold at 100% B; Flow Rate: 15 mL/min; Column Temperature: 25° C. Fractions containing the product were combined and dried via centrifugal evaporation to yield 8-(4-(bis(4-fluorophenyl)methyl)-3,5-dimethylpiperazin-1-yl)-5-methyl-6-oxo-5,6-dihydro-1,5-naphthyridine-2-carbonitrile (7.1 mg, 3.3% yield); LCMS: m/z=500.3 (M+H); rt 2.410 min. Method: Column-X Bridge BEH XP C18 (50× 2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-d$_6$) δ ppm 8.13 (d, J=8.0 Hz, 1H), 8.06 (d, J=8.5 Hz, 1H), 7.59 (dd, J=8.3, 5.8 Hz, 4H), 7.13 (t, J=8.5 Hz, 4H), 6.09 (s, 1H), 5.16 (s, 1H), 3.83 (d, J=11.0 Hz, 2H), 3.53 (s, 3H), 3.15-2.96 (m, 4H), 1.18 (d, J=6.5 Hz, 6H).

Intermediate 122 tert-butyl (R)-4-(bis(4-chlorophenyl)methyl-3-isopropylpiperazine-1-carboxylate

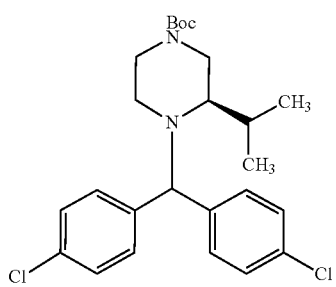

(I-122)

To a stirred solution of (R)-1-Boc-3-isopropyl-piperazine (100 mg, 0.438 mmol) and 4,4'-(bromomethylene)bis(chlorobenzene) (180 mg, 0.569 mmol) in acetonitrile (4 mL) was added DIPEA (0.229 mL, 1.314 mmol). The reaction mixture was heated to 85° C. for 16 h. The reaction mixture was cooled to room temperature and the solvent was removed under reduced pressure to yield crude compound. The crude compound was dissolved in ethyl acetate and washed with water, the organic layer was dried over anhydrous Na$_2$SO$_4$, filtered, and evaporated under reduced pressure. The crude material was dissolved in DCM loaded on a Prep TLC plate. The plate was developed using 5% EA+PE, the product was marked, the silica was dissolved in 10% methanol/DCM, stirred for 10 min, the filtrate was removed under reduced pressure to yield tert-butyl (R)-4-(bis(4-chlorophenyl)methyl)-3-isopropylpiperazine-1-carboxylate (190 mg, 84% yield) as a semisolid; LCMS: m/z=464.2 (M+H); rt 4.233 min. Method: Column-KINETEX-XB-C18 (75×3 mm-2.6 µm); Mobile phase A: 10 mM ammonium formate in water: acetonitrile (98:2); Mobile phase B: 10 mM ammonium formate in water: acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 123

(R)-1-(bis(4-chlorophenyl)methyl)-2-isopropylpiperazine, HCl

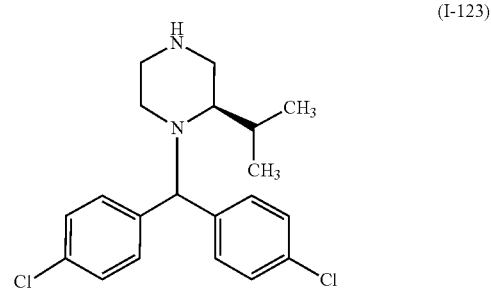 [SMILES: CC(C)[C@@H]1CNCCN1C(c1ccc(Cl)cc1)c1ccc(Cl)cc1]

(I-123)

To a stirred solution of tert-butyl (R)-4-(bis(4-chlorophenyl)methyl)-3-isopropylpiperazine-1-carboxylate (190 mg, 0.410 mmol) in DCM (4 mL) was added HCl in dioxane (6 mL, 197 mmol). The reaction mixture was stirred at room temperature for 2 h. The solvent was removed under reduced pressure to yield (R)-1-(bis(4-chlorophenyl)methyl)-2-isopropylpiperazine, HCl (160 mg, 81% yield) as an off-white solid; LCMS: m/z=363.3 (M+H); rt 1.92 min. Method: Column-AQUITY UPLC BEH C18 (3.0×50 mm) 1.7 µm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.3 minute hold at 100% B, flow rate 0.7 mL/min.

Example 167

(R)-8-(4-(bis(4-chlorophenyl)methyl)-3-isopropylpiperazin-1-yl)-5-methyl-6-oxo-5,6-dihydro-1,5-naphthyridine-2-carbonitrile

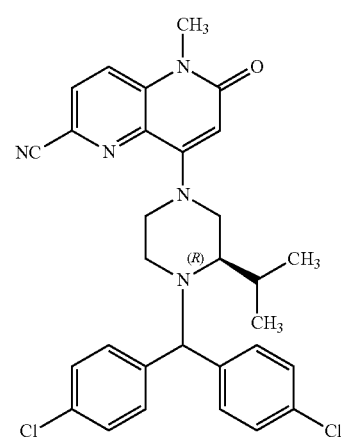

(167)

To a stirred solution of (R)-1-(bis(4-chlorophenyl)methyl)-2-isopropylpiperazine, HCl (0.07 g, 0.175 mmol) in dry acetonitrile (5 mL) was added DIPEA (0.092 mL, 0.525 mmol), followed by the addition of 6-cyano-1-methyl-2- oxo-1,2-dihydro-1,5-naphthyridin-4-yl trifluoromethanesulfonate (0.064 g, 0.193 mmol). The reaction mixture was heated 85° C. for 2 h. The reaction mixture was cooled to room temperature and the solvent was removed under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 20% B, 20-85% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield (R)-8-(4-(bis(4-chlorophenyl)methyl)-3-isopropylpiperazin-1-yl)-5-methyl-6-oxo-5,6-dihydro-1,5-naphthyridine-2-carbonitrile (33.9 mg, 35.2% yield); LCMS: m/z=546.2 (M+H); rt 2.975 min. Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-d$_6$) δ ppm 8.15 (d, J=8.8 Hz, 1H), 8.08 (d, J=8.8 Hz, 1H), 7.55-7.44 (m, 4H), 7.44-7.31 (m, 4H), 6.12 (s, 1H), 5.51 (s, 1H), 3.81 (dd, J=13.0, 3.7 Hz, 1H), 3.62-3.44 (m, 4H), 3.40-3.33 (m, 1H), 3.16-3.03 (m, 2H), 2.54 (br. s., 2H), 2.26 (d, J=8.6 Hz, 1H), 1.09 (d, J=6.8 Hz, 3H), 0.94 (d, J=6.6 Hz, 3H).

Intermediate 124 tert-butyl (R)-4-(bis(4-fluorophenyl)methyl)-3-isopropylpiperazine-1-carboxylate

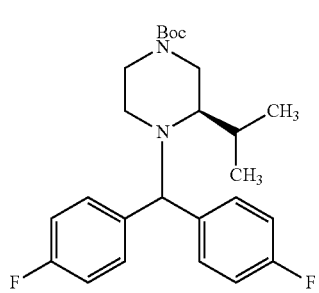 [SMILES: CC(C)[C@@H]1CNCCN1C(c1ccc(F)cc1)c1ccc(F)cc1]

(I-124)

To a stirred solution of (R)-1-Boc-3-isopropyl-piperazine (100 mg, 0.438 mmol) and bis(4-fluorophenyl)methanol (0.113 mL, 0.657 mmol) in acetonitrile (4 mL) was added DIPEA (0.229 mL, 1.314 mmol). The reaction mixture was heated to 85° C. for 16 h. The reaction mixture was cooled to room temperature and the solvent was removed under reduced pressure. The crude material was dissolved in DCM loaded on a Prep TLC plate. The plate was developed using 5% EA+PE and the product was marked and the silica was dissolved in 10% methanol/DCM, stirred for 10 min, the filtrate was removed under reduced pressure to yield tert-butyl (R)-4-(bis(4-fluorophenyl)methyl)-3-isopropylpiperazine-1-carboxylate (80 mg, 34.4% yield as a semisolid); LCMS: m/z 431.4 (M+H); rt 1.80 min. Method: Column-AQUITY UPLC BEH C18 (3.0×50 mm) 1.7 µm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.3 minute hold at 100% B, flow rate 0.7 mL/min.

Intermediate 125

(R)-1-(bis(4-fluorophenyl)methyl)-2-isopropylpiperazine, HCl

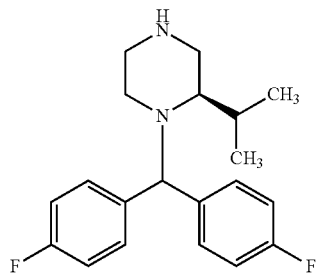

To a stirred solution of tert-butyl (R)-4-(bis(4-fluorophenyl)methyl)-3-isopropylpiperazine-1-carboxylate (80 mg, 0.186 mmol) in dry DCM (3 mL) was added HCl in dioxane (3.0 mL, 12.00 mmol). The reaction mixture was stirred at room temperature for 2 h. The solvent was removed under reduced pressure to yield (R)-1-(bis(4-fluorophenyl)methyl)-2-isopropylpiperazine, HCl (60 mg, 76% yield) as an off-white solid; LCMS: m/z=331.4 (M+H); rt 2.469 min. (LCMS) Method: Column-KINETEX-XB-C18 (75×3 mm-2.6 µm); Mobile phase A: 0.1% TFA in Milli-Q water; Mobile phase B: 0.1% TFA in acetonitrile; Gradient: 20-100% B over 4.0 minutes, flow rate 1.0 mL/min, then a 0.6 minute hold at 100% B flow rate 1.5 mL/min, 100-20% B over 0.1 minutes, flow rate 1.5 mL/min.

Example 168

(R)-8-(4-(bis(4-chlorophenyl)methyl)-3-isopropylpiperazin-1-yl)-5-methyl-6-oxo-5,6-dihydro-1,5-naphthyridine-2-carbonitrile

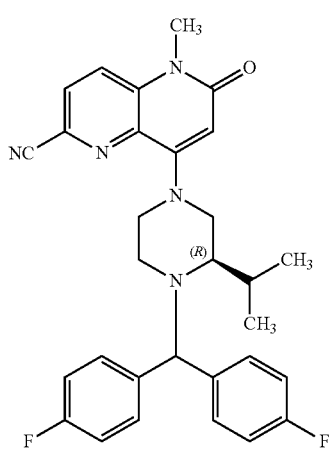

(168)

To a stirred solution of (R)-1-(bis(4-fluorophenyl)methyl)-2-isopropylpiperazine, HCl (60 mg, 0.164 mmol) in acetonitrile (2 mL) were added DIPEA (0.086 mL, 0.491 mmol) and 6-cyano-1-methyl-2-oxo-1,2-dihydro-1,5-naphthyridin-4-yl trifluoromethanesulfonate (59.9 mg, 0.180 mmol). The reaction mixture was heated to 85° C. for 2 h. The reaction mixture was cooled to room temperature and the solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 9% B, 9-38% B over 25 minutes, then a 5 minute hold at 100% B; Flow Rate: 15 mL/min; Column Temperature: 25° C. Fractions containing the product were combined and dried via centrifugal evaporation to yield (R)-8-(4-(bis(4-fluorophenyl) methyl)-3-isopropylpiperazin-1-yl)-5-methyl-6-oxo-5,6-dihydro-1,5-naphthyridine-2-carbonitrile (40.7 mg, 48.5% yield); LCMS: m/z=514.3 (M+H); rt 2.492 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-d$_6$) δ ppm 8.15 (d, J=8.8 Hz, 1H), 8.08 (d, J=8.8 Hz, 1H), 7.62-7.44 (m, 4H), 7.28-7.06 (m, 4H), 6.12 (s, 1H), 5.49 (s, 1H), 3.82 (dd, J=12.5, 3.9 Hz, 1H), 3.66-3.44 (m, 4H), 3.41-3.33 (m, 1H), 3.21-2.99 (m, 2H), 2.90 (s, 1H), 2.55 (br. s., 1H), 2.30-2.17 (m, 1H), 1.09 (d, J=6.6 Hz, 3H), 0.94 (d, J=6.4 Hz, 3H).

Example 169

(R)-8-(4-(bis(4-fluorophenyl)methyl)-3-isopropylpiperazin-1-yl)-5-methyl-6-oxo-5,6-dihydro-1,5-naphthyridine-2,7-dicarbonitrile

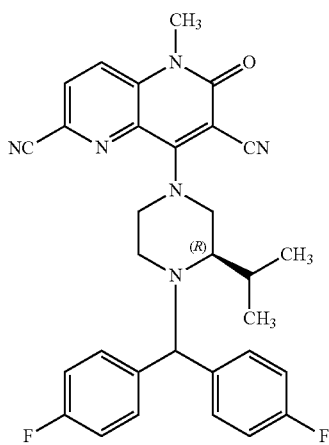

(169)

To a stirred solution of (R)-1-(bis(4-fluorophenyl) methyl)-2-isopropylpiperazine, HCl (30 mg, 0.082 mmol) in acetonitrile (5 mL) were added DIPEA (0.043 mL, 0.245 mmol) and 3,6-dicyano-1-methyl-2-oxo-1,2-dihydro-1,5-naphthyridin-4-yl trifluoromethanesulfonate (32.2 mg, 0.090 mmol). The reaction mixture was heated to 85° C. for 2 h. The reaction mixture was cooled to room temperature and the solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 35% B, 35-82% B over 20 minutes, then a 5 minute hold at 100% B; Flow Rate: 15 mL/min; Column Temperature: 25° C. Fractions containing the product were combined and dried via centrifugal evaporation to yield (R)-8-(4-(bis(4-fluorophenyl) methyl)-3-isopropylpiperazin-1-yl)-5-methyl-6-oxo-5,6-dihydro-1,5-naphthyridine-2,7-dicarbonitrile (17.6 mg, 40.0% yield); LCMS: m/z=539.3 (M+H); rt 2.439 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-d$_6$) δ ppm 8.25 (d, J=8.8 Hz, 1H), 8.15 (d, J=9.0 Hz, 1H), 7.59-7.37 (m, 4H), 7.27-7.05 (m, 4H), 5.56 (s, 1H), 4.26 (dd, J=13.2, 3.4 Hz, 1H), 3.91 (d, J=12.7 Hz, 1H), 3.83-3.64 (m, 2H), 3.53 (s, 3H), 3.42-3.32 (m, 1H), 2.56 (d, J=14.7 Hz, 1H), 2.48 (d, J=3.9, Hz, 1H), 2.26 (dd, J=14.1, 7.2 Hz, 1H), 1.06 (d, J=6.8 Hz, 3H), 0.71 (d, J=6.6 Hz, 3H).

Intermediate 126 tert-butyl (R)-4-(6-cyano-1-methyl-2-oxo-1,2-dihydro-1,5-naphthyridin-4-yl)-3-ethylpiperazine-1-carboxylate

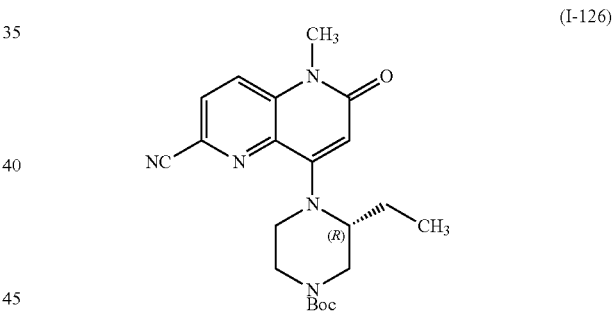

(I-126)

To a stirred solution of (R)-1-BOC-3-ethyl piperazine (100 mg, 0.467 mmol) in DMA (2 mL) were added DIPEA (0.244 mL, 1.400 mmol) and 6-cyano-1-methyl-2-oxo-1,2-dihydro-1,5-naphthyridin-4-yl trifluoromethanesulfonate (171 mg, 0.513 mmol). The reaction mixture was heated to 85° C. for 16 h. The solvent was removed under reduced pressure. The crude compound was purified by Combi (40 g column silica, eluted with 100-80% ethyl acetate/petroleum ether) to afford tert-butyl (R)-4-(6-cyano-1-methyl-2-oxo-1, 2-dihydro-1,5-naphthyridin-4-yl)-3-ethylpiperazine-1-carboxylate (180 mg, 87% yield) as a semisolid; LCMS: m/z=398.2 (M+H); rt 2.702 min. Method: Column-KINETEX-XB-C18 (75×3 mm-2.6 μm); Mobile phase A: 10 mM ammonium formate in water:acetonitrile (98:2); Mobile phase B: 10 mM ammonium formate in water: acetonitrile (2:98); Gradient: 40-100% B over 25 minutes, flow rate 1.0 mL/min, then a 5 minute hold at 100% B flow rate 1.5 mL/min; then Gradient: 100% B over 2 minutes, flow rate 1.5 mL/min; Gradient: 100% B over 4 minutes, flow rate 1.5 mL/min.

Intermediate 127

(R)-8-(2-ethylpiperazin-1-yl)-5-methyl-6-oxo-5,6-dihydro-1,5-naphthyridine-2-carbonitrile, TFA

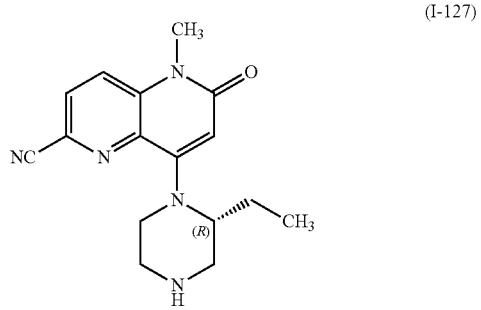

(I-127)

To a stirred solution of tert-butyl (R)-4-(6-cyano-1-methyl-2-oxo-1,2-dihydro-1,5-naphthyridin-4-yl)-3-ethylpiperazine-1-carboxylate (180 mg, 0.453 mmol) in DCM (3 mL) was added TFA (0.035 mL, 0.453 mmol). The reaction mixture was stirred at room temperature for 2 h. The solvent was removed under reduced pressure to yield TFA salt of (R)-8-(2-ethylpiperazin-1-yl)-5-methyl-6-oxo-5,6-dihydro-1,5-naphthyridine-2-carbonitrile (100 mg, 42.9% yield) as a gum; LCMS: m/z=298.4 (M+H); rt 0.66 min. Method: Column-AQUITY UPLC BEH C18 (3.0×50 mm) 1.7 µm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Example 170

(R)-8-(4-(bis(4-fluorophenyl)methyl)-2-ethylpiperazin-1-yl)-5-methyl-6-oxo-5,6-dihydro-1,5-naphthyridine-2-carbonitrile

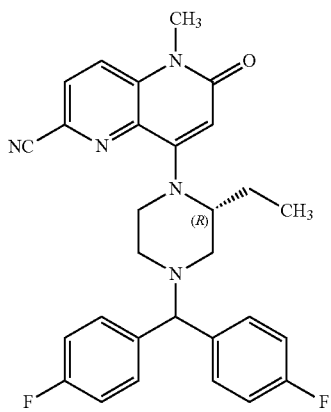

To a stirred solution of (R)-8-(2-ethylpiperazin-1-yl)-5-methyl-6-oxo-5,6-dihydro-1,5-naphthyridine-2-carbonitrile, TFA (100 mg, 0.243 mmol) in acetonitrile (3 mL) were added DIPEA (0.127 mL, 0.729 mmol) and 4,4'-(chloromethylene) bis(fluorobenzene) (0.091 mL, 0.486 mmol). The reaction mixture was heated to 85° C. for 16 h. The reaction mixture was cooled to room temperature and the solvent was removed under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-65% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield (R)-8-(4-(bis(4-fluorophenyl)methyl)-2-ethylpiperazin-1-yl)-5-methyl-6-oxo-5,6-dihydro-1,5-naphthyridine-2-carbonitrile (13.8 mg, 10.8% yield); LCMS: m/z=500.2 (M+H); rt 2.601 min. Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-$d_6$) δ ppm 8.14 (d, J=8.8 Hz, 1H), 8.06 (d, J=9.0 Hz, 1H), 7.50 (dd, J=8.7, 5.5 Hz, 2H), 7.53 (dd, J=8.7, 5.5 Hz, 2H), 7.24-7.06 (m, 4H), 6.02 (s, 1H), 4.63 (br. s., 1H), 4.40 (s, 1H), 3.52 (s, 3H), 3.43 (d, J=6.6 Hz, 2H), 2.83-2.69 (m, 2H), 2.25 (dd, J=11.4, 3.3 Hz, 1H), 2.17-1.98 (m, 2H), 1.74-1.62 (m, 1H), 0.67 (t, J=7.5,Hz, 3H).

Intermediate 128 tert-butyl 4-(6-cyano-1-methyl-2-oxo-1,2-dihydro-1,5-naphthyridin-4-yl)-2,2-dimethylpiperazine-1-carboxylate

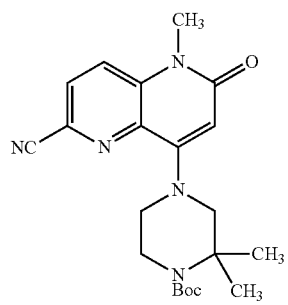

(I-128)

To a stirred solution of 6-cyano-1-methyl-2-oxo-1,2-dihydro-1,5-naphthyridin-4-yl trifluoromethanesulfonate (0.373 g, 1.120 mmol) and tert-butyl 2,2-dimethylpiperazine-1-carboxylate (0.2 g, 0.933 mmol) in acetonitrile (10 mL) was added DIPEA (0.489 mL, 2.80 mmol). The reaction mixture was heated to 85° C. for 16 h. The reaction mixture was cooled to room temperature and the solvent was removed under reduced pressure. The crude compound was purified by Combi (24 g column silica, eluted with 50-60% ethyl acetate/petroleum ether) to yield tert-butyl 4-(6-cyano-1-methyl-2-oxo-1,2-dihydro-1,5-naphthyridin-4-yl)-2,2-dimethylpiperazine-1-carboxylate (0.22 g, 55.1% yield) as a gum; LCMS: m/z=398.4 (M+H); rt 0.65 min. Method: Column-AQUITY UPLC BEH C18 (3.0×50 mm) 1.7 µm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Intermediate 129

8-(3,3-dimethylpiperazin-1-yl)-5-methyl-6-oxo-5,6-dihydro-1,5-naphthyridine-2-carbonitrile, TFA

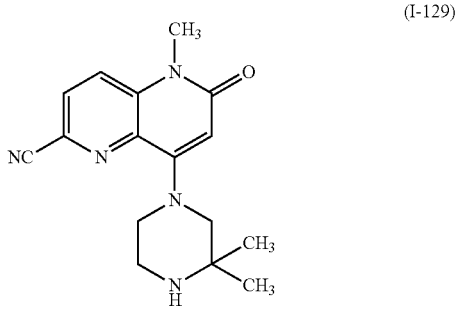 [SMILES: Cn1c(=O)cc(N2CCNC(C)(C)C2)c2nc(C#N)ccc21]

(I-129)

To a stirred solution of tert-butyl 4-(6-cyano-1-methyl-2-oxo-1,2-dihydro-1,5-naphthyridin-4-yl)-2,2-dimethylpiperazine-1-carboxylate (0.1 g, 0.252 mmol) in dry DCM (2 mL) was added TFA (0.5 mL, 6.49 mmol). The reaction mixture was stirred at room temperature for 2 h. The solvent was removed under reduced pressure to yield crude compound and triturated with DCM and petroleum ether to yield 8-(3,3-dimethylpiperazin-1-yl)-5-methyl-6-oxo-5,6-dihydro-1,5-naphthyridine-2-carbonitrile, TFA (0.099 g, 81% yield) as a semisolid; LCMS: m/z=298.4 (M+H); rt 0.61 min. Method: Column-AQUITY UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Example 171

8-(4-(bis(4-fluorophenyl)methyl)-3,3-dimethylpiperazin-1-yl)-5-methyl-6-oxo-5,6-dihydro-1,5-naphthyridine-2-carbonitrile

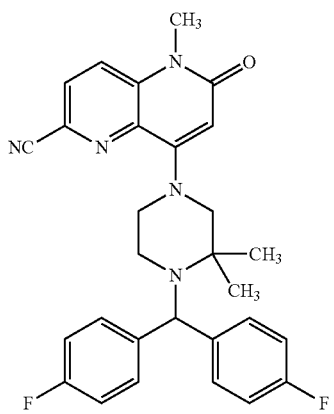

(171)

To a stirred solution of 8-(3,3-dimethylpiperazin-1-yl)-5-methyl-6-oxo-5,6-dihydro-1,5-naphthyridine-2-carbonitrile, TFA (50 mg, 0.168 mmol), and DIPEA (0.088 mL, 0.504 mmol) in acetonitrile (2 mL) was added bis(4-fluorophenyl)methyl trifluoromethanesulfonate (71.1 mg, 0.202 mmol). The reaction mixture was heated to 85° C. for 2 h. The reaction mixture was cooled to room temperature and the solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 40% B, 40-74% B over 20 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield 8-(4-(bis(4-fluorophenyl)methyl)-3,3-dimethylpiperazin-1-yl)-5-methyl-6-oxo-5,6-dihydro-1,5-naphthyridine-2-carbonitrile (6 mg, 7.1% yield); LCMS: m/z=500.3 (M+H); rt 2.456 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-$d_6$) δ ppm 8.15 (d, J=8.8 Hz, 1H), 8.07 (d, J=8.8 Hz, 1H), 7.33 (dd, J=8.6, 5.6 Hz, 4H), 7.24-6.97 (m, 4H), 6.08 (s, 1H), 5.53 (s, 1H), 3.62-3.48 (m, 4H), 3.39 (s, 2H), 2.61 (br. s., 2H), 1.24 (s, 3H), 1.16 (s, 6H). One proton peak was obscured by moisture.

Intermediate 130 tert-butyl (R)-4-(bis(4-fluorophenyl)methyl)-3-ethylpiperazine-1-carboxylate

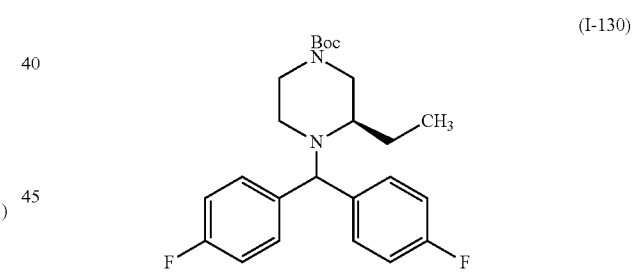

(I-130)

To a stirred solution of tert-butyl (R)-3-ethylpiperazine-1-carboxylate (0.3 g, 1.400 mmol) and DIPEA (0.733 mL, 4.20 mmol) in acetonitrile (5 mL) was added 4,4'-(chloromethylene)bis(fluorobenzene) (0.392 mL, 2.100 mmol). The reaction mixture was heated to 85° C. for 16 h. The reaction mixture was cooled to room temperature and the solvent was removed under reduced pressure. The crude compound was purified by Combi (40 g column silica, eluted with 5-10% ethyl acetate/petroleum ether) to afford tert-butyl (R)-4-(bis(4-fluorophenyl)methyl)-3-ethylpiperazine-1-carboxylate (0.331 g, 48.8% yield) as a colorless gum; LCMS: m/z=417.4 (M+H); rt 1.62 min. Method: Column-AQUITY UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Intermediate 131

(R)-1-(bis(4-fluorophenyl)methyl)-2-ethylpiperazine, HCl

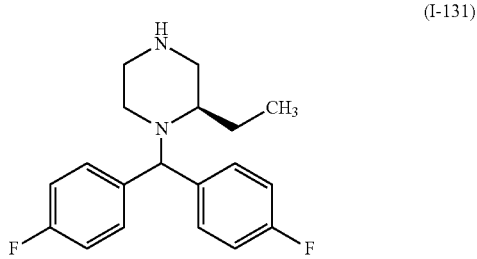 [SMILES: CC[C@@H]1CNCCN1C(c1ccc(F)cc1)c1ccc(F)cc1]

(I-131)

To a stirred solution of tert-butyl (R)-4-(bis(4-fluorophenyl)methyl)-3-ethylpiperazine-1-carboxylate (0.2 g, 0.480 mmol) in DCM (2 mL) was added HCl in dioxane (4 mL, 132 mmol). The reaction mixture was stirred at room temperature for 1 h. The solvent was removed under reduced pressure to yield (R)-1-(bis(4-fluorophenyl)methyl)-2-ethylpiperazine, HCl (0.169 g, 73.8% yield)) as an off-white solid; LCMS: m/z=317.4 (M+H); rt 1.46 min. Method: Column-AQUITY UPLC BEH C18 (3.0×50 mm) 1.7 µm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.3 minute hold at 100% B, flow rate 0.7 mL/min.

Example 172

(R)-8-(4-(bis(4-fluorophenyl)methyl)-3-ethylpiperazin-1-yl)-5-methyl-6-oxo-5,6-dihydro-1,5-naphthyridine-2-carbonitrile

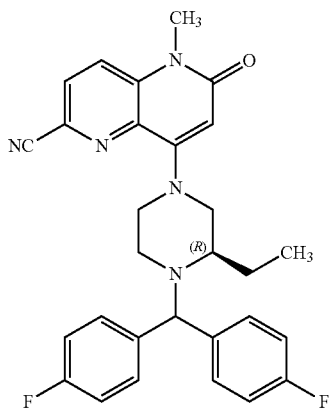

(172)

To a stirred solution of (R)-1-(bis(4-fluorophenyl)methyl)-2-ethylpiperazine, HCl (0.169 g, 0.479 mmol) in acetonitrile (5 mL) were added DIPEA (0.251 mL, 1.437 mmol) and 6-cyano-1-methyl-2-oxo-1,2-dihydro-1,5-naphthyridin-4-yl trifluoromethanesulfonate (0.176 g, 0.527 mmol). The reaction mixture was heated to 85° C. for 2 h. The reaction mixture was cooled to room temperature and the solvent was removed under reduced pressure. The crude material was purified via preparative HPLC Column: X-Bridge Phenyl (250 mm×4.6 mm ID, 5 µm), Mobile phase A=Buffer: 10 mM ammonium acetate in water; Mobile phase B=acetonitrile Flow: 1 mL/min Gradient: 10-40% B over 15 minutes, then a 5 minute hold at 100% B; Flow: 15 mL/min. Fractions containing the product were combined and dried via centrifugal evaporation to yield (R)-8-(4-(bis(4-fluorophenyl)methyl)-3-ethylpiperazin-1-yl)-5-methyl-6-oxo-5,6-dihydro-1,5-naphthyridine-2-carbonitrile (90 mg, 37.2% yield); LCMS: m/z=500.2 (M+H); rt 3.822 min. Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min. $^1$H NMR (400 MHz, DMSO-$d_6$) δ ppm 8.18-8.12 (m, 1H), 8.10-8.05 (m, 1H), 7.61-7.47 (m, 4H), 7.15 (td, J=9.0, 1.0 Hz, 4H), 6.11 (s, 1H), 4.99 (s, 1H), 4.23 (d, J=12.0 Hz, 1H), 3.54 (s, 3H), 3.41 (d, J=11.5 Hz, 1H), 3.12-2.97 (m, 2H), 2.76-2.66 (m, 1H), 2.54 (d, J=6.0 Hz, 2H), 1.94 (ddd, J=13.3, 9.3, 7.5 Hz, 1H), 1.70 (dd, J=12.5, 7.5 Hz, 1H), 0.77 (t, J=7.5 Hz, 3H).

Example 173

(R)-8-(4-(bis(4-fluorophenyl)methyl)-3-ethylpiperazin-1-yl)-5-methyl-6-oxo-5,6-dihydro-1,5-naphthyridine-2,7-dicarbonitrile

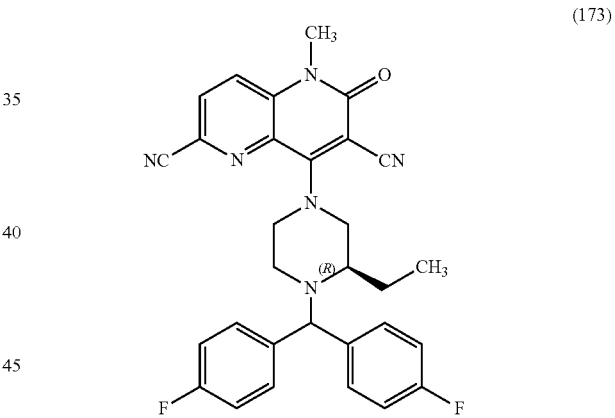

(173)

To a stirred solution of (R)-1-(bis(4-fluorophenyl)methyl)-2-ethylpiperazine, HCl (30 mg, 0.085 mmol) in acetonitrile (5 mL) was added DIPEA (0.045 mL, 0.255 mmol) followed by the dropwise addition of 3,6-dicyano-1-methyl-2-oxo-1,2-dihydro-1,5-naphthyridin-4-yl trifluoromethanesulfonate (33.5 mg, 0.094 mmol). The reaction mixture was heated to 85° C. for 2 h. The reaction mixture was cooled to room temperature and solvent was removed under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 25% B, 25-78% B over 20 minutes, then a 5 minute hold at 100% B; Flow Rate: 15 mL/min; Column Temperature: 25° C. Fractions containing the product were combined and dried via centrifugal evaporation to yield (R)-8-(4-(bis(4-fluorophenyl)methyl)-3-ethylpiperazin-1-yl)-5-methyl-6- oxo-5,6-dihydro-1,5-naphthyridine-2,7-dicarbonitrile (12.4 mg, 27.8% yield); LCMS: m/z 525.3 (M+H); rt 2.364 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-d$_6$) δ ppm 8.25 (d, J=8.8 Hz, 1H), 8.15 (d, J=9.0 Hz, 1H), 7.65-7.44 (m, 4H), 7.16 (t, J=8.7 Hz, 4H), 5.15 (s, 1H), 4.07 (d, J=13.0 Hz, 1H), 4.00-3.86 (m, 2H), 3.62 (t, J=10.1 Hz, 1H), 3.53 (s, 3H), 3.05 (t, J=10.3 Hz, 1H), 2.70-2.62 (m, 1H), 2.56 (d, J=13.0 Hz, 1H), 1.78-1.64 (m, 1H), 1.62-1.47 (m, 1H), 0.63 (t, J=7.5 Hz, 3H).

Example 174

(R)-8-(4-(bis(4-fluorophenyl)methyl)-3-ethylpiperazin-1-yl)-7-fluoro-5-methyl-6-oxo-5,6-dihydro-1,5-naphthyridine-2-carbonitrile

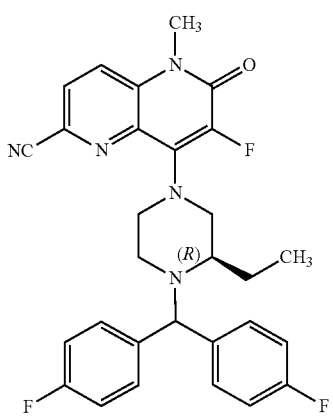

(174)

A solution was prepared by dissolving (R)-8-(4-(bis(4-fluorophenyl)methyl)-3-ethylpiperazin-1-yl)-5-methyl-6-oxo-5,6-dihydro-1,5-naphthyridine-2-carbonitrile (55 mg, 0.110 mmol) in acetonitrile (2 mL). The solution was cooled to 0° C. and Selectfluor (50.7 mg, 0.143 mmol) dissolved in water (0.15 mL) and THF (0.15 mL) was added. The reaction mixture was placed under nitrogen, stirred at 0° C., warmed to room temperature over 1.5 h, and then stirred for 3 h. The solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 35% B, 35-100% B over 20 minutes, then a 5 minute hold at 100% B; Flow Rate: 15 mL/min; Column Temperature: 25° C. Fractions containing the product were combined and dried via centrifugal evaporation to yield (R)-8-(4-(bis(4-fluorophenyl)methyl)-3-ethylpiperazin-1-yl)-7-fluoro-5-methyl-6-oxo-5,6-dihydro-1,5-naphthyridine-2-carbonitrile (4.3 mg, 7.6% yield); LCMS: m/z=518.3 (M+H); rt 2.669 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-d$_6$) δ ppm 8.24-8.03 (m, 2H), 7.67-7.37 (m, 4H), 7.14 (t, J=8.7 Hz, 4H), 5.03 (s, 1H), 3.72-3.52 (m, 4H), 3.52-3.35 (m, 3H), 2.76 (dt, J=12.4, 6.1 Hz, 2H), 2.03-1.90 (m, 1H), 1.80-1.62 (m, 1H), 0.66 (t, J=7.3 Hz, 3H).

Example 175

(R)-8-(4-(bis(4-fluorophenyl)methyl)-3-ethylpiperazin-1-yl)-7-chloro-5-methyl-6-oxo-5,6-dihydro-1,5-naphthyridine-2-carbonitrile

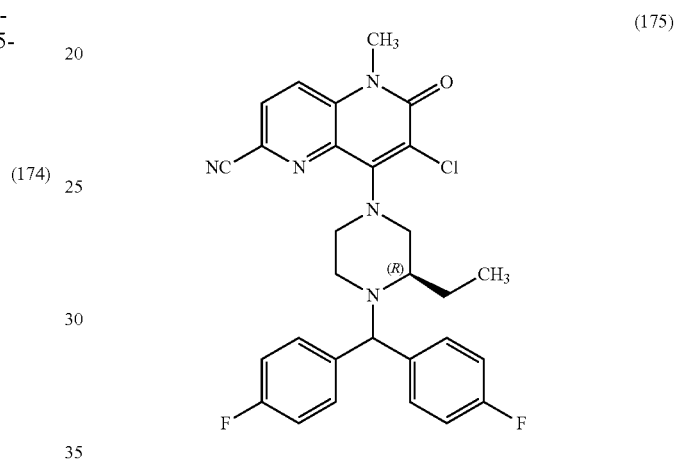

(175)

To a stirred solution of (R)-8-(4-(bis(4-fluorophenyl)methyl)-3-ethylpiperazin-1-yl)-5-methyl-6-oxo-5,6-dihydro-1,5-naphthyridine-2-carbonitrile (40 mg, 0.080 mmol) in dry DCM (3 mL) was added NCS (16.04 mg, 0.120 mmol) at 0° C. The reaction mixture was stirred at room temperature for 16 h. The solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 35% B, 35-100% B over 20 minutes, then a 5 minute hold at 100% B; Flow Rate: 15 mL/min; Column Temperature: 25° C. Fractions containing the product were combined and dried via centrifugal evaporation to yield (R)-8-(4-(bis(4-fluorophenyl)methyl)-3-ethylpiperazin-1-yl)-7-chloro-5-methyl-6-oxo-5,6-dihydro-1,5-naphthyridine-2-carbonitrile (31.4 mg, 69.1% yield); LCMS: m/z=534.3 (M+H); rt 2.752 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-d$_6$) δ ppm 8.17 (q, J=8.8 Hz, 2H), 7.68-7.46 (m, 4H), 7.25-7.06 (m, 4H), 5.05 (s, 1H), 3.82 (d, J=10.0 Hz, 1H), 3.63 (s, 3H), 3.58 (d, J=13.2 Hz, 1H), 3.49-3.33 (m, 2H), 2.98 (t, J=9.7 Hz, 1H), 2.45 (br. s., 1H), 2.08 (s, 1H), 1.82-1.70 (m, 1H), 1.67 (br. s., 1H), 0.53 (t, J=7.5 Hz, 3H).

Intermediate 132 tert-butyl (R)-4-(bis(4-chlorophenyl)methyl)-3-ethylpiperazine-1-carboxylate

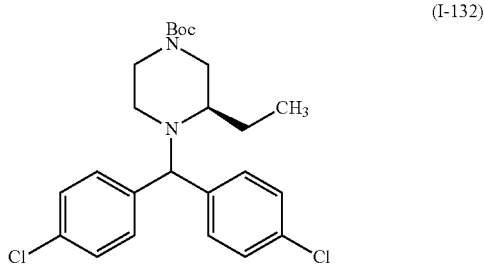 [SMILES: CC[C@@H]1CN(C(=O)OC(C)(C)C)CCN1C(c1ccc(Cl)cc1)c1ccc(Cl)cc1]
(I-132)

To a stirred solution of tert-butyl (R)-3-ethylpiperazine-1-carboxylate (0.18 g, 0.840 mmol) and DIPEA (0.440 mL, 2.52 mmol) in acetonitrile (5 mL) was added DIPEA (0.440 mL, 2.52 mmol) followed by the addition of 4,4'-(bromomethylene) bis(chlorobenzene) (0.292 g, 0.924 mmol). The reaction mixture was heated to 85° C. for 16 h. The reaction mixture was cooled to room temperature and the solvent was removed under reduced pressure. The crude compound was purified by Combi (24 g column silica, eluted with 5-10% ethyl acetate/petroleum ether) to afford tert-butyl (R)-4-(bis (4-chlorophenyl)methyl)-3-ethylpiperazine-1-carboxylate (0.37 g, 98% yield) as a colorless gum; LCMS: m/z=449.2 (M+H); rt 2.02 min. Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min

Intermediate 133

(R)-1-(bis(4-chlorophenyl)methyl)-2-ethylpiperazine, HCl

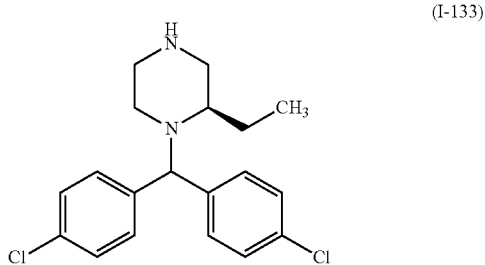 [SMILES: CC[C@@H]1CNCCN1C(c1ccc(Cl)cc1)c1ccc(Cl)cc1]
(I-133)

To a stirred solution of tert-butyl (R)-4-(bis(4-chlorophenyl)methyl)-3-ethylpiperazine-1-carboxylate (0.37 g, 0.823 mmol) in dry DCM (3 mL) was added HCl in dioxane (9 mL, 36.0 mmol). The reaction mixture was stirred at room temperature for 2h. The solvent was removed under reduced pressure to yield (R)-1-(bis(4-chlorophenyl)methyl)-2-ethylpiperazine, HCl (0.3 g, 83% yield) as an off-white solid; LCMS: m/z=349.3 (M+H); rt 1.79 min. Method: Column-AQUITY UPLC BEH C18 (3.0×50 mm) 1.7 μm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.3 minute hold at 100% B, flow rate 0.7 mL/min.

Example 176

(R)-8-(4-(bis(4-chlorophenyl)methyl)-3-ethylpiperazin-1-yl)-5-methyl-6-oxo-5,6-dihydro-1,5-naphthyridine-2-carbonitrile

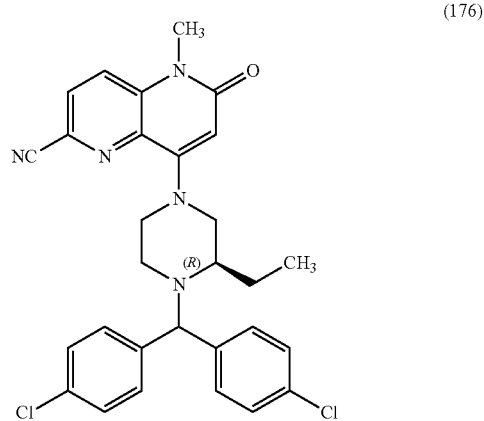
(176)

To a stirred solution of (R)-1-(bis(4-chlorophenyl)methyl)-2-ethylpiperazine, HCl (0.1 g, 0.259 mmol) in acetonitrile (5 mL) were added DIPEA (0.136 mL, 0.778 mmol) and 6-cyano-1-methyl-2-oxo-1,2-dihydro-1,5-naphthyridin-4-yl trifluoromethanesulfonate (0.095 g, 0.285 mmol). The reaction mixture was heated to 85° C. for 2 h. The reaction mixture was cooled to room temperature and the solvent was removed under reduced pressure. The crude compound was purified by combo (12 g column silica, eluted with 5-10% ethyl acetate/petroleum ether) to yield (R)-8-(4-(bis(4-chlorophenyl)methyl)-3-ethylpiperazin-1-yl)-5-methyl-6-oxo-5,6-dihydro-1,5-naphthyridine-2-carbonitrile (125 mg, 49.8% yield) as a gum; LCMS: m/z=532.3 (M+H); rt 2.32 min. Method: Column-AQUITY UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Example 177

(R)-8-(4-(bis(4-chlorophenyl)methyl)-3-ethylpiperazin-1-yl)-7-chloro-5-methyl-6-oxo-5,6-dihydro-1,5-naphthyridine-2-carbonitrile

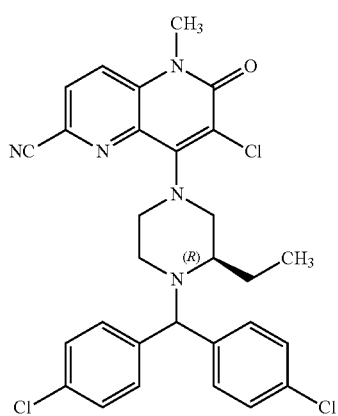

(177)

To a stirred solution of (R)-8-(4-(bis(4-chlorophenyl)methyl)-3-ethylpiperazin-1-yl)-5-methyl-6-oxo-5,6-dihydro-1,5-naphthyridine-2-carbonitrile (30 mg, 0.056 mmol) in dry DCM (3 mL) was added NCS (11.28 mg, 0.085 mmol). The reaction mixture was stirred at room temperature for 16 h. The solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 35% B, 35-100% B over 20 minutes, then a 5 minute hold at 100% B; Flow Rate: 15 mL/min; Column Temperature: 25° C. Fractions containing the product were combined and dried via centrifugal evaporation to yield (R)-8-(4-(bis(4-chlorophenyl)methyl)-3-ethylpiperazin-1-yl)-7-chloro-5-methyl-6-oxo-5,6-dihydro-1,5-naphthyridine-2-carbonitrile (12.9 mg, 40.4% yield); LCMS: m/z=566.2 (M+H); rt 2.864 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water: 5% acetonitrile; 10 mM ammonium acetate; Solvent B: 5% water:95% acetonitrile; 10 mM ammonium acetate. $^1$H NMR (400 MHz, DMSO-$d_6$) δ ppm 8.17 (q, J=9.0 Hz, 2H), 7.58 (d, J=8.6 Hz, 2H), 7.55-7.44 (m, 2H), 7.39 (dd, J=8.6, 1.5 Hz, 4H), 5.06 (s, 1H), 3.82 (dd, J=12.5, 2.4 Hz, 1H), 3.63 (s, 3H), 3.58 (d, J=12.5 Hz, 1H), 3.48-3.33 (m, 2H), 3.00 (dd, J=11.0, 8.6 Hz, 1H), 2.58-2.52 (m, 1H), 2.46, (d, J=12.2 Hz, 1H), 1.85-1.71 (m, 1H), 1.67 (d, J=7.3 Hz, 1H), 0.54 (t, J=7.3 Hz, 3H).

Example 178

(R)-8-(4-(bis(4-chlorophenyl)methyl)-3-ethylpiperazin-1-yl)-7-fluoro-5-methyl-6-oxo-5,6-dihydro-1,5-naphthyridine-2-carbonitrile

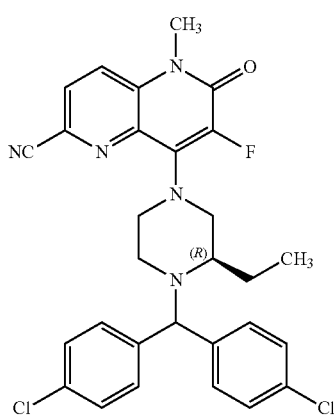

(178)

A solution was prepared by dissolving (R)-8-(4-(bis(4-chlorophenyl)methyl)-3-ethylpiperazin-1-yl)-5-methyl-6-oxo-5,6-dihydro-1,5-naphthyridine-2-carbonitrile (90 mg, 0.169 mmol) in acetonitrile (3 mL). The solution was cooled to 0° C. and Selectfluor (78 mg, 0.220 mmol) dissolved in water (0.2 mL) and tetrahydrofuran (0.2 mL) was added. The reaction mixture was placed under nitrogen, stirred at 0° C., warmed to room temperature over 1.5 h, and then stirred for 3 h. The solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 35% B, 35-100% B over 20 minutes, then a 5 minute hold at 100% B; Flow Rate: 15 mL/min; Column Temperature: 25° C. Fractions containing the product were combined and dried via centrifugal evaporation to yield (R)-8-(4-(bis(4-chlorophenyl)methyl)-3-ethylpiperazin-1-yl)-7-fluoro-5-methyl-6-oxo-5,6-dihydro-1,5-naphthyridine-2-carbonitrile (2 mg, 2.1% yield); LCMS: m/z=550.2 (M+H); rt 2.783 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-$d_6$) δ ppm 8.21-8.09 (m, 2H), 7.57 (d, J=8.6 Hz, 2H), 7.51 (d, J=8.6 Hz, 2H), 7.39 (dd, J=8.6, 1.2 Hz, 4H), 5.05 (s, 1H), 3.72-3.56 (m, 4H), 3.51-3.39 (m, 3H), 2.78 (dd, J=13.0, 5.9 Hz, 1H), 2.45 (br. s., 2H), 1.96 (d, J=8.1 Hz, 1H), 1.71 (br. s., 1H), 0.68 (t, J=7.5 Hz, 3H).

Example 179

(R)-8-(4-(bis(4-chlorophenyl)methyl)-3-ethylpiperazin-1-yl)-5-methyl-6-oxo-5,6-dihydro-1,5-naphthyridine-2,7-dicarbonitrile

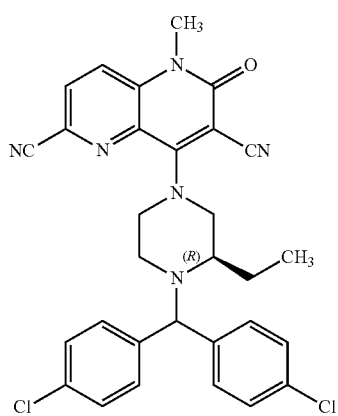

(179)

To a stirred solution of (R)-1-(bis(4-chlorophenyl)methyl)-2-ethylpiperazine, HCl (30 mg, 0.078 mmol) in acetonitrile (5 mL) were added DIPEA (0.041 mL, 0.233 mmol) and 3,6-dicyano-1-methyl-2-oxo-1,2-dihydro-1,5-naphthyridin-4-yl trifluoromethanesulfonate (30.6 mg, 0.086 mmol). The reaction mixture was heated to 85° C. for 2 h. The reaction mixture was cooled to room temperature and the solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 35% B, 35-82% B over 20 minutes, then a 5 minute hold at 100% B; Flow Rate: 15 mL/min; Column Temperature: 25° C. Fractions containing the product were combined and dried via centrifugal evaporation to yield (R)-8-(4-(bis(4-chlorophenyl) methyl)-3-ethylpiperazin-1-yl)-5-methyl-6-oxo-5,6-dihydro-1,5-naphthyridine-2,7-dicarbonitrile (18.5 mg, 42.7% yield); LCMS: m/z=557.2 (M+H); rt 2.635 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-$d_6$) δ ppm 8.25 (d, J=8.8 Hz, 1H), 8.15 (d, J=9.0 Hz, 1H), 7.52 (d, J=8.6 Hz, 2H), 7.56 (d, J=8.6 Hz, 2H), 7.40 (d, J=8.6 Hz, 4H), 5.17 (s, 1H), 4.07 (d, J=13.7 Hz, 1H), 3.94 (br. s., 2H), 3.62 (t, J=10.1 Hz, 1H), 3.53 (s, 3H), 3.06 (t, J=10.4 Hz, 1H), 2.66 (d, J=9.8 Hz, 1H), 2.56 (br. s., 1H), 1.70 (br. s., 1H), 1.62-1.50 (m, 1H), 0.64 (t, J=7.3 Hz, 3H).

Example 180

(R)-8-(4-(bis(4-chlorophenyl)methyl)-3-ethylpiperazin-1-yl)-5-methyl-6-oxo-5,6-dihydro-1,5-naphthyridine-2-carbonitrile

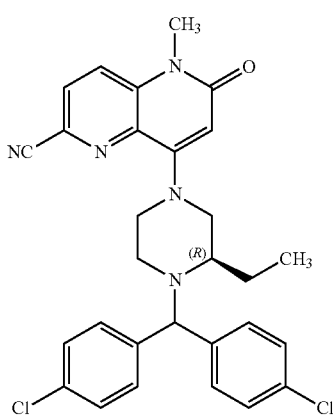

(180)

To a stirred solution of (R)-1-(bis(4-chlorophenyl)methyl)-2-ethylpiperazine, HCl (0.05 g, 0.130 mmol) in acetonitrile (5 mL) were added DIPEA (0.068 mL, 0.389 mmol) and 6-cyano-1-methyl-2-oxo-1,2-dihydro-1,5-naphthyridin-4-yl trifluoromethanesulfonate (0.048 g, 0.143 mmol). The reaction mixture was heated to 85° C. for 2 h. The solvent was removed under reduced pressure. The crude material was purified via preparative HPLC with the following conditions: Column: Waters XBridge C18, 150 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 10% B, 10-45% B over 25 minutes, then a 5 minute hold at 100% B; Flow Rate: 15 mL/min; Column Temperature: 25° C. Fractions containing the product were combined and dried via centrifugal evaporation to yield (R)-8-(4-(bis(4-chlorophenyl)methyl)-3-ethylpiperazin-1-yl)-5-methyl-6-oxo-5,6-dihydro-1,5-naphthyridine-2-carbonitrile (23.5 mg, 33.4% yield); LCMS: m/z=532.2 (M+H); rt 2.873 min. Method: Column-X Bridge BEH XP C18 (50×2.1 mm 2.5 μm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile; 10 mM ammonium acetate. $^1$H NMR (400 MHz, DMSO-$d_6$) δ ppm 8.15 (d, J=8.8 Hz, 1H), 8.08 (d, J=9.0 Hz, 1H), 7.55 (d, J=8.6 Hz, 2H), 7.50 (d, J=8.3 Hz, 2H), 7.39 (d, J=7.1 Hz, 4H), 6.12 (s, 1H), 5.00 (s, 1H), 4.23 (d, J=11.2 Hz, 1H), 3.54 (s, 3H), 3.42 (d, J=12.2 Hz, 1H), 3.10 (d, J=11.5 Hz, 2H), 3.03 (d, J=10.3, Hz, 2H), 2.75 (d, J=14.9 Hz, 1H), 1.93 (s, 1H), 1.71 (br. s., 1H), 0.78 (t, J=7.2 Hz, 3H).

Intermediate 134 tert-butyl (R)-4-(6-cyano-1-methyl-2-oxo-1,2-dihydro-1,5-naphthyridin-4-yl)-3-isopropylpiperazine-1-carboxylate

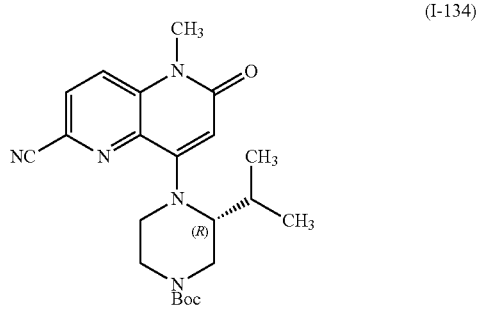

(I-134)

To a stirred solution of (R)-1-Boc-3-isopropyl-piperazine (180 mg, 0.788 mmol) in DMA (1 mL) were added DIPEA (0.413 mL, 2.365 mmol) and 6-cyano-1-methyl-2-oxo-1,2-dihydro-1,5-naphthyridin-4-yl trifluoromethanesulfonate (263 mg, 0.788 mmol). The reaction mixture was heated to 85° C. for 16 h. The reaction mixture was cooled to room temperature and the solvent was removed under reduced pressure. The residue was dissolved in ethyl acetate and washed with water, the organic layer was dried over anhydrous $Na_2SO_4$, filtered, and evaporated under reduced pressure. The crude material was dissolved in DCM and loaded on a Prep TLC plate. The plate was developed using 5% ethyl acetate in petroleum ether and the product was marked and the silica was dissolved in 10% methanol/DCM, stirred for 10 min, filtered and washed with DCM, the filtrate was removed under reduced pressure to yield tert-butyl (R)-4-(6-cyano-1-methyl-2-oxo-1,2-dihydro-1,5-naphthyridin-4-yl)-3-isopropylpiperazine-1-carboxylate (140 mg, 41.9% yield) as a semisolid; LCMS: m/z=412.2 (M+H); rt 2.888 min. Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 135

(R)-8-(2-isopropylpiperazin-1-yl)-5-methyl-6-oxo-5,6-dihydro-1,5-naphthyridine-2-carbonitrile, TFA

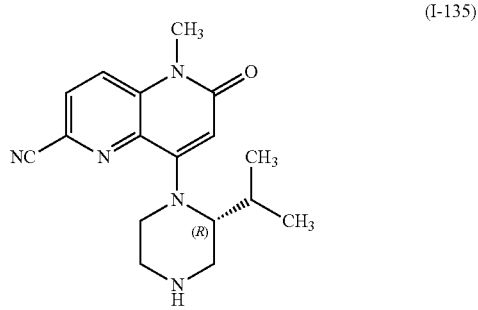

(I-135)

To a stirred solution of tert-butyl (R)-4-(6-cyano-1-methyl-2-oxo-1,2-dihydro-1,5-naphthyridin-4-yl)-3-isopropylpiperazine-1-carboxylate (140 mg, 0.340 mmol) in DCM (3 mL) was added TFA (3 mL, 38.9 mmol). The reaction mixture was stirred at room temperature for 2 h. The solvent was removed under reduced pressure to yield TFA salt of (R)-8-(2-isopropylpiperazin-1-yl)-5-methyl-6-oxo-5,6-dihydro-1,5-naphthyridine-2-carbonitrile (70 mg, 33.9% yield) as a gum; LCMS: m/z=312.2 (M+H); rt 0.81 min. Method: Column-AQUITY UPLC BEH C18 (3.0×50 mm) 1.7 µm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Example 181

(R)-8-(4-(bis(4-fluorophenyl)methyl)-2-isopropylpiperazin-1-yl)-5-methyl-6-oxo-5,6-dihydro-1,5-naphthyridine-2-carbonitrile

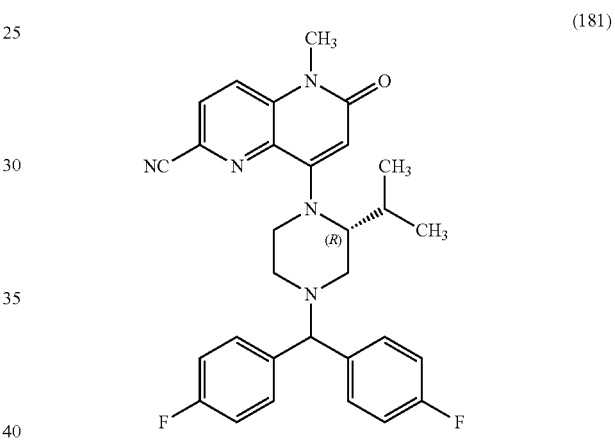

(181)

To a stirred solution of (R)-8-(2-isopropylpiperazin-1-yl)-5-methyl-6-oxo-5,6-dihydro-1,5-naphthyridine-2-carbonitrile, TFA (60 mg, 0.141 mmol) in acetonitrile (3 mL) were added DIPEA (0.074 mL, 0.423 mmol) and 4,4'-(chloromethylene) bis(fluorobenzene) (0.053 mL, 0.282 mmol). The reaction mixture was heated to 85° C. for 16 h. The reaction mixture was cooled to room temperature and the solvent was removed under reduced pressure. The crude material was purified via preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-70% B over 25 minutes, then a 5 minute hold at 100% B; Flow Rate: 15 mL/min; Column Temperature: 25° C. Fraction collection was triggered by MS signals. Fractions containing the product were combined and dried via centrifugal evaporation to yield (R)-8-(4-(bis(4-fluorophenyl)methyl)-2-isopropylpiperazin-1-yl)-5-methyl-6-oxo-5,6-dihydro-1,5-naphthyridine-2-carbonitrile (9.2 mg, 12.7% yield); LCMS: m/z=m/z=514.3 (M+H); rt 2.656 min. Method: Column-X Bridge BEH XP C18 (50×2.1 mm 2.5 µm; flow rate 1.1 mL/min; gradient time 3 min; Temperature: 50° C., 0% Solvent B to 100% Solvent B; monitoring at 220 nm (Solvent A: 95% water:5% acetonitrile; 10 mM ammonium acetate; Solvent B: 5% water:95% acetonitrile;

10 mM ammonium acetate. $^1$H NMR (400 MHz, DMSO-$d_6$) δ ppm 8.13 (d, J=9.0 Hz, 1H), 8.04 (d, J=8.8 Hz, 1H), 7.51 (d, J=5.4 Hz, 4H), 7.25-7.04 (m, 4H), 6.04 (s, 1H), 4.36 (br. s., 2H), 3.51 (br. s., 5H), 2.92-2.73 (m, 3H), 2.18 (d, J=8.8 Hz, 1H), 2.06 (br. s., 1H), 0.77 (d, J=6.6 Hz, 4H), 0.81 (d, J=6.6 Hz, 2H).

Intermediate 136

Methyl 2-ethyl-4-fluorobenzoate

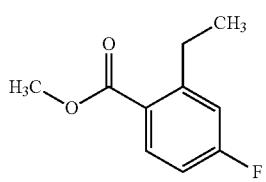
(I-136)

Methyl 2-ethyl-4-fluorobenzoate was prepared according to the general method disclosed in WO 2017/048950.

Zinc bromide (8 g, 35.5 mmol) was dissolved in THF (88 mL) in a 250 mL round bottom flask under nitrogen. Ethylmagnesium bromide (3 M in ether, 11.78 mL, 35.3 mmol) was added dropwise over 10 minutes. A thick slurry formed as the Grignard reagent was added, but the reaction mixture thinned after approximately ½ of the reagent was added. The reaction mixture was cooled in a dry ice bath to form a very thick slurry. Pd(dppf) ([1,1'-bis(diphenylphosphino)ferrocene] dichloropalladium(II)) (1.293 g, 1.767 mmol) and methyl 2-bromo-4-fluorobenzoate (4.12 g, 17.67 mmol) were added to the top of the slurry. The cooling bath was removed. As the temperature increased, the reaction was mixed by hand to homogenize it until the stir bar began to stir. The reaction mixture was stirred at room temperature overnight. TLC analysis in 2:1 hexanes:ethyl acetate showed starting material with about 50% conversion to a higher Rf product. The reaction mixture was heated at reflux for 3 hours. Starting material was shown to be consumed by TLC. The reaction mixture was cooled on an ice bath and 100 mL of saturated ammonium chloride was added. The mixture was partitioned between ethyl acetate and water. The organic portion was concentrated and chromatographed with ethyl acetate and hexanes on an 80 g silica gel column to afford methyl 2-ethyl-4-fluorobenzoate (2.7 g, 14.82 mmol, 84% yield). $^1$H NMR (400 MHz, chloroform-d) δ 7.93 (dd, J=8.8, 6.1 Hz, 1H), 7.00 (dd, J=9.9, 2.6 Hz, 1H), 6.94 (td, J=8.3, 2.7 Hz, 1H), 3.91 (s, 3H), 3.03 (q, J=7.3 Hz, 2H), 1.26 (t, J=7.5 Hz, 3H).

Intermediate 137

(2-Ethyl-4-fluorophenyl)methanol

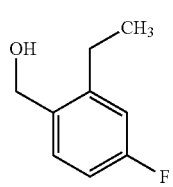
(I-137)

(2-Ethyl-4-fluorophenyl)methanol was prepared using the general procedure described in Vadola, P. A. et al., *J. Org. Chem.* 2012, 77, 6689-6702.

In an oven-dried 500 mL round bottom flask, lithium aluminum hydride (LAH) in THF (11.11 mL, 22.23 mmol) was diluted with dry THF (30 mL) under nitrogen and cooled on an ice bath. Using an oven dried dropping funnel, methyl 2-ethyl-4-fluorobenzoate (2.7 g, 14.82 mmol) in THF (60 mL) was added dropwise to the LAH solution. The reaction mixture was warmed to room temperature. The reaction was monitored by TLC in 30% ethyl acetate in hexanes. After complete reduction of the starting material, the reaction mixture was cooled to 0° C. The reaction was quenched with water (3 mL), stirred 5 minutes, with KOH 20% (9 mL), stirred 5 minutes, and finally water (15 mL). After stirring for 5 min., the suspension was filtered, the filtrate dried over MgSO$_4$ and concentrated in vacuo. The material was redissolved in ethyl acetate, dried over MgSO$_4$, and concentrated in vacuo to give (2-ethyl-4-fluorophenyl)methanol (2.3 g, 100% yield).

Intermediate 138

2-Ethyl-4-fluorobenzaldehyde

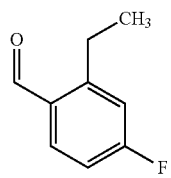
(I-138)

2-Ethyl-4-fluorobenzaldehyde was prepared according to the general method disclosed in Wipf, P. et al., *Org. Lett.*, 2003, 5 (7), pp 1155-1158. In a dry 500 mL round bottom flask, (2-ethyl-4-fluorophenyl)methanol (2.3 g, 14.8 mmol) was dissolved in dichloromethane (74.0 mL), and pyridinium chlorochromate (6.38 g, 29.6 mmol) was added. After 1 hour, TLC in 1:2 ethyl acetate:hexanes showed the reaction was complete. The reaction mixture was filtered through a plug of silica gel. The silica gel was eluted with dichloromethane until UV activity was not detected in the effluent. The organic portions were combined and the solvent was removed to afford 2-ethyl-4-fluorobenzaldehyde (2 g, 13.14 mmol, 89% yield) as a pale yellow oil. $^1$H NMR (400 MHz, chloroform-d) δ 10.24 (s, 1H), 7.87 (dd, J=8.4, 6.0 Hz, 1H), 7.10-6.98 (m, 2H), 3.10 (q, J=7.5 Hz, 2H), 1.31 (t, J=7.6 Hz, 3H).

Intermediate 139

(2-Ethyl-4-fluorophenyl)(4-fluorophenyl)methanol (racemic)

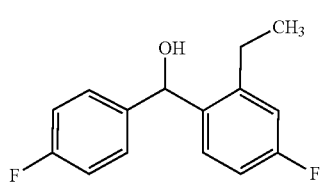
(I-139)

In a 250 mL, dry, round bottom flask, 2-ethyl-4-fluorobenzaldehyde (1 g, 6.57 mmol) was dissolved in THF (32.9 mL) and cooled on an ice bath under nitrogen. To this cold solution, (4-fluorophenyl)magnesium bromide (3.94 mL, 7.89 mmol, 2M in ether) was added. The reaction mixture was stirred at 0° C. for 45 minutes and then at room temperature for 10 minutes. The reaction was quenched by addition of 3 mL saturated aqueous ammonium chloride. The mixture was partitioned between ethyl acetate and water. The organic portion was extracted once with brine, concentrated and the residue chromatographed on a 24 g silica gel column with 0-60% ethyl acetate in hexanes. The sample was dried under high vacuum overnight to provide (2-ethyl-4-fluorophenyl)(4-fluorophenyl)methanol (2 g, 55%) as a crystalline solid. NMR analysis showed this material to be >95% pure. $^1$H NMR (400 MHz, chloroform-d) δ 7.44 (dd, J=9.3, 5.9 Hz, 1H), 7.33-7.29 (m, 2H), 7.04 (t, J=8.6 Hz, 2H), 6.98-6.91 (m, 2H), 6.05 (d, J=3.2 Hz, 1H), 2.79-2.46 (m, 2H), 2.09 (d, J=3.9 Hz, 1H), 1.16 (t, J=7.5 Hz, 3H). Analytical LC\MS conditions: Injection Vol=3 μL, Start % B 2, Final % B 98, Gradient Time 1.5 Minutes, Flow Rate 0.8 mL/min, Wavelength 220 nm, Solvent Pair acetonitrile/water/TFA, Solvent A 100% water/0.05% TFA, Solvent B 100% acetonitrile/0.05% TFA, Column Acquity BEH C18 21. ×50 mm 1.7 μm, Oven Temp=40° C. LC\MS results; retention time 1.6 minutes, observed mass 231.0 (M$^+$-OH).

Intermediate 140

1-(Bromo(phenyl)methyl)-4-fluorobenzene
(racemic)

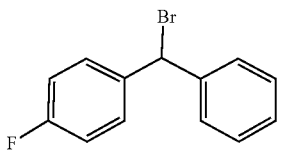

(I-140)

(4-fluorophenyl)(phenyl)methanol (52 mg, 0.257 mmol) and triphenylphosphine (70.8 mg, 0.270 mmol) were combined in tetrahydrofuran (1029 μL). The reaction mixture was cooled to 0° C. and stirred for 2 minutes until homogeneous. Perbromomethane (90 mg, 0.270 mmol) was added and the reaction mixture was stirred at room temperature for 2 hours. LC/MS analysis indicated the reaction was complete. Solids were removed by filtering and the clear solution was concentrated under vacuum to afford 1-(bromo(phenyl) methyl)-4-fluorobenzene as a racemic mixture.

Intermediate 141

1-(Bromo(4-chlorophenyl)methyl)-4-fluorobenzene
(racemic)

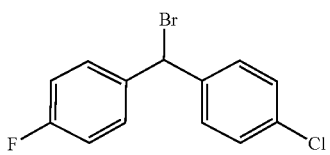

(I-141)

(4-chlorophenyl)(4-fluorophenyl)methanol (52 mg, 0.220 mmol) and triphenylphosphine (60.5 mg, 0.231 mmol) were combined in tetrahydrofuran (879 μl), cooled to 0° C. and stirred for 2 minutes until homogeneous. Perbromomethane (77 mg, 0.231 mmol) was added and the reaction stirred at room temperature for 2 hours. LC/MS analysis indicated the reaction was complete. Solids were removed by filtering and the clear solution was concentrated under vacuum to afford 1-(bromo(4-chlorophenyl) methyl)-4-fluorobenzene as a racemic mixture.

Intermediate 142

Stereochemistry: A
(Cyanomethyl)trimethylphosphonium Iodide

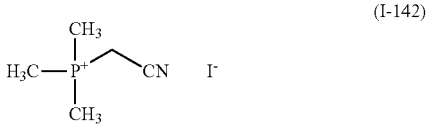

(I-142)

(Cyanomethyl)trimethylphosphonium iodide was prepared according to the general method described in Zaragoza, F., et al., *J. Org. Chem.* 2001, 66, 2518-2521. In a 1 L round bottom flask, trimethylphosphine in toluene (100 mL, 100 mmol) was diluted with THF (50.0 mL) and toluene (50.0 mL), and cooled on an ice bath. The reaction mixture was stirred vigorously while iodoacetonitrile (7 mL, 16.7 g, 68.3 mmol) was added dropwise to produce a tan precipitate. The cooling bath was removed and the reaction mixture was stirred overnight at room temperature. The flask was placed in a sonicator to break up any clumped solids. The reaction mixture was stirred an additional 4 hours. The solids were collected by filtration and dried under vacuum to give (cyanomethyl)trimethylphosphonium iodide (16.6 g, 68.3 mmol, 68.3% yield). $^1$H NMR (400 MHz, DMSO-d$_6$) δ 4.03 (d, J=16.4 Hz, 2H), 2.05 (d, J=15.4 Hz, 9H).

Intermediate 143

Stereochemistry: H 8-((2S,5R)-2,5-Dimethylpiperazin-1-yl)-5-methyl-6-oxo-5,6-dihydro-1,5-naphthyridine-2-carbonitrile,
TFA

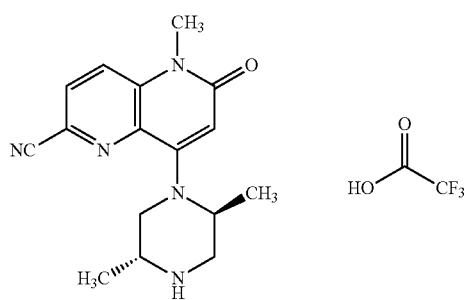

(I-143)

To a solution of 6-cyano-1-methyl-2-oxo-1,2-dihydro-1,5-naphthyridin-4-yl trifluoromethanesulfonate (65 g, 195 mmol) and tert-butyl (2R,5S)-2,5-dimethylpiperazine-1-carboxylate (43.9 g, 205 mmol) in acetonitrile (1.3 L) was added DIPEA (0.102 L, 585 mmol). The solution was stirred at 80° C. for 6 hours. The solvent was removed and the crude residue chromatographed on silica gel (product Rf 0.4 in 100% ethyl acetate). The product, tert-butyl (2R,5S)-4-(6-cyano-1-methyl-2-oxo-1,2-dihydro-1,5-naphthyridin-4-yl)-2,5-dimethylpiperazine-1-carboxylate (75 g, 189 mmol, 97% yield) was obtained. LCMS: m/z=398.2 (M+H); rt 2.7 min. Method: Column-Kinetex XB-C18 (75×3 mm-2.6 µm), flow rate 1 mL/min; gradient time 4 min; 20% Solvent B to 100% Solvent B; monitoring at 254 nm (Solvent A: 98% water:2% acetonitrile; 10 mM ammonium formate; Solvent B: 2% water:98% acetonitrile; 10 mM ammonium formate.

To a solution of tert-butyl (2R,5S)-4-(6-cyano-1-methyl-2-oxo-1,2-dihydro-1,5-naphthyridin-4-yl)-2,5-dimethylpiperazine-1-carboxylate (30 g, 75 mmol) in ethyl acetate (1000 mL) at 0° C. was added HCl (4 M in dioxane) (189 mL, 755 mmol) and the temperature was allowed to reach room temperature while stirring for 6 h. LC/MS analysis showed 90% product mass at 0.60 RT along with 4% of an amide byproduct mass (consistent with nitrile hydrolysis) at 0.44 RT. The reaction mixture was diluted with methyl t-butyl ether (MTBE, 2000 mL), stirred for 15 mins, and the HCl salt of product was filtered, washed with MTBE (100 ml). The HCl salt was dissolved in water (300 ml) and the pH adjusted to ~8 using 10% aqueous sodium bicarbonate. The organic portion was extracted with DCM (5×250 ml). The combined organic layers were washed with water (2×300 mL), dried over sodium sulphate and concentrated to afford 8-((2S,5R)-2,5-dimethylpiperazin-1-yl)-5-methyl-6-oxo-6,6-dihydro-1,5-naphthyridine-2-carbonitrile (20 g, 65.2 mmol, 86% yield). LCMS: m/z=298.2 (M+H); rt 0.5 min. Method: Column-Kinetex XB-C18 (75×3 mm-2.6 µm), flow rate 1 mL/min; gradient time 4 min; 20% Solvent B to 100% Solvent B; monitoring at 254 nm (Solvent A: 98% water:2% acetonitrile; 10 mM ammonium formate; Solvent B: 2% water:98% acetonitrile; 10 mM ammonium formate. $^1$H NMR (400 MHz, CDCl$_3$) δ 7.79 (d, J=8.8 Hz, 1H), 7.70 (d, J=12, 3.2 Hz, 1H), 6.29 (s, 1H), 3.80 (dd, J=8.8 Hz, 1H) 3.70 (m, 1H), 3.65 (s, 3H), 3.29 (m, 2H), 2.80 (m, 2H), 1.19 (d, J=6 Hz, 3H), 1.15 (d, J=6 Hz, 3H). $^{13}$C NMR (75 MHz, Chloroform-d) δ 161.9, 155.0, 138.5, 137.0, 128.2, 125.0, 122.2, 117.2, 111.3, 56.5, 51.9, 50.0, 49.5, 29.0, 18.8, 15.4.

Intermediate 144

Ethyl 3-amino-6-bromopicolinate

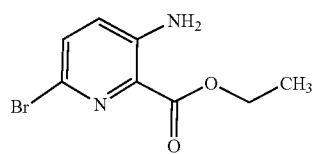

(I-144)

Ethyl 3-aminopicolinate (8.0 g, 48.1 mmol) was suspended in water (66 mL) in a 250 mL three neck round bottom flask equipped with a mechanical stirrer, addition funnel and thermocouple temperature probe. Sulfuric acid (1.7 mL, 31.9 mmol) and acetic acid (3.31 mL, 57.8 mmol) were added slowly while the flask was immersed in a room temperature water bath to control temperature. To the reaction mixture, a solution of bromine (2.5 mL, 48.5 mmol) in acetic acid (17.5 mL, 306 mmol) was added over 15 minutes at ambient temperature with vigorous stirring while maintaining the internal temperature of the reaction mixture below 23° C. The water bath was removed and the reaction mixture was stirred at ambient temperature for 2 hours. The reaction suspension was filtered and rinsed with a small amount of water, and then dried in vacuo at room temperature to yield ethyl 3-amino-6-bromopicolinate (9.305 g) as a yellow solid. LCMS: Column: Waters Acquity UPLC BEH C18, 2.1×50 mm, 1.7 µm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time 0.94 min.; Obs. Adducts: [M+H]; Obs. Masses: 245.0. $^1$H NMR (DMSO-d$_6$) δ 7.44 (d, J=8.8 Hz, 1H), 7.21 (d, J=8.7 Hz, 1H), 6.88 (br. s., 2H), 4.29 (q, J=7.1 Hz, 2H), 1.31 (t, J=7.1 Hz, 3H).

Intermediate 145

Ethyl 3-acetamido-6-bromopicolinate

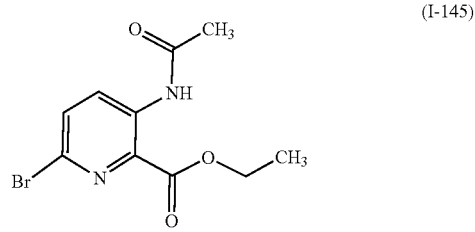 [SMILES: CCOC(=O)c1nc(Br)ccc1NC(C)=O]

(I-145)

Ethyl 3-amino-6-bromopicolinate (1.31 g, 5.35 mmol) was dissolved in THF (6 mL) followed by the addition of acetic anhydride (1.6 mL, 16.96 mmol). The reaction mixture was a suspension/partial solution. The reaction mixture was placed under a nitrogen atmosphere and heated to reflux. The reaction mixture became homogeneous within 15 minutes. The reaction mixture was refluxed for 4 hrs. The reaction volatiles were removed in vacuo using a rotary evaporator. A small amount of ethyl acetate was added to the reaction residue and a nearly colorless solid was filtered off and dried in vacuo to yield ethyl 3-acetamido-6-bromopicolinate (787 mg). LCMS: Column: Waters Acquity UPLC BEH C18, 2.1×50 mm, 1.7 µm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time 0.98 min.; Obs. Adducts: [M+H]; Obs. Masses: 287.0. $^1$H NMR (DMSO-d$_6$) δ 10.40 (s, 1H), 8.32 (d, J=8.7 Hz, 1H), 7.83 (d, J=8.8 Hz, 1H), 4.33 (q, J=7.1 Hz, 2H), 2.12 (s, 3H), 1.32 (t, J=7.2 Hz, 3H). Removal of solvent from the filtrate provided an additional 695 mg of product (87% pure).

Intermediate 146

Ethyl 6-bromo-3-(N-methylacetamido)picolinate

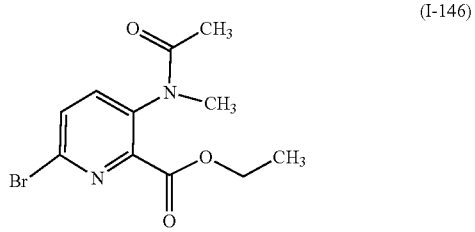 [SMILES: CCOC(=O)c1nc(Br)ccc1N(C)C(C)=O]

(I-146)

A solution was prepared by dissolving ethyl 3-acetamido-6-bromopicolinate (5 g, 17.41 mmol) into DMF (100 mL). Next, cesium carbonate (8.15 g, 25.01 mmol) and methyl iodide (1.75 mL, 28.0 mmol) were added. The reaction mixture was placed under a nitrogen atmosphere and stirred at room temperature for 2 hours and 40 minutes. Solvent was removed in vacuo using a rotary evaporator/vacuum pump combination. Ethyl acetate and DCM were added to the reaction residue along with chloroform and toluene. The mixture was filtered through a celite pad to remove salts. Solvents were again removed in vacuo using a rotary evaporator. The reaction residue was again dissolved in chloroform and toluene and filtered through a celite bed to remove trace insolubles still present. Removal of solvents in vacuo yielded 5.35 g of the product as an orange oil. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time 1.07 min.; Obs. Adducts: [M+H]; Obs. Masses: 301.1. Proton NMR shows characteristics of restricted rotation (rotamers); $^1$H NMR (500 MHz, CHLOROFORM-d) δ 7.72 (d, J=8.4 Hz, 0.8H), 7.66 (d, J=8.4 Hz, 0.2H), 7.51 (d, J=8.4 Hz, 0.8H), 7.45 (d, J=8.4 Hz, 0.2H), 4.50-4.36 (m, 2.0H), 3.37 (s, 0.6H), 3.19 (s, 2.4H), 2.24 (s, 0.6H), 1.82 (s, 2.5H), 1.43-1.36 (m, 3.1H).

Intermediate 147

6-bromo-4-hydroxy-1-methyl-1,5-naphthyridin-2(1H)-one

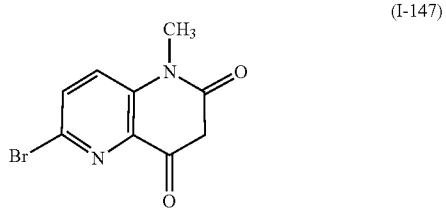

(I-147)

A 25 mL round bottom flask was charged with KHMDS (4.3 mL, 2.150 mmol) (0.5 M in toluene), placed under nitrogen and cooled to −78° C. To the solution of KHMDS was slowly added a solution of ethyl 6-bromo-3-(N-methylacetamido)picolinate (215 mg, 0.714 mmol) in THF (2.5 mL) over approximately 3 minutes. The reaction mixture was warmed to room temperature and a 1:1 mixture of ethyl acetate and water were added to fill the 60 mL separatory funnel. The phases were allowed to separate. The aqueous phase was acidified with 2.5 mL of 1N hydrochloric acid and concentrated on the rotary evaporator using a vacuum pump. The crude residue was swirled in an Erlenmeyer flask with 7 mL of water. A yellow solid collected and dried under vacuum to give the title compound (130.2 mg, 72%). LCMS; Column: Waters Acquity UPLC BEH C18 2.1 mm×50 mm, 1.7 μm particles; Mobile Phase A: 100 water with 0.05% TFA; Mobile Phase B: 100 acetonitrile 0.05% TFA; Temperature: 40° C.; Gradient 2% B to 98% B over 1.5 minutes, then 1 min hold at 100% B; Flow: 0.8 mL/min; Detection: MS and UV (220 nm). Injection volume: 3 μL. Retention Time 0.8 min.; Obs. Adducts: [M+H]; Obs. Masses: 254.9, 256.9.

Intermediate 148

6-Bromo-4-hydroxy-1,5-naphthyridin-2(1H)-one

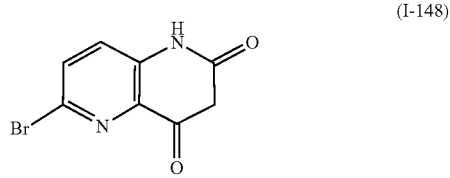 [SMILES: O=C1CC(=O)c2nc(Br)ccc2N1]

(I-148)

To a solution of KHMDS (0.5 M in toluene) (27.2 mL, 13.58 mmol) at −78° C. was slowly added a solution of ethyl 3-acetamido-6-bromopicolinate (1.3 g, 4.53 mmol) in THF (20 mL). The reaction mixture was stirred at −78° C. for 1 hour and then the cooling bath was removed. After warming to room temperature, the yellow solution turned light orange. Ethyl acetate followed by water were added and the color returned to yellow. The phases were separated and the yellow aqueous layer was treated with HCl (1N) and white solid precipitated. The yellow solid was collected by filtration to give the product (950 mg, 76%). LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time 0.7 min.; Obs. Adducts: [M+H]; Obs. Masses: 240.9 242.9.

297

Intermediate 149

6-Bromo-1-methyl-2-oxo-1,2-dihydro-1,5-naphthyridin-4-yl trifluoromethanesulfonate

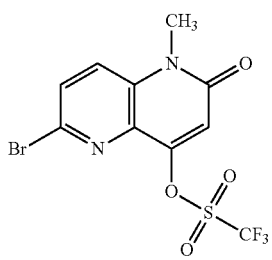

(I-149)

In a round bottom flask, 6-bromo-1-methyl-1,5-naphthyridine-2,4(1H,3H)-dione (200 mg, 0.784 mmol) was combined with DMAP (9.58 mg, 0.078 mmol), DIPEA (0.205 mL, 1.176 mmol) and DCM (20 mL). To the resulting suspension, a solution of trifluoromethanesulfonic anhydride (0.141 mL, 0.863 mmol) in dichloromethane (2 mL) was added dropwise at 0° C. The solution was stirred for 3 hours. LC/MS analysis indicated the reaction was complete. The solvent was removed under reduced pressure and the crude was purified by chromatography with 1:1 hexane:ethyl acetate on a 24 g silica gel column to afford the product as white solid (260 mg, 86%). Analytical LC\MS conditions: Injection Vol=1 µL, Start % B 0, Final % B 100, Gradient Time 2 Minutes, Flow Rate 1 mL/min, Wavelength 220 nm, Solvent Pair acetonitrile/water/TFA, Solvent A 10% Acetonitrile/90% Water/0.1% TFA, Solvent B 90% Acetonitrile/10% Water/0.1% TFA, Column Acquity BEH C18 21. X 50 mm 1.7 µm, Oven Temp=40° C. LC\MS results; retention time 1.5 minutes, observed mass 386.7, 388.7 (M+).

Intermediate 150

Stereochemistry: H tert-Butyl (2R,5S)-4-(6-bromo-1-methyl-2-oxo-1,2-dihydro-1,5-naphthyridin-4-yl)-2,5-dimethylpiperazine-1-carboxylate

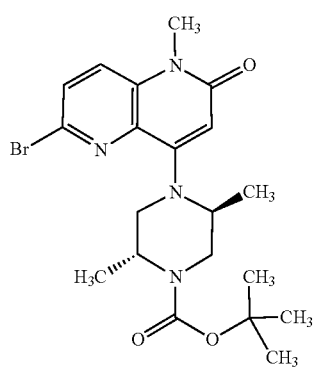

(I-150)

298

To a mixture of (2R,5S)-tert-butyl 2,5-dimethylpiperazine-1-carboxylate (156 mg, 0.705 mmol) and 6-bromo-1-methyl-2-oxo-1,2-dihydro-1,5-naphthyridin-4-yl trifluoromethanesulfonate (260 mg, 0.672 mmol) in acetonitrile (6.7 mL) was added DIPEA (0.352 mL, 2.015 mmol). The reaction was heated at 80° C. overnight. LC/MS analysis indicated the reaction was complete. The solvent was removed and the crude material purified on a silica gel column using a gradient 1-20% methanol in dichloromethane to give the title compound (0.28 g, 92% yield). Analytical LC\MS conditions: Injection Vol=1 µL, Start % B 0, Final % B 100, Gradient Time 2 Minutes, Flow Rate 1 mL/min, Wavelength 220 nm, Solvent Pair acetonitrile/water/TFA, Solvent A 10% acetonitrile/90% water/0.1% TFA, Solvent B 90% acetonitrile/10% water/0.1% TFA, Column Acquity BEH C18 21. X 50 mm 1.7 µm, Oven Temp=40° C. LC\MS results; retention time 1.7 minutes, observed mass 451.0, 453.1 (M+1).

Intermediate 151 tert-Butyl (2R,5S)-4-(6-methoxy-1-methyl-2-oxo-1,2-dihydro-1,5-naphthyridin-4-yl)-2,5-dimethylpiperazine-1-carboxylate

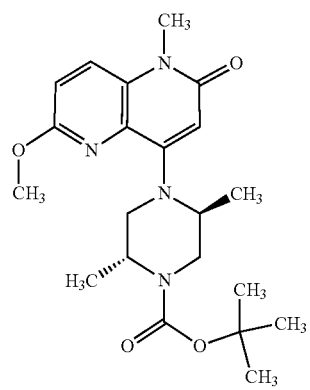

(I-151)

Tert-butyl(2R,5S)-4-(6-bromo-1-methyl-2-oxo-1,2-dihydro-1,5-naphthyridin-4-yl)-2,5-dimethylpiperazine-1-carboxylate (270 mg, 0.598 mmol), palladium(II) acetate (13.43 mg, 0.060 mmol), cesium carbonate (195 mg, 0.598 mmol), and 2-(di-1-adamantylphosphino)-3,6-dimethoxy-2',4',6'-tri-i-propyl-1,1'-biphenyl (77 mg, 0.120 mmol) were charged to a microwave tube under nitrogen. Acetonitrile (2 mL) and methanol (0.1 mL) were added and the mixture heated at 80° C. for 6 hrs. LC/MS indicated completion of the reaction. A portion of the crude material was purified via preparative LC/MS to obtain an analytical sample with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 26% B, 26-66% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 9.3 mg, and its estimated purity by LCMS analysis was 95%. Analytical LC/MS was used to determine the final purity. Injection 1 conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.1%; Observed Mass: 403.16; Retention Time: 1.85 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 95.1%; Observed Mass: 403.17; Retention Time: 1.66 min. $^1$H NMR (500 MHz, DMSO-$d_6$) δ 7.96 (d, J=9.2 Hz, 1H), 7.12 (d, J=9.2 Hz, 1H), 5.93 (s, 1H), 4.99 (br s, 1H), 4.44-4.28 (m, 2H), 3.91 (s, 3H), 3.56 (s, 3H), 3.31-3.17 (m, 1H), 3.14 (br s, 1H), 3.09-2.93 (m, 1H), 1.43 (br s, 9H), 1.20 (br d, J=6.7 Hz, 3H), 0.96 (br d, J=6.4 Hz, 3H).

Intermediate 152

4-((2S,5R)-2,5-Dimethylpiperazin-1-yl)-6-methoxy-1-methyl-1,5-naphthyridin-2(1H)-one, TFA

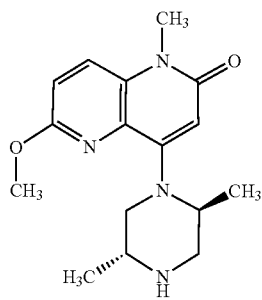

(I-152)

To a dichloromethane (4 mL) solution of tert-butyl (2R,5S)-4-(6-methoxy-1-methyl-2-oxo-1,2-dihydro-1,5-naphthyridin-4-yl)-2,5-dimethylpiperazine-1-carboxylate (220 mg, 0.547 mmol) was added TFA (0.758 mL, 9.84 mmol). The reaction mixture was stirred at room temperature for 3 hours. LC/MS analysis indicated the reaction was complete. The solvent was removed and the crude material was used without further purification. Analytical LC\MS conditions: Injection Vol=3 μL, Start % B 2, Final % B 98, Gradient Time 1.5 Minutes, Flow Rate 0.8 mL/min, Wavelength 220 nm, Solvent Pair acetonitrile/water/TFA, Solvent A 100% Water/0.05% TFA, Solvent B 100% acetonitrile/0.05% TFA, Column Acquity BEH C18 21. X 50 mm 1.7 μm, Oven Temp=40° C. LC\MS results; retention time 1.1 minutes, observed mass 303.3 (M+1). $^1$H NMR (400 MHz, DMSO-$d_6$) δ 7.95 (d, J=9.3 Hz, 1H), 7.09 (d, J=9.0 Hz, 1H), 6.04 (s, 1H), 3.90 (s, 3H), 3.74-3.64 (m, 1H), 3.57-3.43 (m, 3H), 3.31 (s, 3H), 3.16 (dd, J=12.3, 3.3 Hz, 1H), 3.05 (td, J=6.8, 2.9 Hz, 1H), 2.60-2.53 (m, 1H), 1.02 (dd, J=7.8, 6.4 Hz, 6H).

Example 182

8-[(2S,5R)-4-[(4-fluorophenyl)(phenyl)methyl]-2,5-dimethylpiperazin-1-yl]-5-methyl-6-oxo-5,6-dihydro-1,5-naphthyridine-2-carbonitrile

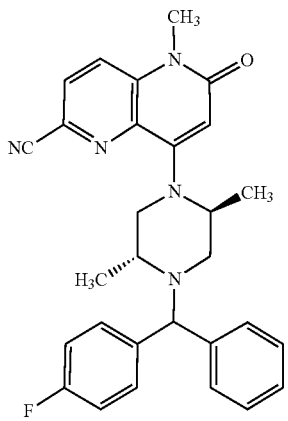

(182)

In a 2 dram sealed reaction vessel, 8-((2S,5R)-2,5-dimethylpiperazin-1-yl)-5-methyl-6-oxo-5,6-dihydro-1,5-naphthyridine-2-carbonitrile, TFA (41.1 mg, 100 μmol), (4-fluorophenyl)(phenyl)methanol (28.3 mg, 140 μmol) and (cyanomethyl) trimethylphosphonium iodide (48.6 mg, 200 μmol) were combined in acetonitrile (200 μl). Hunig's Base (75 μL, 429 μmol) was added and the reaction mixture was heated at 110° C. for 2 hours. The reaction mixture was injected directly onto a 12 g silica gel column and eluted with 20-100% ethyl acetate in hexanes to afford Example 182 as a diasteromeric mixture. Analytical LC\MS conditions: Injection Vol=3 μL, Start % B 0, Final % B 100, Gradient Time 2 Minutes, Flow Rate 1 mL/min, Wavelength 220 nm, Solvent Pair acetonitrile/Water/TFA, Solvent A 10% acetonitrile, 90% water/0.05% TFA, Solvent B 10% Water, 90% acetonitrile/0.05% TFA, Column Acquity BEH C18 21. X 50 mm 1.7 μm, Oven Temp=40° C. LC\MS results; retention time 1.4 minutes, observed mass 482.5 (M$^+$).

The crude material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 47% B, 47-87% B over 20 minutes, then a 4 minute hold at 100% B; Flow Rate: 20 mL/min; Column Temperature: 25° C. Fraction collection was triggered by MS signals. Fractions containing the product were combined and dried via centrifugal evaporation to afford 14.4 mg of the title compound (30% yield). Calculated molecular weight 481.575. LC\MS conditions QC-ACN-TFA-XB: Observed MS Ion 482.2, retention time 1.6 minutes. $^1$H NMR (500 MHz, DMSO-$d_6$) δ 8.18-8.10 (m, 1H), 8.06 (d, J=8.8 Hz, 1H), 7.68-7.48 (m, 4H), 7.39-7.26 (m, 2H), 7.25-7.08 (m, 3H), 6.00 (s, 1H), 4.67 (br s, 1H), 4.59 (br d, J=6.7 Hz, 1H), 3.76-3.62 (m, 1H), 3.55 (br d, J=12.8 Hz, 1H), 3.15-3.04 (m, 1H), 2.90-2.81 (m, 1H), 2.36 (br dd, J=17.4, 11.9 Hz, 1H), 1.35-1.28 (m, 3H), 1.24 (s, 1H), 1.07 (br t, J=5.6 Hz, 3H).

Examples 183 and 184

8-[(2S,5R)-4-[(4-fluorophenyl)(phenyl)methyl]-2,5-dimethylpiperazin-1-yl]-5-methyl-6-oxo-5,6-dihydro-1,5-naphthyridine-2-carbonitrile

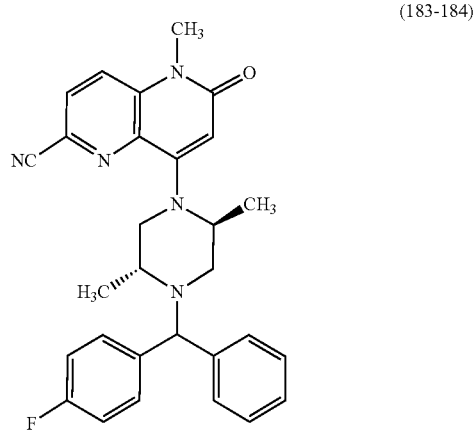 [SMILES: C[C@@H]1CN(c2cc(=O)n(C)c3ccc(C#N)nc23)[C@@H](C)CN1C(c1ccccc1)c1ccc(F)cc1]
(183-184)

Example 182 was separated into individual diastereomers using chiral solid phase chromatography: Column: Chiralpak OJ-H, 21×250 mm; 5 micron, Mobile Phase: 90% $CO_2$/10% methanol, Flow Conditions: 45 mL/min, Detector Wavelength: 225 nm, Injection Details: 500 µL, 15 mg dissolved in 1 mL methanol/acetonitrile.

The first eluting diastereomer, Example 183 (66.4 mg), was isolated in 20.2% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 482.1; Retention Time: 2.49 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 482.11; Retention Time: 1.75 min.

The second eluting diastereomer, Example 184 (71.7 mg), was isolated in 21.9% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 482.11; Retention Time: 2.51 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 482.1; Retention Time: 1.76 min.

Examples 185 and 186

8-[(2S,5R)-4-[1-(4-fluoro-2-methoxyphenyl)-2,2-dimethylpropyl]-2,5-dimethylpiperazin-1-yl]-5-methyl-6-oxo-5,6-dihydro-1,5-naphthyridine-2-carbonitrile

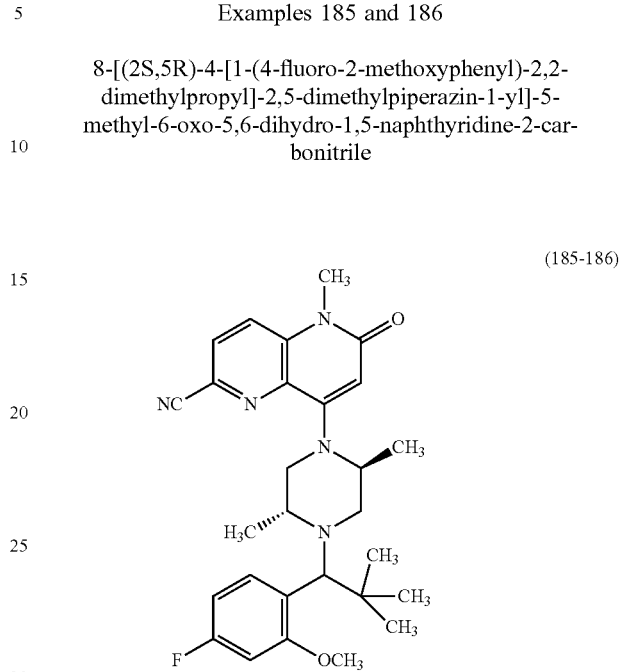
(185-186)

In a 2 dram vial, 8-((2S,5R)-2,5-dimethylpiperazin-1-yl)-5-methyl-6-oxo-5,6-dihydro-1,5-naphthyridine-2-carbonitrile, TFA (60 mg, 0.117 mmol), 1-(1-chloro-2,2-dimethylpropyl)-4-fluoro-2-methoxybenzene (32.3 mg, 0.140 mmol) and sodium iodide (175 mg, 1.167 mmol) were sealed under nitrogen. Hunig's base (0.102 mL, 0.583 mmol) and acetonitrile (2 mL) were added. The reaction mixture was heated at 110° C. for 5 hours in microwave reactor. LC/MS analysis indicated the reaction was complete, with both M+1 and M+42 (M+acetonitrile) observed.

The diastereomers were separated using non-chiral preparative HPLC. The first eluting diastereomer, Example 185 (4.2 mg), was isolated in 7.3% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.3%; Observed Mass: 492.2; Retention Time: 1.55 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.7%; Observed Mass: 492.21; Retention Time: 2.75 min.

The second eluting diastereomer, Example 186 (3.7 mg), was isolated in 6.4% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.4%; Observed Mass: 492.18; Retention Time: 1.58 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.2%; Observed Mass: 492.21; Retention Time: 2.79 min.

Intermediate 153

(4-Chlorophenyl)(3-fluoropyridin-2-yl)methanol

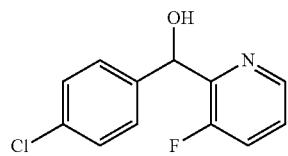

(I-153)

In a 250 mL, dry, round bottom flask, 3-fluoropicolinaldehyde (677 mg, 5.41 mmol) was dissolved in THF (20 mL) and cooled on an ice bath under nitrogen. To this cold solution, (4-chlorophenyl)magnesium bromide in diethyl ether (6.49 mL, 6.49 mmol) was added. The reaction mixture was stirred at 0° C. for 45 minutes and room temperature for 10 minutes. The reaction was quenched by addition of 3 mL saturated aqueous ammonium chloride. The mixture was partitioned between ethyl acetate and brine. The organic portion was concentrated and the residue chromatographed on a 24 g silica gel column with 0-60% ethyl acetate in hexanes. The fractions containing the product were combined, concentrated and dried under high vacuum overnight. NMR analysis showed this material to be >95% pure. $^1$H NMR (400 MHz, chloroform-d) δ 8.43 (br d, J=2.9 Hz, 1H), 7.48-7.17 (m, 6H), 5.98 (br s, 1H), 5.29 (br d, J=4.4 Hz, 1H). Analytical LC\MS conditions: Injection Vol=3 μL, Start % B 2, Final % B 98, Gradient Time 1.5 Minutes, Flow Rate 0.8 mL/min, Wavelength 220 nm, Solvent Pair acetonitrile/water/TFA, Solvent A 100% water/0.05% TFA, Solvent B 100% acetonitrile/0.05% TFA, Column Acquity BEH C18 21. X 50 mm 1.7 μm, Oven Temp=40° C. LC\MS results; retention time 1.3 minutes, observed mass 237.9 (M+1).

Intermediate 154

2-(Chloro(4-chlorophenyl)methyl)-3-fluoropyridine

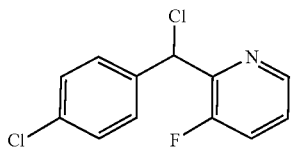

(I-154)

In a 250 mL round bottom flask, (4-chlorophenyl)(3-fluoropyridin-2-yl)methanol (750 mg, 3.16 mmol) was dissolved in dichloromethane (15.779 mL) and thionyl chloride (4.61 mL, 63.1 mmol) was added. The reaction vessel was sealed and heated at 40° C. overnight. The reaction mixture was cooled to room temperature and poured into 100 mL saturated potassium carbonate on an ice water bath. The mixture was partitioned between dichloromethane and water. The organic portions were combined, dried over magnesium sulfate and filtered. The solvent was removed to afford 2-(chloro(4-chlorophenyl)methyl)-3-fluoropyridine (793 mg, 3.10 mmol, 98% yield). $^1$H NMR (400 MHz, CHLOROFORM-d) δ 8.50 (d, J=4.6 Hz, 1H), 7.56 (d, J=8.3 Hz, 2H), 7.43 (ddd, J=9.7, 8.4, 1.2 Hz, 1H), 7.35 (d, J=8.6 Hz, 2H), 7.31 (dd, J=8.3, 4.2 Hz, 1H), 6.40 (s, 1H).

Intermediate 155

(4-Fluorophenyl)(3-fluoropyridin-2-yl)methanol

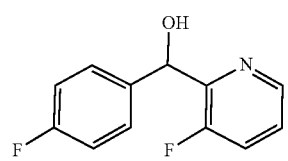

(I-155)

In a 250 mL, dry, round bottom flask, 3-fluoropicolinaldehyde (545 mg, 4.36 mmol) was dissolved in THF (20 mL) and cooled on an ice bath under nitrogen. To this cold solution (4-fluorophenyl)magnesium bromide in diethylether (2.61 mL, 5.23 mmol) was added. The reaction mixture was stirred at 0° C. for 45 minutes and room temperature for 10 minutes. The reaction was quenched by addition of 3 mL saturated aqueous ammonium chloride. The mixture was partitioned between ethyl acetate and brine. The organic portion was concentrated and the residue chromatographed on a 24 g silica gel column with 0-60% ethyl acetate in hexanes. The fractions containing the product were combined, concentrated and dried under high vacuum overnight. NMR analysis showed this material to be >95% pure. $^1$H NMR (400 MHz, chloroform-d) δ 8.44 (br d, J=3.2 Hz, 1H), 7.52-7.23 (m, 4H), 7.02 (br t, J=8.3 Hz, 2H), 5.99 (br d, J=6.1 Hz, 1H), 5.27 (br d, J=6.4 Hz, 1H). Analytical LC\MS conditions: Injection Vol=3 μL, Start % B 2, Final % B 98, Gradient Time 1.5 Minutes, Flow Rate 0.8 mL/min, Wavelength 220 nm, Solvent Pair Acetonitrile/Water/TFA, Solvent A 100% Water/0.05% TFA, Solvent B 100% Acetonitrile/0.05% TFA, Column Acquity BEH C18 21. ×50 mm 1.7 μm, Oven Temp=40° C. LC\MS results; retention time 1.2 minutes, observed mass 221.9 (M+).

Intermediate 156

2-(Chloro(4-fluorophenyl)methyl)-3-fluoropyridine

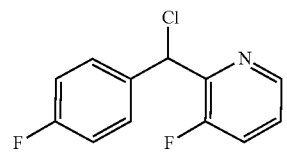

(I-156)

In a 250 mL round bottom flask, (4-fluorophenyl)(3-fluoropyridin-2-yl)methanol (613 mg, 2.77 mmol) was dissolved in dichloromethane (12 mL) and thionyl chloride (4.04 mL, 55.4 mmol) was added. The reaction vessel was sealed and heated at 40° C. overnight. The reaction mixture was cooled to room temperature and poured into 100 mL saturated potassium carbonate on an ice water bath. The mixture was partitioned between dichloromethane and water. The organic portions were combined, dried over magnesium sulfate and filtered. The solvent was removed to yield 2-(chloro(4-fluorophenyl)methyl)-3-fluoropyridine (798 mg, 3.33 mmol) as a clear oil. $^1$H NMR (400 MHz, CHLOROFORM-d) δ 8.51 (d, J=4.4 Hz, 1H), 7.60 (dd, J=8.7, 5.3 Hz, 2H), 7.43 (ddd, J=9.7, 8.4, 1.2 Hz, 1H), 7.33-7.29 (m, 1H), 7.07 (t, J=8.7 Hz, 2H), 6.42 (s, 1H).

Intermediates 157 and 158 tert-butyl (2S,5R)-4-((4-fluorophenyl)(3-fluoropyridin-2-yl)methyl)-2,5-dimethylpiperazine-1-carboxylate

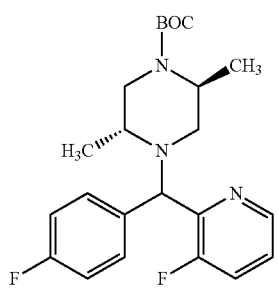

(I-157 and I-158)

In a round bottom flask, 2-(chloro(4-fluorophenyl)methyl)-3-fluoropyridine (790 mg, 3.30 mmol) was dissolved in acetonitrile (16.5 mL). To this solution, potassium iodide (54.7 mg, 0.330 mmol), triethylamine (0.919 mL, 6.59 mmol) and tert-butyl (2S,5R)-2,5-dimethylpiperazine-1-carboxylate (706 mg, 3.30 mmol) were added sequentially. After heating at 75° C. for 5 hours, TLC in 2:3 ethyl acetate/hexanes showed a trace of starting material and two new compounds of lower rf. LS\MS was consistent with 2 major products each having the correct MW corresponding to the two separable diastereomers. The crude material was chromatographed on a 24 g silica gel column with 10-50% ethyl acetate in hexanes to separate two major fractions labeled Isolate-1 and Isolate-02. LCMS showed that each fraction was consistent with a single diastereomer contaminated with a small amount of the other diastereomer.

Intermediate 157: Isolate-1, First eluting fraction. Analytical LC\MS conditions: Injection Vol=1 μL, Start % B 0, Final % B 100, Gradient Time 2 Minutes, Flow Rate 1 mL/min, Wavelength 220 nm, Solvent Pair Acetonitrile/Water/TFA, Solvent A 10% acetonitrile/90% water/0.05% TFA, Solvent B 10 Water 90% acetonitrile/0.05% TFA, Column Acquity BEH C18 21. X 50 mm 1.7 μm, Oven Temp=40° C. LC\MS results; retention time 1.27 minutes, observed mass 418.5 (MH$^+$).

Intermediate 158: Isolate-2, Second eluting fraction. Analytical LC\MS conditions: Injection Vol=1 μL, Start % B 0, Final % B 100, Gradient Time 2 Minutes, Flow Rate 1 mL/min, Wavelength 220 nm, Solvent Pair acetonitrile/water/TFA, Solvent A 10% acetonitrile/90% water/0.05% TFA, Solvent B 10 Water 90% acetonitrile/0.05% TFA, Column Acquity BEH C18 21. X 50 mm 1.7 μm, Oven Temp=40° C. LC\MS results; retention time 1.31 minutes, observed mass 418.1 (MH$^+$).

Intermediates 159 and 160

(2R,5S)-1-((4-Fluorophenyl)(3-fluoropyridin-2-yl)methyl)-2,5-dimethylpiperazine, HCl

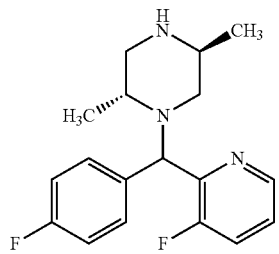

(I-159 and I-160)

A solution of each separated diastereomer of tert-butyl (2S,5R)-4-((4-fluorophenyl)(3-fluoropyridin-2-yl)methyl)-2,5-dimethylpiperazine-1-carboxylate (422 mg, 1.011 mmol) in dichloromethane (20 mL) was cooled on an ice bath and hydrochloric acid (4 M in dioxane) (4 mL, 16.00 mmol) was added. The reaction mixture was stirred overnight at room temperature. The reaction was judged to be complete by TLC. The solvent was removed and the residue dried under high vacuum.

Intermediate 159: Diastereomer 1 from the first eluting sample of tert-butyl (2S,5R)-4-((4-fluorophenyl)(3-fluoropyridin-2-yl)methyl)-2,5-dimethylpiperazine-1-carboxylate (350 mg, 0.989 mmol, 98% yield). Analytical LC\MS conditions: Injection Vol=1 μL, Start % B 0, Final % B 100, Gradient Time 2 Minutes, Flow Rate 1 mL/min, Wavelength 220 nm, Solvent Pair acetonitrile/water/TFA, Solvent A 10% acetonitrile/90% water/0.1% TFA, Solvent B 10 Water 90% acetonitrile/0.1% TFA, Column Acquity BEH C18 21. X 50 mm 1.7 μm, Oven Temp=40° C. LC\MS results; retention time 1.3 minutes, observed mass 318.0 (MH$^+$).

Intermediate 160: Diastereomer 2 from the second eluting sample of tert-butyl (2S,5R)-4-((4-fluorophenyl)(3-fluoropyridin-2-yl)methyl)-2,5-dimethylpiperazine-1-carboxylate (350 mg, 0.989 mmol, 98% yield). Analytical LC\MS conditions: Injection Vol=1 μL, Start % B 0, Final % B 100, Gradient Time 2 Minutes, Flow Rate 1 mL/min, Wavelength 220 nm, Solvent Pair acetonitrile/water/TFA, Solvent A 10% acetonitrile/90% water/0.1% TFA, Solvent B 10 Water 90% acetonitrile/0.1% TFA, Column Acquity BEH C18 21. X 50 mm 1.7 μm, Oven Temp=40° C. LC\MS results; retention time 1.4 minutes, observed mass 318.0 (MH$^+$).

Example 187

8-[(2S,5R)-4-[(4-Fluorophenyl)(3-fluoropyridin-2-yl)methyl]-2,5-dimethylpiperazin-1-yl]-5-methyl-6-oxo-5,6-dihydro-1,5-naphthyridine-2-carbonitrile

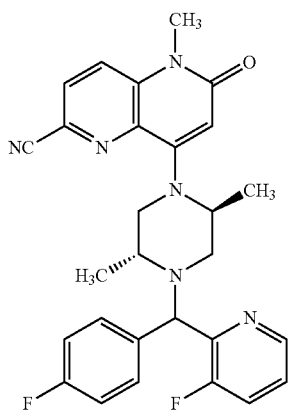

(187)

Intermediate 159, Diastereomer 1 of (2R,5S)-1-((4-fluorophenyl)(3-fluoropyridin-2-yl)methyl)-2,5-dimethylpiperazine, HCl (317 mg, 1.000 mmol) and 6-cyano-1-methyl-2-oxo-1,2-dihydro-1,5-naphthyridin-4-yl trifluoromethanesulfonate (333 mg, 1 mmol) were dissolved in acetonitrile (10 mL). Hunig's base (700 µL, 4.00 mmol) was added and the reaction mixture was heated at 80° C. overnight. The crude material was chromatographed with 0-15% methanol in ethyl acetate on a 24 g silica gel column to afford 8-((2S,5R)-4-((4-fluorophenyl)(3-fluoropyridin-2-yl)methyl)-2,5-dimethylpiperazin-1-yl)-5-methyl-6-oxo-5,6-dihydro-1,5-naphthyridine-2-carbonitrile (73 mg, 0.143 mmol, 14% yield). $^1$H NMR (400 MHz, CHLOROFORM-d) δ 8.43 (d, J=4.4 Hz, 1H), 7.79-7.74 (m, 1H), 7.72-7.64 (m, 3H), 7.33 (ddd, J=10.1, 8.5, 1.2 Hz, 1H), 7.18 (dt, J=8.4, 4.2 Hz, 1H), 7.03 (t, J=8.7 Hz, 2H), 6.11 (s, 1H), 5.19 (s, 1H), 4.57 (br s, 1H), 3.86-3.76 (m, 1H), 3.68-3.63 (m, 1H), 3.62 (s, 3H), 3.27-3.19 (m, 1H), 3.14 (dd, J=11.5, 3.7 Hz, 1H), 2.27 (br d, J=10.8 Hz, 1H), 1.38 (d, J=6.6 Hz, 3H), 1.18 (d, J=6.4 Hz, 3H). Analytical LC\MS conditions: Injection Vol=1 µL, Start % B 0, Final % B 100, Gradient Time 2 Minutes, Flow Rate 1 mL/min, Wavelength 220 nm, Solvent Pair acetonitrile/water/TFA, Solvent A 10% acetonitrile/90% water/0.1% TFA, Solvent B 10 water/90% acetonitrile/0.1% TFA, Column Acquity BEH C18 21. X 50 mm 1.7 µm, Oven Temp=40° C. LC/MS results; retention time 1.7 minutes, observed mass 501.1 (MH$^+$).

Example 188

Stereochemistry 11

8-[(2 S,5R)-4-[(4-fluorophenyl)(3-fluoropyridin-2-yl)methyl]-2,5-dimethylpiperazin-1-yl]-5-methyl-6-oxo-5,6-dihydro-1,5-naphthyridine-2-carbonitrile

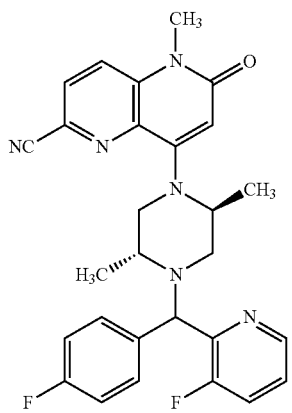

(188)

Example 188 was prepared from Intermediate 160, Diastereomer 2 of (2R,5S)-1-((4-fluorophenyl)(3-fluoropyridin-2-yl)methyl)-2,5-dimethylpiperazine, according the general procedure of Example 187. The compound (175 mg) was isolated in 35% yield. $^1$H NMR (400 MHz, CHLOROFORM-d) δ 8.49 (d, J=4.6 Hz, 1H), 7.80-7.74 (m, 1H), 7.70-7.65 (m, 3H), 7.38 (td, J=9.2, 1.2 Hz, 1H), 7.20 (dt, J=8.4, 4.2 Hz, 1H), 7.01 (t, J=8.7 Hz, 2H), 6.13 (s, 1H), 5.16 (s, 1H), 4.51 (br s, 1H), 3.86 (br d, J=11.0 Hz, 1H), 3.72 (dd, J=12.2, 3.2 Hz, 1H), 3.63 (s, 3H), 3.21-3.13 (m, 1H), 3.03 (dd, J=11.9, 3.5 Hz, 1H), 1.38 (d, J=6.6 Hz, 3H), 1.19 (d, J=6.6 Hz, 3H). Analytical LC\MS conditions: Injection Vol=1 µL, Start % B 0, Final % B 100, Gradient Time 2 Minutes, Flow Rate 1 mL/min, Wavelength 220 nm, Solvent Pair acetonitrile/water/TFA, Solvent A 10% acetonitrile/90% water/0.1% TFA, Solvent B 10% water/90% acetonitrile/0.1% TFA, Column Acquity BEH C18 21. X 50 mm 1.7 µm, Oven Temp=40° C. LCMS results; retention time 1.7 minutes, observed mass 501.1 (MH$^+$).

Examples 189 and 190

8-[(2S,5R)-4-[(4-chlorophenyl)(3-fluoropyridin-2-yl)methyl]-2,5-dimethylpiperazin-1-yl]-5-methyl-6-oxo-5,6-dihydro-1,5-naphthyridine-2-carbonitrile

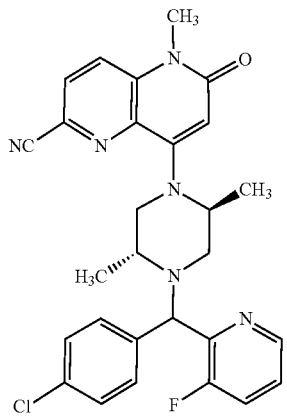

(189-190)

In a 100 mL round bottom flask, 2-(chloro(4-chlorophenyl)methyl)-3-fluoropyridine (775 mg, 3.03 mmol) was dissolved in acetonitrile (8400 μl). To this solution, 8-((2S,5R)-2,5-dimethylpiperazin-1-yl)-5-methyl-6-oxo-5,6-dihydro-1,5-naphthyridine-2-carbonitrile (500 mg, 1.681 mmol), triethylamine (469 μl, 3.36 mmol) and potassium iodide (27.9 mg, 0.168 mmol) were added sequentially. The reaction mixture was sealed under nitrogen and heated at 75° C. for 2 hours. The crude material was chromatographed with 0-100% ethyl acetate in hexanes. Two broad peaks separated and were isolated, each with the correct mass. Coinjection onto the LCMS showed two peaks and H NMR shifts were similar but not identical, consistent with diastereomers.

Example 189: Diastereomer 1 (425 mg, 0.806 mmol, 47.9% yield); Analytical LC\MS conditions: Injection Vol=1 μL, Start % B 0, Final % B 100, Gradient Time 2 Minutes, Flow Rate 1 mL/min, Wavelength 220 nm, Solvent Pair acetonitrile/water/TFA, Solvent A 10% acetonitrile/90% water/0.05% TFA, Solvent B 10 water 90% acetonitrile/0.05% TFA, Column Acquity BEH C18 21. X 50 mm 1.7 μm, Oven Temp=40° C. LC\MS results; retention time 1.8 minutes, observed mass 517.1 (MH+). $^1$H NMR (400 MHz, CHLOROFORM-d) δ 8.40 (d, J=4.4 Hz, 1H), 7.79-7.72 (m, 1H), 7.69-7.61 (m, 3H), 7.36-7.26 (m, 3H), 7.16 (dt, J=8.4, 4.2 Hz, 1H), 6.08 (s, 1H), 5.17 (s, 1H), 4.54 (br s, 1H), 3.78 (br d, J=9.0 Hz, 1H), 3.65-3.60 (m, 1H), 3.59 (s, 3H), 3.25-3.16 (m, 1H), 3.12 (dd, J=11.5, 3.4 Hz, 1H), 2.24 (br d, J=11.5 Hz, 1H), 1.35 (d, J=6.6 Hz, 3H), 1.16 (d, J=6.6 Hz, 3H).

Example 190: Diastereomer 2: (50 mg, 0.081 mmol, 4.83% yield); Analytical LC\MS conditions: Injection Vol=1 μL, Start % B 0, Final % B 100, Gradient Time 2 Minutes, Flow Rate 1 mL/min, Wavelength 220 nm, Solvent Pair acetonitrile/water/TFA, Solvent A 10% acetonitrile/90% water/0.05% TFA, Solvent B 10 water 90% acetonitrile/0.05% TFA, Column Acquity BEH C18 21. X 50 mm 1.7 μm, Oven Temp=40° C. LC\MS results; retention time 1.8 minutes, observed mass 517.1 (MH+). $^1$H NMR (400 MHz, CHLOROFORM-d) δ 8.48 (d, J=4.6 Hz, 1H), 7.81-7.74 (m, 1H), 7.66 (dd, J=12.1, 8.7 Hz, 3H), 7.41-7.34 (m, 1H), 7.34-7.27 (m, 3H), 7.23-7.13 (m, 1H), 6.12 (s, 1H), 5.15 (s, 1H), 4.49 (br s, 1H), 3.86 (br d, J=10.8 Hz, 1H), 3.71 (dd, J=12.2, 2.9 Hz, 1H), 3.63 (s, 3H), 3.19-3.11 (m, 1H), 3.04 (dd, J=11.7, 3.4 Hz, 1H), 2.47 (dd, J=11.9, 1.1 Hz, 1H), 1.38 (d, J=6.6 Hz, 3H), 1.19 (d, J=6.4 Hz, 3H).

Intermediate 161

(4-Chlorophenyl)(5-fluoropyridin-2-yl)methanol

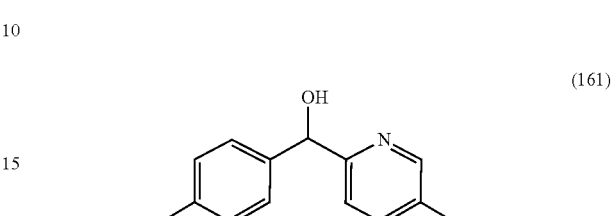

(161)

(4-Chlorophenyl)(5-fluoropyridin-2-yl)methanol was prepared according to the general procedure described for the preparation of Intermediate 153 (4-chlorophenyl)(3-fluoropyridin-2-yl)methanol. $^1$H NMR (400 MHz, CHLOROFORM-d) δ 8.44 (br s, 1H), 7.47-7.27 (m, 5H), 7.19 (br s, 1H), 5.76 (br s, 1H), 5.04-4.49 (br m, 1H).

Examples 191 and 192

8-[(2S,5R)-4-[(4-chlorophenyl)(5-fluoropyridin-2-yl)methyl]-2,5-dimethylpiperazin-1-yl]-5-methyl-6-oxo-5,6-dihydro-1,5-naphthyridine-2-carbonitrile

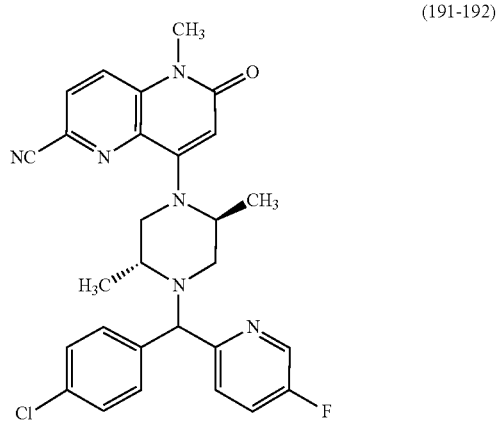 [SMILES: C[C@@H]1CN(c2cc(=O)n(C)c3ccc(C#N)nc23)[C@@H](C)CN1C(c1ccc(Cl)cc1)c1ccc(F)cn1]

(191-192)

(8-[(2S,5R)-4-[(4-chlorophenyl)(5-fluoropyridin-2-yl)methyl]-2,5-dimethylpiperazin-1-yl]-5-methyl-6-oxo-5,6-dihydro-1,5-naphthyridine-2-carbonitrile was prepared according to the general procedure described for the preparation of Example 182, 8-[(2S,5R)-4-[(4-fluorophenyl)(phenyl)methyl]-2,5-dimethylpiperazin-1-yl]-5-methyl-6-oxo-5,6-dihydro-1,5-naphthyridine-2-carbonitrile. The diastereomers were separated using chiral solid phase chromatography: Column: Chiral AD, 30×250 mm, 5 micron, Mobile Phase: 70% $CO_2$/30% IPA w/0.1% DEA, Flow Conditions: 100 mL/min, Detector Wavelength: 220 nm, Injection Details: 1000 μL 15.8 mg dissolved in 3 mL methanol.

Example 191: The first eluting diastereomer (5.5 mg) was isolated in 6.6% yield. Analytical LC/MS was used to determine the final purity. Injection 1 conditions: Column:

Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 517.25; Retention Time: 1.61 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.9%; Observed Mass: 517.07; Retention Time: 2.26 min.

Example 192: The second eluting diastereomer (6.4 mg) was isolated in 7.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.3%; Observed Mass: 517.22; Retention Time: 1.67 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 516.97; Retention Time: 2.26 min.

Intermediate 162

(4-Fluorophenyl)(5-fluoropyridin-2-yl)methanol

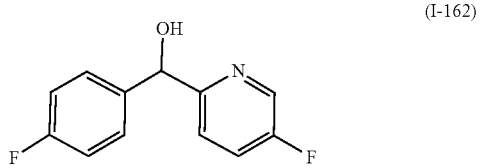 [SMILES: OC(c1ccc(F)cc1)c1ccc(F)cn1]

(I-162)

(4-Fluorophenyl)(5-fluoropyridin-2-yl)methanol was prepared according the general procedure used to prepare Intermediate 153 (4-chlorophenyl)(3-fluoropyridin-2-yl)methanol. $^1$H NMR (400 MHz, CHLOROFORM-d) δ 8.44 (br s, 1H), 7.49-7.27 (m, 3H), 7.18 (br d, J=3.9 Hz, 1H), 7.05 (br t, J=7.9 Hz, 2H), 5.77 (br s, 1H), 4.78 (br s, 1H).

Examples 193 and 194

8-[(2S,5R)-4-[(4-fluorophenyl)(5-fluoropyridin-2-yl)methyl]-2,5-dimethylpiperazin-1-yl]-5-methyl-6-oxo-5,6-dihydro-1,5-naphthyridine-2-carbonitrile

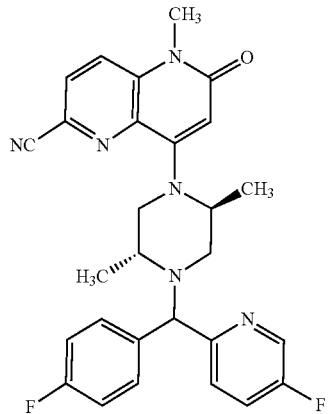

(193-194)

The diastereomers were prepared according to the general procedure used to prepare Examples 183-184.

Example 193: The first eluting diastereomer (16.4 mg) was isolated in 20.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 501.17; Retention Time: 2.26 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 501.18, 501.18; Retention Time: 1.42, 1.45 min.

Example 194: The second eluting diastereomer (6.8 mg) was isolated in 8.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.8%; Observed Mass: 501.2; Retention Time: 1.51 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 501.02; Retention Time: 2.11 min.

Intermediate 163

(4-Chlorophenyl)(6-fluoropyridin-2-yl)methanol

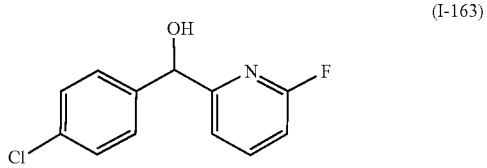 [SMILES: OC(c1ccc(Cl)cc1)c1cccc(F)n1]
(I-163)

(4-Chlorophenyl)(6-fluoropyridin-2-yl)methanol was prepared according to the general procedure used to prepare Intermediate 153, (4-chlorophenyl)(3-fluoropyridin-2-yl)methanol. $^1$H NMR (400 MHz, CHLOROFORM-d) δ 7.78 (q, J=7.8 Hz, 1H), 7.35 (m, 5H), 7.11 (dd, J=7.3, 2.2 Hz, 1H), 6.86 (dd, J=8.1, 2.4 Hz, 1H), 5.75 (d, J=4.4 Hz, 1H), 4.09 (d, J=4.6 Hz, 1H).

Examples 195 and 196

8-[(2S,5R)-4-[(4-chlorophenyl)(6-fluoropyridin-2-yl)methyl]-2,5-dimethylpiperazin-1-yl]-5-methyl-6-oxo-5,6-dihydro-1,5-naphthyridine-2-carbonitrile

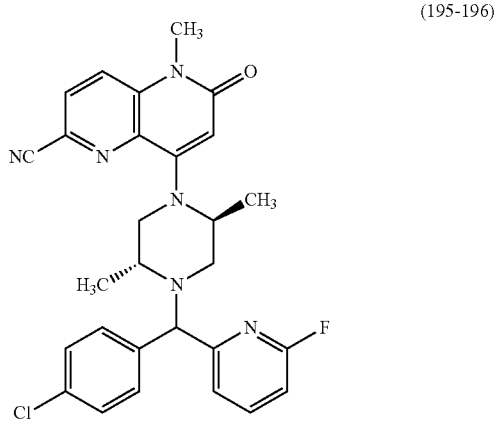 [SMILES: C[C@@H]1CN(c2cc(=O)n(C)c3ccc(C#N)nc23)[C@@H](C)CN1C(c1ccc(Cl)cc1)c1cccc(F)n1]
(195-196)

The diastereomers were prepared and separated according to the general procedure used to prepare Example 182, 8-[(2S,5R)-4-[(4-fluorophenyl)(phenyl) methyl]-2,5-dimethylpiperazin-1-yl]-5-methyl-6-oxo-5,6-dihydro-1,5-naphthyridine-2-carbonitrile.

Example 195: The first eluting diastereomer (4.1 mg) was isolated in 4.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 95.8%; Observed Mass: 516.92; Retention Time: 1.7 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.7%; Observed Mass: 516.93; Retention Time: 2.37 min.

Example 196: The second eluting diastereomer (4 mg) was isolated in 4.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.9%; Observed Mass: 517.05, 517.1; Retention Time: 1.61, 1.71 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.7%; Observed Mass: 517.18; Retention Time: 2.37 min.

Intermediate 164

(4-Fluorophenyl)(pyridin-2-yl)methanol

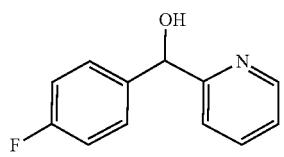
(I-164)

(4-Fluorophenyl)(pyridin-2-yl)methanol was prepared according to the general procedure used to prepare Intermediate 153, (4-chlorophenyl)(3-fluoropyridin-2-yl)methanol. $^1$H NMR (500 MHz, CHLOROFORM-d) δ 8.59 (d, J=4.9 Hz, 1H), 7.65 (td, J=7.6, 1.7 Hz, 1H), 7.36 (dd, J=8.6, 5.4 Hz, 2H), 7.23 (dd, J=7.2, 5.0 Hz, 1H), 7.14 (d, J=7.8 Hz, 1H), 7.04 (t, J=8.7 Hz, 2H), 5.75 (d, J=2.0 Hz, 1H), 5.43-5.14 (m, 1H).

Examples 197 and 198

8-[(2S,5R)-4-[(4-fluorophenyl)(pyridin-2-yl)methyl]-2,5-dimethylpiperazin-1-yl]-5-methyl-6-oxo-5,6-dihydro-1,5-naphthyridine-2-carbonitrile

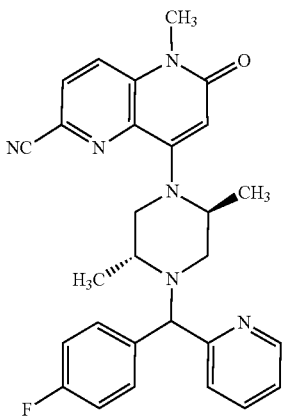
(197-198)

The diastereomers were prepared and separated according to the general procedure used to prepare Examples 183-184.

Example 197: The first eluting diastereomer (5.8 mg) was isolated in 7.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.6%; Observed Mass: 483.24; Retention Time: 1.96 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 483.23; Retention Time: 1.47 min.

Example 198: The second eluting diastereomer (5.2 mg) was isolated in 6.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 93.7%; Observed Mass: 483.24; Retention Time: 1.95 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.3%; Observed Mass: 483.21; Retention Time: 1.46 min.

Intermediate 165

(5-Chloropyridin-2-yl)(p-tolyl)methanol

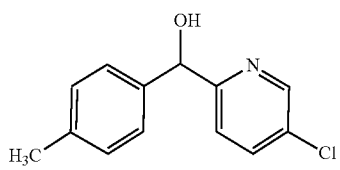

(I-165)

(5-Chloropyridin-2-yl)(p-tolyl)methanol was prepared according to the general procedure used to prepare Intermediate 153, (4-chlorophenyl)(3-fluoropyridin-2-yl)methanol. $^1$H NMR (400 MHz, CHLOROFORM-d) δ 8.53 (s, 1H), 7.61 (dd, J=8.3, 1.7 Hz, 1H), 7.26 (br d, J=7.8 Hz, 2H), 7.21-7.11 (m, 3H), 5.75 (br s, 1H), 4.72 (br s, 1H), 2.36 (s, 3H).

Examples 199 and 200

8-[(2S,5R)-4-[(5-chloropyridin-2-yl)(4-methylphenyl)methyl]-2,5-dimethylpiperazin-1-yl]-5-methyl-6-oxo-5,6-dihydro-1,5-naphthyridine-2-carbonitrile

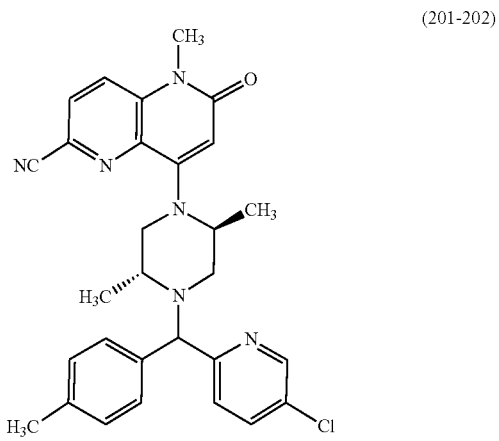 [SMILES: Cc1ccc(C(c2ccc(Cl)cn2)N2C[C@H](C)N(c3cc(=O)n(C)c4ccc(C#N)nc34)C[C@H]2C)cc1]

(201-202)

The diastereomers were prepared and separated according to the general procedure used to prepare Examples 183-184.

Example 199: The first eluting diastereomer (7.5 mg) was isolated in 9.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.1%; Observed Mass: 513.27; Retention Time: 1.58 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 513.03; Retention Time: 2.36 min.

Example 200: The second eluting diastereomer (7 mg) was isolated in 8.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.8%; Observed Mass: 513.25; Retention Time: 1.6 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 513.43; Retention Time: 2.37 min.

Intermediate 166

(4-Chlorophenyl)(5-chloropyridin-2-yl)methanol

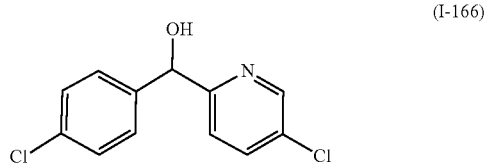 [SMILES: OC(c1ccc(Cl)cc1)c1ccc(Cl)cn1]

(I-166)

(4-Chlorophenyl)(5-chloropyridin-2-yl)methanol was prepared according to the general procedure used to prepare Intermediate 153, (4-chlorophenyl)(3-fluoropyridin-2-yl)methanol. $^1$H NMR (400 MHz, CHLOROFORM-d) δ 8.54 (br s, 1H), 7.64 (br d, J=7.3 Hz, 1H), 7.33 (m, 4H), 7.15 (br d, J=8.3 Hz, 1H), 5.74 (br d, J=3.4 Hz, 1H), 4.76 (br d, J=3.9 Hz, 1H).

Examples 201 and 202

8-[(2S,5R)-4-[(4-chlorophenyl)(5-chloropyridin-2-yl)methyl]-2,5-dimethylpiperazin-1-yl]-5-methyl-6-oxo-5,6-dihydro-1,5-naphthyridine-2-carbonitrile

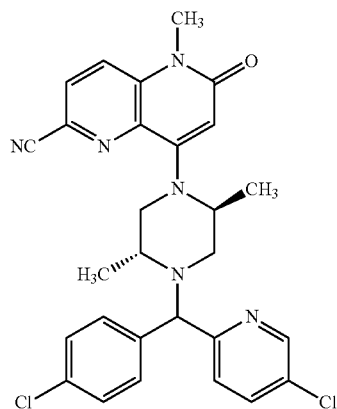

(201-202)

The diastereomers were prepared and separated according to the general procedure described for the preparation of Examples 183-184.

Example 201: The first eluting diastereomer (2.6 mg) was isolated in 3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 95.6%; Observed Mass: 533.2; Retention Time: 1.66 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.8%; Observed Mass: 533.12; Retention Time: 2.43 min.

Example 202: The second eluting diastereomer (2.8 mg) was isolated in 3.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 94.9%; Observed Mass: 533.23; Retention Time: 1.75 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 532.97; Retention Time: 2.43 min.

Intermediate 167

(4-Fluorophenyl)(6-methylpyridin-2-yl)methanol

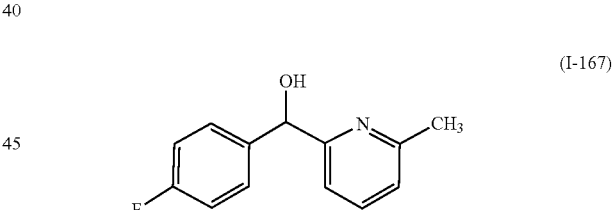

(I-167)

(4-Fluorophenyl)(6-methylpyridin-2-yl)methanol was prepared according to the general procedure used to prepare Intermediate 153, (4-chlorophenyl)(3-fluoropyridin-2-yl)methanol. $^1$H NMR (400 MHz, CHLOROFORM-d) δ 7.53 (t, J=7.7 Hz, 1H), 7.42-7.31 (m, 2H), 7.12-6.98 (m, 3H), 6.88 (d, J=7.6 Hz, 1H), 5.75-5.63 (m, 2H), 2.62 (s, 3H). Analytical LC\MS conditions: Injection Vol=3 μL, Start % B 2, Final % B 98, Gradient Time 1.5 Minutes, Flow Rate 0.8 mL/min, Wavelength 220 nm, Solvent Pair Acetonitrile/Water/TFA, Solvent A 100% Water/0.05% TFA, Solvent B 100% Acetonitrile/0.05% TFA, Column Acquity BEH C18 21. X 50 mm 1.7 um, Oven Temp=40° C. LC\MS results; retention time 1.1 minutes, observed masses 218.3 (M+1) and 200.2 (M$^+$-OH).

Examples 203 and 204

8-[(2S,5R)-4-[(4-fluorophenyl)(6-methylpyridin-2-yl)methyl]-2,5-dimethylpiperazin-1-yl]-5-methyl-6-oxo-5,6-dihydro-1,5-naphthyridine-2-carbonitrile

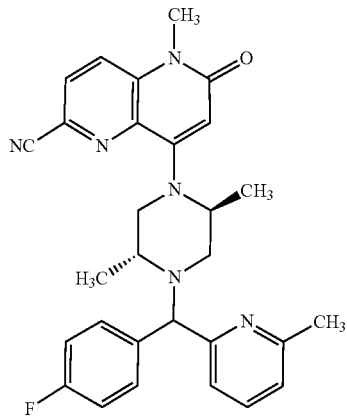

(203-204)

The diastereomers were prepared and separated according to the general procedure described to prepare Examples 183-184.

Example 203: The first eluting diastereomer (6.7 mg) was isolated in 11.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.0%; Observed Mass: 497.3; Retention Time: 1.45 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 96.8%; Observed Mass: 497.25; Retention Time: 2.09 min.

Example 204: The second eluting diastereomer (7.8 mg) was isolated in 13.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.6%; Observed Mass: 497.08; Retention Time: 1.45 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.9%; Observed Mass: 497.31; Retention Time: 2.08 min.

Intermediate 168

(2-Ethoxypyridin-3-yl)(4-fluorophenyl)methanol

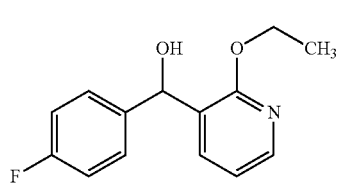

(I-168)

(2-Ethoxypyridin-3-yl)(4-fluorophenyl)methanol was prepared according to the general procedure described to prepare Intermediate 153, (4-chlorophenyl)(3-fluoropyridin-2-yl)methanol. $^1$H NMR (400 MHz, CHLOROFORM-d) δ 8.09 (br d, J=4.6 Hz, 1H), 7.56 (d, J=7.3 Hz, 1H), 7.37 (dd, J=7.9, 5.7 Hz, 2H), 7.04 (t, J=8.6 Hz, 2H), 6.90 (dd, J=6.8, 5.4 Hz, 1H), 5.95 (d, J=3.7 Hz, 1H), 4.40 (q, J=6.9 Hz, 2H), 2.98 (br d, J=4.6 Hz, 1H), 1.36 (t, J=7.1 Hz, 3H). Analytical LC\MS conditions: Injection Vol=1 μL, Start % B 0, Final % B 100, Gradient Time 1.5 Minutes, Flow Rate 1 mL/min, Wavelength 200 nm, Solvent Pair acetonitrile/water/TFA, Solvent A 10% acetonitrile/90% water/0.1% TFA, Solvent B 10% water/90% acetonitrile/0.1% TFA, Column Acquity BEH 21. X 50 mm 1.7 μm, Oven Temp=40° C. LC\MS results; retention time 1.2 minutes, observed mass 248.1 (M$^+$).

Examples 205 and 206

8-[(2S,5R)-4-[(2-ethoxypyridin-3-yl)(4-fluorophenyl)methyl]-2,5-dimethylpiperazin-1-yl]-5-methyl-6-oxo-5,6-dihydro-1,5-naphthyridine-2-carbonitrile

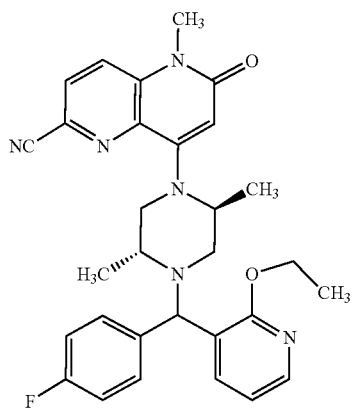

(205-206)

The diastereomers were prepared and separated according to the general procedure used to prepare Examples 183-184.

Example 205: The first eluting diastereomer (5.8 mg) was isolated in 6.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 94.4%; Observed Mass: 527.19;

Retention Time: 2.41 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.8%; Observed Mass: 527.12; Retention Time: 1.71 min.

Example 206: The second eluting diastereomer (6.9 mg) was isolated in 8.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.8%; Observed Mass: 527.1; Retention Time: 2.39 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.8%; Observed Mass: 527.17; Retention Time: 1.68 min.

Intermediate 169

(4-Fluorophenyl)(2-isopropoxypyridin-3-yl)methanol

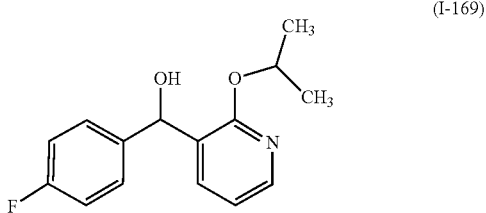 [SMILES: CC(C)Oc1ncccc1C(O)c1ccc(F)cc1]

(I-169)

(4-Fluorophenyl)(2-isopropoxypyridin-3-yl)methanol was prepared according to the general procedure used to prepare Intermediate 153, (4-chlorophenyl)(3-fluoropyridin-2-yl)methanol. $^1$H NMR (400 MHz, Chloroform-d) δ 8.09 (br d, J=4.9 Hz, 1H), 7.56 (d, J=7.3 Hz, 1H), 7.36 (dd, J=7.6, 5.6 Hz, 2H), 7.04 (t, J=8.3 Hz, 2H), 6.91-6.84 (m, 1H), 5.91 (d, J=4.9 Hz, 1H), 5.37 (dt, J=12.3, 6.1 Hz, 1H), 3.02 (d, J=5.4 Hz, 1H), 1.29 (dd, J=8.2, 6.7 Hz, 6H). $^{13}$C NMR (101 MHz, Chloroform-d) δ 163.4, 160.9, 160.1, 145.9, 138.3, 138.3, 135.7, 128.3, 128.3, 126.3, 116.5, 115.1, 114.9, 71.5, 68.4, 22.0. $^{19}$F NMR (376 MHz, Chloroform-d) 6-115 (s, 1F). Analytical LC\MS conditions: Injection Vol=3 μL, Start % B 2, Final % B 98, Gradient Time 1.5 Minutes, Flow Rate 0.8 mL/min, Wavelength 220, Solvent Pair Acetonitrile/Water/TFA, Solvent A 100% Water/0.05% TFA, Solvent B 100% Acetonitrile/0.05% TFA, Column Acquity BEH C18 21. X 50 mm 1.7 um, Oven Temp=40° C. LC\MS results; retention time 1.8 minutes, observed mass 262.0 (M$^+$).

Examples 207 and 208

8-[(2S,5R)-4-[(4-fluorophenyl)[2-(propan-2-yloxy)pyridin-3-yl]methyl]-2,5-dimethylpiperazin-1-yl]-5-methyl-6-oxo-5,6-dihydro-1,5-naphthyridine-2-carbonitrile

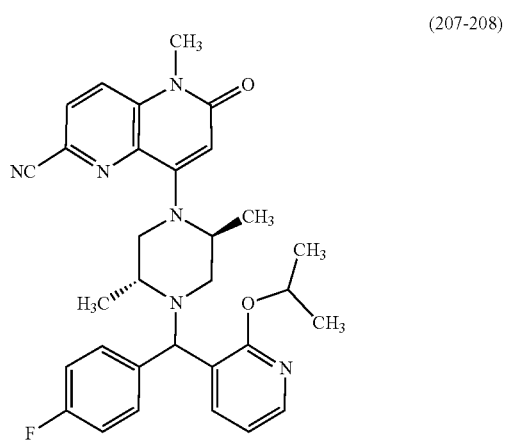 [SMILES: CC(C)Oc1ncccc1C(c1ccc(F)cc1)N1C[C@H](C)N(c2cc(=O)n(C)c3ccc(C#N)nc23)C[C@H]1C]

(207-208)

The diastereomers were prepared and separated according to the general procedure described in the preparation of Examples 183-184.

Example 207: The first eluting diastereomer (6.1 mg) was isolated in 7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.3%; Observed Mass: 541.29; Retention Time: 2.53 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 96.6%; Observed Mass: 541.26; Retention Time: 1.83 min.

Example 208: The second eluting diastereomer (8.6 mg) was isolated in 9.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.9%; Observed Mass: 541.32; Retention Time: 2.5 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100%

B; Flow: 1 mL/min; Detection: MS and UV (220 nm). Injection 2 results: Purity: 97.7%; Observed Mass: 541.26; Retention Time: 1.85 min.

Intermediate 170

(4-Fluorophenyl)(2-methoxypyridin-3-yl)methanol

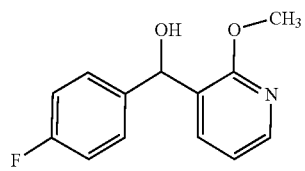

(I-170)

(4-Fluorophenyl)(2-methoxypyridin-3-yl)methanol was prepared according to the general procedure used to prepare Intermediate 153, (4-chlorophenyl)(3-fluoropyridin-2-yl)methanol. $^1$H NMR analysis showed this material to be >95% pure. $^1$H NMR (400 MHz, CHLOROFORM-d) δ 8.12 (d, J=4.9 Hz, 1H), 7.54 (d, J=7.1 Hz, 1H), 7.37 (dd, J=8.3, 5.6 Hz, 2H), 7.05 (t, J=8.6 Hz, 2H), 6.91 (dd, J=7.3, 5.1 Hz, 1H), 5.98 (d, J=4.6 Hz, 1H), 3.98 (s, 3H), 2.92 (d, J=4.6 Hz, 1H).

Examples 209 and 210

8-[(2S,5R)-4-[(4-fluorophenyl)(2-methoxypyridin-3-yl)methyl]-2,5-dimethylpiperazin-1-yl]-5-methyl-6-oxo-5,6-dihydro-1,5-naphthyridine-2-carbonitrile

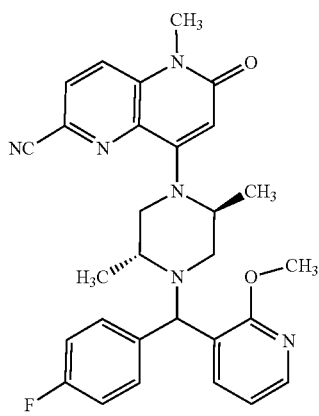

(209-210)

The diastereomers were prepared and separated according to the general procedure used to prepare Examples 183-184.

Example 209: The first eluting diastereomer (4.6 mg) was isolated in 5.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.3%; Observed Mass: 513.19; Retention Time: 2.28 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 513.25; Retention Time: 1.68 min.

Example 210: The second eluting diastereomer (7.5 mg) was isolated in 9.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.6%; Observed Mass: 513.27; Retention Time: 2.26 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 95.7%; Observed Mass: 513.29; Retention Time: 1.58 min.

Intermediate 171

(5-Chloropyridin-2-yl)(4-fluorophenyl)methanol

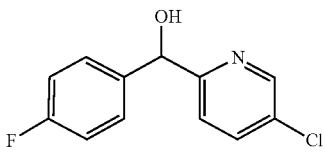

(I-171)

(5-Chloropyridin-2-yl)(4-fluorophenyl)methanol was prepared according to the general procedure used to prepare Intermediate 153, (4-chlorophenyl)(3-fluoropyridin-2-yl)methanol. $^1$H NMR (400 MHz, CHLOROFORM-d) δ 8.52 (br s, 1H), 7.63 (br d, J=7.8 Hz, 1H), 7.38-7.29 (m, 2H), 7.15 (br d, J=8.3 Hz, 1H), 7.04 (br t, J=8.2 Hz, 2H), 5.75 (br s, 1H), 4.84 (br s, 1H).

Examples 211 and 212

8-[(2S,5R)-4-[(5-chloropyridin-2-yl)(4-fluorophenyl)methyl]-2,5-dimethylpiperazin-1-yl]-5-methyl-6-oxo-5,6-dihydro-1,5-naphthyridine-2-carbonitrile

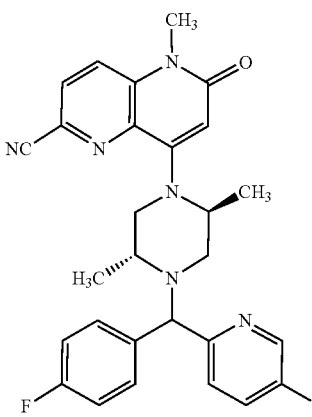

(211-212)

The diastereomers were prepared and separated according to the general procedure used to prepare Example 183-184.

Example 211: The first eluting diastereomer (3.2 mg) was isolated in 3.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.6%; Observed Mass: 517.22; Retention Time: 1.5 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 517.04; Retention Time: 2.27 min.

Example 212: The second eluting diastereomer (3.2 mg) was isolated in 3.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.6%; Observed Mass: 517.23; Retention Time: 1.57 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 517.04; Retention Time: 2.27 min.

Intermediate 172

(4-Chlorophenyl)(5-methylpyridin-2-yl)methanol

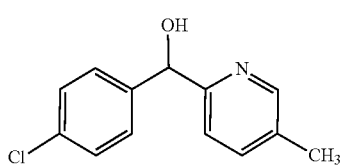

(I-172)

(4-Chlorophenyl)(5-methylpyridin-2-yl)methanol was prepared according to the general procedure used to prepare Intermediate 153, (4-chlorophenyl)(3-fluoropyridin-2-yl)methanol. $^1$H NMR (400 MHz, CHLOROFORM-d) δ 8.38 (br s, 1H), 7.45 (br d, J=6.8 Hz, 1H), 7.32 (br s, 4H), 7.05 (br d, J=7.3 Hz, 1H), 5.72 (br s, 1H), 5.58-5.22 (m, 1H).

Examples 213 to 214

8-[(2S,5R)-4-[(4-chlorophenyl)(5-methylpyridin-2-yl)methyl]-2,5-dimethylpiperazin-1-yl]-5-methyl-6-oxo-5,6-dihydro-1,5-naphthyridine-2-carbonitrile

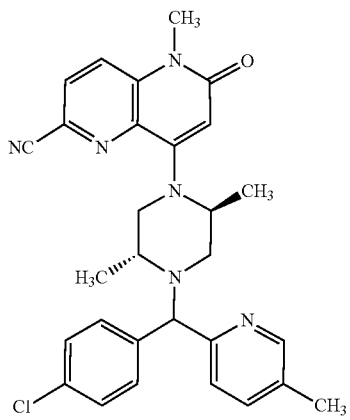

(213-214)

The diastereomers were prepared and separated according to the general procedure used to prepare Examples 183-184.

Example 213: The first eluting diastereomer (9.3 mg) was isolated in 13.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 513.1; Retention Time: 2.26 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 513.07; Retention Time: 1.63 min.

Example 214: The second eluting diastereomer (31.4 mg) was isolated in 45.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 513.13; Retention Time: 2.27 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 513.12; Retention Time: 1.64 min.

Intermediate 173

(3-Fluorophenyl)(5-methylpyridin-2-yl)methanol

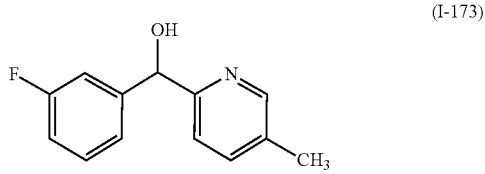 [SMILES: Cc1ccc(C(O)c2cccc(F)c2)nc1]

(I-173)

(3-Fluorophenyl)(5-methylpyridin-2-yl)methanol was prepared according to the general procedure used to prepare Intermediate 153, (4-chlorophenyl)(3-fluoropyridin-2-yl)methanol. $^1$H NMR (400 MHz, CHLOROFORM-d) δ 8.41 (br s, 1H), 7.47 (br d, J=4.2 Hz, 1H), 7.31 (br s, 1H), 7.20 (br s, 1H), 7.09 (br s, 2H), 6.97 (br s, 1H), 5.74 (br s, 1H), 5.33 (br s, 1H).

Examples 215 to 216

8-[(2S,5R)-4-[(3-fluorophenyl)(5-methylpyridin-2-yl)methyl]-2,5-dimethylpiperazin-1-yl]-5-methyl-6-oxo-5,6-dihydro-1,5-naphthyridine-2-carbonitrile

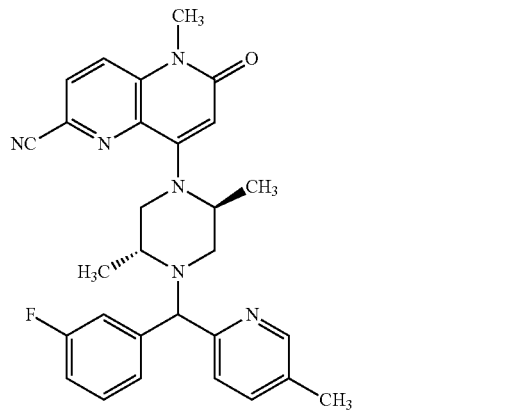

(215-216)

The diastereomers were prepared and separated according to the general procedure used to prepare Examples 183-184.

Example 215: The first eluting diastereomer (8.6 mg) was isolated in 12.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 497.07; Retention Time: 2.09 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.3%; Observed Mass: 497.17; Retention Time: 1.46 min.

Example 216: The second eluting diastereomer (8.8 mg) was isolated in 13.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 497.12; Retention Time: 2.1 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 497.21; Retention Time: 1.47 min.

Examples 217 and 218

7-chloro-8-[(2S,5R)-4-[(4-fluorophenyl)(phenyl)methyl]-2,5-dimethylpiperazin-1-yl]-5-methyl-6-oxo-5,6-dihydro-1,5-naphthyridine-2-carbonitrile

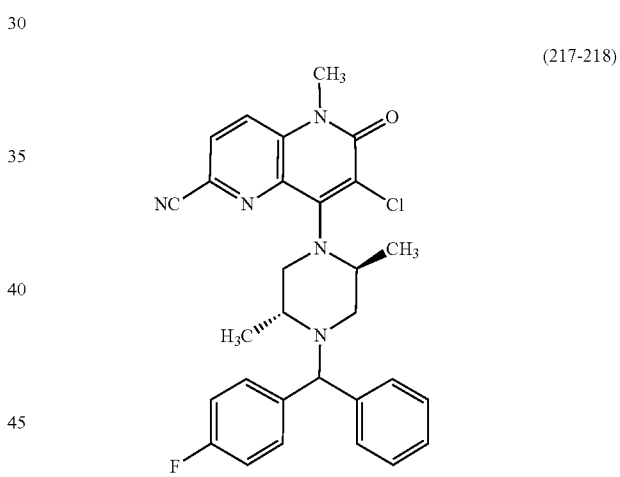

(217-218)

A DMF (1 mL) solution of a mixture of diastereomers of 8-((2S,5R)-4-((4-fluorophenyl)(phenyl)methyl)-2,5-dimethylpiperazin-1-yl)-5-methyl-6-oxo-5,6-dihydro-1,5-naphthyridine-2-carbonitrile (30 mg, 0.062 mmol) was prepared. N-Chlorosuccinimide (12.48 mg, 0.093 mmol) was added and the reaction mixture was stirred at room temperature for 2 hours. LC/MS analysis indicated the reaction was complete. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 44% B, 44-84% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. A solid (22.8 mg) containing a mixture of diastereomers was isolated.

The diastereomers were separated using chiral solid phase chromatography: Column: Chiral OD, 30×250 mm, 5 micron, Mobile Phase: 70% CO$_2$/30% methanol w/0.1% diethyl amine, Flow Conditions: 100 mL/min, Detector Wavelength: 220 nm, Injection Details: 1300 µL 22.8 mg dissolved in 3 mL methanol.

Example 217: The first eluting diastereomer (9.2 mg) was isolated in 28.8% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.2%; Observed Mass: 516.1; Retention Time: 2.68 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.3%

Example 218: The second eluting diastereomer (9.1 mg) was isolated in 28.4% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.1%; Observed Mass: 516.09; Retention Time: 2.68 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.1%; Observed Mass: 516.34; Retention Time: 1.79 min.

Examples 219 and 220

3-chloro-4-{4-[(4-fluorophenyl)(phenyl)methyl]piperazin-1-yl}-6-methoxy-1-methyl-1,2-dihydro-1,5-naphthyridin-2-one The diastereomers were prepared and separated in a similar manner as in Examples 217-218, 7-chloro-8-[(2S,5R)-4-[(4-fluorophenyl)(phenyl)methyl]-2,5-dimethylpiperazin-1-yl]-5-methyl-6-oxo-5,6-dihydro-1,5-naphthyridine-2-carbonitrile.

Example 219: The first eluting diastereomer (13.2 mg) was isolated in 72.4% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 493.17; Retention Time: 2.62 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 520; Retention Time: 1.51 min.

Example 220: The second eluting diastereomer (5.9 mg) was isolated in 32.3% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 493.21; Retention Time: 2.54 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 520; Retention Time: 1.5 min.

Intermediate 174

Phenyl(4-(trifluoromethoxy)phenyl)methanol

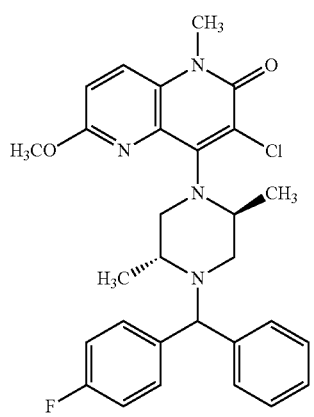

(219-220)

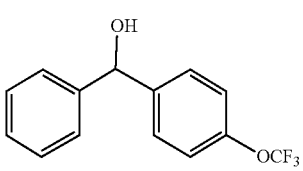

(I-174)

Phenyl(4-(trifluoromethoxy)phenyl)methanol was prepared according to the general procedure used to prepare Intermediate 153, (4-chlorophenyl)(3-fluoropyridin-2-yl)methanol. $^1$H NMR (500 MHz, CHLOROFORM-d) δ 7.43 (d, J=8.5 Hz, 2H), 7.40-7.35 (m, 4H), 7.35-7.29 (m, 1H), 7.24-7.16 (m, 2H), 5.88 (d, J=3.4 Hz, 1H), 2.25 (d, J=3.5 Hz, 1H).

Examples 221 and 222

8-[(2S,5R)-2,5-dimethyl-4-{phenyl[4-(trifluoromethoxy)phenyl]methyl}piperazin-1-yl]-5-methyl-6-oxo-5,6-dihydro-1,5-naphthyridine-2-carbonitrile

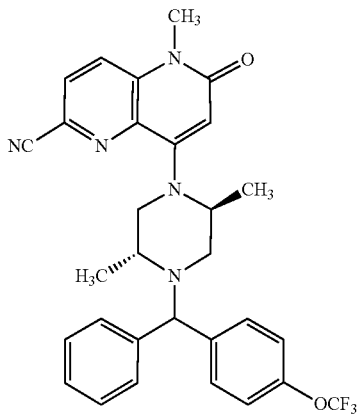

(221-222)

The diastereomers were prepared and separated according to the general procedure used to prepare Examples 183-184.

Example 221: The first eluting diastereomer (6.7 mg) was isolated in 7.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.8%; Observed Mass: 548.26; Retention Time: 2.04 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.8%; Observed Mass: 548; Retention Time: 2.59 min.

Example 222: The second eluting diastereomer (6.4 mg) was isolated in 7.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.5%; Observed Mass: 548.28; Retention Time: 2.02 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.6%; Observed Mass: 548.14; Retention Time: 2.59 min.

Intermediate 175

(4-Fluorophenyl)(m-tolyl)methanol

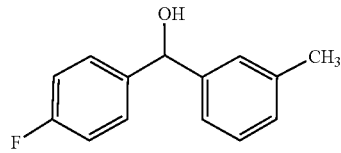

(I-175)

(4-Fluorophenyl)(m-tolyl)methanol was prepared according to the general procedure used to prepare Intermediate 153, (4-chlorophenyl)(3-fluoropyridin-2-yl)methanol. $^1$H NMR (400 MHz, CHLOROFORM-d) δ 7.37 (dd, J=7.7, 5.7 Hz, 2H), 7.25 (d, J=7.6 Hz, 1H), 7.22-7.15 (m, 2H), 7.12 (br d, J=7.3 Hz, 1H), 7.04 (t, J=8.3 Hz, 2H), 5.82 (d, J=2.9 Hz, 1H), 2.36 (s, 3H), 2.18 (d, J=3.2 Hz, 1H). Analytical LC\MS conditions: Injection Vol=3 μL, Start % B 0, Final % B 100, Gradient Time 2 Minutes, Flow Rate 1 mL/min, Wavelength 220 nm, Solvent Pair acetonitrile/water/TFA, Solvent A 10% acetonitrile, 90% water/0.05% TFA, Solvent B 10% Water, 90% acetonitrile/0.05% TFA, Column Acquity BEH C18 21. X 50 mm 1.7 μm, Oven Temp=40° C. LC\MS results; retention time 1.6 minutes, observed mass 198.9 (M$^+$-OH).

Examples 223 and 224

8-[(2S,5R)-4-[(4-fluorophenyl)(3-methylphenyl)methyl]-2,5-dimethylpiperazin-1-yl]-5-methyl-6-oxo-5,6-dihydro-1,5-naphthyridine-2-carbonitrile

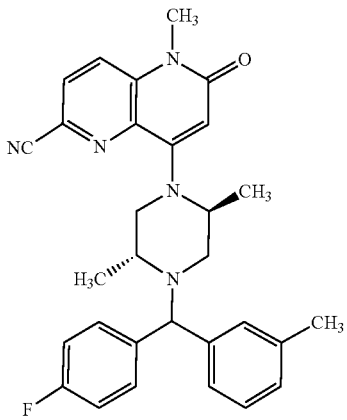

(223-224)

The diastereomers were prepared and separated according to the general procedure used to prepare Examples 183-184.

Example 223: The first eluting diastereomer (5.7 mg) was isolated in 9.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

Injection 1 results: Purity: 100.0%; Observed Mass: 496.21; Retention Time: 2.65 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 496.21; Retention Time: 1.7 min.

Example 224: The second eluting diastereomer (5.3 mg) was isolated in 9.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.0%; Observed Mass: 496.18; Retention Time: 2.54 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 96.1%; Observed Mass: 496.19; Retention Time: 1.83 min.

Intermediate 176

(4-Chlorophenyl)(2-ethyl-4-fluorophenyl)methanol

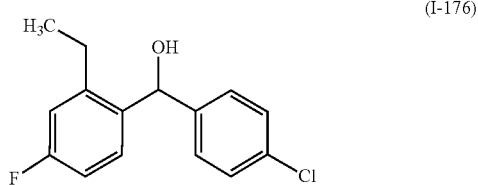 [SMILES: CCc1cc(F)ccc1C(O)c1ccc(Cl)cc1]

(I-176)

(4-Chlorophenyl)(2-ethyl-4-fluorophenyl)methanol was prepared according to the general procedure used to prepare Intermediate 153, (4-chlorophenyl)(3-fluoropyridin-2-yl)methanol. $^1$H NMR (400 MHz, CHLOROFORM-d) δ 7.39 (dd, J=8.3, 6.1 Hz, 1H), 7.36-7.31 (m, 2H), 7.26 (s, 1H), 6.94 (d, J=8.8 Hz, 2H), 6.04 (d, J=3.2 Hz, 1H), 2.77-2.53 (m, 2H), 2.09 (d, J=3.7 Hz, 1H), 1.18 (t, J=7.6 Hz, 3H). Analytical LC\MS conditions: Injection Vol=3 μL, Start % B 2, Final % B 98, Gradient Time 1.5 Minutes, Flow Rate 0.8 mL/min, Wavelength 220 nm, Solvent Pair acetonitrile/water/TFA, Solvent A 100% water/0.05% TFA, Solvent B 100% acetonitrile/0.05% TFA, Column Acquity BEH C18 21. X 50 mm 1.7 μm, Oven Temp=40° C. LC\MS results; retention time 1.7 minutes, observed mass 246.9, 248.7 (M$^+$-OH).

Examples 225 and 226

8-[(2S,5R)-4-[(4-chlorophenyl)(2-ethyl-4-fluorophenyl)methyl]-2,5-dimethylpiperazin-1-yl]-5-methyl-6-oxo-5,6-dihydro-1,5-naphthyridine-2-carbonitrile

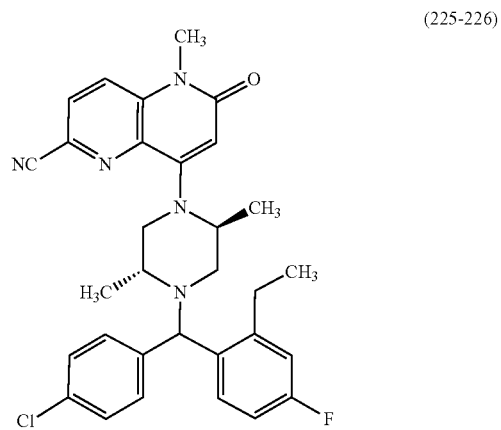 [SMILES: CCc1cc(F)ccc1C(c1ccc(Cl)cc1)N1C[C@H](C)N(c2cc(=O)n(C)c3ccc(C#N)nc23)C[C@H]1C]

(225-226)

The diastereomers were prepared and separated according to the general procedure used to prepare Examples 183-184.

Example 225: The first eluting diastereomer (12.3 mg) was isolated in 16.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 544.26; Retention Time: 2.8 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 544.15; Retention Time: 2.23 min.

Example 226: The second eluting diastereomer (12.4 mg) was isolated in 16.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 544.18; Retention Time: 2.79 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 544.24; Retention Time: 2.23 min.

Examples 227 and 228

8-[(2S,5R)-4-[(2-ethyl-4-fluorophenyl)(4-fluorophenyl)methyl]-2,5-dimethylpiperazin-1-yl]-5-methyl-6-oxo-5,6-dihydro-1,5-naphthyridine-2-carbonitrile

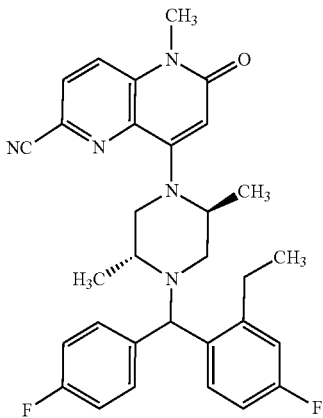

(227-228)

The diastereomers were prepared and separated according to the general procedures used to prepare Examples 183-184.

Example 227: The first eluting diastereomer (16.5 mg) was isolated in 23.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 95.9%; Observed Mass: 528.33; Retention Time: 2.64 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 528.12; Retention Time: 2.01 min.

Example 228: The second eluting diastereomer (14.9 mg) was isolated in 20.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 528.16; Retention Time: 2.68 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 528.14; Retention Time: 2.12 min.

Intermediate 177

(2-Ethoxy-4-fluorophenyl)(4-fluorophenyl)methanol

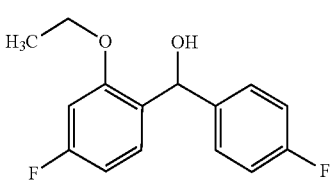

(I-177)

(2-Ethoxy-4-fluorophenyl)(4-fluorophenyl)methanol was prepared according to the general procedure used to prepare Intermediate 153, (4-chlorophenyl)(3-fluoropyridin-2-yl)methanol. NMR analysis showed this material to be >95% pure. $^1$H NMR (400 MHz, Chloroform-d) δ 7.36 (dd, J=7.5, 6.0 Hz, 2H), 7.24 (t, J=7.6 Hz, 1H), 7.03 (t, J=8.3 Hz, 2H), 6.66 (br t, J=8.4 Hz, 1H), 6.61 (br d, J=10.8 Hz, 1H), 6.01 (d, J=5.1 Hz, 1H), 4.02 (q, J=6.8 Hz, 2H), 2.83 (d, J=5.1 Hz, 1H), 1.38 (t, J=6.8 Hz, 3H). Analytical LC\MS conditions: Injection Vol=3 μL, Start % B 2, Final % B 98, Gradient Time 1.5 Minutes, Flow Rate 0.8 mL/min, Wavelength 220, Solvent Pair acetonitrile/water/TFA, Solvent A 100% Water/0.05% TFA, Solvent B 100% acetonitrile/0.05% TFA, Column Acquity BEH C18 21. X 50 mm 1.7 μm, Oven Temp=40° C. LC\MS results; retention time 1.8 minutes, observed mass 247.0 (M$^+$-OH).

Examples 229 and 230

8-[(2S,5R)-4-[(2-ethoxy-4-fluorophenyl)(4-fluorophenyl)methyl]-2,5-dimethylpiperazin-1-yl]-5-methyl-6-oxo-5,6-dihydro-1,5-naphthyridine-2-carbonitrile

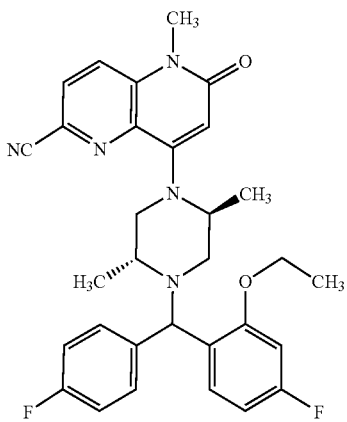

(229-230)

The diastereomers were prepared and separated according to the general procedure used to prepare Examples 183-184.

Example 229: The first eluting diastereomer (12.2 mg) was isolated in 19.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.6%; Observed Mass: 544.32; Retention Time: 2.7 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 544.17; Retention Time: 1.83 min.

Example 230: The second eluting diastereomer (15.4 mg) was isolated in 24.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.1%; Observed Mass: 544.06; Retention Time: 2.69 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 544.15; Retention Time: 1.81 min.

Examples 231 and 232

8-[(2S,5R)-4-[(4-chlorophenyl)(2-ethyl-4-fluorophenyl)methyl]-2,5-dimethylpiperazin-1-yl]-6-methoxy-1-methyl-1,2-dihydro-1,5-naphthyridine-2-one

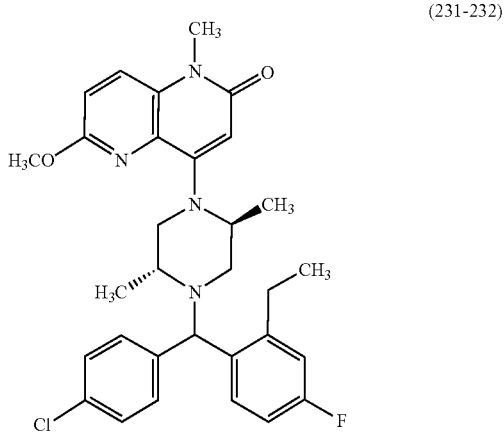 [SMILES: CCc1cc(F)ccc1C(c1ccc(Cl)cc1)N1C[C@H](C)N(c2cc(=O)n(C)c3ccc(OC)nc23)C[C@H]1C]

(231-232)

The diastereomers were prepared and separated according to the general procedure used to prepare Examples 183-184.

Example 231: The first eluting diastereomer (6.6 mg) was isolated in 7.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 548.96; Retention Time: 2.84 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 549.22; Retention Time: 2.28 min.

Example 232: The second eluting diastereomer (8.7 mg) was isolated in 9.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 548.9; Retention Time: 2.82 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 548.92; Retention Time: 2.28 min.

Examples 233 and 234

4-[(2S,5R)-4-[(2-ethyl-4-fluorophenyl)(4-fluorophenyl)methyl]-2,5-dimethylpiperazin-1-yl]-6-methoxy-1-methyl-1,2-dihydro-1,5-naphthyridin-2-one

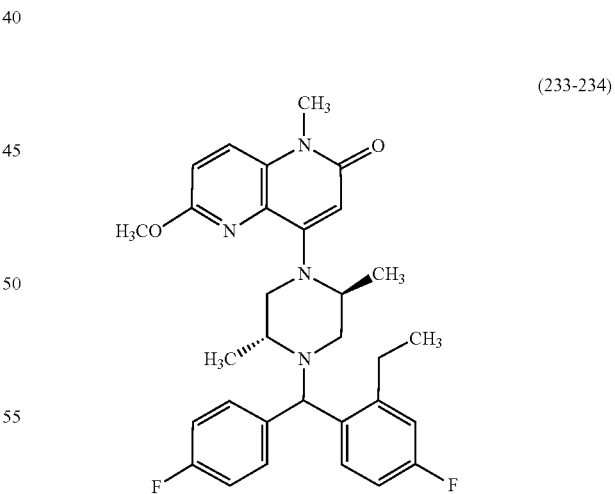

(233-234)

The diastereomers were prepared and separated according to the general procedure used to prepare Examples 183-184.

Examples 233: The first eluting diastereomer (11.4 mg) was isolated in 13% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 95.9%; Observed Mass: 532.94; Retention Time: 2.7 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 96.4%; Observed Mass: 532.93; Retention Time: 2.08 min.

Examples 234: The second eluting diastereomer (13.2 mg) was isolated in 15% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.1%; Observed Mass: 532.95; Retention Time: 2.7 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 94.8%; Observed Mass: 532.96; Retention Time: 2.08 min.

Intermediate 178

(2-Ethylphenyl)(4-fluorophenyl)methanol

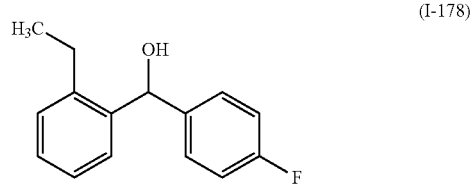 [SMILES: CCc1ccccc1C(O)c1ccc(F)cc1]

(I-178)

(2-Ethylphenyl)(4-fluorophenyl)methanol was prepared according to the general procedure used to prepare Intermediate 153, (4-chlorophenyl)(3-fluoropyridin-2-yl) methanol. NMR analysis showed this material to be >95% pure. $^1$H NMR (400 MHz, chloroform-d) δ 7.47 (d, J=7.1 Hz, 1H), 7.36-7.21 (m, 6H (integrates high due to residual chloroform), 7.03 (t, J=8.6 Hz, 2H), 6.10 (br s, 1H), 2.77-2.52 (m, 2H), 1.17 (t, J=7.6 Hz, 3H). Analytical LC\MS conditions: Injection Vol=1 μL, Start % B 0, Final % B 100, Gradient Time 1.5 Minutes, Flow Rate 1 mL/min, Wavelength 200, Solvent Pair acetonitrile/water/TFA, Solvent A 10% acetonitrile/90% water/0.1% TFA, Solvent B 10% water/90% acetonitrile/0.1% TFA, Column Acquity BEH 21. X 50 mm 1.7 μm, Oven Temp=40° C. LC\MS results; retention time 1.4 minutes, observed mass 213.1 (M$^+$-OH).

Examples 235 and 236

4-[(2S,5R)-4-[(2-ethylphenyl)(4-fluorophenyl) methyl]-2,5-dimethylpiperazin-1-yl]-6-methoxy-1-methyl-1,2-dihydro-1,5-naphthyridin-2-one

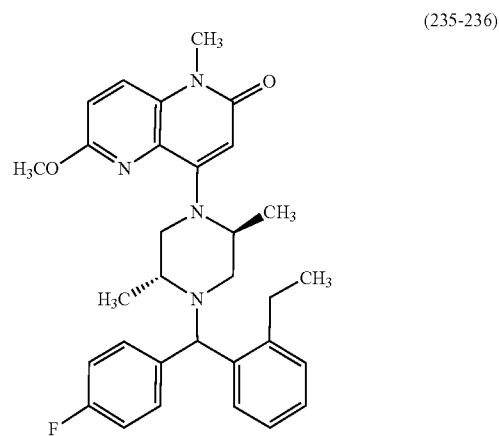 [SMILES: CCc1ccccc1C(c1ccc(F)cc1)N1C[C@H](C)N(c2cc(=O)n(C)c3ccc(OC)nc23)C[C@H]1C]

(235-236)

The diastereomers were prepared and separated according to the general procedure used to prepare Examples 183-184.

Example 235: The first eluting diastereomer (9.7 mg) was isolated in 11.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 514.98; Retention Time: 2.76 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 94.1%; Observed Mass: 514.98; Retention Time: 2 min.

Example 236: The second eluting diastereomer (10.5 mg) was isolated in 12.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 95.8%; Observed Mass: 514.96; Retention Time: 2.76 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 514.97; Retention Time: 1.99 min.

Example 237

8-[(2S,5R)-4-(diphenylmethyl)-2,5-dimethylpiperazin-1-yl]-5-methyl-6-oxo-5,6-dihydro-1,5-naphthyridine-2-carbonitrile

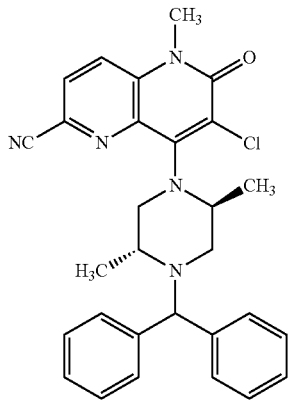

(237)

In a 2 dram sealed reaction vessel, 8-((2S,5R)-2,5-dimethylpiperazin-1-yl)-5-methyl-6-oxo-5,6-dihydro-1,5-naphthyridine-2-carbonitrile, TFA (41.1 mg, 100 µmol), diphenyl methanol (25.8 mg, 140 µmol) and (cyanomethyl)trimethylphosphonium iodide (48.6 mg, 200 µmol) were combined in acetonitrile (200 µl). Hunig's Base (75 µL, 429 µmol) was added and the reaction mixture was heated at 110° C. for 3 hours. LC\MS analysis showed the presence of product. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 42% B, 42-82% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. Calculated molecular weight 463.585. LC\MS conditions QC-ACN-TFA-XB: Observed MS Ion 464.2, retention time 1.54 minutes.

Examples 238 and 239

4-[(2S,5R)-4-[(4-fluorophenyl)(phenyl)methyl]-2,5-dimethylpiperazin-1-yl]-6-methoxy-1-methyl-1,2-dihydro-1,5-naphthyridin-2-one

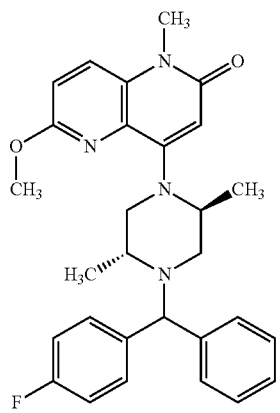

(238-239)

4-((2S,5R)-2,5-dimethylpiperazin-1-yl)-6-methoxy-1-methyl-1,5-naphthyridin-2(1H)-one (50 mg, 0.165 mmol) and 1-(bromo(phenyl)methyl)-4-fluorobenzene (70.1 mg, 0.265 mmol) were combined with diisopropyl ethyl amine (0.173 mL, 0.992 mmol) in acetonitrile (3 mL). The reaction mixture was heated at 55° C. overnight. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 38% B, 38-78% B over 25 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. Calculated molecular weight 486.591. LC\MS conditions QC-ACN-TFA-XB: Observed MS Ion 487.2, retention time 1.62 minutes.

The diastereomers were separated according to the general procedure used to prepare Examples 183-184.

Example 238: The first eluting diastereomer (5.9 mg) was isolated in 7.3% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 487.1; Retention Time: 1.59 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 487.45; Retention Time: 1.75 min.

Example 239: The second eluting diastereomer (6 mg) was isolated in 7.5% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B 10 to 100% B over 3 min, then a 0.50 min hold at 100% B; Flow: 1 mL/min; Detection: MS and UV (220 nm). Injection 1 results: Purity: 95.8%; Observed Mass: 487.22; Retention Time: 1.6 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 487.45; Retention Time: 1.76 min.

Example 240

4-[(2S,5R)-4-[(4-chlorophenyl)(4-fluorophenyl)methyl]-2,5-dimethylpiperazin-1-yl]-6-methoxy-1-methyl-1,2-dihydro-1,5-naphthyridin-2-one

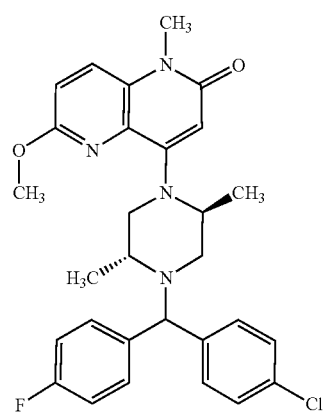

(240)

4-((2S,5R)-2,5-dimethylpiperazin-1-yl)-6-methoxy-1-methyl-1,5-naphthyridin-2(1H)-one (50 mg, 0.165 mmol) and 1-(bromo(4-chlorophenyl)methyl)-4-fluorobenzene (49.5 mg, 0.165 mmol) were combined with diisopropyl ethyl amine (0.173 mL, 0.992 mmol) in acetonitrile (3 mL) and the reaction mixture was heated at 55° C. overnight. LC/MS indicated the reaction was completed. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 42% B, 42-82% B over 25 minutes, then a 5 minute hold at 100% B; Flow Rate: 20 mL/min; Column Temperature: 25° C. Fraction collection was triggered by MS signals. Fractions containing the product were combined and dried via centrifugal evaporation. Calculated molecular weight 521.03. LC\MS conditions QC-ACN-AA-XB: Observed MS Ion 521.1, retention time 2.77 minutes.

Intermediate 179

4,4'-(Bromomethylene)bis(fluorobenzene)

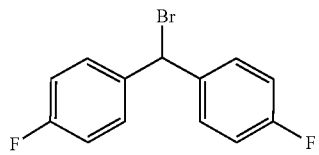

(I-179)

4,4'-(Bromomethylene)bis(fluorobenzene) was prepared according to the general procedure used to prepare 1-(bromo(4-chlorophenyl)methyl)-4-fluorobenzene.

Example 241

4-[(2S,5R)-4-[bis(4-fluorophenyl)methyl]-2,5-dimethylpiperazin-1-yl]-6-methoxy-1-methyl-1,2-dihydro-1,5-naphthyridin-2-one

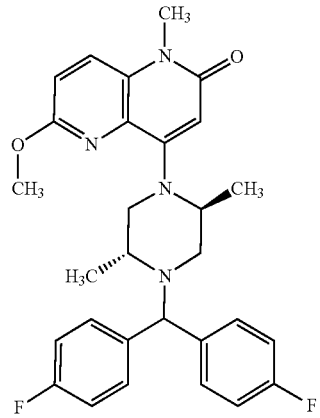

(241)

A solution of 4-((2S,5R)-2,5-dimethylpiperazin-1-yl)-6-methoxy-1-methyl-1,5-naphthyridin-2(1H)-one (128 mg, 0.424 mmol) in acetonitrile (3 mL) was combined with 4,4'-(bromomethylene)bis(fluorobenzene) (100 mg, 0.353 mmol) and diisopropyl ethyl amine (0.185 mL, 1.060 mmol). The reaction mixture was heated at 80° C. in a microwave reactor for 8 hours. LC/MS indicated the starting material was consumed. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 40% B, 40-80% B over 25 minutes, then a 5 minute hold at 100% B; Flow Rate: 20 mL/min; Column Temperature: 25° C. Fraction collection was triggered by UV signals. Fractions containing the product were combined and dried via centrifugal evaporation. Calculated molecular weight 504.582. LC\MS conditions QC-ACN-TFA-XB: Observed MS Ion 505.2, retention time 1.51 minutes.

Example 242

8-[(2S,5R)-4-{[2-(difluoromethyl)-4-fluorophenyl]methyl}-2,5-dimethylpiperazin-1-yl]-5-methyl-6-oxo-5,6-dihydro-1,5-naphthyridine-2-carbonitrile

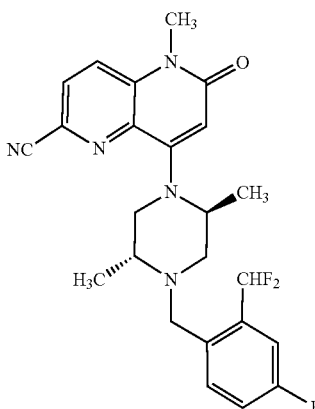

(242)

345

To a DMF (2 mL) solution of 8-((2S,5R)-2,5-dimethylpiperazin-1-yl)-5-methyl-6-oxo-5,6-dihydro-1,5-naphthyridine-2-carbonitrile (30 mg, 0.081 mmol) was added 2-(difluoromethyl)-4-fluorobenzaldehyde (16.86 mg, 0.097 mmol). The solution was stirred at room temperature for 1 hour. Sodium cyanoborohydride (15.22 mg, 0.242 mmol) was added and the reaction mixture was stirred at room temperature overnight. LC/MS analysis indicated the reaction was complete. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 31% B, 31-71% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 13.0 mg, and the estimated purity by LCMS analysis was 100%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 456.08; Retention Time: 1.39 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 456.07; Retention Time: 2.22 min. % B over 3 min, then a 0.50 min hold at 100% B; Flow: 1 mL/min; Detection: MS and UV (220 nm). Injection 2 results: Purity: 100.0%; Observed Mass: 456.07; Retention Time: 2.22 min.

Example 243

8-[(2S,5R)-4-{[2-fluoro-4-(trifluoromethoxy)phenyl]methyl}-2,5-dimethylpiperazin-1-yl]-5-methyl-6-oxo-5,6-dihydro-1,5-naphthyridine-2-carbonitrile

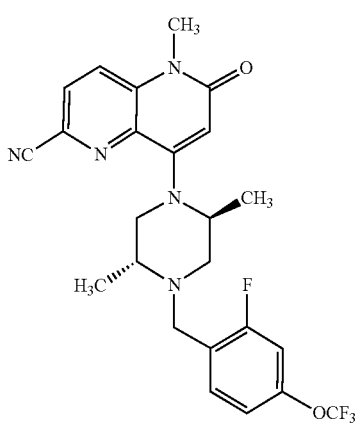

(243)

346

Example 243 was prepared according to the general process used to prepare Example 242, 8-[(2S,5R)-4-{[2-(difluoromethyl)-4-fluorophenyl]methyl}-2,5-dimethylpiperazin-1-yl]-5-methyl-6-oxo-5,6-dihydro-1,5-naphthyridine-2-carbonitrile.

The compound (11 mg) was isolated in 27.7% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 490.12; Retention Time: 2.55 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 490.11; Retention Time: 1.55 min.

Example 244

8-[(2S,5R)-4-[(4-chloro-2-hydroxyphenyl)methyl]-2,5-dimethylpiperazin-1-yl]-5-methyl-6-oxo-5,6-dihydro-1,5-naphthyridine-2-carbonitrile

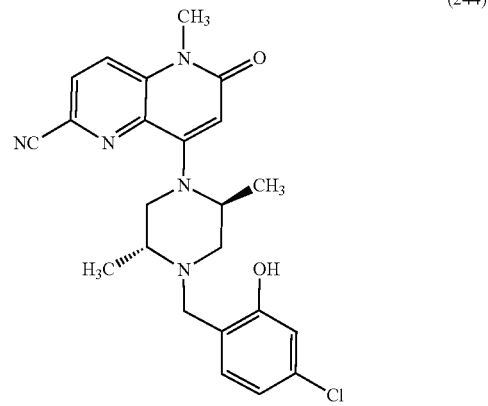

(244)

Example 244 was prepared according to the general process used to prepare Example 242, 8-[(2S,5R)-4-{[2-(difluoromethyl)-4-fluorophenyl]methyl}-2,5-dimethylpiperazin-1-yl]-5-methyl-6-oxo-5,6-dihydro-1,5-naphthyridine-2-carbonitrile.

The compound (17 mg) was isolated in 47.9% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 438.13; Retention Time: 2.33 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 438.12; Retention Time: 1.35 min.

Example 245

8-[(2S,5R)-4-[(2-hydroxyphenyl)methyl]-2,5-dimethylpiperazin-1-yl]-5-methyl-6-oxo-5,6-dihydro-1,5-naphthyridine-2-carbonitrile

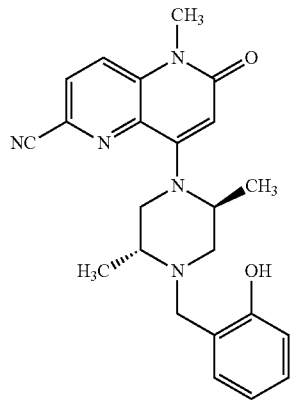

(245)

Example 245 was prepared according to the general process used to prepare Example 242, 8-[(2S,5R)-4-{[2-(difluoromethyl)-4-fluorophenyl]methyl}-2,5-dimethylpiperazin-1-yl]-5-methyl-6-oxo-5,6-dihydro-1,5-naphthyridine-2-carbonitrile.

The compound (15.6 mg) was isolated in 47.7% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 404.16; Retention Time: 2.02 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 404.14; Retention Time: 1.23 min.

Example 246

8-[(2S,5R)-2,5-dimethyl-4-[(2,4,6-trifluorophenyl)methyl]piperazin-1-yl]-5-methyl-6-oxo-5,6-dihydro-1,5-naphthyridine-2-carbonitrile

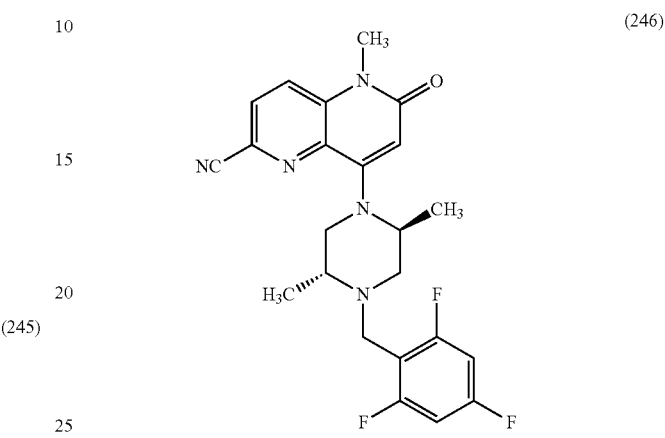

(246)

To a mixture of 2-(bromomethyl)-1,3,5-trifluorobenzene (0.015 mL, 0.114 mmol) and 8-((2S,5R)-2,5-dimethylpiperazin-1-yl)-5-methyl-6-oxo-5,6-dihydro-1,5-naphthyridine-2-carbonitrile, TFA salt (170 mg, 14.5% wt, 0.06 mmol) in acetonitrile (0.3 mL) was added Hunig's base (0.063 mL, 0.360 mmol). The mixture was stirred at 55° C. for 2 hours. LCMS indicated complete conversion to product. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 32% B, 32-72% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 24.3 mg. Calculated molecular weight 441.458. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 442.13; Retention Time: 1.22 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 442.12; Retention Time: 2.24 min.

Example 247

8-[(2S,5R)-4-[(4-chlorophenyl)(4-methylphenyl)methyl]-2,5-dimethylpiperazin-1-yl]-5-methyl-6-oxo-5,6-dihydro-1,5-naphthyridine-2-carbonitrile

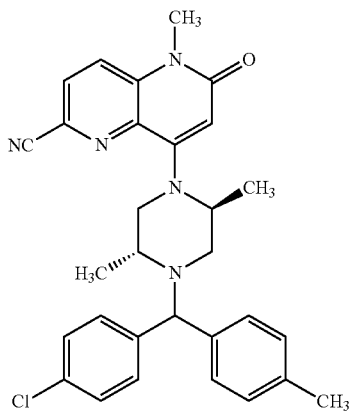
(247)

To the mixture of 8-((2S,5R)-2,5-dimethylpiperazin-1-yl)-5-methyl-6-oxo-5,6-dihydro-1,5-naphthyridine-2-carbonitrile, TFA salt (68.6 mg, 60% wt, 0.1 mmol), (cyanomethyl)trimethylphosphonium iodide (48.6 mg, 0.200 mmol) and (4-chlorophenyl)(p-tolyl)methanol (28.5 mg, 0.120 mmol) in acetonitrile (0.3 mL) was added Hunig's base (0.105 mL, 0.600 mmol). The reaction mixture was stirred at 110° C. for 2 hours, and additional (cyanomethyl)trimethylphosphonium iodide (48.6 mg, 0.200 mmol), (4-chlorophenyl)(p-tolyl)methanol (28.5 mg, 0.120 mmol) and Hunig's base (0.058 mL, 0.300 mmol) were added. The reaction mixture was stirred at 110° C. for another 2 hours. The crude reaction mixture was injected directly on 12 g Si-RediSep Rf for flash chromatography by 20-100% ethyl acetate in hexanes. Product containing fractions were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 51% B, 51-91% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 23.6 mg.

The diastereomeric product was resolved into two diastereomers by using SFC-chiral chromatography with the following conditions: Column: Chiral AD, 30×250 mm, 5 micron particles; Mobile Phase: 75% $CO_2$/25% IPA w/0.1% DEA; Flow Rate: 100 mL/min; Column Temperature: 25° C. Example 249 was collected as the 1$^{st}$ eluent peak, >95% de. Calculated molecular weight 512.05. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.2%; Observed Mass: 512.1; Retention Time: 2.67 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.3%; Observed Mass: 512.44; Retention Time: 1.91 min.

Intermediate 180

(3-Fluorophenyl)(4-fluorophenyl)methanol

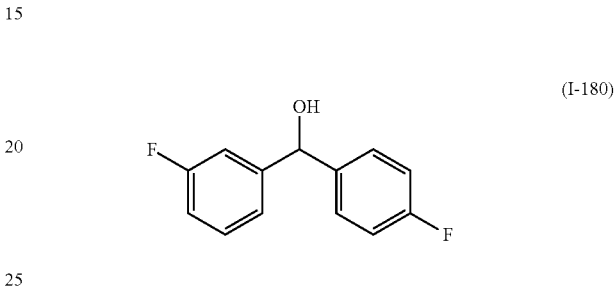
(I-180)

(3-Fluorophenyl)(4-fluorophenyl)methanol was prepared according to the general process used to prepare Intermediate 153, (4-chlorophenyl)(3-fluoropyridin-2-yl) methanol. NMR analysis showed this material to be >95% pure. $^1$H NMR (500 MHz, CHLOROFORM-d) δ 7.40-7.30 (m, 3H), 7.18-7.10 (m, 2H), 7.09-7.02 (m, 2H), 7.02-6.95 (m, 1H), 5.84 (d, J=3.4 Hz, 1H).

Example 248

8-[(2S,5R)-4-[(3-fluorophenyl)(4-fluorophenyl)methyl]-2,5-dimethylpiperazin-1-yl]-5-methyl-6-oxo-5,6-dihydro-1,5-naphthyridine-2-carbonitrile

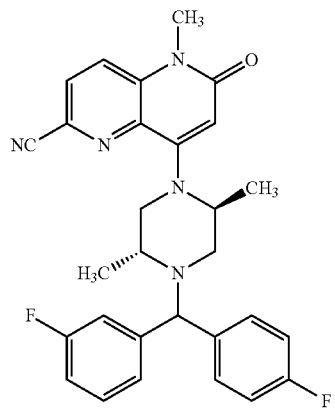
(248)

To the mixture of 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol), (cyanomethyl)trimethylphosphonium iodide (48.6 mg, 0.200 mmol) and (3-fluorophenyl) (4-fluorophenyl)methanol (26.4 mg, 0.120 mmol) in acetonitrile (0.3 mL) was added Hunig's base (0.105 mL, 0.600 mmol). The reaction mixture was stirred at 110° C. for 2 hours. Additional (cyanomethyl)trimethylphosphonium iodide (48.6 mg, 0.200 mmol), (3-fluorophenyl)(4-fluorophenyl)methanol (26.4 mg, 0.120 mmol) and Hunig's base (0.058 mL, 0.300 mmol) were added. The reaction mixture was stirred at 110° C. for another 2 hours. The crude reaction mixture was injected directly on 12 g Si-RediSep Rf for flash chromatography by 20-100% ethyl acetate in hexanes. Product containing fractions were combined and dried by vacuum. The resultant material was further purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 41% B, 41-81% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 20.9 mg.

Example 248 was resolved into two diastereomers by using SFC-chiral chromatography with the following conditions: Column: Chiral AD, 30×250 mm, 5 micron particles; Mobile Phase: 80% $CO_2$/20% IPA w/0.1% DEA; Flow Rate: 100 mL/min; Column Temperature: 25° C. Example 250 was collected as the 2d eluent peak, >90% de. Calculated molecular weight 499.566. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.3%; Observed Mass: 500.12; Retention Time: 2.40 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.1%; Observed Mass: 500.37; Retention Time: 1.86 min.

Example 249

8-[(2S,5R)-4-[(3-fluorophenyl)(4-fluorophenyl)methyl]-2,5-dimethylpiperazin-1-yl]-5-methyl-6-oxo-5,6-dihydro-1,5-naphthyridine-2-carbonitrile

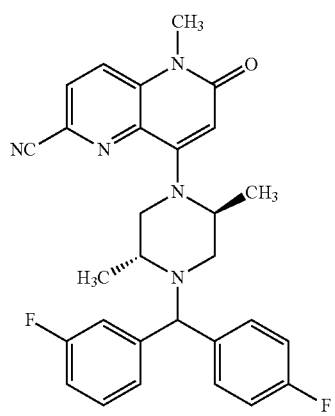

(249)

Example 249 was prepared and separated according to the general procedure used to prepare Example 248. Example 249 was collected as the 1$^{st}$ eluent peak, >95% de. Calculated molecular weight 499.566. Analytical LC/MS was used to determine the final purity. Injection 1 conditions: Column: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: MS and UV (220 nm). Injection 1 results: Purity: 96.3%; Observed Mass: 500.12; Retention Time: 2.40 min. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: MS and UV (220 nm). Injection 2 results: Purity: 97.0%; Observed Mass: 500.37; Retention Time: 1.87 min.

Example 250

8-[(2S,5R)-4-[(4-chlorophenyl)(4-methylphenyl)methyl]-2,5-dimethylpiperazin-1-yl]-5-methyl-6-oxo-5,6-dihydro-1,5-naphthyridine-2-carbonitrile

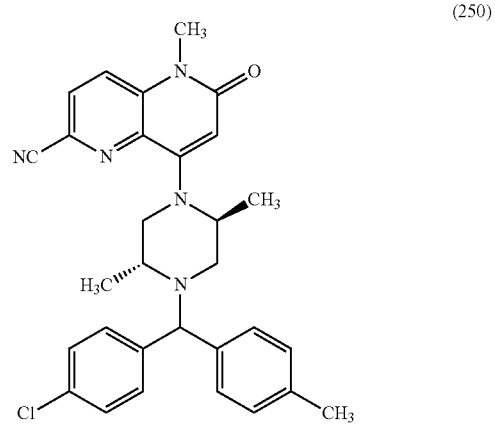

(250)

Example 250 was prepared and separated according to the general procedure used to prepare Example 247. Example 250 was collected as the 2$^{nd}$ eluent peak, >90% de. Calculated molecular weight 512.05. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Purity: 96.4%; Observed Mass: 512.01; Retention Time: 2.67 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.4%; Observed Mass: 512.22; Retention Time: 1.89 min.

Intermediate 181

(4-Fluorophenyl)(p-tolyl)methanol

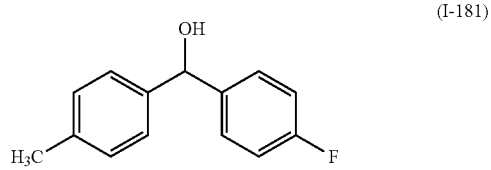 [SMILES: Cc1ccc(C(O)c2ccc(F)cc2)cc1]

(I-181)

(4-Fluorophenyl)(p-tolyl)methanol was prepared according to the general process used to prepare Intermediate 153, (4-chlorophenyl)(3-fluoropyridin-2-yl)methanol. $^1$H NMR (500 MHz, CHLOROFORM-d) δ 7.40-7.33 (m, 2H), 7.26 (d, J=8.1 Hz, 2H), 7.17 (d, J=7.8 Hz, 2H), 7.06-7.00 (m, 2H), 5.83 (d, J=1.8 Hz, 1H), 2.36 (s, 3H).

8-[(2S,5R)-4-[(4-fluorophenyl)(4-methylphenyl)methyl]-2,5-dimethylpiperazin-1-yl]-5-methyl-6-oxo-5,6-dihydro-1,5-naphthyridine-2-carbonitrile

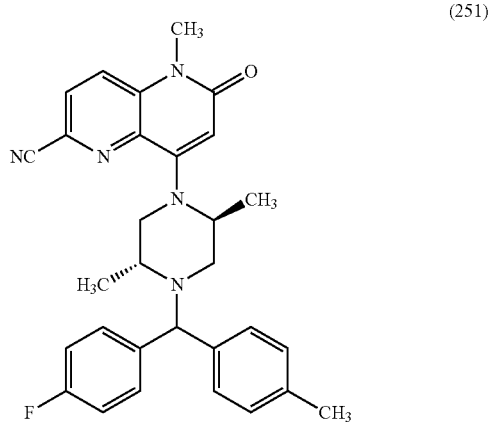

(251)

To the mixture of 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol), (cyanomethyl)trimethylphosphonium iodide (48.6 mg, 0.200 mmol) and (4-fluorophenyl)(p-tolyl)methanol (26.0 mg, 0.120 mmol) in acetonitrile (0.3 mL) was added Hunig's base (0.105 mL, 0.600 mmol). The reaction mixture was stirred at 110° C. for 2 hours, followed by a second addition of (cyanomethyl)trimethylphosphonium iodide (48.6 mg, 0.200 mmol), (4-fluorophenyl)(p-tolyl)methanol (26.0 mg, 0.120 mmol) and Hunig's base (0.058 mL, 0.300 mmol). The reaction mixture was stirred at 110° C. for another 2 hours. The crude reaction mixture was injected directly on 12 g Si-RediSep Rf for flash chromatography by 20-100% ethyl acetate in hexanes. Product containing fractions were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0 minute hold at 20% B, 20-60% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product TFA salt was 47.1 mg.

The diasteromeric product was resolved into two diastereomers by using SFC-chiral chromatography with the following conditions: Column: Chiral AD, 30×250 mm, 5 micron particles; Mobile Phase: 80% CO$_2$/20% IPA w/0.1% DEA; Flow Rate: 100 mL/min; Column Temperature: 25° C. The title compound was collected as the 2$^{nd}$ eluent peak, >91% de. Calculated molecular weight 495.602. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.6%; Observed Mass: 496.26; Retention Time: 2.52 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.2%; Observed Mass: 496.28; Retention Time: 1.73 min.

Example 252

8-[(2S,5R)-4-[(4-fluorophenyl)(4-methylphenyl)methyl]-2,5-dimethylpiperazin-1-yl]-5-methyl-6-oxo-5,6-dihydro-1,5-naphthyridine-2-carbonitrile

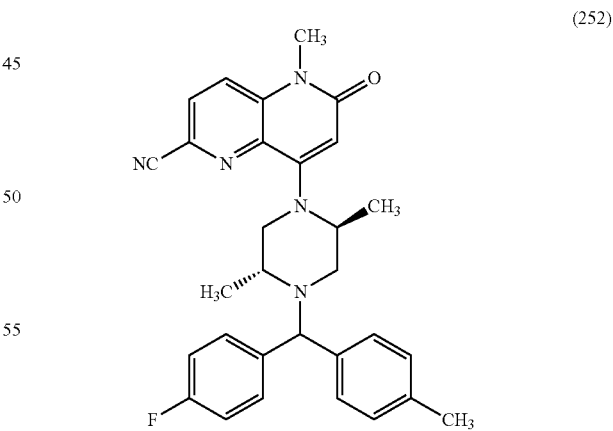

(252)

Example 252 was prepared and separated according to the general procedure used to prepare Example 251. Example 252 was collected as the 1$^{st}$ eluent peak, >95% de. Calculated molecular weight 495.602. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.4%; Observed Mass: 496.14; Retention Time: 2.52 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.0%; Observed Mass: 496.3; Retention Time: 1.71 min.

Example 253

8-[(2S,5R)-4-[(4-cyano-2-fluorophenyl)methyl]-2,5-dimethylpiperazin-1-yl]-5-methyl-6-oxo-5,6-dihydro-1,5-naphthyridine-2-carbonitrile

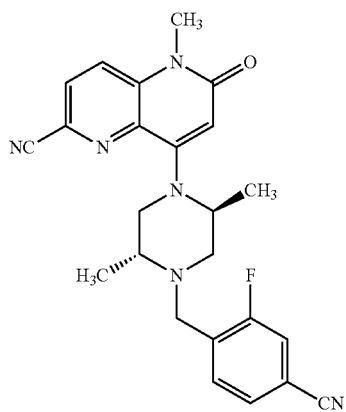

(253)

To a mixture of 4-(bromomethyl)-3-fluorobenzonitrile (16.05 mg, 0.075 mmol) and 8-((2S,5R)-2,5-dimethylpiperazin-1-yl)-5-methyl-6-oxo-5,6-dihydro-1,5-naphthyridine-2-carbonitrile, TFA (142 mg, 14.5% wt, 0.05 mmol) in acetonitrile (0.3 mL) was added Hunig's base (0.052 mL, 0.300 mmol). The mixture was stirred at 55° C. for 2 hours. LCMS indicated complete conversion to product. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 28% B, 28-68% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 18.0 mg. Calculated molecular weight 430.487. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.4%; Observed Mass: 431.13; Retention Time: 2.12 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.1%; Observed Mass: 431.12; Retention Time: 1.14 min.

Example 254

8-[(2S,5R)-4-{[2-fluoro-6-(trifluoromethyl)phenyl]methyl}-2,5-dimethylpiperazin-1-yl]-5-methyl-6-oxo-5,6-dihydro-1,5-naphthyridine-2-carbonitrile

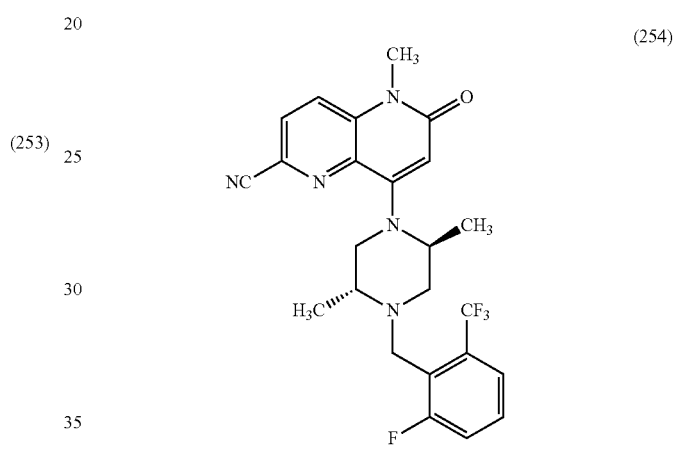

(254)

To a mixture of 2-fluoro-6-(trifluoromethyl)benzyl bromide (25.7 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. LCMS indicated complete conversion to product. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 40% B, 40-80% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 23.4 mg. Calculated molecular weight 473.476. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 474.11; Retention Time: 1.31 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Example 255

8-[(2S,5R)-4-[(2-fluoro-6-methylphenyl)methyl]-2,5-dimethylpiperazin-1-yl]-5-methyl-6-oxo-5,6-dihydro-1,5-naphthyridine-2-carbonitrile

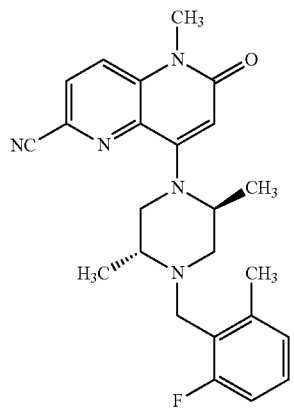

(255)

To a mixture of 2-(bromomethyl)-1-fluoro-3-methylbenzene (20.31 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. LCMS indicated complete conversion to product. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 39% B, 39-79% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 16.0 mg. Calculated molecular weight 419.504. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.6%; Observed Mass: 420.14; Retention Time: 1.19 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 474.11; Retention Time: 2.44 min.

Example 256

8-[(2S,5R)-4-[1-(2,6-difluorophenyl)ethyl]-2,5-dimethylpiperazin-1-yl]-5-methyl-6-oxo-5,6-dihydro-1,5-naphthyridine-2-carbonitrile

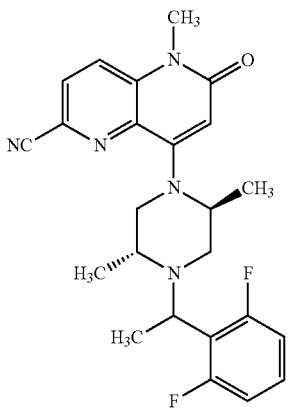

(256)

To a mixture of 2-(1-bromoethyl)-1,3-difluorobenzene (15.12 mg, 0.065 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. LCMS indicated complete conversion to product. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 37% B, 37-77% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 12.1 mg. Calculated molecular weight 437.495. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 438.14; Retention Time: 2.36 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 438.14; Retention Time: 1.2 min.

Example 257

8-[(2S,5R)-4-[bis(3-chlorophenyl)methyl]-2,5-dimethylpiperazin-1-yl]-5-methyl-6-oxo-5,6-dihydro-1,5-naphthyridine-2-carbonitrile

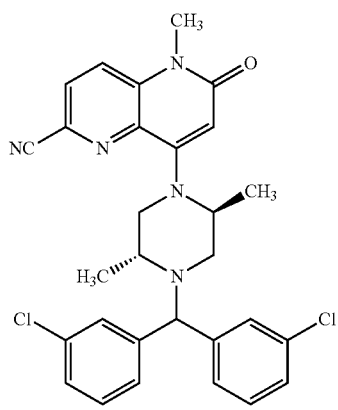

(257)

To the mixture of 8-((2S,5R)-2,5-dimethylpiperazin-1-yl)-5-methyl-6-oxo-5,6-dihydro-1,5-naphthyridine-2-carbonitrile, TFA (48.0 mg, 60% wt, 0.07 mmol), (cyanomethyl)trimethylphosphonium iodide (68.0 mg, 0.280 mmol) and bis(3-chlorophenyl)methanol (53.2 mg, 0.210 mmol) in propanenitrile (0.3 mL) was added Hunig's base (0.122 mL, 0.700 mmol). The reaction mixture was stirred at 110° C. for 2 hours. Next, additional (cyanomethyl)trimethylphosphonium iodide (42.5 mg, 0.125 mmol), bis(3-chlorophenyl)methanol (53.2 mg, 0.210 mmol) and Hunig's base (0.043 mL, 0.245 mmol) were added. The reaction mixture was stirred at 110° C. for another 2 hours. The crude reaction mixture was injected directly on 12 g Si-RediSep Rf for flash chromatography by 20-100% ethyl acetate in hexanes. Product containing fractions were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 50% B, 50-90% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 6.6 mg. Calculated molecular weight 532.47. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 532.09; Retention Time: 2.25 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 532.1; Retention Time: 2.77 min.

Example 258

8-[(2S,5R)-4-[bis(2-fluorophenyl)methyl]-2,5-dimethylpiperazin-1-yl]-5-methyl-6-oxo-5,6-dihydro-1,5-naphthyridine-2-carbonitrile

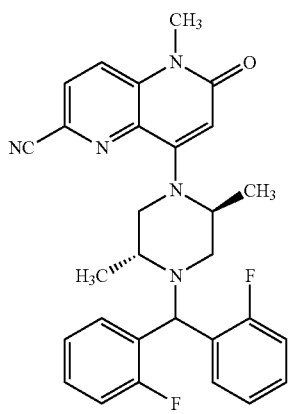

(258)

To the mixture of 8-((2S,5R)-2,5-dimethylpiperazin-1-yl)-5-methyl-6-oxo-5,6-dihydro-1,5-naphthyridine-2-carbonitrile, TFA (48.0 mg, 60% wt, 0.07 mmol), (cyanomethyl)trimethylphosphonium iodide (68.0 mg, 0.280 mmol) and bis(2-fluorophenyl)methanol (46.2 mg, 0.210 mmol) in propanenitrile (0.3 mL) was added Hunig's base (0.122 mL, 0.700 mmol). The reaction mixture was stirred at 110° C. for 2 hours. Next, additional (cyanomethyl)trimethylphosphonium iodide (42.5 mg, 0.125 mmol), bis(2-fluorophenyl)methanol (46.2 mg, 0.210 mmol) and Hunig's base (0.043 mL, 0.245 mmol) were added. The reaction mixture was stirred at 110° C. for another 2 hours. The crude reaction mixture was injected directly on 12 g Si-RediSep Rf for flash chromatography by 20-100% ethyl acetate in hexanes. Product containing fractions were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 42% B, 42-82% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 6.3 mg. Calculated molecular weight 499.566. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 500.15; Retention Time: 1.95 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 500.16; Retention Time: 2.52 min.

Example 259

8-[(2S,5R)-4-[(2-chlorophenyl)(phenyl)methyl]-2,5-dimethylpiperazin-1-yl]-5-methyl-6-oxo-5,6-dihydro-1,5-naphthyridine-2-carbonitrile

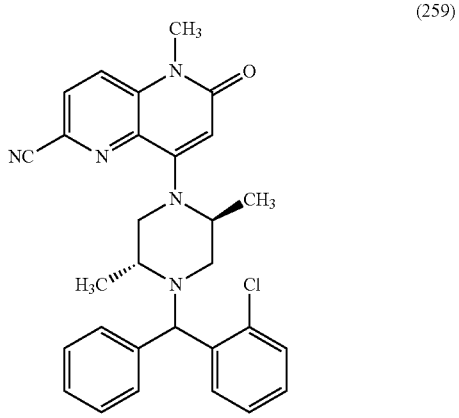 [SMILES: C[C@@H]1CN(c2cc(=O)n(C)c3ccc(C#N)nc23)[C@@H](C)CN1C(c1ccccc1)c1ccccc1Cl]

(259)

To the mixture of 8-((2S,5R)-2,5-dimethylpiperazin-1-yl)-5-methyl-6-oxo-5,6-dihydro-1,5-naphthyridine-2-carbonitrile, TFA (48.0 mg, 60% wt, 0.07 mmol), (cyanomethyl)trimethylphosphonium iodide (68.0 mg, 0.280 mmol) and (2-chlorophenyl)(phenyl)methanol (45.9 mg, 0.210 mmol) in propanenitrile (0.3 mL) was added Hunig's base (0.122 mL, 0.700 mmol). The reaction mixture was stirred at 110° C. for 2 hours. Next, additional (cyanomethyl)trimethylphosphonium iodide (42.5 mg, 0.125 mmol), (2-chlorophenyl)(phenyl)methanol (45.9 mg, 0.210 mmol) and Hunig's base (0.043 mL, 0.245 mmol) were added. The reaction mixture was stirred at 110° C. for another 2 hours. The crude reaction mixture was injected directly on 12 g Si-RediSep Rf for flash chromatography by 20-100% ethyl acetate in hexanes. Product containing fractions were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 47% B, 47-87% B over 20 minutes, then a 5 minute hold at 100% B; Flow Rate: 20 mL/min; Column Temperature: 25° C. Fraction collection was triggered by UV signals. Fractions containing the product were combined and dried via centrifugal evaporation. The yield of the diastereomeric product was 7.8 mg. Calculated molecular weight 498.03. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 498.14; Retention Time: 1.93 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 498.11; Retention Time: 2.66 min.

Example 260

8-[(2S,5R)-4-[(2-chloro-6-cyanophenyl)methyl]-2,5-dimethylpiperazin-1-yl]-5-methyl-6-oxo-5,6-dihydro-1,5-naphthyridine-2-carbonitrile

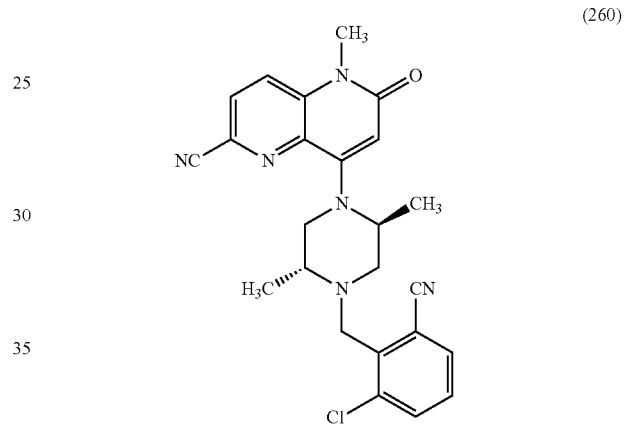

(260)

To a mixture of 2-(bromomethyl)-3-chlorobenzonitrile (23.05 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. LCMS indicated complete conversion to product. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 34% B, 34-74% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 16.4 mg. Calculated molecular weight 446.94. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 447.1; Retention Time: 2.21 min. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 447.1; Retention Time: 1.34 min.

Example 261

8-[(2S,5R)-4-[(2-chloro-6-fluorophenyl)methyl]-2,5-dimethylpiperazin-1-yl]-5-methyl-6-oxo-5,6-dihydro-1,5-naphthyridine-2-carbonitrile

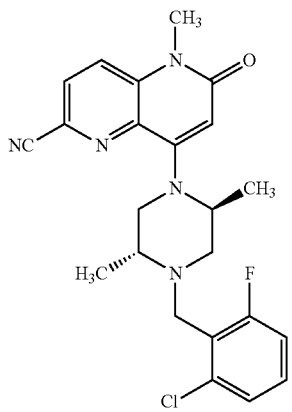

(261)

To a mixture of 2-(bromomethyl)-1-chloro-3-fluorobenzene (22.35 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. LCMS indicated complete conversion to product. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 39% B, 39-79% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 15.8 mg. Calculated molecular weight 439.92. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 440.1; Retention Time: 2.38 min. Injection 2 conditions: Column: Waters Acquity UPLC BEH C18, 2.1×50 mm, 1.7 μm particles; Mobile Phase A: 5:95 Acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 440.1; Retention Time: 1.18 min.

Example 262

8-[(2S,5R)-4-[(2,5-difluorophenyl)methyl]-2,5-dimethylpiperazin-1-yl]-5-methyl-6-oxo-5,6-dihydro-1,5-naphthyridine-2-carbonitrile

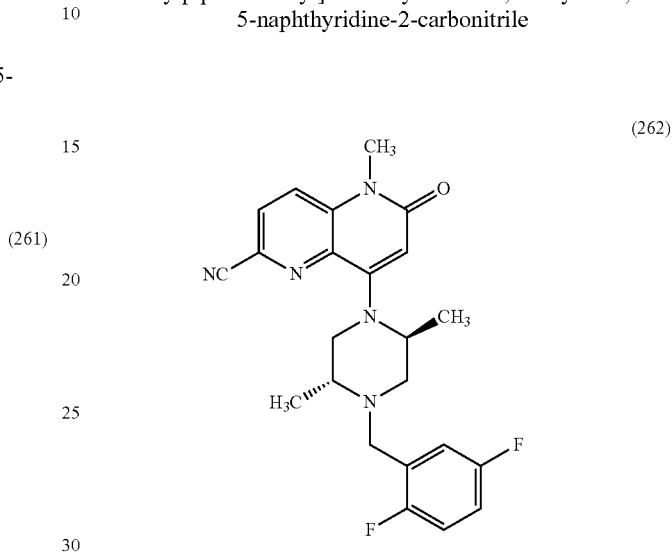

(262)

To a mixture of 2-(bromomethyl)-1,4-difluorobenzene (20.70 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 33% B, 33-73% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 22.5 mg. Calculated molecular weight 423.468. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 424.1; Retention Time: 2.24 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 424.11; Retention Time: 1.15 min.

Example 263

8-[(2S,5R)-4-[(2,6-dichlorophenyl)methyl]-2,5-dimethylpiperazin-1-yl]-5-methyl-6-oxo-5,6-dihydro-1,5-naphthyridine-2-carbonitrile

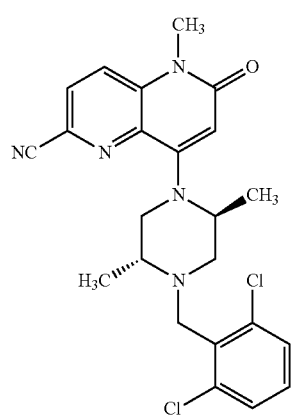

(263)

To a mixture of 2,6-dichlorobenzyl bromide (23.99 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 44% B, 44-84% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. Calculated molecular weight 456.37. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 456.04; Retention Time: 1.26 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 456.03; Retention Time: 2.56 min.

Example 264

8-[(2S,5R)-4-benzyl-2,5-dimethylpiperazin-1-yl]-5-methyl-6-oxo-5,6-dihydro-1,5-naphthyridine-2-carbonitrile

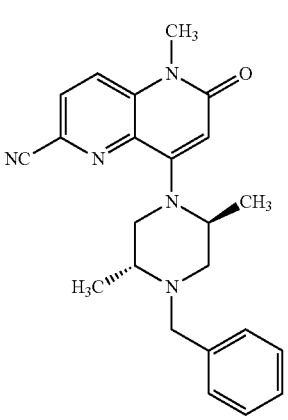

(264)

To a mixture of (bromomethyl)benzene (17.10 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 28% B, 28-68% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 16.5 mg. Calculated molecular weight 387.487. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 388.1; Retention Time: 2.16 min. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 100.0%; Observed Mass: 388.1; Retention Time: 1.14 min.

Example 265

8-[(2S,5R)-4-[(2,6-dimethylphenyl)methyl]-2,5-dimethylpiperazin-1-yl]-5-methyl-6-oxo-5,6-dihydro-1,5-naphthyridine-2-carbonitrile

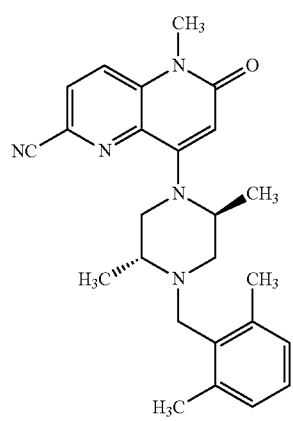

(265)

To a mixture of 2-(bromomethyl)-1,3-dimethylbenzene (19.91 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 43% B, 43-83% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 18.1 mg. Calculated molecular weight 415.541. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 416.16; Retention Time: 1.26 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 416.15; Retention Time: 2.53 min.

Example 266

8-[(2S,5R)-4-[(2-chloro-3,6-difluorophenyl)methyl]-2,5-dimethylpiperazin-1-yl]-5-methyl-6-oxo-5,6-dihydro-1,5-naphthyridine-2-carbonitrile

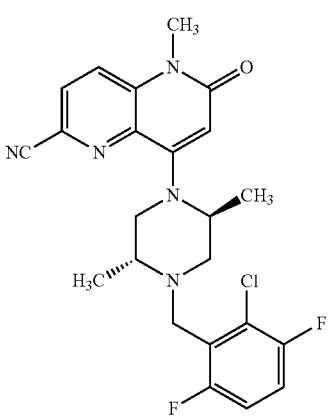

(266)

To a mixture of 2-chloro-3,6-difluorobenzyl bromide (24.15 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 38% B, 38-78% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 22.2 mg. Calculated molecular weight 457.91. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 458.06; Retention Time: 2.38 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 458.06; Retention Time: 1.23 min.

Example 267

8-[(2S,5R)-4-[(4-cyano-2,6-difluorophenyl)methyl]-2,5-dimethylpiperazin-1-yl]-5-methyl-6-oxo-5,6-dihydro-1,5-naphthyridine-2-carbonitrile

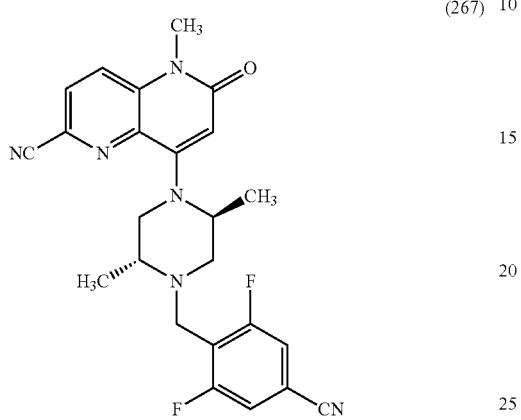

(267)

To a mixture of 4-(bromomethyl)-3,5-difluorobenzonitrile (23.20 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 25% B, 25-65% B over 25 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 16.8 mg. Calculated molecular weight 448.478. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 449.14; Retention Time: 1.12 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 449.12; Retention Time: 2.08 min.

Example 268

8-[(2S,5R)-4-[(4-chloro-2,6-difluorophenyl)methyl]-2,5-dimethylpiperazin-1-yl]-5-methyl-6-oxo-5,6-dihydro-1,5-naphthyridine-2-carbonitrile

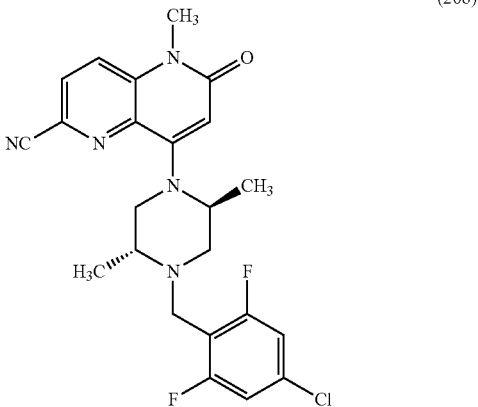

(268)

To a mixture of 4-chloro-2,6-difluorobenzyl bromide (24.15 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 40% B, 40-80% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 18.5 mg. Calculated molecular weight 457.91. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 458.05; Retention Time: 2.43 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 458.07; Retention Time: 1.25 min.

Example 269

8-[(2S,5R)-4-[(2-cyano-6-fluorophenyl)methyl]-2,5-dimethylpiperazin-1-yl]-5-methyl-6-oxo-5,6-dihydro-1,5-naphthyridine-2-carbonitrile

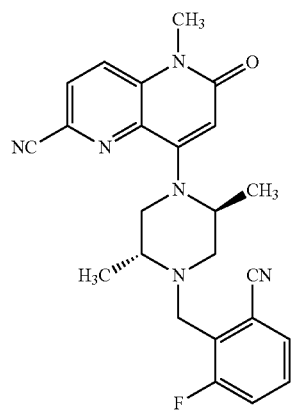

(269)

To a mixture of 2-(bromomethyl)-3-fluorobenzonitrile (21.40 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 24% B, 24-64% B over 25 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 19.6 mg. Calculated molecular weight 430.487. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 431.12; Retention Time: 1.14 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 431.1; Retention Time: 2.07 min.

Example 270

8-[(2S,5R)-4-[bis(3-fluorophenyl)methyl]-2,5-dimethylpiperazin-1-yl]-5-methyl-6-oxo-5,6-dihydro-1,5-naphthyridine-2-carbonitrile

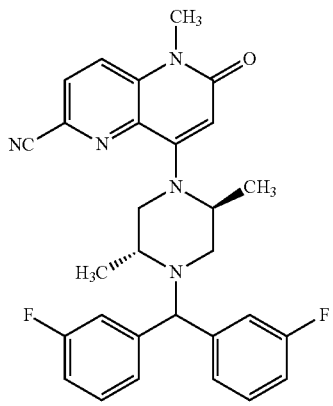

(270)

To the mixture of 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol), bis(3-fluorophenyl)methanol (66.1 mg, 0.300 mmol) and (cyanomethyl)trimethylphosphonium iodide (146.0 mg, 0.6 mmol) in propanenitrile (0.3 mL) was added Hunig's base (0.175 mL, 1.000 mmol). The reaction mixture was stirred at 110° C. for 5 hours. The crude reaction mixture was injected directly on 12 g Si-RediSep Rf for flash chromatography by 20-100% ethyl acetate in hexanes. Product containing fractions were combined and dried by vacuum. The resultant material was further purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 43% B, 43-83% B over 22 minutes, then a 5 minute hold at 100% B; Flow Rate: 20 mL/min; Column Temperature: 25° C. Fraction collection was triggered by MS and UV signals. Fractions containing product were combined and dried via centrifugal evaporation. The yield of the product was 11.6 mg. Calculated molecular weight 499.566. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 92.0%; Observed Mass: 500.18; Retention Time: 1.93 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.9%; Observed Mass: 500.15; Retention Time: 2.6 min.

Example 271

8-[(2S,5R)-4-[(2,6-difluorophenyl)methyl]-2,5-dimethylpiperazin-1-yl]-5-methyl-6-oxo-5,6-dihydro-1,5-naphthyridine-2-carbonitrile

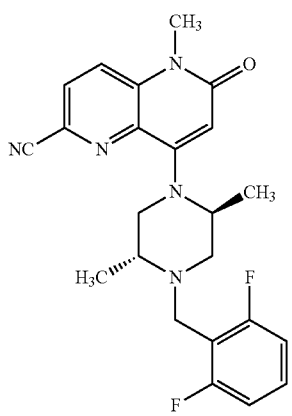

(271)

To a mixture of 2-(bromomethyl)-1,3-difluorobenzene (20.70 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 34% B, 34-74% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 17.2 mg. Calculated molecular weight 423.468. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 424.11; Retention Time: 2.26 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 424.12; Retention Time: 1.11 min.

Intermediate 182

(2,6-difluorophenyl)(phenyl)methanol

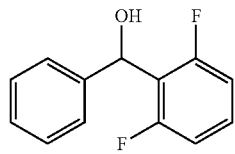

(I-182)

(2,6-Difluorophenyl)(phenyl)methanol was prepared according to the general process used to prepare Intermediate 153, (4-chlorophenyl)(3-fluoropyridin-2-yl)methanol. $^1$H NMR (500 MHz, CHLOROFORM-d) δ 7.45-7.40 (m, 2H), 7.40-7.35 (m, 2H), 7.34-7.22 (m, 2H, overlapping with residual chloroform), 6.98-6.88 (m, 2H), 6.27 (d, J=9.0 Hz, 1H).

Example 272

8-[(2S,5R)-4-[(2,6-difluorophenyl)(phenyl)methyl]-2,5-dimethylpiperazin-1-yl]-5-methyl-6-oxo-5,6-dihydro-1,5-naphthyridine-2-carbonitrile

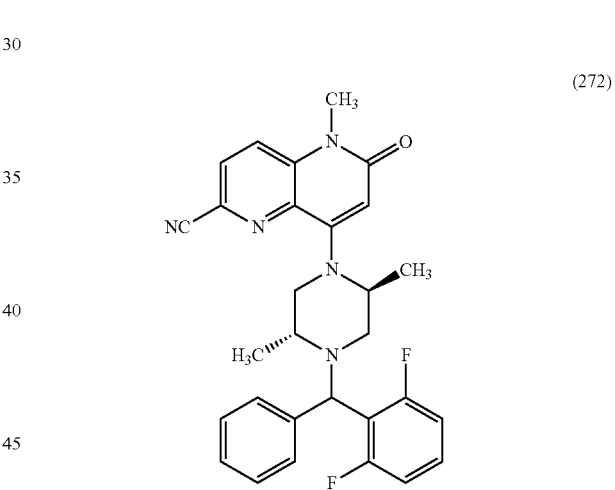

(272)

To the mixture of (2,6-difluorophenyl)(phenyl)methanol (66.1 mg, 0.300 mmol), (cyanomethyl)trimethylphosphonium iodide (97.0 mg, 0.4 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in propanenitrile (0.3 mL) was added Hunig's base (0.175 mL, 1.000 mmol). The reaction mixture was stirred at 110° C. for 5 hours. To the above reaction mixture was added extra (cyanomethyl)trimethylphosphonium iodide (97.0 mg, 0.4 mmol), (2,6-difluorophenyl)(phenyl)methanol (66.1 mg, 0.300 mmol) and Hunig's base (0.14 mL, 0.8 mmol). The reaction mixture was stirred at 110° C. for another 2 hours. The crude reaction mixture was injected directly on 12 g Si-RediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 µm particles; Mobile Phase A: 5:95 acetonitrile:water with 0.1% trifluoroacetic acid; Mobile Phase B: 95:5 acetonitrile: water with 0.1% trifluoroacetic acid; Gradient: a 0 minute hold at 28% B, 28-68% B over 25 minutes, then a 4 minute hold at 100% B; Flow Rate: 20 mL/min; Column Temperature: 25° C. Fraction collection was triggered by MS and UV signals. The two diastereomers were separated under the above condition. The fractions containing the 2$^{nd}$ eluent peak were combined and dried via centrifugal evaporation. The yield of the product as TFA salt was 6.0 mg. Calculated molecular weight 499.566. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.1%; Observed Mass: 500.16; Retention Time: 2 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.1%; Observed Mass: 500.16; Retention Time: 2.64 min.

Example 273

8-[(2S,5R)-4-[(2,6-difluorophenyl)(phenyl)methyl]-2,5-dimethylpiperazin-1-yl]-5-methyl-6-oxo-5,6-dihydro-1,5-naphthyridine-2-carbonitrile, TFA

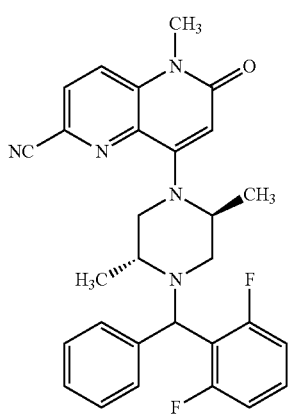

(273)

Example 273 was prepared and separated according to the general procedure used to prepare Example 272. Example 273 was collected as the 1st eluent peak. The yield of the product as a TFA salt was 7.7 mg. Calculated molecular weight 499.566. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.9%; Observed Mass: 500.14; Retention Time: 2.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.1%; Observed Mass: 500.15; Retention Time: 1.72 min.

Intermediate 183

(2,6-difluorophenyl)(4-fluorophenyl)methanol

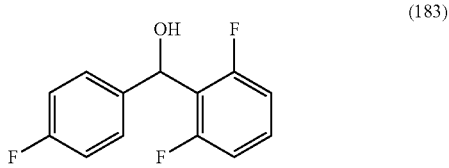 [SMILES: OC(c1ccc(F)cc1)c1c(F)cccc1F]

(183)

(2,6-Difluorophenyl)(4-fluorophenyl)methanol was prepared according to the general process used to prepare Intermediate 153, (4-chlorophenyl)(3-fluoropyridin-2-yl)methanol. $^1$H NMR (500 MHz, CHLOROFORM-d) 7.39 (dd, J=8.5, 5.4 Hz, 2H), 7.33-7.23 (m, 2H), 7.11-7.01 (m, 2H), 6.99-6.89 (m, 2H), 6.24 (d, J=8.9 Hz, 1H).

Example 274

8-[(2S,5R)-4-[(2,6-difluorophenyl)(4-fluorophenyl)methyl]-2,5-dimethylpiperazin-1-yl]-5-methyl-6-oxo-5,6-dihydro-1,5-naphthyridine-2-carbonitrile

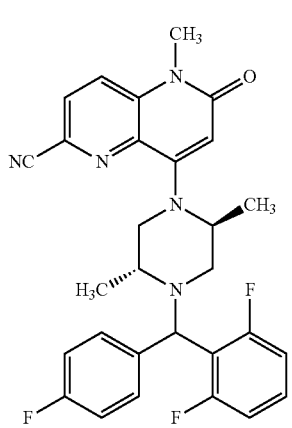

(274)

To the mixture of (2,6-difluorophenyl)(4-fluorophenyl)methanol (71.5 mg, 0.300 mmol), (cyanomethyl)trimethylphosphonium iodide (97.0 mg, 0.4 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in propanenitrile (0.3 mL) was added Hunig's base (0.175 mL, 1.000 mmol). The reaction mixture was stirred at 110° C. for 5 hours. Next, additional (cyanomethyl)trimethylphosphonium iodide (97.0 mg, 0.4 mmol), (2,6-difluorophenyl)(4-fluorophenyl)methanol (71.5 mg, 0.300 mmol) and Hunig's base (0.14 mL, 0.8 mmol) were added.

The reaction mixture was stirred at 110° C. for another 2 hours. The crude reaction mixture was injected directly on 12 g Si-RediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 0.1% trifluoroacetic acid; Mobile Phase B: 95:5 acetonitrile: water with 0.1% trifluoroacetic acid; Gradient: a 0 minute hold at 34% B, 34-74% B over 25 minutes, then a 4 minute hold at 100% B; Flow Rate: 20 mL/min; Column Temperature: 25° C. Fraction collection was triggered by MS and UV signals. The two diastereomers were separated under the above condition. The fractions containing the $2^{nd}$ eluent peak were combined and dried via centrifugal evaporation. The yield of the product as TFA salt was 9.2 mg. Calculated molecular weight 517.556. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.1%; Observed Mass: 518.17; Retention Time: 2.15 min. Injection 2 conditions: Column: Waters XBridge C18, 2.1 mm×50 mm, 1.7 μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.0%; Observed Mass: 518.16; Retention Time: 2.65 min.

Example 275

8-[(2S,5R)-4-[(2,6-difluorophenyl)(4-fluorophenyl)methyl]-2,5-dimethylpiperazin-1-yl]-5-methyl-6-oxo-5,6-dihydro-1,5-naphthyridine-2-carbonitrile

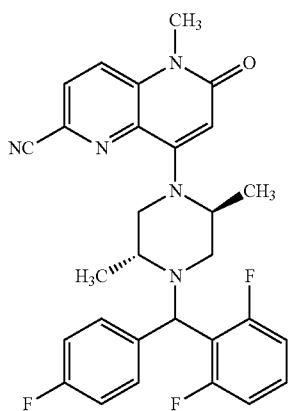

(275)

Example 275 was prepared and separated according to the general procedure used to prepare Example 274. Example 275 was collected as the $1^{st}$ eluent peak. The yield of the product as TFA salt was 10.4 mg. Calculated molecular weight 517.556. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.4%; Observed Mass: 518.16; Retention Time: 1.85 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.3%; Observed Mass: 518.16; Retention Time: 2.64 min.

Intermediate 184

(2,3-Difluorophenyl)(phenyl)methanol

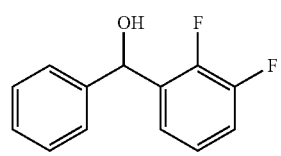

(I-184)

(2,3-Difluorophenyl)(phenyl)methanol was prepared according to the general process used to prepare Intermediate 153, (4-chlorophenyl)(3-fluoropyridin-2-yl)methanol. $^1$H NMR (500 MHz, CHLOROFORM-d) δ 7.45-7.42 (m, 2H), 7.40-7.35 (m, 2H), 7.35-7.29 (m, 2H), 7.16-7.03 (m, 2H), 6.19 (d, J=3.8 Hz, 1H).

Example 276

8-[(2S,5R)-4-[(2,3-difluorophenyl)(phenyl)methyl]-2,5-dimethylpiperazin-1-yl]-5-methyl-6-oxo-5,6-dihydro-1,5-naphthyridine-2-carbonitrile

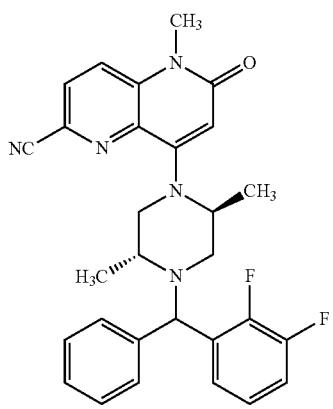

(276)

To the mixture of (2,3-difluorophenyl)(phenyl)methanol (66.1 mg, 0.300 mmol), (cyanomethyl)trimethylphosphonium iodide (97.0 mg, 0.4 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in propanenitrile (0.3 mL) was added Hunig's base (0.175 mL, 1.000 mmol). The reaction mixture was stirred at 110° C. for 5 hours. To the above reaction mixture was added extra (cyanomethyl)trimethylphosphonium iodide (97.0 mg, 0.4 mmol), (2,3-difluorophenyl)(phenyl)methanol (66.1 mg, 0.300 mmol) and Hunig's base (0.14 mL, 0.8 mmol). The reaction mixture was stirred at 110° C. for another 2 hours. The crude material was purified via preparative LC/MS with the following conditions: Column: XBridge C18, 200 mm×19 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0 minute hold at 28% B, 28-68% B over 24 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 14.2 mg. Calculated molecular weight 499.566. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.7%; Observed Mass: 500.17; Retention Time: 2.65 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 93.7%; Observed Mass: 500.16; Retention Time: 1.97 min.

Example 277

8-[(2S,5R)-4-[(2,4-difluorophenyl)methyl]-2,5-dimethylpiperazin-1-yl]-5-methyl-6-oxo-5,6-dihydro-1,5-naphthyridine-2-carbonitrile

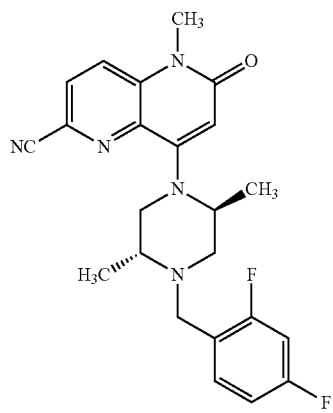

(277)

To a mixture of 1-(bromomethyl)-2,4-difluorobenzene (20.70 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 36% B, 36-76% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 20.6 mg. Calculated molecular weight 423.468. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 424.1; Retention Time: 2.19 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 424.11; Retention Time: 1.19 min.

Example 278

8-[(2S,5R)-2,5-dimethyl-4-{[6-(trifluoromethyl)pyridin-2-yl]methyl}piperazin-1-yl]-5-methyl-6-oxo-5,6-dihydro-1,5-naphthyridine-2-carbonitrile

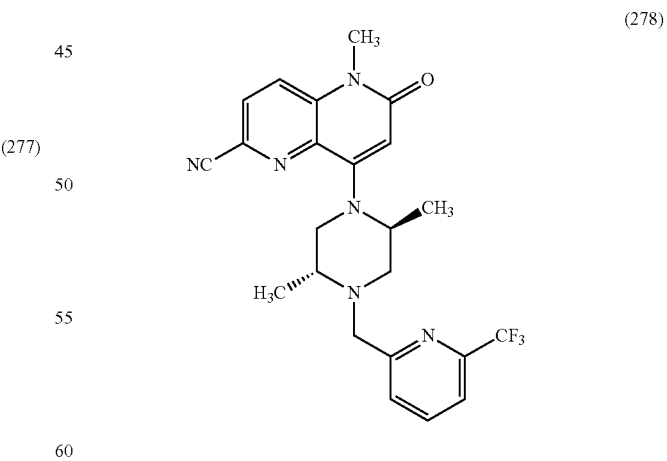

(278)

To a mixture of 2-(chloromethyl)-6-(trifluoromethyl)pyridine (19.56 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 31% B, 31-71% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 20.1 mg. Calculated molecular weight 456.473. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 457.11; Retention Time: 1.24 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 457.12; Retention Time: 2.2 min.

Example 279

8-[(2S,5R)-2,5-dimethyl-4-{[2-methyl-6-(trifluoromethyl)pyridin-3-yl]methyl}piperazin-1-yl]-5-methyl-6-oxo-5,6-dihydro-1,5-naphthyridine-2-carbonitrile

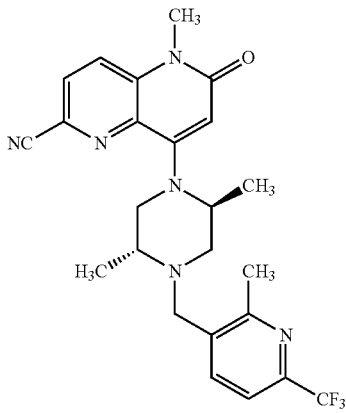

(279)

To a mixture of 3-(chloromethyl)-2-methyl-6-(trifluoromethyl)pyridine (20.96 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 36% B, 36-76% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 20.5 mg. Calculated molecular weight 470.5. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.4%; Observed Mass: 471.13; Retention Time: 1.27 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 471.14; Retention Time: 2.32 min.

Example 280

8-[(2S,5R)-4-{[2-methoxy-6-(trifluoromethyl)pyridin-4-yl]methyl}-2,5-dimethylpiperazin-1-yl]-5-methyl-6-oxo-5,6-dihydro-1,5-naphthyridine-2-carbonitrile

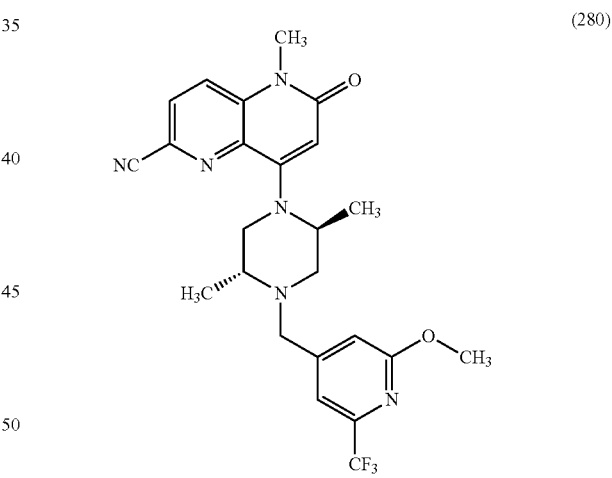

(280)

To a mixture of 4-(bromomethyl)-2-methoxy-6-(trifluoromethyl)pyridine (27.0 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 42% B, 42-82% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 21.4 mg. Calculated molecular weight 486.499. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 487.11; Retention Time: 2.5 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 487.13; Retention Time: 1.41 min.

Example 281

8-[(2S,5R)-4-{[2-chloro-6-(trifluoromethyl)pyridin-3-yl]methyl}-2,5-dimethylpiperazin-1-yl]-5-methyl-6-oxo-5,6-dihydro-1,5-naphthyridine-2-carbonitrile

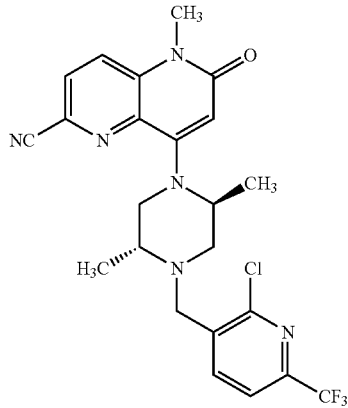

(281)

To a mixture of 2-chloro-3-(chloromethyl)-6-(trifluoromethyl)pyridine (23.00 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 39% B, 39-79% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 20.2 mg. Calculated molecular weight 490.92. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.5%; Observed Mass: 491.07; Retention Time: 1.4 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 491.08; Retention Time: 2.43 min.

Example 282

8-[(2S,5R)-4-[(3-chlorophenyl)(phenyl)methyl]-2,5-dimethylpiperazin-1-yl]-5-methyl-6-oxo-5,6-dihydro-1,5-naphthyridine-2-carbonitrile

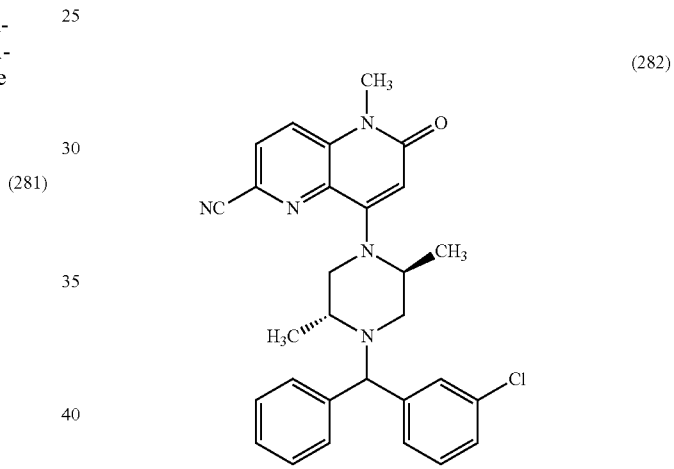

(282)

To the mixture of (3-chlorophenyl)(phenyl)methanol (42.6 mg, 0.195 mmol), (cyanomethyl)trimethylphosphonium iodide (63.2 mg, 0.26 mmol) and 8-((2S,5R)-2,5-dimethylpiperazin-1-yl)-5-methyl-6-oxo-5,6-dihydro-1,5-naphthyridine-2-carbonitrile, TFA (44.6 mg, 60% wt, 0.065 mmol) in propanenitrile (0.3 mL) was added Hunig's base (0.114 mL, 0.65 mmol). The reaction mixture was stirred at 110° C. for 5 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 50% B, 50-90% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of diastereomeric product was 7.4 mg. Calculated molecular weight 498.03. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.4%; Observed Mass: 498.12; Retention Time: 2.74 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.1%; Observed Mass: 498.13; Retention Time: 1.83 min.

Intermediate 185

(2,4-difluorophenyl)(phenyl)methanol

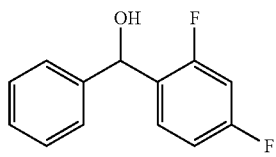

(I-185)

(2,4-difluorophenyl)(phenyl)methanol was prepared according to the general process used to prepare Intermediate 153, (4-chlorophenyl)(3-fluoropyridin-2-yl)methanol. $^1$H NMR (500 MHz, CHLOROFORM-d) δ 7.50 (td, J=8.4, 6.6 Hz, 1H), 7.44-7.35 (m, 4H), 7.34-7.29 (m, 1H), 6.94-6.87 (m, 1H), 6.83-6.77 (m, 1H), 6.13 (d, J=3.8 Hz, 1H).

Example 283

8-[(2S,5R)-4-[(2,4-difluorophenyl)(phenyl)methyl]-2,5-dimethylpiperazin-1-yl]-5-methyl-6-oxo-5,6-dihydro-1,5-naphthyridine-2-carbonitrile

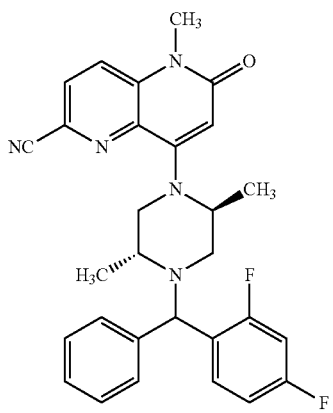

(283)

To the mixture of (2,4-difluorophenyl)(phenyl)methanol (66.1 mg, 0.300 mmol), (cyanomethyl)trimethylphosphonium iodide (97.0 mg, 0.4 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in propanenitrile (0.3 mL) was added Hunig's base (0.175 mL, 1.000 mmol). The reaction mixture was stirred at 110° C. for 5 hours. To the above reaction mixture was added extra (cyanomethyl)trimethylphosphonium iodide (97.0 mg, 0.4 mmol), (2,4-difluorophenyl)(phenyl)methanol (66.1 mg, 0.300 mmol) and Hunig's base (0.14 mL, 0.8 mmol). The reaction mixture was stirred at 100° C. for another 12 hours. The crude reaction mixture was injected directly on 12 g Si-RediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 48% B, 48-88% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of diastereomeric product was 20.3 mg. Calculated molecular weight 499.566. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile: water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.2%; Observed Mass: 500.16; Retention Time: 1.88 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.6%; Observed Mass: 500.16; Retention Time: 2.67 min.

Intermediate 186

(2-fluorophenyl)(4-fluorophenyl)methanol

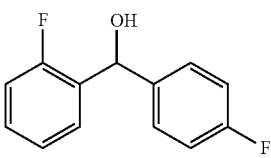

(I-186)

(2-fluorophenyl)(4-fluorophenyl)methanol was prepared according to the general process used to prepare Intermediate 153, (4-chlorophenyl)(3-fluoropyridin-2-yl)methanol. $^1$H NMR (500 MHz, CHLOROFORM-d) δ 7.51 (td, J=7.6, 1.7 Hz, 1H), 7.39 (dd, J=8.6, 5.4 Hz, 2H), 7.32-7.26 (m, 1H), 7.18 (td, J=7.6, 1.1 Hz, 1H), 7.08-7.00 (m, 3H), 6.15 (d, J=3.8 Hz, 1H), 2.35 (d, J=4.0 Hz, 1H).

Example 284

8-[(2S,5R)-4-[(2-fluorophenyl)(4-fluorophenyl)methyl]-2,5-dimethylpiperazin-1-yl]-5-methyl-6-oxo-5,6-dihydro-1,5-naphthyridine-2-carbonitrile

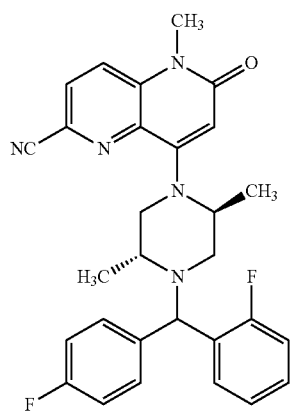

(284)

To the mixture of (2-fluorophenyl)(4-fluorophenyl)methanol (49.5 mg, 0.225 mmol), (cyanomethyl)trimethylphosphonium iodide (72.9 mg, 0.300 mmol) and 8-((2S,5R)-2,5-dimethylpiperazin-1-yl)-5-methyl-6-oxo-5,6-dihydro-1,5-naphthyridine-2-carbonitrile, TFA (51.4 mg, 60% wt, 0.075 mmol) in propanenitrile (0.3 mL) was added Hunig's base (0.131 mL, 0.750 mmol). The reaction mixture was stirred at 110° C. for 5 hours. Next, additional (cyanomethyl)trimethylphosphonium iodide (72.9 mg, 0.300 mmol), (2-fluorophenyl)(4-fluorophenyl)methanol (49.5 mg, 0.225 mmol) and Hunig's base (0.105 mL, 0.60 mmol) were added. The reaction mixture was stirred at 100° C. for another 12 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 44% B, 44-84% B over 22 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 12.2 mg. Calculated molecular weight 499.566. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.6%; Observed Mass: 500.16; Retention Time: 1.83 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.0%; Observed Mass: 500.15; Retention Time: 2.64 min.

Intermediate 187

(2-fluorophenyl)(phenyl)methanol

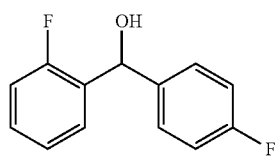

(I-187)

(2-Fluorophenyl)(phenyl)methanol was prepared according to the general process used to prepare Intermediate 153, (4-chlorophenyl)(3-fluoropyridin-2-yl)methanol. $^1$H NMR (500 MHz, CHLOROFORM-d) δ 7.53 (td, J=7.6, 1.8 Hz, 1H), 7.43 (d, J=7.6, 2H), 7.40-7.33 (m, 2H), 7.32-7.23 (m, 3H), 7.18 (td, J=7.6, 1.1 Hz, 1H), 7.04 (ddd, J=10.5, 8.3, 1.1 Hz, 1H), 6.18 (d, J=4.1 Hz, 1H), 2.29 (dd, J=4.2, 0.8 Hz, 1H).

Example 285

8-[(2S,5R)-4-[(2-fluorophenyl)(phenyl)methyl]-2,5-dimethylpiperazin-1-yl]-5-methyl-6-oxo-5,6-dihydro-1,5-naphthyridine-2-carbonitrile

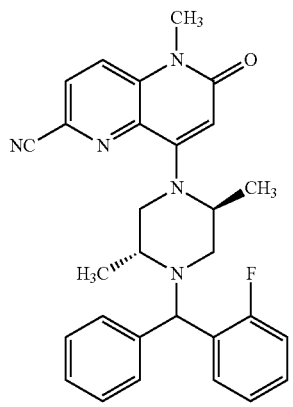

(285)

To the mixture of (2-fluorophenyl)(phenyl)methanol (39.4 mg, 0.195 mmol), (cyanomethyl)trimethylphosphonium iodide (63.2 mg, 0.26 mmol) and 8-((2S,5R)-2,5-dimethylpiperazin-1-yl)-5-methyl-6-oxo-5,6-dihydro-1,5-naphthyridine-2-carbonitrile, TFA (44.6 mg, 60% wt, 0.065 mmol) in propanenitrile (0.3 mL) was added Hunig's base (0.114 mL, 0.65 mmol). The reaction mixture was stirred at 110° C. for 5 hours. To the above reaction mixture was added extra (cyanomethyl)trimethylphosphonium iodide (63.2 mg, 0.26 mmol), (2-fluorophenyl)(phenyl)methanol (39.4 mg, 0.195 mmol) and Hunig's base (0.091 mL, 0.52 mmol). The reaction mixture was stirred at 100° C. for another 12 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 41% B, 41-81% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 14.7 mg. Calculated molecular weight 481.575. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 482.18; Retention Time: 2.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.0%; Observed Mass: 482.18; Retention Time: 1.73 min.

Example 286

8-[(2S,5R)-4-[(2,3-difluorophenyl)methyl]-2,5-dimethylpiperazin-1-yl]-5-methyl-6-oxo-5,6-dihydro-1,5-naphthyridine-2-carbonitrile

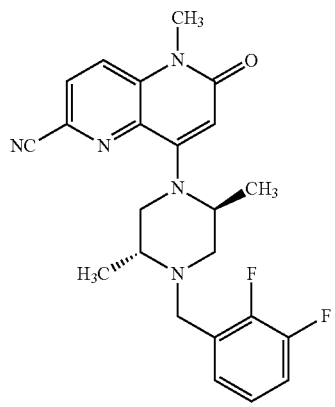

(286)

To a mixture of 1-(bromomethyl)-2,3-difluorobenzene (20.70 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 36% B, 36-76% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 18.6 mg. Calculated molecular weight 423.468. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 424.1; Retention Time: 2.33 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 424.1; Retention Time: 1.16 min.

Example 287

8-[(2S,5R)-4-[(2-fluorophenyl)methyl]-2,5-dimethylpiperazin-1-yl]-5-methyl-6-oxo-5,6-dihydro-1,5-naphthyridine-2-carbonitrile

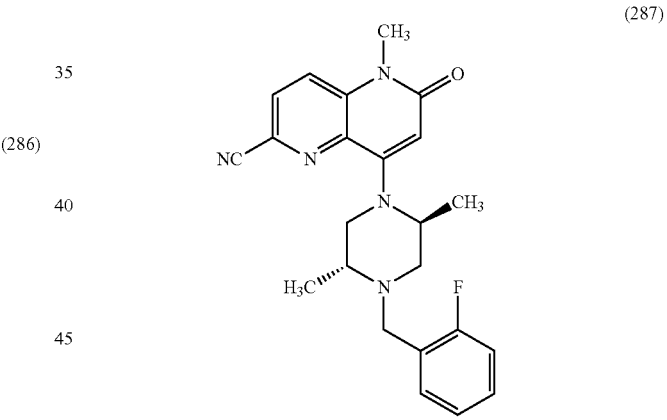

(287)

To a mixture of 1-(bromomethyl)-2-fluorobenzene (18.90 mg, 0.100 mmol) and 5-methyl-6-oxo-8-(piperazin-1-yl)-5,6-dihydro-1,5-naphthyridine-2,7-dicarbonitrile, TFA (34.0 mg, 60% wt, 0.05 mmol) in acetonitrile (0.3 mL) was added Hunig's base (0.052 mL, 0.300 mmol). The mixture was stirred at 55° C. for 2 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 29% B, 29-69% B over 25 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 20.2 mg. Calculated molecular weight 405.477. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 406.14; Retention Time: 1.12 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 406.14; Retention Time: 2.3 min.

Intermediate 188

(3,5-difluorophenyl)(phenyl)methanol

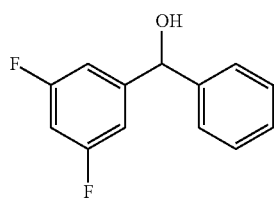

(I-188)

(3,5-difluorophenyl)(phenyl)methanol was prepared according to the general process used to prepare Intermediate 153, (4-chlorophenyl)(3-fluoropyridin-2-yl) methanol. $^1$H NMR (500 MHz, CHLOROFORM-d) δ 7.43-7.31 (m, 5H), 6.98-6.90 (m, 2H), 6.71 (tt, J=8.9, 2.3 Hz, 1H), 5.80 (s, 1H).

Example 288

8-[(2S,5R)-4-[(3,5-difluorophenyl)(phenyl)methyl]-2,5-dimethylpiperazin-1-yl]-5-methyl-6-oxo-5,6-dihydro-1,5-naphthyridine-2-carbonitrile

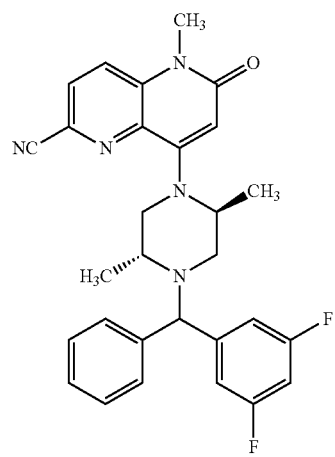

(288)

To the mixture of (3,5-difluorophenyl)(phenyl)methanol (26.4 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. To the above reaction mixture was added extra (cyanomethyl)trimethylphosphonium iodide (194 mg, 0.8 mmol), (3,5-difluorophenyl)(phenyl)methanol (79.2 mg, 0.360 mmol) and Hunig's base (0.21 mL, 1.2 mmol). The reaction mixture was stirred at 110° C. for another 12 hours. The crude reaction mixture was injected directly on 12 g Si-RediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 45% B, 45-95% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 11.9 mg. Calculated molecular weight 499.566. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 500.15, 500.15; Retention Time: 1.94, 1.99 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 500.18; Retention Time: 2.61 min.

Intermediate 189

(3,5-difluorophenyl)(4-fluorophenyl)methanol

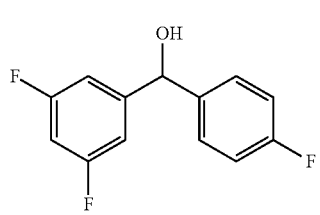

(I-189)

(3,5-difluorophenyl)(4-fluorophenyl)methanol was prepared according to the general process used to prepare Intermediate 153, (4-chlorophenyl)(3-fluoropyridin-2-yl) methanol. $^1$H NMR (500 MHz, CHLOROFORM-d) δ 7.35-

7.27 (m, 2H), 7.10-7.01 (m, 2H), 6.90 (dd, J=8.2, 1.8 Hz, 2H), 6.72 (tt, J=8.8, 2.3 Hz, 1H), 5.74 (s, 1H).

Example 289

8-[(2S,5R)-4-[(3,5-difluorophenyl)(4-fluorophenyl)methyl]-2,5-dimethylpiperazin-1-yl]-5-methyl-6-oxo-5,6-dihydro-1,5-naphthyridine-2-carbonitrile

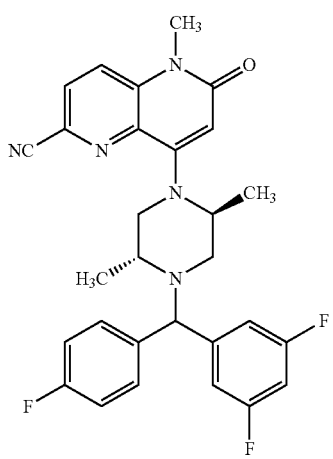

(289)

To the mixture of (3,5-difluorophenyl)(4-fluorophenyl)methanol (28.6 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. Next, additional (cyanomethyl)trimethylphosphonium iodide (194 mg, 0.8 mmol), (3,5-difluorophenyl)(4-fluorophenyl)methanol (85.8 mg, 0.360 mmol) and Hunig's base (0.21 mL, 1.2 mmol) were added. The reaction mixture was stirred at 110° C. for another 12 hours. The crude reaction mixture was injected directly on 12 g Si-RediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 42% B, 42-82% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 11.6 mg. Calculated molecular weight 517.556. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 518.15; Retention Time: 2.61 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 518.12, 518.12; Retention Time: 2.08, 2.11 min.

Example 290

8-[(2S,5R)-4-[(3,5-difluorophenyl)methyl]-2,5-dimethylpiperazin-1-yl]-5-methyl-6-oxo-5,6-dihydro-1,5-naphthyridine-2-carbonitrile

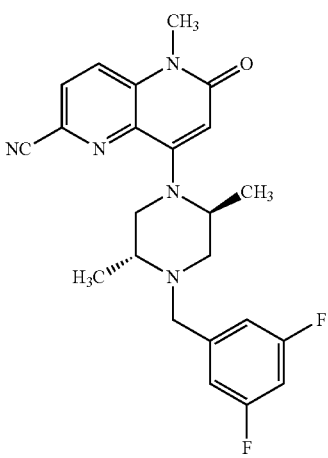

(290)

To a mixture of 1-(bromomethyl)-3,5-difluorobenzene (34.9 mg, 0.160 mmol) and 5-methyl-6-oxo-8-(piperazin-1-yl)-5,6-dihydro-1,5-naphthyridine-2,7-dicarbonitrile, TFA (55 mg, 60% wt, 0.08 mmol) in acetonitrile (0.3 mL) was added Hunig's base (0.084 mL, 0.480 mmol). The mixture was stirred at 55° C. for 1 hour. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 36% B, 36-76% B over 23 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 28.0 mg. Calculated molecular weight 423.468. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 424.1; Retention Time: 2.35 min. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient:

Example 291

8-[(2S,5R)-4-[(3,4-difluorophenyl)methyl]-2,5-dimethylpiperazin-1-yl]-5-methyl-6-oxo-5,6-dihydro-1,5-naphthyridine-2-carbonitrile

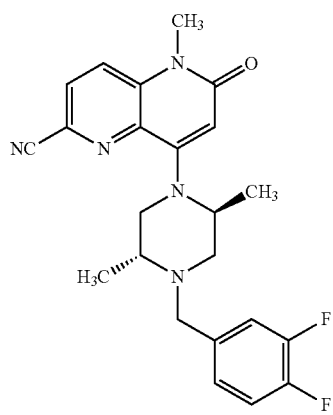

(291)

To a mixture of 4-(bromomethyl)-1,2-difluorobenzene (34.9 mg, 0.160 mmol) and 5-methyl-6-oxo-8-(piperazin-1-yl)-5,6-dihydro-1,5-naphthyridine-2,7-dicarbonitrile, TFA (55 mg, 60% wt, 0.08 mmol) in acetonitrile (0.3 mL) was added Hunig's base (0.084 mL, 0.480 mmol). The mixture was stirred at 55° C. for 1 hour. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 35% B, 35-75% B over 23 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 27.4 mg. Calculated molecular weight 423.468. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 424.1; Retention Time: 2.32 min. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 100.0%; Observed Mass: 424.1; Retention Time: 1.18 min.

Example 292

8-[(2S,5R)-4-[(3-fluorophenyl)methyl]-2,5-dimethylpiperazin-1-yl]-5-methyl-6-oxo-5,6-dihydro-1,5-naphthyridine-2-carbonitrile

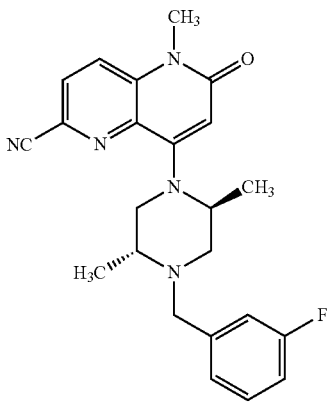

(292)

To a mixture of 1-(bromomethyl)-3-fluorobenzene (38.6 mg, 0.200 mmol) and 5-methyl-6-oxo-8-(piperazin-1-yl)-5,6-dihydro-1,5-naphthyridine-2,7-dicarbonitrile, TFA (68.6 mg, 60% wt, 0.1 mmol) in acetonitrile (0.3 mL) was added Hunig's base (0.105 mL, 0.600 mmol). The mixture was stirred at 55° C. for 1 hour. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 32% B, 32-72% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 37.4 mg. Calculated molecular weight 405.477. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 406.2; Retention Time: 2.27 min. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 406.2; Retention Time: 1.14 min.

Intermediate 190

(3-fluorophenyl)(4-fluorophenyl)methanol

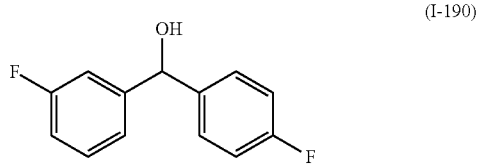 [SMILES: OC(c1ccc(F)cc1)c1cccc(F)c1]

(I-190)

(3-Fluorophenyl)(4-fluorophenyl)methanol was prepared according to the general process used to prepare Intermediate 153, (4-chlorophenyl)(3-fluoropyridin-2-yl) methanol. $^1$H NMR (500 MHz, CHLOROFORM-d) δ 7.38-7.29 (m, 3H), 7.17-7.10 (m, 2H), 7.08-7.02 (m, 2H), 7.01-6.96 (m, 1H), 5.84 (d, J=3.4 Hz, 1H), 2.26 (d, J=3.5 Hz, 1H).

Example 293

8-[(2S,5R)-4-[(3-fluorophenyl)(4-fluorophenyl)methyl]-2,5-dimethylpiperazin-1-yl]-5-methyl-6-oxo-5,6-dihydro-1,5-naphthyridine-2-carbonitrile

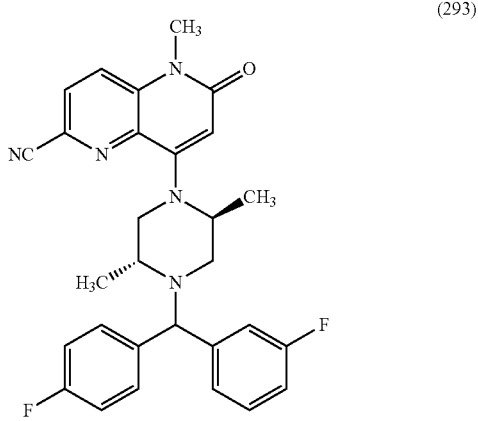 [SMILES: C[C@@H]1CN(c2cc(=O)n(C)c3ccc(C#N)nc23)[C@@H](C)CN1C(c1ccc(F)cc1)c1cccc(F)c1]

(293)

To the mixture of (3-fluorophenyl)(4-fluorophenyl)methanol (26.4 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. Next, additional (cyanomethyl)trimethylphosphonium iodide (194 mg, 0.8 mmol), (3-fluorophenyl)(4-fluorophenyl)methanol (79.2 mg, 0.360 mmol) and Hunig's base (0.21 mL, 1.2 mmol) were added. The reaction mixture was stirred at 110° C. for another 12 hours. The crude reaction mixture was injected directly on 12 g SiRediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 41% B, 41-81% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 20.9 mg. Calculated molecular weight 499.566. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 500.2; Retention Time: 2.57 min. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 95.2%; Observed Mass: 500.2; Retention Time: 1.81 min.

Intermediate 191

(4-fluorophenyl)(4-(trifluoromethyl)phenyl)methanol

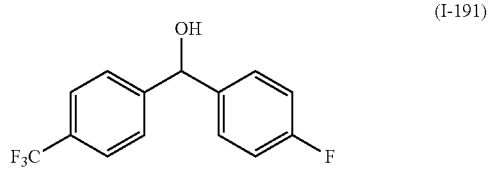 [SMILES: OC(c1ccc(F)cc1)c1ccc(C(F)(F)F)cc1]

(I-191)

(4-fluorophenyl)(4-(trifluoromethyl)phenyl)methanol was prepared according to the general process used to prepare Intermediate 153, (4-chlorophenyl)(3-fluoropyridin-2-yl)methanol. $^1$H NMR (500 MHz, CHLOROFORM-d) δ 7.61 (d, J=8.1 Hz, 2H), 7.50 (d, J=8.5 Hz, 2H), 7.38-7.29 (m, 2H), 7.10-6.98 (m, 2H), 5.88 (s, 1H).

Example 294

8-[(2S,5R)-4-[(4-fluorophenyl)[4-(trifluoromethyl)phenyl]methyl]-2,5-dimethylpiperazin-1-yl]-5-methyl-6-oxo-5,6-dihydro-1,5-naphthyridine-2-carbonitrile

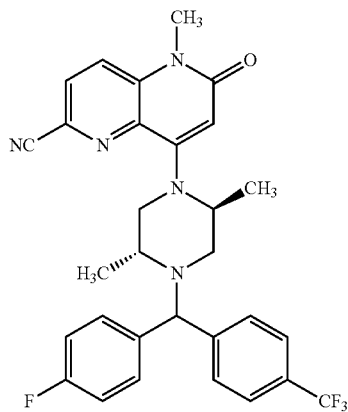

(294)

To the mixture of (4-fluorophenyl)(4-(trifluoromethyl)phenyl)methanol (32.4 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. Next, additional (cyanomethyl)trimethylphosphonium iodide (194 mg, 0.8 mmol), (4-fluorophenyl)(4-(trifluoromethyl)phenyl)methanol (97.2 mg, 0.360 mmol) and Hunig's base (0.21 mL, 1.2 mmol) were added. The reaction mixture was stirred at 110° C. for another 12 hours. The crude reaction mixture was injected directly on 12 g Si-RediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 46% B, 46-86% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 16.8 mg. Calculated molecular weight 549.574. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 550.2; Retention Time: 2.71 min. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 100.0%; Observed Mass: 550.2; Retention Time: 2.10 min.

Intermediate 192

(4-fluorophenyl)(p-tolyl)methanol

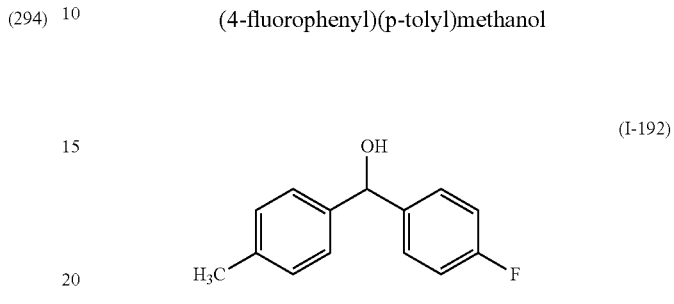

(I-192)

(4-Fluorophenyl)p-tolyl)methanol was prepare according to the general process used to prepare Intermediate 153, (4-chlorophenyl)(3-fluoropyridin-2-yl)methanol. $^1$H NMR (500 MHz, CHLOROFORM-d) δ 7.40-7.32 (m, 2H), 7.26 (d, J=8.1 Hz, 2H), 7.17 (d, J=7.8 Hz, 2H), 7.08-6.97 (m, 2H), 5.83 (d, J=1.8 Hz, 1H), 2.16 (d, J=3.2 Hz, 1H).

Example 295

8-[(2S,5R)-4-[(4-fluorophenyl)(4-methylphenyl)methyl]-2,5-dimethylpiperazin-1-yl]-5-methyl-6-oxo-5,6-dihydro-1,5-naphthyridine-2-carbonitrile

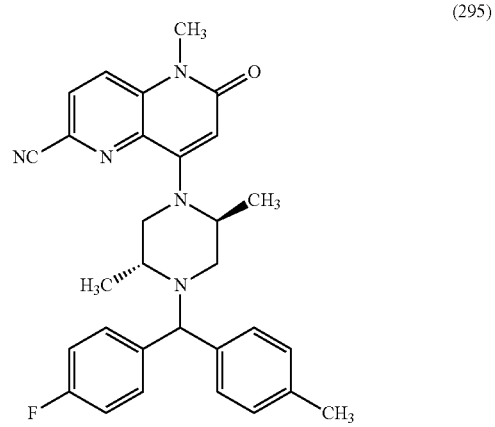 [SMILES: Cc1ccc(C(c2ccc(F)cc2)N2C[C@H](C)N(c3cc(=O)n(C)c4ccc(C#N)nc34)C[C@H]2C)cc1]

(295)

To the mixture of (4-fluorophenyl)(p-tolyl)methanol (26.0 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. To the above reaction mixture was added extra (cyanomethyl)trimethylphosphonium iodide (48.6 mg, 0.2 mmol), (4-fluorophenyl)(p-tolyl)methanol (13.0 mg, 0.060 mmol) and Hunig's base (0.052 mL, 0.3 mmol). The reaction mixture was stirred at 110° C. for another 12 hours. The crude material was purified via preparative LC/MS with the following conditions: Column: XBridge C18, 200 mm×19 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0 minute hold at 20% B, 20-60% B over 25 minutes, then a 5 minute hold at 100% B; Flow Rate: 20 mL/min; Column Temperature: 25° C. Fraction collection was triggered by UV signals. Fractions containing the product were combined and dried via centrifugal evaporation. The yield of the diastereomeric product as TFA salt was 47.1 mg. Calculated molecular weight 495.602. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 94.3%; Observed Mass: 496.2; Retention Time: 2.55 min. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 95.6%; Observed Mass: 496.2; Retention Time: 1.75 min.

Example 296

8-[(2S,5R)-4-[(3-fluorophenyl)(phenyl)methyl]-2,5-dimethylpiperazin-1-yl]-5-methyl-6-oxo-5,6-dihydro-1,5-naphthyridine-2-carbonitrile

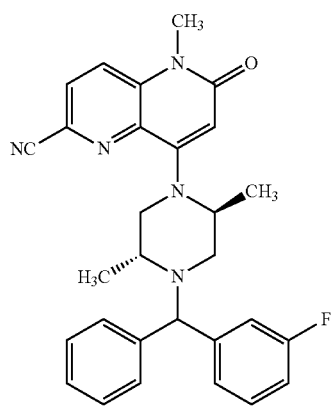

(296)

To the mixture of (3-fluorophenyl)(phenyl)methanol (24.27 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. To the above reaction mixture was added extra (cyanomethyl)trimethylphosphonium iodide (48.6 mg, 0.2 mmol), (3-fluorophenyl)(phenyl)methanol (12.1 mg, 0.060 mmol) and Hunig's base (0.052 mL, 0.3 mmol). The reaction mixture was stirred at 110° C. for another 12 hours. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 42% B, 42-82% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 15.9 mg. Calculated molecular weight 481.575. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 482.2; Retention Time: 2.57 min. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 100.0%; Observed Mass: 482.2; Retention Time: 1.68 min.

Example 297

8-[(2S,5R)-4-[(4-fluorophenyl)methyl]-2,5-dimethylpiperazin-1-yl]-5-methyl-6-oxo-5,6-dihydro-1,5-naphthyridine-2-carbonitrile

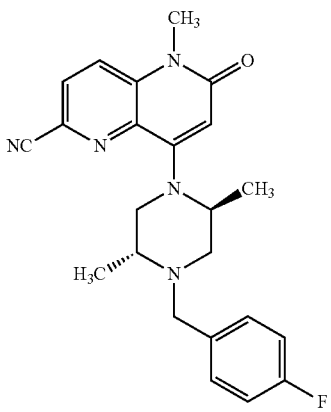

(297)

To a mixture of 1-(bromomethyl)-4-fluorobenzene (30.2 mg, 0.160 mmol) and 5-methyl-6-oxo-8-(piperazin-1-yl)-5,6-dihydro-1,5-naphthyridine-2,7-dicarbonitrile, TFA (55 mg, 60% wt, 0.08 mmol) in acetonitrile (0.3 mL) was added Hunig's base (0.084 mL, 0.480 mmol). The mixture was stirred at 55° C. for 1 hour. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 35%

B, 35-75% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 28.4 mg. Calculated molecular weight 405.477. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 406.1; Retention Time: 2.25 min. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 100.0%; Observed Mass: 406.2; Retention Time: 1.13 min.

Example 298

8-((2S,5R)-4-((4-chlorophenyl)(4-cyanophenyl)methyl)-2,5-dimethylpiperazin-1-yl)-5-methyl-6-oxo-5,6-dihydro-1,5-naphthyridine-2-carbonitrile

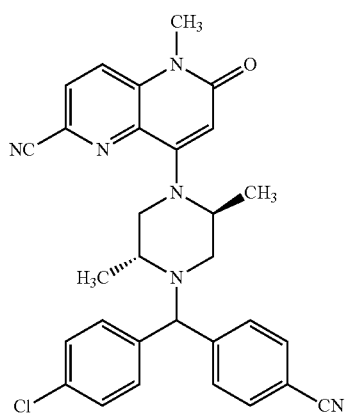

(298)

To the mixture of 4-((4-chlorophenyl)(hydroxy)methyl)benzonitrile (27.3 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. Next, additional (cyanomethyl)trimethylphosphonium iodide (97.2 mg, 0.4 mmol), 4-((4-chlorophenyl)(hydroxy)methyl)benzonitrile (54.6 mg, 0.240 mmol) and Hunig's base (0.105 mL, 0.6 mmol) were added. The reaction mixture was stirred at 110° C. for another 12 hours. The crude reaction mixture was injected directly on 12 g Si-RediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 40% B, 40-80% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 11.1 mg. Calculated molecular weight 506.585. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 507.2; Retention Time: 2.40 min. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 100.0%; Observed Mass: 507.2; Retention Time: 1.86 min.

Example 299

8-[(2S,5R)-4-[(4-chlorophenyl)(4-methylphenyl)methyl]-2,5-dimethylpiperazin-1-yl]-5-methyl-6-oxo-5,6-dihydro-1,5-naphthyridine-2-carbonitrile

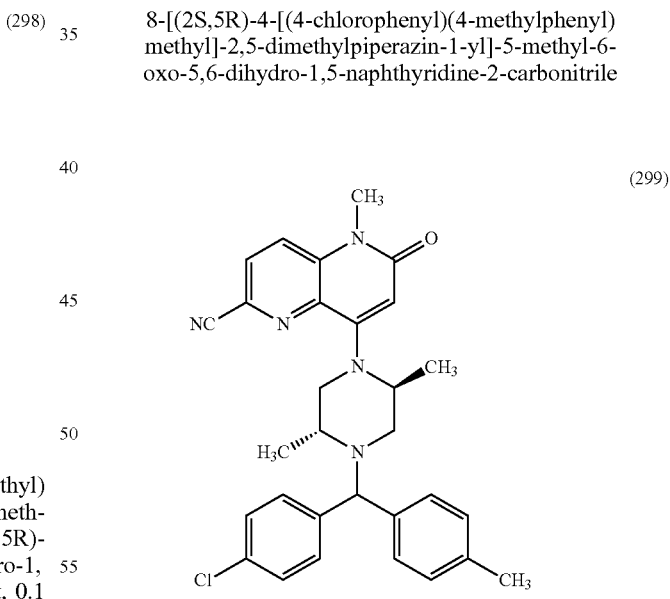

(299)

To the mixture of (4-chlorophenyl)(p-tolyl)methanol (28.5 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. To the above reaction mixture was added extra (cyanomethyl)trimethylphosphonium iodide (48.6 mg, 0.2 mmol), (4-chlorophenyl)(p-tolyl)methanol (28.5 mg, 0.120 mmol) and Hunig's base (0.052 mL, 0.3 mmol). The reaction mixture was stirred at 110° C. for another 12 hours. The crude reaction mixture was injected directly on 12 g Si-RediSep Rf for flash chromatography by 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 51% B, 51-91% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The yield of the diastereomeric product was 23.6 mg. Calculated molecular weight 512.05. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 512.2; Retention Time: 2.83 min. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 100.0%; Observed Mass: 512.2; Retention Time: 1.86 min.

Intermediate 193

(4-chlorophenyl)(4-fluorophenyl)m ethanol

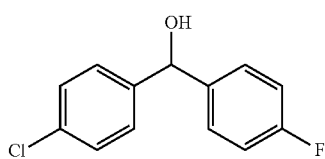

(I-193)

(4-Chlorophenyl)(4-fluorophenyl)methanol was prepared according to the general process used to prepare Intermediate 153, (4-chlorophenyl)(3-fluoropyridin-2-yl)methanol. $^1$H NMR (400 MHz, CHLOROFORM-d) δ 7.40-7.29 (m, 6H), 7.09-6.98 (m, 2H), 5.82 (s, 1H), 2.23 (br d, J=2.5 Hz, 1H).

Example 300

8-[(2S,5R)-4-[(4-chlorophenyl)(4-fluorophenyl)methyl]-2,5-dimethylpiperazin-1-yl]-5-methyl-6-oxo-5,6-dihydro-1,5-naphthyridine-2-carbonitrile

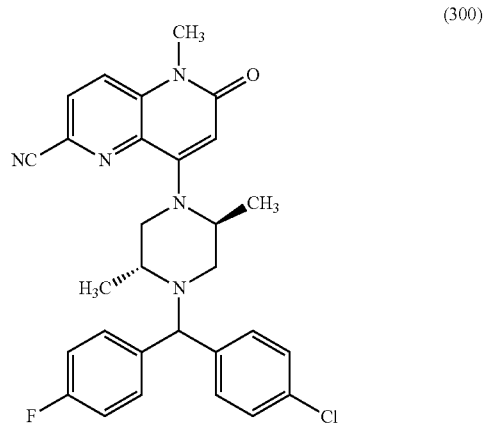 [SMILES: C[C@@H]1CN(c2cc(=O)n(C)c3ccc(C#N)nc23)[C@@H](C)CN1C(c1ccc(F)cc1)c1ccc(Cl)cc1]

(300)

To the mixture of (4-chlorophenyl)(4-fluorophenyl)methanol (28.4 mg, 0.120 mmol), (cyanomethyl)trimethylphosphonium iodide (48.6 mg, 0.2 mmol) and 8-((2S,5R)-2,5-dimethylpiperazin-1-yl)-5-methyl-6-oxo-5,6-dihydro-1,5-naphthyridine-2-carbonitrile, TFA (68.6 mg, 60% wt, 0.1 mmol) in acetonitrile (0.3 mL) was added Hunig's base (0.105 mL, 0.6 mmol). The reaction mixture was stirred at 110° C. for 2 hours. Next, additional (cyanomethyl)trimethylphosphonium iodide (48.6 mg, 0.2 mmol), (4-chlorophenyl)(4-fluorophenyl)methanol (28.4 mg, 0.120 mmol) and Hunig's base (0.052 mL, 0.3 mmol) were added. The reaction mixture was stirred at 110° C. for another 12 hours. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 45% B, 45-85% B over 27 minutes, then a 5 minute hold at 100% B; Flow Rate: 20 mL/min; Column Temperature: 25° C. Fraction collection was triggered by UV signals. Fractions containing the product were combined and dried via centrifugal evaporation. The yield of the diastereomeric product was 14.1 mg. Calculated molecular weight 516.02. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0%; Observed Mass: 516.2; Retention Time: 2.72 min. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: Purity: 100.0%; Observed Mass: 516.2; Retention Time: 1.90 min.

Example 301

8-[(2S,5R)-4-[bis(4-methylphenyl)methyl]-2,5-dimethylpiperazin-1-yl]-5-methyl-6-oxo-5,6-dihydro-1,5-naphthyridine-2-carbonitrile

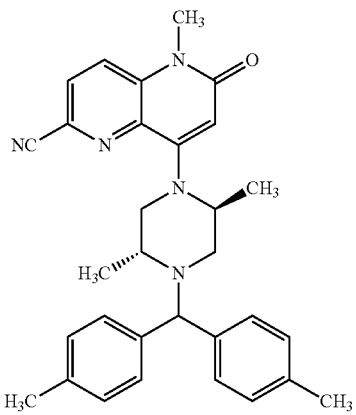

(301)

To the mixture of (cyanomethyl)trimethylphosphonium iodide (46.2 mg, 0.19 mmol), di-p-tolylmethanol (23.46 mg, 0.108 mmol), and 8-((2S,5R)-2,5-dimethylpiperazin-1-yl)-5-methyl-6-oxo-5,6-dihydro-1,5-naphthyridine-2-carbonitrile, TFA (72.4 mg, 54% wt, 0.095 mmol) in acetonitrile (0.3 mL) was added Hunig's base (0.10 mL, 0.57 mmol). The reaction mixture was stirred at 110° C. for 2 hours. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 55% B, 55-95% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. The yield of the product was 23.4 mg. Calculated molecular weight 491.639. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 492.21; Retention Time: 2.77 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 492.2; Retention Time: 1.71 min. $^1$H NMR (400 MHz, DMSO-d$_6$) δ ppm 8.15 (d, J=8.5 Hz, 1H), 8.04-8.09 (m, 1H), 7.81 (s, 4H), 7.57-7.63 (m, 2H), 7.12-7.19 (m, 2H), 6.00 (s, 1H), 4.82 (s, 1H), 4.52-4.63 (m, 1H), 3.64-3.76 (m, 1H), 3.51-3.58 (m, 4H), 2.99-3.10 (m, 1H), 2.86 (br d, J=8.5 Hz, 1H), 2.28-2.37 (m, 1H), 1.31 (d, J=6.5 Hz, 3H), 1.07 (d, J=6.5 Hz, 3H). $^{13}$C NMR (100.66 MHz, DMSO-d$_6$) δ ppm 162.4, 160.9, 159.9, 153.5, 148.0, 138.7, 138.6, 135.0, 132.6, 129.3 (d, J=8.0 Hz), 128.8 (d, J=10.0 Hz), 124.0, 122.8, 118.6, 117.5, 115.6, 115.4, 109.8, 104.8, 69.0, 51.8, 49.4, 48.9, 47.2, 28.6, 13.4, 7.4.

Example 302

8-((2S,5R)-4-((4-chlorophenyl)(4-fluorophenyl)methyl)-2,5-dimethylpiperazin-1-yl)-5-methyl-6-oxo-5,6-dihydro-1,5-naphthyridine-2-carbonitrile

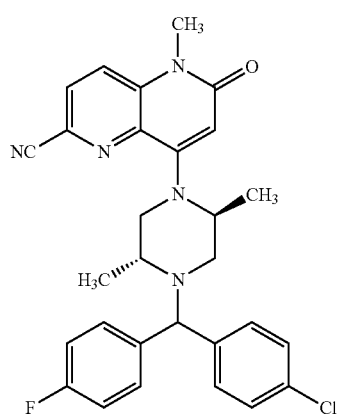

(302)

To the mixture of 1-(bromo(4-chlorophenyl)methyl)-4-fluorobenzene (359 mg, 1.2 mmol) and 8-((2S,5R)-2,5-dimethylpiperazin-1-yl)-5-methyl-6-oxo-5,6-dihydro-1,5-naphthyridine-2-carbonitrile, TFA (288 mg, 0.7 mmol) in acetonitrile (4 mL) was added Hunig's base (0.734 mL, 4.20 mmol). The reaction was stirred at 55° C. for 16 hours. The crude reaction mixture was partitioned between DCM/NaHCO$_3$ (aq). The residue from the concentrated organic layer was charged on to 40 g-Si-RediSepRf for flash chromatography and eluted with 20-100% ethyl acetate in hexanes. Fractions containing the diastereomeric product mixture were combined and dried by vacuum. The resultant material was further purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 0 minute hold at 53% B, 53-93% B over 20 minutes, then a 4 minute hold at 100% B; Flow Rate: 20 mL/min; Column Temperature: 25° C. Fraction collection was triggered by MS and UV signals. Fractions containing the diastereomeric product were combined and dried via centrifugal evaporation.

The dried product was separated into two diastereomers by using SFC-chiral chromatography with the following conditions: Column: Chiral AD, 30×250 mm. 5 micron particles; Mobile Phase: 70% CO$_2$/30% IPA w/0.1% DEA; Flow Rate: 100 mL/min; Column Temperature: 25° C.; Detector Wavelength: 220 nm. The title compound was collected as the 1$^{st}$ eluent peak, >95% de.

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 516.18; Retention Time: 2.59 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 516.22; Retention Time: 2.07 min.

Example 303

8-((2S,5R)-4-((4-chlorophenyl)(4-fluorophenyl)methyl)-2,5-dimethylpiperazin-1-yl)-5-methyl-6-oxo-5,6-dihydro-1,5-naphthyridine-2-carbonitrile

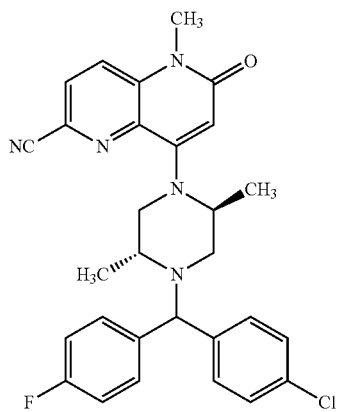

(303)

Example 303 was prepared and purified according to the general procedures for Example 302. Example 303 was collected as the 2' eluent peak, >95% de.

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.5%; Observed Mass: 516.22; Retention Time: 2.6 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.0%; Observed Mass: 515.91; Retention Time: 2.07 min.

Example 304

8-((2S,5R)-4-((2-fluorophenyl)(4-fluorophenyl)methyl)-2,5-dimethylpiperazin-1-yl)-5-methyl-6-oxo-5,6-dihydro-1,5-naphthyridine-2-carbonitrile

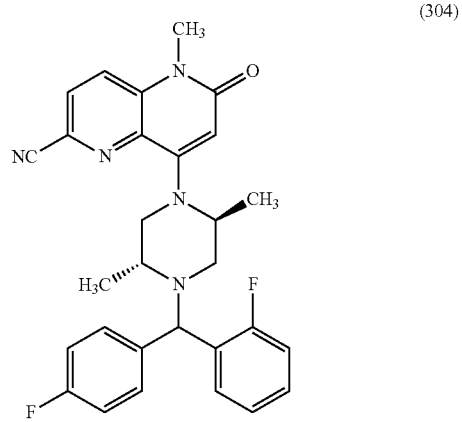 [SMILES: C[C@@H]1CN(c2cc(=O)n(C)c3ccc(C#N)nc23)[C@@H](C)CN1C(c1ccc(F)cc1)c1ccccc1F]

(304)

To the mixture of 8-((2S,5R)-2,5-dimethylpiperazin-1-yl)-5-methyl-6-oxo-5,6-dihydro-1,5-naphthyridine-2-carbonitrile (97 mg, 0.3 mmol), (cyanomethyl) trimethylphosphonium iodide (182 mg, 0.750 mmol) and (2-fluorophenyl)(4-fluorophenyl)methanol (92 mg, 0.420 mmol) in acetonitrile (909 μL)) was added Hunig's base (236 μL, 1.350 mmol). The reaction mixture was stirred on microwave synthesizer at 110° C. for 2 hours. To the reaction mixture was added extra (cyanomethyl) trimethylphosphonium iodide (182 mg, 0.750 mmol), (2-fluorophenyl)(4-fluorophenyl)methanol (92 mg, 0.420 mmol) and Hunig's base (0.184 mL, 1.050 mmol). The reaction was stirred at 110° C. for another 2 hours. The crude reaction mixture was partitioned in to DCM/NaHCO₃ (aq). The residue from the concentrated organic layer was charged on 24 g-Si-RediSep Rf for flash chromatography by 20-100% ethyl acetate in hexanes. Product containing fractions were combined and dried by vacuum. The yield of the diastereomeric product was 110 mg. The diastereomeric material was resolved into two diastereomers by using SFC-chiral chromatography with the following conditions: Column: Chiralpak IC, 21×250 mm, 5 micron particles; Mobile Phase: 35% IPA/65% CO2; Flow Conditions: 45 mL/min, 150 Bar; Column Temperature: 40° C.; Detector Wavelength: 225 nm. The title compound was collected as the 1$^{st}$ eluent peak, >99.5% de. The yield of the homochiral product was 46 mg.

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 500.19; Retention Time: 2.43 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 95.2%; Observed Mass: 500.14; Retention Time: 1.88 min.

Example 305

8-((2S,5R)-4-((2-fluorophenyl)(4-fluorophenyl)methyl)-2,5-dimethylpiperazin-1-yl)-5-methyl-6-oxo-5,6-dihydro-1,5-naphthyridine-2-carbonitrile

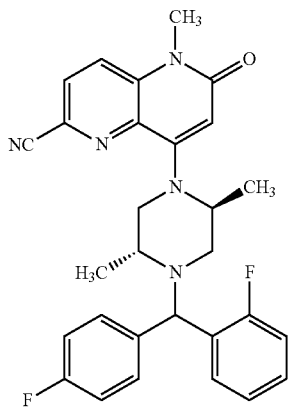

(305)

Example 305 was prepared and purified according to the general procedures for preparing Example 304. Example 305 was collected as the 2d eluent peak, 97.4% de. The yield of the homochiral product was 39 mg.

Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 500.2; Retention Time: 2.41 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 95.2%; Observed Mass: 500.17; Retention Time: 1.92 min.

Example 306

8-((2S,5R)-4-((4-cyanophenyl)(4-fluorophenyl)methyl)-2,5-dimethylpiperazin-1-yl)-5-methyl-6-oxo-5,6-dihydro-1,5-naphthyridine-2-carbonitrile

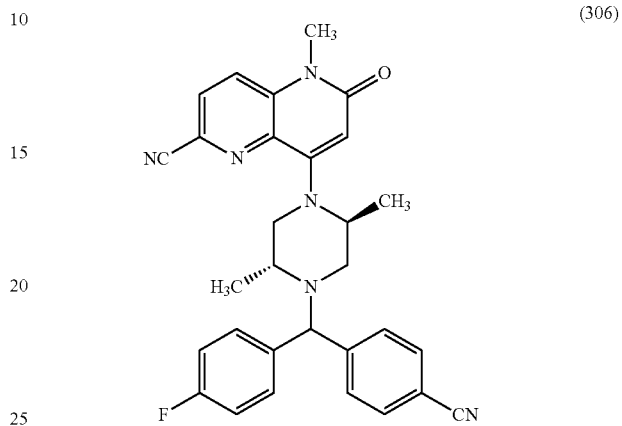

(306)

To a solution of 4-((4-fluorophenyl)(hydroxy)methyl)benzonitrile (4.91 g, 21.18 mmol) in DCM (52.4 ml) and DMF (0.524 ml) at −20° C. was added thionyl bromide (2.171 ml, 27.5 mmol). The mixture was stirred at room temperature for 16 hours. The reaction mixture was extracted with pH 7.4 phosphate buffer/EtOAc twice and then extracted with brine/EtOAc; the organic layer was dried with $MgSO_4$ then concentrated by vacuum to obtain bromobenzhydral, 4-(bromo(4-fluorophenyl)methyl)benzonitrile (6.3 g, 21.28 mmol).

To a mixture of 8-((2S,5R)-2,5-dimethylpiperazin-1-yl)-5-methyl-6-oxo-5,6-dihydro-1,5-naphthyridine-2-carbonitrile (6.27 g, 21.1 mmol) and 4-(bromo(4-fluorophenyl)methyl)benzonitrile (6.25 g, 21.10 mmol) in acetonitrile (140 ml) was added Hunig's base (18.43 ml, 106 mmol). The mixture was stirred at 55° C. for 24 hours. The crude reaction mixture was partitioned between DCM and $NaHCO_3$ (aq). The residue from concentrated organic layer was charged on 220 g-Si-RediSep Rf for flash chromatography by 20-100% ethyl acetate in hexanes. Product containing fractions were combined and dried by vacuum. The yield of the diastereomeric product was 7.8 gram. The diastereomeric material was resolved into two diastereomers by using SFC-chiral chromatography with the following conditions: Column: Cellulose-4 (5×25 cm, 5 µm, #548090); Mobile Phase: $CO_2$/MeOH:MeCN (1:1) w 0.1% $NH_4OH$ (60/40); Flow Conditions: 340 mL/min, 100 Bar; Column Temperature: 35° C.; Detector Wavelength: 220 nm. The title compound was collected as the $2^{nd}$ eluent peak, >99.5% de. The yield of the homochiral product was 3.4 gram.

Analytical LC/MS was used to determine the final purity. Injection 1 conditions: Column: Waters Aquity BEH C18 2.1×50 mm, 1.7 µm particles; Mobile Phase A: 100% Water/0.05% TFA; Mobile Phase B: 100% Acetonitrile/0.05% TFA; Temperature: 50° C.; Gradient: 2% B to 98% B over 1.5 min, then a 1.50 min hold at 98% B; Flow: 0.8 mL/min; Detection: MS and UV (220 nm). Injection 1 results: Purity: 100.0%; Observed Mass: 507.30; Retention Time: 1.75 min.

Example 307

8-((2S,5R)-4-((4-cyanophenyl)(4-fluorophenyl)methyl)-2,5-dimethylpiperazin-1-yl)-5-methyl-6-oxo-5,6-dihydro-1,5-naphthyridine-2-carbonitrile

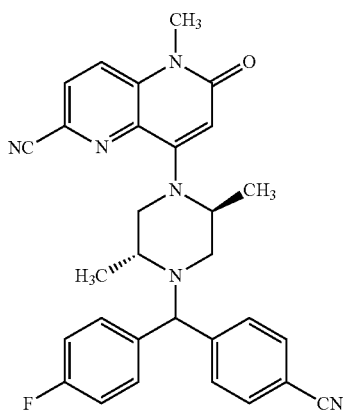

(307)

Example 307 was prepared and purified according to the general procedures for preparing Example 306. Example 307 was collected as the 1$^{st}$ eluent peak, >99.5% de. The yield of the homochiral product was 3.3 gram.

Analytical LC/MS was used to determine the final purity. Injection 1 conditions: Column: Waters Aquity BEH C18 2.1×50 mm, 1.7 μm particles; Mobile Phase A: 100% water/0.05% TFA; Mobile Phase B: 100% acetonitrile/0.05% TFA; Temperature: 50° C.; Gradient: 2% B to 98% B over 1.5 min, then a 1.50 min hold at 98% B; Flow: 0.8 mL/min; Detection: MS and UV (220 nm). Injection 1 results: Purity: 100.0%; Observed Mass: 507.30; Retention Time: 1.76 min.

Examples 308 and 309

8-((2S,5R)-4-(1-((4-fluorophenyl)ethyl)-2,5-dimethylpiperazin-1-yl)-5-methyl-6-oxo-5,6-dihydro-1,5-naphthyridine-2-carbonitrile

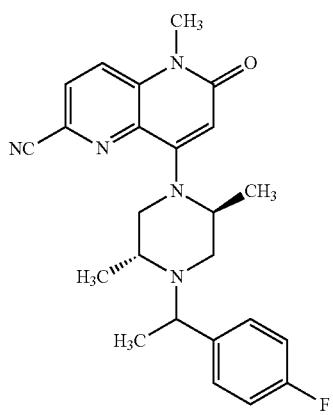

(308-309)

To the mixture of 1-(1-bromoethyl)-4-fluorobenzene (579 mg, 2.85 mmol) and 8-((2S,5R)-2,5-dimethylpiperazin-1-yl)-5-methyl-6-oxo-5,6-dihydro-1,5-naphthyridine-2-carbonitrile (485 mg, 1.5 mmol) in acetonitrile (4 mL) was added Hunig's base (1.048 mL, 6.00 mmol). The reaction mixture was stirred at 55° C. for 16 hours. The crude reaction mixture was partitioned into DCM/NaHCO$_3$ (aq). The residue from the concentrated organic layer was charged on 40 g-Si-RediSep Rf for flash chromatography using 20-100% ethyl acetate in hexanes. Product containing fractions were combined and dried by vacuum. The yield of the diastereomeric product was 480 mg. The diastereomeric product was resolved into two diastereomers by using SFC-chiral chromatography with the following conditions: Column: Chiralpak IF, 30×250 mm. 5 micron particles; Mobile Phase: 20% MeOH/80% CO$_2$ w/0.1% NH$_4$OH; Flow Rate: 85 mL/min, 150 Bar; Column Temperature: 40° C.; Detector wavelength: 226 nm. The yield of the 1$^{st}$ eluting diastereomer (100% de) was 142 mg. The yield of the 2$^{nd}$ eluting diastereomer (97% de) was 161 mg.

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 420.2; Retention Time: 2.06 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 420.2; Retention Time: 1.18 min.

Example 310

8-((2S,5R)-4-((4-cyanophenyl)(p-tolyl)methyl)-2,5-dimethylpiperazin-1-yl)-5-methyl-6-oxo-5,6-dihydro-1,5-naphthyridine-2-carbonitrile, TFA Salt

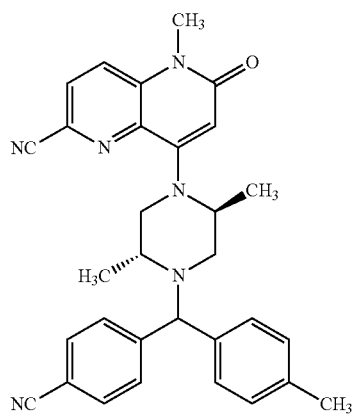

(310)

To the mixture of 8-((2S,5R)-2,5-dimethylpiperazin-1-yl)-5-methyl-6-oxo-5,6-dihydro-1,5-naphthyridine-2-carbonitrile (285 mg, 0.958 mmol), (cyanomethyl) trimethylphosphonium iodide (466 mg, 1.916 mmol), and 4-(hydroxy(p-tolyl)methyl) benzonitrile (262 mg, 1.150 mmol) in acetonitrile (4 mL)) was added Hunig's base (0.837 mL, 4.79 mmol). The reaction mixture was stirred on a microwave synthesizer at 110° C. for 2 hours. To the above reaction mixture was added extra (cyanomethyl) trimethylphosphonium iodide (466 mg, 1.916 mmol), 4-(hydroxy(p-tolyl)methyl) benzonitrile (262 mg, 1.150 mmol), and Hunig's base (0.502 mL, 2.87 mmol). The reaction mixture was stirred at 110° C. for another 2 hours. The crude reaction mixture was partitioned into aqueous DCM/NaHCO$_3$ (aq.) The residue from concentrated organic layer was charged on 40 g-Si-RediSepRf for flash chromatography with 20-100% ethyl acetate in hexanes. Product containing fractions were combined and dried by vacuum. The yield of the diastereomeric product was 180 mg.

The diastereomeric product was resolved via preparative LC/MS with the following conditions: Column: XBridge C18, 200 mm×19 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0 minute hold at 19% B, 19-59% B over 25 minutes, then a 5 minute hold at 100% B; Flow Rate: 20 mL/min; Column Temperature: 25° C. Fraction collection was triggered by MS and UV signals. The diastereomers were collected separately. Fractions containing the product were combined and dried via centrifugal evaporation. The yield of the first eluting diastereomer (Example 310) was 73 mg. The yield of the second eluting diastereomer) was 86 mg. Yields are calculated based on the product as TFA salt.

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 503.21; Retention Time: 1.82 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 503.18; Retention Time: 2.49 min.

Examples 312 and 313

8-((3R)-4-((4-fluorophenyl)(pyrimidin-4-yl)methyl)-3-methylpiperazin-1-yl)-5-methyl-6-oxo-5,6-dihydro-1,5-naphthyridine-2-carbonitrile, TFA Salt

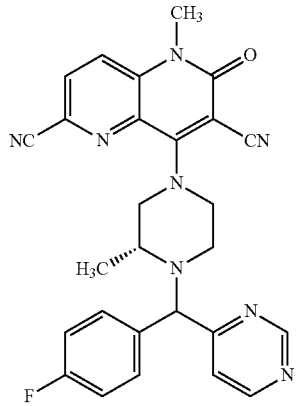

(312-313)

At −20° C., to a solution of (4-fluorophenyl)(pyrimidin-4-yl)methanol (250 mg, 1.224 mmol) in DCM (3 mL) and DMF (0.030 mL) was added thionyl bromide (0.125 mL, 1.592 mmol) dropwise. The reaction mixture was warmed to room temperature and stirred for 2 hours. It was then filtered to yield as 4-(bromo(4-fluorophenyl)methyl) pyrimidine (232 mg, 0.869 mmol, 70.9% yield) an off-white solid. LC/MS: retention time 1.97 minutes, 267.0 (MH$^+$). $^1$H NMR (400 MHz, ACETONITRILE-d3) δ 9.46 (s, 1H), 8.99 (dd, J=6.4, 1.0 Hz, 1H), 8.24 (dd, J=6.4, 1.0 Hz, 1H), 7.73-7.63 (m, 2H), 7.26-7.15 (m, 2H), 6.55 (s, 1H).

To a solution of (R)-5-methyl-8-(3-methylpiperazin-1-yl)-6-oxo-5,6-dihydro-1,5-naphthyridine-2,7-dicarbonitrile (40 mg, 0.130 mmol) in acetonitrile (1.5 ml), N-ethyl-N-isopropylpropan-2-amine (0.113 ml, 0.649 mmol) and 4-(bromo(4-fluorophenyl)methyl) pyrimidine (52.0 mg, 0.195 mmol) were added. The reaction mixture was heated at 65° C. overnight. LC/MS showed formation of the products. The crude material was then purified via preparative LC/MS with the following conditions: Column: XBridge C18, 200 mm×19 mm, 5-μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 27% B, 27-57% B over 20 minutes, then a 4 minute hold at 100% B; Flow Rate: 20 mL/min; Column Temperature: 25° C. Fraction collection was triggered by MS and UV signals. Fractions containing the products were combined and dried via centrifugal evaporation. Two diastereomers were obtained as 8-((3R)-4-((4-fluorophenyl) (pyrimidin-4-yl)methyl)-3-methylpiperazin-1-yl)-5-methyl-6-oxo-5,6-dihydro-1,5-naphthyridine-2,7-dicarbonitrile.

QC Method 1: Analytical LC/MS was used to determine the final purity: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

QC Method 2: Analytical LC/MS was used to determine the final purity. Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

The compounds in Table 1 were prepared from (R)-5-methyl-8-(3-methylpiperazin-1-yl)-6-oxo-5,6-dihydro-1,5-naphthyridine-2,7-dicarbonitrile using similar reaction conditions.

TABLE 1

| Ex. No. | Structure | QC Method | Obs. MS Ion | Stereo Chem | RT (min) |
|---|---|---|---|---|---|
| 312 | 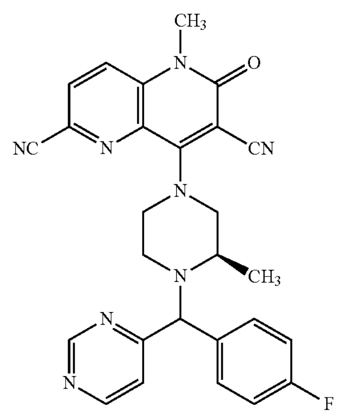 [SMILES: C[C@@H]1CN(c2c(C#N)c(=O)n(C)c3ccc(C#N)nc23)CCN1C(c1ccc(F)cc1)c1ccncn1] | 1.0 | 495.3 | H | 1.66 |
| 313 | 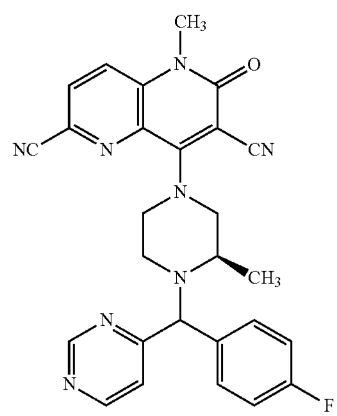 [SMILES: C[C@@H]1CN(c2c(C#N)c(=O)n(C)c3ccc(C#N)nc23)CCN1C(c1ccc(F)cc1)c1ccncn1] | 1.0 | 495.1 | H | 1.72 |
| 314 | 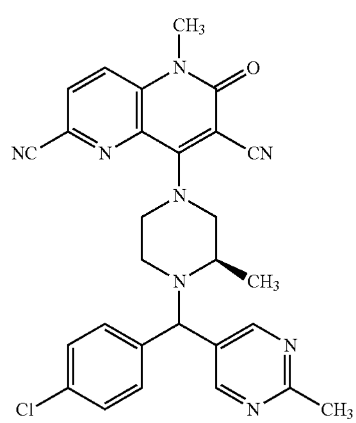 [SMILES: Cc1ncc(C(c2ccc(Cl)cc2)N2CCN(c3c(C#N)c(=O)n(C)c4ccc(C#N)nc34)C[C@H]2C)cn1] | 1.0 | 524.9 | H | 1.97 |

TABLE 1-continued

| Ex. No. | Structure | QC Method | Obs. MS Ion | Stereo Chem | RT (min) |
|---|---|---|---|---|---|
| 315 | 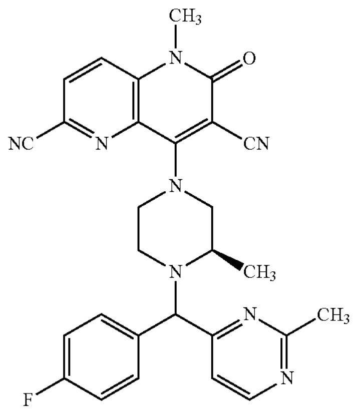 [SMILES: Cc1nccc(C(c2ccc(F)cc2)N2CCN(c3c(C#N)c(=O)n(C)c4ccc(C#N)nc34)C[C@H]2C)n1] | 1.0 | 509.2 | H | 1.72 |
| 316 | 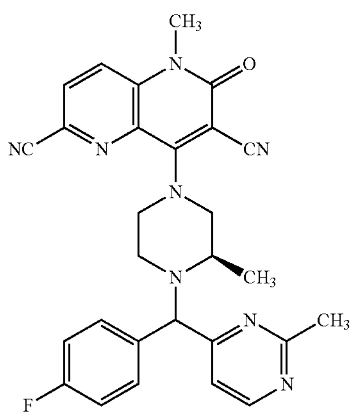 [SMILES: Cc1nccc(C(c2ccc(F)cc2)N2CCN(c3c(C#N)c(=O)n(C)c4ccc(C#N)nc34)C[C@H]2C)n1] | 1.0 | 509.1 | H | 1.68 |
| 317 | 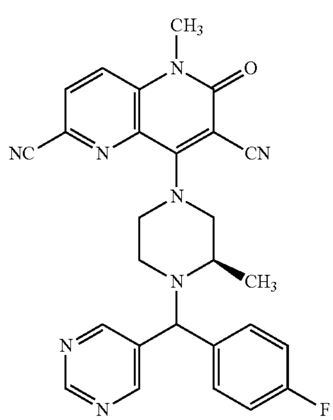 [SMILES: C[C@@H]1CN(c2c(C#N)c(=O)n(C)c3ccc(C#N)nc23)CCN1C(c1ccc(F)cc1)c1cncnc1] | 1.0 | 495.1 | H | 1.77 |

TABLE 1-continued

| Ex. No. | Structure | QC Method | Obs. MS Ion | Stereo Chem | RT (min) |
|---|---|---|---|---|---|
| 318 | 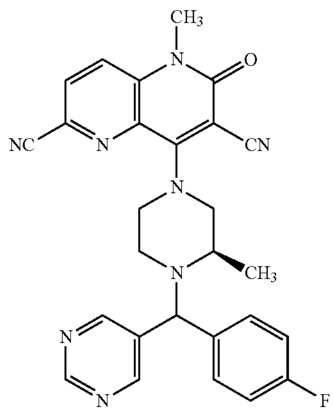 [SMILES: C[C@@H]1CN(c2c(C#N)c(=O)n(C)c3ccc(C#N)nc23)CCN1C(c1ccc(F)cc1)c1cncnc1] | 2.0 | 495.0 | H | 1.62 |
| 319 | 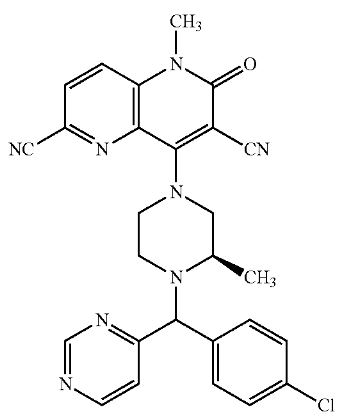 [SMILES: C[C@@H]1CN(c2c(C#N)c(=O)n(C)c3ccc(C#N)nc23)CCN1C(c1ccc(Cl)cc1)c1ccncn1] | 2.0 | 511.2 | H | 1.34 |
| 320 | 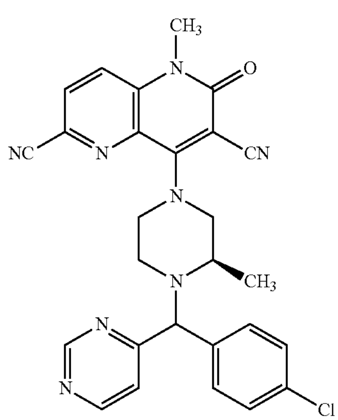 [SMILES: C[C@@H]1CN(c2c(C#N)c(=O)n(C)c3ccc(C#N)nc23)CCN1C(c1ccc(Cl)cc1)c1ccncn1] | 1.0 | 511.3 | H | 1.38 |

TABLE 1-continued

| Ex. No. | Structure | QC Method | Obs. MS Ion | Stereo Chem | RT (min) |
|---|---|---|---|---|---|
| 321 | 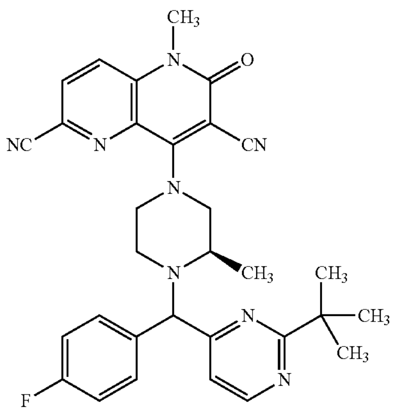 [SMILES: C[C@@H]1CN(c2c(C#N)c(=O)n(C)c3ccc(C#N)nc23)CCN1C(c1ccc(F)cc1)c1ccnc(C(C)(C)C)n1] | 1.0 | 551.4 | D | 2.38 |

TABLE 2

| Ex. No. | Structure | QC Method | Obs. MSI on | Stereo Chem | RT |
|---|---|---|---|---|---|
| 322 | 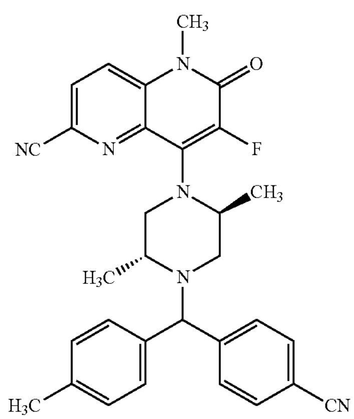 [SMILES: Cc1ccc(C(c2ccc(C#N)cc2)N2C[C@H](C)N(c3c(F)c(=O)n(C)c4ccc(C#N)nc34)C[C@H]2C)cc1] | 1 | 521.2 | D | 2.66 |
| 323 | 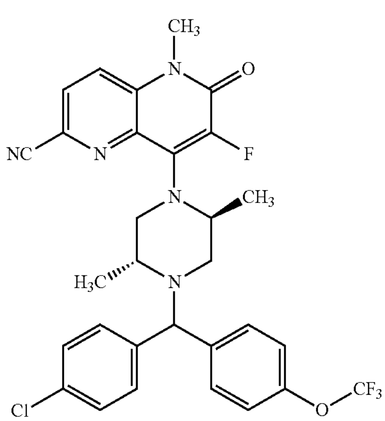 [SMILES: C[C@@H]1CN(c2c(F)c(=O)n(C)c3ccc(C#N)nc23)[C@@H](C)CN1C(c1ccc(Cl)cc1)c1ccc(OC(F)(F)F)cc1] | 1.0 | 600.2 | H | 2.80 |

TABLE 2-continued

| Ex. No. | Structure | QC Method | Obs. MSI on | Stereo Chem | RT |
|---|---|---|---|---|---|
| 324 | 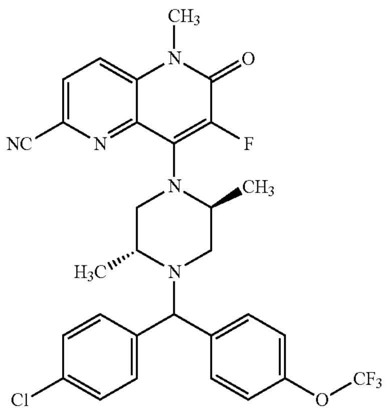 [SMILES: C[C@@H]1CN(c2c(F)c(=O)n(C)c3ccc(C#N)nc23)[C@@H](C)CN1C(c1ccc(Cl)cc1)c1ccc(OC(F)(F)F)cc1] | 1 | 600.1 | H | 2.80 |
| 325 | 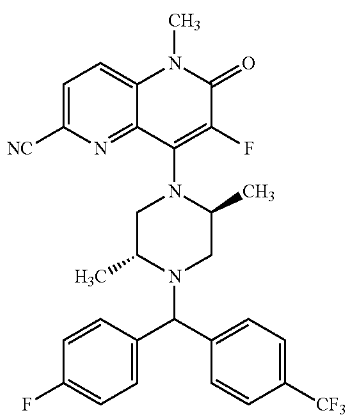 [SMILES: C[C@@H]1CN(c2c(F)c(=O)n(C)c3ccc(C#N)nc23)[C@@H](C)CN1C(c1ccc(F)cc1)c1ccc(C(F)(F)F)cc1] | 2 | 568.3 | H | 2.16 |
| 326 | 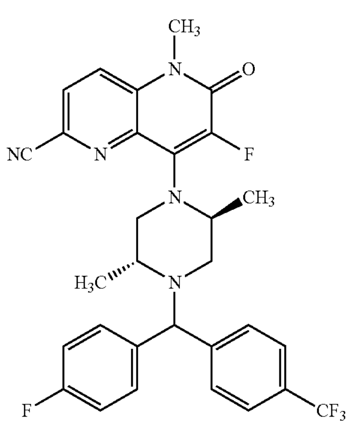 [SMILES: C[C@@H]1CN(c2c(F)c(=O)n(C)c3ccc(C#N)nc23)[C@@H](C)CN1C(c1ccc(F)cc1)c1ccc(C(F)(F)F)cc1] | 2 | 568.3 | H | 2.15 |

TABLE 2-continued

| Ex. No. | Structure | QC Method | Obs. MSI on | Stereo Chem | RT |
|---|---|---|---|---|---|
| 327 | 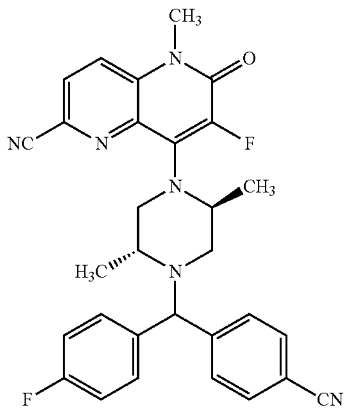 [SMILES: C[C@@H]1CN(c2c(F)c(=O)n(C)c3ccc(C#N)nc23)[C@@H](C)CN1C(c1ccc(F)cc1)c1ccc(C#N)cc1] | 1 | 525.1 | H | 2.30 |
| 328 | 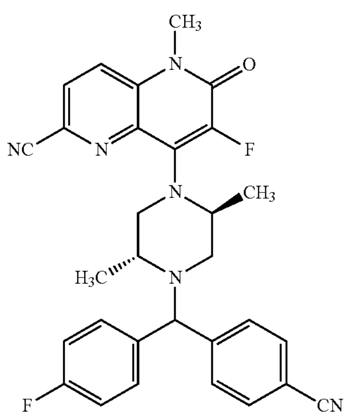 [SMILES: C[C@@H]1CN(c2c(F)c(=O)n(C)c3ccc(C#N)nc23)[C@@H](C)CN1C(c1ccc(F)cc1)c1ccc(C#N)cc1] | 1 | 525.1 | H | 2.29 |
| 329 | 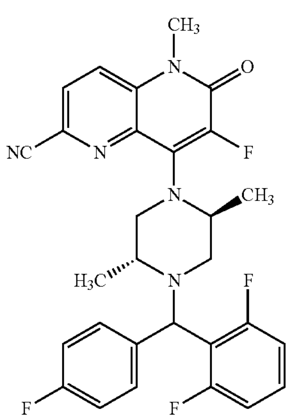 [SMILES: C[C@@H]1CN(c2c(F)c(=O)n(C)c3ccc(C#N)nc23)[C@@H](C)CN1C(c1ccc(F)cc1)c1c(F)cccc1F] | 2.0 | 535.9 | H | 1.91 |

TABLE 2-continued
| Ex. No. | Structure | QC Method | Obs. MSI on | Stereo Chem | RT |
|---|---|---|---|---|---|
| 330 | 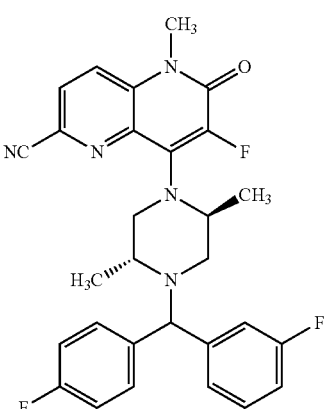 | 2.0 | 518.1 | H | 1.86 |
| 331 | 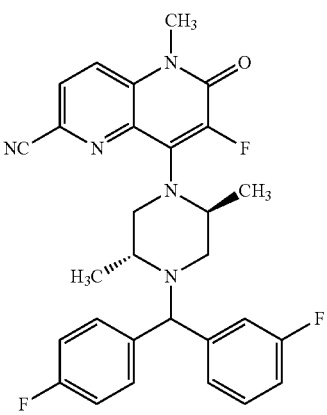 [SMILES: C[C@@H]1CN(c2c(F)c(=O)n(C)c3ccc(C#N)nc23)[C@@H](C)CN1C(c1ccc(F)cc1)c1cccc(F)c1] | 1.0 | 518.2 | H | 2.45 |
| 332 | 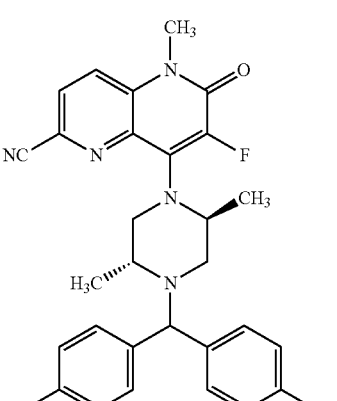 | 1.0 | 514.2 | H | 2.57 |

TABLE 2-continued
| Ex. No. | Structure | QC Method | Obs. MSI on | Stereo Chem | RT |
|---|---|---|---|---|---|
| 333 | 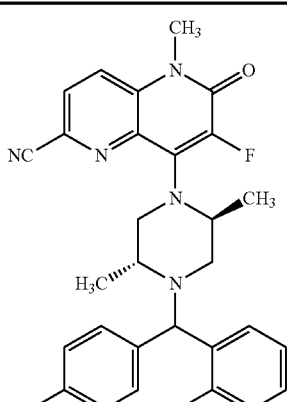 | 2.0 | 518.3 | H | 1.91 |
| 334 | 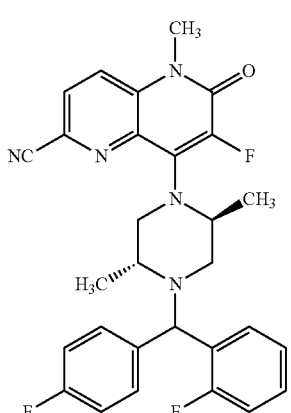 | 1.0 | 518.1 | H | 2.53 |
| 335 | 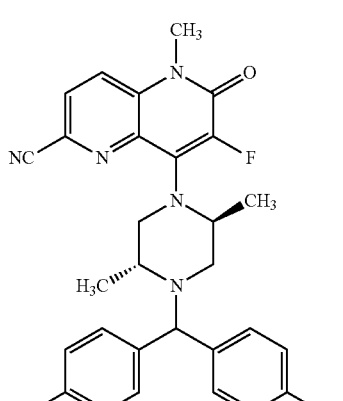 | 2.0 | 514.3 | H | 1.74 |

TABLE 2-continued

| Ex. No. | Structure | QC Method | Obs. MS Ion | Stereo Chem | RT |
|---|---|---|---|---|---|
| 336 | ![structure] | 2.0 | 536.2 | H | 2.18 |

Examples 337-339

8-((2S,5R)-4-(1-(2,4-difluorophenyl)propyl)-2,5-dimethylpiperazin-1-yl)-5-methyl-6-oxo-5,6-dihydro-1,5-naphthyridine-2-carbonitrile

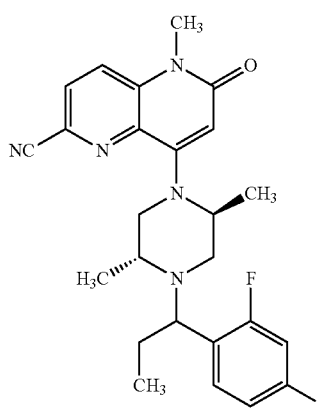

(337-339)

To a mixture of 8-((2S,5R)-2,5-dimethylpiperazin-1-yl)-5-methyl-6-oxo-5,6-dihydro-1,5-naphthyridine-2-carbonitrile (29.7 mg, 0.1 mmol) and 1-(1-bromopropyl)-2,4-difluorobenzene (25.9 mg, 0.110 mmol) in acetonitrile (0.3 mL) was added Hunig's base (87 µL, 0.500 mmol). The mixture was stirred on hot plate at 55° C. for 16 hours. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile: water with 0.1% trifluoroacetic acid; Gradient: a 0 minute hold at 3% B, 3-43% B over 25 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. Stereochemistry: D.

The diastereomeric mixture of Example 337 was further separated to resolve two homochiral diastereomers by using SFC-chiral chromatography with the following conditions: Column: Chiral OD, 30×250 mm. 5 micron particles; Mobile Phase: 15% IPA/85% $CO_2$ w/0.1% DEA; Flow Rate: 100 mL/min; Detector Wavelength: 220 nm.

Example 338 (Isomer 1) was collected as the first eluent peak in 95% de. Stereochemistry: H.

Example 339 (Isomer 2) was collected as the second eluent peak in 95% de. Stereochemistry: H.

Examples 340 and 341

8-[(2S,5R)-5-ethyl-2-methyl-4-[(pyridin-2-yl)[4-(trifluoromethoxy)phenyl]methyl]piperazin-1-yl]-5-methyl-6-oxo-5,6-dihydro-1,5-naphthyridine-2-carbonitrile

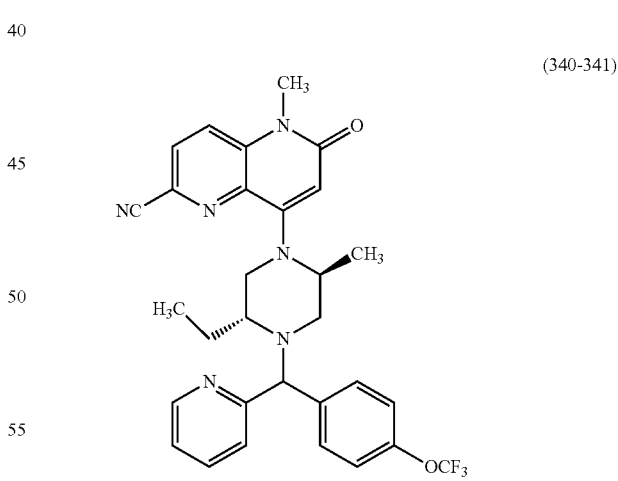

(340-341)

To an acetonitrile (2 mL) solution of 2-(chloro(4-(trifluoromethoxy)phenyl) methyl)pyridine (102 mg, 0.353 mmol) were added 8-((2S,5R)-5-ethyl-2-methylpiperazin-1-yl)-5-methyl-6-oxo-5,6-dihydro-1,5-naphthyridine-2-carbonitrile (55 mg, 0.177 mmol), potassium iodide (2.93 mg, 0.018 mmol) and Hunig's base (0.093 mL, 0.530 mmol). The mixture was heated at 75° C. overnight. After 24 hours, LC/MS analysis indicated the reaction was completed. The reaction mixture was filtered and purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 46% B, 46-86% B over 20 minutes, then a 4 minute hold at 100% B; Flow Rate: 20 mL/min; Column Temperature: 25° C. Fraction collection was triggered by MS and UV signals. Fractions containing the products were combined and dried via centrifugal evaporation to provide Example 340 (9.5 mg) and Example 341 (11.9 mg). Stereochemistry: H.

The compounds of Table 3 were prepared according to the general method disclosed in to Examples 337 and 340 by alkylation of the piperazine nitrogen with either an alkyl chloride or bromide. When the alkylation provided a mixture of diastereomers, the mixture was separated using either preparative chromatography or preparative chiral chromatography. The absolute stereochemistry was not assigned at the newly formed carbon-nitrogen bond.

TABLE 3

| Ex. No. | Structure | QC Method | Obs. MS | Stereo Chem | RT/Meth. |
|---|---|---|---|---|---|
| 344 | 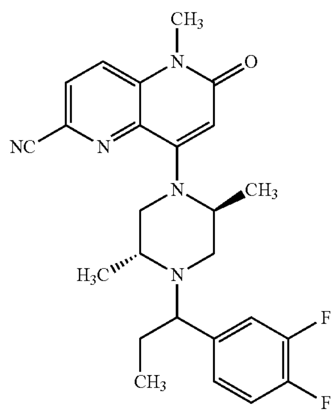 [SMILES: CCC(c1ccc(F)c(F)c1)N1C[C@H](C)N(c2cc(=O)n(C)c3ccc(C#N)nc23)C[C@H]1C] | 1.0 | 452.2 | H | 2.62 A |
| 345 | 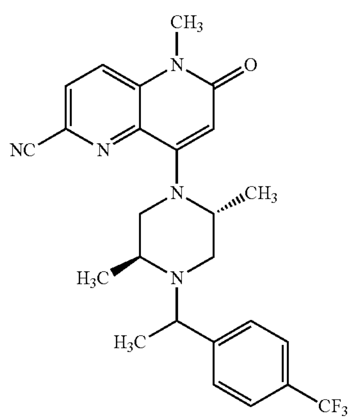 [SMILES: CC(c1ccc(C(F)(F)F)cc1)N1C[C@@H](C)N(c2cc(=O)n(C)c3ccc(C#N)nc23)C[C@@H]1C] | | | | A |
| 346 | 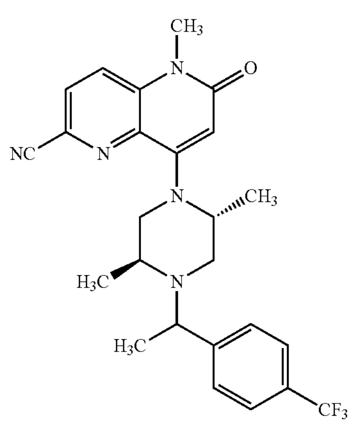 [SMILES: CC(c1ccc(C(F)(F)F)cc1)N1C[C@@H](C)N(c2cc(=O)n(C)c3ccc(C#N)nc23)C[C@@H]1C] | 1.0 | 470.1 | H | 2.38 A |

TABLE 3-continued

| Ex. No. | Structure | QC Method | Obs. MS | Stereo Chem | RT/Meth. |
|---|---|---|---|---|---|
| 350 | 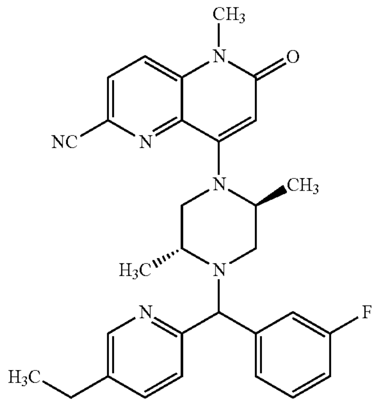 [SMILES: CCc1ccc(C(c2cccc(F)c2)N2C[C@H](C)N(c3cc(=O)n(C)c4ccc(C#N)nc34)C[C@H]2C)nc1] | 1.0 | 511.4 | H | 2.16 B |
| 351 | 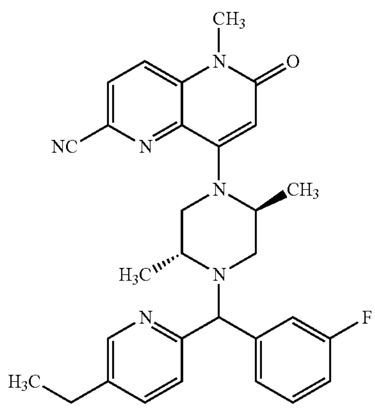 [SMILES: CCc1ccc(C(c2cccc(F)c2)N2C[C@H](C)N(c3cc(=O)n(C)c4ccc(C#N)nc34)C[C@H]2C)nc1] | 1.0 | 511.4 | H | 2.17 B |
| 352 | 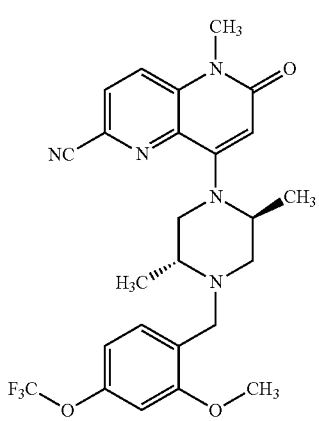 [SMILES: COc1cc(OC(F)(F)F)ccc1CN1C[C@H](C)N(c2cc(=O)n(C)c3ccc(C#N)nc23)C[C@H]1C] | 1.0 | 502.2 | H | 2.39 A |

TABLE 3-continued

| Ex. No. | Structure | QC Method | Obs. MS | Stereo Chem | RT/Meth. |
|---|---|---|---|---|---|
| 353 | 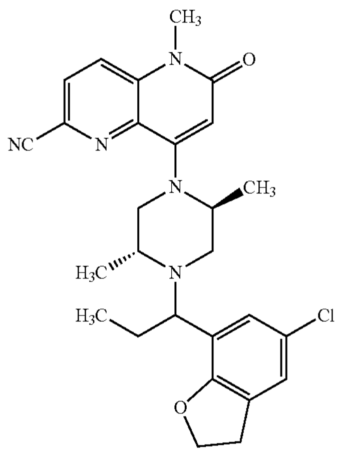 [SMILES: CCC(c1cc(Cl)cc2c1OCC2)N1C[C@H](C)N(c2cc(=O)n(C)c3ccc(C#N)nc23)C[C@H]1C] | 2.0 | 492.2 | D | 1.55 A |
| 354 | 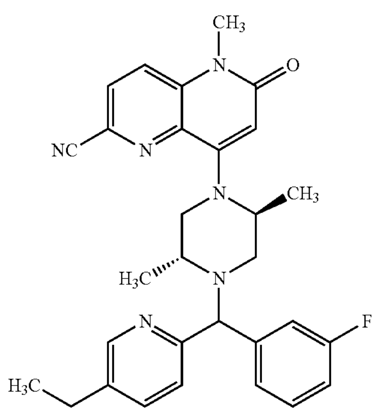 [SMILES: CCc1ccc(C(c2cccc(F)c2)N2C[C@H](C)N(c3cc(=O)n(C)c4ccc(C#N)nc34)C[C@H]2C)nc1] | 1.0 | 511.5 | D | 2.16 B |
| 355 | 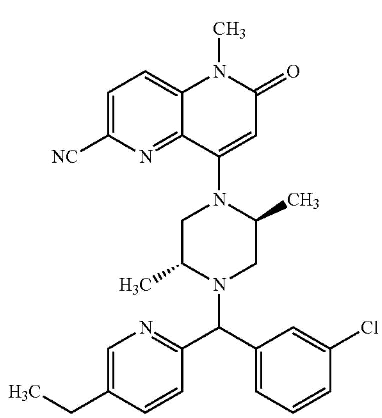 [SMILES: CCc1ccc(C(c2cccc(Cl)c2)N2C[C@H](C)N(c3cc(=O)n(C)c4ccc(C#N)nc34)C[C@H]2C)nc1] | 2.0 | 527.2 | D | 1.65 B |

TABLE 3-continued

| Ex. No. | Structure | QC Method | Obs. MS | Stereo Chem | RT/Meth. |
|---|---|---|---|---|---|
| 356 | 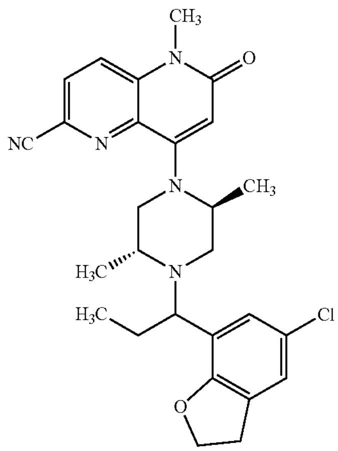 [SMILES: CCC(c1cc(Cl)cc2c1OCC2)N1C[C@H](C)N(c2cc(=O)n(C)c3ccc(C#N)nc23)C[C@H]1C] | 1.0 | 492.1 | H | 2.55 A |
| 357 | 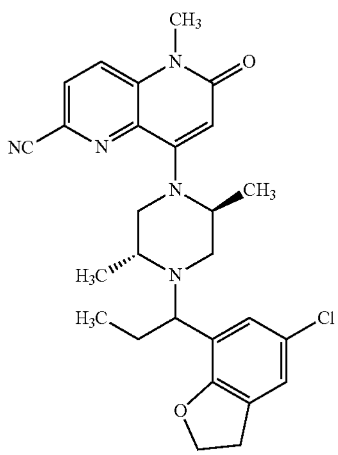 [SMILES: CCC(c1cc(Cl)cc2c1OCC2)N1C[C@H](C)N(c2cc(=O)n(C)c3ccc(C#N)nc23)C[C@H]1C] | 2.0 | 492.1 | H | 1.61 A |
| 358 | 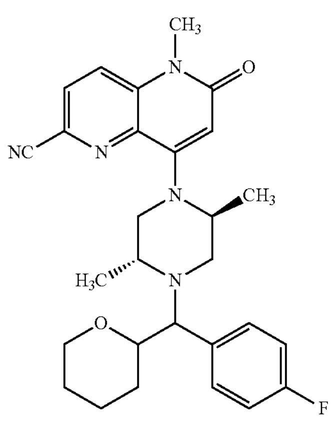 [SMILES: C[C@@H]1CN(c2cc(=O)n(C)c3ccc(C#N)nc23)[C@@H](C)CN1C(c1ccc(F)cc1)C1CCCCO1] | 1.0 | 490.2 | H | 2.33 B |

TABLE 3-continued

| Ex. No. | Structure | QC Method | Obs. MS | Stereo Chem | RT/Meth. |
|---|---|---|---|---|---|
| 359 | 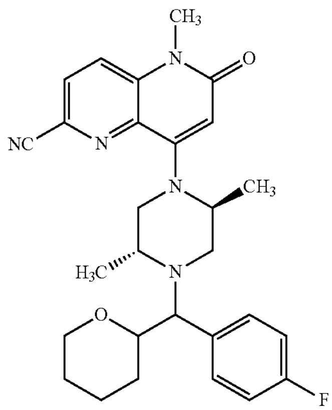 [SMILES: C[C@@H]1CN(c2cc(=O)n(C)c3ccc(C#N)nc23)[C@@H](C)CN1C(c1ccc(F)cc1)C1CCCCO1] | 1.0 | 490.2 | H | 2.38 B |
| 360 | 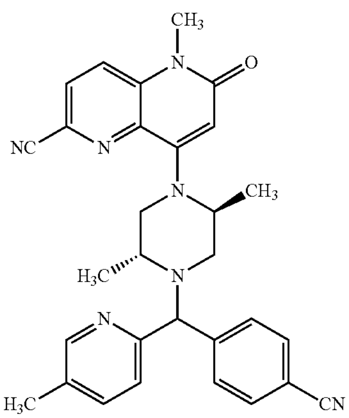 [SMILES: Cc1ccc(C(c2ccc(C#N)cc2)N2C[C@H](C)N(c3cc(=O)n(C)c4ccc(C#N)nc34)C[C@H]2C)nc1] | 2.0 | 504.2 | H | 1.48 B |
| 361 | 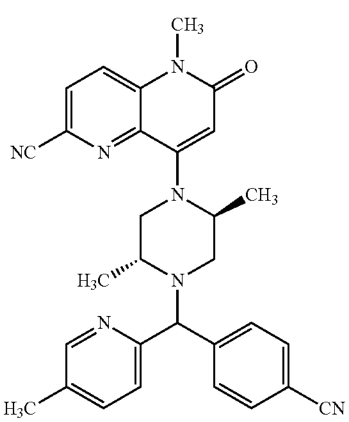 [SMILES: Cc1ccc(C(c2ccc(C#N)cc2)N2C[C@H](C)N(c3cc(=O)n(C)c4ccc(C#N)nc34)C[C@H]2C)nc1] | 1.0 | 504.2 | H | 2.12 B |

TABLE 3-continued

| Ex. No. | Structure | QC Method | Obs. MS | Stereo Chem | RT/Meth. |
|---|---|---|---|---|---|
| 362 | 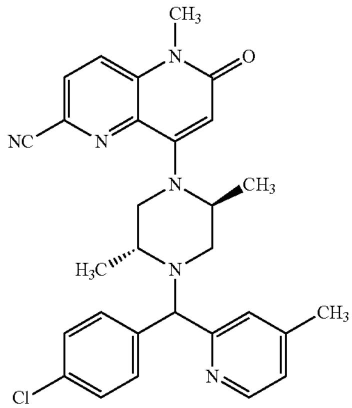 [SMILES: Cc1ccnc(C(c2ccc(Cl)cc2)N2C[C@H](C)N(c3cc(=O)n(C)c4ccc(C#N)nc34)C[C@H]2C)c1] | 1.0 | 513.2 | H | 2.14 B |
| 363 | 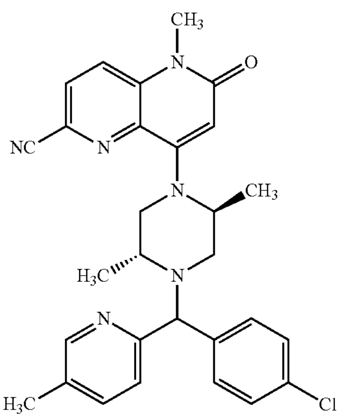 [SMILES: Cc1ccc(C(c2ccc(Cl)cc2)N2C[C@H](C)N(c3cc(=O)n(C)c4ccc(C#N)nc34)C[C@H]2C)nc1] | 1.0 | 513.2 | H | 2.2 B |
| 364 | 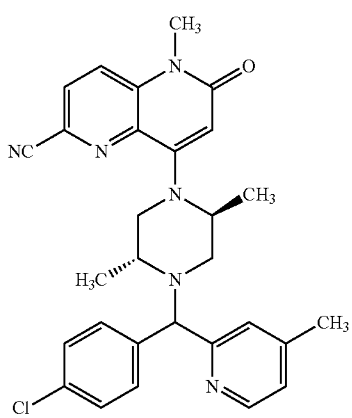 [SMILES: Cc1ccnc(C(c2ccc(Cl)cc2)N2C[C@H](C)N(c3cc(=O)n(C)c4ccc(C#N)nc34)C[C@H]2C)c1] | 1.0 | 513.4 | H | 2.16 B |

TABLE 3-continued

| Ex. No. | Structure | QC Method | Obs. MS | Stereo Chem | RT/Meth. |
|---|---|---|---|---|---|
| 365 | 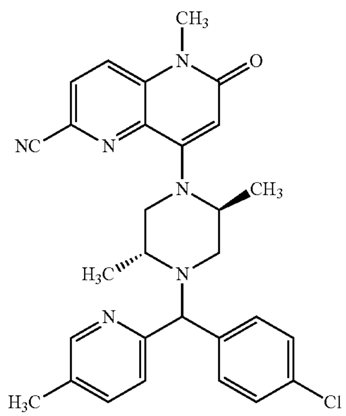 [SMILES: Cc1ccc(C(c2ccc(Cl)cc2)N2C[C@H](C)N(c3cc(=O)n(C)c4ccc(C#N)nc34)C[C@H]2C)nc1] | 1.0 | 513.2 | H | 2.27 B |
| 366 | 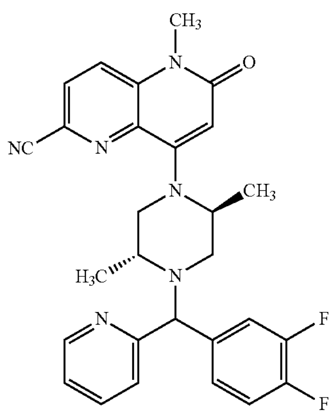 [SMILES: C[C@@H]1CN(c2cc(=O)n(C)c3ccc(C#N)nc23)[C@@H](C)CN1C(c1ccc(F)c(F)c1)c1ccccn1] | 2.0 | 501.32, 501.32 | D | 2.03 B |
| 367 | 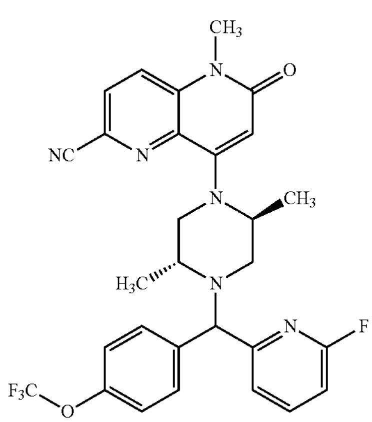 [SMILES: C[C@@H]1CN(c2cc(=O)n(C)c3ccc(C#N)nc23)[C@@H](C)CN1C(c1ccc(OC(F)(F)F)cc1)c1cccc(F)n1] | 1.0 | 567.1 | H | 2.37 B |

TABLE 3-continued

| Ex. No. | Structure | QC Method | Obs. MS | Stereo Chem | RT/Meth. |
|---|---|---|---|---|---|
| 368 | 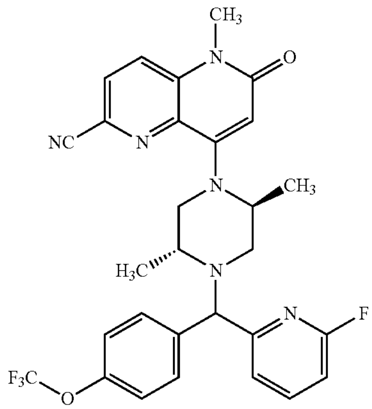 [SMILES: C[C@@H]1CN(c2cc(=O)n(C)c3ccc(C#N)nc23)[C@@H](C)CN1C(c1ccc(OC(F)(F)F)cc1)c1cccc(F)n1] | 1.0 | 567.2 | H | 2.37 B |
| 369 | 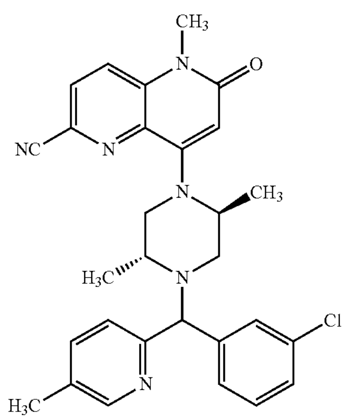 [SMILES: Cc1ccc(C(c2cccc(Cl)c2)N2C[C@H](C)N(c3cc(=O)n(C)c4ccc(C#N)nc34)C[C@H]2C)nc1] | 1.0 | 513.2 | H | 2.17 B |
| 370 | 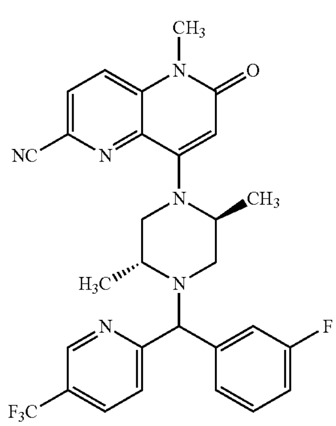 [SMILES: C[C@@H]1CN(c2cc(=O)n(C)c3ccc(C#N)nc23)[C@@H](C)CN1C(c1cccc(F)c1)c1ccc(C(F)(F)F)cn1] | 1.0 | 551.2 | H | 2.49 B |

TABLE 3-continued

| Ex. No. | Structure | QC Method | Obs. MS | Stereo Chem | RT/Meth. |
| --- | --- | --- | --- | --- | --- |
| 371 | 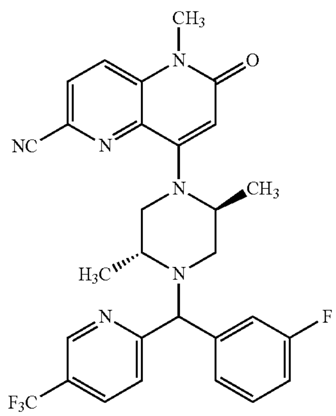 [SMILES: C[C@@H]1CN(c2cc(=O)n(C)c3ccc(C#N)nc23)[C@@H](C)CN1C(c1cccc(F)c1)c1ccc(C(F)(F)F)cn1] | 1.0 | 551.2 | H | 2.5 B |
| 372 | 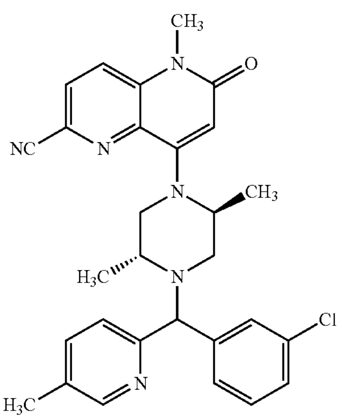 [SMILES: Cc1ccc(C(c2cccc(Cl)c2)N2C[C@H](C)N(c3cc(=O)n(C)c4ccc(C#N)nc34)C[C@H]2C)nc1] | 1.0 | 513.2 | H | 2.19 B |
| 373 | 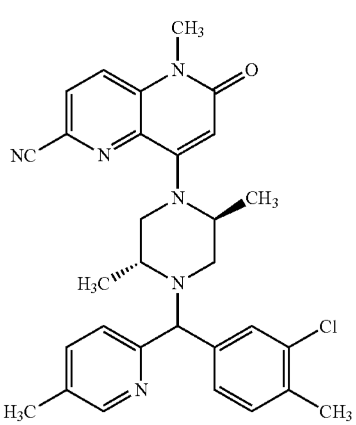 | 2.0 | 527.3 | H | 1.68 |

TABLE 3-continued

| Ex. No. | Structure | QC Method | Obs. MS | Stereo Chem | RT/Meth. |
|---|---|---|---|---|---|
| 374 | 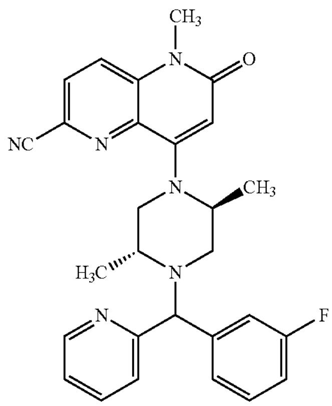 [SMILES: C[C@@H]1CN(c2cc(=O)n(C)c3ccc(C#N)nc23)[C@@H](C)CN1C(c1cccc(F)c1)c1ccccn1] | 2.0 | 483.3 | H | 1.39 B |
| 375 | 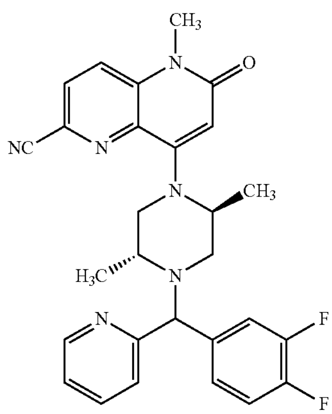 [SMILES: C[C@@H]1CN(c2cc(=O)n(C)c3ccc(C#N)nc23)[C@@H](C)CN1C(c1ccc(F)c(F)c1)c1ccccn1] | 1.0 | 501.2 | H | 2.12 B |
| 376 | 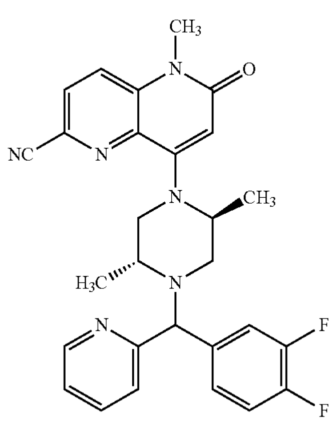 [SMILES: C[C@@H]1CN(c2cc(=O)n(C)c3ccc(C#N)nc23)[C@@H](C)CN1C(c1ccc(F)c(F)c1)c1ccccn1] | 1.0 | 501.2 | H | 2.11 B |

TABLE 3-continued

| Ex. No. | Structure | QC Method | Obs. MS | Stereo Chem | RT/Meth. |
|---|---|---|---|---|---|
| 377 | 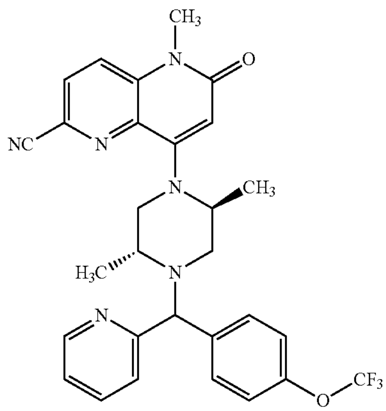 [SMILES: C[C@@H]1CN(c2cc(=O)n(C)c3ccc(C#N)nc23)[C@@H](C)CN1C(c1ccc(OC(F)(F)F)cc1)c1ccccn1] | 1.0 | 549.3 | H | 2.23 B |
| 378 | 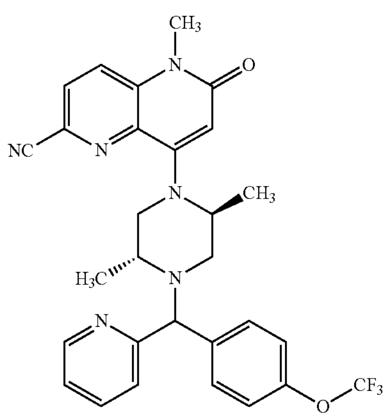 [SMILES: C[C@@H]1CN(c2cc(=O)n(C)c3ccc(C#N)nc23)[C@@H](C)CN1C(c1ccc(OC(F)(F)F)cc1)c1ccccn1] | 1.0 | 549.1 | H | 2.23 B |
| 379 | 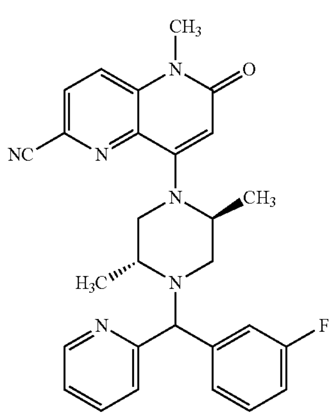 [SMILES: C[C@@H]1CN(c2cc(=O)n(C)c3ccc(C#N)nc23)[C@@H](C)CN1C(c1cccc(F)c1)c1ccccn1] | 1.0 | 483.2 | H | 1.92 B |

TABLE 3-continued

| Ex. No. | Structure | QC Method | Obs. MS | Stereo Chem | RT/Meth. |
| --- | --- | --- | --- | --- | --- |
| 380 | 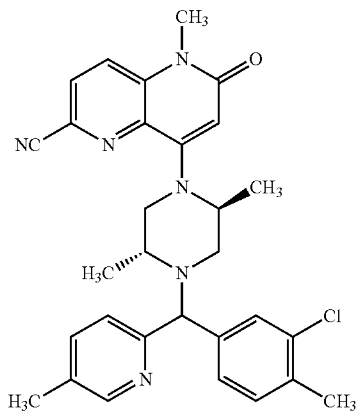 | 1.0 | 527.2 | H | 2.32 B |
| 381 | 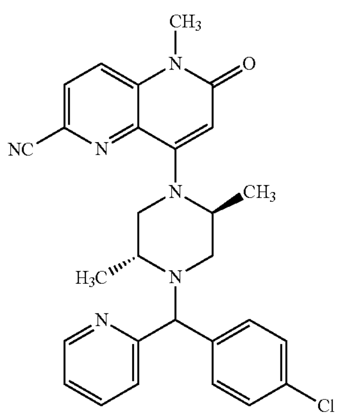 [SMILES: C[C@@H]1CN(c2cc(=O)n(C)c3ccc(C#N)nc23)[C@@H](C)CN1C(c1ccc(Cl)cc1)c1ccccn1] | 1.0 | 499.3 | H | 2.15 B |
| 382 | 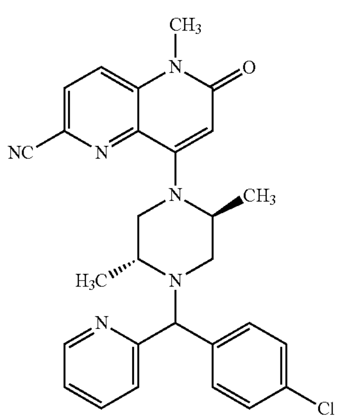 [SMILES: C[C@@H]1CN(c2cc(=O)n(C)c3ccc(C#N)nc23)[C@@H](C)CN1C(c1ccc(Cl)cc1)c1ccccn1] | 1.0 | 499.3 | H | 2.16 B |

TABLE 3-continued

| Ex. No. | Structure | QC Method | Obs. MS | Stereo Chem | RT/Meth. |
|---|---|---|---|---|---|
| 383 | 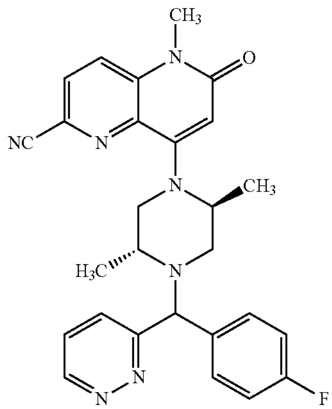 [SMILES: C[C@@H]1CN(c2cc(=O)n(C)c3ccc(C#N)nc23)[C@@H](C)CN1C(c1ccc(F)cc1)c1cccnn1] | 2.0 | 484.2 | H | 1.43 B |
| 384 | 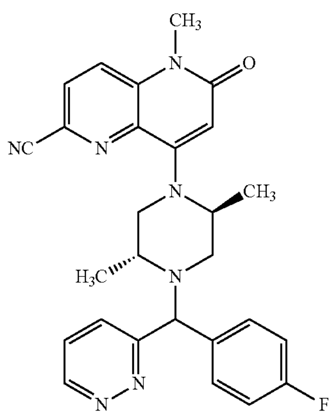 [SMILES: C[C@@H]1CN(c2cc(=O)n(C)c3ccc(C#N)nc23)[C@@H](C)CN1C(c1ccc(F)cc1)c1cccnn1] | 2.0 | 483.9 | H | 1.34 B |
| 385 | 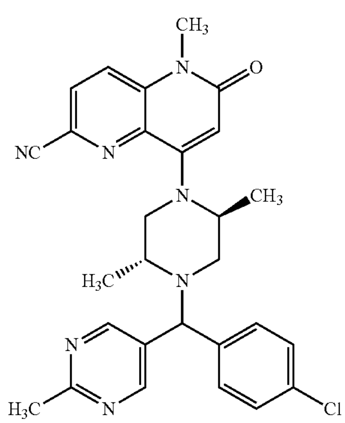 [SMILES: Cc1ncc(C(c2ccc(Cl)cc2)N2C[C@H](C)N(c3cc(=O)n(C)c4ccc(C#N)nc34)C[C@H]2C)cn1] | 1.0 | 514.2 | H | 1.95 B |

TABLE 3-continued
| Ex. No. | Structure | QC Method | Obs. MS | Stereo Chem | RT/Meth. |
|---|---|---|---|---|---|
| 386 | 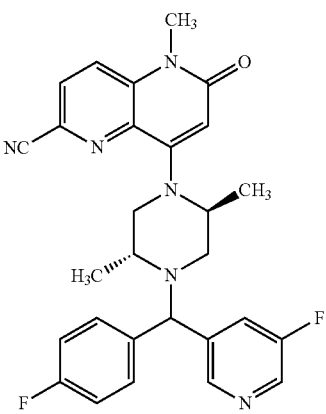 | 1.0 | 501.2 | H | 2.01 B |
| 387 | 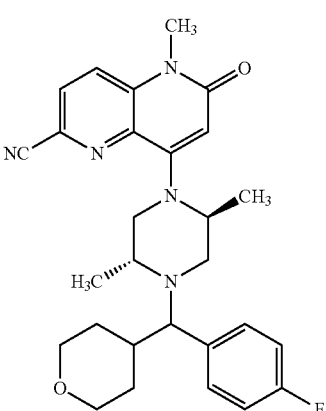 | 1.0 | 490.2 | H | 2.29 B |
| 388 | 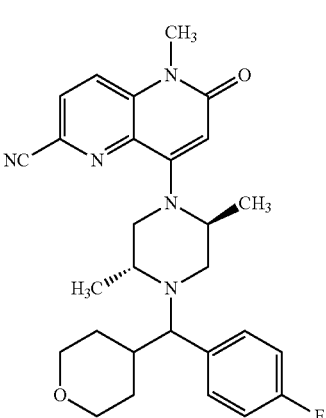 | 2.0 | 490.2 | H | 1.44 B |

TABLE 3-continued
| Ex. No. | Structure | QC Method | Obs. MS | Stereo Chem | RT/Meth. |
|---|---|---|---|---|---|
| 389 | 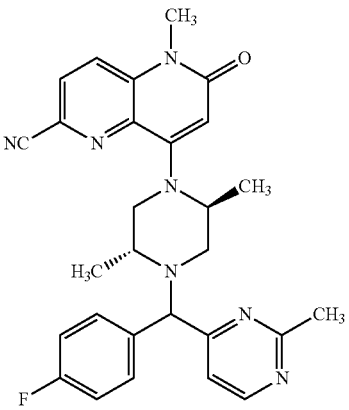 [SMILES: Cc1nccc(C(c2ccc(F)cc2)N2C[C@H](C)N(c3cc(=O)n(C)c4ccc(C#N)nc34)C[C@H]2C)n1] | 1.0 | 497.9 | H | 1.91 B |
| 390 | 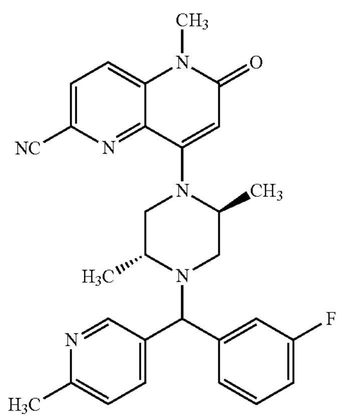 | 1.0 | 497.3 | D | 2.02 B |
| 391 | 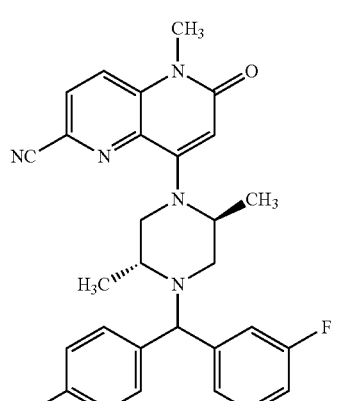 | 2.0 | 497.6 | H | 1.8 B |

TABLE 3-continued
| Ex. No. | Structure | QC Method | Obs. MS | Stereo Chem | RT/Meth. |
|---------|-----------|-----------|---------|-------------|----------|
| 392 | 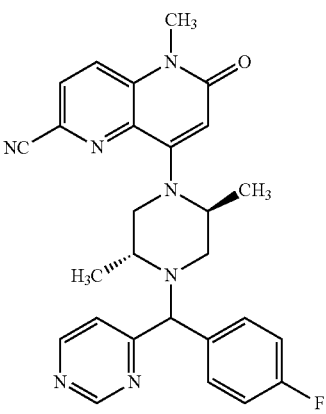 [SMILES: C[C@@H]1CN(c2cc(=O)n(C)c3ccc(C#N)nc23)[C@@H](C)CN1C(c1ccc(F)cc1)c1ccncn1] | 2.0 | 484.3 | H | 1.25 B |
| 393 | 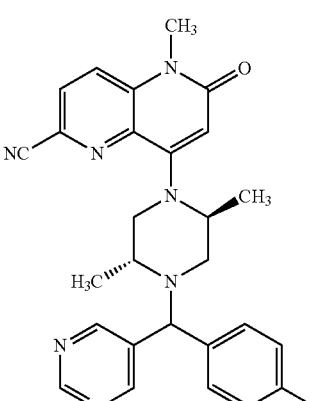 | 1.0 | 484.2 | H | 1.75 B |
| 394 | 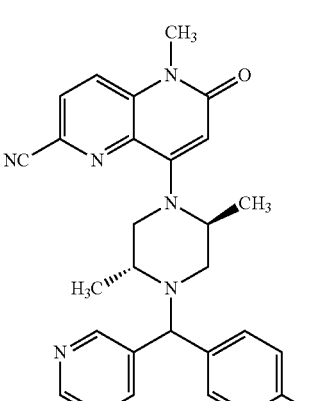 | 1.0 | 484.3 | H | 1.8 B |

TABLE 3-continued

| Ex. No. | Structure | QC Method | Obs. MS | Stereo Chem | RT/Meth. |
|---|---|---|---|---|---|
| 395 | 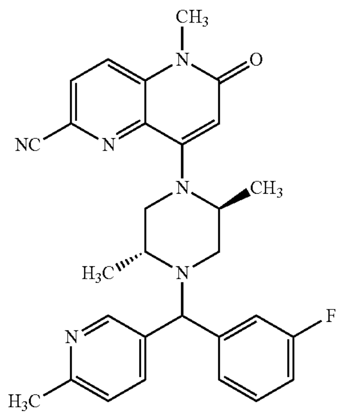 | 1.0 | 497.2 | H | 2.03 B |
| 396 | 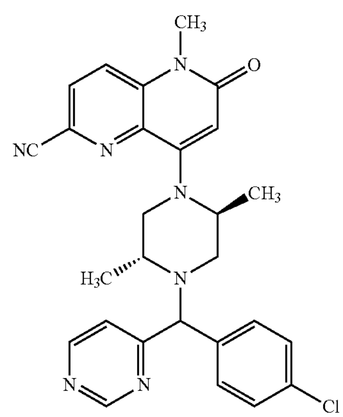 [SMILES: C[C@@H]1CN(c2cc(=O)n(C)c3ccc(C#N)nc23)[C@@H](C)CN1C(c1ccc(Cl)cc1)c1ccncn1] | 2.0 | 500.4 | H | 1.44 B |
| 397 | 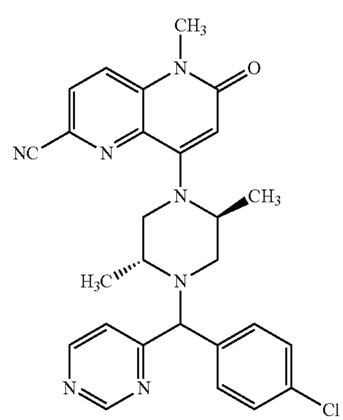 | 2.0 | 500.3 | H | 1.57 B |

TABLE 3-continued

| Ex. No. | Structure | QC Method | Obs. MS | Stereo Chem | RT/Meth. |
|---|---|---|---|---|---|
| 398 | 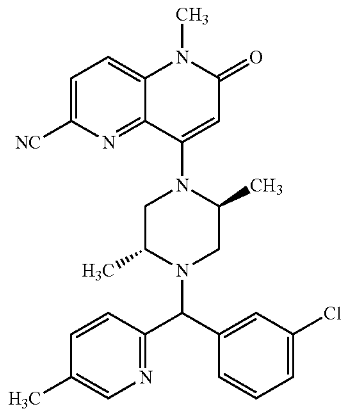 [SMILES: Cc1ccc(C(c2cccc(Cl)c2)N2C[C@H](C)N(c3cc(=O)n(C)c4ccc(C#N)nc34)C[C@H]2C)nc1] | 1.0 | 513.16, 513.16 | D | 1.52 B |
| 399 | 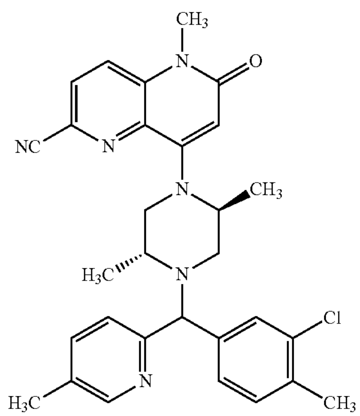 | 1.0 | 527.2 | D | 2.29 B |
| 400 | 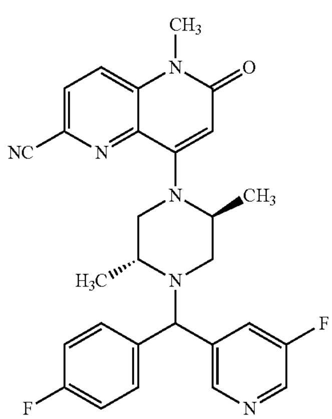 [SMILES: C[C@@H]1CN(c2cc(=O)n(C)c3ccc(C#N)nc23)[C@@H](C)CN1C(c1ccc(F)cc1)c1cncc(F)c1] | 1.0 | 501.2 | D | 2.01 B |

TABLE 3-continued

| Ex. No. | Structure | QC Method | Obs. MS | Stereo Chem | RT/Meth. |
|---|---|---|---|---|---|
| 401 | 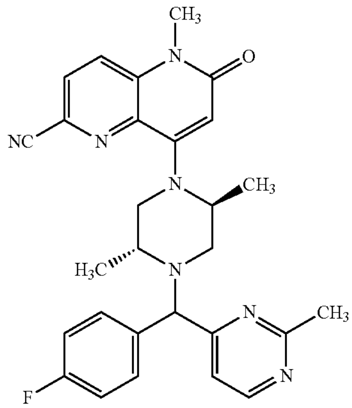 [SMILES: Cc1nccc(C(c2ccc(F)cc2)N2C[C@H](C)N(c3cc(=O)n(C)c4ccc(C#N)nc34)C[C@H]2C)n1] | 2.0 | 498.1 | H | 1.45 B |
| 402 | 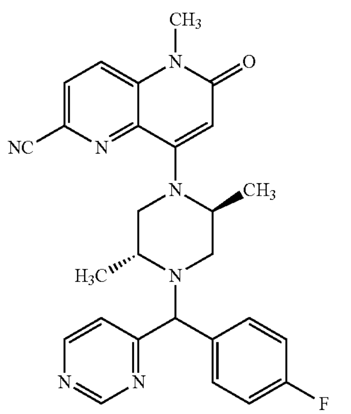 [SMILES: C[C@@H]1CN(c2cc(=O)n(C)c3ccc(C#N)nc23)[C@@H](C)CN1C(c1ccc(F)cc1)c1ccncn1] | 2.0 | 484.3 | H | 1.35 B |
| 403 | 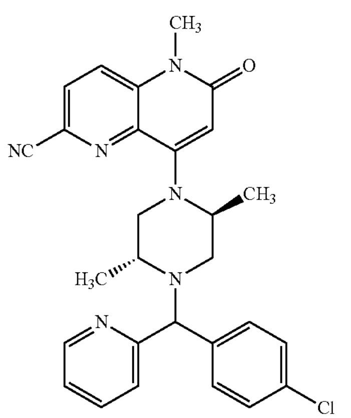 [SMILES: C[C@@H]1CN(c2cc(=O)n(C)c3ccc(C#N)nc23)[C@@H](C)CN1C(c1ccc(Cl)cc1)c1ccccn1] | 1.0 | 499.3 | D | 2.13 B |

TABLE 3-continued

| Ex. No. | Structure | QC Method | Obs. MS | Stereo Chem | RT/Meth. |
|---|---|---|---|---|---|
| 404 | 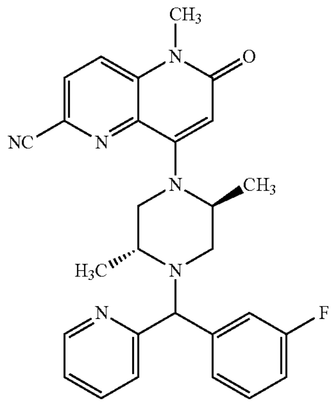 [SMILES: C[C@@H]1CN(c2cc(=O)n(C)c3ccc(C#N)nc23)[C@@H](C)CN1C(c1cccc(F)c1)c1ccccn1] | 1.0 | 483.4 | D | 1.92 B |
| 405 | 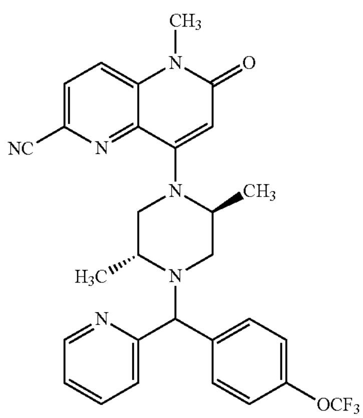 [SMILES: C[C@@H]1CN(c2cc(=O)n(C)c3ccc(C#N)nc23)[C@@H](C)CN1C(c1ccc(OC(F)(F)F)cc1)c1ccccn1] | 1.0 | 549.3 | D | 2.2 B |
| 406 | 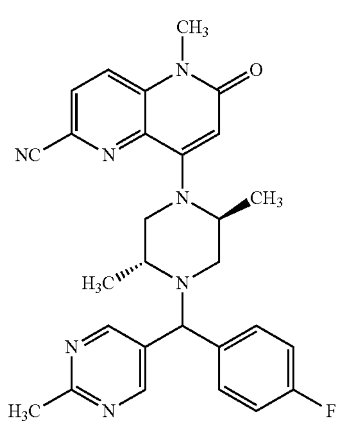 [SMILES: Cc1ncc(C(c2ccc(F)cc2)N2C[C@H](C)N(c3cc(=O)n(C)c4ccc(C#N)nc34)C[C@H]2C)cn1] | 2.0 | 498.2 | H | 1.64 B |

TABLE 3-continued

| Ex. No. | Structure | QC Method | Obs. MS | Stereo Chem | RT/Meth. |
|---|---|---|---|---|---|
| 407 | 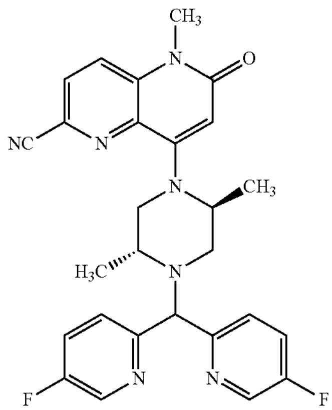 [SMILES: C[C@@H]1CN(c2cc(=O)n(C)c3ccc(C#N)nc23)[C@@H](C)CN1C(c1ccc(F)cn1)c1ccc(F)cn1] | 2.0 | 502.2 | H | 1.35 B |
| 408 | 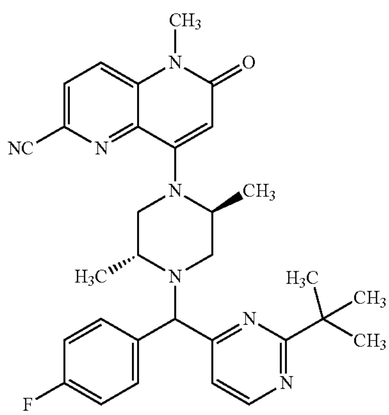 [SMILES: C[C@@H]1CN(c2cc(=O)n(C)c3ccc(C#N)nc23)[C@@H](C)CN1C(c1ccc(F)cc1)c1ccnc(C(C)(C)C)n1] | 2.0 | 540.0 | H | 1.62 B |
| 409 | 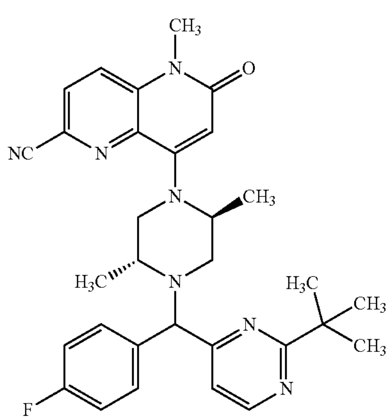 [SMILES: C[C@@H]1CN(c2cc(=O)n(C)c3ccc(C#N)nc23)[C@@H](C)CN1C(c1ccc(F)cc1)c1ccnc(C(C)(C)C)n1] | 1.0 | 540.2 | H | 2.56 B |

TABLE 3-continued

| Ex. No. | Structure | QC Method | Obs. MS | Stereo Chem | RT/Meth. |
|---|---|---|---|---|---|
| 410 | 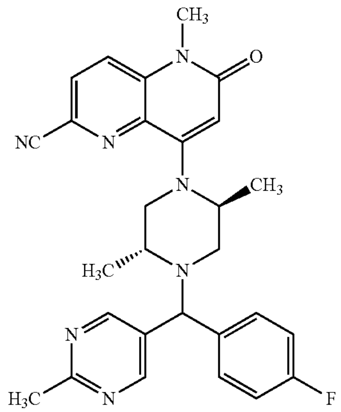 [SMILES: Cc1ncc(C(c2ccc(F)cc2)N2C[C@H](C)N(c3cc(=O)n(C)c4ccc(C#N)nc34)C[C@H]2C)cn1] | 1.0 | 498.2 | H | 1.81 B |
| 411 | 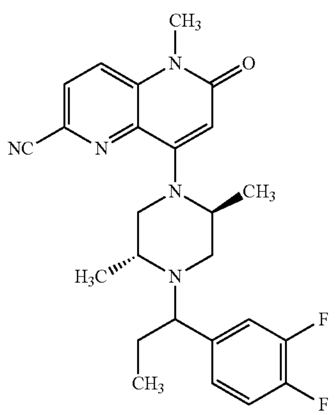 [SMILES: CCC(c1ccc(F)c(F)c1)N1C[C@H](C)N(c2cc(=O)n(C)c3ccc(C#N)nc23)C[C@H]1C] | 2.0 | 452.2 | H | 1.45 A |
| 412 | 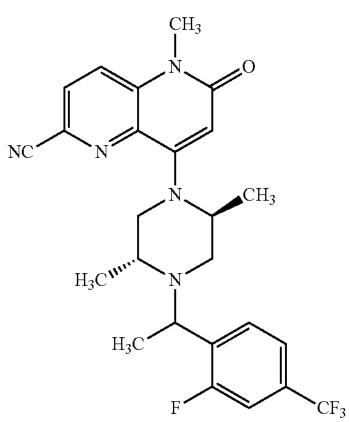 [SMILES: CC(c1ccc(C(F)(F)F)cc1F)N1C[C@H](C)N(c2cc(=O)n(C)c3ccc(C#N)nc23)C[C@H]1C] | 2.0 | 488.2 | H | 1.38 A |

TABLE 3-continued

| Ex. No. | Structure | QC Method | Obs. MS | Stereo Chem | RT/Meth. |
|---|---|---|---|---|---|
| 413 | 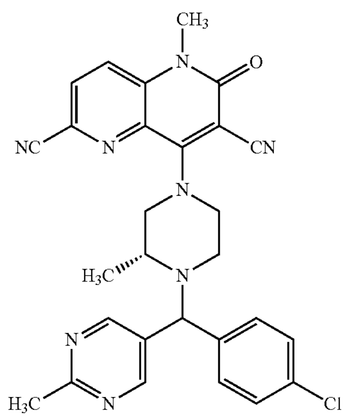 [SMILES: Cc1ncc(C(c2ccc(Cl)cc2)N2CCN(c3c(C#N)c(=O)n(C)c4ccc(C#N)nc34)C[C@H]2C)cn1] | 1.0 | 525.1 | H | 1.93 B |
| 414 | 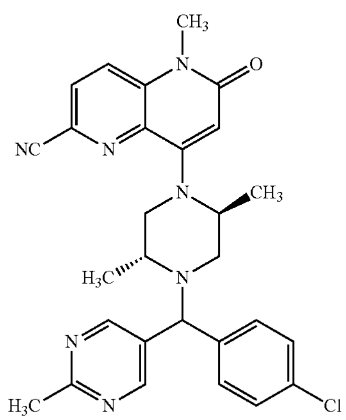 [SMILES: Cc1ncc(C(c2ccc(Cl)cc2)N2C[C@H](C)N(c3cc(=O)n(C)c4ccc(C#N)nc34)C[C@H]2C)cn1] | 2.0 | 514.0 | H | 1.9 B |
| 415 | 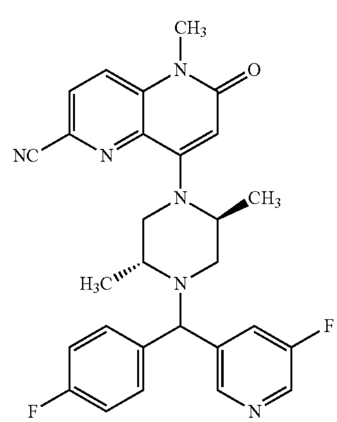 [SMILES: C[C@@H]1CN(c2cc(=O)n(C)c3ccc(C#N)nc23)[C@@H](C)CN1C(c1ccc(F)cc1)c1cncc(F)c1] | 1.0 | 501.1 | H | 2.1 B |

TABLE 3-continued

| Ex. No. | Structure | QC Method | Obs. MS | Stereo Chem | RT/Meth. |
|---|---|---|---|---|---|
| 416 | 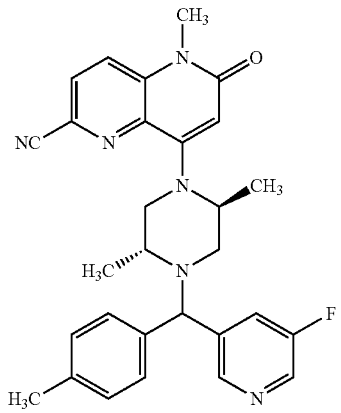 [SMILES: Cc1ccc(C(c2cncc(F)c2)N2C[C@H](C)N(c3cc(=O)n(C)c4ccc(C#N)nc34)C[C@H]2C)cc1] | 2.0 | 497.2 | H | 1.8 B |
| 417 | 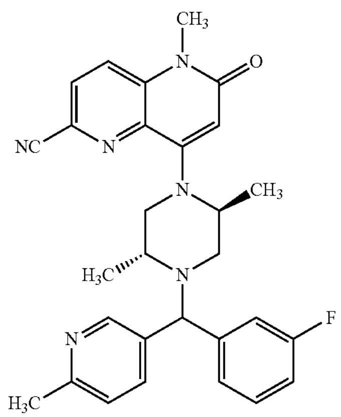 | 1.0 | 497.3 | H | 2.03 B |
| 418 | 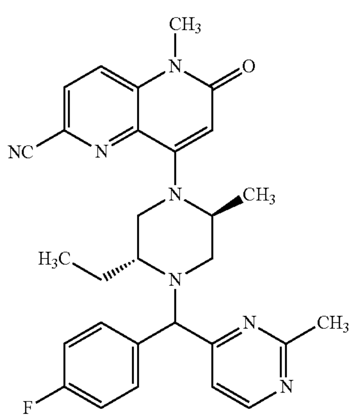 [SMILES: CC[C@@H]1CN(c2cc(=O)n(C)c3ccc(C#N)nc23)[C@@H](C)CN1C(c1ccc(F)cc1)c1ccnc(C)n1] | 1.0 | 512.2 | H | 2.0 B |

TABLE 3-continued

| Ex. No. | Structure | QC Method | Obs. MS | Stereo Chem | RT/Meth. |
|---|---|---|---|---|---|
| 419 | 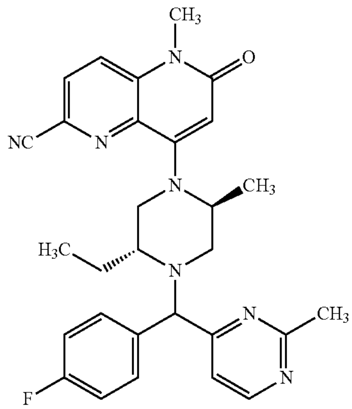 [SMILES: CC[C@@H]1CN(c2cc(=O)n(C)c3ccc(C#N)nc23)[C@@H](C)CN1C(c1ccc(F)cc1)c1ccnc(C)n1] | 1.0 | 512.2 | H | 2.0 B |
| 420 | 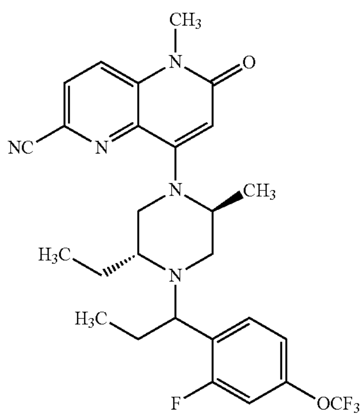 [SMILES: CCC(c1ccc(OC(F)(F)F)cc1F)N1C[C@H](C)N(c2cc(=O)n(C)c3ccc(C#N)nc23)C[C@H]1CC] | 1.0 | 532.1 | H | 1.8 B |
| 421 | 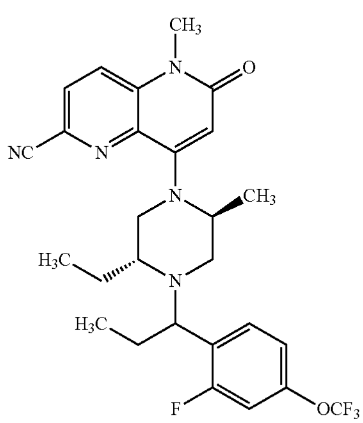 [SMILES: CCC(c1ccc(OC(F)(F)F)cc1F)N1C[C@H](C)N(c2cc(=O)n(C)c3ccc(C#N)nc23)C[C@H]1CC] | 2.0 | 532.1 | H | 1.7 B |

TABLE 3-continued

| Ex. No. | Structure | QC Method | Obs. MS | Stereo Chem | RT/Meth. |
|---|---|---|---|---|---|
| 422 | 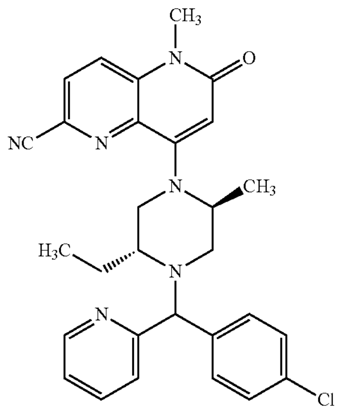 [SMILES: CC[C@@H]1CN(c2cc(=O)n(C)c3ccc(C#N)nc23)[C@@H](C)CN1C(c1ccc(Cl)cc1)c1ccccn1] | 2.0 | 512.9 | H | 1.6 B |
| 423 | 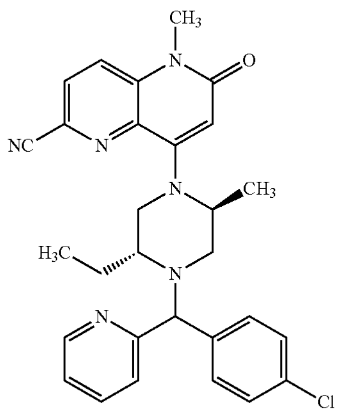 [SMILES: CC[C@@H]1CN(c2cc(=O)n(C)c3ccc(C#N)nc23)[C@@H](C)CN1C(c1ccc(Cl)cc1)c1ccccn1] | 1.0 | 513.1 | H | 2.3 B |

Examples 424 and 425

7-fluoro-8-((2S,5R)-4-(1-(4-fluorophenyl)ethyl-1-d)-2,5-dimethylpiperazin-1-yl)-5-methyl-6-oxo-5,6-dihydro-1,5-naphthyridine-2-carbonitrile and 7-fluoro-8-((2S,5R)-4-(1-(4-fluorophenyl)ethyl-1-d)-2,5-dimethylpiperazin-1-yl)-5-methyl-6-oxo-5,6-dihydro-1,5-naphthyridine-2-carbonitrile (424-425)

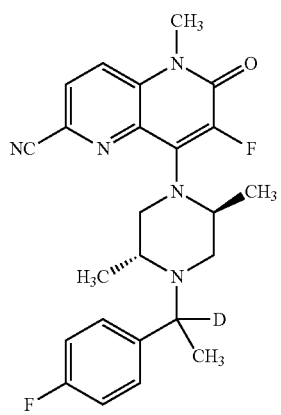

8-((2S,5R)-2,5-dimethylpiperazin-1-yl)-7-fluoro-5-methyl-6-oxo-5,6-dihydro-1,5-naphthyridine-2-carbonitrile bis-hydrochloride (120 mg, 0.309 mmol) was added to a solution of 1-(4-fluorophenyl)ethan-1-d-1-ol (98 mg, 0.694 mmol) and DIEA (0.28 ml, 1.603 mmol) in acetonitrile (4 mL) in a 20 mL pressure vial. (Cyanomethyl)trimethylphosphonium iodide (155 mg, 0.638 mmol) was added and the mixture was placed under nitrogen and heated at 110° C. overnight. Next, additional 1-(4-fluorophenyl)ethan-1-d-1-ol (57 mg, 0.404 mmol), DIEA (0.054 ml, 0.309 mmol) and (cyanomethyl)trimethylphosphonium iodide (75 mg, 0.309 mmol) were added and heating was continued for an additional 5 h. The mixture was then cooled, and evaporated in vacuo. The brown/amber colored residue (562 mg) was adsorbed onto silica gel and fractionated using flash chromatography using 15% EtOAc in DCM as eluent. Homogeneous fractions were combined and evaporated under reduced pressure to yield 62 mg of a brown colored oil. This material was then fractionated using SFC-chiral chromatography to afford two products.

Example 424: 15.5 mg; purity was 100% as determined by analytical LC/MS. Proton NMR was acquired in deuterated DMSO. Proton NMR: Water suppression at 3.38 ppm appears to have reduced adjacent peak intensities. NMR data is reported uncorrected. $^1$H NMR (500 MHz, DMSO-$d_6$) δ 8.18-8.11 (m, 2.0H), 7.45 (dd, J=8.2, 5.8 Hz, 2.0H), 7.14 (t, J=8.7 Hz, 2.0H), 3.89 (br s, 1.0H), 3.77 (br d, J=12.2 Hz, 1.0H), 3.62 (s, 2.2H), 3.24 (br d, J=4.6 Hz, 0.4H), 3.06-2.95 (m, 0.7H), 2.68 (br dd, J=11.4, 2.9 Hz, 0.9H), 2.06 (br dd, J=11.6, 4.9 Hz, 1.0H), 1.25 (s, 3.0H), 1.08 (d, J=6.4 Hz, 3.0H), 0.98 (br d, J=6.1 Hz, 3.0H).

Example 425: 16.5 mg; purity was 100% as determined by analytical LC/MS. Proton NMR was acquired in deuterated DMSO. Proton NMR: Water suppression at 3.38 ppm appears to have reduced adjacent peak intensities. NMR data is reported uncorrected: $^1$H NMR (500 MHz, DMSO-$d_6$) δ 8.20-8.09 (m, 2.0H), 7.40 (br t, J=6.9 Hz, 2.0H), 7.17 (br t, J=8.5 Hz, 2.0H), 4.07 (br s, 1.1H), 3.61 (s, 2.1H), 3.54 (br d, J=12.2 Hz, 0.6H), 3.12-3.05 (m, 0.5H), 2.90-2.83 (m, 0.7H), 2.30 (br dd, J=10.4, 4.9 Hz, 1.1H), 1.31 (s, 2.8H), 1.10 (br d, J=6.4 Hz, 3.0H), 1.00 (br d, J=6.1 Hz, 3.0H).

A chiral SFC separation method was developed as described in the experimental details below. Approximately 62 mg of sample was resolved into two peaks collected in MeOH w/0.1% DEA. The chiral purity for the isolates were determined using the analytical chromatographic conditions below.

| Isolate | Chiral Purity |
|---|---|
| First eluting peak | >95% |
| Second eluting peak | =94% |

Chiral SFC Preparative Chromatographic Conditions:
Instrument: Waters 100 Prep SFC
Column: Chiral IC, 21 × 250 mm. 5 micron
Mobile Phase: 70% $CO_2$/30% MeOH w/0.1% DEA
Flow Conditions: 60 mL/min
Detector Wavelength: 220 nm
Injection Details: 300 μL 62 mg dissolved in 3 mL MeOH The Examples in Table 4A were prepared from the appropriate piperazine and alcohol using (cyanomethyl)trimethylphosphonium iodide according to the general procedures disclosed in Examples 182, 424, and 425. When the reaction provided a mixture of diastereomers, the mixture was separated using either preparative chromatography or preparative chiral chromatography. The absolute stereochemistry was not assigned at the newly formed carbon-nitrogen bond.

TABLE 4A

| Ex. No. | Structure | QC Method | Obs. MS Ion | Stereo Chem | RT |
|---|---|---|---|---|---|
| 424 | 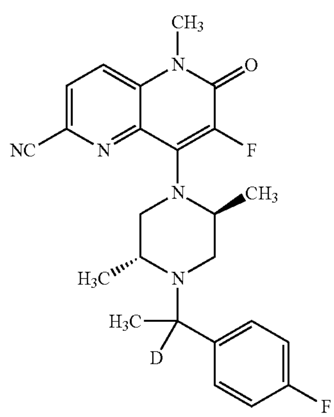 [SMILES: [2H]C(C)(c1ccc(F)cc1)N1C[C@H](C)N(c2c(F)c(=O)n(C)c3ccc(C#N)nc23)C[C@H]1C] | 2.0 | 439.2 | H | 1.21 |
| 425 | 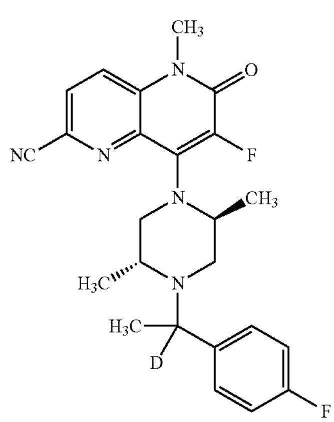 [SMILES: [2H]C(C)(c1ccc(F)cc1)N1C[C@H](C)N(c2c(F)c(=O)n(C)c3ccc(C#N)nc23)C[C@H]1C] | 2.0 | 439.2 | H | 1.21 |

TABLE 4A-continued

| Ex. No. | Structure | QC Method | Obs. MS Ion | Stereo Chem | RT |
|---|---|---|---|---|---|
| 426 | 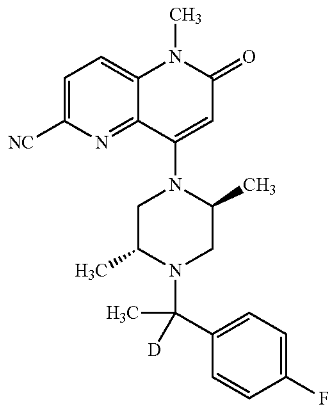 [SMILES: [2H]C(C)(c1ccc(F)cc1)N1C[C@H](C)N(c2cc(=O)n(C)c3ccc(C#N)nc23)C[C@H]1C] | 2.0 | 421.3 | H | 1.18 |
| 427 | 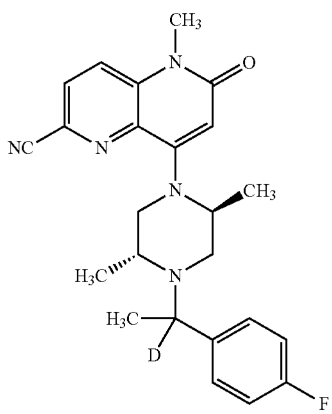 [SMILES: [2H]C(C)(c1ccc(F)cc1)N1C[C@H](C)N(c2cc(=O)n(C)c3ccc(C#N)nc23)C[C@H]1C] | 2.0 | 421.3 | H | 1.19 |
| 428 | 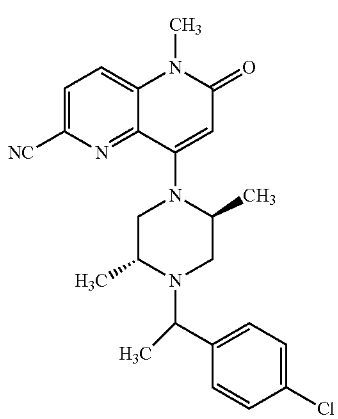 [SMILES: CC(c1ccc(Cl)cc1)N1C[C@H](C)N(c2cc(=O)n(C)c3ccc(C#N)nc23)C[C@H]1C] | | | H | |

TABLE 4A-continued

| Ex. No. | Structure | QC Method | Obs. MS Ion | Stereo Chem | RT |
|---|---|---|---|---|---|
| 429 | 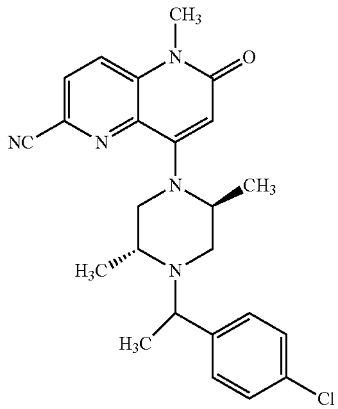 [SMILES: CC(c1ccc(Cl)cc1)N1C[C@H](C)N(c2cc(=O)n(C)c3ccc(C#N)nc23)C[C@H]1C] | | | H | |
| 430 | 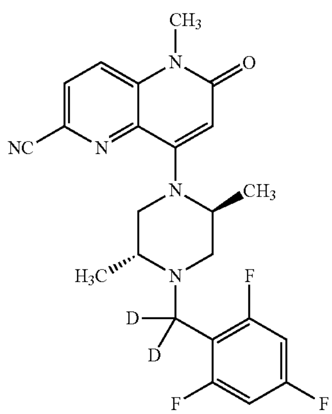 [SMILES: [2H]C([2H])(c1c(F)cc(F)cc1F)N1C[C@H](C)N(c2cc(=O)n(C)c3ccc(C#N)nc23)C[C@H]1C] | 1.0 | 441.2 | H | 2.28 |
| 431 | 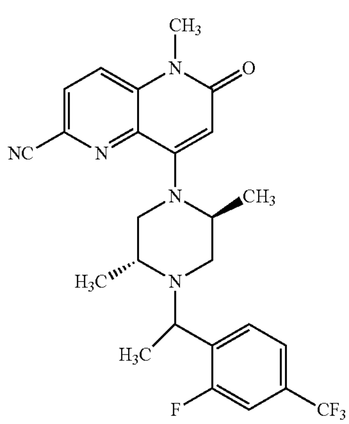 [SMILES: CC(c1ccc(C(F)(F)F)cc1F)N1C[C@H](C)N(c2cc(=O)n(C)c3ccc(C#N)nc23)C[C@H]1C] | 1.0 | 488.2 | D | 2.64 |

TABLE 4A-continued

| Ex. No. | Structure | QC Method | Obs. MS Ion | Stereo Chem | RT |
|---|---|---|---|---|---|
| 432 | 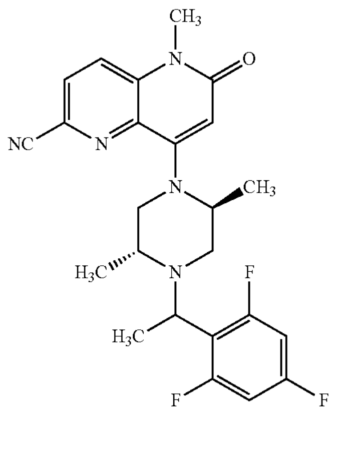 [SMILES: CC(c1c(F)cc(F)cc1F)N1C[C@H](C)N(c2cc(=O)n(C)c3ccc(C#N)nc23)C[C@H]1C] | 1.0 | 456.1 | H | 2.51 |
| 433 | 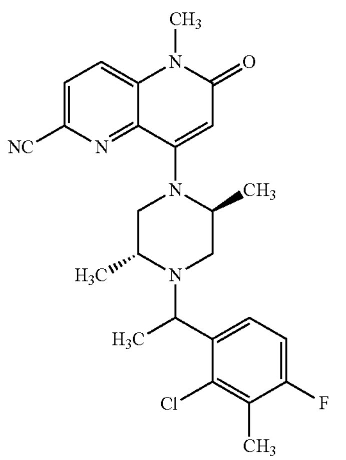 [SMILES: Cc1c(F)ccc(C(C)N2C[C@H](C)N(c3cc(=O)n(C)c4ccc(C#N)nc34)C[C@H]2C)c1Cl] | 1.0 | 468.2 | H | 2.82 |
| 434 | 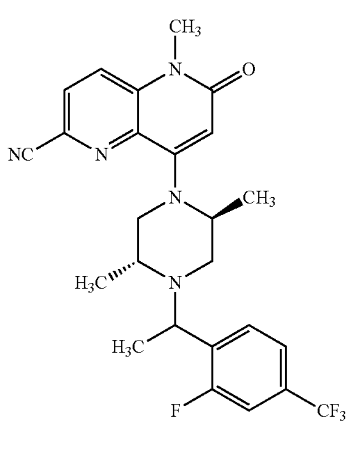 [SMILES: CC(c1ccc(C(F)(F)F)cc1F)N1C[C@H](C)N(c2cc(=O)n(C)c3ccc(C#N)nc23)C[C@H]1C] | 2.0 | 488.2 | H | 1.41 |

TABLE 4A-continued

| Ex. No. | Structure | QC Method | Obs. MS Ion | Stereo Chem | RT |
|---|---|---|---|---|---|
| 435 | 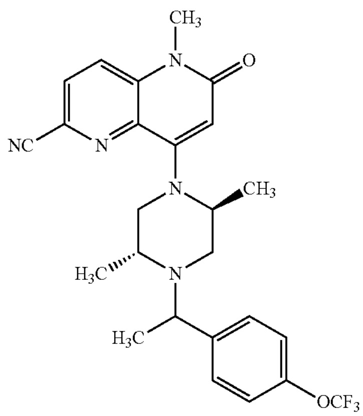 [SMILES: CC(c1ccc(OC(F)(F)F)cc1)N1C[C@H](C)N(c2cc(=O)n(C)c3ccc(C#N)nc23)C[C@H]1C] | 2.0 | 486.2 | H | 1.53 |
| 436 | 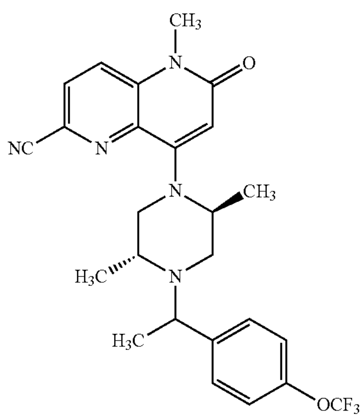 [SMILES: CC(c1ccc(OC(F)(F)F)cc1)N1C[C@H](C)N(c2cc(=O)n(C)c3ccc(C#N)nc23)C[C@H]1C] | 2.0 | 486.2 | H | 1.52 |
| 437 | 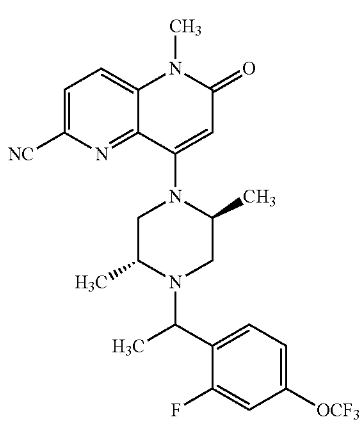 [SMILES: CC(c1ccc(OC(F)(F)F)cc1F)N1C[C@H](C)N(c2cc(=O)n(C)c3ccc(C#N)nc23)C[C@H]1C] | 2.0 | 504.2 | H | 1.72 |

TABLE 4A-continued

| Ex. No. | Structure | QC Method | Obs. MS Ion | Stereo Chem | RT |
|---|---|---|---|---|---|
| 438 | 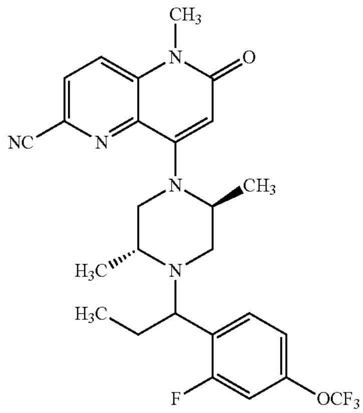 [SMILES: CCC(c1ccc(OC(F)(F)F)cc1F)N1C[C@H](C)N(c2cc(=O)n(C)c3ccc(C#N)nc23)C[C@H]1C] | 2.0 | 518.2 | D | 1.66 |
| 439 | 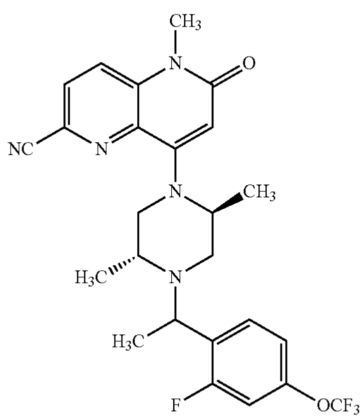 [SMILES: CC(c1ccc(OC(F)(F)F)cc1F)N1C[C@H](C)N(c2cc(=O)n(C)c3ccc(C#N)nc23)C[C@H]1C] | 1.0 | 504.1 | H | 2.67 |
| 440 | 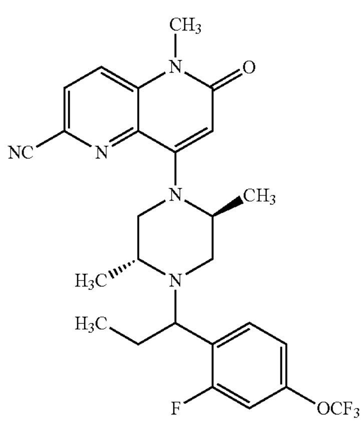 [SMILES: CCC(c1ccc(OC(F)(F)F)cc1F)N1C[C@H](C)N(c2cc(=O)n(C)c3ccc(C#N)nc23)C[C@H]1C] | 2.0 | 518.3 | H | 1.67 |

TABLE 4A-continued
| Ex. No. | Structure | QC Method | Obs. MS Ion | Stereo Chem | RT |
|---|---|---|---|---|---|
| 441 | 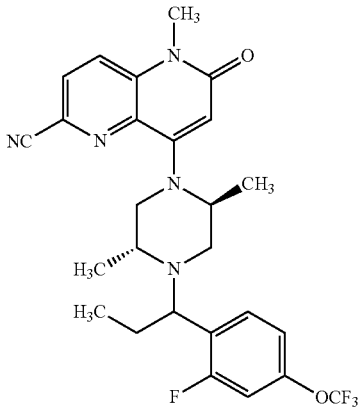 | 1.0 | 518.3 | H | 2.78 |
| 442 | 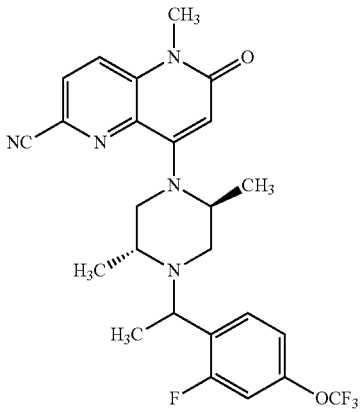 | 1.0 | 504.3 | H | 2.67 |
| 443 | 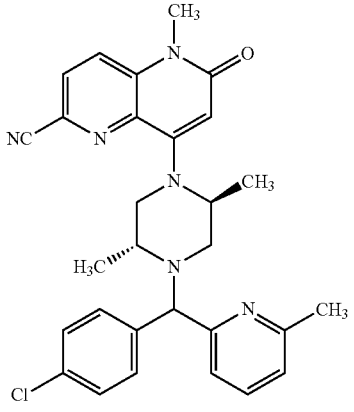 [SMILES: Cc1cccc(C(c2ccc(Cl)cc2)N2C[C@H](C)N(c3cc(=O)n(C)c4ccc(C#N)nc34)C[C@H]2C)n1] | 1.0 | 513.1 | H | 2.28 |

TABLE 4A-continued

| Ex. No. | Structure | QC Method | Obs. MS Ion | Stereo Chem | RT |
|---|---|---|---|---|---|
| 444 | 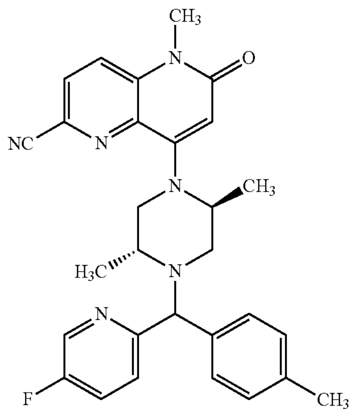 [SMILES: Cc1ccc(C(c2ccc(F)cn2)N2C[C@H](C)N(c3cc(=O)n(C)c4ccc(C#N)nc34)C[C@H]2C)cc1] | 1.0 | 497.2 | H | 2.12 |
| 445 | 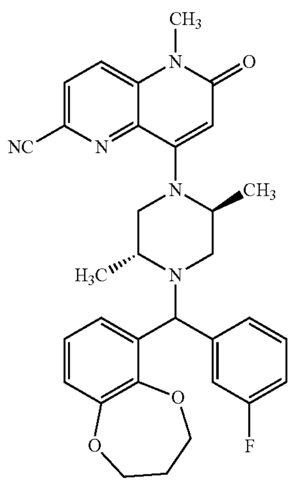 [SMILES: C[C@@H]1CN(c2cc(=O)n(C)c3ccc(C#N)nc23)[C@@H](C)CN1C(c1cccc(F)c1)c1cccc2c1OCCCO2] | 1.0 | 554.1 | H | 2.36 |
| 446 | 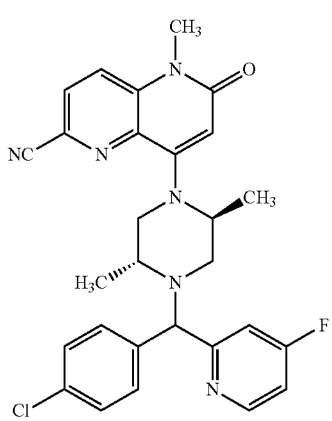 [SMILES: C[C@@H]1CN(c2cc(=O)n(C)c3ccc(C#N)nc23)[C@@H](C)CN1C(c1ccc(Cl)cc1)c1cc(F)ccn1] | 1.0 | 517.2 | D | 2.43 |

TABLE 4A-continued

| Ex. No. | Structure | QC Method | Obs. MS Ion | Stereo Chem | RT |
|---|---|---|---|---|---|
| 447 | 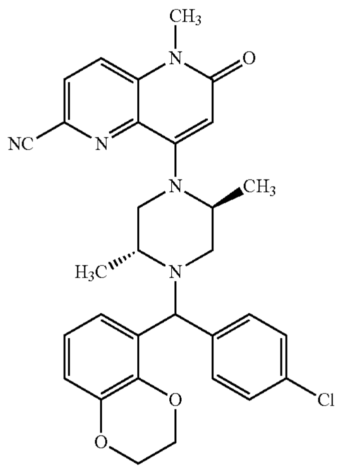 [SMILES: C[C@@H]1CN(c2cc(=O)n(C)c3ccc(C#N)nc23)[C@@H](C)CN1C(c1ccc(Cl)cc1)c1cccc2c1OCCO2] | 1.0 | 556.4 | H | 2.55 |
| 448 | 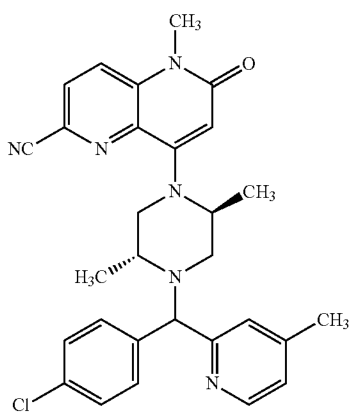 [SMILES: Cc1ccnc(C(c2ccc(Cl)cc2)N2C[C@H](C)N(c3cc(=O)n(C)c4ccc(C#N)nc34)C[C@H]2C)c1] | 1.0 | 513.1 | H | 2.25 |
| 449 | 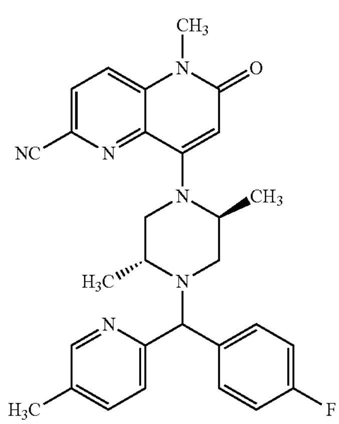 [SMILES: Cc1ccc(C(c2ccc(F)cc2)N2C[C@H](C)N(c3cc(=O)n(C)c4ccc(C#N)nc34)C[C@H]2C)nc1] | 1.0 | 497.2 | H | 1.47 |

TABLE 4A-continued
| Ex. No. | Structure | QC Method | Obs. MS Ion | Stereo Chem | RT |
|---|---|---|---|---|---|
| 450 | 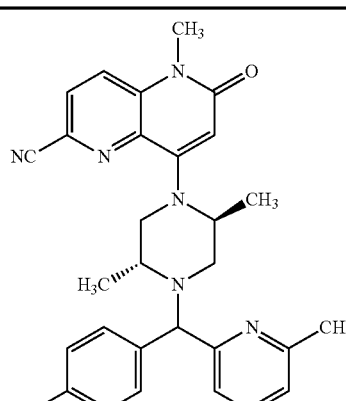 | 1.0 | 493.2 | H | 1.99 |
| 451 | 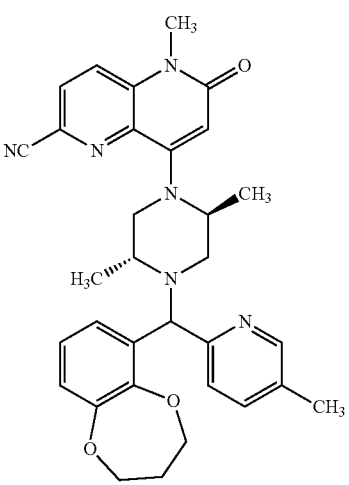 [SMILES: Cc1ccc(C(c2cccc3c2OCCCO3)N2C[C@H](C)N(c3cc(=O)n(C)c4ccc(C#N)nc34)C[C@H]2C)nc1] | 1.0 | 551.2 | H | 2.28 |
| 452 | 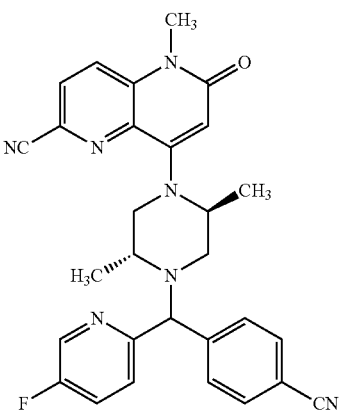 [SMILES: C[C@@H]1CN(c2cc(=O)n(C)c3ccc(C#N)nc23)[C@@H](C)CN1C(c1ccc(C#N)cc1)c1ccc(F)cn1] | 1.0 | 508.2 | D | 2.20 |

TABLE 4A-continued

| Ex. No. | Structure | QC Method | Obs. MS Ion | Stereo Chem | RT |
|---|---|---|---|---|---|
| 453 | 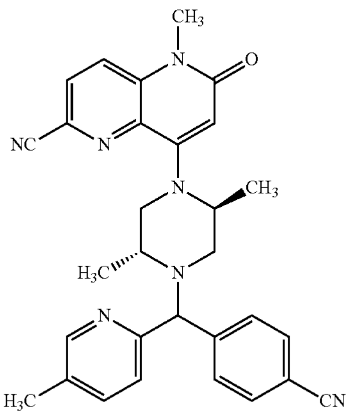 [SMILES: Cc1ccc(C(c2ccc(C#N)cc2)N2C[C@H](C)N(c3cc(=O)n(C)c4ccc(C#N)nc34)C[C@H]2C)nc1] | 1.0 | 504.2 | D | 2.2 |
| 454 | 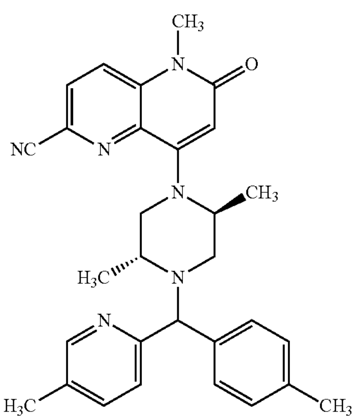 | 1.0 | 493.4 | H | 2.15 |
| 455 | 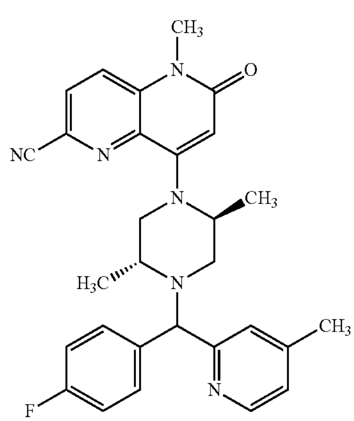 [SMILES: Cc1ccnc(C(c2ccc(F)cc2)N2C[C@H](C)N(c3cc(=O)n(C)c4ccc(C#N)nc34)C[C@H]2C)c1] | 1.0 | 496.9 | H | 2.10 |

TABLE 4A-continued

| Ex. No. | Structure | QC Method | Obs. MS Ion | Stereo Chem | RT |
|---|---|---|---|---|---|
| 456 | 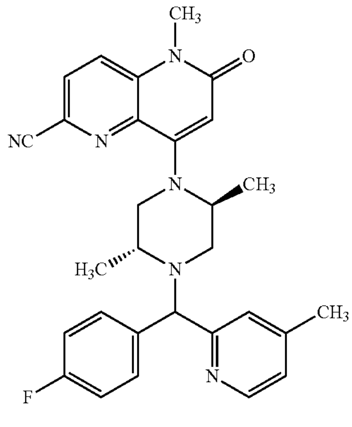 [SMILES: Cc1ccnc(C(c2ccc(F)cc2)N2C[C@H](C)N(c3cc(=O)n(C)c4ccc(C#N)nc34)C[C@H]2C)c1] | 1.0 | 497.2 | H | 2.10 |
| 457 | 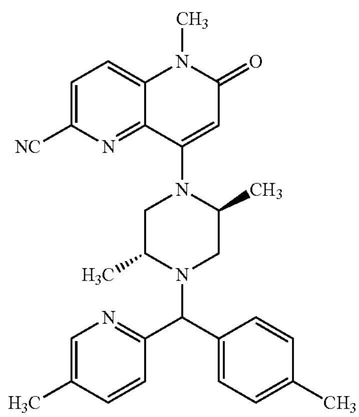 | 1.0 | 493.4 | H | 2.16 |
| 458 | 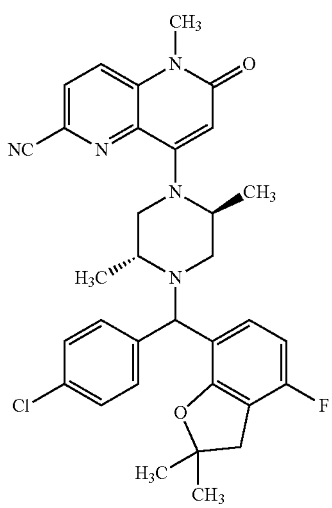 [SMILES: C[C@@H]1CN(c2cc(=O)n(C)c3ccc(C#N)nc23)[C@@H](C)CN1C(c1ccc(Cl)cc1)c1ccc(F)c2c1OC(C)(C)C2] | 1.0 | 586.0 | H | 2.83 |

TABLE 4A-continued

| Ex. No. | Structure | QC Method | Obs. MS Ion | Stereo Chem | RT |
|---|---|---|---|---|---|
| 459 | 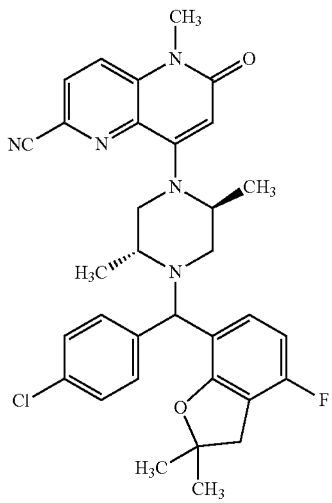 [SMILES: C[C@@H]1CN(c2cc(=O)n(C)c3ccc(C#N)nc23)[C@@H](C)CN1C(c1ccc(Cl)cc1)c1ccc(F)c2c1OC(C)(C)C2] | 1.0 | 585.9 | H | 2.82 |
| 460 | 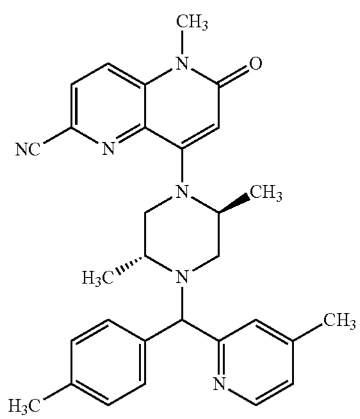 | 1.0 | 493.3 | H | 2.15 |
| 461 | 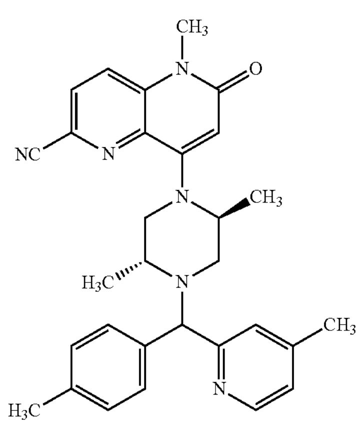 | 1.0 | 493.3 | H | 2.16 |

TABLE 4A-continued
| Ex. No. | Structure | QC Method | Obs. MS Ion | Stereo Chem | RT |
|---|---|---|---|---|---|
| 462 | 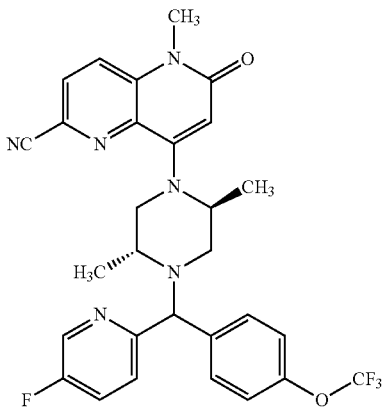 [SMILES: C[C@@H]1CN(c2cc(=O)n(C)c3ccc(C#N)nc23)[C@@H](C)CN1C(c1ccc(OC(F)(F)F)cc1)c1ccc(F)cn1] | 1.0 | 567.2 | D | 2.49 |
| 463 | 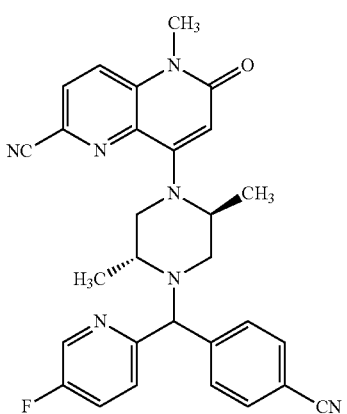 [SMILES: C[C@@H]1CN(c2cc(=O)n(C)c3ccc(C#N)nc23)[C@@H](C)CN1C(c1ccc(C#N)cc1)c1ccc(F)cn1] | 1.0 | 508.2 | H | 2.12 |
| 464 | 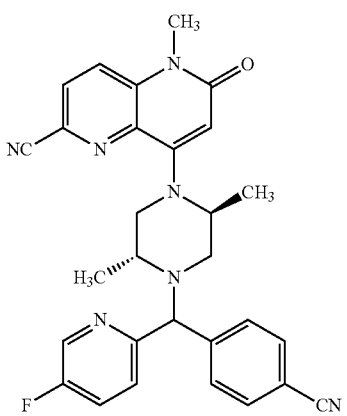 [SMILES: C[C@@H]1CN(c2cc(=O)n(C)c3ccc(C#N)nc23)[C@@H](C)CN1C(c1ccc(C#N)cc1)c1ccc(F)cn1] | 1.0 | 508.2 | H | 2.13 |

TABLE 4A-continued
| Ex. No. | Structure | QC Method | Obs. MS Ion | Stereo Chem | RT |
|---|---|---|---|---|---|
| 465 | 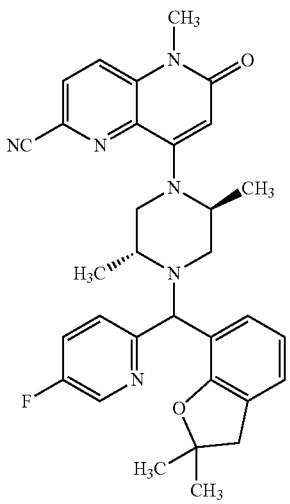 [SMILES: C[C@@H]1CN(c2cc(=O)n(C)c3ccc(C#N)nc23)[C@@H](C)CN1C(c1ccc(F)cn1)c1cccc2c1OC(C)(C)C2] | 1.0 | 553.0 | H | 2.34 |
| 466 | 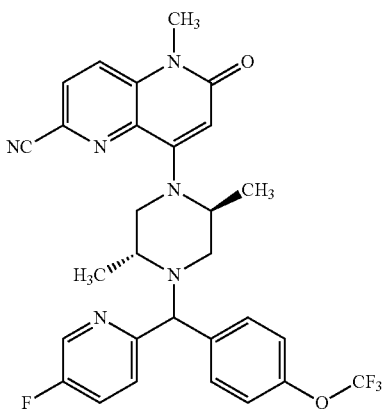 [SMILES: C[C@@H]1CN(c2cc(=O)n(C)c3ccc(C#N)nc23)[C@@H](C)CN1C(c1ccc(OC(F)(F)F)cc1)c1ccc(F)cn1] | 1.0 | 567.2 | H | 2.50 |
| 467 | 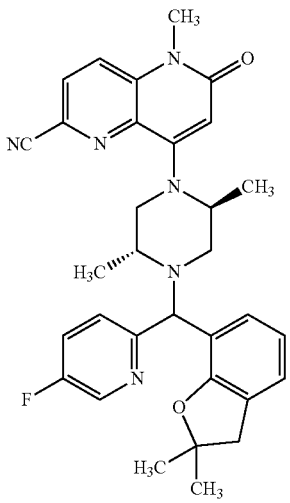 [SMILES: C[C@@H]1CN(c2cc(=O)n(C)c3ccc(C#N)nc23)[C@@H](C)CN1C(c1ccc(F)cn1)c1cccc2c1OC(C)(C)C2] | 1.0 | 553.3 | H | 2.36 |

TABLE 4A-continued

| Ex. No. | Structure | QC Method | Obs. MS Ion | Stereo Chem | RT |
|---|---|---|---|---|---|
| 468 | 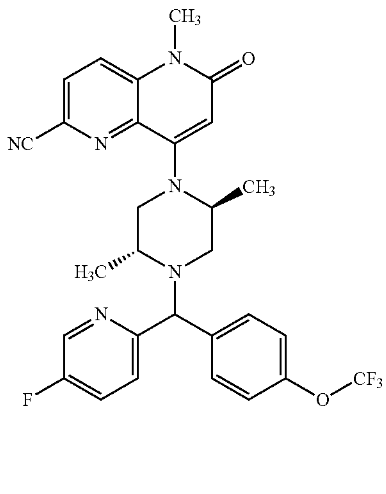 [SMILES: C[C@@H]1CN(c2cc(=O)n(C)c3ccc(C#N)nc23)[C@@H](C)CN1C(c1ccc(OC(F)(F)F)cc1)c1ccc(F)cn1] | 1.0 | 567.2 | H | 2.50 |
| 469 | 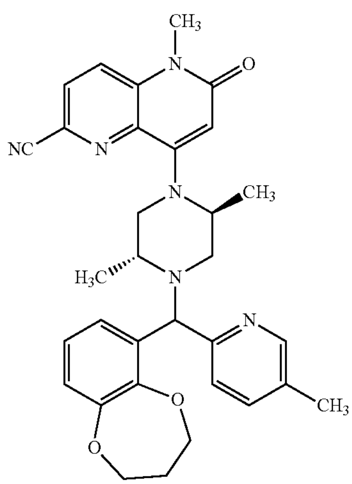 [SMILES: Cc1ccc(C(c2cccc3c2OCCCO3)N2C[C@H](C)N(c3cc(=O)n(C)c4ccc(C#N)nc34)C[C@H]2C)nc1] | 1.0 | 551.2 | H | 2.3 |
| 470 | 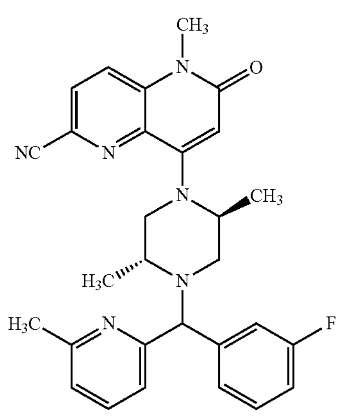 [SMILES: Cc1cccc(C(c2cccc(F)c2)N2C[C@H](C)N(c3cc(=O)n(C)c4ccc(C#N)nc34)C[C@H]2C)n1] | 1.0 | 497.1 | H | 2.19 |

TABLE 4A-continued

| Ex. No. | Structure | QC Method | Obs. MS Ion | Stereo Chem | RT |
|---|---|---|---|---|---|
| 471 | 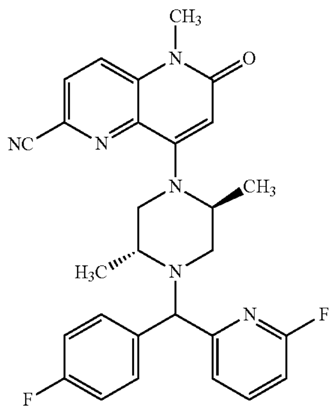 [SMILES: C[C@@H]1CN(c2cc(=O)n(C)c3ccc(C#N)nc23)[C@@H](C)CN1C(c1ccc(F)cc1)c1cccc(F)n1] | 2.0 | 501.3 | H | 1.44 |
| 472 | 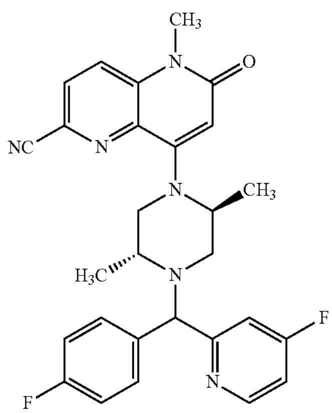 [SMILES: C[C@@H]1CN(c2cc(=O)n(C)c3ccc(C#N)nc23)[C@@H](C)CN1C(c1ccc(F)cc1)c1cc(F)ccn1] | 2.0 | 501.3 | D | 2.33 |
| 473 | 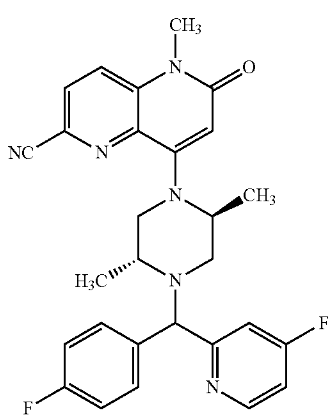 | 2.0 | 501.3 | H | 1.51 |

TABLE 4A-continued
| Ex. No. | Structure | QC Method | Obs. MS Ion | Stereo Chem | RT |
|---|---|---|---|---|---|
| 474 | 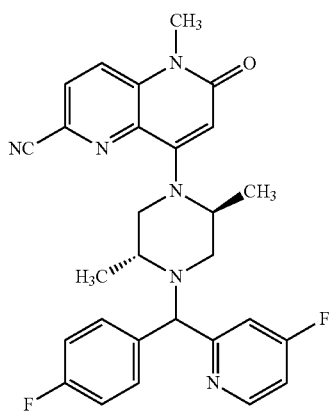 [SMILES: C[C@@H]1CN(c2cc(=O)n(C)c3ccc(C#N)nc23)[C@@H](C)CN1C(c1ccc(F)cc1)c1cc(F)ccn1] | 2.0 | 501.2 | H | 1.48 |
| 475 | 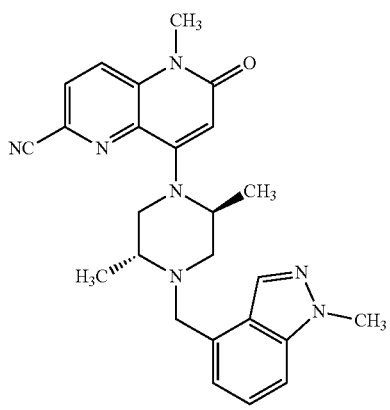 [SMILES: C[C@@H]1CN(c2cc(=O)n(C)c3ccc(C#N)nc23)[C@@H](C)CN1Cc1cccc2c1cnn2C] | | | H | |
| 476 | 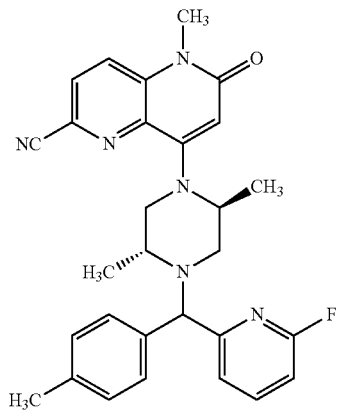 [SMILES: Cc1ccc(C(c2cccc(F)n2)N2C[C@H](C)N(c3cc(=O)n(C)c4ccc(C#N)nc34)C[C@H]2C)cc1] | 1.0 | 497.2 | D | 2.24 |

TABLE 4A-continued
| Ex. No. | Structure | QC Method | Obs. MS Ion | Stereo Chem | RT |
|---|---|---|---|---|---|
| 477 | 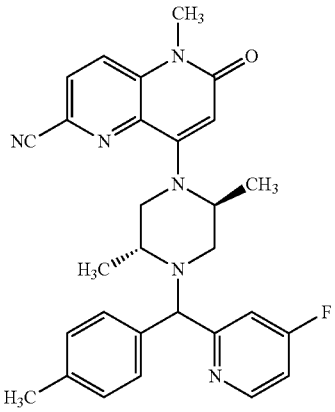 [SMILES: Cc1ccc(C(c2cc(F)ccn2)N2C[C@H](C)N(c3cc(=O)n(C)c4ccc(C#N)nc34)C[C@H]2C)cc1] | 1.0 | 497.1 | H | 2.13 |
| 478 | 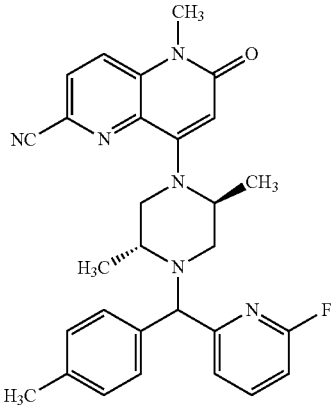 [SMILES: Cc1ccc(C(c2cccc(F)n2)N2C[C@H](C)N(c3cc(=O)n(C)c4ccc(C#N)nc34)C[C@H]2C)cc1] | 1.0 | 497.2 | H | 2.14 |
| 479 | 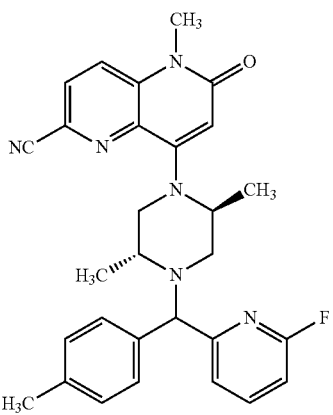 [SMILES: Cc1ccc(C(c2cccc(F)n2)N2C[C@H](C)N(c3cc(=O)n(C)c4ccc(C#N)nc34)C[C@H]2C)cc1] | 1.0 | 497.1 | H | 2.24 |

TABLE 4A-continued
| Ex. No. | Structure | QC Method | Obs. MS Ion | Stereo Chem | RT |
|---|---|---|---|---|---|
| 480 | 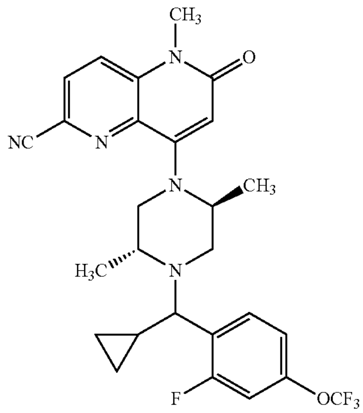 [SMILES: C[C@@H]1CN(c2cc(=O)n(C)c3ccc(C#N)nc23)[C@@H](C)CN1C(c1ccc(OC(F)(F)F)cc1F)C1CC1] | 2.0 | 530.4 | H | 1.81 |
| 481 | 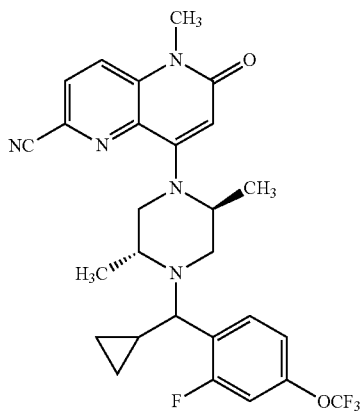 [SMILES: C[C@@H]1CN(c2cc(=O)n(C)c3ccc(C#N)nc23)[C@@H](C)CN1C(c1ccc(OC(F)(F)F)cc1F)C1CC1] | 1.0 | 530.4 | H | 2.61 |
| 482 | 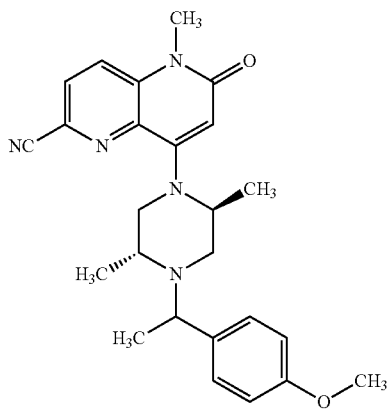 [SMILES: COc1ccc(C(C)N2C[C@H](C)N(c3cc(=O)n(C)c4ccc(C#N)nc34)C[C@H]2C)cc1] | 2.0 | 446.3 | H | 2.25 |

TABLE 4A-continued

| Ex. No. | Structure | QC Method | Obs. MS Ion | Stereo Chem | RT |
| --- | --- | --- | --- | --- | --- |
| 483 | 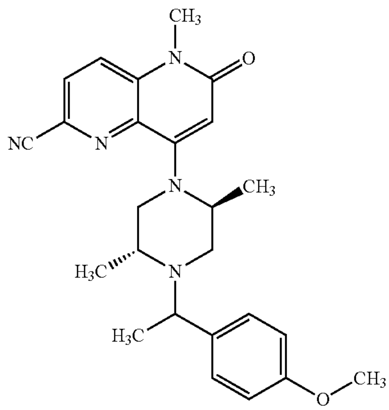 [SMILES: COc1ccc(C(C)N2C[C@H](C)N(c3cc(=O)n(C)c4ccc(C#N)nc34)C[C@H]2C)cc1] | 2.0 | 446.3 | H | 2.18 |
| 484 | 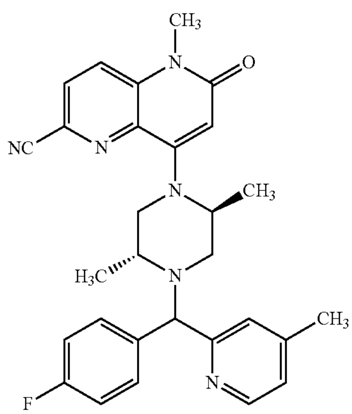 [SMILES: Cc1ccnc(C(c2ccc(F)cc2)N2C[C@H](C)N(c3cc(=O)n(C)c4ccc(C#N)nc34)C[C@H]2C)c1] | 1.0 | 497.3 | D | 2.0 |
| 485 | 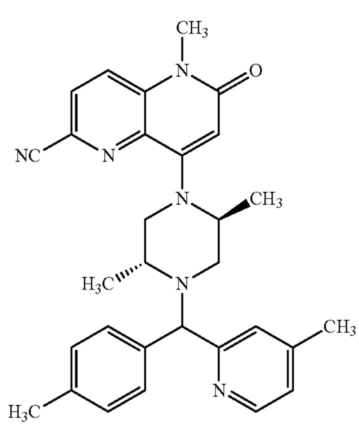 | 1.0 | 493.4 | D | 2.1 |

TABLE 4A-continued
| Ex. No. | Structure | QC Method | Obs. MS Ion | Stereo Chem | RT |
|---|---|---|---|---|---|
| 486 | 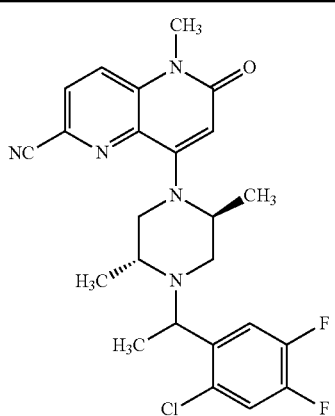 | 1.0 | 472.1 | H | 1.5 |
| 487 | 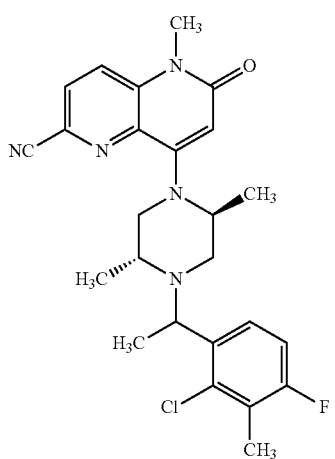 | 1.0 | 468.2 | H | 2.8 |
| 488 | 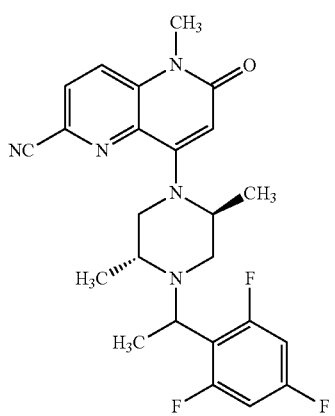 [SMILES: CC(c1c(F)cc(F)cc1F)N1C[C@H](C)N(c2cc(=O)n(C)c3ccc(C#N)nc23)C[C@H]1C] | 1.0 | 456.1 | H | 2.5 |

TABLE 4A-continued

| Ex. No. | Structure | QC Method | Obs. MS Ion | Stereo Chem | RT |
|---|---|---|---|---|---|
| 489 | 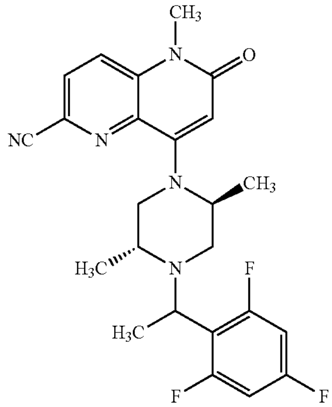 [SMILES: CC(c1c(F)cc(F)cc1F)N1C[C@H](C)N(c2cc(=O)n(C)c3ccc(C#N)nc23)C[C@H]1C] | | | | |

TABLE 4B

| Ex. No. | Structure | Obs. MS Ion | QC Method | Stereo Chem | RT |
|---|---|---|---|---|---|
| 555 | 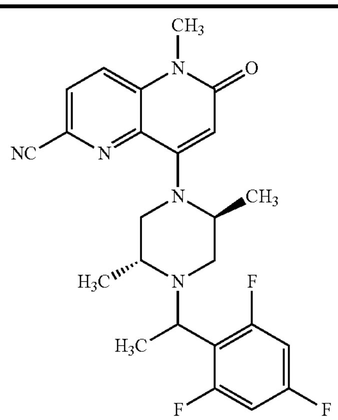 | | | | |

Example 556

8-[(2S,5R)-4-[2-fluoro-1-(4-fluorophenyl)ethyl]-2,5-dimethylpiperazin-1-yl]-5-methyl-6-oxo-5,6-dihydro-1,5-naphthyridine-2-carbonitrile

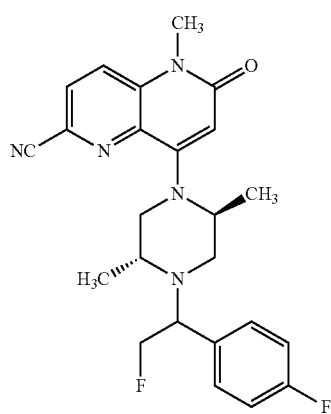

(556)

In a sealed vial, 8-((2S,5R)-4-(1-(4-fluorophenyl)-2-hydroxyethyl)-2,5-dimethylpiperazin-1-yl)-5-methyl-6-oxo-5,6-dihydro-1,5-naphthyridine-2-carbonitrile (70 µL, 0.166 mmol) was dissolved in dichloromethane (828 µL) and cooled on an ice bath. After stirring for 5 minutes, bis(2-methoxyethyl)aminosulfur trifluoride (36.6 mg, 0.166 mmol) was added. The reaction was sealed and allowed to slowly warm to room temperature over 3 hours. LC/MS analysis showed the starting material was consumed and a new major peak present consistent with the product. A saturated solution of aqueous sodium carbonate was added dropwise until gas evolution ceased. The aqueous portion was extracted 2 times with dichloromethane. The combined organic portions were dried under a stream of nitrogen. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 30% B, 30-70% B over 20 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation to provide 42 mg of the title compound. Stereochemistry: D Examples 557 and 558

8-((2S,5R)-4-(1-(4-fluorophenyl)-2-hydroxyethyl)-2,5-dimethylpiperazin-1-yl)-5-methyl-6-oxo-5,6-dihydro-1,5-naphthyridine-2-carbonitrile

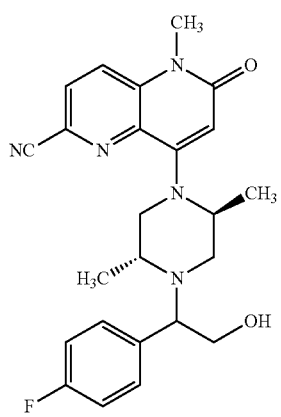

(557-558)

Crude 2-((2R,5S)-2,5-dimethylpiperazin-1-yl)-2-(4-fluorophenyl)ethan-1-ol, TFA (546 mg, 1.490 mmol) and 6-cyano-1-methyl-2-oxo-1,2-dihydro-1,5-naphthyridin-4-yl trifluoromethanesulfonate (497 mg, 1.490 mmol) were dissolved in acetonitrile (14.9 mL). Hunig's base (0.260 mL, 1.490 mmol) was added and the reaction mixture was heated at 80° C. overnight. The crude material was chromatographed with 0-15% methanol in dichloromethane on a 24 g silica gel column to give the product as a mixture of diastereomers. The crude material was purified via preparative LC/MS with the following conditions: Column: XBridge C18, 200 mm×19 mm, 5-μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-55% B over 25 minutes, then a 5 minute hold at 100% B; Flow Rate: 20 mL/min; Column Temperature: 25° C. Fraction collection was triggered by MS and UV signals. Fractions containing the products were combined and dried via centrifugal evaporation. Example 557 (3.3 mg) was isolated as the first eluting product and its estimated purity by LCMS analysis was 100%. Example 558 (16.7 mg) was isolated as the second eluting product and its estimated purity by LCMS analysis was 98%.

Examples 559 to 561

8-((2S,5R)-4-(1-(4-fluorophenyl)-2-methoxyethyl)-2,5-dimethylpiperazin-1-yl)-5-methyl-6-oxo-5,6-dihydro-1,5-naphthyridine-2-carbonitrile (559-560) and 8-((2S,5R)-4-(2-(4-fluorophenyl)-2-methoxyethyl)-2,5-dimethylpiperazin-1-yl)-5-methyl-6-oxo-5,6-dihydro-1,5-naphthyridine-2-carbonitrile (561)

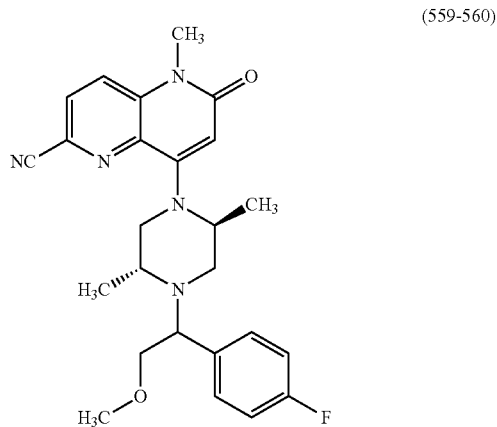

(559-560)

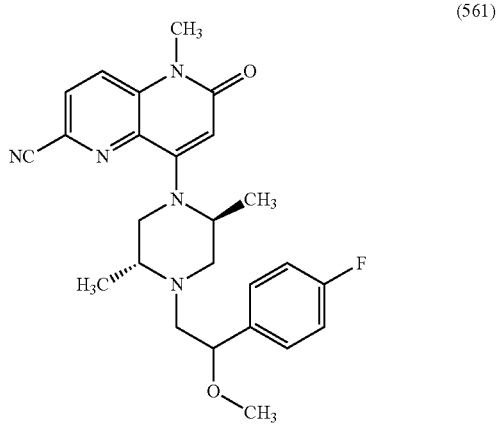

(561)

Intermediates 559A, 560A, and 561 A: 8-((2S,5R)-4-(1-(4-fluorophenyl)-2-hydroxyethyl)-2,5-dimethylpiperazin-1-yl)-5-methyl-6-oxo-5,6-dihydro-1,5-naphthyridine-2-carbonitrile (559A and 560A) and 8-((2S,5R)-4-(2-(4-fluorophenyl)-2-hydroxyethyl)-2,5-dimethylpiperazin-1-yl)-5-methyl-6-oxo-5,6-dihydro-1,5-naphthyridine-2-carbonitrile (561A)

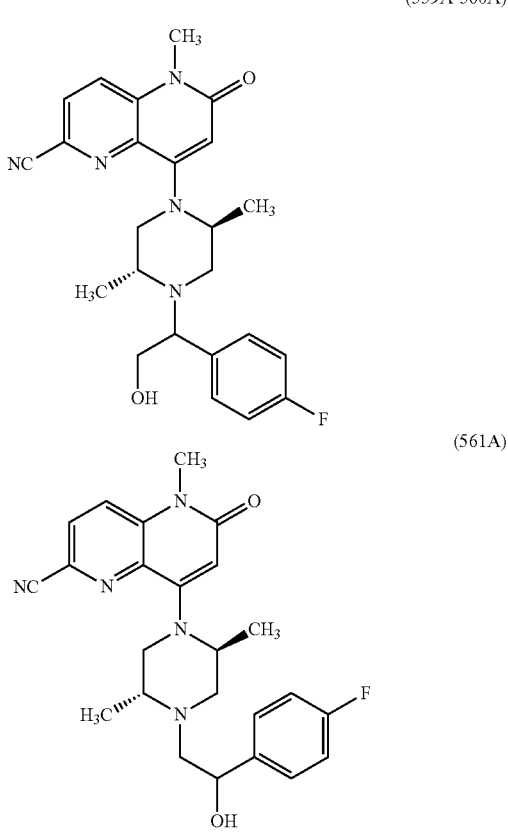

The mixture of 2-(4-fluorophenyl)oxirane (0.022 mL, 0.180 mmol) and 8-((2S,5R)-2,5-dimethylpiperazin-1-yl)-5-methyl-6-oxo-5,6-dihydro-1,5-naphthyridine-2-carbonitrile (44.6 mg, 0.15 mmol) in MeCN (0.3 mL) was heated in a microwave synthesizer at 100° C. for 10 hour. The three intermediates were separated via preparative LC/MS with the following conditions: Column: XBridge C18, 200 mm×19 mm, 5-μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 18% B, 18-58% B over 25 minutes, then a 5 minute hold at 100% B; Flow Rate: 20 mL/min; Column Temperature: 25° C. Fraction collection was triggered by MS and UV signals. Fractions containing Intermediates 559A was combined and dried via centrifugal evaporation. Fractions containing Intermediates 560A was combined and dried via centrifugal evaporation. Fractions containing Intermediates 561A was combined and dried via centrifugal evaporation.

Example 559: 8-((2S,5R)-4-(1-(4-fluorophenyl)-2-methoxyethyl)-2,5-dimethylpiperazin-1-yl)-5-methyl-6-oxo-5,6-dihydro-1,5-naphthyridine-2-carbonitrile, Isomer 1

To the mixture of Intermediate 559A (9 mg, 0.021 mmol) and iodomethane (4.52 μL, 0.072 mmol) in DMF (0.3 mL) was added NaH (2.89 mg, 0.072 mmol) 60% powder, followed by addition of THF (0.3 mL). The mixture was stirred at room temperature for 1 hour. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 31% B, 31-71% B over 20 minutes, then a 4 minute hold at 100% B; Flow Rate: 20 mL/min; Column Temperature: 25° C. Fraction collection was triggered by MS and UV signals. Fractions containing the Example 559 were combined and dried via centrifugal evaporation. Stereochemistry: H Example 560: 8-((2S,5R)-4-(1-(4-fluorophenyl)-2-methoxyethyl)-2,5-dimethylpiperazin-1-yl)-5-methyl-6-oxo-5,6-dihydro-1,5-naphthyridine-2-carbonitrile, Isomer 2

Example 560 was prepared according to the general procedure for the preparation of Example 559, except the Intermediate 560A was used in place of Intermediate 559A. Stereochemistry: H Example 561: 8-((2S,5R)-4-(2-(4-fluorophenyl)-2-methoxyethyl)-2,5-dimethylpiperazin-1-yl)-5-methyl-6-oxo-5,6-dihydro-1,5-naphthyridine-2-carbonitrile Example 561 was prepared according to the general procedure for the preparation of Example 559, except the Intermediate 561A was used in place of Intermediate 559A. Stereochemistry: H

TABLE 5

| Ex. No. | Structure | QC Method | Obs. MS Ion | Stereo Chem | RT |
|---|---|---|---|---|---|
| 567 | (structure) | 2.0 | 453.2 | H | 1.27 |

TABLE 5-continued

| Ex. No. | Structure | QC Method | Obs. MS Ion | Stereo Chem | RT |
|---|---|---|---|---|---|
| 568 | 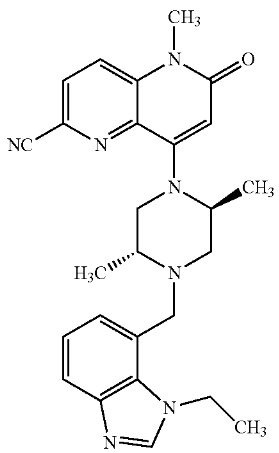 [SMILES: CCn1cnc2cccc(CN3C[C@H](C)N(c4cc(=O)n(C)c5ccc(C#N)nc45)C[C@H]3C)c21] | | | H | |
| 569 | 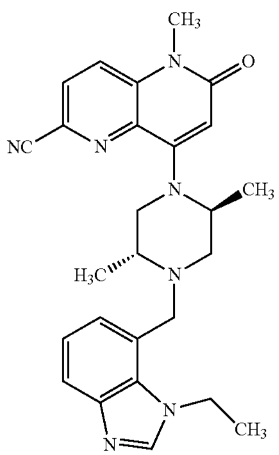 [SMILES: CCn1cnc2cccc(CN3C[C@H](C)N(c4cc(=O)n(C)c5ccc(C#N)nc45)C[C@H]3C)c21] | | | H | |
| 570 | 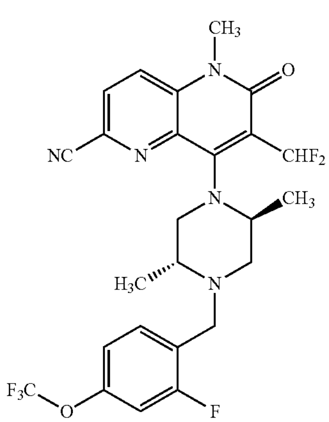 [SMILES: C[C@@H]1CN(c2c(C(F)F)c(=O)n(C)c3ccc(C#N)nc23)[C@@H](C)CN1Cc1ccc(OC(F)(F)F)cc1F] | 1.0 | 540.2 | H | 2.6 |

Example 573

8-((2S,5R)-4-(3-(dimethylamino)benzyl)-2,5-dimethylpiperazin-1-yl)-5-methyl-6-oxo-5,6-dihydro-1,5-naphthyridine-2-carbonitrile (573)

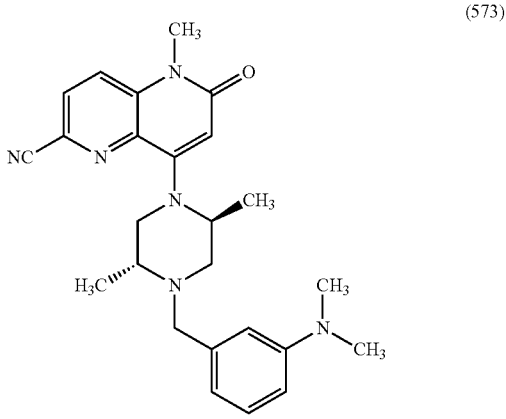 [SMILES: C[C@@H]1CN(c2cc(=O)n(C)c3ccc(C#N)nc23)[C@@H](C)CN1Cc1cccc(N(C)C)c1]

To a mixture of 3-(dimethylamino) benzaldehyde (8.95 mg, 0.060 mmol) and 8-((2S,5R)-2,5-dimethylpiperazin-1-yl)-5-methyl-6-oxo-5,6-dihydro-1,5-naphthyridine-2-carbonitrile (0.018 g, 0.06 mmol) in DCE (0.3 mL) was added acetic acid (0.014 mL, 0.240 mmol), then added sodium triacetoxyborohydride (0.025 g, 0.120 mmol). The reaction mixture was stirred at room temperature for 16 hours. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 39% B, 39-79% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation. Stereochemistry: H.

Examples 574 and 575

8-((2S,5R)-4-(1-(4-fluorophenyl)propyl-1-yl)-2,5-dimethylpiperazin-1-yl)-5-methyl-6-oxo-5,6-dihydro-1,5-naphthyridine-2-carbonitrile (574-575)

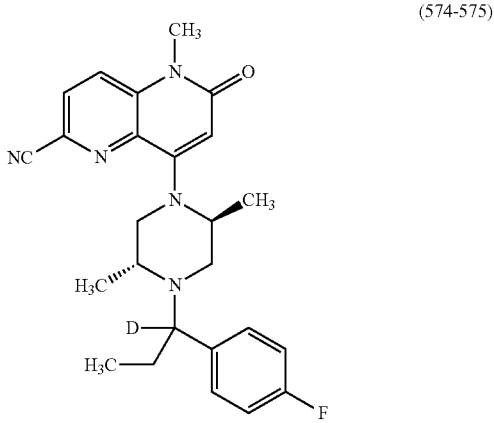 [SMILES: [2H]C(CC)(c1ccc(F)cc1)N1C[C@H](C)N(c2cc(=O)n(C)c3ccc(C#N)nc23)C[C@H]1C]

A mixture of 8-((2S,5R)-2,5-dimethylpiperazin-1-yl)-5-methyl-6-oxo-5,6-dihydro-1,5-naphthyridine-2-carbonitrile (100 mg, 0.336 mmol), 4'-fluoropropiophenone (0.056 mL, 0.404 mmol), and titanium(IV) isopropoxide (0.4 mL, 1.365 mmol) in anhydrous THF (0.5 mL) were placed in a 1 dram vial and sealed under nitrogen. The mixture was heated at 70° C. overnight, during which time it became an orange colored solution. After cooling, sodium cyanoborodeuteride (44.0 mg, 0.668 mmol) and methanol-d4 (0.4 mL) (Aldrich >99.8 atom % D) were added and heating was continued at 45° C. for 2 h. The reaction mixture was then cooled and quenched by the addition of 1 mL of D20. The resultant mixture was suspended in water and chloroform. This suspension was filtered, the solid material was washed with chloroform and the washings combined with the filtrate and transferred to a separatory funnel. The organic layer was collected, dried over $Na_2SO_4$, filtered and concentrated in vacuo. The residue (142 mg) was then fractionated using flash chromatography using silica gel eluted with 15% EtOAc in DCM. Homogeneous fractions were combined and evaporated under reduced pressure to give 57.8 mg of a pale yellow foam. This material was dissolved in 2 mL of acetonitrile and further purified using preparative HPLC. [Column: Sunfire C18 19 mm×150 mm, Solvent A: 10% ACN-90% $H_2O$-0.1% TFA, Solvent B: 90% ACN-10% $H_2O$-0.1% TFA: Start % B 10, Finish % B100, Gradient Time 20 min. Collection by UV, wavelength, 220 nm.]. The main peak was collected and concentrated in vacuo. The residue was partitioned between DCM and 1 M $Na_2CO_3$ solution. The organic phase was collected and the aqueous phase re-extracted with DCM. The combined extracts were dried over $Na_2SO_4$, filtered and concentrated to give 32.2 mg of a pale yellow solid. This material was then fractionated using SFC-chiral chromatography to provide two diastereomeric products The yield of the Example 574 was 6.9 mg, and its purity was 95% as determined by analytical LC/MS. Proton NMR was acquired in deuterated DMSO. Water suppression at 3.52 ppm appeared to have reduced adjacent peak intensities and obscured some peaks with remaining residual water. NMR is reported uncorrected: $^1$H NMR (500 MHz, DMSO-$d_6$) δ 8.10 (d, J=8.8 Hz, 1.0H), 8.05-8.00 (m, 1.0H), 7.34 (br dd, J=8.4, 5.6 Hz, 2.1H), 7.13 (br t, J=8.7 Hz, 2.0H), 5.98 (s, 1.0H), 4.39 (br s, 0.8H), 2.72 (br dd, J=11.6, 3.1 Hz, 1.0H), 2.06 (br d, J=11.3 Hz, 1.0H), 1.94-1.79 (m, 0.8H), 1.55-1.38 (m, 0.8H), 1.12 (br d, J=6.4 Hz, 3.0H), 1.06 (br d, J=6.4 Hz, 3.1H), 0.64-0.54 (m, 3.0H).

The yield of Example 575 was 3.4 mg, and its purity was 95% as determined by analytical LC/MS. Proton NMR was acquired in deuterated DMSO. Water suppression at 3.50 ppm appears to have reduced adjacent peak intensities and obscured some peaks with remaining residual water. NMR is reported uncorrected: $^1$H NMR (500 MHz, DMSO-$d_6$) δ 8.13-8.08 (m, 1.0H), 8.05-8.01 (m, 1.1H), 7.37 (dd, J=8.2, 5.8 Hz, 2.0H), 7.16 (t, J=8.7 Hz, 2.0H), 6.00 (s, 1.0H), 4.46 (br s, 0.7H), 3.36 (br s, 0.6H), 2.97 (dd, J=11.1, 3.2 Hz, 0.9H), 2.75-2.67 (m, 1.0H), 2.63 (br dd, J=11.4, 3.2 Hz, 0.9H), 1.89-1.75 (m, 0.8H), 1.58-1.47 (m, 0.8H), 1.21 (d, J=6.4 Hz, 3.0H), 0.97 (d, J=6.4 Hz, 3.0H), 0.66-0.56 (m, 3.0H).

A chiral SFC separation method was developed as described in the experimental details below. Approximately 33.5 mg of sample was resolved into two peaks collected in IPA w/0.1% DEA. The chiral purity for the isolates were determined using the analytical chromatographic conditions below.

| Isolate | Chiral Purity |
|---|---|
| First eluting peak | >95% |
| Second eluting peak | >95% |

Preparative Chiral SFC Chromatographic Conditions:
Instrument: Waters 100 Prep SFC
Column: Chiral AD, 30 × 250 mm. 5 micron
Mobile Phase: 85% $CO_2$/15% MeOH w/0.1% DEA
Flow Conditions: 100 mL/min
Detector Wavelength: 220 nm
Injection Details: 400 μL 29.2 mg dissolved in 3 mL MeOH The compounds in Table 7 were prepared from (R)-5-methyl-8-(3-methylpiperazin-1-yl)-6-oxo-5,6-dihydro-1,5-naphthyridine-2,7-dicarbonitrile or 8-((2S,5R)-2,5-dimethylpiperazin-1-yl)-7-fluoro-5-methyl-6-oxo-5,6-dihydro-1,5-naphthyridine-2-carbonitrile bis-hydrochloride using similar reaction conditions as those used to prepare Examples 573 to 575. When the reaction provided a mixture of diastereomers, the mixture was separated using either preparative chromatography or preparative chiral chromatography. The absolute stereochemistry was not assigned at the newly formed carbon-nitrogen bond.

TABLE 7

| Ex. No. | Structure | QC Method | Obs. MS Ion | Stereo Chem | RT |
|---|---|---|---|---|---|
| 581 | 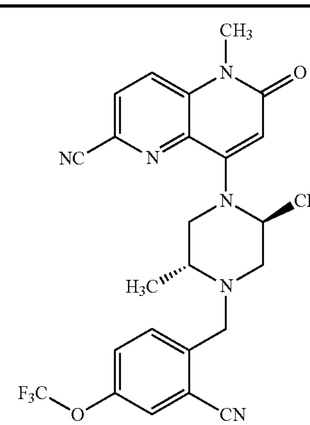 | 2.0 | 497.1 | H | 1.51 |

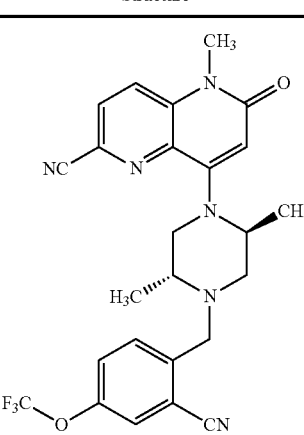

TABLE 7-continued

| Ex. No. | Structure | QC Method | Obs. MS Ion | Stereo Chem | RT |
|---|---|---|---|---|---|
| 582 | 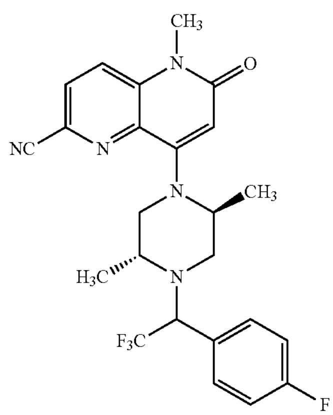 [SMILES: C[C@@H]1CN(c2cc(=O)n(C)c3ccc(C#N)nc23)[C@@H](C)CN1C(c1ccc(F)cc1)C(F)(F)F] | 2.0 | 474.2 | H | 2.23 |
| 583 | 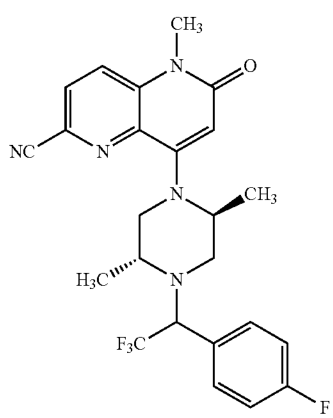 [SMILES: C[C@@H]1CN(c2cc(=O)n(C)c3ccc(C#N)nc23)[C@@H](C)CN1C(c1ccc(F)cc1)C(F)(F)F] | 2.0 | 474.2 | H | 2.25 |
| 584 | 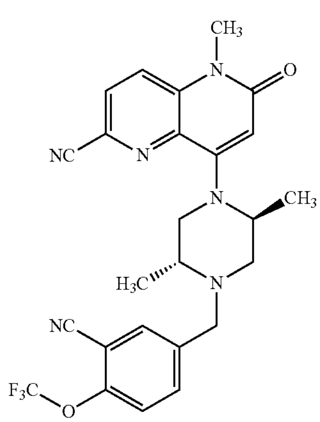 [SMILES: C[C@@H]1CN(c2cc(=O)n(C)c3ccc(C#N)nc23)[C@@H](C)CN1Cc1ccc(OC(F)(F)F)c(C#N)c1] | 1.0 | 497.2 | H | 2.33 |

TABLE 7-continued

| Ex. No. | Structure | QC Method | Obs. MS Ion | Stereo Chem | RT |
|---|---|---|---|---|---|
| 585 | 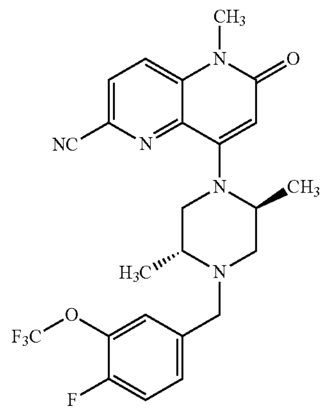 [SMILES: C[C@@H]1CN(c2cc(=O)n(C)c3ccc(C#N)nc23)[C@@H](C)CN1Cc1ccc(F)c(OC(F)(F)F)c1] | 2.0 | 490.1 | H | 1.49 |
| 586 | 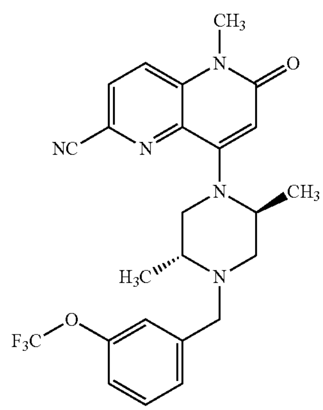 [SMILES: C[C@@H]1CN(c2cc(=O)n(C)c3ccc(C#N)nc23)[C@@H](C)CN1Cc1cccc(OC(F)(F)F)c1] | 2.0 | 472.2 | H | 1.44 |
| 587 | 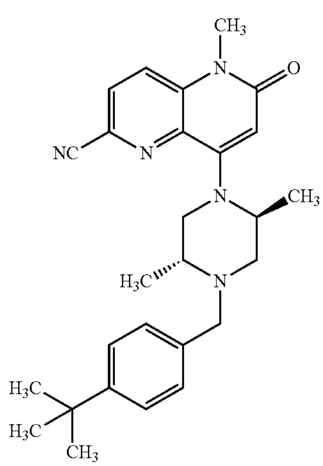 [SMILES: C[C@@H]1CN(c2cc(=O)n(C)c3ccc(C#N)nc23)[C@@H](C)CN1Cc1ccc(C(C)(C)C)cc1] | 1.0 | 444.2 | H | 2.61 |

TABLE 7-continued

| Ex. No. | Structure | QC Method | Obs. MS Ion | Stereo Chem | RT |
|---|---|---|---|---|---|
| 588 | 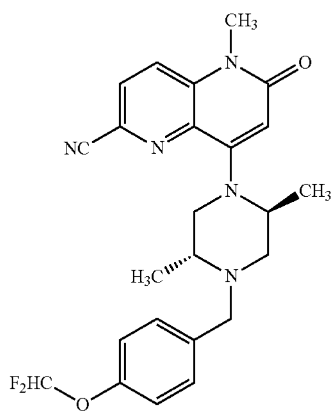 [SMILES: C[C@@H]1CN(c2cc(=O)n(C)c3ccc(C#N)nc23)[C@@H](C)CN1Cc1ccc(OC(F)F)cc1] | 2.0 | 454.1 | H | 1.39 |
| 589 | 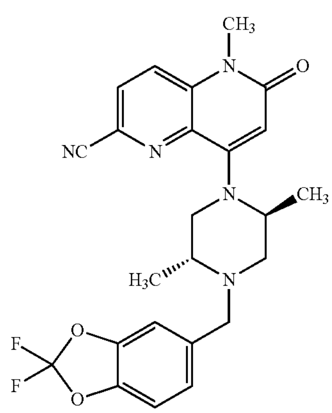 [SMILES: C[C@@H]1CN(c2cc(=O)n(C)c3ccc(C#N)nc23)[C@@H](C)CN1Cc1ccc2c(c1)OC(F)(F)O2] | 2.0 | 468.2 | H | 1.46 |
| 590 | 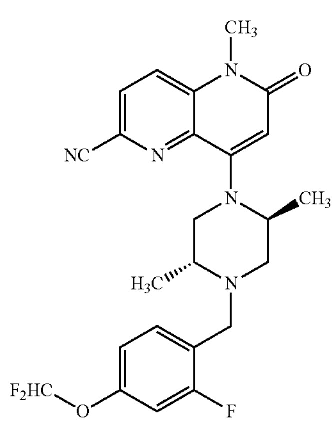 [SMILES: C[C@@H]1CN(c2cc(=O)n(C)c3ccc(C#N)nc23)[C@@H](C)CN1Cc1ccc(OC(F)F)cc1F] | 2.0 | 472.2 | H | 1.6 |

TABLE 7-continued

| Ex. No. | Structure | QC Method | Obs. MS Ion | Stereo Chem | RT |
|---|---|---|---|---|---|
| 591 | 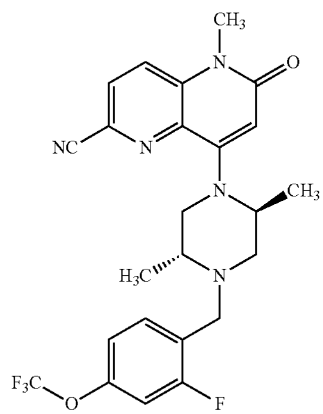 [SMILES: C[C@@H]1CN(c2cc(=O)n(C)c3ccc(C#N)nc23)[C@@H](C)CN1Cc1ccc(OC(F)(F)F)cc1F] | 2.0 | 490.2 | H | 1.43 |
| 592 | 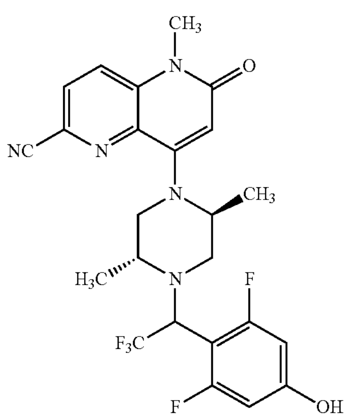 [SMILES: C[C@@H]1CN(c2cc(=O)n(C)c3ccc(C#N)nc23)[C@@H](C)CN1C(c1c(F)cc(O)cc1F)C(F)(F)F] | 1.0 | 508.2 | D | 1.97 |
| 593 | 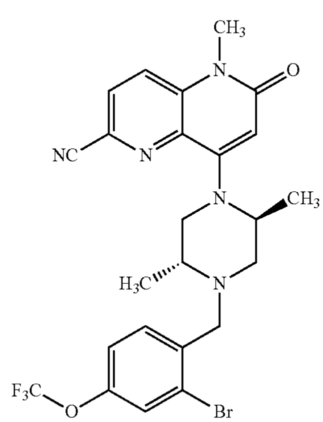 [SMILES: C[C@@H]1CN(c2cc(=O)n(C)c3ccc(C#N)nc23)[C@@H](C)CN1Cc1ccc(OC(F)(F)F)cc1Br] | 1.0 | 551.4 | H | 2.74 |

TABLE 7-continued
| Ex. No. | Structure | QC Method | Obs. MS Ion | Stereo Chem | RT |
|---|---|---|---|---|---|
| 594 | 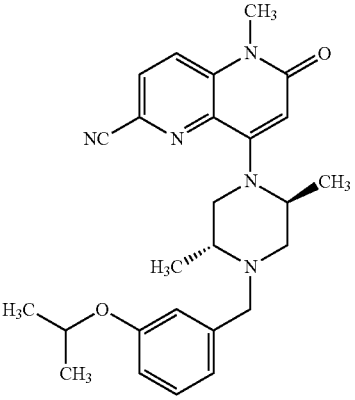 [SMILES: CC(C)Oc1cccc(CN2C[C@H](C)N(c3cc(=O)n(C)c4ccc(C#N)nc34)C[C@H]2C)c1] | | | | |
| 595 | 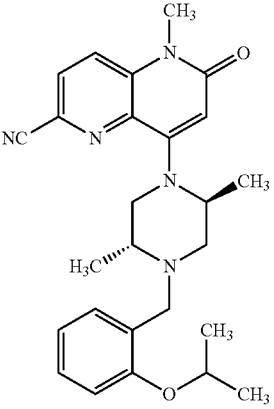 [SMILES: CC(C)Oc1ccccc1CN1C[C@H](C)N(c2cc(=O)n(C)c3ccc(C#N)nc23)C[C@H]1C] | | | | |
| 596 | 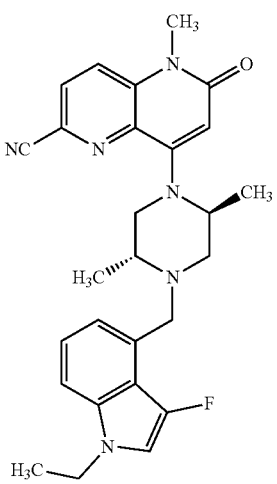 [SMILES: CCn1cc(F)c2c(CN3C[C@H](C)N(c4cc(=O)n(C)c5ccc(C#N)nc45)C[C@H]3C)cccc21] | | | | |

TABLE 7-continued
| Ex. No. | Structure | QC Method | Obs. MS Ion | Stereo Chem | RT |
|---|---|---|---|---|---|
| 598 | 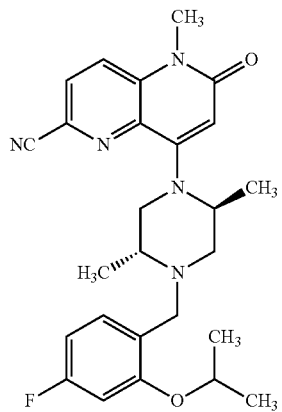 [SMILES: CC(C)Oc1cc(F)ccc1CN1C[C@H](C)N(c2cc(=O)n(C)c3ccc(C#N)nc23)C[C@H]1C] | | | | |
| 599 | 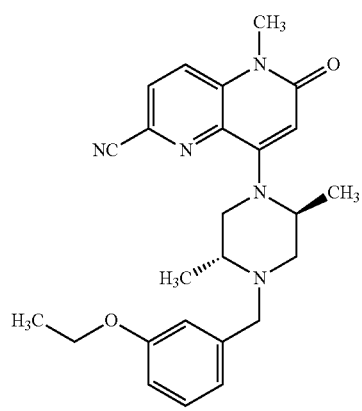 [SMILES: CCOc1cccc(CN2C[C@H](C)N(c3cc(=O)n(C)c4ccc(C#N)nc34)C[C@H]2C)c1] | | | | |
| 601 | 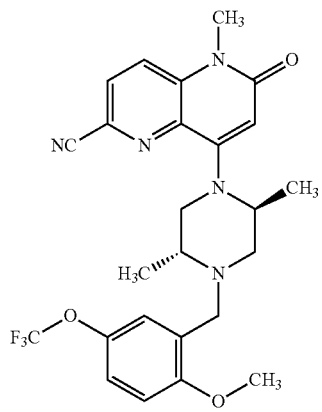 [SMILES: COc1ccc(OC(F)(F)F)cc1CN1C[C@H](C)N(c2cc(=O)n(C)c3ccc(C#N)nc23)C[C@H]1C] | 1.0 | 502.2 | H | 2.42 |

TABLE 7-continued

| Ex. No. | Structure | QC Method | Obs. MS Ion | Stereo Chem | RT |
|---|---|---|---|---|---|
| 602 | 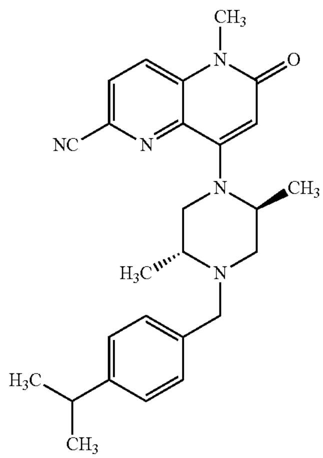 [SMILES: CC(C)c1ccc(CN2C[C@H](C)N(c3cc(=O)n(C)c4ccc(C#N)nc34)C[C@H]2C)cc1] | 2.0 | 430.2 | H | 1.5 |
| 604 | 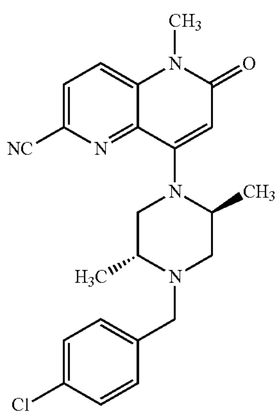 [SMILES: C[C@@H]1CN(c2cc(=O)n(C)c3ccc(C#N)nc23)[C@@H](C)CN1Cc1ccc(Cl)cc1] | | | | |
| 606 | 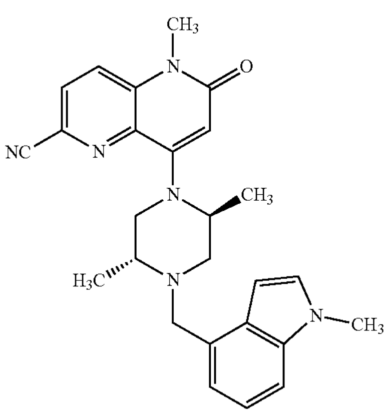 [SMILES: C[C@@H]1CN(c2cc(=O)n(C)c3ccc(C#N)nc23)[C@@H](C)CN1Cc1cccc2c1ccn2C] | 1.0 | 441.2 | H | 2.19 |

TABLE 7-continued

| Ex. No. | Structure | QC Method | Obs. MS Ion | Stereo Chem | RT |
|---|---|---|---|---|---|
| 607 | 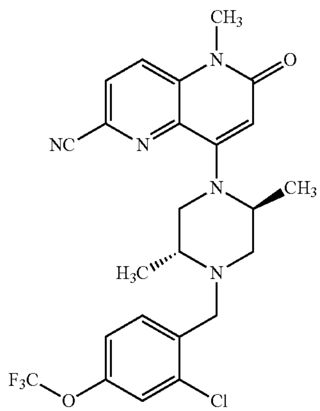 [SMILES: C[C@@H]1CN(c2cc(=O)n(C)c3ccc(C#N)nc23)[C@@H](C)CN1Cc1ccc(OC(F)(F)F)cc1Cl] | 2.0 | 506.1 | H | 1.59 |
| 608 | 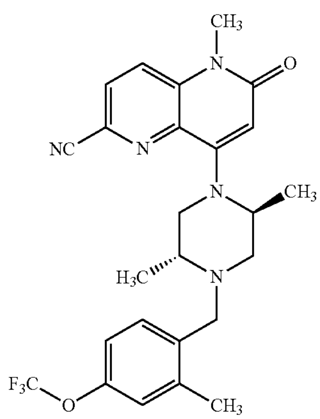 [SMILES: Cc1cc(OC(F)(F)F)ccc1CN1C[C@H](C)N(c2cc(=O)n(C)c3ccc(C#N)nc23)C[C@H]1C] | 1.0 | 486.1 | H | 2.67 |
| 609 | 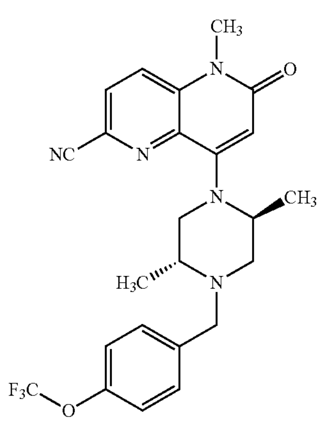 [SMILES: C[C@@H]1CN(c2cc(=O)n(C)c3ccc(C#N)nc23)[C@@H](C)CN1Cc1ccc(OC(F)(F)F)cc1] | 1.0 | 472.1 | H | 2.5 |

TABLE 7-continued
| Ex. No. | Structure | QC Method | Obs. MS Ion | Stereo Chem | RT |
|---|---|---|---|---|---|
| 610 | 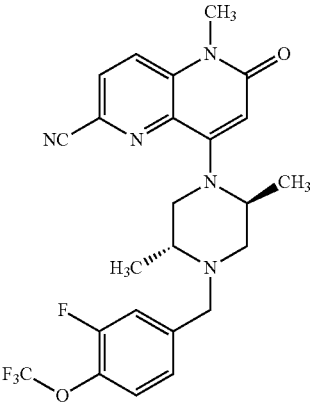 [SMILES: C[C@@H]1CN(c2cc(=O)n(C)c3ccc(C#N)nc23)[C@@H](C)CN1Cc1ccc(OC(F)(F)F)c(F)c1] | 2.0 | 490.2 | H | 1.54 |
| 611 | 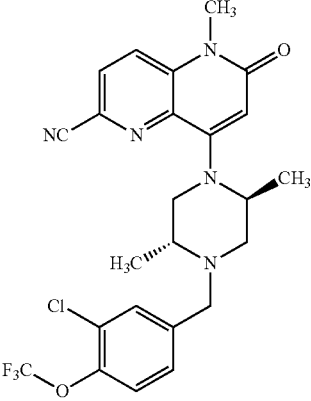 [SMILES: C[C@@H]1CN(c2cc(=O)n(C)c3ccc(C#N)nc23)[C@@H](C)CN1Cc1ccc(OC(F)(F)F)c(Cl)c1] | 2.0 | 506.1 | H | 1.61 |
| 623 | 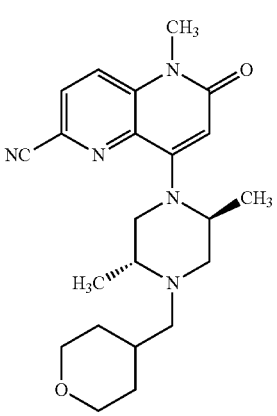 [SMILES: C[C@@H]1CN(c2cc(=O)n(C)c3ccc(C#N)nc23)[C@@H](C)CN1CC1CCOCC1] | 2.0 | 396.2 | H | 1.2 |

TABLE 7-continued
| Ex. No. | Structure | QC Method | Obs. MS Ion | Stereo Chem | RT |
|---|---|---|---|---|---|
| 624 | 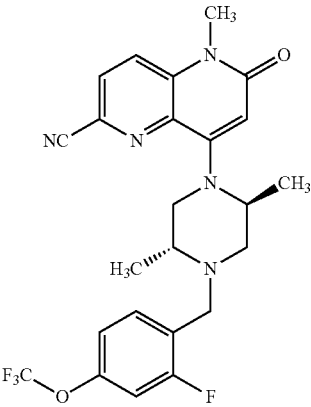 [SMILES: C[C@@H]1CN(c2cc(=O)n(C)c3ccc(C#N)nc23)[C@@H](C)CN1Cc1ccc(OC(F)(F)F)cc1F] | 1.0 | 490.2 | H | 2.5 |
| 625 | 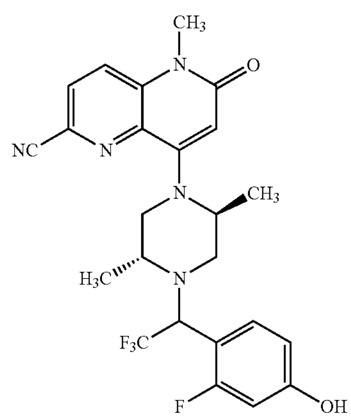 [SMILES: C[C@@H]1CN(c2cc(=O)n(C)c3ccc(C#N)nc23)[C@@H](C)CN1C(c1ccc(O)cc1F)C(F)(F)F] | 1.0 | 490.2 | D | 2.43 |
| 626 | 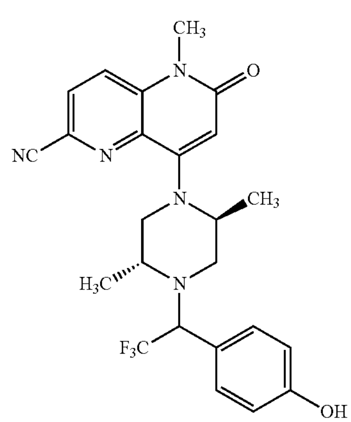 [SMILES: C[C@@H]1CN(c2cc(=O)n(C)c3ccc(C#N)nc23)[C@@H](C)CN1C(c1ccc(O)cc1)C(F)(F)F] | 2.0 | 472.1 | D | 1.38 |

TABLE 7-continued
| Ex. No. | Structure | QC Method | Obs. MS Ion | Stereo Chem | RT |
|---|---|---|---|---|---|
| 627 | 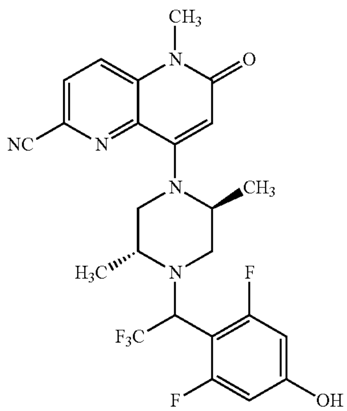 [SMILES: C[C@@H]1CN(c2cc(=O)n(C)c3ccc(C#N)nc23)[C@@H](C)CN1C(c1c(F)cc(O)cc1F)C(F)(F)F] | 1.0 | 508.3 | H | 1.89 |
| 628 | 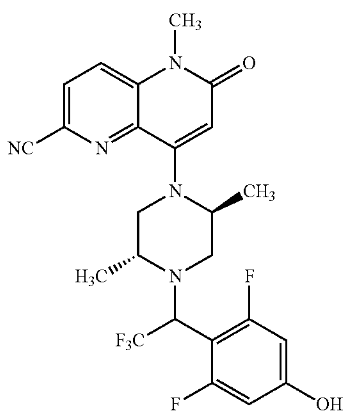 [SMILES: C[C@@H]1CN(c2cc(=O)n(C)c3ccc(C#N)nc23)[C@@H](C)CN1C(c1c(F)cc(O)cc1F)C(F)(F)F] | 1.0 | 508.1 | H | 1.89 |
| 629 | 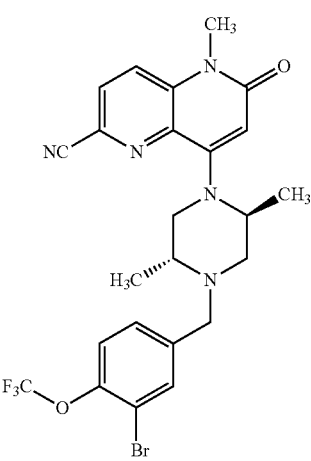 [SMILES: C[C@@H]1CN(c2cc(=O)n(C)c3ccc(C#N)nc23)[C@@H](C)CN1Cc1ccc(OC(F)(F)F)c(Br)c1] | 1.0 | 550.1 | H | 2.7 |

LCMS Methods

Method A: Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm.

Method B: Column: XBridge BEH XP C18 (2.1×50 mm), 2.5 μm; Mobile phase A: 0.1% TFA: acetonitrile (95:5), Mobile phase B: 0.1% TFA: acetonitrile (5:95), Gradient=0-100% B over 3 minutes; Temperature: 50° C.; Flow rate: 1.1 mL/min; Detection: UV at 220 nm.

Method C: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Method D: Column: Ascentis Express C8 (50×2.1 mm) 2.7 μm; Mobile phase A: 10 mM ammonium formate:acetonitrile (98:2), Mobile phase B: 10 mM ammonium formate: acetonitrile (2:98), Gradient=0-100% B over 1.5 minutes, then a 0.6 minute hold at 100% B; Temperature: 27° C.; Flow rate: 1.0 mL/min; Detection: UV at 220 nm.

The examples in the Table 8 were prepared according to the general procedure described in Example 246 by alkylation of the piperazine nitrogen with either an alkyl chloride or bromide. The crude material was purified by preparative HPLC to obtain the product.

TABLE 8

| Ex. No. | Structure | LCMS RT and Method | M + H | Stereo chem. |
|---|---|---|---|---|
| 630 | 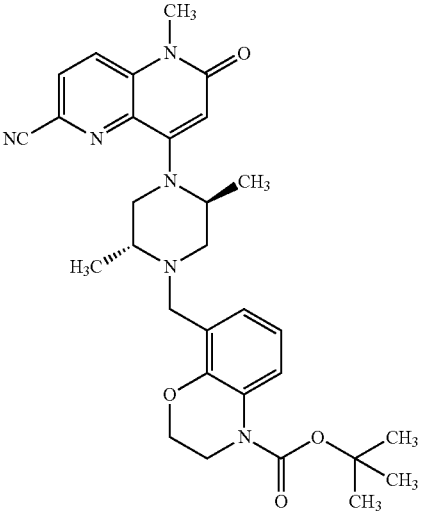 [SMILES: C[C@@H]1CN(c2cc(=O)n(C)c3ccc(C#N)nc23)[C@@H](C)CN1Cc1cccc2c1OCCN2C(=O)OC(C)(C)C] | 2.54 A | 545.3 | H |
| 631 | 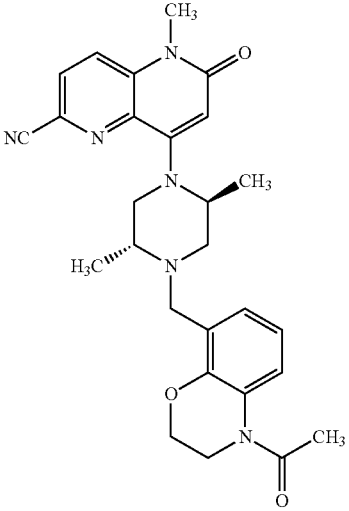 [SMILES: CC(=O)N1CCOc2c(CN3C[C@H](C)N(c4cc(=O)n(C)c5ccc(C#N)nc45)C[C@H]3C)cccc21] | 1.6 A | 487.2 | H |

TABLE 8-continued
| Ex. No. | Structure | LCMS RT and Method | M + H | Stereo chem. |
|---|---|---|---|---|
| 632 | 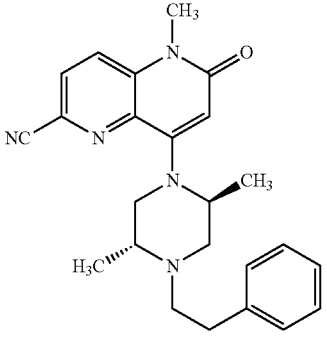 [SMILES: C[C@@H]1CN(c2cc(=O)n(C)c3ccc(C#N)nc23)[C@@H](C)CN1CCc1ccccc1] | 1.95 A | 402.2 | H |
| 633 | 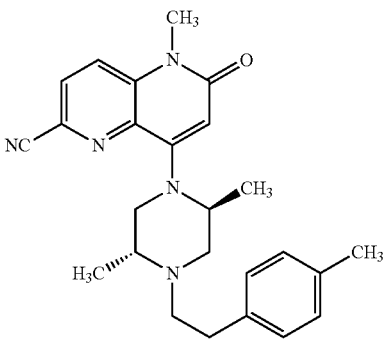 [SMILES: Cc1ccc(CCN2C[C@H](C)N(c3cc(=O)n(C)c4ccc(C#N)nc34)C[C@H]2C)cc1] | 2.09 A | 416.2 | H |
| 634 | 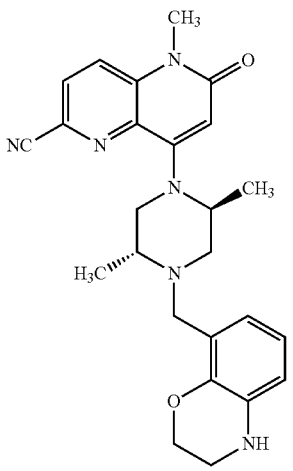 [SMILES: C[C@@H]1CN(c2cc(=O)n(C)c3ccc(C#N)nc23)[C@@H](C)CN1Cc1cccc2c1OCCN2] | 1.54 A | 445.2 | H |

TABLE 8-continued

| Ex. No. | Structure | LCMS RT and Method | M + H | Stereo chem. |
|---|---|---|---|---|
| 635 | 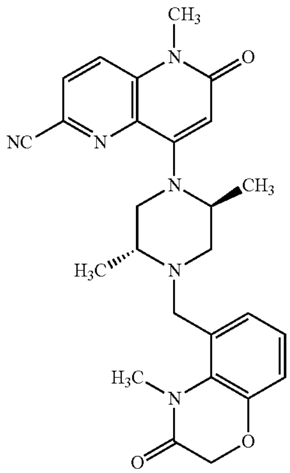 [SMILES: C[C@@H]1CN(c2cc(=O)n(C)c3ccc(C#N)nc23)[C@@H](C)CN1Cc1cccc2c1N(C)C(=O)CO2] | 2.11 A | 473.2 | H |

The compounds in Table 9 were prepared from the appropriate piperazine using the corresponding α-methyl benzyl chloride/bromide as described for Examples 308 and 309. When the synthesis provided a mixture of diastereomers, the mixture was separated at the final stage using either preparative chromatography or preparative chiral chromatography. The absolute stereochemistry was not assigned at the newly formed carbon-nitrogen-bond.

TABLE 9

| Ex. No. | Structure | LCMS RT and Method | M + H | Stereo chem. |
|---|---|---|---|---|
| 636 | 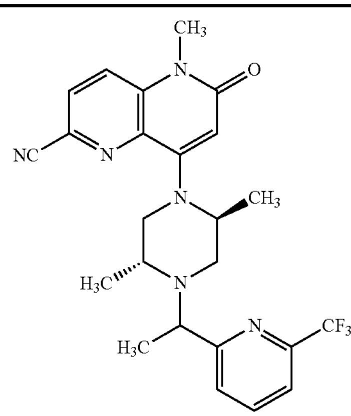 | 2.09 A | 471.2 | H |
| 637 | 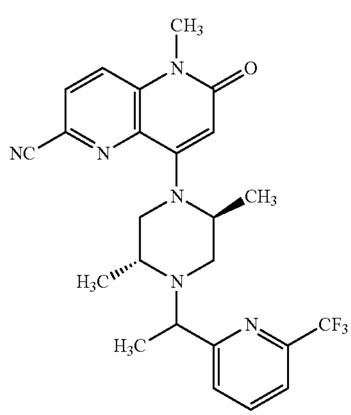 [SMILES: CC(c1cccc(C(F)(F)F)n1)N1C[C@H](C)N(c2cc(=O)n(C)c3ccc(C#N)nc23)C[C@H]1C] | 2.08 A | 471.2 | H |

TABLE 9-continued
| Ex. No. | Structure | LCMS RT and Method | M + H | Stereo chem. |
|---|---|---|---|---|
| 638 | 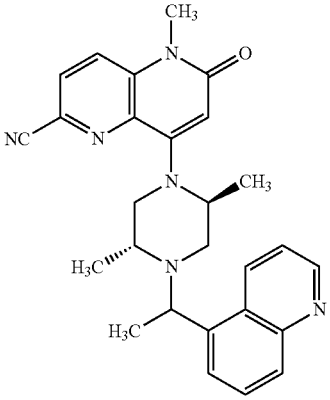 [SMILES: CC(c1cccc2ncccc12)N1C[C@H](C)N(c2cc(=O)n(C)c3ccc(C#N)nc23)C[C@H]1C] | 1.91 B | 453.2 | H |
| 639 | 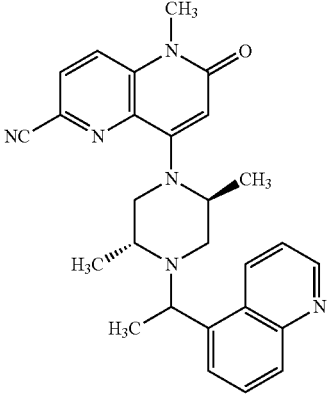 [SMILES: CC(c1cccc2ncccc12)N1C[C@H](C)N(c2cc(=O)n(C)c3ccc(C#N)nc23)C[C@H]1C] | 1.89 B | 453.2 | H |
| 640 | 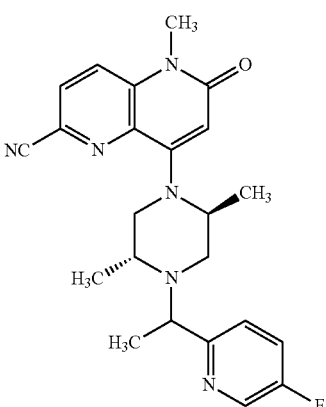 | 1.77 A | 421.2 | H |

TABLE 9-continued

| Ex. No. | Structure | LCMS RT and Method | M + H | Stereo chem. |
|---|---|---|---|---|
| 641 | 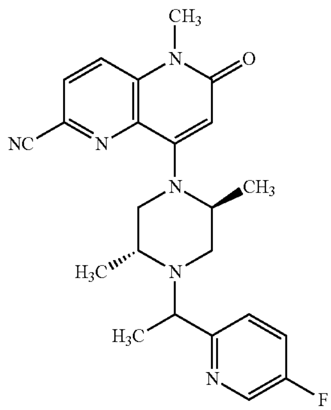 [SMILES: CC(c1ccc(F)cn1)N1C[C@H](C)N(c2cc(=O)n(C)c3ccc(C#N)nc23)C[C@H]1C] | 1.79 A | 421.1 | H |
| 642 | 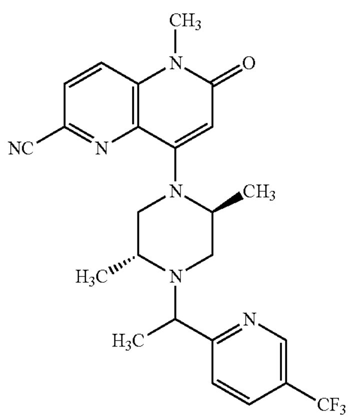 [SMILES: CC(c1ccc(C(F)(F)F)cn1)N1C[C@H](C)N(c2cc(=O)n(C)c3ccc(C#N)nc23)C[C@H]1C] | 2.08 A | 471.2 | H |
| 643 | 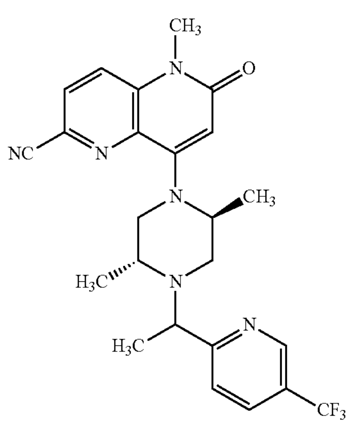 [SMILES: CC(c1ccc(C(F)(F)F)cn1)N1C[C@H](C)N(c2cc(=O)n(C)c3ccc(C#N)nc23)C[C@H]1C] | 2.08 A | 471.2 | H |

TABLE 9-continued

| Ex. No. | Structure | LCMS RT and Method | M + H | Stereo chem. |
|---|---|---|---|---|
| 644 | 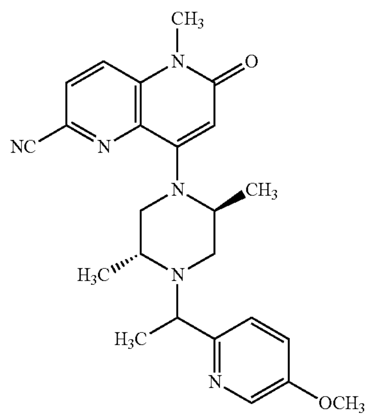 [SMILES: COc1ccc(C(C)N2C[C@H](C)N(c3cc(=O)n(C)c4ccc(C#N)nc34)C[C@H]2C)nc1] | 1.72 A | 433.2 | H |
| 645 | 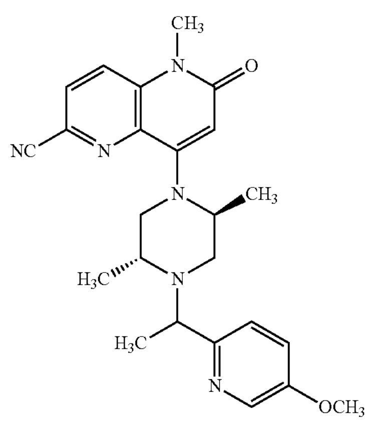 [SMILES: COc1ccc(C(C)N2C[C@H](C)N(c3cc(=O)n(C)c4ccc(C#N)nc34)C[C@H]2C)nc1] | 1.68 A | 433.2 | H |
| 646 | 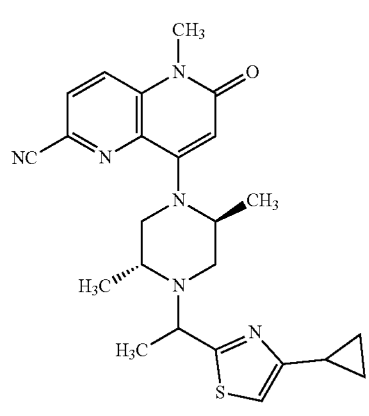 [SMILES: CC(c1nc(C2CC2)cs1)N1C[C@H](C)N(c2cc(=O)n(C)c3ccc(C#N)nc23)C[C@H]1C] | 2.03 A | 449.2 | H |

TABLE 9-continued

| Ex. No. | Structure | LCMS RT and Method | M + H | Stereo chem. |
|---|---|---|---|---|
| 647 | 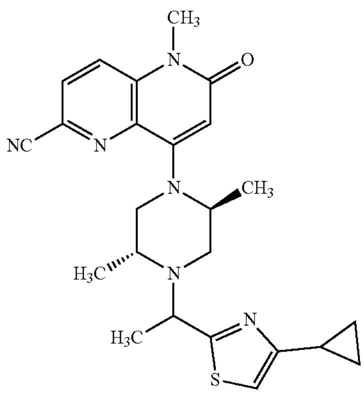 [SMILES: CC(c1nc(C2CC2)cs1)N1C[C@H](C)N(c2cc(=O)n(C)c3ccc(C#N)nc23)C[C@H]1C] | 2.03 A | 449.2 | H |
| 648 | 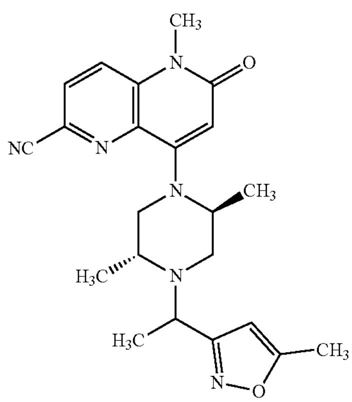 [SMILES: Cc1cc(C(C)N2C[C@H](C)N(c3cc(=O)n(C)c4ccc(C#N)nc34)C[C@H]2C)no1] | 1.62 A | 407.2 | H |
| 649 | 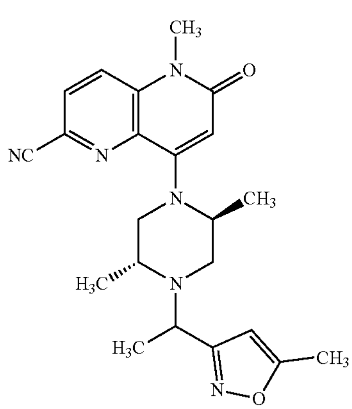 [SMILES: Cc1cc(C(C)N2C[C@H](C)N(c3cc(=O)n(C)c4ccc(C#N)nc34)C[C@H]2C)no1] | 1.70 A | 407.2 | H |

TABLE 9-continued

| Ex. No. | Structure | LCMS RT and Method | M + H | Stereo chem. |
|---|---|---|---|---|
| 650 | 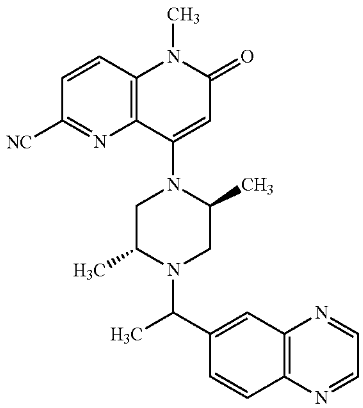 [SMILES: CC(c1ccc2nccnc2c1)N1C[C@H](C)N(c2cc(=O)n(C)c3ccc(C#N)nc23)C[C@H]1C] | 1.79 A | 454.2 | H |
| 651 | 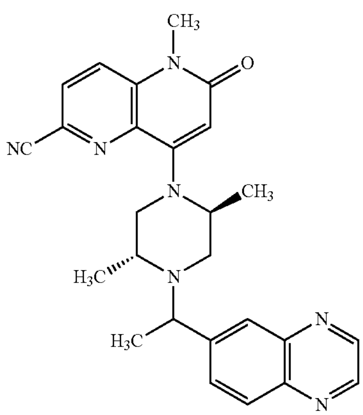 [SMILES: CC(c1ccc2nccnc2c1)N1C[C@H](C)N(c2cc(=O)n(C)c3ccc(C#N)nc23)C[C@H]1C] | 1.8 A | 454.1 | H |
| 652 | 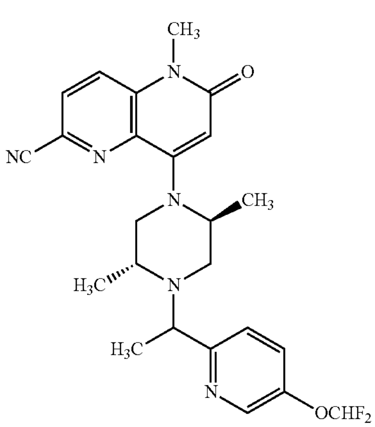 [SMILES: CC(c1ccc(OC(F)F)cn1)N1C[C@H](C)N(c2cc(=O)n(C)c3ccc(C#N)nc23)C[C@H]1C] | 2.19 A | 468.2 | H |

TABLE 9-continued

| Ex. No. | Structure | LCMS RT and Method | M + H | Stereo chem. |
|---|---|---|---|---|
| 653 | 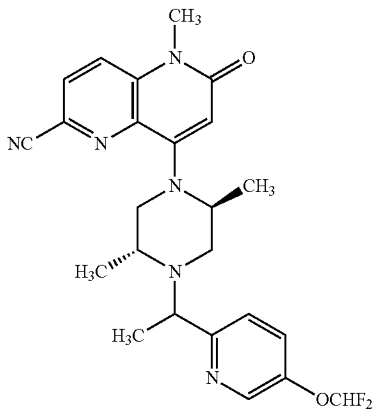 [SMILES: CC(c1ccc(OC(F)F)cn1)N1C[C@H](C)N(c2cc(=O)n(C)c3ccc(C#N)nc23)C[C@H]1C] | 2.22 A | 468.2 | H |
| 654 | 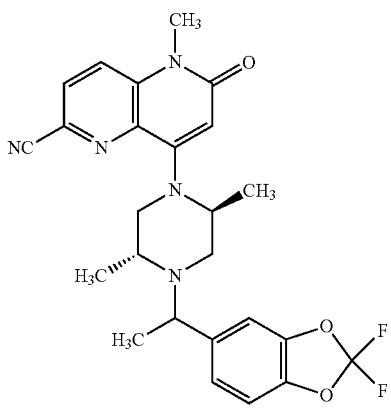 [SMILES: CC(c1ccc2c(c1)OC(F)(F)O2)N1C[C@H](C)N(c2cc(=O)n(C)c3ccc(C#N)nc23)C[C@H]1C] | 2.46 A | 482.2 | H |
| 655 | 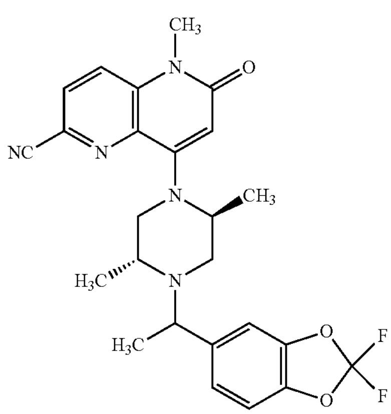 [SMILES: CC(c1ccc2c(c1)OC(F)(F)O2)N1C[C@H](C)N(c2cc(=O)n(C)c3ccc(C#N)nc23)C[C@H]1C] | 2.48 A | 482.2 | H |

The compounds in Table 10 were prepared from the appropriate piperazine using the corresponding benzhydryl chloride/bromide as described for Example 302. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 10

| Ex. No. | Structure | LCMS RT and Method | M + H | Stereo chem. |
|---|---|---|---|---|
| 656 | 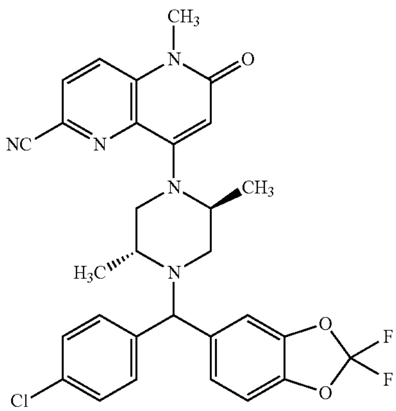 [SMILES: C[C@@H]1CN(c2cc(=O)n(C)c3ccc(C#N)nc23)[C@@H](C)CN1C(c1ccc(Cl)cc1)c1ccc2c(c1)OC(F)(F)O2] | 2.72 A | 579.2 | H |
| 657 | 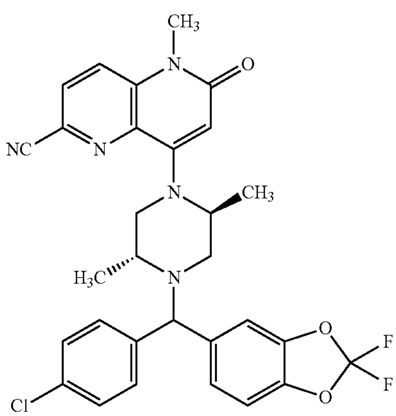 [SMILES: C[C@@H]1CN(c2cc(=O)n(C)c3ccc(C#N)nc23)[C@@H](C)CN1C(c1ccc(Cl)cc1)c1ccc2c(c1)OC(F)(F)O2] | 2.71 A | 579.2 | H |
| 658 | 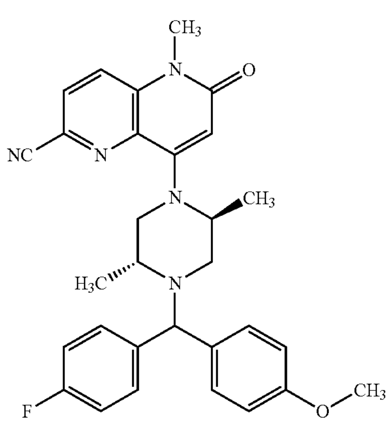 [SMILES: COc1ccc(C(c2ccc(F)cc2)N2C[C@H](C)N(c3cc(=O)n(C)c4ccc(C#N)nc34)C[C@H]2C)cc1] | 2.39 A | 512.3 | H |

TABLE 10-continued
| Ex. No. | Structure | LCMS RT and Method | M + H | Stereo chem. |
|---|---|---|---|---|
| 659 | 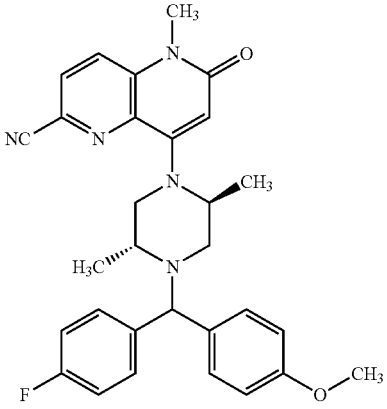 [SMILES: COc1ccc(C(c2ccc(F)cc2)N2C[C@H](C)N(c3cc(=O)n(C)c4ccc(C#N)nc34)C[C@H]2C)cc1] | 2.40 A | 512.3 | H |
| 660 | 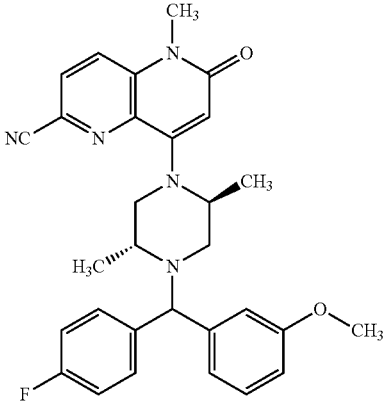 [SMILES: COc1cccc(C(c2ccc(F)cc2)N2C[C@H](C)N(c3cc(=O)n(C)c4ccc(C#N)nc34)C[C@H]2C)c1] | 2.32 A | 512.3 | H |
| 661 | 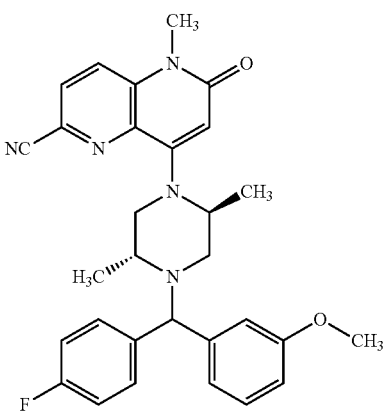 [SMILES: COc1cccc(C(c2ccc(F)cc2)N2C[C@H](C)N(c3cc(=O)n(C)c4ccc(C#N)nc34)C[C@H]2C)c1] | 2.32 A | 512.2 | H |

TABLE 10-continued
| Ex. No. | Structure | LCMS RT and Method | M + H | Stereo chem. |
|---|---|---|---|---|
| 662 | 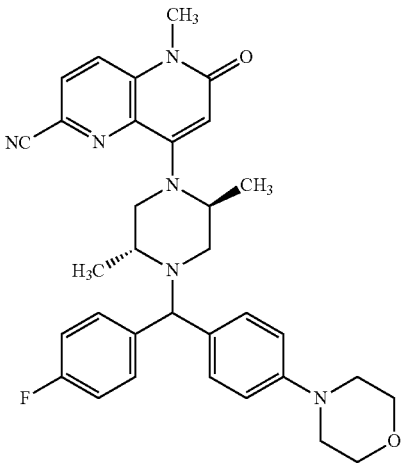 [SMILES: C[C@@H]1CN(c2cc(=O)n(C)c3ccc(C#N)nc23)[C@@H](C)CN1C(c1ccc(F)cc1)c1ccc(N2CCOCC2)cc1] | 2.40 A | 567.3 | H |
| 663 | 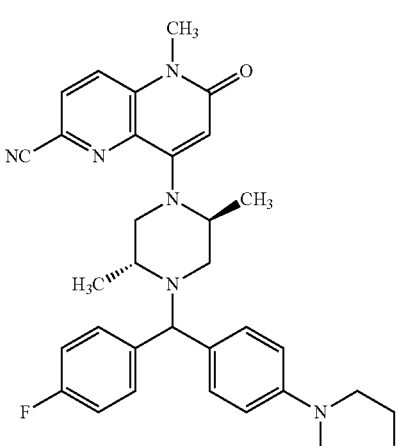 | 2.36 A | 567.3 | H |
| 664 | 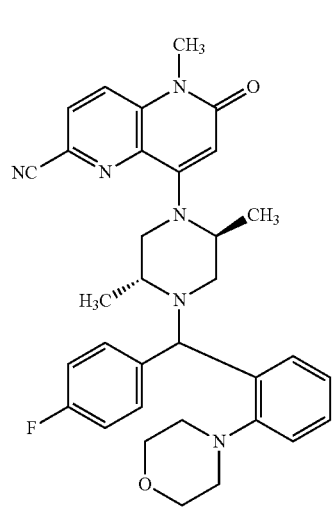 [SMILES: C[C@@H]1CN(c2cc(=O)n(C)c3ccc(C#N)nc23)[C@@H](C)CN1C(c1ccc(F)cc1)c1ccccc1N1CCOCC1] | 2.36 A | 567.3 | H |

TABLE 10-continued
| Ex. No. | Structure | LCMS RT and Method | M + H | Stereo chem. |
|---|---|---|---|---|
| 665 | 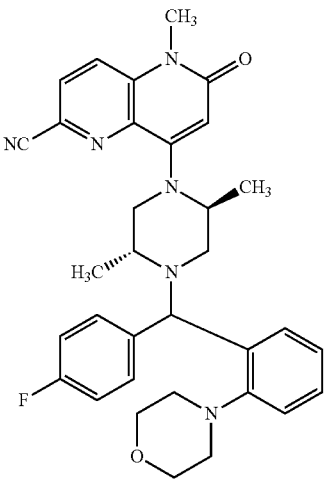 [SMILES: C[C@@H]1CN(c2cc(=O)n(C)c3ccc(C#N)nc23)[C@@H](C)CN1C(c1ccc(F)cc1)c1ccccc1N1CCOCC1] | 2.38 A | 567.2 | H |
| 666 | 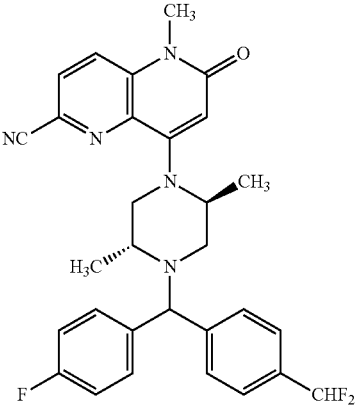 [SMILES: C[C@@H]1CN(c2cc(=O)n(C)c3ccc(C#N)nc23)[C@@H](C)CN1C(c1ccc(F)cc1)c1ccc(C(F)F)cc1] | 2.63 A | 532.2 | H |
| 667 | 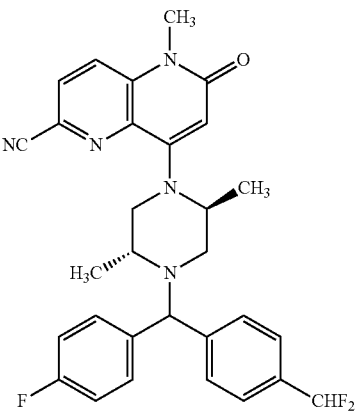 [SMILES: C[C@@H]1CN(c2cc(=O)n(C)c3ccc(C#N)nc23)[C@@H](C)CN1C(c1ccc(F)cc1)c1ccc(C(F)F)cc1] | 2.63 A | 532.2 | H |

TABLE 10-continued

| Ex. No. | Structure | LCMS RT and Method | M + H | Stereo chem. |
|---|---|---|---|---|
| 668 | 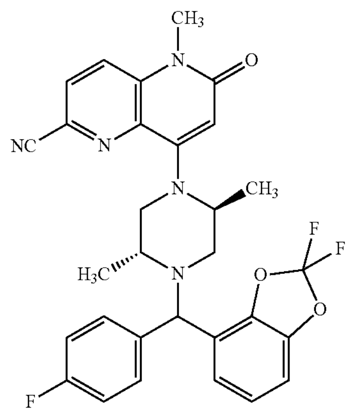 [SMILES: C[C@@H]1CN(c2cc(=O)n(C)c3ccc(C#N)nc23)[C@@H](C)CN1C(c1ccc(F)cc1)c1cccc2c1OC(F)(F)O2] | 2.54 A | 562.2 | H |
| 669 | 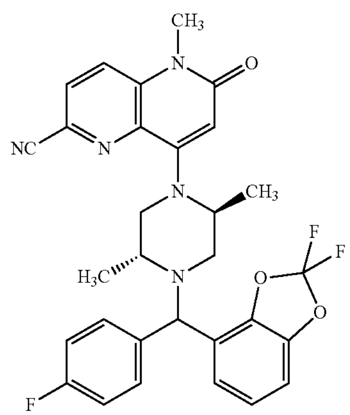 [SMILES: C[C@@H]1CN(c2cc(=O)n(C)c3ccc(C#N)nc23)[C@@H](C)CN1C(c1ccc(F)cc1)c1cccc2c1OC(F)(F)O2] | 2.5 A | 562.2 | H |
| 670 | 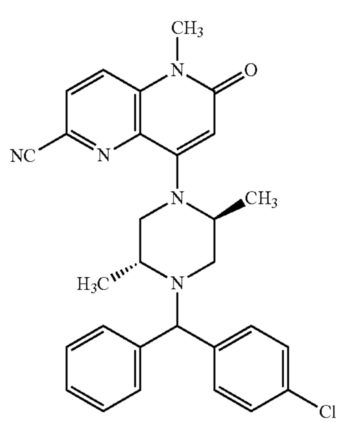 [SMILES: C[C@@H]1CN(c2cc(=O)n(C)c3ccc(C#N)nc23)[C@@H](C)CN1C(c1ccccc1)c1ccc(Cl)cc1] | 2.52 A | 498.2 | H |

TABLE 10-continued

| Ex. No. | Structure | LCMS RT and Method | M + H | Stereo chem. |
|---|---|---|---|---|
| 671 | 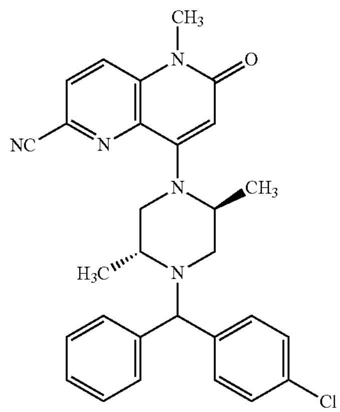 [SMILES: C[C@@H]1CN(c2cc(=O)n(C)c3ccc(C#N)nc23)[C@@H](C)CN1C(c1ccccc1)c1ccc(Cl)cc1] | 2.54 A | 498.2 | H |
| 672 | 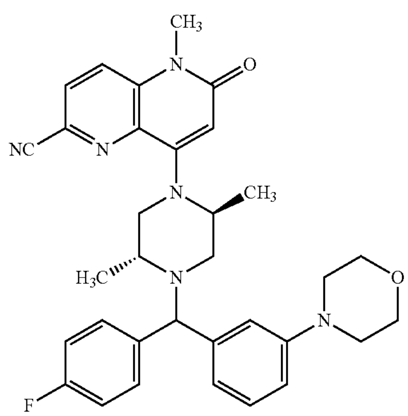 [SMILES: C[C@@H]1CN(c2cc(=O)n(C)c3ccc(C#N)nc23)[C@@H](C)CN1C(c1ccc(F)cc1)c1cccc(N2CCOCC2)c1] | 2.26 A | 567.3 | H |
| 673 | 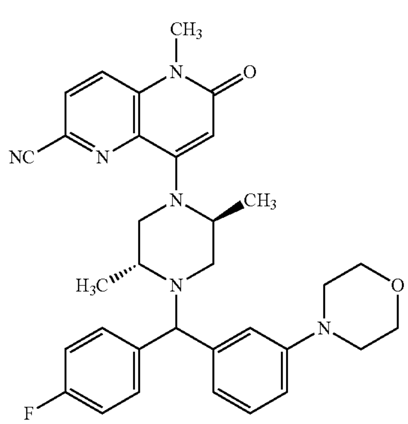 [SMILES: C[C@@H]1CN(c2cc(=O)n(C)c3ccc(C#N)nc23)[C@@H](C)CN1C(c1ccc(F)cc1)c1cccc(N2CCOCC2)c1] | 2.27 A | 567.3 | H |

TABLE 10-continued

| Ex. No. | Structure | LCMS RT and Method | M + H | Stereo chem. |
|---|---|---|---|---|
| 674 | 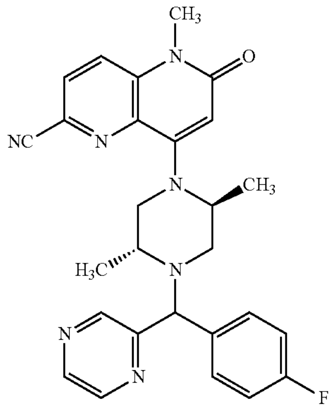 [SMILES: C[C@@H]1CN(c2cc(=O)n(C)c3ccc(C#N)nc23)[C@@H](C)CN1C(c1ccc(F)cc1)c1cnccn1] | 1.90 A | 484.2 | H |
| 675 | 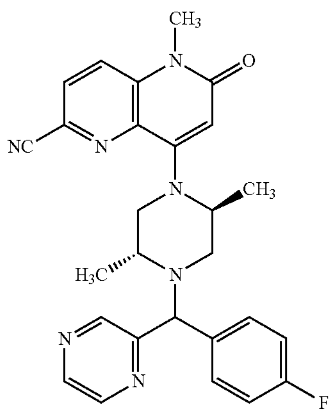 [SMILES: C[C@@H]1CN(c2cc(=O)n(C)c3ccc(C#N)nc23)[C@@H](C)CN1C(c1ccc(F)cc1)c1cnccn1] | 1.90 A | 484.2 | H |
| 676 | 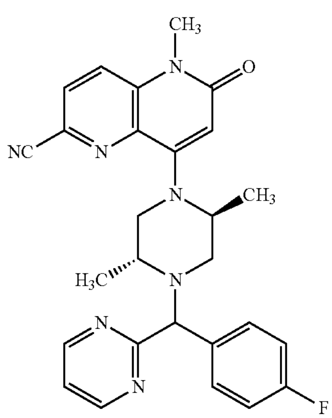 [SMILES: C[C@@H]1CN(c2cc(=O)n(C)c3ccc(C#N)nc23)[C@@H](C)CN1C(c1ccc(F)cc1)c1ncccn1] | 1.79 A | 484.2 | H |

TABLE 10-continued
| Ex. No. | Structure | LCMS RT and Method | M + H | Stereo chem. |
|---|---|---|---|---|
| 677 | 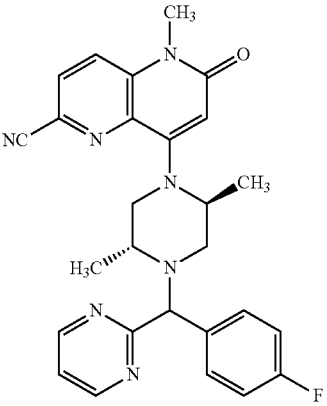 [SMILES: C[C@@H]1CN(c2cc(=O)n(C)c3ccc(C#N)nc23)[C@@H](C)CN1C(c1ccc(F)cc1)c1ncccn1] | 1.80 A | 484.2 | H |
| 678 | 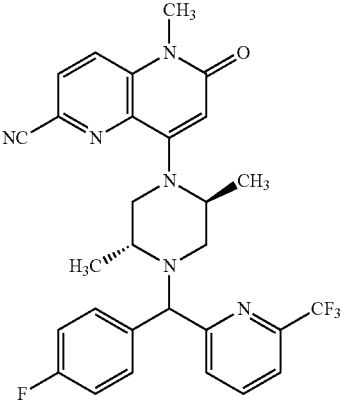 [SMILES: C[C@@H]1CN(c2cc(=O)n(C)c3ccc(C#N)nc23)[C@@H](C)CN1C(c1ccc(F)cc1)c1cccc(C(F)(F)F)n1] | 2.49 A | 551.2 | H |
| 679 | 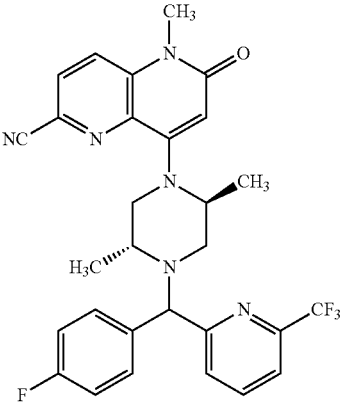 [SMILES: C[C@@H]1CN(c2cc(=O)n(C)c3ccc(C#N)nc23)[C@@H](C)CN1C(c1ccc(F)cc1)c1cccc(C(F)(F)F)n1] | 2.48 A | 551.2 | H |

TABLE 10-continued
| Ex. No. | Structure | LCMS RT and Method | M + H | Stereo chem. |
|---|---|---|---|---|
| 680 | 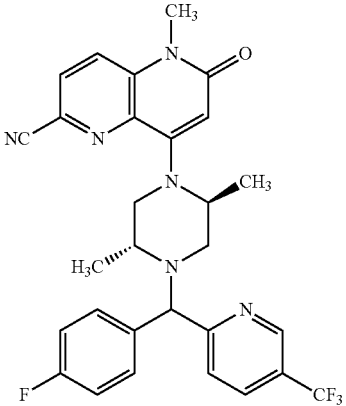 [SMILES: C[C@@H]1CN(c2cc(=O)n(C)c3ccc(C#N)nc23)[C@@H](C)CN1C(c1ccc(F)cc1)c1ccc(C(F)(F)F)cn1] | 2.62 A | 551.2 | H |
| 681 | 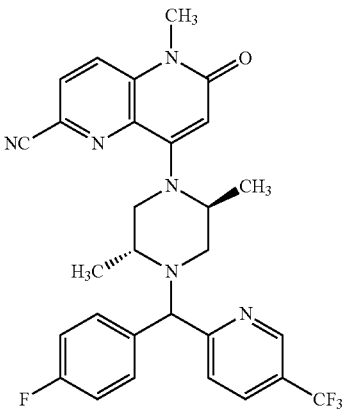 | 2.62 A | 551.2 | H |
| 682 | 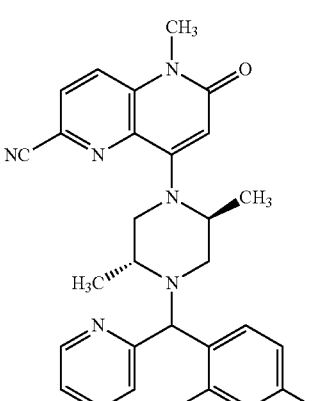 | 2.00 A | 501.1 | H |

TABLE 10-continued
| Ex. No. | Structure | LCMS RT and Method | M + H | Stereo chem. |
|---|---|---|---|---|
| 683 | 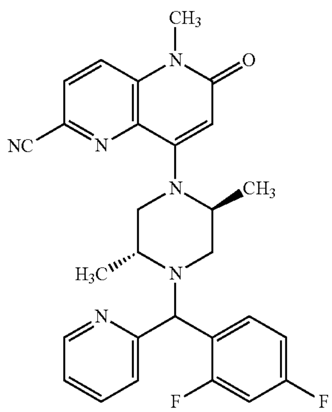 [SMILES: C[C@@H]1CN(c2cc(=O)n(C)c3ccc(C#N)nc23)[C@@H](C)CN1C(c1ccccn1)c1ccc(F)cc1F] | 2.00 A | 501.2 | H |
| 684 | 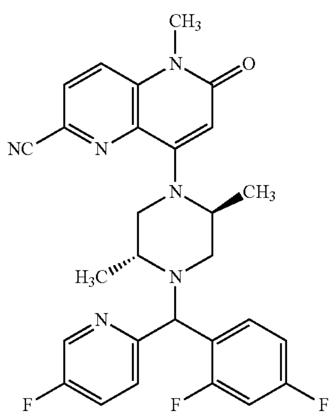 [SMILES: C[C@@H]1CN(c2cc(=O)n(C)c3ccc(C#N)nc23)[C@@H](C)CN1C(c1ccc(F)cn1)c1ccc(F)cc1F] | 2.15 A | 519.2 | H |
| 685 | 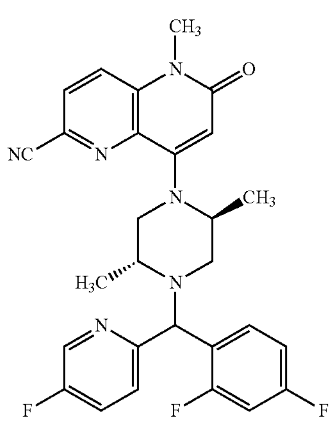 [SMILES: C[C@@H]1CN(c2cc(=O)n(C)c3ccc(C#N)nc23)[C@@H](C)CN1C(c1ccc(F)cn1)c1ccc(F)cc1F] | 2.15 A | 519.2 | H |

TABLE 10-continued

| Ex. No. | Structure | LCMS RT and Method | M + H | Stereo chem. |
|---|---|---|---|---|
| 686 | 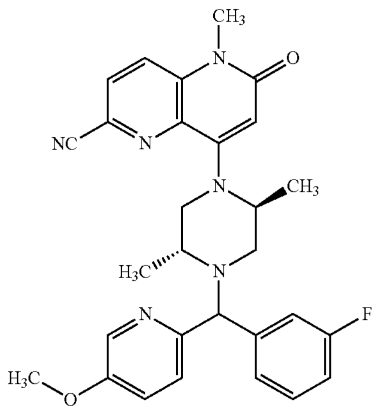 [SMILES: COc1ccc(C(c2cccc(F)c2)N2C[C@H](C)N(c3cc(=O)n(C)c4ccc(C#N)nc34)C[C@H]2C)nc1] | 2.02 A | 513.2 | H |
| 687 | 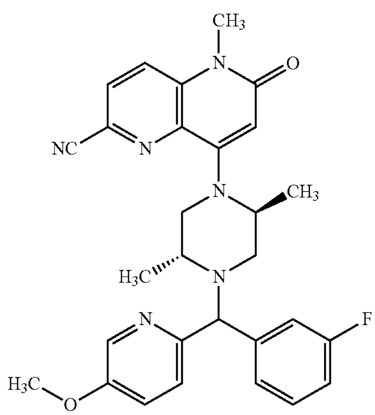 [SMILES: COc1ccc(C(c2cccc(F)c2)N2C[C@H](C)N(c3cc(=O)n(C)c4ccc(C#N)nc34)C[C@H]2C)nc1] | 2.03 A | 513.2 | H |
| 688 | 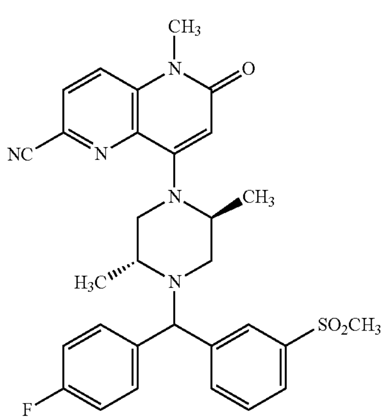 [SMILES: C[C@@H]1CN(c2cc(=O)n(C)c3ccc(C#N)nc23)[C@@H](C)CN1C(c1ccc(F)cc1)c1cccc(S(C)(=O)=O)c1] | 1.92 A | 560.2 | H |

TABLE 10-continued
| Ex. No. | Structure | LCMS RT and Method | M + H | Stereo chem. |
|---|---|---|---|---|
| 689 | 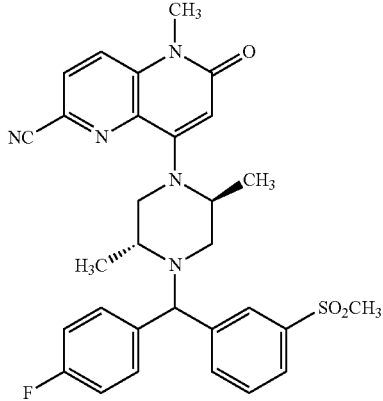 [SMILES: C[C@@H]1CN(c2cc(=O)n(C)c3ccc(C#N)nc23)[C@@H](C)CN1C(c1ccc(F)cc1)c1cccc(S(C)(=O)=O)c1] | 1.99 A | 560.2 | H |
| 690 | 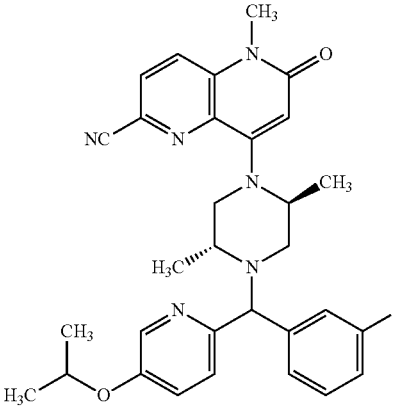 | 2.27 A | 541.2 | H |
| 691 | 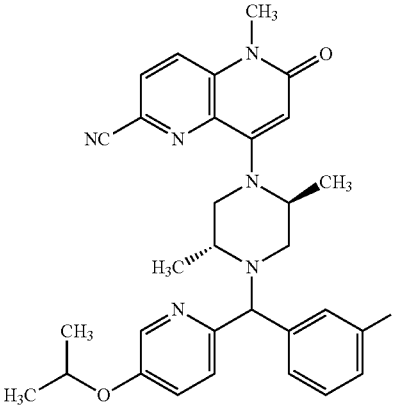 | 2.26 A | 541.2 | H |

TABLE 10-continued
| Ex. No. | Structure | LCMS RT and Method | M + H | Stereo chem. |
|---|---|---|---|---|
| 692 | 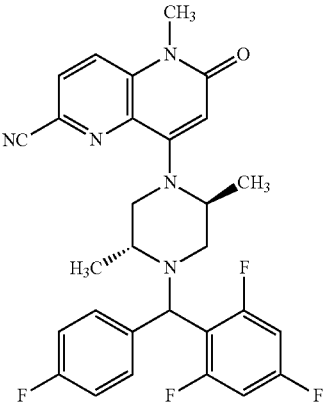 [SMILES: C[C@@H]1CN(c2cc(=O)n(C)c3ccc(C#N)nc23)[C@@H](C)CN1C(c1ccc(F)cc1)c1c(F)cc(F)cc1F] | 2.47 A | 536.2 | H |
| 693 | 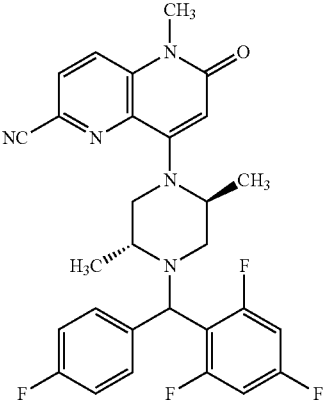 [SMILES: C[C@@H]1CN(c2cc(=O)n(C)c3ccc(C#N)nc23)[C@@H](C)CN1C(c1ccc(F)cc1)c1c(F)cc(F)cc1F] | 2.47 A | 536.2 | H |
| 694 | 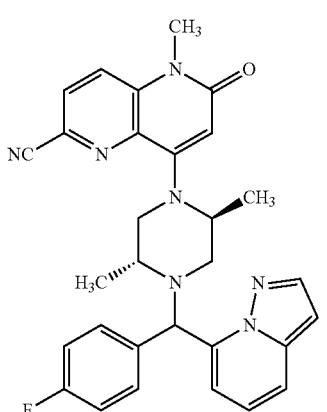 | 2.27 A | 522.2 | H |

TABLE 10-continued
| Ex. No. | Structure | LCMS RT and Method | M + H | Stereo chem. |
|---|---|---|---|---|
| 695 | 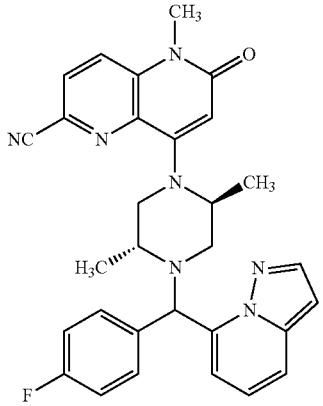 [SMILES: C[C@@H]1CN(c2cc(=O)n(C)c3ccc(C#N)nc23)[C@@H](C)CN1C(c1ccc(F)cc1)c1cccc2ccnn12] | 2.27 A | 522.2 | H |
| 696 | 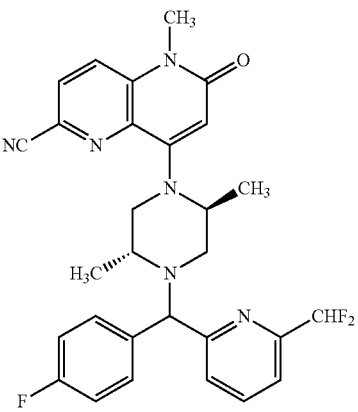 [SMILES: C[C@@H]1CN(c2cc(=O)n(C)c3ccc(C#N)nc23)[C@@H](C)CN1C(c1ccc(F)cc1)c1cccc(C(F)F)n1] | 2.19 A | 533.2 | H |
| 697 | 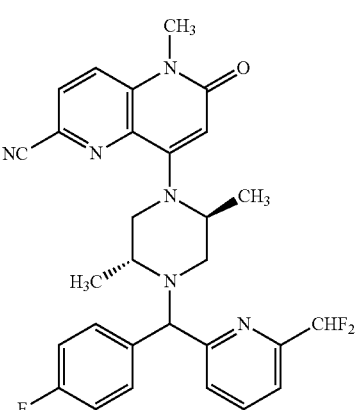 | 2.18 A | 533.2 | H |

TABLE 10-continued

| Ex. No. | Structure | LCMS RT and Method | M + H | Stereo chem. |
|---|---|---|---|---|
| 698 | 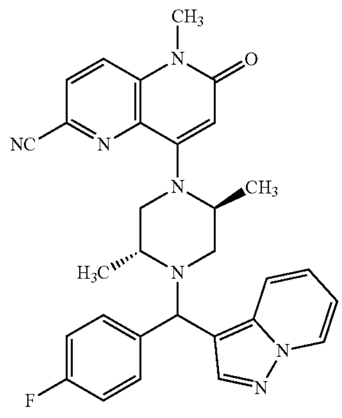 [SMILES: C[C@@H]1CN(c2cc(=O)n(C)c3ccc(C#N)nc23)[C@@H](C)CN1C(c1ccc(F)cc1)c1cnn2ccccc12] | 2.25 A | 522.2 | H |
| 699 | 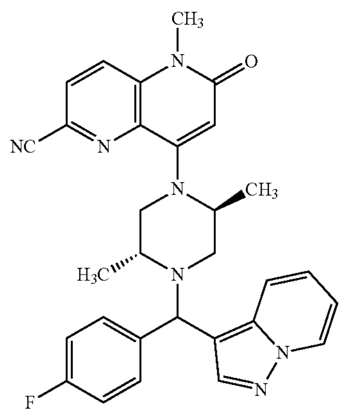 [SMILES: C[C@@H]1CN(c2cc(=O)n(C)c3ccc(C#N)nc23)[C@@H](C)CN1C(c1ccc(F)cc1)c1cnn2ccccc12] | 2.25 A | 522.2 | H |

Examples 700 and 701

8-((2S,5R)-4-((4-cyclopropylthiazol-2-yl)(4-fluorophenyl) methyl)-2, 5-dimethylpiperazin-1-yl)-5-methyl-6-oxo-5,6-dihydro-1,5-naphthyridine-2-carbonitrile

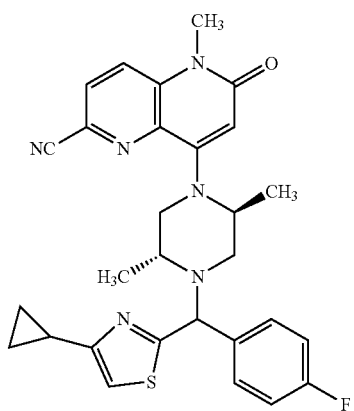

(700-701)

Intermediate 700A: (4-cyclopropylthiazol-2-yl)(4-fluorophenyl) methanol

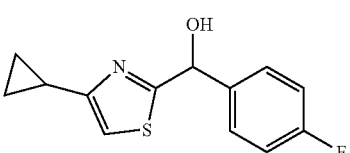

(700A)

To a stirred solution of 4-cyclopropylthiazole-2-carbaldehyde (0.3 g, 1.96 mmol) in tetrahydrofuran (8 mL) at 0° C. was added (4-fluorophenyl)magnesium bromide 1 M solution in THF (3.1 mL, 3.1 mmol) dropwise under nitrogen over 3 min. The reaction mixture was slowly warmed to room temperature and was stirred for 3 h. The reaction was quenched with saturated aqueous ammonium chloride solution (50 mL). The reaction mixture was extracted with EtOAc (3×100 mL). The combined organic layer was dried over anhydrous sodium sulphate, filtered and evaporated under reduced pressure to obtain crude compound. The crude compound was purified by flash column chromatography (using 12 g silica gel column; using 12%-15% ethyl acetate/Pet. ether) to yield (4-cyclopropylthiazol-2-yl)(4- fluorophenyl)methanol (0.42 g, 1.685 mmol, 86% yield) as a brown oil. ¹H NMR (300 MHz, DMSO-d₆) δ ppm 7.49-7.40 (m, 2H), 7.22-7.10 (m, 3H), 6.77-6.70 (m, 1H), 5.90-5.83 (m, 1H), 2.06-1.95 (m, 1H), 0.88-0.81 (m, 2H), 0.75-0.66 (m, 2H).

Intermediate 700B: 2-(chloro(4-fluorophenyl)methyl)-4-cyclopropylthiazole

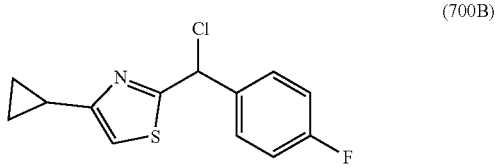 [SMILES: Fc1ccc(C(Cl)c2nc(C3CC3)cs2)cc1]

(700B)

To a stirred solution of (4-cyclopropylthiazol-2-yl)(4-fluorophenyl)methanol (0.15 g, 0.60 mmol) in DCM (4 mL) was added thionyl chloride (0.178 mL, 2.41 mmol) at 0° C. The reaction mixture was heated to 40° C. for 3 h. The reaction mixture was cooled to room temperature, concentrated under reduced pressure to yield the crude product. ¹H NMR (300 MHz, DMSO-d₆) δ ppm 7.66-7.56 (m, 2H), 7.33 (s, 3H), 5.55-5.11 (m, 1H), 2.11-1.95 (m, 1H), 0.94-0.83 (m, 3H), 0.78-0.67 (m, 1H).

Examples 700 and 701: 8-((2S, 5R)-4-((4-cyclopropylthiazol-2-yl) (4-fluorophenyl) methyl)-2,5-dimethylpiperazin-1-yl)-5-methyl-6-oxo-5,6-dihydro-1,5-naphthyridine-2-carbonitrile To a stirred solution of 8-((2S, 5R)-2,5-dimethylpiperazin-1-yl)-5-methyl-6-oxo-5,6-dihydro-1,5-naphthyridine-2-carbonitrile, HCl (80 mg, 0.24 mmol) in acetonitrile (8 mL) was added DIPEA (0.21 mL, 1.2 mmol). The reaction mixture was stirred for 5 min and then 2-(chloro(4-fluorophenyl) methyl)-4-cyclopropylthiazole (77 mg, 0.29 mmol) was added. The reaction mixture was heated to 85° C. for 16 h. The reaction mixture was cooled to room temperature and concentrated under reduced pressure to yield crude product which was purified by preparative chiral HPLC. (Chiral HPLC Method: Column: CELLULOSE-C4 (250×21.2) mm, 5 micron, M. Phase: 0.1% TFA in acetonitrile, 0.1% DEA in MeOH 90:10, ISOCRETIC to obtain Peak 1 (Example 700) and Peak 2 (Example 701).

Example 700: (1.6 mg, 2.97 μmol, 1.24% yield). LCMS: m/z, 529.2 (M+H); rt 2.27 min; (LCMS method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%. ¹H NMR (400 MHz, DMSO-d₆) δ ppm 8.17-8.11 (m, 1H), 8.09-8.02 (m, 1H), 7.69-7.50 (m, 2H), 7.27-7.13 (m, 3H), 6.00 (s, 1H), 5.02 (s, 1H), 4.61-4.47 (m, 1H), 3.70-3.60 (m, 1H), 3.54-3.44 (m, 4H), 3.06-2.93 (m, 2H), 2.42-2.35 (m, 1H), 1.27 (d, J=6.6 Hz, 3H), 1.02 (d, J=6.4 Hz, 3H), 0.90-0.80 (m, 2H), 0.76-0.63 (m, 2H).

Example 701: (1.5 mg, 2.84 μmol, 1.2% yield). LCMS: m/z, 529.2 (M+H); rt 2.30 min; (LCMS method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%. ¹H NMR (400 MHz, DMSO-d₆) δ ppm 8.17-8.10 (m, 1H), 8.09-8.02 (m, 1H), 7.56 (dd, J=5.5, 8.7 Hz, 2H), 7.29-7.13 (m, 3H), 6.01 (s, 1H), 5.09 (s, 1H), 4.63-4.50, (m, 1H), 3.62 (br d, J=12.2 Hz, 1H), 3.54-3.44 (m, 4H), 3.07 (br dd, J=2.4, 3.4 Hz, 1H), 2.85 (dd, J=3.4, 12.0 Hz, 1H), 2.23 (br d, J=11.0, Hz, 1H), 1.19 (dd, J=6.5, 13.6 Hz, 6H), 0.91-0.83 (m, 2H), 0.77-0.68 (m, 2H).

The examples in the Table 11 were prepared from the appropriate piperazine according to the general procedure described in Examples 700 and 701, substituting 4-cyclopropylthiazole-2-carbaldehyde with the appropriate heterocyclic aldehyde in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 11

| Ex. No. | Structure | LCMS RT and Method | M + H | Stereo chem. |
|---|---|---|---|---|
| 702 | 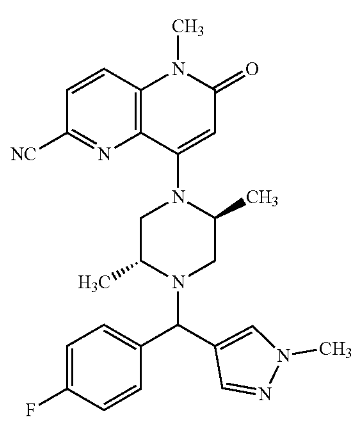 [SMILES: C[C@@H]1CN(c2cc(=O)n(C)c3ccc(C#N)nc23)[C@@H](C)CN1C(c1ccc(F)cc1)c1cnn(C)c1] | 1.873 A | 486.2 | H |

TABLE 11-continued
| Ex. No. | Structure | LCMS RT and Method | M + H | Stereo chem. |
|---|---|---|---|---|
| 703 | 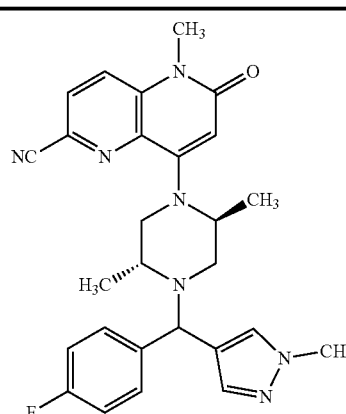 | 1.878 A | 486.2 | H |
| 704 | 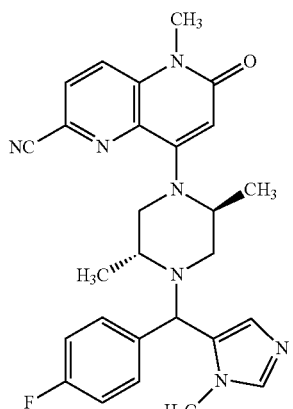 | 1.759 A | 486.3 | H |
| 705 | 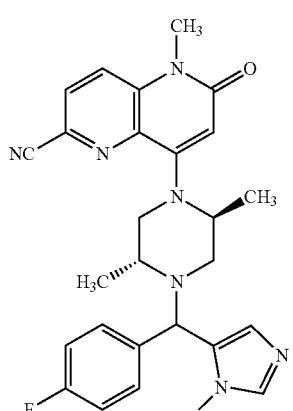 | 1.771 A | 486.3 | H |

TABLE 11-continued
| Ex. No. | Structure | LCMS RT and Method | M + H | Stereo chem. |
|---|---|---|---|---|
| 706 | 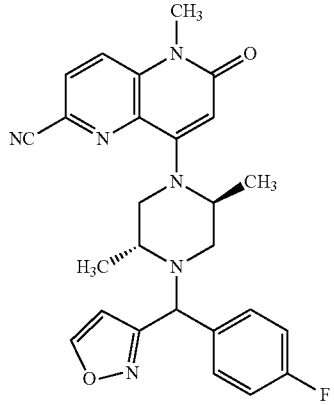 [SMILES: C[C@@H]1CN(c2cc(=O)n(C)c3ccc(C#N)nc23)[C@@H](C)CN1C(c1ccc(F)cc1)c1ccon1] | 1.998 A | 473.2 | H |
| 707 | 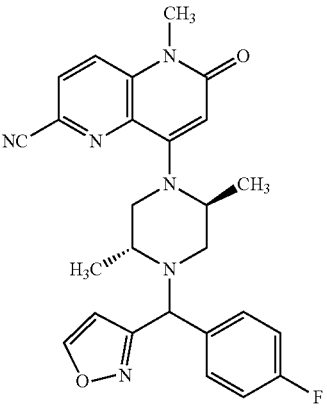 [SMILES: C[C@@H]1CN(c2cc(=O)n(C)c3ccc(C#N)nc23)[C@@H](C)CN1C(c1ccc(F)cc1)c1ccon1] | 1.983 A | 473.2 | H |
| 708 | 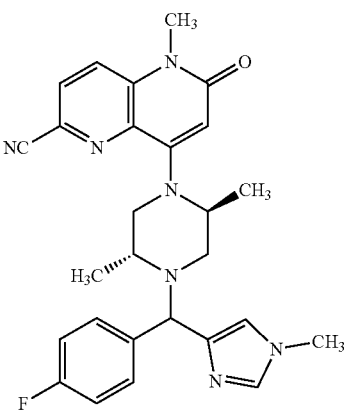 [SMILES: C[C@@H]1CN(c2cc(=O)n(C)c3ccc(C#N)nc23)[C@@H](C)CN1C(c1ccc(F)cc1)c1cn(C)cn1] | 1.741 A | 486.3 | H |

TABLE 11-continued
| Ex. No. | Structure | LCMS RT and Method | M + H | Stereo chem. |
|---|---|---|---|---|
| 709 | 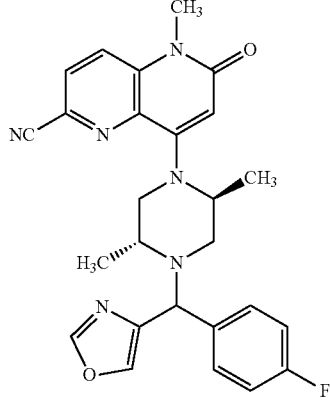 [SMILES: C[C@@H]1CN(c2cc(=O)n(C)c3ccc(C#N)nc23)[C@@H](C)CN1C(c1ccc(F)cc1)c1cocn1] | 1.901 A | 473.2 | H |
| 710 | 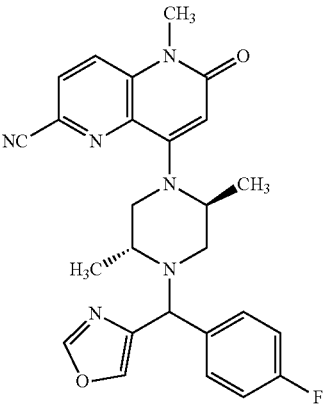 [SMILES: C[C@@H]1CN(c2cc(=O)n(C)c3ccc(C#N)nc23)[C@@H](C)CN1C(c1ccc(F)cc1)c1cocn1] | 1.89 A | 473.2 | H |
| 711 | 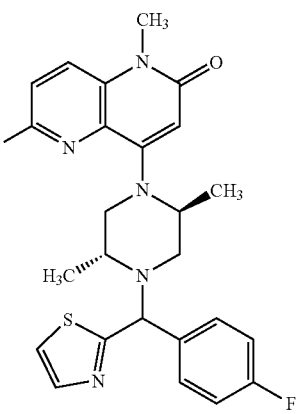 | 2.004 A | 489.2 | H |

TABLE 11-continued

| Ex. No. | Structure | LCMS RT and Method | M + H | Stereo chem. |
|---------|-----------|--------------------|-------|--------------|
| 712 | 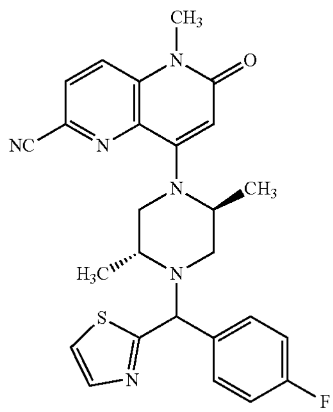 [SMILES: C[C@@H]1CN(c2cc(=O)n(C)c3ccc(C#N)nc23)[C@@H](C)CN1C(c1ccc(F)cc1)c1nccs1] | 1.983 A | 489.2 | H |
| 713 | 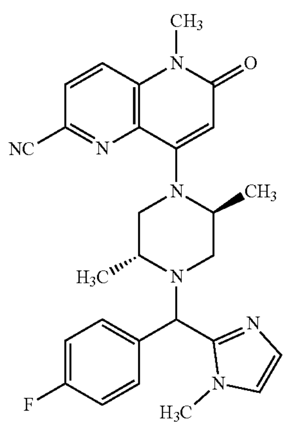 [SMILES: C[C@@H]1CN(c2cc(=O)n(C)c3ccc(C#N)nc23)[C@@H](C)CN1C(c1ccc(F)cc1)c1nccn1C] | 1.855 A | 486.2 | H |
| 714 | 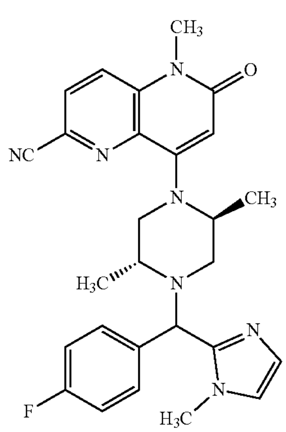 [SMILES: C[C@@H]1CN(c2cc(=O)n(C)c3ccc(C#N)nc23)[C@@H](C)CN1C(c1ccc(F)cc1)c1nccn1C] | 1.831 A | 486.2 | H |

TABLE 11-continued
| Ex. No. | Structure | LCMS RT and Method | M + H | Stereo chem. |
|---|---|---|---|---|
| 715 | 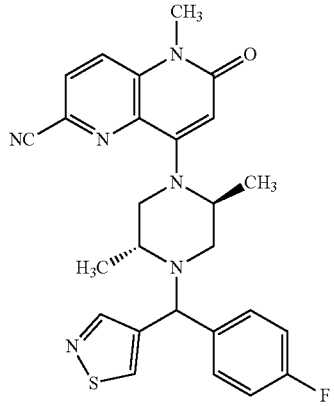 [SMILES: C[C@@H]1CN(c2cc(=O)n(C)c3ccc(C#N)nc23)[C@@H](C)CN1C(c1ccc(F)cc1)c1cnsc1] | 1.835 A | 489.2 | H |
| 716 | 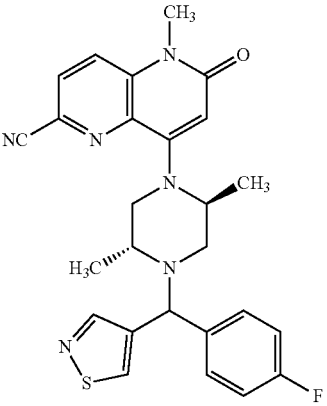 [SMILES: C[C@@H]1CN(c2cc(=O)n(C)c3ccc(C#N)nc23)[C@@H](C)CN1C(c1ccc(F)cc1)c1cnsc1] | 2.377 A | 489.1 | H |
| 717 | 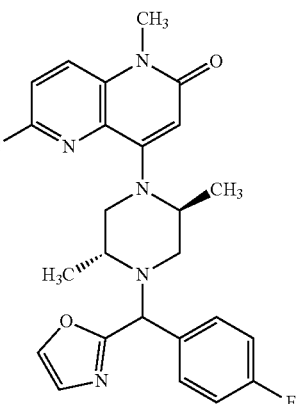 | 1.917 A | 473.2 | H |

TABLE 11-continued
| Ex. No. | Structure | LCMS RT and Method | M + H | Stereo chem. |
|---|---|---|---|---|
| 718 | 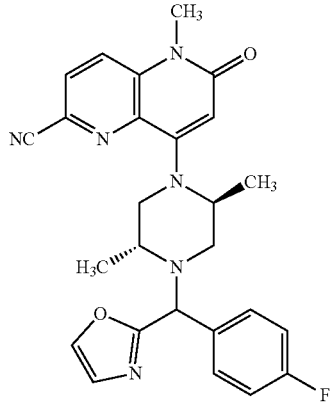 [SMILES: C[C@@H]1CN(c2cc(=O)n(C)c3ccc(C#N)nc23)[C@@H](C)CN1C(c1ccc(F)cc1)c1ncco1] | 1.916 A | 473.1 | H |
| 719 | 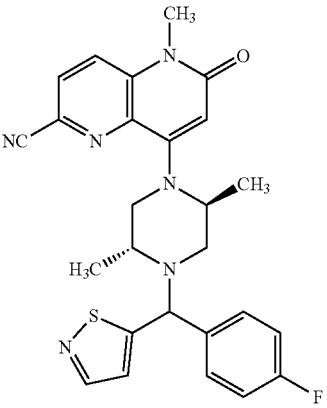 | 2.047 A | 489.1 | H |
| 720 | 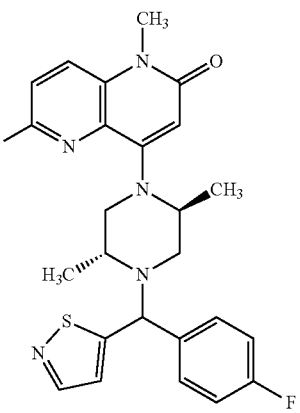 | 2.066 A | 489.1 | H |

TABLE 11-continued
| Ex. No. | Structure | LCMS RT and Method | M + H | Stereo chem. |
|---|---|---|---|---|
| 721 | 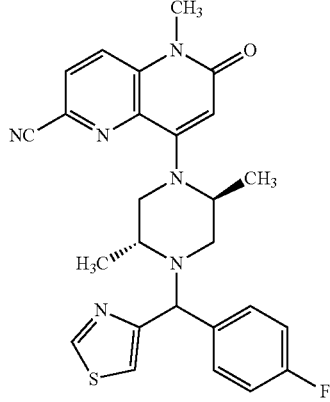 [SMILES: C[C@@H]1CN(c2cc(=O)n(C)c3ccc(C#N)nc23)[C@@H](C)CN1C(c1ccc(F)cc1)c1cscn1] | 1.922 A | 489.1 | H |
| 722 | 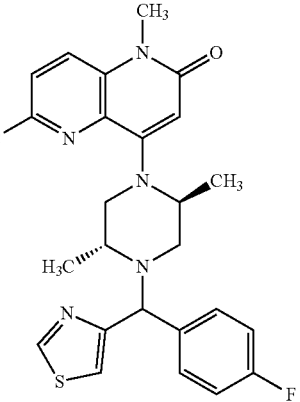 | 1.922 A | 489.2 | H |
| 723 | 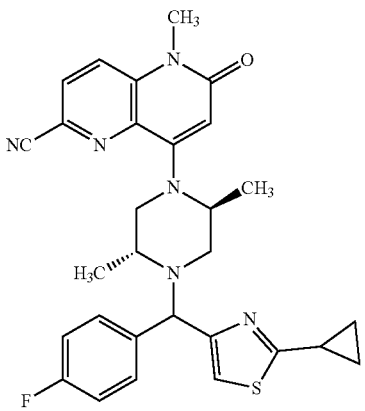 [SMILES: C[C@@H]1CN(c2cc(=O)n(C)c3ccc(C#N)nc23)[C@@H](C)CN1C(c1ccc(F)cc1)c1csc(C2CC2)n1] | 2.277 A | 529.2 | H |

TABLE 11-continued

| Ex. No. | Structure | LCMS RT and Method | M + H | Stereo chem. |
|---|---|---|---|---|
| 724 | 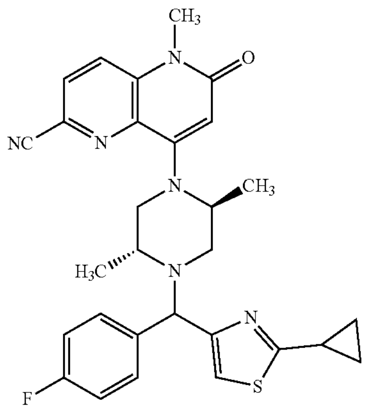 [SMILES: C[C@@H]1CN(c2cc(=O)n(C)c3ccc(C#N)nc23)[C@@H](C)CN1C(c1ccc(F)cc1)c1csc(C2CC2)n1] | 2.299 A | 529.2 | H |
| 725 | 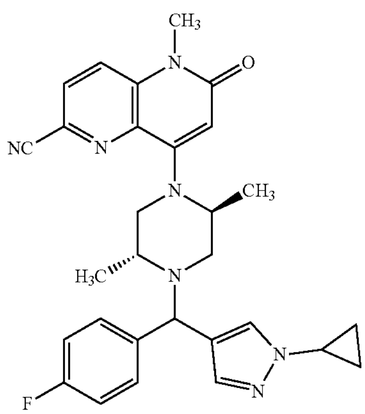 [SMILES: C[C@@H]1CN(c2cc(=O)n(C)c3ccc(C#N)nc23)[C@@H](C)CN1C(c1ccc(F)cc1)c1cnn(C2CC2)c1] | 2 A | 512.3 | H |
| 726 | 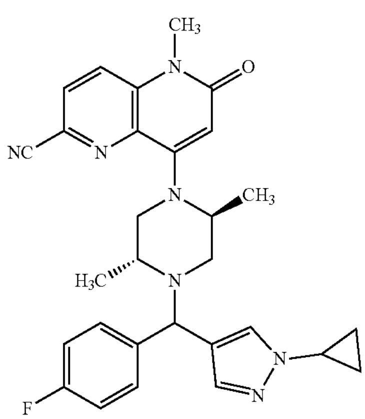 [SMILES: C[C@@H]1CN(c2cc(=O)n(C)c3ccc(C#N)nc23)[C@@H](C)CN1C(c1ccc(F)cc1)c1cnn(C2CC2)c1] | 2.01 A | 512.3 | H |

TABLE 11-continued

| Ex. No. | Structure | LCMS RT and Method | M + H | Stereo chem. |
|---|---|---|---|---|
| 727 | 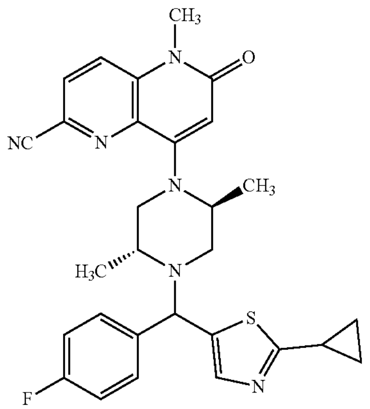 [SMILES: C[C@@H]1CN(c2cc(=O)n(C)c3ccc(C#N)nc23)[C@@H](C)CN1C(c1ccc(F)cc1)c1cnc(C2CC2)s1] | 2.221 A | 529.2 | H |
| 728 | 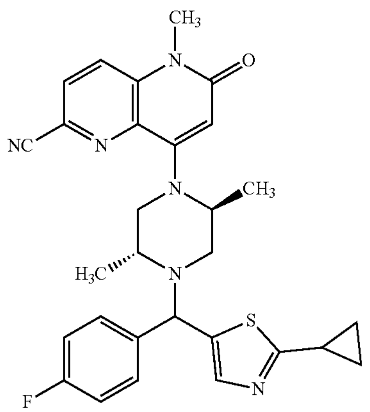 [SMILES: C[C@@H]1CN(c2cc(=O)n(C)c3ccc(C#N)nc23)[C@@H](C)CN1C(c1ccc(F)cc1)c1cnc(C2CC2)s1] | 2.2 A | 529.3 | H |

Examples 729 and 730

8-((2S,5R)-4-((5-cyclopropylisoxazol-3-yl)(4-fluoro-phenyl)methyl)-2,5-dimethylpiperazin-1-yl)-5-methyl-6-oxo-5,6-dihydro-1,5-naphthyridine-2-car-bonitrile (729-730)

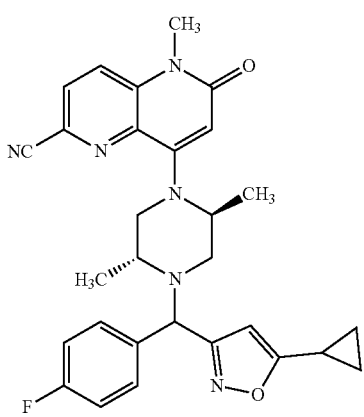

Intermediate 729A: 5-cyclopropyl-N-methoxy-N-methylisoxazole-3-carboxamide

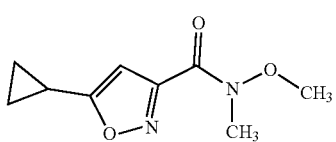

(729A)

To a solution of 5-cyclopropylisoxazole-3-carboxylic acid (650 mg, 4.24 mmol) in DMF (2 mL) were added N,O-dimethylhydroxylamine hydrochloride (497 mg, 5.09 mmol), DIPEA (2.22 mL, 12.73 mmol) and 1-propaneph-osphonic anhydride (3.75 mL, 6.37 mmol) at room temperature. The reaction mixture was stirred at the same temperature for 16 h. The reaction mixture was diluted with water and extracted twice with ethyl acetate (20 mL). The combined organic layer was dried over $Na_2SO_4$ and evaporated under reduced pressure to dryness. The crude product was purified by flash column chromatography (Column: 24 g silica; Solvent run: 0-50% EtOAc in pet ether). The product was eluted at 30% EtOAc in pet ether to yield 5-cyclopro-pyl-N-methoxy-N-methylisoxazole-3-carboxamide (450 mg, 2.16 mmol, 50.8% yield). LCMS: m/z, 197.1 (M+H); rt 1.07 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 729B: (5-cyclopropylisoxazol-3-yl)(4-fluorophenyl)methanone

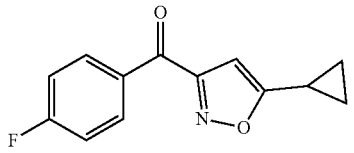

(729B)

To a solution of 5-cyclopropyl-N-methoxy-N-methylisoxazole-3-carboxamide (350 mg, 1.78 mmol) in tetrahydrofuran (20 mL) was added (4-fluorophenyl)magnesium bromide (4.46 mL, 3.57 mmol) at 0° C. After complete addition, the reaction mixture was stirred at room temperature for 16 h. The reaction was quenched with saturated aqueous NH$_4$Cl solution. The reaction mixture was extracted twice with ethyl acetate (40 mL). The combined organic layer was dried over Na$_2$SO$_4$ and evaporated to dryness to obtain (5-cyclopropylisoxazol-3-yl)(4-fluorophenyl)methanone (300 mg, 69.8% yield) as a colorless viscous oil. LCMS: m/z, 232.1 (M+H); rt 1.92 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 729C: (5-cyclopropylisoxazol-3-yl)(4-fluorophenyl)methanol

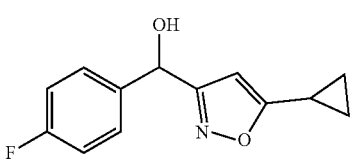

(729C)

To a solution of (5-cyclopropylisoxazol-3-yl)(4-fluorophenyl)methanone (300 mg, 1.30 mmol) in MeOH (5 mL) was added sodium borohydride (98 mg, 2.59 mmol) at 0° C. The reaction mixture was stirred at room temperature for 3 h. The reaction mixture was diluted with water and extracted twice with ethyl acetate (20 mL). The organic layer was separated, dried over Na$_2$SO$_4$ and evaporated to dryness to obtain the (5-cyclopropylisoxazol-3-yl)(4-fluorophenyl)methanol (250 mg, 83% yield) as a colorless liquid. $^1$H NMR (300 MHz, Chloroform-d) δ ppm 7.40-7.27 (m, 2H), 7.05-6.90 (m, 2H), 5.82 (d, J=3.6 Hz, 1H), 5.70 (s, 1H), 1.96-1.82 (m, 1H), 1.03-0.93 (m, 2H), 0.91-0.79 (m, 2H).

Intermediate 729D: 3-(bromo(4-fluorophenyl)methyl)-5-cyclopropylisoxazole

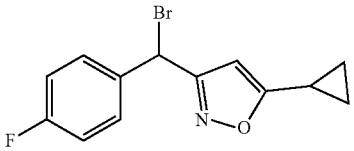

(729D)

To a solution of (5-cyclopropylisoxazol-3-yl)(4-fluorophenyl)methanol (100 mg, 0.43 mmol) in dichloromethane (5 mL) was added acetyl bromide (0.063 mL, 0.86 mmol) at room temperature. The reaction mixture was stirred at room temperature for 3 h. The reaction mixture was diluted with water and extracted twice with dichloromethane (20 mL). The organic layer was separated, dried over Na$_2$SO$_4$ and evaporated to dryness to yield 3-(bromo(4-fluorophenyl)methyl)-5-cyclopropylisoxazole (100 mg, 28.4% yield) as a pale yellow liquid. $^1$H NMR (300 MHz, Chloroform-d) δ ppm 7.56-7.33 (m, 2H), 7.15-6.96 (m, 2H), 6.10 (d, J=15.0 Hz, 1H), 5.84 (s, 1H), 2.08-1.88 (m, 1H), 1.15-0.88 (m, 4H).

Examples 729 and 730: 8-((2S,5R)-4-((5-cyclopropylisoxazol-3-yl)(4-fluorophenyl) methyl)-2,5-dimethylpiperazin-1-yl)-5-methyl-6-oxo-5,6-dihydro-1,5-naphthyridine-2-carbonitrile To a stirred solution of 8-((2S,5R)-2,5-dimethylpiperazin-1-yl)-5-methyl-6-oxo-5,6-dihydro-1,5-naphthyridine-2-carbonitrile, HCl (100 mg, 0.3 mmol) in acetonitrile (5 mL) were added DIPEA (0.16 mL, 0.9 mmol) and 3-(bromo(4-fluorophenyl)methyl)-5-cyclopropylisoxazole (115 mg, 0.39 mmol). The reaction mixture was stirred at 80° C. overnight. The reaction mixture was cooled to room temperature and concentrated under reduced pressure. The residue was dissolved in ethyl acetate (100 mL). The organic layer was washed with brine, dried over Na$_2$SO$_4$, concentrated under reduced pressure to afford crude product, which was purified by preparative HPLC (Prep HPLC Method: LUX COLUMN C2 (250 mm×21.2 mm ID, 5 μm) Mobile phase A-0.1% DEA in acetonitrile, Mobile phase B-0.1% DEA in MeOH, % B-0/0, 12/100 Flow: 20 mL/min) to afford Examples 729 and 730.

Example 729: (10 mg, 6.19% yield); LCMS: m/z, 513.2 (M+H); rt 2.188 min; (LCMS method: Column: XBridge BEH XP C18 (50×2.1) mm, 2.5 μm; Mobile phase A: 95% water:5% acetonitrile; 10 mM ammonium acetate; Mobile phase B: 5% water: 95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.13 (d, J=8.8 Hz, 1H), 8.03-8.08 (m, 1H), 7.58 (dd, J=8.6, 5.6 Hz, 2H), 7.15-7.21 (m, 2H), 6.40 (s, 1H), 6.00 (s, 1H), 4.79 (s, 1H), 4.50 (br s, 1H), 3.64-3.72 (m, 1H), 3.49-3.55 (m, 4H), 2.98-3.07 (m, 1H), 2.79-2.91 (m, 1H), 2.16-2.25 (m, 1H), 2.03-2.15 (m, 1H), 1.19 (d, J=6.6 Hz, 3H), 1.12 (d, J=6.6 Hz, 3H), 0.98-1.05 (m, 2H), 0.84-0.90 (m, 2H).

Example 730: (10 mg, 6.19% yield); LCMS: m/z, 513.2 (M+H); rt 2.16 min; (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.13

(d, J=8.8 Hz, 1H), 8.02-8.08 (m, 1H), 7.59-7.66 (m, 2H), 7.17-7.24 (m, 2H), 6.36 (s, 1H), 5.98 (s, 1H), 4.78 (s, 1H), 4.50-4.64 (m, 1H), 3.61-3.71 (m, 1H), 3.51 (s, 3H), 3.44 (br dd, J=12.3, 3.1 Hz, 1H), 2.89-2.99 (m, 2H), 2.21-2.28 (m, 1H), 2.04-2.14 (m, 1H), 1.26 (d, J=6.6 Hz, 3H), 0.99-1.07 (m, 5H), 0.77-0.91 (m, 2H).

The examples in the Table 12 were prepared from the appropriate piperazine according to the general procedure described in Examples 729 and 730, substituting 5-cyclopropylisoxazole-3-carboxylic acid with the appropriate isoxazole-3-carboxylic acid in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 12

| Ex. No. | Structure | LCMS RT and Method | M + H | Stereo chem. |
|---|---|---|---|---|
| 731 | 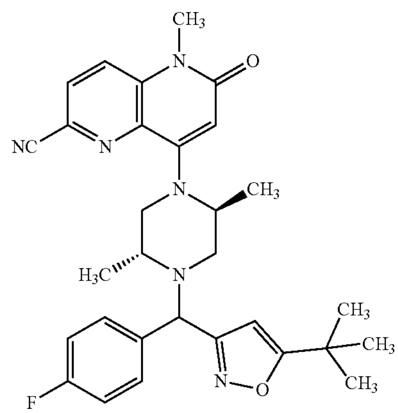 [SMILES: C[C@@H]1CN(c2cc(=O)n(C)c3ccc(C#N)nc23)[C@@H](C)CN1C(c1ccc(F)cc1)c1cc(C(C)(C)C)on1] | 2.349 A | 529.2 | H |
| 732 | 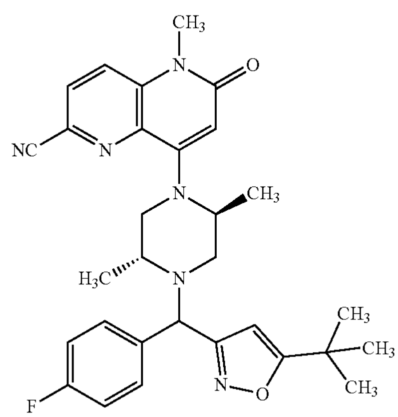 [SMILES: C[C@@H]1CN(c2cc(=O)n(C)c3ccc(C#N)nc23)[C@@H](C)CN1C(c1ccc(F)cc1)c1cc(C(C)(C)C)on1] | 2.338 A | 529.3 | H |
| 733 | 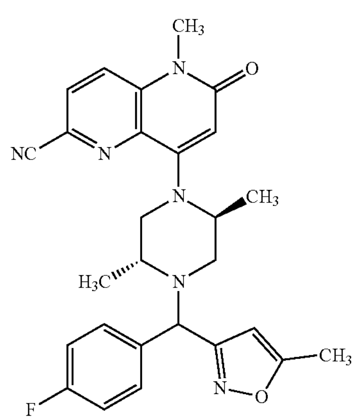 [SMILES: Cc1cc(C(c2ccc(F)cc2)N2C[C@H](C)N(c3cc(=O)n(C)c4ccc(C#N)nc34)C[C@H]2C)no1] | 2.059 A | 487.1 | H |

TABLE 12-continued

| Ex. No. | Structure | LCMS RT and Method | M + H | Stereo chem. |
|---|---|---|---|---|
| 734 | 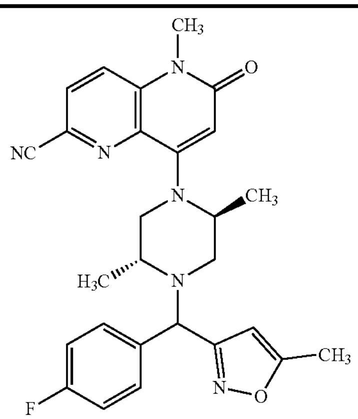 | 2.039 A | 487.2 | H |

Examples 735 and 736

8-((2S,5R)-4-((3-cyclopropyl-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile

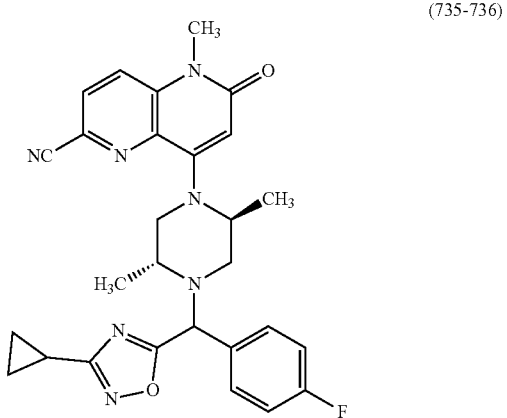 [SMILES: C[C@@H]1CN(c2cc(=O)n(C)c3ccc(C#N)nc23)[C@@H](C)CN1C(c1ccc(F)cc1)c1nc(C2CC2)no1]

(735-736)

To a solution of tert-butyl (2S,5R)-2,5-dimethylpiperazine-1-carboxylate (1.5 g, 7.0 mmol) in acetonitrile (5 mL) were added (4-fluorophenyl)boronic acid (0.98 g, 7.0 mmol) and glyoxylic acid (0.39 mL, 7.0 mmol) at room temperature. The reaction mixture was stirred at 85° C. for 2 h. The reaction mixture was concentrated to yield a brown solid. Diethyl ether (50 mL) was added to the solid and the mixture was stirred for 10 minutes, followed by the filtration of the solid. The filtrate was concentrated to yield 2-((2R,5S)-4-(tert-butoxycarbonyl)-2,5-dimethylpiperazin-1-yl)-2-(4-fluorophenyl)acetic acid (1.34 g, 29.3% yield) as a brown solid. LCMS: m/z, 367.1 (M+H); rt, 0.99 and 1.04 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Intermediate 735A: 2-((2R,5S)-4-(tert-butoxycarbonyl)-2,5-dimethylpiperazin-1-yl)-2-(4-fluorophenyl)acetic acid Intermediate 735B: Tert-butyl(2S,5R)-4-((3-cyclopropyl-1,2,4-oxadiazol-5-yl)(4-fluorophenyl)methyl)-2,5-dimethylpiperazine-1-carboxylate

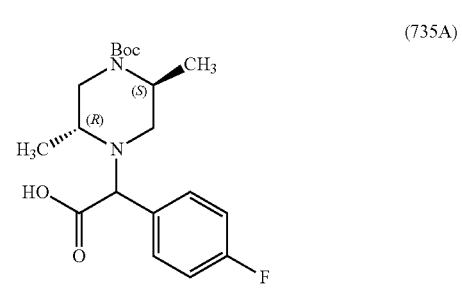

(735A)

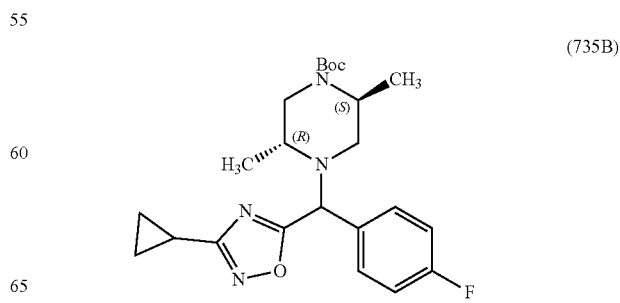

(735B)

To a stirred solution of 2-((2R,5S)-4-(tert-butoxycarbonyl)-2,5-dimethylpiperazin-1-yl)-2-(4-fluorophenyl)acetic acid (400 mg, 1.1 mmol), (Z)—N'-hydroxycyclopropane carboximidamide (219 mg, 2.18 mmol) in DMF (8.0 mL), BOP (724 mg, 1.64 mmol) and triethyl amine (0.46 mL, 3.27 mmol) were added at room temperature. The mixture was stirred for 2 h at room temperature. The reaction mixture was heated to 110° C. for 16 h. The reaction mixture was cooled to room temperature and concentrated under reduced pressure to yield crude product, which was purified by using silica gel flash chromatography using 0%-100% ethyl acetate/Pet. Ether). The fractions were concentrated under reduced pressure to yield tert-butyl (2S,5R)-4-((3-cyclopropyl-1,2,4-oxadiazol-5-yl)(4-fluorophenyl)methyl)-2,5-dimethylpiperazine-1-carboxylate (400 mg, 85% yield). LCMS: m/z, 431.2 (M+H); rt 2.28 min. LC-MS Method: Column-AQUITY UPLC BEH C18 (3.0×50 mm) 1.7 μm); Mobile phase A: 10 mM ammonium acetate in water:acetonitrile (98:02); Mobile phase B: 10 mM ammonium acetate in water: acetonitrile (2:98); Gradient: 20%-100% B over 2 minutes, then a 0.2 minute hold at 100% B flow rate 0.7 mL/min.

Intermediate 735C: 3-cyclopropyl-5-(((2R,5S)-2,5-dimethylpiperazin-1-yl)(4-fluorophenyl)methyl)-1,2,4-oxadiazole

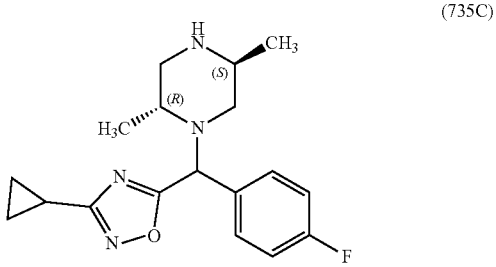

(735C)

To a stirred solution of tert-butyl (2S,5R)-4-((3-cyclopropyl-1,2,4-oxadiazol-5-yl) (4-fluorophenyl)methyl)-2,5-dimethylpiperazine-1-carboxylate (400 mg, 0.93 mmol) in DCM (8.0 mL) was added TFA (0.8 mL, 10.38 mmol). The mixture was stirred at room temperature for 4 h. The solvent was removed under reduced pressure to yield a TFA salt of 3-cyclopropyl-5-(((2R,5S)-2,5-dimethylpiperazin-1-yl)(4-fluorophenyl) methyl)-1,2,4-oxadiazole (250 mg, 81% yield) as a brown semisolid. LCMS: m/z, 331.0 (M+H); rt 0.94-1.06 min. LCMS Method: Column-Luna 3.0 C18(2) 100 Å; LC column (20×4.0 mm) Mercury MS TM; Mobile phase A: 0.1% TFA in Milli-Q water; Mobile phase B: 0.1% TFA in acetonitrile; Gradient: 20-100% B over 2.8 minutes, flow rate 2.0 mL/min, then a 0.1 minute hold at 100% B flow rate 1.5 mL/min, 100-20% B over 0.2 minutes, flow rate 1.5 mL/min.

Examples 735 and 736: 8-((2S,5R)-4-((3-cyclopropyl-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile To a stirred solution of 6-cyano-1-methyl-2-oxo-1,2-dihydro-1,5-naphthyridin-4-yl trifluoromethanesulfonate (200 mg, 0.6 mmol), 3-cyclopropyl-5-(((2R,5S)-2,5-dimethylpiperazin-1-yl)(4-fluorophenyl)methyl)-1,2,4-oxadiazole, TFA (347 mg, 0.78 mmol) in acetonitrile (8 mL) was added sodium bicarbonate (151 mg, 1.8 mmol). The reaction mixture was heated up to 85° C. for 16 h. The reaction mixture was cooled to room temperature and evaporated under reduced pressure to yield crude product, which was purified via preparative HPLC. Chiral Separation Method: Column: DAD-1-Cellulose-2 (250×4.6 mm), 5 micron; DAD-2-Cellulose-4 (250×4.6 mm), 5 micron. Mobile Phase: 0.1% DEA in acetonitrile, Flow: 2.0 mL\min.

Example 735: (13.4 mg, 17.4% yield): LCMS: m/z, 514.2 (M+H); rt 2.18 min; LCMS method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min) Time (min): 0-3; % B: 0-100%). $^1$H NMR (400 MHz, DMSO-$d_6$) δ ppm 8.19-8.13 (m, 1H), 8.09-8.03 (m, 1H), 7.66 (dd, J=5.6, 8.6 Hz, 2H), 7.25 (t, J=8.8 Hz, 2H), 6.04 (s, 1H), 5.25 (s, 1H), 4.48-4.38 (m, 1H), 3.63-3.47 (m, 4H), 3.18 (d, J=5.1 Hz, 1H), 2.91-2.83 (m, 2H), 2.20 (dd, J=1.8, 11.6 Hz, 1H), 2.17-2.09 (m, 1H), 1.21-1.11 (m, 6H), 1.11-1.03 (m, 2H), 0.94-0.88 (m, 2H).

Example 736: (12.4 mg, 16.1% yield): LCMS: m/z, 514.2 (M+H); rt 2.18 min; LCMS method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min) Time (min): 0-3; % B: 0-100%). $^1$H NMR (400 MHz, DMSO-$d_6$) δ ppm 8.18-8.12 (m, 1H), 8.10-8.02 (m, 1H), 7.69-7.58 (m, 2H), 7.27 (t, J=8.8 Hz, 2H), 6.00 (s, 1H), 5.25 (s, 1H), 4.61-4.50 (m, 1H), 3.66-3.56 (m, 1H), 3.52 (s, 3H), 3.47 (dd, J=3.2, 12.5 Hz, 1H), 3.20-3.09 (m, H), 3.02-2.87 (m, 1H), 2.17-2.08 (m, 2H), 1.22 (d, J=6.6 Hz, 2H), 1.19-0.99 (m, 6H), 0.96-0.78 (m, 2H).

The examples in the Table 13 were prepared from the appropriate piperazine according to the general procedure disclosed in Examples 735 and 736, substituting (Z)—N'-hydroxycyclopropane carboximidamide with the appropriate amidoximes in the synthetic sequence. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 13

| Ex. No. | Structure | LCMS RT and Method | M + H | Stereo chem. |
|---|---|---|---|---|
| 737 | 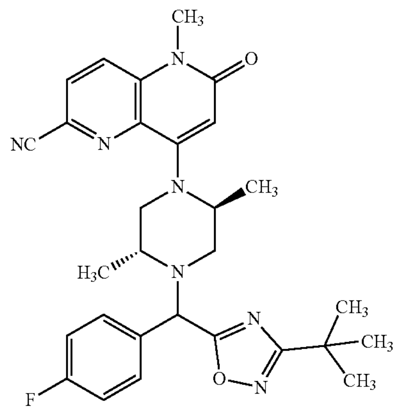 [SMILES: C[C@@H]1CN(c2cc(=O)n(C)c3ccc(C#N)nc23)[C@@H](C)CN1C(c1ccc(F)cc1)c1nc(C(C)(C)C)no1] | 2.67 A | 531.2 | H |
| 738 | 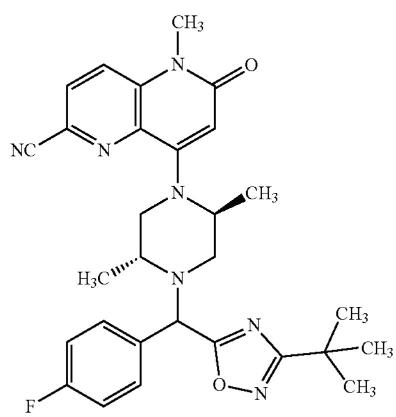 [SMILES: C[C@@H]1CN(c2cc(=O)n(C)c3ccc(C#N)nc23)[C@@H](C)CN1C(c1ccc(F)cc1)c1nc(C(C)(C)C)no1] | 2.67 A | 531.2 | H |
| 739 | 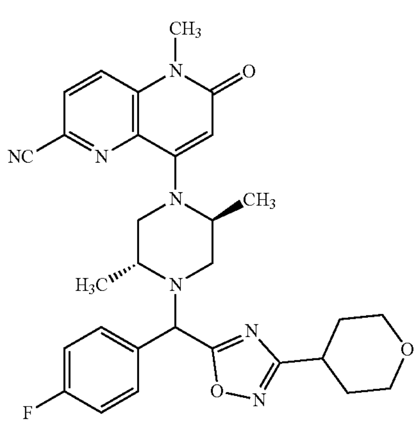 [SMILES: C[C@@H]1CN(c2cc(=O)n(C)c3ccc(C#N)nc23)[C@@H](C)CN1C(c1ccc(F)cc1)c1nc(C2CCOCC2)no1] | 2.04 A | 558.3 | H |

TABLE 13-continued

| Ex. No. | Structure | LCMS RT and Method | M + H | Stereo chem. |
|---|---|---|---|---|
| 740 | 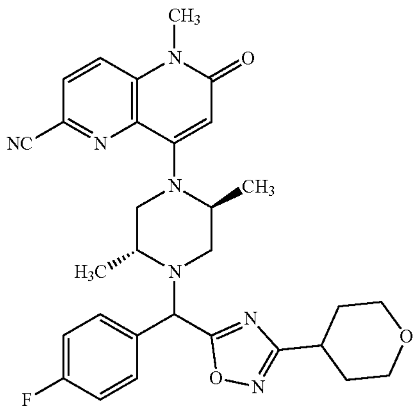 | 2.04 A | 558.3 | H |
| 741 | 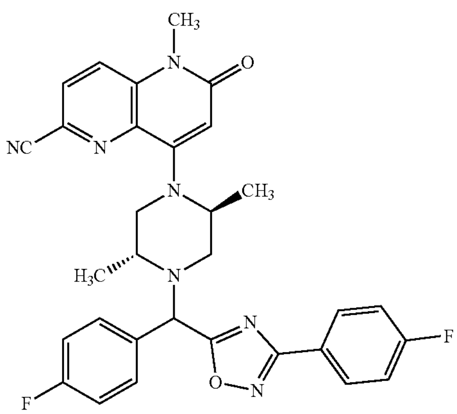 [SMILES: C[C@@H]1CN(c2cc(=O)n(C)c3ccc(C#N)nc23)[C@@H](C)CN1C(c1ccc(F)cc1)c1nc(-c2ccc(F)cc2)no1] | 2.46 A | 568.3 | H |
| 742 | 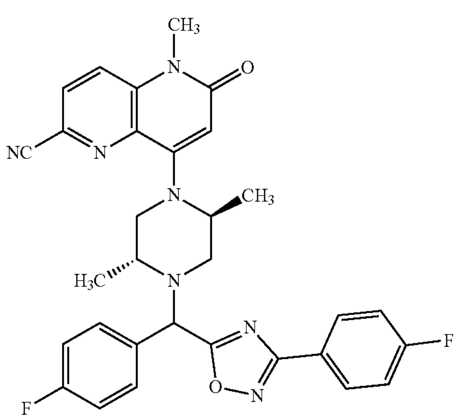 [SMILES: C[C@@H]1CN(c2cc(=O)n(C)c3ccc(C#N)nc23)[C@@H](C)CN1C(c1ccc(F)cc1)c1nc(-c2ccc(F)cc2)no1] | 2.44 A | 568.3 | H |

TABLE 13-continued
| Ex. No. | Structure | LCMS RT and Method | M + H | Stereo chem. |
|---|---|---|---|---|
| 743 | 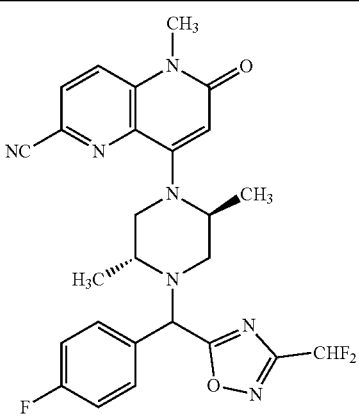 | 2.1 A | 524.3 | H |
| 744 | 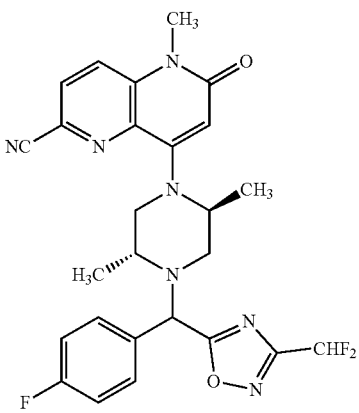 [SMILES: C[C@@H]1CN(c2cc(=O)n(C)c3ccc(C#N)nc23)[C@@H](C)CN1C(c1ccc(F)cc1)c1nc(C(F)F)no1] | 2.1 A | 524.3 | H |
| 745 | 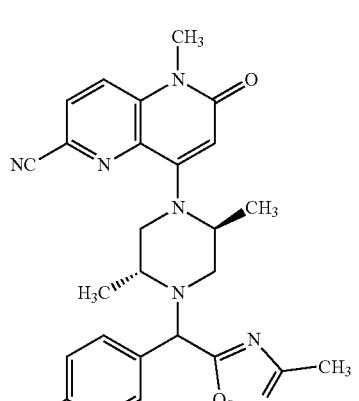 | 2.02 A | 488.2 | H |

TABLE 13-continued
| Ex. No. | Structure | LCMS RT and Method | M + H | Stereo chem. |
|---|---|---|---|---|
| 746 | 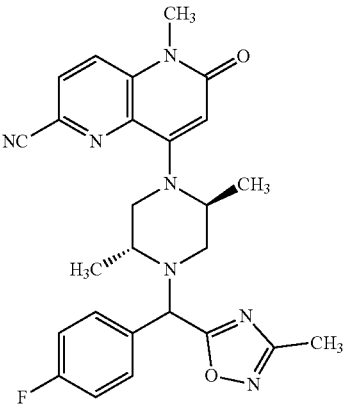 [SMILES: Cc1noc(C(c2ccc(F)cc2)N2C[C@H](C)N(c3cc(=O)n(C)c4ccc(C#N)nc34)C[C@H]2C)n1] | 2.02 A | 488.2 | H |
| 747 | 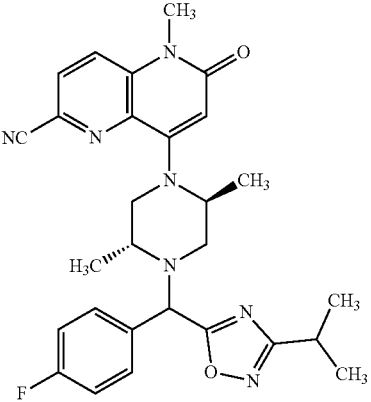 [SMILES: CC(C)c1noc(C(c2ccc(F)cc2)N2C[C@H](C)N(c3cc(=O)n(C)c4ccc(C#N)nc34)C[C@H]2C)n1] | 2.279 A | 516.2 | H |
| 748 | 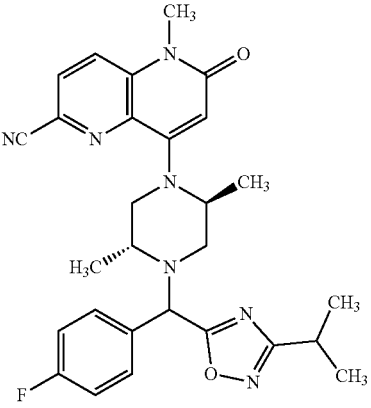 [SMILES: CC(C)c1noc(C(c2ccc(F)cc2)N2C[C@H](C)N(c3cc(=O)n(C)c4ccc(C#N)nc34)C[C@H]2C)n1] | 2.269 A | 516.2 | H |

TABLE 13-continued
| Ex. No. | Structure | LCMS RT and Method | M + H | Stereo chem. |
|---|---|---|---|---|
| 749 | 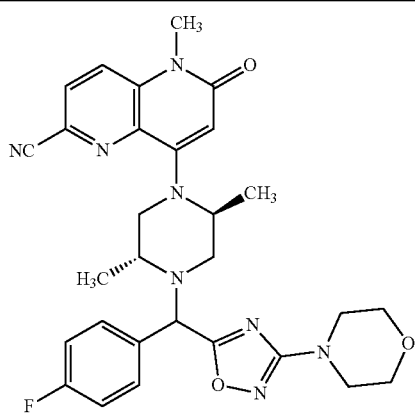 | 2.061 A | 559.3 | H |
| 750 | 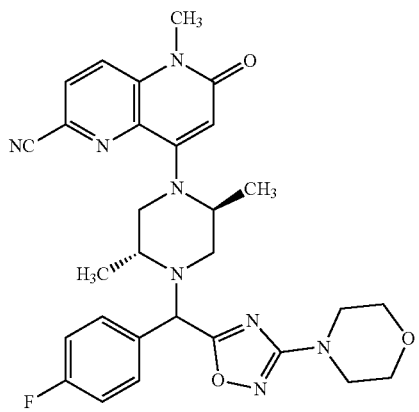 | 2.068 A | 559.2 | H |
| 751 | 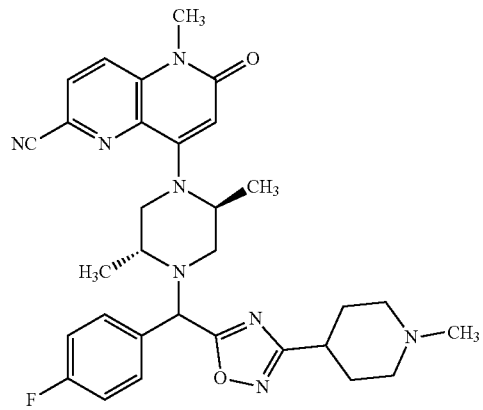 [SMILES: C[C@@H]1CN(c2cc(=O)n(C)c3ccc(C#N)nc23)[C@@H](C)CN1C(c1ccc(F)cc1)c1nc(C2CCN(C)CC2)no1] | 2.805 A | 571.4 | H |

TABLE 13-continued
| Ex. No. | Structure | LCMS RT and Method | M + H | Stereo chem. |
|---|---|---|---|---|
| 752 | 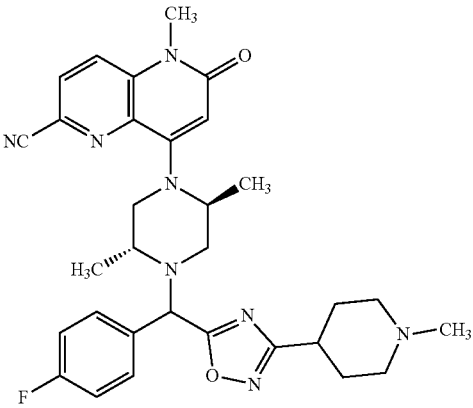 [SMILES: C[C@@H]1CN(c2cc(=O)n(C)c3ccc(C#N)nc23)[C@@H](C)CN1C(c1ccc(F)cc1)c1nc(C2CCN(C)CC2)no1] | 2.765 A | 571.2 | H |
| 753 | 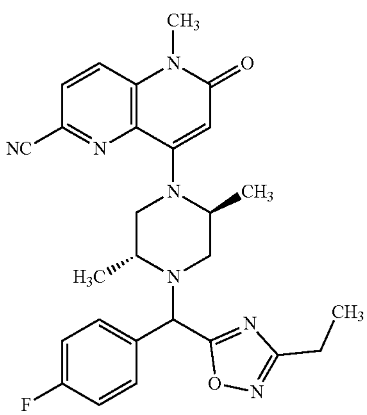 [SMILES: CCc1noc(C(c2ccc(F)cc2)N2C[C@H](C)N(c3cc(=O)n(C)c4ccc(C#N)nc34)C[C@H]2C)n1] | 2.078 A | 502.2 | H |
| 754 | 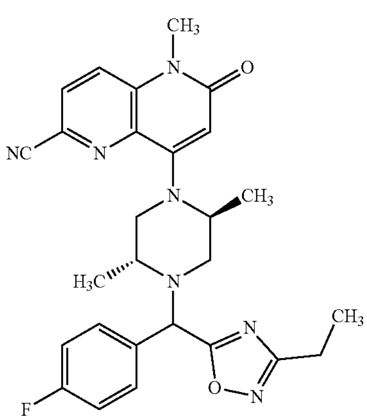 [SMILES: CCc1noc(C(c2ccc(F)cc2)N2C[C@H](C)N(c3cc(=O)n(C)c4ccc(C#N)nc34)C[C@H]2C)n1] | 2.117 A | 502.2 | H |

TABLE 13-continued

| Ex. No. | Structure | LCMS RT and Method | M + H | Stereo chem. |
|---|---|---|---|---|
| 755 | 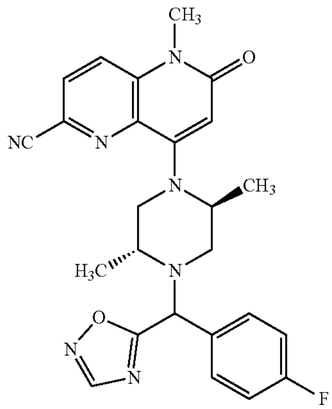 [SMILES: C[C@@H]1CN(c2cc(=O)n(C)c3ccc(C#N)nc23)[C@@H](C)CN1C(c1ccc(F)cc1)c1ncno1] | 1.135 A | 474.2 | D |
| 756 | 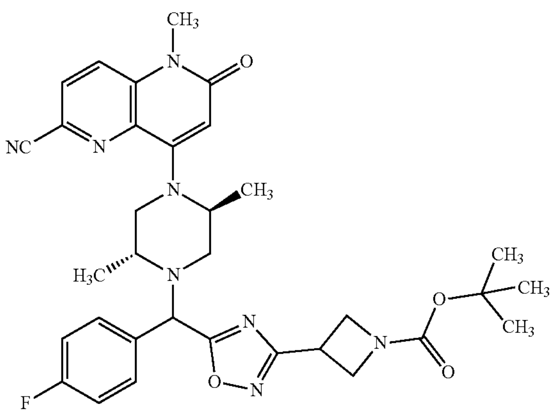 [SMILES: C[C@@H]1CN(c2cc(=O)n(C)c3ccc(C#N)nc23)[C@@H](C)CN1C(c1ccc(F)cc1)c1nc(C2CN(C(=O)OC(C)(C)C)C2)no1] | 2.269 A | 629.3 | H |
| 757 | 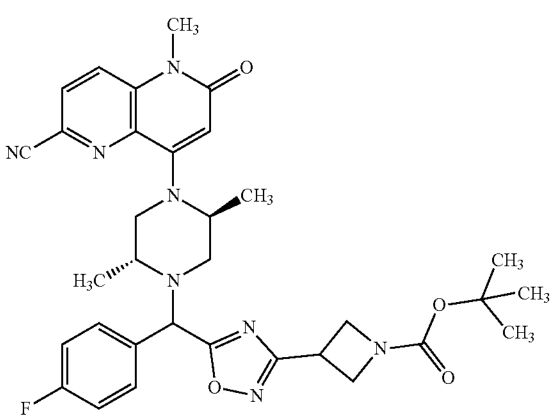 [SMILES: C[C@@H]1CN(c2cc(=O)n(C)c3ccc(C#N)nc23)[C@@H](C)CN1C(c1ccc(F)cc1)c1nc(C2CN(C(=O)OC(C)(C)C)C2)no1] | 2.260 A | 629.3 | H |

The examples in the Table 14 were prepared from the appropriate piperazine according to the general procedure described in Examples 735 and 736, substituting 4-fluorophenylboronic acid with the appropriate aryl boronic acid in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 13

| Ex. No. | Structure | LCMS RT and Method | M + H | Stereo chem. |
|---|---|---|---|---|
| 758 | 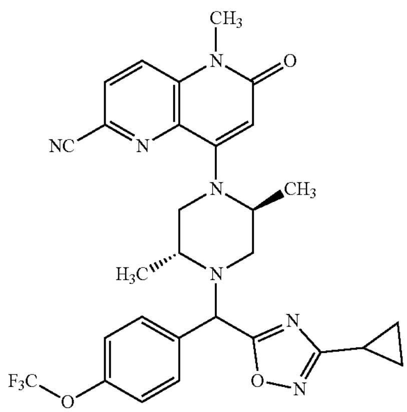 [SMILES: C[C@@H]1CN(c2cc(=O)n(C)c3ccc(C#N)nc23)[C@@H](C)CN1C(c1ccc(OC(F)(F)F)cc1)c1nc(C2CC2)no1] | 3.79 C | 580.2 | H |
| 759 | 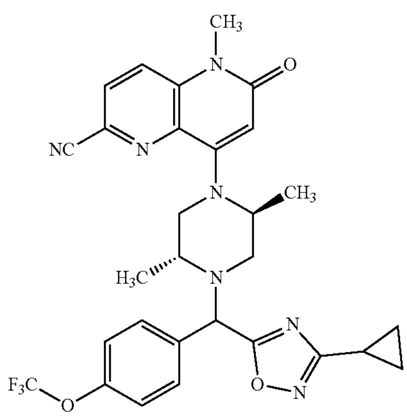 [SMILES: C[C@@H]1CN(c2cc(=O)n(C)c3ccc(C#N)nc23)[C@@H](C)CN1C(c1ccc(OC(F)(F)F)cc1)c1nc(C2CC2)no1] | 3.77 C | 580.2 | H |
| 760 | 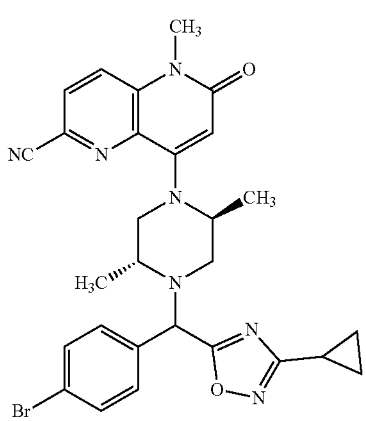 [SMILES: C[C@@H]1CN(c2cc(=O)n(C)c3ccc(C#N)nc23)[C@@H](C)CN1C(c1ccc(Br)cc1)c1nc(C2CC2)no1] | 2.37 A | 575.2 | H |

TABLE 13-continued

| Ex. No. | Structure | LCMS RT and Method | M + H | Stereo chem. |
|---|---|---|---|---|
| 761 | 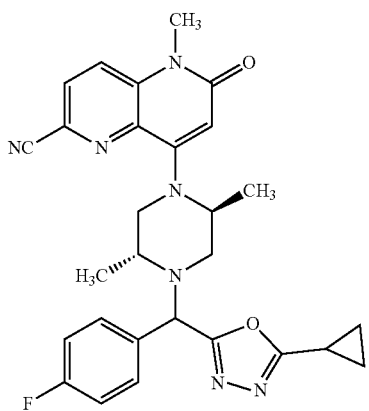 | 2.37 A | 575.2 | H |

Examples 762 and 763

8-((2R,5S)-4-((cyclopropyl-1,3,4-oxadiazol-2-yl)(4-fluorophenyl)methyl)-2,5-dimethylpiperazin-1-yl)-5-methyl-6-oxo-5,6-dihydro-1,5-naphthyridine-2-carbonitrile (762-763)

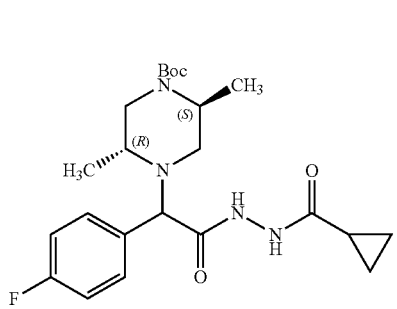

Intermediate 762A: tert-butyl (2S,5R)-4-(2-(2-(cyclopropanecarbonyl)hydrazineyl)-1-(4-fluorophenyl)-2-oxoethyl)-2,5-dimethylpiperazine-1-carboxylate To a solution of 2-((2R,5S)-4-(tert-butoxycarbonyl)-2,5-dimethylpiperazin-1-yl)-2-(4-fluorophenyl)acetic acid (0.4 g, 1.1 mmol) in DMF (5 mL) were added HATU (0.83 g, 2.2 mmol), DIPEA (0.58 mL, 3.27 mmol) and cyclopropanecarbohydrazide (0.11 g, 1.1 mmol) at room temperature. The reaction mixture was stirred at room temperature for 2 h. The reaction mixture was concentrated under reduced pressure to remove DMF and washed with water (2×10 mL) and extracted with ethyl acetate (2×10 mL). The combined organic layer was dried over sodium sulphate, which was concentrated under reduced pressure to give the crude compound as a gummy liquid. The crude product was purified by silica gel column chromatography eluting with 10% MeOH in DCM. The fractions were concentrated under reduced pressure to yield tert-butyl (2S,5R)-4-(2-(2-(cyclopropanecarbonyl)hydrazineyl)-1-(4-fluorophenyl)-2-oxoethyl)-2,5-dimethylpiperazine-1-carboxylate (450 mg, 46.0% yield). LCMS: m/z, 449.3 (M+H); rt 1.60-1.62 min. (LCMS Method: Column: Aquity UPLC BEH C18 (3.0×50 mm) 1.7 μm; Mobile phase A: 10 mM ammonium acetate:acetonitrile (98:2), Mobile phase B: 10 mM ammonium acetate:acetonitrile (2:98), Gradient=20-100% B over 4 minutes, then a 0.6 minute hold at 100% B; Temperature: 27° C.; Flow rate: 0.7 mL/min; Detection: UV at 220 nm).

Intermediate 762B: 2-cyclopropyl-5-(((2R,5S)-2,5-dimethylpiperazin-1-yl)(4-fluorophenyl)methyl)-1,3,4-oxadiazole (762A)

(762B)

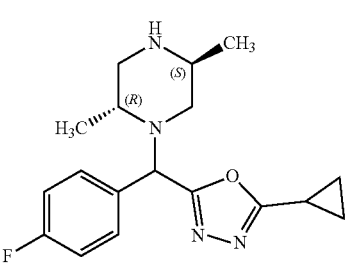

To a solution of tert-butyl (2S,5R)-4-(2-(2-(cyclopropanecarbonyl)hydrazineyl)-1-(4-fluorophenyl)-2-oxoethyl)-2, 5-dimethylpiperazine-1-carboxylate (0.13 g, 0.29 mmol) in acetonitrile (2 mL) was added phosphoryl chloride (0.03 mL, 0.348 mmol) at room temperature. The reaction mixture was stirred at 85° C. for 2 h. The reaction mixture was allowed to come to room temperature and then concentrated under reduced pressure to give the crude compound, 2-cyclopropyl-5-(((2R,5S)-2,5-dimethylpiperazin-1-yl)(4-fluorophenyl)methyl)-1,3,4-oxadiazole (130 mg, 54.3% yield), as a gummy liquid. LCMS: m/z, 331.2 (M+H); rt 2.28 min. (LCMS Method: Column: AQUITY UPLC BEH C18 (3.0× 50 mm) 1.7 μm; Mobile phase A: 10 mM ammonium acetate:acetonitrile (95:5), Mobile phase B: 10 mM ammonium acetate:acetonitrile (5:95), Gradient=20-100% B over 4 minutes, then a 0.6 minute hold at 100% B; Temperature: 27° C.; Flow rate: 0.7 mL/min; Detection: UV at 220 nm).

Examples 762 and 763: 8-((2S,5R)-4-((5-cyclopropyl-1,3,4-oxadiazol-2-yl)(4-fluorophenyl)methyl)-2,5-dimethylpiperazin-1-yl)-5-methyl-6-oxo-5,6-dihydro-1,5-naphthyridine-2-carbonitrile To a stirred solution of 2-cyclopropyl-5-(((2R,5S)-2,5-dimethylpiperazin-1-yl)(4-fluorophenyl)methyl)-1,3,4-oxadiazole (119 mg, 0.36 mmol) in acetonitrile (2 mL), sodium bicarbonate (91 mg, 1.08 mmol) was added at room temperature. The mixture was refluxed at 85° C. for 16 h. The reaction mixture was concentrated under reduced pressure to give the crude compound as a gummy liquid. The crude product was purified on a 12 g silica gel column chromatography by eluting with 10% MeOH in DCM. The fractions were concentrated under reduced pressure to yield 8-((2S,5R)-4-((5-cyclopropyl-1,3,4-oxadiazol-2-yl)(4-fluorophenyl)methyl)-2,5-dimethylpiperazin-1-yl)-5-methyl-6-oxo-5,6-dihydro-1,5-naphthyridine-2-carbonitrile as brown gummy liquid. The crude material was purified via preparative HPLC followed by chiral HPLC. (Chiral HPLC Method: Column: INERTSIL ODS (250 mm×19 mm ID, 5 μm); Mobile Phase A: 10 mM ammonium acetate in water; Mobile Phase B: acetonitrile; Gradient: 0-100% B over 18 minutes, then a 5 minute hold at 100% B; Flow: 18 mL/min).

The fraction containing Example 762 was concentrated under reduced pressure and the residue was diluted with EtOH water mixture (1:5) and lyophilized to yield Example 762 (7.0 mg, 3.76% yield); LCMS: m/z, 514.2 (M+H); rt 2.99 min; (LCMS method: Column: Column-Kinetex XB-C18 (75×3 mm-2.6 μm); Mobile phase A: 98% water: 2% acetonitrile; 10 mM ammonium acetate; Mobile phase B: 2% water:98% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.15 (d, J=9.0 Hz, 1H), 8.06 (d, J=8.5 Hz, 1H), 7.69-7.60 (m, 2H), 7.26-7.22 (m, 2H), 6.03 (s, 1H), 5.18 (s, 1H), 4.43-4.41 (m, 1H), 3.62-3.58 (m, 2H), 3.52 (s, 3H), 2.90-2.86 (m, 2H), 2.27-2.15 (m, 2H), 1.17-1.13 (m, 8H), 1.00-0.97 (m, 2H).

The fraction containing Example 763 was concentrated under reduced pressure and the residue was diluted with EtOH water mixture (1:5) and lyophilized to yield Example 763 (6.4 mg, 3.39% yield); LCMS: m/z, 514.2 (M+H); rt 2.98 min; (LCMS Method: Column: XBridge BEH XP C18 (50×2.1) mm, 2.5 μm; Mobile phase A: 98% water:2% acetonitrile; 10 mM ammonium acetate; Mobile phase B: 2% water:98% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.15 (d, J=9.0 Hz, 1H), 8.06 (d, J=9.0 Hz, 1H), 7.65 (dd, J=8.8, 5.3 Hz, 2H), 7.28-7.26 (m, 2H), 5.99 (s, 1H), 5.17 (s, 1H), 4.57 (br. s., 1H), 3.60 (d, J=11.0 Hz, 1H), 3.52 (s, 3H), 3.46-3.42 (m, 1H), 3.09-3.05 (m, 1H), 2.96-2.92 (m, 1H), 2.10-2.06 (m, 1H), 2.13-2.09 (m, 1H), 1.22 (d, J=6.5 Hz, 3H), 1.13 (dd, J=8.0, 2.5 Hz, 2H), 1.03 (d, J=6.5 Hz, 3H), 1.00-0.91 (m, 2H).

Examples 764 and 765

8-((2S,5R)-4-((5-(tert-butyl)-1,2,4-oxadiazol-3-yl)(4-fluorophenyl)methyl)-2,5-dimethylpiperazin-1-yl)-5-methyl-6-oxo-5,6-dihydro-1,5-naphthyridine-2-carbonitrile

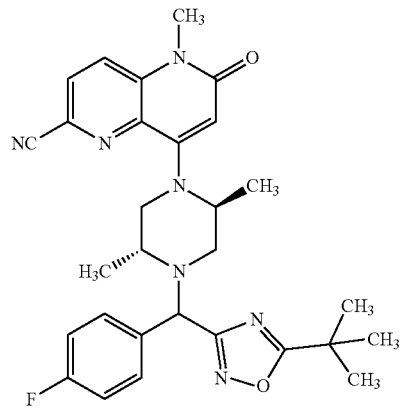

(764-765)

Intermediate 764A: tert-butyl (2S,5R)-4-(cyano(4-fluorophenyl)methyl)-2,5-dimethylpiperazine-1-carboxylate

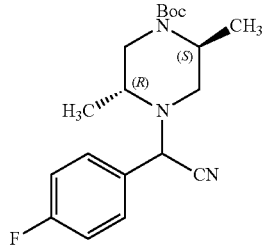

(764A)

To a solution of tert-butyl (2S,5R)-2,5-dimethylpiperazine-1-carboxylate (500 mg, 2.3 mmol) and 4-fluorobenzaldehyde (290 mg, 2.3 mmol) in acetonitrile (5.0 mL), trimethylsilyl cyanide (0.31 mL, 2.3 mmol) was added under nitrogen atmosphere. The reaction mixture was stirred for 16 h at room temperature. The reaction mixture was concentrated under reduced pressure to afford a yellow liquid. The crude product was purified by silica gel column chromatography eluting with 10% ethyl acetate in petroleum ether. The fractions were concentrated under reduced pressure to yield tert-butyl (2S,5R)-4-(cyano(4-fluorophenyl)methyl)-2,5-dimethylpiperazine-1-carboxylate (550 mg, 67.9% yield). LCMS: m/z, 348.2 (M+H); rt 2.07 min. LCMS Method: Column: AQUITY UPLC BEH C18 (3.0×50 mm) 1.7 μm; Mobile phase A: 10 mM ammonium acetate: acetonitrile (98:2), Mobile phase B: 10 mM ammonium acetate:acetonitrile (2:98), Gradient=20-100% B over 4 minutes, then a 0.6

Intermediate 764B: tert-butyl (2S,5R)-4-((Z)-2-amino-1-(4-fluorophenyl)-2-(hydroxyimino)ethyl)-2,5-dimethylpiperazine-1-carboxylate

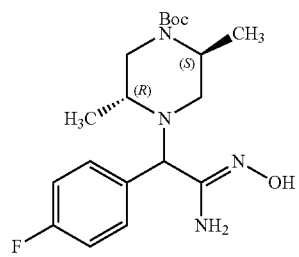
(764B)

To a mixture of the product of tert-butyl (2S,5R)-4-(cyano(4-fluorophenyl)methyl)-2,5-dimethylpiperazine-1-carboxylate (500 mg, 1.44 mmol) in ethanol (15 mL) was added hydroxylamine (0.13 mL, 2.16 mmol). The resulting mixture was stirred at room temperature for 20 h. The reaction mixture was concentrated under reduced pressure and was purified by silica gel (12 g) chromatography by using 0-100% EtOAc/Pet ether as eluent. The fractions were concentrated under reduced pressure to yield tert-butyl (2S,5R)-4-((E)-2-amino-1-(4-fluorophenyl)-2-(hydroxyimino)ethyl)-2,5-dimethylpiperazine-1-carboxylate (400 mg, 73.1% yield). LCMS: m/z, 381.3 (M+H); rt 1.60 min. LCMS Method: Column: AQUITY UPLC BEH C18 (3.0×50 mm) 1.7 µm; Mobile phase A: 10 mM ammonium acetate:acetonitrile (98:2), Mobile phase B: 10 mM ammonium acetate:acetonitrile (2:98), Gradient=20-100% B over 4 minutes, then a 0.6 minute hold at 100% B; Temperature: 27° C.; Flow rate: 0.7 mL/min; Detection: UV at 220 nm).

Intermediate 764C: tert-butyl (2S,5R)-4-((5-(tert-butyl)-1,2,4-oxadiazol-3-yl)(4-fluorophenyl)methyl)-2,5-dimethylpiperazine-1-carboxylate

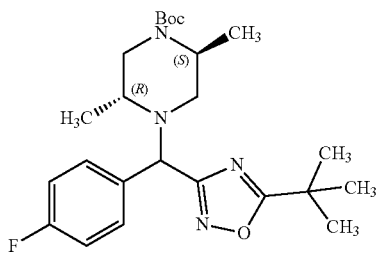
(764C)

To a stirred solution of tert-butyl (2S,5R)-4-((Z)-2-amino-1-(4-fluorophenyl)-2-(hydroxyimino)ethyl)-2,5-dimethylpiperazine-1-carboxylate (100 mg, 0.26 mmol), DIPEA (0.14 mL, 0.8 mmol) in DMF (2.0 mL), pivaloyl chloride (47.5 mg, 0.39 mmol) was added at room temperature. The mixture was stirred for 16 h. The reaction mixture was heated to 90° C. for 12 h. The reaction mixture cooled to room temperature, concentrated under reduced pressure, dissolved in DCM (100 mL), washed with saturated aqueous NaHCO$_3$ (20 mL), water (20 mL), brine (20 mL), dried over Na$_2$SO$_4$ and concentrated under reduced pressure to obtain the crude product, which was purified by silica gel (12 g) chromatography by using 0-100% EtOAc/Pet Ether as eluent. The fractions were concentrated under reduced pressure to yield tert-butyl (2S,5R)-4-((5-(tert-butyl)-1,2,4-oxadiazol-3-yl)(4-fluorophenyl)methyl)-2,5-dimethylpiperazine-1-carboxylate (80 mg, 68% yield). LCMS: m/z, 447.3 (M+H); rt 2.05 and 2.08 min. LCMS Method: Column: AQUITY UPLC BEH C18 (3.0×50 mm) 1.7 µm; Mobile phase A: 10 mM ammonium acetate:acetonitrile (98:2), Mobile phase B: 10 mM ammonium acetate:acetonitrile (2:98), Gradient=20-100% B over 4 minutes, then a 0.6 minute hold at 100% B; Temperature: 27° C.; Flow rate: 0.7 mL/min; Detection: UV at 220 nm).

Intermediate 764D: 5-(tert-butyl)-3-(((2R,5S)-2,5-dimethylpiperazin-1-yl)(4-fluorophenyl)methyl)-1,2,4-oxadiazole

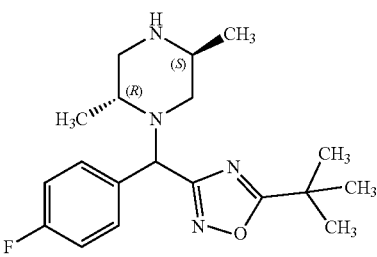
(764D)

To a solution of tert-butyl (2S,5R)-4-((5-(tert-butyl)-1,2,4-oxadiazol-3-yl)(4-fluorophenyl)methyl)-2,5-dimethylpiperazine-1-carboxylate (80 mg, 0.18 mmol) in DCM (2 mL) at room temperature was added TFA (0.18 mL, 2.33 mmol). The reaction mixture was stirred for 4 h. The reaction mixture was concentrated under reduced pressure. DCM (5 mL) and the mixture was rotovapped again. The crude material was dried under vacuum to obtain 5-(tert-butyl)-3-(((2R,5S)-2,5-dimethylpiperazin-1-yl)(4-fluorophenyl)methyl)-1,2,4-oxadiazole (41 mg, 0.16 mmol, 66% yield) as a TFA salt. LCMS: m/z, 347.2 (M+H); rt 1.12 min. (LCMS Method: Column: AQUITY UPLC BEH C18 (3.0×50 mm) 1.7 µm; Mobile phase A: 10 mM ammonium acetate:acetonitrile (95:5), Mobile phase B: 10 mM ammonium acetate:acetonitrile (5:95), Gradient=20-100% B over 4 minutes, then a 0.6 minute hold at 100% B; Temperature: 27° C.; Flow rate: 0.7 mL/min; Detection: UV at 220 nm).

Examples 764 and 765: 8-((2S,5R)-4-((5-(tert-butyl)-1,2,4-oxadiazol-3-yl)(4-fluorophenyl)methyl)-2,5-dimethylpiperazin-1-yl)-5-methyl-6-oxo-5,6-dihydro-1,5-naphthyridine-2-carbonitrile To a solution of 5-(tert-butyl)-3-(((2R,5S)-2,5-dimethylpiperazin-1-yl)(4-fluorophenyl)methyl)-1,2,4-oxadiazole (41.6 mg, 0.12 mmol) in dry acetonitrile (3 mL), 6-cyano-1-methyl-2-oxo-1,2-dihydro-1,5-naphthyridin-4-yl trifluoromethanesulfonate (40 mg, 0.120 mmol), sodium bicarbonate (30.3 mg, 0.36 mmol) was added at room temperature under an argon atmosphere. The reaction mixture was stirred for 10 minutes at room temperature. The reaction mixture was heated to 85° C. for 16 h. The reaction mixture was cooled to room temperature and evaporated to dryness. The residue was purified by silica gel (12 g) chromatography by using 0-10% MeOH/CHCl₃ as eluent. The fractions were concentrated under reduced pressure to yield a diastereomeric mixture of 8-((2S,5R)-4-((5-(tert-butyl)-1,2,4-oxadiazol-3-yl)(4-fluorophenyl)methyl)-2,5-dimethylpiperazin-1-yl)-5-methyl-6-oxo-5,6-dihydro-1,5-naphthyridine-2-carbonitrile. The crude material was purified via preparative HPLC followed by chiral separation. Chiral Separation Method: Column: Cellulose-2 (250×4.6) mm, 5 micron Mobile Phase: 0.1% TFA in Methanol, Flow: 1.0 mL\min.

Example 764: (1 mg, 1.6% yield); LCMS: m/z, 530.2 (M+H); rt 2.35 min; LCMS method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). ¹H NMR (400 MHz, DMSO-d₆) δ ppm 8.17-8.12 (m, 1H), 8.09-8.02 (m, 1H), 7.71 (dd, J=6.2, 8.4 Hz, 2H), 7.23 (t, J=8.9 Hz, 2H), 5.98 (s, 1H), 5.01 (s, 1H), 4.62-4.53 (m, 1H), 3.56 (br dd, J=2.0, 3.4 Hz, 1H), 3.51 (s, 3H), 3.46 (br d, J=0.7 Hz, 1H), 3.07-3.01 (m, 1H), 2.96-2.90 (m, 2H), 1.36 (s, 9H), 1.28-1.14 (m, 3H), 1.04 (d, J=6.6 Hz, 3H).

Example 765: (1 mg, 1.6% yield); LCMS: m/z, 530.2 (M+H); rt 2.33 min; LCMS method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). ¹H NMR (400 MHz, DMSO-d₆) δ ppm 8.16-8.12 (m, 1H), 8.08-7.99 (m, 1H), 7.72-7.60 (m, 2H), 7.25-7.16 (m, 2H), 6.03 (s, 1H), 5.01 (s, 1H), 4.46-4.35 (m, 1H), 3.68-3.61 (m, 1H), 3.56-3.50 (m, 4H), 2.99-2.85 (m, 3H), 1.37 (s, 9H), 1.21-1.09 (m, 6H).

Examples 766 and 767

8-((2S,5R)-4-((5-cyclopropyl-4H-1,2,4-triazol-3-yl)(4-fluorophenyl)methyl)-2,5-dimethylpiperazin-1-yl)-5-methyl-6-oxo-5,6-dihydro-1,5-naphthyridine-2-carbonitrile

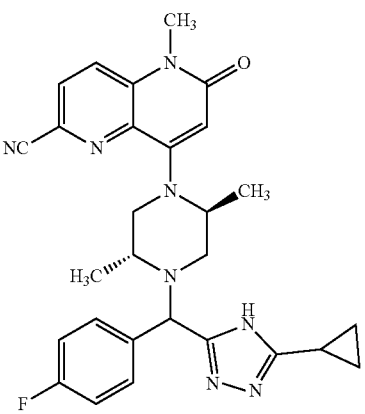
(766-767)

Intermediate 766A: tert-butyl (2S,5R)-4-(2-(2-(cyclopropyl(imino)methyl)hydrazineyl)-1-(4-fluorophenyl)-2-oxoethyl)-2,5-dimethylpiperazine-1-carboxylate

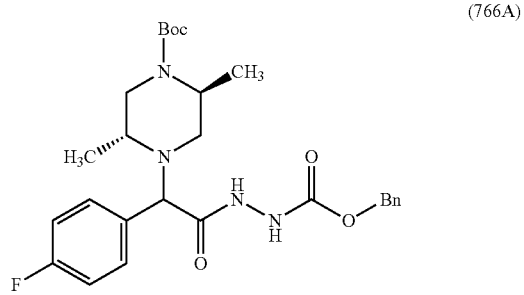 [SMILES: C[C@@H]1CN(C(=O)OC(C)(C)C)[C@@H](C)CN1C(C(=O)NNC(=O)OCc1ccccc1)c1ccc(F)cc1]
(766A)

To a stirred solution of 2-((2R,5S)-4-(tert-butoxycarbonyl)-2,5-dimethylpiperazin-1-yl)-2-(4-fluorophenyl)acetic acid (600 mg, 1.64 mmol) in EtOAc (4 mL) were added benzylhydrazinecarboxylate (272 mg, 1.64 mmol), Et₃N (0.46 mL, 3.27 mmol), followed by 1-propanephosphonic anhydride (1250 mg, 1.97 mmol) at 0° C. The reaction mixture was allowed to reach room temperature and stirred for 16 h. The reaction mixture was extracted with EtOAc (2×100 mL), washed with water and brine, dried over Na₂SO₄ and concentrated to give tert-butyl (2S,5R)-4-(2-(2-benzyloxy) carbonyl)hydrazineyl)-1-(4-fluorophenyl)-2-oxoethyl)-2,5-dimethylpiperazine-1-carboxylate (700 mg, 83% yield). LCMS: m/z, 515.4 (M+H); rt 1.89 & 1.92 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Temperature: 50° C.; Flow rate: 0.7 mL/min; Detection: UV at 220 nm).

Intermediate 766B: tert-butyl (2S,5R)-4-(1-(4-fluorophenyl)-2-hydrazineyl-2-oxoethyl)-2,5-dimethylpiperazine-1-carboxylate

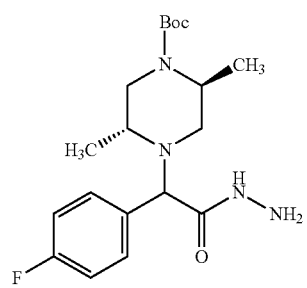
(766B)

To a stirred solution of tert-butyl (2S,5R)-4-(2-(2-((benzyloxy)carbonyl) hydrazineyl)-1-(4-fluorophenyl)-2-oxoethyl)-2,5-dimethylpiperazine-1-carboxylate (800 mg, 1.56 mmol) in EtOH (15 mL) was added Pd—C (10% on carbon) (83 mg, 0.78 mmol) and hydrogenated using a hydrogen bladder at ~1 atm pressure for 16 h. The reaction mixture was filtered through a Celite pad, washed with excess EtOH, and the filtrate was concentrated under reduced pressure to give tert-butyl (2S,5R)-4-(1-(4-fluorophenyl)-2-hydrazineyl-2-oxoethyl)-2,5-dimethylpiperazine-1-carboxylate (600 mg, 1.10 mmol, 71.0% yield). LCMS: m/z, 381.3 (M+H); rt 1.47 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 766C: tert-butyl (2S,5R)-4-(2-(2-(cyclopropyl(imino)methyl)hydrazineyl)-1-(4-fluorophenyl)-2-oxoethyl)-2,5-dimethylpiperazine-1-carboxylate

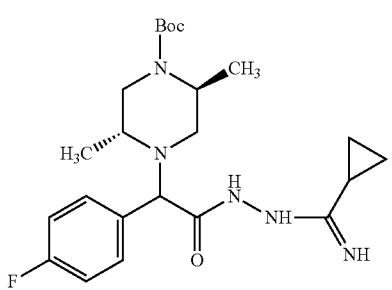

(766C)

To a stirred solution of methyl cyclopropanecarbimidate, HCl (125 mg, 0.92 mmol) in benzene (5 mL) was added Et₃N (0.36 mL, 2.58 mmol). The reaction mixture was stirred for 30 min. The reaction mixture was filtered. The filtrate was added to the tert-butyl (2S,5R)-4-(1-(4-luorophenyl)-2-hydrazineyl-2-oxoethyl)-2,5-dimethylpiperazine-1-carboxylate (350 mg, 0.92 mmol) and heated at 85° C. for 2 h. The reaction mixture was cooled to room temperature and extracted with EtOAc (2×100 mL), washed with water, brine, dried over Na₂SO₄ and concentrated to give crude product. The crude product was purified by flash chromatography using silica gel 12 g column and eluted with 5% MeOH/CHCl₃ to afford tert-butyl (2S,5R)-4-(2-(2-cyclopropyl(imino)methyl)hydrazineyl)-1-(4-fluorophenyl)-2-oxoethyl)-2,5-dimethylpiperazine-1-carboxylate (200 mg, 48.6% yield). LCMS: m/z, 448.3 (M+H); rt 1.46 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 766D: tert-butyl (2S,5R)-4-((5-cyclopropyl-4H-1,2,4-triazol-3-yl)(4-fluorophenyl)methyl)-2,5-dimethylpiperazine-1-carboxylate

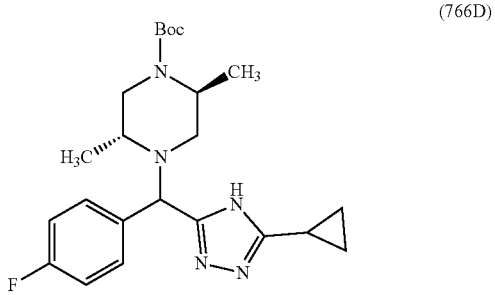 [SMILES: C[C@@H]1CN(C(=O)OC(C)(C)C)[C@@H](C)CN1C(c1ccc(F)cc1)c1nnc(C2CC2)[nH]1]

(766D)

In a round bottom flask, tert-butyl (2S,5R)-4-(2-(2-(cyclopropyl(imino)methyl) hydrazineyl)-1-(4-fluorophenyl)-2-oxoethyl)-2,5-dimethylpiperazine-1-carboxylate (200 mg, 0.45 mmol) was heated at 180° C. for 2-5 min. The reaction mixture was cooled to room temperature and the crude product was purified via flash chromatography using 12 g silica gel column and eluted with 3% MeOH/CHCl₃. The fractions were concentrated to afford tert-butyl (2S,5R)-4-((5-cyclopropyl-4H-1,2,4-triazol-3-yl)(4-fluorophenyl)methyl)-2,5-dimethylpiperazine-1-carboxylate (100 mg, 52.1% yield). LCMS: m/z, 430.3 (M+H); rt 1.73 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 766E: (2R,5S)-1-((5-cyclopropyl-4H-1, 2,4-triazol-3-yl)(4-fluorophenyl) methyl)-2,5-dimethylpiperazine

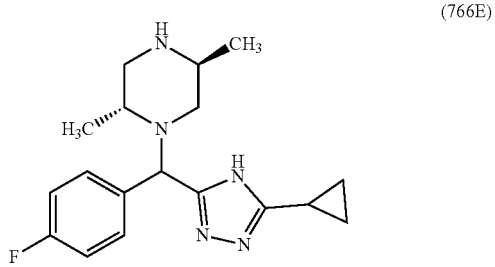 [SMILES: C[C@@H]1CN[C@@H](C)CN1C(c1ccc(F)cc1)c1nnc(C2CC2)[nH]1]

(766E)

To a stirred solution of tert-butyl (2S,5R)-4-((5-cyclopropyl-4H-1,2,4-triazol-3-yl)(4-fluorophenyl)methyl)-2,5-dimethylpiperazine-1-carboxylate (100 mg, 0.23 mmol), in DCM (4 mL), was added TFA (0.18 mL, 2.33 mmol) at 0° C. The reaction mixture was allowed to reach room temperature and stirred for 3 h. The solvent was evaporated under reduced pressure to afford (2R,5S)-1-((5-cyclopropyl-4H-1,2,4-triazol-3-yl)(4-fluorophenyl)methyl)-2,5-dimeth ylpiperazine, TFA salt (70 mg, 73.0% yield). LCMS: m/z, 330.1 (M+H); rt 0.80 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm.

Examples 766 and 767: 8-((2S,5R)-4-((5-cyclopropyl-4H-1,2,4-triazol-3-yl)(4-fluorophenyl)methyl)-2,5-dimethylpiperazin-1-yl)-5-methyl-6-oxo-5,6-dihydro-1,5-naphthyridine-2-carbonitrile To a stirred solution of (2R,5S)-1-((5-cyclopropyl-4H-1,2,4-triazol-3-yl)(4-fluorophenyl)methyl)-2,5-dimethylpiperazine, TFA salt (70 mg, 0.21 mmol) in acetonitrile (5 mL) was added DIPEA (0.15 mL, 0.85 mmol) and stirred for 2-5 min at room temperature. Then 6-cyano-1-methyl-2-oxo-1,2-dihydro-1,5-naphthyridin-4-yltrifluoromethanesulfonate (70.8 mg, 0.212 mmol) was added. The reaction mixture was heated at 80° C. for 4 h. The solvent was evaporated under reduced pressure to obtain crude product which was purified by SFC. Column/dimensions: Whelk(R,R)(250×21) mm, 5 µm, % $CO_2$: 65%, % Co solvent: 35% of acetonitrile:MeOH (50:50), Total Flow: 80.0 g/min, Back Pressure: 100 bar, Temperature: 30° C., UV: 225 nm.

Example 766: (4.3 mg, 4.13% yield); LCMS: m/z, 513.2 (M+H); rt 1.67 min; (LCMS method: Column: XBridge BEH XP C18 (50×2.1) mm, 2.5 µm; Mobile phase A: 95% water:5% acetonitrile; 10 mM ammonium acetate; Mobile phase B: 5% water: 95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.18-8.10 (m, 1H), 8.08-8.00 (m, 1H), 7.62 (dd, J=5.7, 8.4 Hz, 2H), 7.13 (t, J=8.7 Hz, 2H), 6.00 (s, 1H), 4.77 (s, 1H), 4.42 (br d, J=2.2 Hz, 1H), 3.57-3.48 (m, 5H), 3.42 (br s, 1H), 2.93 (br dd, J=3.1, 6.0 Hz, 1H), 2.82 (br dd, J=3.4, 11.5 Hz, 1H), 2.23-2.17 (m, 1H), 2.01-1.90 (m, 1H), 1.11 (dd, J=6.6, 12.5 Hz, 6H), 0.92 (br dd, J=2.2, 8.3 Hz, 2H), 0.84-0.77 (m, 2H).

Example 767: (4.5 mg, 4.13% yield); LCMS: m/z, 513.2 (M+H); rt 1.66 min; (LCMS method: Column: XBridge BEH XP C18 (50×2.1) mm, 2.5 µm; Mobile phase A: 95% water:5% acetonitrile; 10 mM ammonium acetate; Mobile phase B: 5% water: 95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 13.62-13.16 (m, 1H), 8.18-8.10 (m, 1H), 8.08-8.00 (m, 1H), 7.67 (dd, J=5.9, 8.3 Hz, 2H), 7.17 (br t, J=8.8 Hz, 2H), 5.97 (s, 1H), 4.86-4.74 (m, 1H), 4.57-4.34 (m, 2H), 3.70-3.59 (m, 1H), 3.51 (s, 3H), 3.45-3.39 (m, 1H), 2.97-2.86 (m, 2H), 2.17-2.04 (m, 1H), 1.30-1.16 (m, 4H), 1.01 (d, J=6.6 Hz, 2H), 0.96-0.70 (m, 4H).

Examples 768 and 769

8-((2S,5R)-4-((3-cyclopropyl-1-methyl-1H-1,2,4-triazol-5-yl)(4-fluorophenyl)methyl)-2,5-dimethylpiperazin-1-yl)-5-methyl-6-oxo-5,6-dihydro-1,5-naphthyridine-2-carbonitrile

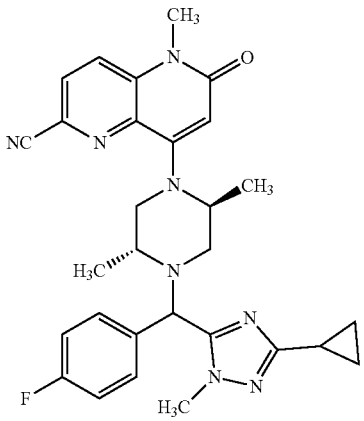

(768-769)

Intermediate 768A: tert-butyl (2S,5R)-4-((3-cyclopropyl-1-methyl-1H-1,2,4-triazol-5-yl) (4-fluorophenyl)methyl)-2,5-dimethylpiperazine-1-carboxylate

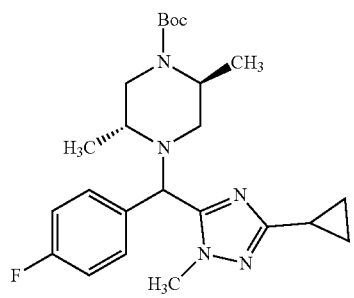

(768A)

To a stirred solution of 2-((2R,5S)-4-(tert-butoxycarbonyl)-2,5-dimethylpiperazin-1-yl)-2-(4-fluorophenyl)acetic acid (300 mg, 0.82 mmol) in DMF (3 mL) were added cyclopropanecarboximidamide, HCl (148 mg, 1.23 mmol), DIPEA (0.57 mL, 3.27 mmol) followed by HATU (342 mg, 0.90 mmol) at 0° C. The reaction mixture was allowed to reach room temperature and stirred for 16 h. Methylhydrazine sulfate (130 mg, 0.9 mmol) was added to the reaction mixture and heated at 80° C. for 1 h. The reaction mixture was cooled to room temperature and extracted with EtOAc (2×50 mL), washed with water, brine, dried over $Na_2SO_4$ and concentrated to afford crude product. The crude product was purified via flash chromatography by using 12 silica gel column and eluted with 35% EtOAc in Pet. ether. The required fractions were concentrated to afford tert-butyl (2S,5R)-4-((3-cyclopropyl-1-methyl-H-1,2,4-triazol-5-yl) (4-fluorophenyl)methyl)-2,5-dimethylpiperazine-1-carboxylate (120 mg, 33.0% yield). LCMS: m/z, 444 (M+H); rt 1.93 & 1.97 min. (LCMS Method: Column: Waters Acquity UPLC BEH C18 (2.1×50 mm) 1.7 µm, Mobile phase A: 10

Intermediate 768B: (2R,5S)-1-((3-cyclopropyl-1-methyl-1H-1,2,4-triazol-5-yl)(4-fluorophenyl)methyl)-2,5-dimethylpiperazine

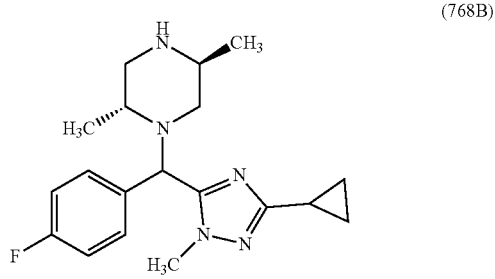 [SMILES: C[C@@H]1CN[C@@H](C)CN1C(c1ccc(F)cc1)c1nc(C2CC2)nn1C]

(768B)

To a stirred solution of tert-butyl (2S,5R)-4-((3-cyclopropyl-1-methyl-1H-1,2,4-triazol-5-yl)(4-fluorophenyl)methyl)-2,5-dimethylpiperazine-1-carboxylate (120 mg, 0.27 mmol), in DCM (3 mL) was added TFA (0.52 µm, 6.76 mmol) at 0° C. The reaction mixture was allowed to reach room temperature and stirred for 2 h. The solvent was evaporated under reduced pressure to afford (2R,5S)-1-((3-cyclopropyl-1-methyl-1H-1,2,4-triazol-5-yl)(4-fluorophenyl)methyl)-2,5-dimethylpiperazine, TFA. LCMS: m/z, 344 (M+H); rt 0.88 & 0.96 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Examples 768 and 769: 8-((2S,5R)-4-((3-cyclopropyl-1-methyl-H-1,2,4-triazol-5-yl)(4-fluorophenyl)methyl)-2,5-dimethylpiperazin-1-yl)-5-methyl-6-oxo-5,6-dihydro-,5-naphthyridine-2-carbonitrile To a stirred solution of (2R,5S)-1-((3-cyclopropyl-1-methyl-H-1,2,4-triazol-5-yl)(4-fluorophenyl)methyl)-2,5-dimethylpiperazine (100 mg, 0.29 mmol) in acetonitrile (5 mL) was added DIPEA (0.26 mL, 1.46 mmol). The reaction mixture was stirred at room temperature for 5 min. Next, 6-cyano-1-methyl-2-oxo-1,2-dihydro-1,5-naphthyridin-4-yl trifluoromethanesulfonate (146 mg, 0.44 mmol) was added and the reaction mixture was heated at 80° C. for 3 h. The reaction mixture was cooled to room temperature and evaporated under reduced pressure to obtain crude product, which was purified by prep-HPLC (HPLC Method: Column: Waters XBridge C18, 150 mm×19 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0 minute hold at 10% B, 10-35% B over 20 minutes, then a 5 minute hold at 100% B; Flow Rate: 15 mL/min; Column Temperature: 25° C.).

Example 768: (28 mg, 17.7% yield); LCMS: m/z, 527.2 (M+H); rt 1.86 min; (LCMS Method: Column: XBridge BEH XP C18 (50×2.1) mm, 2.5 µm; Mobile phase A: 95% water:5% acetonitrile; 0.1% TFA; Mobile phase B: 5% water:95% acetonitrile; 0.1% TFA; Flow: 1.1 mL/min; Temp: 50° C.; Time (min): 0-3; % B: 0-100%).). $^1$H NMR (400 MHz, DMSO-$d_6$) δ ppm 8.19-8.12 (m, 1H), 8.11-8.02 (m, 1H), 7.71 (dd, J=5.6, 8.3 Hz, 2H), 7.26 (br t, J=8.6 Hz, 2H), 6.04 (s, 1H), 5.47-5.30 (m, 1H), 4.64-4.51 (m, 1H), 3.80 (s, 3H), 3.71-3.58 (m, 2H), 3.50 (s, 3H), 3.20-3.02 (m, 2H), 1.98-1.87 (m, 1H), 1.23 (d, J=6.6 Hz, 3H), 1.13 (br d, J=5.4 Hz, 3H), 0.90 (dd, J=3.4, 8.3 Hz, 2H), 0.85-0.67 (m, 2H). One proton peak merged with solvent residual peak.

Example 769: (16 mg, 10.3% yield); LCMS: m/z, 527.3 (M+H); rt 1.61 min; (LCMS Method: Column: XBridge BEH XP C18 (50×2.1) mm, 2.5 µm; Mobile phase A: 95% water:5% acetonitrile; 0.1% TFA; Mobile phase B: 5% water:95% acetonitrile; 0.1% TFA; Flow: 1.1 mL/min; Temp: 50° C.; Time (min): 0-3; % B: 0-100%). $^1$H NMR (400 MHz, DMSO-$d_6$) δ ppm 8.20-8.13 (m, 1H), 8.10-8.02 (m, 1H), 7.66 (dd, J=5.5, 8.4 Hz, 2H), 7.22 (t, J=8.8 Hz, 2H), 6.06 (s, 1H), 5.27-5.18 (m, 1H), 4.59-4.50 (m, 1H), 3.88 (s, 3H), 3.72-3.58 (m, 2H), 3.53 (s, 3H), 3.24-3.10 (m, 1H), 3.05-2.93 (m, 1H), 2.47-2.36 (m, 1H), 1.99-1.88 (m, 1H), 1.18 (d, J=6.4 Hz, 3H), 1.10 (d, J=6.6 Hz, 3H), 0.93-0.85 (m, 2H), 0.82-0.73 (m, 2H).

Examples 770 and 771

8-((2S,5R)-4-((1-(tert-butyl)-1H-tetrazol-5-l)(4-fluorophenyl)methyl)-2,5-dimethylpiperazin-1-yl)-5-methyl-6-oxo-5,6-dihydro-1,5-naphthyridine-2-carbonitrile

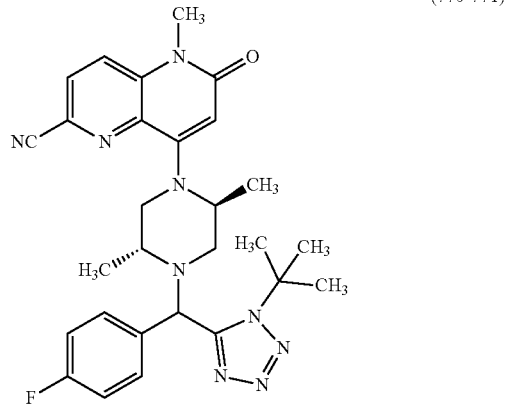

(770-771)

Intermediate 770A: tert-butyl (2S,5R)-4-(4-fluorobenzoyl)-2,5-dimethylpiperazine-1-carboxylate

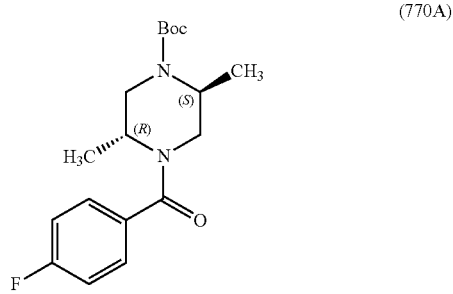

(770A)

To a solution of 4-fluorobenzoic acid (0.98 g, 7 mmol) in DMF (10 mL) were added TEA (1.95 mL, 14.0 mmol), BOP (2.06 g, 4.67 mmol) and tert-butyl (2S,5R)-2,5-dimethylpiperazine-1-carboxylate (1.0 g, 4.67 mmol). The reaction mixture was stirred at room temperature for 4 h. The solvent was removed under reduced pressure and the crude compound was purified by flash chromatography (12 g column silica, eluted with 25-40% ethyl acetate/Pet ether) to obtain tert-butyl (2S,5R)-4-(4-fluorobenzoyl)-2,5-dimethylpiperazine-1-carboxylate (1.1 g, 70.1% yield) as an off white solid; LCMS: m/z, 337.2 (M+H); rt 1.95 min. LCMS Method Column Name: AQUITY UPLC BEH C18 (3.0×50 mm) 1.7 μm Buffer: 10 mM ammonium acetate Mobile phase A: Buffer acetonitrile (95:5) Mobile phase B: Buffer:acetonitrile (5:95) Method: % B: 0 min-20:2 min-100:2.2 min-100 Flow: 0.7 mL/min.

Intermediate 770B: tert-butyl (2S,5R)-4-((1-(tert-butyl)-1H-tetrazol-5-yl)(4-fluorophenyl) methyl)-2,5-dimethylpiperazin-1-carboxylate

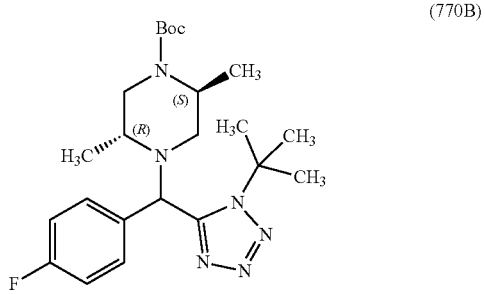

(770B)

To a solution of tert-butyl (2S,5R)-4-(4-fluorobenzoyl)-2,5-dimethylpiperazine-1-carboxylate (350 mg, 1.040 mmol) in DCM (8 mL) was added carbonyl chlorobis(triphenylphosphine)iridium(I) (40.6 mg, 0.05 mmol), AcOH (0.119 mL, 2.08 mmol), and 1,1,3,3-tetramethyldisiloxane (0.4 mL, 2.1 mmol). The reaction mixture was stirred at room temperature for 5-10 min, and tert-butyl isocyanide (173 mg, 2.08 mmol) and TMS-$N_3$ (0.28 mL, 2.08 mmol) were added. The reaction mixture was stirred at room temperature for 14 h. The solvent was removed under reduced pressure and the crude compound was purified by flash chromatography (12 g column silica, eluted with 15-30% ethyl acetate/Pet ether) to obtain tert-butyl(2S,5R)-4-((1-(tert-butyl)-1H-tetrazol-5-yl) (4-fluorophenyl) methyl)-2,5-dimethylpiperazine-1-carboxylate (200 mg, 43.0% yield) as an off white solid; LCMS: m/z, 447.2 (M+H); ret. Time 2.30 min. LCMS Method info: LCMS Method Column Name: AQUITY UPLC BEH C18 (3.0×50 mm) 1.7 μm Buffer: 10 mM ammonium acetate Mobile phase A: Buffer: acetonitrile (95:5) Mobile phase B: Buffer: acetonitrile (5:95) Method B: 0 min-20:2 min-100:+2.2 min-100 Flow: 0.7 mL/min.

Intermediate 770C: ((2R,5S)-1-((1-(tert-butyl)-1H-tetrazol-5-yl)(4-fluorophenyl) methyl)-2,5-dimethylpiperazine.HCl salt

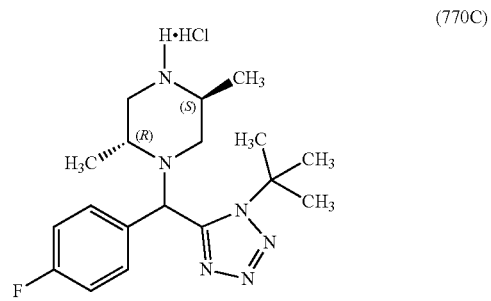

(770C)

To a solution of tert-butyl(2S,5R)-4-((1-(tert-butyl)-1H-tetrazol-5-yl) (4-fluorophenyl) methyl)-2,5-dimethylpiperazine-1-carboxylate (200 mg, 0.45 mmol) in DCM (4 mL) was added 4 N HCl in dioxane (0.11 mL, 0.45 mmol). The mixture was stirred at room temperature for 2 h. The solvent was removed under reduced pressure to obtain (2R,5S)-1-((1-(tert-butyl)-1H-tetrazol-5-yl)(4-fluorophenyl)methyl)-2,5-dimethylpiperazine, HCl (85 mg, 54.8% yield) as a diastereomeric mixture; LCMS: m/z, 347.2 (M+H); rt 1.10 and 1.20 min LCMS Method Column Name: AQUITY UPLC BEH C18 (3.0×50 mm) 1.7 μm Buffer: 10 mM ammonium acetate Mobile phase A: Buffer: acetonitrile (95:5) Mobile phase B: Buffer:acetonitrile (5:95) Method: % B: 0 min-20:2 min-100:2.2 min-100 Flow: 0.7 mL/min.

Examples 770 and 771: 8-((2S,5R)-4-((1-(tert-butyl)-1H-tetrazol-5-yl)(4-fluorophenyl) methyl)-2,5-dimethylpiperazin-1-yl)-5-methyl-6-oxo-5,6-dihydro-1,5-naphthyridine-2-carbonitrile To a solution of (2R,5S)-1-((1-(tert-butyl)-1H-tetrazol-5-yl)(4-fluorophenyl) methyl)-2,5-dimethylpiperazine, HCl (100 mg, 0.29 mmol) in acetonitrile (5 mL) was added DIPEA (0.050 mL, 0.289 mmol) at room temperature. After 5 min, 6-cyano-1-methyl-2-oxo-1,2-dihydro-1,5-naphthyridin-4-yl trifluoromethanesulfonate (96 mg, 0.29 mmol) was added and the reaction mixture was heated at 85° C. for 3 h. The reaction mixture was cooled to room temperature and evaporated under reduced pressure. The crude material was purified via preparative HPLC with the following conditions: Column: CELLULOSE-4 (250×21.2) mm, 5-micron M. Phase: 0.1% DEA in MeOH; Flow: 20 mL/min; Fractions containing the product were combined and dried via centrifugal evaporation to obtain Peak 1 (Example 770) and Peak 2 (Example 771).

Example 770: (4.9 mg, 3.05% yield); LCMS: m/z, 530.2 (M+H); rt 1.99 min. LC MS condition Column: Waters XBridge BEH C18 XP (50×2.1 mm) 2.5 μm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.1 mL/min. $^1$H NMR (400 MHz, DMSO-$d_6$) δ ppm 8.15 (d, J=8.6 Hz, 1H), 8.06 (d, J=9.0 Hz, 1H), 7.62 (dd, J=8.7, 5.5 Hz, 2H), 7.23 (t, J=8.9 Hz, 2H), 6.03 (s, 1H), 5.70 (s, 1H), 4.30 (br. s., 1H), 3.61-3.47 (m, 4H), 3.17 (d, J=6.8 Hz, 1H), 2.92 (dd, J=11.9, 3.3 Hz, 1H), 2.72-2.59 (m, 2H), 1.66 (s, 9H), 1.09-1.05 (m, 3H), 1.00 (d, J=6.6 Hz, 3H).

Example 771: (3.1 mg, 1.926% yield); LCMS: m/z, 530.2 (M+H); rt 1.99 min. LC MS condition: Column: Waters XBridge BEH C18 XP (50×2.1 mm) 2.5 µm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.1 mL/min. $^1$H NMR (400 MHz, DMSO-$d_6$) δ ppm 8.13 (br d, J=9.3 Hz, 1H), 8.01-8.09 (m, 1H), 7.64 (br t, J=6.5 Hz, 2H), 7.22 (br t, J=8.3 Hz, 2H), 5.95-6.02 (m, 1H), 5.66-5.72 (m, 1H), 4.37-4.49 (m, 1H), 3.57-3.63 (m, 1H), 3.51 (s, 3H), 3.49-3.49 (m, 1H), 3.14-3.23 (m, 2H), 2.11-2.17 (m, 1H), 1.68 (s, 9H), 1.08 (br d, J=6.6 Hz, 3H), 0.93 (br d, J=6.1 Hz, 3H).

Examples 772 and 773

8-((2S,5R)-4-((4-fluorophenyl)(5-isopropyl-1,3,4-thiazol-2-yl)methyl)-2,5-dimethylpiperazin-1-yl)-5-methyl-6-oxo-5,6-dihydro-1,5-naphthyridine-2-carbonitrile

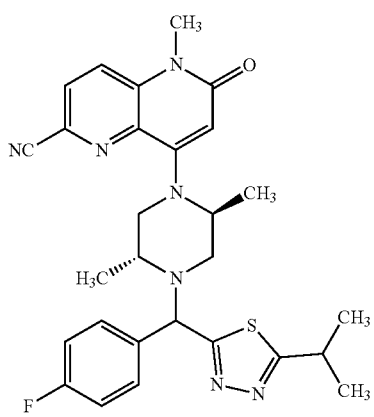

(772-773)

Intermediate 772A: tert-butyl (2S,5R)-4-(1-(4-fluorophenyl)-2-(2-isobutyrylhydrazineyl)-2-oxoethyl)-2,5-dimethylpiperazine-1-carboxylate

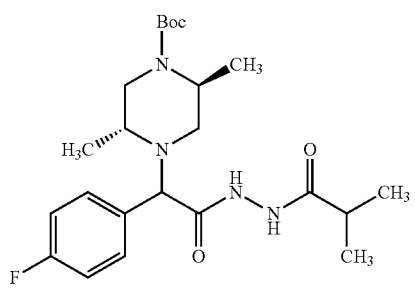

(772A)

To a stirred solution of 2-((2R,5S)-4-(tert-butoxycarbonyl)-2,5-dimethylpiperazin-1-yl)-2-(4-fluorophenyl)acetic acid (500 mg, 1.37 mmol) in EtOAc (6 mL) were added isobutyrohydrazide (139 mg, 1.36 mmol), Et$_3$N (0.38 mL, 2.73 mmol) followed by 1-propanephosphonicanhydride (1042 mg, 1.64 mmol) at 0° C. The reaction mixture was allowed to reach room temperature and stirred for 16 h. The reaction mixture was extracted with ethyl acetate, washed with water, brine, dried over Na$_2$SO$_4$ and concentrated under reduced pressure to give tert-butyl (2S,5R)-4-(1-(4-fluorophenyl)-2-(2-isobutyrylhydrazineyl)-2-oxoethyl)-2,5-dimethylpiperazine-1-carboxylate (0.55 g, 1.22 mmol, 89% yield). LCMS: m/z, 451.5 (M+H); rt 1.64 min. (LCMS Method: Column: Waters Acquity UPLC BEH C18 (2.1×50 mm) 1.7 µm, Mobile phase A: 10 mM ammonium acetate: acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 772B: 2-(((2R,5S)-2,5-dimethylpiperazin-1-yl)(4-fluorophenyl)methyl)-5-isopropyl-1,3,4-thiadiazole

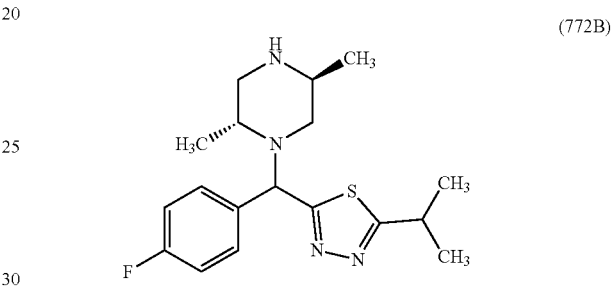

(772B)

To a stirred solution of tert-butyl (2S,5R)-4-(1-(4-fluorophenyl)-2-(2-isobutyrylhydrazineyl)-2-oxoethyl)-2,5-dimethylpiperazine-1-carboxylate (600 mg, 1.33 mmol) in toluene (6 mL) was added Lawesson's reagent (539 mg, 1.33 mmol) at room temperature. The reaction mixture was heated at 110° C. for 16 h. The reaction mixture was cooled to room temperature and evaporated under reduced pressure to give crude product. The crude product was purified via flash chromatography on a 12 g silica gel column and eluted with 35% EtOAc/Pet. ether. The required fractions were concentrated to afford 2-(((2R,5S)-2,5-dimethylpiperazin-1-yl)(4-fluorophenyl)methyl)-5-isopropyl-1,3,4-thiadiazole (200 mg, 21.5% yield). LCMS: m/z, 349.5 (M+H); rt 0.95 and 1.1 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Example 772 and 773: 8-((2S,5R)-4-((4-fluorophenyl)(5-isopropyl-1,3,4-thiadiazol-2-yl) methyl)-2,5-dimethylpiperazin-1-yl)-5-methyl-6-oxo-5,6-dihydro-1,5-naphthyridine-2-carbonitrile To a stirred solution of 2-(((2R,5S)-2,5-dimethylpiperazin-1-yl)(4-fluorophenyl) methyl)-5-isopropyl-1,3,4-thiadiazole (100 mg, 0.29 mmol) in acetonitrile (5 mL) was added DIPEA (0.25 mL, 1.44 mmol). The reaction mixture was stirred at room temperature for 5 min. Next, 6-cyano-1-methyl-2-oxo-1,2-dihydro-1,5-naphthyridin-4-yltrifluoromethanesulfonate (96 mg, 0.29 mmol) was added and the reaction mixture was heated at 80° C. for 3 h. The reaction mixture was cooled to room temperature and evaporated under reduced pressure to obtain crude product, which was purified by prep-HPLC method as follows Column: YMC EXRS (250 mm×19 mm ID, 5 μm); Mobile phase A=10 mm ammonium bicarbonate in water pH 9.5; Mobile phase B=acetonitrile; Flow 17 mL/min; Grad (T/% B): 0/50, 2/60, 15/75).

Example 772: (4 mg, 2.5% yield); LCMS: m/z, 532 (M+H); rt 3.26 min; (LCMS method: Column-Kinetex XB-C18 (75×3 mm-2.6 μm) Mphase A: 10 mM ammonium formate in water:acetonitrile (98:2), Mphase B: 10 mM ammonium formate in water: acetonitrile (2:98). $^1$H NMR (400 MHz, DMSO-$d_6$) δ ppm 8.15 (d, J=8.3 Hz, 1H), 8.08 (d, J=9.0 Hz, 1H), 7.67 (s, 2H), 7.27 (t, J=8.1 Hz, 2H), 6.01 (s, 1H), 5.24 (s, 1H), 4.5-4.60 (m, 1H), 3.60-3.65 (m, 1H), 3.52 (s, 3H), 3.45-3.35 (m, 2H), 3.29-3.19 (m, 3H), 1.35-1.23 (m, 9H), 1.05 (d, J=6.4 Hz, 3H).

Example 773: (6 mg, 3.81% yield); LCMS: m/z, 532 (M+H); rt 3.27 min; (LCMS method: Column-Kinetex XB-C18 (75×3 mm-2.6 μm) Mphase A: 10 mM ammonium formate in water:acetonitrile (98:2), Mphase B: 10 mM ammonium formate in water: acetonitrile (2:98). $^1$H NMR (400 MHz, DMSO-$d_6$) δ ppm 8.15 (d, J=8.8 Hz, 1H), 8.07 (d, J=8.8 Hz, 1H), 7.61 (dd, J=5.5, 8.7 Hz, 2H), 7.25 (t, J=8.8 Hz, 2H), 6.02 (s, 1H), 5.31 (s, 1H), 4.5-4.60 (m, 1H), 3.65-3.70 (m, 1H), 3.52 (s, 3H), 3.45-3.34 (m, 2H), 2.89-3.01 (m, 2H), 1.36-1.32 (m, 7H), 1.28-1.16 (m, 6H).

Examples 774 and 775

8-((2S,5R)-4-((5-cyclopropyl-1,3,4-thiadiazol-2-yl)(4-fluorophenyl)methyl)-2,5-dimethylpiperazin-1-yl)-5-methyl-6-oxo-5,6-dihydro-1,5-naphthyridine-2-carbonitrile

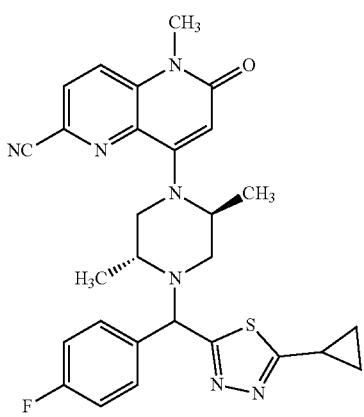
(774-775)

Intermediate 774A: tert-butyl (2S,5R)-4-(2-(2-(cyclopropanecarbonyl)hydrazineyl)-1-(4-fluorophenyl)-2-oxoethyl)-2,5-dimethylpiperazine-1-carboxylate

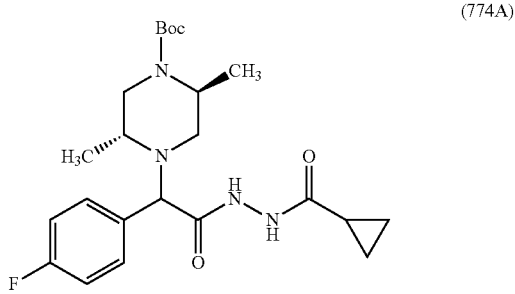 [SMILES: C[C@@H]1CN(C(=O)OC(C)(C)C)[C@@H](C)CN1C(C(=O)NNC(=O)C1CC1)c1ccc(F)cc1]
(774A)

To a stirred solution of 2-((2R,5S)-4-(tert-butoxycarbonyl)-2,5-dimethylpiperazin-1-yl)-2-(4-fluorophenyl)acetic acid (300 mg, 0.82 mmol) in EtOAc (6 mL) were added cyclopropanecarbohydrazide (90 mg, 0.901 mmol), Et$_3$N (0.23 mL, 1.64 mmol) followed by 1-propanephosphonic anhydride (391 mg, 1.23 mmol) at 0° C. The reaction mixture was allowed to reach room temperature and stirred for 16 h. The reaction mixture was extracted with ethyl acetate, washed with water, brine, dried over Na$_2$SO$_4$ and concentrated under reduced pressure to give tert-butyl (2S,5R)-4-(2-(2-(cyclopropanecarbonyl)hydrazineyl)-1-(4-fluorophenyl)-2-oxoethyl)-2,5-dimethylpiperazine-1-carboxylate (400 mg, 54.5% yield). LCMS: m/z, 449.4 (M+H); rt 1.62 and 1.64 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 774B: tert-butyl (2S,5R)-4-((5-cyclopropyl-1,3,4-thiadiazol-2-yl)(4-fluorophenyl)methyl)-2,5-dimethylpiperazine-1-carboxylate

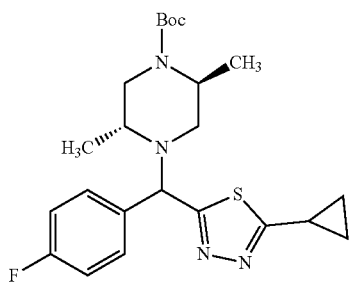
(774B)

To a stirred solution of tert-butyl (2S,5R)-4-(2-(2-(cyclopropanecarbonyl) hydrazineyl)-1-(4-fluorophenyl)-2-oxoethyl)-2,5-dimethylpiperazine-1-carboxylate (300 mg, 0.67 mmol) in toluene (1 mL) was added Lawesson's reagent (271 mg, 0.67 mmol). The reaction mixture was heated at 110° C. for 16 h. The reaction mixture was cooled to room temperature and evaporated under reduced pressure to yield crude product, which was purified by flash chromatography using 12 g silica gel column and eluted with 35% EtOAc in Pet ether. The required fractions were concentrated to afford tert-butyl (2S,5R)-4-((5-cyclopropyl-1,3,4-thiadiazol-2-yl)(4-fluorophenyl)methyl)-2,5-dimethylpiperazine-1-carboxylate (130 mg, 43.5% yield). LCMS: m/z, 447.3 (M+H); rt 2.18 and 2.22 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 774C: 2-cyclopropyl-5-(((2R,5S)-2,5-dimethylpiperazin-1-yl)(4-fluorophenyl)methyl)-1,3,4-thiadiazole

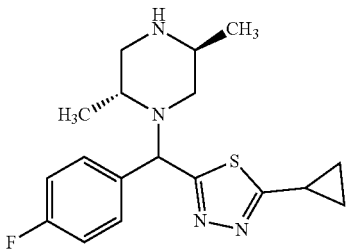

(774C)

To a stirred solution of tert-butyl (2S,5R)-4-((5-cyclopropyl-1,3,4-thiadiazol-2-yl) (4-fluorophenyl)methyl)-2,5-dimethylpiperazine-1-carboxylate (130 mg, 0.29 mmol) in EtOAc (3 mL) was added HCl (4 M in dioxane) (0.73 mL, 2.9 mmol) at 0° C. The reaction mixture was allowed to reach room temperature and stirred for 2 h. The solvent was evaporated under reduced pressure to afford 2-cyclopropyl-5-(((2R,5S)-2,5-dimethylpiperazin-1-yl)(4-fluorophenyl)methyl)-1,3,4-thiadiazole (80 mg, 79% yield). LCMS: m/z, 347.1 (M+H); rt 0.90 and 1.1 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 774 and 775: 8-((2S,5R)-4-((5-cyclopropyl-1,3,4-thiadiazol-2-yl)(4-fluorophenyl)methyl)-2,5-dimethylpiperazin-1-yl)-5-methyl-6-oxo-5,6-dihydro-1,5-naphthyridine-2-carbonitrile To a stirred solution of 2-cyclopropyl-5-(((2R,5S)-2,5-dimethylpiperazin-1-yl)(4-fluorophenyl)methyl)-1,3,4-thiadiazole (100 mg, 0.29 mmol) in acetonitrile (5 mL) was added DIPEA (0.202 mL, 1.155 mmol). The reaction mixture was stirred for 5 min at room temperature. Next, 6-cyano-1-methyl-2-oxo-1,2-dihydro-1,5-naphthyridin-4-yl trifluoromethanesulfonate (115 mg, 0.35 mmol) was added and the reaction mixture was heated at 80° C. for 4 h. The reaction mixture was cooled to room temperature and evaporated under reduced pressure to obtain crude product which was purified via preparative HPLC. Column: Waters XBridge C18, 150 mm×19 mm, 5-µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 15% B, 15-55% B over 25 minutes, then a 5 minute hold at 100% B; Flow Rate: 15 mL/min; Column Temperature: 25° C. Fractions containing the product were combined and dried via centrifugal evaporation to give Example 774 (2 mg, 1.308% yield) and Example 775 (1 mg, 0.65% yield).

Example 774: LCMS: m/z, 530.2 (M+H); rt 1.98 min; (LCMS Method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.17-8.10 (m, 1H), 8.08-8.01 (m, 1H), 7.63 (dd, J=5.6, 8.8 Hz, 2H), 7.30-7.21 (m, 2H), 6.00 (s, 1H), 5.20 (s, 1H), 4.64-4.56 (m, 1H), 3.66-3.60 (m, 1H), 3.54-3.50 (m, 4H), 3.08-3.00 (m, 2H), 2.89 (d, J=7.3 Hz, 1H), 2.47-2.43 (m, 1H), 1.29-1.23 (m, 4H), 1.19-1.11 (m, 4H), 1.04 (d, J=6.6 Hz, 2H).

Example 775: LCMS: m/z, 530.2 (M+H); rt 2.02 min; (LCMS Method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.18-8.11 (m, 1H), 8.09-8.01 (m, 1H), 7.62-7.52 (m, 2H), 7.29-7.17 (m, 2H), 6.01 (s, 1H), 5.27 (s, 1H), 4.60-4.50 (m, 1H), 3.69 (br dd, J=2.1, 12.1 Hz, 1H), 3.54-3.49 (m, 4H), 3.05-3.01 (m, 1H), 2.87 (dd, J=3.1, 11.4 Hz, 1H), 2.46 (d, J=3.4 Hz, 1H), 2.28 (br d, J=10.8 Hz, 1H), 1.27-1.15 (m, 8H), 1.03-0.97 (m, 2H).

Examples 776 and 777

8-((2S,5R)-4-((4-cyclopropyloxazol-2-yl)(4-fluorophenyl)methyl)-2,5-dimethylpiperazin-1-yl)-5-methyl-6-oxo-5,6-dihydro-1,5-naphthyridine-2-carbonitrile

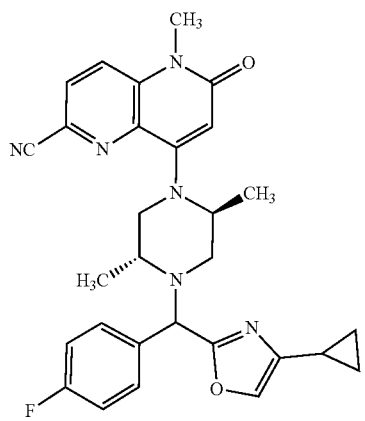

(776-777)

Intermediate 776A: tert-butyl (2S,5R)-4-(2-amino-1-(4-fluorophenyl)-2-oxoethyl)-2,5-dimethylpiperazine-1-carboxylate

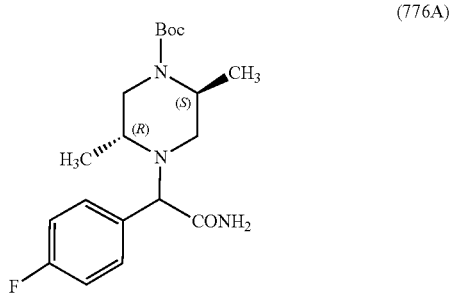

(776A)

To a solution of 2-((2R,5S)-4-(tert-butoxycarbonyl)-2,5-dimethylpiperazin-1-yl)-2-(4-fluorophenyl)acetic acid (400 mg, 1.1 mmol) in tetrahydrofuran (8 mL) were added TEA (0.46 mL, 3.27 mmol) and ethyl chloroformate (0.16 mL, 1.64 mmol) at room temperature. The reaction mixture was stirred at room temperature for 2 h. Next, ammonium hydroxide (0.21 mL, 5.46 mmol) was added. The reaction mixture was stirred for 30 min and evaporated to dryness to yield tert-butyl (2S,5R)-4-(2-amino-1-(4-fluorophenyl)-2-oxoethyl)-2,5-dimethylpiperazine-1-carboxylate (350 mg, 19.3%). LCMS: m/z, 366.5 (M+H); rt 1.57 min; Method Info: AQUITY UPLC BEH C18 (3.0×50 mm) 1.7 µm, Mobile phase A: 95% water:5% acetonitrile; 10 mM ammonium acetate; Mobile phase B: 5% water:95% acetonitrile; 10 mM ammonium acetate, Flow: 0.7 mL/min.

Intermediate 776B: tert-butyl (2S,5R)-4-((4-cyclopropyloxazol-2-yl)(4-fluorophenyl) methyl)-2,5-dimethylpiperazine-1-carboxylate

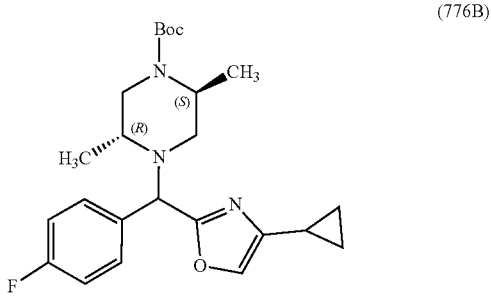

(776B)

A mixture of 2-bromo-1-cyclopropylethan-1-one (161 mg, 0.99 mmol), tert-butyl (2S,5R)-4-(2-amino-1-(4-fluorophenyl)-2-oxoethyl)-2,5-dimethylpiperazine-1-carboxylate (300 mg, 0.82 mmol), and silver trifluoromethanesulfonate (264 mg, 1.03 mmol) in ethyl acetate (4 mL) was heated to 60° C. The reaction mixture was cooled to room temperature and filtered through a sintered funnel. Water was added and the mixture was extracted twice with ethyl acetate (20 mL). The combined organic layer was dried over $Na_2SO_4$ and evaporated to dryness to obtain tert-butyl (2S,5R)-4-((4-cyclopropyloxazol-2-yl)(4-fluorophenyl)methyl)-2,5-dimethylpiperazine-1-carboxylate (220 mg, 24.9% yield). LCMS: m/z, 330.2 (M-Boc); rt 1.57 min; Method Info: Luna 3.0 C18(2) 100 Å LC column (20×4.0 mm) Mercury MS TM, Mobile phase A: 0.1% TFA in Milli-Q water, Mobile phase B: 0.1% TFA in acetonitrile, Flow: 1.5 mL/min.

Intermediate 776C: 4-cyclopropyl-2-(((2R,5S)-2,5-dimethylpiperazin-1-yl)(4-fluorophenyl)methyl)oxazole, HCl

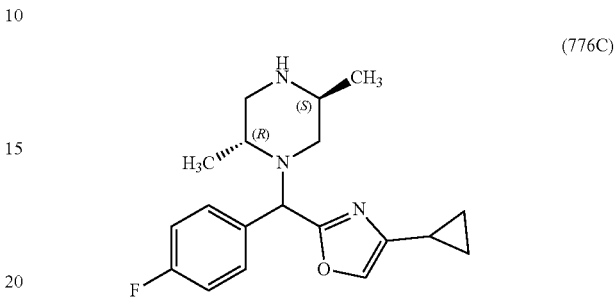

(776C)

To a solution of tert-butyl (2S,5R)-4-((4-cyclopropyloxazol-2-yl)(4-fluorophenyl) methyl)-2,5-dimethylpiperazine-1-carboxylate (400 mg, 0.93 mmol) in 1,4-dioxane (5 mL) was added HCl in dioxane (0.28 mL, 9.31 mmol) at room temperature. The reaction mixture was stirred at room temperature for 3 h. The reaction mixture was evaporated to dryness to yield 4-cyclopropyl-2-(((2R,5S)-2,5-dimethylpiperazin-1-yl)(4-fluorophenyl) methyl)oxazole, HCl (280 mg, 18.1% yield). LCMS: m/z, 330.1 (M+H); rt 1.31 min; Method Info: AQUITY UPLC BEH C18 (3.0×50 mm) 1.7 µm, Mobile phase A: 95% water:5% acetonitrile; 10 mM ammonium acetate, Mobile phase B: 5% water:95% acetonitrile; 10 mM ammonium acetate, Flow: 0.7 mL/min.

Examples 776 and 777: 8-((2S,5R)-4-((4-cyclopropyloxazol-2-yl)(4-fluorophenyl) methyl)-2,5-dimethylpiperazin-1-yl)-5-methyl-6-oxo-5,6-dihydro-1,5-naphthyridine-2-carbonitrile To a stirred solution of 4-cyclopropyl-2-(((2R,5S)-2,5-dimethylpiperazin-1-yl)(4-fluorophenyl)methyl)oxazole, HCl (300 mg, 0.82 mmol) in acetonitrile (3 mL) were added DIPEA (0.43 mL, 2.46 mmol) and 6-cyano-1-methyl-2-oxo-1,2-dihydro-1,5-naphthyridin-4-yl trifluoromethanesulfonate (328 mg, 0.98 mmol). The reaction mixture was stirred at 80° C. overnight. The crude LCMS had shown formation of the product. The solvent was removed under reduced pressure and the residue was dissolved in ethyl acetate (100 mL). The organic layer was washed with brine, dried over $Na_2SO_4$, concentrated under reduced pressure to afford crude product which was purified by preparative Chiral HPLC (Chiral Prep HPLC method: CELLULOSE-2 (250×4.6 mm), 5 micron M. Phase: 0.1% DEA in acetonitrile) to afford Examples 776 and 777.

Example 776: (8.1 mg, 1.9% yield); LCMS: m/z, 513.2 (M+H); rt 2.188 min; (LCMS method: Column: XBridge BEH XP C18 (50×2.1) mm, 2.5 µm; Mobile phase A: 95% water:5% acetonitrile; 10 mM ammonium acetate; Mobile phase B: 5% water: 95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.18-8.12 (m, 1H), 8.10-8.03 (m, 1H), 7.85 (s, 1H), 7.63 (dd, J=5.7, 8.4 Hz, 2H), 7.21 (t, J=8.8 Hz, 2H), 6.03 (s, 1H), 4.92 (s, 1H), 4.45 (td, J=2.5, 3.8 Hz, 1H), 3.63-3.55 (m, 1H), 3.55-3.46 (m, 4H), 2.86 (dd, J=3.4, 11.7 Hz, 1H), 2.77-2.69

(m, 1H), 2.17 (dd, J=1.5, 12.0 Hz, 1H), 1.84-1.75 (m, 1H), 1.15 (dd, J=6.6, 12.5 Hz, 6H), 0.88-0.76 (m, 2H), 0.69-0.60 (m, 2H).

Example 777: (3.4 mg, 2.2% yield); LCMS: m/z, 513.2 (M+H); rt 2.19 min; (LCMS Method: Column: XBridge BEH XP C18 (50×2.1) mm, 2.5 µm; Mobile phase A: 95% water:5% acetonitrile; 10 mM ammonium acetate; Mobile phase B: 5% water: 95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.21-8.11 (m, 1H), 8.09-8.00 (m, 1H), 7.84 (s, 1H), 7.64 (dd, J=5.9, 8.1 Hz, 2H), 7.23 (t, J=8.7 Hz, 2H), 5.99 (s, 1H), 4.95 (s, 1H), 4.54 (br d, J=2.7 Hz, 1H), 3.78 (s, 1H), 3.63 (br d, J=13.0 Hz, 1H), 3.52 (s, 3H), 3.45 (br dd, J=2.3, 12.1 Hz, 1H), 3.05 (br dd, J=2.7, 11.2 Hz, 1H), 2.94 (br d, J=6.1 Hz, 1H), 2.00 (br d, J=11.2 Hz, 1H), 1.22 (d, J=6.4 Hz, 3H), 1.03 (dd, J=6.2, 11.6 Hz, 3H), 0.81 (br d, J=8.1 Hz, 2H), 0.70-0.57 (m, 2H).

The compounds in Table 15 were prepared from the appropriate piperazine according to the general procedure described in Examples 776 and 777, substituting 2-bromo-1-cyclopropylethan-1-one with the appropriate acyl bromides in the synthetic sequence. The synthesis provided a mixture of diastereomers, the mixture was separated at the final stage using either preparative chromatography or preparative chiral chromatography. The absolute stereochemistry was not assigned at the newly formed carbon-nitrogen bond Examples 780 and 781

8-((2S,5R)-4-(1-(2,6-difluorophenyl)ethyl)-2,5-dimethylpiperazin-1-yl)-5-methyl-6-oxo-5,6-dihydro-1,5-naphthyridine-2,7-dicarbonitrile

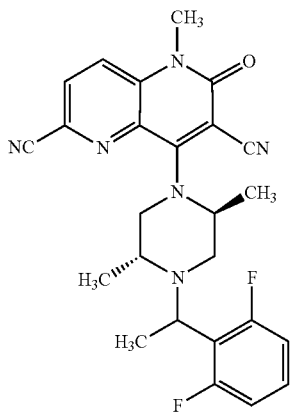

(780-781)

TABLE 15

| Ex. No. | Structure | LCMS RT and Method | M + H | Stereo chem. |
|---|---|---|---|---|
| 778 | 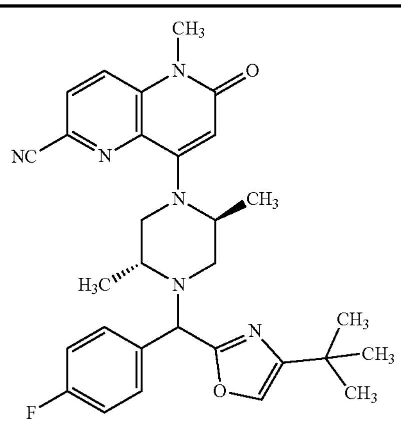 | 2.39 A | 529.3 | H |
| 779 | 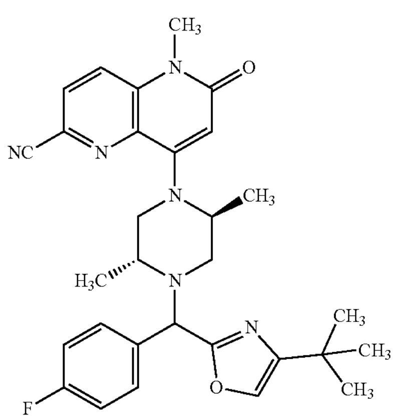 [SMILES: C[C@@H]1CN(c2cc(=O)n(C)c3ccc(C#N)nc23)[C@@H](C)CN1C(c1ccc(F)cc1)c1nc(C(C)(C)C)co1] | 2.39 A | 529.3 | H |

Intermediate 780A: Ethyl 3-amino-6-bromopicolinate

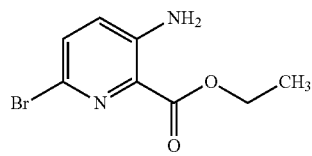

(780A)

To a suspension of ethyl 3-aminopicolinate (12.0 g, 72.2 mmol) in water (54 mL) were added sulfuric acid (3.9 mL, 72.2 mmol) and acetic acid (4.1 mL, 72.2 mmol). The reaction mixture was stirred for 5 min. Next, bromine (3.72 mL, 72.2 mmol) in acetic acid (15 mL) was slowly added through an addition funnel over 15 min. The reaction mixture was stirred at room temperature for 16 h. The reaction was quenched with water (500 mL). The reaction mixture was filtered through a Buchner funnel to obtain ethyl 3-amino-6-bromopicolinate (12.9 g, 47.4 mmol, 65.6% yield) as a pale yellow solid. LCMS: m/z, 247.1 (M+2); rt 1.18 min. (LC-MS Method info: Column-AQUITY UPLC BEH C18 (3.0×50 mm) 1.7 µm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min).

Intermediate 780B: Ethyl 6-bromo-3-(2-cyanoacetamido) picolinate

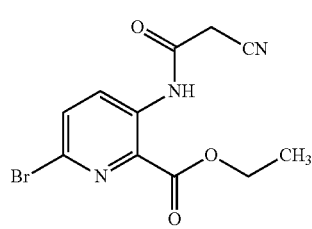

(780B)

To a stirred solution of ethyl 3-amino-6-bromopicolinate (2.0 g, 8.16 mmol) in DMF (15 mL) were added 2-cyano-acetic acid (1.39 g, 16.32 mmol) and TEA (2.84 mL, 20.4 mmol), followed by 1-propanephosphonic anhydride (10.8 mL, 18 mmol). The reaction mixture was stirred at room temperature for 16 h. The reaction mixture was quenched with water (100 mL) and was stirred for 15 min to obtain a solid which was filtered through Buchner funnel to obtain ethyl 6-bromo-3-(2-cyanoacetamido)picolinate (2.45 g, 7.85 mmol, 96% yield) as yellow solid; LCMS: m/z, 314.0 (M+2); rt 2.023 min. (LC-MS Method info: Column-KINE-TEX-XB-C18 (75×3 mm-2.6 µm); M phase A: 10 mM ammonium formate in water:acetonitrile (98:2); M phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min).

Intermediate 780C: ethyl 6-cyano-3-(2-cyanoacetamido)picolinate

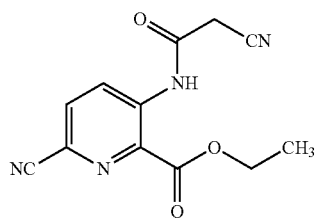

(780C)

To a stirred solution of ethyl 6-bromo-3-(2-cyanoacet-amido)picolinate (200 mg, 0.64 mmol) in NMP (8 mL) were added zinc (8.38 mg, 0.128 mmol) and zinc cyanide (150 mg, 1.28 mmol) under nitrogen. The nitrogen purging was continued for 3 min and was dppf (21.3 mg, 0.04 mmol) and $Pd_2(dba)_3$ (58.7 mg, 0.06 mmol) were added. Nitrogen purging was continued for another 3 min. The reaction mixture was heated up to 80° C. for 1 h. The reaction mixture was cooled to room temperature. The reaction was quenched with water. The reaction mixture was filtered through a Celite pad. The filtrate was extracted with ethyl acetate (3×100 mL). The combined organic layer was washed with brine solution (50 mL) and was dried over anhydrous sodium sulfate, filtered and evaporated under reduced pressure. The crude compound was purified by silica gel column (12 g, eluting with 34%-39% ethyl acetate/Pet ether) to obtain ethyl 6-cyano-3-(2-cyanoacetamido) picolinate (70 mg, 0.271 mmol, 42.3% yield) as a brown solid. LCMS: m/z, 257.2 (M–H); rt 1.10 min. (LC-MS Method info: Column-AQUITY UPLC BEH C18 (3.0×50 mm) 1.7 µm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min).

Intermediate 780D: 6,8-dioxo-5,6,7,8-tetrahydro-1,5-naphthyridine-2,7-dicarbonitrile

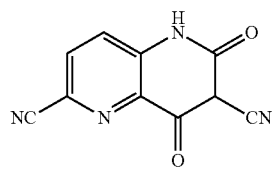

(780D)

To a stirred solution of ethyl 6-cyano-3-(2-cyanoacet-amido) picolinate (70 mg, 0.27 mmol) in DCM (5 mL) was added trimethylamine (0.11 mL, 0.81 mmol). The reaction mixture was warmed to 45° C. and was stirred for 3 h. The reaction mixture cooled to room temperature and concentrated under reduced pressure. Next, 10% ethyl acetate in hexane was added. The reaction mixture was stirred for 15 min and was filtered through Buchner funnel to obtain 6,8-dioxo-5, 6, 7, 8-tetrahydro-1, 5-naphthyridine-2,7-dicarbonitrile (54 mg, 0.26 mmol, 94% yield) as brown solid. LCMS: m/z, 211.1 (M–H); rt 0.41 min. (LC-MS Method info: Column-AQUITY UPLC BEH C18 (3.0×50 mm) 1.7 µm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.3 minute hold at 100% B, flow rate 0.7 mL/min.

Intermediate 780E: 5-methyl-6,8-dioxo-5,6,7,8-tetrahydro-1,5-naphthyridine-2,7-dicarbonitrile

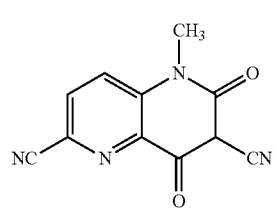

(780E)

To a stirred solution of 6,8-dioxo-5,6,7,8-tetrahydro-1,5-naphthyridine-2,7-dicarbonitrile (50 mg, 0.24 mmol) in DMF (3 mL) was added NaH (28.3 mg, 0.71 mmol) at 0° C. The reaction mixture was stirred at room temperature for 30 min, then methyl iodide (0.05 mL, 0.7 mmol) was added. The reaction mixture was stirred at room temperature for another 3 h. The reaction mixture was quenched with water (10 mL) and was acidified with 1.5 N HCl to adjust the pH ~6 at 0° C. The reaction mixture was stirred for 15 min to obtain a solid residue which was filtered through Buchner funnel to obtain 5-methyl-6,8-dioxo-5,6,7,8-tetrahydro-1,5-naphthyridine-2,7-dicarbonitrile (20 mg, 0.088 mmol, 37.5% yield) as a brown solid. LCMS: m/z, 225.0 (M–H); rt 1.30 min. (LC-MS Method info: Column-KINETEX-XB-C18 (75×3 mm-2.6 µm); M phase A: 10 mM ammonium formate in water:acetonitrile (98:02); M phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 780F: 3,6-dicyano-1-methyl-2-oxo-1,2-dihydro-1,5-naphthyridin-4-yl trifluoromethanesulfonate

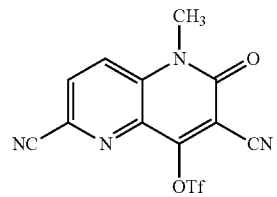

(780F)

To a stirred solution of 5-methyl-6,8-dioxo-5,6,7,8-tetrahydro-1,5-naphthyridine-2,7-dicarbonitrile (0.3 g, 1.33 mmol) in DCM (8 mL) were added TEA (0.56 mL, 3.9 mmol) and DMAP (0.02 g, 0.14 mmol) at 0° C., followed by trifluoromethanesulfonic anhydride (0.45 mL, 2.7 mmol). The reaction mixture was slowly warmed to room temperature and was stirred for 1.5 h. The reaction was quenched with water (50 mL). The reaction mixture was extracted with DCM (3×100 mL). The combined organic layer was dried over anhydrous sodium sulfate, filtered and evaporated under reduced pressure to obtain 3,6-dicyano-1-methyl-2-oxo-1,2-dihydro-1,5-naphthyridin-4-yl trifluoromethanesulfonate (0.32 g, 67.3%) as a brown solid. $^1$H NMR (400 MHz, CDCl$_3$) δ ppm 8.06-8.03 (d, 1H), 7.95-7.92 (d, 1H), 3.80 (s, 3H).

Intermediate 780G: tert-butyl (2R,5S)-4-(3,6-dicyano-1-methyl-2-oxo-1,2-dihydro-1,5-naphthyridin-4-yl)-2,5-dimethylpiperazine-1-carboxylate

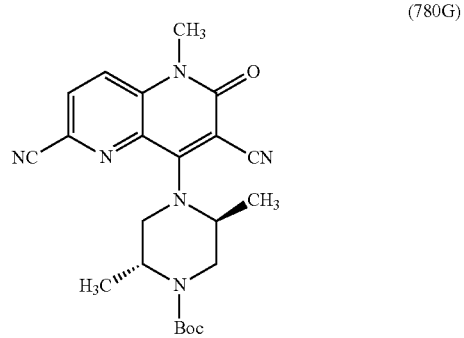 [SMILES: C[C@@H]1CN(c2c(C#N)c(=O)n(C)c3ccc(C#N)nc23)[C@@H](C)CN1C(=O)OC(C)(C)C]

(780G)

To a stirred solution of (2R,5S)-tert-butyl 2,5-dimethylpiperazine-1-carboxylate (126 mg, 0.59 mmol) in acetonitrile (5 mL) were added DIPEA (0.2 mL, 1.17 mmol) and 3,6-dicyano-1-methyl-2-oxo-1,2-dihydro-1,5-naphthyridin-4-yl trifluoromethanesulfonate (140 mg, 0.39 mmol). The reaction mixture was heated to 85° C. for 2 h. The reaction mixture was cooled to room temperature and evaporated under reduced pressure to obtain crude product. The crude product was purified by silica gel column (24 g, eluted with 100-80% ethyl acetate/Pet ether) to yield tert-butyl (2R,5S)-4-(3,6-dicyano-1-methyl-2-oxo-1,2-dihydro-1,5-naphthyridin-4-yl)-2,5-dimethylpiperazine-1-carboxylate (120 mg, 0.24 mmol, 61.8% yield) as a light brown solid. LCMS: m/z, 423.0 (M+H); rt 1.58 min; (LCMS method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Intermediate 780H: 8-((2S,5R)-2,5-dimethylpiperazin-1-yl)-5-methyl-6-oxo-5,6-dihydro-1,5-naphthyridine-2,7-dicarbonitrile.TFA

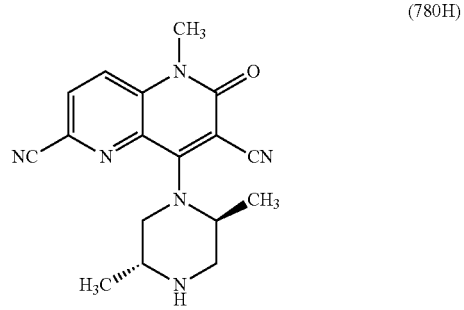 [SMILES: C[C@@H]1CN(c2c(C#N)c(=O)n(C)c3ccc(C#N)nc23)[C@@H](C)CN1]

(780H)

To a stirred solution of tert-butyl (2R,5S)-4-(3,6-dicyano-1-methyl-2-oxo-1,2-dihydro-1,5-naphthyridin-4-yl)-2,5-dimethylpiperazine-1-carboxylate (80 mg, 0.19 mmol) in DCM (10 mL) was added TFA (1 mL, 12.98 mmol). The reaction mixture was stirred at room temperature for 16 h. The solvent was removed under reduced pressure to obtain 8-((2S,5R)-2,5-dimethylpiperazin-1-yl)-5-methyl-6-oxo-5,6-dihydro-1,5-naphthyridine-2,7-dicarbonitrile, TFA (80 mg, 0.115 mmol, 61.0% yield) as a gum. LCMS: m/z, 323.3 (M+H); rt 0.59 min; (LCMS method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Examples 780 and 781: 8-((2S,5R)-4-(1-(2,6-difluorophenyl)ethyl)-2,5-dimethylpiperazin-1-yl)-5-methyl-6-oxo-5,6-dihydro-1,5-naphthyridine-2,7-dicarbonitrile To a stirred solution of 8-((2S,5R)-2,5-dimethylpiperazin-1-yl)-5-methyl-6-oxo-5,6-dihydro-1,5-naphthyridine-2,7-dicarbonitrile, TFA (60 mg, 0.19 mmol) in acetonitrile (2 mL) was added DIPEA (0.1 mL, 0.6 mmol), followed by 2-(1-bromoethyl)-1,3-difluorobenzene (61.7 mg, 0.28 mmol). The reaction mixture was heated to 85° C. for 16 h. The reaction mixture was cooled to room temperature and evaporated under reduced pressure. The residue was dissolved in ethyl acetate (100 mL). The organic layer was washed with brine, dried over $Na_2SO_4$, concentrated under reduced pressure to obtain crude product, which was purified by preparative HPLC (Prep HPLC Method: column: DAD 1: Bridge Phenyl (250 mm×4.6 mm) 5 µm, DAD-2: Inersil ODS (250 mm×4.6 mm) 5 µm ID, 5 µm) Mobile phase 10 mM ammonium acetate in water pH: 4.5, MeOH: acetonitrile: 50:50 A-0.1% DEA in acetonitrile, Mobile phase B-0.1% DEA in MeOH, % B-0/70, 20/100 Flow: 2 mL/min) to yield Examples 780 and 781.

Example 780: (8.9 mg, 10.23% yield); LCMS: m/z, 463.2 (M+H); rt 2.349 min; (LCMS method: Column: XBridge BEH XP C18 (50×2.1) mm, 2.5 µm; Mobile phase A: 95% water:5% acetonitrile; 10 mM ammonium acetate; Mobile phase B: 5% water: 95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.32-8.22 (m, 1H), 8.21-8.10 (m, 1H), 7.44-7.31 (m, 1H), 7.14-6.99 (m, 2H), 4.84 (br. s., 1H), 4.15 (q, J=6.5 Hz, 1H), 3.96 (dd, J=3.5, 12.5 Hz, 1H), 3.54 (s, 3H), 3.25-3.14 (m, 1H), 2.88-2.73 (m, 2H), 1.45 (d, J=6.5 Hz, 3H), 1.36 (d, J=6.5 Hz, 3H), 0.90 (d, J=6.5 Hz, 3H), one proton merged with residual water.

Example 781: (8.9 mg, 10.23% yield); LCMS: m/z, 463.2 (M+H); rt 2.383 min; (LCMS method: Column: XBridge BEH XP C18 (50×2.1) mm, 2.5 µm; Mobile phase A: 95% water:5% acetonitrile; 10 mM ammonium acetate; Mobile phase B: 5% water: 95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.31-8.23 (m, 1H), 8.19-8.09 (m, 1H), 7.41-7.32 (m, 1H), 7.12-6.99 (m, 2H), 4.71-4.59 (m, 1H), 4.17-4.02 (m, 2H), 3.54-3.46 (m, 5H), 3.18-3.11 (m, 1H), 2.22-2.14 (m, 1H), 1.50-1.40 (m, 3H), 1.22-1.12 (m, 3H), 1.01-0.91 (m, 3H).

The examples in the Table 16 were prepared from the appropriate piperazine according to the general procedure described in Examples 780 and 781 substituting 2-(1-bromoethyl)-1,3-difluorobenzene with the appropriate α-methyl benzylbromides in the synthetic sequence. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 16

| Ex. No. | Structure | LCMS RT and Method | M + H | Stereo chem. |
|---|---|---|---|---|
| 782 | 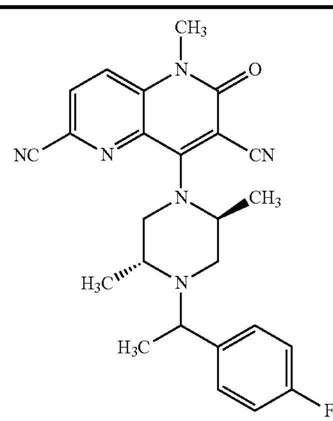 | 2.24 A | 445.3 | H |

TABLE 16-continued

| Ex. No. | Structure | LCMS RT and Method | M + H | Stereo chem. |
|---|---|---|---|---|
| 783 | 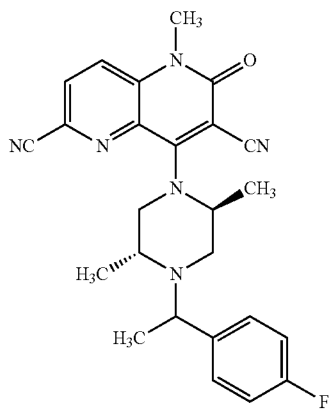 [SMILES: CC(c1ccc(F)cc1)N1C[C@H](C)N(c2c(C#N)c(=O)n(C)c3ccc(C#N)nc23)C[C@H]1C] | 2.24 A | 445.3 | H |
| 784 | 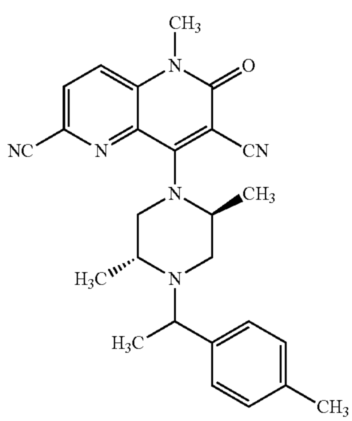 [SMILES: Cc1ccc(C(C)N2C[C@H](C)N(c3c(C#N)c(=O)n(C)c4ccc(C#N)nc34)C[C@H]2C)cc1] | 2.37 A | 441.3 | H |
| 785 | 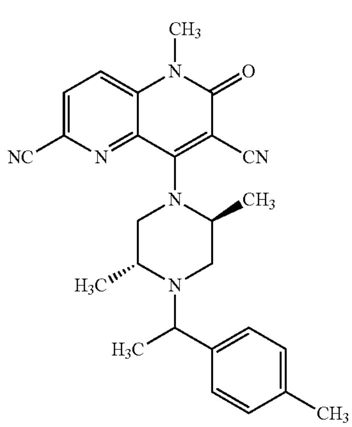 [SMILES: Cc1ccc(C(C)N2C[C@H](C)N(c3c(C#N)c(=O)n(C)c4ccc(C#N)nc34)C[C@H]2C)cc1] | 2.36 A | 441.3 | H |

TABLE 16-continued
| Ex. No. | Structure | LCMS RT and Method | M + H | Stereo chem. |
|---|---|---|---|---|
| 786 | 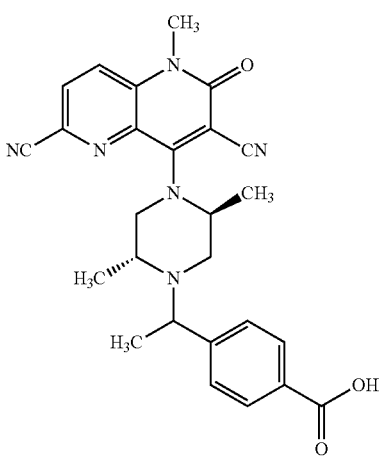 [SMILES: CC(c1ccc(C(=O)O)cc1)N1C[C@H](C)N(c2c(C#N)c(=O)n(C)c3ccc(C#N)nc23)C[C@H]1C] | 1.22 A | 471.2 | H |
| 787 | 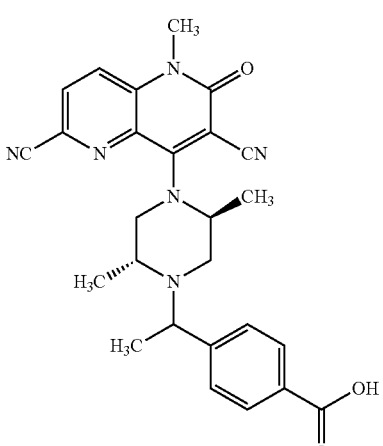 | 1.21 A | 471.2 | H |
| 788 | 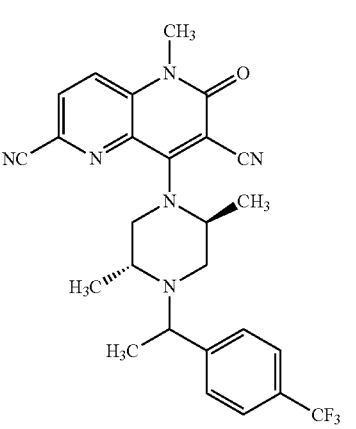 [SMILES: CC(c1ccc(C(F)(F)F)cc1)N1C[C@H](C)N(c2c(C#N)c(=O)n(C)c3ccc(C#N)nc23)C[C@H]1C] | 2.4 A | 495.2 | H |

TABLE 16-continued

| Ex. No. | Structure | LCMS RT and Method | M + H | Stereo chem. |
|---|---|---|---|---|
| 789 | 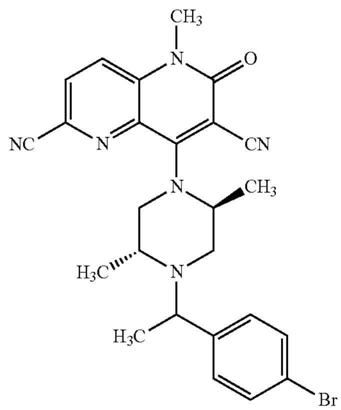 [SMILES: CC(c1ccc(Br)cc1)N1C[C@H](C)N(c2c(C#N)c(=O)n(C)c3ccc(C#N)nc23)C[C@H]1C] | 2.40 A | 505.1 | H |
| 790 | 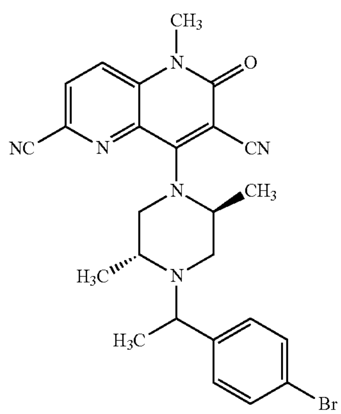 [SMILES: CC(c1ccc(Br)cc1)N1C[C@H](C)N(c2c(C#N)c(=O)n(C)c3ccc(C#N)nc23)C[C@H]1C] | 2.40 A | 505.1 | H |
| 791 | 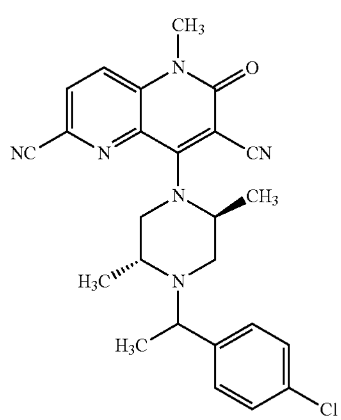 [SMILES: CC(c1ccc(Cl)cc1)N1C[C@H](C)N(c2c(C#N)c(=O)n(C)c3ccc(C#N)nc23)C[C@H]1C] | 2.41 A | 461.2 | H |

TABLE 16-continued
| Ex. No. | Structure | LCMS RT and Method | M + H | Stereo chem. |
|---|---|---|---|---|
| 792 | 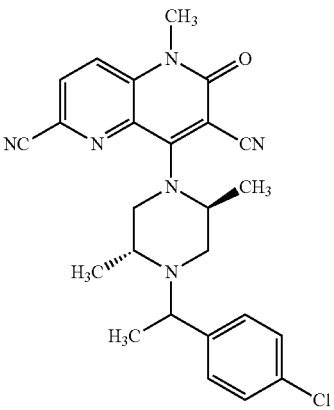 [SMILES: CC(c1ccc(Cl)cc1)N1C[C@H](C)N(c2c(C#N)c(=O)n(C)c3ccc(C#N)nc23)C[C@H]1C] | 2.4 A | 461.2 | H |
| 793 | 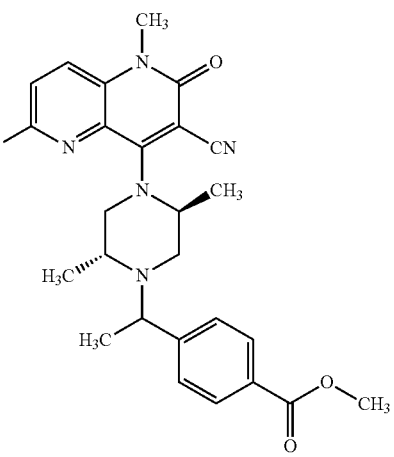 | 2.11 A | 485.2 | H |
| 794 | 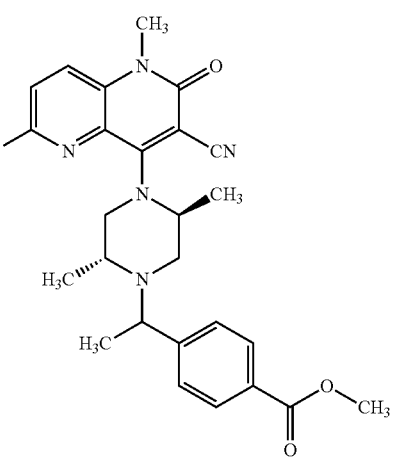 | 2.10 A | 485.2 | H |

TABLE 16-continued
| Ex. No. | Structure | LCMS RT and Method | M + H | Stereo chem. |
|---|---|---|---|---|
| 795 | 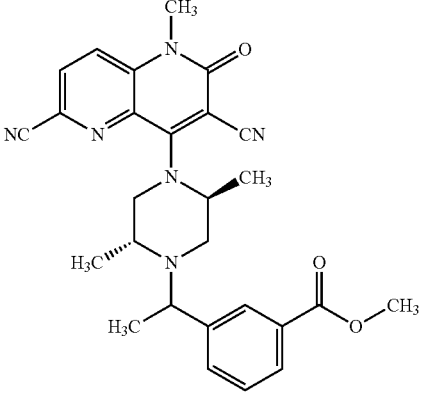 [SMILES: COC(=O)c1cccc(C(C)N2C[C@H](C)N(c3c(C#N)c(=O)n(C)c4ccc(C#N)nc34)C[C@H]2C)c1] | 2.14 A | 485.2 | H |
| 796 | 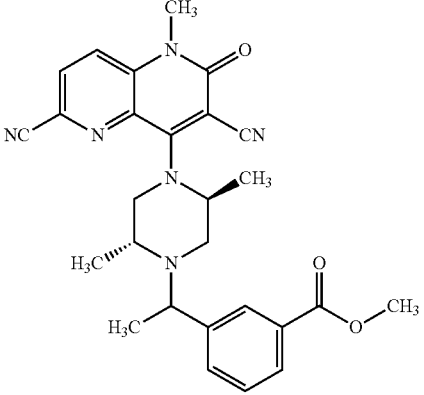 [SMILES: COC(=O)c1cccc(C(C)N2C[C@H](C)N(c3c(C#N)c(=O)n(C)c4ccc(C#N)nc34)C[C@H]2C)c1] | 2.14 A | 485.2 | H |
| 797 | 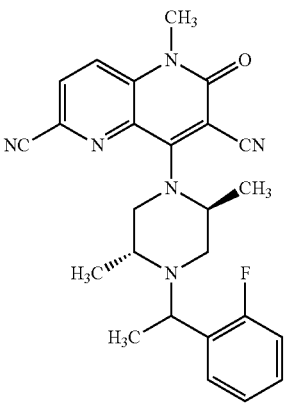 [SMILES: CC(c1ccccc1F)N1C[C@H](C)N(c2c(C#N)c(=O)n(C)c3ccc(C#N)nc23)C[C@H]1C] | 2.24 A | 445.2 | H |

TABLE 16-continued
| Ex. No. | Structure | LCMS RT and Method | M + H | Stereo chem. |
|---|---|---|---|---|
| 798 | 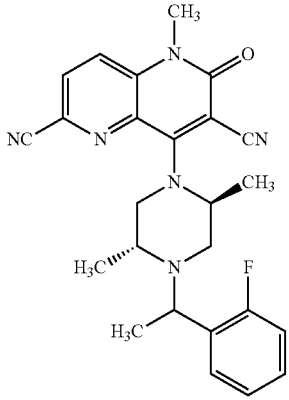 [SMILES: CC(c1ccccc1F)N1C[C@H](C)N(c2c(C#N)c(=O)n(C)c3ccc(C#N)nc23)C[C@H]1C] | 2.22 A | 445.2 | H |
| 799 | 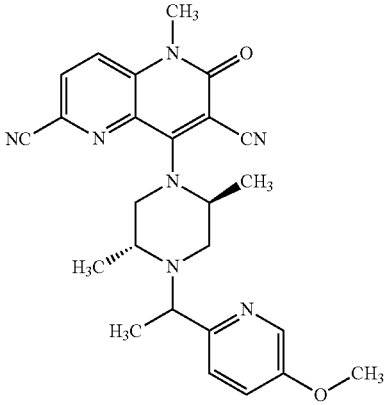 [SMILES: COc1ccc(C(C)N2C[C@H](C)N(c3c(C#N)c(=O)n(C)c4ccc(C#N)nc34)C[C@H]2C)nc1] | 1.73 A | 458.2 | H |
| 800 | 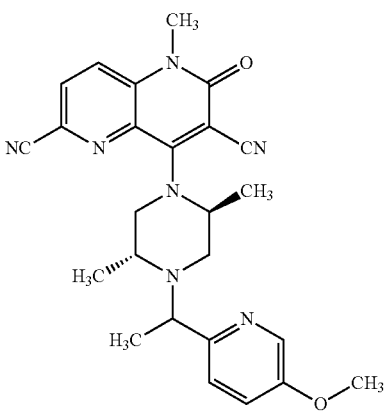 [SMILES: COc1ccc(C(C)N2C[C@H](C)N(c3c(C#N)c(=O)n(C)c4ccc(C#N)nc34)C[C@H]2C)nc1] | 1.14 T | 458.2 | H |

TABLE 16-continued
| Ex. No. | Structure | LCMS RT and Method | M + H | Stereo chem. |
|---|---|---|---|---|
| 801 | 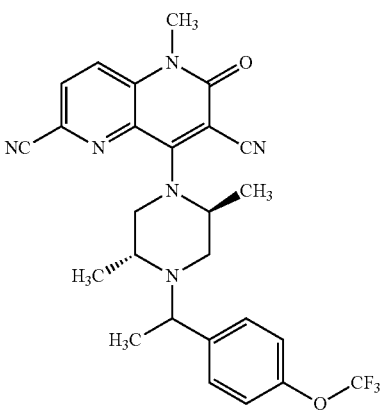 [SMILES: CC(c1ccc(OC(F)(F)F)cc1)N1C[C@H](C)N(c2c(C#N)c(=O)n(C)c3ccc(C#N)nc23)C[C@H]1C] | 2.43 A | 511.2 | H |
| 802 | 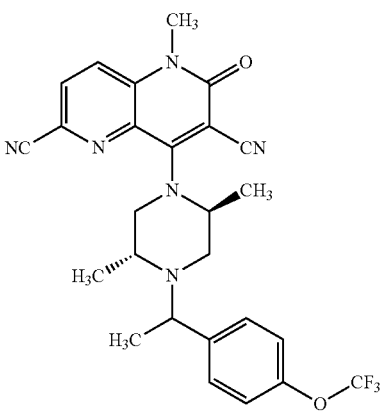 [SMILES: CC(c1ccc(OC(F)(F)F)cc1)N1C[C@H](C)N(c2c(C#N)c(=O)n(C)c3ccc(C#N)nc23)C[C@H]1C] | 2.43 A | 511.2 | H |
| 803 | 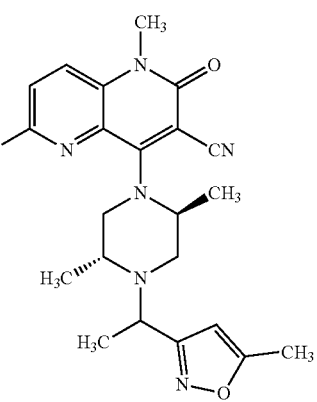 | 1.75 A | 432.2 | H |

TABLE 16-continued

| Ex. No. | Structure | LCMS RT and Method | M + H | Stereo chem. |
|---|---|---|---|---|
| 804 | 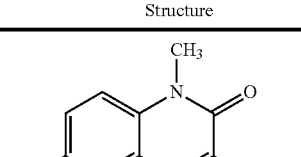 | 1.75 A | 432.2 | H |

The examples in the Table 17 were prepared from the appropriate piperazine according to the general procedure described in Examples 780 and 781, substituting 2-(1-bromoethyl)-1,3-difluorobenzene with the appropriate benzhydryl chloride/bromides in the synthetic sequence. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 17

| Ex. No. | Structure | LCMS RT and Method | M + H | Stereo chem. |
|---|---|---|---|---|
| 805 | 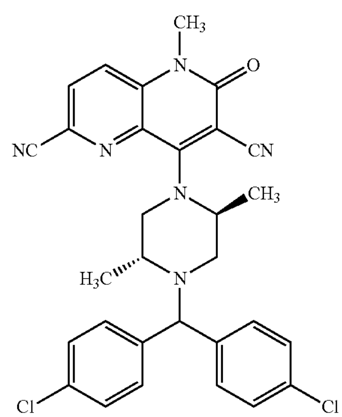 [SMILES: C[C@@H]1CN(c2c(C#N)c(=O)n(C)c3ccc(C#N)nc23)[C@@H](C)CN1C(c1ccc(Cl)cc1)c1ccc(Cl)cc1] | 2.78 A | 557.2 | H |
| 806 | 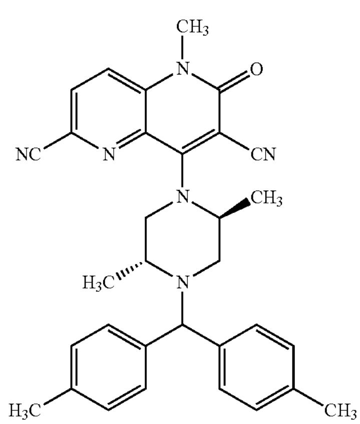 | 2.56 A | 517.3 | H |

TABLE 17-continued
| Ex. No. | Structure | LCMS RT and Method | M + H | Stereo chem. |
|---|---|---|---|---|
| 807 | 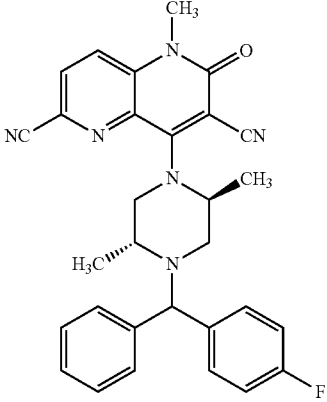 [SMILES: C[C@@H]1CN(c2c(C#N)c(=O)n(C)c3ccc(C#N)nc23)[C@@H](C)CN1C(c1ccccc1)c1ccc(F)cc1] | 2.34 A | 507.3 | H |
| 808 | 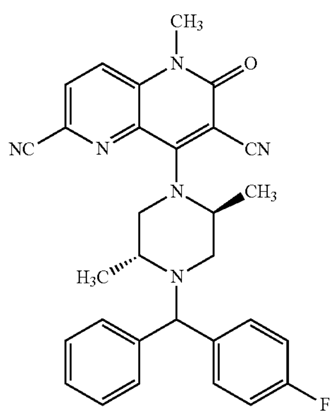 [SMILES: C[C@@H]1CN(c2c(C#N)c(=O)n(C)c3ccc(C#N)nc23)[C@@H](C)CN1C(c1ccccc1)c1ccc(F)cc1] | 2.35 A | 507.2 | H |
| 809 | 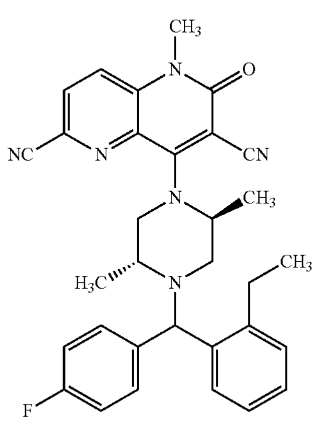 [SMILES: CCc1ccccc1C(c1ccc(F)cc1)N1C[C@H](C)N(c2c(C#N)c(=O)n(C)c3ccc(C#N)nc23)C[C@H]1C] | 2.52 A | 535.3 | H |

TABLE 17-continued
| Ex. No. | Structure | LCMS RT and Method | M + H | Stereo chem. |
|---|---|---|---|---|
| 810 | 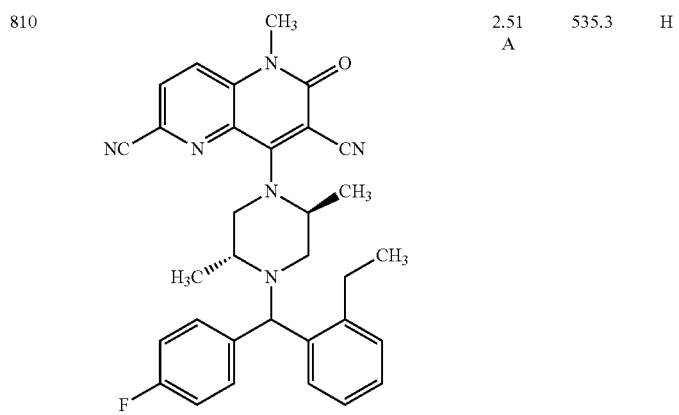 | 2.51 A | 535.3 | H |
| 811 | 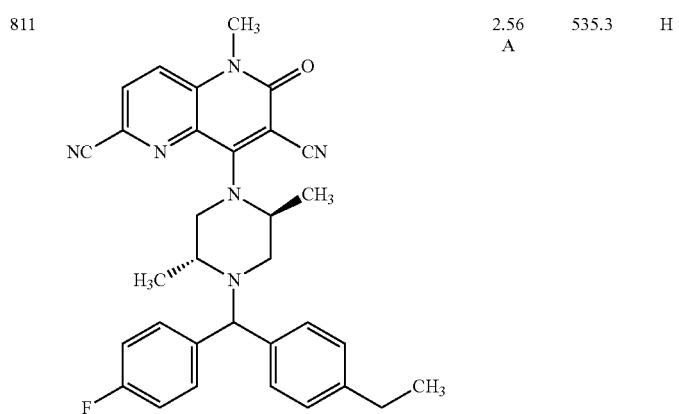 | 2.56 A | 535.3 | H |
| 812 | 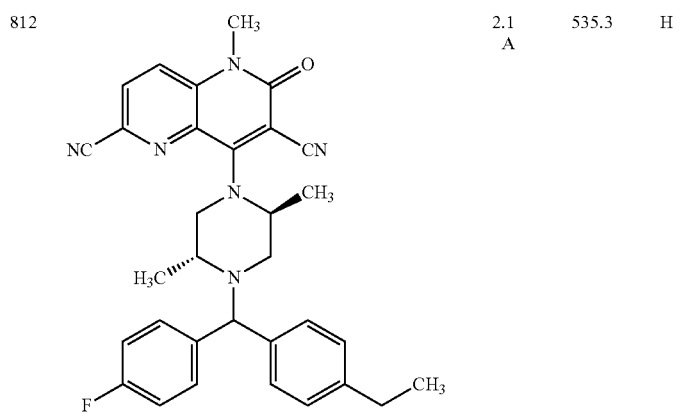 | 2.1 A | 535.3 | H |

TABLE 17-continued

| Ex. No. | Structure | LCMS RT and Method | M + H | Stereo chem. |
|---|---|---|---|---|
| 813 | 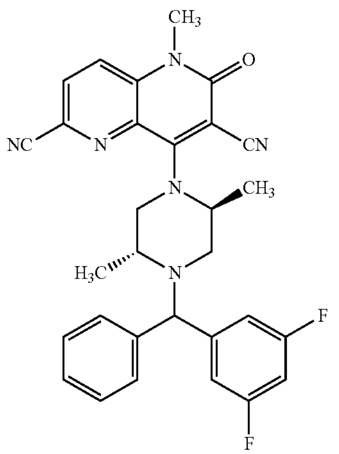 [SMILES: C[C@@H]1CN(c2c(C#N)c(=O)n(C)c3ccc(C#N)nc23)[C@@H](C)CN1C(c1ccccc1)c1cc(F)cc(F)c1] | 2.37 A | 525.3 | H |
| 814 | 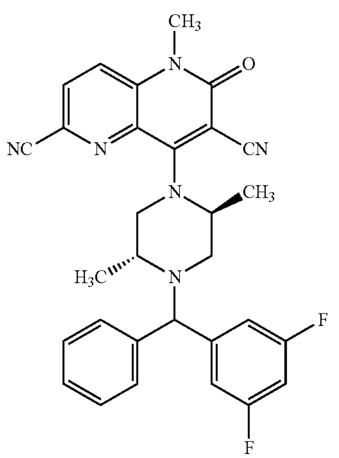 [SMILES: C[C@@H]1CN(c2c(C#N)c(=O)n(C)c3ccc(C#N)nc23)[C@@H](C)CN1C(c1ccccc1)c1cc(F)cc(F)c1] | 2.38 A | 525.3 | H |
| 815 | 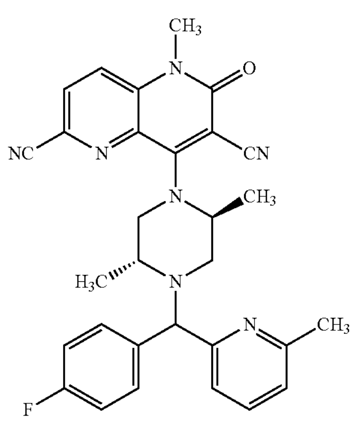 [SMILES: Cc1cccc(C(c2ccc(F)cc2)N2C[C@H](C)N(c3c(C#N)c(=O)n(C)c4ccc(C#N)nc34)C[C@H]2C)n1] | 2.23 A | 522.2 | H |

TABLE 17-continued
| Ex. No. | Structure | LCMS RT and Method | M + H | Stereo chem. |
|---|---|---|---|---|
| 816 | 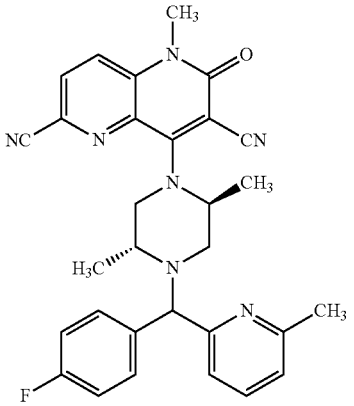 [SMILES: Cc1cccc(C(c2ccc(F)cc2)N2C[C@H](C)N(c3c(C#N)c(=O)n(C)c4ccc(C#N)nc34)C[C@H]2C)n1] | 2.30 A | 522.2 | H |
| 817 | 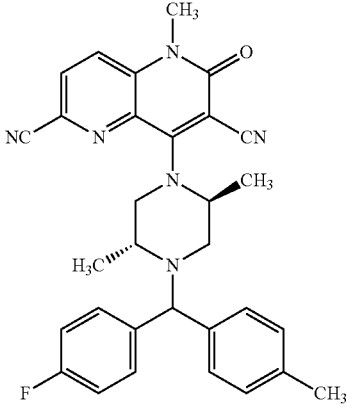 [SMILES: Cc1ccc(C(c2ccc(F)cc2)N2C[C@H](C)N(c3c(C#N)c(=O)n(C)c4ccc(C#N)nc34)C[C@H]2C)cc1] | 2.45 A | 521.3 | H |
| 818 | 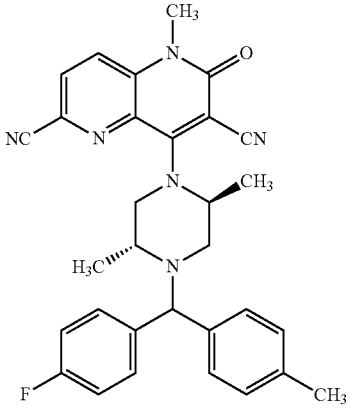 [SMILES: Cc1ccc(C(c2ccc(F)cc2)N2C[C@H](C)N(c3c(C#N)c(=O)n(C)c4ccc(C#N)nc34)C[C@H]2C)cc1] | 2.45 A | 521.2 | H |

TABLE 17-continued

| Ex. No. | Structure | LCMS RT and Method | M + H | Stereo chem. |
|---|---|---|---|---|
| 819 | 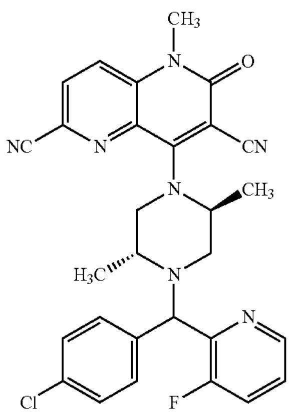 [SMILES: C[C@@H]1CN(c2c(C#N)c(=O)n(C)c3ccc(C#N)nc23)[C@@H](C)CN1C(c1ccc(Cl)cc1)c1ncccc1F] | 2.23 A | 542.2 | H |
| 820 | 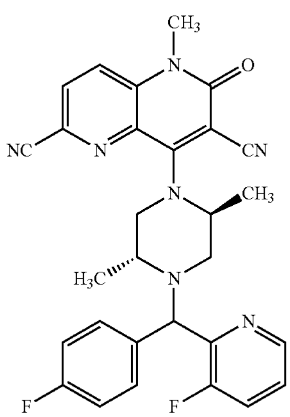 [SMILES: C[C@@H]1CN(c2c(C#N)c(=O)n(C)c3ccc(C#N)nc23)[C@@H](C)CN1C(c1ccc(F)cc1)c1ncccc1F] | 1.56 A | 526.3 | H |
| 821 | 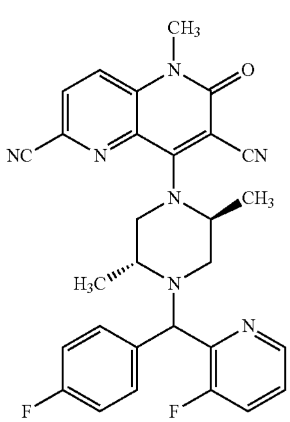 [SMILES: C[C@@H]1CN(c2c(C#N)c(=O)n(C)c3ccc(C#N)nc23)[C@@H](C)CN1C(c1ccc(F)cc1)c1ncccc1F] | 1.46 A | 526.3 | H |

TABLE 17-continued
| Ex. No. | Structure | LCMS RT and Method | M + H | Stereo chem. |
|---|---|---|---|---|
| 822 | 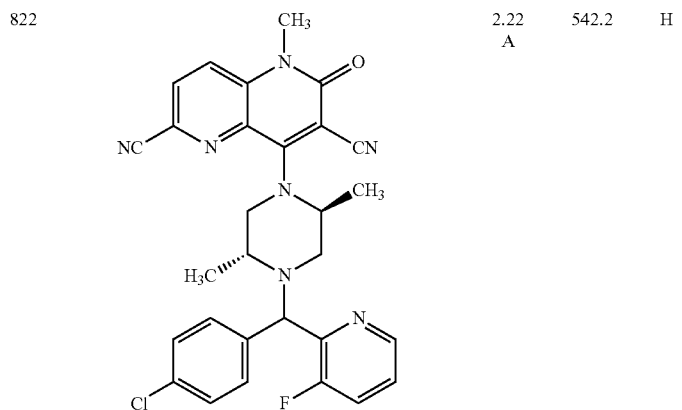 | 2.22 A | 542.2 | H |
| 823 | 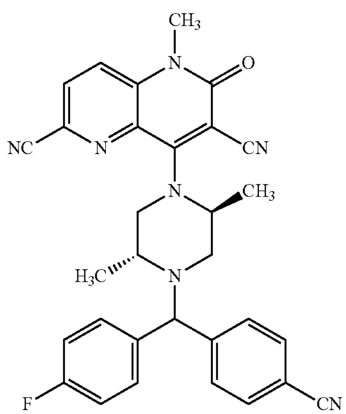 [SMILES: C[C@@H]1CN(c2c(C#N)c(=O)n(C)c3ccc(C#N)nc23)[C@@H](C)CN1C(c1ccc(F)cc1)c1ccc(C#N)cc1] | 2.36 A | 532.2 | H |
| 824 | 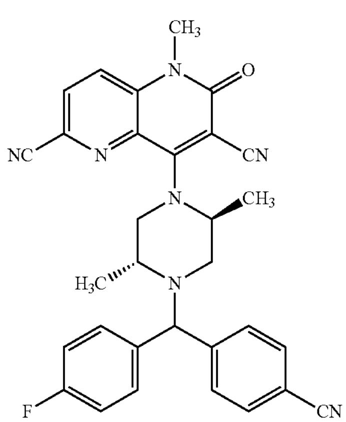 [SMILES: C[C@@H]1CN(c2c(C#N)c(=O)n(C)c3ccc(C#N)nc23)[C@@H](C)CN1C(c1ccc(F)cc1)c1ccc(C#N)cc1] | 2.33 A | 532.2 | H |

TABLE 17-continued

| Ex. No. | Structure | LCMS RT and Method | M + H | Stereo chem. |
|---|---|---|---|---|
| 825 | 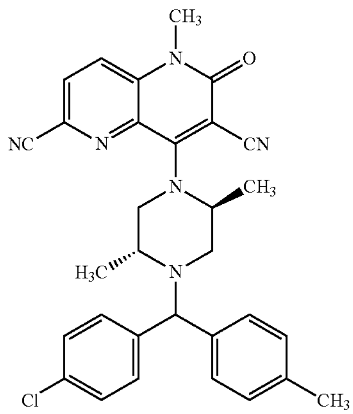 [SMILES: Cc1ccc(C(c2ccc(Cl)cc2)N2C[C@H](C)N(c3c(C#N)c(=O)n(C)c4ccc(C#N)nc34)C[C@H]2C)cc1] | 2.62 A | 537.3 | H |
| 826 | 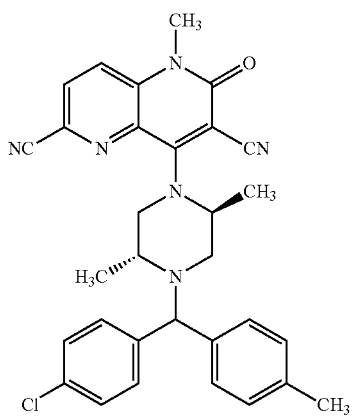 [SMILES: Cc1ccc(C(c2ccc(Cl)cc2)N2C[C@H](C)N(c3c(C#N)c(=O)n(C)c4ccc(C#N)nc34)C[C@H]2C)cc1] | 2.62 A | 537.3 | H |
| 827 | 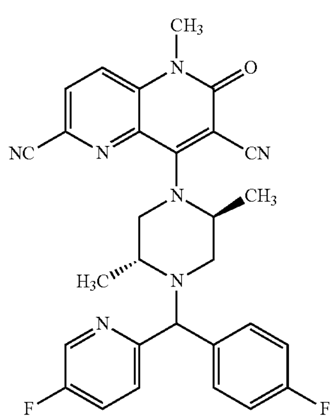 [SMILES: C[C@@H]1CN(c2c(C#N)c(=O)n(C)c3ccc(C#N)nc23)[C@@H](C)CN1C(c1ccc(F)cc1)c1ccc(F)cn1] | 2.12 A | 526.2 | H |

TABLE 17-continued
| Ex. No. | Structure | LCMS RT and Method | M + H | Stereo chem. |
|---|---|---|---|---|
| 828 | 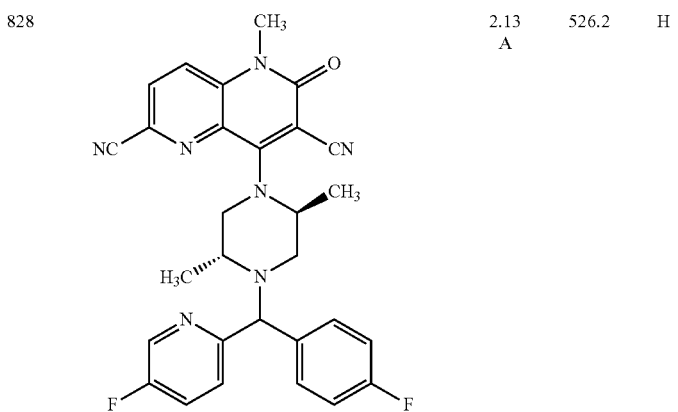 | 2.13 A | 526.2 | H |
| 829 | 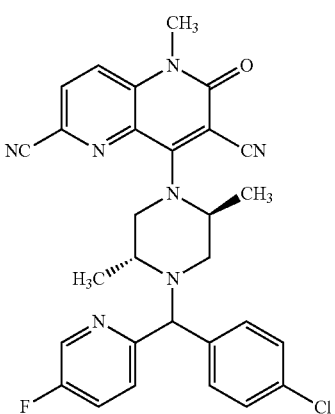 [SMILES: C[C@@H]1CN(c2c(C#N)c(=O)n(C)c3ccc(C#N)nc23)[C@@H](C)CN1C(c1ccc(Cl)cc1)c1ccc(F)cn1] | 2.37 A | 542.2 | H |
| 830 | 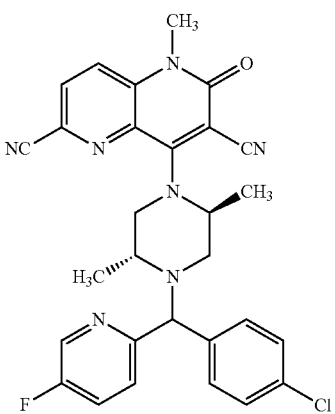 [SMILES: C[C@@H]1CN(c2c(C#N)c(=O)n(C)c3ccc(C#N)nc23)[C@@H](C)CN1C(c1ccc(Cl)cc1)c1ccc(F)cn1] | 2.4 A | 542.2 | H |

TABLE 17-continued
| Ex. No. | Structure | LCMS RT and Method | M + H | Stereo chem. |
|---|---|---|---|---|
| 831 | 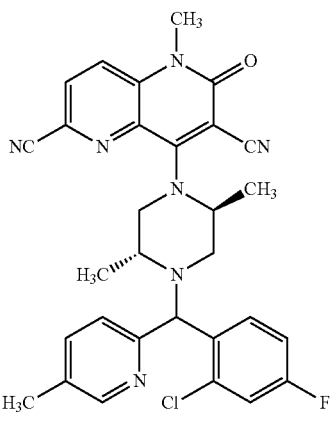 [SMILES: Cc1ccc(C(c2ccc(F)cc2Cl)N2C[C@H](C)N(c3c(C#N)c(=O)n(C)c4ccc(C#N)nc34)C[C@H]2C)nc1] | 2.2 A | 556.2 | H |
| 832 | 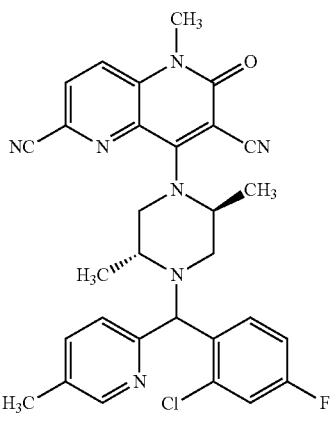 [SMILES: Cc1ccc(C(c2ccc(F)cc2Cl)N2C[C@H](C)N(c3c(C#N)c(=O)n(C)c4ccc(C#N)nc34)C[C@H]2C)nc1] | 2.22 A | 556.2 | H |
| 833 | 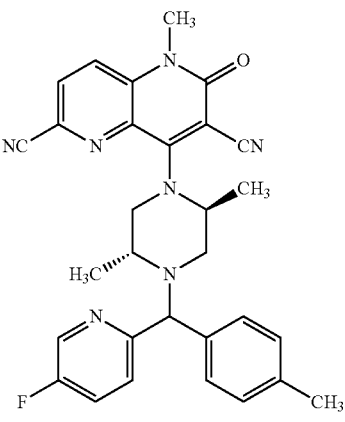 [SMILES: Cc1ccc(C(c2ccc(F)cn2)N2C[C@H](C)N(c3c(C#N)c(=O)n(C)c4ccc(C#N)nc34)C[C@H]2C)cc1] | 2.18 A | 522.2 | H |

TABLE 17-continued
| Ex. No. | Structure | LCMS RT and Method | M + H | Stereo chem. |
|---|---|---|---|---|
| 834 | 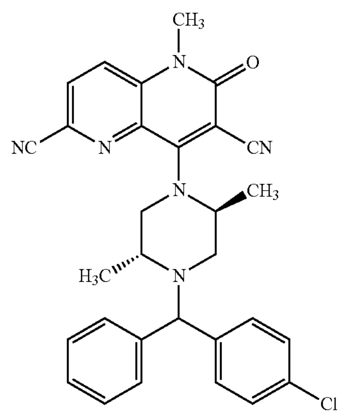 [SMILES: C[C@@H]1CN(c2c(C#N)c(=O)n(C)c3ccc(C#N)nc23)[C@@H](C)CN1C(c1ccccc1)c1ccc(Cl)cc1] | 2.47 A | 523.2 | H |
| 835 | 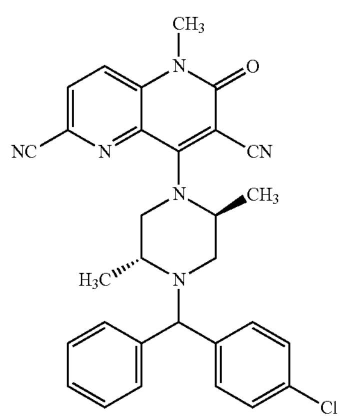 [SMILES: C[C@@H]1CN(c2c(C#N)c(=O)n(C)c3ccc(C#N)nc23)[C@@H](C)CN1C(c1ccccc1)c1ccc(Cl)cc1] | 2.47 A | 523.2 | H |
| 836 | 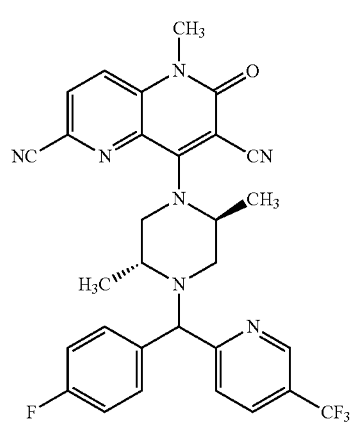 [SMILES: C[C@@H]1CN(c2c(C#N)c(=O)n(C)c3ccc(C#N)nc23)[C@@H](C)CN1C(c1ccc(F)cc1)c1ccc(C(F)(F)F)cn1] | 2.29 A | 576.2 | H |

TABLE 17-continued
| Ex. No. | Structure | LCMS RT and Method | M + H | Stereo chem. |
|---|---|---|---|---|
| 837 | 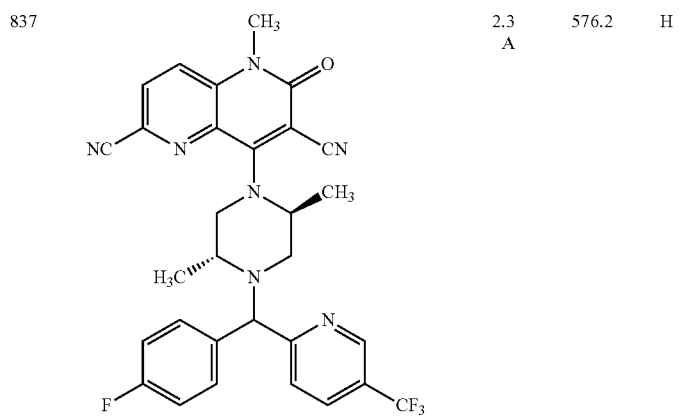 | 2.3 A | 576.2 | H |
| 838 | 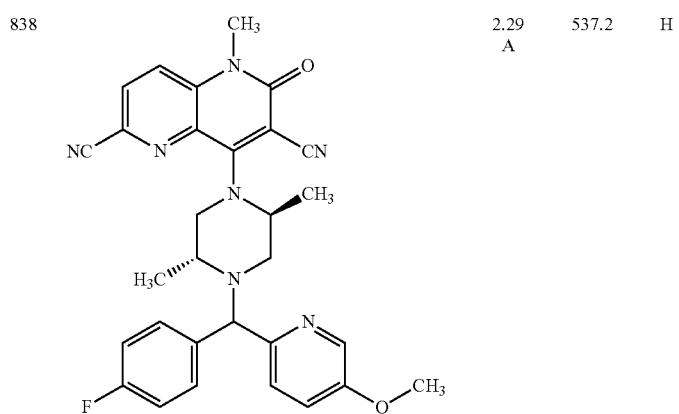 | 2.29 A | 537.2 | H |
| 839 | 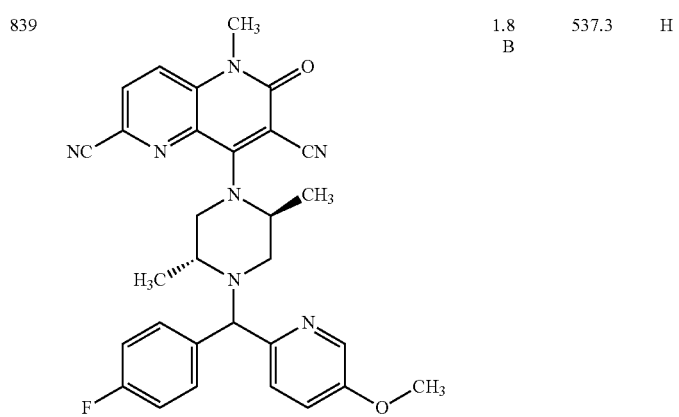 | 1.8 B | 537.3 | H |

TABLE 17-continued
| Ex. No. | Structure | LCMS RT and Method | M + H | Stereo chem. |
|---|---|---|---|---|
| 840 | 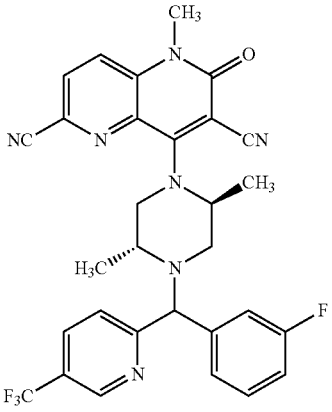 [SMILES: C[C@@H]1CN(c2c(C#N)c(=O)n(C)c3ccc(C#N)nc23)[C@@H](C)CN1C(c1cccc(F)c1)c1ccc(C(F)(F)F)cn1] | 2.29 A | 576.2 | H |
| 841 | 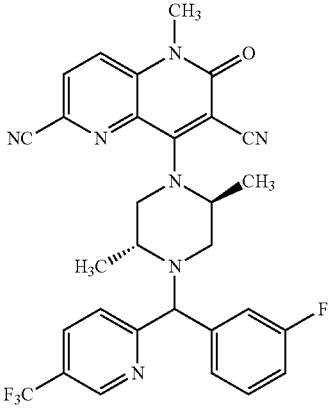 [SMILES: C[C@@H]1CN(c2c(C#N)c(=O)n(C)c3ccc(C#N)nc23)[C@@H](C)CN1C(c1cccc(F)c1)c1ccc(C(F)(F)F)cn1] | 2.30 A | 576.2 | H |
| 842 | 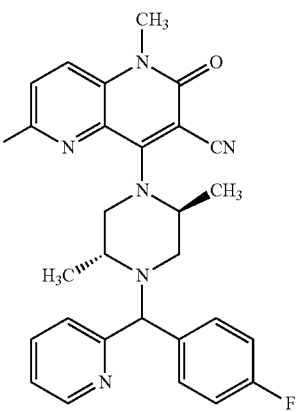 | 1.98 A | 508.2 | H |

TABLE 17-continued

| Ex. No. | Structure | LCMS RT and Method | M + H | Stereo chem. |
|---|---|---|---|---|
| 843 | 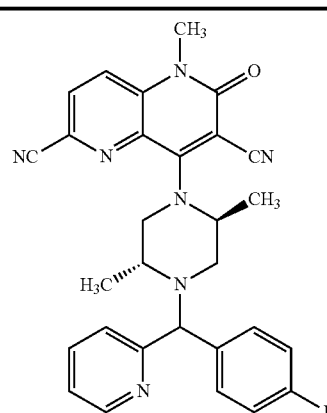 | 1.97 A | 508.2 | H |
| 844 | 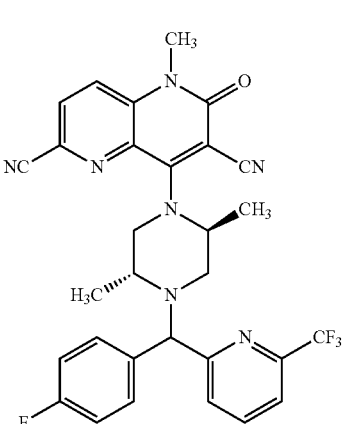 | 2.29 A | 576.2 | H |
| 845 | 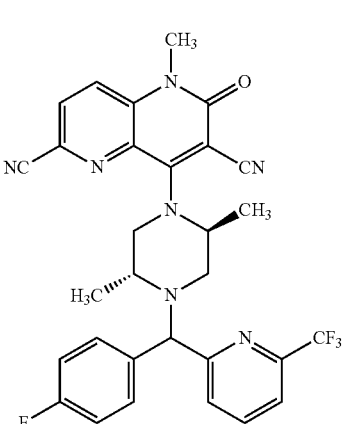 | 2.30 A | 576.2 | H |

The examples in the Table 18 were prepared from the appropriate piperazine according to the general procedure described in Examples 700 and 701, substituting 4-cyclopropylthiazole-2-carbaldehyde with the appropriate heterocyclic aldehyde and Intermediate 780H in the synthetic sequence. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 18
| Ex. No. | Structure | LCMS RT and Method | M + H | Stereo Chem. |
|---|---|---|---|---|
| 846 | 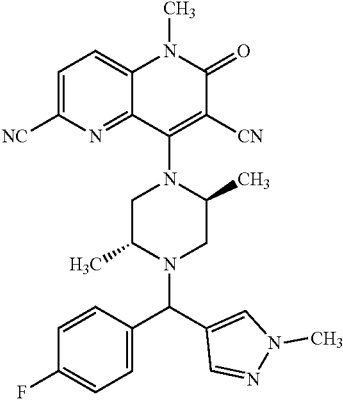 [SMILES: C[C@@H]1CN(c2c(C#N)c(=O)n(C)c3ccc(C#N)nc23)[C@@H](C)CN1C(c1ccc(F)cc1)c1cnn(C)c1] | 1.87 A | 511.3 | H |
| 847 | 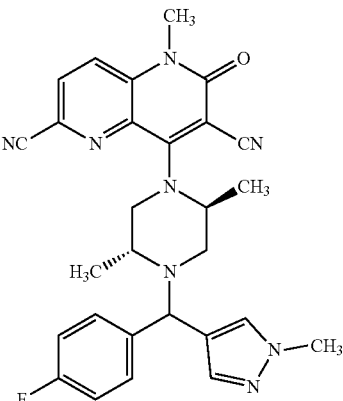 | 1.87 A | 511.2 | H |
| 848 | 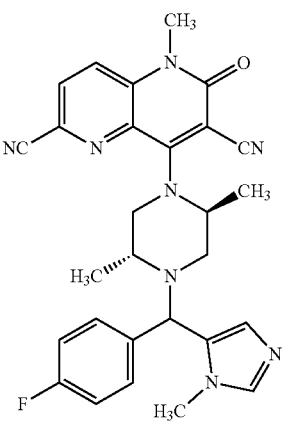 [SMILES: C[C@@H]1CN(c2c(C#N)c(=O)n(C)c3ccc(C#N)nc23)[C@@H](C)CN1C(c1ccc(F)cc1)c1cncn1C] | 1.70 A | 511.2 | H |

TABLE 18-continued

| Ex. No. | Structure | LCMS RT and Method | M + H | Stereo Chem. |
|---|---|---|---|---|
| 849 | 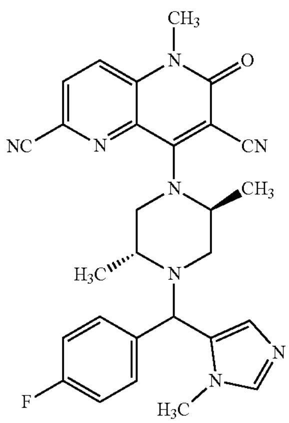 [SMILES: C[C@@H]1CN(c2c(C#N)c(=O)n(C)c3ccc(C#N)nc23)[C@@H](C)CN1C(c1ccc(F)cc1)c1cncn1C] | 1.73 A | 511.3 | H |
| 850 | 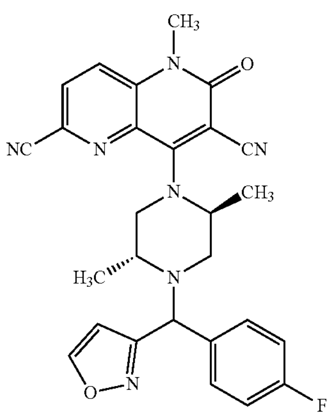 [SMILES: C[C@@H]1CN(c2c(C#N)c(=O)n(C)c3ccc(C#N)nc23)[C@@H](C)CN1C(c1ccc(F)cc1)c1ccon1] | 1.98 A | 498.1 | H |
| 851 | 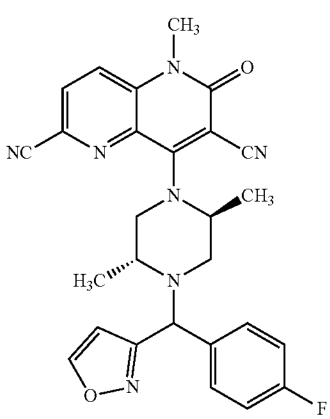 [SMILES: C[C@@H]1CN(c2c(C#N)c(=O)n(C)c3ccc(C#N)nc23)[C@@H](C)CN1C(c1ccc(F)cc1)c1ccon1] | 2.00 A | 498.2 | H |

TABLE 18-continued
| Ex. No. | Structure | LCMS RT and Method | M + H | Stereo Chem. |
|---|---|---|---|---|
| 852 | 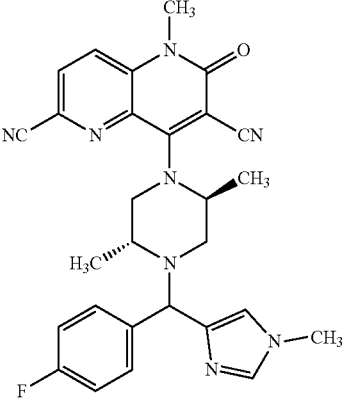 [SMILES: C[C@@H]1CN(c2c(C#N)c(=O)n(C)c3ccc(C#N)nc23)[C@@H](C)CN1C(c1ccc(F)cc1)c1cn(C)cn1] | 1.74 A | 511.2 | H |
| 853 | 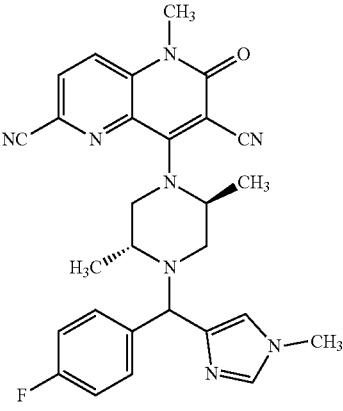 [SMILES: C[C@@H]1CN(c2c(C#N)c(=O)n(C)c3ccc(C#N)nc23)[C@@H](C)CN1C(c1ccc(F)cc1)c1cn(C)cn1] | 1.71 A | 511.2 | H |
| 854 | 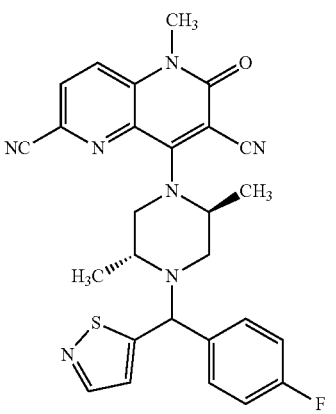 [SMILES: C[C@@H]1CN(c2c(C#N)c(=O)n(C)c3ccc(C#N)nc23)[C@@H](C)CN1C(c1ccc(F)cc1)c1ccns1] | 2.01 A | 514.1 | H |

TABLE 18-continued
| Ex. No. | Structure | LCMS RT and Method | M + H | Stereo Chem. |
|---|---|---|---|---|
| 855 | 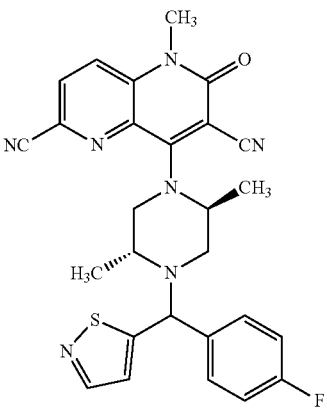 [SMILES: C[C@@H]1CN(c2c(C#N)c(=O)n(C)c3ccc(C#N)nc23)[C@@H](C)CN1C(c1ccc(F)cc1)c1ccns1] | 2.02 A | 514.2 | H |
| 856 | 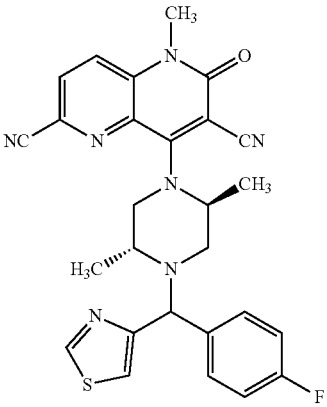 [SMILES: C[C@@H]1CN(c2c(C#N)c(=O)n(C)c3ccc(C#N)nc23)[C@@H](C)CN1C(c1ccc(F)cc1)c1cscn1] | 1.94 A | 514.7 | H |
| 857 | 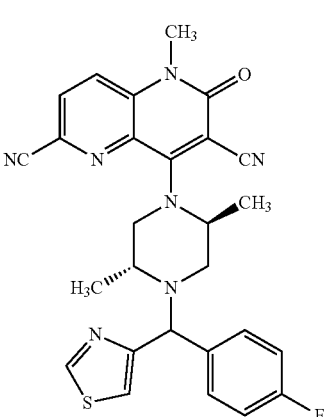 | 1.94 A | 514.1 | H |

TABLE 18-continued

| Ex. No. | Structure | LCMS RT and Method | M + H | Stereo Chem. |
|---|---|---|---|---|
| 858 | 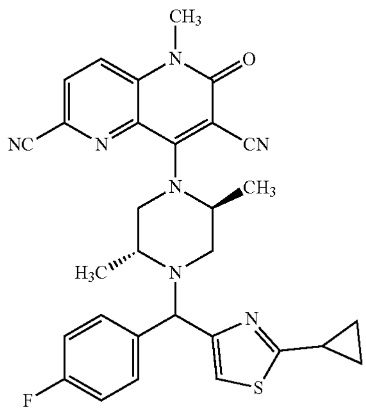 [SMILES: C[C@@H]1CN(c2c(C#N)c(=O)n(C)c3ccc(C#N)nc23)[C@@H](C)CN1C(c1ccc(F)cc1)c1csc(C2CC2)n1] | 1.66 A | 554.2 | H |
| 859 | 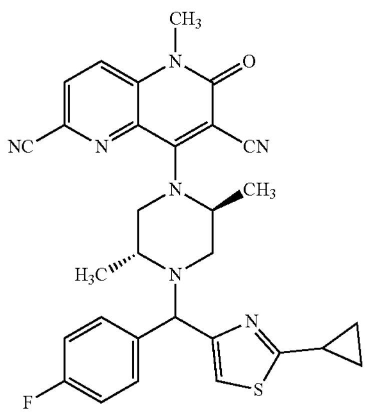 [SMILES: C[C@@H]1CN(c2c(C#N)c(=O)n(C)c3ccc(C#N)nc23)[C@@H](C)CN1C(c1ccc(F)cc1)c1csc(C2CC2)n1] | 2.25 A | 554.2 | H |

The examples in the Table 19 were prepared from the appropriate piperazine according to the general procedure described in Examples 735 and 736 substituting (Z)—N'-hydroxycyclopropane carboximidamide with the appropriate amidoximes and Intermediate 780F in the synthetic sequence. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 19

| Ex. No. | Structure | LCMS RT and Method | M + H | Stereo chem. |
|---|---|---|---|---|
| 860 | 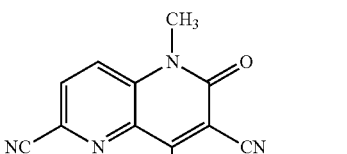 | 2.18 A | 539.2 | H |

TABLE 19-continued

| Ex. No. | Structure | LCMS RT and Method | M + H | Stereo chem. |
|---|---|---|---|---|
| 861 | 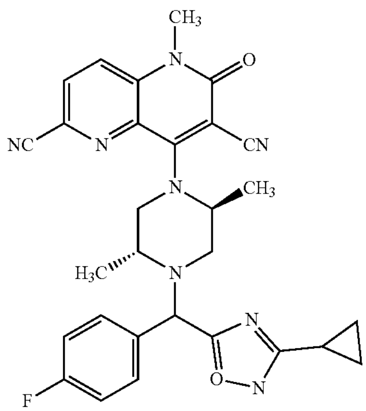 | 2.18 A | 539.2 | H |
| 862 | 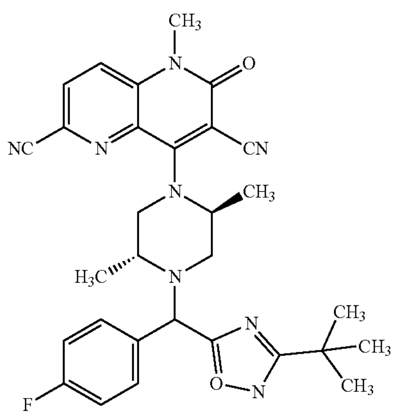 | 2.37 A | 555.2 | H |
| 863 | 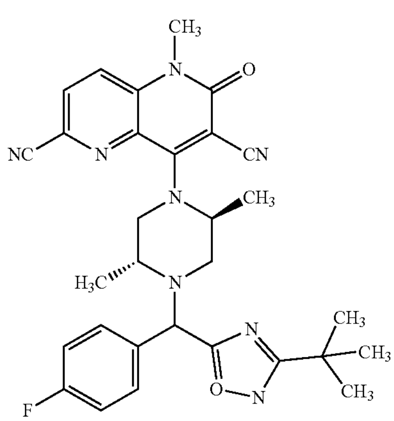 | 2.37 A | 555.2 | H |

The examples in the Table 20 were prepared from the appropriate piperazine according to the general procedure described in Examples 729 and 730, substituting 5-cyclopropylisoxazole-3-carboxylic acid with the appropriate isoxazole-3-carboxylic acid and using Intermediate 780F in the synthetic sequence. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 20

| Ex. No. | Structure | LCMS RT and Method | M + H | Stereo chem. |
|---|---|---|---|---|
| 864 | 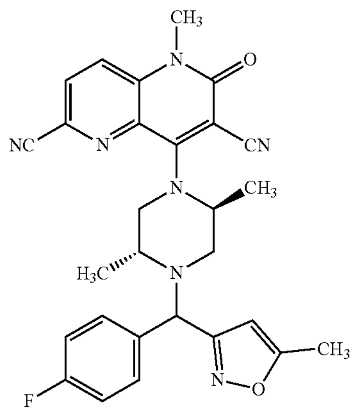 [SMILES: Cc1cc(C(c2ccc(F)cc2)N2C[C@H](C)N(c3c(C#N)c(=O)n(C)c4ccc(C#N)nc34)C[C@H]2C)no1] | 2.07 A | 512.2 | H |
| 865 | 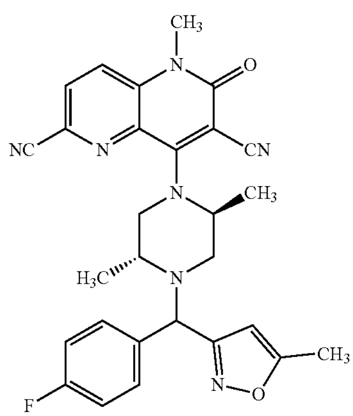 [SMILES: Cc1cc(C(c2ccc(F)cc2)N2C[C@H](C)N(c3c(C#N)c(=O)n(C)c4ccc(C#N)nc34)C[C@H]2C)no1] | 2.06 A | 512.2 | H |
| 866 | 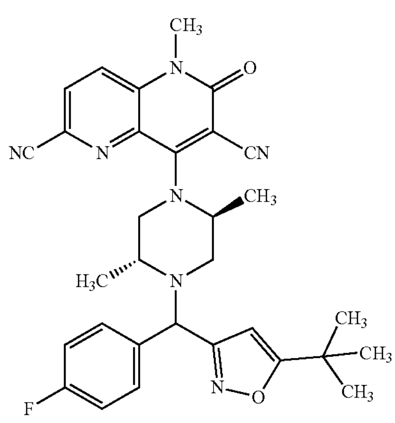 [SMILES: C[C@@H]1CN(c2c(C#N)c(=O)n(C)c3ccc(C#N)nc23)[C@@H](C)CN1C(c1ccc(F)cc1)c1cc(C(C)(C)C)on1] | 2.38 A | 554.3 | H |

TABLE 20-continued

| Ex. No. | Structure | LCMS RT and Method | M + H | Stereo chem. |
|---|---|---|---|---|
| 867 | 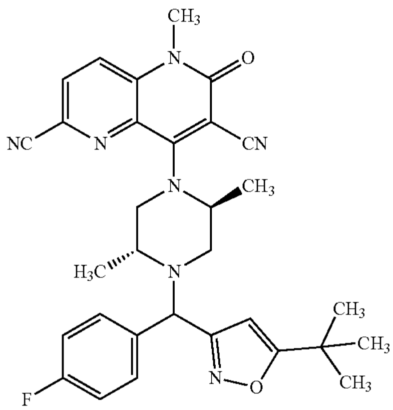 [SMILES: C[C@@H]1CN(c2c(C#N)c(=O)n(C)c3ccc(C#N)nc23)[C@@H](C)CN1C(c1ccc(F)cc1)c1cc(C(C)(C)C)on1] | 2.39 A | 554.2 | H |
| 868 | 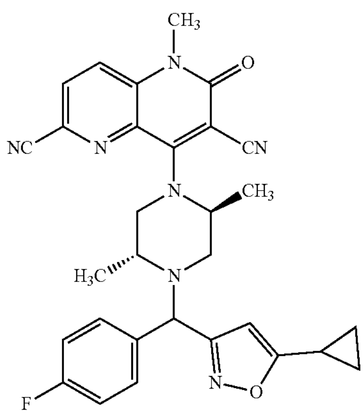 [SMILES: C[C@@H]1CN(c2c(C#N)c(=O)n(C)c3ccc(C#N)nc23)[C@@H](C)CN1C(c1ccc(F)cc1)c1cc(C2CC2)on1] | 2.17 A | 538.2 | H |
| 869 | 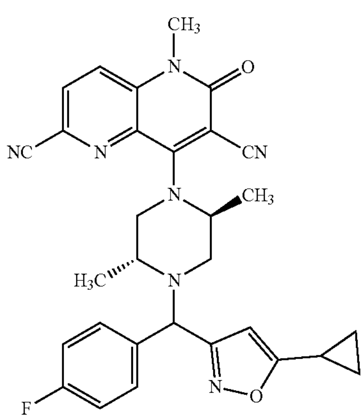 [SMILES: C[C@@H]1CN(c2c(C#N)c(=O)n(C)c3ccc(C#N)nc23)[C@@H](C)CN1C(c1ccc(F)cc1)c1cc(C2CC2)on1] | 2.19 A | 538.2 | H |

The examples in the Table 21 were prepared from the appropriate piperazine according to the general procedure described in Examples 780 and 781, substituting 2-(1-bromoethyl)-1,3-difluorobenzene with the appropriate benzhydryl chloride/bromides in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 21
| Ex. No. | Structure | LCMS RT and Method | M + H | Stereo chem. |
|---|---|---|---|---|
| 870 | 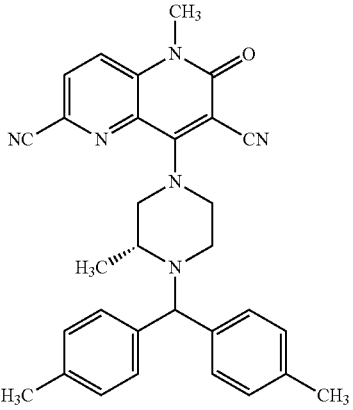 | 2.49 A | 503.3 | H |
| 871 | 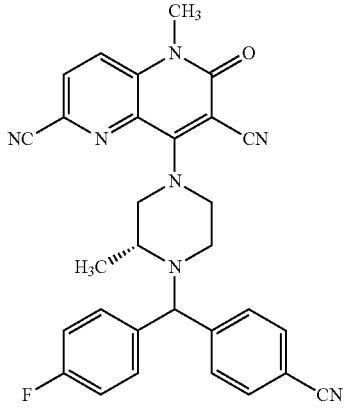 [SMILES: C[C@@H]1CN(c2c(C#N)c(=O)n(C)c3ccc(C#N)nc23)CCN1C(c1ccc(F)cc1)c1ccc(C#N)cc1] | 2.1 A | 518.3 | H |
| 872 | 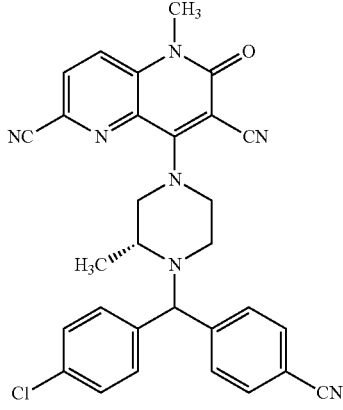 [SMILES: C[C@@H]1CN(c2c(C#N)c(=O)n(C)c3ccc(C#N)nc23)CCN1C(c1ccc(Cl)cc1)c1ccc(C#N)cc1] | 2.24 A | 534.3 | H |

TABLE 21-continued
| Ex. No. | Structure | LCMS RT and Method | M + H | Stereo chem. |
|---|---|---|---|---|
| 873 | 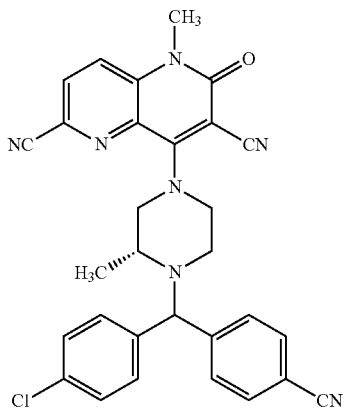 [SMILES: C[C@@H]1CN(c2c(C#N)c(=O)n(C)c3ccc(C#N)nc23)CCN1C(c1ccc(Cl)cc1)c1ccc(C#N)cc1] | 2.23 A | 534.2 | H |
| 874 | 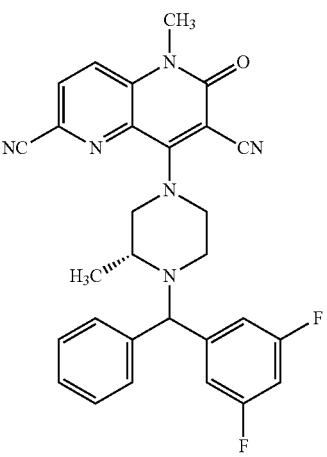 [SMILES: C[C@@H]1CN(c2c(C#N)c(=O)n(C)c3ccc(C#N)nc23)CCN1C(c1ccccc1)c1cc(F)cc(F)c1] | 2.32 A | 511.2 | D |
| 875 | 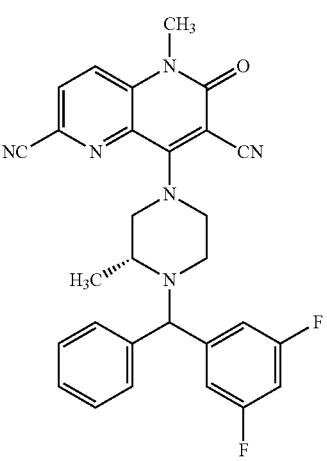 [SMILES: C[C@@H]1CN(c2c(C#N)c(=O)n(C)c3ccc(C#N)nc23)CCN1C(c1ccccc1)c1cc(F)cc(F)c1] | 2.33 A | 511.2 | H |

TABLE 21-continued
| Ex. No. | Structure | LCMS RT and Method | M + H | Stereo chem. |
|---|---|---|---|---|
| 876 | 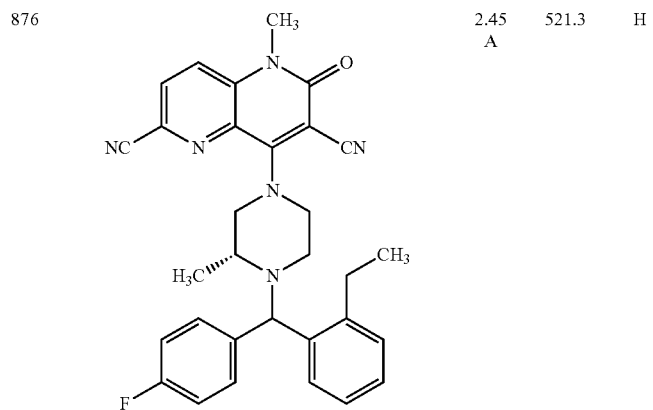 | 2.45 A | 521.3 | H |
| 877 | 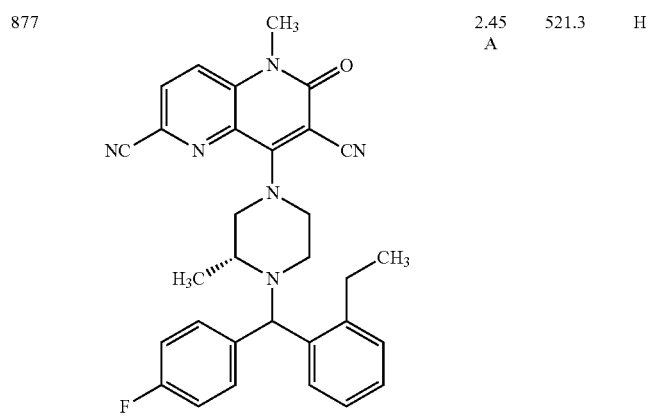 | 2.45 A | 521.3 | H |
| 878 | 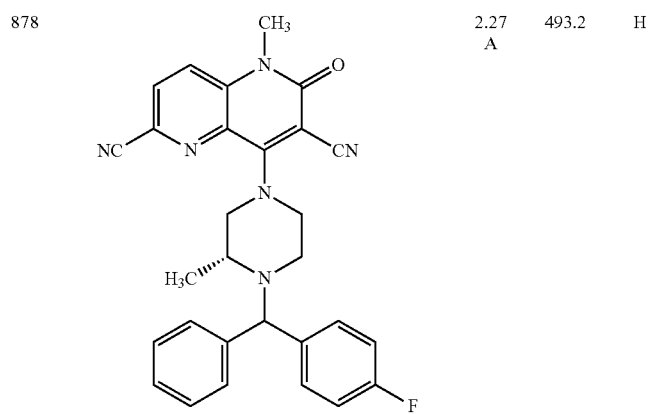 | 2.27 A | 493.2 | H |

TABLE 21-continued

| Ex. No. | Structure | LCMS RT and Method | M + H | Stereo chem. |
|---|---|---|---|---|
| 879 | 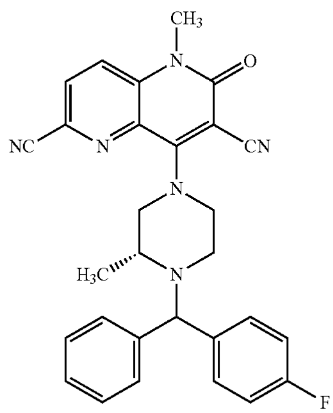 | 2.27 A | 493.2 | H |
| 880 | 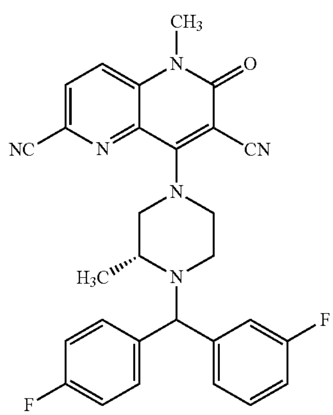 [SMILES: C[C@@H]1CN(c2c(C#N)c(=O)n(C)c3ccc(C#N)nc23)CCN1C(c1ccc(F)cc1)c1cccc(F)c1] | 2.29 A | 511.2 | H |
| 881 | 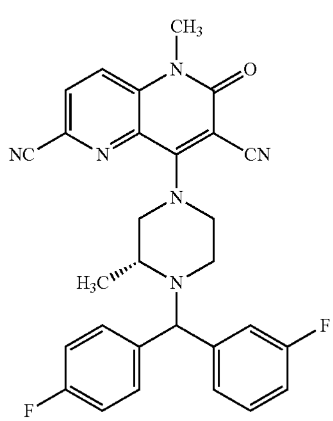 [SMILES: C[C@@H]1CN(c2c(C#N)c(=O)n(C)c3ccc(C#N)nc23)CCN1C(c1ccc(F)cc1)c1cccc(F)c1] | 2.28 A | 511.2 | H |

TABLE 21-continued

| Ex. No. | Structure | LCMS RT and Method | M + H | Stereo chem. |
|---|---|---|---|---|
| 882 | 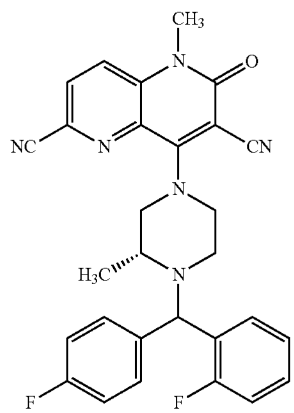 [SMILES: C[C@@H]1CN(c2c(C#N)c(=O)n(C)c3ccc(C#N)nc23)CCN1C(c1ccc(F)cc1)c1ccccc1F] | 2.27 A | 511.3 | H |
| 883 | 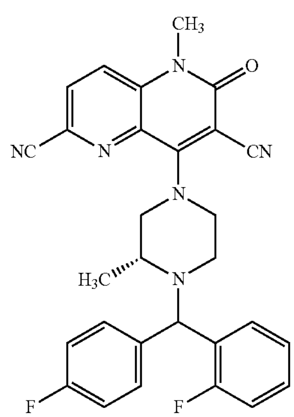 [SMILES: C[C@@H]1CN(c2c(C#N)c(=O)n(C)c3ccc(C#N)nc23)CCN1C(c1ccc(F)cc1)c1ccccc1F] | 2.29 A | 511.3 | H |
| 884 | 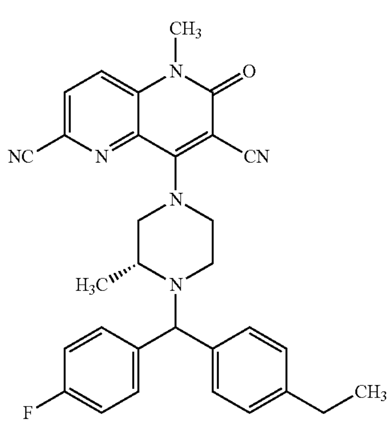 [SMILES: CCc1ccc(C(c2ccc(F)cc2)N2CCN(c3c(C#N)c(=O)n(C)c4ccc(C#N)nc34)C[C@H]2C)cc1] | 2.49 A | 521.3 | H |

TABLE 21-continued

| Ex. No. | Structure | LCMS RT and Method | M + H | Stereo chem. |
|---|---|---|---|---|
| 885 | 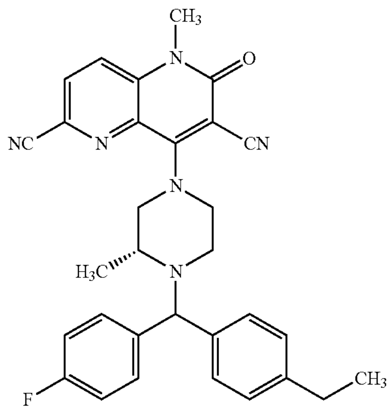 [SMILES: CCc1ccc(C(c2ccc(F)cc2)N2CCN(c3c(C#N)c(=O)n(C)c4ccc(C#N)nc34)C[C@H]2C)cc1] | 2.49 A | 521.3 | H |
| 886 | 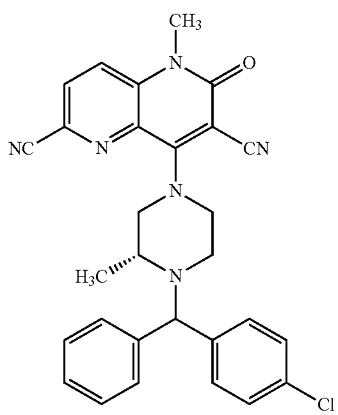 [SMILES: C[C@@H]1CN(c2c(C#N)c(=O)n(C)c3ccc(C#N)nc23)CCN1C(c1ccccc1)c1ccc(Cl)cc1] | 2.41 A | 509.3 | H |
| 887 | 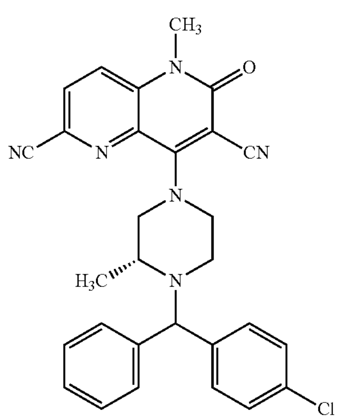 [SMILES: C[C@@H]1CN(c2c(C#N)c(=O)n(C)c3ccc(C#N)nc23)CCN1C(c1ccccc1)c1ccc(Cl)cc1] | 2.4 A | 509.2 | H |

TABLE 21-continued
| Ex. No. | Structure | LCMS RT and Method | M + H | Stereo chem. |
|---|---|---|---|---|
| 888 | 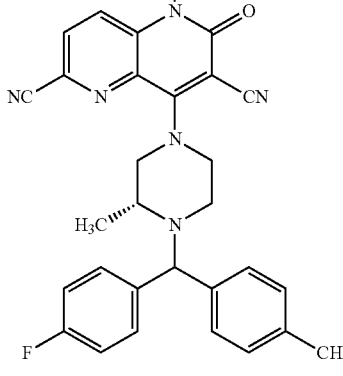 | 2.39 A | 507.3 | H |
| 889 | 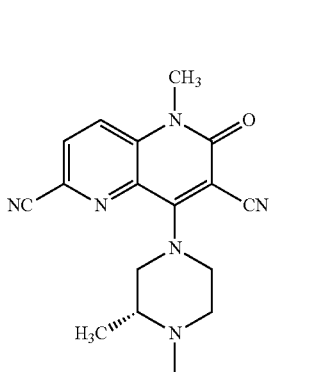 | 2.39 A | 507.3 | H |
| 890 | 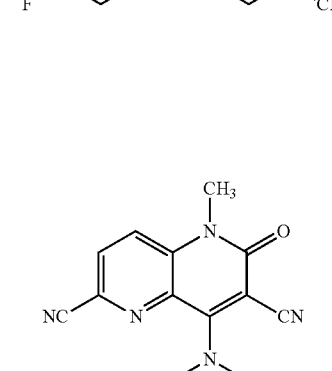 | 2.0 A | 508.3 | H |

TABLE 21-continued

| Ex. No. | Structure | LCMS RT and Method | M + H | Stereo chem. |
|---|---|---|---|---|
| 891 | 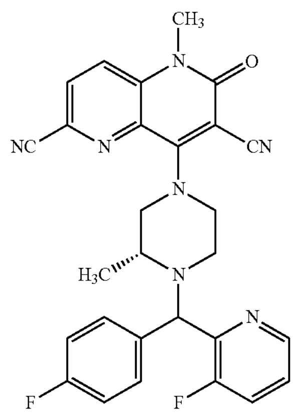 | 1.93 A | 512.2 | H |
| 892 | 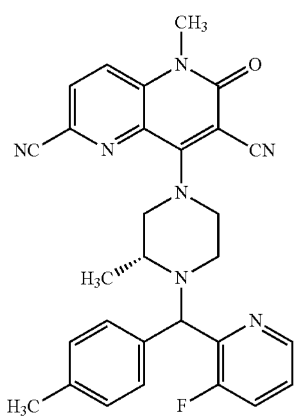 [SMILES: Cc1ccc(C(c2ncccc2F)N2CCN(c3c(C#N)c(=O)n(C)c4ccc(C#N)nc34)C[C@H]2C)cc1] | 2.07 A | 508.3 | H |
| 893 | 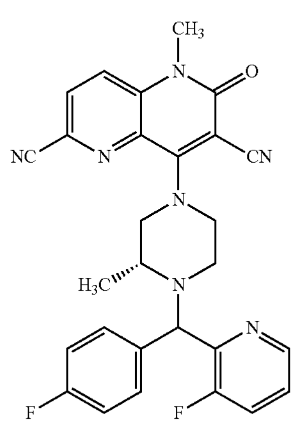 [SMILES: C[C@@H]1CN(c2c(C#N)c(=O)n(C)c3ccc(C#N)nc23)CCN1C(c1ccc(F)cc1)c1ncccc1F] | 1.36 A | 512.3 | H |

TABLE 21-continued
| Ex. No. | Structure | LCMS RT and Method | M + H | Stereo chem. |
|---|---|---|---|---|
| 894 | 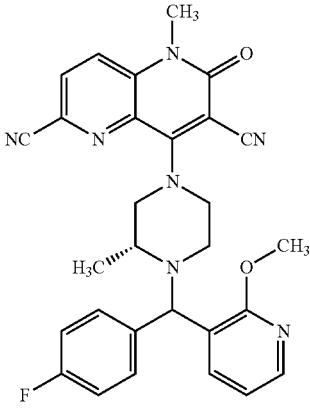 [SMILES: COc1ncccc1C(c1ccc(F)cc1)N1CCN(c2c(C#N)c(=O)n(C)c3ccc(C#N)nc23)C[C@H]1C] | 2.13 A | 524.3 | H |
| 895 | 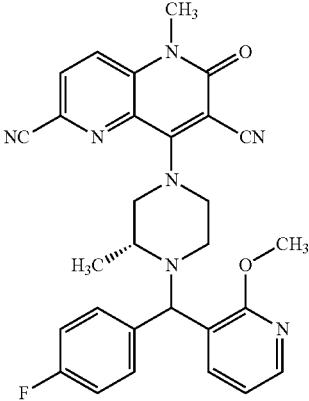 [SMILES: COc1ncccc1C(c1ccc(F)cc1)N1CCN(c2c(C#N)c(=O)n(C)c3ccc(C#N)nc23)C[C@H]1C] | 2.16 A | 524.3 | H |
| 896 | 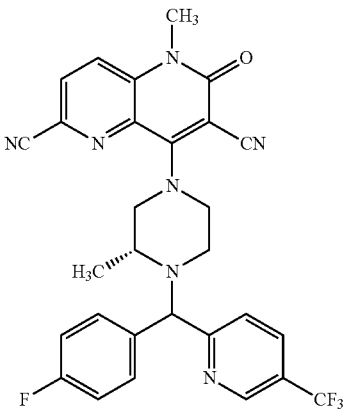 [SMILES: C[C@@H]1CN(c2c(C#N)c(=O)n(C)c3ccc(C#N)nc23)CCN1C(c1ccc(F)cc1)c1ccc(C(F)(F)F)cn1] | 2.19 A | 562.3 | H |

TABLE 21-continued
| Ex. No. | Structure | LCMS RT and Method | M + H | Stereo chem. |
|---|---|---|---|---|
| 897 | 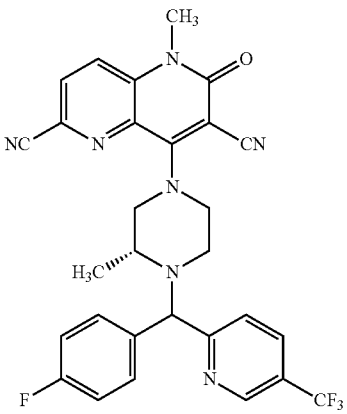 [SMILES: C[C@@H]1CN(c2c(C#N)c(=O)n(C)c3ccc(C#N)nc23)CCN1C(c1ccc(F)cc1)c1ccc(C(F)(F)F)cn1] | 2.22 A | 562.2 | H |
| 898 | 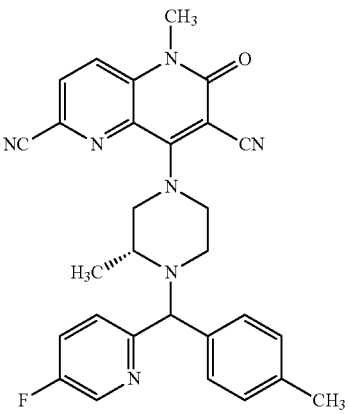 | 2.07 A | 508.3 | H |
| 899 | 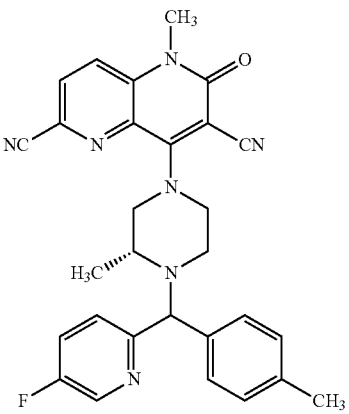 [SMILES: Cc1ccc(C(c2ccc(F)cn2)N2CCN(c3c(C#N)c(=O)n(C)c4ccc(C#N)nc34)C[C@H]2C)cc1] | 2.11 A | 508.3 | H |

TABLE 21-continued
| Ex. No. | Structure | LCMS RT and Method | M + H | Stereo chem. |
|---|---|---|---|---|
| 900 | 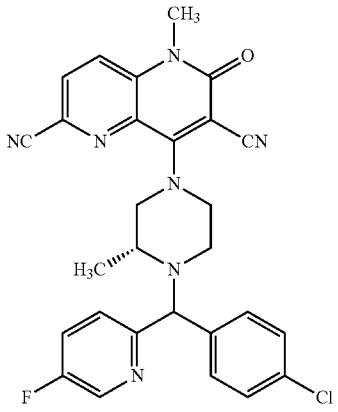 [SMILES: C[C@@H]1CN(c2c(C#N)c(=O)n(C)c3ccc(C#N)nc23)CCN1C(c1ccc(Cl)cc1)c1ccc(F)cn1] | 2.12 A | 528.2 | H |
| 901 | 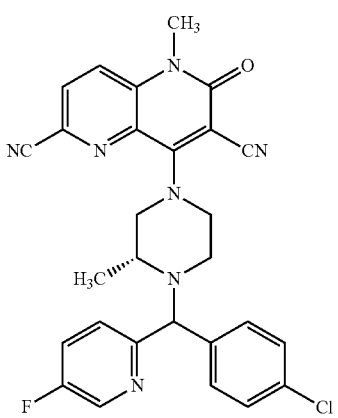 [SMILES: C[C@@H]1CN(c2c(C#N)c(=O)n(C)c3ccc(C#N)nc23)CCN1C(c1ccc(Cl)cc1)c1ccc(F)cn1] | 2.17 A | 528.2 | H |
| 902 | 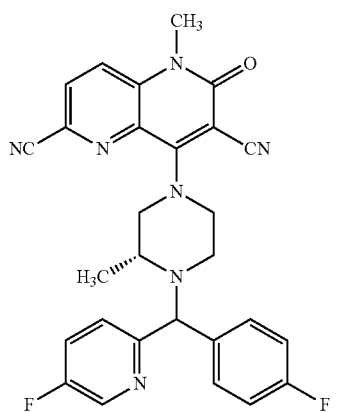 [SMILES: C[C@@H]1CN(c2c(C#N)c(=O)n(C)c3ccc(C#N)nc23)CCN1C(c1ccc(F)cc1)c1ccc(F)cn1] | 1.98 A | 512.2 | H |

TABLE 21-continued
| Ex. No. | Structure | LCMS RT and Method | M + H | Stereo chem. |
|---|---|---|---|---|
| 903 | 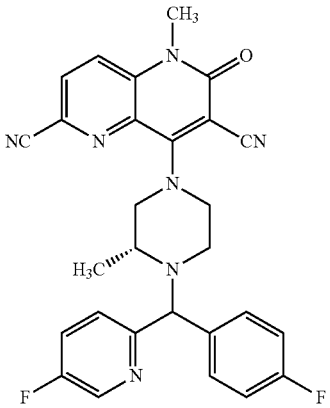 [SMILES: C[C@@H]1CN(c2c(C#N)c(=O)n(C)c3ccc(C#N)nc23)CCN1C(c1ccc(F)cc1)c1ccc(F)cn1] | 2.01 A | 512.2 | H |
| 904 | 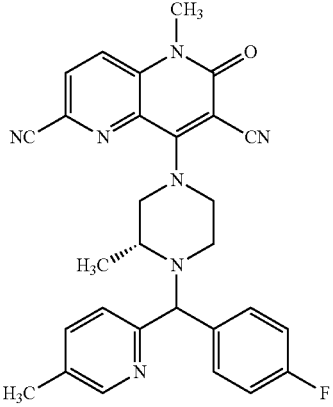 [SMILES: Cc1ccc(C(c2ccc(F)cc2)N2CCN(c3c(C#N)c(=O)n(C)c4ccc(C#N)nc34)C[C@H]2C)nc1] | 2.07 A | 508.2 | H |
| 905 | 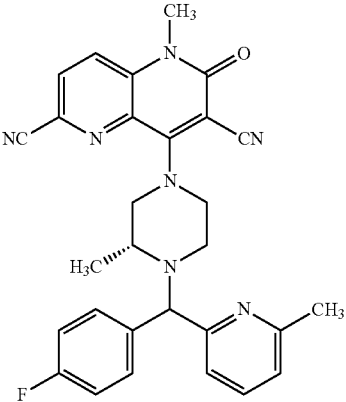 [SMILES: Cc1cccc(C(c2ccc(F)cc2)N2CCN(c3c(C#N)c(=O)n(C)c4ccc(C#N)nc34)C[C@H]2C)n1] | 1.99 A | 508.2 | H |

TABLE 21-continued

| Ex. No. | Structure | LCMS RT and Method | M + H | Stereo chem. |
|---|---|---|---|---|
| 906 | 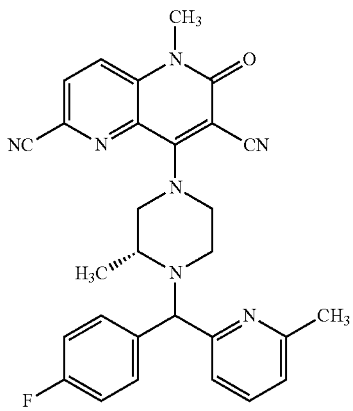 [SMILES: Cc1cccc(C(c2ccc(F)cc2)N2CCN(c3c(C#N)c(=O)n(C)c4ccc(C#N)nc34)C[C@H]2C)n1] | 2.02 A | 508.2 | H |
| 907 | 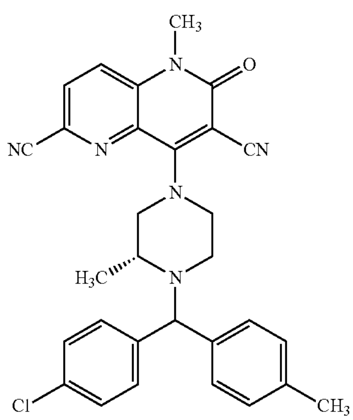 [SMILES: Cc1ccc(C(c2ccc(Cl)cc2)N2CCN(c3c(C#N)c(=O)n(C)c4ccc(C#N)nc34)C[C@H]2C)cc1] | 2.83 A | 523.2 | Diastereomer Mixture |
| 908 | 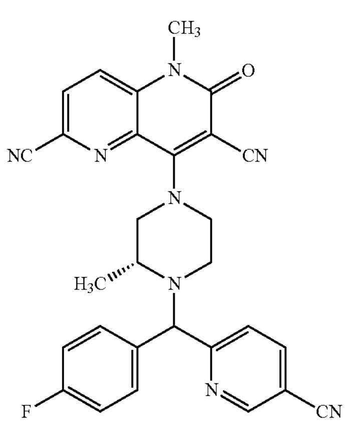 [SMILES: C[C@@H]1CN(c2c(C#N)c(=O)n(C)c3ccc(C#N)nc23)CCN1C(c1ccc(F)cc1)c1ccc(C#N)cn1] | 1.90 A | 519.2 | H |

TABLE 21-continued

| Ex. No. | Structure | LCMS RT and Method | M + H | Stereo chem. |
|---|---|---|---|---|
| 909 | 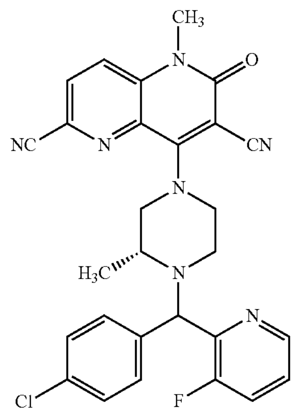 [SMILES: C[C@@H]1CN(c2c(C#N)c(=O)n(C)c3ccc(C#N)nc23)CCN1C(c1ccc(Cl)cc1)c1ncccc1F] | 2.08 A | 528.2 | H |
| 910 | 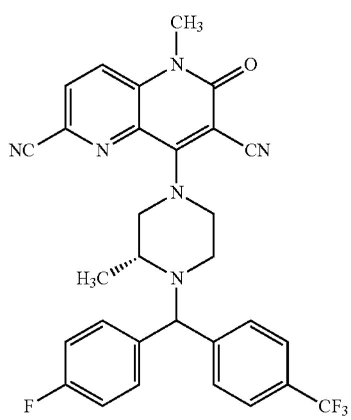 | 2.54 A | 561.2 | H |
| 911 | 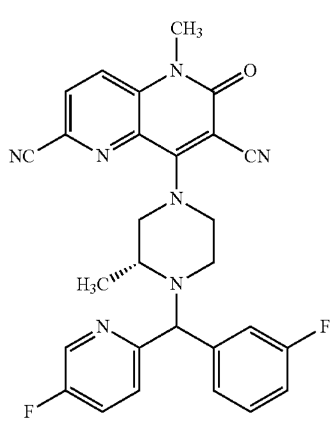 [SMILES: C[C@@H]1CN(c2c(C#N)c(=O)n(C)c3ccc(C#N)nc23)CCN1C(c1cccc(F)c1)c1ccc(F)cn1] | 1.99 A | 512.2 | H |

TABLE 21-continued

| Ex. No. | Structure | LCMS RT and Method | M + H | Stereo chem. |
|---|---|---|---|---|
| 912 | 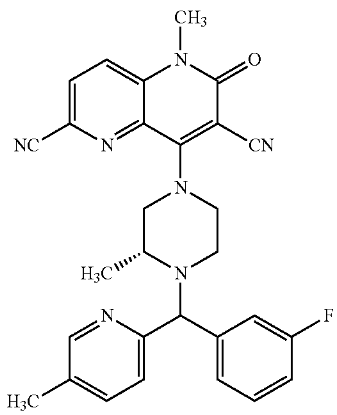 [SMILES: Cc1ccc(C(c2cccc(F)c2)N2CCN(c3c(C#N)c(=O)n(C)c4ccc(C#N)nc34)C[C@H]2C)nc1] | 1.98 A | 508.2 | H |
| 913 | 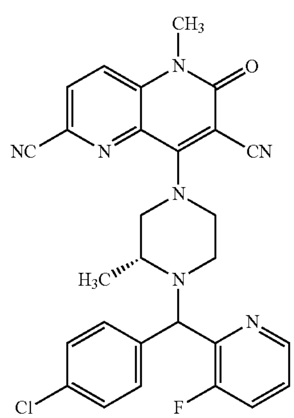 [SMILES: C[C@@H]1CN(c2c(C#N)c(=O)n(C)c3ccc(C#N)nc23)CCN1C(c1ccc(Cl)cc1)c1ncccc1F] | 2.16 A | 528.2 | H |
| 914 | 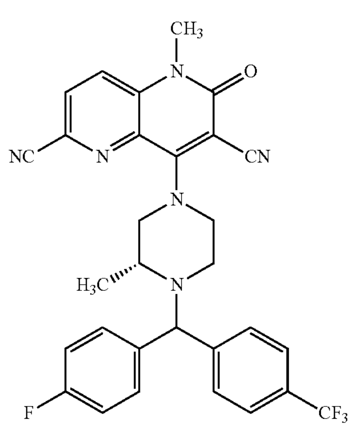 | 2.53 A | 561.2 | H |

TABLE 21-continued
| Ex. No. | Structure | LCMS RT and Method | M + H | Stereo chem. |
|---|---|---|---|---|
| 915 | 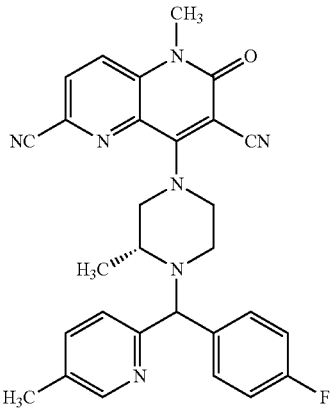 [SMILES: Cc1ccc(C(c2ccc(F)cc2)N2CCN(c3c(C#N)c(=O)n(C)c4ccc(C#N)nc34)C[C@H]2C)nc1] | 2.11 A | 508.2 | H |
| 916 | 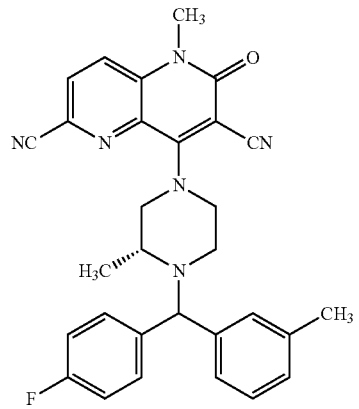 [SMILES: Cc1cccc(C(c2ccc(F)cc2)N2CCN(c3c(C#N)c(=O)n(C)c4ccc(C#N)nc34)C[C@H]2C)c1] | 2.37 A | 507.3 | H |
| 917 | 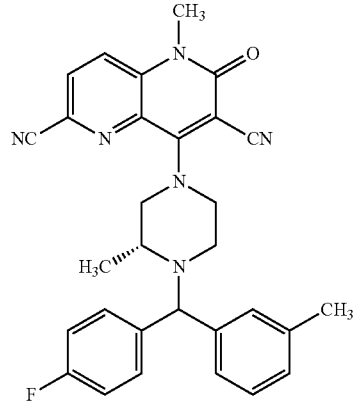 [SMILES: Cc1cccc(C(c2ccc(F)cc2)N2CCN(c3c(C#N)c(=O)n(C)c4ccc(C#N)nc34)C[C@H]2C)c1] | 2.37 A | 507.2 | H |

TABLE 21-continued

| Ex. No. | Structure | LCMS RT and Method | M + H | Stereo chem. |
|---|---|---|---|---|
| 918 | 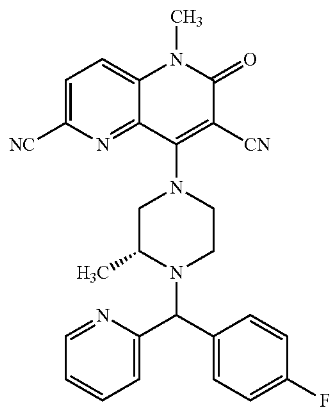 [SMILES: C[C@@H]1CN(c2c(C#N)c(=O)n(C)c3ccc(C#N)nc23)CCN1C(c1ccc(F)cc1)c1ccccn1] | 1.83 A | 494.2 | H |
| 919 | 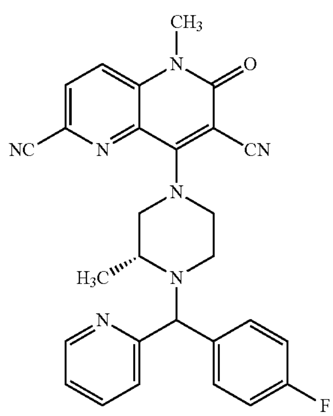 [SMILES: C[C@@H]1CN(c2c(C#N)c(=O)n(C)c3ccc(C#N)nc23)CCN1C(c1ccc(F)cc1)c1ccccn1] | 1.87 A | 494.2 | H |
| 920 | 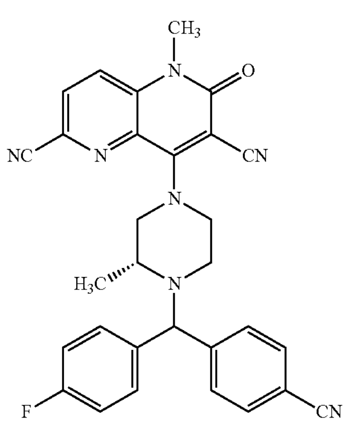 [SMILES: C[C@@H]1CN(c2c(C#N)c(=O)n(C)c3ccc(C#N)nc23)CCN1C(c1ccc(F)cc1)c1ccc(C#N)cc1] | 3.44 C | 518.2 | H |

TABLE 21-continued
| Ex. No. | Structure | LCMS RT and Method | M + H | Stereo chem. |
|---|---|---|---|---|
| 921 | 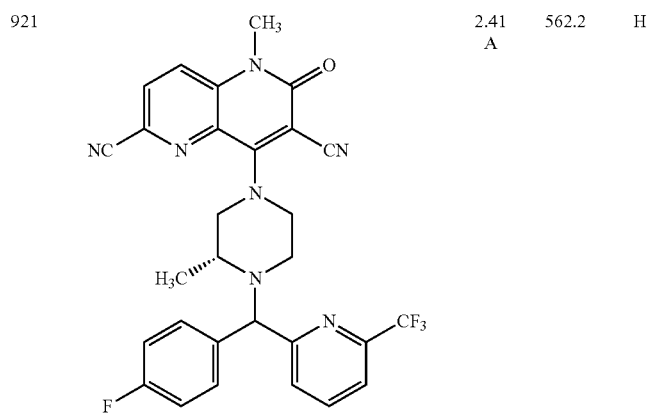 | 2.41 A | 562.2 | H |
| 922 | 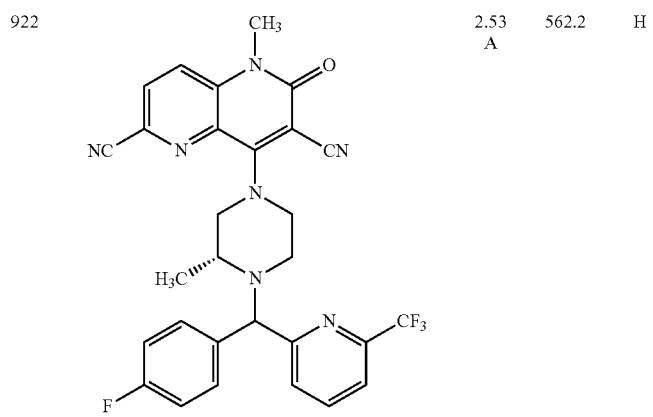 | 2.53 A | 562.2 | H |
| 923 | 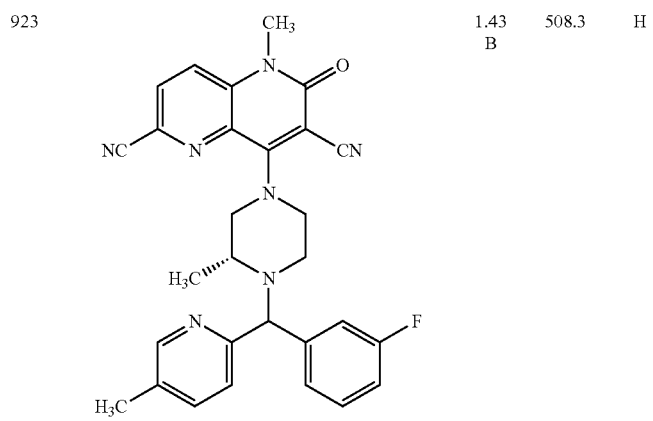 | 1.43 B | 508.3 | H |

TABLE 21-continued

| Ex. No. | Structure | LCMS RT and Method | M + H | Stereo chem. |
|---|---|---|---|---|
| 924 | 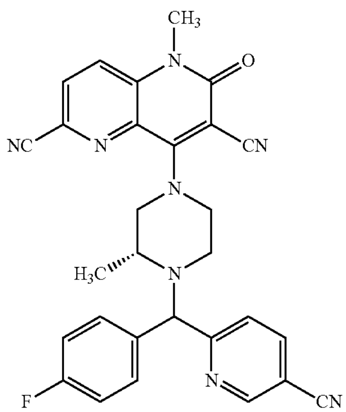 [SMILES: C[C@@H]1CN(c2c(C#N)c(=O)n(C)c3ccc(C#N)nc23)CCN1C(c1ccc(F)cc1)c1ccc(C#N)cn1] | 1.94 A | 519.2 | H |
| 925 | 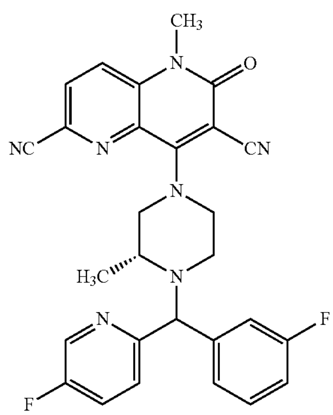 [SMILES: C[C@@H]1CN(c2c(C#N)c(=O)n(C)c3ccc(C#N)nc23)CCN1C(c1cccc(F)c1)c1ccc(F)cn1] | 2.03 A | 512.2 | H |
| 926 | 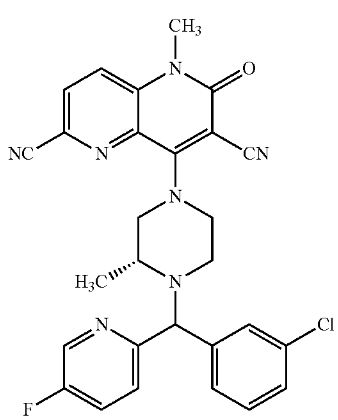 [SMILES: C[C@@H]1CN(c2c(C#N)c(=O)n(C)c3ccc(C#N)nc23)CCN1C(c1cccc(Cl)c1)c1ccc(F)cn1] | 2.15 A | 528.2 | H |

TABLE 21-continued
| Ex. No. | Structure | LCMS RT and Method | M + H | Stereo chem. |
|---|---|---|---|---|
| 927 | 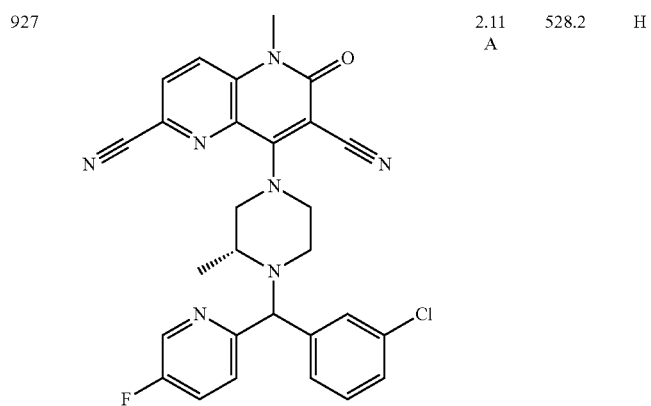 | 2.11 A | 528.2 | H |
| 928 | 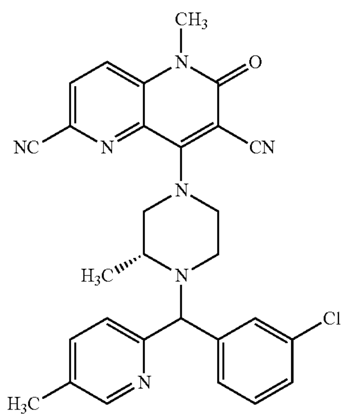 [SMILES: Cc1ccc(C(c2cccc(Cl)c2)N2CCN(c3c(C#N)c(=O)n(C)c4ccc(C#N)nc34)C[C@H]2C)nc1] | 2.1 A | 524.2 | H |
| 929 | 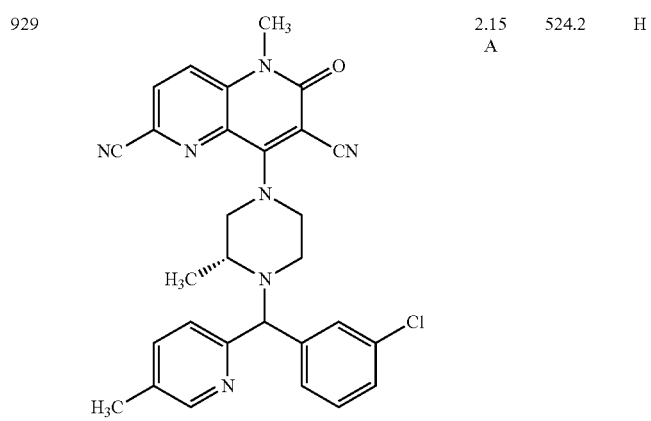 | 2.15 A | 524.2 | H |

TABLE 21-continued

| Ex. No. | Structure | LCMS RT and Method | M + H | Stereo chem. |
|---|---|---|---|---|
| 930 | 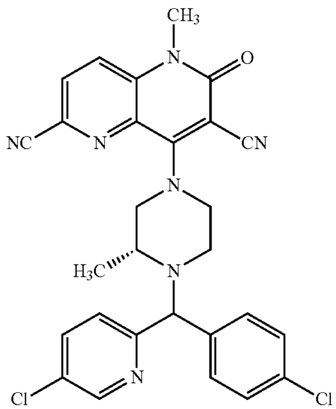 [SMILES: C[C@@H]1CN(c2c(C#N)c(=O)n(C)c3ccc(C#N)nc23)CCN1C(c1ccc(Cl)cc1)c1ccc(Cl)cn1] | 2.32 A | 546.1 | H |
| 931 | 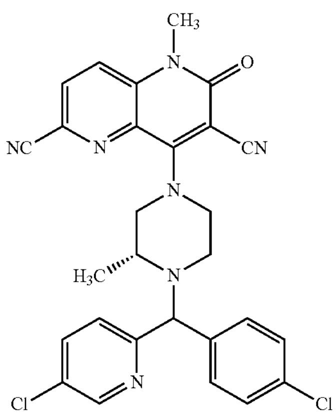 [SMILES: C[C@@H]1CN(c2c(C#N)c(=O)n(C)c3ccc(C#N)nc23)CCN1C(c1ccc(Cl)cc1)c1ccc(Cl)cn1] | 2.36 A | 546.2 | H |
| 932 | 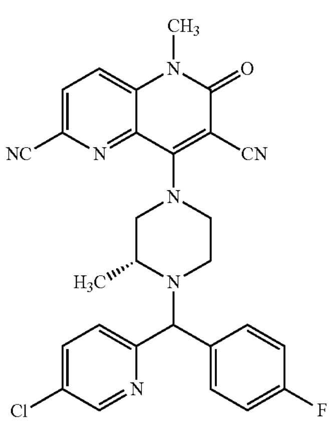 [SMILES: C[C@@H]1CN(c2c(C#N)c(=O)n(C)c3ccc(C#N)nc23)CCN1C(c1ccc(F)cc1)c1ccc(Cl)cn1] | 2.18 A | 528.2 | H |

TABLE 21-continued
| Ex. No. | Structure | LCMS RT and Method | M + H | Stereo chem. |
|---|---|---|---|---|
| 933 | 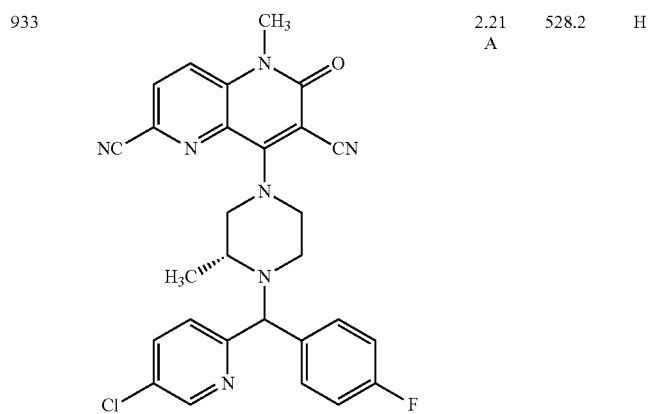 | 2.21 A | 528.2 | H |
| 934 | 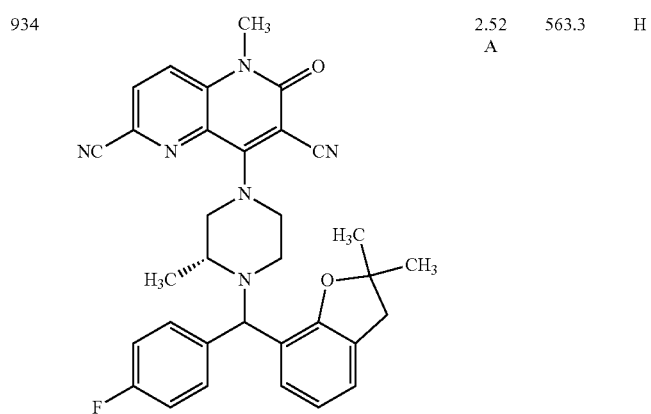 | 2.52 A | 563.3 | H |
| 935 | 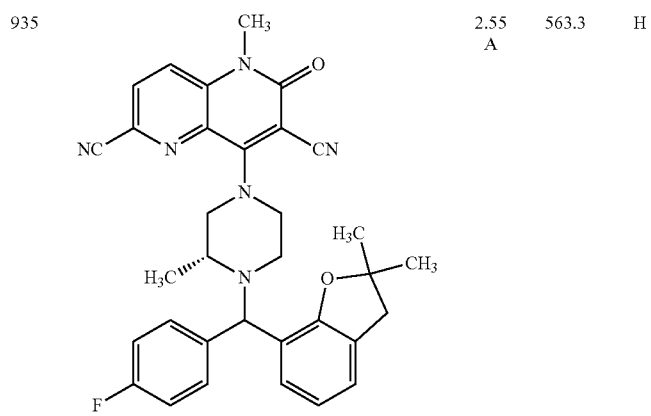 | 2.55 A | 563.3 | H |

TABLE 21-continued

| Ex. No. | Structure | LCMS RT and Method | M + H | Stereo chem. |
|---|---|---|---|---|
| 936 | 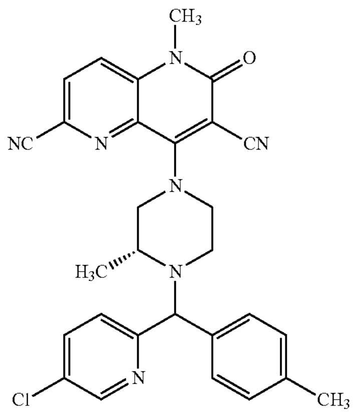 [SMILES: Cc1ccc(C(c2ccc(Cl)cn2)N2CCN(c3c(C#N)c(=O)n(C)c4ccc(C#N)nc34)C[C@H]2C)cc1] | 2.23 A | 524.2 | H |
| 937 | 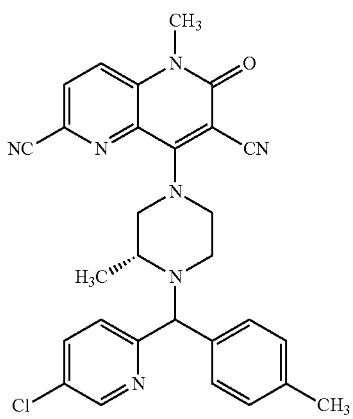 [SMILES: Cc1ccc(C(c2ccc(Cl)cn2)N2CCN(c3c(C#N)c(=O)n(C)c4ccc(C#N)nc34)C[C@H]2C)cc1] | 2.20 A | 524.2 | H |
| 938 | 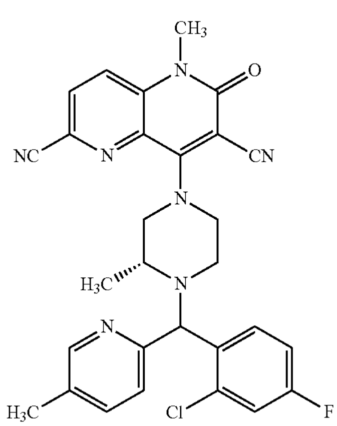 [SMILES: Cc1ccc(C(c2ccc(F)cc2Cl)N2CCN(c3c(C#N)c(=O)n(C)c4ccc(C#N)nc34)C[C@H]2C)nc1] | 2.16 A | 542.2 | H |

TABLE 21-continued
| Ex. No. | Structure | LCMS RT and Method | M + H | Stereo chem. |
|---|---|---|---|---|
| 939 | 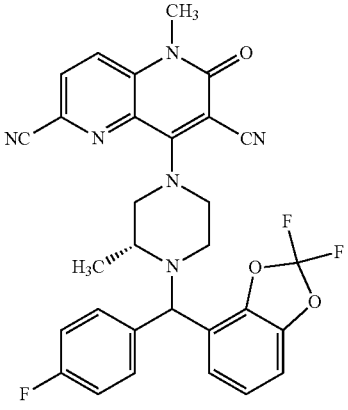 [SMILES: C[C@@H]1CN(c2c(C#N)c(=O)n(C)c3ccc(C#N)nc23)CCN1C(c1ccc(F)cc1)c1cccc2c1OC(F)(F)O2] | 2.41 A | 573.2 | H |
| 940 | 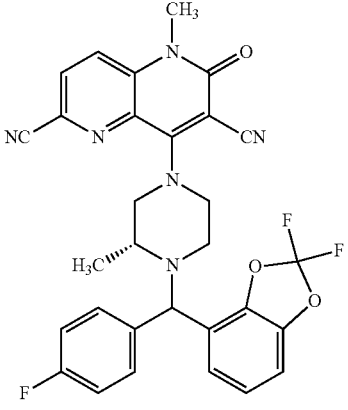 [SMILES: C[C@@H]1CN(c2c(C#N)c(=O)n(C)c3ccc(C#N)nc23)CCN1C(c1ccc(F)cc1)c1cccc2c1OC(F)(F)O2] | 2.42 A | 573.2 | H |
| 941 | 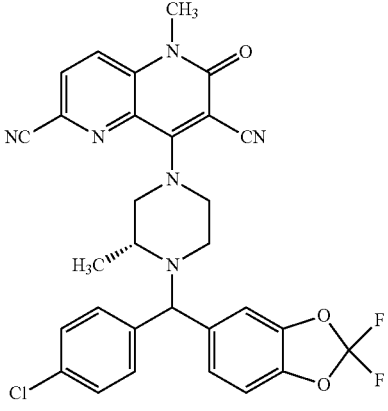 [SMILES: C[C@@H]1CN(c2c(C#N)c(=O)n(C)c3ccc(C#N)nc23)CCN1C(c1ccc(Cl)cc1)c1ccc2c(c1)OC(F)(F)O2] | 2.57 A | 589.2 | H |

TABLE 21-continued

| Ex. No. | Structure | LCMS RT and Method | M + H | Stereo chem. |
|---|---|---|---|---|
| 942 | 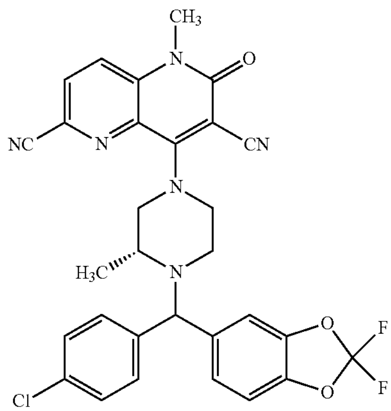 [SMILES: C[C@@H]1CN(c2c(C#N)c(=O)n(C)c3ccc(C#N)nc23)CCN1C(c1ccc(Cl)cc1)c1ccc2c(c1)OC(F)(F)O2] | 2.57 A | 589.2 | H |
| 943 | 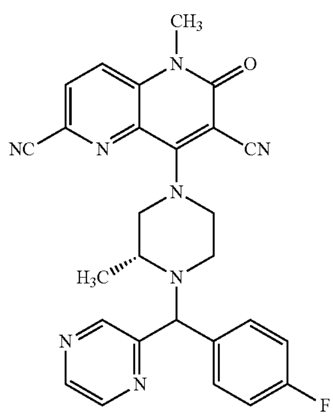 [SMILES: C[C@@H]1CN(c2c(C#N)c(=O)n(C)c3ccc(C#N)nc23)CCN1C(c1ccc(F)cc1)c1cnccn1] | 1.72 A | 495.2 | H |
| 944 | 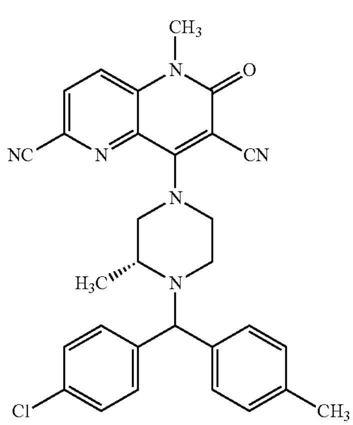 [SMILES: Cc1ccc(C(c2ccc(Cl)cc2)N2CCN(c3c(C#N)c(=O)n(C)c4ccc(C#N)nc34)C[C@H]2C)cc1] | 2.53 A | 523.2 | H |

TABLE 21-continued

| Ex. No. | Structure | LCMS RT and Method | M + H | Stereo chem. |
|---|---|---|---|---|
| 945 | 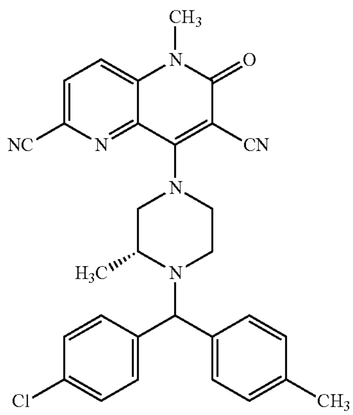 [SMILES: Cc1ccc(C(c2ccc(Cl)cc2)N2CCN(c3c(C#N)c(=O)n(C)c4ccc(C#N)nc34)C[C@H]2C)cc1] | 2.54 A | 523.2 | H |
| 946 | 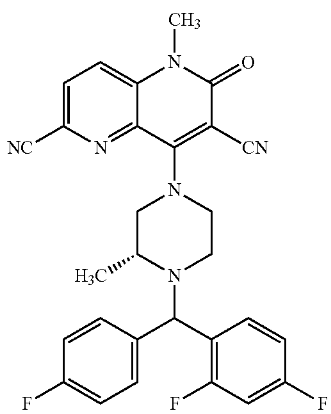 [SMILES: C[C@@H]1CN(c2c(C#N)c(=O)n(C)c3ccc(C#N)nc23)CCN1C(c1ccc(F)cc1)c1ccc(F)cc1F] | 2.34 A | 529.2 | H |
| 947 | 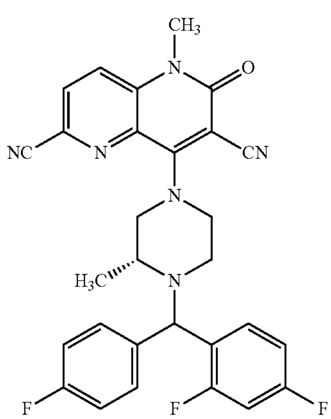 [SMILES: C[C@@H]1CN(c2c(C#N)c(=O)n(C)c3ccc(C#N)nc23)CCN1C(c1ccc(F)cc1)c1ccc(F)cc1F] | 2.35 A | 529.1 | Homo chiral |

TABLE 21-continued

| Ex. No. | Structure | LCMS RT and Method | M + H | Stereo chem. |
|---|---|---|---|---|
| 948 | 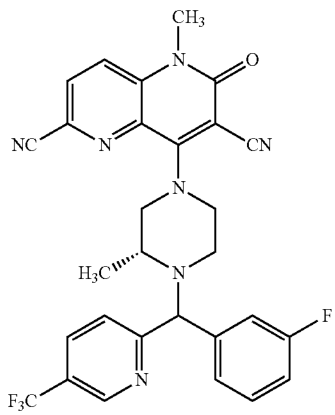 [SMILES: C[C@@H]1CN(c2c(C#N)c(=O)n(C)c3ccc(C#N)nc23)CCN1C(c1cccc(F)c1)c1ccc(C(F)(F)F)cn1] | 2.19 A | 562.5 | H |
| 949 | 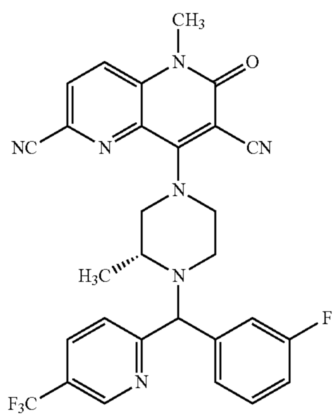 [SMILES: C[C@@H]1CN(c2c(C#N)c(=O)n(C)c3ccc(C#N)nc23)CCN1C(c1cccc(F)c1)c1ccc(C(F)(F)F)cn1] | 2.23 A | 562.5 | H |

The examples in the Table 22 were prepared from the appropriate piperazine according to the general procedure described in Examples 780 and 781, substituting 2-(1-bromoethyl)-1,3-difluorobenzene with the appropriate α-methyl benzyl chlorides/bromides in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 22

| Ex. No. | Structure | LCMS RT and Method | M + H | Stereo chem. |
|---|---|---|---|---|
| 950 | 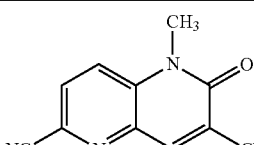 | 2.09 A | 449.2 | H |

TABLE 22-continued
| Ex. No. | Structure | LCMS RT and Method | M + H | Stereo chem. |
|---|---|---|---|---|
| 951 | 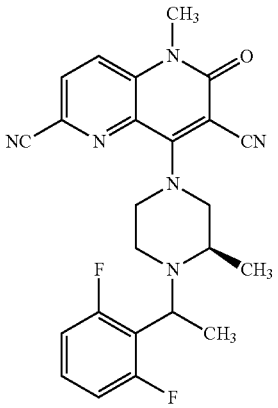 [SMILES: CC(c1c(F)cccc1F)N1CCN(c2c(C#N)c(=O)n(C)c3ccc(C#N)nc23)C[C@H]1C] | 2.17 A | 449.2 | H |
| 952 | 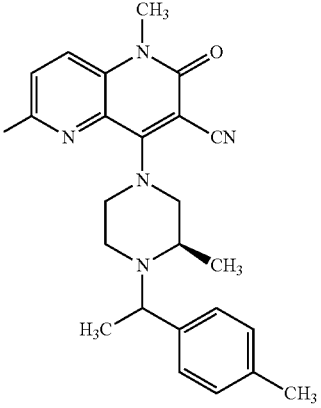 | 2.13 A | 427.3 | H |
| 953 | 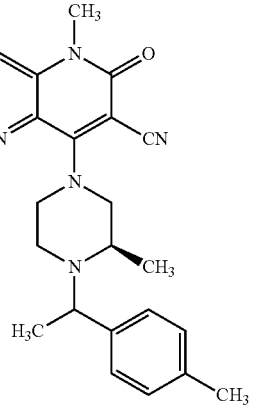 | 2.34 A | 427.3 | H |

TABLE 22-continued

| Ex. No. | Structure | LCMS RT and Method | M + H | Stereo chem. |
|---|---|---|---|---|
| 954 | 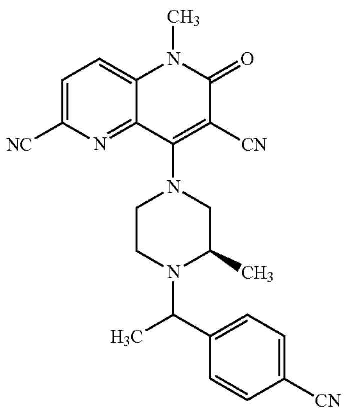 [SMILES: CC(c1ccc(C#N)cc1)N1CCN(c2c(C#N)c(=O)n(C)c3ccc(C#N)nc23)C[C@H]1C] | 1.90 A | 438.3 | H |
| 955 | 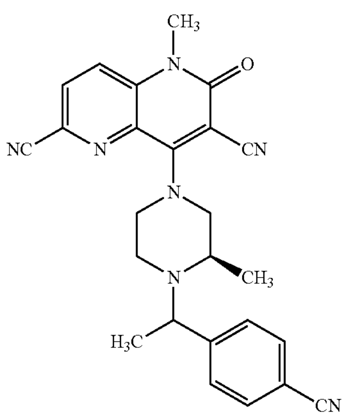 [SMILES: CC(c1ccc(C#N)cc1)N1CCN(c2c(C#N)c(=O)n(C)c3ccc(C#N)nc23)C[C@H]1C] | 1.76 A | 438.3 | H |
| 956 | 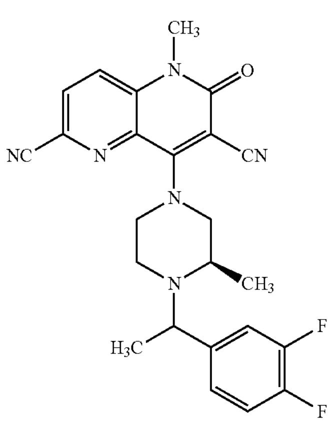 [SMILES: CC(c1ccc(F)c(F)c1)N1CCN(c2c(C#N)c(=O)n(C)c3ccc(C#N)nc23)C[C@H]1C] | 1.96 A | 449.2 | H |

TABLE 22-continued
| Ex. No. | Structure | LCMS RT and Method | M + H | Stereo chem. |
|---|---|---|---|---|
| 957 | 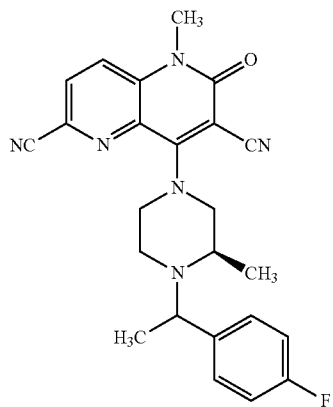 | 1.88 A | 431.2 | H |
| 958 | 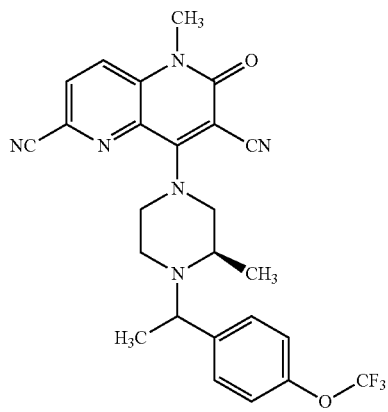 [SMILES: CC(c1ccc(OC(F)(F)F)cc1)N1CCN(c2c(C#N)c(=O)n(C)c3ccc(C#N)nc23)C[C@H]1C] | 1.39 A | 497.3 | H |
| 959 | 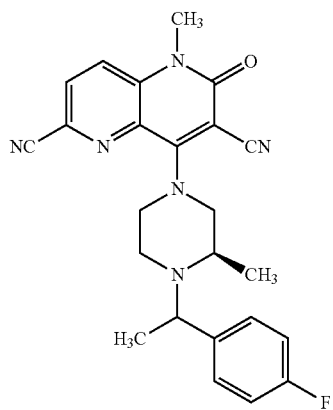 [SMILES: CC(c1ccc(F)cc1)N1CCN(c2c(C#N)c(=O)n(C)c3ccc(C#N)nc23)C[C@H]1C] | 2.06 A | 431.2 | H |

TABLE 22-continued
| Ex. No. | Structure | LCMS RT and Method | M + H | Stereo chem. |
|---|---|---|---|---|
| 960 | 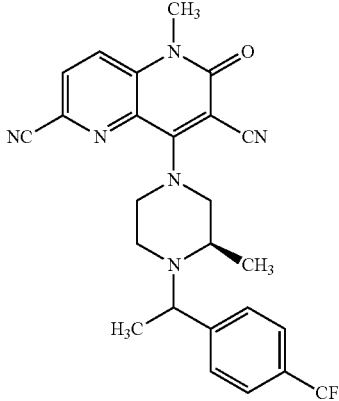 | 2.12 A | 481.2 | H |
| 961 | 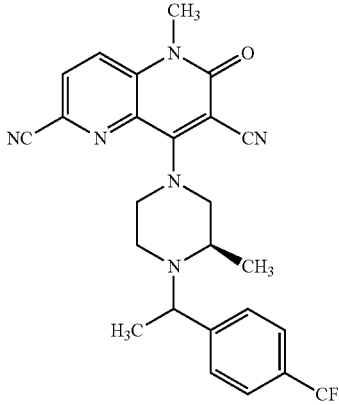 | 2.28 A | 481.2 | H |
| 962 | 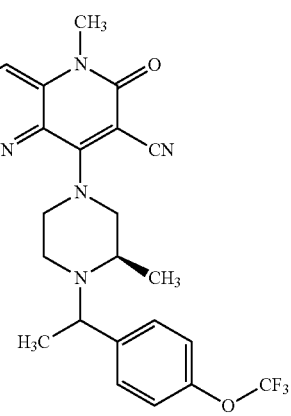 | 2.32 A | 497.3 | H |

TABLE 22-continued

| Ex. No. | Structure | LCMS RT and Method | M + H | Stereo chem. |
|---|---|---|---|---|
| 963 | 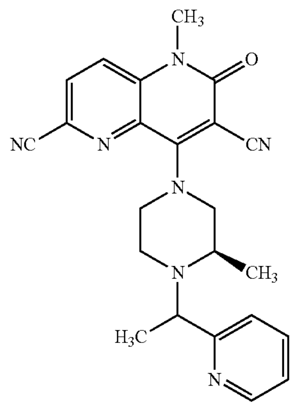 [SMILES: CC(c1ccccn1)N1CCN(c2c(C#N)c(=O)n(C)c3ccc(C#N)nc23)C[C@H]1C] | 1.43 A | 414.1 | H |
| 964 | 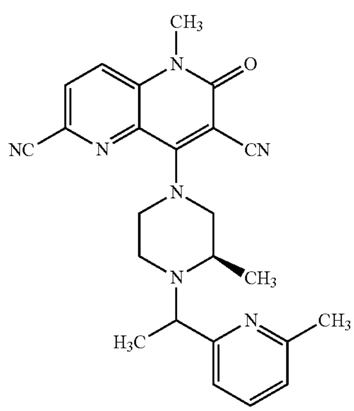 [SMILES: Cc1cccc(C(C)N2CCN(c3c(C#N)c(=O)n(C)c4ccc(C#N)nc34)C[C@H]2C)n1] | 1.60 A | 428.2 | H |
| 965 | 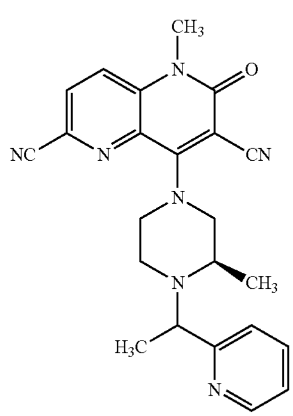 [SMILES: CC(c1ccccn1)N1CCN(c2c(C#N)c(=O)n(C)c3ccc(C#N)nc23)C[C@H]1C] | 1.54 A | 414.3 | H |

TABLE 22-continued

| Ex. No. | Structure | LCMS RT and Method | M + H | Stereo chem. |
|---|---|---|---|---|
| 966 | 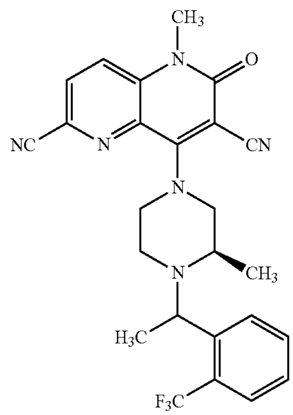 [SMILES: CC(c1ccccc1C(F)(F)F)N1CCN(c2c(C#N)c(=O)n(C)c3ccc(C#N)nc23)C[C@H]1C] | 2.28 A | 481.2 | H |
| 967 | 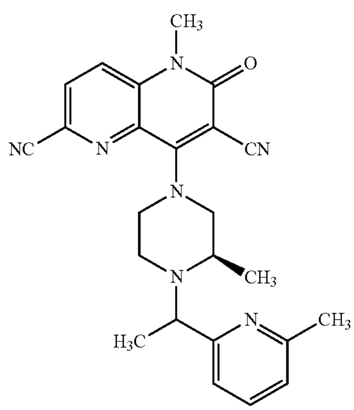 [SMILES: Cc1cccc(C(C)N2CCN(c3c(C#N)c(=O)n(C)c4ccc(C#N)nc34)C[C@H]2C)n1] | 1.69 A | 428.2 | H |
| 968 | 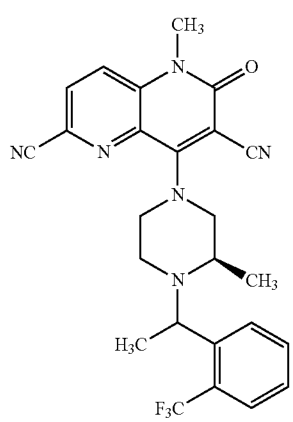 [SMILES: CC(c1ccccc1C(F)(F)F)N1CCN(c2c(C#N)c(=O)n(C)c3ccc(C#N)nc23)C[C@H]1C] | 2.30 A | 481.2 | H |

TABLE 22-continued

| Ex. No. | Structure | LCMS RT and Method | M + H | Stereo chem. |
|---|---|---|---|---|
| 969 | 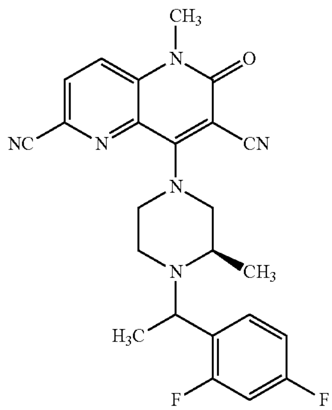 [SMILES: CC(c1ccc(F)cc1F)N1CCN(c2c(C#N)c(=O)n(C)c3ccc(C#N)nc23)C[C@H]1C] | 1.97 A | 449.2 | H |
| 970 | 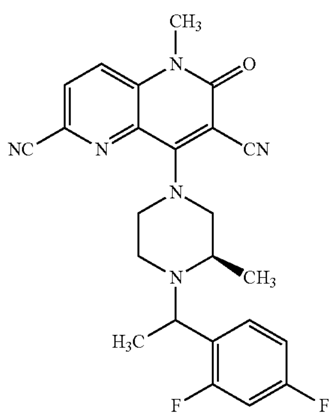 [SMILES: CC(c1ccc(F)cc1F)N1CCN(c2c(C#N)c(=O)n(C)c3ccc(C#N)nc23)C[C@H]1C] | 2.09 A | 449.2 | H |
| 971 | 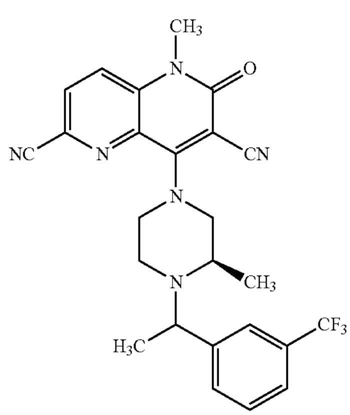 [SMILES: CC(c1cccc(C(F)(F)F)c1)N1CCN(c2c(C#N)c(=O)n(C)c3ccc(C#N)nc23)C[C@H]1C] | 2.13 A | 481.2 | H |

TABLE 22-continued

| Ex. No. | Structure | LCMS RT and Method | M + H | Stereo chem. |
|---|---|---|---|---|
| 972 | 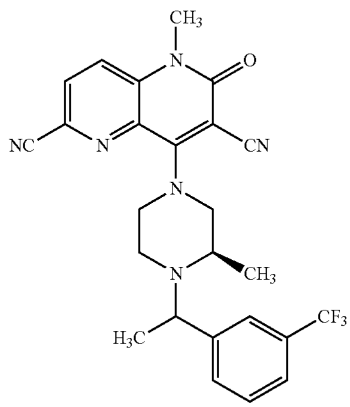 [SMILES: CC(c1cccc(C(F)(F)F)c1)N1CCN(c2c(C#N)c(=O)n(C)c3ccc(C#N)nc23)C[C@H]1C] | 2.29 A | 481.2 | H |
| 973 | 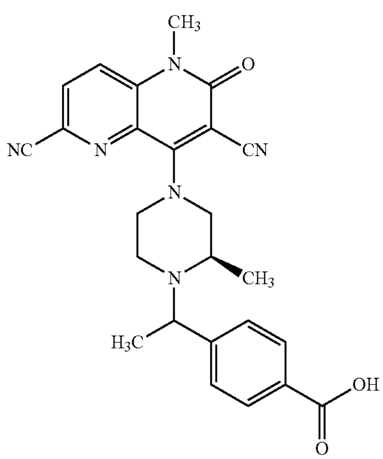 [SMILES: CC(c1ccc(C(=O)O)cc1)N1CCN(c2c(C#N)c(=O)n(C)c3ccc(C#N)nc23)C[C@H]1C] | 0.93 A | 457.2 | H |
| 974 | 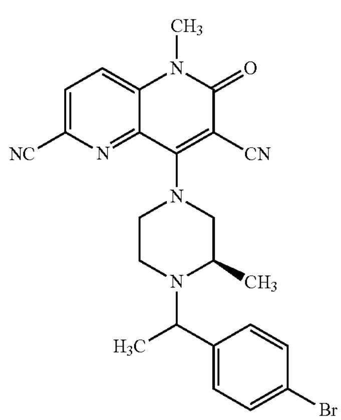 [SMILES: CC(c1ccc(Br)cc1)N1CCN(c2c(C#N)c(=O)n(C)c3ccc(C#N)nc23)C[C@H]1C] | 2.06 A | 491.1 | H |

TABLE 22-continued
| Ex. No. | Structure | LCMS RT and Method | M + H | Stereo chem. |
|---|---|---|---|---|
| 975 | 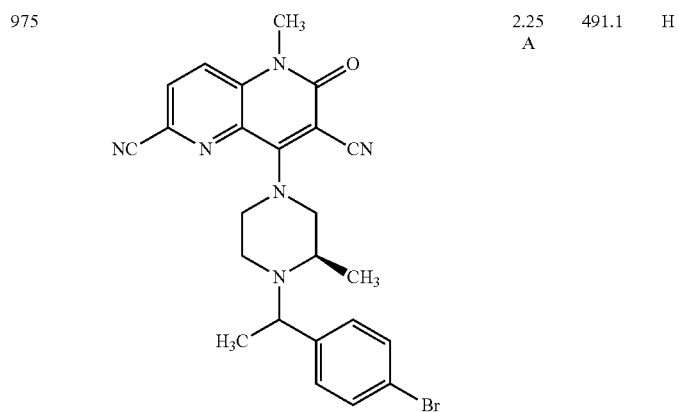 | 2.25 A | 491.1 | H |
| 976 | 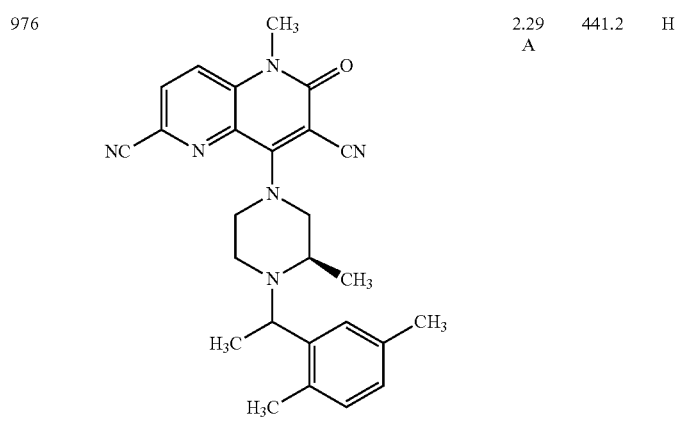 | 2.29 A | 441.2 | H |
| 977 | 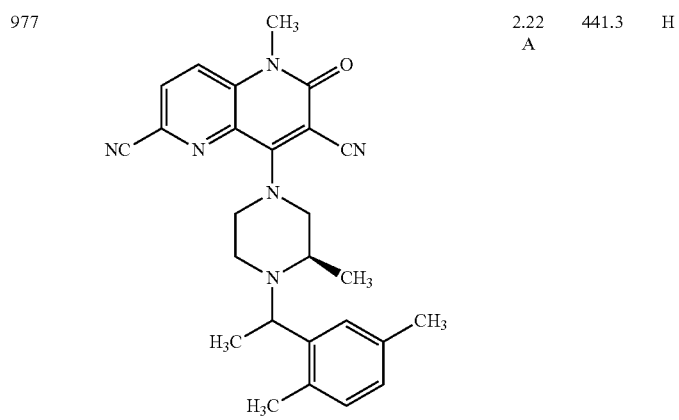 | 2.22 A | 441.3 | H |

TABLE 22-continued

| Ex. No. | Structure | LCMS RT and Method | M + H | Stereo chem. |
|---|---|---|---|---|
| 978 | 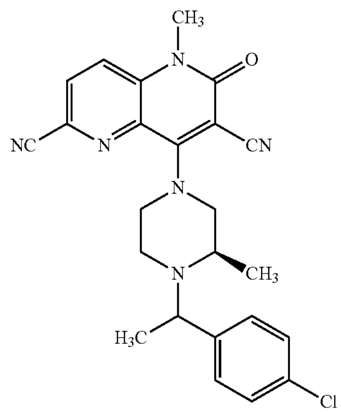 [SMILES: CC(c1ccc(Cl)cc1)N1CCN(c2c(C#N)c(=O)n(C)c3ccc(C#N)nc23)C[C@H]1C] | 2.02 A | 447.1 | H |
| 979 | 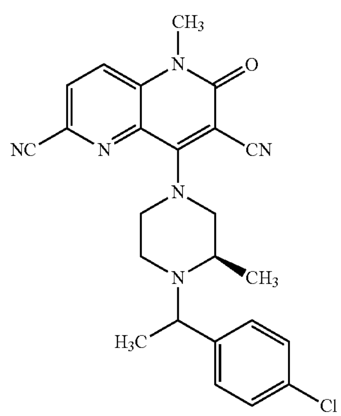 [SMILES: CC(c1ccc(Cl)cc1)N1CCN(c2c(C#N)c(=O)n(C)c3ccc(C#N)nc23)C[C@H]1C] | 2.20 A | 447.2 | H |
| 980 | 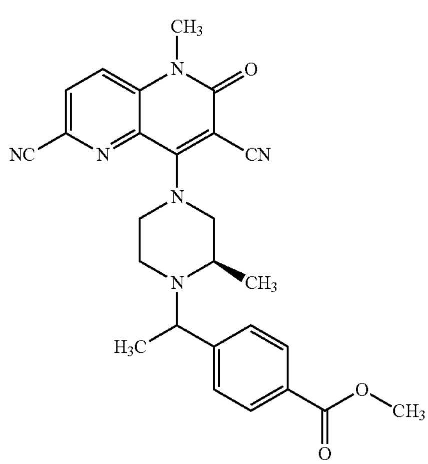 [SMILES: COC(=O)c1ccc(C(C)N2CCN(c3c(C#N)c(=O)n(C)c4ccc(C#N)nc34)C[C@H]2C)cc1] | 1.70 A | 471.2 | H |

TABLE 22-continued

| Ex. No. | Structure | LCMS RT and Method | M + H | Stereo chem. |
|---|---|---|---|---|
| 981 | 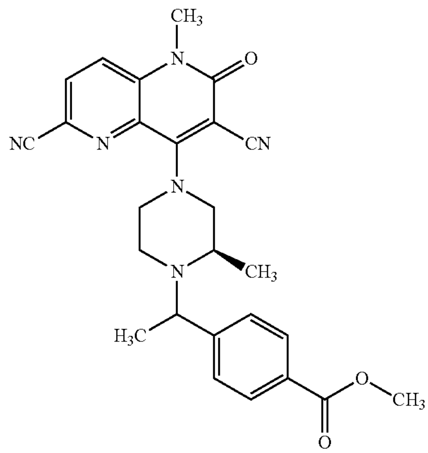 [SMILES: COC(=O)c1ccc(C(C)N2CCN(c3c(C#N)c(=O)n(C)c4ccc(C#N)nc34)C[C@H]2C)cc1] | 1.96 A | 471.2 | H |
| 982 | 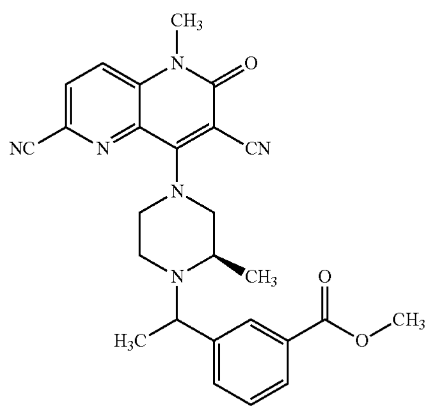 [SMILES: COC(=O)c1cccc(C(C)N2CCN(c3c(C#N)c(=O)n(C)c4ccc(C#N)nc34)C[C@H]2C)c1] | 1.70 A | 471.2 | H |
| 983 | 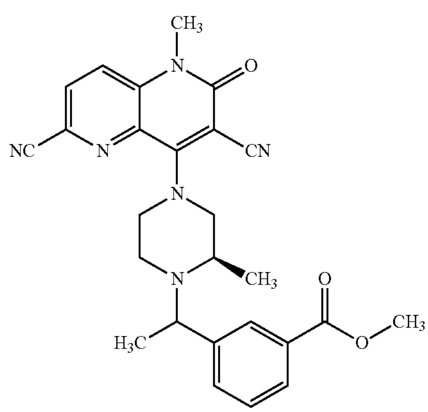 [SMILES: COC(=O)c1cccc(C(C)N2CCN(c3c(C#N)c(=O)n(C)c4ccc(C#N)nc34)C[C@H]2C)c1] | 1.95 A | 471.2 | H |

The examples in the Table 23 were prepared from the appropriate piperazine according to the general procedure described in Example 780 and 781, substituting 2-(1-bromoethyl)-1,3-difluorobenzene with the appropriate benzyl chlorides/bromides in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 23
| Ex. No. | Structure | LCMS RT and Method | M + H | Stereo chem. |
|---|---|---|---|---|
| 984 | 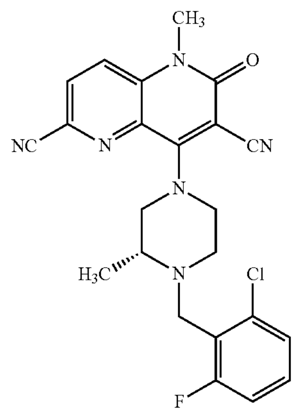 [SMILES: C[C@@H]1CN(c2c(C#N)c(=O)n(C)c3ccc(C#N)nc23)CCN1Cc1c(F)cccc1Cl] | 1.30 A | 451.1 | H |
| 985 | 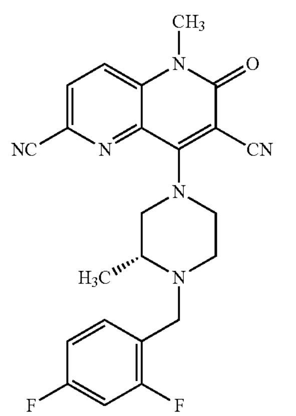 [SMILES: C[C@@H]1CN(c2c(C#N)c(=O)n(C)c3ccc(C#N)nc23)CCN1Cc1ccc(F)cc1F] | 1.88 A | 435.2 | H |
| 986 | 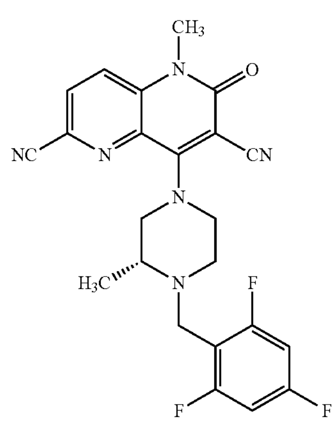 [SMILES: C[C@@H]1CN(c2c(C#N)c(=O)n(C)c3ccc(C#N)nc23)CCN1Cc1c(F)cc(F)cc1F] | 1.90 A | 453.2 | H |
| 987 | 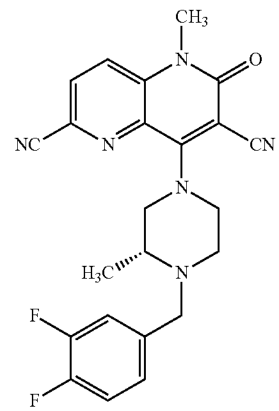 [SMILES: C[C@@H]1CN(c2c(C#N)c(=O)n(C)c3ccc(C#N)nc23)CCN1Cc1ccc(F)c(F)c1] | 1.95 A | 435.2 | H |
| 988 | 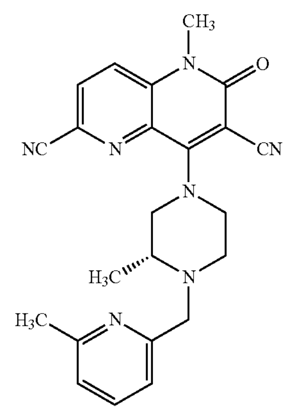 [SMILES: Cc1cccc(CN2CCN(c3c(C#N)c(=O)n(C)c4ccc(C#N)nc34)C[C@H]2C)n1] | 1.57 A | 414.2 | H |
| 989 | 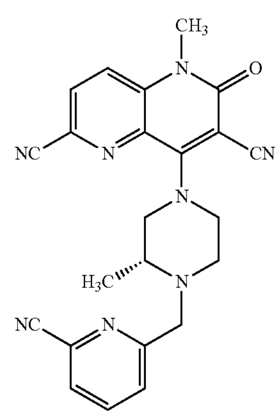 [SMILES: C[C@@H]1CN(c2c(C#N)c(=O)n(C)c3ccc(C#N)nc23)CCN1Cc1cccc(C#N)n1] | 1.56 A | 425.2 | H |
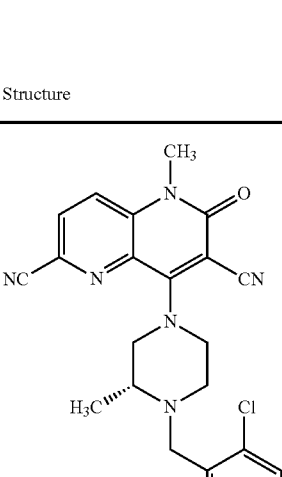

TABLE 23-continued

| Ex. No. | Structure | LCMS RT and Method | M + H | Stereo chem. |
|---|---|---|---|---|
| 990 | 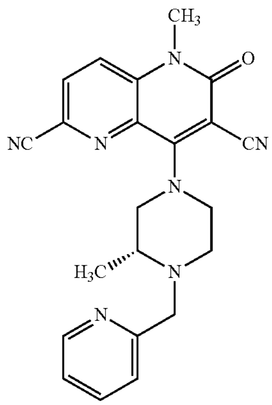 [SMILES: C[C@@H]1CN(c2c(C#N)c(=O)n(C)c3ccc(C#N)nc23)CCN1Cc1ccccn1] | 1.40 A | 400.2 | H |
| 991 | 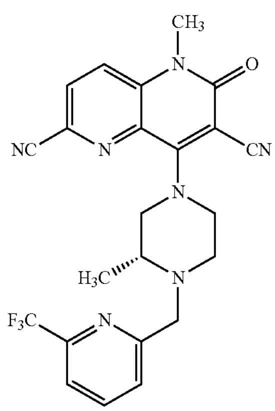 [SMILES: C[C@@H]1CN(c2c(C#N)c(=O)n(C)c3ccc(C#N)nc23)CCN1Cc1cccc(C(F)(F)F)n1] | 1.89 A | 468.2 | H |
| 992 | 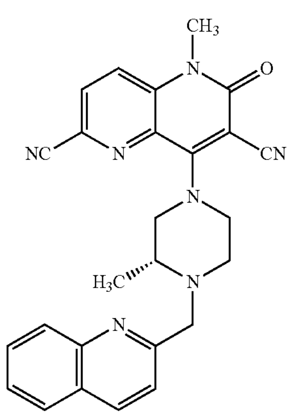 [SMILES: C[C@@H]1CN(c2c(C#N)c(=O)n(C)c3ccc(C#N)nc23)CCN1Cc1ccc2ccccc2n1] | 1.80 A | 450.2 | H |
| 993 | 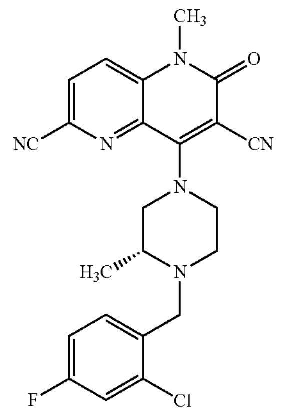 [SMILES: C[C@@H]1CN(c2c(C#N)c(=O)n(C)c3ccc(C#N)nc23)CCN1Cc1ccc(F)cc1Cl] | 2.14 A | 452.2 | H |
| 994 | 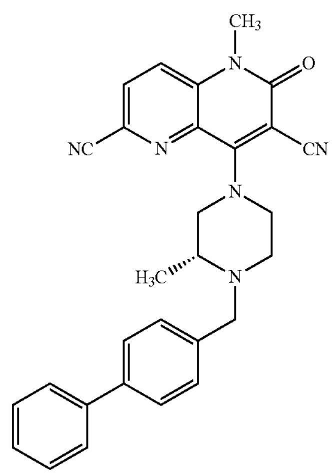 [SMILES: C[C@@H]1CN(c2c(C#N)c(=O)n(C)c3ccc(C#N)nc23)CCN1Cc1ccc(-c2ccccc2)cc1] | 1.43 B | 475.2 | H |
| 995 | 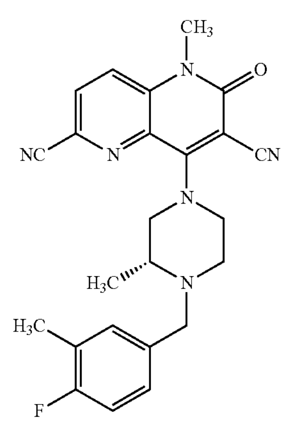 [SMILES: Cc1cc(CN2CCN(c3c(C#N)c(=O)n(C)c4ccc(C#N)nc34)C[C@H]2C)ccc1F] | 1.97 A | 431.2 | H |

TABLE 23-continued
| Ex. No. | Structure | LCMS RT and Method | M + H | Stereo chem. |
|---|---|---|---|---|
| 996 | 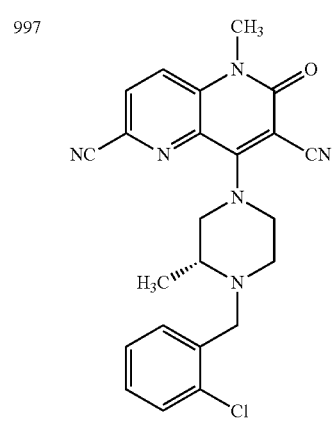 | 2.27 A | 467.1 | H |
| 997 | 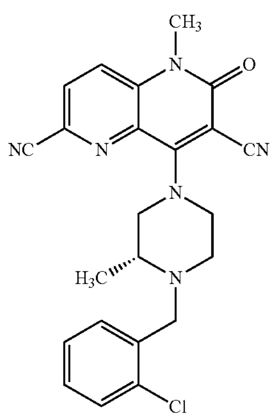 [SMILES: C[C@@H]1CN(c2c(C#N)c(=O)n(C)c3ccc(C#N)nc23)CCN1Cc1ccccc1Cl] | 2.07 A | 433.2 | H |
| 998 | 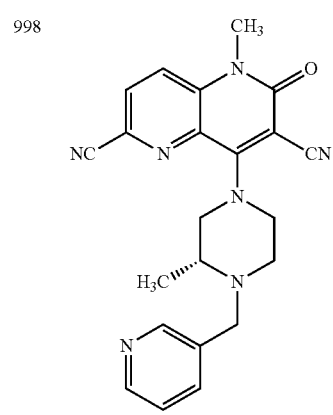 | 1.30 A | 400.2 | H |
TABLE 23-continued
| Ex. No. | Structure | LCMS RT and Method | M + H | Stereo chem. |
|---|---|---|---|---|
| 999 | 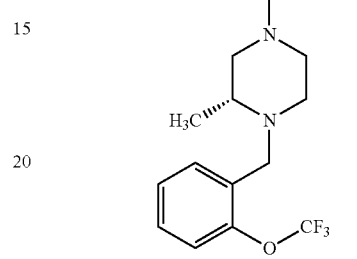 | 2.17 A | 483.2 | H |
| 1000 | 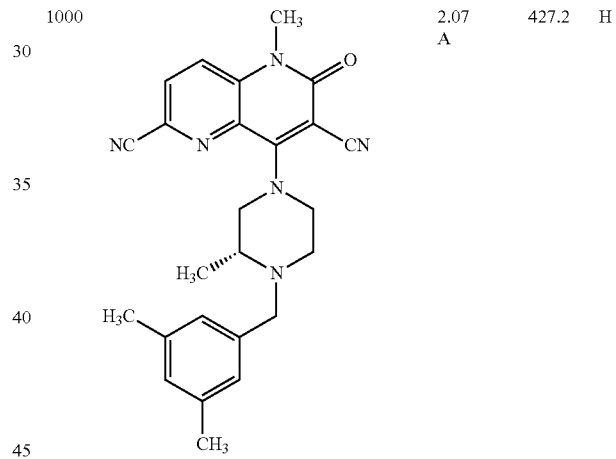 | 2.07 A | 427.2 | H |
| 1001 | 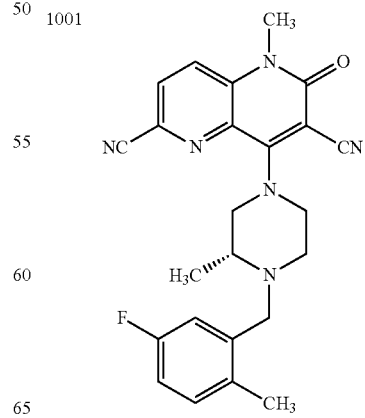 | 2.1 A | 431.2 | H |

TABLE 23-continued
| Ex. No. | Structure | LCMS RT and Method | M + H | Stereo chem. |
|---|---|---|---|---|
| 1002 | 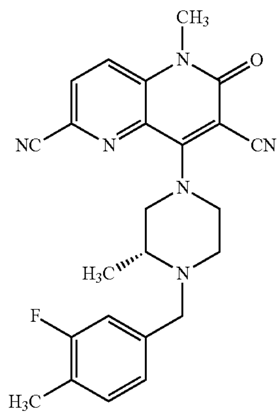 [SMILES: Cc1ccc(CN2CCN(c3c(C#N)c(=O)n(C)c4ccc(C#N)nc34)C[C@H]2C)cc1F] | 2.01 A | 431.2 | H |
| 1003 | 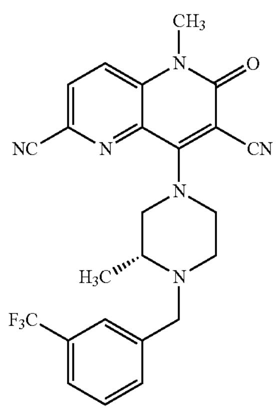 [SMILES: C[C@@H]1CN(c2c(C#N)c(=O)n(C)c3ccc(C#N)nc23)CCN1Cc1cccc(C(F)(F)F)c1] | 2.10 A | 467.2 | H |
| 1004 | 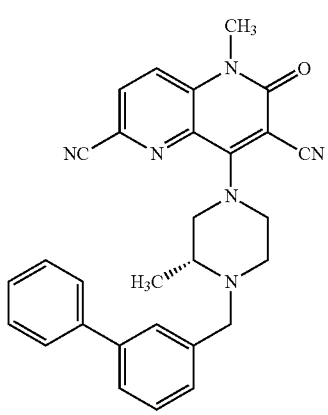 [SMILES: C[C@@H]1CN(c2c(C#N)c(=O)n(C)c3ccc(C#N)nc23)CCN1Cc1cccc(-c2ccccc2)c1] | 2.19 A | 475.2 | H |
| 1005 | 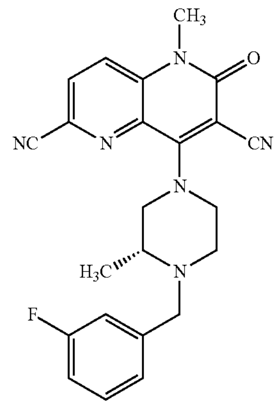 [SMILES: C[C@@H]1CN(c2c(C#N)c(=O)n(C)c3ccc(C#N)nc23)CCN1Cc1cccc(F)c1] | 1.90 A | 417.2 | H |
| 1006 | 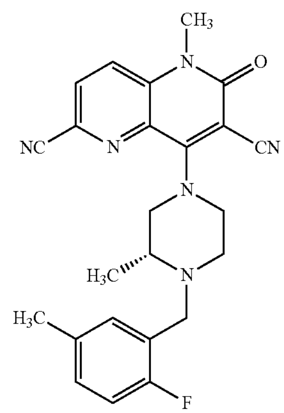 [SMILES: Cc1ccc(F)c(CN2CCN(c3c(C#N)c(=O)n(C)c4ccc(C#N)nc34)C[C@H]2C)c1] | 1.95 A | 431.2 | H |
| 1007 | 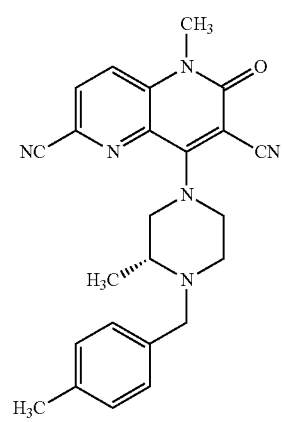 [SMILES: Cc1ccc(CN2CCN(c3c(C#N)c(=O)n(C)c4ccc(C#N)nc34)C[C@H]2C)cc1] | 1.96 A | 413.2 | H |
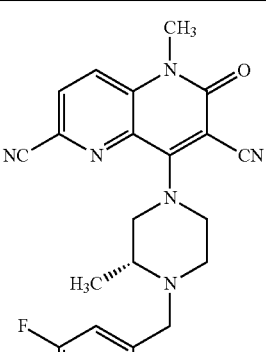

TABLE 23-continued

| Ex. No. | Structure | LCMS RT and Method | M + H | Stereo chem. |
|---|---|---|---|---|
| 1008 | 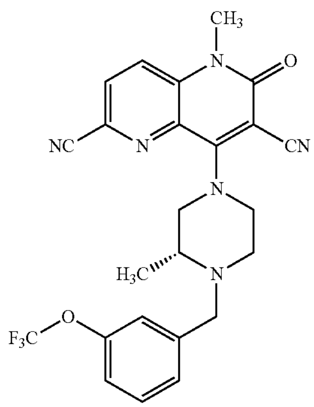 [SMILES: C[C@@H]1CN(c2c(C#N)c(=O)n(C)c3ccc(C#N)nc23)CCN1Cc1cccc(OC(F)(F)F)c1] | 2.16 A | 483.2 | H |
| 1009 | 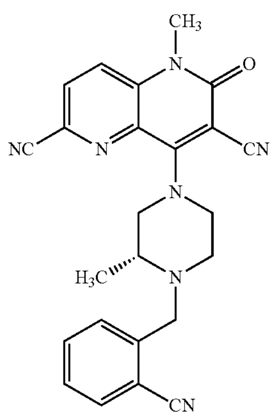 [SMILES: C[C@@H]1CN(c2c(C#N)c(=O)n(C)c3ccc(C#N)nc23)CCN1Cc1ccccc1C#N] | 1.76 A | 424.2 | H |
| 1010 | 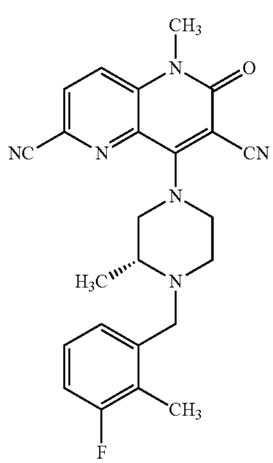 [SMILES: Cc1c(F)cccc1CN1CCN(c2c(C#N)c(=O)n(C)c3ccc(C#N)nc23)C[C@H]1C] | 2.10 A | 431.2 | H |
| 1011 | 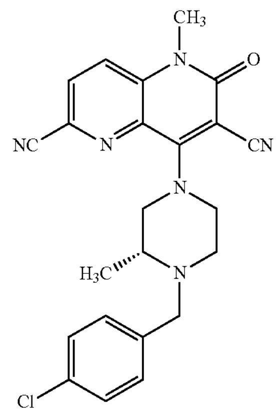 [SMILES: C[C@@H]1CN(c2c(C#N)c(=O)n(C)c3ccc(C#N)nc23)CCN1Cc1ccc(Cl)cc1] | 2.04 A | 433.2 | H |
| 1012 | 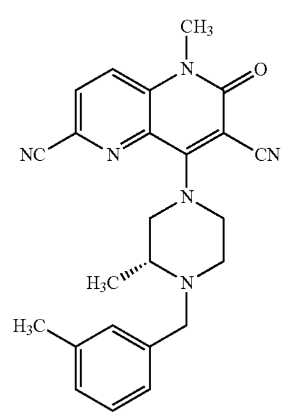 [SMILES: Cc1cccc(CN2CCN(c3c(C#N)c(=O)n(C)c4ccc(C#N)nc34)C[C@H]2C)c1] | 1.14 B | 413.3 | H |

TABLE 23-continued

| Ex. No. | Structure | LCMS RT and Method | M + H | Stereo chem. |
|---|---|---|---|---|
| 1013 | 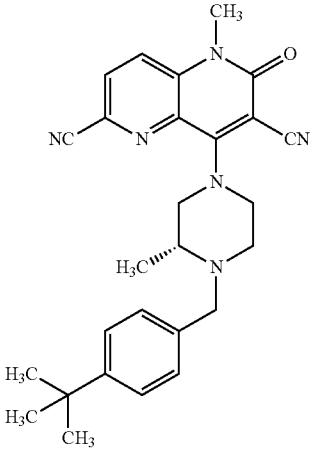 [SMILES: C[C@@H]1CN(c2c(C#N)c(=O)n(C)c3ccc(C#N)nc23)CCN1Cc1ccc(C(C)(C)C)cc1] | 2.32 A | 455.3 | H |
| 1014 | 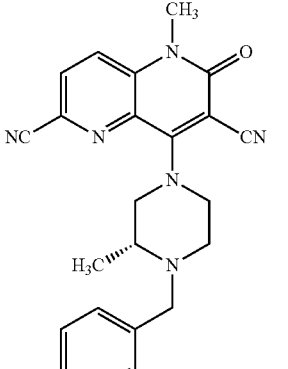 | 2.21 A | 467.2 | H |
| 1015 | (structure) | 2.07 A | 451.1 | H |

The examples in the Table 24 were prepared from the appropriate piperazine according to the general procedure described in Examples 700 and 701, substituting 4-cyclopropylthiazole-2-carbaldehyde with the appropriate heterocyclic aldehyde and Intermediate 780F in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 24

| Ex. No. | Structure | LCMS RT and Method | M + H | Stereo chem. |
|---|---|---|---|---|
| 1016 | (structure) | 2.78 C | 497.2 | H |

TABLE 24-continued

| Ex. No. | Structure | LCMS RT and Method | M + H | Stereo chem. |
|---|---|---|---|---|
| 1017 | 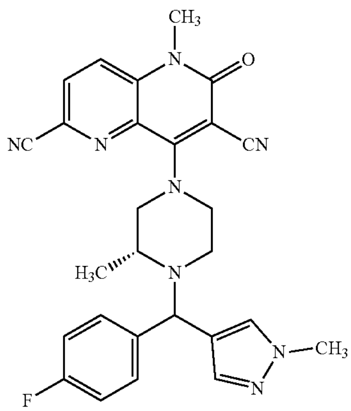 [SMILES: C[C@@H]1CN(c2c(C#N)c(=O)n(C)c3ccc(C#N)nc23)CCN1C(c1ccc(F)cc1)c1cnn(C)c1] | 2.91 C | 497.2 | H |
| 1018 | 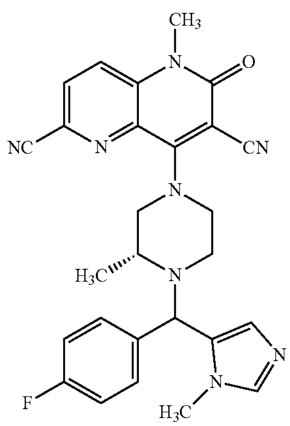 [SMILES: C[C@@H]1CN(c2c(C#N)c(=O)n(C)c3ccc(C#N)nc23)CCN1C(c1ccc(F)cc1)c1cncn1C] | 1.57 C | 497.2 | H |
| 1019 | 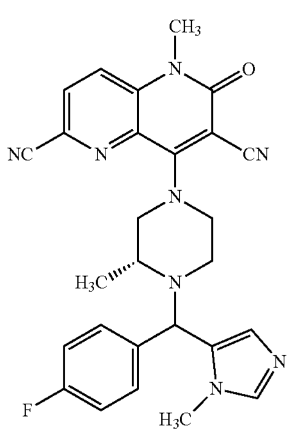 [SMILES: C[C@@H]1CN(c2c(C#N)c(=O)n(C)c3ccc(C#N)nc23)CCN1C(c1ccc(F)cc1)c1cncn1C] | 1.63 A | 497.2 | H |

TABLE 24-continued

| Ex. No. | Structure | LCMS RT and Method | M + H | Stereo chem. |
|---|---|---|---|---|
| 1022 | 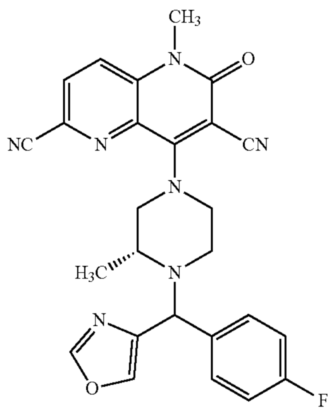 [SMILES: C[C@@H]1CN(c2c(C#N)c(=O)n(C)c3ccc(C#N)nc23)CCN1C(c1ccc(F)cc1)c1cocn1] | 1.72 A | 484.2 | H |
| 1023 | 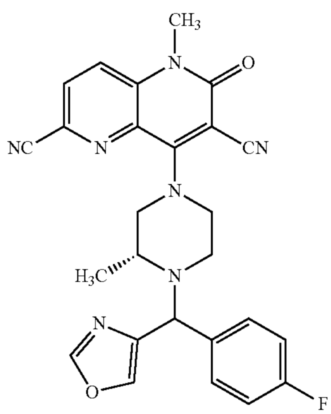 [SMILES: C[C@@H]1CN(c2c(C#N)c(=O)n(C)c3ccc(C#N)nc23)CCN1C(c1ccc(F)cc1)c1cocn1] | 1.81 A | 484.2 | H |
| 1024 | 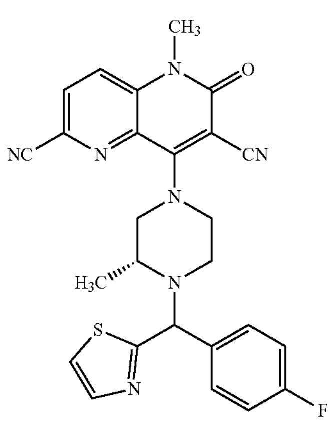 [SMILES: C[C@@H]1CN(c2c(C#N)c(=O)n(C)c3ccc(C#N)nc23)CCN1C(c1ccc(F)cc1)c1nccs1] | 1.85 A | 500.1 | H |

TABLE 24-continued

| Ex. No. | Structure | LCMS RT and Method | M + H | Stereo chem. |
|---|---|---|---|---|
| 1025 | 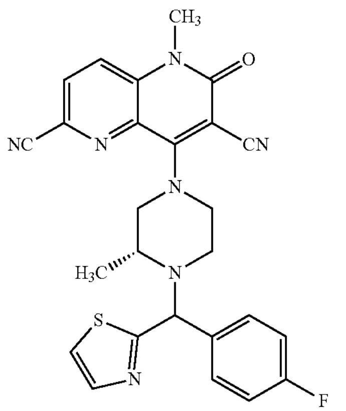 [SMILES: C[C@@H]1CN(c2c(C#N)c(=O)n(C)c3ccc(C#N)nc23)CCN1C(c1ccc(F)cc1)c1nccs1] | 1.92 A | 500.2 | H |
| 1026 | 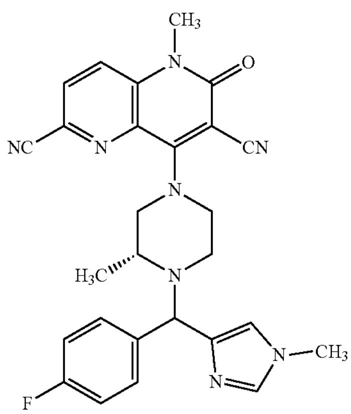 [SMILES: C[C@@H]1CN(c2c(C#N)c(=O)n(C)c3ccc(C#N)nc23)CCN1C(c1ccc(F)cc1)c1cn(C)cn1] | 1.72 A | 497.2 | H |
| 1027 | 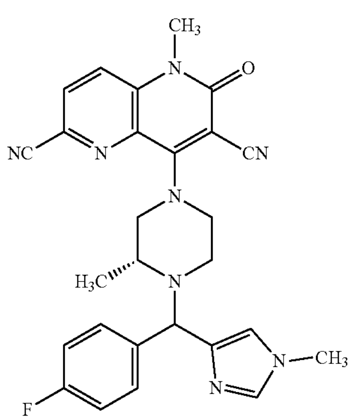 [SMILES: C[C@@H]1CN(c2c(C#N)c(=O)n(C)c3ccc(C#N)nc23)CCN1C(c1ccc(F)cc1)c1cn(C)cn1] | 1.80 A | 497.2 | H |

TABLE 24-continued

| Ex. No. | Structure | LCMS RT and Method | M + H | Stereo chem. |
|---|---|---|---|---|
| 1028 | 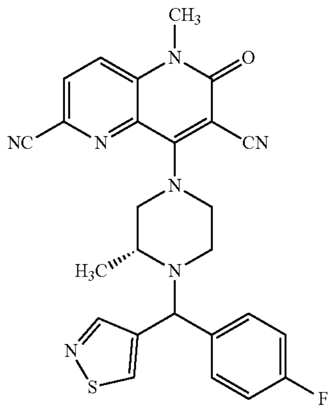 [SMILES: C[C@@H]1CN(c2c(C#N)c(=O)n(C)c3ccc(C#N)nc23)CCN1C(c1ccc(F)cc1)c1cnsc1] | 1.95 A | 500.1 | H |

The examples in the Table 25 were prepared from the appropriate piperazine according to the general procedure described in Examples 735 and 736 substituting (Z)—N'-hydroxycyclopropane carboximidamide and Intermediate 780F in the synthetic sequence. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 25

| Ex. No. | Structure | LCMS RT and Method | M + H | Stereo chem. |
|---|---|---|---|---|
| 1029 | 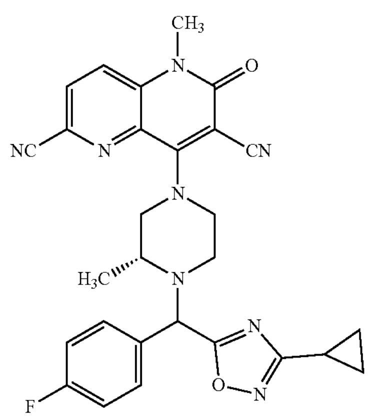 [SMILES: C[C@@H]1CN(c2c(C#N)c(=O)n(C)c3ccc(C#N)nc23)CCN1C(c1ccc(F)cc1)c1nc(C2CC2)no1] | 2.03 A | 525.2 | H |
| 1030 | 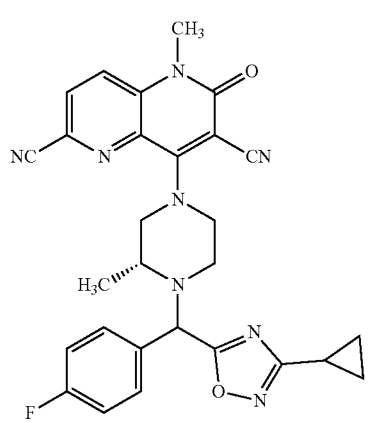 [SMILES: C[C@@H]1CN(c2c(C#N)c(=O)n(C)c3ccc(C#N)nc23)CCN1C(c1ccc(F)cc1)c1nc(C2CC2)no1] | 2.12 A | 525.2 | H |

The compounds in Table 26 were prepared from the appropriate piperazine using corresponding benzhydryl chloride/bromide as described for Example 302. When the reaction provided a mixture of diastereomers, the mixture was separated using either preparative chromatography or preparative chiral chromatography. The absolute stereochemistry was not assigned at the newly formed carbon-nitrogen bond.

TABLE 26

| Ex. No. | Structure | LCMS RT and Method | M + H | Stereo chem. |
|---------|-----------|--------------------|-------|--------------|
| 1031 | 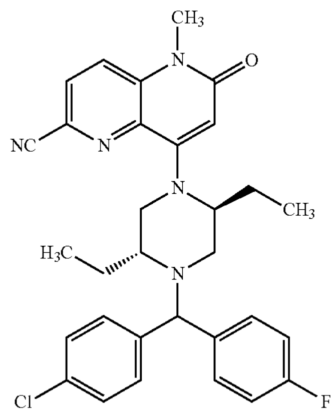 [SMILES: CC[C@H]1CN(C(c2ccc(F)cc2)c2ccc(Cl)cc2)[C@H](CC)CN1c1cc(=O)n(C)c2ccc(C#N)nc12] | 2.68 A | 544.2 | H |
| 1032 | 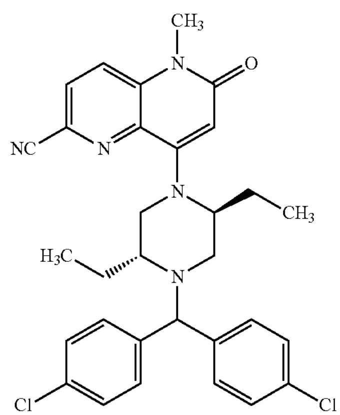 [SMILES: CC[C@H]1CN(C(c2ccc(Cl)cc2)c2ccc(Cl)cc2)[C@H](CC)CN1c1cc(=O)n(C)c2ccc(C#N)nc12] | 1.93 C | 560.2 | H |
| 1033 | 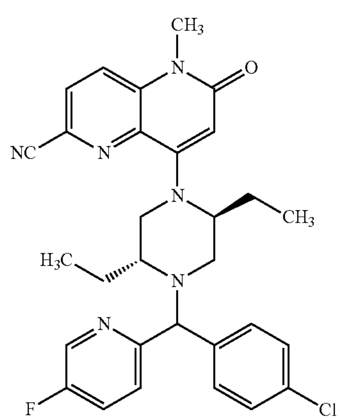 [SMILES: CC[C@H]1CN(C(c2ccc(Cl)cc2)c2ccc(F)cn2)[C@H](CC)CN1c1cc(=O)n(C)c2ccc(C#N)nc12] | 2.67 A | 545.2 | H |

TABLE 26-continued

| Ex. No. | Structure | LCMS RT and Method | M + H | Stereo chem. |
|---|---|---|---|---|
| 1034 | 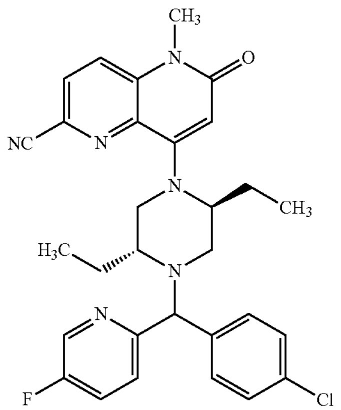 [SMILES: CC[C@H]1CN(C(c2ccc(Cl)cc2)c2ccc(F)cn2)[C@H](CC)CN1c1cc(=O)n(C)c2ccc(C#N)nc12] | 2.69 A | 545.2 | H |
| 1035 | 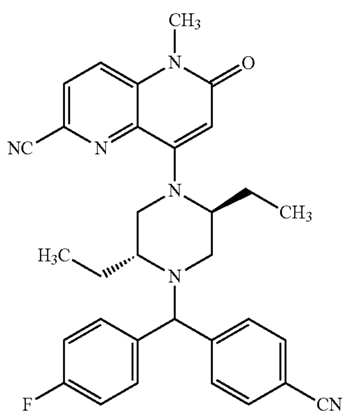 [SMILES: CC[C@H]1CN(C(c2ccc(F)cc2)c2ccc(C#N)cc2)[C@H](CC)CN1c1cc(=O)n(C)c2ccc(C#N)nc12] | 2.5 A | 535.2 | H |
| 1036 | 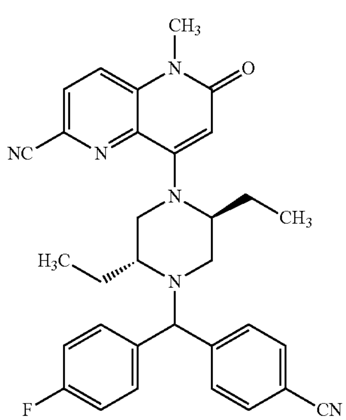 [SMILES: CC[C@H]1CN(C(c2ccc(F)cc2)c2ccc(C#N)cc2)[C@H](CC)CN1c1cc(=O)n(C)c2ccc(C#N)nc12] | 2.49 A | 535.2 | H |

TABLE 26-continued

| Ex. No. | Structure | LCMS RT and Method | M + H | Stereo chem. |
|---|---|---|---|---|
| 1037 | 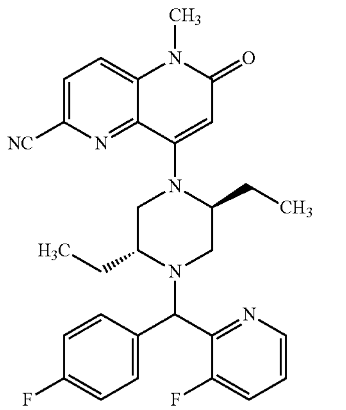 [SMILES: CC[C@H]1CN(C(c2ccc(F)cc2)c2ncccc2F)[C@H](CC)CN1c1cc(=O)n(C)c2ccc(C#N)nc12] | 2.27 A | 529.2 | H |
| 1038 | 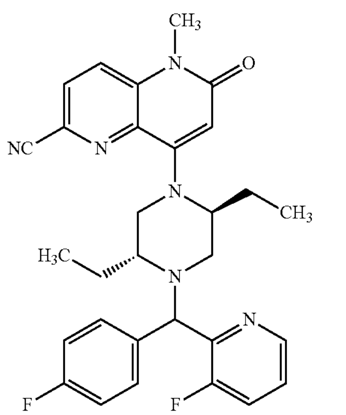 [SMILES: CC[C@H]1CN(C(c2ccc(F)cc2)c2ncccc2F)[C@H](CC)CN1c1cc(=O)n(C)c2ccc(C#N)nc12] | 2.24 A | 529.2 | H |
| 1039 | 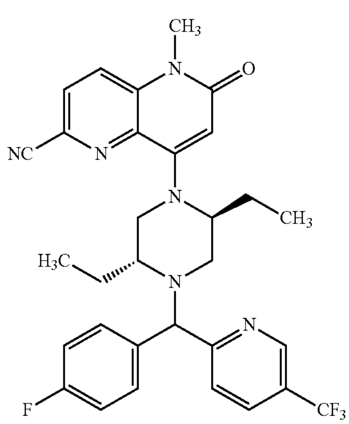 [SMILES: CC[C@H]1CN(C(c2ccc(F)cc2)c2ccc(C(F)(F)F)cn2)[C@H](CC)CN1c1cc(=O)n(C)c2ccc(C#N)nc12] | 2.46 A | 579.2 | H |

TABLE 26-continued

| Ex. No. | Structure | LCMS RT and Method | M + H | Stereo chem. |
|---|---|---|---|---|
| 1040 | 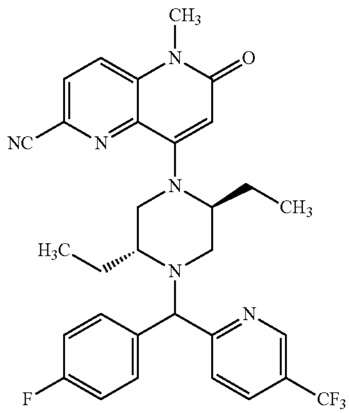 [SMILES: CC[C@H]1CN(C(c2ccc(F)cc2)c2ccc(C(F)(F)F)cn2)[C@H](CC)CN1c1cc(=O)n(C)c2ccc(C#N)nc12] | 2.46 A | 579.2 | H |
| 1041 | 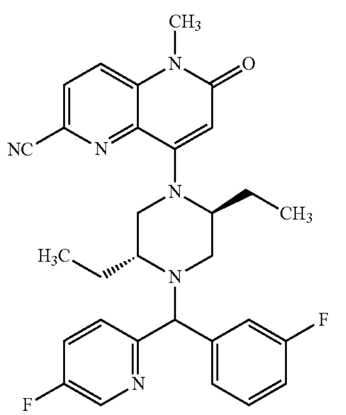 [SMILES: CC[C@H]1CN(C(c2cccc(F)c2)c2ccc(F)cn2)[C@H](CC)CN1c1cc(=O)n(C)c2ccc(C#N)nc12] | 2.27 A | 529.2 | H |
| 1042 | 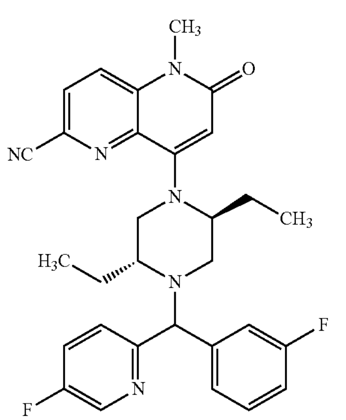 [SMILES: CC[C@H]1CN(C(c2cccc(F)c2)c2ccc(F)cn2)[C@H](CC)CN1c1cc(=O)n(C)c2ccc(C#N)nc12] | 2.27 A | 529.2 | H |

TABLE 26-continued
| Ex. No. | Structure | LCMS RT and Method | M + H | Stereo chem. |
|---|---|---|---|---|
| 1043 | 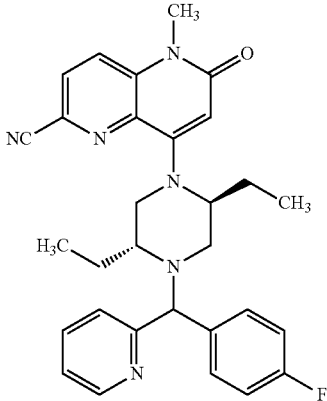 [SMILES: CC[C@H]1CN(C(c2ccc(F)cc2)c2ccccn2)[C@H](CC)CN1c1cc(=O)n(C)c2ccc(C#N)nc12] | 2.15 A | 511.2 | H |
| 1044 | 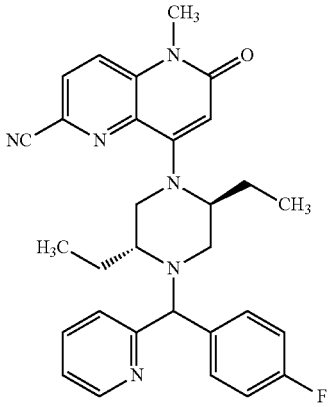 [SMILES: CC[C@H]1CN(C(c2ccc(F)cc2)c2ccccn2)[C@H](CC)CN1c1cc(=O)n(C)c2ccc(C#N)nc12] | 2.14 A | 511.2 | H |
| 1045 | 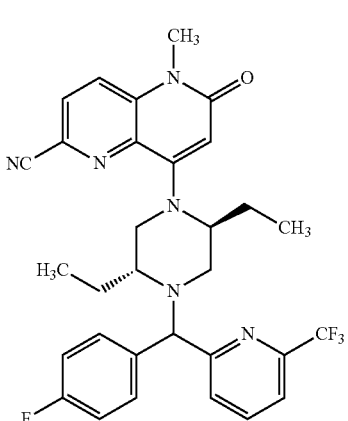 | 2.43 A | 579.2 | H |

TABLE 26-continued

| Ex. No. | Structure | LCMS RT and Method | M + H | Stereo chem. |
|---|---|---|---|---|
| 1046 | 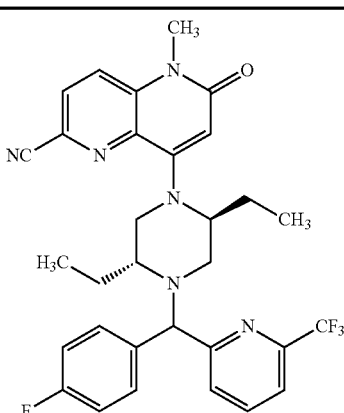 | 2.44 A | 579.3 | H |
| 1047 | 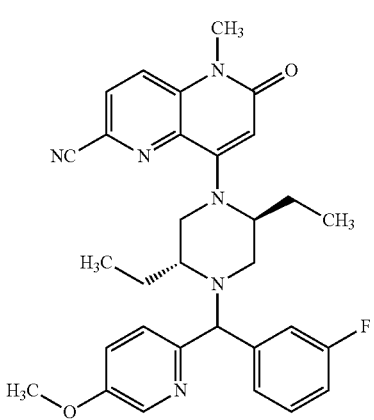 [SMILES: CC[C@H]1CN(C(c2cccc(F)c2)c2ccc(OC)cn2)[C@H](CC)CN1c1cc(=O)n(C)c2ccc(C#N)nc12] | 2.16 A | 541.3 | H |
| 1048 | 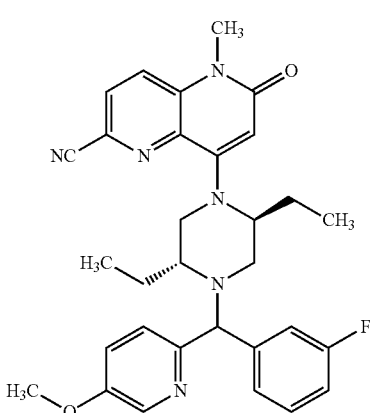 | 2.18 A | 541.3 | H |

The compounds in Table 27 were prepared from the appropriate piperazine using corresponding benzyl chloride/bromide as described for Examples 308 and 309. When the synthesis provided a mixture of diastereomers, the mixture was separated using either preparative chromatography or preparative chiral chromatography. The absolute stereochemistry was not assigned at the newly formed carbon-nitrogen bond

TABLE 27

| Ex. No. | Structure | LCMS RT and Method | M + H | Stereo chem. |
|---|---|---|---|---|
| 1049 | 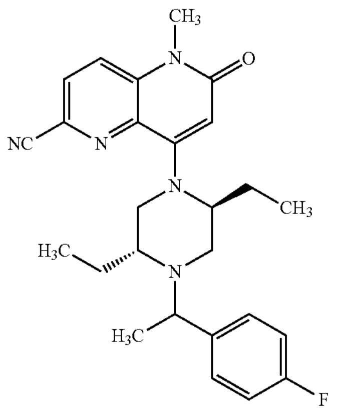 [SMILES: CC[C@H]1CN(C(C)c2ccc(F)cc2)[C@H](CC)CN1c1cc(=O)n(C)c2ccc(C#N)nc12] | 2.47 A | 448.2 | H |
| 1050 | 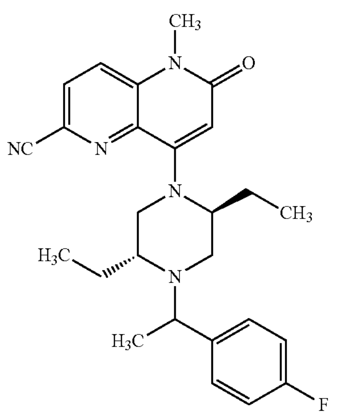 [SMILES: CC[C@H]1CN(C(C)c2ccc(F)cc2)[C@H](CC)CN1c1cc(=O)n(C)c2ccc(C#N)nc12] | 2.47 A | 448.2 | H |
| 1051 | 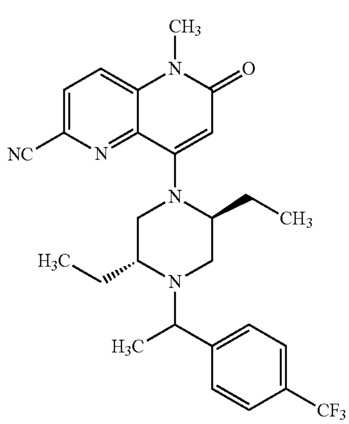 [SMILES: CC[C@H]1CN(C(C)c2ccc(C(F)(F)F)cc2)[C@H](CC)CN1c1cc(=O)n(C)c2ccc(C#N)nc12] | 2.53 A | 498.2 | H |

TABLE 27-continued
| Ex. No. | Structure | LCMS RT and Method | M + H | Stereo chem. |
|---|---|---|---|---|
| 1052 | 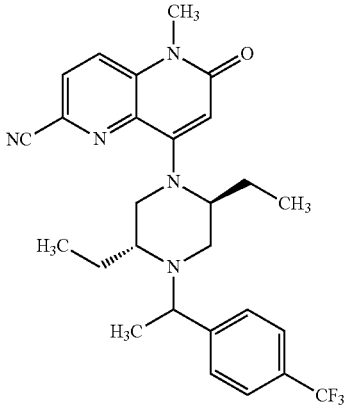 | 2.54 A | 498.2 | H |
| 1053 | 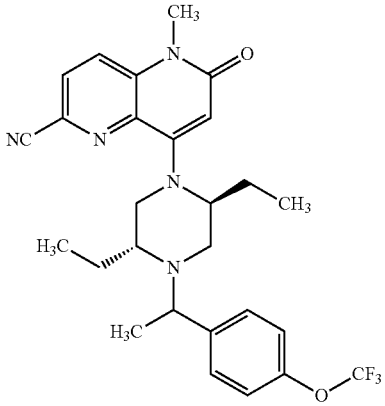 [SMILES: CC[C@H]1CN(C(C)c2ccc(OC(F)(F)F)cc2)[C@H](CC)CN1c1cc(=O)n(C)c2ccc(C#N)nc12] | 2.61 A | 514.2 | H |
| 1054 | 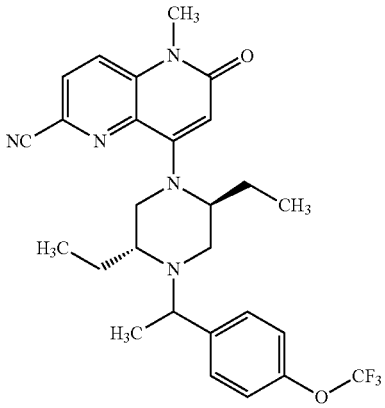 [SMILES: CC[C@H]1CN(C(C)c2ccc(OC(F)(F)F)cc2)[C@H](CC)CN1c1cc(=O)n(C)c2ccc(C#N)nc12] | 2.62 A | 514.2 | H |

TABLE 27-continued

| Ex. No. | Structure | LCMS RT and Method | M + H | Stereo chem. |
|---|---|---|---|---|
| 1055 | 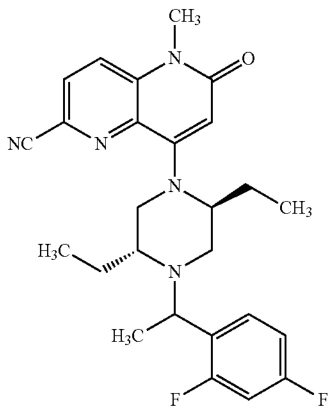 [SMILES: CC[C@H]1CN(C(C)c2ccc(F)cc2F)[C@H](CC)CN1c1cc(=O)n(C)c2ccc(C#N)nc12] | 2.47 A | 466.2 | H |
| 1056 | 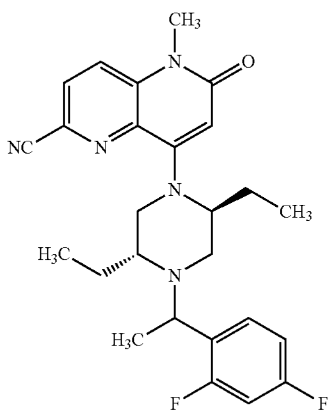 [SMILES: CC[C@H]1CN(C(C)c2ccc(F)cc2F)[C@H](CC)CN1c1cc(=O)n(C)c2ccc(C#N)nc12] | 2.48 A | 466.2 | H |
| 1057 | 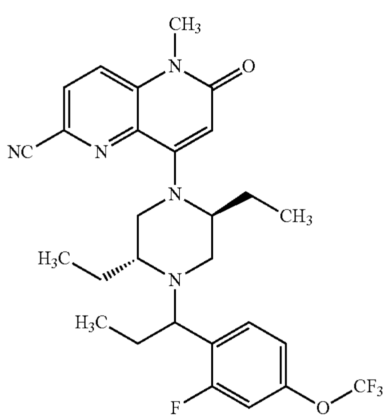 [SMILES: CCC(c1ccc(OC(F)(F)F)cc1F)N1C[C@H](CC)N(c2cc(=O)n(C)c3ccc(C#N)nc23)C[C@H]1CC] | 2.73 A | 546.2 | H |

TABLE 27-continued

| Ex. No. | Structure | LCMS RT and Method | M + H | Stereo chem. |
|---|---|---|---|---|
| 1058 | 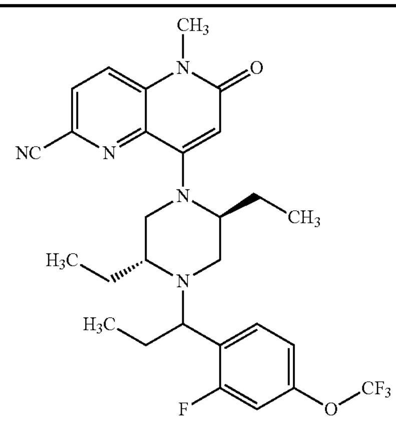 | 2.75 A | 546.2 | H |
| 1059 | 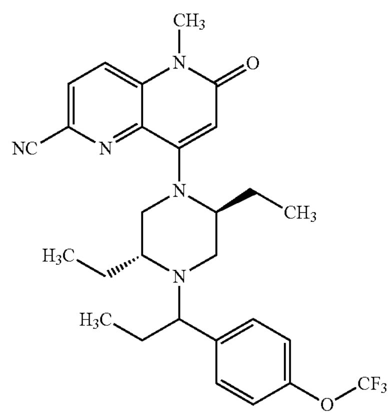 [SMILES: CCC(c1ccc(OC(F)(F)F)cc1)N1C[C@H](CC)N(c2cc(=O)n(C)c3ccc(C#N)nc23)C[C@H]1CC] | 2.70 A | 528.2 | H |
| 1060 | 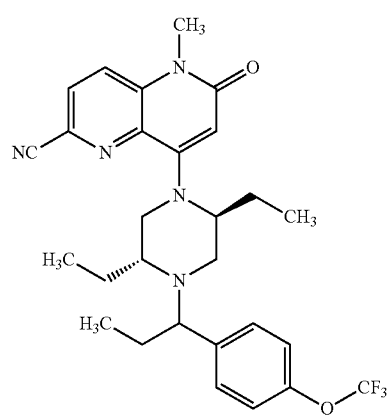 [SMILES: CCC(c1ccc(OC(F)(F)F)cc1)N1C[C@H](CC)N(c2cc(=O)n(C)c3ccc(C#N)nc23)C[C@H]1CC] | 2.74 A | 528.3 | H |

The compounds in Table 28 were prepared from the appropriate piperazine using the corresponding benzyl chloride/bromide as described in the procedure for Example 246. The crude material was purified by preparative HPLC to obtain the product.

TABLE 28

| Ex. No. | Structure | LCMS RT and Method | M + H | Stereo chem. |
|---|---|---|---|---|
| 1061 | 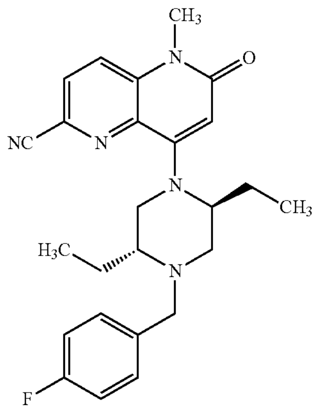 [SMILES: CC[C@@H]1CN(c2cc(=O)n(C)c3ccc(C#N)nc23)[C@@H](CC)CN1Cc1ccc(F)cc1] | 2.31 A | 434.2 | H |
| 1062 | 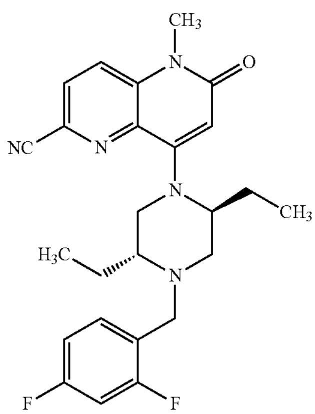 [SMILES: CC[C@@H]1CN(c2cc(=O)n(C)c3ccc(C#N)nc23)[C@@H](CC)CN1Cc1ccc(F)cc1F] | 2.35 A | 452.2 | H |
| 1063 | 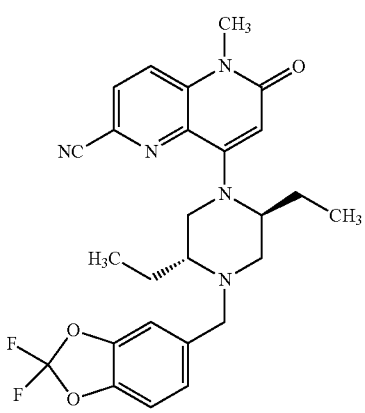 [SMILES: CC[C@@H]1CN(c2cc(=O)n(C)c3ccc(C#N)nc23)[C@@H](CC)CN1Cc1ccc2c(c1)OC(F)(F)O2] | 2.50 A | 496.2 | H |

The examples in the Table 29 were prepared from the appropriate piperazine according to the general procedure described in Examples 735 and 736. When the reaction provided mixture of diastereomers, the mixture was separated at the final stage using either preparative chromatography or preparative chiral chromatography. The absolute stereochemistry was not assigned at the newly formed carbon-nitrogen bond.

TABLE 29

| Ex. No. | Structure | LCMS RT and Method | M + H | Stereo chem. |
|---|---|---|---|---|
| 1064 | 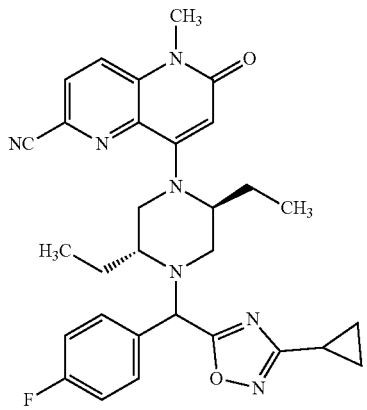 [SMILES: CC[C@H]1CN(C(c2ccc(F)cc2)c2nc(C3CC3)no2)[C@H](CC)CN1c1cc(=O)n(C)c2ccc(C#N)nc12] | 2.38 A | 542.2 | H |
| 1065 | 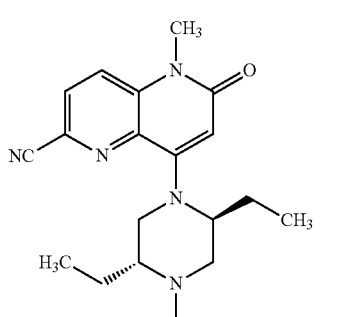 | 2.36 A | 542.2 | H |

The examples in the Table 30 were prepared from the appropriate piperazine according to the general procedure described in Examples 700 and 701, substituting 4-cyclopropylthiazole-2-carbaldehyde with the appropriate heterocyclic aldehyde and Intermediate 780F in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 30

| Ex. No. | Structure | LCMS RT and Method | M + H | Stereo chem. |
|---|---|---|---|---|
| 1171 | 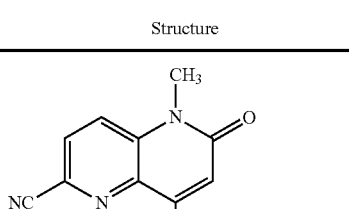 | 2.43 A | 557.3 | H |

TABLE 30-continued

| Ex. No. | Structure | LCMS RT and Method | M + H | Stereo chem. |
|---|---|---|---|---|
| 1067 | 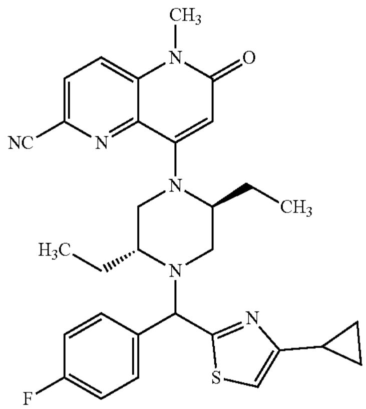 [SMILES: CC[C@H]1CN(C(c2ccc(F)cc2)c2nc(C3CC3)cs2)[C@H](CC)CN1c1cc(=O)n(C)c2ccc(C#N)nc12] | 2.47 A | 557.3 | H |
| 1068 | 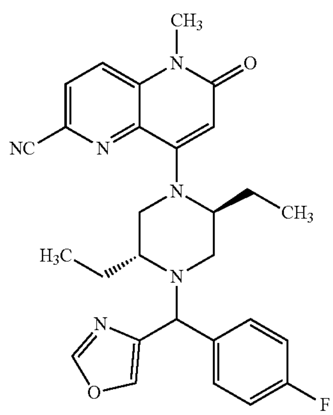 [SMILES: CC[C@H]1CN(C(c2ccc(F)cc2)c2cocn2)[C@H](CC)CN1c1cc(=O)n(C)c2ccc(C#N)nc12] | 2.08 A | 501.2 | H |
| 1069 | 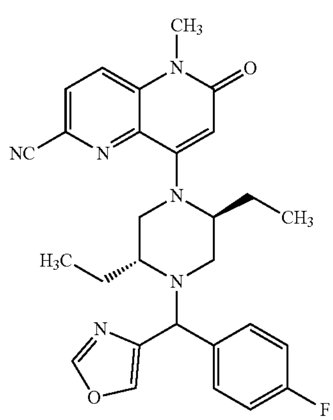 [SMILES: CC[C@H]1CN(C(c2ccc(F)cc2)c2cocn2)[C@H](CC)CN1c1cc(=O)n(C)c2ccc(C#N)nc12] | 2.06 A | 501.2 | H |

TABLE 30-continued

| Ex. No. | Structure | LCMS RT and Method | M + H | Stereo chem. |
|---|---|---|---|---|
| 1070 | 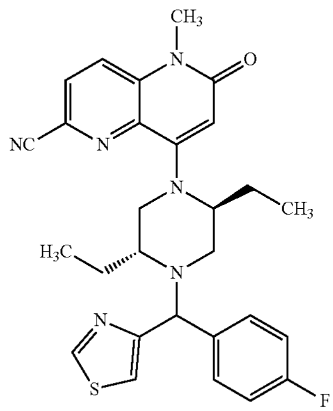 [SMILES: CC[C@H]1CN(C(c2ccc(F)cc2)c2cscn2)[C@H](CC)CN1c1cc(=O)n(C)c2ccc(C#N)nc12] | 2.14 A | 517.2 | H |
| 1071 | 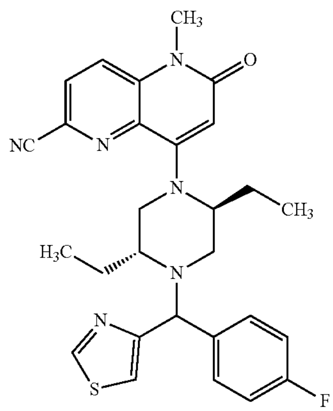 [SMILES: CC[C@H]1CN(C(c2ccc(F)cc2)c2cscn2)[C@H](CC)CN1c1cc(=O)n(C)c2ccc(C#N)nc12] | 2.15 A | 517.2 | H |

The examples in the Table 31 were prepared from the appropriate piperazine according to the general procedure described in Examples 729 and 730, substituting 5-cyclopropylisoxazole-3-carboxylic acid with the appropriate isoxazole-3-carboxylic acid and using Intermediate 780F in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 31

| Ex. No. | Structure | LCMS RT and Method | M + H | Stereo chem. |
|---|---|---|---|---|
| 1072 | 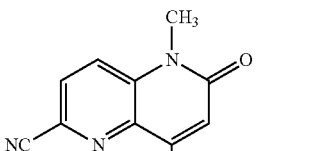 | 2.16 A | 501.2 | H |

TABLE 31-continued
| Ex. No. | Structure | LCMS RT and Method | M + H | Stereo chem. |
|---|---|---|---|---|
| 1073 | 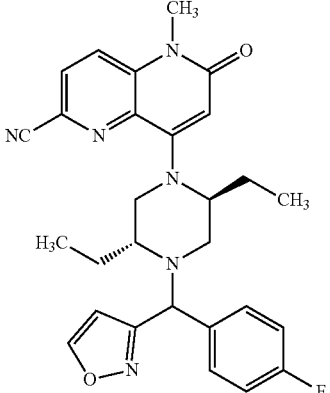 | 2.13 A | 501.2 | H |
| 1074 | 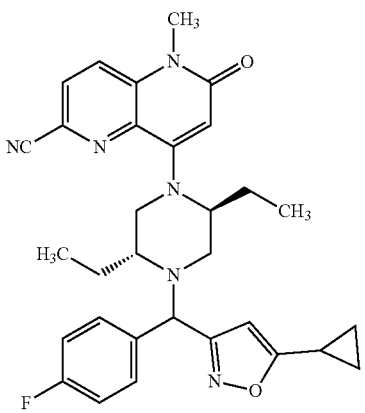 [SMILES: CC[C@H]1CN(C(c2ccc(F)cc2)c2cc(C3CC3)on2)[C@H](CC)CN1c1cc(=O)n(C)c2ccc(C#N)nc12] | 2.34 A | 541.3 | H |
| 1075 | 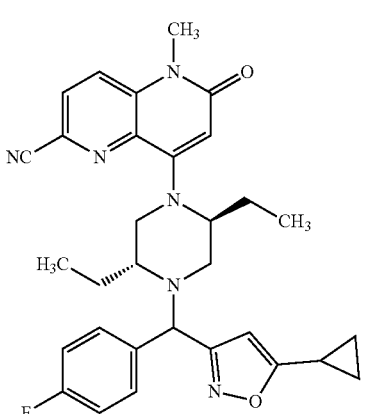 | 2.32 A | 541.3 | H |
The compounds in Table 32 were prepared from the appropriate piperazine using corresponding benzyl chloride/bromide as described for Example 246. The crude material was purified by preparative HPLC to obtain the product.

TABLE 32
| Ex. No. | Structure | LCMS RT and Method | M + H | Stereo chem. |
|---|---|---|---|---|
| 1076 | 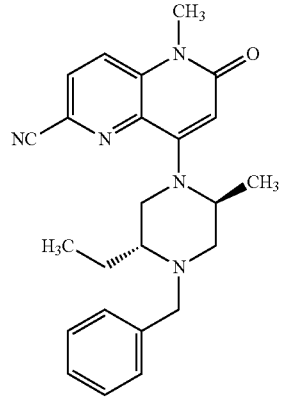 [SMILES: CC[C@@H]1CN(c2cc(=O)n(C)c3ccc(C#N)nc23)[C@@H](C)CN1Cc1ccccc1] | 2.16 A | 402.1 | H |
| 1077 | 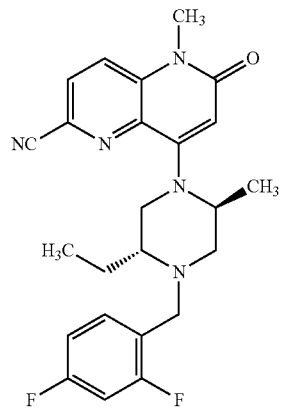 [SMILES: CC[C@@H]1CN(c2cc(=O)n(C)c3ccc(C#N)nc23)[C@@H](C)CN1Cc1ccc(F)cc1F] | 2.22 A | 438.1 | H |
| 1078 | 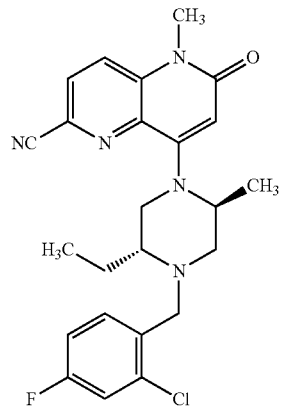 [SMILES: CC[C@@H]1CN(c2cc(=O)n(C)c3ccc(C#N)nc23)[C@@H](C)CN1Cc1ccc(F)cc1Cl] | 2.40 A | 454.1 | H |

TABLE 32-continued
| Ex. No. | Structure | LCMS RT and Method | M + H | Stereo chem. |
|---|---|---|---|---|
| 1079 | 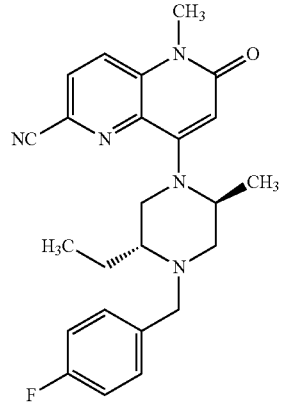 [SMILES: CC[C@@H]1CN(c2cc(=O)n(C)c3ccc(C#N)nc23)[C@@H](C)CN1Cc1ccc(F)cc1] | 2.18 A | 420.2 | H |
| 1080 | 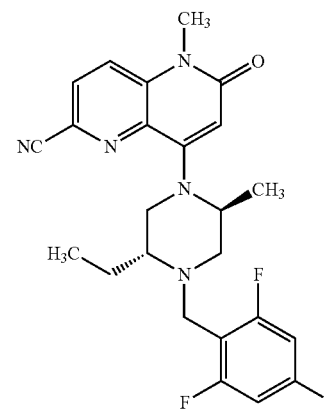 | 2.22 A | 456.2 | H |
| 1081 | 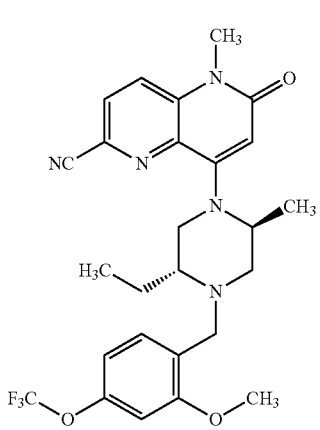 [SMILES: CC[C@@H]1CN(c2cc(=O)n(C)c3ccc(C#N)nc23)[C@@H](C)CN1Cc1ccc(OC(F)(F)F)cc1OC] | 2.41 A | 516.3 | H |

TABLE 32-continued

| Ex. No. | Structure | LCMS RT and Method | M + H | Stereo chem. |
|---|---|---|---|---|
| 1082 | 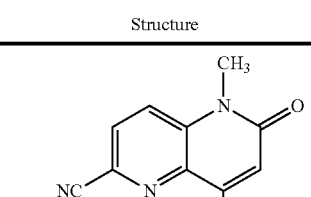 | 2.38 A | 482.2 | H |

The compounds in Table 33 were prepared from the appropriate piperazine using corresponding α-methyl benzyl chloride/bromide as described for Examples 308 and 309. When the synthesis provided a mixture of diastereomers, the mixture was separated using either preparative chromatography or preparative chiral chromatography. The absolute stereochemistry was not assigned at the newly formed carbon-nitrogen bond.

TABLE 33

| No. | Structure | LCMS RT and Method | M + H | Stereo chem. |
|---|---|---|---|---|
| 1083 | 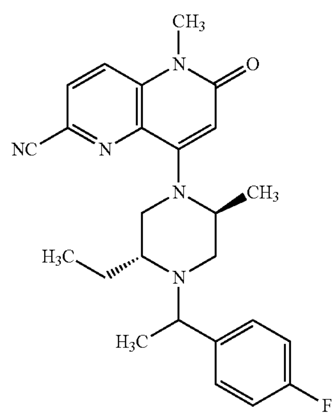 [SMILES: CC[C@@H]1CN(c2cc(=O)n(C)c3ccc(C#N)nc23)[C@@H](C)CN1C(C)c1ccc(F)cc1] | 2.32 A | 434.2 | H |
| 1084 | 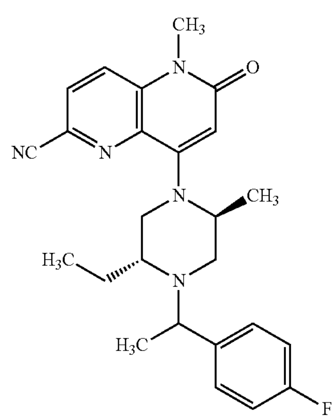 [SMILES: CC[C@@H]1CN(c2cc(=O)n(C)c3ccc(C#N)nc23)[C@@H](C)CN1C(C)c1ccc(F)cc1] | 2.38 A | 434.2 | H |

TABLE 33-continued
| No. | Structure | LCMS RT and Method | M + H | Stereo chem. |
|-----|-----------|---------------------|-------|--------------|
| 1085 | 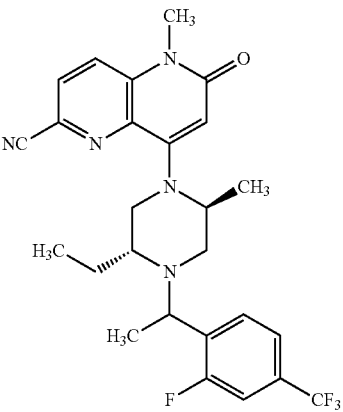 [SMILES: CC[C@@H]1CN(c2cc(=O)n(C)c3ccc(C#N)nc23)[C@@H](C)CN1C(C)c1ccc(C(F)(F)F)cc1F] | 2.52 A | 502.2 | H |
| 1086 | 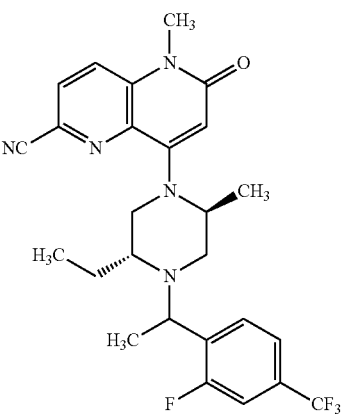 [SMILES: CC[C@@H]1CN(c2cc(=O)n(C)c3ccc(C#N)nc23)[C@@H](C)CN1C(C)c1ccc(C(F)(F)F)cc1F] | 2.57 A | 502.2 | H |
| 1087 | 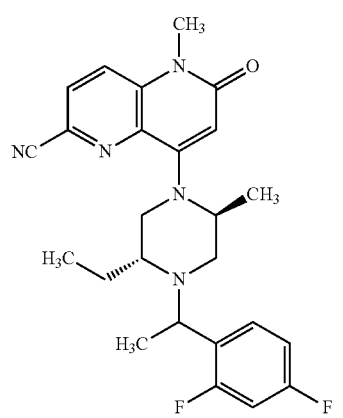 [SMILES: CC[C@@H]1CN(c2cc(=O)n(C)c3ccc(C#N)nc23)[C@@H](C)CN1C(C)c1ccc(F)cc1F] | 2.34 A | 452.3 | H |

TABLE 33-continued

| No. | Structure | LCMS RT and Method | M + H | Stereo chem. |
|---|---|---|---|---|
| 1088 | 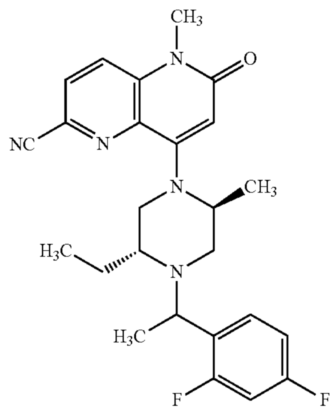 [SMILES: CC[C@@H]1CN(c2cc(=O)n(C)c3ccc(C#N)nc23)[C@@H](C)CN1C(C)c1ccc(F)cc1F] | 2.38 A | 452.2 | H |
| 1089 | 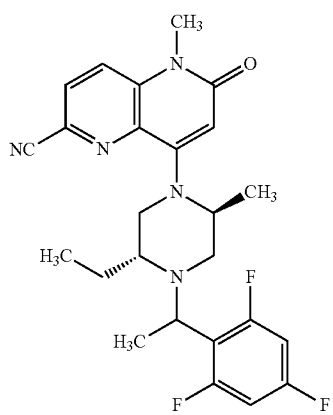 [SMILES: CC[C@@H]1CN(c2cc(=O)n(C)c3ccc(C#N)nc23)[C@@H](C)CN1C(C)c1c(F)cc(F)cc1F] | 2.35 A | 470.2 | H |
| 1090 | 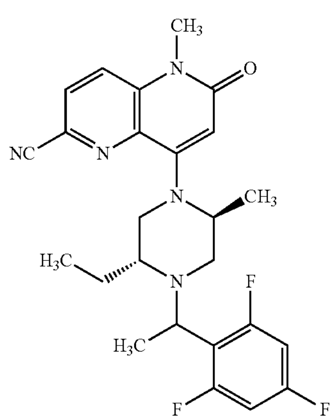 [SMILES: CC[C@@H]1CN(c2cc(=O)n(C)c3ccc(C#N)nc23)[C@@H](C)CN1C(C)c1c(F)cc(F)cc1F] | 2.38 A | 470.2 | H |

TABLE 33-continued
| No. | Structure | LCMS RT and Method | M + H | Stereo chem. |
|---|---|---|---|---|
| 1091 | 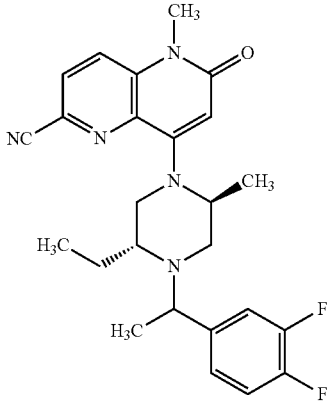 [SMILES: CC[C@@H]1CN(c2cc(=O)n(C)c3ccc(C#N)nc23)[C@@H](C)CN1C(C)c1ccc(F)c(F)c1] | 2.33 A | 452.2 | H |
| 1092 | 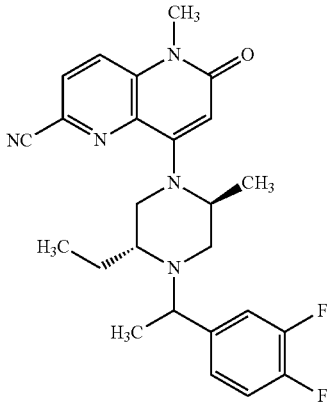 [SMILES: CC[C@@H]1CN(c2cc(=O)n(C)c3ccc(C#N)nc23)[C@@H](C)CN1C(C)c1ccc(F)c(F)c1] | 2.38 A | 452.2 | H |
| 1093 | 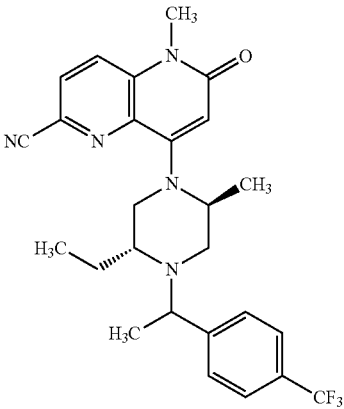 [SMILES: CC[C@@H]1CN(c2cc(=O)n(C)c3ccc(C#N)nc23)[C@@H](C)CN1C(C)c1ccc(C(F)(F)F)cc1] | 2.48 A | 484.2 | H |

TABLE 33-continued

| No. | Structure | LCMS RT and Method | M + H | Stereo chem. |
|---|---|---|---|---|
| 1094 | 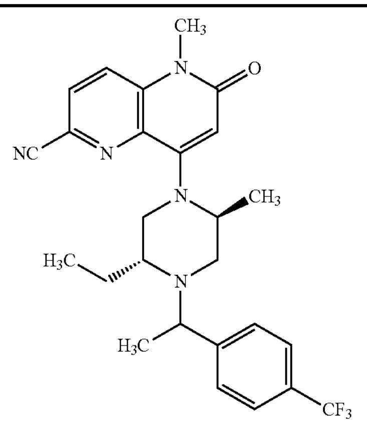 | 2.52 A | 484.3 | H |
| 1095 | 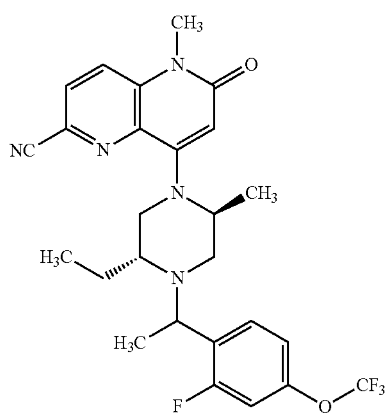 [SMILES: CC[C@@H]1CN(c2cc(=O)n(C)c3ccc(C#N)nc23)[C@@H](C)CN1C(C)c1ccc(OC(F)(F)F)cc1F] | 2.55 A | 518.2 | H |
| 1096 | 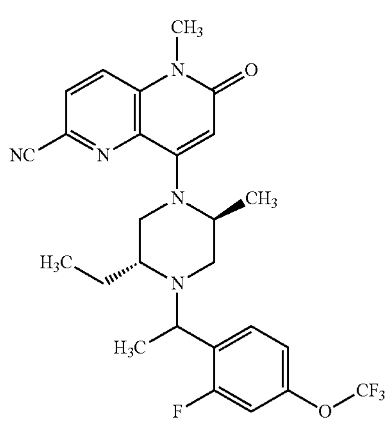 [SMILES: CC[C@@H]1CN(c2cc(=O)n(C)c3ccc(C#N)nc23)[C@@H](C)CN1C(C)c1ccc(OC(F)(F)F)cc1F] | 2.59 A | 518.2 | H |

The compounds in Table 34 were prepared from the appropriate piperazine using corresponding benzhydryl chloride/bromide as described for Example 302. When the reaction provided a mixture of diastereomers, the mixture was separated using either preparative chromatography or preparative chiral chromatography. The absolute stereochemistry was not assigned at the newly formed carbon-nitrogen bond.

TABLE 34

| Ex. No. | Structure | LCMS RT and Method | M + H | Stereo chem. |
|---|---|---|---|---|
| 1097 | 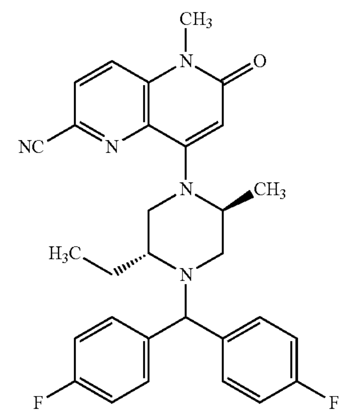 [SMILES: CC[C@@H]1CN(c2cc(=O)n(C)c3ccc(C#N)nc23)[C@@H](C)CN1C(c1ccc(F)cc1)c1ccc(F)cc1] | 2.46 A | 514.2 | H |
| 1098 | 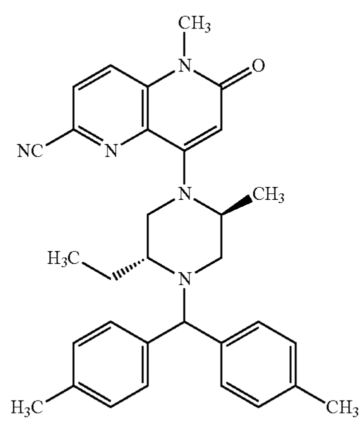 [SMILES: CC[C@@H]1CN(c2cc(=O)n(C)c3ccc(C#N)nc23)[C@@H](C)CN1C(c1ccc(C)cc1)c1ccc(C)cc1] | 2.67 A | 506.3 | H |
| 1099 | 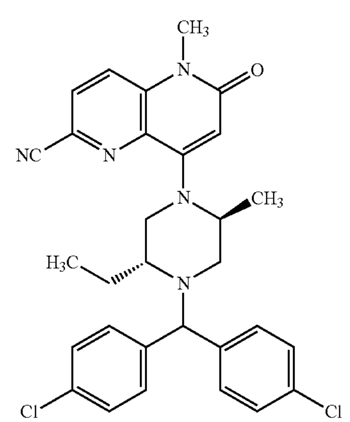 [SMILES: CC[C@@H]1CN(c2cc(=O)n(C)c3ccc(C#N)nc23)[C@@H](C)CN1C(c1ccc(Cl)cc1)c1ccc(Cl)cc1] | 2.75 A | 548.2 | H |

TABLE 34-continued
| Ex. No. | Structure | LCMS RT and Method | M + H | Stereo chem. |
|---|---|---|---|---|
| 1100 | 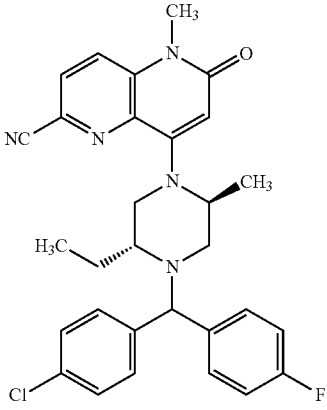 [SMILES: CC[C@@H]1CN(c2cc(=O)n(C)c3ccc(C#N)nc23)[C@@H](C)CN1C(c1ccc(F)cc1)c1ccc(Cl)cc1] | 2.58 A | 530.2 | H |
| 1101 | 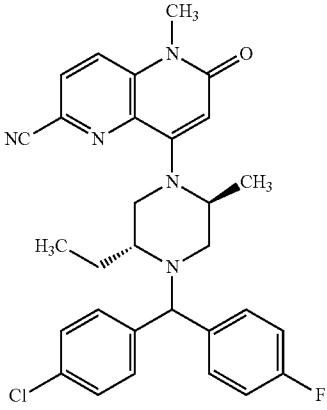 [SMILES: CC[C@@H]1CN(c2cc(=O)n(C)c3ccc(C#N)nc23)[C@@H](C)CN1C(c1ccc(F)cc1)c1ccc(Cl)cc1] | 2.58 A | 530.2 | H |
| 1102 | 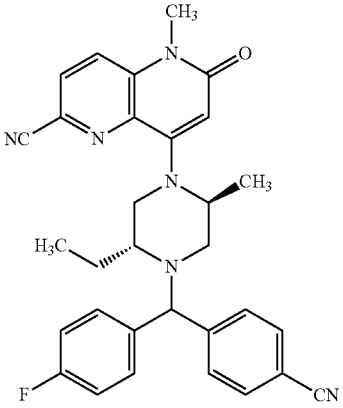 [SMILES: CC[C@@H]1CN(c2cc(=O)n(C)c3ccc(C#N)nc23)[C@@H](C)CN1C(c1ccc(F)cc1)c1ccc(C#N)cc1] | 2.29 A | 521.2 | H |

TABLE 34-continued

| Ex. No. | Structure | LCMS RT and Method | M + H | Stereo chem. |
|---|---|---|---|---|
| 1103 | 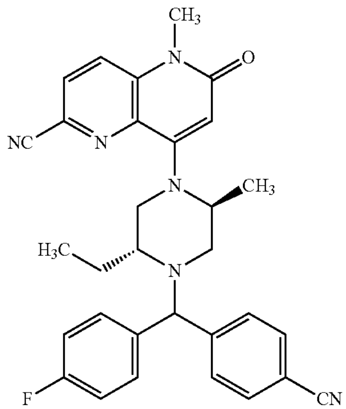 [SMILES: CC[C@@H]1CN(c2cc(=O)n(C)c3ccc(C#N)nc23)[C@@H](C)CN1C(c1ccc(F)cc1)c1ccc(C#N)cc1] | 2.27 A | 521.2 | H |
| 1104 | 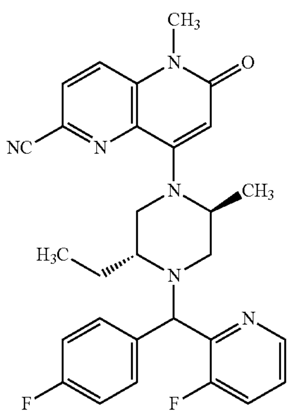 [SMILES: CC[C@@H]1CN(c2cc(=O)n(C)c3ccc(C#N)nc23)[C@@H](C)CN1C(c1ccc(F)cc1)c1ncccc1F] | 2.51 A | 515.2 | H |
| 1105 | 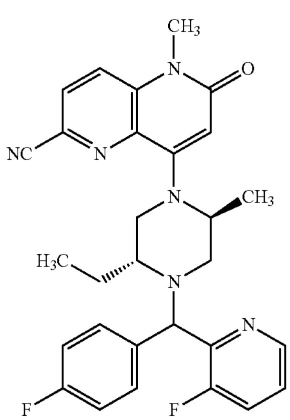 [SMILES: CC[C@@H]1CN(c2cc(=O)n(C)c3ccc(C#N)nc23)[C@@H](C)CN1C(c1ccc(F)cc1)c1ncccc1F] | 2.46 A | 515.2 | H |

TABLE 34-continued

| Ex. No. | Structure | LCMS RT and Method | M + H | Stereo chem. |
|---|---|---|---|---|
| 1106 | 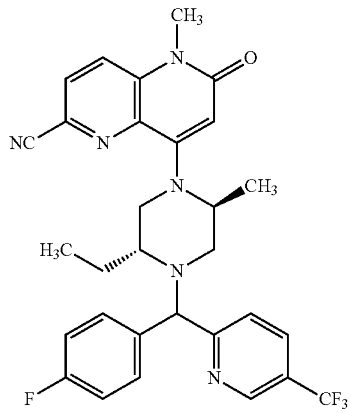 [SMILES: CC[C@@H]1CN(c2cc(=O)n(C)c3ccc(C#N)nc23)[C@@H](C)CN1C(c1ccc(F)cc1)c1ccc(C(F)(F)F)cn1] | 2.39 A | 565.2 | H |
| 1107 | 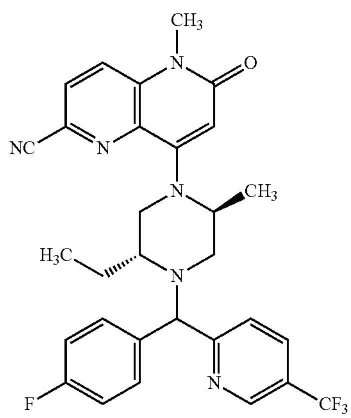 [SMILES: CC[C@@H]1CN(c2cc(=O)n(C)c3ccc(C#N)nc23)[C@@H](C)CN1C(c1ccc(F)cc1)c1ccc(C(F)(F)F)cn1] | 2.40 A | 565.2 | H |
| 1108 | 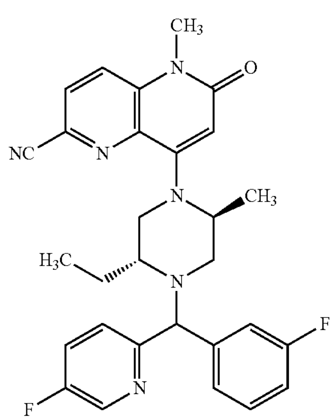 [SMILES: CC[C@@H]1CN(c2cc(=O)n(C)c3ccc(C#N)nc23)[C@@H](C)CN1C(c1cccc(F)c1)c1ccc(F)cn1] | 2.2 A | 515.2 | H |

TABLE 34-continued

| Ex. No. | Structure | LCMS RT and Method | M + H | Stereo chem. |
|---|---|---|---|---|
| 1109 | 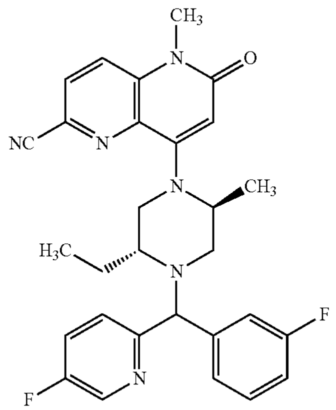 [SMILES: CC[C@@H]1CN(c2cc(=O)n(C)c3ccc(C#N)nc23)[C@@H](C)CN1C(c1cccc(F)c1)c1ccc(F)cn1] | 2.18 A | 515.3 | H |
| 1110 | 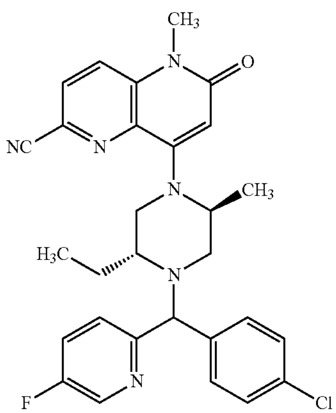 [SMILES: CC[C@@H]1CN(c2cc(=O)n(C)c3ccc(C#N)nc23)[C@@H](C)CN1C(c1ccc(Cl)cc1)c1ccc(F)cn1] | 2.34 A | 531.2 | H |
| 1111 | 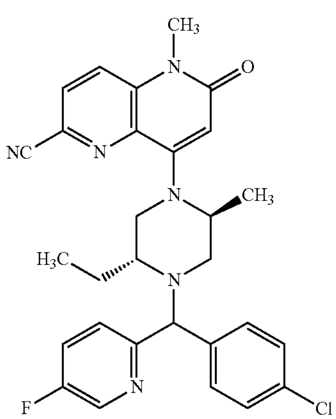 [SMILES: CC[C@@H]1CN(c2cc(=O)n(C)c3ccc(C#N)nc23)[C@@H](C)CN1C(c1ccc(Cl)cc1)c1ccc(F)cn1] | 2.33 A | 531.2 | H |

TABLE 34-continued

| Ex. No. | Structure | LCMS RT and Method | M + H | Stereo chem. |
|---|---|---|---|---|
| 1112 | 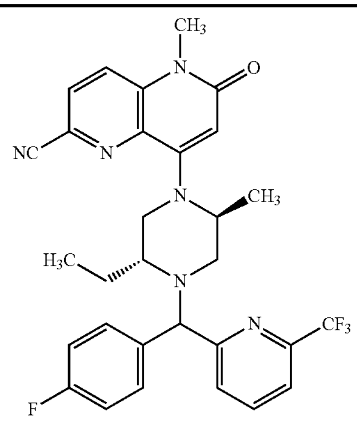 | 2.37 A | 565.2 | H |
| 1113 | 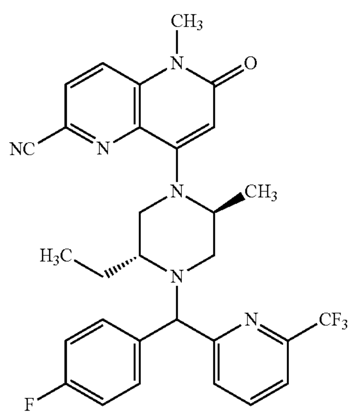 [SMILES: CC[C@@H]1CN(c2cc(=O)n(C)c3ccc(C#N)nc23)[C@@H](C)CN1C(c1ccc(F)cc1)c1cccc(C(F)(F)F)n1] | 2.39 A | 565.2 | H |

The examples in the Table 35 were prepared from the appropriate piperazine according to the general procedure described in Examples 729 and 730. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 35

| No. | Structure | LCMS RT and Method | M + H | Stereo chem. |
|---|---|---|---|---|
| 1114 | 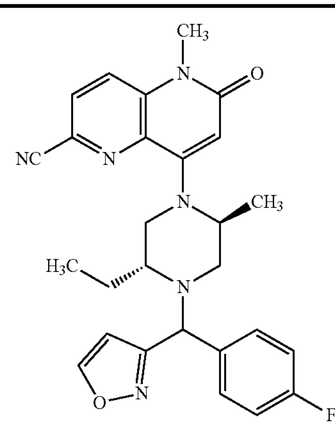 | 2.04 A | 487.2 | H |

TABLE 35-continued

| No. | Structure | LCMS RT and Method | M + H | Stereo chem. |
|---|---|---|---|---|
| 1115 | 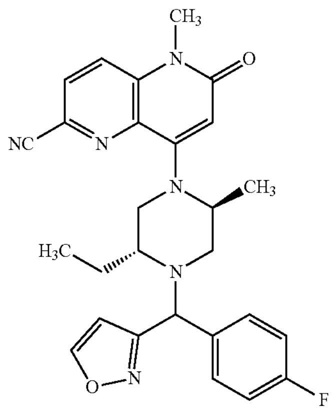 [SMILES: CC[C@@H]1CN(c2cc(=O)n(C)c3ccc(C#N)nc23)[C@@H](C)CN1C(c1ccc(F)cc1)c1ccon1] | 2.05 A | 487.2 | H |

The examples in the Table 36 were prepared from the appropriate piperazine according to the general procedure described in Examples 735 and 736. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 36

| Ex. No. | Structure | LCMS RT and Method | M + H | Stereo chem. |
|---|---|---|---|---|
| 1116 | 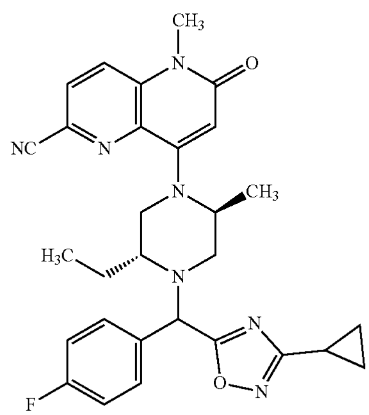 [SMILES: CC[C@@H]1CN(c2cc(=O)n(C)c3ccc(C#N)nc23)[C@@H](C)CN1C(c1ccc(F)cc1)c1nc(C2CC2)no1] | 2.27 A | 528.3 | H |
| 1117 | 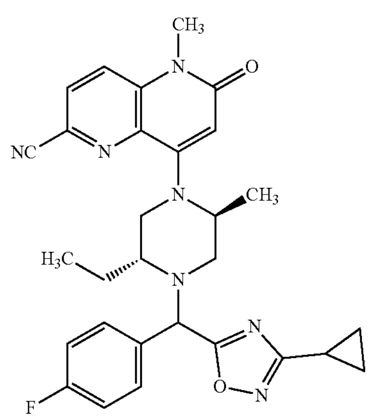 [SMILES: CC[C@@H]1CN(c2cc(=O)n(C)c3ccc(C#N)nc23)[C@@H](C)CN1C(c1ccc(F)cc1)c1nc(C2CC2)no1] | 2.59 A | 528.2 | H |

The compounds in Table 37 were prepared from the appropriate piperazine using corresponding benzhydryl chloride/bromide as described for Example 302. When the synthesis provided a mixture of diastereomers, the mixture was separated using either preparative chromatography or preparative chiral chromatography. The absolute stereochemistry was not assigned at the newly formed carbon-nitrogen bond.

TABLE 37

| Ex. No. | Structure | LCMS RT and Method | M + H | Stereo chem. |
|---------|-----------|--------------------|-------|--------------|
| 1118 | 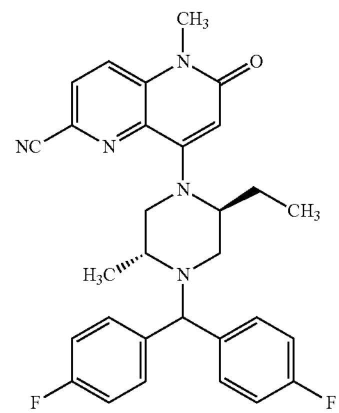 [SMILES: CC[C@H]1CN(C(c2ccc(F)cc2)c2ccc(F)cc2)[C@H](C)CN1c1cc(=O)n(C)c2ccc(C#N)nc12] | 2.42 A | 514.2 | H |
| 1119 | 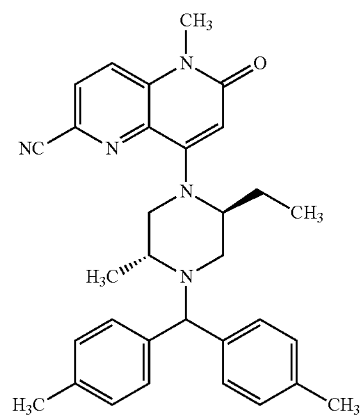 | 2.64 A | 506.3 | H |
| 1120 | 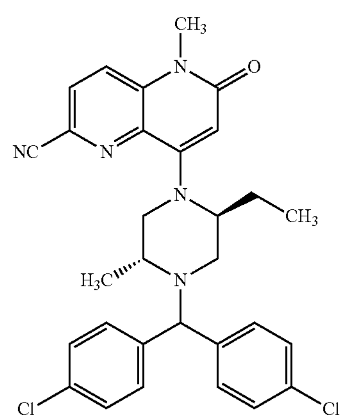 [SMILES: CC[C@H]1CN(C(c2ccc(Cl)cc2)c2ccc(Cl)cc2)[C@H](C)CN1c1cc(=O)n(C)c2ccc(C#N)nc12] | 2.7 A | 548.2 | H |

TABLE 37-continued

| Ex. No. | Structure | LCMS RT and Method | M + H | Stereo chem. |
|---------|-----------|--------------------|-------|--------------|
| 1121 | 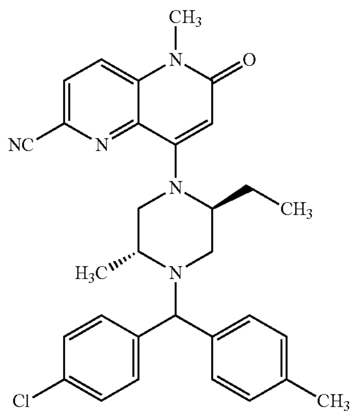 [SMILES: CC[C@H]1CN(C(c2ccc(C)cc2)c2ccc(Cl)cc2)[C@H](C)CN1c1cc(=O)n(C)c2ccc(C#N)nc12] | 2.69 A | 527.2 | H |
| 1122 | 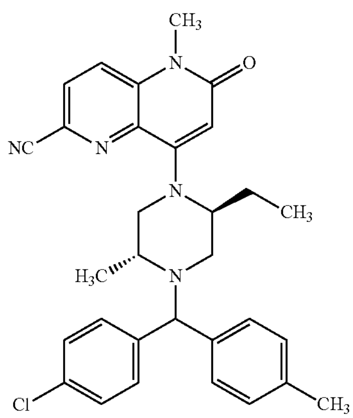 [SMILES: CC[C@H]1CN(C(c2ccc(C)cc2)c2ccc(Cl)cc2)[C@H](C)CN1c1cc(=O)n(C)c2ccc(C#N)nc12] | 2.69 A | 527.2 | H |
| 1123 | 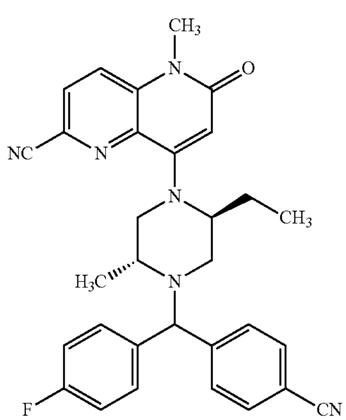 [SMILES: CC[C@H]1CN(C(c2ccc(F)cc2)c2ccc(C#N)cc2)[C@H](C)CN1c1cc(=O)n(C)c2ccc(C#N)nc12] | 2.28 A | 521.2 | H |

TABLE 37-continued
| Ex. No. | Structure | LCMS RT and Method | M + H | Stereo chem. |
|---|---|---|---|---|
| 1124 | 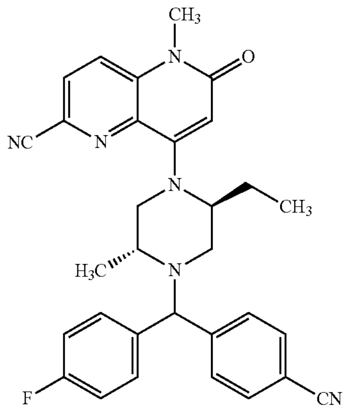 [SMILES: CC[C@H]1CN(C(c2ccc(F)cc2)c2ccc(C#N)cc2)[C@H](C)CN1c1cc(=O)n(C)c2ccc(C#N)nc12] | 2.28 A | 521.2 | H |
| 1125 | 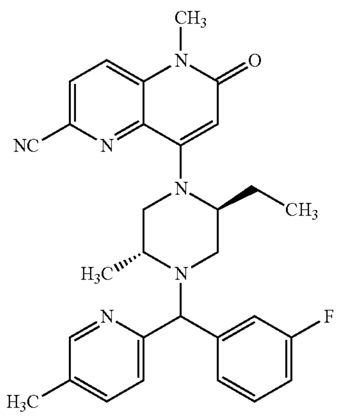 [SMILES: CC[C@H]1CN(C(c2cccc(F)c2)c2ccc(C)cn2)[C@H](C)CN1c1cc(=O)n(C)c2ccc(C#N)nc12] | 2.16 A | 511.2 | H |
| 1126 | 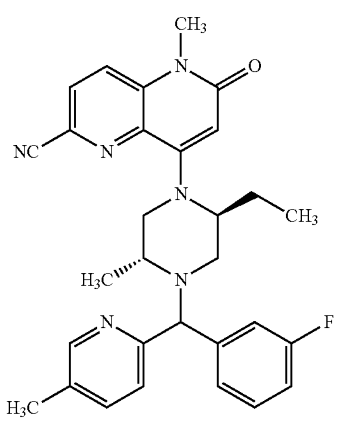 [SMILES: CC[C@H]1CN(C(c2cccc(F)c2)c2ccc(C)cn2)[C@H](C)CN1c1cc(=O)n(C)c2ccc(C#N)nc12] | 2.44 A | 511.2 | H |

TABLE 37-continued
| Ex. No. | Structure | LCMS RT and Method | M + H | Stereo chem. |
|---|---|---|---|---|
| 1127 | 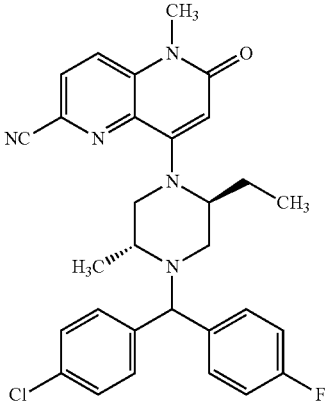 [SMILES: CC[C@H]1CN(C(c2ccc(F)cc2)c2ccc(Cl)cc2)[C@H](C)CN1c1cc(=O)n(C)c2ccc(C#N)nc12] | 2.87 A | 532.2 | H |
| 1128 | 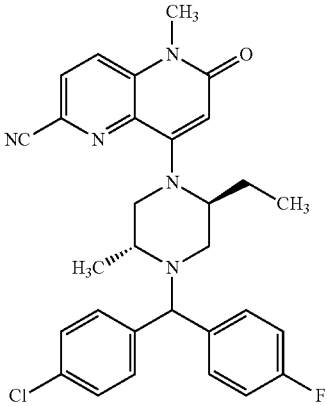 [SMILES: CC[C@H]1CN(C(c2ccc(F)cc2)c2ccc(Cl)cc2)[C@H](C)CN1c1cc(=O)n(C)c2ccc(C#N)nc12] | 2.87 A | 532.2 | H |
| 1129 | 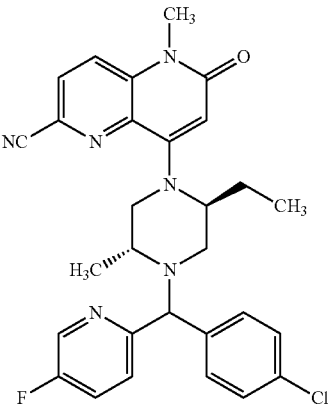 [SMILES: CC[C@H]1CN(C(c2ccc(Cl)cc2)c2ccc(F)cn2)[C@H](C)CN1c1cc(=O)n(C)c2ccc(C#N)nc12] | 2.3 A | 531.2 | H |

TABLE 37-continued
| Ex. No. | Structure | LCMS RT and Method | M + H | Stereo chem. |
|---|---|---|---|---|
| 1130 | 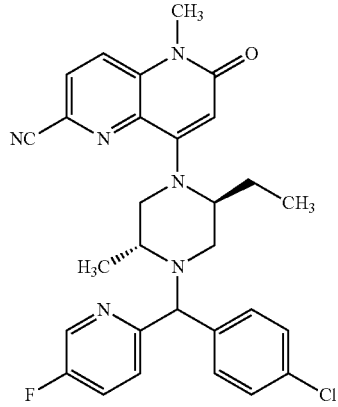 [SMILES: CC[C@H]1CN(C(c2ccc(Cl)cc2)c2ccc(F)cn2)[C@H](C)CN1c1cc(=O)n(C)c2ccc(C#N)nc12] | 2.32 A | 531.2 | H |
| 1131 | 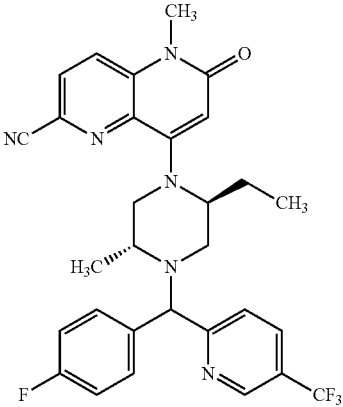 [SMILES: CC[C@H]1CN(C(c2ccc(F)cc2)c2ccc(C(F)(F)F)cn2)[C@H](C)CN1c1cc(=O)n(C)c2ccc(C#N)nc12] | 2.34 A | 565.2 | H |
| 1132 | 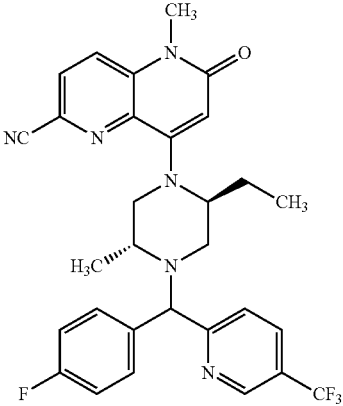 [SMILES: CC[C@H]1CN(C(c2ccc(F)cc2)c2ccc(C(F)(F)F)cn2)[C@H](C)CN1c1cc(=O)n(C)c2ccc(C#N)nc12] | 2.34 A | 565.2 | H |

TABLE 37-continued

| Ex. No. | Structure | LCMS RT and Method | M + H | Stereo chem. |
|---|---|---|---|---|
| 1133 | 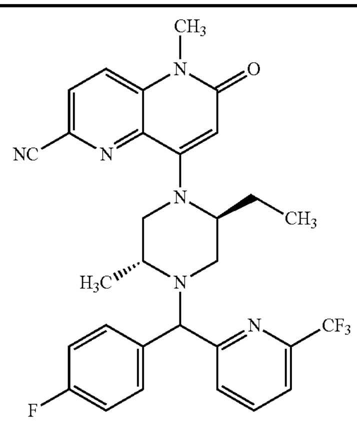 | 2.37 A | 565.2 | H |
| 1134 | 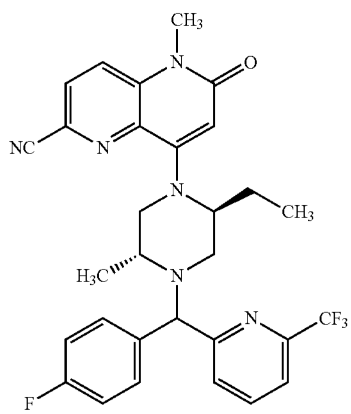 [SMILES: CC[C@H]1CN(C(c2ccc(F)cc2)c2cccc(C(F)(F)F)n2)[C@H](C)CN1c1cc(=O)n(C)c2ccc(C#N)nc12] | 2.38 A | 565.2 | H |

The compounds in Table 38 were prepared from the appropriate piperazine using corresponding α-alkyl benzyl chloride/bromide as described for Example 308/309. When the synthesis provided a mixture of diastereomers, the mixture was separated using either preparative chromatography or preparative chiral chromatography. The absolute stereochemistry was not assigned at the newly formed carbon-nitrogen bond.

TABLE 38

| Ex. No. | Structure | LCMS RT and Method | M + H | Stereo chem. |
|---|---|---|---|---|
| 1135 | 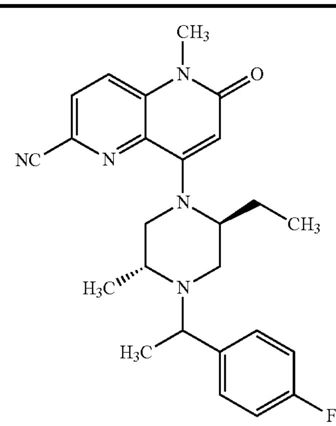 | 2.36 A | 434.2 | H |

TABLE 38-continued

| Ex. No. | Structure | LCMS RT and Method | M + H | Stereo chem. |
|---|---|---|---|---|
| 1136 | 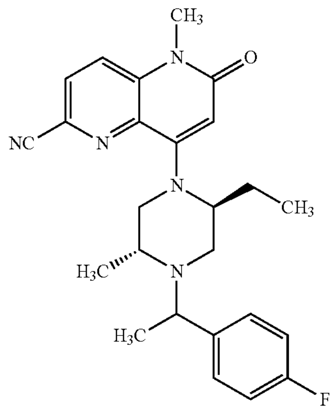 [SMILES: CC[C@H]1CN(C(C)c2ccc(F)cc2)[C@H](C)CN1c1cc(=O)n(C)c2ccc(C#N)nc12] | 2.34 A | 434.2 | H |
| 1137 | 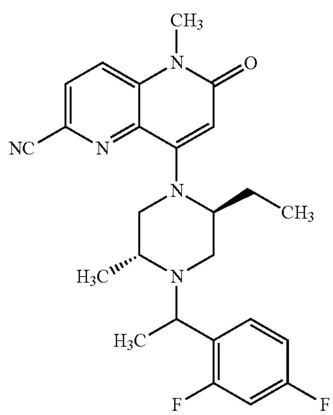 [SMILES: CC[C@H]1CN(C(C)c2ccc(F)cc2F)[C@H](C)CN1c1cc(=O)n(C)c2ccc(C#N)nc12] | 2.37 A | 452.2 | H |
| 1138 | 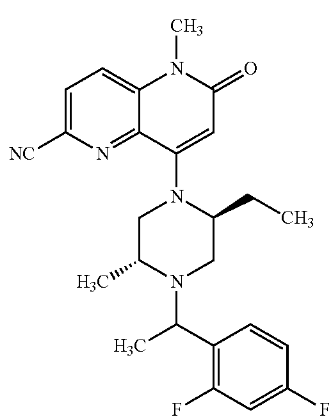 [SMILES: CC[C@H]1CN(C(C)c2ccc(F)cc2F)[C@H](C)CN1c1cc(=O)n(C)c2ccc(C#N)nc12] | 2.35 A | 452.2 | H |

TABLE 38-continued
| Ex. No. | Structure | LCMS RT and Method | M + H | Stereo chem. |
|---|---|---|---|---|
| 1139 | 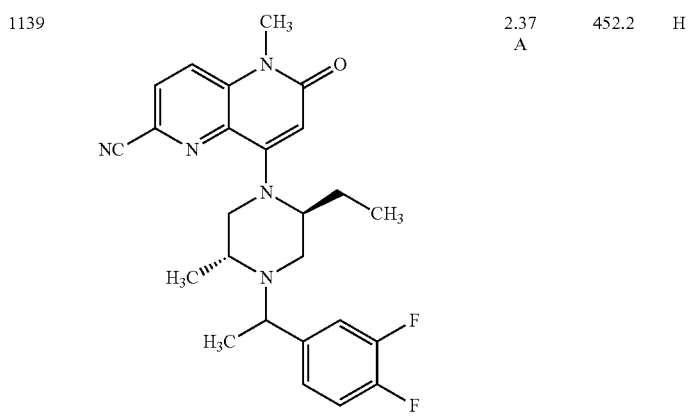 | 2.37 A | 452.2 | H |
| 1140 | 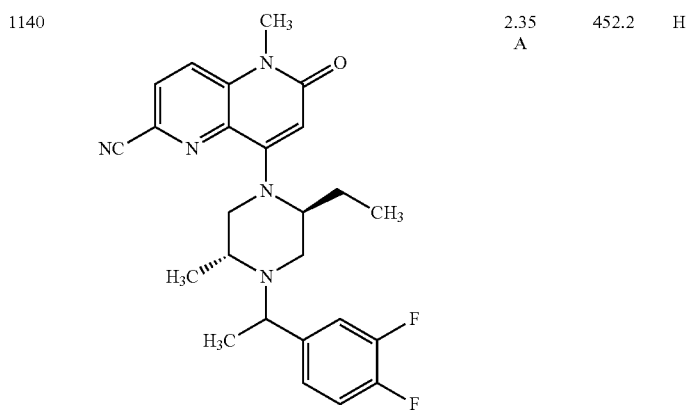 | 2.35 A | 452.2 | H |
| 1141 | 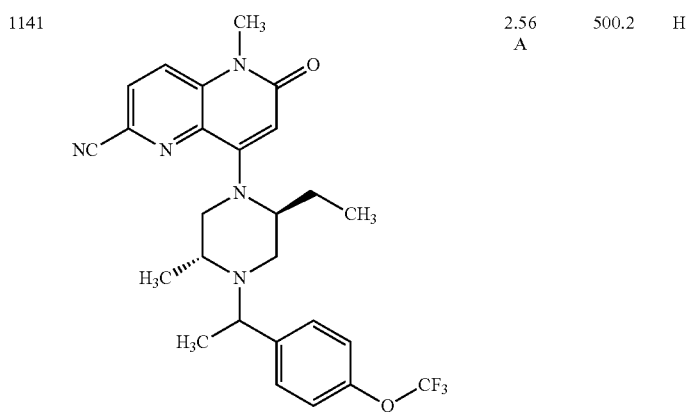 | 2.56 A | 500.2 | H |

TABLE 38-continued
| Ex. No. | Structure | LCMS RT and Method | M + H | Stereo chem. |
|---|---|---|---|---|
| 1142 | 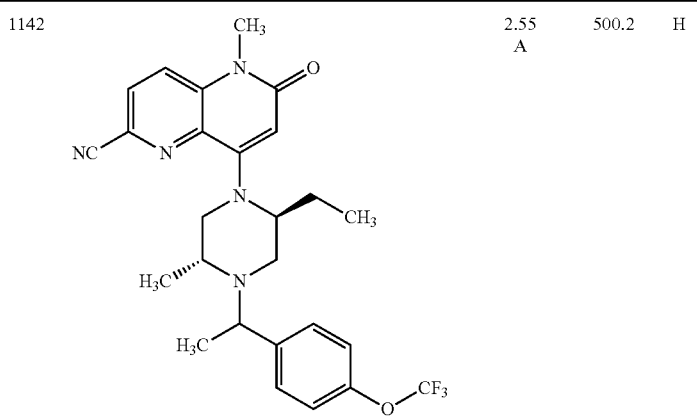 | 2.55 A | 500.2 | H |
| 1143 | 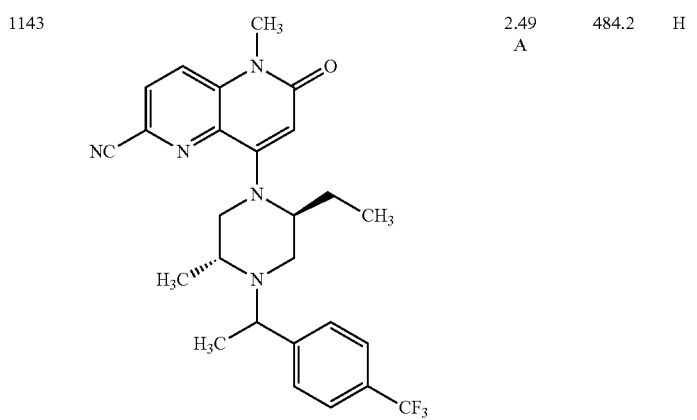 | 2.49 A | 484.2 | H |
| 1144 | 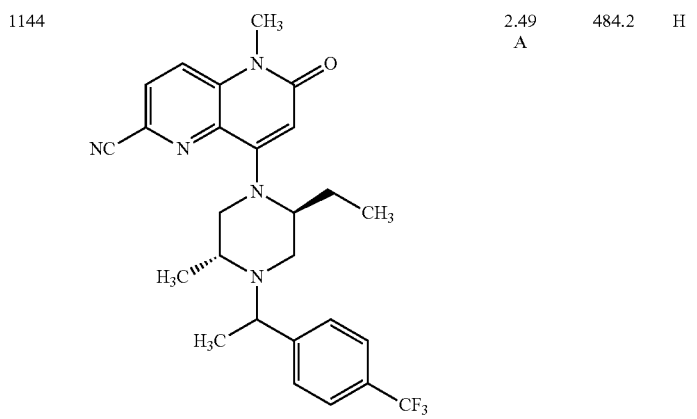 | 2.49 A | 484.2 | H |

TABLE 38-continued

| Ex. No. | Structure | LCMS RT and Method | M + H | Stereo chem. |
|---|---|---|---|---|
| 1145 | 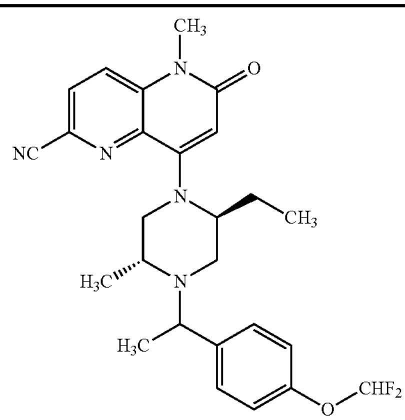 | 2.29 A | 482.3 | H |
| 1146 | 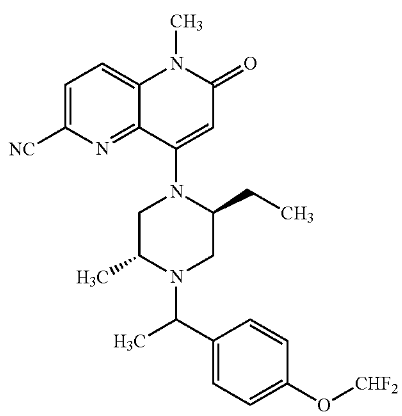 [SMILES: CC[C@H]1CN(C(C)c2ccc(OC(F)F)cc2)[C@H](C)CN1c1cc(=O)n(C)c2ccc(C#N)nc12] | 2.63 A | 514.2 | H |
| 1147 | 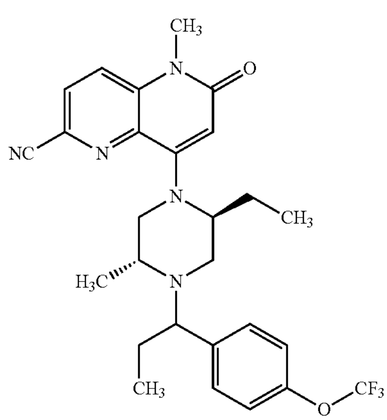 [SMILES: CCC(c1ccc(OC(F)(F)F)cc1)N1C[C@H](CC)N(c2cc(=O)n(C)c3ccc(C#N)nc23)C[C@H]1C] | 2.63 A | 514.2 | H |

The compounds of Table 39 were prepared according to the general procedure described in Example 246 by alkylation of the piperazine nitrogen with either an alkyl chloride or bromide. The crude material was purified by preparative HPLC to obtain the product.

TABLE 39

| Ex. No. | Structure | LCMS RT and Method | M + H | Stereo chem. |
|---|---|---|---|---|
| 1148 | 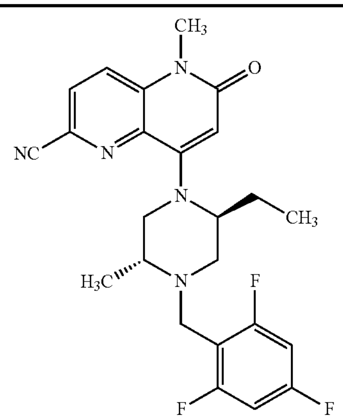 | 2.22 A | 456.2 | H |
| 1149 | 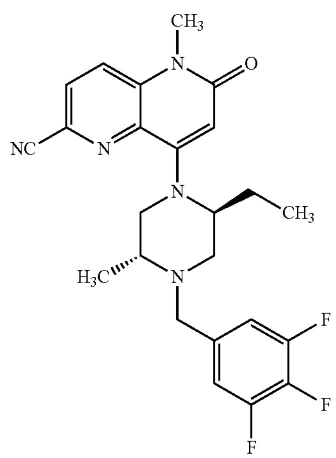 [SMILES: CC[C@H]1CN(Cc2cc(F)c(F)c(F)c2)[C@H](C)CN1c1cc(=O)n(C)c2ccc(C#N)nc12] | 2.31 A | 456.1 | H |

Example 1150

8-(4-(bis(4-fluorophenyl)methyl)-3-(hydroxymethyl)piperazin-1-yl)-5-methyl-6-oxo-5,6-dihydro-1,5-naphthyridine-2-carbonitrile

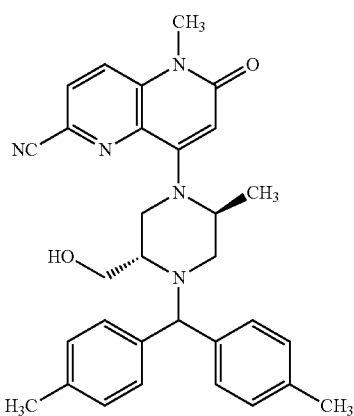

(1150)

Intermediate 1150A: methyl ((benzyloxy)carbonyl)-D-seryl-L-alaninate

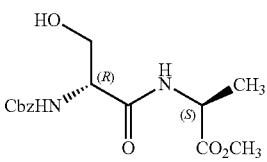

(1150)

Diisopropylethylamine (75 mL, 430 mmol) was added dropwise to a cooled mixture of methyl L-alaninate (20 g, 143 mmol), 1-(3-dimethylaminopropyl)-3-ethylcarbodiimide hydrochloride (33.0 g, 172 mmol), ((benzyloxy)carbonyl)-D-serine (34.3 g, 143 mmol) in dichloromethane (36 mL). The resulting mixture was stirred under nitrogen at ambient temperature for 16 h. After removing solvent in vacuo at 40° C., the residue was diluted with saturated sodium carbonate (200 mL), water (200 mL) and extracted with EtOAc (500 mL×2). The combined organic phases were washed with 1.5 M hydrochloric acid (200 mL), saturated brine solution (200 mL), dried over sodium sulfate and concentrated in vacuo at 40° C. to give methyl((benzyloxy)carbonyl)-D-seryl-L-alaninate (30 g, 64.6% yield) as a colorless solid. LCMS: m/z, 325.1 (M+H); rt 0.90 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Intermediate 1150B: (3R,6S)-3-(hydroxymethyl)-6-methylpiperazine-2,5-dione

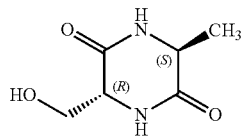

(1150B)

To a stirred solution of methyl ((benzyloxy)carbonyl)-D-seryl-L-alaninate (10 g, 30.8 mmol) in MeOH (100 mL) was added Pd—C (10% on carbon) (0.66 g, 6.17 mmol). The reaction mixture was stirred under a hydrogen bladder at 1 atm for 16 h. The reaction mixture was filtered through a Celite pad, washed with excess MeOH (150 mL) and the filtrate was refluxed at 70° C. for 16 h. The solvent was removed under reduced pressure to give (3R,6S)-3-(hydroxymethyl)-6-methylpiperazine-2,5-dione (4.5 g, 92% yield). $^1$H NMR (300 MHz, DMSO-$d_6$) δ ppm 8.09 (s, 1H), 7.91 (br s, 1H), 5.13 (br s, 1H), 3.92 (q, J=6.9 Hz, 1H), 3.49-3.77 (m, 3H), 1.23 (d, J=7.1 Hz, 3H).

Intermediate 1150C: ((2S,5S)-5-methylpiperazin-2-yl)methanol

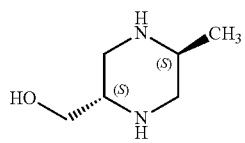

(1150C)

To (3R,6S)-3-(hydroxymethyl)-6-methylpiperazine-2,5-dione (5 g, 31.6 mmol) was added a solution of borane in THF (1M, 237 mL, 237 mmol). The mixture was heated to 70° C. for 18 h. The reaction mixture was cooled to 0° C. Methanol (65 mL) was added gradually, followed by 5 M hydrochloric acid (16 mL) and the reaction mixture was heated to 70° C. for 2 h. The reaction mixture was cooled to room temperature, the resulting solid was filtered, the cake was washed with THF (40 mL) and dried to give ((2S,5S)-5-methylpiperazin-2-yl)methanol, 2 HCl (4.4 g, 68.5% yield) as an off-white solid. $^1$H NMR (300 MHz, D20) δ ppm 3.80-3.89 (m, 1H), 3.53-3.73 (m, 5H), 3.10-3.33 (m, 2H), 1.35 (d, J=6.4 Hz, 3H).

Intermediate 1150D: 8-((2S,5S)-5-(hydroxymethyl)-2-methylpiperazin-1-yl)-5-methyl-6-oxo-5,6-dihydro-1,5-naphthyridine-2-carbonitrile

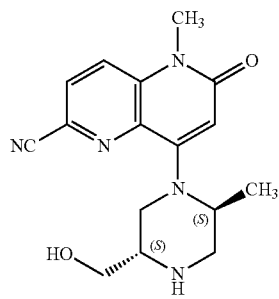

(1150D)

To a stirred solution of ((2S,5S)-5-methylpiperazin-2-yl)methanol, 2 HCl (500 mg, 2.46 mmol) in acetonitrile (5 mL), DIPEA (2.58 mL, 14.77 mmol) and 6-cyano-1-methyl-2-oxo-1,2-dihydro-1,5-naphthyridin-4-yl trifluoromethanesulfonate (820 mg, 2.46 mmol) were added sequentially at room temperature. The reaction mixture was heated at 85° C. for 6 h. The solvent was removed under reduced pressure to give crude product which was purified via silica gel chromatography (15% MeOH (10% aq. NH$_3$)CHCl$_3$) to afford 8-((2S,5S)-5-(hydroxymethyl)-2-methylpiperazin-1-yl)-5-methyl-6-oxo-5,6-dihydro-1,5-naphthyridine-2-carbonitrile (250 mg, 32.4% yield). LCMS: m/z, 314.3 (M+H); rt 0.54 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Example 1150: 8-(4-(bis(4-fluorophenyl)methyl)-3-(hydroxymethyl)piperazin-1-yl)-5-methyl-6-oxo-5,6-dihydro-1,5-naphthyridine-2-carbonitrile To a stirred solution of 8-((2S,5S)-5-(hydroxymethyl)-2-methylpiperazin-1-yl)-5-methyl-6-oxo-5,6-dihydro-1,5-naphthyridine-2-carbonitrile (40 mg, 0.13 mmol), 6-cyano-1-methyl-2-oxo-1,2-dihydro-1,5-naphthyridin-4-yl trifluoromethanesulfonate (25 mg, 0.075 mmol) in acetonitrile (5 mL) was added DIPEA (0.09 mL, 0.51 mmol). After 5 min at room temperature, 4,4'-(bromomethylene)bis(methylbenzene) (70.3 mg, 0.26 mmol) was added. The reaction mixture was heated at 85° C. for 6 h. The solvent was removed under reduced pressure and the crude product was purified by preparative HPLC. Column: Waters XBridge C18, 150 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0 minute hold at 15% B, 15-46% B over 20 minutes, then a 5 minute hold at 100% B; Flow Rate: 15 mL/min; Column Temperature: 25° C. Fractions containing the product were combined and dried via centrifugal evaporation to give 8-((2S,5S)-4-(di-p-tolylmethyl)-5-(hydroxymethyl)-2-methylpiperazin-1-yl)-5-methyl-6-oxo-5,6-dihydro-1,5-naphthyridine-2-carbonitrile (2 mg, 3.09% yield). LCMS: m/z, 508.3 (M+H); rt 2.296 min; (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min):0-3; % B: 0-100%. $^1$H NMR (400 MHz, DMSO-d$_6$) δ ppm 8.17-8.10 (m, 1H), 8.08-8.01 (m, 1H), 7.41 (d, J=8.1 Hz, 2H), 7.36 (d, J=8.1 Hz, 2H), 7.11 (d, J=7.8 Hz, 2H), 7.07 (d, J=8.1 Hz, 2H), 6.12 (s, 1H), 4.84 (s, 1H), 4.82-4.73 (m, 1H), 4.31 (t, J=4.4 Hz, 1H), 3.77-3.64 (m, 2H), 3.63-3.57 (m, 1H), 3.52 (s, 4H), 2.96-2.82 (m, 2H), 2.43-2.38 (m, 1H), 2.24 (s, 3H), 2.21 (s, 3H), 1.23 (d, J=6.6 Hz, 3H).

The examples in the Table 40 were prepared according to the general procedure described in Example 1150, substituting (4,4'-(bromomethylene)bis(methylbenzene) with the appropriate benzhydryl bromides in the synthetic sequence. When the synthesis provided a mixture of diastereomers, the mixture was separated at the final stage using either preparative chromatography or preparative chiral chromatography. The absolute stereochemistry was not assigned at the newly formed carbon-nitrogen bond.

TABLE 40

| Ex. No. | Structure | LCMS RT and Method | M + H | Stereo chem. |
|---------|-----------|--------------------|-------|--------------|
| 1151 | 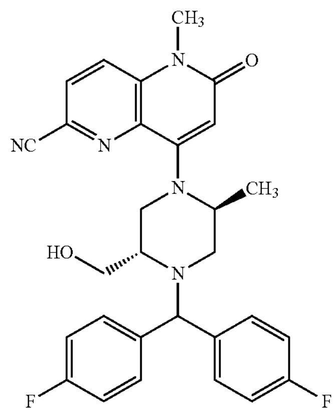 [SMILES: C[C@H]1CN(C(c2ccc(F)cc2)c2ccc(F)cc2)[C@H](CO)CN1c1cc(=O)n(C)c2ccc(C#N)nc12] | 2.07 A | 516.2 | H |
| 1152 | 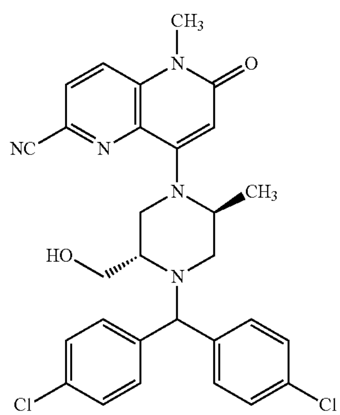 [SMILES: C[C@H]1CN(C(c2ccc(Cl)cc2)c2ccc(Cl)cc2)[C@H](CO)CN1c1cc(=O)n(C)c2ccc(C#N)nc12] | 2.35 A | 549.1 | H |
| 1153 | 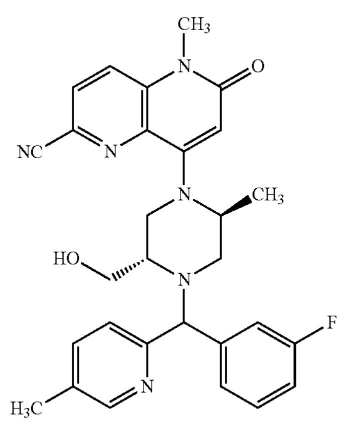 [SMILES: Cc1ccc(C(c2cccc(F)c2)N2C[C@H](C)N(c3cc(=O)n(C)c4ccc(C#N)nc34)C[C@H]2CO)nc1] | 1.80 A | 513.2 | H |

TABLE 40-continued

| Ex. No. | Structure | LCMS RT and Method | M + H | Stereo chem. |
|---|---|---|---|---|
| 1154 | 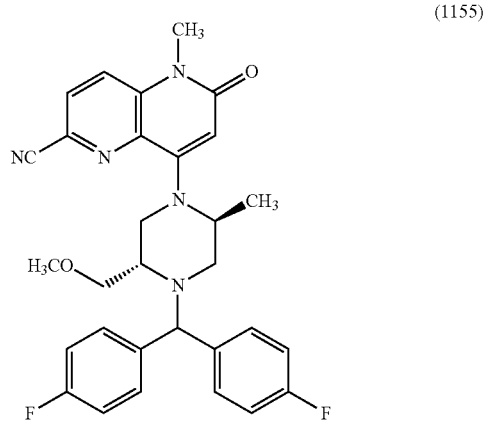 [SMILES: COC[C@@H]1CN(c2cc(=O)n(C)c3ccc(C#N)nc23)[C@@H](C)CN1C(c1ccc(F)cc1)c1ccc(F)cc1] | 1.82 A | 513.2 | H |

Example 1155

8-((2S,5S)-4-(bis(4-fluorophenyl)methyl)-5-(methoxymethyl)-2-methylpiperazin-1-yl)-5-methyl-6-oxo-5,6-dihydro-1,5-naphthyridine-2-carbonitrile (1155)

Intermediate A85: tert-butyl (2S,5S)-5-(hydroxymethyl)-2-methylpiperazine-1-carboxylate

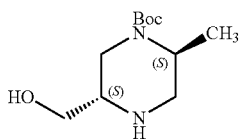
(1155A)

To an ice cooled, stirred solution of ((2S,5S)-5-methylpiperazin-2-yl)methanol, 2 HCl (2.1 g, 10.34 mmol) in MeOH (10 mL), Et₃N (4.32 mL, 31.0 mmol) was added. After 5 min., Boc-anhydride (5.76 mL, 24.81 mmol) in MeOH (14.5 mL) was added dropwise over a period of 15 min. The reaction mixture was allowed to reach room temperature, stirred for 1 h followed by heating at 50° C. for 16 h. The reaction mixture was concentrated and the residue was dissolved in EtOH (40 mL). A solution of NaOH (2.1 g, 52 mmol) in water (40 mL) was added and the reaction mixture was heated at 100° C. for 16 h. The reaction mixture was cooled to room temperature, neutralized with aqueous 1.5 N HCl (~300 mL) to pH 9 and extracted with chloroform (3×100 mL). The combined organic extracts were dried over sodium sulfate, filtered and concentrated to give tert-butyl (2S,5S)-5-(hydroxymethyl)-2-methylpiperazine-1-carboxylate (2.0 g, 84% yield). LCMS: m/z, 231.3 (M+H); rt 0.70 min. (LCMS Method: Column: Waters Acquity UPLC BEH C18 (2.1×50 mm) 1.7 μm, Mobile phase A: 10 mM ammonium acetate: acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm). ¹H NMR (400 MHz, METHANOL-d4) δ ppm 4.06-4.14 (m, 1H), 3.76 (dd, J=13.8, 1.8 Hz, 1H), 3.57-3.65 (m, 1H), 3.52 (dd, J=10.8, 6.8 Hz, 1H), 3.22 (dd, J=13.8, 4.3 Hz, 1H), 3.03 (dd, J=13.1, 5.0 Hz, 1H), 2.88-2.96 (m, 1H), 2.52 (dd, J=13.1, 3.0 Hz, 1H), 1.46 (s, 9H), 1.23 (d, J=7.0 Hz, 3H).

Intermediate 1155B: tert-butyl (2S,5S)-4-(bis(4-fluorophenyl)methyl)-5-(hydroxymethyl)-2-methylpiperazine-1-carboxylate

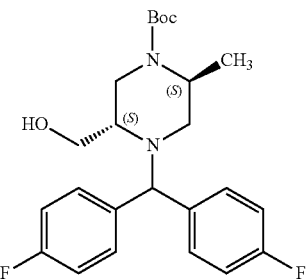
(1155B)

To a stirred solution of tert-butyl (2S,5S)-5-(hydroxymethyl)-2-methylpiperazine-1-carboxylate (0.5 g, 2.17 mmol)

in acetonitrile (5 mL), DIPEA (1.2 mL, 6.51 mmol), and 4,4'-(bromomethylene)bis(fluorobenzene) (0.62 g, 2.2 mmol) were added sequentially at room temperature, followed by heating at 80° C. for 3 h. The solvent was removed under reduced pressure to give the crude product which was purified by silica gel column chromatography using a 24 g silica gel flash column, eluting with 0-7% MeOH in DCM to afford tert-butyl (2S,5S)-4-(bis(4-fluorophenyl)methyl)-5-(hydroxymethyl)-2-methylpiperazine-1-carboxylate (650 mg, 69.2% yield) as an off-white solid. LCMS: m/z, 433.3 (M+H); rt 2.12 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Temperature: 50° C.; Flow rate: 0.7 mL/min; Detection: UV at 220 nm).

Intermediate 1155C: ((2S,5S)-1-(bis(4-fluorophenyl)methyl)-5-methylpiperazin-2-yl) methanol hydrochloride

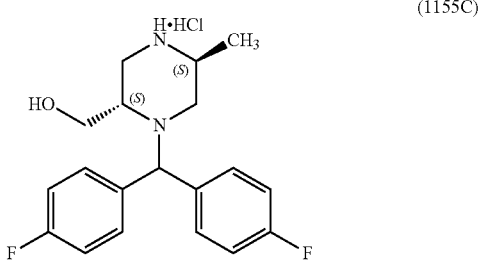

(1155C)

To a stirred solution of tert-butyl (2S,5S)-4-(bis(4-fluorophenyl)methyl)-5-(hydroxymethyl)-2-methylpiperazine-1-carboxylate (300 mg, 0.7 mmol) in DCM (5 mL), HCl (4N in dioxane) (1.73 mL, 6.94 mmol) was added drop wise at room temperature. After stirring for 3 h., solvent was removed under reduced pressure, co-distilled with acetonitrile (3×10 mL), crude was triturated with diethyl ether (10 mL) and dried to afford ((2S,5S)-1-(bis(4-fluorophenyl)methyl)-5-methylpiperazin-2-yl)methanol hydrochloride (235 mg, 92% yield) as an off-white solid. LCMS: m/z, 333.2 (M+H); rt 1.19 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Temperature: 50° C.; Flow rate: 0.7 mL/min; Detection: UV at 220 nm).

Intermediate 1155D: 8-((2S,5S)-4-(bis(4-fluorophenyl)methyl)-5-(hydroxymethyl)-2-methylpiperazin-1-yl)-5-methyl-6-oxo-5,6-dihydro-1,5-naphthyridine-2-carbonitrile

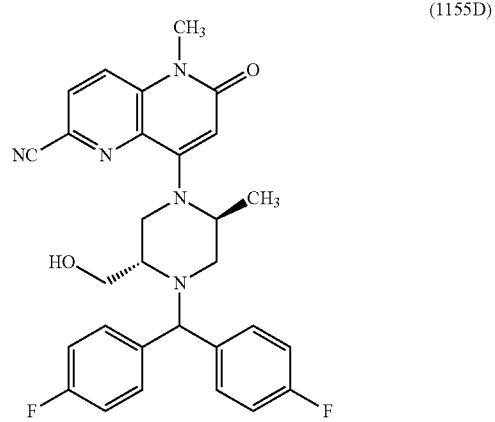

(1155D)

To a stirred solution of ((2S,5S)-1-(bis(4-fluorophenyl)methyl)-5-methylpiperazin-2-yl)methanol hydrochloride (230 mg, 0.624 mmol) in acetonitrile (5 mL), DIPEA (0.33 mL, 1.9 mmol) and 6-cyano-1-methyl-2-oxo-1,2-dihydro-1,5-naphthyridin-4-yl trifluoromethanesulfonate (208 mg, 0.624 mmol) were added sequentially at room temperature followed by heating at 80° C. for 4 h. The solvent was removed under reduced pressure, crude was purified by silica gel column chromatography using 24 g flash column, eluting with 40-100% EtOAc/hexane followed by 0-10% MeOH in CHCl₃ to afford 8-((2S,5S)-4-(bis(4-fluorophenyl)methyl)-5-(hydroxymethyl)-2-methylpiperazin-1-yl)-5-methyl-6-oxo-5,6-dihydro-1,5-naphthyridine-2-carbonitrile (160 mg, 49.8% yield). LCMS: m/z, 516.6 (M+H); rt 0.79 min. (LCMS Method: Column: Waters Acquity UPLC BEH C18 (3.0×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Example 1155: 8-((2S,5S)-4-(bis(4-fluorophenyl)methyl)-5-(methoxymethyl)-2-methylpiperazin-1-yl)-5-methyl-6-oxo-5,6-dihydro-1,5-naphthyridine-2-carbonitrile To a stirred solution of 8-((2S,5S)-4-(bis(4-fluorophenyl)methyl)-5-(hydroxymethyl)-2-methylpiperazin-1-yl)-5-methyl-6-oxo-5,6-dihydro-1,5-naphthyridine-2-carbonitrile (30 mg, 0.06 mmol) in THF (2 mL), NaH (4.65 mg, 0.12 mmol, 60%) was added at 0° C. After stirring for 5 min., methyl iodide (5.46 µL, 0.09 mmol) was added. The reaction mixture was allowed to reach room temperature. The reaction mixture was stirred for 4 h at room temperature. The reaction was quenched with ice-cold water and extracted with EtOAc (3×20 mL). The combined organic extracts were washed with brine, dried over sodium sulphate and concentrated to give crude product. The crude product was purified by preparative HPLC. Column: Waters XBridge C18, 150 mm×19 mm, 5-μm particles; Mobile Phase A: 5:95 acetonitrile:water with 10 mM ammonium acetate; Mobile Phase B: 95:5 acetonitrile:water with 10 mM ammonium acetate; Gradient: a 3 minute hold at 40% B, 40-61% B over 15 minutes, then a 5 minute hold at 100% B; Flow Rate: 15 mL/min; Column Temperature: 25° C. Fraction collection was triggered by MS signals. Fractions containing the product were combined and dried via centrifugal evaporation to give 8-((2S,5S)-4-(bis(4-fluorophenyl) methyl)-5-(methoxymethyl)-2-methylpiperazin-1-yl)-5-methyl-6-oxo-5,6-dihydro-1,5-naphthyridine-2-carbonitrile (5.9 mg, 18.2% yield). LCMS: m/z, 530.2 (M+H); rt 2.286 min; (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%. $^1$H NMR (400 MHz, DMSO-$d_6$) δ ppm 8.13-8.17 (m, 1H), 8.03-8.10 (m, 1H), 7.50-7.64 (m, 4H), 7.06-7.21 (m, 4H), 6.07 (s, 1H), 5.00 (s, 1H), 4.64-4.75 (m, 1H), 3.64-3.76 (m, 3H), 3.49-3.55 (m, 4H) 3.05 (s, 3H) 3.00 (td, J=6.24, 1.47 Hz, 1H) 2.81-2.88 (m, 1H) 2.35-2.42 (m, 1H) 1.29 (d, J=6.36 Hz, 3H).

The examples in the Table 41 were prepared according to the general procedure described in Example 1155, substituting (4,4'-(bromomethylene)bis(fluorobenzene) with the appropriate benzyhydryl bromides in the synthetic sequence.

Examples 1157 and 1158

8-((2S,5S)-4-((4-cyanophenyl)(4-fluorophenyl) methyl)-5-(methoxymethyl)-2-methylpiperazin-1-yl)-5-methyl-6-oxo-5,6-dihydro-1,5-naphthyridine-2-carbonitrile

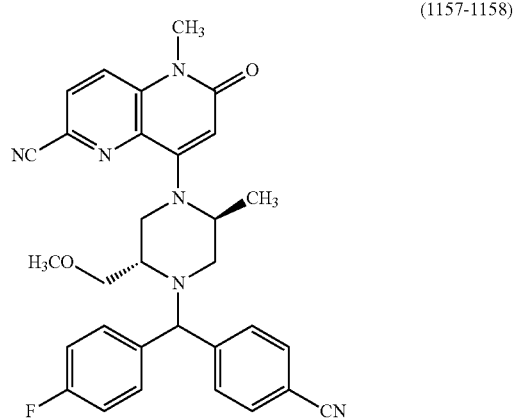 [SMILES: COC[C@@H]1CN(c2cc(=O)n(C)c3ccc(C#N)nc23)[C@@H](C)CN1C(c1ccc(F)cc1)c1ccc(C#N)cc1]

(1157-1158)

Intermediate 1157A: tert-butyl (2S,5S)-4-((4-cyanophenyl)(4-fluorophenyl)methyl)-5-(hydroxymethyl)-2-methylpiperazine-1-carboxylate

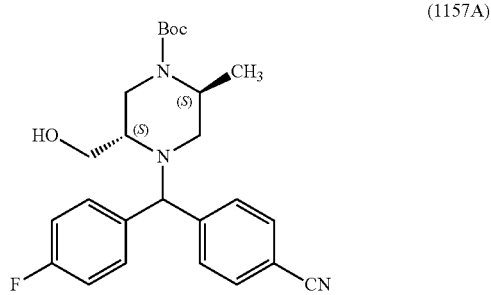

(1157A)

TABLE 41

| Ex. No. | Structure | LCMS RT and Method | M + H | Stereo chem. |
|---|---|---|---|---|
| 1156 | (structure shown) | 2.52 A | 522.3 | H |

To a solution of tert-butyl (2S,5S)-5-(hydroxymethyl)-2-methylpiperazine-1-carboxylate (250 mg, 1.09 mmol) in acetonitrile (10 mL) was added DIPEA (1.9 mL, 11 mmol) at room temperature. After 5 min, 4-(bromo(4-fluorophenyl)methyl)benzonitrile (315 mg, 1.09 mmol) was added followed by heating at 80° C. for 2 h. The solvent was removed under reduced pressure to obtain crude product, which was purified by flash chromatography (0-10% MeOH in DCM; 12 g column) to afford tert-butyl (2S,5S)-4-((4-cyanophenyl)(4-fluorophenyl)methyl)-5-(hydroxymethyl)-2-methylpiperazine-1-carboxylate (250 mg, 52.4% yield) as a diasteromeric mixture. LCMS: m/z, 438.3 (M–H); rt 1.96 and 2.04 min. (LCMS Method: Column: AQUITY UPLC BEH C18 (3.0×50 mm) 1.7 μm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100, Temperature: 27° C.; Flow rate: 0.7 mL/min; Detection: UV at 220 nm).

Intermediate 1157B: tert-butyl (2S,5S)-4-((4-cyanophenyl)(4-fluorophenyl)methyl)-5-(methoxymethyl)-2-methylpiperazine-1-carboxylate

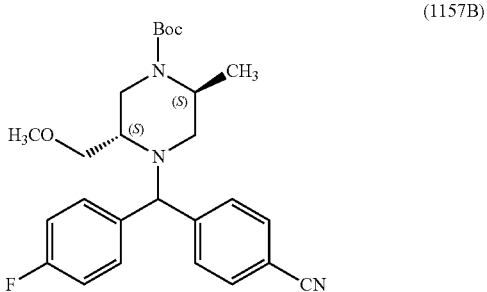

(1157B)

To a solution of tert-butyl (2S,5S)-4-((4-cyanophenyl)(4-fluorophenyl)methyl)-5-(hydroxymethyl)-2-methylpiperazine-1-carboxylate (200 mg, 0.46 mmol) in THF (2 mL) was added NaH (32.8 mg, 1.37 mmol, 60%) at 0° C. The reaction mixture was stirred for 5 min. Methyl iodide (0.09 mL, 1.4 mmol) was added and the reaction mixture was allowed to reach room temperature. The reaction mixture was stirred for 2 h. The reaction mixture was cooled to 0° C. The reaction was quenched with ice cold water. The reaction mixture was extracted with EtOAc (2×50 mL). The combined organic extracts were washed with brine, dried over $Na_2SO_4$ and concentrated to give crude product. The crude product was purified by silica gel flash column chromatography (5-10% MeOH in DCM; 12 g column) to afford tert-butyl (2S,5S)-4-((4-cyanophenyl)(4-fluorophenyl)methyl)-5-(methoxymethyl)-2-methylpiperazine-1-carboxylate (140 mg, 67.8% yield) as a diasteromeric mixture. LCMS: m/z, 454.3 (M+H); rt 2.16 and 2.18 min. (LCMS Method: Column: AQUITY UPLC BEH C18 (3.0×50 mm) 1.7 μm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100, Temperature: 27° C.; Flow rate: 0.7 mL/min; Detection: UV at 220 nm).

Intermediate 1157C: 4-((4-fluorophenyl)((2S,5S)-2-(methoxymethyl)-5-methylpiperazin-1-yl)methyl)benzonitrile hydrochloride

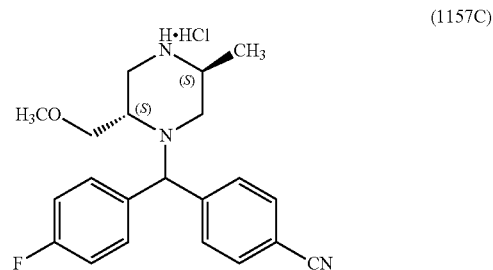

(1157C)

To a solution of tert-butyl (2S,5S)-4-((4-cyanophenyl)(4-fluorophenyl)methyl)-5-(methoxymethyl)-2-methylpiperazine-1-carboxylate (200 mg, 0.44 mmol) in DCM (4 mL) was added 4N HCl in dioxane (1.1 mL, 4.41 mmol) at 0° C. The reaction mixture was allowed to reach room temperature and stirred for 2 h. The reaction mixture was concentrated under reduced pressure to give 4-((4-fluorophenyl)((2S,5S)-2-(methoxymethyl)-5-methylpiperazin-1-yl)methyl)benzonitrile (140 mg, 90% yield). LCMS: m/z, 354.4 (M+H); rt 1.45 min. (LCMS Method: Column: AQUITY UPLC BEH C18 (3.0×50 mm) 1.7 μm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100, Temperature: 27° C.; Flow rate: 0.7 mL/min; Detection: UV at 220 nm).

Examples 1157 and 1158: 8-((2S,5S)-4-((4-cyanophenyl)(4-fluorophenyl)methyl)-5-(methoxymethyl)-2-methylpiperazin-1-yl)-5-methyl-6-oxo-5,6-dihydro-1,5-naphthyridine-2-carbonitrile To a solution of 4-((4-fluorophenyl)((2S,5S)-2-(methoxymethyl)-5-methylpiperazin-1-yl)methyl)benzonitrile (140 mg, 0.4 mmol) in acetonitrile (4 mL), DIPEA (0.7 mL, 3.96 mmol) and 6-cyano-1-methyl-2-oxo-1,2-dihydro-1,5-naphthyridin-4-yl trifluoromethanesulfonate (158 mg, 0.475 mmol) were added sequentially at room temperature followed by heating at 80° C. for 3 h. Solvent was removed under reduced pressure to obtain crude product, which was purified by flash column chromatography (75-90% EtOAc in hexane; 12 g column) to give 8-((2S,5S)-4-((4-cyanophenyl)(4-fluorophenyl)methyl)-5-(methoxymethyl)-2-methylpiperazin-1-yl)-5-methyl-6-oxo-5,6-dihydro-1,5-naphthyridine-2-carbonitrile as a diastereomeric mixture. The diasteromeric mixture was further purified by prep-HPLC method as follows: column: YMC EXRS (250 mm×20 mm ID, 5 μm); Mobile phase A=10 mM ammonium bicarbonate in water pH-9.5; Mobile phase B=acetonitrile:MeOH (50:50); Flow: 20 mL/min; Gradient: 0-100% B over 20 minutes, then a 1 minute hold at 100% B. The fractions were concentrated to give Example 1157 (20 mg, 9.13% yield) and Example 1158 (20 mg, 9.13% yield).

Example 1157: LCMS: 537.2 μm/z, (M+H); rt 3.260 min Column: Column-Kinetex XB-C18 (75×3 mm-2.6 μm), Mphase A: 10 mM ammonium formate in water: acetonitrile (98:2); Mphase B: 10 mM ammonium formate in water: acetonitrile (2:98); Flow: 1 mL/min; Gradient: 20-100% B over 4 minutes then 0.6 min hold at 100% B. $^1$H NMR (400

MHz, DMSO-d$_6$) δ ppm 8.13-8.17 (m, 1H), 8.05-8.09 (m, 1H), 7.72-7.81 (m, 4H), 7.59-7.65 (m, 2H), 7.14-7.21 (m, 2H), 6.07 (s, 1H), 5.11 (s, 1H), 4.67-4.76 (m, 1H), 3.66-3.73 (m, 3H), 3.56 (br d, J=3.0 Hz, 1H), 3.53 (s, 3H), 3.05 (s, 3H), 2.97-3.03 (m, 1H), 2.86-2.93 (m, 1H), 2.34-2.37 (m, 1H), 1.30 (d, J=6.5 Hz, 3H).

Example 1158: LCMS: 537.2 μm/z, (M+H); rt 3.307 min Column: Column-Kinetex XB-C18 (75×3 mm-2.6 μm), Mphase A: 10 mM ammonium formate in water: acetonitrile (98:2); Mphase B: 10 mM ammonium formate in water: acetonitrile (2:98); Flow: 1 mL/min; Gradient: 20-100% B over 4 minutes then 0.6 min hold at 100% B. $^1$H NMR (400 MHz, DMSO-d$_6$) δ ppm 8.13-8.17 (m, 1H), 8.05-8.10 (m, 1H), 7.77-7.83 (m, 4H), 7.57 (dd, J=8.8, 5.8 Hz, 2H), 7.15 (t, J=8.8 Hz, 2H), 6.06 (s, 1H), 5.12 (s, 1H), 4.68 (br s, 1H), 3.60-3.84 (m, 3H), 3.54-3.58 (m, 1H), 3.53 (s, 3H), 3.06 (s, 3H), 2.95-3.02 (m, 1H), 2.83-2.89 (m, 1H), 2.36-2.42 (m, 1H), 1.30 (d, J=6.5 Hz, 3H).

Examples 1159 and 1160

8-((2S,5S)-4-(1-(4-fluorophenyl)ethyl)-5-(methoxymethyl)-2-methylpiperazin-1-yl)-5-methyl-6-oxo-5,6-dihydro-1,5-naphthyridine-2-carbonitrile

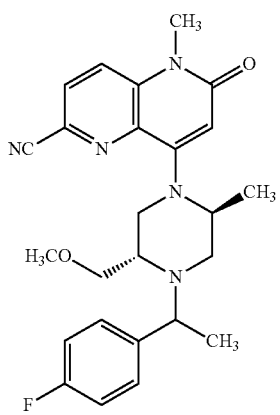
(1159-1160)

Intermediate 1159A: methyl N-benzyl-N-(N-(tert-butoxycarbonyl)-O-methyl-D-seryl)-L-alaninate

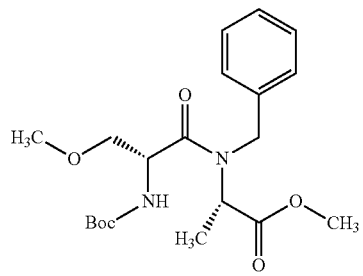
(1159A)

To a solution of methyl benzyl-L-alaninate (1 g, 5.17 mmol) in DMF (10 mL) were added HATU (2.95 g, 7.76 mmol), DIPEA (2.71 mL, 15.52 mmol) followed by N-(tert-butoxycarbonyl)-O-methyl-D-serine (1.13 g, 5.17 mmol).

The reaction mixture was stirred at room temperature for 2 h. The reaction mixture was extracted with EtOAc (2×50 mL), washed with water (30 mL), brine, dried over Na$_2$SO$_4$ and concentrated under reduced pressure to give crude product. The crude product was purified by flash chromatography (0-50% EtOAc/Pet ether; 24 g column) to afford methyl N-benzyl-N—(N-(tert-butoxycarbonyl)-O-methyl-D-seryl)-L-alaninate (1.6 g, 77% yield). LCMS: m/z, 395.2 (M+H); rt 2.75 min. (LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 1159B: (3S,6R)-1-benzyl-6-(methoxymethyl)-3-methylpiperazine-2,5-dione

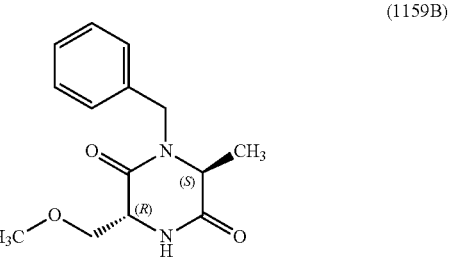
(1159B)

To a solution of methyl N-benzyl-N—(N-(tert-butoxycarbonyl)-O-methyl-D-seryl)-L-alaninate (1.3 g, 3.30 mmol) in DCM (10 mL) at 0° C. was added TFA (3.81 mL, 49.4 mmol). The reaction mixture was stirred at room temperature for 3 h. The reaction mixture was concentrated under reduced pressure to afford crude product. The crude product was purified by flash chromatography (0-10% MeOH/chloroform; 24 g column) to afford (3S,6R)-1-benzyl-6-(methoxymethyl)-3-methylpiperazine-2,5-dione (0.6 g, 68.0% yield). LCMS: m/z, 263.2 (M+H); rt 1.34 min. (LCMS Method: Column: Kinetex XB-C18 (3×75 mm) 2.6 μm; Mobile phase A: 10 mM ammonium formate:acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 1159C: (2S,5S)-1-benzyl-5-(methoxymethyl)-2-methylpiperazine

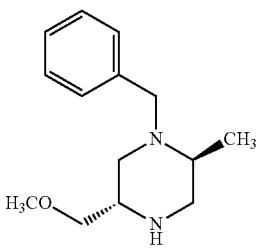
(1159C)

A stirred solution of (3S, 6R)-1-benzyl-3-(methoxymethyl)-6-methylpiperazine-2,5-dione (1.3 g, 4.96 mmol) in tetrahydrofuran (7 mL) was cooled to 0° C. and BH₃-THF (24.8 mL, 24.8 mmol) was added drop wise. The reaction mixture was allowed to reach room temperature and heated at 65° C. for 12 h. The reaction mixture was cooled to 0° C. The reaction was quenched with MeOH (5 mL) and HCl (11 N, 0.5 mL). The reaction mixture was refluxed for 3 h. The reaction mixture was concentrated reduced pressure to obtain (2S,5S)-1-benzyl-5-(methoxymethyl)-2-methylpiperazine (0.8 g, 68.2% yield). LCMS: m/z, 235.4 (M+H); rt 0.43 min. (LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 1159D: (2S,5S)-4-benzyl-2-(methoxymethyl)-5-methylpiperazine-1-carboxylate

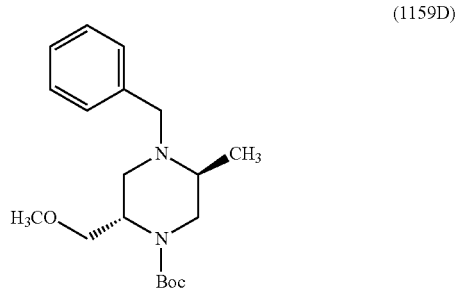 [SMILES: COC[C@@H]1CN(Cc2ccccc2)[C@@H](C)CN1C(=O)OC(C)(C)C]

(1159D)

To a solution of (2S,5S)-1-benzyl-5-(methoxymethyl)-2-methylpiperazine (0.8 g, 3.41 mmol) in DCM (15 mL) were added TEA (0.714 mL, 5.12 mmol) and Boc-anhydride (0.793 mL, 3.41 mmol). The reaction mixture was stirred at room temperature for 12 h. The reaction mixture was extracted with EtOAc (2×30 mL), washed with ice cold water (20 mL), dried over Na₂SO₄ and concentrated under reduced pressure to obtain crude product. The crude product was purified by flash chromatography (0-50% EtOAc in Pet ether; 24 g silica column) to afford (2S,5S)-4-benzyl-2-(methoxymethyl)-5-methylpiperazine-1-carboxylate (0.4 g, 35.0% yield). LCMS: m/z, 335.2 (M+H); rt 3.75 min. (LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 1159E: tert-butyl (2S,5S)-2-(methoxymethyl)-5-methylpiperazine-1-carboxylate

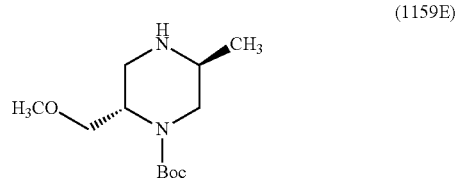 [SMILES: COC[C@@H]1CN[C@@H](C)CN1C(=O)OC(C)(C)C]

(1159E)

To a stirred solution of tert-butyl (2S,5S)-4-benzyl-2-(methoxymethyl)-5-methylpiperazine-1-carboxylate (0.4 g, 1.2 mmol) in MeOH (5 mL) were added 10% Pd—C (0.04 g, 0.36 mmol) and AcOH (0.07 mL, 1.2 mmol). The reaction mixture was hydrogenated under 5 kg pressure at room temperature. The reaction mixture was filtered through a Celite pad, washed with excess methanol (20 mL), and the filtrate was concentrated under reduced pressure to obtain tert butyl(2S,5S)-2-(methoxymethyl)-5-methylpiperazine-1-carboxylate (250 mg, 85% yield). ¹H NMR (400 MHz, DMSO-d₆) δ ppm 3.94-4.11 (m, 1H), 3.40-3.64 (m, 2H), 3.20-3.29 (m, 3H), 2.94-3.11 (m, 2H), 2.65 (br d, J=13.6 Hz, 1H), 1.95-1.92 (m, 2H), 1.40 (d, J=1.5 Hz, 9H), 0.92-1.10 (m, 3H).

Intermediate 1159F: tert-butyl(2S,5R)-4-(6-cyano-1-methyl-2-oxo-1,2-dihydro-1,5-naphthyridin-4-yl)-2-(methoxymethyl)-5-methylpiperazine-1-carboxylate

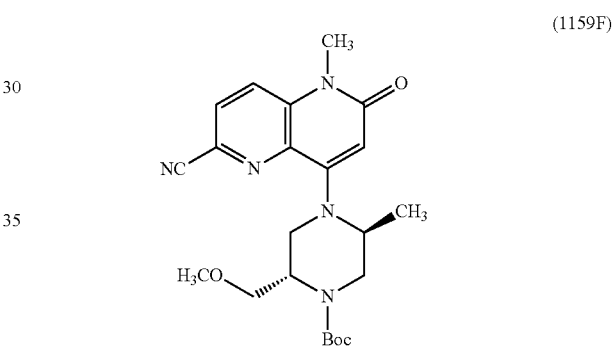

(1159F)

To a solution of 6-cyano-1-methyl-2-oxo-1,2-dihydro-1,5-naphthyridin-4-yl trifluoromethanesulfonate (0.25 g, 0.75 mmol) in acetonitrile (2 mL) were added sodium bicarbonate (0.32 g, 3.75 mmol) and tert-butyl (2S,5S)-2-(methoxymethyl)-5-methylpiperazine-1-carboxylate (0.18 g, 0.75 mmol). The reaction mixture was stirred at 80° C. for 12 h. The reaction mixture was concentrated under reduced pressure to afford crude product. The crude product was purified by flash chromatography (0-100% EtOAc in Pet ether; 24 g column) to afford tert-butyl(2S,5S)-4-(6-cyano-1-methyl-2-oxo-1,2-dihydro-1,5-naphthyridin-4-yl)-2-(methoxymethyl)-5-methylpiperazine-1-carboxylate (150 mg, 39.3% yield). LCMS: 428.2 μm/z, (M+H); rt 2.66 min. (LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 1159G: 8-((2S,5S)-5-(methoxymethyl)-2-methylpiperazin-1-yl)-5-methyl-6-oxo-5,6-dihydro-1,5-naphthyridine-2-carbonitrile

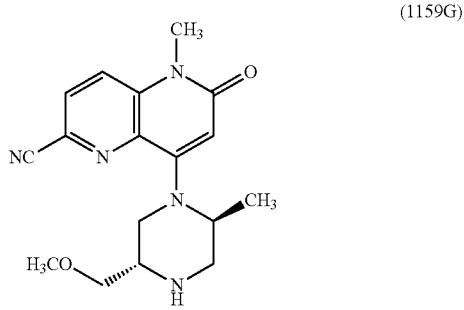 [SMILES: COC[C@@H]1CN(c2cc(=O)n(C)c3ccc(C#N)nc23)[C@@H](C)CN1]

(1159G)

To a solution of tert-butyl (2S,5S)-4-(6-cyano-1-methyl-2-oxo-1,2-dihydro-1,5-naphthyridin-4-yl)-2-(methoxymethyl)-5-methylpiperazine-1-carboxylate (150 mg, 0.35 mmol) in DCM (5 mL) were added 2,6-lutidine (0.245 mL, 2.11 mmol) and TMS-OTf (0.45 mL, 2.46 mmol) at 0° C. The reaction mixture was allowed to reach room temperature and stirred for 4 h. The reaction mixture was concentrated under reduced pressure and co-distilled with acetonitrile (2×10 mL) to afford 8-((2S,5S)-5-(methoxymethyl)-2-methylpiperazin-1-yl)-5-methyl-6-oxo-5,6-dihydro-1,5-naphthyridine-2-carbonitrile (120 mg, 89% yield). LCMS: m/z, 328.2 (M+H); rt 0.52 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Examples 1159 and 1160: 8-((2S,5S)-4-(1-(4-fluorophenyl)ethyl)-5-(methoxymethyl)-2-methylpiperazin-1-yl)-5-methyl-6-oxo-5,6-dihydro-1,5-naphthyridine-2-carbonitrile To a solution of 8-((2S,5S)-5-(methoxymethyl)-2-methylpiperazin-1-yl)-5-methyl-6-oxo-5,6-dihydro-1,5-naphthyridine-2-carbonitrile (70 mg, 0.214 mmol) in acetonitrile (2 mL) were added 1-(1-bromoethyl)-4-fluorobenzene (65.1 mg, 0.32 mmol) and sodium bicarbonate (35.9 mg, 0.43 mmol). The reaction mixture was stirred at 80° C. overnight. The solvent was removed under reduced pressure. The crude product was extracted with EtOAc (2×25 mL), washed with water, brine, dried over $Na_2SO_4$ and concentrated under reduced pressure to obtain crude product. The crude material was purified via preparative HPLC. Column: Waters XBridge C18, 150 mm×19 mm, 5-µm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 18% B, 18-59% B over 25 minutes, then a 5 minute hold at 100% B; Flow Rate: 15 mL/min; Column Temperature: 25° C. The diastereomeric mixture was further purified by prep-HPLC method as Column: Cellulose-4 (250×4.6 mm) 5 µm, Mobile Phase: 0.1% DEA in acetonitrile; Flow: 1.0 mL/min and column fractions were concentrated to afford Example 1159 (3.9 mg, 4% yield) and Example 1160 (3.6 mg, 4% yield).

Example 1159: LCMS: 450.2 µm/z, (M+H); rt 2.11 min; Column: Waters Xbridge BEH C18 XP (50×2.1 mm) 2.5 µm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.1 mL/min. $^1$H NMR (400 MHz, DMSO-$d_6$) δ ppm 8.20-8.14 (m, 1H), 8.11-8.02 (m, 1H), 7.43 (dd, J=5.9, 8.6 Hz, 2H), 7.18 (t, J=8.8 Hz, 2H), 6.04 (s, 1H), 4.72-4.63 (m, 1H), 3.98-3.91 (m, 1H), 3.71-3.61 (m, 1H), 3.57-3.45 (m, 5H), 3.41-3.34 (m, 1H), 3.07 (s, 3H), 2.94 (dd, J=3.7, 11.5 Hz, 1H), 2.82-2.73 (m, 2H), 1.28 (d, J=6.6 Hz, 3H), 1.21 (d, J=6.4 Hz, 3H).

Example 1160: LCMS: 450.2 µm/z, (M+H); rt 2.13 min. Column: Waters XBridge BEH C18 XP (50×2.1 mm) 2.5 µm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.1 mL/min. $^1$H NMR (400 MHz, DMSO-$d_6$) δ ppm 8.19-8.12 (m, 1H), 8.10-8.02 (m, 1H), 7.41 (dd, J=5.6, 8.6 Hz, 2H), 7.15 (t, J=8.9 Hz, 2H), 6.07 (s, 1H), 4.47 (br dd, J=1.6, 3.3 Hz, 1H), 3.93-3.86 (m, 1H), 3.84-3.78 (m, 1H), 3.63 (d, J=6.6 Hz, 2H), 3.56-3.48 (m, 4H), 3.42-3.35 (m, 1H), 3.22 (s, 3H), 2.72 (dd, J=3.2, 11.7 Hz, 1H), 2.27-2.18 (m, 1H), 1.33 (d, J=6.4 Hz, 3H), 1.07 (d, J=6.4 Hz, 3H).

The examples in the Table 42 were prepared according to the general procedure described in Examples 1159 and 1160 substituting 1-(1-bromoethyl)-4-fluorobenzene with the appropriate benzyl bromides in the synthetic sequence. When the reaction provided a mixture of diastereomers, the mixture was separated at the final stage using either preparative chromatography or preparative chiral chromatography. The absolute stereochemistry was not assigned at the newly formed carbon-nitrogen bond TABLE 42
| Ex. No. | Structure | LCMS RT and Method | M + H | Stereo chem. |
|---|---|---|---|---|
| 1161 | 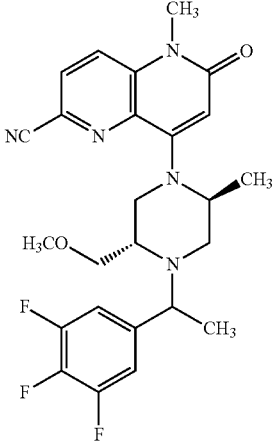 [SMILES: COC[C@@H]1CN(c2cc(=O)n(C)c3ccc(C#N)nc23)[C@@H](C)CN1C(C)c1cc(F)c(F)c(F)c1] | 2.13 A | 472.1 | H |
| 1162 | 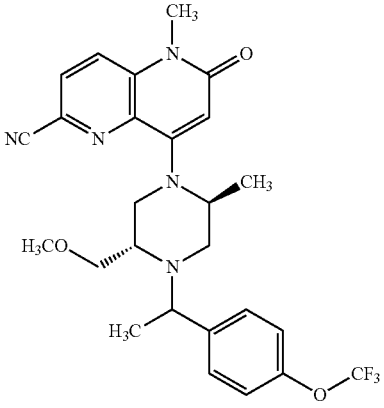 [SMILES: COC[C@@H]1CN(c2cc(=O)n(C)c3ccc(C#N)nc23)[C@@H](C)CN1C(C)c1ccc(OC(F)(F)F)cc1] | 2.34 A | 516.2 | H |
| 1163 | 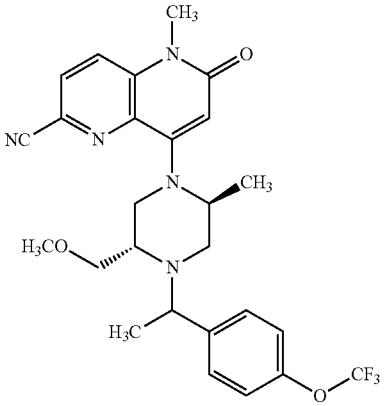 [SMILES: COC[C@@H]1CN(c2cc(=O)n(C)c3ccc(C#N)nc23)[C@@H](C)CN1C(C)c1ccc(OC(F)(F)F)cc1] | 2.36 A | 516.2 | H |

Example 1164

8-((2S,5S)-4-(bis(4-fluorophenyl)methyl)-5-(ethoxymethyl)-2-methylpiperazin-1-yl)-5-methyl-6-oxo-5,6-dihydro-1,5-naphthyridine-2-carbonitrile

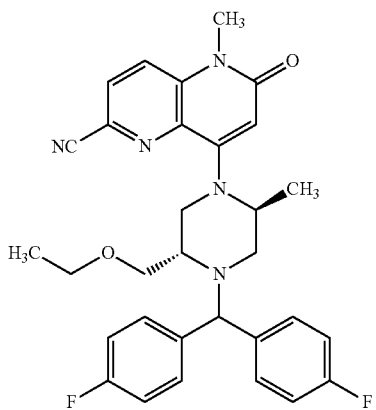

(1164)

Intermediate 1164A: tert-butyl (2S,5S)-4-(bis(4-fluorophenyl)methyl)-5-(ethoxymethyl)-2-methylpiperazine-1-carboxylate

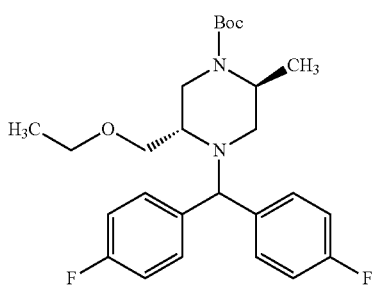

(1164A)

To an ice cooled stirred solution of tert-butyl (2S,5S)-4-(bis(4-fluorophenyl) methyl)-5-(hydroxymethyl)-2-methylpiperazine-1-carboxylate (100 mg, 0.23 mmol) in THF (5 mL), sodium hydride (11.1 mg, 0.46 mmol) was added under argon and stirred for 10 min. Iodoethane (0.04 mL, 0.46 mmol) was added and the reaction mixture was allowed to reach room temperature and stirred for 6 h. The reaction was quenched with ice-cold water. The reaction mixture was extracted with EtOAc (3×30 mL). The organic portion was washed with brine, dried over sodium sulphate and concentrated. The crude product was purified by silica gel column chromatography using 12 g flash column, eluting with 40-60% EtOAc/Hexane to afford tert-butyl (2S,5S)-4-(bis(4-fluorophenyl) methyl)-5-(ethoxymethyl)-2-methylpiperazine-1-carboxylate (45 mg, 42.3% yield) as off-white solid. LCMS: m/z, 461.6 (M+H); rt 1.68 min. (LCMS Method: Column: AQUITY UPLC BEH C18 (3.0×50 mm) 1.7 µm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100; Temperature: 27° C.; Flow rate: 0.7 mL/min; Detection: UV at 220 nm).

Intermediate 1164B: (2S,5S)-1-(bis(4-fluorophenyl)methyl)-2-(ethoxymethyl)-5-methylpiperazine hydrochloride

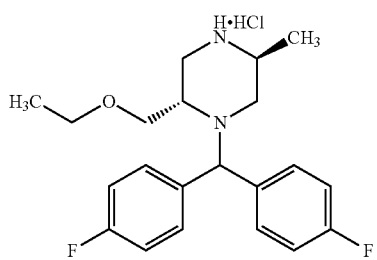

(1164B)

To a stirred solution of tert-butyl (2S,5S)-4-(bis(4-fluorophenyl)methyl)-5-(ethoxymethyl)-2-methylpiperazine-1-carboxylate (40 mg, 0.09 mmol) in DCM (4 mL), HCl (4 N in dioxane) (0.217 mL, 0.87 mmol) was added dropwise at room temperature. After stirring for 4 h., the solvent was removed under reduced pressure to obtain the crude product, which was triturated with diethyl ether to afford (2S,5S)-1-(bis(4-fluorophenyl)methyl)-2-(ethoxymethyl)-5-methylpiperazine hydrochloride (30 mg, 87% yield). LCMS: m/z, 361.5 (M+H); rt 1.72 min. (LCMS Method: Column: AQUITY UPLC BEH C18 (3.0×50 mm) 1.7 µm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100; Temperature: 27° C.; Flow rate: 0.7 mL/min; Detection: UV at 220 nm).

Example 1164: 8-((2S,5S)-4-(bis(4-fluorophenyl)methyl)-5-(ethoxymethyl)-2-methylpiperazin-1-yl)-5-methyl-6-oxo-5,6-dihydro-1,5-naphthyridine-2-carbonitrile To a stirred solution of (2S,5S)-1-(bis(4-fluorophenyl)methyl)-2-(ethoxymethyl)-5-methylpiperazine hydrochloride (30 mg, 0.076 mmol) in acetonitrile (1 mL), DIPEA (0.04 mL, 0.23 mmol) and 6-cyano-1-methyl-2-oxo-1,2-dihydro-1,5-naphthyridin-4-yl trifluoromethanesulfonate (25.2 mg, 0.08 mmol) were added sequentially at room temperature. The reaction mixture was heated at 80° C. for 4 h. The reaction mixture was cooled to room temperature. The solvent was removed under reduced pressure to give crude product, which was purified via preparative HPLC. Column: Waters XBridge C18, 19×150 mm, 5 µm particles; Mobile Phase A: 10 mM ammonium acetate; Mobile Phase B: acetonitrile; Gradient: 15-50% B over 20 minutes, then a 5 minute hold at 100% B; Flow: 15 mL/min. Fraction collection was triggered by MS signals. Fractions containing the product were combined and dried via centrifugal evaporation to give 8-((2S,5S)-4-(bis(4-fluorophenyl)methyl)-5-(ethoxymethyl)-2-methylpiperazin-1-yl)-5-methyl-6-oxo-5,6-dihydro-1,5-naphthyridine-2-carbonitrile (16 mg, 38.6% yield). LCMS: m/z, 544.2 (M+H); rt 2.408 min. (LCMS Method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-$d_6$) δ ppm 8.11-8.19 (m, 1H), 8.01-8.10 (m, 1H), 7.45-7.64 (m, 4H), 7.15 (dt, J=11.19, 8.83 Hz, 4H), 6.09 (s, 1H), 5.00 (s, 1H), 4.64-4.76 (m, 1H), 3.61-3.76 (m, 3H), 3.47-3.60 (m, 4H), 3.11-3.27 (m, 2H), 2.95-3.04 (m, 1H), 2.85 (dd, J=11.49, 3.42 Hz, 1H), 2.35-2.42 (m, 1H), 1.30 (d, J=6.60 Hz, 3H), 0.94 (t, J=6.97 Hz, 3H).

Example 1165

N-(((2R,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)acetamide

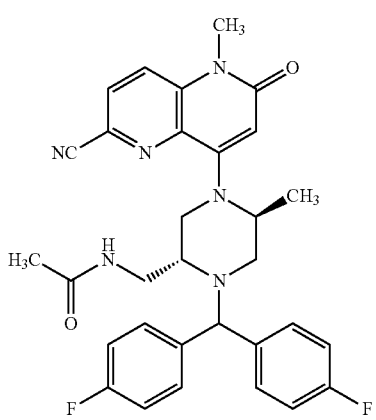

(1165)

Intermediate 1165A: 8-((2S,5S)-4-(bis(4-fluorophenyl)methyl)-5-(chloromethyl)-2-methylpiperazin-1-yl)-5-methyl-6-oxo-5,6-dihydro-1,5-naphthyridine-2-carbonitrile

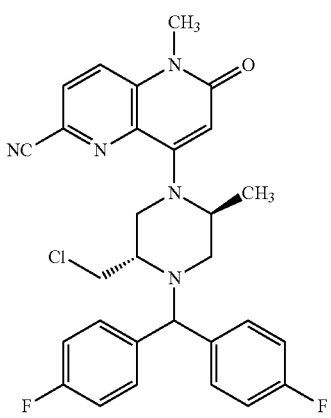

(1165A)

To a stirred solution of 8-((2S,5S)-4-(bis(4-fluorophenyl)methyl)-5-(hydroxymethyl)-2-methylpiperazin-1-yl)-5-methyl-6-oxo-5,6-dihydro-1,5-naphthyridine-2-carbonitrile (170 mg, 0.33 mmol) in DCM (5 mL), triethylamine (0.14 mL, 1 mmol), Mesyl-Cl (0.05 mL, 0.66 mmol) and catalytic amount of DMAP were added sequentially at 0° C. under nitrogen. The reaction mixture was allowed to reach room temperature and stirred overnight. The reaction mixture was extracted with DCM (2×30 mL), washed with water, brine and dried over sodium sulphate. Solvent was removed under reduced pressure to obtain 8-((2S,5S)-4-(bis(4-fluorophenyl)methyl)-5-(chloromethyl)-2-methylpiperazin-1-yl)-5-methyl-6-oxo-5,6-dihydro-1,5-naphthyridine-2-carbonitrile (150 mg, 85% yield). LCMS: m/z, 534.2 (M+H); rt 2.08 min. (LCMS Method: Column: AQUITY UPLC BEH C18 (3.0×50 mm) 1.7 μm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100; Temperature: 27° C.; Flow rate: 0.7 mL/min; Detection: UV at 220 nm).

Intermediate 1165B: 8-((2S,5S)-5-(azidomethyl)-4-(bis(4-fluorophenyl)methyl)-2-methylpiperazin-1-yl)-5-methyl-6-oxo-5,6-dihydro-1,5-naphthyridine-2-carbonitrile

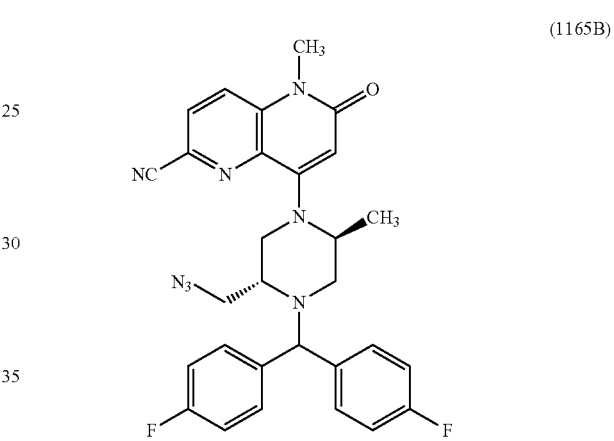

(1165B)

To a stirred solution of 8-((2S,5S)-4-(bis(4-fluorophenyl)methyl)-5-(chloromethyl)-2-methylpiperazin-1-yl)-5-methyl-6-oxo-5,6-dihydro-1,5-naphthyridine-2-carbonitrile (70 mg, 0.13 mmol) in DMF (3 mL), sodium azide (25.6 mg, 0.39 mmol) was added at room temperature. The reaction mixture was heated at 80° C. overnight. The reaction mixture was cooled to room temperature and extracted with EtOAc (3×30 mL), washed with water, brine and dried over sodium sulphate. Solvent was removed under reduced pressure to give crude product, which was purified by silica gel column chromatography using 12 g flash column, eluting with 25-100% EtOAc in Pet ether. The fractions were concentrated under reduced pressure to obtain 8-((2S,5S)-5-(azidomethyl)-4-(bis(4-fluorophenyl) methyl)-2-methylpiperazin-1-yl)-5-methyl-6-oxo-5,6-dihydro-1,5-naphthyridine-2-carbonitrile (60 mg, 85% yield) as a pale yellow solid. LCMS: m/z, 541.2 (M+H); rt 2.07 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Intermediate 1165C: 8-((2S,5R)-5-(aminomethyl)-4-(bis(4-fluorophenyl)methyl)-2-methylpiperazin-1-yl)-5-methyl-6-oxo-5,6-dihydro-1,5-naphthyridine-2-carbonitrile

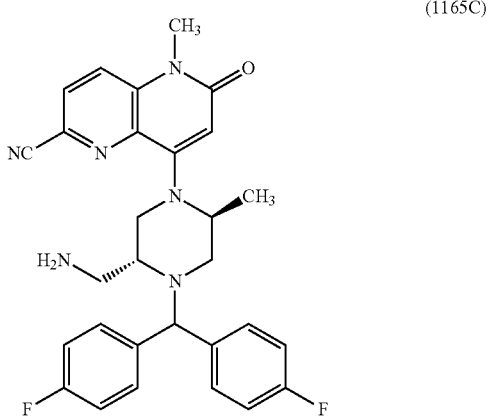 [SMILES: C[C@H]1CN(C(c2ccc(F)cc2)c2ccc(F)cc2)[C@H](CN)CN1c1cc(=O)n(C)c2ccc(C#N)nc12]

(1165C)

To a stirred solution of 8-((2S,5S)-5-(azidomethyl)-4-(bis(4-fluorophenyl) methyl)-2-methylpiperazin-1-yl)-5-methyl-6-oxo-5,6-dihydro-1,5-naphthyridine-2-carbonitrile (60 mg, 0.11 mmol) in THF (2 mL)/water (1 mL), triphenylphosphine (87 mg, 0.33 mmol) was added. The reaction mixture was heated at 65° C. for 6 h. The reaction mixture was cooled to room temperature and the solvent was removed under reduced pressure, co-distilled with toluene (3×5 mL) and dried to afford 8-((2S,5R)-5-(aminomethyl)-4-(bis(4-fluorophenyl)methyl)-2-methylpiperazin-1-yl)-5-methyl-6-oxo-5,6-dihydro-1,5-naphthyridine-2-carbonitrile (50 mg, 88% yield). LCMS: m/z, 515.4 (M+H); rt 1.49 min. (LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Example 1165: N-(((2R,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)acetamide To a stirred solution of 8-((2S,5R)-5-(aminomethyl)-4-(bis(4-fluorophenyl) methyl)-2-methylpiperazin-1-yl)-5-methyl-6-oxo-5,6-dihydro-1,5-naphthyridine-2-carbonitrile (25 mg, 0.05 mmol) in pyridine (1 mL), Ac2O (0.02 mL) was added at 0° C. The reaction mixture was allowed to reach room temperature and stirred overnight. The reaction mixture was extracted with DCM (3×20 mL), washed with water, brine and dried over sodium sulphate. The solvent was removed under reduced pressure to afford the crude product, which was purified via preparative HPLC. Column: Waters XBridge C18, 19×150 mm, 5 µm particles; Mobile Phase A: 10 mM ammonium acetate; Mobile Phase B: acetonitrile; Gradient: 15-50% B over 20 minutes, then a 5 minute hold at 100% B; Flow: 15 mL/min. Fraction collection was triggered by MS signals. Fractions containing the product were combined and dried via centrifugal evaporation to give N-(((2R,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)acetamide (2 mg, 7.10% yield). LCMS: m/z, 557.3 (M+H); rt 1.98 min. (LCMS Method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d6) S ppm 8.19-8.10 (m, 1H), 8.09-8.02 (m, 1H), 7.54 (ddd, J=5.9, 8.7, 15.0 Hz, 4H), 7.45 (br t, J=4.9 Hz, 1H), 7.13 (dt, J=5.6, 8.6 Hz, 4H), 6.03 (s, 1H), 5.01 (s, 1H), 4.91-4.73 (m, 1H), 3.61-3.49 (m, 5H), 3.41 (br s, 2H), 3.02-2.85 (m, 2H), 2.35 (br d, J=12.0 Hz, 1H), 1.60 (s, 3H), 1.19 (d, J=6.6 Hz, 3H).

Example 1166 methyl (((2R,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)carbamate

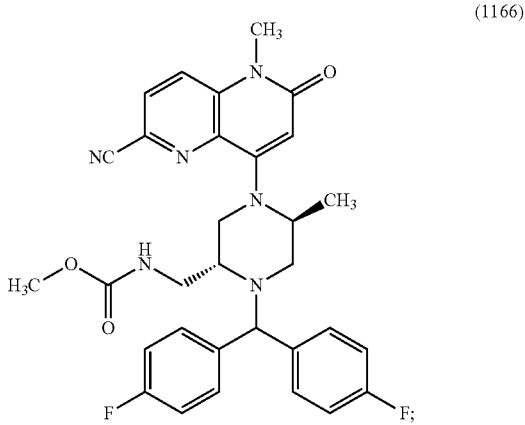 [SMILES: COC(=O)NC[C@@H]1CN(c2cc(=O)n(C)c3ccc(C#N)nc23)[C@@H](C)CN1C(c1ccc(F)cc1)c1ccc(F)cc1]

(1166)

To a stirred solution of 8-((2S,5R)-5-(aminomethyl)-4-(bis(4-fluorophenyl) methyl)-2-methylpiperazin-1-yl)-5-methyl-6-oxo-5,6-dihydro-1,5-naphthyridine-2-carbonitrile (25 mg, 0.05 mmol) in DCM (1 mL), DIPEA (0.025 mL, 0.146 mmol), methyl chloroformate (8 µL, 0.1 mmol) were added sequentially at 0° C. The reaction mixture was allowed to reach room temperature and stirred overnight. The reaction mixture was extracted with DCM (3×20 mL), washed with water, brine and dried over sodium sulphate. The solvent was removed under reduced pressure to obtain crude product, which was purified via preparative HPLC with the following conditions: Column: Waters XBridge C18, 19×150 mm, 5 µm particles; Mobile Phase A: 10 mM ammonium acetate; Mobile Phase B: acetonitrile; Column Temperature: 25° C. Fraction collection was triggered by MS signals. The fractions containing the product were combined and dried via centrifugal evaporation to give methyl (((2R,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)carbamate (1 mg, 3.6% yield). LCMS: m/z, 573.3 (M+H); rt 2.121 min. (LCMS Method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.17-8.10 (m, 1H), 8.09-8.00 (m, 1H), 7.63-7.44 (m, 4H), 7.22-7.07 (m, 4H), 6.85 (br d, J=1.7 Hz, 1H), 6.03 (s, 1H), 5.03 (s, 1H), 4.90-4.75 (m, 1H), 3.58-3.47 (m, 5H), 3.36 (br s, 5H), 3.04-2.91 (m, 2H), 2.35 (br d, J=12.2 Hz, 1H), 1.18 (br d, J=6.4 Hz, 3H).

Example 1167

8-((2S,5R)-4-(bis(4-fluorophenyl)methyl)-2-methyl-5-(morpholinomethyl)piperazin-1-yl)-5-methyl-6-oxo-5,6-dihydro-1,5-naphthyridine-2-carbonitrile

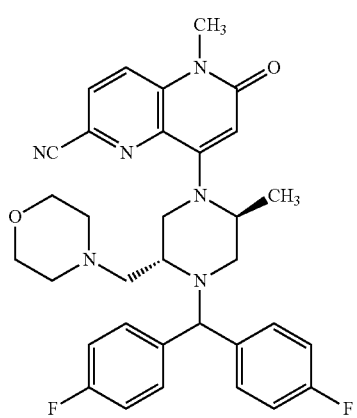

(1167)

To a stirred solution of 8-((2S,5S)-4-(bis(4-fluorophenyl)methyl)-5-(chloromethyl)-2-methylpiperazin-1-yl)-5-methyl-6-oxo-5,6-dihydro-1,5-naphthyridine-2-carbonitrile (70 mg, 0.13 mmol) in acetonitrile (3 mL), potassium carbonate (54.3 mg, 0.39 mmol), potassium iodide (37.0 mg, 0.22 mmol), morpholine (0.02 mL) were added sequentially at room temperature. The reaction mixture was heated at 70° C. overnight. The reaction mixture was cooled to room temperature, filtered through syringe filter, the filtrate was concentrated under reduced pressure to give the crude product. The crude product was purified via preparative HPLC with the following conditions: Column: Waters XBridge C18, 150 mm×19 mm, 5 μm particles; Mobile Phase A: 5:95 acetonitrile:water with 0.1% trifluoroacetic acid; Mobile Phase B: 95:5 acetonitrile: water with 0.1% trifluoroacetic acid; Gradient: a 2 minute hold at 20% B, 20-60% B over 25 minutes, then a 5 minute hold at 100% B; Flow Rate: 15 mL/min; Column Temperature: 25° C. Fraction collection was triggered by MS signals. The fractions containing the product were combined and dried via centrifugal evaporation to obtain 8-((2S,5R)-4-(bis(4-fluorophenyl)methyl)-2-methyl-5-(morpholinomethyl)piperazin-1-yl)-5-methyl-6-oxo-5,6-dihydro-1,5-naphthyridine-2-carbonitrile (16 mg, 20.88% yield). LCMS: m/z, 585.2 (M+H); rt 2.325 min. (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.12-8.19 (m, 1H) 8.01-8.09 (m, 1H) 7.48-7.67 (m, 4H) 7.15 (dt, J=11.86, 8.86 Hz, 4H) 6.19 (s, 1H) 4.94 (s, 1H) 4.64-4.75 (m, 1H) 3.82-3.92 (m, 1H) 3.60 (br dd, J=12.84, 2.08 Hz, 1H) 3.51 (s, 3H) 3.24-3.32 (m, 3H) 2.95-3.07 (m, 1H) 2.81 (dd, J=11.86, 3.30 Hz, 1H) 2.60 (br t, J=11.00 Hz, 1H) 2.32-2.44 (m, 2H) 1.92-2.02 (m, 2H) 1.74-1.90 (m, 2H) 1.35 (d, J=6.60 Hz, 3H). One proton peak merged with moisture peak.

The examples in the Table 43 were prepared according to the general procedure described in Example 1167, substituting morpholine with the appropriate amines in the synthetic sequence. The reaction mixture was purified by preparative HPLC to obtain the pure product.

TABLE 43

| Ex. No. | Structure | LCMS RT and Method | M + H | Stereo chem. |
|---|---|---|---|---|
| 1168 | ![structure] | 1.91 A | 571.2 | H |

TABLE 43-continued

| Ex. No. | Structure | LCMS RT and Method | M + H | Stereo chem. |
|---|---|---|---|---|
| 1169 | 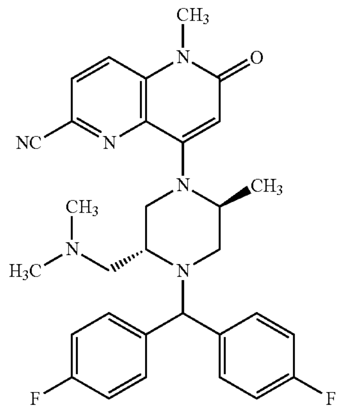 [SMILES: C[C@H]1CN(C(c2ccc(F)cc2)c2ccc(F)cc2)[C@H](CN(C)C)CN1c1cc(=O)n(C)c2ccc(C#N)nc12] | 2.15 A | 543.2 | H |

Examples 1170 and 1171

8-((2S,5S)-4-((4-cyanophenyl)(4-fluorophenyl)methyl)-2-ethyl-5-(methoxymethyl) piperazin-1-yl)-5-methyl-6-oxo-5,6-dihydro-1,5-naphthyridine-2-carbonitrile (1170-1171)

Intermediate 1170A: tert-butyl (2S,5S)-4-(6-cyano-1-methyl-2-oxo-1,2-dihydro-1,5-naphthyridin-4-yl)-5-ethyl-2-(methoxymethyl)piperazine-1-carboxylate

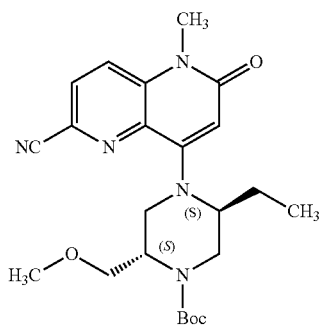
(1170A)

Intermediate 1170A was synthesized according to the general procedure described for Intermediate 1159F, by substituting methyl benzyl-L-alaninate with methyl (S)-2-(benzylamino)butanoate in the synthetic sequence. LCMS: m/z, 386.2, (M+H-56); rt-1.67 min. LCMS Method Column Name: AQUITY UPLC BEH C18 (3.0×50 mm) 1.7 μm Buffer: 10 mM ammonium acetate Mobile Phase A: Buffer:acetonitrile (95:5) Mobile phase B: Buffer:acetonitrile (5:95) Method: % B:0 min-20:2 min-100:2.2 min-100 Flow: 0.7 mL/min.

Intermediate 1170B: 8-((2S,5S)-2-ethyl-5-(methoxymethyl) piperazin-1-yl)-5-methyl-6-oxo-5,6-dihydro-1,5-naphthyridine-2-carbonitrile. TFA Salt

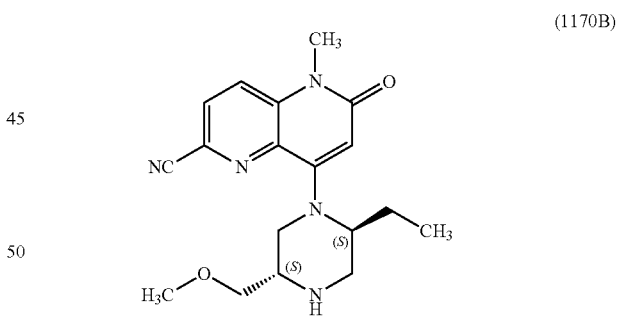
(1170B)

To a solution of tert-butyl (2S,5S)-4-(6-cyano-1-methyl-2-oxo-1,2-dihydro-1,5-naphthyridin-4-yl)-5-ethyl-2-(methoxymethyl) piperazine-1-carboxylate (100 mg, 0.23 mmol) in DCM (4 mL) was added TFA (0.02 mL, 0.24 mmol) at 0° C. The reaction mixture was allowed to reach room temperature and stirred for 2 h. The reaction mixture was concentrated under reduced pressure to obtain 8-((2S,5S)-2-ethyl-5-(methoxymethyl) piperazin-1-yl)-5-methyl-6-oxo-5,6-dihydro-1,5-naphthyridine-2-carbonitrile, TFA salt (60 mg, 78% yield). LCMS: m/z, 342.2, (M+H); rt-0.77 min. LCMS Method Column Name: AQUITY UPLC BEH C18 (3.0×50 mm) 1.7 μm Buffer: 10 mM ammonium acetate Mobile Phase A: Buffer: acetonitrile (95:5) Mobile phase B:

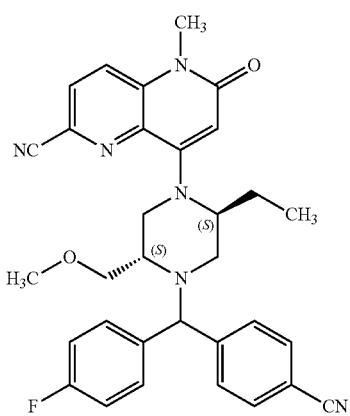

Buffer:acetonitrile (5:95) Method: % B: 0 min-20:2 min-100:2.2 min-100 Flow: 0.7 mL/min.

Examples 1170 and 1171: 8-((2S,5S)-4-((4-cyanophenyl) (4-fluorophenyl) methyl)-2-ethyl-5-(methoxymethyl) piperazin-1-yl)-5-methyl-6-oxo-5,6-dihydro-1,5-naphthyridine-2-carbonitrile To a solution of 8-((2S,5S)-2-ethyl-5-(methoxymethyl) piperazin-1-yl)-5-methyl-6-oxo-5,6-dihydro-1,5-naphthyridine-2-carbonitrile, TFA salt (60 mg, 0.18 mmol) in acetonitrile (4 mL) was added sodium bicarbonate (14.8 mg, 0.18 mmol) at room temperature. After 5 min, 4-(bromo(4-fluorophenyl)methyl)benzonitrile (51.0 mg, 0.18 mmol) was added followed by heating at 85° C. for 14 h. The solvent was removed under reduced pressure. The crude material was purified via preparative HPLC. Column: X-Bridgephenyl (250×19) mm 5 μm Mobile Phase A-10 mM ammonium acetate in water, pH:4.5 Mobile phase B-acetonitrile:Methanol (1:1) Flowrate: 20 mL/min. Fractions containing the product were combined and dried via centrifugal evaporation to give Example 1170 (5.4 mg, 5.0% yield) and Example 1171 (4.8 mg, 4.76% yield).

Example 1170: LCMS: m/z, 551.2 (M+H); rt 2.16 min. (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.15 (d, J=8.8 Hz, 1H), 8.06 (d, J=9.0 Hz, 1H), 7.79 (d, J=8.3 Hz, 2H), 7.74 (d, J=8.3 Hz, 2H), 7.63 (dd, J=8.7, 5.5 Hz, 2H), 7.17 (t, J=8.8 Hz, 2H), 6.05 (s, 1H), 5.09 (s, 1H), 4.44 (br. s., 1H), 3.76 (d, J=13.2 Hz, 1H), 3.68-3.61 (m, 2H), 3.60-3.53 (m, 1H), 3.02-2.95 (m, 4H), 2.85-2.79 (m, 1H), 2.42 (d, J=12.0 Hz, 2H), 2.16-2.06 (m, 2H), 1.91-1.81 (m, 1H), 1.76 (br. s., 1H), 0.67 (t, J=7.5 Hz, 3H).

Example A1171: LCMS: m/z, 551.2 (M+H); rt 2.16 min. (LCMS Method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.15 (d, J=8.8 Hz, 1H), 8.06 (d, J=8.8 Hz, 1H), 7.84-7.76 (m, 4H), 7.57 (dd, J=8.8, 5.6 Hz, 2H), 7.16 (t, J=8.8 Hz, 2H), 6.03 (s, 1H), 5.11 (s, 1H), 4.41 (br. s., 1H), 3.82-3.69 (m, 2H), 3.65-3.50 (m, 5H), 3.03 (s, 3H), 2.95 (br. s., 1H), 2.82-2.74 (m, 1H), 2.47 (d, J=12.5 Hz, 1H), 2.21-2.06 (m, 1H), 1.88-1.74 (m, 1H), 0.67 (t, J=7.3 Hz, 3H).

Example 1172

8-((2R,5R)-4-(bis(4-fluorophenyl) methyl)-5-(hydroxymethyl)-2-methylpiperazin-1-yl)-5-methyl-6-oxo-5,6-dihydro-1,5-naphthyridine-2-carbonitrile

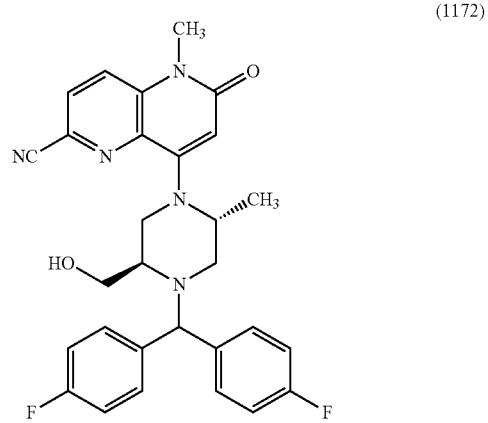 [SMILES: C[C@@H]1CN(C(c2ccc(F)cc2)c2ccc(F)cc2)[C@@H](CO)CN1c1cc(=O)n(C)c2ccc(C#N)nc12]

(1172)

Intermediate 1172A: tert-butyl (2R,5R)-4-(bis(4-fluorophenyl)methyl)-5-(hydroxymethyl)-2-methylpiperazine-1-carboxylatecarboxylate

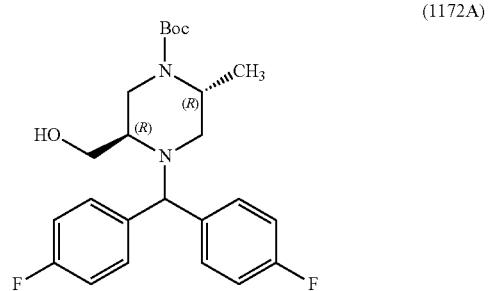

(1172A)

To a solution of tert-butyl (2R,5R)-5-(hydroxymethyl)-2-methylpiperazine-1-carboxylate (100 mg, 0.43 mmol) in acetonitrile (5 mL) was added DIPEA (0.76 mL, 4.34 mmol) at room temperature. After 5 min, 4,4'-(bromomethylene) bis(fluorobenzene) (148 mg, 0.52 mmol) was added and the reaction mixture was heated at 80° C. for 12 h. The reaction mixture was cooled to room temperature, the solvent was removed under reduced pressure and the crude product was purified by Combiflash using a 12 g silica gel column and eluted with 5-10% MeOH in DCM. The required fractions concentrated to obtain tert-butyl (2R,5R)-4-(bis(4-fluorophenyl)methyl)-5-(hydroxymethyl)-2-methylpiperazine-1-carboxylate (130 mg, 69.2% yield) as an off-white solid; LCMS: m/z, 433.4 (M+H); rt 2.15 min. LCMS Method Column Name: AQUITY UPLC BEH C18 (3.0×50 mm) 1.7 μm Buffer:10 mM ammonium acetate Mobile Phase A: Buffer:acetonitrile (95:5) Mobile phase B: Buffer:acetonitrile (5:95) Method: % B: 0 min-20:2 min-100:2.2 min-100 Flow: 0.7 mL/min.

Intermediate 1172B: ((2R,5R)-1-(bis(4-fluorophenyl)methyl)-5-methylpiperazin-2-yl) methanol hydrochloride

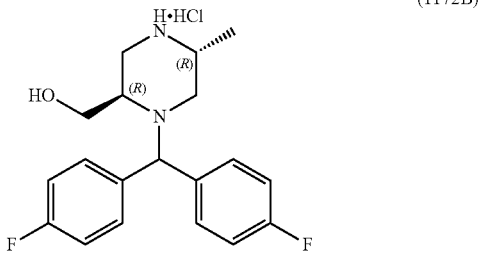

(1172B)

To a solution of tert-butyl (2R,5R)-4-(bis(4-fluorophenyl)methyl)-5-(hydroxymethyl)-2-methylpiperazine-1-carboxylate (100 mg, 0.23 mmol) in DCM (4 mL) was added 4 N HCl in dioxane (0.58 mL, 2.31 mmol) at 0° C. The reaction mixture was allowed to reach room temperature and stirred for 2 h. The solvent was removed under reduced pressure and the solid material was dried to afford ((2R,5R)-1-(bis(4-fluorophenyl)methyl)-5-methylpiperazin-2-yl)methanol hydrochloride (70 mg, 91% yield) as a gummy solid. LCMS: m/z, 333.2 (M+H); rt 1.44 min. LCMS Method Column Name: AQUITY UPLC BEH C18 (3.0×50 mm) 1.7 μm Buffer: 10 mM ammonium acetate Mobile Phase A: Buffer:acetonitrile (95:5) Mobile phase B: Buffer:acetonitrile (5:95) Method: % B: 0 min-20:2 min-100:2.2 min-100 Flow: 0.7 mL/min.

Example 1172: 8-((2R,5R)-4-(bis(4-fluorophenyl)methyl)-5-(hydroxymethyl)-2-methylpiperazin-1-yl)-5-methyl-6-oxo-5,6-dihydro-1,5-naphthyridine-2-carbonitrile To a solution of ((2R,5R)-1-(bis(4-fluorophenyl) methyl)-5-methylpiperazin-2-yl) methanol hydrochloride (59.8 mg, 0.18 mmol) in acetonitrile (2 mL) was add DIPEA (0.08 mL, 0.54 mmol) at room temperature. The reaction mixture was stirred at room temperature for 10 min and 6-cyano-1-methyl-2-oxo-1,2-dihydro-1,5-naphthyridin-4-yl trifluoromethanesulfonate (50 mg, 0.15 mmol) in acetonitrile (2 mL) was added. The reaction mixture was heated at 80° C. for 2 h. The solvent was removed under reduced pressure. The crude material was purified via preparative HPLC. Column: Waters XBridge C18, 150 mm×19 mm, 5-μm particles; Mobile Phase A: 5:95 acetonitrile:water with 10 mM ammonium acetate; Mobile Phase B: 95:5 acetonitrile:water with 10 mM ammonium acetate; Gradient: a 2 minute hold at 15% B, 15-55% B over 25 minutes, then a 5 minute hold at 100% B; Flow Rate: 15 mL/min; Column Temperature: 25° C. Fraction collection was triggered by signals. Fractions containing the product were combined and dried via centrifugal evaporation to obtain 8-((2R,5R)-4-(bis(4-fluorophenyl)methyl)-5-(hydroxymethyl)-2-methylpiperazin-1-yl)-5-methyl-6-oxo-,6-dihydro-1,5-naphthyridine-2-carbonitrile (3.2 mg, 4.00% yield); LCMS: m/z, 516.3 (M+H); rt 2.10 min. LCMS condition: Column: Waters XBridge BEH C18 XP (50×2.1 mm) 2.5 μm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.1 mL/min. $^1$H NMR (400 MHz, DMSO-$d_6$) δ ppm 8.17-8.10 (m, 1H), 8.08-8.02 (m, 1H), 7.59 (dd, J=5.6, 8.8 Hz, 2H), 7.53 (dd, J=5.6, 8.6 Hz, 2H), 7.20-7.05 (m, 4H), 6.13 (s, 1H), 5.01 (s, 1H), 4.85-4.74 (m, 1H), 4.36 (t, J=4.6 Hz, 1H), 3.76-3.67 (m, 2H), 3.63-3.57 (m, 1H), 3.55-3.47 (m, 3H), 2.92-2.81 (m, 2H), 2.35 (br dd, J=1.7, 13.4 Hz, 1H), 1.24 (d, J=6.6 Hz, 3H).

The examples in the Table 44 were prepared according to the general procedure described in Example 1172, substituting 4,4'-(bromomethylene)bis(fluorobenzene) with the appropriate benzhydryl bromides or benzyl bromides in the synthetic sequence. When the synthesis provided a mixture of diastereomers, the mixture was separated using either preparative chromatography or preparative chiral chromatography. The absolute stereochemistry was not assigned at the newly formed carbon-nitrogen bond.

TABLE 44

| Ex. No. | Structure | LCMS RT and Method | M + H | Stereo chem. |
|---|---|---|---|---|
| 1173 | 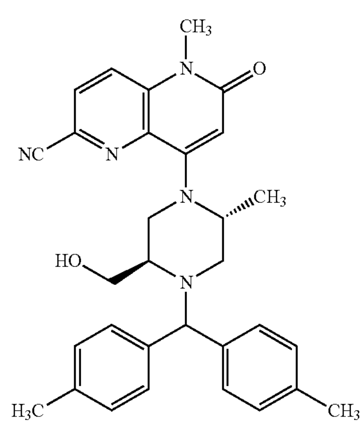 | 2.27 A | 508.3 | H |

TABLE 44-continued
| Ex. No. | Structure | LCMS RT and Method | M + H | Stereo chem. |
|---|---|---|---|---|
| 1174 | 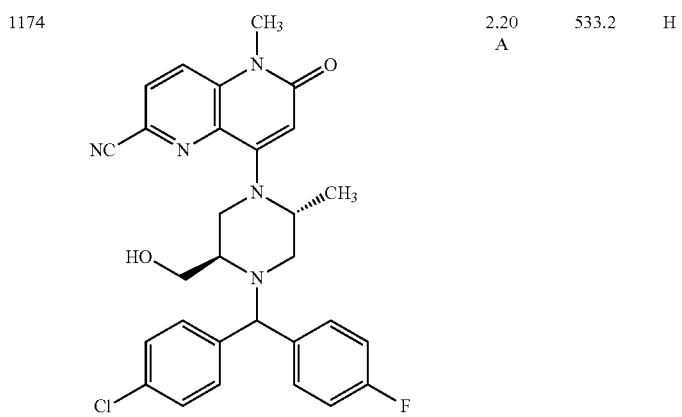 | 2.20 A | 533.2 | H |
| 1175 | 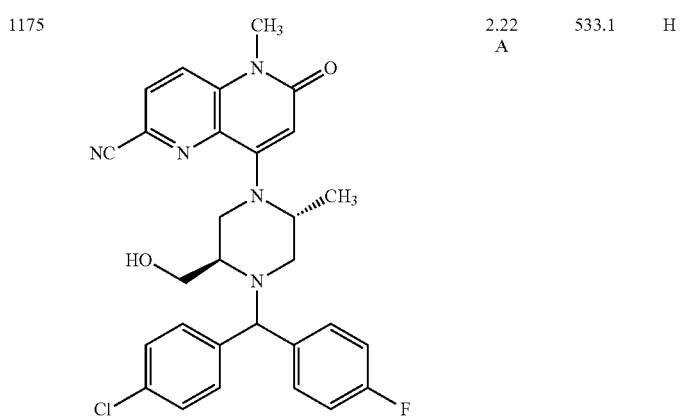 | 2.22 A | 533.1 | H |
| 1176 | 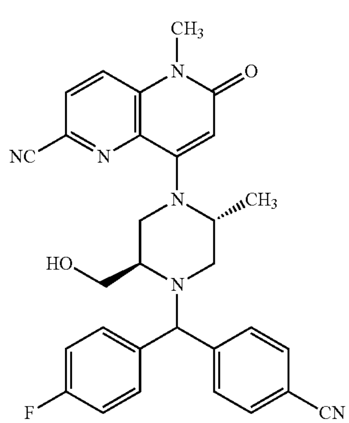 [SMILES: C[C@@H]1CN(C(c2ccc(F)cc2)c2ccc(C#N)cc2)[C@@H](CO)CN1c1cc(=O)n(C)c2ccc(C#N)nc12] | 1.91 A | 523.2 | H |

TABLE 44-continued
| Ex. No. | Structure | LCMS RT and Method | M + H | Stereo chem. |
|---|---|---|---|---|
| 1177 | 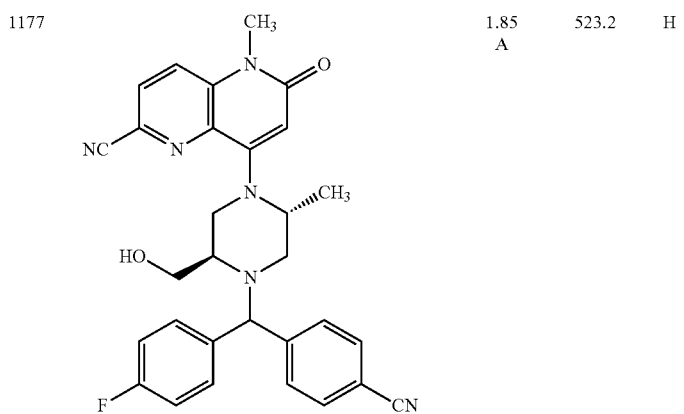 | 1.85 A | 523.2 | H |
| 1178 | 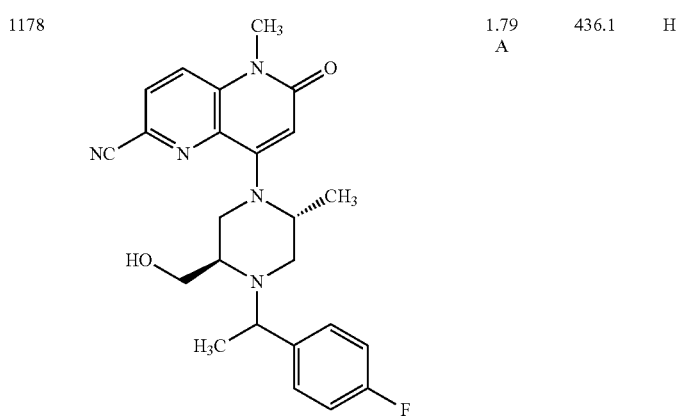 | 1.79 A | 436.1 | H |
| 1179 | 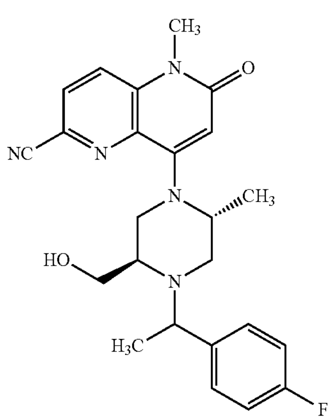 [SMILES: CC(c1ccc(F)cc1)N1C[C@@H](C)N(c2cc(=O)n(C)c3ccc(C#N)nc23)C[C@@H]1CO] | 1.80 A | 436.1 | H |

TABLE 44-continued
| Ex. No. | Structure | LCMS RT and Method | M + H | Stereo chem. |
|---|---|---|---|---|
| 1180 | 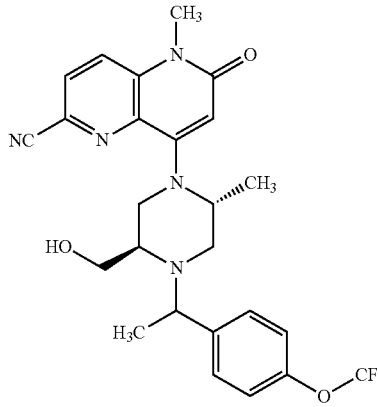 | 2.07 A | 502.1 | H |
| 1181 | 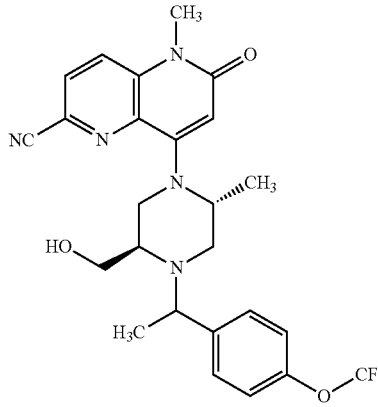 | 2.09 A | 502.2 | H |
| 1182 | 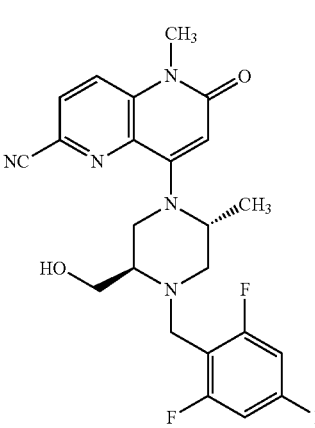 | 1.73 A | 458.2 | H |

Example 1183

8-((2R,5R)-4-(bis(4-fluorophenyl) methyl)-5-(methoxymethyl)-2-methylpiperazin-1-yl)-5-methyl-6-oxo-5,6-dihydro-1,5-naphthyridine-2-carbonitrile

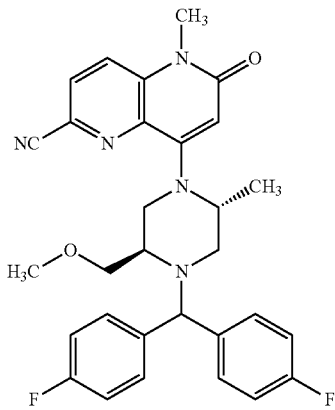

(1183)

Intermediate 1183A: tert-butyl (2R,5R)-4-(bis(4-fluorophenyl)methyl)-5-(methoxymethyl)-2-methylpiperazine-1-carboxylate

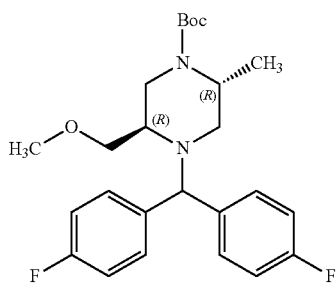

(1183A)

To a solution of tert-butyl (2R,5R)-4-(bis(4-fluorophenyl) methyl)-5-(hydroxymethyl)-2-methylpiperazine-1-carboxylate (150 mg, 0.35 mmol) in THF (4 mL) was added NaH (20.8 mg, 0.87 mmol) at 0° C. The reaction mixture was stirred for 5 min. Methyl iodide (0.07 mL, 1.04 mmol) was added drop wise, the reaction mixture was allowed to reach room temperature and stirred for 2 h. The reaction mixture was cooled to 0° C. The reaction was quenched with ice cold water. The reaction mixture was extracted with EtOAc (2×50 mL). The combined organic extracts were washed with brine, dried over Na$_2$SO$_4$ and concentrated under reduced pressure to obtain tert-butyl (2R,5R)-4-(bis(4-fluorophenyl) methyl)-5-(methoxymethyl)-2-methylpiperazine-1-carboxylate (120 mg, 77% yield). LCMS: m/z, 447.4 (M+H); rt 2.33 min. LCMS Method Column Name: AQUITY UPLC BEH C18 (3.0×50 mm) 1.7 µm Buffer: 10 mM ammonium acetate Mobile Phase A: Buffer: acetonitrile (95:5) Mobile phase B: Buffer: acetonitrile (5:95) Method: % B: 0 min-20:2 min-100:2.2 min-100 Flow: 0.7 mL/min.

Intermediate 1183B: (2R,5R)-1-(bis(4-fluorophenyl) methyl)-2-(methoxymethyl)-5-methylpiperazine hydrochloride

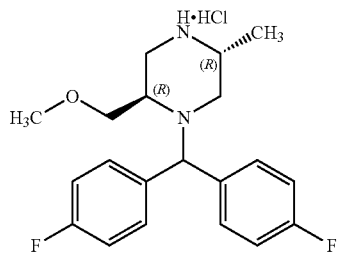

(1183B)

To a solution of tert-butyl (2R,5R)-4-(bis(4-fluorophenyl) methyl)-5-(methoxymethyl)-2-methylpiperazine-1-carboxylate (100 mg, 0.23 mmol) in DCM (2 mL) was added 4 M HCl in dioxane (1 mL) at 0° C. The reaction mixture was allowed to reach room temperature and stirred for 2 h. The solvent was removed under reduced pressure to obtain (2R,5R)-1-(bis(4-fluorophenyl)methyl)-2-(methoxymethyl)-5-methylpiperazine hydrochloride (65 mg, 84% yield). LCMS: m/z, 347.3 (M+H); rt 1.49 min. LCMS Method Column Name: AQUITY UPLC BEH C18 (3.0×50 mm) 1.7 µm Buffer: 10 mM ammonium acetate Mobile Phase A: Buffer: acetonitrile (95:5) Mobile phase B: Buffer: acetonitrile (5:95) Method: % B: 0 min-20:2 min-100:2.2 min-100 Flow: 0.7 mL/min.

Example 1183: 8-((2R,5R)-4-(bis(4-fluorophenyl) methyl)-5-(methoxymethyl)-2-methylpiperazin-1-yl)-5-methyl-6-oxo-5,6-dihydro-1,5-naphthyridine-2-carbonitrile To a solution of (2R,5R)-1-(bis(4-fluorophenyl) methyl)-2-(methoxymethyl)-5-methylpiperazine hydrochloride (50 mg, 0.14 mmol) in acetonitrile (4 mL) was added DIPEA (0.03 mL, 0.14 mmol) at room temperature. After 5 min., 6-cyano-,1-methyl-2-oxo-1,2-dihydro-1,5-naphthyridin-4-yl trifluoromethanesulfonate (48.1 mg, 0.14 mmol) was added. The reaction mixture was heated at 80° C. for 2 h. The solvent was removed under reduced pressure and the crude material was purified via preparative HPLC. Column: Waters XBridge C18, 150 mm×19 mm, 5 µm particles; Mobile Phase A: 5:95 acetonitrile:water with 10 mM ammonium acetate; Mobile Phase B: 95:5 acetonitrile: water with 10 mM ammonium acetate; Gradient: a 2 minute hold at 18% B, 18-67% B over 25 minutes, then a 5 minute hold at 100% B; Flow Rate: 15 mL/min; Column Temperature: 25° C. Fractions containing the product were combined and dried via centrifugal evaporation to obtain 8-((2R,5R)-4-(bis (4-fluorophenyl)methyl)-5-(methoxymethyl)-2-methylpiperazin-1-yl)-5-methyl-6-oxo-5,6-dihydro-1,5-naphthyridine-2-carbonitrile (14.4 mg, 18.8% yield). LCMS: m/z, 530.2 (M+H); rt 2.31 min. Column: Waters XBridge BEH C18 XP (50×2.1 mm) 2.5 μm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.1 mL/min. $^1$H NMR (400 MHz, DMSO-$d_6$) δ ppm 8.10-8.18 (m, 1H), 8.01-8.08 (m, 1H), 7.46-7.68 (m, 4H), 7.14 (dt, J=11.74, 8.80 Hz, 4H), 6.05 (s, 1H), 4.98 (s, 1H), 4.60-4.75 (m, 1H), 3.63-3.79 (m, 3H), 3.45-3.57 (m, 4H), 3.04 (s, 4H), 2.83 (br dd, J=11.74, 3.18 Hz, 1H), 2.37 (br d, J=11.25 Hz, 1H), 1.28 (d, J=6.36 Hz, 3H).

Examples 1184 and 1185

8-(4-(2-chloro-4-fluorobenzyl)-3-((difluoromethoxy)methyl)piperazin-1-yl)-5-methyl-6-oxo-5,6-dihydro-1,5-naphthyridine-2-carbonitrile

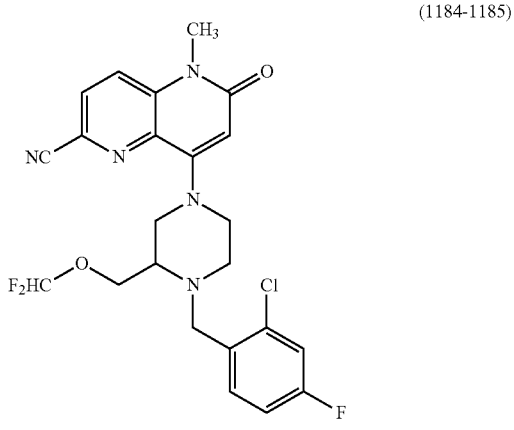 [SMILES: Cn1c(=O)cc(N2CCN(Cc3ccc(F)cc3Cl)C(COC(F)F)C2)c2nc(C#N)ccc21]

(1184-1185)

Intermediate 1184A: tert-butyl 4-(6-cyano-1-methyl-2-oxo-1,2-dihydro-1,5-naphthyridin-4-yl)-2-(hydroxymethyl)piperazine-1-carboxylate

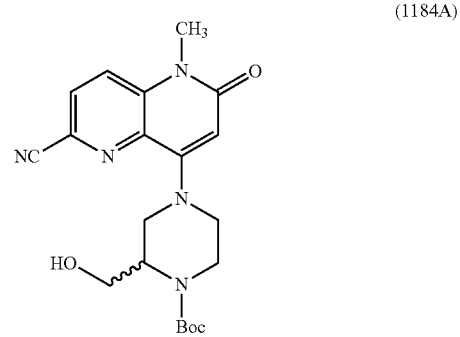 [SMILES: Cn1c(=O)cc(N2CCN(C(=O)OC(C)(C)C)C(CO)C2)c2nc(C#N)ccc21]

(1184A)

To a solution of 6-cyano-1-methyl-2-oxo-1,2-dihydro-1,5-naphthyridin-4-yl trifluoromethanesulfonate (3.47 g, 10.4 mmol) in acetonitrile (15 mL) was added tert-butyl 2-(hydroxymethyl)piperazine-1-carboxylate (1.5 g, 6.94 mmol), followed by DIPEA (3.63 mL, 20.81 mmol). The reaction mixture was stirred at 85° C. overnight. The reaction mixture was concentrated under reduced pressure to remove volatiles and the residue was dissolved in ethyl acetate and washed with water. The aqueous layer was back extracted with ethyl acetate (150 mL×2). The combined organic layer was flushed with brine, dried over Na$_2$SO$_4$, concentrated under reduced pressure to give crude product. The crude product was purified via flash chromatography (5-10% methanol/chloroform; 40 g silica gel column) to afford tert-butyl 4-(6-cyano-1-methyl-2-oxo-1,2-dihydro-1,5-naphthyridin-4-yl)-2-(hydroxymethyl)piperazine-1-carboxylate (2.415 g, 6.05 mmol, 87% yield). LCMS: m/z=400.1 (M+H); rt 1.18 min. (LCMS Condition: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Intermediate 1184B: tert-butyl 4-(6-cyano-1-methyl-2-oxo-1,2-dihydro-1,5-naphthyridin-4-yl)-2-((difluoromethoxy)methyl)piperazine-1-carboxylate

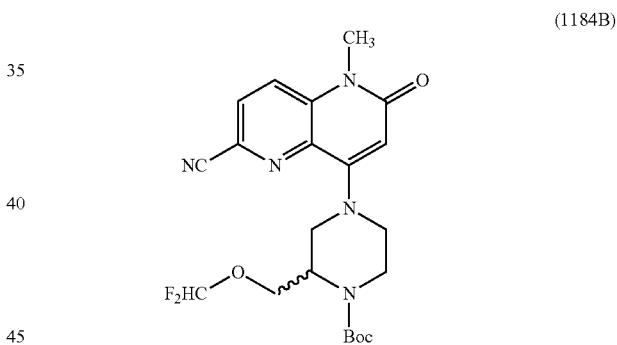

(1184B)

To a solution of tert-butyl 4-(6-cyano-1-methyl-2-oxo-1,2-dihydro-1,5-naphthyridin-4-yl)-2-(hydroxymethyl)piperazine-1-carboxylate (0.27 g, 0.68 mmol) in CH$_2$Cl$_2$ (3 mL)/water (3 mL) was added potassium acetate (0.27 g, 2.7 mmol). The reaction mixture was stirred at room temperature for 10 min and (bromodifluoromethyl) trimethylsilane (1.05 mL, 6.8 mmol) was added. The reaction mixture was stirred at the same temperature for 10 h. After 10 h, the reaction mixture was diluted with CH$_2$Cl$_2$ (20 mL), and was treated with water (10 mL) and extracted with CH$_2$Cl$_2$ (3×15 mL). The organic layer was combined and dried over anhydrous sodium sulfate to give tert-butyl 4-(6-cyano-1-methyl-2-oxo-1,2-dihydro-1,5-naphthyridin-4-yl)-2-((difluoromethoxy) methyl)piperazine-1-carboxylate (175 mg, 0.389 mmol, 57.6% yield). LCMS: m/z=450.1 (M+H); rt 1.50 min. (LCMS Condition: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Intermediate 1184C: 8-(3-((difluoromethoxy)methyl)piperazin-1-yl)-5-methyl-6-oxo-5,6-dihydro-1,5-naphthyridine-2-carbonitrile HCl

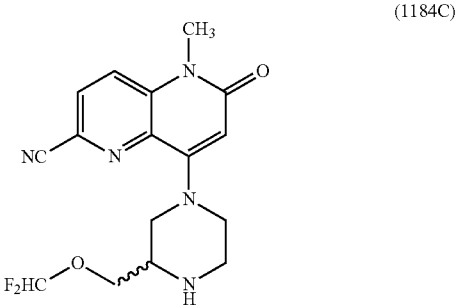 [SMILES: Cn1c(=O)cc(N2CCNC(COC(F)F)C2)c2nc(C#N)ccc21]

(1184C)

To a solution of tert-butyl 4-(6-cyano-1-methyl-2-oxo-1,2-dihydro-1,5-naphthyridin-4-yl)-2-((difluoromethoxy)methyl)piperazine-1-carboxylate (170 mg, 0.38 mmol) in ethyl acetate (5 mL) was added 4 N HCl in dioxane (0.1 mL). The reaction mixture was stirred at room temperature for 3 h. The reaction mixture was concentrated under reduced pressure and triturated with hexane to obtain 8-(3-((difluoromethoxy) methyl)piperazin-1-yl)-5-methyl-6-oxo-5,6-dihydro-1,5-naphthyridine-2-carbonitrile, HCl (134 mg, 0.35 mmol, 92% yield). LCMS: m/z=350.1 (M+H); rt 0.88 min. (LCMS Condition: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm).

Example 1184 and 1185: 8-(4-(2-chloro-4-fluorobenzyl)-3-((difluoromethoxy)methyl) piperazin-1-yl)-5-methyl-6-oxo-5,6-dihydro-1,5-naphthyridine-2-carbonitrile To a solution of 8-(3-((difluoromethoxy)methyl)piperazin-1-yl)-5-methyl-6-oxo-5,6-dihydro-1,5-naphthyridine-2-carbonitrile, HCl (80 mg, 0.21 mmol) in acetonitrile (3 mL) was added DIPEA (0.11 mL, 0.62 mmol), followed by 1-(bromomethyl)-2-chloro-4-fluorobenzene (93 mg, 0.42 mmol). The reaction mixture was stirred at 85° C. overnight. The reaction mixture was concentrated under reduced pressure to remove volatiles and dissolved in ethyl acetate, washed with water. The aqueous layer was back extracted with ethyl acetate (20 mL×2). The combined organic layer was flushed with brine, dried over Na₂SO₄, concentrated under reduced pressure to give crude product. The crude compound was purified by preparative HPLC (Method info: COLUMN: CHIRALPAK-ADH (250*4.6) 5 μm; M. Phase-A: 0.1% ammonia in n-hexane:70; M. Phase-B: 0.1% ammonia in IPA: 30; FLOW: 1 mL/min) to give Example 1184 (4.4 mg, 4.3%) and Example 1185 (6.0 mg, 5.9%).

Example 1184: LCMS: m/z, 492.1 (M+H); rt 2.21 min; Column: XBridge BEH XP C18 (2.1×50 mm), 2.5 μm; Mobile phase A: 10 mM ammonium acetate:acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm. ¹H NMR (400 MHz, DMSO-d₆) δ ppm 8.22-8.15 (m, 1H), 8.13-8.05 (m, 1H), 7.61 (dd, J=6.5, 8.7 Hz, 1H), 7.43 (dd, J=2.6, 8.9 Hz, 1H), 7.24 (dt, J=2.7, 8.4 Hz, 1H), 6.91-6.45 (m, 1H), 6.14 (s, 1H), 4.31 (dd, J=5.0, 10.6 Hz, 1H), 4.14 (dd, J=5.9, 10.8 Hz, 1H), 4.00 (d, J=14.2 Hz, 1H), 3.70 (d, J=14.4 Hz, 1H), 3.56 (m, 2H), 3.55 (s, 3H), 3.50-3.42 (m, 1H), 3.29-3.21 (m, 1H), 3.11-3.04 (m, 1H), 2.92-2.82 (m, 1H), 2.55 (s, 1H).

Example 1185: LCMS: m/z, 492.2 (M+H); rt 2.21 min; Column: XBridge BEH XP C18 (2.1×50 mm), 2.5 μm; Mobile phase A: 10 mM ammonium acetate:acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm. ¹H NMR (400 z, DMSO-d₆) δ ppm 8.21-8.16 (m, 1H), 8.13-8.05 (m, 1H), 7.61 (dd, J=6.4, 8.6 Hz, 1H), 7.43 (dd, J=2.6, 8.9 Hz, 1H), 7.24 (dt, J=2.7, 8.6 Hz, 1H), 6.92-6.50 (m, 1H), 6.14 (s, 1H), 4.31 (dd, J=5.0, 10.6 Hz, 1H), 4.14 (dd, J=5.9, 10.8 Hz, 1H), 4.00 (d, J=14.2 Hz, 1H), 3.70 (d, J=14.2 Hz, 1H), 3.65-3.57 (m, 2H), 3.55 (s, 3H), 3.50-3.42 (m, 1H), 3.30-3.23 (m, 1H), 3.11-3.03 (m, 1H), 2.91-2.83 (m, 1H), 2.55 (s, 1H).

The examples in the Table 45 were prepared according to the general procedure described in Examples 1184 and 1185, substituting 1-(bromomethyl)-2-chloro-4-fluorobenzene with the appropriate benzhydryl bromides or benzyl bromides in the synthetic sequence. When the synthesis provided a mixture of diastereomers, the mixture was separated using either preparative chromatography or preparative chiral chromatography. The absolute stereochemistry was not assigned at the newly formed carbon-nitrogen bond.

TABLE 45

| Ex. No. | Structure | LCMS RT and Method | M + H | Stereo chem. |
|---|---|---|---|---|
| 1186 | 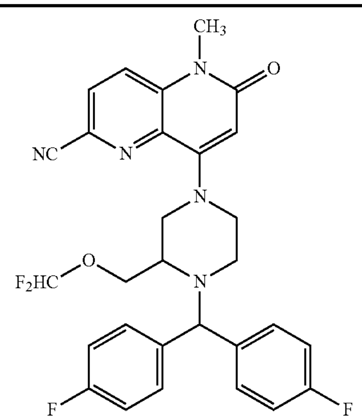 | 2.29 A | 552.2 | H |
| 1187 | 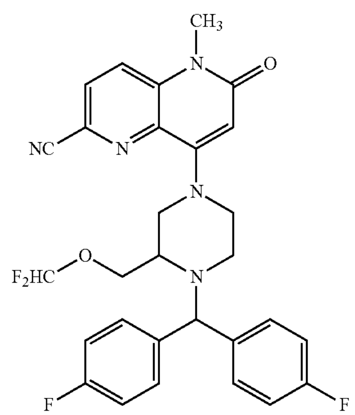 [SMILES: Cn1c(=O)cc(N2CCN(C(c3ccc(F)cc3)c3ccc(F)cc3)C(COC(F)F)C2)c2nc(C#N)ccc21] | 2.29 A | 552.2 | H |

Examples 1188 and 1189

8-((2S,5R)-4-(2-(difluoromethoxy)-1-(4-fluorophenyl)ethyl)-2,5-dimethylpiperazin-1-yl)-5-methyl-6-oxo-5,6-dihydro-1,5-naphthyridine-2-carbonitrile (1188-1189)

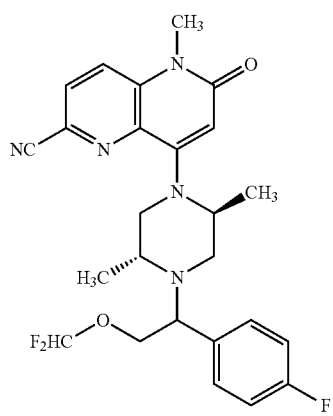

Intermediate 1188A: tert-butyl (2S,5R)-4-(1-(4-fluorophenyl)-2-methoxy-2-oxoethyl)-2,5-dimethylpiperazine-1-carboxylate

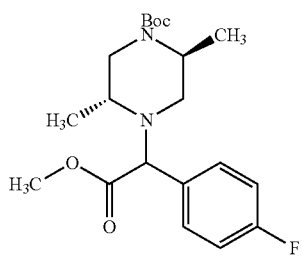

(1188A)

To a stirred solution of tert-butyl (2S,5R)-2,5-dimethylpiperazine-1-carboxylate (1.5 g, 7. mmol) in acetonitrile (15 mL) was added DIPEA (3.7 mL, 21 mmol) and methyl 2-bromo-2-(4-fluorophenyl)acetate (1.9 g, 7.7 mmol). The reaction mixture was heated up to 85° C. over 10 min and was stirred for 16 h. The reaction mixture was concentrated under reduced pressure to obtain a brown gummy solid. The crude compound was purified by flash chromatography (using 24 g silica gel column; using 5%-10% ethylacetate/ Pet. ether) to obtain tert-butyl (2S,5R)-4-(1-(4-fluorophenyl)-2-methoxy-2-oxoethyl)-2,5-dimethylpiperazine-1-carboxylate (2.35 g, 6.18 mmol, 88% yield) as brown solid. LCMS: m/z, 379.3 (M−H); rt 1.13 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1188B: tert-butyl (2S,5R)-4-(1-(4-fluorophenyl)-2-hydroxyethyl)-2,5-dimethylpiperazine-1-carboxylate

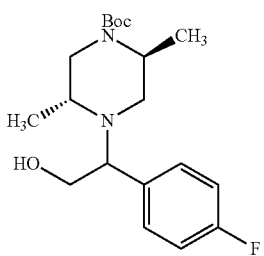

(1188B)

To a stirred solution of tert-butyl (2S,5R)-4-(1-(4-fluorophenyl)-2-methoxy-2-oxoethyl)-2,5-dimethylpiperazine-1-carboxylate (0.9 g, 2.37 mmol) in ethanol (10 mL) was added NaBH$_4$ (0.45 g, 11.83 mmol) and calcium chloride (1.3 g, 11.83 mmol). The reaction mixture was stirred at room temperature for 24 h. The reaction was quenched with water (10 mL). The reaction mixture was concentrated under reduced pressure. The residue was extracted with ethyl acetate (3×100 mL) and washed with brine. The combined organic layer was dried over anhydrous sodium sulfate, filtered and evaporated under reduced pressure to obtain tert-butyl (2S,5R)-4-(1-(4-fluorophenyl)-2-hydroxyethyl)-2,5-dimethylpiperazine-1-carboxylate (0.75 g, 90% yield) as a brown oil. LCMS: m/z, 353.5 (M+H); rt 1.84 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1188C: 2-((2R,5S)-2,5-dimethylpiperazine-1-yl)-2-(4-fluorophenyl)-ethan-1-ol, HCl

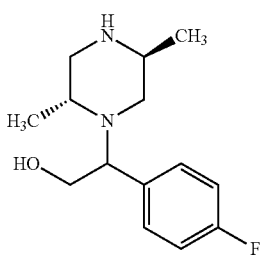

(1188C)

To a stirred solution of tert-butyl (2S,5R)-4-(1-(4-fluorophenyl)-2-hydroxyethyl)-2,5-dimethylpiperazine-1-carboxylate (300 mg, 0.85 mmol) in DCM (5 mL) was added HCl in dioxane (2 mL, 65.8 mmol). The reaction mixture was stirred at room temperature for 1 h. The reaction mixture was concentrated under reduced pressure to obtain as a brown solid. The crude compound was triturated with DCM and hexane (1:4) to obtain a solid residue. The solid material was filtered to obtain 2-((2R,5S)-2,5-dimethylpiperazin-1-yl)-2-(4-fluorophenyl)ethan-1-ol, HCl (0.2 g, 71% yield) as a brown oil. LCMS: m/z, 253.4 (M+H); rt 0.45 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Temperature: 50° C.; Flow rate: 0.7 mL/min; Detection: UV at 220 nm.

Intermediate 1188D: 8-((2S,5R)-4-(1-(4-fluorophenyl)-2-hydroxyethyl)-2,5-dimethylpiperazin-1-yl)-5-methyl-6-oxo-5,6-dihydro-1,5-naphthyridine-2-carbonitrile

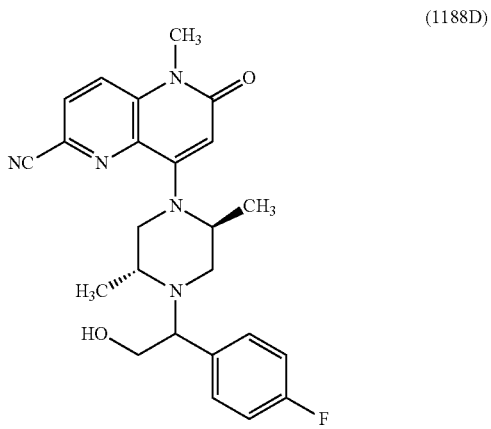 [SMILES: C[C@@H]1CN(c2cc(=O)n(C)c3ccc(C#N)nc23)[C@@H](C)CN1C(CO)c1ccc(F)cc1]

(1188D)

To a stirred solution of 2-((2R,5S)-2,5-dimethylpiperazin-1-yl)-2-(4-fluorophenyl)ethan-1-ol, HCl (208 mg, 0.72 mmol) in acetonitrile (8 mL) was added DIPEA (0.31 mL, 1.8 mmol). The reaction mixture was stirred for 5 min and 6-cyano-1-methyl-2-oxo-1,2-dihydro-1,5-naphthyridin-4-yl trifluoromethanesulfonate (200 mg, 0.6 mmol) was added. The reaction mixture was heated up to 85° C. over 5 min and was stirred for 3 h. The reaction mixture was filtered through Celite bed and was concentrated under high vacuum pump to obtain a brown gum. The crude compound was purified by flash chromatography (using 24 g silica gel column; using 88%-95% ethylacetate/Pet. ether) to obtain 8-((2S,5R)-4-(1-(4-fluorophenyl)-2-hydroxyethyl)-2,5-dimethylpiperazin-1-yl)-5-methyl-6-oxo-5,6-dihydro-1,5-naphthyridine-2-carbonitrile (200 mg, 0.46 mmol, 77% yield) as a brown solid. LCMS: m/z, 436.2 (M+H); rt 1.12-1.15 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Temperature: 50° C.; Flow rate: 0.7 mL/min; Detection: UV at 220 nm.

Examples 1188 and 1189: 8-((2S,5R)-4-(2-(difluoromethoxy)-1-(4-fluorophenyl)ethyl)-2,5-dimethylpiperazin-1-yl)-5-methyl-6-oxo-5,6-dihydro-1,5-naphthyridine-2-carbonitrile To a stirred solution of 8-((2S,5R)-4-(1-(4-fluorophenyl)-2-hydroxyethyl)-2,5-dimethylpiperazin-1-yl)-5-methyl-6- oxo-5,6-dihydro-1,5-naphthyridine-2-carbonitrile (100 mg, 0.23 mmol) in DCM (3 mL)/water (3 mL) were added (bromodifluoromethyl) trimethylsilane (466 mg, 2.30 mmol) and KOAc (90 mg, 0.918 mmol). The reaction mixture was stirred at room temperature for 2 h. The reaction quenched with water (5 mL). The reaction mixture was extracted with ethyl acetate (3×10 mL). The combined organic layer was dried over anhydrous sodium sulfate, filtered and evaporated under reduced pressure to obtain a brown oil. The crude material was purified by preparative HPLC (Column: Cellulose 4 (250×21.2) mm, 5 μm; M. Phase: 0.1% DEA in acetonitrile; Flow rate: 20 mL/min; Isocratic) to obtain 8-((2S,5R)-4-(2-(difluoromethoxy)-1-(4-fluorophenyl)ethyl)-2,5-dimethylpiperazin-1-yl)-5-methyl-6-oxo-5,6-dihydro-1,5-naphthyridine-2-carbonitrile.

Example 1188: (1.0 mg, 1.94 μmol, 0.84% yield). LCMS: m/z, 486.2 (M+H); rt 2.147 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.11-8.17 (m, 1H), 8.04-8.09 (m, 1H), 7.43-7.53 (m, 2H), 7.21 (t, J=8.80 Hz, 2H), 6.63 (s, 1H), 6.02 (s, 1H), 4.32-4.44 (m, 1H), 4.13 (dd, J=10.39, 5.26 Hz, 1H), 3.98-4.08 (m, 1H), 3.90 (t, J=5.38 Hz, 1H), 3.68-3.77 (m, 1H), 2.09-2.15 (m, 1H), 3.52 (s, 4H), 1.21 (d, J=6.36 Hz, 3H), 1.02 (d, J=6.36 Hz, 3H).

Example 1189: (1.0 mg, 2.06 μmol, 0.9% yield). LCMS: m/z, 486.1 (M+H); rt 2.161 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.13-8.17 (m, 1H), 8.02-8.08 (m, 1H), 7.42-7.49 (m, 2H), 7.11-7.22 (m, 2H), 6.56-6.67 (m, 1H), 6.01 (s, 1H), 4.31-4.43 (m, 1H), 4.14-4.22 (m, 1H), 4.05 (dd, J=10.39, 6.24 Hz, 1H), 3.82 (t, J=5.14 Hz, 1H), 3.67-3.76 (m, 1H), 3.52 (s, 4H), 3.32 (m, 1H), 2.77-2.82 (m, 1H), 2.09-2.15 (m, 1H), 1.19 (d, J=6.11 Hz, 3H), 1.09 (d, J=6.36 Hz, 3H).

The examples in the Table 46 were prepared according to the general procedure described in Examples 1188-1189.

| Ex. No. | Structure | QC Method IDs | Obs. MS Ion | Stereo Chem | RT | Method |
|---|---|---|---|---|---|---|
| 1190 | 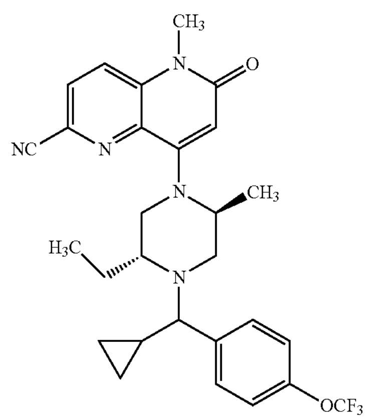 [SMILES: CC[C@@H]1CN(c2cc(=O)n(C)c3ccc(C#N)nc23)[C@@H](C)CN1C(c1ccc(OC(F)(F)F)cc1)C1CC1] | 2 | 526.1 | D | 1.81 | A |
| 1191 | 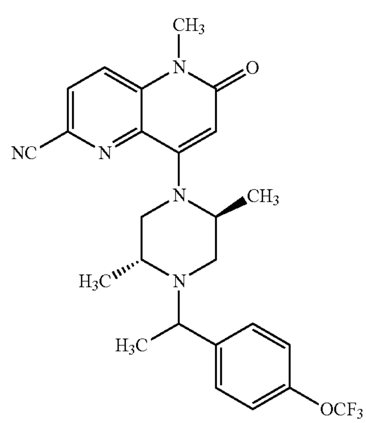 [SMILES: CC(c1ccc(OC(F)(F)F)cc1)N1C[C@H](C)N(c2cc(=O)n(C)c3ccc(C#N)nc23)C[C@H]1C] | 2 | 499.9 | H | 1.58 | B |

-continued

| Ex. No. | Structure | QC Method IDs | Obs. MS Ion | Stereo Chem | RT | Method |
|---|---|---|---|---|---|---|
| 1192 | 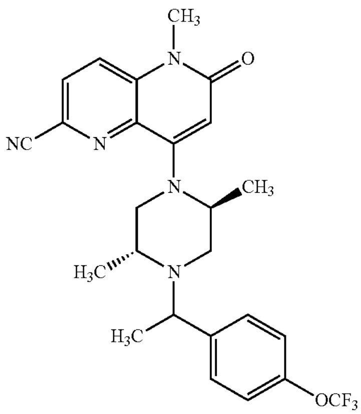 [SMILES: CC(c1ccc(OC(F)(F)F)cc1)N1C[C@H](C)N(c2cc(=O)n(C)c3ccc(C#N)nc23)C[C@H]1C] | 1 | 499.9 | H | 2.53 | B |
| 1193 | 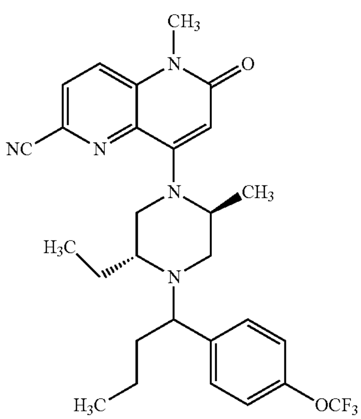 [SMILES: CCCC(c1ccc(OC(F)(F)F)cc1)N1C[C@H](C)N(c2cc(=O)n(C)c3ccc(C#N)nc23)C[C@H]1CC] | 1 | 444.1 | H | 2.78 | A |
| 1194 | 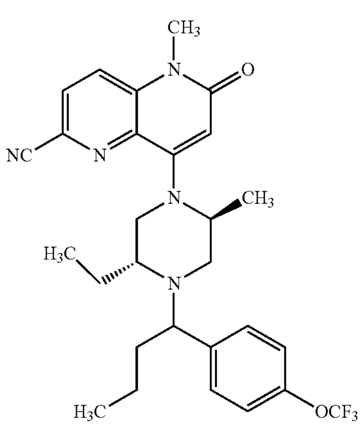 [SMILES: CCCC(c1ccc(OC(F)(F)F)cc1)N1C[C@H](C)N(c2cc(=O)n(C)c3ccc(C#N)nc23)C[C@H]1CC] | 1 | 444.1 | H | 2.72 | A |

-continued

| Ex. No. | Structure | QC Method IDs | Obs. MS Ion | Stereo Chem | RT | Method |
|---|---|---|---|---|---|---|
| 1195 | 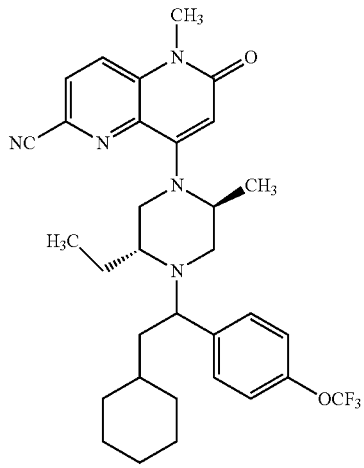 [SMILES: CC[C@@H]1CN(c2cc(=O)n(C)c3ccc(C#N)nc23)[C@@H](C)CN1C(CC1CCCCC1)c1ccc(OC(F)(F)F)cc1] | 2 | 582.2 | H | 2.09 | A |
| 1196 | 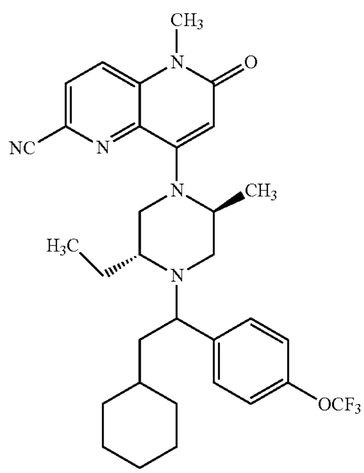 [SMILES: CC[C@@H]1CN(c2cc(=O)n(C)c3ccc(C#N)nc23)[C@@H](C)CN1C(CC1CCCCC1)c1ccc(OC(F)(F)F)cc1] | 1 | 582.2 | H | 2.96 | A |
| 1197 | 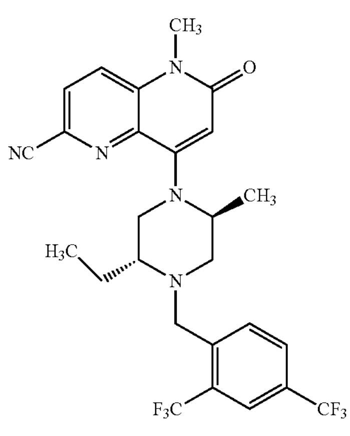 [SMILES: CC[C@@H]1CN(c2cc(=O)n(C)c3ccc(C#N)nc23)[C@@H](C)CN1Cc1ccc(C(F)(F)F)cc1C(F)(F)F] | 1 | 538.3 | H | 2.71 | A |

| Ex. No. | Structure | QC Method IDs | Obs. MS Ion | Stereo Chem | RT | Method |
|---|---|---|---|---|---|---|
| 1198 | 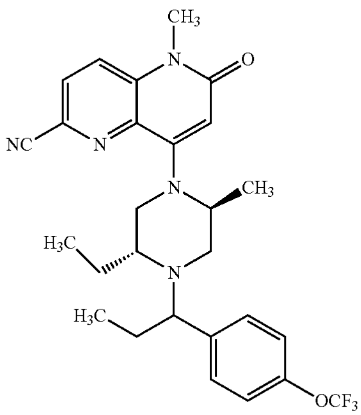 [SMILES: CCC(c1ccc(OC(F)(F)F)cc1)N1C[C@H](C)N(c2cc(=O)n(C)c3ccc(C#N)nc23)C[C@H]1CC] | 1 | 514.3 | H | 2.79 | A |
| 1199 | 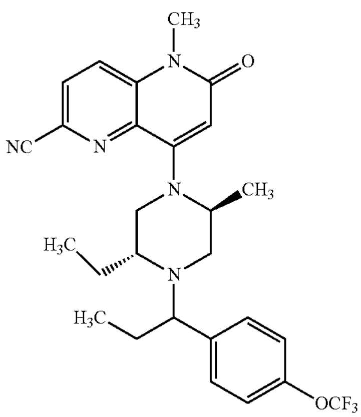 [SMILES: CCC(c1ccc(OC(F)(F)F)cc1)N1C[C@H](C)N(c2cc(=O)n(C)c3ccc(C#N)nc23)C[C@H]1CC] | 1 | 514.3 | H | 2.68 | A |

Examples 1200 and 1201

8-((2S,5R)-4-(1-(4-cyclopropyl-2-fluorophenyl)ethyl)-2,5-dimethylpiperazin-1-yl)-5-methyl-6-oxo-5,6-dihydro-1,5-naphthyridine-2-carbonitrile (1200-1201)

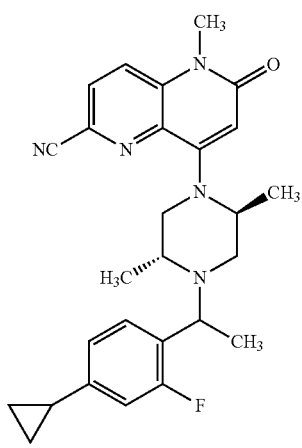

Intermediate 1200A: 1-(4-cyclopropyl-2-fluorophenyl)-ethan-1-ol (1200A)

To a stirred solution of 4-cyclopropyl-2-fluorobenzaldehyde (0.65 g, 3.96 mmol) in tetrahydrofuran (10 mL) was added methylmagnesium chloride (1.98 mL, 5.94 mmol, 3M in THF) drop wise at 0° C. under nitrogen over 5 min. The reaction mixture was slowly warmed to room temperature. The reaction mixture was stirred for 2 h. The reaction was quenched with saturated aqueous ammonium chloride solution (80 mL). The reaction mixture was extracted with ethyl acetate (3×100 mL). The combined organic layer was dried over anhydrous sodium sulfate, filtered and evaporated under reduced pressure to yield the crude product. $^1$H NMR (400 MHz, DMSO-$d_6$) δ ppm 7.4-7.29 (m, 1H), 6.96-6.88 (m, 1H), 6.85-6.74 (m, 1H), 5.17 (d, J=4.5 Hz, 1H), 4.98-4.84 (m, 1H), 1.94-1.83 (m, 1H), 1.28 (d, J=6.0 Hz, 3H), 0.97-0.86 (m, 2H), 0.68-0.58 (m, 2H).

Intermediate 1200B:
1-(1-chloroethyl)-4-cyclopropyl-2-fluorobenzene

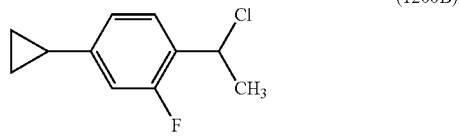

(1200B)

To a stirred solution of 1-(4-cyclopropyl-2-fluorophenyl)ethan-1-ol (0.6 g, 3.33 mmol) in DCM (4 mL) was added $SOCl_2$ (0.97 mL, 13.32 mmol) at room temperature. The reaction mixture was heated at 40° C. for 3 h. The reaction mixture was cooled to room temperature and concentrated under reduced pressure to obtain 1-(1-chloroethyl)-4-cyclopropyl-2-fluorobenzene (0.59 g, 91% yield) as a brown oil. $^1$H NMR (400 MHz, DMSO-$d_6$) δ ppm 7.59-7.37 (m, 1H), 7.06-6.85 (m, 2H), 5.50-5.42 (m, 1H), 2.03-1.90 (m, 1H), 1.81 (d, J=7.0 Hz, 3H), 1.04-0.92 (m, 2H), 0.78-0.65 (m, 2H).

Examples 1200 and 1201: 8-((2S,5R)-4-(1-(4-cyclopropyl-2-fluorophenyl)ethyl)-2,5-dimethylpiperazin-1-yl)-5-methyl-6-oxo-5,6-dihydro-1,5-naphthyridine-2-carbonitrile To a stirred suspension of 8-((2S,5R)-2,5-dimethylpiperazin-1-yl)-5-methyl-6-oxo-5,6-dihydro-1,5-naphthyridine-2-carbonitrile hydrochloride salt (100 mg, 0.30 mmol) in acetonitrile (8 mL) were added DIPEA (0.16 mL, 0.9 mmol) and 1-(1-chloroethyl)-4-cyclopropyl-2-fluorobenzene (71.4 mg, 0.36 mmol) at room temperature. The reaction mixture was heated at 85° C. for 16 h, cooled to room temperature and concentrated under reduced pressure to obtain the crude product, which was purified by preparative HPLC (Prep HPLC Method info: Column CELLULOSE 5 [250×30 mm], 5 micron; M. Phase: 0.1% DEA in MeOH; ISOCRATIC) to obtain Example 1200 and Example 1201.

Example 1200: (28.6 mg, 20% yield). LCMS: m/z=460.3 (M+H); retention time 2.46 min [LCMS method info: A: 95% water:5% acetonitrile; 10 mM $NH_4OAc$; B: 5% water: 95% acetonitrile; 10 mM $NH_4OAc$; Flow: 1.1 mL/min; Temp: 50° C.; Column: Ascentis Express C18 (50×2.1) mm, 2.7 μm; Time (min): 0-3% B: 0-100). $^1$H NMR (400 MHz, DMSO-$d_6$) δ ppm 8.18-8.12 (m, 1H), 8.09-8.02 (m, 1H), 7.34-7.43 (m, 1H), 6.95 (dd, J=1.5, 8.1 Hz, 1H), 6.86 (dd, J=1.7, 12.0 Hz, 1H), 5.99 (s, 1H), 4.63 (br d, J=3.7 Hz, 1H), 3.97 (q, J=6.8 Hz, 1H), 3.52 (s, 3H), 3.45-3.38 (m, 1H), 3.35 (br d, J=3.2 Hz, 1H), 2.98, (dd, J=3.4, 11.5 Hz, 1H), 2.80 (br dd, J=3.1, 5.7 Hz, 1H), 2.71 (dd, J=2.3, 11.6 Hz, 1H), 1.96-1.86 (m, 1H), 1.26 (d, J=6.6 Hz, 3H), 1.23 (d, J=6.4 Hz, 3H), 1.00 (d, J=6.6 Hz, 3H), 0.98-0.91 (m, 2H), 0.73-0.65 (m, 2H).

Example 1200: (30.4 mg, 21% yield). LCMS: m/z=460.3 (M+H); retention time 2.47 min [LCMS method: A: 95% Water:5% acetonitrile; 10 mM $NH_4OAc$; B: 5% water:95% acetonitrile; 10 mM $NH_4OAc$; Flow: 1.1 mL/min; Temp: 50° C.; Column: Ascentis Express C18 (50×2.1) mm, 2.7 μm; Time (min): 0-3; % B: 0-100). $^1$H NMR (400 MHz, DMSO-$d_6$) δ ppm 8.19-8.13 (m, 1H), 8.10-8.03 (m, 1H), 7.37-7.46 (m, 1H), 6.94 (dd, J=1.5, 8.1 Hz, 1H), 6.83 (dd, J=1.7, 12.0 Hz, 1H), 6.01 (s, 1H), 4.43-4.31 (m, 1H), 3.93-3.74 (m, 3H), 3.57-3.43 (m, 3H), 3.17 (d, J=4.6 Hz, 1H), 2.75 (dd, J=3.2, 11.5 Hz, 1H), 2.17-2.10 (m, 1H), 1.98-1.85 (m, 1H), 1.27 (d, J=6.6 Hz, 3H), 1.16 (d, J=6.4 Hz, 3H), 1.10 (d, J=6.6 Hz, 3H), 0.97-0.91 (m, 2H), 0.73-0.66 (m, 2H).

The examples in the Table 47 were prepared from the general procedure described in Examples 1200 and 1201, using the appropriate aldehyde. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 47

| Ex. No. | Structure | M + H | Stereo chem | LCMS RT and Method |
|---|---|---|---|---|
| 1202 | 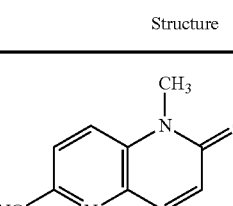 | 504.2 | H | 2.49 A |

TABLE 47-continued
| Ex. No. | Structure | M + H | Stereo chem | LCMS RT and Method |
|---|---|---|---|---|
| 1203 | 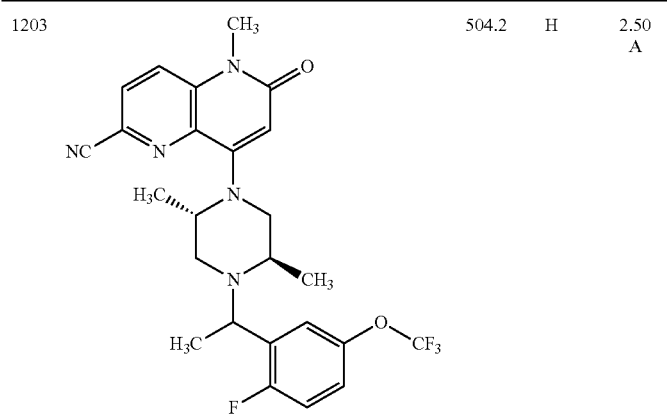 | 504.2 | H | 2.50 A |
| 1204 | 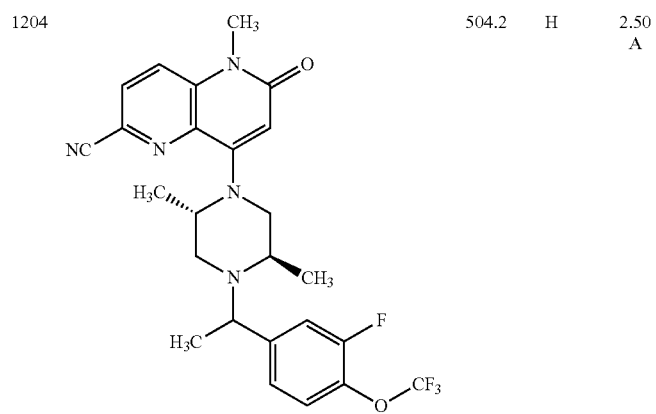 | 504.2 | H | 2.50 A |
| 1205 | 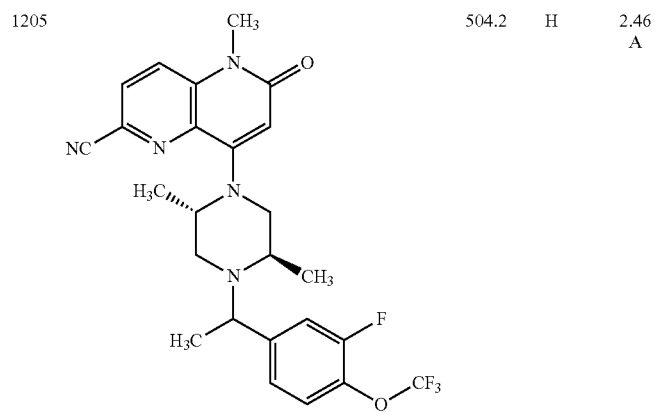 | 504.2 | H | 2.46 A |

TABLE 47-continued
| Ex. No. | Structure | M + H | Stereo chem | LCMS RT and Method |
|---|---|---|---|---|
| 1206 | 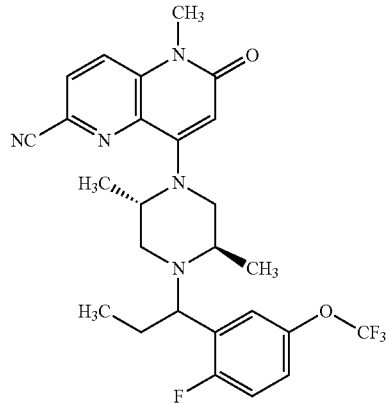 [SMILES: CCC(c1cc(OC(F)(F)F)ccc1F)N1C[C@H](C)N(c2cc(=O)n(C)c3ccc(C#N)nc23)C[C@H]1C] | 518.2 | H | 2.52 A |
| 1207 | 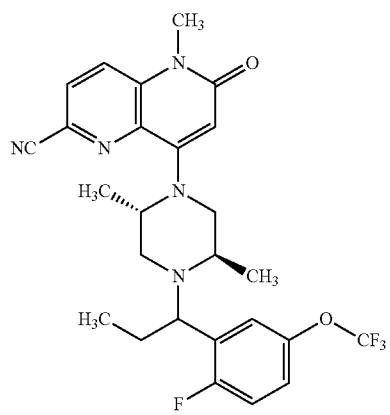 [SMILES: CCC(c1cc(OC(F)(F)F)ccc1F)N1C[C@H](C)N(c2cc(=O)n(C)c3ccc(C#N)nc23)C[C@H]1C] | 518.2 | H | 2.55 A |
| 1208 | 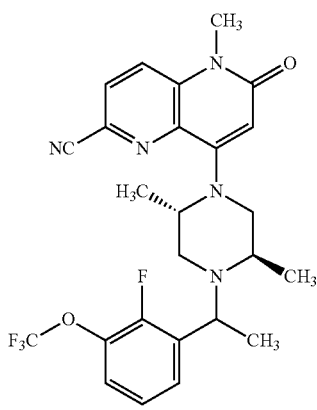 [SMILES: CC(c1cccc(OC(F)(F)F)c1F)N1C[C@H](C)N(c2cc(=O)n(C)c3ccc(C#N)nc23)C[C@H]1C] | 504.2 | H | 2.44 A |

TABLE 47-continued

| Ex. No. | Structure | M + H | Stereo chem | LCMS RT and Method |
|---|---|---|---|---|
| 1209 | 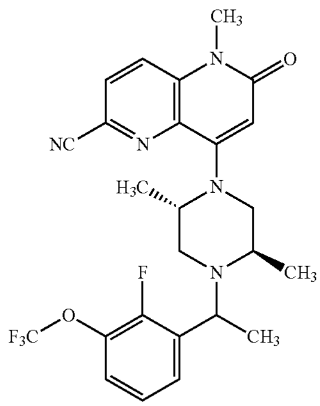 [SMILES: CC(c1cccc(OC(F)(F)F)c1F)N1C[C@H](C)N(c2cc(=O)n(C)c3ccc(C#N)nc23)C[C@H]1C] | 504.2 | H | 2.45 A |
| 1210 | 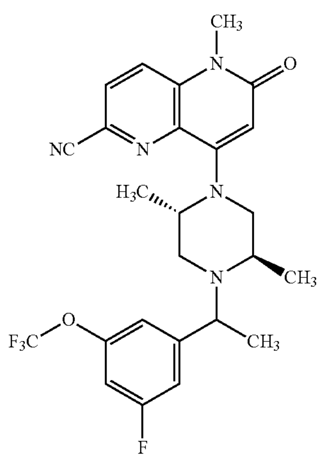 [SMILES: CC(c1cc(F)cc(OC(F)(F)F)c1)N1C[C@H](C)N(c2cc(=O)n(C)c3ccc(C#N)nc23)C[C@H]1C] | 504.2 | H | 2.49 A |
| 1211 | 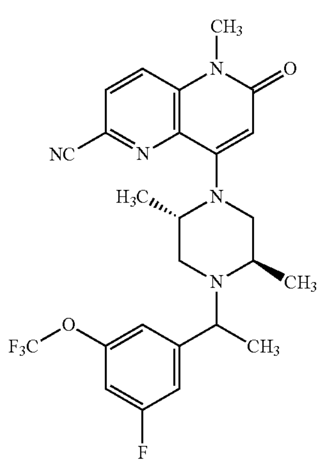 [SMILES: CC(c1cc(F)cc(OC(F)(F)F)c1)N1C[C@H](C)N(c2cc(=O)n(C)c3ccc(C#N)nc23)C[C@H]1C] | 504.1 | H | 2.49 A |

TABLE 47-continued

| Ex. No. | Structure | M + H | Stereo chem | LCMS RT and Method |
|---|---|---|---|---|
| 1212 | 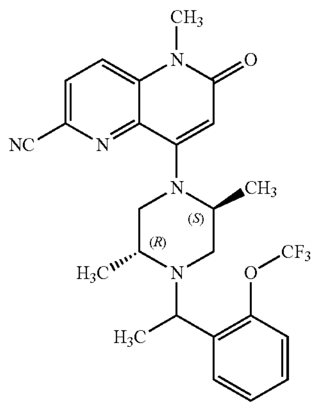 | 486.2 | H | 2.5 A |
| 1213 | 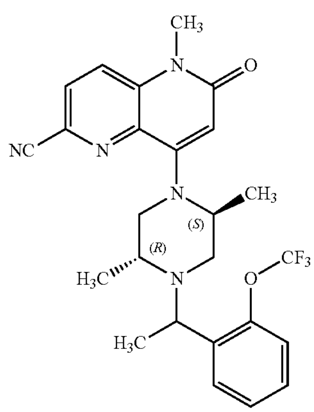 | 486.2 | H | 2.48 A |
| 1214 | 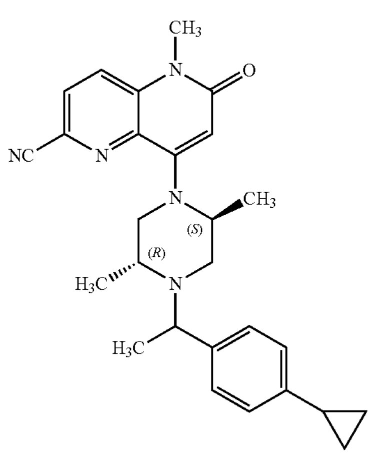 | 442.2 | H | 2.46 A |

TABLE 47-continued
| Ex. No. | Structure | M + H | Stereo chem | LCMS RT and Method |
|---|---|---|---|---|
| 1215 | 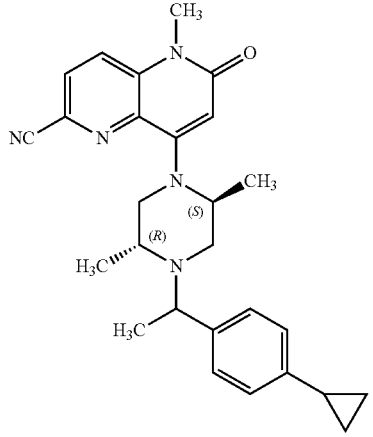 | 442.2 | H | 2.49 A |
| 1216 | 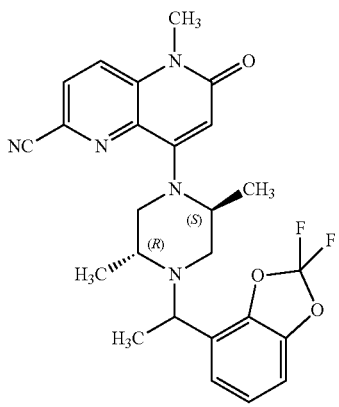 | 482.2 | H | 2.41 A |
| 1217 | 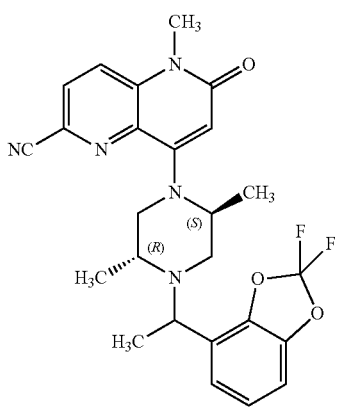 | 482.2 | H | 2.36 A |

TABLE 47-continued
| Ex. No. | Structure | M + H | Stereo chem | LCMS RT and Method |
|---|---|---|---|---|
| 1218 | 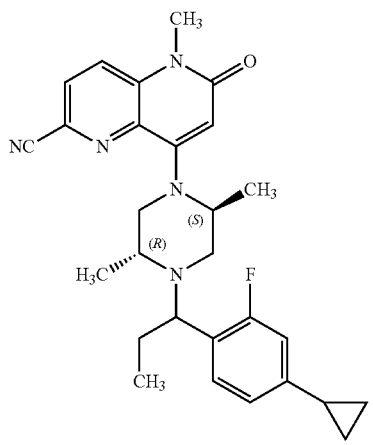 | 474.3 | H | 2.57 A |
| 1219 | 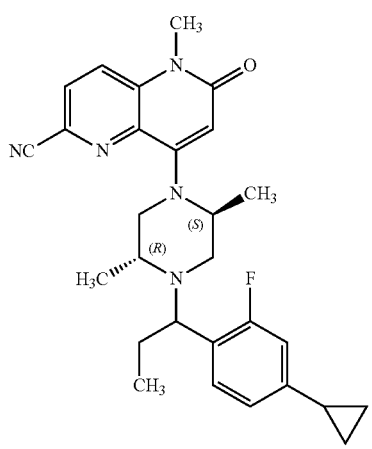 | 474.3 | H | 2.59 A |
| 1220 | 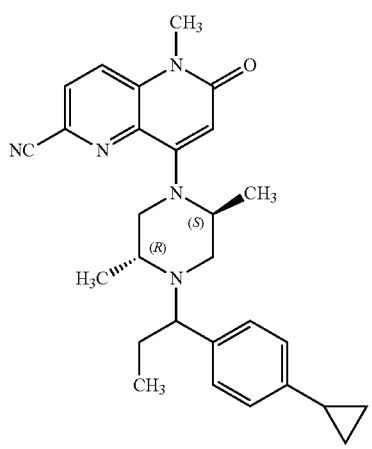 | 456.3 | H | 2.55 A |

TABLE 47-continued
| Ex. No. | Structure | M + H | Stereo chem | LCMS RT and Method |
|---|---|---|---|---|
| 1221 | 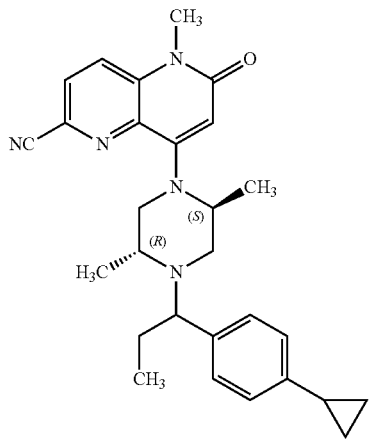 | 456.3 | H | 2.59 A |
| 1222 | 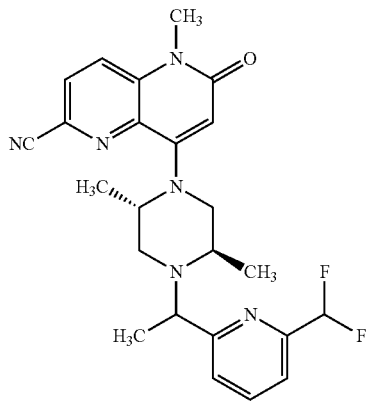 [SMILES: CC(c1cccc(C(F)F)n1)N1C[C@H](C)N(c2cc(=O)n(C)c3ccc(C#N)nc23)C[C@H]1C] | 453.2 | H | 1.96 A |
| 1223 | 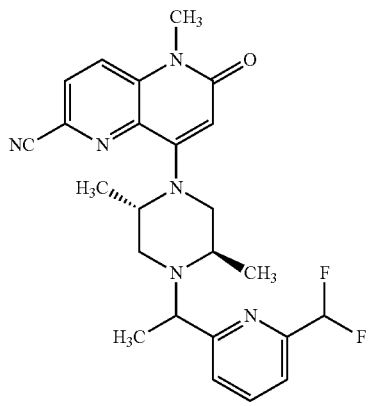 [SMILES: CC(c1cccc(C(F)F)n1)N1C[C@H](C)N(c2cc(=O)n(C)c3ccc(C#N)nc23)C[C@H]1C] | 453.2 | H | 1.95 A |

TABLE 47-continued
| Ex. No. | Structure | M + H | Stereo chem | LCMS RT and Method |
|---|---|---|---|---|
| 1224 | 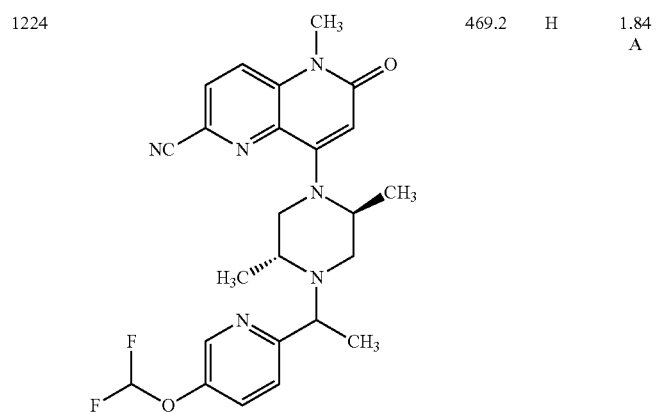 | 469.2 | H | 1.84 A |
| 1225 | 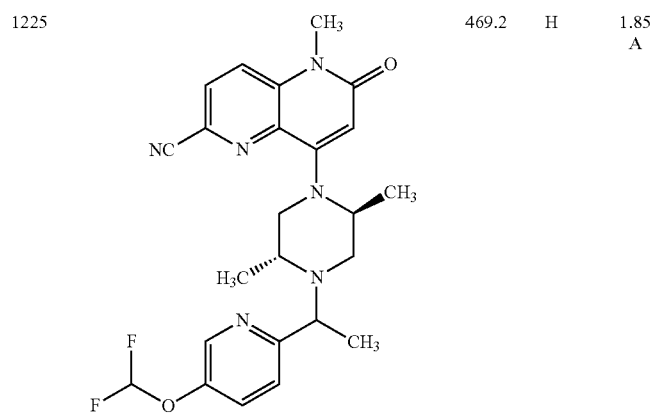 | 469.2 | H | 1.85 A |
| 1226 | 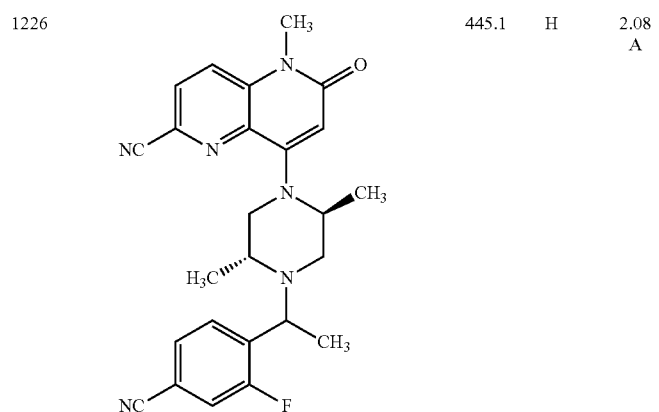 | 445.1 | H | 2.08 A |

TABLE 47-continued
| Ex. No. | Structure | M + H | Stereo chem | LCMS RT and Method |
|---|---|---|---|---|
| 1227 | 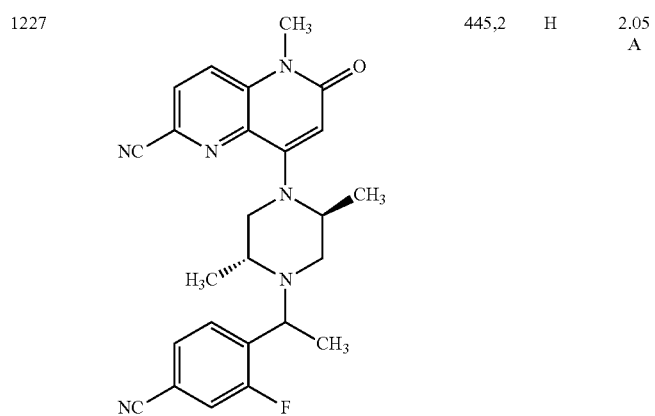 | 445,2 | H | 2.05 A |
| 1228 | 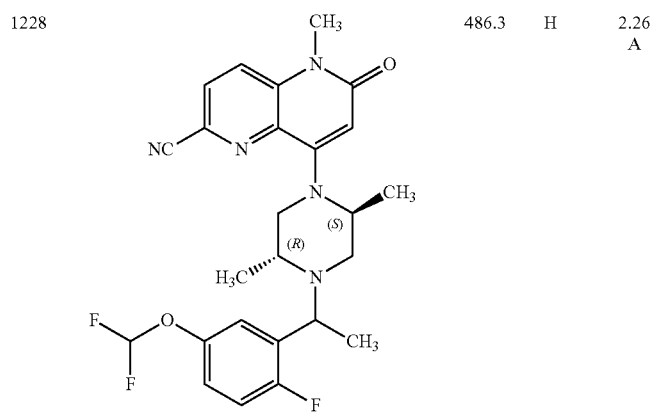 | 486.3 | H | 2.26 A |
| 1229 | 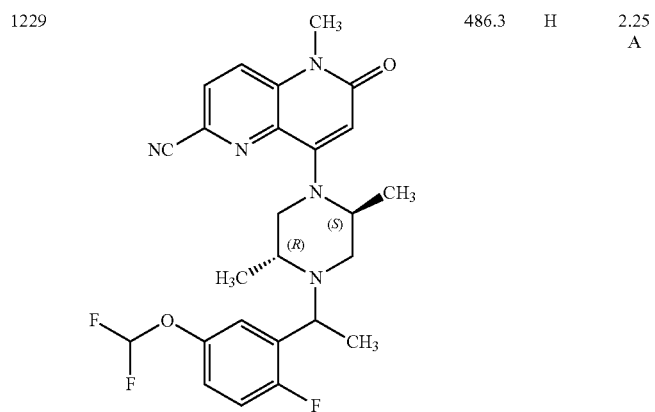 | 486.3 | H | 2.25 A |

TABLE 47-continued
| Ex. No. | Structure | M + H | Stereo chem | LCMS RT and Method |
|---|---|---|---|---|
| 1230 | 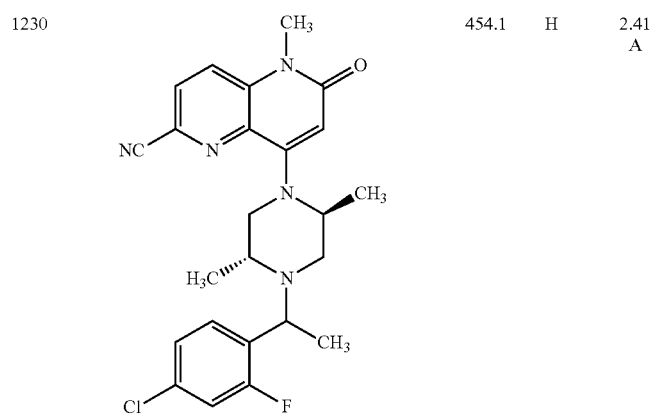 | 454.1 | H | 2.41 A |
| 1231 | 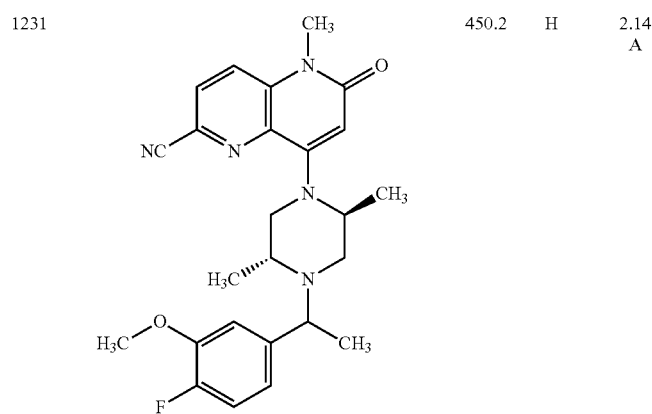 | 450.2 | H | 2.14 A |
| 1232 | 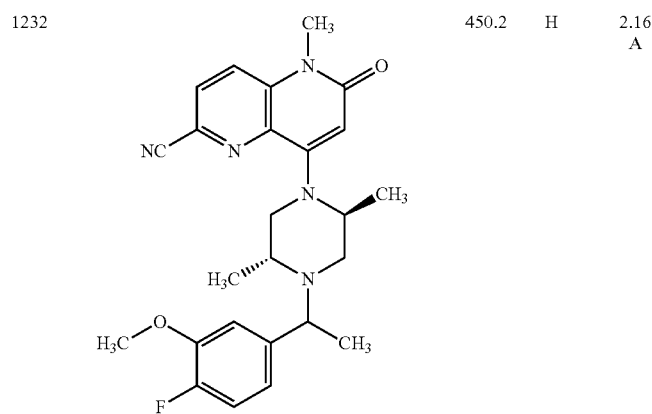 | 450.2 | H | 2.16 A |

TABLE 47-continued
| Ex. No. | Structure | M + H | Stereo chem | LCMS RT and Method |
|---|---|---|---|---|
| 1233 | 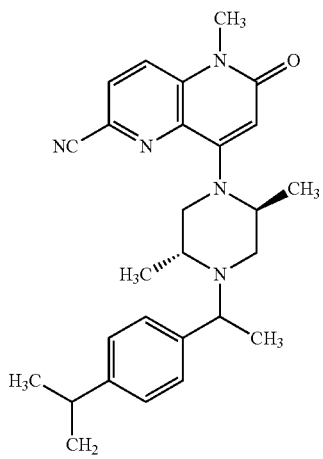 [SMILES: CC(C)c1ccc(C(C)N2C[C@H](C)N(c3cc(=O)n(C)c4ccc(C#N)nc34)C[C@H]2C)cc1] | 444.3 | H | 2.53 A |
| 1234 | 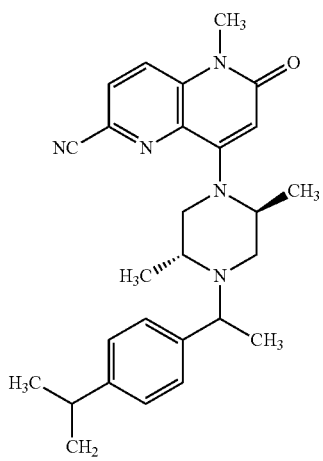 [SMILES: CC(C)c1ccc(C(C)N2C[C@H](C)N(c3cc(=O)n(C)c4ccc(C#N)nc34)C[C@H]2C)cc1] | 444.3 | H | 2.56 A |
| 1235 | 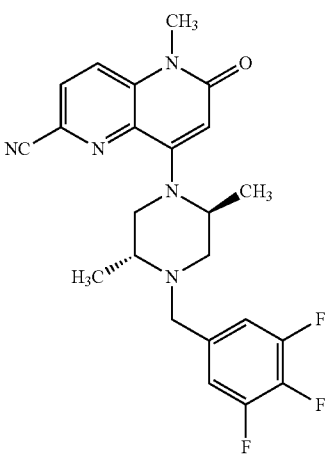 [SMILES: C[C@@H]1CN(c2cc(=O)n(C)c3ccc(C#N)nc23)[C@@H](C)CN1Cc1cc(F)c(F)c(F)c1] | 442.1 | H | 2.21 A |

TABLE 47-continued
| Ex. No. | Structure | M + H | Stereo chem | LCMS RT and Method |
|---|---|---|---|---|
| 1236 | 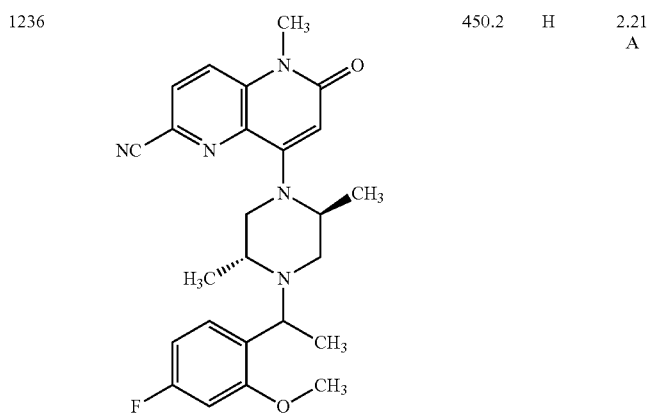 | 450.2 | H | 2.21 A |
| 1237 | 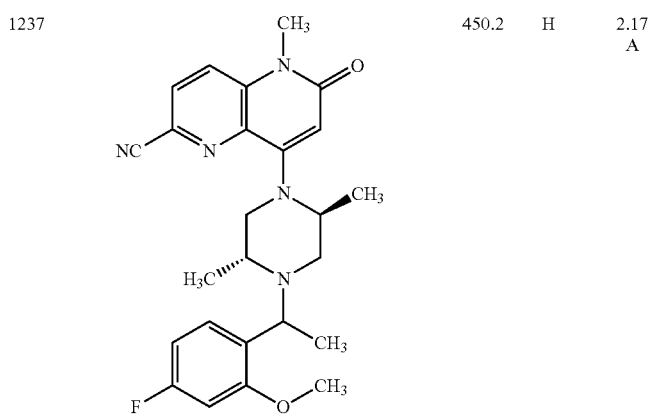 | 450.2 | H | 2.17 A |
| 1238 | 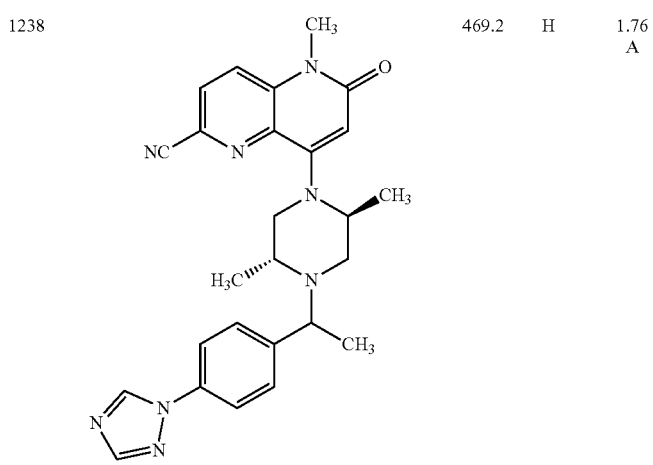 | 469.2 | H | 1.76 A |

TABLE 47-continued

| Ex. No. | Structure | M + H | Stereo chem | LCMS RT and Method |
|---|---|---|---|---|
| 1239 | 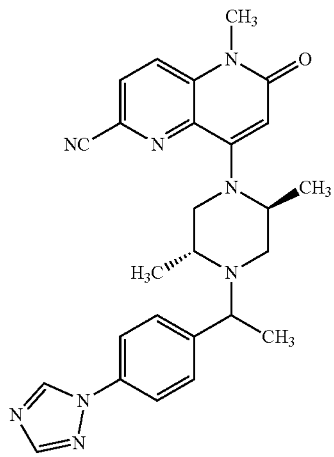 [SMILES: CC(c1ccc(-n2cncn2)cc1)N1C[C@H](C)N(c2cc(=O)n(C)c3ccc(C#N)nc23)C[C@H]1C] | 469.1 | H | 1.78 A |
| 1240 | 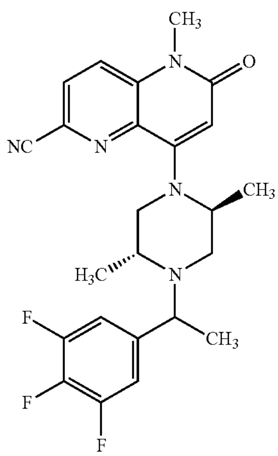 [SMILES: CC(c1cc(F)c(F)c(F)c1)N1C[C@H](C)N(c2cc(=O)n(C)c3ccc(C#N)nc23)C[C@H]1C] | 456.1 | H | 2.32 A |
| 1241 | 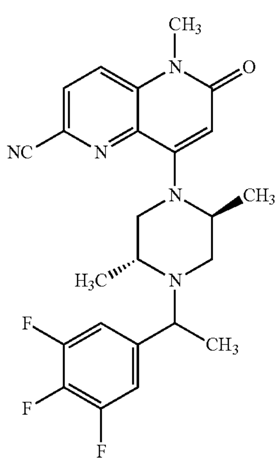 [SMILES: CC(c1cc(F)c(F)c(F)c1)N1C[C@H](C)N(c2cc(=O)n(C)c3ccc(C#N)nc23)C[C@H]1C] | 456.1 | H | 2.35 A |

TABLE 47-continued
| Ex. No. | Structure | M + H | Stereo chem | LCMS RT and Method |
|---|---|---|---|---|
| 1242 | 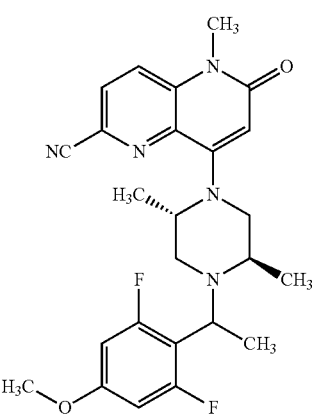 | 468.3 | H | 2.22 A |
| 1243 | 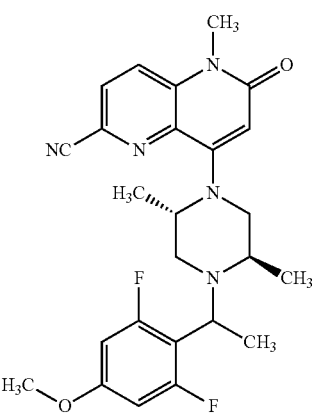 | 468.3 | H | 2.23 A |
| 1244 | 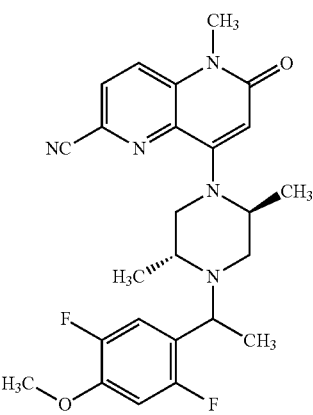 | 468.3 | H | 2.17 A |

TABLE 47-continued
| Ex. No. | Structure | M + H | Stereo chem | LCMS RT and Method |
|---|---|---|---|---|
| 1245 | 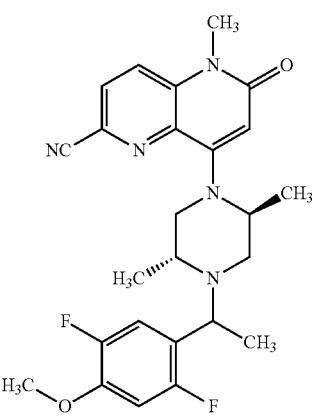 | 468.3 | H | 2.18 A |
| 1246 | 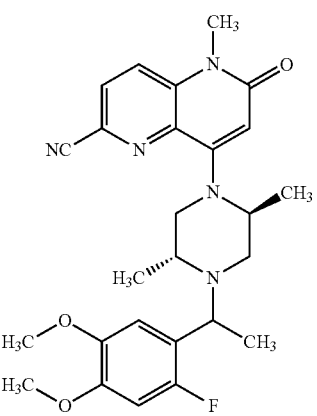 | 480.3 | H | 2.02 A |
| 1247 | 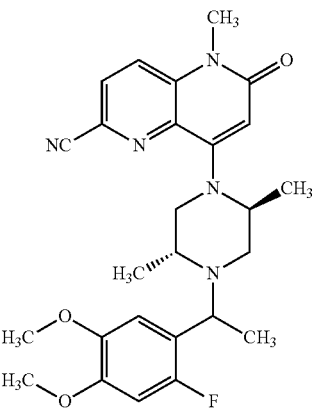 | 480.3 | H | 2.01 A |

TABLE 47-continued

| Ex. No. | Structure | M + H | Stereo chem | LCMS RT and Method |
|---|---|---|---|---|
| 1249 | (structure) | 500.3 | H | 2.28 A |
| 1250 | (structure) | 500.3 | H | 2.31 A |

Examples 1251 and 1252

8-((2S,5R)-4-(1-(4-(1-cyanocyclopropyl)-2-fluorophenyl)ethyl)-2,5-dimethylpiperazin-1-yl)-5-methyl-6-oxo-5,6-dihydro-1,5-naphthyridine-2-carbonitrile (1251-1252)

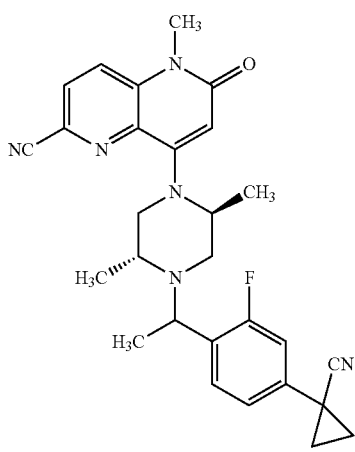

Intermediate 1251 A: 1-(4-acetyl-3-fluorophenyl)cyclopropane-1-carbonitrile

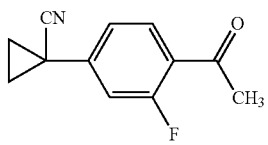

(1251A)

To a stirred solution of 1-(4-bromo-3-fluorophenyl)cyclopropane-1-carbonitrile (0.15 g, 0.63 mmol) in 1,4-dioxane (5 mL) were added tributyl(1-ethoxyvinyl)stannane (0.25 mL, 0.75 mmol) and Pd(PPh$_3$)$_4$ (36.1 mg, 0.03 mmol) at room temperature. The reaction mixture was degassed with nitrogen and heated at 90° C. for 16 h, cooled to room temperature and the volatiles were removed under reduced pressure to obtain the crude product, which was purified by silica gel column chromatography (24 g, Solvent run: 0-50% EtOAc in pet ether) to yield 1-(4-acetyl-3-fluorophenyl)cyclopropane-1-carbonitrile (80 mg, 63% yield). $^1$H NMR (300 MHz, DMSO-d$_6$) δ ppm 7.79-7.89 (m, 1H), 7.45-7.05 (m, 2H), 2.57 (d, J=4.1 Hz, 3H), 1.94-1.85 (m, 2H), 1.73-1.62 (m, 2H).

Intermediate 1251B: 1-(3-fluoro-4-(1-hydroxyethyl)phenyl)cyclopropane-1-carbonitrile

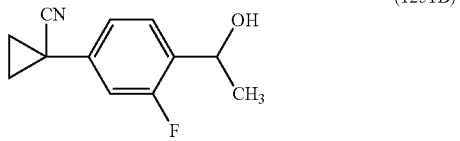

(1251B)

To a solution of 1-(4-acetyl-3-fluorophenyl)cyclopropane-1-carbonitrile (120 mg, 0.59 mmol) in methanol (5 mL) was added NaBH$_4$ (45 mg, 1.18 mmol) at room temperature. The reaction mixture was stirred for 2 h. The reaction was quenched with water (5 mL). The reaction mixture was extracted with ethyl acetate (2×20 mL). The combined organic layer was dried over anhydrous Na$_2$SO$_4$, evaporated under reduced pressure to obtain 1-(3-fluoro-4-(1-hydroxyethyl)phenyl)cyclopropane-1-carbonitrile (100 mg, 83% yield). $^1$H NMR (300 MHz, Chloroform-d) δ ppm 7.44-7.54 (m, 1H), 7.09 (br d, J=8.1 Hz, 1H), 6.95 (d, J=11.4 Hz, 1H), 5.18 (br dd, J=3.8, 5.9 Hz, 1H), 4.12 (q, J=7.1 Hz, 1H), 1.50 (d, J=6.4 Hz, 3H), 1.45-1.35 (m, 2H), 1.26 (t, J=7.1 Hz, 2H).

Intermediate 1251C: 1-(4-(1-chloroethyl)-3-fluorophenyl)cyclopropane-1-carbonitrile

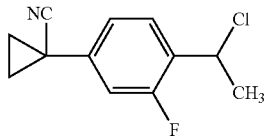

(1251C)

To a solution of 1-(3-fluoro-4-(1-hydroxyethyl)phenyl)cyclopropane-1-carbonitrile (80 mg, 0.39 mmol) in dichloromethane (1.0 mL) was added SOCl$_2$ (0.14 mL, 1.95 mmol) at 0° C. The reaction mixture was stirred at room temperature for 2 h. The volatiles were removed from the reaction mixture under reduced pressure to obtain the crude product. $^1$H NMR (400 MHz, Chloroform-d) δ ppm 7.36-7.46 (m, 1H), 6.79-6.65 (m, 1H), 6.60 (dd, J=2.5, 12.0 Hz, 1H), 5.38 (q, J=7.0 Hz, 1H), 1.84 (d, J=6.5 Hz, 3H), 0.75-0.60 (m, 2H), 0.42-0.25 (m, 2H).

Examples 1251 and 1252: 8-((2S,5R)-4-(1-(4-(1-cyanocyclopropyl)-2-fluorophenyl) ethyl)-2,5-dimethylpiperazin-1-yl)-5-methyl-6-oxo-5,6-dihydro-1,5-naphthyridine-2-carbonitrile To a stirred suspension of 8-((2S,5R)-2,5-dimethylpiperazin-1-yl)-5-methyl-6-oxo-5,6-dihydro-1,5-naphthyridine-2-carbonitrile (100 mg, 0.3 mmol) hydrochloride in acetonitrile (2.0 mL) were added DIPEA (0.16 mL, 0.9 mmol) and 1-(4-(1-chloroethyl)-3-fluorophenyl)cyclopropane-1-carbonitrile (80 mg, 0.36 mmol) at room temperature. The reaction mixture was heated at 80° C. for 4 h, cooled to room temperature, dissolved in ethyl acetate (40 mL) and washed with water (5 mL×2). The organic layer dried over anhydrous Na$_2$SO$_4$ and evaporated under reduced pressure to obtain the crude product, which was purified via preparative HPLC (Method Information: Column CELLULOSE 5 [(250×4.6 mm), 5 micron; MOBILE PHASE A: 0.1% DEA in acetonitrile; MOBILE PHASE B: 0.1% DEA in methanol] to obtain Examples 1251 and 1252.

Example 1251: (7 mg, 5% yield). LCMS: m/z=485.2 (M+H); retention time 1.25 min [LCMS method: Column: XBridge BEH XP C18 (2.1×50 mm), 2.5 μm; Mobile phase A: 0.1% TFA: acetonitrile (95:5), Mobile phase B: 0.1% TFA: acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-d$_6$) δ ppm 8.20-8.14 (m, 1H), 8.11-8.03 (m, 1H), 7.53-7.63 (m, 1H), 7.27 (dd, J=1.8, 8.2 Hz, 1H), 7.11 (dd, J=2.0, 11.5 Hz, 1H), 6.00 (s, 1H), 4.71-4.58 (m, 1H), 4.03 (q, J=6.4 Hz, 1H), 3.53 (s, 3H), 3.46-3.40 (m, 1H), 3.37 (d, J=3.2 Hz, 1H), 3.00 (dd, J=3.5, 11.1 Hz, 1H), 2.82-2.70 (m, 2H), 1.80-1.75 (m, 2H), 1.61-1.56 (m, 2H), 1.28 (d, J=6.6 Hz, 3H), 1.24 (d, J=6.6 Hz, 3H), 1.02 (d, J=6.4 Hz, 3H).

Example 1252: (8.9 mg, 6% yield). LCMS: m/z=485.2 (M+H); retention time 1.26 min [LCMS method: Column: XBridge BEH XP C18 (2.1×50 mm), 2.5 μm; Mobile phase A: 0.1% TFA: acetonitrile (95:5), Mobile phase B: 0.1% TFA: acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-d$_6$) δ ppm 8.20-8.13 (m, 1H), 8.11-8.01 (m, 1H), 7.55-7.65 (m, 1H), 7.25 (dd, J=2.0, 8.1 Hz, 1H), 7.08 (dd, J=2.0, 11.5 Hz, 1H), 6.02 (s, 1H), 4.46-4.34 (m, 1H), 3.94-3.75 (m, 2H), 3.58-3.46 (m, 5H), 3.17 (d, J=5.4 Hz, 1H), 2.81-2.73 (m, 1H), 1.81-1.74 (m, 2H), 1.60-1.53 (m, 2H), 1.29 (d, J=6.4 Hz, 3H), 1.17 (d, J=6.4 Hz, 3H), 1.12 (d, J=6.6 Hz, 3H).

The examples in the Table 48 were prepared from general procedure described in Examples 1251 and 1252, using appropriate bromide. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 48
| Ex. No. | Structure | M + H | Stereo chem | LCMS RT and Method |
|---|---|---|---|---|
| 1253 | 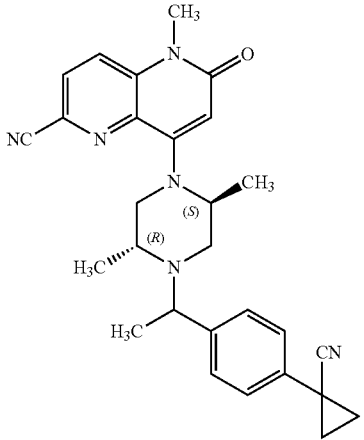 | 467.2 | H | 2.09 A |
| 1254 | 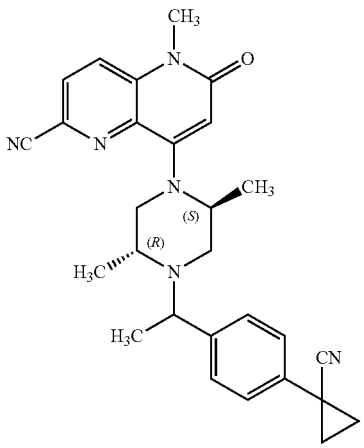 | 467.2 | H | 1.23 B |
| 1255 | 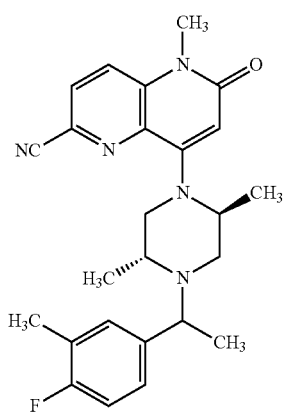 [SMILES: Cc1cc(C(C)N2C[C@H](C)N(c3cc(=O)n(C)c4ccc(C#N)nc34)C[C@H]2C)ccc1F] | 434.2 | H | 2.42 A |

TABLE 48-continued

| Ex. No. | Structure | M + H | Stereo chem | LCMS RT and Method |
|---|---|---|---|---|
| 1256 | 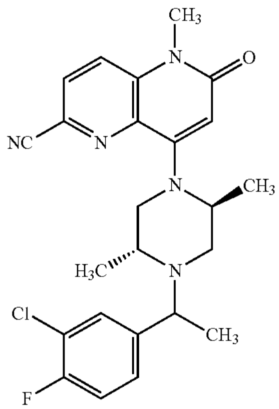 [SMILES: CC(c1ccc(F)c(Cl)c1)N1C[C@H](C)N(c2cc(=O)n(C)c3ccc(C#N)nc23)C[C@H]1C] | 454.1 | H | 2.35 A |
| 1257 | 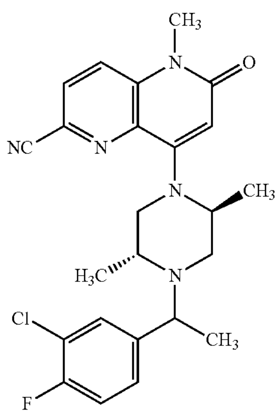 [SMILES: CC(c1ccc(F)c(Cl)c1)N1C[C@H](C)N(c2cc(=O)n(C)c3ccc(C#N)nc23)C[C@H]1C] | 454.1 | H | 2.38 A |
| 1258 | 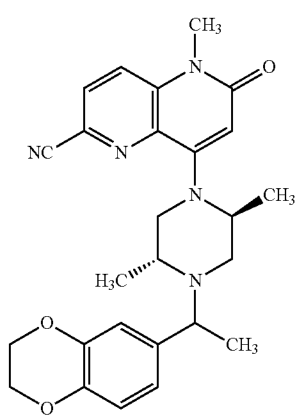 [SMILES: CC(c1ccc2c(c1)OCCO2)N1C[C@H](C)N(c2cc(=O)n(C)c3ccc(C#N)nc23)C[C@H]1C] | 460.3 | H | 2.00 A |

TABLE 48-continued

| Ex. No. | Structure | M + H | Stereo chem | LCMS RT and Method |
|---|---|---|---|---|
| 1259 | 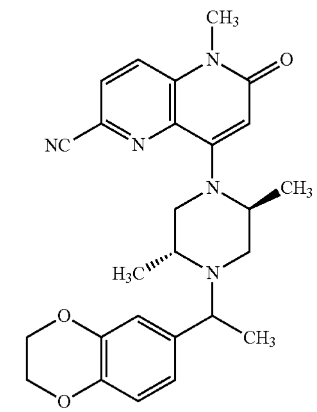 [SMILES: CC(c1ccc2c(c1)OCCO2)N1C[C@H](C)N(c2cc(=O)n(C)c3ccc(C#N)nc23)C[C@H]1C] | 460.1 | H | 2.04 A |
| 1260 | 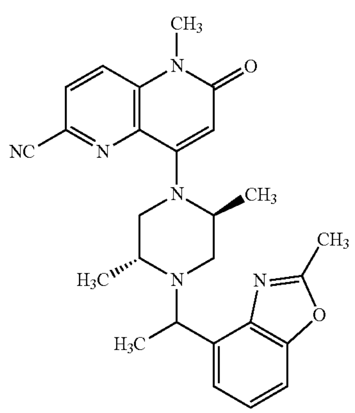 [SMILES: Cc1nc2c(C(C)N3C[C@H](C)N(c4cc(=O)n(C)c5ccc(C#N)nc45)C[C@H]3C)cccc2o1] | 457.3 | H | 1.99 A |
| 1261 | 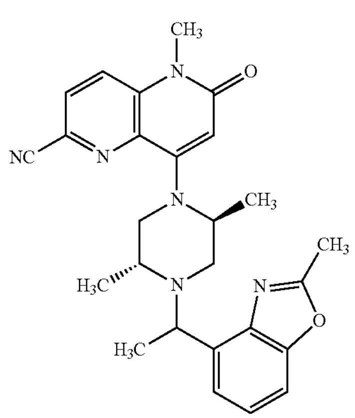 [SMILES: Cc1nc2c(C(C)N3C[C@H](C)N(c4cc(=O)n(C)c5ccc(C#N)nc45)C[C@H]3C)cccc2o1] | 457.3 | H | 1.99 A |

TABLE 48-continued
| Ex. No. | Structure | M + H | Stereo chem | LCMS RT and Method |
|---|---|---|---|---|
| 1262 | 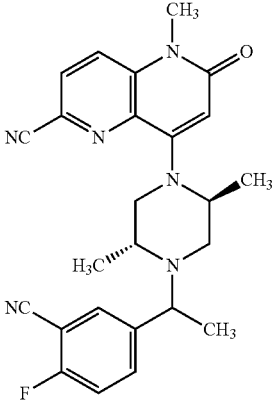 [SMILES: CC(c1ccc(F)c(C#N)c1)N1C[C@H](C)N(c2cc(=O)n(C)c3ccc(C#N)nc23)C[C@H]1C] | 445.3 | H | 2.05 A |
| 1263 | 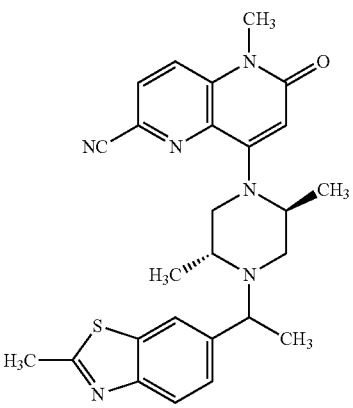 | 473.3 | H | 2.01 A |
| 1264 | 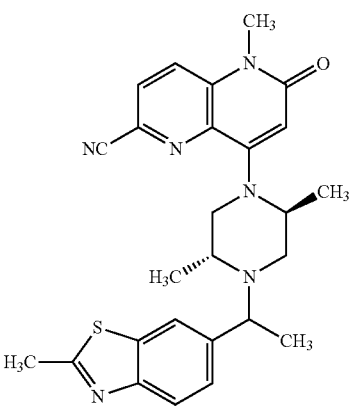 | 473.3 | H | 2.04 A |

TABLE 48-continued

| Ex. No. | Structure | M + H | Stereo chem | LCMS RT and Method |
|---|---|---|---|---|
| 1265 | ![structure] | 446.3 | H | 2.07 A |
| 1266 | ![structure] | 446.3 | H | 2.1 A |

Examples 1267 and 1268

8-((2S,5R)-2,5-dimethyl-4-(1-(3-(trifluoromethoxy)phenyl)ethyl)piperazin-1-yl)-5-methyl-6-oxo-5,6-dihydro-1,5-naphthyridine-2-carbonitrile

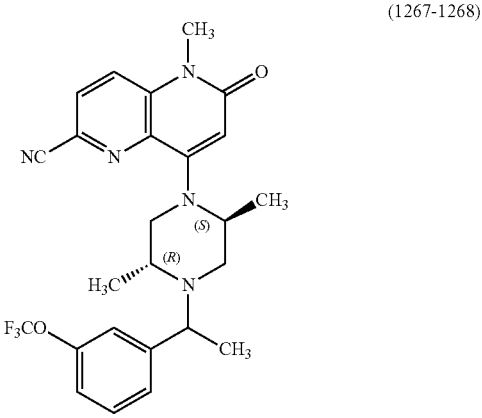

(1267-1268)

To a suspension of 8-((2S,5R)-2,5-dimethylpiperazin-1-yl)-5-methyl-6-oxo-5,6-dihydro-1,5-naphthyridine-2-carbonitrile (100 mg, 0.3 mmol) in acetonitrile (2 mL) were added DIPEA (0.16 mL, 0.90 mmol) and 1-(1-bromoethyl)-3-(trifluoromethoxy)benzene (97 mg, 0.36 mmol) at room temperature. The reaction mixture was heated at 80° C. for 4 h. The reaction mixture was cooled to room temperature and diluted with water and extracted twice with ethyl acetate (20 mL). The combined organic layer was dried over anhydrous $Na_2SO_4$ and evaporated under reduced pressure to obtain the crude product which was purified via preparative HPLC (Method Information: Column CELLULOSE-2 [(250×4.6 mm), 5 micron; MOBILE PHASE: 0.1% DEA in methanol] to obtain Examples 1267 and 1268.

Example 1267: The pure fractions were evaporated to dryness to yield Example 1267 (6.3 mg, 4% yield). LCMS: m/z=486.2 (M+H); retention time 1.44 min [LCMS method: Column: XBridge BEH XP C18 (2.1×50 mm), 2.5 µm; Mobile phase A: 0.1% TFA: acetonitrile (95:5), Mobile phase B: 0.1% TFA: acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-$d_6$) δ ppm 8.19-8.14 (m, 1H), 8.11-8.04 (m, 1H), 7.44-7.52 (m, 2H), 7.39 (s, 1H), 7.25 (br d, J=8.3 Hz, 1H), 6.00 (s, 1H), 4.66 (br dd, J=2.8, 3.8 Hz, 1H), 3.78 (q, J=6.5 Hz, 1H), 3.53 (s, 3H), 3.47-3.36 (m, 2H), 3.01 (dd, J=3.5, 11.4 Hz, 1H), 2.80-2.70 (m, 2H), 1.23-1.29 (m, 6H), 1.03 (d, J=6.4 Hz, 3H).

Example 1268: (14 mg, 9% yield). LCMS: m/z=486.2 (M+H); retention time 1.44 min [LCMS method: Column: XBridge BEH XP C18 (2.1×50 mm), 2.5 µm; Mobile phase A: 0.1% TFA: acetonitrile (95:5), Mobile phase B: 0.1%

TFA: acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-d$_6$) δ ppm 8.19-8.12 (m, 1H), 8.10-8.03 (m, 1H), 7.51-7.43 (m, 1H), 7.41 (d, J=7.6 Hz, 2H), 7.23 (br d, J=7.3 Hz, 1H), 6.02 (s, 1H), 4.45-4.32 (m, 1H), 3.85-3.76 (m, 1H), 3.68-3.60 (m, 1H), 3.59-3.49 (m, 5H), 2.78 (dd, J=3.7, 12.0 Hz, 1H), 2.11-2.00 (m, 1H), 1.29 (d, J=6.6 Hz, 3H), 1.18 (d, J=6.4 Hz, 3H), 1.10 (d, J=6.4 Hz, 3H).

The examples in Table 49 were prepared from general procedure as described in Examples 1267 and 1268, using appropriate benzyl bromide/chloride. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 49

| Ex. No. | Structure | M + H | Stereo chem | LCMS RT and Method |
|---|---|---|---|---|
| 1269 | 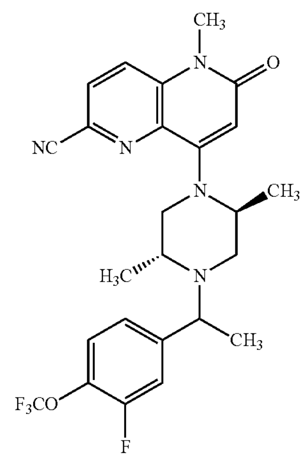 [SMILES: CC(c1ccc(OC(F)(F)F)c(F)c1)N1C[C@H](C)N(c2cc(=O)n(C)c3ccc(C#N)nc23)C[C@H]1C] | 504.2 | H | 2.51 A |
| 1270 | 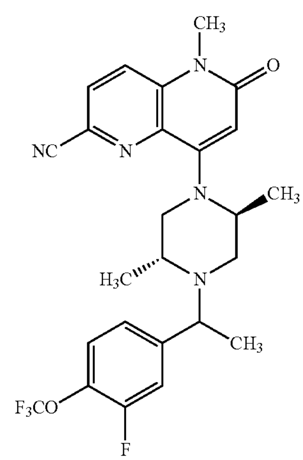 [SMILES: CC(c1ccc(OC(F)(F)F)c(F)c1)N1C[C@H](C)N(c2cc(=O)n(C)c3ccc(C#N)nc23)C[C@H]1C] | 504.2 | H | 2.46 A |
| 1271 | 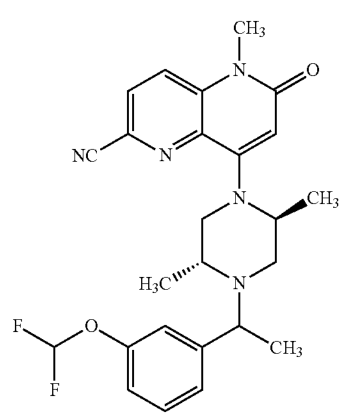 [SMILES: CC(c1cccc(OC(F)F)c1)N1C[C@H](C)N(c2cc(=O)n(C)c3ccc(C#N)nc23)C[C@H]1C] | 468.2 | H | 2.20 A |

TABLE 49-continued

| Ex. No. | Structure | M + H | Stereo chem | LCMS RT and Method |
|---|---|---|---|---|
| 1272 | 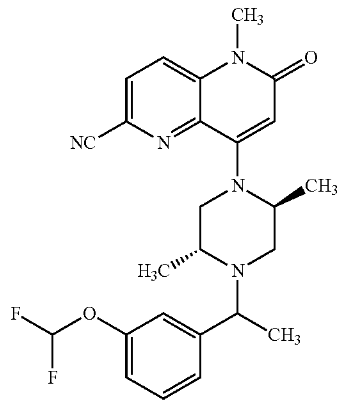 [SMILES: CC(c1cccc(OC(F)F)c1)N1C[C@H](C)N(c2cc(=O)n(C)c3ccc(C#N)nc23)C[C@H]1C] | 468.2 | H | 2.22 A |
| 1273 | 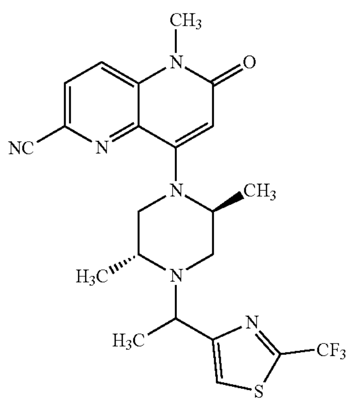 [SMILES: CC(c1csc(C(F)(F)F)n1)N1C[C@H](C)N(c2cc(=O)n(C)c3ccc(C#N)nc23)C[C@H]1C] | 477.2 | H | 2.03 A |
| 1274 | 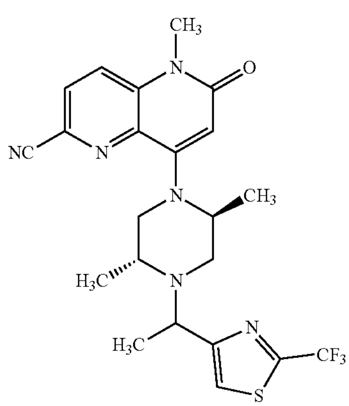 [SMILES: CC(c1csc(C(F)(F)F)n1)N1C[C@H](C)N(c2cc(=O)n(C)c3ccc(C#N)nc23)C[C@H]1C] | 477.1 | H | 2.09 A |

TABLE 49-continued

| Ex. No. | Structure | M + H | Stereo chem | LCMS RT and Method |
|---|---|---|---|---|
| 1275 | 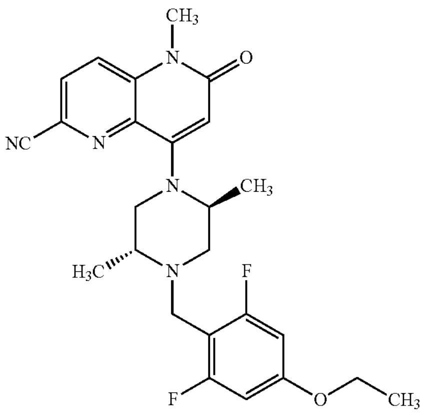 [SMILES: CCOc1cc(F)c(CN2C[C@H](C)N(c3cc(=O)n(C)c4ccc(C#N)nc34)C[C@H]2C)c(F)c1] | 468.3 | H | 2.21 A |
| 1276 | 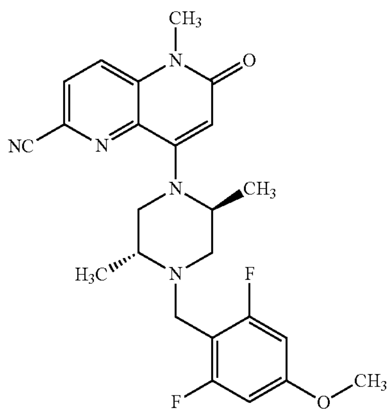 [SMILES: COc1cc(F)c(CN2C[C@H](C)N(c3cc(=O)n(C)c4ccc(C#N)nc34)C[C@H]2C)c(F)c1] | 454.2 | H | 2.05 A |

Examples 1277 and 1278

8-((2S,5R)-4-(2-methoxy-1-(5-(trifluoromethyl)pyridin-2-yl)ethyl)-2,5-dimethylpiperazin-1-yl)-5-methyl-6-oxo-5,6-dihydro-1,5-naphthyridine-2-carbonitrile (1277-1278)

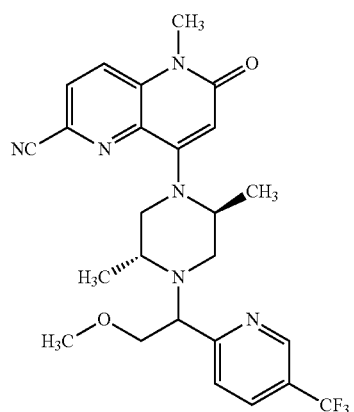

Intermediate 1277A: tert-butyl (2S,5R)-4-(2-methoxy-2-oxo-1-(5-(trifluoromethyl) pyridin-2-yl)ethyl)-2,5-dimethylpiperazine-1-carboxylate (1277A)

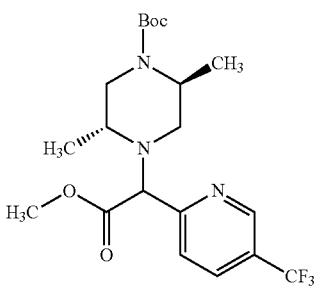

To a stirred solution of tert-butyl (2S,5R)-2,5-dimethylpiperazine-1-carboxylate (0.35 g, 1.63 mmol) in acetonitrile (8 mL) were added DIPEA (0.9 mL, 4.9 mmol) and methyl 2-bromo-2-(5-(trifluoromethyl)pyridin-2-yl)acetate (0.54 g, 1.79 mmol) at room temperature. The reaction mixture was heated at 85° C. for 16 h. The reaction mixture was cooled to room temperature, concentrated under reduced pressure to obtain the crude product, which was purified by silica gel chromatography (24 g; using 6%-10% ethyl acetate/petroleum ether) to obtain tert-butyl (2S,5R)-4-(2-methoxy-2-oxo-1-(5-(trifluoromethyl)pyridin-2-yl)ethyl)-2,5-dimethylpiperazine-1-carboxylate (0.52 g, 74% yield). LCMS: m/z=432.2 (M+H); retention time 2.19 min [LCMS method: Column: Waters Acquity UPLC BEH C18 (2.1×50 mm), 1.7 μm; Mobile phase A: 0.1% TFA in water; Mobile phase B: 0.1% TFA in acetonitrile; Gradient=20-90% B over 1.1 minute, then a 0.6 minute hold at 90% B; Temperature: 50° C.; Flow rate: 0.7 mL/min; Detection: UV at 220 nm].

Intermediate 1277B: tert-butyl (2S,5R)-4-(2-hydroxy-1-(5-(trifluoromethyl)pyridin-2-yl) ethyl)-2,5-dimethylpiperazine-1-carboxylate

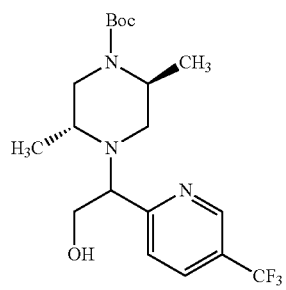

(1277B)

To a solution of tert-butyl (2S,5R)-4-(2-methoxy-2-oxo-1-(5-(trifluoromethyl) pyridin-2-yl)ethyl)-2,5-dimethylpiperazine-1-carboxylate (0.15 g, 0.35 mmol) in ethanol (5 mL) was added NaBH$_4$ (0.07 g, 1.74 mmol) and calcium chloride (0.19 g, 1.74 mmol) at room temperature. The reaction mixture was stirred for 3 h. The reaction was quenched with water (10 mL). The reaction mixture was extracted with ethyl acetate (3×100 mL), the combined organic layer was dried over anhydrous sodium sulfate and evaporated under reduced pressure to obtain the crude product. LCMS: m/z=404.2 (M+H); retention time 1.84 min [LCMS method: Column: Ascentis Express C8 (50×2.1 mm) 2.7 μm; Mobile phase A: 10 mM ammonium formate:acetonitrile (98:2), Mobile phase B: 10 mM ammonium formate:acetonitrile (2:98), Gradient=0-100% B over 1.5 minutes, then a 0.6 minute hold at 100% B; Temperature: 27° C.; Flow rate: 1.0 mL/min; Detection: UV at 220 nm].

Intermediate 1277C: tert-butyl (2S,5R)-4-(2-methoxy-1-(5-(trifluoromethyl)pyridin-2-yl) ethyl)-2,5-dimethylpiperazine-1-carboxylate

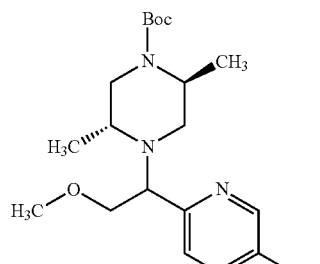

(1277C)

To a stirred solution of tert-butyl (2S,5R)-4-(2-hydroxy-1-(5-(trifluoromethyl) pyridin-2-yl)ethyl)-2,5-dimethylpiperazine-1-carboxylate (0.25 g, 0.62 mmol) in DMF (5 mL) was added NaH (50 mg, 1.24 mmol, 60% w/w) at 0° C. After 30 min., methyl iodide (0.06 mL, 0.93 mmol) was added and the reaction mixture was stirred at room temperature for 3 h. The reaction was quenched with water (50 mL). The reaction mixture was extracted with ethyl acetate (3×100 mL), the organic layer dried over anhydrous sodium sulfate, filtered, evaporated under reduced pressure to obtain the crude product which was purified by silica gel chromatography (12 g silica gel column; using 42%-48% ethyl acetate/petroleum ether) to obtain tert-butyl (2S,5R)-4-(2-methoxy-1-(5-(trifluoromethyl)pyridin-2-yl)ethyl)-2,5-dimethylpiperazine-1-carboxylate (110 mg, 42% yield). LCMS: m/z=418.2 (M+H); retention time 2.25 min [LCMS method: Column: Ascentis Express C8 (50×2.1 mm) 2.7 μm; Mobile phase A: 10 mM ammonium formate:acetonitrile (98:2), Mobile phase B: 10 mM ammonium formate:acetonitrile (2:98), Gradient=0-100% B over 1.5 minutes, then a 0.6 minute hold at 100% B; Temperature: 27° C.; Flow rate: 1.0 mL/min; Detection: UV at 220 nm].

Intermediate 1277D: (2R,5S)-1-(2-methoxy-1-(5-(trifluoromethyl)pyridin-2-yl)ethyl)-2,5-dimethylpiperazine.TFA

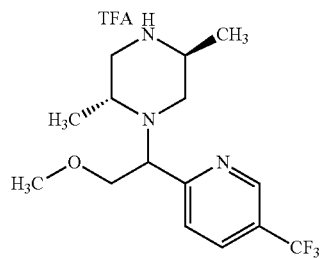

(1277D)

To a solution of tert-butyl (2S,5R)-4-(2-methoxy-1-(5-(trifluoromethyl)pyridin-2-yl)ethyl)-2,5-dimethylpiperazine-1-carboxylate (110 mg, 0.26 mmol) in DCM (3 mL) was added TFA (0.2 mL, 2.6 mmol). The reaction mixture was stirred at room temperature for 2 h. The reaction mixture was concentrated under reduced pressure to obtain the crude product (2R,5S)-1-(2-methoxy-1-(5-(trifluoromethyl)pyridin-2-yl)ethyl)-2,5-dimethylpiperazine.TFA (100 mg, 88% yield) as brown solid. LCMS: m/z=318.2 (M+H); retention time 0.87 min [LCMS method: Column: Ascentis Express C8 (50×2.1 mm) 2.7 μm; Mobile phase A: 10 mM ammonium formate:acetonitrile (98:2), Mobile phase B: 10 mM ammonium formate:acetonitrile (2:98), Gradient=0-100% B over 1.5 minutes, then a 0.6 minute hold at 100% B; Temperature: 27° C.; Flow rate: 1.0 mL/min; Detection: UV at 220 nm].

Examples 1277 and 1278: 8-((2S,5R)-4-(2-methoxy-1-(5-(trifluoromethyl)pyridin-2-yl) ethyl)-2,5-dimethylpiperazin-1-yl)-5-methyl-6-oxo-5,6-dihydro-1,5-naphthyridine-2-carbonitrile To a stirred solution of (2R,5S)-1-(2-methoxy-1-(5-(trifluoromethyl)pyridin-2-yl) ethyl)-2,5-dimethylpiperazine, TFA (0.10 g, 0.24 mmol) in acetonitrile (8 mL) was added DIPEA (0.13 mL, 0.72 mmol), 6-cyano-1-methyl-2-oxo-1, 2-dihydro-1,5-naphthyridin-4-yl trifluoromethanesulfonate (0.08 g, 0.24 mmol) at room temperature. The reaction mixture was heated at 85° C. for 16 h. The reaction mixture was cooled to room temperature and concentrated under reduced pressure to obtain the crude product, which was purified by preparative HPLC (Method Information: Column CELLULOSE-2 (250×4.6 mm), 5 micron, MOBILE PHASE: 0.1% DEA in acetonitrile, Isocratic) to obtain Examples 1277 and 1278.

Example 1277: (3.5 mg, 3% yield). LCMS: m/z=501.3 (M+H); retention time 1.99 min [LCMS method: Column: Ascentis Express C8 (50×2.1 mm) 2.7 µm; Mobile phase A: 10 mM ammonium formate:acetonitrile (98:2), Mobile phase B: 10 mM ammonium formate:acetonitrile (2:98), Gradient=0-100% B over 1.5 minutes, then a 0.6 min hold at 100% B; Temperature: 27° C.; Flow rate: 1.0 mL/min; Detection: UV at 220 nm]. $^1$H NMR (400 MHz, DMSO-$d_6$) δ ppm 8.94 (s, 1H), 8.21 (dd, J=1.6, 8.4 Hz, 1H), 8.17-8.12 (m, 1H), 8.09-8.03 (m, 1H), 7.78 (d, J=8.1 Hz, 1H), 6.03 (s, 1H), 4.50-4.33 (m, 1H), 4.11 (t, J=5.6 Hz, 1H), 3.69-3.81 (m, 2H), 3.52 (s, 3H), 3.47-3.41 (m, 1H), 3.35 (br s, 1H), 3.21 (s, 3H), 3.17 (br dd, J=3.4, 11.7 Hz, 1H), 2.76-2.63 (m, 2H), 1.19 (d, J=6.4 Hz, 3H), 1.08 (d, J=6.4 Hz, 3H).

Example 1278: (11.9 mg, 10% yield). LCMS: m/z=501.2 (M+H); retention time 1.96 min [LCMS method: Column: Ascentis Express C8 (50×2.1 mm) 2.7 µm; Mobile phase A: 10 mM ammonium formate:acetonitrile (98:2), Mobile phase B: 10 mM ammonium formate:acetonitrile (2:98), Gradient=0-100% B over 1.5 minutes, then a 0.6 minute hold at 100% B; Temperature: 27° C.; Flow rate: 1.0 mL/min; Detection: UV at 220 nm]. $^1$H NMR (400 MHz, DMSO-$d_6$) δ 8.90 (s, 1H), 8.20 (dd, J=2.1, 8.2 Hz, 1H), 8.17-8.12 (m, 1H), 8.10-8.01 (m, 1H), 7.80 (d, J=8.3 Hz, 1H), 6.03 (s, 1H), 4.35 (br dd, J=2.1, 3.3 Hz, 1H), 3.99 (t, J=5.3 Hz, 1H), 3.87-3.80 (m, 1H), 3.73 (dd, J=5.0, 10.1 Hz, 1H), 3.66-3.43 (m, 5H), 3.21 (s, 3H), 3.18 (d, J=5.4 Hz, 1H), 2.92 (dd, J=3.7, 11.7 Hz, 1H), 2.13 (dd, J=2.3, 11.6 Hz, 1H), 1.17 (d, J=6.4 Hz, 3H), 1.11 (d, J=6.4 Hz, 3H).

Examples 1279 and 1280

8-((2S,5R)-4-(2-hydroxy-1-(5-(trifluoromethyl)pyridin-2-yl)ethyl)-2,5-dimethylpiperazin-1-yl)-5-methyl-6-oxo-5,6-dihydro-1,5-naphthyridine-2-carbonitrile

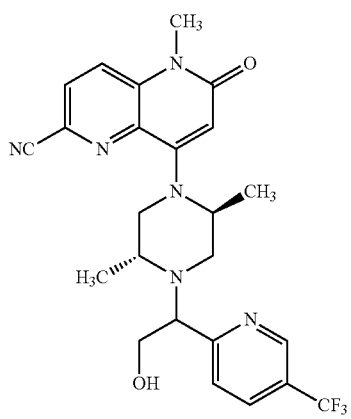

(1279-1280)

Intermediate 1279A: 2-((2R,5S)-2,5-dimethylpiperazin-1-yl)-2-(5-(trifluoromethyl) pyridin-2-yl)ethan-1-ol

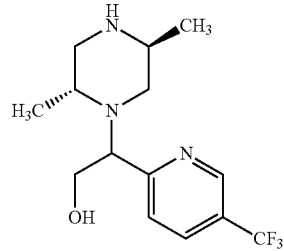

(1297A)

To a solution of tert-butyl (2S,5R)-4-(2-hydroxy-1-(5-(trifluoromethyl)pyridin-2-yl)ethyl)-2,5-dimethylpiperazine-1-carboxylate (120 mg, 0.29 mmol) in DCM (3 mL) was added TFA (0.2 mL, 2.6 mmol) at room temperature. The reaction mixture was stirred for 2 h. The reaction mixture was concentrated under reduced pressure to obtain 2-((2R,5S)-2,5-dimethylpiperazin-1-yl)-2-(5-(trifluoromethyl)pyridin-2-yl)ethan-1-ol (100 mg, 63% yield) as brown solid. LCMS: m/z=304.2 (M+H); retention time 0.53 min [LCMS method: Column: Ascentis Express C8 (50×2.1 mm) 2.7 µm; Mobile phase A: 10 mM ammonium formate: acetonitrile (98:2), Mobile phase B: 10 mM ammonium formate:acetonitrile (2:98), Gradient=0-100% B over 1.5 minutes, then a 0.6 minute hold at 100% B; Temperature: 27° C.; Flow rate: 1.0 mL/min; Detection: UV at 220 nm].

Examples 1279 and 1280: 8-((2S,5R)-4-(2-hydroxy-1-(5-(trifluoromethyl)pyridin-2-yl) ethyl)-2,5-dimethylpiperazin-1-yl)-5-methyl-6-oxo-5,6-dihydro-1,5-naphthyridine-2-carbonitrile To a stirred solution of 2-((2R,5S)-2,5-dimethylpiperazin-1-yl)-2-(5-(trifluoromethyl)pyridin-2-yl)ethan-1-ol, TFA (0.1 g, 0.24 mmol) in acetonitrile (8 mL) were added DIPEA (0.13 mL, 0.72 mmol) and 6-cyano-1-methyl-2-oxo-1,2-dihydro-1,5-naphthyridin-4-yl trifluoromethanesulfonate (0.08 g, 0.24 mmol) at room temperature. The reaction mixture was heated at 85° C. for 16 h. The reaction mixture was cooled to room temperature and concentrated under reduced pressure to obtain the crude product, which was purified by preparative HPLC (Method information: Column CELLULOSE-2 (250×4.6 mm), 5 micron; MOBILE PHASE: 0.1% DEA MeOH; Isocratic) to obtain Examples 1279 and 1280.

Example 1279: (9.1 mg, 8% yield). LCMS: m/z=487.2 (M+H); retention time 1.65 min [LCMS method: Column: Ascentis Express C8 (50×2.1 mm) 2.7 µm; Mobile phase A: 10 mM ammonium formate:acetonitrile (98:2), Mobile phase B: 10 mM ammonium formate:acetonitrile (2:98), Gradient=0-100% B over 1.5 minutes, then a 0.6 min hold at 100% B; Temperature: 27° C.; Flow rate: 1.0 mL/min; Detection: UV at 220 nm]. $^1$H NMR (400 MHz, DMSO-$d_6$) δ ppm 8.94 (s, 1H), 8.24-8.12 (m, 2H), 8.11-8.02 (m, 1H), 7.78 (d, J=8.3 Hz, 1H), 6.04 (s, 1H), 4.65 (br t, J=4.8 Hz, 1H), 4.53-4.38 (m, 1H), 4.04-3.94 (m, 1H), 3.90-3.73 (m, 2H), 3.53 (s, 3H), 3.49-3.43 (m, 1H), 3.26 (br d, J=7.3 Hz, 1H), 2.80-2.69 (m, 2H), 2.57-2.53 (m, 1H), 1.27-1.14 (m, 3H), 1.12-1.03 (m, 3H).

Example 1280: (11.1 mg, 9.3% yield). LCMS: m/z=487.2 (M+H); retention time 1.65 min [LCMS method: Column: Ascentis Express C8 (50×2.1 mm) 2.7 μm; Mobile phase A: 10 mM ammonium formate:acetonitrile (98:2), Mobile phase B: 10 mM ammonium formate:acetonitrile (2:98), Gradient=0-100% B over 1.5 minutes, then a 0.6 minute hold at 100% B; Temperature: 27° C.; Flow rate: 1.0 mL/min; Detection: UV at 220 nm]. $^1$H NMR (400 MHz, DMSO-$d_6$) δ ppm 8.89 (d, J=1.0 Hz, 1H), 8.25-8.12 (m, 2H), 8.10-8.04 (m, 1H), 7.80 (d, J=8.3 Hz, 1H), 6.03 (s, 1H), 4.70-4.59 (m, 1H), 4.45-4.30 (m, 1H), 3.98-3.89 (m, 1H), 3.85-3.73 (m, 2H), 3.65 (br s, 1H), 3.62-3.55 (m, 2H), 3.53 (s, 3H), 2.92 (dd, J=3.7, 12.0 Hz, 1H), 2.14-2.06 (m, 1H), 1.18 (d, J=6.4 Hz, 3H), 1.13 (d, J=6.4 Hz, 3H).

Examples 1281 and 1282

8-((2S,5R)-4-(1-(5-cyclopropylisoxazol-3-yl)ethyl)-2,5-dimethylpiperazin-1-yl)-5-methyl-6-oxo-5,6-dihydro-1,5-naphthyridine-2-carbonitrile (1281-1282)

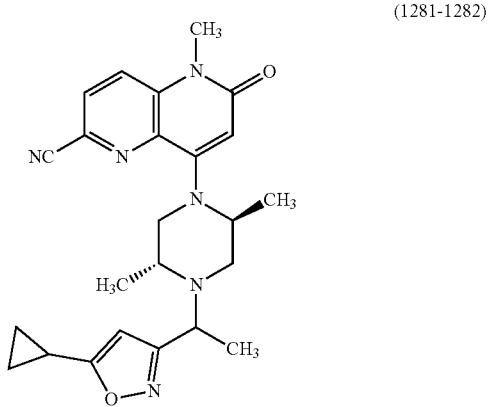 [SMILES: CC(c1cc(C2CC2)on1)N1C[C@H](C)N(c2cc(=O)n(C)c3ccc(C#N)nc23)C[C@H]1C]

To a solution of 8-((2S,5R)-2,5-dimethylpiperazin-1-yl)-5-methyl-6-oxo-5,6-dihydro-1,5-naphthyridine-2-carbonitrile (130 mg, 0.44 mmol) in acetonitrile (5 mL) was added DIPEA (0.38 mL, 2.19 mmol), 1-(5-cyclopropylisoxazol-3-yl)ethan-1-ol (94 mg, 0.61 mmol) and (cyanomethyl) trimethyl phosphonium iodide (212 mg, 0.87 mmol) at room temperature. The reaction mixture was heated at 110° C. in a microwave reactor for 2 h. The reaction mixture was cooled to room temperature, diluted with water and extracted twice with ethyl acetate (20 mL). The combined organic layer was dried over anhydrous $Na_2SO_4$ and evaporated under reduced pressure to obtain the crude product, which was purified by preparative HPLC (Method Information: Column: DAD:1-XBRIDGE C18 (150×4.6) mm 5 micron DAD:2-SUNFIRE C18 (150×4.6) mm 5 micron; MOBILE PHASE: A: 10 mM ammonium acetate in water B: ACN; FLOW: 2.0 mL/min). The fractions were evaporated and taken for chiral Prep HPLC purification (Chiral Prep Method: Column: DAD-1-CELLULOSE-2 (250×4.6 mm), 5 micron; DAD-2-CELLULOSE-4 (250×4.6 mm), 5 micron; MOBILE PHASE A: 0.1% DEA in ACN; MOBILE PHASE B: 0.1% DEA in MeOH) to obtain Example 1281: (5.0 mg, 3% yield). LCMS: m/z=433.2 (M+H); retention time 1.80 min [LCMS method: Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-$d_6$) δ ppm 8.20-8.13 (m, 1H), 8.10-8.03 (m, 1H), 6.23 (s, 1H), 6.09 (s, 1H), 4.34-4.06 (m, 1H), 3.96 (q, J=6.5 Hz, 1H), 3.54 (s, 3H), 3.52-3.45 (m, 1H), 3.25-3.18 (m, 1H), 3.03 (dd, J=3.4, 11.5 Hz, 1H), 2.84-2.74 (m, 1H), 2.45 (br d, J=4.6 Hz, 1H), 2.18-2.09 (m, 1H), 1.33 (d, J=6.8 Hz, 3H), 1.14 (d, J=6.4 Hz, 3H), 1.09-0.99 (m, 5H), 0.94-0.87 (m, 2H); and Example 1282 (4.4 mg, 2% yield). LCMS: m/z=433.2 (M+H); retention time 1.18 min (Column: XBridge BEH XP C18 (2.1×50 mm), 2.5 μm; Mobile phase A: 0.1% TFA: acetonitrile (95:5), Mobile phase B: 0.1% TFA: acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-$d_6$) δ ppm 8.19-8.14 (m, 1H), 8.11-8.03 (m, 1H), 6.16 (s, 1H), 6.04 (s, 1H), 4.37-4.27 (m, 1H), 3.80-3.73 (m, 1H), 3.69-3.63 (m, 1H), 3.55-3.48 (m, 4H), 3.42-3.36 (m, 1H), 2.79 (dd, J=3.5, 11.6 Hz, 1H), 2.18 (dd, J=3.1, 11.6 Hz, 1H), 2.15-2.08 (m, 1H), 1.30 (d, J=6.8 Hz, 3H), 1.08-1.12 (m, 6H), 1.07-1.02 (m, 2H), 0.93-0.81 (m, 2H).

The examples in the Table 50 were prepared from general procedure described in Examples 1281 and 1282, using appropriate alcohol. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 50

| Ex. No. | Structure | M + H | Stereo chem | LCMS RT and Method |
|---|---|---|---|---|
| 1283 | 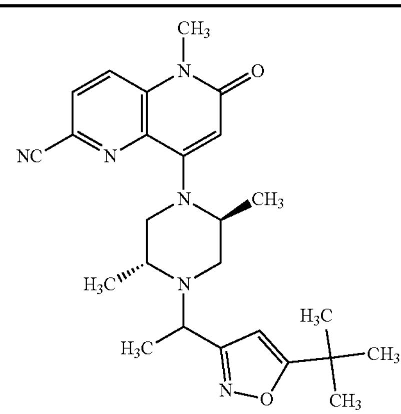 | 449.3 | H | 1.41 A |

TABLE 50-continued

| Ex. No. | Structure | M + H | Stereo chem | LCMS RT and Method |
|---|---|---|---|---|
| 1284 | 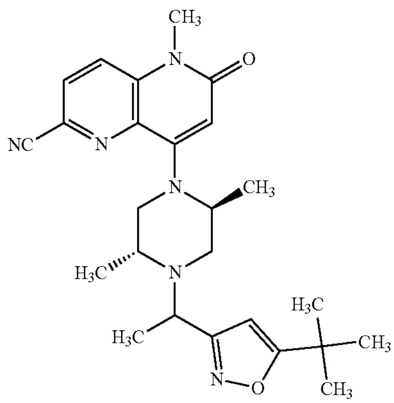 [SMILES: CC(c1cc(C(C)(C)C)on1)N1C[C@H](C)N(c2cc(=O)n(C)c3ccc(C#N)nc23)C[C@H]1C] | 449.3 | H | 1.38 A |

The examples in the Table 51 were prepared from general procedure described in Examples 735 and 736, using appropriate boronic acid. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 51

| Ex. No. | Structure | M + H | Stereo chem | LCMS RT and Method |
|---|---|---|---|---|
| 1285 | 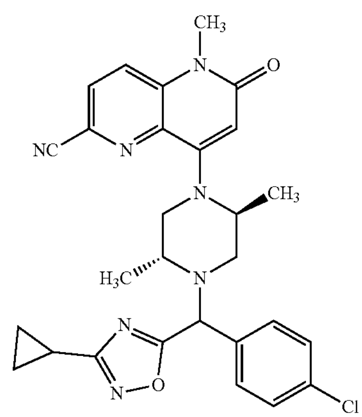 [SMILES: C[C@@H]1CN(c2cc(=O)n(C)c3ccc(C#N)nc23)[C@@H](C)CN1C(c1ccc(Cl)cc1)c1nc(C2CC2)no1] | 530.2 | H | 2.31 A |
| 1286 | 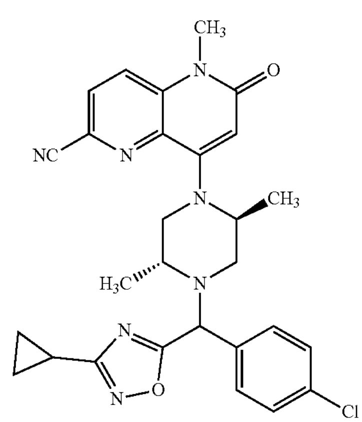 [SMILES: C[C@@H]1CN(c2cc(=O)n(C)c3ccc(C#N)nc23)[C@@H](C)CN1C(c1ccc(Cl)cc1)c1nc(C2CC2)no1] | 530.3 | H | 2.3 A |

Examples 1287 and 1288

8-((2S,5R)-4-((2-(dimethylphosphoryl)phenyl)(4-fluorophenyl)methyl)-2,5-dimethylpiperazin-1-yl)-5-methyl-6-oxo-5,6-dihydro-1,5-naphthyridine-2-carbonitrile

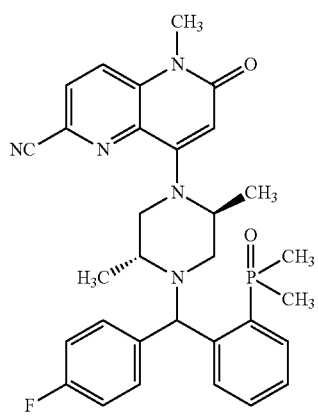
(1287-1288)

Intermediate 1287A:
(2-bromophenyl)(4-fluorophenyl)methanol

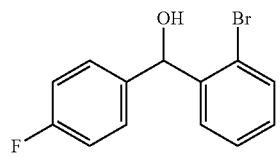
(1287A)

To a stirred solution of 2-bromobenzaldehyde (2.0 g, 10.81 mmol) in dry tetrahydrofuran (20 mL) was added (4-fluorophenyl)magnesium bromide (10 mL, 10 mmol, 1M in THF) at 0° C. The reaction mixture was stirred for 16 h at room temperature. The reaction was quenched with saturated aqueous NH$_4$Cl solution (20 mL). The reaction mixture was extracted with ethyl acetate (100 mL). The organic layer was washed with water (20 mL), brine (20 mL), dried over anhydrous Na$_2$SO$_4$ and evaporated under reduced pressure to obtain the crude compound which was purified by 24 g silica gel chromatography by using 0-30% ethyl acetate/petroleum ether as eluent to obtain (2-bromophenyl)(4-fluorophenyl) methanol (2.1 g, 89% yield). $^1$H NMR (300 MHz, CDCl$_3$) δ ppm 7.50-7.62 (m, 2H), 7.34-7.46 (m, 3H), 7.14-7.24 (m, 1H), 6.92-7.07 (m, 2H), 6.20 (s, 1H).

Intermediate 1287B:
1-bromo-2-(bromo(4-fluorophenyl)methyl)benzene

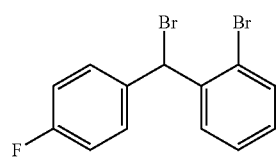
(1287B)

To a stirred solution of (2-bromophenyl)(4-fluorophenyl)methanol (500 mg, 1.78 mmol) in DCM (10 mL) was added dropwise BBr$_3$ (3.56 mL, 3.56 mmol, 1 M in DCM) at room temperature. The reaction mixture was stirred for 4 h. The reaction was quenched with saturated aqueous NaHCO$_3$ solution (20 mL). The reaction mixture was extracted with DCM (100 mL). The organic layer was dried over anhydrous sodium sulfate, filtered and evaporated under reduced pressure to yield 1-bromo-2-(bromo(4-fluorophenyl)methyl) benzene (580 mg, 95% yield). LCMS: m/z, 263.1 (M-Br); retention time 2.13 min. LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Flow rate: 0.7 mL/min; Detection: UV at 220 nm.

Intermediate 1287C: tert-butyl (2S,5R)-4-((2-bromophenyl)(4-fluorophenyl)methyl)-2,5-dimethylpiperazine-1-carboxylate

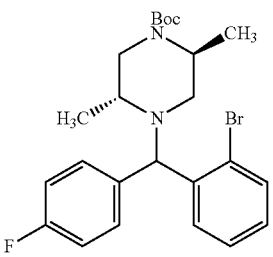
(1287C)

To a solution of tert-butyl (2S,5R)-2,5-dimethylpiperazine-1-carboxylate (500 mg, 2.33 mmol) in dry acetonitrile (3.0 mL), were added 1-bromo-2-(bromo(4-fluorophenyl) methyl)benzene (883 mg, 2.57 mmol) and DIPEA (1.22 mL, 7.0 mmol) at room temperature. The reaction mixture was heated at 85° C. for 24 h. The reaction mixture was cooled to room temperature and concentrated under reduced pressure to obtain the crude product, which was purified by Combi flash 12 g silica gel chromatography by using 0-100% ethyl acetate/petroleum ether as eluent to obtain tert-butyl (2S,5R)-4-((2-bromophenyl)(4-fluorophenyl) methyl)-2,5-dimethylpiperazine-1-carboxylate (0.45 g, 40% yield). $^1$H NMR (300 MHz, CDCl$_3$) δ ppm 7.75-7.89 (m, 1H), 7.25-7.60 (m, 4H), 6.91-7.17 (m, 3H), 5.02 (d, J=9.6 Hz, 1H), 4.12 (m, 1H), 3.51-3.72 (m, 1H), 3.30 (m, 1H), 2.93 (m, 1H), 2.57-2.71 (m, 1H), 2.17-2.31 (m, 1H), 1.37-1.65 (m, 9H), 1.14-1.33 (m, 3H), 0.82-1.05 (m, 3H).

Intermediate 1287D: tert-butyl (2S,5R)-4-((2-(dimethylphosphoryl)phenyl)(4-fluorophenyl)methyl)-2,5-dimethylpiperazine-1-carboxylate

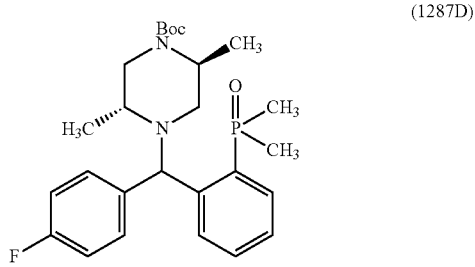 [SMILES: C[C@@H]1CN(C(=O)OC(C)(C)C)[C@@H](C)CN1C(c1ccc(F)cc1)c1ccccc1P(C)(C)=O]
(1287D)

A stirred suspension of tert-butyl (2S,5R)-4-((2-bromophenyl)(4-fluorophenyl) methyl)-2,5-dimethylpiperazine-1-carboxylate (75 mg, 0.16 mmol), dimethylphosphine oxide (15 mg, 0.19 mmol), XantPhos (6 mg, 9.43 µmol) and potassium phosphate, tribasic (33 mg, 0.19 mmol) in DMF (2 mL) was purged with argon for 10 min, followed by addition of palladium(II) acetate (2 mg, 7.85 µmol). The reaction mixture was heated at 120° C. overnight. The reaction mixture was cooled to room temperature, concentrated under reduced pressure and was purified by 12 g silica gel chromatography by using 0-50% ethyl acetate/petroleum ether as eluent to obtain tert-butyl (2S,5R)-4-((2-(dimethylphosphoryl)phenyl)(4-fluorophenyl)methyl)-2,5-dimethylpiperazine-1-carboxylate (50 mg, 67% yield). LCMS: m/z, 475.5 (M+H); retention time 1.94 and 1.98 min. [LCMS Method: Column: Waters Acquity UPLC BEH C18 (2.1×50 mm) 1.7 µm, Mobile phase A: 10 mM ammonium acetate: acetonitrile (95:5); Mobile phase B: 10 mM ammonium acetate:acetonitrile (5:95), Gradient=20-100% B over 2 minute, then a 0.3 minute hold at 100% B; Flow rate: 0.7 mL/min; Detection: UV at 220 nm].

Intermediate 1287E: (2-(((2R,5S)-2,5-dimethylpiperazin-1-yl)(4-fluorophenyl)methyl) phenyl)dimethylphosphine oxide, TFA

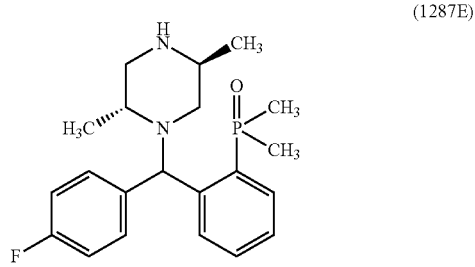 [SMILES: C[C@@H]1CN[C@@H](C)CN1C(c1ccc(F)cc1)c1ccccc1P(C)(C)=O]
(1287E)

To a stirred solution of tert-butyl (2S,5R)-4-((2-(dimethylphosphoryl)phenyl)(4-fluorophenyl)methyl)-2,5-dimethylpiperazine-1-carboxylate (50 mg, 0.11 mmol) in DCM (2 mL) was added TFA (0.11 mL, 1.37 mmol). The reaction mixture was stirred at room temperature for 4 h. The solvent was removed under reduced pressure to yield the TFA salt of (2-(((2R,5S)-2,5-dimethylpiperazin-1-yl)(4-fluorophenyl) methyl)phenyl) dimethylphosphine oxide as a brown semisolid. LCMS: m/z, 375.4 (M+H); retention time 1.03 min. LC-MS Method: Column-AQUITY UPLC BEH C18 (3.0× 50 mm) 1.7 µm; Mobile phase A: 10 mM ammonium acetate in water:acetonitrile (98:2); Mobile phase B: 10 mM ammonium acetate in water:acetonitrile (2:98); Gradient: 20%-100% B over 2 minutes, then a 0.2 minute hold at 100% B flow rate 0.7 mL/min, Detection: UV at 220 nm.

Examples 1287 and 1288: 8-((2S,5R)-4-((2-(dimethylphosphoryl)phenyl)(4-fluorophenyl)methyl)-2,5-dimethylpiperazin-1-yl)-5-methyl-6-oxo-5,6-dihydro-1,5-naphthyridine-2-carbonitrile To a suspension of (2-(((2R,5S)-2,5-dimethylpiperazin-1-yl)(4-fluorophenyl) methyl)phenyl)dimethylphosphine oxide, TFA (88 mg, 0.18 mmol) in dry acetonitrile (3 mL), were added 6-cyano-1-methyl-2-oxo-1,2-dihydro-1,5-naphthyridin-4-yl trifluoromethanesulfonate (60 mg, 0.18 mmol) and sodium bicarbonate (45 mg, 0.54 mmol) at room temperature under an argon atmosphere. The reaction mixture was heated to 85° C. for 16 h. The reaction mixture was cooled to room temperature, concentrated under reduced pressure to yield the crude product, which was purified by preparative chiral HPLC (Chiral HPLC Method: Column: LUX COLUMN C4 (250×21.2) 5 µm, Mobile phase: 0.1% DEA in MeOH, Flow: 23 mL/min) to afford Examples 1287 and 1288.

Example 1287 (2 mg, 2% yield); LCMS: m/z, 558.3 (M+H); retention time 1.85 min; [LCMS method: Column: XBridge BEH XP C18 (50×2.1 mm) 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%)]; $^1$H NMR (400 MHz, DMSO-$d_6$) δ ppm 8.20-8.01 (m, 2H), 7.85 (dd, J=6.0, 8.4 Hz, 2H), 7.59-7.42 (m, 2H), 7.36-7.24 (m, 1H), 7.08-7.18 (m, 2H), 6.51 (s, 1H), 6.39 (s, 1H), 5.99 (s, 1H), 4.59 (br s, 1H), 3.73-3.45 (m, 5H), 3.16-3.06 (m, 1H), 2.96 (br dd, J=3.3, 11.4 Hz, 1H), 2.35-2.21 (m, 1H), 1.83-1.61 (m, 6H), 1.33-1.15 (m, 3H), 1.11-0.95 (m, 3H).

Example 1288: (2 mg, 1.8% yield); LCMS: m/z, 558.2 (M+H); retention time 1.89 min; [LCMS method: Column: XBridge BEH XP C18 (50×2.1 mm) 2.5 µm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%)]; $^1$H NMR (400 MHz, DMSO-$d_6$) δ ppm 8.41-8.09 (m, 1H), 8.09-7.99 (m, 1H), 7.71 (dd, J=5.9, 8.3 Hz, 2H), 7.63-7.50 (m, 2H), 7.38-7.26 (m, 1H), 7.07-7.17 (m, 2H), 6.52 (br s, 1H), 5.99 (s, 1H), 4.77-4.55 (m, 1H), 3.72-3.46 (m, 5H), 3.17-3.07 (m, 1H), 3.02-2.86 (m, 1H), 2.82 (dd, J=3.3, 11.4 Hz, 1H), 2.27 (br d, J=11.2 Hz, 1H), 1.85-1.71 (m, 3H), 1.61-1.47 (m, 3H), 1.30 (d, J=6.6 Hz, 3H), 1.24-1.06 (m, 3H).

The compounds in Table 52 were prepared using the corresponding bromide as described for Example 1287 and 1288. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 52

| Ex. No. | Structure | M + H | Stereo chem | LCMS RT and Method |
|---|---|---|---|---|
| 1289 | 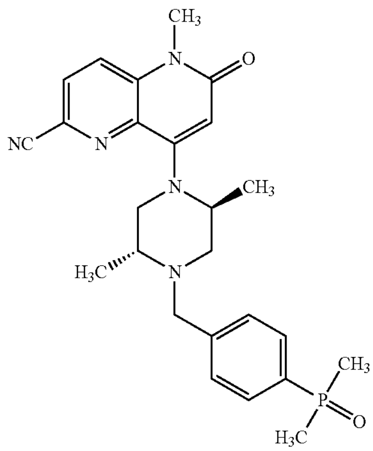 [SMILES: C[C@@H]1CN(c2cc(=O)n(C)c3ccc(C#N)nc23)[C@@H](C)CN1Cc1ccc(P(C)(C)=O)cc1] | 464.2 | H | 1.27 A |
| 1290 | 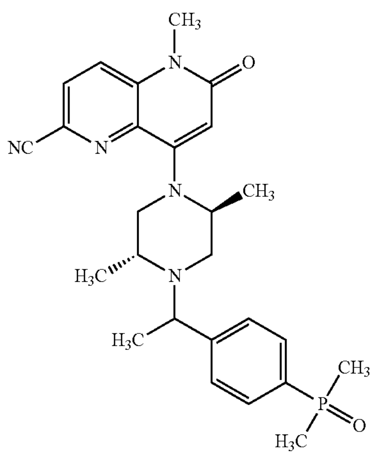 [SMILES: CC(c1ccc(P(C)(C)=O)cc1)N1C[C@H](C)N(c2cc(=O)n(C)c3ccc(C#N)nc23)C[C@H]1C] | 478.2 | H | 1.47 A |
| 1291 | 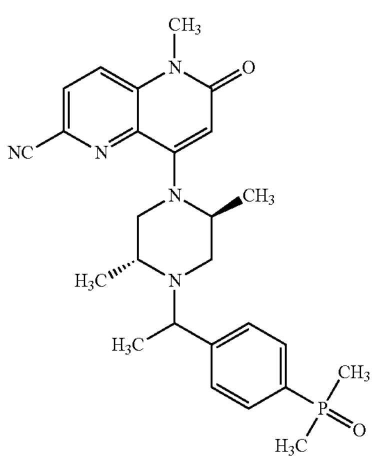 [SMILES: CC(c1ccc(P(C)(C)=O)cc1)N1C[C@H](C)N(c2cc(=O)n(C)c3ccc(C#N)nc23)C[C@H]1C] | 478.2 | H | 1.49 A |

TABLE 52-continued

| Ex. No. | Structure | M + H | Stereo chem | LCMS RT and Method |
|---|---|---|---|---|
| 1292 | 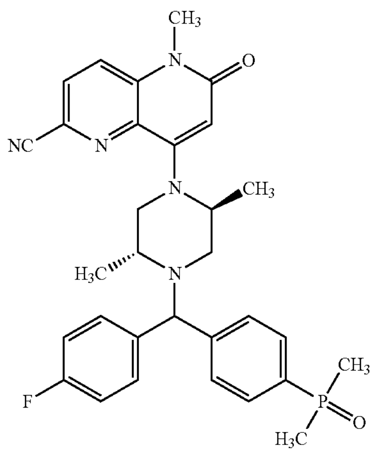 [SMILES: C[C@@H]1CN(c2cc(=O)n(C)c3ccc(C#N)nc23)[C@@H](C)CN1C(c1ccc(F)cc1)c1ccc(P(C)(C)=O)cc1] | 558.2 | H | 1.73 A |
| 1293 | 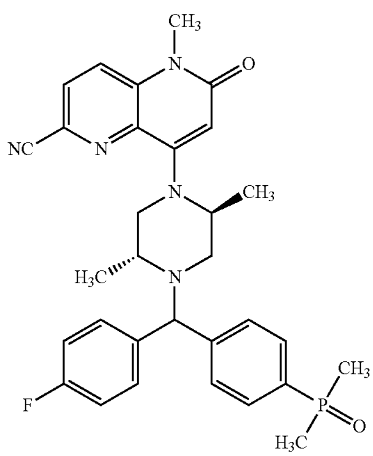 [SMILES: C[C@@H]1CN(c2cc(=O)n(C)c3ccc(C#N)nc23)[C@@H](C)CN1C(c1ccc(F)cc1)c1ccc(P(C)(C)=O)cc1] | 558.3 | H | 1.32 B |
| 1294 | 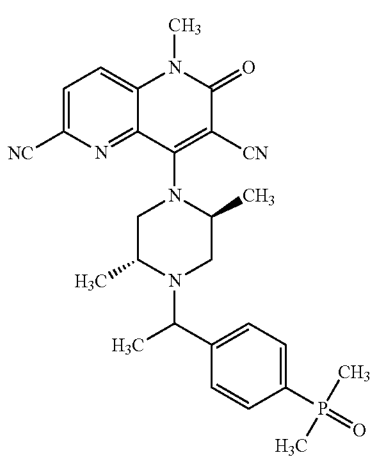 [SMILES: CC(c1ccc(P(C)(C)=O)cc1)N1C[C@H](C)N(c2c(C#N)c(=O)n(C)c3ccc(C#N)nc23)C[C@H]1C] | 503.2 | H | 1.48 A |

TABLE 52-continued

| Ex. No. | Structure | M + H | Stereo chem | LCMS RT and Method |
|---|---|---|---|---|
| 1295 | 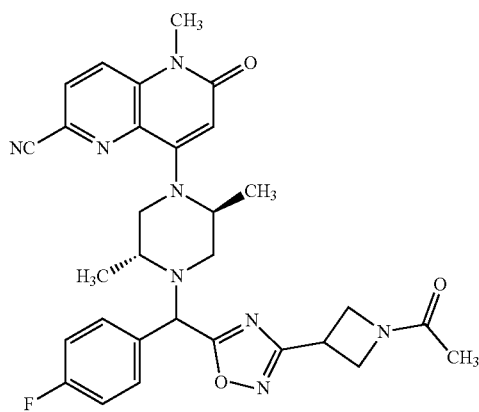 | 503.2 | H | 1.50 A |

Examples 1296 and 1297

8-((2S,5R)-4-((3-(1-acetylazetidin-3-yl)-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile (1296-1297)

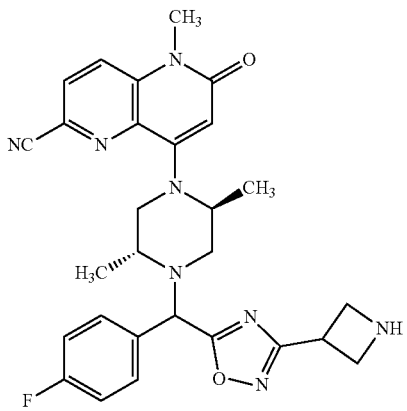

Intermediate 1296A: 8-((2S,5R)-4-((3-(azetidin-3-yl)-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile, TFA (1296A)

To a stirred solution of tert-butyl 3-(5-(((2R,5S)-4-(6-cyano-1-methyl-2-oxo-1,2-dihydro-1,5-naphthyridin-4-yl)-2,5-dimethylpiperazin-1-yl)(4-fluorophenyl)methyl)-1,2,4-oxadiazol-3-yl)azetidine-1-carboxylate (0.15 g, 0.24 mmol) in DCM (5 mL) was added TFA (0.18 mL, 2.39 mmol). The reaction mixture was stirred at room temperature for 3 h. The solvent was removed under reduced pressure to obtain the crude compound, which was purified by prep HPLC to obtain 8-((2S,5R)-4-((3-(azetidin-3-yl)-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile, TFA (150 mg, 99% yield). LCMS: m/z, 529.3 (M+H); retention time 1.56 min. Column: XBridge BEH XP C18 (2.1×50 mm), 2.5 μm; Mobile phase A: 10 mM ammonium acetate:acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.20-7.95 (m, 2H), 7.75-7.61 (m, 2H), 7.37-7.19 (m, 2H), 6.04 (br d, J=15.4 Hz, 1H), 5.38-5.26 (m, 1H), 3.82-3.73 (m, 2H), 3.61-3.50 (m, 6H), 3.17 (d, J=4.9 Hz, 1H), 3.01-2.77 (m, 2H), 1.28-0.80 (m, 10H).

Examples 1296 and 1297: 8-((2S,5R)-4-((3-(1-acetylazetidin-3-yl)-1,2,4-oxadiazol-5-yl) (4-fluorophenyl)methyl)-2,5-dimethylpiperazin-1-yl)-5-methyl-6-oxo-5,6-dihydro-1,5-naphthyridine-2-carbonitrile To a solution of 8-((2S,5R)-4-((3-(azetidin-3-yl)-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile (0.07 g, 0.13 mmol) in DCM (5 mL) at 0° C. were added triethylamine (0.07 mL, 0.53 mmol) and acetyl chloride (0.02 mL, 0.27 mmol). The reaction mixture was stirred at room temperature for 3 h. The reaction was quenched with saturated aqueous NaHCO$_3$ solution (5 mL). The mixture was dissolved in DCM (100 mL) and washed with water (20 mL), brine (20 mL), dried over anhydrous sodium sulfate, evaporated under reduced pressure to obtain the crude product, which was purified on a 12 g silica gel column chromatography by eluting with 10% MeOH in DCM. The desired fractions were concentrated under reduced pressure to yield 8-((2S,5R)-4-((3-(1-acetylazetidin-3-yl)-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile which was purified by preparative HPLC followed by chiral HPLC. (Chiral Separation Method: Column: Cellulose-2 (250×4.6 mm), 5 μm; Mobile Phase: 0.1% DEA in acetonitrile:methanol (90:10)) to afford Examples 1296 and 1297.

Example 1296: (4.7 mg, 6% yield); LCMS: m/z, 571.3 μm/z, (M+H); retention time 1.74 min; [LCMS method: Column: XBridge BEH XP C18 (50×2.1 mm) 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$) δ 8.18-8.10 (m, 1H), 8.10-8.03 (m, 1H), 7.69 (dd, J=5.4, 8.6 Hz, 2H), 7.21-7.31 (m, 2H), 6.04 (s, 1H), 5.36 (s, 1H), 4.55-4.34 (m, 2H), 4.29-4.15 (m, 2H), 4.11-3.99 (m, 1H), 3.98-3.91 (m, 1H), 3.67-3.47 (m, 5H), 2.98-2.82 (m, 2H), 1.83-1.72 (m, 3H), 1.17 (m, 6H).

Example 1297: (4.2 mg, 5.3% yield); LCMS: m/z, 571.2 (M+H); retention time 1.73 min; [LCMS method: Column: XBridge BEH XP C18 (50×2.1 mm) 2.5 μm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$) δ ppm 8.18-8.12 (m, 1H), 8.10-8.03 (m, 1H), 7.74-7.64 (m, 2H), 7.22-7.32 (m, 2H), 6.00 (s, 1H), 5.35 (d, J=2.2 Hz, 1H), 4.64-4.54 (m, 1H), 4.42-4.54 (m, 1H), 4.27-4.15 (m, 2H), 4.05-3.87 (m, 2H), 3.62-3.46 (m, 5H), 3.18-3.12 (m, 1H), 3.00 (br dd, J=1.8, 2.8 Hz, 1H), 2.24-2.14 (m, 1H), 1.76 (d, J=3.2 Hz, 3H), 1.22 (d, J=6.8 Hz, 3H), 1.03 (d, J=6.6 Hz, 3H).

Examples 1298 and 1299

8-((2S,5R)-4-((4-fluorophenyl)(3-(1-methylazetidin-3-yl)-1,2,4-oxadiazol-5-yl)methyl)-2,5-dimethylpiperazin-1-yl)-5-methyl-6-oxo-5,6-dihydro-1,5-naphthyridine-2-carbonitrile

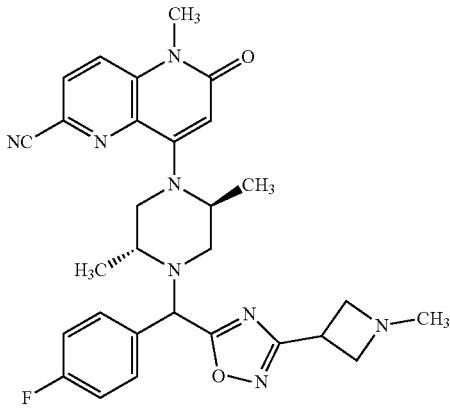

(1298-1299)

To a stirred solution of 8-((2S,5R)-4-((3-(azetidin-3-yl)-1,2,4-oxadiazol-5-yl)(4 fluorophenyl)methyl)-2,5-dimethylpiperazin-1-yl)-5-methyl-6-oxo-5,6-dihydro-1,5-naphthyridine-2-carbonitrile (0.05 g, 0.1 mmol) in THF (1 mL) and MeOH (1 mL) was added formaldehyde (4.3 mg, 0.14 mmol). The reaction mixture was stirred at room temperature for 2 h. Sodium cyanoborohydride (0.01 g, 0.19 mmol) was added and the reaction mixture was stirred at room temperature for 16 h. The reaction was quenched with saturated aqueous NaHCO$_3$ solution (5 mL). The reaction mixture was dissolved in DCM (100 mL), and washed with water (20 mL), brine (20 mL), dried over anhydrous sodium sulfate, filtered and evaporated under reduced pressure to yield 8-((2S,5R)-4-((3-(1-acetylazetidin-3-yl)-1,2,4-oxadiazol-5-yl)(4-fluorophenyl)methyl)-2,5-dimethylpiperazin-1-yl)-5-methyl-6-oxo-5,6-dihydro-1,5-naphthyridine-2-carbonitrile which was purified by preparative HPLC followed by chiral HPLC. (Chiral Separation Method: Column: Cellulose-4 (250×4.6 mm) 5 μm; Mobile Phase: 0.1% DEA in acetonitrile:isopropanol (90:10), Isocratic) to afford Examples 1298 and 1299.

Example 1298 (3.6 mg, 7% yield); LCMS: m/z=543.2 (M+H); retention time 1.74 min; [LCMS method: Column: XBridge BEH XP C18 (50×2.1 mm) 2.5 μm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$): δ ppm 8.15-8.13 (m, 1H), 8.07-8.04 (m, 1H), 7.69-7.66 (m, 2H), 7.29-7.24 (m, 2H), 6.00 (s, 1H), 5.32 (s, 1H), 4.63-4.51 (m, 1H), 3.72-3.67 (m, 2H), 3.58-3.48 (m, 6H), 3.30-3.13 (m, 4H), 2.21 (s, 3H), 2.16-2.07 (m, 1H), 1.34-1.22 (m, 6H).

Example 1299 (2.1 mg, 4% yield); LCMS: m/z, 543.3 (M+H); retention time 1.73 min; [LCMS method: Column: XBridge BEH XP C18 (50×2.1 mm) 2.5 μm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$) δ ppm 8.15-8.13 (m, 1H), 8.07-8.05 (m, 1H), 7.70-7.66 (m, 2H), 7.27-7.23 (m, 2H), 6.04 (s, 1H), 5.32 (s, 1H), 4.37-4.49 (m, 1H), 3.74-3.68 (m, 1H), 3.62-3.46 (m, 7H), 3.30-3.22 (m, 2H), 3.19-3.16 (m, 2H), 2.32-2.09 (m, 4H), 1.23-1.13 (m, 6H).

Examples 1300 and 1301

8-((2S,5R)-4-((1,1-dioxidotetrahydro-2H-thiopyran-4-yl)(4-fluorophenyl)methyl)-2,5-dimethylpiperazin-1-yl)-5-methyl-6-oxo-5,6-dihydro-1,5-naphthyridine-2-carbonitrile

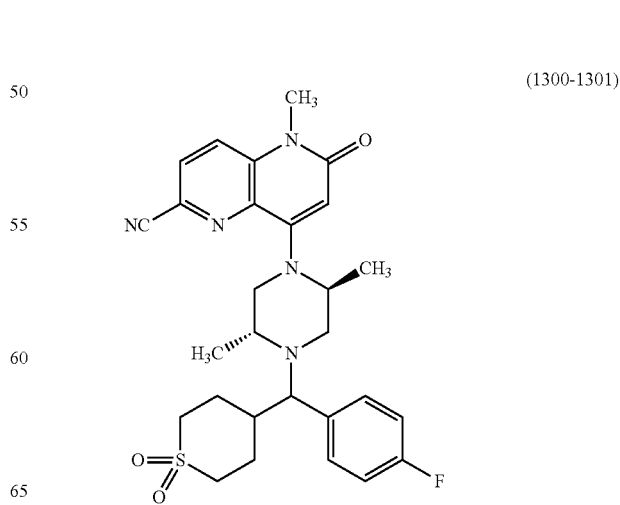

(1300-1301)

Intermediate 1300A: N-methoxy-N-methyltetrahydro-2H-thiopyran-4-carboxamide 1,1-dioxide

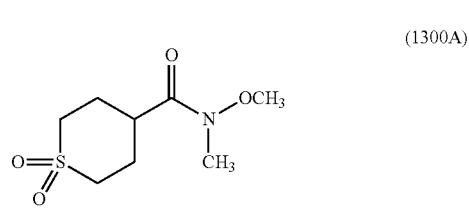
(1300A)

To a stirred solution of tetrahydro-2H-thiopyran-4-carboxylic acid 1,1-dioxide (1.0 g, 5.61 mmol) in DCM (15 mL) was added 1,1'-carbonyldiimidazole (0.91 g, 5.61 mmol) at room temperature. After 1 h., N,O-dimethylhydroxylamine hydrochloride (0.82 g, 8.42 mmol) was added and the reaction mixture was stirred for 16 h. The reaction mixture was diluted with water and extracted with DCM (2×50 mL), the combined organic layer was washed with water (50 mL), brine (50 mL), dried over anhydrous $Na_2SO_4$ and evaporated under reduced pressure to obtain N-methoxy-N-methyltetrahydro-2H-thiopyran-4-carboxamide 1,1-dioxide (1.2 g, 97% yield). $^1H$ NMR (400 MHz, DMSO-$d_6$) δ ppm 3.70 (s, 3H), 3.28-3.20 (m, 2H), 3.10-3.06 (m, 6H), 2.07-1.92 (m, 4H).

Intermediate 1300B: (1,1-dioxidotetrahydro-2H-thiopyran-4-yl)(4-fluorophenyl) methanone

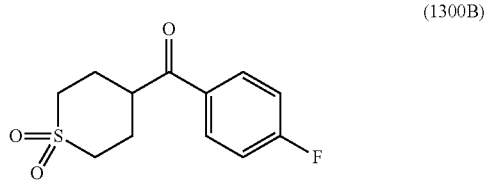 [SMILES: O=C(c1ccc(F)cc1)C1CCS(=O)(=O)CC1]
(1300B)

To a stirred solution of N-methoxy-N-methyltetrahydro-2H-thiopyran-4-carboxamide 1,1-dioxide (0.700 g, 3.16 mmol) in tetrahydrofuran (7 mL) was added (4-fluorophenyl)magnesium bromide (11.9 mL, 9.49 mmol, 0.8 Min THF) at 0° C. The reaction mixture was stirred at room temperature for 4 h. The reaction was quenched with saturated aqueous $NH_4Cl$ solution. The reaction mixture was extracted with ethyl acetate (2×40 mL), the combined organic layer was dried over anhydrous $Na_2SO_4$ and evaporated to dryness to yield the crude product, which was purified by 12 g silica gel chromatography by using 0-30% ethyl acetate/petroleum ether as eluent to obtain (1,1-dioxidotetrahydro-2H-thiopyran-4-yl)(4-fluorophenyl)methanone (620 mg, 76% yield). LCMS: m/z, 274.0 (M+$NH_4$); retention time 1.02 min; LCMS Method: Column-Luna 3.0 C18 (2) 100 Å; LC column (20×4.0 mm) Mercury MS TM; Mobile phase A: 10 mM $NH_4OAc$ in water:acetonitrile (98:2); Mobile phase B: 10 mM $NH_4OAc$ in water:acetonitrile (2:98); Gradient: 15-100% B over 2.5 minutes, flow rate 1.5 mL/min, then a 0.3 minute hold at 100% B flow rate 2.0 mL/min, then 100-15% B over 0.1 minutes; 0.1 minute hold at 15% B, flow rate 1.5 mL/min.

Intermediate 1300C: 4-((4-fluorophenyl)(hydroxy)methyl)tetrahydro-2H-thiopyran 1,1-dioxide

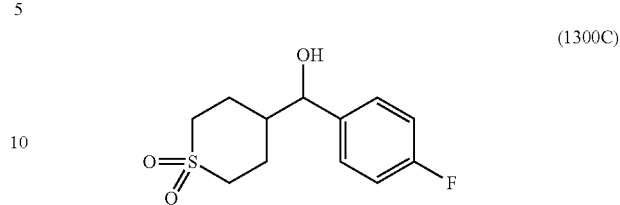
(1300C)

To a solution of (1,1-dioxidotetrahydro-2H-thiopyran-4-yl)(4-fluorophenyl) methanone (620 mg, 2.42 mmol) in MeOH (6 mL) was added sodium borohydride (275 mg, 7.26 mmol) at room temperature. The reaction mixture was stirred for 16 h. The reaction mixture was diluted with water and extracted twice with ethyl acetate (20 mL), the organic layer was separated, dried over anhydrous $Na_2SO_4$ and concentrated under reduced pressure to obtain 4-((4-fluorophenyl)(hydroxy)methyl)tetrahydro-2H-thiopyran 1,1-dioxide (550 mg, 88% yield) as a white solid. LCMS: m/z, 276.2 (M+$NH_4$); retention time 1.00 min. [LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Temperature: 50° C.; Flow rate: 0.7 mL/min; Detection: UV at 220 nm].

Examples 1300 and 1301: 8-((2S,5R)-4-((1,1-dioxidotetrahydro-2H-thiopyran-4-yl)(4-fluorophenyl)methyl)-2,5-dimethylpiperazin-1-yl)-5-methyl-6-oxo-5,6-dihydro-1,5-naphthyridine-2-carbonitrile To a stirred solution of 8-((2S,5R)-2,5-dimethylpiperazin-1-yl)-5-methyl-6-oxo-5,6-dihydro-1,5-naphthyridine-2-carbonitrile (170 mg, 0.57 mmol) in acetonitrile (2 mL) were added 4-((4-fluorophenyl)(hydroxy)methyl)tetrahydro-2H-thiopyran 1,1-dioxide (222 mg, 0.86 mmol), (cyanomethyl)trimethylphosphonium iodide (278 mg, 1.14 mmol), and DIPEA (0.5 mL, 2.86 mmol). The reaction mixture was heated at 110° C. in a microwave for 2 h, cooled to room temperature and concentrated under reduced pressure to yield the crude product, which was purified by preparative HPLC followed by chiral HPLC. (Chiral HPLC Method: Column: Cellulose 4 (250 mm×30 mm), 5 µm, Mobile phase: 0.1% DEA in (acetonitrile:MeOH=70:30)) to afford Examples 1300 and 1301).

Example 1300 (4.1 mg, 1.3% yield); LCMS: m/z, 538.3 (M+H); retention time 1.8 min; [LCMS method: Column: XBridge BEH XP C18 (50×2.1 mm) 2.5 µm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); $^1H$ NMR (400 MHz, DMSO-$d_6$) δ ppm 8.16-8.14 (m, 1H), 8.08-8.06 (m, 1H), 7.38 (dd, J=5.7, 8.7 Hz, 2H), 7.25-7.20 (m, 2H), 6.07 (s, 1H), 4.40 (m, 1H), 3.66 (d, J=6.6 Hz, 1H), 3.53 (s, 3H), 3.48 (dd, J=3.4, 12.5 Hz, 1H), 3.20-3.12 (m, 4H), 3.10-2.96 (m, 4H), 2.48 (br dd, J=1.7, 3.7 Hz, 1H), 2.22-2.10 (m, 1H), 2.05-1.90 (m, 1H), 1.50-1.35 (m, 1H), 1.23-1.16 (m, 4H) 0.98 (d, J=6.4 Hz, 3H).

Example 1301 (1 mg, 0.33% yield); LCMS: m/z, 538.3 (M+H); retention time 1.82 min; [LCMS method: Column: XBridge BEH XP C18 (50×2.1) mm), 2.5 µm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); $^1$H NMR (400 MHz, DMSO-$d_6$) δ ppm 8.16-8.14 (m, 1H), 8.07-8.04 (m, 1H), 7.35 (dd, J=5.7, 8.7 Hz, 2H), 7.20-7.16 (m, 2H), 5.99 (s, 1H), 4.40 (m, 1H), 4.10-3.90 (m, 1H), 3.59-3.49 (m, 6H), 3.33-3.10 (m, 2H), 2.98 (br d, J=12.5 Hz, 2H), 2.67-2.52 (m, 1H), 2.33-2.32 (m, 1H), 2.20-2.10 (m, 2H), 2.06-1.98 (m, 1H), 1.37-1.13 (m, 1H), 1.23-1.08 (m, 7H).

Examples 1302 and 1303

8-((2S,5R)-4-(1-(4-methoxy-3-(2-methoxyethoxy)phenyl)ethyl)-2,5-dimethylpiperazin-1-yl)-5-methyl-6-oxo-5,6-dihydro-1,5-naphthyridine-2-carbonitrile

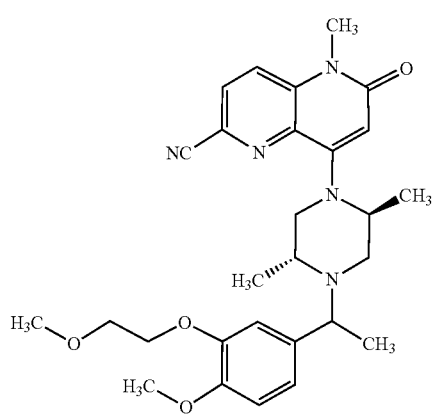
(1302-1303)

Intermediate 1302A:
5-(1-hydroxyethyl)-2-methoxyphenol

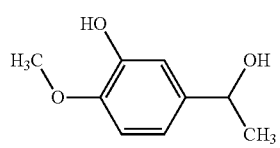
(1302A)

To a solution of 3-hydroxy-4-methoxybenzaldehyde (2 g, 13.15 mmol) in THF (30 mL), methylmagnesium chloride (9.6 mL, 28.9 mmol, 3M in THF) at 0° C. was added slowly over 5 min. The reaction mixture was stirred for 4 h at room temperature. The reaction was quenched with saturated aqueous NH$_4$Cl solution (20 mL). The reaction mixture was dissolved in ethyl acetate (100 mL), the organic layer was washed with water (20 mL), brine (20 mL), dried over anhydrous Na$_2$SO$_4$ and evaporated under reduced pressure to yield the crude product, which was purified on a 24 g silica gel column chromatography by eluting with 0-100% ethyl acetate in petroleum ether to obtain 5-(1-hydroxyethyl)-2-methoxyphenol (2.2 g, quantitative yield) as a white solid. LCMS: m/z, 167.1 (M–H); retention time 0.58 min., [LCMS Method: Column: Waters Acquity UPLC BEH C18 (2.1×50 mm) 1.7 μm, Mobile phase A: 10 mM ammonium acetate: acetonitrile (95:5); Mobile phase B: 10 mM ammonium acetate:acetonitrile (5:95), Gradient=20-100% B over 2 minute, then a 0.2 minute hold at 100% B; Flow rate: 0.7 mL/min; Detection: UV at 220 nm].

Intermediate 1302B:
5-(1-chloroethyl)-2-methoxyphenol

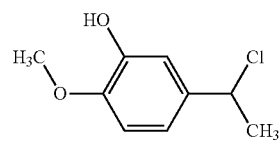
(1302B)

To a stirred solution of 5-(1-hydroxyethyl)-2-methoxyphenol (340 mg, 2.02 mmol) in DCM (3 mL), thionyl chloride (0.44 mL, 6.06 mmol) was added dropwise at room temperature. The reaction mixture was stirred for 3 h and evaporated to dryness to obtain 5-(1-chloroethyl)-2-methoxyphenol (375 mg, 99% yield). LCMS: m/z, 151.0 (M-Cl); retention time 0.95 min; [LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Flow rate: 0.7 mL/min; Detection: UV at 220 nm].

Intermediate 1302C: 8-((2S,5R)-4-(1-(3-hydroxy-4-methoxyphenyl)ethyl)-2,5-dimethylpiperazin-1-yl)-5-methyl-6-oxo-5,6-dihydro-1,5-naphthyridine-2-carbonitrile

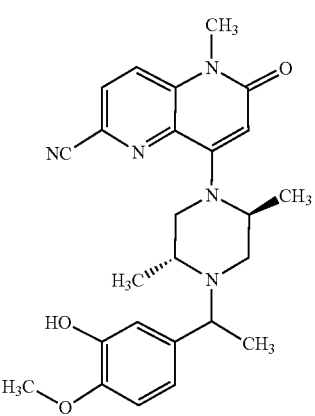
(1302C)

To a solution of 8-((2S,5R)-2,5-dimethylpiperazin-1-yl)-5-methyl-6-oxo-5,6-dihydro-1,5-naphthyridine-2-carbonitrile (200 mg, 0.67 mmol) in dry acetonitrile (3 mL), 5-(1-chloroethyl)-2-methoxyphenol (251 mg, 1.35 mmol), DIPEA (0.35 mL, 2.02 mmol) were added at room temperature. The reaction mixture was heated at 85° C. for 24 h. The reaction mixture cooled to room temperature and concentrated under reduced pressure to yield the crude product, which was purified on a 12 g silica gel column chromatography by eluting with 10% MeOH in DCM. The desired fractions were concentrated under reduced pressure to yield 8-((2S,5R)-4-(1-(3-hydroxy-4-methoxyphenyl)ethyl)-2,5- dimethylpiperazin-1-yl)-5-methyl-6-oxo-5,6-dihydro-1,5-naphthyridine-2-carbonitrile (250 mg, 83% yield). LCMS: m/z, 448.2 (M+H); retention time 1.45 and 1.46 min; [LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Flow rate: 0.7 mL/min; Detection: UV at 220 nm].

Examples 1302 and 1303: 8-((2S,5R)-4-(1-(4-methoxy-3-(2-methoxyethoxy)phenyl) ethyl)-2,5-dimethylpiperazin-1-yl)-5-methyl-6-oxo-5,6-dihydro-1,5-naphthyridine-2-carbonitrile To a stirred solution of 8-((2S,5R)-4-(1-(3-hydroxy-4-methoxyphenyl)ethyl)-2,5-dimethylpiperazin-1-yl)-5-methyl-6-oxo-5,6-dihydro-1,5-naphthyridine-2-carbonitrile (100 mg, 0.22 mmol) in dry DMF (3 mL), K$_2$CO$_3$ (93 mg, 0.67 mmol) was added at room temperature under argon atmosphere. The reaction mixture was stirred for 5 min and 1-bromo-2-methoxyethane (62 mg, 0.45 mmol) was added. The reaction mixture was heated 85° C. for 16 h. The reaction mixture cooled to room temperature, filtered through Celite and the filtrate was concentrated under reduced pressure to yield crude product, which was purified by preparative HPLC followed by chiral HPLC. [Chiral HPLC Method: Column: CELLULOSE 5 (250 mm×30 mm) 5 µm, Mobile phase: 0.1% DEA in MeOH, ISOCRATIC) to afford Examples 1302 and 1303.

Example 1302 (7.7 mg, 6.7% yield); LCMS: m/z, 506.3 (M+H); retention time 1.9 min; [LCMS method: Column: XBridge BEH XP C18 (50×2.1 mm) 2.5 [m; Mobile phase A: 95% Water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%].

Example 1303 (6.6 mg, 5.8% yield); LCMS: m/z, 506.4 (M+H); retention time 1.92 min; [LCMS method: Column: XBridge BEH XP C18 (50×2.1 mm) 2.5 µm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%).

The compounds in Table 53 were prepared from the phenol intermediate using the corresponding alkyl bromides as described for Examples 1302 and 1303. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 53

| Ex No. | Structure | M + H | Stereo chem | LCMS RT and Method |
|---|---|---|---|---|
| 1304 | 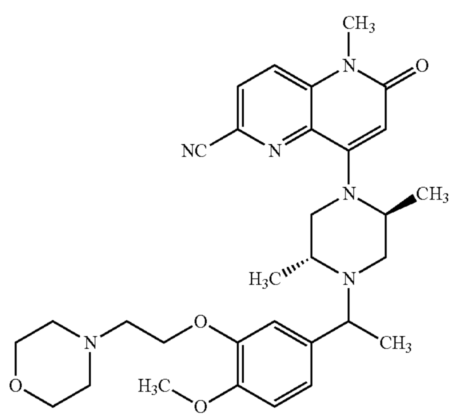 [SMILES: COc1ccc(C(C)N2C[C@H](C)N(c3cc(=O)n(C)c4ccc(C#N)nc34)C[C@H]2C)cc1OCCN1CCOCC1] | 561.4 | H | 1.77 A |
| 1305 | 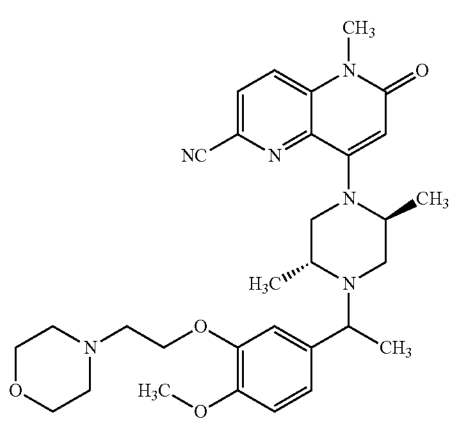 [SMILES: COc1ccc(C(C)N2C[C@H](C)N(c3cc(=O)n(C)c4ccc(C#N)nc34)C[C@H]2C)cc1OCCN1CCOCC1] | 561.4 | H | 1.79 A |

Examples 1306 and 1307

8-((2S,5R)-4-(1-(3-cyclopropyl-1,2,4-oxadiazol-5-yl)ethyl)-2,5-dimethylpiperazin-1-yl)-5-methyl-6-oxo-5,6-dihydro-1,5-naphthyridine-2,7-dicarbonitrile

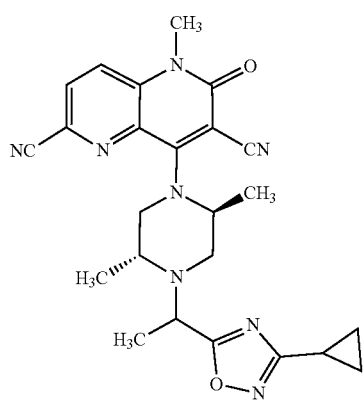
(1306-1307)

Intermediate 1306A: tert-butyl (2S,5R)-4-(1-methoxy-1-oxopropan-2-yl)-2,5-dimethylpiperazine-1-carboxylate

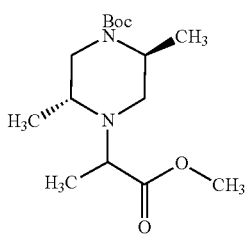
(1306A)

To a stirred solution of tert-butyl (2S,5R)-2,5-dimethylpiperazine-1-carboxylate (500 mg, 2.33 mmol) in dry acetonitrile (10 mL), methyl 2-bromopropanoate (468 mg, 2.80 mmol) and DIPEA (1.22 mL, 7.00 mmol) were added at room temperature. The reaction mixture was heated to 85° C. for 16 h. The reaction mixture was cooled to room temperature and concentrated under reduced pressure to obtain the crude product, which was purified by Combi flash 24 g silica gel chromatography by using 0-30% ethyl acetate in petroleum ether as eluent to obtain tert-butyl (2S,5R)-4-(1-methoxy-1-oxopropan-2-yl)-2,5-dimethylpiperazine-1-carboxylate (620 mg, 88% yield) as a light yellow liquid. LCMS: m/z, 301.2 (M+H); retention time 2.941 and 3.094 min. Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 1306B: 2-((2R,5S)-4-(tert-butoxycarbonyl)-2,5-dimethylpiperazin-1-yl) Propanoic Acid

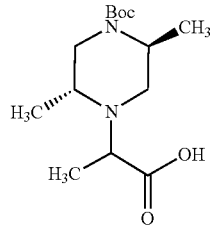
(1306B)

To a solution of tert-butyl (2S,5R)-4-(1-methoxy-1-oxopropan-2-yl)-2,5-dimethylpiperazine-1-carboxylate (320 mg, 1.07 mmol) in dry MeOH (6.0 mL), water (1.5 mL) and KOH (179 mg, 3.20 mmol) were added at room temperature. The reaction mixture was stirred for 6 h. The reaction mixture was concentrated under reduced pressure to obtain crude product, which was diluted with toluene (3×10 mL), evaporated and dried under high vacuum to yield potassium salt of 2-((2R,5S)-4-(tert-butoxycarbonyl)-2,5-dimethylpiperazin-1-yl)propanoic acid (350 mg, 86% yield) as an off-white solid. LCMS: m/z, 287.3 (M+H); retention time 0.67 and 0.69 min. LC-MS Method: Column-AQUITY UPLC BEH C18 (3.0×50 mm) 1.7 µm; Mobile phase A: 10 mM ammonium acetate in water:acetonitrile (98:2); Mobile phase B: 10 mM ammonium acetate in water:acetonitrile (2:98); Gradient: 20%-100% B over 2 minutes, then a 0.2 minute hold at 100% B, flow rate 0.7 mL/min.

Intermediate 1306C: tert-butyl (2S,5R)-4-(1-(3-cyclopropyl-1,2,4-oxadiazol-5-yl)ethyl)-2,5-dimethylpiperazine-1-carboxylate

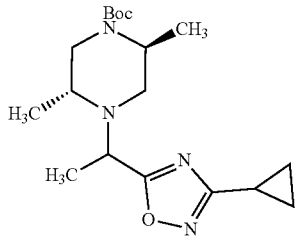
(1306C)

To a stirred solution of 2-((2R,5S)-4-(tert-butoxycarbonyl)-2,5-dimethylpiperazin-1-yl)propanoic acid, potassium salt (450 mg, 1.38 mmol) in DMF (8.0 mL), BOP (1.22 g, 2.77 mmol) and triethyl amine (0.58 mL, 4.15 mmol) were added at room temperature. After 2 h., the reaction mixture was heated at 100° C. for 16 h, cooled to room temperature, concentrated under reduced pressure to yield the crude product, which was purified on 24 g silica gel chromatography by using 0-100% ethyl acetate/petroleum ether. The fractions were concentrated under reduced pressure to yield tert-butyl (2S,5R)-4-(1-(3-cyclopropyl-1,2,4-oxadiazol-5-yl)ethyl)-2,5-dimethylpiperazine-1-carboxylate (450 mg, 93% yield). LCMS: m/z, 351.2 (M+H); retention time 2.218 min. [LCMS Method: Column-Luna 3.0 C18 (2) 100 Å LC column (20×4.0 mm) Mercury MS TM; Mobile phase A: 0.1% TFA in Milli-Q Water; Mobile phase B: 0.1% TFA in acetonitrile; Gradient: 15-100% B over 2.5 minutes, flow rate 1.5 mL/min, then a 0.3 minute hold at 100% B flow rate 2.0 mL/min, then 100-15% B over 0.1 minutes, flow rate 1.5 mL/min; 0.1 minute hold at 15% B, flow rate 1.5 mL/min].

Intermediate 1306D: 3-cyclopropyl-5-(1-((2R,5S)-2,5-dimethylpiperazin-1-yl)ethyl)-1,2,4-oxadiazole, TFA

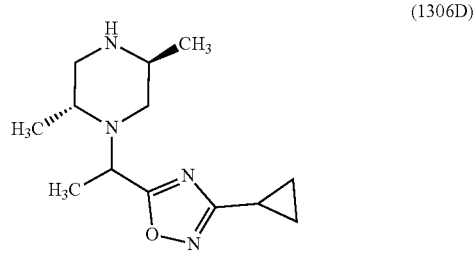 [SMILES: CC(c1nc(C2CC2)no1)N1C[C@H](C)NC[C@H]1C]

(1306D)

To a solution of tert-butyl (2S,5R)-4-(1-(3-cyclopropyl-1,2,4-oxadiazol-5-yl) ethyl)-2,5-dimethylpiperazine-1-carboxylate (450 mg, 1.28 mmol) in DCM (8 mL) was added TFA (0.1 mL, 1.28 mmol). The reaction mixture was stirred at room temperature for 4 h. The solvent was removed under reduced pressure to yield the TFA salt of 3-cyclopropyl-5-(1-((2R,5S)-2,5-dimethylpiperazin-1-yl)ethyl)-1,2,4-oxadiazole (320 mg, 68.4% yield). LCMS: m/z, 251.0 (M+H); retention time 0.87 min. LCMS Method: Column-Kinetex XB-C18 (75×3 mm-2.6 µm); Mobile phase A: 0.1% TFA in Milli-Q Water; Mobile phase B: 0.1% TFA in acetonitrile; Gradient: 20-100% B over 4 minutes, flow rate 1.0 mL/min, then a 0.6 minute hold at 100% B flow rate 1.5 mL/min, then 100-20% B over 0.1 minutes, flow rate 1.5 mL/min; 1 minute hold at 20% B, flow rate 1.5 mL/min.

Examples 1306 and 1307:8-((2S,5R)-4-(1-(3-cyclopropyl-1,2,4-oxadiazol-5-yl)ethyl)-2,5-dimethylpiperazin-1-yl)-5-methyl-6-oxo-5,6-dihydro-1,5-naphthyridine-2,7-dicarbonitrile To a stirred solution of 3-cyclopropyl-5-(1-((2R,5S)-2,5-dimethylpiperazin-1-yl) ethyl)-1,2,4-oxadiazole, TFA (132 mg, 0.36 mmol) in acetonitrile (4 mL), 3,6-dicyano-1-methyl-2-oxo-1,2-dihydro-1,5-naphthyridin-4-yl trifluoromethanesulfonate (100 mg, 0.28 mmol) and DIPEA (0.15 mL, 0.84 mmol) were added. The reaction mixture was heated at 85° C. for 3 h. The reaction mixture cooled to room temperature and evaporated under reduced pressure to yield the crude product, which was purified by preparative HPLC followed by chiral SFC (Chiral SFC Method: Column: Luxcellulose-2 (250×50 mm) 5 [m, % CO$_2$=65%; Percentage of Solvent: 35% of Methanol (100%), Total Flow: 4.0 g/min. Back pressure: 120 bar; temperature: 35° C.; UV detection: 235 nm] to afford Examples 1306 and 1307.

Example 1306: (42.2 mg, 64.6% yield): LCMS: m/z, 459.2 (M+H); retention time 1.86 min; LCMS method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.33-8.24 (m, 1H), 8.24-8.11 (m, 1H), 4.70-4.48 (m, 1H), 4.34 (q, J=7.0 Hz, 1H), 3.91 (dd, J=3.1, 12.3 Hz, 1H), 3.56 (s, 3H), 3.34 (br s, 1H), 3.27 (dd, J=4.4, 12.7 Hz, 1H), 3.06-2.97 (m, 1H), 2.41 (dd, J=5.1, 11.5 Hz, 1H), 2.18-2.08 (m, 1H), 1.49 (d, J=6.8 Hz, 3H), 1.16 (d, J=6.4 Hz, 3H), 1.11-1.03 (m, 2H), 0.92 (d, J=6.1 Hz, 5H).

Example 1307: (18.4 mg, 28.2% yield): LCMS: m/z, 459.2 (M+H); retention time 1.88 min; LCMS method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.30-8.24 (m, 1H), 8.20-8.13 (m, 1H), 4.77-4.67 (m, 1H), 4.24 (q, J=7.0 Hz, 1H), 4.11 (dd, J=3.3, 12.6 Hz, 1H), 3.55 (s, 3H), 3.42-3.33 (m, 2H), 3.21 (dd, J=3.5, 11.6 Hz, 1H), 2.48 (br d, J=3.4 Hz, 1H), 2.17-2.10 (m, 1H), 1.42 (d, J=6.8 Hz, 3H), 1.24 (d, J=6.6 Hz, 3H), 1.12-1.02 (m, 2H), 0.95-0.88 (m, 2H), 0.86 (d, J=6.4 Hz, 3H).

Examples 1308 and 1309

8-((2S,5R)-4-(1-(4-fluorophenyl)-2-hydroxy-2-methylpropyl)-2,5-dimethylpiperazin-1-yl)-5-methyl-6-oxo-5,6-dihydro-1,5-naphthyridine-2-carbonitrile

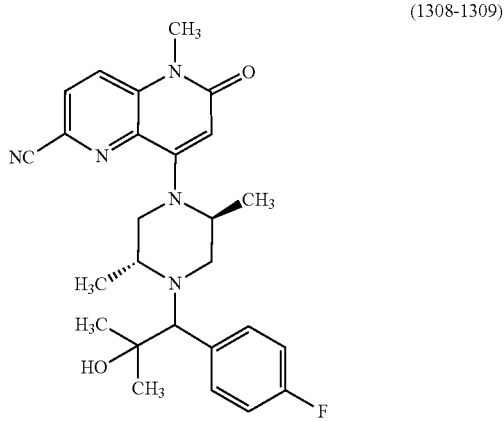 [SMILES: C[C@@H]1CN(c2cc(=O)n(C)c3ccc(C#N)nc23)[C@@H](C)CN1C(c1ccc(F)cc1)C(C)(C)O]

(1308-1309)

Intermediate 1308A: tert-butyl (2S,5R)-4-(1-(4-fluorophenyl)-2-hydroxy-2-methylpropyl)-2,5-dimethylpiperazine-1-carboxylate

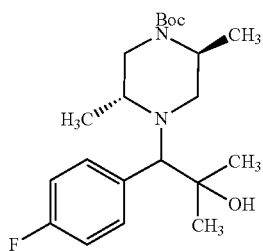

(1308B)

To a solution of tert-butyl (2S,5R)-4-(1-(4-fluorophenyl)-2-methoxy-2-oxoethyl)-2,5-dimethylpiperazine-1-carboxylate (500 mg, 1.314 mmol) in dry tetrahydrofuran (6 mL) was added methylmagnesium bromide (2.63 mL, 5.26 mmol) at 0° C. The reaction mixture was stirred at room temperature for 16 h. The reaction was quenched with saturated aqueous NH₄Cl solution (20 mL). The reaction mixture was extracted with ethyl acetate (100 mL), the organic layer was washed with water (20 mL), brine (20 mL), dried over anhydrous Na₂SO₄ and evaporated under reduced pressure to obtain the crude product, which was purified by 12 g silica gel chromatography by using 0-100% ethyl acetate/petroleum ether as eluent to obtain tert-butyl (2S,5R)-4-(1-(4-fluorophenyl)-2-hydroxy-2-methylpropyl)-2,5-dimethylpiperazine-1-carboxylate (410 mg, 82% yield). LCMS: m/z, 381.2 (M+H); retention time 3.63 min; Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 1308B: 1-((2R,5S)-2,5-dimethylpiperazin-1-yl)-1-(4-fluorophenyl)-2-methylpropan-2-ol, TFA

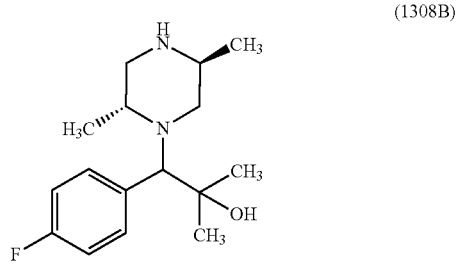 [SMILES: C[C@@H]1CN[C@@H](C)CN1C(c1ccc(F)cc1)C(C)(C)O]

(1308B)

To a solution of tert-butyl (2S,5R)-4-(1-(4-fluorophenyl)-2-hydroxy-2-methylpropyl)-2,5-dimethylpiperazine-1-carboxylate (200 mg, 0.53 mmol) in DCM (4 mL), was added TFA (0.4 mL, 5.26 mmol) and the mixture was stirred at room temperature for 4 h. The solvent was removed under reduced pressure to yield the TFA salt of 1-((2R,5S)-2,5-dimethylpiperazin-1-yl)-1-(4-fluorophenyl)-2-methylpropan-2-ol (200 mg, 96% yield). LCMS: m/z, 281.4 (M+H); retention time 1.09 min.; LCMS Method: Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Flow rate: 0.7 mL/min; Detection: UV at 220 nm.

Examples 1308 and 1309: 8-((2S,5R)-4-(1-(4-fluorophenyl)-2-hydroxy-2-methylpropyl)-2,5-dimethylpiperazin-1-yl)-5-methyl-6-oxo-5,6-dihydro-1,5-naphthyridine-2-carbonitrile To a suspension of 1-((2R,5S)-2,5-dimethylpiperazin-1-yl)-1-(4-fluorophenyl)-2-methylpropan-2-ol, TFA (84 mg, 0.3 mmol) in dry acetonitrile (3 mL), 6-cyano-1-methyl-2-oxo-1,2-dihydro-1,5-naphthyridin-4-yl trifluoromethanesulfonate (100 mg, 0.3 mmol) and sodium bicarbonate (76 mg, 0.9 mmol) were added at room temperature under argon atmosphere. The reaction mixture was heated to 85° C. for 16 h. The reaction mixture was cooled to room temperature and concentrated under reduced pressure to yield the crude product, which was purified by preparative HPLC followed by chiral HPLC (Chiral HPLC Method: Column: Cellulose 4 (250 mm×21.2 mm) 5 µm, Mobile phase: 0.1% DEA in MeOH, Flow: 20 mL/min) to afford Examples 1308 and 1309.

Examples 1308: (24 mg, 16% yield): LCMS: m/z, 464.2 (M+H); retention time 2.0 min; [LCMS method: Column: XBridge BEH XP C18 (50×2.1 mm) 2.5 µm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); ¹H NMR (400 MHz, DMSO-d₆) δ ppm 8.12-8.17 (m, 1H), 8.03-8.08 (m, 1H), 7.50 (dd, J=8.4, 6.0 Hz, 2H), 7.13-7.21 (m, 2H), 6.06 (s, 1H), 4.55 (s, 1H), 4.15-4.26 (m, 1H), 3.50-3.57 (m, 5H), 3.42-3.50 (m, 3H), 2.73-2.82 (m, 1H), 1.13 (d, J=6.1 Hz, 3H), 1.09 (s, 6H), 0.97 (d, J=6.4 Hz, 3H).

Example 1309: (15.4 mg, 11% yield): LCMS: m/z, 464.2 (M+H); retention time 1.98 min; [LCMS method: Column: XBridge BEH XP C18 (50×2.1 mm) 2.5 µm; Mobile phase A: 95% Water:5% acetonitrile; 10 mM ammonium acetate; Mobile phase B: 5% Water:95% acetonitrile; 10 mM ammonium acetate; Flow: 1.1 mL/min; Temp: 50° C.; Time (min): 0-3; % B: 0-100%); ¹H NMR (400 MHz, DMSO-d₆) δ ppm 8.10-8.15 (m, 1H) 8.01-8.07 (m, 1H) 7.48 (dd, J=8.56, 5.87 Hz, 2H) 7.10-7.16 (m, 2H) 5.97 (s, 1H) 4.52-4.63 (m, 1H) 4.32 (s, 1H) 3.54-3.64 (m, 3H) 3.49-3.53 (m, 4H) 2.79 (d, J=1.71 Hz, 2H) 1.24 (d, J=6.60 Hz, 3H) 1.15 (s, 3H) 0.98-1.08 (m, 6H).

Examples 1310 and 1311

8-((2S,5R)-4-(2,2-difluoro-1-(4-fluorophenyl)-3-hydroxypropyl)-2,5-dimethylpiperazin-1-yl)-5-methyl-6-oxo-5,6-dihydro-1,5-naphthyridine-2-carbonitrile

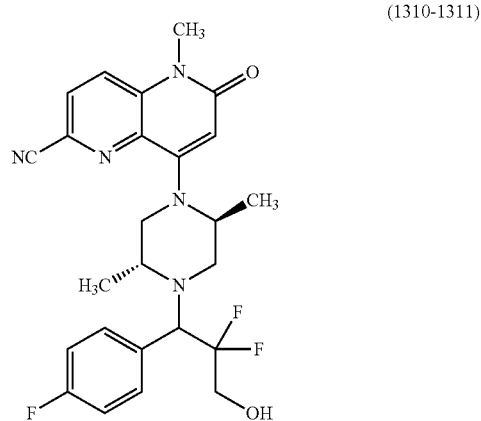 [SMILES: C[C@@H]1CN(c2cc(=O)n(C)c3ccc(C#N)nc23)[C@@H](C)CN1C(c1ccc(F)cc1)C(F)(F)CO]

(1310-1311)

Intermediate 1310A: tert-butyl (2S,5R)-4-(4-fluorobenzoyl)-2,5-dimethylpiperazine-1-carboxylate

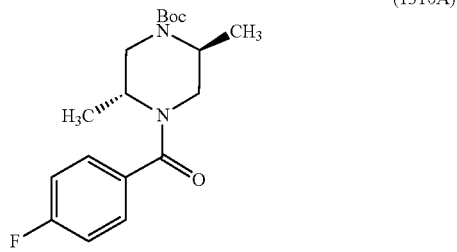

To a solution of 4-fluorobenzoic acid (330 mg, 2.36 mmol) in DMF (5 mL) were added DIPEA (0.6 mL, 3.53 mmol) and HATU (1.35 g, 3.53 mmol) at room temperature. The reaction mixture was stirred for 30 min. The reaction mixture was cooled to 0° C., tert-butyl (2S,5R)-2,5-dimethylpiperazine-1-carboxylate (505 mg, 2.36 mmol) in DMF (5 mL) was added dropwise under nitrogen atmosphere and the reaction mixture was stirred at room temperature for 16 h. Solvent was removed under reduced pressure, the mixture was extracted with EtOAc (2×50 mL), washed with water, brine, dried over anhydrous sodium sulphate and concentrated under reduced pressure to obtain the crude product which was purified by flash column chromatography (Column: 24 g silica; Solvent run: 45-50% EtOAc in pet ether) to obtain (2S,5R)-4-(4-fluorobenzoyl)-2,5-dimethylpiperazine-1-carboxylate (400 mg, 50% yield). LCMS: m/z, 337.3 (M+H); retention time 1.70 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1310B: tert-butyl (2S,5R)-4-(3-ethoxy-2,2-difluoro-1-(4-fluorophenyl)-3-oxopropyl)-2,5-dimethylpiperazine-1-carboxylate

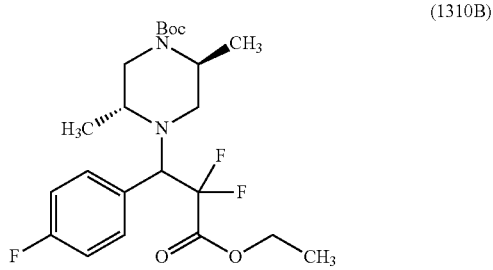 [SMILES: CCOC(=O)C(F)(F)C(c1ccc(F)cc1)N1C[C@H](C)N(C(=O)OC(C)(C)C)C[C@H]1C]

Step-1: To a solution of tert-butyl (2S,5R)-4-(4-fluorobenzoyl)-2,5-dimethylpiperazine-1-carboxylate (1 g, 2.97 mmol) in DCM (10 mL) was added carbonyl chlorobis(triphenylphosphine)iridium(I) (0.23 g, 0.30 mmol) at room temperature. After 10 min, 1,1,3,3-tetramethyldisiloxane (1.1 mL, 5.95 mmol) was added and the reaction mixture was stirred for 10 min.

Step-2: In a separate round bottom flask, zinc (1.3 g, 19.32 mmol) was suspended in tetrahydrofuran (10 mL) and the mixture was refluxed at 70° C. for 5 min. Next, ethyl 2-bromo-2,2-difluoroacetate (3.9 g, 19.32 mmol) was added at 70° C. After 5 min, the Step-1 solution was added and reaction mixture was maintained at 70° C. for another 2 h., and then cooled to room temperature. The reaction was quenched with 10% aqueous NaHCO₃ and the mixture was extracted with EtOAc (3×50 mL). The combined organic extracts were washed with water, brine, dried over anhydrous sodium sulphate and concentrated under reduced pressure to obtain the crude product, which was purified by flash column chromatography (Column: 24 g silica; Solvent run: 40-50% EtOAc in pet ether) to obtain tert-butyl (2S,5R)-4-(3-ethoxy-2,2-difluoro-1-(4-fluorophenyl)-3-oxopropyl)-2,5-dimethylpiperazine-1-carboxylate (600 mg, 45% yield) as a diastereomeric mixture. LCMS: m/z, 445.4 (M+H); retention time 2.27 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1310C: tert-butyl (2S,5R)-4-(2,2-difluoro-1-(4-fluorophenyl)-3-hydroxypropyl)-2,5-dimethylpiperazine-1-carboxylate

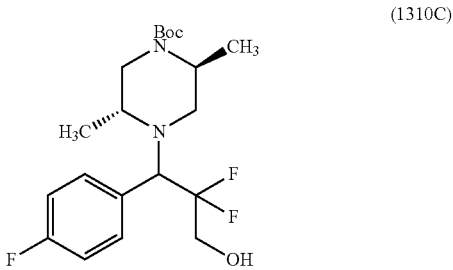 [SMILES: C[C@@H]1CN(C(=O)OC(C)(C)C)[C@@H](C)CN1C(c1ccc(F)cc1)C(F)(F)CO]

To a solution of tert-butyl (2S,5R)-4-(3-ethoxy-2,2-difluoro-1-(4-fluorophenyl)-3-oxopropyl)-2,5-dimethylpiperazine-1-carboxylate (200 mg, 0.45 mmol) in THF (2 mL) was added LAH (0.4 mL, 0.90 mmol, 2.4 M in THF) drop wise over a period of 2 min at 0° C. The reaction mixture was stirred for 3 h at room temperature. The reaction mixture was cooled to 0° C. The reaction was quenched with saturated aqueous NH₄Cl solution, and the mixture was extracted with EtOAc (2×25 mL). The combined organic extracts were dried over anhydrous sodium sulphate and concentrated under reduced pressure to obtain the crude product, which was purified by flash column chromatography (Column: 12 g silica; Solvent run: 2-3% MeOH in chloroform) to obtain tert-butyl (2S,5R)-4-(2,2-difluoro-1-(4-fluorophenyl)-3-hydroxypropyl)-2,5-dimethylpiperazine-1-carboxylate (120 mg, 66% yield) as a diastereomeric mixture. LCMS: m/z, 403.4 (M+H); retention time 1.99 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1310D: 3-((2R,5S)-2,5-dimethylpiperazin-1-yl)-2,2-difluoro-3-(4-fluorophenyl)propan-1-ol.TFA

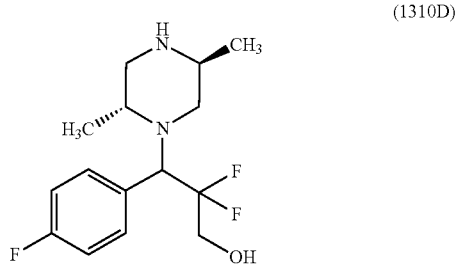 [SMILES: C[C@@H]1CN[C@@H](C)CN1C(c1ccc(F)cc1)C(F)(F)CO]

(1310D)

To a solution of tert-butyl (2S,5R)-4-(2,2-difluoro-1-(4-fluorophenyl)-3-hydroxypropyl)-2,5-dimethylpiperazine-1-carboxylate (120 mg, 0.30 mmol) in DCM (4 mL) was added TFA (0.23 mL, 2.98 mmol) at 0° C. The reaction mixture was stirred at room temperature for 4 h. The solvent was removed under reduced pressure to yield 3-((2R,5S)-2,5-dimethylpiperazin-1-yl)-2,2-difluoro-3-(4-fluorophenyl)propan-1-ol, TFA (120 mg, 97%) as a diastereomeric mixture. LCMS: m/z, 303.3 (M+H); retention time 0.80 min; Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Examples 1310 and 1311: 8-((2S,5R)-4-(2,2-difluoro-1-(4-fluorophenyl)-3-hydroxypropyl)-2,5-dimethylpiperazin-1-yl)-5-methyl-6-oxo-5,6-dihydro-1,5-naphthyridine-2-carbonitrile To a stirred suspension of 3-((2R,5S)-2,5-dimethylpiperazin-1-yl)-2,2-difluoro-3-(4-fluorophenyl)propan-1-ol, TFA (135 mg, 0.45 mmol) in acetonitrile (5 mL) were added DIPEA (0.4 mL, 2.24 mmol) and 6-cyano-1-methyl-2-oxo-1,2-dihydro-1,5-naphthyridin-4-yl trifluoromethanesulfonate (100 mg, 0.22 mmol). The reaction mixture was heated at 80° C. for 3 h. The reaction mixture was cooled to room temperature and solvent was removed under reduced pressure to obtain the crude product, which was purified by flash column chromatography (Column: 12 g silica; Solvent run: 2-3% MeOH in chloroform) to obtain a diastereomeric mixture. The mixture was purified by preparative HPLC (Chiral Separation Method: Column: Cellulose-2 (250×4.6) mm, 5 micron Mobile Phase: 10 mM ammonium acetate in MeOH, Flow rate: 20 mL/min; Isocratic) to obtain Examples 1310 and 1311.

Example 1310: (8.7 mg, 8% yield); LCMS: m/z, 486.2 (M+H); retention time 1.80 min; Column: XBridge BEH XP C18 (2.1×50 mm), 2.5 µm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.19-8.13 (m, 1H), 8.11-8.05 (m, 1H), 7.52 (dd, J=5.7, 8.2 Hz, 2H), 7.21-7.30 (m, 2H), 6.15 (s, 1H), 4.45-4.34 (m, 1H), 4.03 (br d, J=1.2 Hz, 1H), 3.90-3.75 (m, 1H), 3.68-3.50 (m, 5H), 3.23-3.07 (m, 3H), 2.79-2.71 (m, 1H), 2.36 (br dd, J=7.2, 11.6 Hz, 1H), 1.07-1.02 (m, 6H).

Example 1311: (7.4 mg, 7% yield). LCMS: m/z, 486.2 (M+H); retention time 1.81 min; Column: XBridge BEH XP C18 (2.1×50 mm), 2.5 µm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.13 (d, J=8.8 Hz, 1H), 8.02-8.08 (m, 1H), 7.54 (dd, J=8.4, 5.7 Hz, 2H), 7.17-7.26 (m, 2H), 5.99 (s, 1H), 5.53 (t, J=6.1 Hz, 1H), 4.51-4.60 (m, 1H), 4.32-4.44 (m, 1H), 3.83-4.00 (m, 1H), 3.42-3.70 (m, 7H), 2.83 (dd, J=11.6, 3.1 Hz, 1H), 2.63 (br d, J=11.2 Hz, 1H), 1.18 (d, J=6.6 Hz, 3H), 1.05 (d, J=6.4 Hz, 3H).

Examples 1312 and 1313

8-((2S,5R)-4-(2,2-difluoro-1-(4-fluorophenyl)-3-methoxypropyl)-2,5-dimethylpiperazin-1-yl)-5-methyl-6-oxo-5,6-dihydro-1,5-naphthyridine-2-carbonitrile

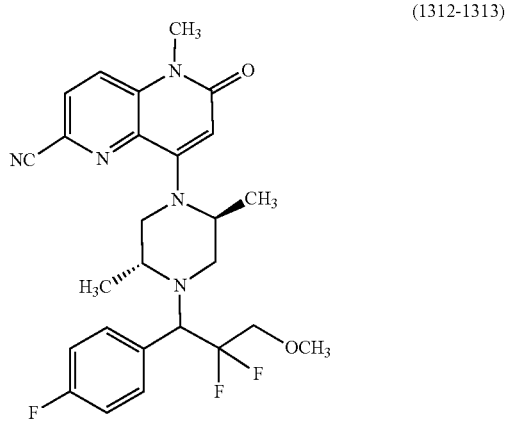 [SMILES: COCC(F)(F)C(c1ccc(F)cc1)N1C[C@H](C)N(c2cc(=O)n(C)c3ccc(C#N)nc23)C[C@H]1C]

(1312-1313)

Intermediate 1312A: tert-butyl (2S,5R)-4-(2,2-difluoro-1-(4-fluorophenyl)-3-methoxypropyl)-2,5-dimethylpiperazine-1-carboxylate

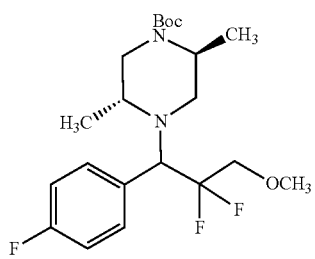

(1312A)

To a stirred solution of tert-butyl (2S,5R)-4-(2,2-difluoro-1-(4-fluorophenyl)-3-hydroxypropyl)-2,5-dimethylpiperazine-1-carboxylate (200 mg, 0.50 mmol) in THF (4 mL) was added NaH (60 mg, 1.50 mmol, 60% w/w) at 0° C. The reaction mixture was stirred for 5 min. Methyl iodide (0.062 mL, 0.99 mmol) was added at 0° C. and the reaction mixture was stirred at room temperature for 4 h. The reaction was quenched with ice cold water and extracted with EtOAc (2×50 mL), the combined organic extracts were dried over anhydrous sodium sulphate and concentrated to obtain the crude product, which was purified by flash column chromatography (Column: 12 g silica; Solvent run: 2-3% MeOH in chloroform) to obtain tert-butyl (2S,5R)-4-(2,2-difluoro-1-(4-fluorophenyl)-3-methoxypropyl)-2,5-dimethylpiperazine-1-carboxylate (150 mg, 73% yield) as a diastereomeric mixture. LCMS: m/z, 417.4 (M+H); retention time 2.25 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1312B: (2R,5S)-1-(2,2-difluoro-1-(4-fluorophenyl)-3-methoxypropyl)-2,5-dimethylpiperazine, TFA

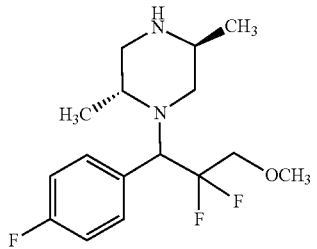

(1312B)

To a solution of tert-butyl (2S,5R)-4-(2,2-difluoro-1-(4-fluorophenyl)-3-methoxypropyl)-2,5-dimethylpiperazine-1-carboxylate (100 mg, 0.24 mmol) in DCM (4 mL) was added TFA (0.2 mL, 2.40 mmol) at 0° C. The reaction mixture was stirred at room temperature for 4 h. The solvent was removed under reduced pressure to afford (2R,5S)-1-(2,2-difluoro-1-(4-fluorophenyl)-3-methoxypropyl)-2,5-dimethylpiperazine, TFA (80 mg, 77% yield) as a diastereomeric mixture. LCMS: m/z, 317.3 (M+H); retention time 1.11 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Examples 1312 and 1313: 8-((2S,5R)-4-(2,2-difluoro-1-(4-fluorophenyl)-3-methoxypropyl)-2,5-dimethylpiperazin-1-yl)-5-methyl-6-oxo-5,6-dihydro-1,5-naphthyridine-2-carbonitrile To a stirred solution of (2R,5S)-1-(2,2-difluoro-1-(4-fluorophenyl)-3-methoxypropyl)-2,5-dimethylpiperazine, TFA (150 mg, 0.35 mmol) in acetonitrile (5 mL), were added DIPEA (0.6 mL, 3.49 mmol) and 6-cyano-1-methyl-2-oxo-1,2-dihydro-1,5-naphthyridin-4-yl trifluoromethanesulfonate (175 mg, 0.52 mmol). The reaction mixture was heated at 80° C. for 3 h. The reaction mixture was cooled to room temperature and the solvent was removed under reduced pressure to obtain the crude product, which was purified by flash column chromatography (Column: 12 g silica; Solvent run: 2-3% MeOH in chloroform) to obtain a diastereomeric mixture. The mixture of diastereomers were further purified by preparative HPLC (Chiral Separation Method: Column: Cellulose-2 (250×4.6) mm, 5 μm, Mobile Phase A: 0.1% DEA in ACN, Mobile Phase B: 0.1% DEA in MeOH, Gradient=0-100% B over 12 minutes) to obtain Examples 1312 and 1313.

Example 1312: (7.1 mg, 4% yield); LCMS: m/z, 500.3 (M+H); retention time 2.09 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.16 (d, J=8.8 Hz, 1H), 8.06-8.11 (m, 1H), 7.53 (dd, J=8.6, 5.6 Hz, 2H), 7.21-7.34 (m, 2H), 6.15 (s, 1H), 4.31-4.44 (m, 1H), 3.98-4.10 (m, 1H), 3.78-3.94 (m, 1H), 3.52-3.65 (m, 5H), 3.34 (s, 3H, merged with solvent moisture peak), 3.09-3.23 (m, 2H), 2.72-2.82 (m, 1H), 2.29-2.36 (m, 1H), 1.06 (d, J=6.1 Hz, 3H), 1.02 (d, J=6.4 Hz, 3H).

Example 1313: (10 mg, 6% yield). LCMS: m/z, 500.2 (M+H); retention time 2.11 min; Column: XBridge BEH XP C18 (2.1×50 mm), 2.5 μm; Mobile phase A: 10 mM ammonium acetate:acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.15 (d, J=8.8 Hz, 1H), 7.98-8.12 (m, 1H), 7.51-7.60 (m, 2H), 7.19-7.26 (m, 2H), 6.00 (s, 1H), 4.54-4.63 (m, 1H), 4.30-4.42 (m, 1H), 3.86-4.01 (m, 1H), 3.49-3.71 (m, 5H), 3.42-3.47 (m, 1H), 3.34 (s, 3H), 2.79-2.87 (m, 1H), 2.64-2.67 (m, 1H), 2.62-2.70 (m, 1H), 1.19 (d, J=6.6 Hz, 3H), 1.05 (d, J=6.1 Hz, 3H).

Examples 1314 and 1315

8-((2S,5R)-4-(1-(4-fluoro-2-(methoxymethyl)phenyl)ethyl)-2,5-dimethylpiperazin-1-yl)-5-methyl-6-oxo-5,6-dihydro-1,5-naphthyridine-2-carbonitrile

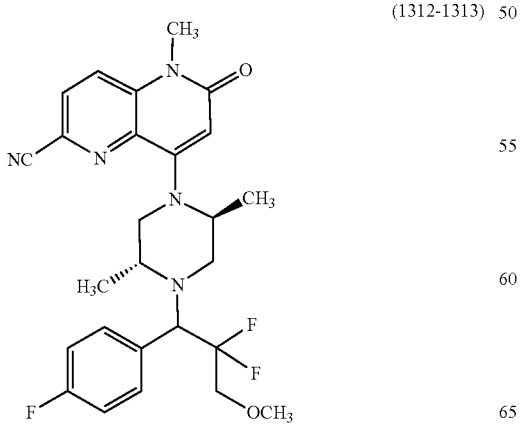

(1312-1313)

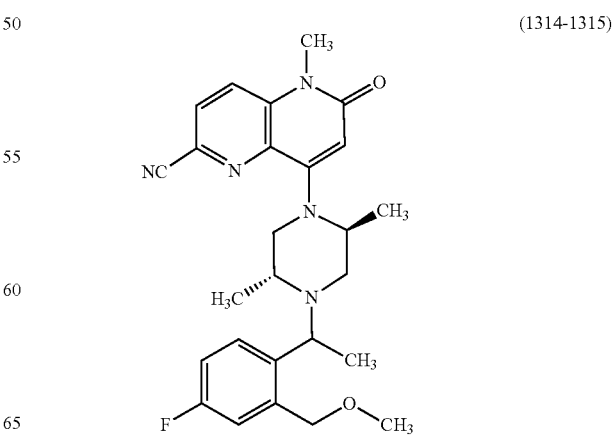

(1314-1315)

Intermediate 1314A:
1-(4-fluoro-2-(methoxymethyl)phenyl)ethan-1-ol

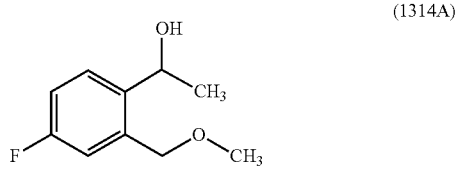
(1314A)

To a stirred solution of 1-bromo-4-fluoro-2-(methoxymethyl)benzene (1 g, 4.57 mmol) in THF (10 mL) was added n-butyl lithium (2.2 mL, 5.48 mmol, 2.5 M in n-hexane) dropwise at −78° C. The reaction mixture was stirred for 1 h and then acetaldehyde (1.3 mL, 22.83 mmol) was added. The reaction mixture was slowly warmed to room temperature. The reaction mixture was stirred for 12 h. and cooled to 0° C. The reaction was quenched with saturated aqueous $NH_4Cl$ (10 mL) solution. The mixture was extracted with EtOAc (3×50 mL). The combined organic extracts were washed with water and brine, dried over anhydrous sodium sulphate and concentrated to afford the crude product, which was purified by flash column chromatography (Column: 24 g silica; Solvent run: 65-70% EtOAc in petroleum ether) to obtain 1-(4-fluoro-2-(methoxymethyl) phenyl)ethan-1-ol (0.3 g, 36% yield) as a racemate. LCMS: m/z, 202.2 (M+H); retention time 1.50 min. (LC-MS Method info: Column-KINETEX-XB-C18 (75×3 mm-2.6 μm); Mphase A: 10 mM ammonium formate in water:acetonitrile (98:2); Mphase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min).

Intermediate 1314B: 1-(1-chloroethyl)-4-fluoro-2-(methoxymethyl)benzene

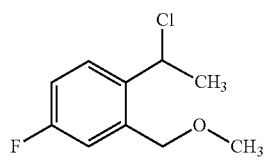
(1314B)

To a solution of 1-(4-fluoro-2-(methoxymethyl)phenyl) ethan-1-ol (0.2 g, 1.09 mmol) in DCM (5 mL) was added thionyl chloride (0.4 mL, 5.43 mmol) at 0° C. The reaction mixture was stirred at room temperature for 3 h. The solvent was removed under reduced pressure, co-distilled with acetonitrile (2×5 mL) and dried to afford 1-(1-chloroethyl)-4-fluoro-2-(methoxymethyl)benzene (150 mg, 68% yield).

$^1$H NMR (400 MHz, DMSO-$d_6$) δ ppm 7.67 (dd, J=8.3, 5.8 Hz, 1H), 7.14-7.28 (m, 2H), 5.53 (q, J=6.9 Hz, 1H), 4.63 (d, J=12.5 Hz, 1H), 4.49 (d, J=13.1 Hz, 1H), 3.34 (s, 3H), 1.80 (d, J=7.0 Hz, 3H).

Examples 1325 and 1326: 8-((2S,5R)-4-(1-(4-fluoro-2-(methoxymethyl)phenyl)ethyl)-2,5-dimethylpiperazin-1-yl)-5-methyl-6-oxo-5,6-dihydro-1,5-naphthyridine-2-carbonitrile To a stirred solution of 8-((2S,5R)-2,5-dimethylpiperazin-1-yl)-5-methyl-6-oxo-5,6-dihydro-1,5-naphthyridine-2-carbonitrile (0.1 g, 0.34 mmol) in acetonitrile (3 mL) were added sodium bicarbonate (0.14 g, 1.68 mmol) and 1-(1-chloroethyl)-4-fluoro-2-(methoxymethyl)benzene (0.07 g, 0.34 mmol) at room temperature. The reaction mixture was heated at 80° C. for 12 h. The reaction mixture was cooled to room temperature and solvent was removed under reduced pressure to obtain the crude product, which was purified by preparative HPLC (Chiral Separation Method: Column: Cellulose-5 (250×30) mm, 5 μm, Mobile Phase: 0.1% DEA in MeOH, Flow rate: 35 mL/min, isocratic) to obtain Examples 1314 and 1315.

Example 1314: (19 mg, 12% yield); LCMS: m/z, 464.2 (M+H); retention time 2.24 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.21-8.13 (m, 1H), 8.11-8.00 (m, 1H), 7.59 (dd, J=6.4, 8.3 Hz, 1H), 7.24-7.09 (m, 2H), 5.99 (s, 1H), 4.82-4.70 (m, 1H), 4.67-4.53 (m, 2H), 3.88 (q, J=6.1 Hz, 1H), 3.57-3.42 (m, 4H), 3.39-3.36 (m, 1H), 3.34 (s, 3H), 2.98 (dd, J=3.4, 11.5 Hz, 1H), 2.89-2.76 (m, 2H), 1.26 (d, J=6.6 Hz, 3H), 1.22 (d, J=6.6 Hz, 3H), 1.01 (d, J=6.4 Hz, 3H).

Example 1315: (25 mg, 16% yield). LCMS: m/z, 464.2 (M+H); retention time 2.21 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.15 (d, J=8.8 Hz, 1H), 8.00-8.13 (m, 1H), 7.63 (dd, J=9.4, 6.0 Hz, 1H), 7.07-7.16 (m, 2H), 6.02 (s, 1H), 4.47-4.59 (m, 2H), 4.29-4.42 (m, 1H), 3.66-3.87 (m, 2H), 3.45-3.60 (m, 5H), 3.34 (s, 3H, obscured with moisture peak), 2.70-2.80 (m, 1H), 1.96-2.05 (m, 1H), 1.25 (d, J=6.4 Hz, 3H), 1.18 (d, J=6.4 Hz, 3H), 1.06 (d, J=6.6 Hz, 3H).

The examples in the Table 54 were prepared according to the general method described for Examples 1314 and 1315, using the appropriate aryl bromides. When the reaction provided a mixture of diastereomers, the mixture was separated at the final stage using either preparative chromatography or preparative chiral chromatography. The absolute stereochemistry was not assigned at the newly formed carbon-nitrogen bond

TABLE 54

| Ex. No. | Structure | M + H | Stereo chem | LCMS RT and Method |
|---|---|---|---|---|
| 1316 | 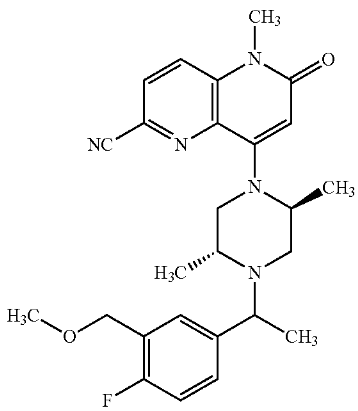 | 464.2 | H | 2.17 A |
| 1317 | 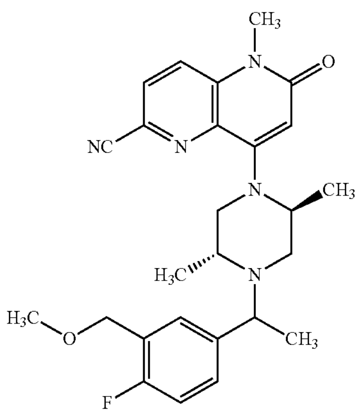 | 464.2 | H | 2.29 A |

Examples 1318 and 1319

8-((2S,5R)-4-(1-(4-fluorophenyl)-2-(methylthio)ethyl)-2,5-dimethylpiperazin-1-yl)-5-methyl-6-oxo-5,6-dihydro-1,5-naphthyridine-2-carbonitrile

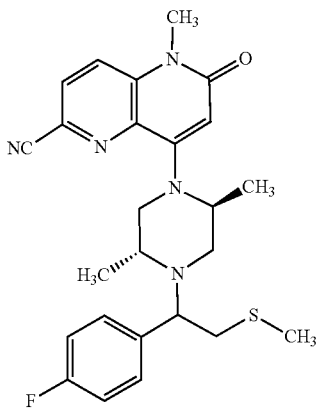
(1318-1319)

Intermediate 1318A:
1-(4-fluorophenyl)-2-(methylthio)ethan-1-one

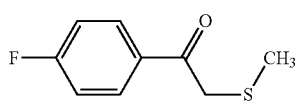
(1318A)

To a solution of 2-bromo-1-(4-fluorophenyl)ethan-1-one (3 g, 13.82 mmol) in MeOH (30 mL) was added sodium thiomethoxide (1.94 g, 27.6 mmol) portion wise at 0° C. The reaction mixture was stirred at room temperature for 4 h. The solvent was removed under reduced pressure, extracted with EtOAc (100 mL), washed with water, brine, dried over anhydrous sodium sulphate and concentrated under reduced pressure. The crude product was purified by flash column chromatography (Column: 40 g silica; Solvent run: 40-45% EtOAc in petroleum ether) to obtain 1-(4-fluorophenyl)-2-(methylthio)ethan-1-one (2 g, 79% yield). $^1$H NMR (300 MHz, DMSO-$d_6$) δ ppm 8.08 (dd, J=5.5, 9.0 Hz, 2H), 7.47-7.21 (m, 2H), 3.96 (s, 2H), 2.04 (s, 3H).

Intermediate 1318B:
1-(4-fluorophenyl)-2-(methylthio)ethan-1-ol

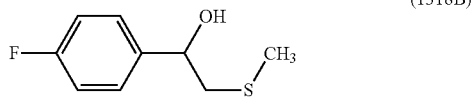
(1318B)

To a solution of 1-(4-fluorophenyl)-2-(methylthio)ethan-1-one (0.6 g, 3.26 mmol) in MeOH (10 mL) was added sodium borohydride (0.37 g, 9.77 mmol) at 0° C. The reaction mixture was stirred at room temperature for 2 h. The reaction was quenched with saturated aqueous NH$_4$Cl solution. Methanol was evaporated under reduced pressure. The mixture was extracted with EtOAc (3×50 mL), washed with water, brine, dried over anhydrous sodium sulphate and concentrated under reduced pressure to obtain the crude product, which was purified by flash column chromatography (Column: 12 g silica; Solvent run: 40-45% EtOAc in petroleum ether) to obtain 1-(4-fluorophenyl)-2-(methylthio)ethan-1-ol (0.5 g, 82% yield). $^1$H NMR (300 MHz, DMSO-d$_6$) δ ppm 7.35-7.44 (m, 2H), 7.09-7.20 (m, 2H), 5.42-5.54 (m, 1H), 4.62-4.75 (m, 1H), 2.69 (dd, J=8.7, 6.5 Hz, 2H), 2.00 (s, 3H).

Intermediate 1318C:
(2-chloro-2-(4-fluorophenyl)ethyl)(methyl)sulfane

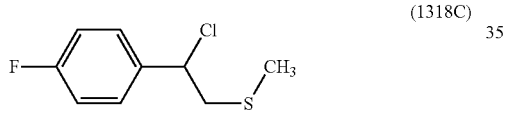
(1318C)

To a solution of 2-(methylthio)-1-phenylethan-1-ol (0.4 g, 2.38 mmol) in DCM (5 mL) was added thionyl chloride (0.9 mL, 11.89 mmol) at 0° C. The reaction mixture was stirred at room temperature for 3 h. The solvent was removed under reduced pressure, diluted with acetonitrile (2×5 mL), solvent was evaporated and dried to yield (2-chloro-2-phenylethyl)(methyl)sulfane (0.3 g, 68% yield). $^1$H NMR (400 MHz, DMSO-d$_6$) δ ppm 7.51-7.59 (m, 2H), 7.16-7.25 (m, 2H), 5.31 (t, J=7.5 Hz, 1H), 3.19-3.23 (m, 2H), 2.00 (s, 3H).

Examples 1318 and 1319: 8-((2S,5R)-4-(1-(4-fluorophenyl)-2-(methylthio)ethyl)-2,5-dimethylpiperazin-1-yl)-5-methyl-6-oxo-5,6-dihydro-1,5-naphthyridine-2-carbonitrile To a stirred solution of 8-((2S,5R)-2,5-dimethylpiperazin-1-yl)-5-methyl-6-oxo-5,6-dihydro-1,5-naphthyridine-2-carbonitrile (0.3 g, 1.01 mmol) in acetonitrile (3 mL) were added sodium bicarbonate (0.42 g, 5.04 mmol) and (2-chloro-2-(4-fluorophenyl) ethyl)(methyl)sulfane (0.21 g, 1.01 mmol) at room temperature. The reaction mixture was heated at 80° C. for 12 h. The reaction mixture was cooled to room temperature, solvent was removed under reduced pressure to obtain the crude product, which was purified by preparative HPLC (Chiral Separation Method: Column: Cellulose-4 (250×21.2) mm, 5 micron, Mobile Phase: 10 mM ammonium acetate in MeOH, Flow rate: 20 mL/min, isocratic) to obtain Example 1318 and Example 1319.

Example 1318: (6 mg, 1.3%); LCMS: m/z, 466.2 (M+H); retention time 2.16 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.19-8.12 (m, 1H), 8.10-8.03 (m, 1H), 7.51-7.40 (m, 2H), 7.24-7.14 (m, 2H), 6.03 (s, 1H), 4.52-4.43 (m, 1H), 3.83 (dd, J=4.9, 8.3 Hz, 1H), 3.52 (s, 3H), 3.44-3.37 (m, 1H), 3.31-3.25 (m, 1H), 3.08-2.96 (m, 2H), 2.87-2.78 (m, 1H), 2.78-2.70 (m, 1H), 2.69-2.62 (m, 1H), 1.92 (s, 3H), 1.20 (d, J=6.4 Hz, 3H), 1.00 (d, J=6.4 Hz, 3H).

Example 1319: (1.0 mg 0.2%). LCMS: m/z, 466.3 (M+H); retention time 2.19 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.12-8.19 (m, 1H), 8.05-8.08 (m, 1H), 7.38-7.45 (m, 2H), 7.19-7.26 (m, 2H), 6.01 (s, 1H), 4.31-4.43 (m, 1H), 3.72 (br d, J=3.7 Hz, 2H), 3.48-3.58 (m, 5H), 2.95-3.03 (m, 1H), 2.72-2.88 (m, 2H), 2.10-2.16 (m, 1H), 1.90 (s, 3H), 1.16 (d, J=6.4 Hz, 3H), 1.09 (d, J=6.6 Hz, 3H).

Examples 1320 and 1321

8-((2S,5R)-4-(1-(4-cyano-3-(2-methoxyethoxy)phenyl)ethyl)-2,5-dimethylpiperazin-1-yl)-5-methyl-6-oxo-5,6-dihydro-1,5-naphthyridine-2-carbonitrile

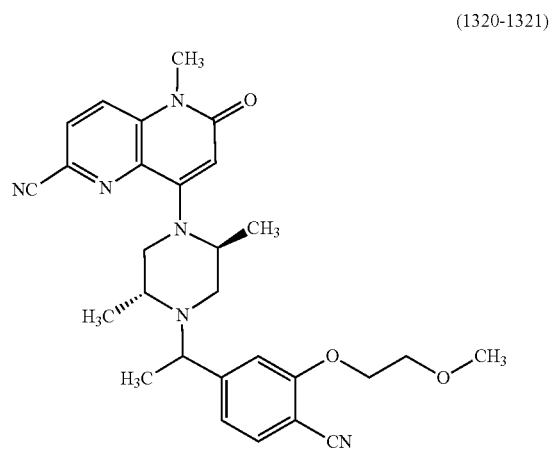 [SMILES: COCCOc1cc(C(C)N2C[C@H](C)N(c3cc(=O)n(C)c4ccc(C#N)nc34)C[C@H]2C)ccc1C#N]
(1320-1321)

Intermediate 1320A:
1-bromo-4-(1-bromoethyl)-2-fluorobenzene

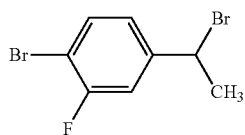
(1320A)

To a stirred solution of 1-(4-bromo-3-fluorophenyl)ethan-1-ol (1 g, 4.57 mmol) in DCM (5 mL) was added BBr$_3$ (9.1 mL, 9.13 mmol, 1 M in DCM) at 0° C. The reaction mixture was stirred at room temperature for 3 h. The reaction was quenched with ice cold water (30 mL). The reaction mixture was extracted with EtOAc (2×30 mL), dried over anhydrous sodium sulphate and concentrated under reduced pressure to obtain 1-bromo-4-(1-bromoethyl)-2-fluorobenzene (1.1 g, 85% yield). $^1$H NMR (400 MHz, DMSO-$d_6$) δ ppm 7.69-7.73 (m, 1H), 7.47-7.66 (m, 1H), 7.25-7.39 (m, 1H), 5.50 (q, J=6.8 Hz, 1H), 1.98 (d, J=6.8 Hz, 3H).

Intermediate 1320B: tert-butyl (2S,5R)-4-(1-(4-bromo-3-fluorophenyl)ethyl)-2,5-dimethylpiperazine-1-carboxylate

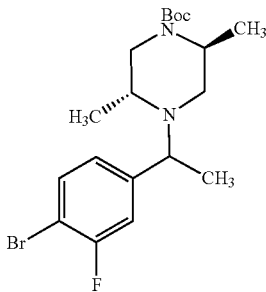

(1320B)

To a stirred solution of tert-butyl (2S,5R)-2,5-dimethylpiperazine-1-carboxylate (0.5 g, 2.33 mmol) in acetonitrile (10 mL) were added sodium bicarbonate (0.98 g, 11.67 mmol) and 1-bromo-4-(1-bromoethyl)-2-fluorobenzene (0.66 g, 2.33 mmol) at room temperature. The reaction mixture was heated at 80° C. for 12 h. The reaction mixture was cooled to room temperature and the solvent was removed under reduced pressure to obtain the crude product, which was purified by flash column chromatography (Column: 24 g silica; Solvent run: 40-45% EtOAc in petroleum ether) to obtain a diastereomeric mixture of tert-butyl (2S,5R)-4-(1-(4-bromo-3-fluorophenyl)ethyl)-2,5-dimethylpiperazine-1-carboxylate (0.3 g, 27% yield) as an off-white solid. LCMS: m/z, 416.2 (M+2); retention time 3.55 min. (LC-MS Method info: Column-KINETEX-XB-C18 (75×3 mm-2.6 μm); Mphase A: 10 mM ammonium formate in water:acetonitrile (98:2); Mphase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min).

Intermediate 1320C: tert-butyl (2S,5R)-4-(1-(4-cyano-3-fluorophenyl)ethyl)-2,5-dimethylpiperazine-1-carboxylate

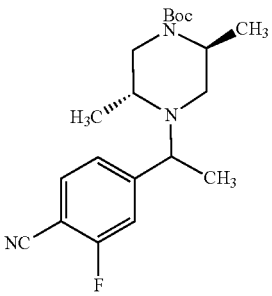

(1320C)

To a stirred solution of tert-butyl (2S,5R)-4-(1-(4-bromo-3-fluorophenyl)ethyl)-2,5-dimethylpiperazine-1-carboxylate (1.6 g, 3.85 mmol) in DMF (5 mL) were added zinc (0.38 g, 5.78 mmol) and zinc cyanide (1.35 g, 11.56 mmol) under an atmosphere of argon, followed by dichloro[9,9-dimethyl-4,5-bis(diphenylphosphino)xanthene]palladium (II) (0.29 g, 0.38 mmol) and TEA (2.2 mL, 15.41 mmol). The reaction mixture was heated at 90° C. for 12 h. The reaction mixture was cooled to room temperature, filtered through Celite pad, washed with EtOAc (30 mL) and filtrate was concentrated under reduced pressure to obtain the crude product, which was purified by flash column chromatography (Column: 40 g silica; Solvent run: 40-45% EtOAc in petroleum ether) to obtain tert-butyl (2S,5R)-4-(1-(4-cyano-3-fluorophenyl)ethyl)-2,5-dimethylpiperazine-1-carboxylate (1.2 g, 86% yield). LCMS: m/z, 362.1 (M+H); retention time 2.17 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1320D: tert-butyl (2S,5R)-4-(1-(4-cyano-3-(2-methoxyethoxy)phenyl) ethyl)-2,5-dimethylpiperazine-1-carboxylate

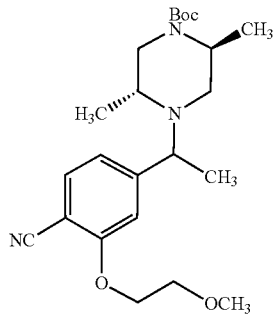

(1320D)

To a solution of tert-butyl (2S,5R)-4-(1-(4-cyano-3-fluorophenyl)ethyl)-2,5-dimethylpiperazine-1-carboxylate (300 mg, 0.83 mmol) in DMSO (5 mL) were added 2-methoxyethan-1-ol (63 mg, 0.83 mmol) and potassium tert-butoxide (190 mg, 1.66 mmol) at 0° C. The reaction mixture was stirred at room temperature for 2 h. The reaction mixture was extracted with EtOAc (30 mL), washed with water and brine solution, the organic extracts were dried over anhydrous sodium sulphate and concentrated under reduced pressure to obtain the crude product, which was purified by flash column chromatography (Column: 12 g silica; Solvent run: 40-45% EtOAc in petroleum ether) to obtain diastereomeric mixture of tert-butyl (2S,5R)-4-(1-(4-cyano-3-(2-methoxyethoxy)phenyl)ethyl)-2,5-dimethylpiperazine-1-carboxylate (250 mg, 72% yield). LCMS: m/z, 418.2 (M+H); retention time 2.09 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1320E: 4-(1-((2R,5S)-2,5-dimethylpip-erazin-1-yl)ethyl)-2-(2-methoxyethoxy)benzonitrile, TFA

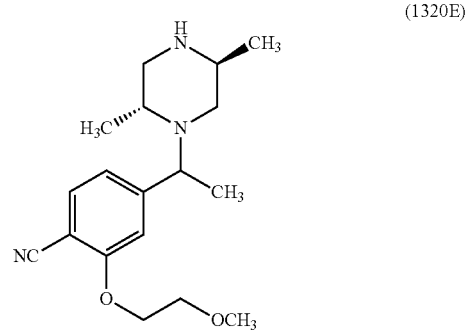 [SMILES: COCCOc1cc(C(C)N2C[C@H](C)NC[C@H]2C)ccc1C#N]

(1320E)

To a stirred solution of tert-butyl (2S,5R)-4-(1-(4-cyano-3-(2-methoxyethoxy) phenyl)ethyl)-2,5-dimethylpiperazine-1-carboxylate (150 mg, 0.36 mmol) in DCM (5 mL) was added TFA (0.14 mL, 1.80 mmol) at 0° C. The reaction mixture was stirred at room temperature for 4 h. The solvent was removed under reduced pressure and dried to afford the diastereomeric mixture of 4-(1-((2R,5S)-2,5-dimethylpiperazin-1-yl)ethyl)-2-(2-methoxyethoxy)benzonitrile, TFA (120 mg, 63% yield). LCMS: m/z, 318.2 (M+H); retention time 0.89 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Examples 1320 and 1321: 8-((2S,5R)-4-(1-(4-cyano-3-(2-methoxyethoxy)phenyl)ethyl)-2,5-dimethylpiperazin-1-yl)-5-methyl-6-oxo-5,6-dihydro-1,5-naphthyridine-2-carbonitrile To a stirred solution of 4-(1-((2R,5S)-2,5-dimethylpiperazin-1-yl)ethyl)-2-(2-methoxyethoxy)benzonitrile (100 mg, 0.32 mmol) in acetonitrile (3 mL) were added sodium bicarbonate (130 mg, 1.57 mmol) and 6-cyano-1-methyl-2-oxo-1,2-dihydro-1,5-naphthyridin-4-yl trifluoromethanesulfonate (105 mg, 0.32 mmol) at room temperature. The reaction mixture was heated at 80° C. for 12 h. The reaction mixture was cooled to room temperature and solvent was removed under reduced pressure to obtain the crude product, which was purified by preparative HPLC (Chiral Separation Method: Column: Cellulose-5 (250×19) mm, 5 μm, Mobile Phase: 0.1% DEA in ACN:MeOH (1:1), Flow rate: 20 mL/min, isocratic) to obtain Examples 1320 and 1321.

Example 1320: (2.6 mg, 1.6%); LCMS: m/z, 501.3 (M+H); retention time 1.99 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.13-8.18 (m, 1H), 8.05-8.09 (m, 1H), 7.69 (d, J=7.8 Hz, 1H), 7.29 (s, 1H), 7.15 (d, J=7.8 Hz, 1H), 5.99 (s, 1H), 4.63-4.74 (m, 1H), 4.27-4.34 (m, 2H), 3.66-3.79 (m, 3H), 3.52 (s, 3H), 3.37-3.47 (m, 2H), 3.34 (s, 3H), 3.00 (dd, J=11.4, 3.3 Hz, 1H), 2.76 (br d, J=2.2 Hz, 2H), 1.24-1.29 (m, 6H), 1.03 (d, J=6.4 Hz, 3H).

Example 1321: (4.7 mg, 3.0%). LCMS: m/z, 501.3 (M+H); retention time 1.99 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.14-8.18 (m, 1H), 8.06-8.10 (m, 1H), 7.68 (d, J=7.8 Hz, 1H), 7.29 (s, 1H), 7.10-7.15 (m, 1H), 6.02 (s, 1H), 4.37-4.46 (m, 1H), 4.29-4.36 (m, 1H), 4.18-4.25 (m, 1H), 3.75-3.83 (m, 1H), 3.72 (t, J=4.4 Hz, 2H), 3.50-3.66 (m, 6H), 3.34 (s, 3H), 2.75-2.83 (m, 1H), 2.01-2.11 (m, 1H), 1.29 (d, J=6.4 Hz, 3H), 1.18 (d, J=6.4 Hz, 3H), 1.13 (d, J=6.6 Hz, 3H).

The examples in Table 55 were prepared according to the general procedure described in Examples 1320 and 1321 using the appropriate 2-(dimethylamino)ethan-1-ol. When the reaction provided a mixture of diastereomers, the mixture was separated at the final stage using either preparative chromatography or preparative chiral chromatography. The absolute stereochemistry was not assigned at the newly formed carbon-nitrogen bond

TABLE 55

| Ex. No. | Structure | M + H | Stereo chem | LCMS RT and Method |
|---|---|---|---|---|
| 1322 | ![structure] | 514.3 | H | 1.68 A |

TABLE 55-continued

| Ex. No. | Structure | M + H | Stereo chem | LCMS RT and Method |
|---|---|---|---|---|
| 1323 | 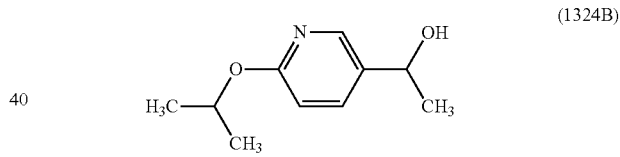 | 514.3 | H | 1.69 A |

Examples 1324 and 1325

8-((2S,5R)-4-(1-(6-isopropoxypyridin-3-yl)ethyl)-2,5-dimethylpiperazin-1-yl)-5-methyl-6-oxo-5,6-dihydro-1,5-naphthyridine-2-carbonitrile

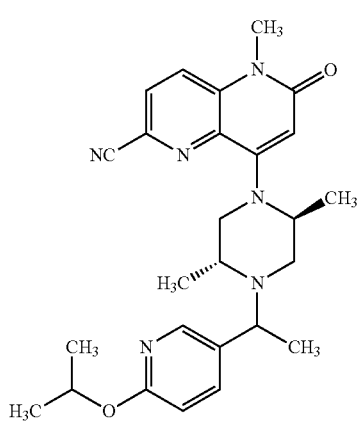

(1324-1325)

Intermediate 13 24A: 1-(6-isopropoxypyridin-3-yl)ethan-1-one

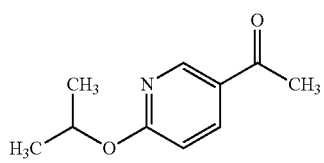

(1324A)

To a solution of 1-(6-fluoropyridin-3-yl)ethan-1-one (0.6 g, 4.31 mmol) in DMSO (5 mL), propan-2-ol (0.26 g, 4.31 mmol) and potassium tert-butoxide (0.97 g, 8.63 mmol) were added sequentially at 0° C. The reaction mixture was stirred at room temperature for 2 h. The reaction mixture was diluted with EtOAc (20 mL) and washed with water (2×20 mL), the organic layer was dried over anhydrous $Na_2SO_4$, filtered and concentrated under reduced pressure to obtain the crude product, which was purified by flash column chromatography (Column: 12 g silica; Solvent run: 30-40% EtOAc in petroleum ether) to obtain 1-(6-isopropoxypyridin-3-yl)ethan-1-one (0.4 g, 52% yield). LCMS: m/z, 180.1 (M+H); retention time 1.37 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1324B: 1-(6-isopropoxypyridin-3-yl)ethan-1-ol (1324B)

To a stirred solution of 1-(6-isopropoxypyridin-3-yl)ethan-1-one (0.4 g, 2.23 mmol) in MeOH (10 mL) was added sodium borohydride (0.25 g, 6.70 mmol) at 0° C. The reaction mixture was stirred at room temperature for 2 h. The reaction was quenched with saturated aqueous $NH_4Cl$ solution. Methanol was evaporated under reduced pressure. The crude product was extracted with EtOAc (3×50 mL), washed with water, brine, dried over anhydrous sodium sulphate and concentrated to obtain a racemic mixture of 1-(6-isopropoxypyridin-3-yl)ethan-1-ol (250 mg, 40% yield). LCMS: m/z, 182.1 (M+H); retention time 1.01 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Examples 1324 and 1325: 8-((2S,5R)-4-(1-(6-isopropoxypyridin-3-yl)ethyl)-2,5-dimethylpiperazin-1-yl)-5-methyl-6-oxo-5,6-dihydro-1,5-naphthyridine-2-carbonitrile To a stirred solution of 8-((2S,5R)-2,5-dimethylpiperazin-1-yl)-5-methyl-6-oxo-5,6-dihydro-1,5-naphthyridine-2-carbonitrile (200 mg, 0.67 mmol) in acetonitrile (3 mL) were added (cyanomethyl)trimethylphosphonium iodide (327 mg, 1.34 mmol), 1-(6-isopropoxypyridin-3-yl)ethan-1-ol (122 mg, 0.67 mmol) and DIPEA (0.4 mL, 2.02 mmol) at room temperature. The reaction mixture was heated at 100° C. under microwave irradiation for 2 h. The reaction mixture was concentrated under reduced pressure to obtain the crude product, which was purified by preparative HPLC (Chiral Separation Method: Column: Cellulose-4 (250×19) mm, 5 micron, Mobile Phase: 10 mM ammonium acetate in MeOH, Flow rate: 20 mL/min, isocratic) to obtain Examples 1324 and 1325.

Example 1324: (4.7 mg, 2% yield); LCMS: m/z, 461.2 (M+H); retention time 2.21 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.14-8.18 (m, 1H), 8.05-8.12 (m, 2H), 7.68-7.72 (m, 1H), 6.75 (d, J=8.6 Hz, 1H), 6.00 (s, 1H), 5.23 (quin, J=6.2 Hz, 1H), 4.57-4.64 (m, 1H), 3.68 (q, J=6.6 Hz, 1H), 3.52 (s, 3H), 3.36-3.43 (m, 2H), 2.98 (dd, J=11.7, 3.4 Hz, 1H), 2.67-2.78 (m, 2H), 1.25-1.31 (m, 9H), 1.23 (d, J=6.6 Hz, 3H), 1.02 (d, J=6.6 Hz, 3H).

Example 1325: (2.8 mg, 1% yield). LCMS: m/z, 461.2 (M+H); retention time 2.24 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.13-8.18 (m, 1H), 8.04-8.09 (m, 2H), 7.68 (dd, J=8.6, 2.4 Hz, 1H), 6.71 (d, J=8.6 Hz, 1H), 6.01 (s, 1H), 5.17-5.26 (m, 1H), 4.32-4.40 (m, 1H), 3.71-3.79 (m, 1H), 3.48-3.59 (m, 6H), 2.70-2.80 (m, 1H), 2.09 (dd, J=12.2, 1.5 Hz, 1H), 1.27-1.29 (m, 9H), 1.16 (d, J=6.4 Hz, 3H), 1.07 (d, J=6.4 Hz, 3H).

Examples 1326 and 1327

8-((2S,5R)-4-(2-(3-cyclopropyl-1,2,4-oxadiazol-5-yl)-1-(4-fluorophenyl)ethyl)-2,5-dimethylpiperazin-1-yl)-5-methyl-6-oxo-5,6-dihydro-1,5-naphthyridine-2-carbonitrile

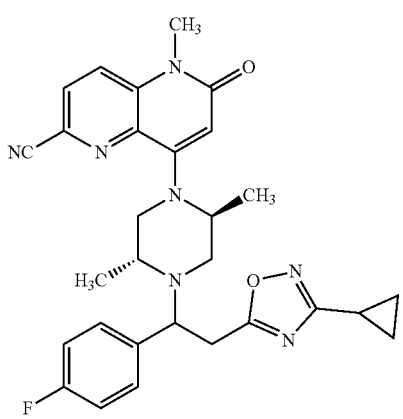

(1326-1327)

Intermediate 1326A: 3-((2R,5S)-4-(tert-butoxycarbonyl)-2,5-dimethylpiperazin-1-yl)-3-(4-fluorophenyl)propanoic acid

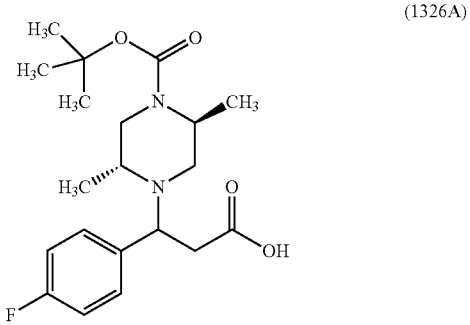 [SMILES: C[C@@H]1CN(C(=O)OC(C)(C)C)[C@@H](C)CN1C(CC(=O)O)c1ccc(F)cc1]

(1326A)

To a solution of tert-butyl (2S,5R)-4-(1-(4-fluorophenyl)-3-methoxy-3-oxopropyl)-2,5-dimethylpiperazine-1-carboxylate (1.0 g, 2.53 mmol) in THF (20 mL) and water (10 mL) was added lithium hydroxide monohydrate (0.53 g, 12.67 mmol) at room temperature. The reaction mixture was stirred for 16 h. The reaction mixture was neutralized with aqueous 1.5 N HCl and extracted with EtOAc (2×100 mL), washed with water, brine, dried over anhydrous sodium sulphate and concentrated to afford 3-((2R,5S)-4-(tert-butoxycarbonyl)-2,5-dimethylpiperazin-1-yl)-3-(4-fluorophenyl) propanoic acid (0.85 g, 88% yield). LCMS: m/z, 381.3 (M+H); retention time 1.11 min. [LCMS Method: Column: AQUITY UPLC BEH C18 (3.0×50 mm) 1.7 μm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100, Temperature: 27° C.; Flow rate: 0.7 mL/min; Detection: UV at 220 nm].

Intermediate 1326B: tert-butyl (2S,5R)-4-(3-((((E)-amino(cyclopropyl)methylene)amino) oxy)-1-(4-fluorophenyl)-3-oxopropyl)-2,5-dimethylpiperazine-1-carboxylate

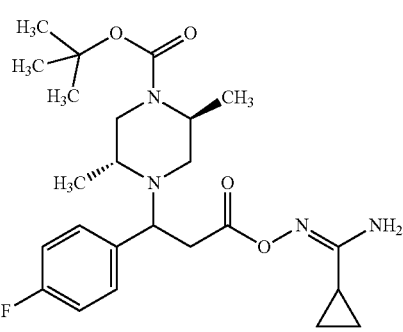

(1326B)

To a solution of 3-((2R,5S)-4-(tert-butoxycarbonyl)-2,5-dimethylpiperazin-1-yl)-3-(4-fluorophenyl)propanoic acid (500 mg, 1.31 mmol) in EtOAc (10 mL) were added (E)-N'-hydroxycyclopropanecarboximidamide (145 mg, 1.45 mmol), Et$_3$N (0.37 mL, 2.63 mmol) and 1-propanephosphonic anhydride (50% in EtOAc) (1 mL, 1.58 mmol) at 0° C. The reaction mixture was stirred at room temperature for 16 h. The reaction mixture was extracted with EtOAc (2×50 mL), washed with water, brine, dried over anhydrous sodium sulphate and concentrated to obtain tert-butyl (2S, 5R)-4-(3-((((E)-amino(cyclopropyl)methylene) amino) oxy)-1-(4-fluorophenyl)-3-oxopropyl)-2,5-dimethylpiperazine-1-carboxylate (500 mg, 82% yield) as a diastereomeric mixture. LCMS: m/z, 463.4 (M+H); retention time 1.81 min. [LCMS Method: Column: AQUITY UPLC BEH C18 (3.0× 50 mm) 1.7 µm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100, Temperature: 27° C.; Flow rate: 0.7 mL/min; Detection: UV at 220 nm].

Intermediate 1326C: tert-butyl (2S,5R)-4-(2-(3-cyclopropyl-1,2,4-oxadiazol-5-yl)-1-(4-fluorophenyl)ethyl)-2,5-dimethylpiperazine-1-carboxylate

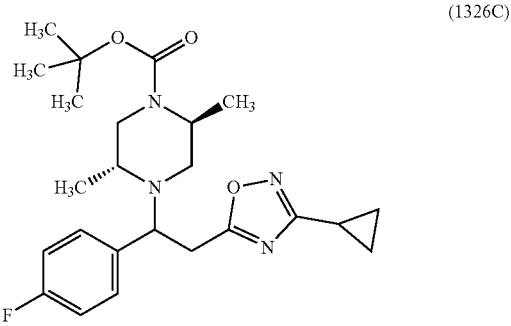 [SMILES: C[C@@H]1CN(C(=O)OC(C)(C)C)[C@@H](C)CN1C(Cc1nc(C2CC2)no1)c1ccc(F)cc1]

(1326C)

To a stirred solution of tert-butyl (2S,5R)-4-(3-((((E)-amino(cyclopropyl) methylene)amino)oxy)-1-(4-fluorophenyl)-3-oxopropyl)-2,5-dimethylpiperazine-1-carboxylate (320 mg, 0.69 mmol) in 1,4-dioxane (6 mL) was added $Et_3N$ (0.4 mL, 2.77 mmol) at room temperature. The reaction mixture was heated at 160° C. under microwave for 1 h. The reaction mixture was cooled to room temperature and solvent was removed under reduced pressure to obtain the crude product, which was purified silica gel flash column chromatography (30% EtOAc in n-hexane; 24 g column) to afford tert-butyl (2S,5R)-4-(2-(3-cyclopropyl-1,2,4-oxadiazol-5-yl)-1-(4-fluorophenyl)ethyl)-2,5-dimethylpiperazine-1-carboxylate (175 mg, 57% yield) as a diastereomeric mixture. LCMS: m/z, 445.4 (M+H); retention time 2.15 min. [LCMS Method: Column: Waters Acquity UPLC BEH C18 (2.1×50 mm) 1.7 µm, Mobile phase A: 10 mM $NH_4OAc$:acetonitrile (95:5); Mobile phase B: 10 mM $NH_4OAc$:acetonitrile (5:95), Gradient=20-100% B over 2 minute, then a 0.3 minute hold at 100% B; Temperature: 50° C.; Flow rate: 0.7 mL/min; Detection: UV at 220 nm].

Intermediate 1326D: 3-cyclopropyl-5-(2-((2R,5S)-2,5-dimethylpiperazin-1-yl)-2-(4-fluorophenyl)ethyl)-1,2,4-oxadiazole

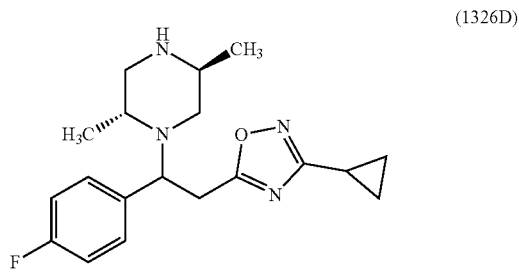 [SMILES: C[C@@H]1CN[C@@H](C)CN1C(Cc1nc(C2CC2)no1)c1ccc(F)cc1]

(1326D)

To a solution of tert-butyl (2S,5R)-4-(2-(3-cyclopropyl-1,2,4-oxadiazol-5-yl)-1-(4-fluorophenyl)ethyl)-2,5-dimethylpiperazine-1-carboxylate (150 mg, 0.34 mmol) in DCM (1 mL) were added 2,6-lutidine (0.24 mL, 2.02 mmol) and TMS-OTf (0.43 mL, 2.36 mmol) at 0° C. The reaction mixture was stirred at room temperature for 3 h. The reaction mixture was extracted with DCM (2×30 mL), washed with aqueous $NaHCO_3$ solution, water and brine. The combined organic extracts were dried over anhydrous sodium sulphate, concentrated and dried to afford 3-cyclopropyl-5-(2-((2R,5S)-2,5-dimethylpiperazin-1-yl)-2-(4-fluorophenyl)ethyl)-1,2,4-oxadiazole (70 mg, 60% yield). LCMS: m/z, 345.2 (M+H); retention time 1.08 and 1.11 min. [LCMS Method: Column: Waters Acquity UPLC BEH C18 (2.1×50 mm) 1.7 µm, Mobile phase A: 10 mM $NH_4OAc$:acetonitrile (95:5); Mobile phase B: 10 mM $NH_4OAc$:acetonitrile (5:95), Gradient=20-100% B over 2 minute, then a 0.3 minute hold at 100% B; Temperature: 50° C.; Flow rate: 0.7 mL/min; Detection: UV at 220 nm].

Examples 1326 and 1327: 8-((2S,5R)-4-(2-(3-cyclopropyl-1,2,4-oxadiazol-5-yl)-1-(4-fluorophenyl) ethyl)-2,5-dimethylpiperazin-1-yl)-5-methyl-6-oxo-5,6-dihydro-1,5-naphthyridine-2-carbonitrile To a stirred solution of 3-cyclopropyl-5-(2-((2R,5S)-2,5-dimethylpiperazin-1-yl)-2-(4-fluorophenyl)ethyl)-1,2,4-oxadiazole (70 mg, 0.20 mmol) in acetonitrile (5 mL), were added DIPEA (0.15 mL, 0.81 mmol) and 6-cyano-1-methyl-2-oxo-1,2-dihydro-1,5-naphthyridin-4-yl trifluoromethanesulfonate (68 mg, 0.20 mmol) at room temperature. The reaction mixture was heated at 80° C. for 4 h. The reaction mixture was cooled to room temperature and the solvent was removed under reduced pressure to obtain the crude product, which was purified by prep-HPLC (Chiral Separation Method: Column: cellulose-4 (250×4.6) mm, 5 micron, Mobile Phase: 0.1% DEA in MeOH, isocratic) to obtain Examples 1326 and 1327.

Example 1326: (14 mg, 13% yield); LCMS: m/z, 528.2 (M+H); retention time 2.13 min; Column: XBridge BEH XP C18 (2.1×50 mm), 2.5 µm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.13-8.17 (m, 1H), 8.05-8.08 (m, 1H), 7.33 (dd, J=8.4, 5.7 Hz, 2H), 7.08-7.20 (m, 2H), 6.01 (s, 1H), 4.30-4.44 (m, 1H), 4.00-4.14 (m, 1H), 3.66-3.76 (m, 1H), 3.45-3.61 (m, 6H), 3.10-3.20 (m, 1H), 2.74-2.82 (m, 1H), 2.18-

2.27 (m, 1H), 1.97-2.08 (m, 1H), 1.14 (d, J=6.4 Hz, 3H), 1.04 (d, J=6.6 Hz, 3H), 0.99-1.02 (m, 2H), 0.70-0.85 (m, 2H).

Example 1327: (3.6 mg, 3% yield). LCMS: m/z, 528.2 (M+H); retention time 2.10 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.15 (d, J=8.8 Hz, 1H), 8.02-8.11 (m, 1H), 7.39 (dd, J=8.1, 5.6 Hz, 2H), 7.13-7.23 (m, 2H), 6.03 (s, 1H), 4.20-4.29 (m, 2H), 3.62-3.72 (m, 1H), 3.53 (s, 3H), 3.37-3.45 (m, 1H), 3.10-3.24 (m, 3H), 2.75-2.85 (m, 1H), 1.99-2.07 (m, 1H), 1.12 (d, J=6.1 Hz, 3H), 0.99-1.04 (m, 2H), 0.95 (d, J=6.4 Hz, 3H), 0.71-0.87 (m, 2H).

Examples 1328 and 1329

8-((2S,5R)-5-ethyl-2-methyl-4-(1-(4-(trifluoromethoxy)phenyl)ethyl)piperazin-1-yl)-7-fluoro-5-methyl-6-oxo-5,6-dihydro-1,5-naphthyridine-2-carbonitrile

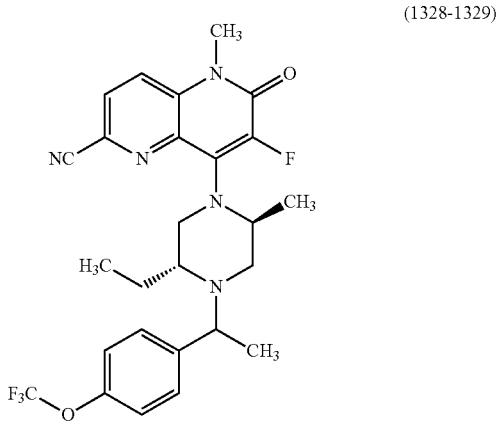 [SMILES: CC[C@@H]1CN(c2c(F)c(=O)n(C)c3ccc(C#N)nc23)[C@@H](C)CN1C(C)c1ccc(OC(F)(F)F)cc1]

(1328-1329)

To a solution of Selectfluor® (0.125 g, 0.35 mmol) in acetonitrile (2 mL) at room temperature was added 8-((2S,5R)-5-ethyl-2-methyl-4-(1-(4-(trifluoromethoxy)phenyl)ethyl)piperazin-1-yl)-5-methyl-6-oxo-5,6-dihydro-1,5-naphthyridine-2-carbonitrile (0.16 g, 0.32 mmol) in acetonitrile (2 mL). The reaction mixture was stirred at room temperature for 30 min. The reaction was quenched with water. The reaction mixture was extracted with ethyl acetate (2×100 mL). The combined organic layer was washed with water, brine and dried over anhydrous sodium sulfate. The solvent was evaporated under reduced pressure to obtain the crude product which was purified by preparative HPLC (Method Information: LC conditions: Column: Sunfire C18 (150 mm×19.2 mm ID, 5u); Mobile phase A=10 mM AA in water; Mobile phase B=acetonitrile:MeOH; Flow 18 mL/min) to obtain Examples 1328 and 1329.

Example 1328: (3.4 mg, 2.0% yield). LCMS: m/z=518.2 (M+H); retention time 2.54 min [LCMS method: Column: XBridge BEH XP C18 (2.1×50 mm), 2.5 μm; Mobile phase A: 10 mM ammonium acetate:acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-$d_6$) δ ppm 8.23-8.08 (m, 2H), 7.51 (d, J=8.6 Hz, 2H), 7.35 (d, J=8.1 Hz, 2H), 4.22-4.12 (m, 1H), 4.02-3.91 (m, 1H), 3.70-3.57 (m, 4H), 3.11 (dd, J=3.1, 11.1 Hz, 1H), 3.03-2.89 (m, 1H), 2.45-2.51 (m, 1H), 2.31-2.22 (m, 1H), 1.73-1.51 (m, 2H), 1.33 (d, J=6.6 Hz, 3H), 1.18 (d, J=6.4 Hz, 3H), 0.58 (t, J=7.3 Hz, 3H).

Example 1329: (4.4 mg, 2.6% yield). LCMS: m/z=518.2 (M+H); retention time 2.62 min [LCMS method: Column: XBridge BEH XP C18 (2.1×50 mm), 2.5 μm; Mobile phase A: 10 mM ammonium acetate:acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.20-8.04 (m, 2H), 7.55 (d, J=7.3 Hz, 2H), 7.31 (br d, J=7.6 Hz, 2H), 4.00-3.92 (m, 1H), 3.91-3.77 (m, 2H), 3.61 (s, 3H), 3.17-3.07 (m, 2H), 3.01-2.91 (m, 1H), 2.11-2.00 (m, 1H), 1.81-1.65 (m, 1H), 1.61-1.47 (m, 1H), 1.25 (br d, J=6.4 Hz, 3H), 1.00 (d, J=6.8 Hz, 3H), 0.79 (br t, J=7.5 Hz, 3H).

Example 1330

8-((2S,5R)-4-(4-(difluoromethoxy)benzyl)-5-ethyl-2-methylpiperazin-1-yl)-5-methyl-6-oxo-5,6-dihydro-1,5-naphthyridine-2-carbonitrile

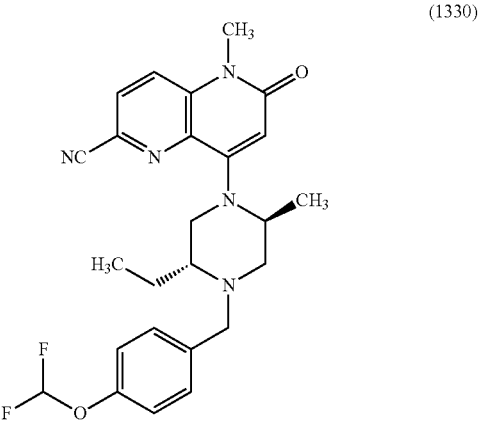 [SMILES: CC[C@@H]1CN(c2cc(=O)n(C)c3ccc(C#N)nc23)[C@@H](C)CN1Cc1ccc(OC(F)F)cc1]

(1330)

Intermediate 1330A: 4-(difluoromethoxy)benzyl methanesulfonate

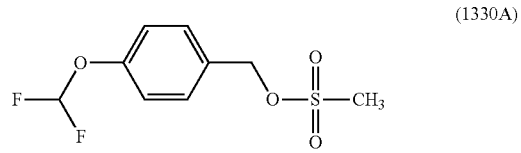

(1330A)

To a solution of (4-(difluoromethoxy)phenyl)methanol (0.5 g, 2.8 mmol) in DCM (2 mL) at 0° C. were added triethylamine (0.8 mL, 5.7 mmol) and methanesulfonyl chloride (0.34 mL, 4.31 mmol). The reaction mixture was stirred at room temperature for 3 h. The reaction was quenched with water. The reaction mixture was extracted with ethyl acetate (2×100 mL), the combined organic layer was washed with water, brine and dried over anhydrous

1087 sodium sulfate and evaporated under reduced pressure to obtain 4-(difluoromethoxy)benzyl methanesulfonate (0.5 g, 69% yield). $^1$H NMR (400 MHz, Chloroform-d) δ ppm 7.49-7.35 (m, 2H), 7.22-7.06 (m, 2H), 6.77-6.27 (m, 1H), 4.65-4.53 (m, 2H), 3.41-3.26 (m, 3H).

Example 1330: 8-((2S,5R)-4-(4-(difluoromethoxy)benzyl)-5-ethyl-2-methylpiperazin-1-yl)-5-methyl-6-oxo-5,6-dihydro-1,5-naphthyridine-2-carbonitrile To a solution of 8-((2S,5R)-5-ethyl-2-methylpiperazin-1-yl)-5-methyl-6-oxo-5,6-dihydro-1,5-naphthyridine-2-carbonitrile (0.03 g, 0.1 mmol) in acetonitrile (2 mL) was added DIPEA (0.05 mL, 0.29 mmol) and 4-(difluoromethoxy)benzyl methanesulfonate (49 mg, 0.193 mmol) at room temperature. The reaction mixture was heated at 85° C. overnight. The reaction was quenched with water. The reaction mixture was extracted with ethyl acetate (2×100 mL), the combined organic layer was washed with water, brine and dried over anhydrous sodium sulfate, evaporated under reduced pressure to obtain the crude product, which was purified by preparative HPLC (Method Information: Column: Waters XBridge C18, 150 mm×19 mm, 5 µm particles; Mobile Phase A: 5:95 acetonitrile:water with 10-mM ammonium acetate; Mobile Phase B: 95:5 acetonitrile: water with 10-mM ammonium acetate; Gradient: 0 minute hold at 21% B, 21-65% B over 25 minutes, then a 5-minute hold at 100% B; Flow Rate: 15 mL/min; Column Temperature: 25° C.) to obtain 8-((2S,5R)-4-(4-(difluoromethoxy)benzyl)-5-ethyl-2-methylpiperazin-1-yl)-5-methyl-6-oxo-5,6-dihydro-1,5-naphthyridine-2-carbonitrile (8.3 mg, 18.2% yield). LCMS: m/z=468.2 (M+H); retention time 2.18 min [LCMS method: Column: XBridge BEH XP C18 (2.1×50 mm), 2.5 µm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.19-8.12 (m, 1H), 8.11-8.04 (m, 1H), 7.48-6.97 (m, 5H), 6.09 (s, 1H), 4.37 (br dd, J=1.0, 2.9 Hz, 1H), 3.73-3.60 (m, 3H), 3.57-3.44 (m, 4H), 2.93 (dd, J=3.4, 11.5 Hz, 1H), 2.68-2.62 (m, 1H), 2.28 (dd, J=3.3, 11.6 Hz, 1H), 1.79-1.57 (m, 2H), 1.13 (d, J=6.4 Hz, 3H), 0.85 (t, J=7.3 Hz, 3H).

The examples in Table 56 were prepared according to the general procedure described in Example 1330 with the appropriate alcohol.

TABLE 56

| Ex. No. | Structure | M + H | Stereo chem. | LCMS RT and Method |
|---|---|---|---|---|
| 1331 | 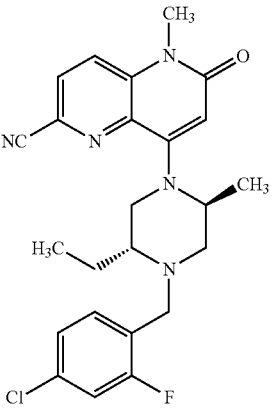 [SMILES: CC[C@@H]1CN(c2cc(=O)n(C)c3ccc(C#N)nc23)[C@@H](C)CN1Cc1ccc(Cl)cc1F] | 441.2 | H | 2.11 A |
| 1332 | 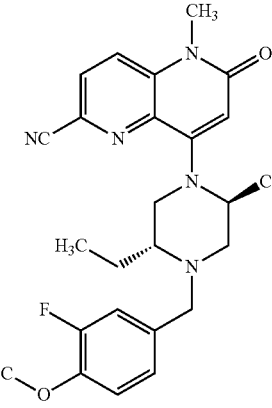 | 504.3 | H | 2.46 A |

Examples 1333 and 1334

8-((2S,5R)-4-((4-fluorophenyl)(2-(trifluoromethyl)thiazol-4-yl)methyl)-2,5-dimethylpiperazin-1-yl)-5-methyl-6-oxo-5,6-dihydro-1,5-naphthyridine-2-carbonitrile (1333-1334)

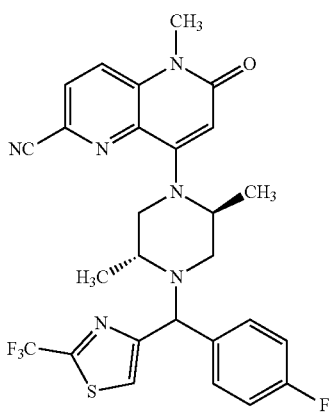

Intermediate 1333A: N-methoxy-N-methyl-2-(trifluoromethyl)thiazole-4-carboxamide (1333A)

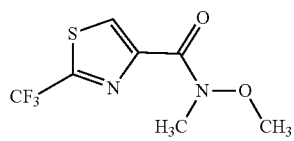

To a solution of 2-(trifluoromethyl)thiazole-4-carboxylic acid (1.0 g, 5.07 mmol) in DMF (15 mL) were added 1-propanephosphonic anhydride (6.34 mL, 10.15 mmol, 50% in ethyl acetate), followed by DIPEA (2.66 mL, 15.22 mmol) and N,O-dimethylhydroxylamine hydrochloride (0.99 g, 10.15 mmol) at room temperature. The reaction mixture was stirred for 5 h. The reaction mixture was concentrated under reduced pressure to remove volatiles and the crude product was dissolved in ethyl acetate (150 mL), washed with water (100 mL), the aqueous layer was back extracted with ethyl acetate (50 mL×2) and the combined organic layer was washed with brine, dried over anhydrous Na$_2$SO$_4$, concentrated under reduced pressure to obtain the crude product, which was purified by silica gel chromatography (1-5% methanol/chloroform; 40 g column) to afford N-methoxy-N-methyl-2-(trifluoromethyl)thiazole-4-carboxamide (925 mg, 76% yield). LCMS: m/z=241.1 (M+H); retention time 1.17 min [LCMS method: Column: Waters Acquity UPLC BEH C18 (2.1×50 mm) 1.7 μm, Mobile phase A: 10 mM NH$_4$OAc:acetonitrile (95:5); Mobile phase B: 10 mM NH$_4$OAc:acetonitrile (5:95), Gradient=20-90% B over 1.1 minute, then a 0.6 minute hold at 90% B; Temperature: 50° C.; Flow rate: 0.7 mL/min; Detection: UV at 220 nm].

Intermediate 1333B: (4-fluorophenyl)(2-(trifluoromethyl)thiazol-4-yl)methanone (1333B)

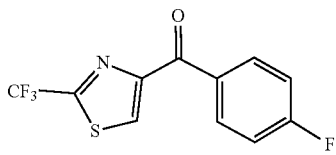

To a solution of N-methoxy-N-methyl-2-(trifluoromethyl)thiazole-4-carboxamide (500 mg, 2.08 mmol) in tetrahydrofuran (10 mL) at 0° C. was added 4-fluorophenylmagnesium bromide (4.16 mL, 4.16 mmol, 1.0 M in THF). The reaction mixture was warmed to room temperature. The reaction mixture was stirred overnight. The reaction was quenched with saturated aqueous ammonium chloride solution (20 mL). The reaction mixture was extracted with ethyl acetate (2×50 mL). The combined organic layer was dried over anhydrous sodium sulfate, filtered and evaporated under reduced pressure to obtain the crude product, which was purified by Silica gel chromatography (50-100% EA/Petroleum ether; 24 g column) to afford (4-fluorophenyl) (2-(trifluoromethyl)thiazol-4-yl)methanone (355 mg, 62.0% yield). LCMS: m/z=276.2 (M+H); retention time 1.86 min [LCMS method: Column: Waters Acquity UPLC BEH C18 (2.1×50 mm) 1.7 μm, Mobile phase A: 10 mM NH$_4$OAc:acetonitrile (95:5); Mobile phase B: 10 mM NH$_4$OAc:acetonitrile (5:95), Gradient=20-90% B over 1.1 minute, then a 0.6 minute hold at 90% B; Temperature: 50° C.; Flow rate: 0.7 mL/min; Detection: UV at 220 nm].

Intermediate 1333C: (4-fluorophenyl)(2-(trifluoromethyl)thiazol-4-yl)methanol (1333C)

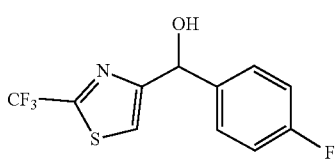

To a solution of (4-fluorophenyl)(2-(trifluoromethyl)thiazol-4-yl)methanone (425 mg, 1.54 mmol) in MeOH (5 mL) at 4-5° C. was added NaBH$_4$ (117 mg, 3.09 mmol) portionwise. The reaction mixture was stirred at room temperature overnight. The reaction mixture was concentrated under reduced pressure to remove volatiles and the crude product was dissolved in ethyl acetate (60 mL) and was washed with water. The aqueous layer was back extracted with ethyl acetate (50 mL×2). The combined organic layer was washed with brine, dried over anhydrous Na$_2$SO$_4$, concentrated under reduced pressure to obtain the crude product, which was purified by silica gel chromatography (50-100% ethyl acetate/petroleum ether; 24 g column) to afford (4-fluorophenyl)(2-(trifluoromethyl)thiazol-4-yl)methanol (421 mg, 98% yield). LCMS: m/z=276.1 (M−H); retention time 1.57 min [LCMS method: Column: Waters Acquity UPLC BEH C18 (2.1×50 mm) 1.7 μm, Mobile phase A: 10 mM NH$_4$OAc:acetonitrile (95:5); Mobile phase B: 10 mM NH$_4$OAc:acetonitrile (5:95), Gradient=20-90% B over 1.1

Intermediate 1333D: 4-(chloro(4-fluorophenyl)
methyl)-2-(trifluoromethyl)thiazole

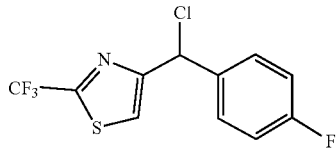
(1333D)

To a stirred solution of (4-fluorophenyl)(2-(trifluoromethyl)thiazol-4-yl)methanol (420 mg, 1.52 mmol) in $CH_2Cl_2$ (10 mL) at 0° C. was added $SOCl_2$ (1.11 mL, 15.15 mmol) dropwise under nitrogen over 3 min. The reaction mixture was slowly warm to room temperature and was stirred for 3 h. The volatiles were removed from the reaction mixture under reduced pressure. The crude product was dissolved in DCM and was washed with water and brine. The organic layer was dried over anhydrous sodium sulfate, concentrated under reduced pressure to obtain 4-(chloro(4-fluorophenyl)methyl)-2-(trifluoromethyl)thiazole (471 mg). The crude material was taken to the next step without further purification. $^1$H NMR (400 MHz, DMSO-$d_6$) δ ppm 8.15 (s, 1H), 7.52-7.65 (m, 2H), 7.19-7.29 (m, 2H), 6.75 (s, 1H).

Examples 1333 and 1334: 8-((2S,5R)-4-((4-fluorophenyl)(2-(trifluoromethyl)thiazol-4-yl)methyl)-2,5-dimethylpiperazin-1-yl)-5-methyl-6-oxo-5,6-dihydro-1,5-naphthyridine-2-carbonitrile To a solution of 8-((2S,5R)-2,5-dimethylpiperazin-1-yl)-5-methyl-6-oxo-5,6-dihydro-1,5-naphthyridine-2-carbonitrile (80 mg, 0.27 mmol) in acetonitrile (5 mL) was added DIPEA (0.24 mL, 1.35 mmol), followed by 4-(chloro(4-fluorophenyl)methyl)-2-(trifluoromethyl)thiazole (80 mg, 0.27 mmol) and the reaction mixture was stirred at 85° C. overnight. The reaction mixture was concentrated under reduced pressure to remove volatiles and the crude product was dissolved in ethyl acetate, washed with water. The aqueous layer was back extracted with ethyl acetate (20 mL×2). The combined organic layer was washed with brine, dried over anhydrous $Na_2SO_4$, concentrated under reduced pressure to obtain the crude product, which was purified by preparative HPLC (Method Information: Column Cellulose 2 (250×4.6 mm), 5 micron; Mobile phase: 0.1% DEA in acetonitrile; Isocratic) to obtain Examples 1333 and 1334.

Example 1333: (11 mg, 7.3% yield). LCMS: m/z=557.2 (M+H); retention time 2.33 min [LCMS method: Column: XBridge BEH XP C18 (2.1×50 mm), 2.5 μm; Mobile phase A: 10 mM ammonium acetate:acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-$d_6$) δ ppm 8.27 (s, 1H), 8.18-8.11 (m, 1H), 8.10-8.03 (m, 1H), 7.64 (dd, J=5.7, 8.7 Hz, 2H), 7.13-7.23 (m, 2H), 6.01 (s, 1H), 5.07 (s, 1H), 4.42-4.54 (m, 1H), 3.71-3.62 (m, 1H), 3.52 (s, 4H), 2.96-2.84 (m, 2H), 2.26-2.17 (m, 1H), 1.20 (d, J=6.6 Hz, 3H), 1.14 (d, J=6.6 Hz, 3H).

Example 1334: (11 mg, 7.3% yield). LCMS: m/z=557.2 (M+H); retention time 2.35 min [LCMS method: Column: XBridge BEH XP C18 (2.1×50 mm), 2.5 μm; Mobile phase A: 10 mM ammonium acetate:acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm]. $^1$H NMR (400 MHz, DMSO-$d_6$) δ ppm 8.19-8.12 (m, 2H), 8.09-8.03 (m, 1H), 7.73-7.61 (m, 2H), 7.16-7.26 (m, 2H), 6.00 (s, 1H), 5.06 (s, 1H), 4.64-4.52 (m, 1H), 3.65-3.56 (m, 1H), 3.54-3.43 (m, 4H), 2.97 (br dd, J=2.9, 11.2 Hz, 2H), 2.24 (br d, J=11.5 Hz, 1H), 1.26 (d, J=6.6 Hz, 3H), 1.10-1.02 (m, 3H).

Example 1335

8-((2S,5R)-4-(bis(4-(hydroxymethyl)phenyl)methyl)-2,5-dimethylpiperazin-1-yl)-5-methyl-6-oxo-5,6-dihydro-1,5-naphthyridine-2-carbonitrile

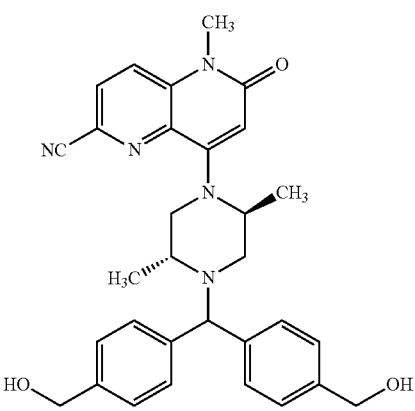
(1335)

Intermediate 1335A: dimethyl 4,4'-(((2R,5S)-4-(tert-butoxycarbonyl)-2,5-dimethylpiperazin-1-yl)methylene)dibenzoate

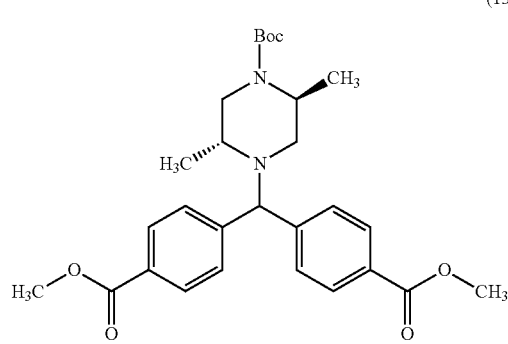
(1335A)

To a stirred solution of tert-butyl (2S,5R)-2,5-dimethylpiperazine-1-carboxylate (0.2 g, 0.93 mmol) in acetonitrile (6 mL) were added DIPEA (0.5 mL, 2.80 mmol) and dimethyl 4,4'-(bromomethylene)dibenzoate (0.373 g, 1.03 mmol) at room temperature. The reaction mixture was heated at 85° C. for 16 h. The volatiles were removed from the reaction mixture under reduced pressure to obtain the crude product, which was purified by silica gel column chromatography (24 g, 12%-17% ethyl acetate/petroleum ether) to obtain dimethyl 4,4'-(((2R,5S)-4-(tert-butoxycarbonyl)-2,5-dimethylpiperazin-1-yl) methylene)dibenzoate (140 mg, 30.2% yield). LCMS: m/z=497.2 (M+H); retention time 2.52 min [LCMS method: Column: Waters Acquity UPLC BEH C18 (2.1×50 mm) 1.7 μm, Mobile phase A: 10 mM NH₄OAc: acetonitrile (95:5); Mobile phase B: 10 mM NH₄OAc:acetonitrile (5:95), Gradient=20-90% B over 1.1 minute, then a 0.6 minute hold at 90% B; Temperature: 50° C.; Flow rate: 0.7 mL/min; Detection: UV at 220 nm].

Intermediate 1335B: tert-butyl (2S,5R)-4-(bis(4-(hydroxymethyl)phenyl)methyl)-2,5-dimethylpiperazine-1-carboxylate

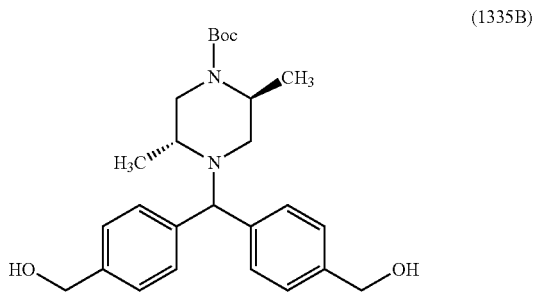 [SMILES: C[C@@H]1CN(C(=O)OC(C)(C)C)[C@@H](C)CN1C(c1ccc(CO)cc1)c1ccc(CO)cc1]

(1335B)

To a solution of dimethyl 4,4'-(((2R,5S)-4-(tert-butoxycarbonyl)-2,5-dimethylpiperazin-1-yl)methylene)dibenzoate (140 mg, 0.28 mmol) in tetrahydrofuran (8 mL) were added LiBH₄ (49.1 mg, 2.26 mmol) and methanol (0.1 mL) at 0° C. The reaction mixture was stirred at room temperature for 2 h. The reaction was quenched with water (20 mL). The reaction mixture was extracted with ethyl acetate (3×50 mL), dried over anhydrous sodium sulfate, filtered and evaporated under reduced pressure to obtain the crude product. LCMS: m/z=441.2 (M+H); retention time 1.75 min [LCMS method: Column: Ascentis Express C8 (50×2.1 mm) 2.7 μm; Mobile phase A: 10 mM ammonium formate: acetonitrile (98:2), Mobile phase B: 10 mM ammonium formate:acetonitrile (2:98), Gradient=0-100% B over 1.5 minutes, then a 0.6 min hold at 100% B; Temperature: 27° C.; Flow rate: 1.0 mL/min; Detection: UV at 220 nm].

Intermediate 1335C: ((((2R,5S)-2,5-dimethylpiperazin-1-yl)methylene)bis(4,1-phenylene))dimethanol

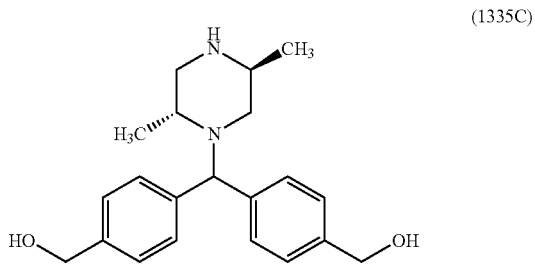 [SMILES: C[C@@H]1CN[C@@H](C)CN1C(c1ccc(CO)cc1)c1ccc(CO)cc1]

(1335C)

To a solution of tert-butyl (2S,5R)-4-(bis(4-(hydroxymethyl)phenyl)methyl)-2,5-dimethylpiperazine-1-carboxylate (0.1 g, 0.23 mmol) in DCM (8 mL) was added HCl in dioxane (0.5 mL, 16.46 mmol, 4 M in dioxane) at room temperature. The reaction mixture was stirred for 1 h. The reaction mixture was concentrated under reduced pressure, triturated with DCM and hexane (1:4) to obtain solid product, which was filtered through a Buchner funnel to obtain (2R,5S)-2,5-dimethylpiperazin-1-yl) methylene)bis(4,1-phenylene))dimethanol hydrochloride (82 mg, 96%). LCMS: m/z=341.2 (M+H); retention time 0.44 min [LCMS method: Column: Ascentis Express C8 (50×2.1 mm) 2.7 μm; Mobile phase A: 10 mM ammonium formate:acetonitrile (98:2), Mobile phase B: 10 mM ammonium formate:acetonitrile (2:98), Gradient=0-100% B over 1.5 minutes, then a 0.6 min hold at 100% B; Temperature: 27° C.; Flow rate: 1.0 mL/min; Detection: UV at 220 nm].

Example 1335: 8-((2S,5R)-4-(bis(4-(hydroxymethyl)phenyl)methyl)-2,5-dimethylpiperazin-1-yl)-5-methyl-6-oxo-5,6-dihydro-1,5-naphthyridine-2-carbonitrile To a stirred solution of ((((2R,5S)-2,5-dimethylpiperazin-1-yl)methylene)bis(4,1-phenylene))dimethanol hydrochloride (0.079 g, 0.21 mmol) in acetonitrile (6 mL) were added DIPEA (0.11 mL, 0.63 mmol) and 6-cyano-1-methyl-2-oxo-1,2-dihydro-1,5-naphthyridin-4-yl trifluoromethanesulfonate (0.07 g, 0.21 mmol) at room temperature. The reaction mixture was heated 85° C. for 16 h. The reaction mixture was filtered through syringe filter and the filtrate was concentrated under reduced pressure to obtain the crude product, which was purified by preparative HPLC (Method Information: Column: Inersil ODS, 250×20 mm ID, 5 μm; Mobile Phase A: 10 mM NH₄OAc in water; Mobile Phase B: Methanol; Gradient: 10-100% B over 25 minutes, then a 5 minute hold at 100% B; Flow: 17 mL/min) to obtain 8-((2S,5R)-4-(bis(4-(hydroxymethyl)phenyl)methyl)-2,5-dimethylpiperazin-1-yl)-5-methyl-6-oxo-5,6-dihydro-1,5-naphthyridine-2-carbonitrile (54 mg, 49.0% yield) as a pale yellow solid. LCMS: m/z=524.2 (M+H); retention time 2.17 min [LCMS method: Column: Ascentis Express C8 (50×2.1 mm) 2.7 μm; Mobile phase A: 10 mM ammonium formate: acetonitrile (98:2), Mobile phase B: 10 mM ammonium formate:acetonitrile (2:98), Gradient=0-100% B over 1.5 minutes, then a 0.6 min hold at 100% B; Temperature: 27° C.; Flow rate: 1.0 mL/min; Detection: UV at 220 nm]. ¹H NMR (400 MHz, DMSO-d₆) δ ppm 8.17-8.10 (m, 1H), 8.09-8.02 (m, 1H), 7.45-7.55 (m, 4H), 7.29-7.20 (m, 4H), 6.01 (s, 1H), 5.11-5.01 (m, 2H), 4.62-4.54 (m, 2H), 4.45-4.38 (m, 4H), 3.75-3.67 (m, 1H), 3.55-3.49 (m, 4H), 3.18-3.09 (m, 1H), 2.90-2.82 (m, 1H), 1.35-1.28 (m, 3H), 1.10-1.01 (m, 3H).

Examples 1336 and 1337

8-((2S,5R)-4-((4-cyanophenyl)(4-fluorophenyl)methyl)-2,5-dimethylpiperazin-1-yl)-6-oxo-5,6-dihydro-1,5-naphthyridine-2-carbonitrile

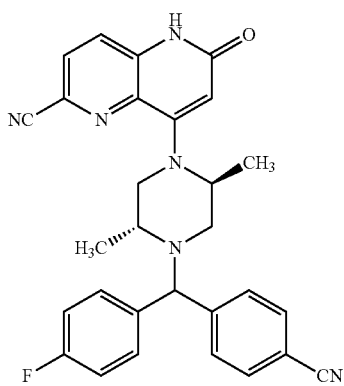

(1336-1337)

Intermediate 1336A: ethyl 6-bromo-3-(N-(4-methoxybenzyl)acetamido)picolinate

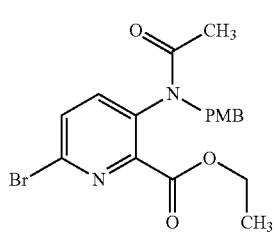

(1336A)

To a solution of ethyl 3-acetamido-6-bromopicolinate (1.0 g, 3.48 mmol) in DMF (15 mL) was added $Cs_2CO_3$ (3.40 g, 10.45 mmol) and 1-(chloromethyl)-4-methoxybenzene (0.705 mL, 6.97 mmol) at room temperature. The reaction mixture was stirred for 16 h. The reaction was quenched with water (100 mL). The reaction mixture was extracted with ethyl acetate (3×100 mL). The combined organic layer was dried over anhydrous sodium sulfate, filtered and evaporated under reduced pressure to obtain the crude product, which was purified by silica gel chromatography (24 g, using 40%-60% ethyl acetate/petroleum ether) to obtain ethyl 6-bromo-3-(N-(4-methoxybenzyl) acetamido) picolinate (1.1 g, 78% yield). LCMS: m/z=409.0 (M+H); retention time 1.53 min [LCMS method: Column-Luna 3.0 C18(2) 100 Å LC column (20×4.0 mm) Mercury MS TM; Mphase A: 10 mM $NH_4OAc$ in water: ACN (98:2); Mphase B: 10 mM $NH_4OAc$ in water:ACN (2:98); Gradient=15-100% B over 2.5 minute, then a 2.6 min hold at 100% B; Flow rate: 1.5 mL/min; Detection: UV at 220 nm].

Intermediate 1336B: 6-bromo-4-hydroxy-1-(4-methoxybenzyl)-1,5-naphthyridin-2(1H)-one

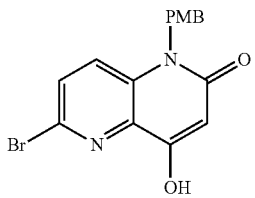

(1336B)

To a stirred solution of ethyl 6-bromo-3-(N-(4-methoxybenzyl)acetamido) picolinate (0.2 g, 0.49 mmol) in tetrahydrofuran (6 mL) was added dropwise KHMDS (1.57 mL, 1.57 mmol, 1M in THF) in THF (3 mL) at −78° C. over 10 min. The reaction mixture was stirred at 0° C. for 1 h. The reaction was quenched with water (15 mL). The mixture was washed with ethyl acetate (2×50 mL). The aqueous layer was collected, acidified with 1.5 N HCl to adjust pH-3.0 and was stirred for 15 min. The crude product obtained was filtered through Buchner funnel to obtain 6-bromo-4-hydroxy-1-(4-methoxybenzyl)-1,5-naphthyridin-2(1H)-one (110 mg, 62.0% yield). LCMS: m/z=361.0 (M+H); retention time 0.99 min [LCMS method: Column-Luna 3.0 C18(2) 100 Å LC column (20×4.0 mm) Mercury MS TM; Mphase A: 10 mM $NH_4OAc$ in water: ACN (98:2); Mphase B: 10 mM $NH_4OAc$ in water:ACN (2:98); Gradient=15-100% B over 2.5 minute, then a 2.6 min hold at 100% B; Flow rate: 1.5 mL/min; Detection: UV at 220 nm].

Intermediate 1336C: 6-bromo-1-(4-methoxybenzyl)-2-oxo-1,2-dihydro-1,5-naphthyridin-4-yl trifluoromethanesulfonate

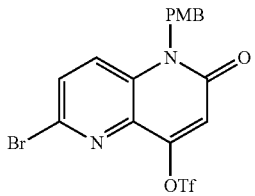

(1336C)

To a solution of 6-bromo-4-hydroxy-1-(4-methoxybenzyl)-1,5-naphthyridin-2(1H)-one (0.3 g, 0.831 mmol) in DCM (6 mL) were added TEA (0.347 mL, 2.492 mmol) and DMAP (10.15 mg, 0.083 mmol) at 0° C., followed by trifluoromethanesulfonic anhydride (0.281 mL, 1.661 mmol). The reaction mixture was stirred at room temperature for 1.5 h. The reaction mixture was then quenched with water (50 mL) and was extracted with DCM (3×50 mL), the combined organic layer was dried over anhydrous sodium sulfate, filtered and evaporated under reduced pressure to obtain (6-bromo-1-(4-methoxybenzyl)-2-oxo-1,2-dihydro-1,5-naphthyridin-4-yl (350 mg, 85% yield). The crude material was taken to the next step without further purification. LCMS: m/z=493.0 (M+2); retention time 2.13 min [LCMS method: Column-Luna 3.0 C18(2) 100 Å LC column (20×4.0 mm) Mercury MS TM; Mphase A: 10 mM $NH_4OAc$ in water:ACN (98:2); Mphase B: 10 mM $NH_4OAc$ in water: ACN (2:98); Gradient=15-100% B over 2.5 minute, then a 2.6 min hold at 100% B; Flow rate: 1.5 mL/min; Detection: UV at 220 nm].

Intermediate 1336D: 4-(((2R,5S)-4-(6-bromo-1-(4-methoxybenzyl)-2-oxo-1,2-dihydro-1,5-naphthyridin-4-yl)-2,5-dimethylpiperazin-1-yl)(4-fluorophenyl)methyl)benzonitrile

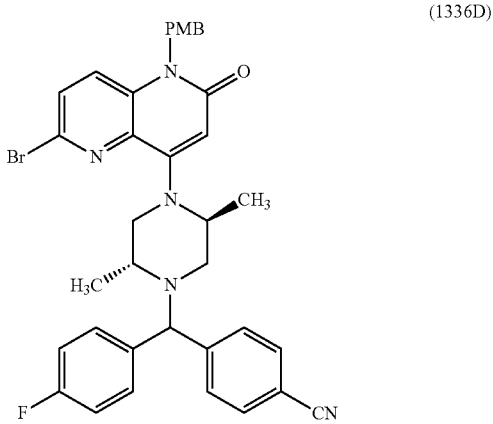

(1336D)

To a solution of 4-(((2R,5S)-2,5-dimethylpiperazin-1-yl)(4-fluorophenyl)methyl) benzonitrile, TFA (310 mg, 0.71 mmol) in acetonitrile (8 mL) was added DIPEA (0.37 mL, 2.13 mmol). The reaction mixture was stirred for 5 min and was added 6-bromo-1-(4-methoxybenzyl)-2-oxo-1,2-dihydro-1,5-naphthyridin-4-yl trifluoromethanesulfonate (350 mg, 0.71 mmol) and heated at 85° C. for 16 h. The reaction mixture was cooled to room temperature, concentrated under reduced pressure to obtain the crude compound, which was purified by silica gel chromatography (24 g, using 34%-40% ethyl acetate/Petroleum ether) to obtain 4-(((2R,5S)-4-(6-bromo-1-(4-methoxybenzyl)-2-oxo-1,2-dihydro-1,5-naphthyridin-4-yl)-2,5-dimethylpiperazin-1-yl)(4-fluorophenyl)methyl) benzonitrile (120 mg, 25.4% yield). LCMS: m/z=666.0 (M+H); retention time 2.62 min [LCMS method: Column-Luna 3.0 C18(2) 100 Å LC column (20×4.0 mm) Mercury MS™; Mphase A: 10 mM NH$_4$OAc in water:acetonitrile (98:2); Mphase B: 10 mM NH$_4$OAc in water:acetonitrile (2:98); Gradient=15-100% B over 2.5 minute, then a 2.6 min hold at 100% B; Flow rate: 1.5 mL/min; Detection: UV at 220 nm].

Intermediate 1336E: 8-((2S,5R)-4-((4-cyanophenyl)(4-fluorophenyl)methyl)-2,5-dimethylpiperazin-1-yl)-5-(4-methoxybenzyl)-6-oxo-5,6-dihydro-1,5-naphthyridine-2-carbonitrile

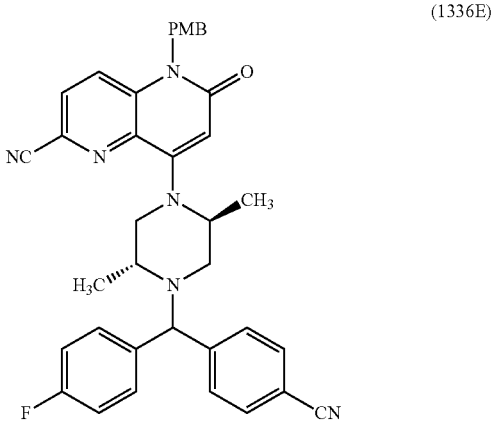

(1336E)

To a solution of 4-(((2R,5S)-4-(6-bromo-1-(4-methoxybenzyl)-2-oxo-1,2-dihydro-1,5-naphthyridin-4-yl)-2,5-dimethylpiperazin-1-yl)(4-fluorophenyl)methyl) benzonitrile (140 mg, 0.21 mmol) in NMP (5 mL) were added zinc (2.8 mg, 0.04 mmol), dppf (7.0 mg, 0.013 mmol) and zinc cyanide (49 mg, 0.42 mmol) at room temperature. The reaction mixture was degassed under N$_2$, Pd$_2$(dba)$_3$ (19 mg, 0.02 mmol) was added, and the reaction mixture was heated at 90° C. for 16 h. The reaction mixture was diluted with water and extracted twice with ethyl acetate (2×20 mL), the combined organic layer was dried over anhydrous Na$_2$SO$_4$ and evaporated under reduced pressure to obtain the crude product, which was purified by silica gel chromatography (24 g, using 10%-50% ethyl acetate/petroleum ether) to obtain 8-((2S,5R)-4-((4-cyanophenyl)(4-fluorophenyl)methyl)-2,5-dimethylpiperazin-1-yl)-5-(4-methoxybenzyl)-6-oxo-5,6-dihydro-1,5-naphthyridine-2-carbonitrile (105 mg, 37% yield). LCMS: m/z=613.2 (M+H); retention time 1.09 min [LCMS method: Column: Waters Acquity UPLC BEH C18 (2.1×50 mm) 1.7 µm, Mobile phase A: 10 mM NH$_4$OAc:acetonitrile (95:5); Mobile phase B: 10 mM NH$_4$OAc:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Examples 1336 and 1337: 8-((2S,5R)-4-((4-cyanophenyl)(4-fluorophenyl)methyl)-2,5-dimethylpiperazin-1-yl)-6-oxo-5,6-dihydro-1,5-naphthyridine-2-carbonitrile To a solution of 8-((2S,5R)-4-((4-cyanophenyl)(4-fluorophenyl)methyl)-2,5-dimethylpiperazin-1-yl)-5-(4-methoxybenzyl)-6-oxo-5,6-dihydro-1,5-naphthyridine-2-carbonitrile (50 mg, 0.082 mmol) in TFA (0.5 mL, 6.49 mmol) was added triflic acid (0.2 mL, 2.252 mmol) at 0° C. The reaction mixture was stirred at room temperature for 4 h. The reaction mixture was poured into a 10% aqueous NaHCO$_3$ solution and extracted twice with dichloromethane (2×20 mL). The combined organic layer was dried over anhydrous Na$_2$SO$_4$, evaporated under reduced pressure to obtain the crude product, which was purified by preparative HPLC (Method Information: Column: Cellulose-4 (150×19) mm-5 µm; Mobile phase A=10 mM ammonium acetate in MeOH; Flow=20 mL/min) to obtain Examples 1336 and 1337.

Example 1336: (9 mg, 22% yield). LCMS: m/z=491.2 (M−H); retention time 2.94 min [LCMS method: Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 min hold at 100% B; Temperature: 27° C.; Flow rate: 1.0 mL/min; Detection: UV at 220 nm. $^1$H NMR (400 MHz, DMSO-d$_6$) δ ppm 11.69-11.44 (m, 1H), 8.01 (d, J=8.5 Hz, 1H), 7.80-7.81 (m, 4H), 7.72 (d, J=8.5 Hz, 1H), 7.64-7.55 (m, 2H), 7.10-7.20 (m, 2H), 5.84 (s, 1H), 4.82 (s, 1H), 4.68-4.53 (m, 1H), 3.78-3.66 (m, 1H), 3.55 (dd, J=3.3, 12.8 Hz, 1H), 3.03 (dd, J=2.8, 5.3 Hz, 1H), 2.85 (dd, J=3.0, 12.0 Hz, 1H), 2.37-2.27 (m, 1H), 1.30 (d, J=6.5 Hz, 3H), 1.06 (d, J=6.5 Hz, 3H).

Example 1337: (8 mg, 19.3% yield). LCMS: m/z=493.2 (M+H); retention time 2.95 min [LCMS method: Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 min hold at 100% B; Temperature: 27° C.; Flowrate: 1.0 mL/min; Detection: UV at 220 nm. $^1$H NMR (400 MHz, DMSO-d$_6$) δ ppm 8.01 (d, J=8.5 Hz, 1H), 7.70-7.82 (m, 5H), 7.60-7.67 (m, 2H), 7.13-7.22 (m, 2H) 5.84 (s, 1H), 4.82 (s, 1H), 4.67-4.56 (m, 1H), 3.78-3.65 (m, 1H), 3.59-3.50 (m, 1H), 3.08-3.01 (m, 1H), 2.85 (dd, J=3.8, 11.8 Hz, 1H), 2.36-2.28 (m, 1H), 1.30 (d, J=6.5 Hz, 3H), 1.06 (d, J=6.5 Hz, 3H).

The examples in Table 57 were prepared according to the general procedures described in Examples 337 and 340 using the appropriate substituted piperazine and halo benzyl/alpha-methyl benzyl/benzhydryl. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 57

| Ex. No. | Structure | M + H | Stereo chem | LCMS RT and Method |
|---|---|---|---|---|
| 1338 | 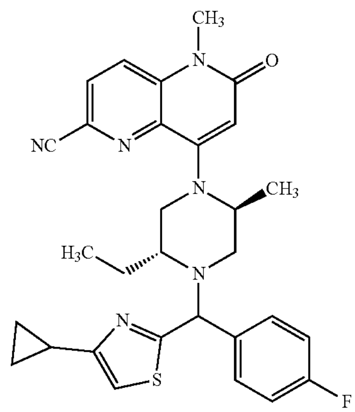 [SMILES: CC[C@@H]1CN(c2cc(=O)n(C)c3ccc(C#N)nc23)[C@@H](C)CN1C(c1ccc(F)cc1)c1nc(C2CC2)cs1] | 543.2 | H | 2.34 A |
| 1339 | 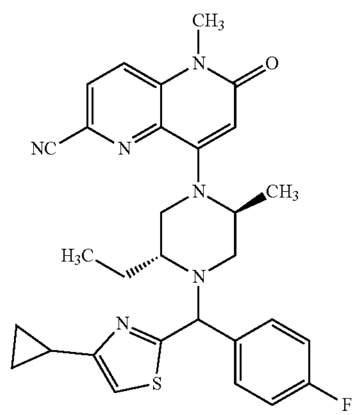 [SMILES: CC[C@@H]1CN(c2cc(=O)n(C)c3ccc(C#N)nc23)[C@@H](C)CN1C(c1ccc(F)cc1)c1nc(C2CC2)cs1] | 543.2 | H | 2.39 A |
| 1340 | 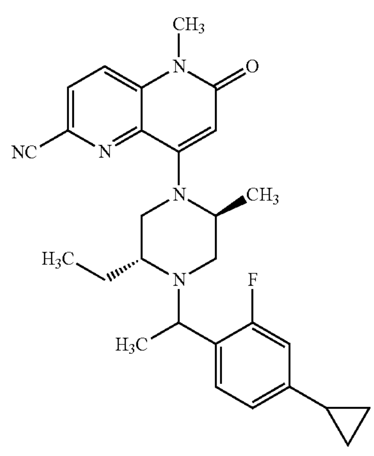 [SMILES: CC[C@@H]1CN(c2cc(=O)n(C)c3ccc(C#N)nc23)[C@@H](C)CN1C(C)c1ccc(C2CC2)cc1F] | 474.3 | H | 2.54 A |

TABLE 57-continued

| Ex. No. | Structure | M + H | Stereo chem | LCMS RT and Method |
|---|---|---|---|---|
| 1341 | 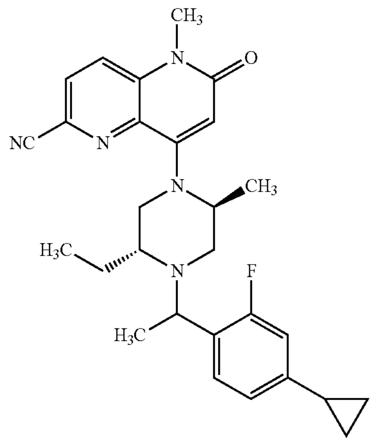 [SMILES: CC[C@@H]1CN(c2cc(=O)n(C)c3ccc(C#N)nc23)[C@@H](C)CN1C(C)c1ccc(C2CC2)cc1F] | 474.3 | H | 2.59 A |
| 1342 | 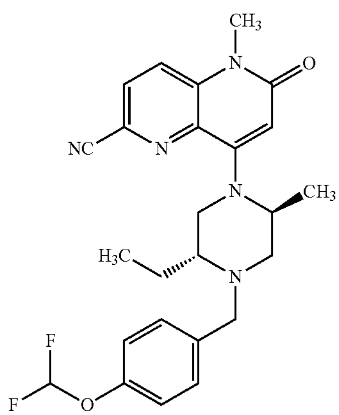 [SMILES: CC[C@@H]1CN(c2cc(=O)n(C)c3ccc(C#N)nc23)[C@@H](C)CN1Cc1ccc(OC(F)F)cc1] | 468.2 | H | 2.184 A |
| 1343 | 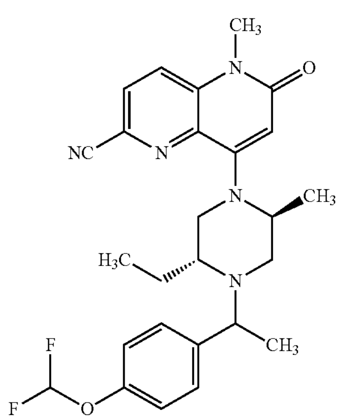 [SMILES: CC[C@@H]1CN(c2cc(=O)n(C)c3ccc(C#N)nc23)[C@@H](C)CN1C(C)c1ccc(OC(F)F)cc1] | 482.3 | H | 2.276 A |

TABLE 57-continued
| Ex. No. | Structure | M + H | Stero chem | LCMS RT and Method |
|---|---|---|---|---|
| 1344 | 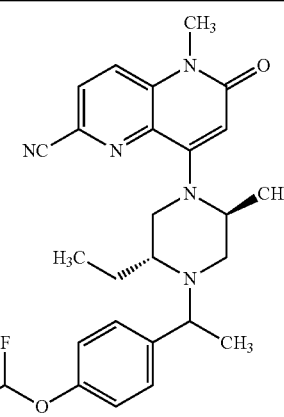 | 482.3 | H | 2.329 A |
| 1345 | 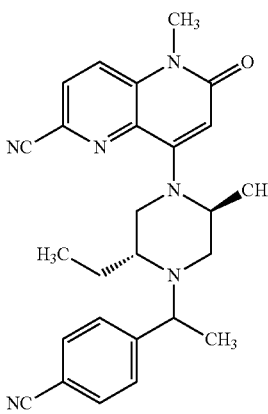 | 441.2 | H | 2.107 A |
| 1346 | 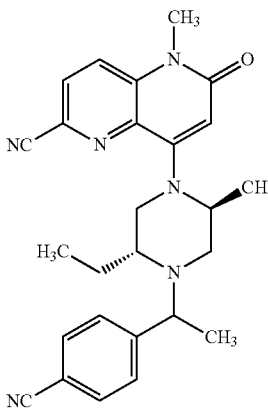 | 441.2 | H | 1.17 B |

TABLE 57-continued

| Ex. No. | Structure | M + H | Stereo chem | LCMS RT and Method |
|---|---|---|---|---|
| 1347 | 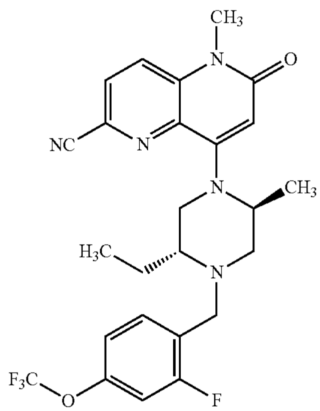 [SMILES: CC[C@@H]1CN(c2cc(=O)n(C)c3ccc(C#N)nc23)[C@@H](C)CN1Cc1ccc(OC(F)(F)F)cc1F] | 504.3 | H | 2.46 A |
| 1348 | 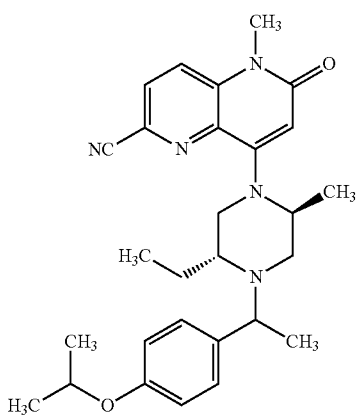 [SMILES: CC[C@@H]1CN(c2cc(=O)n(C)c3ccc(C#N)nc23)[C@@H](C)CN1C(C)c1ccc(OC(C)C)cc1] | 474.3 | H | 2.45 A |
| 1349 | 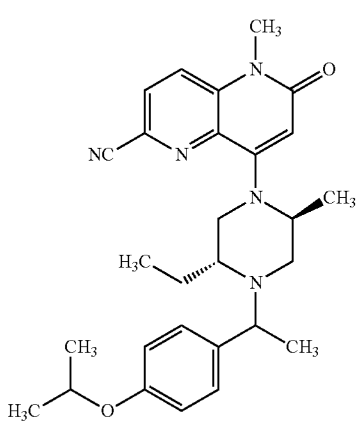 [SMILES: CC[C@@H]1CN(c2cc(=O)n(C)c3ccc(C#N)nc23)[C@@H](C)CN1C(C)c1ccc(OC(C)C)cc1] | 474.3 | H | 2.51 A |

TABLE 57-continued

| Ex. No. | Structure | M + H | Stero chem | LCMS RT and Method |
|---|---|---|---|---|
| 1350 | 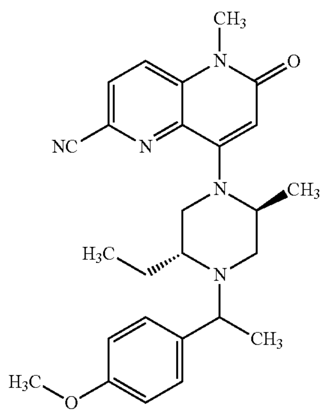 | 446.3 | H | 2.18 A |
| 1351 | 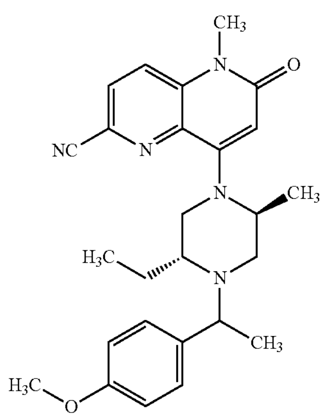 | 446.3 | H | 2.25 A |
| 1352 | 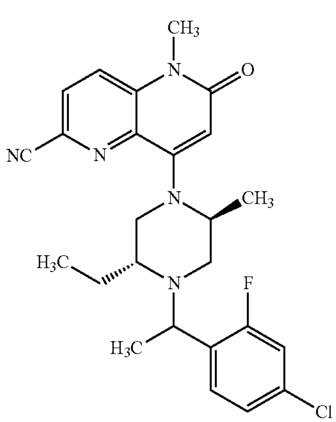 [SMILES: CC[C@@H]1CN(c2cc(=O)n(C)c3ccc(C#N)nc23)[C@@H](C)CN1C(C)c1ccc(Cl)cc1F] | 468.2 | H | 2.53 A |

TABLE 57-continued

| Ex. No. | Structure | M + H | Stereo chem | LCMS RT and Method |
|---|---|---|---|---|
| 1353 | 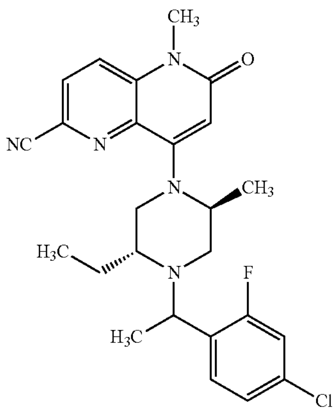 [SMILES: CC[C@@H]1CN(c2cc(=O)n(C)c3ccc(C#N)nc23)[C@@H](C)CN1C(C)c1ccc(Cl)cc1F] | 468.3 | H | 2.57 A |
| 1354 | 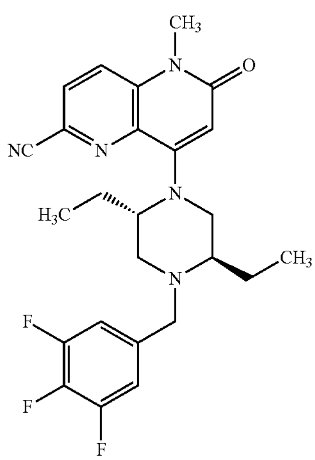 [SMILES: CC[C@@H]1CN(c2cc(=O)n(C)c3ccc(C#N)nc23)[C@@H](CC)CN1Cc1cc(F)c(F)c(F)c1] | 470.1 | H | 2.41 A |
| 1355 | 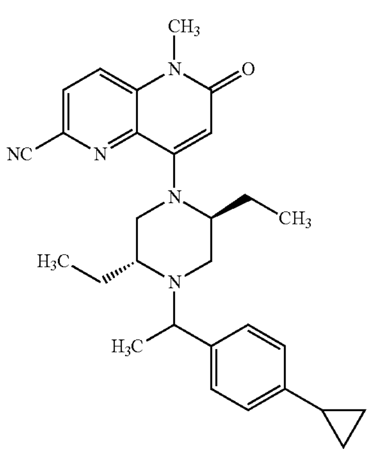 [SMILES: CC[C@H]1CN(C(C)c2ccc(C3CC3)cc2)[C@H](CC)CN1c1cc(=O)n(C)c2ccc(C#N)nc12] | 470.3 | H | 2.66 A |

TABLE 57-continued

| Ex. No. | Structure | M + H | Stereo chem | LCMS RT and Method |
|---|---|---|---|---|
| 1356 | 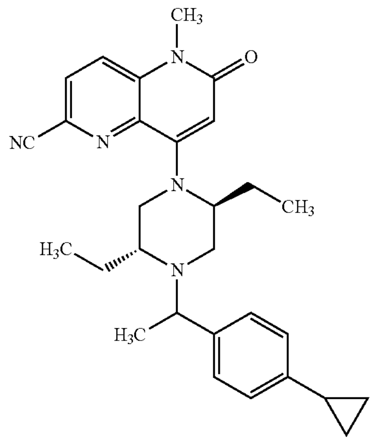 [SMILES: CC[C@H]1CN(C(C)c2ccc(C3CC3)cc2)[C@H](CC)CN1c1cc(=O)n(C)c2ccc(C#N)nc12] | 470.3 | H | 2.67 A |
| 1357 | 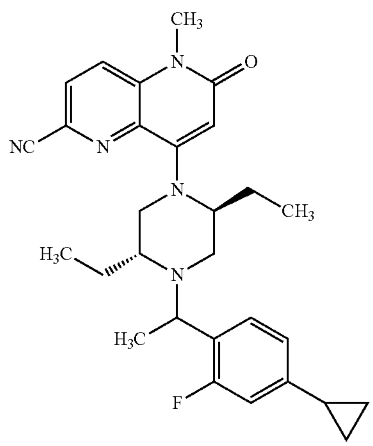 [SMILES: CC[C@H]1CN(C(C)c2ccc(C3CC3)cc2F)[C@H](CC)CN1c1cc(=O)n(C)c2ccc(C#N)nc12] | 488.4 | H | 2.66 A |
| 1358 | 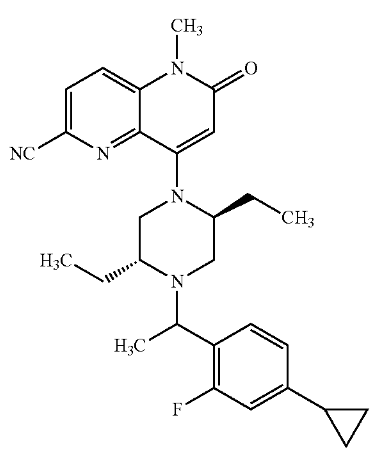 [SMILES: CC[C@H]1CN(C(C)c2ccc(C3CC3)cc2F)[C@H](CC)CN1c1cc(=O)n(C)c2ccc(C#N)nc12] | 488.3 | H | 2.67 A |

TABLE 57-continued
| Ex. No. | Structure | M + H | Stereo chem | LCMS RT and Method |
|---|---|---|---|---|
| 1359 | 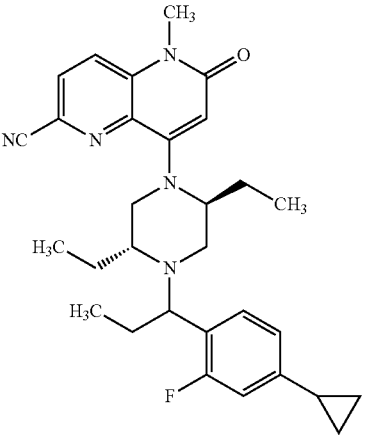 [SMILES: CCC(c1ccc(C2CC2)cc1F)N1C[C@H](CC)N(c2cc(=O)n(C)c3ccc(C#N)nc23)C[C@H]1CC] | 502.4 | H | 2.76 A |
| 1360 | 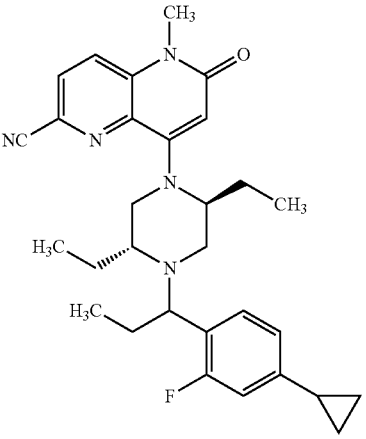 [SMILES: CCC(c1ccc(C2CC2)cc1F)N1C[C@H](CC)N(c2cc(=O)n(C)c3ccc(C#N)nc23)C[C@H]1CC] | 502.3 | H | 2.78 A |
| 1361 | 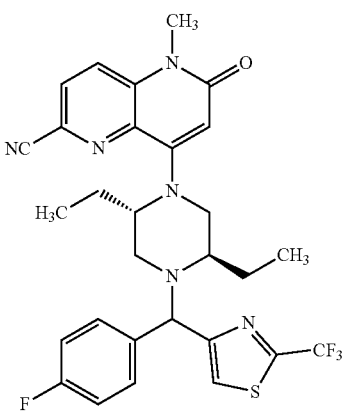 [SMILES: CC[C@H]1CN(C(c2ccc(F)cc2)c2csc(C(F)(F)F)n2)[C@H](CC)CN1c1cc(=O)n(C)c2ccc(C#N)nc12] | 585.2 | H | 2.49 A |

TABLE 57-continued
| Ex. No. | Structure | M + H | Stereo chem | LCMS RT and Method |
|---|---|---|---|---|
| 1362 | 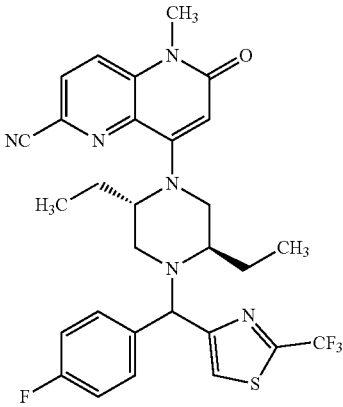 [SMILES: CC[C@H]1CN(C(c2ccc(F)cc2)c2csc(C(F)(F)F)n2)[C@H](CC)CN1c1cc(=O)n(C)c2ccc(C#N)nc12] | 585.2 | H | 2.49 A |
| 1363 | 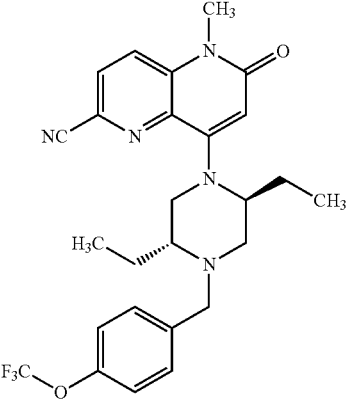 [SMILES: CC[C@@H]1CN(c2cc(=O)n(C)c3ccc(C#N)nc23)[C@@H](CC)CN1Cc1ccc(OC(F)(F)F)cc1] | 500.2 | H | 2.54 A |
| 1364 | 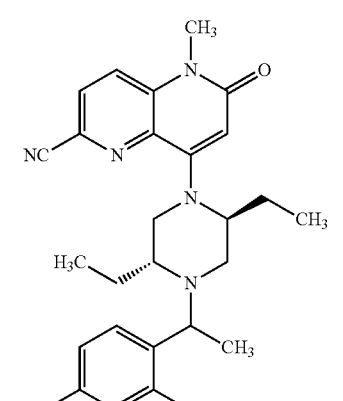 | 516.2 | H | 2.55 A |

TABLE 57-continued
| Ex. No. | Structure | M + H | Stereo chem | LCMS RT and Method |
|---|---|---|---|---|
| 1365 | 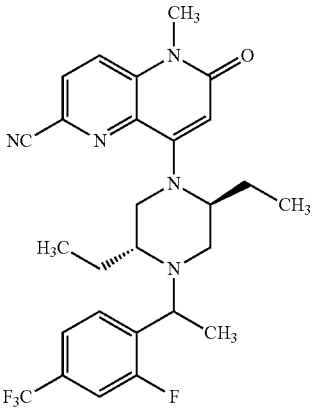 [SMILES: CC[C@H]1CN(C(C)c2ccc(C(F)(F)F)cc2F)[C@H](CC)CN1c1cc(=O)n(C)c2ccc(C#N)nc12] | 516.3 | H | 2.61 A |
| 1366 | 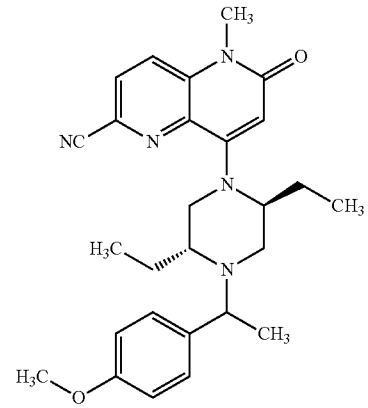 [SMILES: CC[C@H]1CN(C(C)c2ccc(OC)cc2)[C@H](CC)CN1c1cc(=O)n(C)c2ccc(C#N)nc12] | 460.3 | H | 2.37 A |
| 1367 | 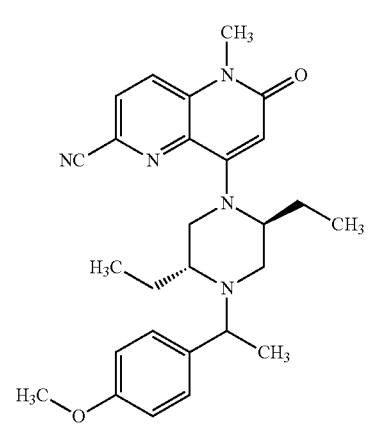 | 460.4 | H | 2.36 A |

TABLE 57-continued

| Ex. No. | Structure | M + H | Stereo chem | LCMS RT and Method |
|---------|-----------|-------|-------------|--------------------|
| 1368 | 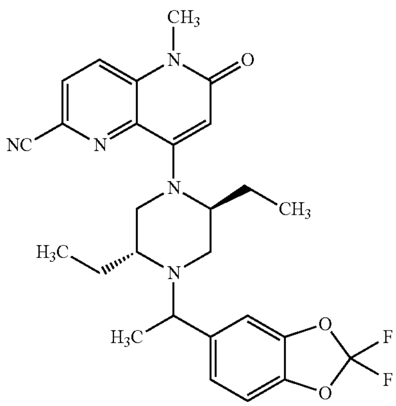 [SMILES: CC[C@H]1CN(C(C)c2ccc3c(c2)OC(F)(F)O3)[C@H](CC)CN1c1cc(=O)n(C)c2ccc(C#N)nc12] | 510.3 | H | 2.60 A |
| 1369 | 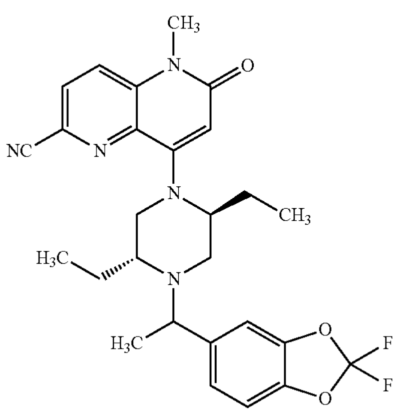 [SMILES: CC[C@H]1CN(C(C)c2ccc3c(c2)OC(F)(F)O3)[C@H](CC)CN1c1cc(=O)n(C)c2ccc(C#N)nc12] | 510.3 | H | 2.61 A |
| 1370 | 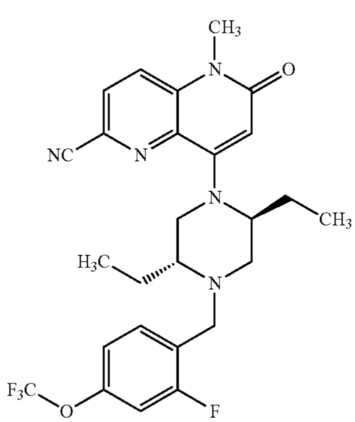 [SMILES: CC[C@@H]1CN(c2cc(=O)n(C)c3ccc(C#N)nc23)[C@@H](CC)CN1Cc1ccc(OC(F)(F)F)cc1F] | 518.3 | H | 2.57 A |

TABLE 57-continued
| Ex. No. | Structure | M + H | Stereo chem | LCMS RT and Method |
|---|---|---|---|---|
| 1371 | 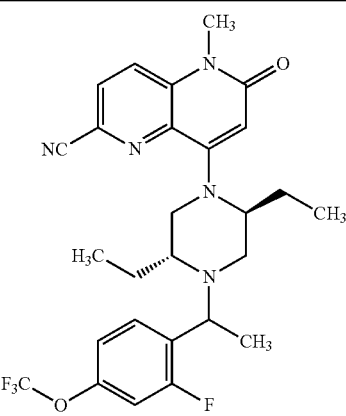 | 532.2 | H | 2.64 A |
| 1372 | 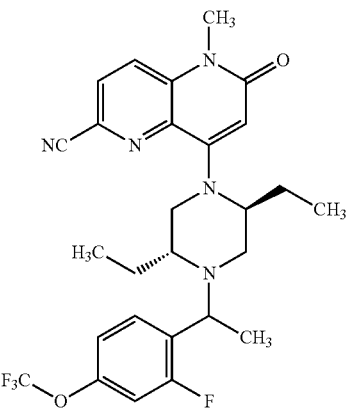 [SMILES: CC[C@H]1CN(C(C)c2ccc(OC(F)(F)F)cc2F)[C@H](CC)CN1c1cc(=O)n(C)c2ccc(C#N)nc12] | 532.2 | H | 2.66 A |
| 1373 | 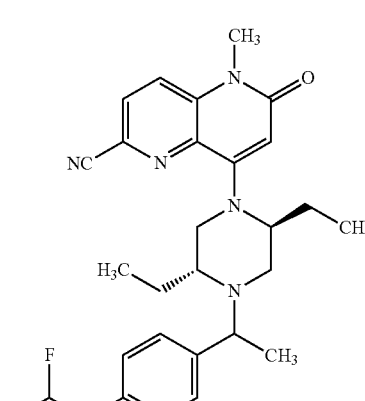 | 496.2 | H | 2.39 A |

TABLE 57-continued

| Ex. No. | Structure | M + H | Stereo chem | LCMS RT and Method |
|---|---|---|---|---|
| 1374 | 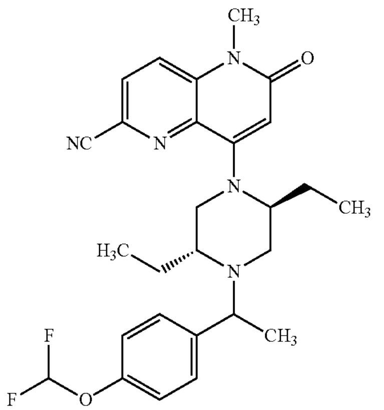 [SMILES: CC[C@H]1CN(C(C)c2ccc(OC(F)F)cc2)[C@H](CC)CN1c1cc(=O)n(C)c2ccc(C#N)nc12] | 496.2 | H | 2.40 A |
| 1375 | 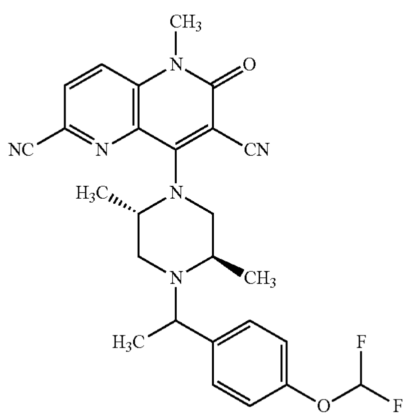 [SMILES: CC(c1ccc(OC(F)F)cc1)N1C[C@H](C)N(c2c(C#N)c(=O)n(C)c3ccc(C#N)nc23)C[C@H]1C] | 493.2 | H | 2.21 A |
| 1376 | 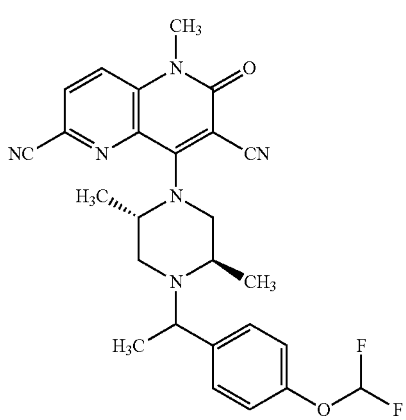 [SMILES: CC(c1ccc(OC(F)F)cc1)N1C[C@H](C)N(c2c(C#N)c(=O)n(C)c3ccc(C#N)nc23)C[C@H]1C] | 493.2 | H | 2.2 A |

TABLE 57-continued

| Ex. No. | Structure | M + H | Stero chem | LCMS RT and Method |
|---|---|---|---|---|
| 1377 | 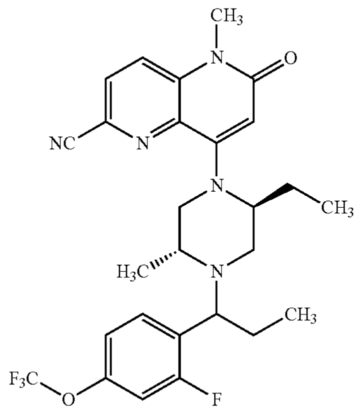 [SMILES: CCC(c1ccc(OC(F)(F)F)cc1F)N1C[C@H](CC)N(c2cc(=O)n(C)c3ccc(C#N)nc23)C[C@H]1C] | 532.2 | H | 2.74 A |
| 1378 | 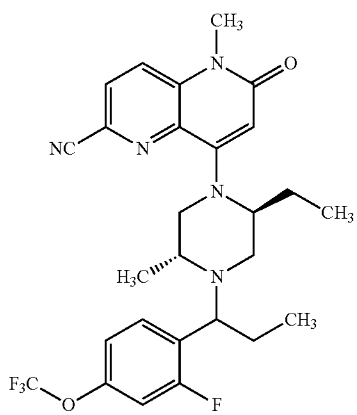 [SMILES: CCC(c1ccc(OC(F)(F)F)cc1F)N1C[C@H](CC)N(c2cc(=O)n(C)c3ccc(C#N)nc23)C[C@H]1C] | 532.2 | H | 2.73 A |
| 1379 | 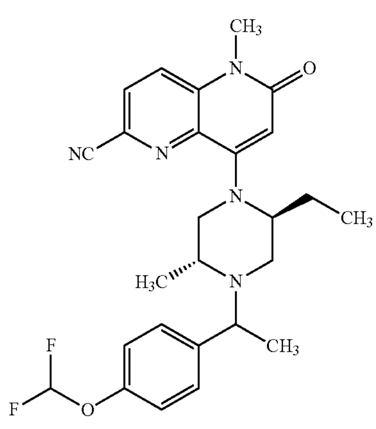 [SMILES: CC[C@H]1CN(C(C)c2ccc(OC(F)F)cc2)[C@H](C)CN1c1cc(=O)n(C)c2ccc(C#N)nc12] | 482.2 | H | 2.31 A |

TABLE 57-continued

| Ex. No. | Structure | M + H | Stero chem | LCMS RT and Method |
|---|---|---|---|---|
| 1380 | 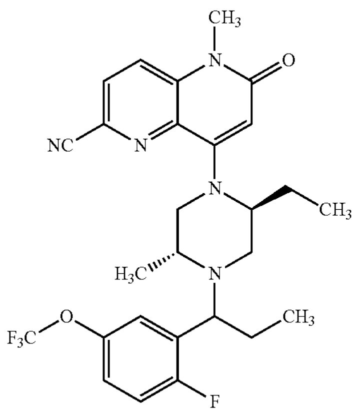 [SMILES: CCC(c1cc(OC(F)(F)F)ccc1F)N1C[C@H](CC)N(c2cc(=O)n(C)c3ccc(C#N)nc23)C[C@H]1C] | 532.2 | H | 2.62 A |
| 1381 | 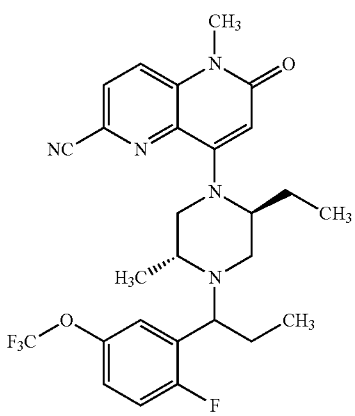 [SMILES: CCC(c1cc(OC(F)(F)F)ccc1F)N1C[C@H](CC)N(c2cc(=O)n(C)c3ccc(C#N)nc23)C[C@H]1C] | 532.2 | H | 2.61 A |
| 1382 | 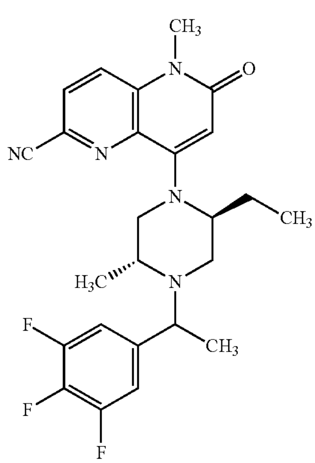 [SMILES: CC[C@H]1CN(C(C)c2cc(F)c(F)c(F)c2)[C@H](C)CN1c1cc(=O)n(C)c2ccc(C#N)nc12] | 470.2 | H | 2.43 A |

TABLE 57-continued

| Ex. No. | Structure | M + H | Stereo chem | LCMS RT and Method |
|---|---|---|---|---|
| 1383 | (structure) | 470.2 | H | 2.42 A |
| 1384 | (structure) | 518.3 | H | 2.57 A |
| 1385 | (structure) | 518.3 | H | 2.57 A |

The examples in Table 58 were prepared according to the general method described for Intermediate 1155D, using appropriate benzyl bromides/chlorides. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 58
| Ex. No. | Structure | M + H | Stereo chem | LCMS RT and Method |
|---|---|---|---|---|
| 1386 | 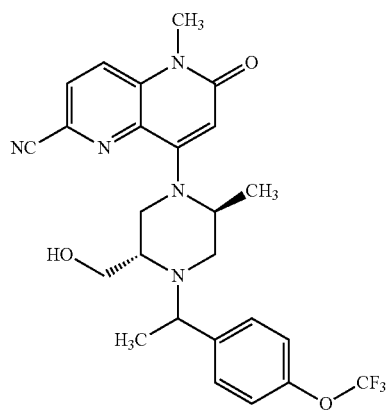 [SMILES: CC(c1ccc(OC(F)(F)F)cc1)N1C[C@H](C)N(c2cc(=O)n(C)c3ccc(C#N)nc23)C[C@H]1CO] | 502.2 | H | 2.08 A |
| 1387 | 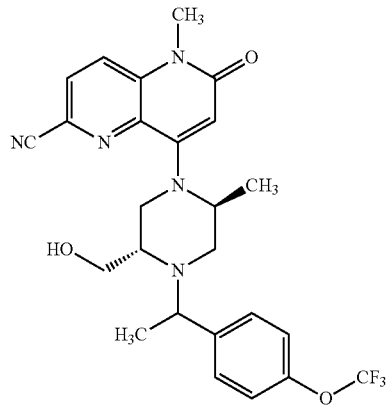 [SMILES: CC(c1ccc(OC(F)(F)F)cc1)N1C[C@H](C)N(c2cc(=O)n(C)c3ccc(C#N)nc23)C[C@H]1CO] | 502.2 | H | 2.08 A |
| 1388 | 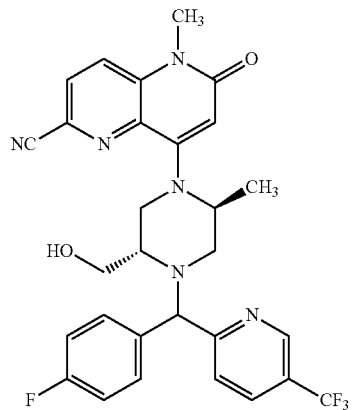 [SMILES: C[C@H]1CN(C(c2ccc(F)cc2)c2ccc(C(F)(F)F)cn2)[C@H](CO)CN1c1cc(=O)n(C)c2ccc(C#N)nc12] | 567.2 | H | 2.02 A |

TABLE 58-continued
| Ex. No. Structure | M + H | Stereo chem | LCMS RT and Method |
|---|---|---|---|
| 1389 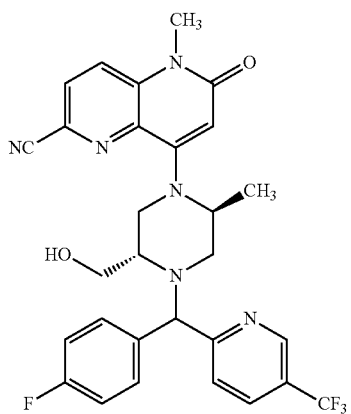 [SMILES: C[C@H]1CN(C(c2ccc(F)cc2)c2ccc(C(F)(F)F)cn2)[C@H](CO)CN1c1cc(=O)n(C)c2ccc(C#N)nc12] | 567.2 | H | 2.00 A |
| 1390 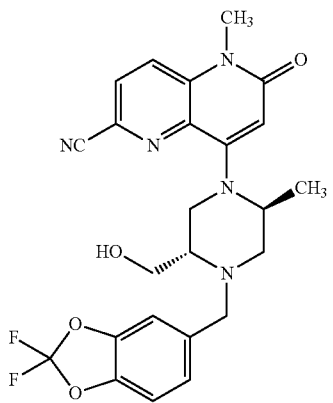 [SMILES: C[C@H]1CN(Cc2ccc3c(c2)OC(F)(F)O3)[C@H](CO)CN1c1cc(=O)n(C)c2ccc(C#N)nc12] | 484.1 | H | 1.94 A |
| 1391 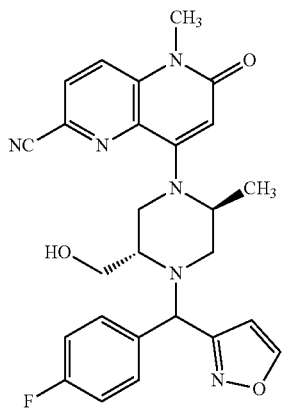 [SMILES: C[C@H]1CN(C(c2ccc(F)cc2)c2ccon2)[C@H](CO)CN1c1cc(=O)n(C)c2ccc(C#N)nc12] | 489.3 | H | 1.62 A |

TABLE 58-continued

| Ex. No. | Structure | M + H | Stereo chem | LCMS RT and Method |
|---|---|---|---|---|
| 1392 | 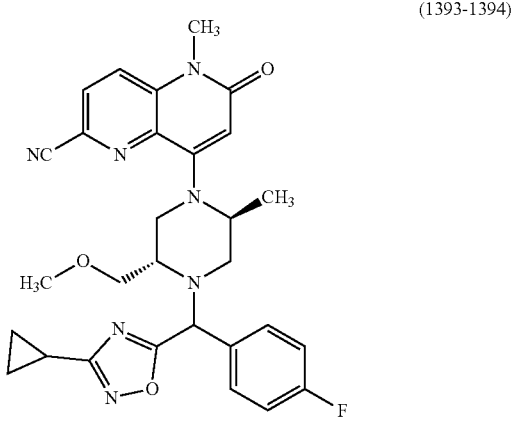 [SMILES: COC[C@@H]1CN(c2cc(=O)n(C)c3ccc(C#N)nc23)[C@@H](C)CN1C(c1ccc(F)cc1)c1nc(C2CC2)no1] | 489.3 | H | 1.69 A |

Examples 1393 and 1394

8-((2S,5S)-4-((3-cyclopropyl-1,2,4-oxadiazol-5-yl) (4-fluorophenyl)methyl)-5-(methoxymethyl)-2-methylpiperazin-1-yl)-5-methyl-6-oxo-5,6-dihydro-1,5-naphthyridine-2-carbonitrile (1393-1394)

Intermediate 1393A: tert-butyl (2S,5S)-4-(2-ethoxy-1-(4-fluorophenyl)-2-oxoethyl)-5-(hydroxymethyl)-2-methylpiperazine-1-carboxylate

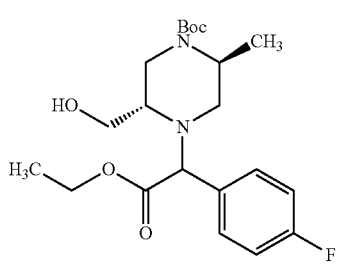

(1393A)

To a solution of tert-butyl (2S,5S)-5-(hydroxymethyl)-2-methylpiperazine-1-carboxylate (500 mg, 2.17 mmol) in dry acetonitrile (10 mL), ethyl 2-bromo-2-(4-fluorophenyl)acetate (624 mg, 2.39 mmol) and DIPEA (1.14 mL, 6.51 mmol) were added at room temperature. The reaction mixture was heated to 85° C. for 16 h. The reaction mixture was cooled to room temperature and concentrated under reduced pressure to obtain the crude product, which was purified by 24 g silica gel chromatography by using 0-10% MeOH/CHCl₃ as eluent to obtain tert-butyl (2S,5S)-4-(2-ethoxy-1-(4-fluorophenyl)-2-oxoethyl)-5-(hydroxymethyl)-2-methylpiperazine-1-carboxylate (755 mg, 85% yield). LCMS: m/z, 412.3 (M+H); retention time 1.97 and 2.01 min. LC-MS Method: Column-AQUITY UPLC BEH C18 (3.0×50 mm) 1.7 μm; Mobile phase A: 10 mM ammonium acetate in water:acetonitrile (98:2); Mobile phase B: 10 mM ammonium acetate in water:acetonitrile (2:98); Gradient: 20%-100% B over 2 minutes, then a 0.2 minute hold at 100% B, flow rate 0.7 mL/min.

Intermediate 1393B: 2-((2S,5S)-4-(tert-butoxycarbonyl)-2-(methoxymethyl)-5-methylpiperazin-1-yl)-2-(4-fluorophenyl)acetic acid

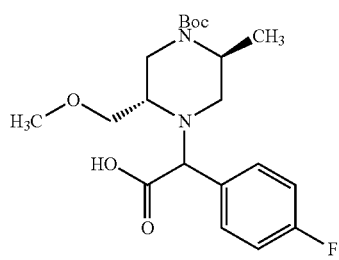

(1393B)

To a stirred suspension of NaH (48.7 mg, 1.22 mmol, 60% w/w) in DMF (5.0 mL) was added tert-butyl (2S,5S)-4-(2-ethoxy-1-(4-fluorophenyl)-2-oxoethyl)-5-(hydroxymethyl)-2-methylpiperazine-1-carboxylate (250 mg, 0.61 mmol) at 0° C. After 30 minutes, MeI (0.08 mL, 1.22 mmol) was added. The reaction mixture was stirred for 16 h at room temperature. The reaction was quenched with ice water (10 mL). The reaction mixture was extracted in ethyl acetate (100 mL), organic layer separated, dried over anhydrous Na$_2$SO$_4$ and evaporated under reduced pressure to obtain the sodium salt of 2-((2S,5S)-4-(tert-butoxycarbonyl)-2-(methoxymethyl)-5-methylpiperazin-1-yl)-2-(4-fluorophenyl) acetic acid (220 mg, 85% yield). LCMS: m/z, 397.2 (M+H); retention time 0.33 min. LC-MS Method: Column-AQUITY UPLC BEH C18 (3.0×50 mm) 1.7 µm; Mobile phase A: 10 mM ammonium acetate in water:acetonitrile (98:2); Mobile phase B: 10 mM ammonium acetate in water:acetonitrile (2:98); Gradient: 20%-100% B over 2 minutes, then a 0.2 minute hold at 100% B, flow rate 0.7 mL/min.

Intermediate 1393C: tert-butyl (2S,5S)-4-((3-cyclopropyl-1,2,4-oxadiazol-5-yl)(4-fluorophenyl)methyl)-5-(methoxymethyl)-2-methylpiperazine-1-carboxylate

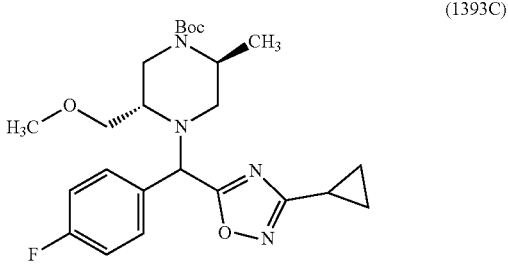 [SMILES: COC[C@@H]1CN(C(=O)OC(C)(C)C)[C@@H](C)CN1C(c1ccc(F)cc1)c1nc(C2CC2)no1]

(1393C)

To a stirred solution of 2-((2S,5S)-4-(tert-butoxycarbonyl)-2-(methoxymethyl)-5-methylpiperazin-1-yl)-2-(4-fluorophenyl)acetic acid (200 mg, 0.5 mmol), (Z)—N'-hydroxycyclopropane carboximidamide (101 mg, 1.01 mmol) in DMF (8.0 mL), BOP (335 mg, 0.76 mmol) and triethyl amine (0.21 mL, 1.51 mmol) were added at room temperature. The reaction mixture was stirred for 2 h at room temperature and heated 110° C. for 16 h. The reaction mixture cooled to room temperature and concentrated under reduced pressure to yield crude compound, which was purified by using 12 g silica gel flash chromatography using 0-100% ethyl acetate/petroleum ether), the fractions containing the product were concentrated under reduced pressure to yield tert-butyl (2S,5S)-4-((3-cyclopropyl-1,2,4-oxadiazol-5-yl)(4-fluorophenyl)methyl)-5-(methoxymethyl)-2-methylpiperazine-1-carboxylate (155 mg, 67% yield). LCMS: m/z, 461.2 (M+H); retention time 1.30 min. LC-MS Method: Column-AQUITY UPLC BEH C18 (3.0×50 mm) 1.7 µm; Mobile phase A: 10 mM ammonium acetate in water: acetonitrile (98:2); Mobile phase B: 10 mM ammonium acetate in water:acetonitrile (2:98); Gradient: 20%-100% B over 2 minutes, then a 0.2 minute hold at 100% B, flow rate 0.7 mL/min.

Intermediate 1393D: 3-cyclopropyl-5-((4-fluorophenyl)((2S,5S)-2-(methoxymethyl)-5-methylpiperazin-1-yl)methyl)-1,2,4-oxadiazole, TFA

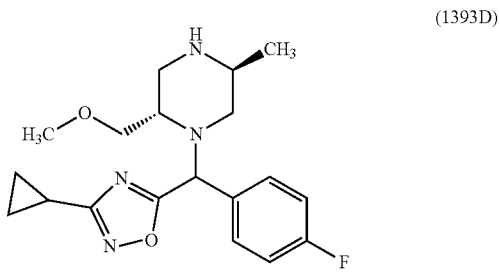 [SMILES: COC[C@@H]1CN[C@@H](C)CN1C(c1ccc(F)cc1)c1nc(C2CC2)no1]

(1393D)

To a stirred solution of tert-butyl (2S,5S)-4-((3-cyclopropyl-1,2,4-oxadiazol-5-yl) (4-fluorophenyl)methyl)-5-(methoxymethyl)-2-methylpiperazine-1-carboxylate (110 mg, 0.24 mmol) in DCM (3 mL) was added TFA (0.3 mL, 3.89 mmol). The mixture was stirred at room temperature for 4 h. The solvent was removed under reduced pressure to yield the TFA salt of 3-cyclopropyl-5-((4-fluorophenyl)((2S, 5S)-2-(methoxymethyl)-5-methylpiperazin-1-yl)methyl)-1, 2,4-oxadiazole (85 mg, 75% yield). LCMS: m/z, 361.2 (M+H); retention time 1.21 and 1.28 min. LC-MS Method: Column-AQUITY UPLC BEH C18 (3.0×50 mm) 1.7 µm; Mobile phase A: 10 mM ammonium acetate in water: acetonitrile (98:2); Mobile phase B: 10 mM ammonium acetate in water:acetonitrile (2:98); Gradient: 20%-100% B over 2 minutes, then a 0.2 minute hold at 100% B, flow rate 0.7 mL/min.

Examples 1393 and 1394: 8-((2S,5S)-4-((3-cyclopropyl-1,2,4-oxadiazol-5-yl)(4-fluorophenyl)methyl)-5-(methoxymethyl)-2-methylpiperazin-1-yl)-5-methyl-6-oxo-5,6-dihydro-1,5-naphthyridine-2-carbonitrile To a stirred solution of 3-cyclopropyl-5-((4-fluorophenyl)((2S,5S)-2-(methoxymethyl)-5-methylpiperazin-1-yl) methyl)-1,2,4-oxadiazole (70 mg, 0.19 mmol) in acetonitrile (8 mL), 6-cyano-1-methyl-2-oxo-1,2-dihydro-1,5-naphthyridin-4-yl trifluoromethanesulfonate (64.7 mg, 0.19 mmol) and DIPEA (0.1 mL, 0.58 mmol) were added at room temperature. The reaction mixture was heated at 85° C. for 16 h. The reaction mixture cooled to room temperature and evaporated under reduced pressure to yield the crude product, which was purified by preparative HPLC followed by chiral HPLC (Chiral HPLC Method: Column: Cellulose-2 (250×4.6 mm) 5 µm, Mobile phase: 0.1% DEA in MeOH: acetonitrile (50:50), Flow: 1.0 mL/min) to afford Examples 1393 and 1394.

Example 1393: (4.2 mg, 4.0% yield): LCMS: m/z, 544.3 (M+H); retention time 2.11 min; LCMS method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.19-8.13 (m, 1H), 8.11-8.02 (m, 1H), 7.64-7.51 (m, 2H), 7.30-7.17 (m, 2H), 6.07 (s, 1H), 5.50 (s, 1H), 4.54-4.40 (m, 1H), 3.86-3.71 (m, 2H), 3.63-3.48 (m, 5H), 3.11 (s, 3H), 3.03-2.94 (m, 1H), 2.87 (dd, J=3.5, 11.6 Hz, 1H), 2.37 (dd, J=3.5, 11.6 Hz, 1H), 2.18-2.10 (m, 1H), 1.14-1.05 (m, 5H), 0.95-0.81 (m, 2H).

Example 1394: (5.0 mg, 4.6% yield): LCMS: m/z, 544.3 (M+H); retention time 2.11 min; LCMS method: Column: XBridge BEH XP C18 (50×2.1) mm, 2.5 μm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.20-8.12 (m, 1H), 8.10-7.98 (m, 1H), 7.56-7.44 (m, 2H), 7.29-7.15 (m, 2H), 6.03 (s, 1H), 5.58 (s, 1H), 4.57-4.44 (m, 1H), 3.77 (br d, J=11.2 Hz, 1H), 3.63 (dd, J=6.1, 9.8 Hz, 1H), 3.56-3.45 (m, 5H), 3.25 (dd, J=3.4, 11.7 Hz, 1H), 3.15-3.08 (m, 1H), 3.00 (s, 3H), 2.29 (dd, J=2.4, 11.7 Hz, 1H), 2.18-2.10 (m, 1H), 1.14 (d, J=6.4 Hz, 3H), 1.07 (dd, J=2.0, 8.3 Hz, 2H), 0.94-0.80 (m, 2H).

The examples in Table 59 were prepared according to the general procedures described in Examples 1393 and 1394, using the appropriate benzyl bromides/chlorides. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 59

| Ex. No. | Structure | M + H | Stereochem | LCMS RT and Method |
|---|---|---|---|---|
| 1395 | 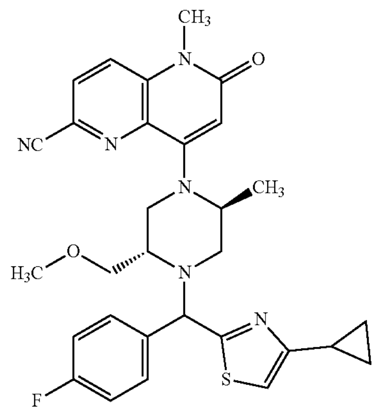 [SMILES: COC[C@@H]1CN(c2cc(=O)n(C)c3ccc(C#N)nc23)[C@@H](C)CN1C(c1ccc(F)cc1)c1nc(C2CC2)cs1] | 559.2 | H | 2.2 A |
| 1396 | 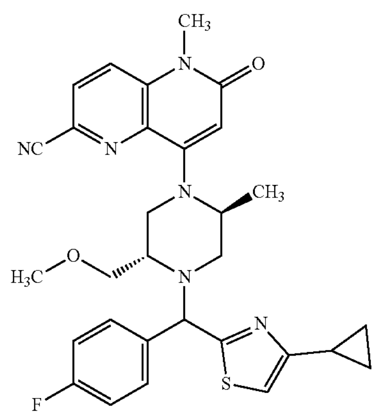 [SMILES: COC[C@@H]1CN(c2cc(=O)n(C)c3ccc(C#N)nc23)[C@@H](C)CN1C(c1ccc(F)cc1)c1nc(C2CC2)cs1] | 559.2 | H | 2.24 A |
| 1397 | 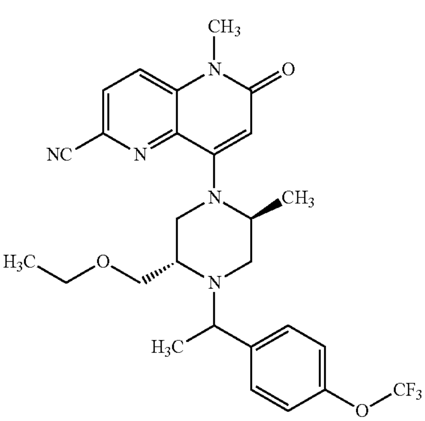 [SMILES: CCOC[C@@H]1CN(c2cc(=O)n(C)c3ccc(C#N)nc23)[C@@H](C)CN1C(C)c1ccc(OC(F)(F)F)cc1] | 530.2 | H | 2.46 A |

TABLE 59-continued
| Ex. No. | Structure | M + H | Stereo chem | LCMS RT and Method |
|---|---|---|---|---|
| 1398 | 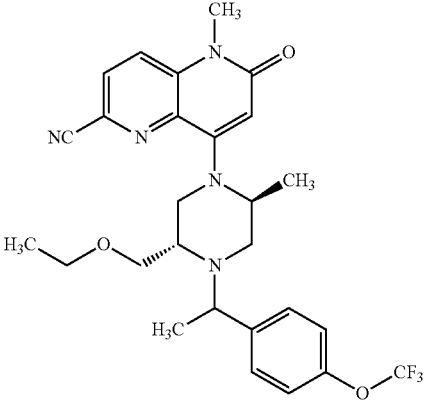 [SMILES: CCOC[C@@H]1CN(c2cc(=O)n(C)c3ccc(C#N)nc23)[C@@H](C)CN1C(C)c1ccc(OC(F)(F)F)cc1] | 530.3 | H | 2.47 A |
| 1399 | 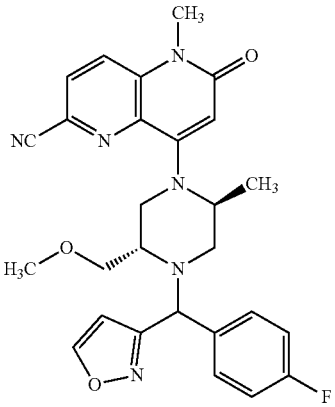 [SMILES: COC[C@@H]1CN(c2cc(=O)n(C)c3ccc(C#N)nc23)[C@@H](C)CN1C(c1ccc(F)cc1)c1ccon1] | 503.3 | H | 1.9 A |
| 1400 | 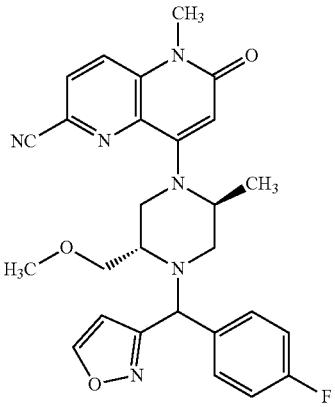 [SMILES: COC[C@@H]1CN(c2cc(=O)n(C)c3ccc(C#N)nc23)[C@@H](C)CN1C(c1ccc(F)cc1)c1ccon1] | 503.3 | H | 1.87 A |

TABLE 59-continued
| Ex. No. Structure | M + H | Stereo chem | LCMS RT and Method |
|---|---|---|---|
| 1401 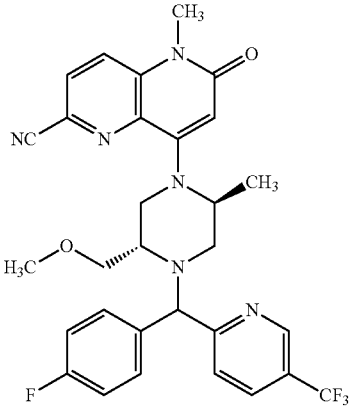 [SMILES: COC[C@@H]1CN(c2cc(=O)n(C)c3ccc(C#N)nc23)[C@@H](C)CN1C(c1ccc(F)cc1)c1ccc(C(F)(F)F)cn1] | 581.3 | H | 2.21 A |
| 1402 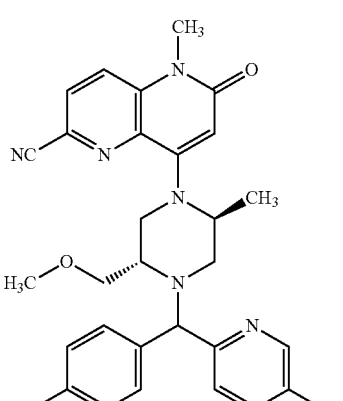 | 581.3 | H | 2.22 A |
| 1403 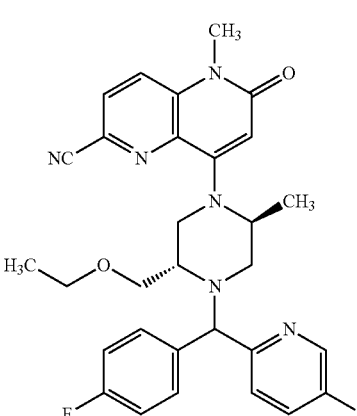 | 595.3 | H | 2.3 A |

TABLE 59-continued

| Ex. No. | Structure | M + H | Stereo chem | LCMS RT and Method |
|---|---|---|---|---|
| 1404 | 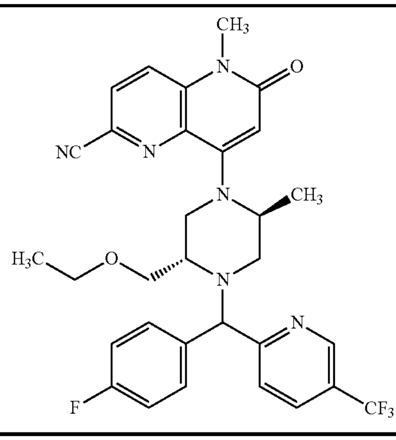 | 595.2 | H | 2.31 A |

Examples 1405 and 1406

8-((2S,5S)-5-((2-methoxyethoxy)methyl)-2-methyl-4-(1-(4-(trifluoromethoxy)phenyl) ethyl)piperazin-1-yl)-5-methyl-6-oxo-5,6-dihydro-1,5-naphthyridine-2-carbonitrile (1405-1406)

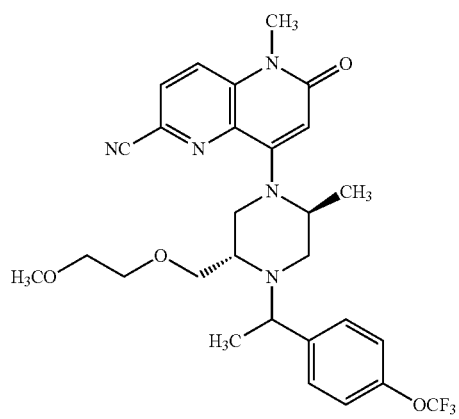

Intermediate 1405A: tert-butyl (2S,5S)-5-((2-methoxyethoxy)methyl)-2-methyl-4-(1-(4-(trifluoromethoxy)phenyl)ethyl)piperazine-1-carboxylate To a solution of tert-butyl (2S,5S)-5-(hydroxymethyl)-2-methyl-4-(1-(4-(trifluoromethoxy)phenyl)ethyl)piperazine-1-carboxylate (200 mg, 0.48 mmol) in THF (8 mL) was added NaH (57 mg, 1.43 mmol, 60% w/w) at 0° C. After 5 min., 1-bromo-2-methoxyethane (75 mg, 0.53 mmol) was added. The reaction mixture was stirred at room temperature for 2 h. The reaction mixture was cooled to 0° C., quenched with ice cold water and extracted with EtOAc (2×50 mL). The combined organic extracts were washed with brine, dried over anhydrous $Na_2SO_4$ and concentrated to obtain the crude product, which was purified by silica gel flash column chromatography (5-10% MeOH in DCM; 12 g column) to afford the diastereomeric mixture of tert-butyl (2S,5S)-5-((2-methoxyethoxy)methyl)-2-methyl-4-(1-(4-(trifluoromethoxy)phenyl)ethyl)piperazine-1-carboxylate (100 mg, 44% yield). LCMS: m/z, 477.8 (M+H); retention time 1.53 and 1.55 min. [LCMS Method: Column: AQUITY UPLC BEH C18 (3.0×50 mm) 1.7 μm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100, Temperature: 27° C.; Flow rate: 0.7 mL/min; Detection: UV at 220 nm].

Intermediate 1405B: (2S,5S)-2-((2-methoxyethoxy)methyl)-5-methyl-1-(1-(4-(trifluoromethoxy)phenyl)ethyl)piperazine.HCl

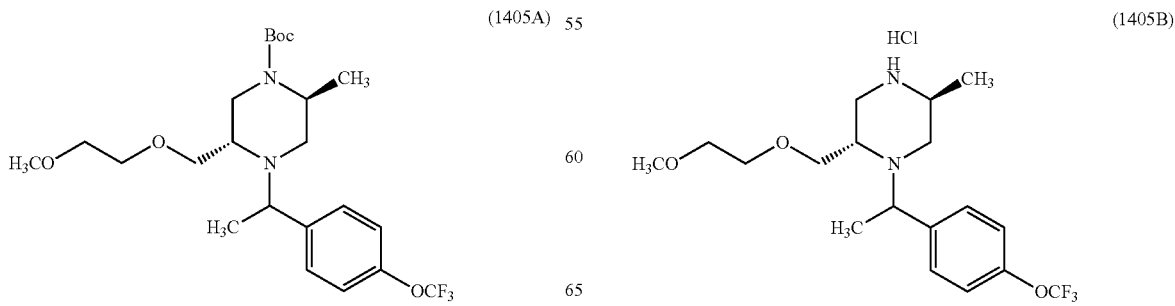

To a solution of tert-butyl (2S,5S)-5-((2-methoxyethoxy)methyl)-2-methyl-4-(1-(4-(trifluoromethoxy)phenyl)ethyl)piperazine-1-carboxylate (100 mg, 0.21 mmol) in DCM (6 mL) was added 4 N HCl in dioxane (0.3 mL, 1.05 mmol) at 0° C. The reaction mixture was stirred at room temperature for 2 h. The reaction mixture was concentrated under reduced pressure to obtain the diastereomeric mixture of (2S,5S)-2-((2-methoxyethoxy)methyl)-5-methyl-1-(1-(4-(trifluoromethoxy)phenyl)ethyl)piperizine hydrochloride (65 mg, 76% yield). LCMS: m/z, 377.2 (M+H); retention time 1.27 and 1.36 min. [LCMS Method: Column: AQUITY UPLC BEH C18 (3.0×50 mm) 1.7 μm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100, Temperature: 27° C.; Flow rate: 0.7 mL/min; Detection: UV at 220 nm].

Examples 1405 and 1406: 8-((2S,5S)-5-((2-methoxyethoxy)methyl)-2-methyl-4-(1-(4-(trifluoromethoxy)phenyl)ethyl)piperazin-1-yl)-5-methyl-6-oxo-5,6-dihydro-1,5-naphthyridine-2-carbonitrile To a solution of (2S,5S)-2-((2-methoxyethoxy)methyl)-5-methyl-1-(1-(4-(trifluoromethoxy)phenyl)ethyl)piperizine hydrochloride (80 mg, 0.19 mmol) in acetonitrile (8 mL), sodium bicarbonate (148 mg, 1.76 mmol) and 6-cyano-1-methyl-2-oxo-1,2-dihydro-1,5-naphthyridin-4-yl trifluoromethanesulfonate (59 mg, 0.18 mmol) were added sequentially at room temperature. The reaction mixture was heated at 80° C. for 14 h. The reaction mixture was cooled to room temperature and the solvent was removed under reduced pressure to obtain the diastereomeric mixture of product, which was further purified by prep-HPLC (Chiral Separation Method: Column: Cellulose-5 (250*19) mm, 5 micron, Mobile Phase: 0.1% DEA in MeOH, Flow rate: 20 mL/min, isocratic) to obtain Examples 1405 and 1406.

Example 1405: (7.5 mg, 7% yield); LCMS: m/z, 560.3 (M+H); retention time 2.32 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.16-8.19 (m, 1H), 8.06-8.10 (m, 1H), 7.51-7.56 (m, 2H), 7.34 (d, J=7.8 Hz, 2H), 6.04 (s, 1H), 4.60-4.74 (m, 1H), 3.90-4.05 (m, 1H), 3.58-3.73 (m, 2H), 3.34-3.55 (m, 6H), 3.23 (br d, J=1.0 Hz, 3H), 3.08 (s, 3H), 2.91-3.00 (m, 1H), 2.76-2.86 (m, 2H), 1.28 (d, J=6.6 Hz, 3H), 1.19 (d, J=6.6 Hz, 3H).

Example 1406: (5.4 mg, 5% yield). LCMS: m/z, 560.3 (M+H); retention time 2.33 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.16 (d, J=8.8 Hz, 1H), 8.04-8.10 (m, 1H), 7.50 (d, J=8.8 Hz, 2H), 7.32 (d, J=7.8 Hz, 2H), 6.08 (s, 1H), 4.39-4.59 (m, 1H), 3.78-3.95 (m, 2H), 3.50-3.72 (m, 6H), 3.43-3.50 (m, 1H), 3.35-3.40 (m, 2H), 3.29-3.33 (m, 2H), 3.14 (s, 3H), 2.75 (dd, J=11.9, 3.8 Hz, 1H), 2.25 (dd, J=11.9, 3.8 Hz, 1H), 1.34 (d, J=6.6 Hz, 3H), 1.06 (d, J=6.6 Hz, 3H).

The examples in Table 60 were prepared according to the general procedures described for Examples 1170 and 1171, using the appropriate benzyl bromides/chlorides. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 60

| Ex. No. | Structure | M + H | Stereo chem. | LCMS RT and Method |
|---|---|---|---|---|
| 1407 | 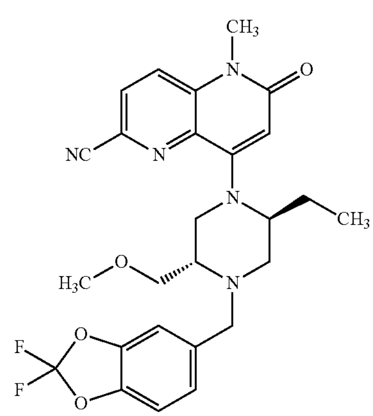 [SMILES: CC[C@H]1CN(Cc2ccc3c(c2)OC(F)(F)O3)[C@H](COC)CN1c1cc(=O)n(C)c2ccc(C#N)nc12] | 512.2 | H | 2.32 A |

TABLE 60-continued

| Ex. No. | Structure | M + H | Stereo chem. | LCMS RT and Method |
|---|---|---|---|---|
| 1408 | 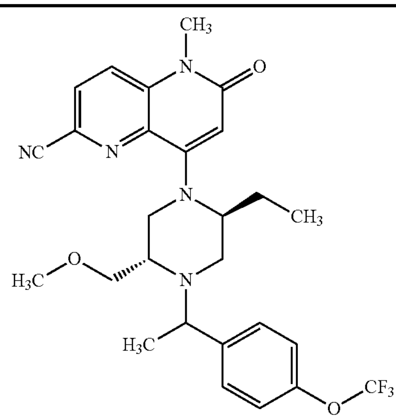 | 530.3 | H | 2.47 A |
| 1409 | 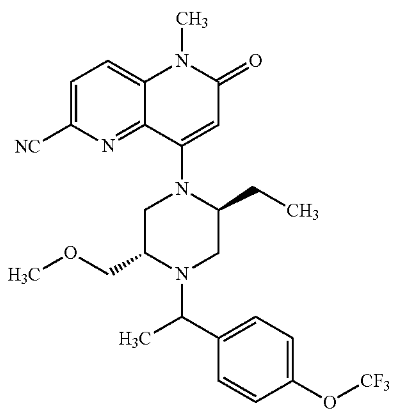 [SMILES: CC[C@H]1CN(C(C)c2ccc(OC(F)(F)F)cc2)[C@H](COC)CN1c1cc(=O)n(C)c2ccc(C#N)nc12] | 530.2 | H | 2.45 A |

Example 1410

N-(((2S,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)methanesulfonamide

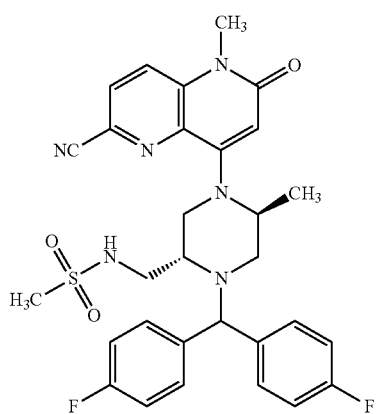

(1410)

Intermediate 1410A: tert-butyl (2S,5S)-4-(bis(4-fluorophenyl)methyl)-2-methyl-5-(((methylsulfonyl)oxy)methyl)piperazine-1-carboxylate

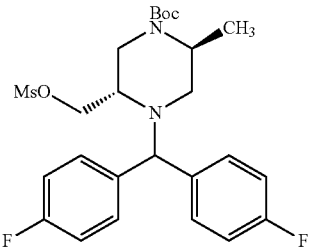

(1410A)

To a stirred solution of tert-butyl (2S,5S)-4-(bis(4-fluorophenyl)methyl)-5-(hydroxymethyl)-2-methylpiperazine-1-carboxylate (620 mg, 1.43 mmol) in DCM (10 mL) were added Et₃N (0.6 mL, 4.3 mmol) and DMAP (9 mg, 0.07 mmol) followed by methanesulfonyl chloride (0.23 mL, 2.87 mmol) at 0° C. The reaction mixture was stirred at room temperature for 16 h. The reaction was quenched with water. The reaction mixture was extracted with DCM (2×30 mL), washed with water, brine and dried over anhydrous sodium sulphate, evaporated under reduced pressure to afford tert-butyl (2S,5S)-4-(bis(4-fluorophenyl)methyl)-2-methyl-5-(((methylsulfonyl)oxy)methyl) piperazine-1-carboxylate (650 mg, 89% yield). LCMS: m/z, 511.2 (M+H); retention time 1.24 min. [LCMS Method: Column: Waters Acquity UPLC BEH C18 (2.1×50 mm) 1.7 μm, Mobile phase A: 10 mM NH₄OAc:acetonitrile (95:5); Mobile phase B: 10 mM NH₄OAc:acetonitrile (5:95), Gradient=20-100% B over 2 minute, then a 0.3 minute hold at 100% B; Temperature: 50° C.; Flow rate: 0.7 mL/min; Detection: UV at 220 nm].

Intermediate 1410B: tert-butyl (2S,5S)-5-(azidomethyl)-4-(bis(4-fluorophenyl)methyl)-2-methylpiperazine-1-carboxylate

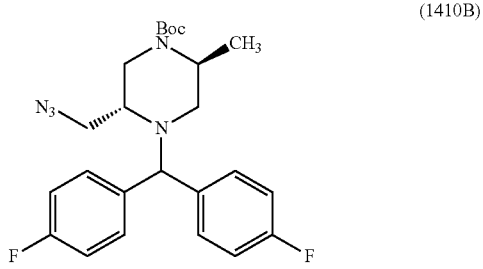 [SMILES: C[C@H]1CN(C(c2ccc(F)cc2)c2ccc(F)cc2)[C@H](CN=[N+]=[N-])CN1C(=O)OC(C)(C)C]

(1410B)

To a stirred solution of tert-butyl (2S,5S)-4-(bis(4-fluorophenyl)methyl)-2-methyl-5-(((methylsulfonyl)oxy)methyl)piperazine-1-carboxylate (600 mg, 1.17 mmol) in DMF (15 mL) were added TBAI (43 mg, 0.12 mmol) and tert-butyl (2S,5S)-4-(bis(4-fluorophenyl)methyl)-2-methyl-5-(((methylsulfonyl)oxy)methyl)piperazine-1-carboxylate (600 mg, 1.18 mmol) at room temperature. The reaction mixture was heated at 80° C. for 16 h. The reaction mixture was cooled to room temperature and solvent was concentrated under reduced pressure to obtain the crude product, which was purified by silica gel flash column chromatography 3-5% MeOH in DCM; 12 g column) to afford tert-butyl (2S,5S)-5-(azidomethyl)-4-(bis(4-fluorophenyl)methyl)-2-methylpiperazine-1-carboxylate (500 mg, 93% yield). LCMS: m/z, 458.2 (M+H); retention time 2.26 min. [LCMS Method: Column: Waters Acquity UPLC BEH C18 (2.1×50 mm) 1.7 μm, Mobile phase A: 10 mM NH₄OAc:acetonitrile (95:5); Mobile phase B: 10 mM NH₄OAc:acetonitrile (5:95), Gradient=20-100% B over 2 minute, then a 0.3 minute hold at 100% B; Temperature: 50° C.; Flow rate: 0.7 mL/min; Detection: UV at 220 nm].

Intermediate 1410C: tert-butyl (2S,5R)-5-(aminomethyl)-4-(bis(4-fluorophenyl)methyl)-2-methylpiperazine-1-carboxylate

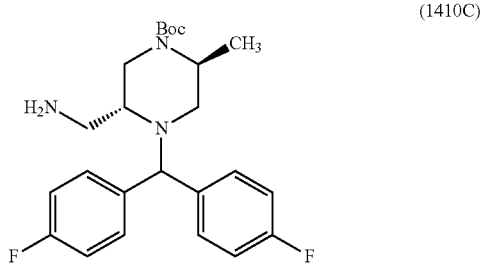 [SMILES: C[C@H]1CN(C(c2ccc(F)cc2)c2ccc(F)cc2)[C@H](CN)CN1C(=O)OC(C)(C)C]

(1410C)

To a stirred solution of tert-butyl (2S,5S)-5-(azidomethyl)-4-(bis(4-fluorophenyl) methyl)-2-methylpiperazine-1-carboxylate (200 mg, 0.44 mmol) in THF (8 mL) and water (4 mL) was added triphenylphosphine (345 mg, 1.31 mmol) at room temperature. The reaction mixture was heated at 65° C. for 16 h. The reaction mixture was cooled to room temperature and solvent was removed under reduced pressure to afford tert-butyl (2S,5R)-5-(aminomethyl)-4-(bis(4-fluorophenyl)methyl)-2-methylpiperazine-1-carboxylate which was taken to the next step without further purification. LCMS: m/z, 432.3 (M+H); retention time 1.81 min. [LCMS Method: Column: Waters Acquity UPLC BEH C18 (2.1×50 mm) 1.7 μm, Mobile phase A: 10 mM NH₄OAc:acetonitrile (95:5); Mobile phase B: 10 mM NH₄OAc:acetonitrile (5:95), Gradient=20-100% B over 2 minute, then a 0.3 minute hold at 100% B; Temperature: 50° C.; Flow rate: 0.7 mL/min; Detection: UV at 220 nm].

Intermediate 1410D: tert-butyl (2S,5S)-4-(bis(4-fluorophenyl)methyl)-2-methyl-5-(methylsulfonamidomethyl)piperazine-1-carboxylate

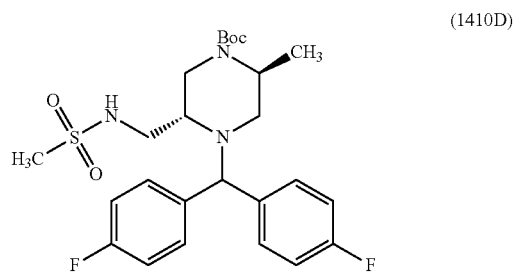 [SMILES: C[C@H]1CN(C(c2ccc(F)cc2)c2ccc(F)cc2)[C@H](CNS(C)(=O)=O)CN1C(=O)OC(C)(C)C]

(1410D)

To a stirred solution of tert-butyl (2S,5R)-5-(aminomethyl)-4-(bis(4-fluorophenyl) methyl)-2-methylpiperazine-1-carboxylate (100 mg, 0.23 mmol) in DCM (4 mL) were added DIPEA (0.08 mL, 0.46 mmol) and methanesulfonyl chloride (0.03 mL, 0.35 mmol) at room temperature. The reaction mixture was stirred for 3 h. The reaction was quenched with water. The reaction mixture was extracted with EtOAc (2×30 mL), washed with water and brine, the combined organic extracts were dried over anhydrous sodium sulphate, concentrated under reduced pressure to obtain tert-butyl (2S,5S)-4-(bis(4-fluorophenyl)methyl)-2-methyl-5-(methylsulfonamidomethyl)piperazine-1-carboxylate (120 mg) of crude product. LCMS: m/z, 510.1 (M+H); retention time 2.04 min. [LCMS Method: Column: Waters Acquity UPLC BEH C18 (2.1×50 mm) 1.7 μm, Mobile phase A: 10 mM NH₄OAc:acetonitrile (95:5); Mobile phase B: 10 mM NH₄OAc:acetonitrile (5:95), Gradient=20-100% B over 2 minute, then a 0.3 minute hold at 100% B; Temperature: 50° C.; Flow rate: 0.7 mL/min; Detection: UV at 220 nm].

Intermediate 1410E: N-(((2S,5S)-1-(bis(4-fluorophenyl)methyl)-5-methylpiperazin-2-yl) methyl) methanesulfonamide hydrochloride

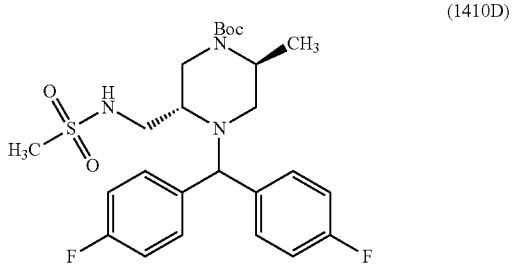 [SMILES: C[C@H]1CN(C(c2ccc(F)cc2)c2ccc(F)cc2)[C@H](CNS(C)(=O)=O)CN1C(=O)OC(C)(C)C]

(1410D)

To a stirred solution of tert-butyl (2S,5S)-4-(bis(4-fluorophenyl)methyl)-2-methyl-5-(methylsulfonamidomethyl) piperazine-1-carboxylate (100 mg, 0.20 mmol) in DCM (20 mL) was added 4 M HCl (in dioxane) (1 mL, 3.92 mmol) at 0° C. The reaction mixture was stirred at room temperature for 3 h. The solvent was removed under reduced pressure to afford N-(((2S,5S)-1-(bis(4-fluorophenyl)methyl)-5-methylpiperazin-2-yl) methyl)methanesulfonamide hydrochloride which was taken to the next step without further purification. LCMS: m/z, 410.2 (M+H); retention time 1.23 min. [LCMS Method: Column: Waters Acquity UPLC BEH C18 (2.1×50 mm) 1.7 µm, Mobile phase A: 10 mM NH$_4$OAc: acetonitrile (95:5); Mobile phase B: 10 mM NH$_4$OAc:acetonitrile (5:95), Gradient=20-100% B over 2 minute, then a 0.3 minute hold at 100% B; Temperature: 50° C.; Flow rate: 0.7 mL/min; Detection: UV at 220 nm].

Example 1410: N-(((2S,5S)-1-(bis(4-fluorophenyl) methyl)-4-(6-cyano-1-methyl-2-oxo-1,2-dihydro-1, 5-naphthyridin-4-yl)-5-methylpiperazin-2-yl)methyl) methanesulfonamide To a stirred solution of N-(((2S,5S)-1-(bis(4-fluorophenyl)methyl)-5-methylpiperazin-2-yl)methyl)methanesulfonamide (100 mg, 0.24 mmol) in acetonitrile (5 mL) were added DIPEA (0.2 mL, 1.22 mmol) and 6-cyano-1-methyl-2-oxo-1,2-dihydro-1,5-naphthyridin-4-yl trifluoromethanesulfonate (81 mg, 0.24 mmol) at room temperature. The reaction mixture was heated at 80° C. for 3 h., and then cooled to room temperature. The solvent was removed under reduced pressure to obtain the crude product, which was purified by preparative HPLC. Column: Waters XBridge C18, 150 mm×19 mm, 5-µm particles; Mobile Phase A: 5:95 acetonitrile:water with 10 mM ammonium acetate; Mobile Phase B: 95:5 acetonitrile:water with 10 mM ammonium acetate; Gradient: a 3 minute hold at 40% B, 40-61% B over 15 minutes, then a 5 minute hold at 100% B; Flow Rate: 15 mL/min; Column Temperature: 25° C. Fractions containing the product were combined and dried by centrifugal evaporation to obtain N-(((2S,5S)-1-(bis(4-fluorophenyl)methyl)-4-(6-cyano-1-methyl-2-oxo-1,2-dihydro-1,5-naphthyridin-4-yl)-5-methylpiperazin-2-yl)methyl)methanesulfonamide (8.4 mg, 6% yield). LCMS: m/z, 593.2 (M+H); retention time 2.06 min; [LCMS Method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%. $^1$H NMR (400 MHz, DMSO-d$_6$) δ ppm 8.15 (d, J=8.8 Hz, 1H), 8.06-8.10 (m, 1H), 7.50-7.63 (m, 4H), 7.10-7.19 (m, 4H), 6.72-6.83 (m, 1H), 6.09 (s, 1H), 5.03 (s, 1H), 4.95 (br s, 1H), 3.53 (s, 3H), 3.44-3.50 (m, 1H), 3.33-3.43 (m, 2H), 3.24-3.31 (m, 1H), 2.90-3.03 (m, 2H), 2.65 (s, 3H), 2.34-2.40 (m, 1H), 1.16 (d, J=6.6 Hz, 3H).

Examples 1411 and 1412

8-((2S,5R)-5-(cyanomethyl)-2-methyl-4-(1-(4-(trifluoromethoxy)phenyl)ethyl)piperazin-1-yl)-5-methyl-6-oxo-5,6-dihydro-1,5-naphthyridine-2-carbonitrile

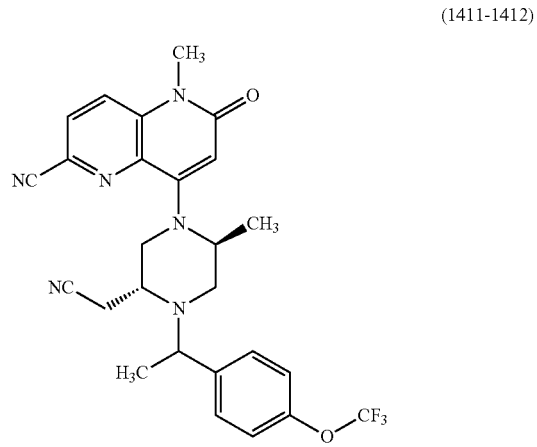 [SMILES: CC(c1ccc(OC(F)(F)F)cc1)N1C[C@H](C)N(c2cc(=O)n(C)c3ccc(C#N)nc23)C[C@H]1CC#N]

(1411-1412)

Intermediate 1411A: tert-butyl (2S,5S)-5-(hydroxymethyl)-2-methyl-4-(1-(4-(trifluoromethoxy) phenyl)ethyl)piperazine-1-carboxylate

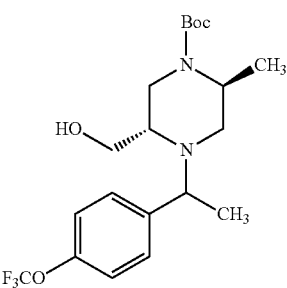

(1412A)

To a stirred solution of tert-butyl (2S,5S)-5-(hydroxymethyl)-2-methylpiperazine-1-carboxylate (1.0 g, 4.34 mmol) in acetonitrile (8 mL), sodium bicarbonate (0.37 g, 4.34 mmol) and 1-(1-bromoethyl)-4-(trifluoromethoxy)benzene (1.2 g, 4.34 mmol) were added at room temperature. The reaction mixture was heated at 85° C. for 14 h. The reaction mixture was cooled to room temperature, the solvent was removed under reduced pressure, extracted with EtOAc (2×100 mL) and washed with water. The combined organic extracts were dried over anhydrous sodium sulphate and concentrated under reduced pressure to obtain the crude product, which was purified by silica gel column chromatography using a 24 g silica gel column, eluting with 0-7% MeOH in DCM to afford diastereomeric mixture of tert-butyl (2S,5S)-5-(hydroxymethyl)-2-methyl-4-(1-(4-(trifluoromethoxy)phenyl)ethyl)piperazine-1-carboxylate (1.0 g, 55% yield). LCMS: m/z, 419.3 (M+H); retention time 2.35 min. [LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Temperature: 50° C.; Flow rate: 0.7 mL/min; Detection: UV at 220 nm].

Intermediate 1411B: ((2S,5S)-5-methyl-1-(1-(4-(trifluoromethoxy)phenyl)ethyl) piperazine-2-yl)methanol hydrochloride

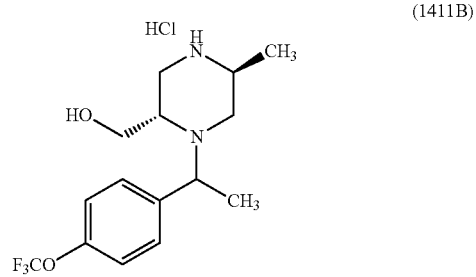 [SMILES: Cl ; CC(c1ccc(OC(F)(F)F)cc1)N1C[C@H](C)NC[C@H]1CO]

(1411B)

To a stirred solution of tert-butyl (2S,5S)-5-(hydroxymethyl)-2-methyl-4-(1-(4-(trifluoromethoxy)phenyl)ethyl) piperazine-1-carboxylate (200 mg, 0.48 mmol) in DCM (5 mL), HCl (4N in dioxane) (0.6 mL, 2.39 mmol) was added drop wise at 0° C. The reaction mixture was stirred at room temperature for 2 h. The solvent was removed under reduced pressure and dried to afford diastereomeric mixture of ((2S,5S)-5-methyl-1-(1-(4-(trifluoromethoxy)phenyl)ethyl) piperazin-2-yl)methanol hydrochloride (130 mg, 85% yield). LCMS: m/z, 319.1 (M+H); retention time 1.06 and 1.15 min. [LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.2 minute hold at 100% B; Temperature: 50° C.; Flow rate: 0.7 mL/min; Detection: UV at 220 nm].

Intermediate 1411C: 8-((2S,5S)-5-(hydroxymethyl)-2-methyl-4-(1-(4-(trifluoromethoxy) phenyl)ethyl) piperazin-1-yl)-5-methyl-6-oxo-5,6-dihydro-1,5-naphthyridine-2-carbonitrile

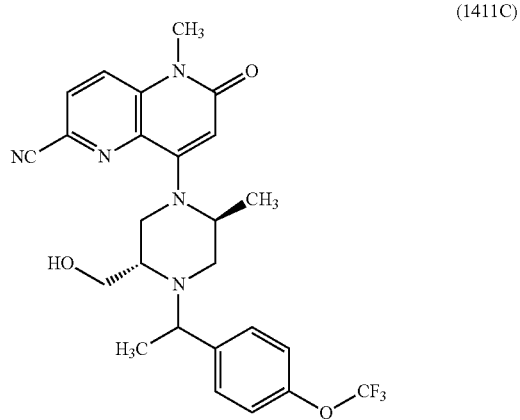 [SMILES: CC(c1ccc(OC(F)(F)F)cc1)N1C[C@H](C)N(c2cc(=O)n(C)c3ccc(C#N)nc23)C[C@H]1CO]

(1411C)

To a stirred solution of ((2S,5S)-5-methyl-1-(1-(4-(trifluoromethoxy)phenyl) ethyl)piperazin-2-yl)methanol, HCl (400 mg, 1.26 mmol) in acetonitrile (8 mL), DIPEA (0.7 mL, 3.75 mmol) and 6-cyano-1-methyl-2-oxo-1,2-dihydro-1,5-naphthyridin-4-yl trifluoromethanesulfonate (420 mg, 1.26 mmol) were added sequentially at room temperature. The reaction mixture was heated at 80° C. for 14 h. The reaction mixture cooled to at room temperature and the solvent was removed under reduced pressure to obtain the crude product, which was purified by silica gel column chromatography using 24 g flash column, eluting with 40-100% EtOAc/hexane followed by 0-10% MeOH in CHCl₃ to afford the diastereomeric mixture of 8-((2S,5S)-5-(hydroxymethyl)-2-methyl-4-(1-(4-(trifluoromethoxy)phenyl)ethyl)piperazin-1-yl)-5-methyl-6-oxo-5,6-dihydro-1,5-naphthyridine-2-carbonitrile (400 mg, 64% yield). LCMS: m/z, 502.4 (M+H); retention time 1.86 min. [LCMS Method: Column: Waters Acquity UPLC BEH C18 (3.0×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm].

Examples 1411 and 1412: 8-((2S,5S)-5-(chloromethyl)-2-methyl-4-(1-(4-(trifluoromethoxy)phenyl) ethyl)piperazin-1-yl)-5-methyl-6-oxo-5,6-dihydro-1, 5-naphthyridine-2-carbonitrile To a stirred solution of 8-((2S,5S)-5-(hydroxymethyl)-2-methyl-4-(1-(4-(trifluoromethoxy)phenyl)ethyl)piperazin-1-yl)-5-methyl-6-oxo-5,6-dihydro-1,5-naphthyridine-2-carbonitrile (500 mg, 1.00 mmol) in DCM (10 mL), TEA (0.42 mL, 2.99 mmol), methanesulfonyl chloride (0.16 mL, 1.99 mmol) and 4-dimethylaminopyridine (12 mg, 0.10 mmol) were added sequentially at 0° C. The reaction mixture was stirred at room temperature overnight. The reaction mixture was extracted with DCM (2×50 mL), washed with water, brine and dried over anhydrous sodium sulphate. Solvent was removed under reduced pressure to obtain the diastereomeric mixture of 8-((2S,5S)-5-(chloromethyl)-2-methyl-4-(1-(4-(trifluoromethoxy)phenyl)ethyl)piperazin-1-yl)-5-methyl-6-oxo-5,6-dihydro-1,5-naphthyridine-2-carbonitrile (450 mg, 87% yield). LCMS: m/z, 520.2 (M+H); retention time 2.20 and 2.23 min. [LCMS Method: Column: AQUITY UPLC BEH C18 (3.0×50 mm) 1.7 μm; Mobile phase A: 10 mM ammonium acetate:acetonitrile (95:5), Mobile phase B: 10 mM ammonium acetate:acetonitrile (5:95), Method: % B: 0 min-20:2 min-100:2.3 min-100; Temperature: 27° C.; Flow rate: 0.7 mL/min; Detection: UV at 220 nm].

To a stirred solution of 8-((2S,5S)-5-(chloromethyl)-2-methyl-4-(1-(4-(trifluoromethoxy)phenyl)ethyl)piperazin- 1-yl)-5-methyl-6-oxo-5,6-dihydro-1,5-naphthyridine-2-carbonitrile (100 mg, 0.19 mmol) in DMSO (5 mL), was added KCN (63 mg, 0.96 mmol) at room temperature. The reaction mixture was heated at 70° C. overnight. The reaction mixture was cooled to room temperature, extracted with EtOAc (2×50 mL) and washed with water. The combined organic extracts were washed with brine, dried over anhydrous sodium sulphate and concentrated to obtain the crude product, which was purified by preparative HPLC (Chiral Separation Method: Column: Cellulose-5 (250×19) mm, 5 micron, Mobile Phase: 0.1% DEA in MeOH, Flow rate: 20 mL/min, isocratic) to obtain Examples 1411 and 1412.

Example 1411: (12.2 mg, 12% yield)); LCMS: m/z, 511.2 (M+H); retention time 2.2 min; Column: XBridge BEH XP C18 (2.1×50 mm), 2.5 µm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.22-8.16 (m, 1H), 8.13-8.07 (m, 1H), 7.63-7.52 (m, 2H), 7.38 (d, J=8.1 Hz, 2H), 6.10 (s, 1H), 4.84-4.75 (m, 1H), 3.95-3.88 (m, 1H), 3.55 (s, 3H), 3.44 (br s, 2H), 3.10-3.03 (m, 1H), 3.02-2.80 (m, 4H), 1.30 (d, J=6.6 Hz, 3H), 1.18 (d, J=6.6 Hz, 3H).

Example 1412: (18 mg, 18% yield). LCMS: m/z, 511.2 (M+H); retention time 2.20 min; Column: XBridge BEH XP C18 (2.1×50 mm), 2.5 µm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.20-8.14 (m, 1H), 8.12-8.06 (m, 1H), 7.51 (d, J=8.6 Hz, 2H), 7.34 (d, J=8.1 Hz, 2H), 6.14 (s, 1H), 4.54 (br dd, J=2.9, 6.4 Hz, 1H), 3.83-3.73 (m, 2H), 3.73-3.61 (m, 2H), 3.55 (s, 3H), 3.06-2.95 (m, 1H), 2.88-2.80 (m, 1H), 2.74 (dd, J=3.4, 12.2 Hz, 1H), 2.20 (dd, J=2.3, 12.1 Hz, 1H), 1.35 (d, J=6.4 Hz, 3H), 1.01 (d, J=6.6 Hz, 3H).

Examples 1413 and 1414

8-((2S,5S)-5-((dimethylamino)methyl)-2-methyl-4-(1-(4-(trifluoromethoxy)phenyl)ethyl) piperazin-1-yl)-5-methyl-6-oxo-5,6-dihydro-1,5-naphthyridine-2-carbonitrile

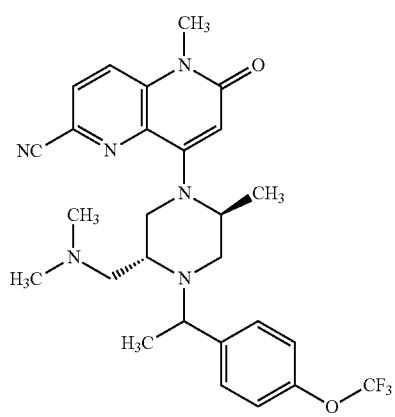

(1413-1414)

To a stirred solution of 8-((2S,5S)-5-(chloromethyl)-2-methyl-4-(1-(4-(trifluoromethoxy)phenyl)ethyl)piperazin-1-yl)-5-methyl-6-oxo-5,6-dihydro-1,5-naphthyridine-2-carbonitrile (100 mg, 0.19 mmol) in acetonitrile (3 mL), potassium carbonate (80 mg, 0.58 mmol), potassium iodide (54 mg, 0.33 mmol), dimethylamine hydrochloride (24 mg, 0.29 mmol) were added sequentially at room temperature. The reaction mixture was heated at 70° C. overnight. The reaction mixture was cooled to room temperature, filtered through syringe filter and the filtrate was concentrated under reduced pressure to obtain the crude product, which was purified by preparative HPLC (Chiral Separation Method: Column: Cellulose-5 (250×19) mm, 5 micron, Mobile Phase: 0.1% DEA in MeOH, Flow rate: 20 mL/min, isocratic) to obtain Examples 1413 and 1414.

Example 1413: (14 mg, 13% yield); LCMS: m/z, 529.3 (M+H); retention time 2.16 min; Column: XBridge BEH XP C18 (2.1×50 mm), 2.5 µm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.11-8.20 (m, 1H), 8.03-8.10 (m, 1H), 7.53 (d, J=8.3 Hz, 2H), 7.31-7.40 (m, 2H), 6.08 (s, 1H), 4.70-4.81 (m, 1H), 3.91-4.00 (m, 1H), 3.58-3.68 (m, 1H), 3.52 (s, 3H), 3.35-3.43 (m, 1H), 2.87-2.97 (m, 1H), 2.74-2.83 (m, 1H), 2.65-2.73 (m, 1H), 2.10-2.23 (m, 1H), 1.84 (br s, 6H), 1.28-1.25 (m, 6H), (1H might have obscured with moisture peak).

Example 1414: (21 mg, 20% yield). LCMS: m/z, 529.3 (M+H); retention time 2.17 min; Column: XBridge BEH XP C18 (2.1×50 mm), 2.5 µm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-$d_6$) δ ppm 8.12-8.17 (m, 1H), 8.04-8.08 (m, 1H), 7.49-7.54 (m, 2H), 7.32 (d, J=7.8 Hz, 2H), 6.16 (s, 1H), 4.49-4.57 (m, 1H), 3.78-3.87 (m, 2H), 3.49-3.66 (m, 4H), 3.30-3.32 (m, 2H, obscured with moisture peak), 2.58-2.79 (m, 2H), 1.99-2.28 (m, 7H), 1.34 (d, J=5.4 Hz, 3H), 1.11 (d, J=5.4 Hz, 3H).

The examples in Table 61 were prepared according to the general procedure described for Example 1413 and 1414 using the appropriate amines. When the reaction provided a mixture of diastereomers, the mixture was separated at the final stage using either preparative chromatography or preparative chiral chromatography. The absolute stereochemistry was not assigned at the newly formed carbon-nitrogen bond TABLE 61
| Ex. No. | Structure | M + H | Stereo chem | LCMS RT and Method |
|---|---|---|---|---|
| 1415 | 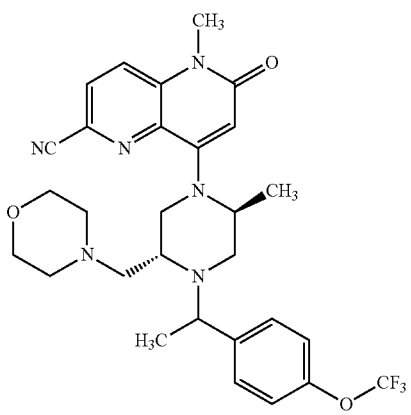 [SMILES: CC(c1ccc(OC(F)(F)F)cc1)N1C[C@H](C)N(c2cc(=O)n(C)c3ccc(C#N)nc23)C[C@H]1CN1CCOCC1] | 571.3 | H | 2.34 A |
| 1416 | 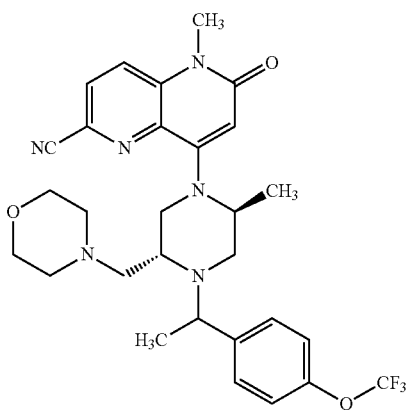 [SMILES: CC(c1ccc(OC(F)(F)F)cc1)N1C[C@H](C)N(c2cc(=O)n(C)c3ccc(C#N)nc23)C[C@H]1CN1CCOCC1] | 571.3 | H | 2.35 A |
| 1417 | 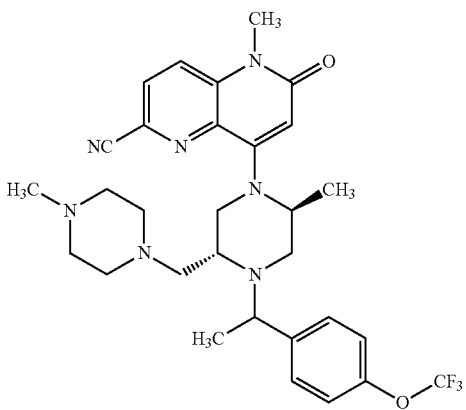 [SMILES: CC(c1ccc(OC(F)(F)F)cc1)N1C[C@H](C)N(c2cc(=O)n(C)c3ccc(C#N)nc23)C[C@H]1CN1CCN(C)CC1] | 584.3 | H | 2.08 A |

TABLE 61-continued

| Ex. No. | Structure | M + H | Stereo chem | LCMS RT and Method |
|---|---|---|---|---|
| 1418 | 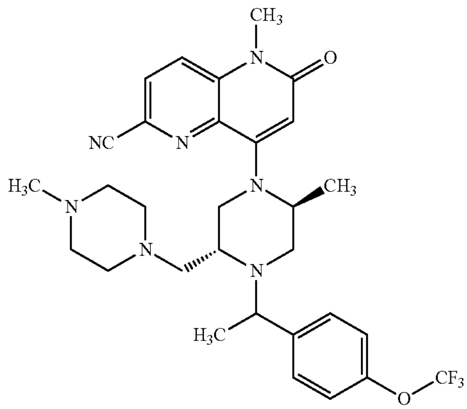 [SMILES: CC(c1ccc(OC(F)(F)F)cc1)N1C[C@H](C)N(c2cc(=O)n(C)c3ccc(C#N)nc23)C[C@H]1CN1CCN(C)CC1] | 584.3 | H | 2.09 A |

Examples 1419 and 1420

8-((2R,5R)-2-(hydroxymethyl)-5-methyl-4-(1-(4-(trifluoromethoxy)phenyl)ethyl) piperazin-1-yl)-5-methyl-6-oxo-5,6-dihydro-1,5-naphthyridine-2-carbonitrile

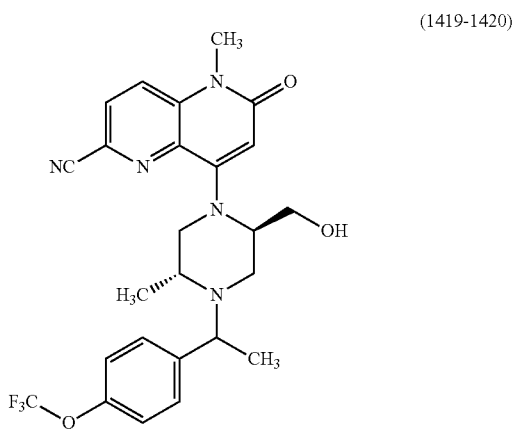 [SMILES: CC(c1ccc(OC(F)(F)F)cc1)N1C[C@H](CO)N(c2cc(=O)n(C)c3ccc(C#N)nc23)C[C@H]1C]
(1419-1420)

Intermediate 1419A: tert-butyl (2R,5R)-4-(6-cyano-1-methyl-2-oxo-1,2-dihydro-1,5-naphthyridin-4-yl)-5-(hydroxymethyl)-2-methylpiperazine-1-carboxylate

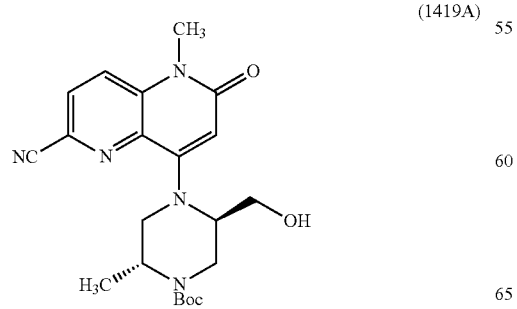
(1419A)

To a stirred solution of tert-butyl (2R,5R)-5-(hydroxymethyl)-2-methylpiperazine-1-carboxylate (100 mg, 0.43 mmol) in acetonitrile (5 mL), were added DIPEA (0.8 mL, 4.34 mmol) and 6-cyano-1-methyl-2-oxo-1,2-dihydro-1,5-naphthyridin-4-yl trifluoromethanesulfonate (145 mg, 0.43 mmol) at room temperature. The reaction mixture was heated at 80° C. for 3 h. The reaction mixture was cooled to room temperature and solvent was removed under reduced pressure to obtain the crude product, which was purified by flash column chromatography (Column: 12 g silica; Solvent run: 2-3% MeOH (10% $NH_4OH$ in chloroform) to obtain a tert-butyl (2R,5R)-4-(6-cyano-1-methyl-2-oxo-1,2-dihydro-1,5-naphthyridin-4-yl)-5-(hydroxymethyl)-2-methylpiperazine-1-carboxylate (120 mg, 67% yield). LCMS: m/z, 414.2 (M+H); retention time 1.36 min. [LCMS Method: Column: Waters Acquity UPLC BEH C18 (2.1×50 mm) 1.7 μm, Mobile phase A: 10 mM $NH_4OAc$:acetonitrile (95:5); Mobile phase B: 10 mM $NH_4OAc$:acetonitrile (5:95), Gradient=20-100% B over 2 minute, then a 0.3 minute hold at 100% B; Temperature: 50° C.; Flow rate: 0.7 mL/min; Detection: UV at 220 nm].

Intermediate 1419B: 8-((2R,5R)-2-(hydroxymethyl)-5-methylpiperazin-1-yl)-5-methyl-6-oxo-5,6-dihydro-1,5-naphthyridine-2-carbonitrile.TFA salt

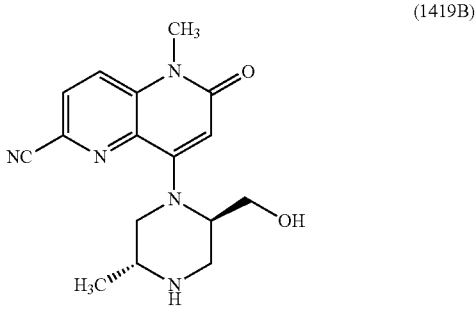 [SMILES: C[C@@H]1CN(c2cc(=O)n(C)c3ccc(C#N)nc23)[C@@H](CO)CN1]
(1419B)

To a solution of tert-butyl (2R,5R)-4-(6-cyano-1-methyl-2-oxo-1,2-dihydro-1,5-naphthyridin-4-yl)-5-(hydroxymethyl)-2-methylpiperazine-1-carboxylate (70 mg, 0.17 mmol) in DCM (4 mL) was added TFA (0.07 mL, 0.85 mmol) at 0° C. The reaction mixture was stirred at room temperature for 2 h. Solvent was removed under reduced pressure and dried to afford TFA salt of 8-((2R,5R)-2-(hydroxymethyl)-5-methylpiperazin-1-yl)-5-methyl-6-oxo-5,6-dihydro-1,5-naphthyridine-2-carbonitrile (48 mg, 69% yield). LCMS: m/z, 314.2 (M+H); retention time 0.63 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Examples 1419 and 1420: 8-((2R,5R)-2-(hydroxymethyl)-5-methyl-4-(1-(4-(trifluoromethoxy)phenyl)ethyl)piperazin-1-yl)-5-methyl-6-oxo-5,6-dihydro-1,5-naphthyridine-2-carbonitrile To a stirred suspension of 8-((2R,5R)-2-(hydroxymethyl)-5-methylpiperazin-1-yl)-5-methyl-6-oxo-5,6-dihydro-1,5-naphthyridine-2-carbonitrile, TFA salt (80 mg, 0.25 mmol) in acetonitrile (5 mL) were added sodium bicarbonate (65 mg, 0.75 mmol) and 1-(1-bromoethyl)-4-(trifluoromethoxy)benzene (69 mg, 0.25 mmol) at room temperature and heated at 80° C. for 12 h. The reaction mixture was cooled to room temperature and solvent was removed under reduced pressure to obtain the crude product, which was purified by preparative HPLC (Method: Column: Sunfire C18 (150×19) mm, 5 μm, Mobile Phase A: 0.1% DEA in ACN, Mobile Phase B: 0.1% DEA in IPA, Gradient=0-50% B over 12 minutes Flow rate: 20 mL/min) to obtain Example 1419 and 1420.

Example 1419: (3.2 mg, 2% yield); LCMS: m/z, 502.3 (M+H); retention time 2.11 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.19-8.14 (m, 1H), 8.10-8.00 (m, 1H), 7.57-7.46 (m, 2H), 7.34 (d, J=8.1 Hz, 2H), 6.00 (s, 1H), 4.79-4.67 (m, 1H), 4.65-4.59 (m, 1H), 3.87-3.77 (m, 1H), 3.77-3.63 (m, 2H), 3.52 (s, 3H), 3.30 (dd, J=2.6, 4.0 Hz, 1H), 3.09 (br d, J=11.2 Hz, 1H), 2.92 (dd, J=3.7, 11.7 Hz, 1H), 2.79-2.70 (m, 1H), 1.25 (d, J=6.4 Hz, 3H), 0.99 (d, J=6.4 Hz, 3H).

Example 1420: (3.1 mg, 2% yield). LCMS: m/z, 502.3 (M+H); retention time 2.12 min; Column: XBridge BEH XP C18 (2.1×50 mm), 2.5 μm; Mobile phase A: 10 mM ammonium acetate:acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.19-8.14 (m, 1H), 8.10-8.00 (m, 1H), 7.57-7.46 (m, 2H), 7.34 (d, J=8.1 Hz, 2H), 6.00 (s, 1H), 4.79-4.67 (m, 1H), 4.65-4.59 (m, 1H), 3.87-3.77 (m, 1H), 3.77-3.63 (m, 2H), 3.52 (s, 3H), 3.30 (dd, J=2.6, 4.0 Hz, 1H), 3.09 (br d, J=11.2 Hz, 1H), 2.92 (dd, J=3.7, 11.7 Hz, 1H), 2.79-2.70 (m, 1H), 1.25 (d, J=6.4 Hz, 3H), 0.99 (d, J=6.4 Hz, 3H).

Example 1421

8-((2R,5R)-4-(bis(4-fluorophenyl)methyl)-2-(methoxymethyl)-5-methylpiperazin-1-yl)-5-methyl-6-oxo-5,6-dihydro-1,5-naphthyridine-2-carbonitrile

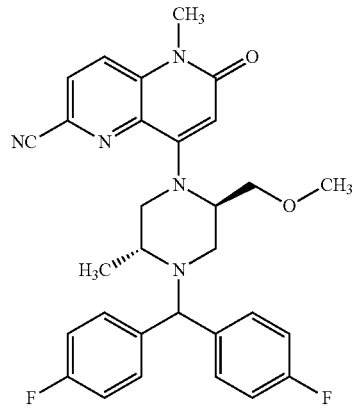

(1421)

Intermediate 1421A: tert-butyl (2R,5R)-4-(6-cyano-1-methyl-2-oxo-1,2-dihydro-1,5-naphthyridin-4-yl)-5-(methoxymethyl)-2-methylpiperazine-1-carboxylate

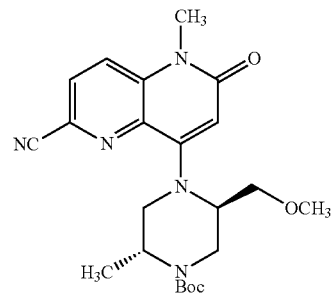

(1421A)

To a stirred suspension of NaH (20 mg, 0.48 mmol, 60% w/w) in THF (4 mL) was added tert-butyl (2R,5R)-4-(6-cyano-1-methyl-2-oxo-1,2-dihydro-1,5-naphthyridin-4-yl)-5-(hydroxymethyl)-2-methylpiperazine-1-carboxylate (100 mg, 0.24 mmol) at 0° C. After 5 min, MeI (0.03 mL, 0.48 mmol) was added. The reaction mixture was stirred at room temperature for 4 h. The reaction was quenched with ice cold water. The reaction mixture was extracted with EtOAc (2×30 mL), dried over anhydrous sodium sulphate and concentrated under reduced pressure to obtain tert-butyl (2R,5R)-4-(6-cyano-1-methyl-2-oxo-1,2-dihydro-1,5-naphthyridin-4-yl)-5-(methoxymethyl)-2-methylpiperazine-1-carboxylate (100 mg, 97% yield). LCMS: m/z, 428.4 (M+H); retention time 1.63 min; Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 1421B: 8-((2R,5R)-2-(methoxymethyl)-5-methylpiperazin-1-yl)-5-methyl-6-oxo-5,6-dihydro-1,5-naphthyridine-2-carbonitrile, TFA Salt

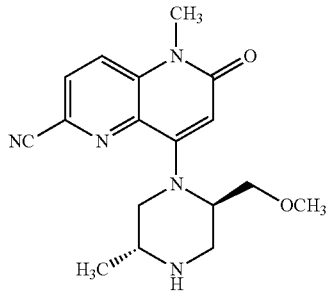

(1421B)

To a solution of tert-butyl (2R,5R)-4-(6-cyano-1-methyl-2-oxo-1,2-dihydro-1,5-naphthyridin-4-yl)-5-(methoxymethyl)-2-methylpiperazine-1-carboxylate (80 mg, 0.19 mmol) in DCM (4 mL) was added TFA (0.07 mL, 0.94 mmol) at 0° C. The reaction mixture was stirred at room temperature for 2 h. Solvent was removed under reduced pressure and dried to afford TFA salt of 8-((2R,5R)-2-(methoxymethyl)-5-methylpiperazin-1-yl)-5-methyl-6-oxo-5,6-dihydro-1,5-naphthyridine-2-carbonitrile (45 mg, 74% yield). LCMS: m/z, 328.2 (M+H); retention time 0.78 min; Column: Waters Acquity UPLC BEH C18 (2.1×50 mm) 1.7 µm, Mobile phase A: 10 mM ammonium acetate:acetonitrile (95:5); Mobile phase B: 10 mM ammonium acetate:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Example 1421: 8-((2R,5R)-4-(bis(4-fluorophenyl)methyl)-2-(methoxymethyl)-5-methylpiperazin-1-yl)-5-methyl-6-oxo-5,6-dihydro-1,5-naphthyridine-2-carbonitrile To a stirred suspension of 8-((2R,5R)-2-(methoxymethyl)-5-methylpiperazin-1-yl)-5-methyl-6-oxo-5,6-dihydro-1,5-naphthyridine-2-carbonitrile TFA (30 mg, 0.09 mmol) in acetonitrile (5 mL) were added DIPEA (0.5 mL, 0.28 mmol) and 4,4'-(bromomethylene)bis(fluorobenzene) (26 mg, 0.09 mmol) at room temperature. The reaction mixture was heated at 80° C. for 14 h. The reaction mixture was cooled to room temperature and the solvent was removed under reduced pressure to obtain the crude product, which was purified by prep-HPLC (Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 0-minute hold at 15% B, 15-55% B over 25 minutes, then a 5 minute hold at 100% B; Flow Rate: 15 mL/min, column temperature: 25° C.) to afford 8-((2S,5R)-4-(4-(4-fluorophenyl)thiazol-2-yl)-2,5-dimethylpiperazin-1-yl)-5-methyl-6-oxo-5,6-dihydro-1,5-naphthyridine-2-carbonitrile (4.3 mg, 6% yield). LCMS: m/z, 530.1 (M+H); retention time 1.82 min; [LCMS method: Column: XBridge BEH XP C18 (50×2.1) mm, 2.5 µm; Mobile phase A: 95% water:5% acetonitrile; 10 mM ammonium acetate; Mobile phase B: 5% water:95% acetonitrile; 10 mM ammonium acetate; Flow: 1.1 mL/min; Temp: 50° C.; Time (min): 0-3; % B: 0-100%). ¹H NMR (400 MHz, DMSO-d₆) δ ppm 8.15-8.12 (m, 1H), 8.08-8.04 (m, 1H), 7.62-7.58 (m, 2H), 7.54 (dd, J=5.5, 8.8 Hz, 2H), 7.18-7.14 (m, 2H), 7.13-7.09 (m, 2H), 6.01 (s, 1H), 4.83-4.77 (m, 1H), 4.69 (s, 1H), 3.84-3.77 (m, 1H), 3.75-3.69 (m, 1H), 3.54-3.57 (m, 1H), 3.52 (s, 3H), 3.13 (s, 3H), 3.05-3.09 (m, 1H), 3.05-3.09 (m, 1H), 2.83-2.80 (m, 1H), 1.02 (d, J=6.5 Hz, 3H).

Example 1422

8-((2S,5R)-4-((4-cyanothiophen-2-yl)methyl)-2,5-dimethylpiperazin-1-yl)-5-methyl-6-oxo-5,6-dihydro-1,5-naphthyridine-2-carbonitrile

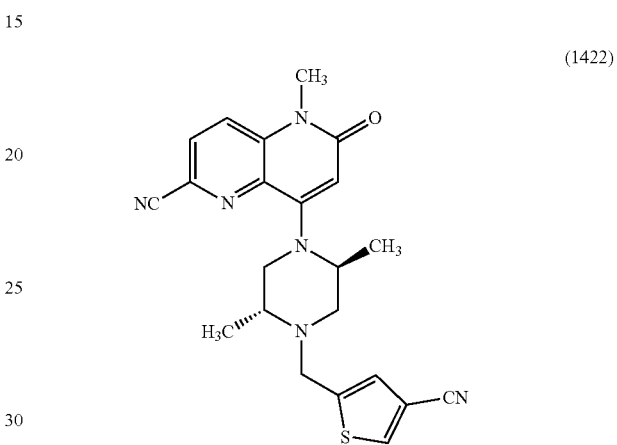

(1422)

To a solution of 8-((2S,5R)-2,5-dimethylpiperazin-1-yl)-5-methyl-6-oxo-5,6-dihydro-1,5-naphthyridine-2-carbonitrile (0.03 g, 0.101 mmol) in acetonitrile (4 mL) at room temperature were added DIEA (0.039 mL, 0.222 mmol) and 5-(chloromethyl) thiophene-3-carbonitrile (0.016 g, 0.101 mmol). The reaction vessel was capped and heated at 80° C. overnight. The progress of the reaction was monitored by LC-MS (Acquity UPLC BEH C18 2.1×50 mm 1.7 µm column. 0-100% B; 2 minute gradient, 3 minute run time 0.8 mL/min flow rate (Solvent A: 90% water, 10% methanol, 0.1% TFA: Solvent B: 10% water, 90% methanol, 0.1% TFA). The reaction mixture was concentrated and the residue was redissolved in methanol and purified by reverse phase HPLC to obtain 8-((2S,5R)-4-((4-cyanothiophen-2-yl)methyl)-2,5-dimethylpiperazin-1-yl)-5-methyl-6-oxo-5,6-dihydro-1,5-naphthyridine-2-carbonitrile (6.9 mg, 17% yield). LC-MS: Showed (M+H) peak at 419; Re: 1.17 min.

The crude material was purified via preparative LC/MS with the following conditions: Column: XBridge C18, 200 mm×19 mm, 5 µm particles; Mobile Phase A: 5:95 acetonitrile:water with 10-mM ammonium acetate; Mobile Phase B: 95:5 acetonitrile:water with 10 mM ammonium acetate; Gradient: a zero minute hold at 31% B, 31-71% B over 20 minutes, then a 4-minute hold at 100% B; Flow Rate: 20 mL/min; Column Temperature: 25° C. The yield of the product was 6.9 mg, and its estimated purity by LCMS analysis was 96%. Analytical LC/MS was used to determine the final purity. Conditions for QC were Conditions 1 and 2 as mentioned earlier. ¹H NMR (500 MHz, DMSO-d₆) δ 8.19-8.13 (m, 1H), 8.11-8.04 (m, 1H), 7.90 (dd, J=7.2, 1.7 Hz, 2H), 7.58-7.48 (m, 3H), 7.00 (s, 1H), 6.12 (s, 1H), 4.34-4.20 (m, 1H), 3.98-3.80 (m, 2H), 3.63-3.53 (m, 2H), 3.47 (br dd, J=7.0, 1.9 Hz, 2H), 3.05 (br dd, J=11.0, 3.1 Hz, 2H), 2.55 (s, 1H), 2.43 (br dd, J=11.4, 3.7 Hz, 1H), 1.16 (dd, J=6.2, 3.5 Hz, 6H).

The examples in Table 62 were prepared from (R)-7-fluoro-5-methyl-8-(3-methylpiperazin-1-yl)-6-oxo-5,6-dihydro-1,5-naphthyridine-2-carbonitrile using the general method described in Example 1422.
TABLE 62
| Ex. No. | Structure | QC Method | Obs. MS Ion | Stereo Chem | RT |
|---|---|---|---|---|---|
| 1423 | 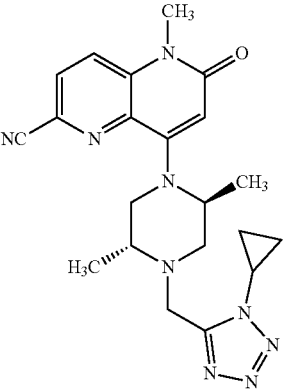 [SMILES: C[C@@H]1CN(c2cc(=O)n(C)c3ccc(C#N)nc23)[C@@H](C)CN1Cc1nnnn1C1CC1] | 1 | 420.03 | H | 1.54 |
| 1424 | 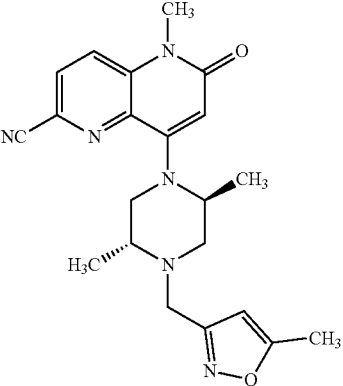 [SMILES: Cc1cc(CN2C[C@H](C)N(c3cc(=O)n(C)c4ccc(C#N)nc34)C[C@H]2C)no1] | 1 | 393.37 | H | 1.49 |
| 1425 | 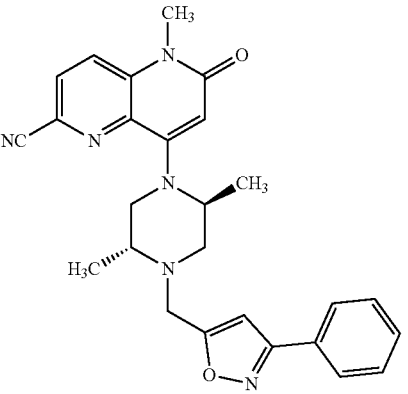 [SMILES: C[C@@H]1CN(c2cc(=O)n(C)c3ccc(C#N)nc23)[C@@H](C)CN1Cc1cc(-c2ccccc2)no1] | 1 | 455.05 | H | 2.01 |

TABLE 62-continued
| Ex. No. | Structure | QC Method | Obs. MS Ion | Stereo Chem | RT |
|---|---|---|---|---|---|
| 1426 | 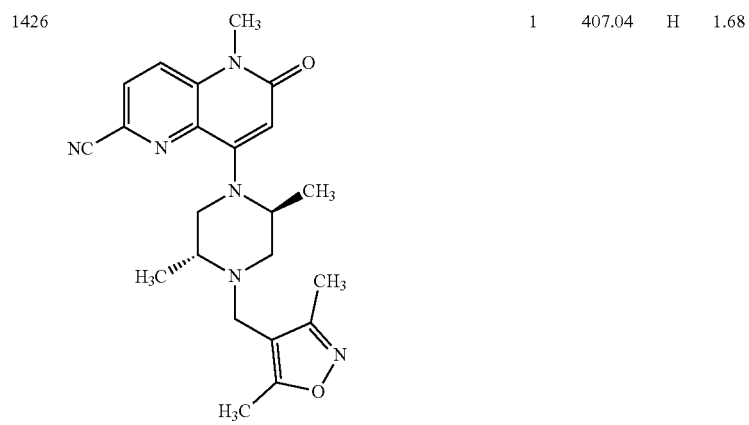 | 1 | 407.04 | H | 1.68 |
| 1427 | 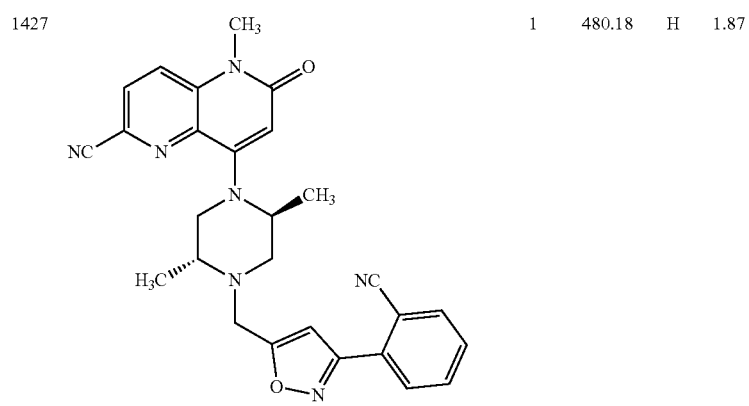 | 1 | 480.18 | H | 1.87 |
| 1428 | 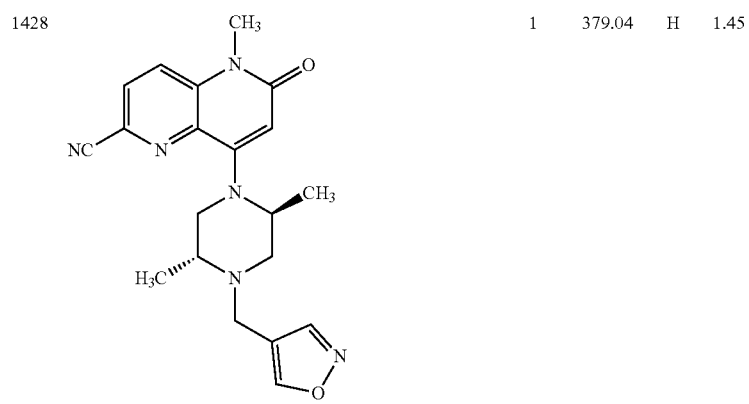 | 1 | 379.04 | H | 1.45 |

TABLE 62-continued

| Ex. No. Structure | QC Method | Obs. MS Ion | Stereo Chem | RT |
|---|---|---|---|---|
| 1429 | 1 | 487.22 | H | 2.16 |
| 1430 | 1 | 486.91 | H | 2.13 |
| 1431 | 1 | 393.06 | H | 1.57 |

TABLE 62-continued

| Ex. No. | Structure | QC Method | Obs. MS Ion | Stereo Chem | RT |
|---|---|---|---|---|---|
| 1432 | 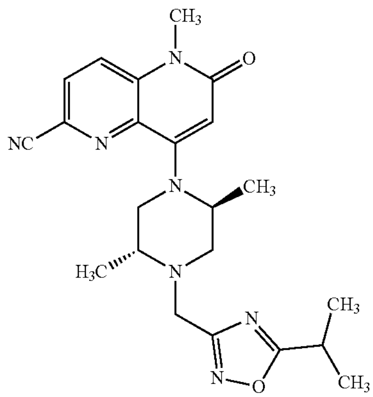 [SMILES: CC(C)c1nc(CN2C[C@H](C)N(c3cc(=O)n(C)c4ccc(C#N)nc34)C[C@H]2C)no1] | 1 | 422.08 | H | 1.24 |
| 1433 | 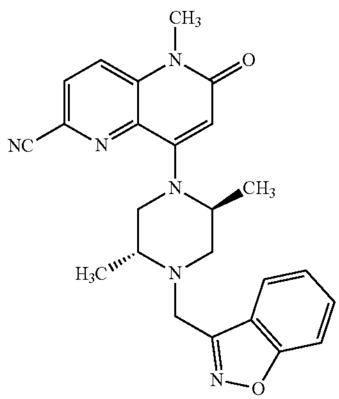 [SMILES: C[C@@H]1CN(c2cc(=O)n(C)c3ccc(C#N)nc23)[C@@H](C)CN1Cc1noc2ccccc12] | 1 | 429.08 | H | 1.95 |
| 1434 | 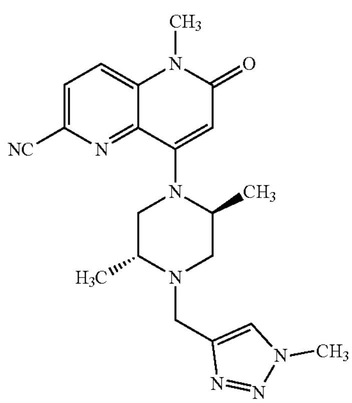 [SMILES: C[C@@H]1CN(c2cc(=O)n(C)c3ccc(C#N)nc23)[C@@H](C)CN1Cc1cn(C)nn1] | 1 | 461.24 | H | 1.86 |
| 1435 | 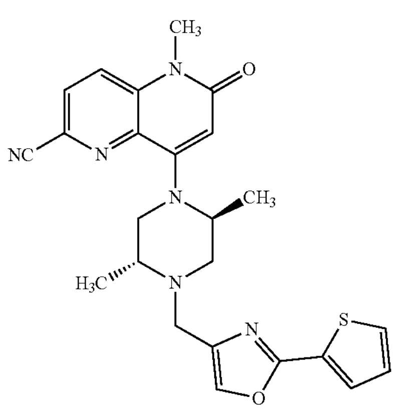 [SMILES: C[C@@H]1CN(c2cc(=O)n(C)c3ccc(C#N)nc23)[C@@H](C)CN1Cc1coc(-c2cccs2)n1] | 1 | 393.14 | H | 1.02 |

TABLE 62-continued

| Ex. No. | Structure | QC Method | Obs. MS Ion | Stereo Chem | RT |
|---|---|---|---|---|---|
| 1436 | 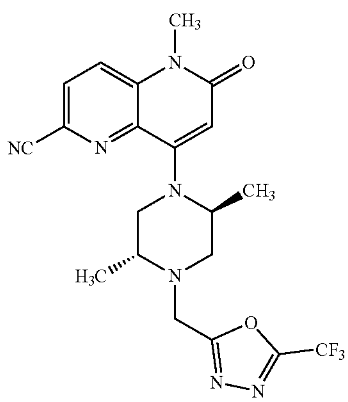 [SMILES: C[C@@H]1CN(c2cc(=O)n(C)c3ccc(C#N)nc23)[C@@H](C)CN1Cc1nnc(C(F)(F)F)o1] | 1 | 448.06 | H | 1.52 |
| 1437 | 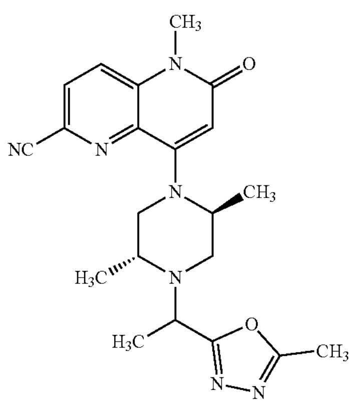 [SMILES: Cc1nnc(C(C)N2C[C@H](C)N(c3cc(=O)n(C)c4ccc(C#N)nc34)C[C@H]2C)o1] | 1 | 408.3 | H | 1.34 |
| 1438 | 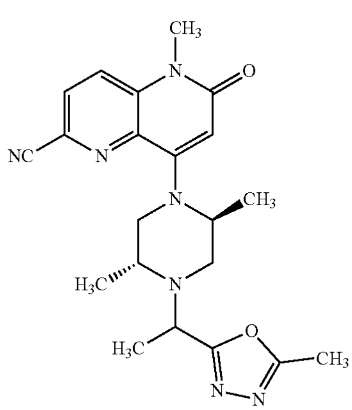 [SMILES: Cc1nnc(C(C)N2C[C@H](C)N(c3cc(=O)n(C)c4ccc(C#N)nc34)C[C@H]2C)o1] | 1 | 408.3 | H | 1.39 |

Examples 1439 and 1440

8-((2S,5R)-4-(1-(4-(cyclopropylmethoxy)phenyl)propyl)-2,5-dimethylpiperazin-1-yl)-5-methyl-6-oxo-5,6-dihydro-1,5-naphthyridine-2-carbonitrile

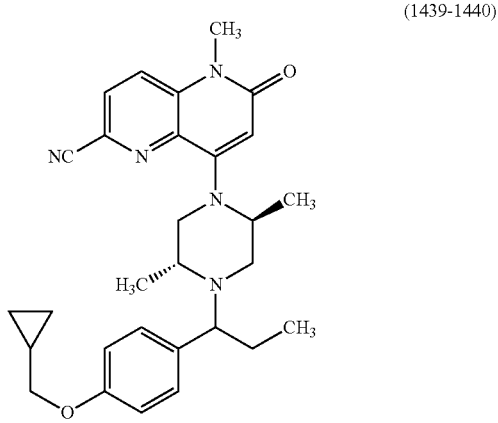 [SMILES: CCC(c1ccc(OCC2CC2)cc1)N1C[C@H](C)N(c2cc(=O)n(C)c3ccc(C#N)nc23)C[C@H]1C]

(1439-1440)

Intermediate 1439A:
4-(cyclopropylmethoxy)benzaldehyde

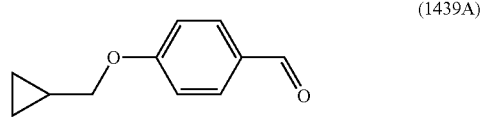

(1439A)

To a solution of 4-hydroxybenzaldehyde (3 g, 24.57 mmol) in acetonitrile (10 mL) at room temperature were added (bromomethyl)cyclopropane (3.65 g, 27.0 mmol) and potassium carbonate (6.79 g, 49.1 mmol). The reaction vial was capped and heated at 80° C. overnight. The progress of the reaction was monitored by LC-MS (Acquity UPLC BEH C18 2.1×50 mm 1.7 μm column. 0-100% B; 2 minute gradient, 3 minute run time 0.8 mL/min flow rate (Solvent A: 90% water, 10% methanol, 0.1% TFA: Solvent B: 10% water, 90% methanol, 0.1% TFA). The reaction mixture was filtered and concentrated. The residue was redissolved in dichloromethane and purified by silica gel chromatography using 40 g ISCO column and eluted with hexanes, ethyl acetate gradient (100:0 to 20:80, 500 mL). The required fractions were concentrated to obtain 4-(cyclopropylmethoxy)benzaldehyde (3.62 g, 20.54 mmol, 84% yield). LC-MS: (M+H) peak at 177, Rt=0.9 min.

Intermediate 1439B:
1-(4-(cyclopropylmethoxy)phenyl)propan-1-ol

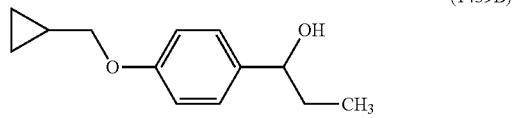

(1439B)

To an ice-cold solution of 4-(cyclopropylmethoxy)benzaldehyde (3.2 g, 18.16 mmol) in THF (30 mL) was added dropwise, ethylmagnesium bromide (7.57 mL, 22.70 mmol) (M in Et$_2$O). The reaction mixture was stirred at room temperature for 2 h. The progress of the reaction was monitored by LC-MS (Acquity UPLC BEH C18 2.1×50 mm 1.7 μm column. 0-100% B; 2 minute gradient run time 0.8 mL/min flow rate (Solvent A: 100% water, 0.1% TFA: Solvent B: 100% acetonitrile, 0.1% TFA). No starting material was observed. The reaction was quenched with saturated aqueous NH$_4$Cl. The reaction mixture was diluted with ethyl acetate. The organic phase was washed with water, brine and dried (MgSO$_4$). The filtrate was rotovapped and residue purified by silica gel chromatography using 40 g ISCO column and eluted with hexanes, ethyl acetate gradient (100:0 to 0:100, 500 mL). The required fractions were concentrated to obtain 1-(4-(cyclopropylmethoxy)phenyl)propan-1-ol (3.29 g, 15.95 mmol, 88% yield). $^1$H NMR (499 MHz, CHLOROFORM-d) δ 7.28-7.23 (m, 2H), 6.92-6.87 (m, 2H), 4.54 (t, J=6.7 Hz, 1H), 3.81 (d, J=6.8 Hz, 2H), 1.96 (s, 1H), 1.88-1.69 (m, 2H), 1.33-1.25 (m, 1H), 0.91 (t, J=7.4 Hz, 3H), 0.70-0.63 (m, 2H), 0.40-0.33 (m, 2H).

Examples 1439 and 1440: 8-((2S,5R)-4-(1-(4-(cyclopropylmethoxy)phenyl)propyl)-2,5-dimethylpiperazin-1-yl)-5-methyl-6-oxo-5,6-dihydro-1,5-naphthyridine-2-carbonitrile To a solution of 8-((2S,5R)-2,5-dimethylpiperazin-1-yl)-5-methyl-6-oxo-5,6-dihydro-1,5-naphthyridine-2-carbonitrile (0.05 g, 0.168 mmol) in acetonitrile (5 mL) at room temperature were added 1-(4-(cyclopropylmethoxy)phenyl)propan-1-ol (0.052 g, 0.252 mmol), (cyanomethyl)trimethylphosphonium iodide (0.082 g, 0.336 mmol) and Hunig's base (0.147 mL, 0.841 mmol). The reaction vial was sealed and heated at 110° C. overnight. The progress of the reaction was monitored by LC-MS (Acquity UPLC BEH C18 2.1×50 mm 1.7 μm column. 0-100% B; 2 minute gradient run time 0.8 mL/min flow rate (Solvent A: 100% water, 0.1% TFA: Solvent B: 100% acetonitrile, 0.1% TFA). Some product formation was observed along with starting material. Next, 1.5 equiv. of the alcohol, 2.0 equiv. phosphonium iodide and 5.0 equiv. DIEA were added and the heating was continued for 16 more hours. LC-MS shows more product. The reaction mixture was cooled to room temperature, concentrated and the residue was redissolved in DMF. The mixture was filtered and purified by reverse phase HPLC following the same conditions as mentioned earlier. Fractions containing the product were combined and dried via centrifugal evaporation to obtain Example 1439 (1.4 mg) and its estimated purity by LCMS analysis was 100%. R$_f$=1.66 min, Obs MS ion: 486.08. Second peak yield of Example 1440 was 1.5 mg, and its estimated purity by LCMS analysis was 97%. R$_f$=1.74 min, Obs MS ion: 486.12. QC conditions 1 and 2. $^1$H NMR (500 MHz, DMSO-d$_6$) δ 7.88 (d, J=8.8 Hz, 1H), 7.83-7.77 (m, 1H), 6.96 (d, J=8.7 Hz, 2H), 6.62 (d, J=8.5 Hz, 2H), 5.74 (s, 1H), 4.13 (br dd, J=3.2, 1.5 Hz, 1H), 3.54 (d, J=6.9 Hz, 2H), 3.27 (br s, 2H), 3.01 (br dd, J=9.3, 3.1 Hz, 1H), 2.45 (br dd, J=11.7, 3.2 Hz, 1H), 2.31 (s, 4H), 1.92-1.84 (m, 1H), 1.70-1.58 (m, 1H), 1.30-1.18 (m, 1H), 1.03-0.92 (m, 1H), 0.88 (br d, J=6.5 Hz, 3H), 0.83 (d, J=6.5 Hz, 3H), 0.42-0.26 (m, 5H), 0.13-0.01 (m, 2H).

The examples in Table 63 were prepared from 8-((2S,5R)-2,5-dimethylpiperazin-1-yl)-5-methyl-6-oxo-5,6-dihydro-1,5-naphthyridine-2-carbonitrile using the general method of Examples 1439 and 1440.

TABLE 63
| Ex. No. | Structure | QC Method | Obs. MS Ion | Stereo Chem | RT |
|---|---|---|---|---|---|
| 1441 | 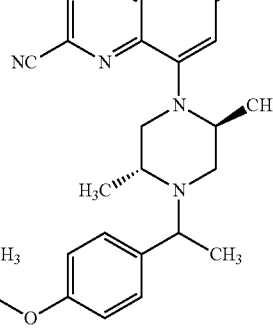 | 1 | 473.9 | H | 1.46 |
| 1442 | 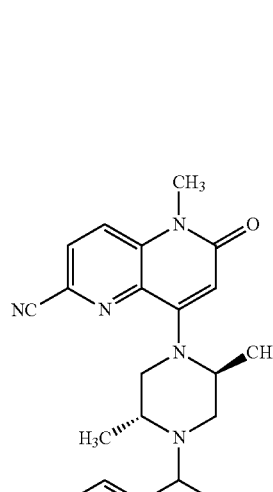 | 1 | 474.17 | H | 1.47 |
| 1443 | 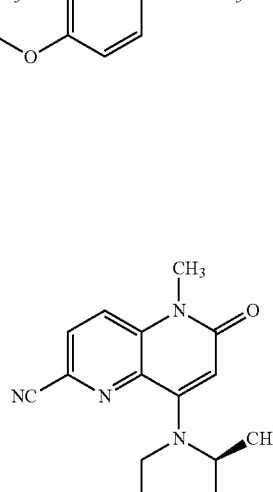 | 1 | 488.46 | H | 1.57 |

TABLE 63-continued
| Ex. No. | Structure | QC Method | Obs. MS Ion | Stereo Chem | RT |
|---|---|---|---|---|---|
| 1444 | 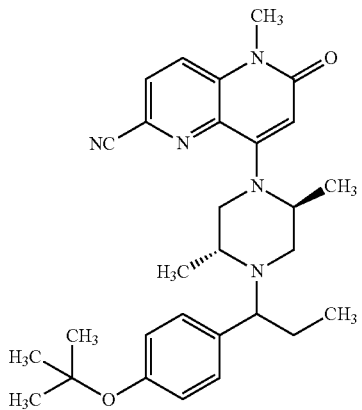 [SMILES: CCC(c1ccc(OC(C)(C)C)cc1)N1C[C@H](C)N(c2cc(=O)n(C)c3ccc(C#N)nc23)C[C@H]1C] | 1 | 488.49 | H | 1.57 |
| 1445 | 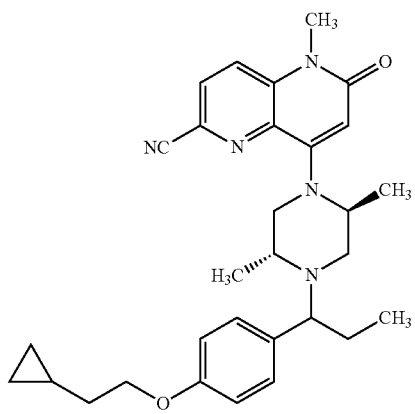 [SMILES: CCC(c1ccc(OCCC2CC2)cc1)N1C[C@H](C)N(c2cc(=O)n(C)c3ccc(C#N)nc23)C[C@H]1C] | 1 | 500.19 | H | 1.72 |
| 1446 | 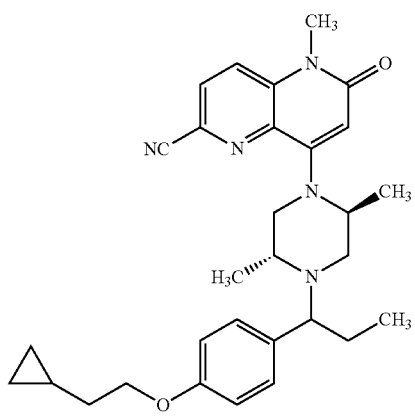 [SMILES: CCC(c1ccc(OCCC2CC2)cc1)N1C[C@H](C)N(c2cc(=O)n(C)c3ccc(C#N)nc23)C[C@H]1C] | 1 | 500.09 | H | 1.73 |

TABLE 63-continued

| Ex. No. | Structure | QC Method | Obs. MS Ion | Stereo Chem | RT |
|---|---|---|---|---|---|
| 1447 | 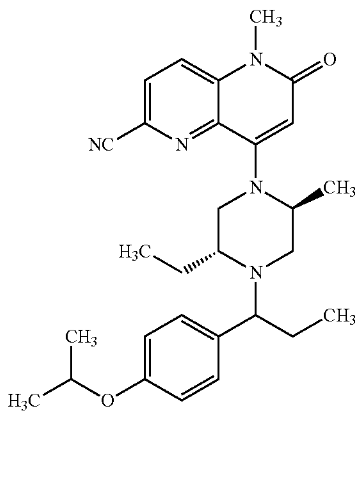 [SMILES: CCC(c1ccc(OC(C)C)cc1)N1C[C@H](C)N(c2cc(=O)n(C)c3ccc(C#N)nc23)C[C@H]1CC] | 1 | 488.32 | H | 2.71 |
| 1448 | 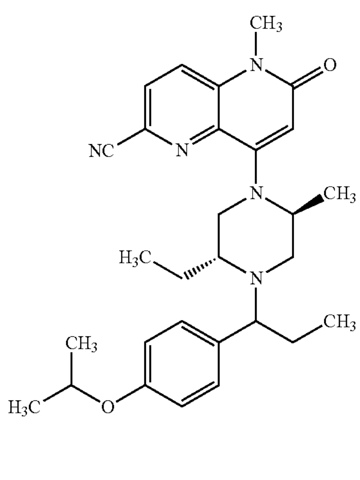 [SMILES: CCC(c1ccc(OC(C)C)cc1)N1C[C@H](C)N(c2cc(=O)n(C)c3ccc(C#N)nc23)C[C@H]1CC] | 1 | 488.07 | H | 2.78 |
| 1449 | 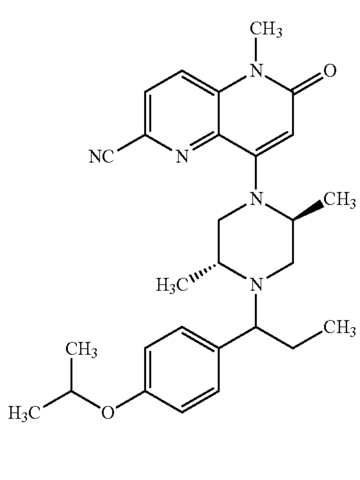 [SMILES: CCC(c1ccc(OC(C)C)cc1)N1C[C@H](C)N(c2cc(=O)n(C)c3ccc(C#N)nc23)C[C@H]1C] | 1 | 474.05 | H | 1.59 |

TABLE 63-continued
| Ex. No. | Structure | QC Method | Obs. MS Ion | Stereo Chem | RT |
|---|---|---|---|---|---|
| 1450 | 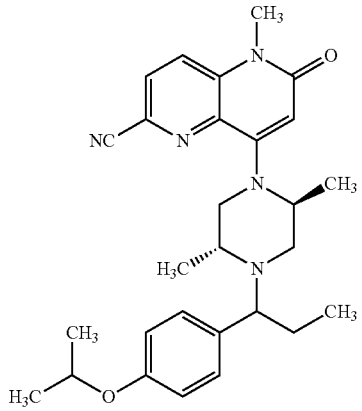 [SMILES: CCC(c1ccc(OC(C)C)cc1)N1C[C@H](C)N(c2cc(=O)n(C)c3ccc(C#N)nc23)C[C@H]1C] | 1 | 474.14 | H | 1.7 |
| 1451 | 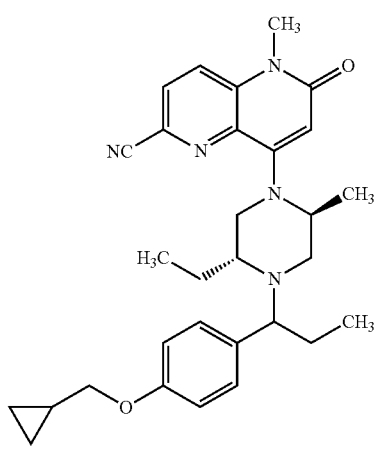 [SMILES: CCC(c1ccc(OCC2CC2)cc1)N1C[C@H](C)N(c2cc(=O)n(C)c3ccc(C#N)nc23)C[C@H]1CC] | 1 | 500.5 | D | 2.71 |
| 1452 | 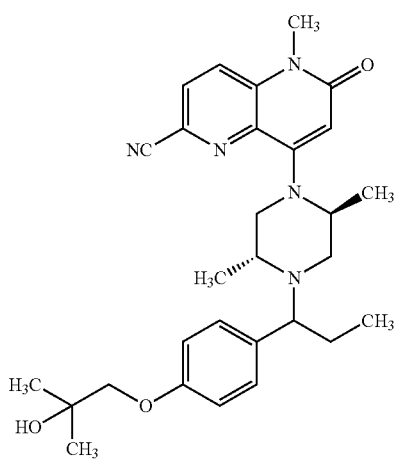 [SMILES: CCC(c1ccc(OCC(C)(C)O)cc1)N1C[C@H](C)N(c2cc(=O)n(C)c3ccc(C#N)nc23)C[C@H]1C] | 1 | 504.5 | D | 1.79 |

TABLE 63-continued

| Ex. No. | Structure | QC Method | Obs. MS Ion | Stereo Chem | RT |
|---|---|---|---|---|---|
| 1453 | 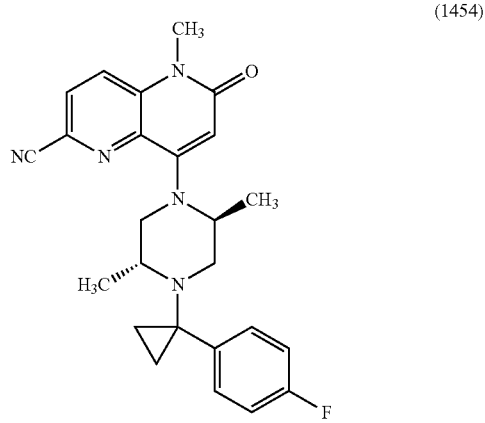 [SMILES: C[C@@H]1CN(c2cc(=O)n(C)c3ccc(C#N)nc23)[C@@H](C)CN1C1(c2ccc(F)cc2)CC1] | 1 | 514.12 | D | 2.80 |

Example 1454

8-((2S,5R)-4-(1-(4-fluorophenyl)cyclopropyl)-2,5-dimethylpiperazin-1-yl)-5-methyl-6-oxo-5,6-dihydro-1,5-naphthyridine-2-carbonitrile (1454)

Intermediate 1454A: tert-butyl (2S,5R)-4-(4-fluorobenzoyl)-2,5-dimethylpiperazine-1-carboxylate

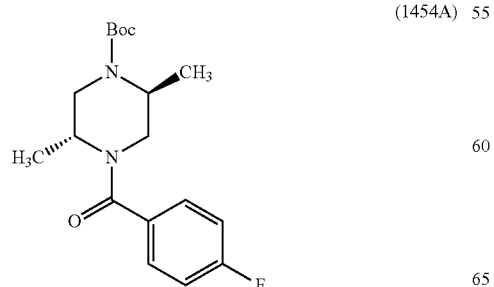
(1454A)

To a stirred solution of 4-fluorobenzoyl chloride (1.0 g, 7.14 mmol) in acetonitrile (10 mL) were added DIPEA (3.74 mL, 21.41 mmol) and HATU (3.53 g, 9.28 mmol) at room temperature. After 30 min., tert-butyl (2S,5R)-2,5-dimethylpiperazine-1-carboxylate (1.83 g, 8.56 mmol) was added and the reaction mixture was stirred overnight. The reaction mixture was concentrated under reduced pressure to remove volatiles and the residue dissolved in ethyl acetate (100 mL) and washed with water (50 mL). The aqueous layer was back extracted with ethyl acetate (100 mL×2) and the combined organic layer was washed with brine, dried over anhydrous $Na_2SO_4$, concentrated under reduced pressure to obtain the crude product, which was purified by silica gel chromatography (50-100% EtOAc in petroleum ether; 40 g column) to afford tert-butyl (2S,5R)-4-(4-fluorobenzoyl)-2,5-dimethylpiperazine-1-carboxylate (1.99 g, 83% yield). LCMS: m/z=337.1 (M+H); retention time 1.62 min. [LCMS Condition: Column: Waters Acquity UPLC BEH C18 (2.1×50 mm) 1.7 μm, Mobile phase A: 10 mM $NH_4OAc$:acetonitrile (95:5); Mobile phase B: 10 mM $NH_4OAc$:acetonitrile (5:95), Gradient=20-90% B over 1.1 minute, then a 0.6 minute hold at 90% B; Temperature: 50° C.; Flow rate: 0.7 mL/min; Detection: UV at 220 nm].

Intermediate 1454B: tert-butyl (2S,5R)-4-(1-(4-fluorophenyl)cyclopropyl)-2,5-dimethylpiperazine-1-carboxylate

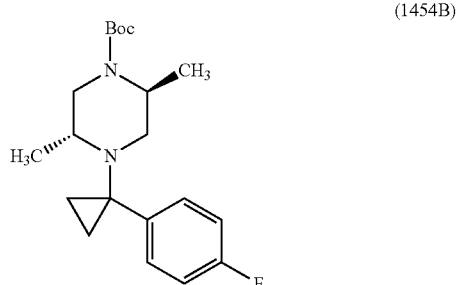
(1454B)

To a stirred solution of methyl titanium triisopropoxide (3.0 mL, 2.97 mmol, 1 M in DCM) in tetrahydrofuran (15 mL) at −78° C. was added ethylmagnesium bromide (6 mL, 5.95 mmol, 1M in THF). After 30 min., a solution of tert-butyl (2S,5R)-4-(4-fluorobenzoyl)-2,5-dimethylpiperazine-1-carboxylate (500 mg, 1.49 mmol in 5.0 mL THF) was added. The reaction mixture was stirred for 30 min at −78° C. and then, 1 h at room temperature. The reaction mixture was poured into water (100 mL) and extracted with ether (50 mL×3), the combined organic layer was washed with brine, dried over anhydrous Na$_2$SO$_4$, concentrated under reduced pressure to obtain the crude product, which was purified by silica gel chromatography (5-10% ethyl acetate/petroleum ether; 24 g column) to afford tert-butyl (2S,5R)-4-(1-(4-fluorophenyl)cyclopropyl)-2,5-dimethylpiperazine-1-carboxylate (425 mg, 82% yield). LCMS: m/z=349.2 (M+H); retention time 4.21 min. [LCMS Condition: Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 1454C: (2S,5R)-4-(1-(4-fluorophenyl) cyclopropyl)-2,5-dimethylpiperazin-1-ium chloride

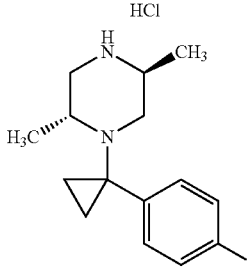

(1454C)

To a solution of tert-butyl (2S,5R)-4-(1-(4-fluorophenyl) cyclopropyl)-2,5-dimethylpiperazine-1-carboxylate (200 mg, 0.57 mmol) in DCM (10 mL) was added 4 N HCl (0.17 mL, 5.74 mmol) (in dioxane) at room temperature. The reaction mixture was stirred for 3 h. The reaction mixture was evaporated under reduced pressure to obtain the HCl salt of (2R,5S)-1-(1-(4-fluorophenyl)cyclopropyl)-2,5-dimethylpiperazine (131 mg, 80% yield). LCMS: m/z=249.3 (M+H); retention time 1.08 min. [LCMS Condition: Column: Waters Acquity UPLC BEH C18 (2.1×50 mm) 1.7 µm, Mobile phase A: 10 mM NH$_4$OAc: acetonitrile (95:5); Mobile phase B: 10 mM NH$_4$OAc: acetonitrile (5:95), Gradient=20-90% B over 1.1 minute, then a 0.6 minute hold at 90% B; Temperature: 50° C.; Flow rate: 0.7 mL/min; Detection: UV at 220 nm].

Example 1454: 8-((2S,5R)-4-(1-(4-fluorophenyl) cyclopropyl)-2,5-dimethylpiperazin-1-yl)-5-methyl-6-oxo-5,6-dihydro-1,5-naphthyridine-2-carbonitrile To a stirred suspension of (2R,5S)-1-(1-(4-fluorophenyl) cyclopropyl)-2,5-dimethylpiperazine hydrochloride (50 mg, 0.17 mmol) in acetonitrile (3 mL) were added DIPEA (0.09 mL, 0.53 mmol) and 6-cyano-1-methyl-2-oxo-1,2-dihydro-1,5-naphthyridin-4-yl trifluoromethanesulfonate (88 mg, 0.26 mmol) at room temperature. The reaction mixture was heated at 85° C. for 16 h. The reaction mixture was cooled to room temperature, concentrated under reduced pressure to remove volatiles and the residue was dissolved in ethyl acetate (20 mL), washed with water (15 mL). The aqueous layer was back extracted with ethyl acetate (20 mL×2). The combined organic layer was washed with brine, dried over anhydrous Na$_2$SO$_4$, concentrated under reduced pressure to obtain the crude product, which was purified by preparative HPLC with the following conditions: Column: Waters XBridge C18, 150 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 10% B, 10-45% B over 20 minutes, then a 5-minute hold at 100% B; Flow Rate: 15 mL/min; Column Temperature: 25° C. Fraction collection was triggered by signals. Fractions containing the product were combined and dried by centrifugal evaporation to obtain 8-((2S,5R)-4-(1-(4-fluorophenyl)cyclopropyl)-2,5-dimethylpiperazin-1-yl)-5-methyl-6-oxo-5,6-dihydro-1,5-naphthyridine-2-carbonitrile (3.6 mg, 5% yield). LCMS: m/z=432.2 (M+H); retention time 2.1 min. [LCMS Condition: Column: XBridge BEH XP C18 (2.1×50 mm), 2.5 µm; Mobile phase A: 10 mM ammonium acetate: acetonitrile (95:5), Mobile phase B: 10 mM ammonium acetate:acetonitrile (5:95), Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.12-8.16 (m, 1H), 8.04-8.09 (m, 1H), 7.39-7.50 (m, 2H), 7.15-7.24 (m, 2H), 6.17 (s, 1H), 3.68-3.82 (m, 1H), 3.48-3.61 (m, 4H), 3.16-3.24 (m, 1H), 2.69-2.84 (m, 2H), 2.36-2.44 (m, 1H), 1.13-1.20 (m, 1H), 0.98-1.09 (m, 6H), 0.76-0.96 (m, 3H).

Biological Assays

The pharmacological properties of the compounds of this invention may be confirmed by a number of biological assays. The exemplified biological assays, which follow, have been carried out with compounds of the invention.

1. In Vitro DGK Inhibition Assays

The DGKα and DGKζ reactions were performed using either extruded liposome (DGKα and DGKζ LIPGLO assays) or detergent/lipid micelle substrate (DGKα and DGKζ assays). The reactions were carried out in 50 mM MOPS pH 7.5, 100 mM NaCl, 10 mM MgCl$_2$, 1 µM CaCl$_2$), and 1 mM DTT (assay buffer). The reactions using a detergent/lipid micelle substrate also contained 50 mM octyl B-D-glucopyranoside. The lipid substrate concentrations were 11 mM PS and 1 mM DAG for the detergent/lipid micelle reactions. The lipid substrate concentrations were 2 mM PS, 0.25 mM DAG, and 2.75 mM PC for the extruded liposome reactions. The reactions were carried out in 150 µM ATP. The enzyme concentrations for the DGKα and DGKζ were 5 nM The compound inhibition studies were carried out as follows: 50 nL droplets of each test compound (top concentration 10 mM with 11 point, 3-fold dilution series for each compound) solubilized in DMSO were transferred to wells of a white 1536 well plate (Corning 3725). A 5 mL enzyme/substrate solution at 2× final reaction concentration was prepared by combining 2.5 mL 4× enzyme solution (20 nM DGKα or DGKζ (prepared as described below) in assay buffer) and 2.5 mL of either 4× liposome or 4× detergent/lipid micelle solution (compositions described below) and incubated at room temperature for 10 minutes. Next, 1 µL 2× enzyme/substrate solution was added to wells containing the test compound and reactions were initiated with the addition of 1 µL 300 uM ATP. The reactions were allowed to proceed for 1 hr, after which 2 µL Glo Reagent (Promega V9101) was added and incubated for 40 minutes. Next, 4 µL Kinase Detection Reagent was added and incubated for 30 minutes. Luminescence was recorded using an EnVision microplate reader. The percent inhibition was calculated from the ATP conversion generated by no enzyme control reactions for 100% inhibition and vehicle-only reactions for 0% inhibition. The compounds were evaluated at 11 concentrations to determine $IC_{50}$.

4× Detergent/Lipid Micelle Preparation

The detergent/lipid micelle was prepared by combining 15 g phosphatidylserine (Avanti 840035P) and 1 g diacylglycerol (8008110) and dissolving into 150 mL chloroform in a 2 L round bottom flask. Chloroform was removed under high vacuum by rotary evaporation. The resulting colorless, tacky oil was resuspended in 400 mL 50 mM MOPS pH 7.5, 100 mM NaCl, 20 mM NaF, 10 mM $MgCl_2$, 1 µM $CaCl_2$), 1 mM DTT, and 200 mM octyl glucoside by vigorous mixing. The lipid/detergent solution was split into 5 mL aliquots and stored at −80° C.

4× Liposome Preparation

The lipid composition was 5 mol % DAG (Avanti 8008110), 40 mol % PS (Avanti 840035P), and 55 mol % PC (Avanti 850457) at a total lipid concentration of 15.2 mg/mL for the 4× liposome solution. The PC, DAG, and PS were dissolved in chloroform, combined, and dried in vacuo to a thin film. The lipids were hydrated to 20 mM in 50 mM MOPS pH 7.5, 100 mM NaCl, 5 mM $MgCl_2$, and were freeze-thawed five times. The lipid suspension was extruded through a 100 nm polycarbonate filter eleven times. Dynamic light scattering was carried out to confirm liposome size (50-60 nm radius). The liposome preparation was stored at 4° C. for as long as four weeks.

Baculovirus Expression of Human DGKα and DGKζ

Human DGK-alpha-TVMV-His-pFBgate and human DGK-zeta-transcript variant-2-TVMV-His-pFBgate baculovirus samples were generated using the Bac-to-Bac baculovirus expression system (Invitrogen) according to the manufacturer's protocol. The DNA used for expression of DGK-alpha and DGK-zeta have SEQ ID NOs: 1 and 3, respectively. Baculovirus amplification was achieved using infected Sf9 cells at 1:1500 virus/cell ratios, and grown for 65 hours at 27° C. post-transfection.

The expression scale up for each protein was carried out in the Cellbag 50L WAVE-Bioreactor System 20/50 from GE Healthcare Bioscience. 12 L of 2×10⁶ cells/mL Sf9 cells (Expression System, Davis, Calif.) grown in ESF921 insect medium (Expression System) were infected with virus stock at 1:200 virus/cell ratios, and grown for 66-68 hours at 27° C. post-infection. The infected cell culture was harvested by centrifugation at 2000 rpm for 20 min 4° C. in a SORVALL® RC12BP centrifuge. The cell pellets were stored at −70° C. until purification.

Purification of Human DGK-Alpha and DGK-Zeta

Full length human DGKα and DGKζ, each expressed containing a TVMV-cleavable C-terminal Hexa-His tag sequence (SEQ ID NOs: 2 and 4, respectively) and produced as described above, were purified from Sf9 baculovirus-infected insect cell paste. The cells were lysed using nitrogen cavitation method with a nitrogen bomb (Parr Instruments), and the lysates were clarified by centrifugation. The clarified lysates were purified to ~90% homogeneity, using three successive column chromatography steps on an ÄKTA Purifier Plus system. The three steps column chromatography included nickel affinity resin capture (i.e. HisTrap FF crude, GE Healthcare), followed by size exclusion chromatography (i.e. HiLoad 26/600 Superdex 200 prep grade, GE Healthcare for DGK-alpha, and HiPrep 26/600 Sephacryl S 300_HR, GE Healthcare for DGK-zeta). The third step was ion exchange chromatography, and differed for the two isoforms. DGKα was polished using Q-Sepharose anion exchange chromatography (GE Healthcare). DGKζ was polished using SP Sepharose cation exchange chromatography (GE Healthcare). The proteins were delivered at concentrations of ≥2 mg/mL. The formulation buffers were identical for both proteins: 50 mM Hepes, pH 7.2, 500 mM NaCl, 10% v/v glycerol, 1 mM TCEP, and 0.5 mM EDTA.

2. Raji CD4 T Cell IL2 Assay

A 1536-well IL-2 assay was performed in 4 µL volume using pre-activated CD4 T cells and Raji cells. Prior to the assay, CD4 T cells were pre-activated by treatment with α-CD3, α-CD28 and PHA at 1.5 µg/mL, 1 µg/mL, and 10 µg/mL, respectively. Raji cells were treated with Staphylococcal enterotoxin B (SEB) at 10,000 ng/mL. Serially diluted compounds were first transferred to 1536-well assay plate (Corning, #3727), followed by addition of 2 µL of pre-activated CD4 T cells (final density at 6000 cells/well) and 2 µL of SEB-treated Raji cells (2000 cells/well). After 24 hours incubation at a 37° C./5% $CO_2$ incubator, 4 µl of IL-2 detection reagents were added to the assay plate (Cisbio, #64IL2PEC). The assay plates were read on an Envision reader. To assess compound cytotoxicity, either Raji or CD4 T cells were incubated with the serially diluted compounds. After 24 hours incubation, 4 µL of Cell Titer Glo (Promega, #G7572) were added, and the plates were read on an Envision reader. The 50% effective concentration ($IC_{50}$) was calculated using the four-parameter logistic formula $y=A+((B-A)/(1+((C/x)^D)))$, where A and B denote minimal and maximal % activation or inhibition, respectively, C is the $IC_{50}$, D is hill slope and x represent compound concentration.

3. CellTiter-Glo CD8 T Cell Proliferation Assay

Frozen naïve human CD8 T cells were thawed in RPMI+ 10% FBS, incubated for 2 h in 37° C., and counted. The 384-well tissue culture plate was coated overnight at 4° C. with 20 µl anti-human CD3 at 0.1 µg/mL in plain RPMI, which was removed off the plate before 20 k/40 µL CD8 T cells with 0.5 µg/ml soluble anti-human CD28 were added to each well. The compounds were echoed to the cell plate immediately after the cells were plated. After 72 h incubation at 37° C. incubator, 10 µL CellTiter-glo reagent (Promega catalog number G7570) was added to each well. The plate was vigorously shaken for 5 mins, incubated at room temperature for another 15 mins and read on Envision for CD8 T cell proliferation. In analysis, 0.1 µg/mL anti-CD3 and 0.5 µg/mL anti-CD28 stimulated CD8 T cell signal was background. The reference compound, 8-(4-(bis(4-fluorophenyl)methyl) piperazin-1-yl)-5-methyl-7-nitro-6-oxo-5,6-dihydro-1,5-naphthyridine-2-carbonitrile, at 3 µM was used to set the 100% range and $EC_{50}$ was at absolute 50% to normalize the data.

4. DGK AP1-Reporter Assay

The Jurkat AP1-luciferase Reporter was generated using the Cignal Lenti AP1 Reporter (luc) Kit from SABiosciences (CLS-011L).

The compounds were transferred from an Echo LDV plate to individual wells of a 384-well plate (white, solid-bottom, opaque PE CulturPlate 6007768) using an Echo550 instrument. The sample size was 30 nL per well; and one destination plate per source plate. The cell suspensions were prepared by transferring 40 mL cells (2×20 mL) to clean 50 mL conical tubes. The cells were concentrated by centrifugation (1200 rpm; 5 mins; ambient temperature). The supernatant was removed and all cells were suspended in RPMI (Gibco 11875)+10% FBS to make a $1.35 \times 10^6$ cells/ml concentration. The cells were added manually using a multi-channel pipette, 30 [L/well of cell suspension to a 384-well TC plate containing the compounds, $4.0 \times 10^4$ cells per well. The cell plates were incubated for 20 minutes at 37° C. and 5% $CO_2$.

During the incubation, anti-CD3 antibody (aCD3) solutions were prepared by mixing 3 μL aCD3 (1.3 mg/mL) with 10 mL medium [final conc=0.4 μg/mL]. Next, 1.5 μl aCD3 (1.3 mg/mL) was mixed with 0.5 mL medium [final conc=4 μg/ml]. After 20 minutes, 10 μL medium was added to all wells in column 1, wells A to M, and 10 μL aCD3 (4 ug/mL) per well was added in column 1, rows N to P for reference. Then using a multi-channel pipette, 10 μL aCD3 (0.4 ug/mL) per well was added. The aCD3 stimulated+/−compound-treated cells were incubated at 37° C., 5% $CO_2$ for 6 hours.

During this incubation period, Steady-Glo (Promega E2520) reagent was slowly thawed to ambient temperature. Next, 20 μL Steady-Glo reagent per well was added using a multi-drop Combi-dispenser. Bubbles were removed by centrifugation (2000 rpm, ambient temperature, 10 secs). The cells were incubated at room temperature for 5 minutes. Samples were characterized by measuring the Relative Light Units (RLU) with an using Envision Plate Reader Instrument on a luminescence protocol. The data was analyzed using the reference compound, 8-(4-(bis(4-fluorophenyl)methyl)piperazin-1-yl)-5-methyl-7-nitro-6-oxo-5,6-dihydro-1,5-naphthyridine-2-carbonitrile, to normalize 100% inhibition.

5. Murine Cytotoxic T Lymphocyte Assay

An antigen-specific cytolytic T-cell (CTL) assay was developed to evaluate functionally the ability of DGKα and DGKζ inhibitors to enhance effector T cell mediated tumor cell killing activity. CD8+ T-cells isolated from the OT-1 transgenic mouse recognize antigen presenting cells, MC38, that present the ovalbumin derived peptide SIINFEKL. Recognition of the cognate antigen initiates the cytolytic activity of the OT-1 antigen-specific CD8+ T cells.

Functional CTL cells were generated as follows: OT-1 splenocytes from 8-12 week old mice were isolated and expanded in the presence of the SIINFEKL peptide at 1 μg/mL and mIL2 at 10 U/mL. After three days, fresh media with mIL2 U/ml was added. On day 5 of the expansion, the CD8+ T cells were isolated and ready for use. Activated CTL cells may be stored frozen for 6 months. Separately, one million MC38 tumor cells were pulsed with 1 μg/mL of SIINFEKL-OVA peptide for 3 hours at 37° C. The cells were washed (3x) with fresh media to remove excess peptide. Finally, CTL cells that were pretreated with DGK inhibitors for 1 hour in a 96-well U bottom plate were combined with the antigen loaded MC38 tumor cells at a 1:10 ratio. The cells were then spun at 700 rpm for 5 min and placed in an incubator overnight at 37° C. After 24 hours, the supernatant was collected for analysis of IFN-γ cytokine levels by AlphaLisa purchased from Perkin Elmer.

6. PHA Proliferation Assay

Phytohaemagglutinin (PHA)-stimulated blast cells from frozen stocks were incubated in RPMI medium (Gibco, ThermoFisher Scientific, Waltham, Mass.) supplemented with 10% fetal bovine serum (Sigma Aldrich, St. Louis, Mo.) for one hour prior to adding to individual wells of a 384-well plate (10,000 cells per well). The compounds were transferred to individual wells of a 384-well plate and treated cells are maintained at 37° C., 5% $CO_2$ for 72 h in culture medium containing human IL2 (20 ng/mL) prior to measuring growth using MTS reagent [3-(4,5-dimethyl-2-yl)-5-(3-carboxymethoxyphenyl)-2-(4-sulfophenyl)-2H-tetrazolium] following manufacturer's instructions (Promega, Madison, Wis.). Percent inhibition was calculated comparing values between IL2 stimulated (0% inhibition) and unstimulated control (100% inhibition). Inhibition concentration ($IC_{50}$) determinations were calculated based on 50% inhibition on the fold-induction between IL2 stimulated and unstimulated treatments.

7. Human CD8 T Cells IFN-γ Assay

Frozen naïve human CD8 T cells were thawed in AIM-V media, incubated for 2 h in 37° C., and counted. The 384-well tissue culture plate was coated overnight at 4° C. with 20 μL anti-human CD3 at 0.05 μg/mL in PBS, which was removed off the plate before 40,000 cells per 40 microliters CD8 T cells with 0.1 μg/mL soluble anti-human CD28 were added to each well. The compounds were transferred using an Echo liquid handler to the cell plate immediately after the cells were plated. After 20 h incubation at 37° C. incubator, 3 microliters per well supernatants transferred into a new 384-well white assay plate for cytokine measurement.

Interferon-γ (IFN-γ) was quantitated using the AlphLISA kit (Cat #AL217) as described by the manufacturer manual (Perkin Elmer). The counts from each well were converted to IFN-γ concentration (μg/mL). The compound $EC_{50}$ values were determined by setting 0.05 μg/mL anti-CD3 plus 0.1 μg/mL anti-CD28 as the baseline, and co-stimulation of 3 μM of the reference compound, 8-(4-(bis(4-fluorophenyl)methyl) piperazin-1-yl)-5-methyl-7-nitro-6-oxo-5,6-dihydro-1,5-naphthyridine-2-carbonitrile, with anti-CD3 plus anti-CD28 as 100% activation.

8. Human CD8 T cells pERK Assay

Frozen naïve human CD8 T cells were thawed in AIM-V media, incubated for 2 h in 37° C., and counted. The CD8 positive T cells were added to 384-well tissue culture plate at 20,000 cells per well in AIM-V media. One compound was added to each well, then bead bound anti-human CD3 and anti-CD28 mAb were added at final concentration of 0.3 μg/mL. The cells were incubated at 37° C. for 10 minutes. The reaction was stopped by adding lysis buffer from the AlphaLISA Surefire kit. (Perkin Elmer, cat #ALSU-PERK-A). Lysate (5 μL per well) was transferred into a new 384-well white assay plate for pERK activation measurement.

Compound $EC_{50}$ was determined as setting anti-CD3 plus anti-CD28 as baseline, and co-stimulation of 3 μM 8-(4-(bis (4-fluorophenyl)methyl)piperazin-1-yl)-5-methyl-7-nitro-6-oxo-5,6-dihydro-1,5-naphthyridine-2-carbonitrile with anti-CD3 plus anti-CD28 as 100% activation.

9. Human Whole Blood IFN-γ Assay

Human venous whole blood (22.5 μL per well), obtained from healthy donors, was pre-treated with compounds for one hour at 37° C. in a humidified 95% air/5% $CO_2$ incubator. The blood was stimulated with 2.5 μL anti-human CD3 and anti-CD28 mAb at a final concentration of 1 μg/mL each for 24 hours at 37° C. IFN-γ in the supernatants was measured using AlphLISA kit (Cat #AL217).

Compound $EC_{50}$ determined as setting anti-CD3 plus anti-CD28 as baseline, and co-stimulation of 3 μM of the reference compound, 8-(4-(bis(4-fluorophenyl)methyl) piperazin-1-yl)-5-methyl-7-nitro-6-oxo-5,6-dihydro-1,5-naphthyridine-2-carbonitrile, with anti-CD3 plus anti-CD28 as 100% activation.

TABLE A

In vitro DGK Inhibition $IC_{50}$ Activity Values

| x. No. | DGKa LIPGLO $IC_{50}$ (μM) | DGKz LIPGLO $IC_{50}$ (μM) | HuCD8 INFG Normalized $EC_{50}$ (μM) | msCTL INFg $IC_{50}$ (μM) | INFg Whole Blood Normalized Agonist $EC_{50}$ (μM) |
|---|---|---|---|---|---|
| 1 | 3.0 | 0.48 | 0.096 | 0.23 | 0.82 |
| 2 | 2.6 | 3.3 | 0.12 | 0.21 | 2.7 |
| 3 | 0.19 | 0.40 | 0.043 | 0.070 | 0.46 |
| 4 | 8.1 | 1.7 | 0.30 | 0.32 | 3.5 |
| 5 | 23 | 42 | — | — | — |
| 6 | 25 | 16 | 0.56 | — | — |
| 8 | 17 | 5.0 | 0.23 | 1.0 | 14 |
| 9 | 2.1 | 9.5 | — | — | 1.6 |
| 10 | 97 | 5.1 | 0.15 | — | 5.0 |
| 11 | 3.6 | 240 | — | — | — |
| 12 | 2.7 | 58 | 10 | — | 13 |
| 15 | 5.1 | 6.6 | 10 | 0.91 | — |
| 16 | 7.5 | 12 | 0.53 | 1.4 | — |
| 17 | 2.3 | 19 | 6.5 | — | — |
| 18 | 0.80 | 12 | 0.25 | 10 | 20 |
| 19 | 42 | 240 | 10 | 8.7 | 20 |
| 20 | 95 | 130 | 10 | 10 | 20 |
| 22 | 44 | 37 | 10 | 10 | 20 |
| 23 | 240 | 100 | — | 1.4 | 10 |
| 24 | 1.5 | 3.9 | — | 0.20 | 13 |
| 25 | 0.65 | 0.25 | 0.0043 | 0.041 | 0.39 |
| 26 | 24 | 3.0 | 2.3 | 10 | 20 |
| 27 | 240 | 1.7 | 0.062 | 0.064 | 0.52 |
| 28 | 4.6 | 2.1 | 0.038 | 0.57 | 5.3 |
| 29 | 1.5 | 0.46 | 0.018 | 0.037 | 1.3 |
| 30 | 0.50 | 0.43 | 0.43 | 0.015 | 1.6 |
| 32 | 0.98 | 0.85 | 0.017 | 0.043 | 0.40 |
| 34 | 0.69 | 0.51 | 0.18 | — | 1.3 |
| 35 | 21 | 0.77 | 0.061 | 1.1 | 2.2 |
| 36 | 3.3 | 3.3 | 1.2 | 1.2 | 4.6 |
| 38 | 2.2 | 1.8 | 0.067 | 0.078 | 3.2 |
| 39 | 240 | 9.4 | 0.22 | 1.9 | 9.7 |
| 40 | 1.2 | 0.63 | 0.028 | 0.071 | 0.78 |
| 41 | 14 | 46 | 1.5 | — | — |
| 42 | 180 | 9.7 | 0.61 | 2.6 | 3.1 |
| 43 | 6.2 | 3.1 | 0.087 | — | 1.2 |
| 44 | 2.9 | 5.5 | 0.46 | 0.59 | 3.9 |
| 45 | 7.2 | 2.4 | 0.53 | 0.91 | 2.3 |
| 46 | 240 | 3.5 | 4.7 | — | — |
| 47 | 260 | 5.2 | 10 | — | 5.0 |
| 48 | 240 | 20 | 3.8 | — | — |
| 49 | 25 | 8.7 | 0.49 | — | 6.3 |
| 50 | 2.2 | 0.75 | 0.072 | 0.15 | 1.5 |
| 51 | — | 2.1 | 0.51 | 1.9 | 1.6 |
| 52 | 24 | 150 | — | — | — |
| 53 | 140 | 94 | 10 | — | — |
| 54 | 200 | 120 | 10 | 10 | — |
| 55 | 240 | 180 | 6.4 | — | — |
| 57 | 52 | 140 | 6.0 | — | — |
| 58 | 7.2 | 180 | — | — | — |
| 60 | 240 | 72 | 10 | 10 | — |
| 61 | 240 | 170 | 10 | 10 | — |
| 62 | 240 | 15 | 1.8 | 10 | — |
| 63 | 240 | 240 | 0.21 | 1.6 | — |
| 64 | 240 | 240 | 10 | 8.8 | — |
| 65 | 240 | — | 1.7 | 8.4 | 16 |
| 66 | 2.4 | 1.2 | 0.16 | 0.066 | — |
| 67 | 48 | 0.92 | 0.030 | — | — |
| 68 | 18 | 0.25 | 0.011 | — | — |
| 69 | 21 | 0.85 | — | 0.22 | 2.5 |
| 70 | 220 | 19 | — | — | 10 |
| 71 | 240 | 52 | — | 3.8 | 10 |
| 72 | 40 | 0.76 | — | 0.078 | 1.2 |
| 73 | 0.52 | 0.31 | — | 0.15 | 0.29 |
| 74 | 23 | 8.6 | — | 0.29 | 8.6 |
| 75 | 0.99 | 0.40 | — | 0.023 | — |
| 76 | 3.4 | 5.2 | 10 | 0.28 | 1.6 |
| 77 | 81 | 240 | 10 | 3.3 | 1.7 |
| 78 | 18 | 1.9 | 0.21 | 2.0 | 8.4 |
| 79 | 6.7 | 240 | 10 | 8.0 | 10 |
| 80 | 0.67 | 240 | — | 3.1 | 10 |
| 81 | 25 | 16 | 1.7 | 0.58 | 8.7 |
| 84 | 81 | 240 | 10 | 10 | 20 |
| 85 | 240 | 240 | — | 10 | 20 |
| 86 | 7.4 | 1.2 | — | 0.20 | 2.9 |
| 87 | 28 | 6.6 | — | 0.45 | — |
| 88 | 140 | 240 | 2.0 | 0.99 | 10 |
| 89 | 240 | 77 | — | 2.6 | 20 |
| 90 | 240 | 240 | — | 4.8 | 20 |
| 91 | 240 | 240 | — | — | — |
| 92 | 96 | 5.4 | 9.7 | 0.69 | 9.0 |
| 93 | 4.3 | 0.68 | 0.063 | 0.081 | 1.4 |
| 94 | 27 | 4.4 | 0.40 | — | — |
| 95 | 2.6 | 0.76 | 0.021 | — | — |
| 96 | 240 | 14 | — | — | 13 |
| 97 | 14 | 1.7 | 0.057 | 0.096 | 1.7 |
| 99 | 7.0 | 2.8 | 0.17 | 1.2 | 2.8 |
| 100 | 1.9 | 3.1 | 0.089 | 0.11 | 1.4 |
| 101 | 3.3 | 1.6 | 0.077 | 0.14 | 2.3 |
| 102 | 2.9 | 8.3 | — | — | — |
| 103 | 0.77 | 0.83 | 0.028 | 0.076 | 0.73 |
| 104 | 4.4 | 4.4 | 0.18 | 0.56 | 6.5 |
| 105 | 1.4 | 0.82 | — | 0.074 | 4.3 |
| 106 | 240 | 13 | 0.61 | 2.9 | 8.5 |
| 107 | 40 | 0.20 | 0.027 | 0.75 | 11 |
| 108 | 3.4 | 0.13 | 0.033 | 0.13 | 0.44 |
| 109 | 24 | 0.10 | 0.015 | 0.48 | 1.3 |
| 111 | 62 | 1.6 | 0.073 | — | — |
| 112 | 77 | 2.6 | — | 1.6 | 7.0 |
| 114 | 0.42 | 1.6 | 0.057 | — | 0.49 |
| 115 | 1.0 | 8.8 | 0.39 | — | 2.0 |
| 116 | 9.5 | 3.6 | 0.16 | 0.56 | 3.3 |
| 117 | 0.35 | 7.2 | 0.28 | 0.27 | 2.5 |
| 118 | 10 | 63 | 0.71 | — | — |
| 119 | 29 | 1.7 | 0.61 | 6.3 | 5.1 |
| 120 | 110 | 240 | 1.0 | 4.7 | 20 |
| 121 | 240 | 52 | — | — | — |
| 122 | 210 | 4.8 | — | 3.8 | 10 |
| 123 | 2.4 | 240 | — | 2.4 | 35 |
| 124 | 9.9 | 15 | — | 0.39 | 4.8 |
| 125 | 36 | 240 | — | — | — |
| 126 | 230 | 31 | — | 10 | 20 |
| 127 | 1.5 | 2.3 | — | 0.36 | 4.3 |
| 128 | 47 | 2.0 | 1.4 | 0.94 | 20 |
| 129 | 12 | 0.82 | — | 0.71 | 5.4 |
| 130 | 18 | 0.96 | — | 0.75 | 4.0 |
| 131 | 10 | 15 | 0.40 | 5.9 | 12 |
| 132 | 51 | 2.7 | 2.1 | 7.1 | 8.3 |
| 133 | 6.4 | 12 | 0.84 | 1.1 | 5.8 |
| 134 | 13 | 4.9 | 0.59 | 0.39 | — |
| 135 | 110 | 10 | 10 | 3.6 | 61 |
| 136 | 25 | 39 | 0.95 | 0.52 | — |
| 137 | 240 | 33 | 1.5 | 10 | — |
| 138 | 82 | 95 | 10 | — | — |
| 139 | 240 | 110 | 50 | 10 | — |
| 140 | 150 | 25 | 6.6 | 10 | — |
| 141 | 240 | 200 | — | — | — |
| 142 | 40 | 65 | 10 | — | — |
| 143 | 5.4 | 6.4 | — | 0.33 | 5.7 |
| 144 | 1.4 | 2.4 | 1.2 | — | — |
| 145 | 9.0 | 23 | — | — | — |
| 146 | 84 | 14 | 0.66 | — | — |
| 147 | 48 | 15 | 2.0 | — | — |
| 148 | 240 | 75 | 0.42 | — | — |
| 149 | 35 | 21 | — | — | — |
| 150 | 240 | 29 | 10 | — | — |
| 151 | 3.6 | 8.8 | 0.15 | — | — |
| 152 | 7.7 | 240 | — | — | — |
| 153 | 240 | 240 | — | — | — |
| 155 | 240 | 240 | — | 10 | 20 |
| 156 | 8.5 | 9.8 | — | 0.40 | 6.9 |
| 157 | 0.35 | 0.38 | 0.072 | 0.078 | 0.53 |
| 158 | 3.6 | 13 | 0.11 | — | — |
| 159 | 2.8 | 0.96 | 0.035 | 0.14 | 1.0 |

TABLE A-continued

In vitro DGK Inhibition IC$_{50}$ Activity Values

| x. No. | DGKa LIPGLO IC$_{50}$ (μM) | DGKz LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) |
|---|---|---|---|---|---|
| 160 | 2.4 | 44 | 10 | 10 | 20 |
| 161 | 68 | 29 | 0.52 | 1.5 | 8.6 |
| 162 | 1.9 | 2.4 | — | — | — |
| 163 | 16 | 12 | 1.5 | 2.1 | — |
| 167 | 7.7 | 58 | 10 | 10 | 20 |
| 168 | 7.5 | 240 | 10 | 0.51 | 10 |
| 169 | 3.2 | 77 | 0.44 | 2.6 | 13 |
| 170 | 240 | 7.0 | 0.19 | 2.6 | 12 |
| 171 | 0.24 | 94 | 10 | — | — |
| 172 | 1.9 | 1.4 | 0.036 | 0.039 | 1.3 |
| 173 | 0.95 | 1.4 | 0.025 | 0.045 | 0.99 |
| 174 | 0.82 | 0.43 | 0.034 | 0.11 | 2.2 |
| 175 | 2.4 | 0.33 | 0.051 | 0.61 | 4.3 |
| 177 | 5.5 | 2.7 | 0.13 | 0.87 | 5.0 |
| 178 | 0.61 | 0.39 | — | — | 0.58 |
| 179 | 0.88 | 0.88 | 0.052 | 0.049 | 1.0 |
| 180 | 4.1 | 1.5 | 0.070 | 0.40 | 0.83 |
| 181 | 240 | 240 | 10 | 10 | 20 |
| 182 | 0.87 | 1.6 | 0.030 | — | 0.68 |
| 183 | 0.66 | 0.42 | 0.039 | 0.033 | 0.70 |
| 184 | 0.46 | 0.51 | 0.047 | 0.064 | 0.57 |
| 185 | 4.4 | 0.21 | 10 | — | 2.0 |
| 186 | 3.3 | 14 | 10 | — | 20 |
| 187 | 0.18 | 1.3 | 0.11 | — | 1.4 |
| 188 | 0.69 | 3.8 | 0.014 | — | 0.66 |
| 189 | 0.20 | 0.55 | 0.10 | — | 1.2 |
| 190 | 0.22 | 1.1 | 0.17 | — | 0.70 |
| 191 | 0.20 | 0.59 | 0.031 | — | 0.43 |
| 192 | 0.12 | 1.5 | 0.056 | — | 0.60 |
| 194 | 0.20 | 0.68 | 0.040 | — | 0.98 |
| 195 | 1.1 | 1.1 | 0.0099 | — | 1.8 |
| 196 | 1.3 | 3.0 | 0.047 | — | 1.4 |
| 197 | 0.20 | 3.7 | 0.035 | 0.082 | 1.1 |
| 198 | 0.24 | 0.87 | 0.021 | — | 0.59 |
| 199 | 0.10 | 0.10 | 0.061 | — | 0.25 |
| 200 | 0.061 | 0.20 | 0.040 | — | 0.54 |
| 201 | 0.45 | 0.79 | 0.031 | — | 0.50 |
| 202 | 0.11 | 0.49 | 0.0083 | — | 0.38 |
| 203 | 0.19 | 0.029 | 0.032 | — | 0.29 |
| 204 | 1.3 | 0.22 | 0.012 | — | 0.62 |
| 205 | 37 | 0.67 | 0.15 | — | 0.99 |
| 206 | 24 | 0.44 | 0.039 | — | 1.4 |
| 207 | 71 | 3.1 | 0.43 | — | 3.5 |
| 208 | 11 | 0.68 | 0.25 | — | 1.0 |
| 209 | 15 | 0.32 | 0.17 | — | 1.5 |
| 210 | 14 | 0.26 | 0.13 | 0.12 | 1.1 |
| 211 | 0.039 | 0.15 | 0.029 | — | 0.80 |
| 212 | 0.21 | 0.59 | 0.057 | — | 0.89 |
| 213 | 0.36 | 0.79 | 1.1 | — | 0.46 |
| 214 | 0.072 | 0.29 | 0.12 | — | 0.62 |
| 215 | 0.66 | 0.53 | 0.033 | — | 2.1 |
| 216 | 0.18 | 0.21 | 0.074 | — | 0.13 |
| 217 | 50 | 140 | 7.8 | — | 20 |
| 218 | 9.5 | >250 | 10 | — | 20 |
| 220 | 15 | 0.36 | 3.3 | — | 21 |
| 221 | 1.2 | 0.75 | 0.042 | — | 3.0 |
| 222 | 0.29 | 0.71 | 0.046 | — | 0.68 |
| 223 | 0.28 | 0.034 | 0.029 | — | 0.87 |
| 224 | 1.5 | 0.057 | 0.024 | — | 1.0 |
| 225 | — | 0.57 | 0.061 | — | 7.6 |
| 226 | 67 | 1.4 | 0.067 | — | 1.7 |
| 227 | >250 | 1.0 | 0.016 | — | 13 |
| 228 | 58 | 1.4 | 0.031 | — | 2.8 |
| 229 | 58 | 0.45 | 1.0 | — | 8.3 |
| 230 | 26 | 0.49 | 0.37 | — | 5.3 |
| 231 | 240 | 3.7 | 1.1 | — | 20 |
| 232 | 240 | 1.7 | 10 | — | 20 |
| 233 | 27 | 3.6 | 10 | — | 20 |
| 234 | 240 | 8.7 | 2.5 | — | 20 |
| 235 | 81 | 4.8 | 1.5 | — | 20 |
| 236 | 240 | 11 | 10 | — | 20 |
| 237 | 0.93 | 1.4 | 0.039 | — | — |
| 238 | 17 | 79 | 5.0 | — | — |
| 239 | 5.9 | 64 | 10 | — | — |
| 240 | 15 | 20 | 12 | — | — |
| 241 | 8.3 | 17 | 1.6 | — | 16 |
| 242 | 4.4 | 0.97 | 0.17 | — | 1.5 |
| 243 | 0.29 | 1.9 | 0.16 | — | 1.5 |
| 244 | 0.26 | 1.1 | 0.11 | — | 1.7 |
| 245 | 0.0086 | 1.1 | 0.75 | — | 5.2 |
| 246 | 0.12 | 0.46 | 0.027 | — | 0.55 |
| 247 | 0.37 | 0.21 | 0.12 | 0.11 | 0.39 |
| 248 | 1.3 | 0.79 | 0.053 | — | 0.71 |
| 249 | 0.82 | 0.44 | 0.032 | — | 0.69 |
| 250 | 0.60 | 0.63 | 0.12 | 0.19 | 0.71 |
| 251 | 0.67 | 0.32 | 0.023 | 0.032 | 0.44 |
| 252 | 0.66 | 0.44 | 0.16 | 0.022 | 0.43 |
| 253 | 0.20 | 0.69 | 0.087 | — | 3.0 |
| 254 | 0.14 | 1.6 | 0.21 | — | 2.2 |
| 255 | 0.77 | 1.7 | 0.18 | — | 3.2 |
| 256 | 0.14 | 0.57 | 0.022 | — | 0.65 |
| 257 | 25 | 0.83 | 0.81 | — | 6.2 |
| 258 | 0.24 | 0.82 | 0.056 | — | 1.4 |
| 259 | 3.1 | 0.84 | 0.55 | — | 2.1 |
| 260 | 3.8 | 1.1 | 0.9 | — | 4.4 |
| 261 | 0.39 | 1.1 | 0.23 | — | 0.88 |
| 262 | 0.64 | 2.5 | 0.31 | — | 7.1 |
| 263 | 6.5 | 1.7 | 0.61 | — | 6.3 |
| 264 | 0.035 | 3.0 | 0.26 | — | 11 |
| 265 | 23 | 2.6 | 1.6 | — | 3.8 |
| 266 | 1.4 | 2.1 | 1.1 | — | 2.8 |
| 267 | 0.39 | 1.6 | 10 | — | — |
| 268 | 0.23 | 1.2 | 0.054 | — | 1.7 |
| 269 | 78 | 240 | 1.2 | — | 8.8 |
| 270 | 3.4 | 0.57 | 0.062 | — | 2.0 |
| 271 | 0.13 | 1.9 | 0.55 | — | 1.4 |
| 272 | 0.99 | 0.45 | 0.079 | — | 2.5 |
| 273 | 3.8 | 15 | — | — | 7.1 |
| 274 | 5.7 | 2.5 | 0.042 | — | 3.6 |
| 275 | 1.9 | 3.6 | 0.23 | — | 3.7 |
| 276 | 1.2 | 1.0 | 0.18 | — | 2.4 |
| 277 | 0.25 | 1.5 | 0.066 | — | 0.84 |
| 278 | 0.87 | 1.5 | 2.2 | — | 3.2 |
| 279 | 2.3 | 4.6 | 1.2 | — | 3.7 |
| 280 | 7.9 | 7.3 | 0.68 | — | 7.7 |
| 281 | 2.8 | 4.4 | 0.56 | — | 2.7 |
| 282 | 1.2 | 0.94 | 0.069 | — | 3.8 |
| 283 | 0.65 | 1.1 | 0.068 | — | 0.89 |
| 284 | 0.25 | 0.51 | 0.036 | — | 0.78 |
| 285 | 0.27 | 0.68 | 0.15 | — | 1.5 |
| 286 | 1.9 | 3.2 | 0.37 | — | 2.2 |
| 287 | 0.034 | 1.6 | 12 | — | 7.1 |
| 288 | 2.0 | 2.2 | 0.026 | — | 0.81 |
| 289 | 3.0 | 0.76 | 0.22 | — | 1.0 |
| 290 | 1.7 | 3.5 | 2.0 | — | 7.9 |
| 291 | 0.60 | 1.5 | 0.034 | 0.47 | 1.3 |
| 292 | 0.28 | 3.0 | 1.7 | — | 2.2 |
| 293 | 0.33 | 0.16 | — | — | 0.46 |
| 294 | 0.19 | 0.33 | 0.020 | — | 0.56 |
| 295 | 1.8 | 1.3 | 0.20 | — | 0.64 |
| 296 | 0.63 | 0.90 | 0.40 | — | 1.2 |
| 297 | 0.015 | 0.74 | 0.49 | — | 1.5 |
| 298 | 1.5 | 2.4 | 0.029 | — | 0.57 |
| 299 | 1.7 | 1.1 | 0.017 | — | 0.65 |
| 300 | 0.89 | 1.0 | 0.021 | — | 0.12 |
| 301 | 1.5 | 0.87 | 0.0095 | 0.072 | 0.52 |
| 302 | 0.17 | 0.64 | 0.023 | 0.024 | 0.57 |
| 303 | 0.50 | 0.69 | 0.16 | 0.057 | 0.65 |
| 304 | 0.19 | 0.26 | 0.0085 | 0.047 | 0.49 |
| 305 | 0.58 | 0.33 | 0.026 | 0.023 | 0.68 |
| 306 | 0.47 | 1.3 | 0.054 | 0.053 | 0.53 |
| 307 | 0.47 | 1.0 | 0.030 | 0.031 | 0.33 |
| 308 | 0.025 | 0.16 | 0.29 | 0.081 | 0.52 |
| 309 | 0.72 | 0.49 | 0.036 | — | 0.88 |

TABLE A-continued

In vitro DGK Inhibition IC$_{50}$ Activity Values

| x. No. | DGKa LIPGLO IC$_{50}$ (μM) | DGKz LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) |
|---|---|---|---|---|---|
| 310 | 1.3 | 1.6 | — | — | 1.9 |
| 312 | 0.71 | 3.4 | — | — | — |
| 313 | 2.3 | 4.8 | — | — | — |
| 314 | 8.5 | 31 | — | — | — |
| 315 | 4.1 | 1.8 | — | — | — |
| 316 | 2.4 | 0.93 | — | — | — |
| 317 | 3.8 | 13 | — | — | — |
| 318 | 4.9 | 14 | — | — | 7.4 |
| 319 | 2.2 | 6.6 | — | — | 1.6 |
| 320 | 9.3 | 28 | — | — | — |
| 321 | 4.3 | 0.24 | — | — | 0.95 |
| 322 | 2.7 | 2.2 | — | — | 2.2 |
| 323 | 2.1 | — | — | — | 5.7 |
| 324 | 1.2 | 4.1 | — | — | 4.7 |
| 325 | 0.68 | 2.3 | — | — | 3.2 |
| 326 | — | 6.5 | — | — | 20 |
| 327 | 3.2 | 4.9 | 1.2 | — | 0.70 |
| 328 | 1.2 | 2.6 | 6.0 | — | 1.0 |
| 329 | 3.6 | 4.5 | — | — | 13 |
| 330 | 0.26 | 0.50 | — | — | 1.2 |
| 331 | 1.7 | 1.9 | — | — | 20 |
| 332 | 3.1 | 1.0 | — | — | 1.9 |
| 333 | 0.83 | 1.1 | — | — | 1.2 |
| 334 | 0.50 | 0.56 | — | — | 1.9 |
| 335 | 1.2 | 2.5 | — | — | 1.2 |
| 336 | 0.74 | 0.23 | — | — | 2.0 |
| 337 | 0.57 | 0.46 | 0.048 | — | 0.44 |
| 338 | 0.15 | 0.33 | 0.020 | — | 0.13 |
| 339 | 1.7 | 3.7 | — | — | — |
| 340 | 0.32 | 0.22 | — | — | 0.08 |
| 341 | 0.069 | 0.55 | — | — | 0.12 |
| 344 | 1.0 | 1.0 | 0.024 | — | 0.46 |
| 345 | 4.0 | 33 | — | — | 6.8 |
| 346 | 1.3 | 1.5 | — | — | 1.1 |
| 350 | 1.9 | 1.8 | 0.20 | — | 0.85 |
| 351 | 0.64 | 1.3 | 0.031 | — | 0.089 |
| 352 | 0.52 | 1.7 | — | — | 0.79 |
| 353 | 72 | 1.4 | — | — | — |
| 354 | 0.45 | 1.0 | — | — | 0.35 |
| 355 | 0.89 | 0.74 | — | — | 0.34 |
| 356 | >250 | 0.42 | — | — | 20 |
| 357 | — | 0.89 | — | — | 13 |
| 358 | 9.0 | 21 | — | — | 1.0 |
| 359 | 0.28 | 1.1 | 0.038 | — | 0.66 |
| 360 | 0.57 | 2.5 | 0.13 | — | 0.31 |
| 361 | 0.21 | 1.1 | — | — | 1.1 |
| 362 | 0.23 | 0.34 | 0.23 | — | 0.72 |
| 363 | 0.15 | 0.40 | 0.099 | — | 0.13 |
| 364 | 1.6 | 3.9 | — | — | — |
| 365 | 0.27 | 0.77 | — | — | 0.36 |
| 366 | 0.57 | 2.0 | — | — | 0.49 |
| 367 | 1.3 | 2.7 | 0.013 | — | 0.46 |
| 368 | 1.7 | 2.5 | 0.010 | — | 0.46 |
| 369 | 2.8 | 1.4 | 0.15 | — | 0.48 |
| 370 | 1.1 | 0.76 | — | — | — |
| 371 | 3.0 | 2.1 | — | — | — |
| 372 | 0.55 | 0.27 | 0.022 | — | 0.27 |
| 373 | 6.5 | 0.74 | 0.18 | — | 0.32 |
| 374 | 0.57 | 3.8 | — | — | — |
| 375 | 0.27 | 2.7 | 0.049 | — | 0.33 |
| 376 | 2.9 | 1.1 | 0.028 | — | 0.38 |
| 377 | 0.31 | 3.9 | — | — | — |
| 378 | 0.69 | 2.5 | 0.0053 | — | 0.49 |
| 379 | 2.0 | 2.1 | — | — | 1.1 |
| 380 | 3.1 | 1.6 | — | — | 0.63 |
| 381 | 0.36 | 0.50 | 0.0039 | — | 0.18 |
| 382 | 0.22 | 2.5 | — | — | 2.6 |
| 383 | 5.6 | 13 | — | — | 3.2 |
| 384 | 1.5 | 6.9 | — | — | — |
| 385 | 3.3 | 6.3 | — | — | — |
| 386 | 2.3 | 4.6 | — | — | — |
| 387 | 1.5 | 3.1 | — | — | 3.6 |
| 388 | 8.5 | 14 | — | — | — |
| 389 | 2.2 | 1.1 | 0.025 | — | 0.28 |
| 390 | 17 | 7.4 | — | — | 2.6 |
| 391 | 3.1 | 2.4 | 0.081 | — | 0.89 |
| 392 | 0.18 | 2.1 | 0.066 | — | 0.33 |
| 393 | 1.6 | 7.1 | — | — | 3.5 |
| 394 | 42 | 49 | — | — | 18 |
| 395 | 48 | 7.8 | — | — | 6.3 |
| 396 | 1.3 | 3.6 | — | — | 0.19 |
| 397 | 1.8 | 16 | — | — | — |
| 398 | 1.1 | 1.4 | — | — | 0.41 |
| 399 | 2.3 | 0.69 | — | — | 0.57 |
| 400 | 4.2 | 3.2 | — | — | — |
| 401 | 7.8 | 4.5 | — | — | 0.93 |
| 402 | 0.82 | 9.3 | — | — | — |
| 403 | 0.14 | 0.46 | — | — | 0.17 |
| 404 | 0.36 | 4.1 | — | — | — |
| 405 | 0.46 | 4.0 | — | — | — |
| 406 | 2.4 | 2.8 | — | — | 11 |
| 407 | 0.029 | 1.0 | — | — | 20 |
| 408 | 7.5 | 0.80 | — | — | 0.80 |
| 409 | 5.3 | 0.053 | — | — | 0.43 |
| 411 | 22 | 19 | — | — | — |
| 412 | 12 | 13 | — | — | — |
| 413 | 12 | 15 | — | — | — |
| 414 | 24 | 11 | — | — | 8.5 |
| 415 | 35 | 19 | — | — | 16 |
| 416 | 21 | 14 | — | — | 5.2 |
| 417 | 20 | 11 | — | — | 7.7 |
| 418 | 1.5 | 0.13 | — | — | 0.28 |
| 419 | 0.95 | 0.34 | — | — | 0.96 |
| 420 | 0.31 | 0.25 | — | — | 0.15 |
| 421 | 7.8 | 1.8 | — | — | 2.6 |
| 422 | 0.12 | 0.089 | — | — | 0.22 |
| 423 | 0.027 | 0.17 | — | — | 0.74 |
| 424 | 0.29 | 37 | — | — | 16 |
| 425 | 0.058 | 1.5 | 0.11 | — | 0.27 |
| 426 | 0.77 | 11 | — | — | 2.3 |
| 427 | 0.032 | 1.2 | 0.047 | — | 0.20 |
| 428 | 0.25 | 0.70 | — | — | 20 |
| 429 | 0.86 | 16 | — | — | 2.4 |
| 430 | 0.41 | 2.0 | 0.046 | — | 0.50 |
| 431 | 7.3 | 1.1 | — | — | 1.6 |
| 432 | 0.51 | 0.50 | 0.015 | — | 0.067 |
| 433 | 79 | 0.24 | — | — | 1.3 |
| 434 | 1.8 | 0.70 | 0.0057 | — | 0.60 |
| 435 | 1.1 | 4.9 | — | — | 2.5 |
| 436 | 0.065 | 0.81 | — | — | 0.44 |
| 437 | 0.40 | 0.67 | — | — | 0.54 |
| 438 | 0.32 | 0.81 | — | — | 0.74 |
| 439 | — | 0.32 | — | — | 0.68 |
| 440 | 0.081 | 0.32 | — | — | 1.0 |
| 441 | 1.5 | 2.4 | — | — | 7.9 |
| 442 | 1.4 | 1.8 | — | — | 7.5 |
| 443 | 1.4 | 0.11 | 0.094 | — | 0.37 |
| 444 | 0.13 | 0.76 | 0.049 | — | 0.51 |
| 445 | 40 | 0.42 | — | — | 2.6 |
| 446 | 1.7 | 2.1 | — | — | 1.1 |
| 447 | 7.7 | 0.29 | 0.050 | — | 0.60 |
| 448 | 0.66 | 0.66 | — | — | 1.1 |
| 450 | 2.6 | 0.29 | 0.070 | — | 0.28 |
| 451 | 24 | 0.53 | — | — | 7.6 |
| 452 | 0.29 | 1.9 | 0.20 | — | 0.55 |
| 453 | 0.31 | 1.0 | — | — | 2.8 |
| 454 | 0.23 | 0.54 | — | — | 0.47 |
| 455 | 1.0 | 2.4 | 0.097 | — | 0.74 |
| 456 | 0.23 | 1.0 | — | — | 1.1 |
| 457 | 0.14 | 1.1 | — | — | 0.59 |
| 458 | 1.1 | 0.11 | — | — | 0.51 |
| 459 | 36 | 1.1 | — | — | — |
| 460 | 0.030 | 0.038 | 0.027 | — | 0.52 |
| 461 | 1.4 | 3.6 | — | — | 2.1 |

TABLE A-continued

In vitro DGK Inhibition IC$_{50}$ Activity Values

| x. No. | DGKa LIPGLO IC$_{50}$ (µM) | DGKz LIPGLO IC$_{50}$ (µM) | HuCD8 INFG Normalized EC$_{50}$ (µM) | msCTL INFg IC$_{50}$ (µM) | INFg Whole Blood Normalized Agonist EC$_{50}$ (µM) |
|---|---|---|---|---|---|
| 462 | 0.14 | 1.8 | 0.020 | — | 0.45 |
| 463 | 0.33 | 4.6 | — | — | 3.7 |
| 464 | 0.28 | 1.7 | — | — | — |
| 465 | 0.20 | 0.98 | — | — | 20 |
| 466 | 0.19 | 1.8 | — | — | 5.5 |
| 467 | 0.98 | 0.45 | — | — | 20 |
| 468 | 0.14 | 1.6 | — | — | 1.3 |
| 469 | 1.7 | 0.51 | — | — | 3.2 |
| 470 | 13 | 2.0 | — | — | 0.37 |
| 471 | 0.25 | 0.52 | 0.20 | — | 0.57 |
| 472 | 1.3 | 2.9 | — | — | 1.3 |
| 473 | 1.7 | 4.0 | — | — | 0.88 |
| 474 | 0.26 | 1.2 | — | — | 0.26 |
| 475 | 16 | 2.0 | — | — | 20 |
| 476 | 0.94 | 0.30 | 0.16 | — | 0.63 |
| 477 | 0.27 | 0.30 | 0.0096 | — | 0.95 |
| 478 | 2.1 | 2.4 | — | — | 3.8 |
| 479 | 0.91 | 1.9 | — | — | 2.1 |
| 480 | 1.6 | 1.8 | — | — | 4.9 |
| 481 | 1.4 | 1.8 | — | — | — |
| 482 | 0.13 | 0.17 | — | — | 0.29 |
| 483 | 3.3 | 3.9 | — | — | 4.3 |
| 486 | 27 | 14 | — | — | — |
| 487 | 41 | 11 | — | — | — |
| 488 | 15 | 11 | — | — | — |
| 556 | 2.6 | 6.0 | — | — | — |
| 557 | 0.50 | 5.3 | — | — | 1.6 |
| 558 | 10 | 100 | — | — | 15 |
| 559 | 0.065 | 2.7 | — | — | 0.27 |
| 560 | 0.58 | 2.9 | — | — | — |
| 561 | 7.1 | 10 | — | — | — |
| 567 | 2.8 | 18 | — | — | 20 |
| 568 | 23 | 20 | — | — | 20 |
| 569 | 22 | 0.49 | — | — | 15 |
| 570 | >250 | >250 | — | — | — |
| 573 | 4.3 | 0.64 | — | — | — |
| 574 | 1.8 | 28 | — | — | 7.3 |
| 575 | 0.18 | 1.6 | — | — | 0.36 |
| 581 | 1.3 | 6.7 | — | — | 2.7 |
| 582 | 0.44 | 6.0 | — | — | 1.7 |
| 583 | 0.10 | 0.95 | — | — | 0.46 |
| 584 | 5.9 | 7.9 | — | — | 3.4 |
| 585 | 9.3 | 1.5 | — | — | 2.1 |
| 586 | 7.3 | 5.6 | — | — | 2.3 |
| 587 | 4.6 | 6.6 | — | — | 2.3 |
| 588 | 0.091 | 7.4 | — | — | — |
| 589 | 1.9 | 4.1 | 0.039 | — | 0.94 |
| 590 | 0.33 | 5.1 | — | — | 1.9 |
| 591 | 3.1 | 3.9 | — | — | 19 |
| 592 | 5.5 | 19 | — | — | 3.6 |
| 593 | 3.1 | 5.9 | — | — | 1.2 |
| 594 | 7.0 | 1.4 | — | — | — |
| 595 | 0.39 | 4.7 | — | — | — |
| 596 | 8.9 | 0.58 | — | — | 15 |
| 598 | 0.34 | 1.8 | — | — | — |
| 599 | 3.1 | 1.9 | — | — | — |
| 601 | 2.1 | 7.7 | — | — | 3.3 |
| 602 | 0.85 | 3.7 | — | — | 1.1 |
| 604 | 0.31 | 2.0 | — | — | 4.8 |
| 606 | 5.2 | 0.066 | — | — | 1.1 |
| 607 | 1.9 | 7.6 | — | — | 2.0 |
| 608 | 1.6 | 9.2 | — | — | — |
| 609 | 0.021 | 13 | — | — | 2.2 |
| 610 | 0.69 | 13 | — | — | 1.8 |
| 611 | 6.8 | 21 | — | — | 3.7 |
| 623 | 130 | >250 | — | — | 20 |
| 624 | 0.66 | 24 | — | — | — |
| 625 | 0.23 | 2.4 | — | — | 0.70 |
| 626 | 1.7 | 7.9 | — | — | 2.5 |
| 627 | 5.4 | 5.9 | — | — | 5.1 |
| 628 | 5.9 | 7.4 | — | — | 4.8 |
| 629 | 11 | 18 | — | — | 4.2 |
| 630 | 0.39 | 13 | — | — | — |
| 631 | 1.4 | 4.3 | — | — | — |
| 632 | 6.5 | 11 | — | — | — |
| 633 | 6.7 | 10 | — | — | — |
| 634 | 4.3 | 9.0 | — | — | 2.9 |
| 635 | 8.0 | 150 | — | — | — |
| 636 | 12 | 8.0 | — | — | 3.9 |
| 637 | 0.17 | 0.84 | — | — | 10 |
| 638 | 110 | 1.8 | — | — | 20 |
| 639 | 98 | 18 | — | — | 20 |
| 640 | 0.036 | 3.9 | — | — | 1.6 |
| 641 | 1.7 | 15 | — | — | 5.9 |
| 642 | | 0.19 | — | — | 3.3 |
| 643 | 0.31 | 1.6 | — | — | 5.3 |
| 644 | 0.16 | 0.50 | — | — | 3.8 |
| 645 | 1.9 | 18 | — | — | 17 |
| 646 | 1.6 | 2.7 | — | — | 6.7 |
| 647 | 0.22 | 0.075 | — | — | 5.2 |
| 648 | 0.59 | 3.9 | — | — | — |
| 649 | 3.6 | 3.4 | — | — | 20 |
| 650 | 2.5 | 0.011 | — | — | 0.29 |
| 651 | 50 | 0.95 | — | — | 20 |
| 652 | 0.018 | 0.25 | — | — | — |
| 653 | 0.094 | 1.1 | — | — | — |
| 654 | 2.0 | 0.13 | — | — | 0.40 |
| 655 | 4.2 | 1.3 | — | — | 6.6 |
| 656 | 23 | 4.0 | — | — | — |
| 657 | 2.4 | 1.6 | 0.027 | — | 0.66 |
| 658 | 0.69 | 0.59 | — | — | 1.5 |
| 659 | 1.4 | 0.31 | — | — | 17 |
| 660 | 17 | 0.51 | — | — | 0.66 |
| 661 | 4.1 | 1.7 | — | — | 1.0 |
| 662 | >250 | >250 | — | — | 20 |
| 663 | >250 | 24 | — | — | 20 |
| 664 | >250 | 4.5 | — | — | — |
| 665 | >250 | >250 | — | — | — |
| 666 | 0.72 | 2.0 | 0.0056 | — | 0.92 |
| 667 | 2.8 | 2.7 | 0.027 | — | 0.85 |
| 668 | 120 | 3.1 | 0.035 | — | 0.60 |
| 669 | 140 | 4.8 | 0.096 | — | 0.86 |
| 670 | 1.1 | 3.6 | — | — | 2.8 |
| 671 | 3.3 | 3.2 | — | — | 1.2 |
| 672 | 92 | 1.7 | — | — | 9.5 |
| 673 | 4.7 | 2.3 | — | — | 1.3 |
| 674 | 0.40 | 4.3 | — | — | — |
| 675 | 4.6 | 23 | — | — | — |
| 676 | 0.062 | 5.4 | — | — | 1.8 |
| 677 | 0.15 | 2.7 | — | — | 1.8 |
| 678 | 3.6 | 1.5 | — | — | 0.44 |
| 679 | 5.4 | 0.72 | — | — | 1.3 |
| 680 | 1.2 | 2.5 | — | — | 0.48 |
| 681 | 0.10 | 0.35 | — | — | 0.27 |
| 682 | 0.58 | 1.5 | 0.039 | — | 0.32 |
| 683 | 0.47 | 23 | — | — | 1.5 |
| 684 | 0.0069 | 0.49 | — | — | 0.35 |
| 685 | 0.30 | 1.0 | 0.012 | — | 0.10 |
| 686 | 4.3 | 3.4 | — | — | 0.56 |
| 687 | 1.6 | 0.73 | 0.017 | — | 0.27 |
| 688 | 83 | 24 | — | — | 13 |
| 689 | 7.6 | 3.0 | — | — | 1.5 |
| 690 | 1.5 | 0.39 | — | — | 3.5 |
| 691 | 4.5 | 0.56 | — | — | 2.7 |
| 692 | 0.81 | 2.5 | — | — | 0.68 |
| 693 | 2.2 | 0.57 | — | — | 0.29 |
| 694 | 0.84 | 0.12 | — | — | — |
| 695 | 12 | 0.28 | — | — | 4.9 |
| 696 | 0.24 | 0.24 | — | — | 0.42 |
| 697 | 0.74 | 0.059 | — | — | 0.20 |
| 698 | 1.7 | 0.40 | — | — | 1.0 |
| 699 | 47 | 2.1 | — | — | 0.98 |
| 700 | 0.38 | 0.095 | — | — | 0.12 |
| 701 | 0.21 | 0.032 | — | — | 0.05 |

TABLE A-continued

In vitro DGK Inhibition IC$_{50}$ Activity Values

| x. No. | DGKa LIPGLO IC$_{50}$ (μM) | DGKz LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) |
|---|---|---|---|---|---|
| 702 | 1.3 | 2.9 | — | — | 4.7 |
| 703 | 4.0 | 2.5 | — | — | 1.2 |
| 704 | 86 | 46 | — | — | 17 |
| 705 | 220 | 19 | — | — | 9.1 |
| 706 | 1.3 | 12 | — | — | 2.9 |
| 707 | 0.15 | 1.7 | 0.044 | — | 0.40 |
| 708 | 1.0 | 37 | — | — | — |
| 709 | 0.67 | 14 | — | — | 2.1 |
| 710 | 0.12 | 2.6 | 0.022 | — | 0.55 |
| 711 | 0.069 | 3.6 | — | — | 1.7 |
| 712 | 0.32 | 0.72 | — | — | 2.8 |
| 713 | 6.6 | 51 | — | — | 13 |
| 714 | 18 | 28 | — | — | 3.9 |
| 715 | 0.36 | 3.9 | 0.042 | — | 0.68 |
| 716 | 6.6 | 20 | — | — | 3.1 |
| 717 | 0.22 | 8.1 | — | — | 1.6 |
| 718 | 0.090 | 4.6 | — | — | 0.83 |
| 719 | 0.40 | 0.38 | — | — | 0.50 |
| 720 | 1.1 | 0.94 | — | — | 1.9 |
| 721 | 0.072 | 1.1 | — | — | 3.5 |
| 722 | 0.12 | 0.56 | — | — | 0.84 |
| 723 | 0.31 | 0.011 | — | — | 0.45 |
| 724 | 0.084 | 0.098 | — | — | 0.26 |
| 725 | 0.55 | 0.49 | — | — | 1.5 |
| 726 | 1.9 | 0.059 | — | — | 0.80 |
| 727 | 37 | 1.6 | — | — | 1.3 |
| 728 | 0.063 | 0.044 | — | — | 0.92 |
| 729 | 1.1 | 1.8 | — | — | 2.2 |
| 730 | 0.044 | 0.64 | — | — | 0.87 |
| 731 | 8.5 | 0.33 | — | — | 0.95 |
| 732 | 0.044 | 0.15 | — | — | 0.44 |
| 733 | 4.1 | 1.5 | — | — | 3.5 |
| 734 | 0.18 | 0.29 | — | — | 1.4 |
| 735 | 0.24 | 0.061 | 0.00074 | — | 0.14 |
| 736 | 0.16 | 0.48 | 0.025 | — | 0.15 |
| 737 | 1.1 | 0.13 | 0.00031 | — | 0.043 |
| 738 | 0.019 | 0.16 | — | — | 0.082 |
| 739 | 0.13 | 0.76 | 0.052 | — | 0.19 |
| 740 | 0.61 | 1.3 | — | — | 0.12 |
| 741 | 0.87 | 1.4 | 0.0037 | — | 0.21 |
| 742 | 0.15 | 0.79 | 0.0015 | — | 0.14 |
| 743 | 0.12 | 1.6 | — | — | 0.42 |
| 744 | 0.049 | 0.62 | — | — | 0.31 |
| 745 | 0.38 | 0.47 | — | — | 1.1 |
| 746 | — | 0.17 | — | — | 0.96 |
| 747 | 0.30 | 0.069 | — | — | 0.18 |
| 748 | 0.054 | 0.22 | — | — | 0.41 |
| 749 | 0.67 | 0.58 | — | — | 1.2 |
| 750 | 0.48 | 0.24 | — | — | 0.15 |
| 751 | — | 17 | — | — | 4.5 |
| 752 | 1.0 | 4.1 | — | — | 1.7 |
| 753 | 0.40 | 0.16 | — | — | 0.64 |
| 754 | 0.058 | 0.23 | — | — | 0.091 |
| 755 | 2.6 | 61 | — | — | 18 |
| 756 | 0.19 | 1.9 | — | — | 6.0 |
| 757 | 0.023 | 0.16 | — | — | 1.0 |
| 758 | 0.86 | 0.075 | — | — | 0.30 |
| 759 | 0.085 | 0.29 | — | — | 0.27 |
| 760 | 0.070 | 0.022 | — | — | 0.048 |
| 761 | 0.048 | 0.041 | — | — | 0.17 |
| 763 | 4.5 | 0.76 | — | — | 1.8 |
| 764 | 0.051 | 0.53 | — | — | — |
| 765 | 0.62 | 0.13 | — | — | — |
| 766 | 0.66 | 9.4 | — | — | 3.5 |
| 767 | 0.44 | 6.6 | — | — | 2.3 |
| 768 | 14 | 3.2 | — | — | 1.8 |
| 769 | 16 | 0.20 | — | — | 0.46 |
| 770 | 21 | 1.7 | — | — | 8.5 |
| 771 | 6.3 | 8.5 | — | — | 10 |
| 772 | 0.0047 | 0.027 | — | — | 1.4 |
| 773 | 0.76 | 0.70 | — | — | 7.9 |
| 774 | 0.63 | 1.1 | — | — | — |
| 775 | 5.8 | 6.6 | — | — | — |
| 776 | 0.055 | 0.038 | — | — | — |
| 777 | 0.068 | 0.75 | — | — | 0.77 |
| 778 | 0.15 | 0.34 | — | — | — |
| 779 | 0.11 | 0.012 | — | — | 0.010 |
| 780 | 1.5 | 31 | — | — | 14 |
| 781 | 0.074 | 0.12 | — | — | 0.83 |
| 782 | 0.18 | 3.4 | — | — | 1.1 |
| 783 | 1.2 | >250 | — | — | — |
| 784 | 1.2 | 2.6 | — | — | 2.0 |
| 785 | 0.69 | >250 | — | — | 6.4 |
| 786 | >250 | 83 | — | — | — |
| 787 | 200 | 83 | — | — | — |
| 788 | 4.8 | >250 | — | — | — |
| 789 | 1.2 | 7.0 | — | — | — |
| 790 | 0.61 | >250 | — | — | — |
| 791 | 1.9 | 5.7 | — | — | 1.3 |
| 792 | 1.5 | 83 | — | — | 21 |
| 793 | 6.9 | 11 | — | — | — |
| 794 | 24 | 120 | — | — | — |
| 795 | 13 | 160 | — | — | 20 |
| 796 | 240 | 2.2 | — | — | 20 |
| 797 | 1.8 | 8.6 | — | — | 1.8 |
| 798 | 9.8 | >250 | — | — | 20 |
| 799 | 0.86 | 9.9 | — | — | 20 |
| 800 | 0.38 | 0.33 | — | — | 5.9 |
| 801 | 0.068 | 2.2 | — | — | 13 |
| 802 | 1.3 | 24 | — | — | 10 |
| 803 | 2.0 | 7.0 | — | — | 20 |
| 804 | 6.9 | 32 | — | — | 20 |
| 805 | 11 | 1.7 | — | — | 9.8 |
| 806 | 6.3 | 0.39 | 0.018 | — | 0.69 |
| 807 | 5.0 | 2.6 | — | — | 2.5 |
| 808 | 4.2 | 1.6 | — | — | 1.3 |
| 809 | 140 | 2.3 | — | — | 20 |
| 810 | 240 | 23 | — | — | 20 |
| 811 | 9.3 | 2.6 | — | — | 2.1 |
| 812 | 17 | 0.51 | — | — | 2.8 |
| 813 | 85 | 3.7 | — | — | 20 |
| 814 | 35 | 1.0 | — | — | 5.5 |
| 815 | 7.7 | 4.1 | — | — | 1.9 |
| 816 | 2.6 | 3.1 | — | — | 1.1 |
| 817 | 22 | 8.6 | — | — | 1.1 |
| 818 | 58 | 7.3 | — | — | 4.2 |
| 819 | 2.3 | 2.9 | — | — | 2.2 |
| 820 | 0.92 | 2.0 | — | — | 2.2 |
| 821 | 2.7 | 6.5 | — | — | 3.4 |
| 822 | 2.7 | 13 | — | — | 3.2 |
| 823 | 18 | 40 | — | — | 7.6 |
| 824 | 16 | 11 | — | — | 3.2 |
| 825 | 23 | 3.2 | — | — | — |
| 826 | 43 | 3.1 | — | — | — |
| 827 | 4.4 | 10 | — | — | 1.3 |
| 828 | 4.2 | 16 | — | — | 2.7 |
| 829 | 5.5 | 8.0 | — | — | 1.2 |
| 830 | 1.5 | 9.6 | — | — | 1.9 |
| 831 | 42 | 6.5 | — | — | 2.5 |
| 832 | 19 | 2.7 | — | — | 1.8 |
| 833 | 2.0 | 2.8 | 0.32 | — | 0.68 |
| 834 | 22 | 6.0 | — | — | 3.6 |
| 835 | 11 | 11 | — | — | 20 |
| 836 | 4.7 | 4.9 | — | — | 1.1 |
| 837 | 5.7 | 35 | — | — | — |
| 838 | — | 2.1 | — | — | 17 |
| 839 | — | 3.3 | — | — | 20 |
| 840 | 22 | 2.8 | — | — | 0.81 |
| 841 | 83 | 11 | — | — | 3.3 |
| 842 | 1.2 | 3.3 | — | — | 20 |
| 843 | 0.75 | 0.88 | — | — | 3.8 |
| 844 | 100 | 5.2 | — | — | 2.7 |
| 845 | 2.5 | 6.2 | — | — | 1.5 |
| 846 | 12 | 8.6 | — | — | 5.1 |

TABLE A-continued

In vitro DGK Inhibition IC$_{50}$ Activity Values

| x. No. | DGKa LIPGLO IC$_{50}$ (μM) | DGKz LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) |
|---|---|---|---|---|---|
| 847 | 22 | 7.4 | — | — | 5.0 |
| 848 | 230 | 100 | — | — | 20 |
| 849 | >250 | 130 | — | — | 20 |
| 850 | 0.51 | 5.4 | — | — | 3.6 |
| 851 | 1.3 | 27 | — | — | 20 |
| 852 | 1.3 | 5.7 | — | — | — |
| 853 | 19 | 38 | — | — | 20 |
| 854 | 5.1 | 1.9 | — | — | 10 |
| 855 | 27 | 20 | — | — | — |
| 856 | 0.33 | 5.6 | — | — | — |
| 857 | 1.0 | 1.9 | — | — | 1.4 |
| 858 | 0.48 | 0.15 | — | — | 1.7 |
| 859 | 3.0 | 0.36 | — | — | 3.7 |
| 860 | 0.41 | 1.3 | — | — | 0.72 |
| 861 | 0.42 | 0.63 | — | — | 0.42 |
| 862 | 0.29 | 0.60 | — | — | 1.2 |
| 863 | 0.53 | 0.19 | — | — | 0.72 |
| 864 | 0.17 | 1.0 | — | — | 6.5 |
| 865 | 18 | 14 | — | — | — |
| 866 | 0.39 | 0.94 | — | — | 2.3 |
| 867 | >250 | 7.9 | — | — | 20 |
| 868 | 0.44 | 2.4 | — | — | 2.2 |
| 869 | 17 | 14 | — | — | — |
| 870 | 2.5 | 0.31 | — | — | 1.4 |
| 871 | 1.1 | 1.3 | — | — | 3.0 |
| 872 | 1.5 | 1.4 | — | — | — |
| 873 | 2.6 | 7.2 | — | — | — |
| 874 | 14 | 2.2 | — | — | — |
| 875 | 1.7 | 0.51 | — | — | 3.1 |
| 876 | 2.4 | 0.51 | — | — | 2.2 |
| 877 | 5.1 | 0.24 | — | — | 6.0 |
| 878 | 1.9 | 1.3 | — | — | 0.57 |
| 879 | 0.60 | 1.1 | — | — | 1.2 |
| 880 | 6.5 | 2.5 | — | — | 20 |
| 881 | 5.3 | 3.0 | — | — | 2.1 |
| 882 | 0.82 | 0.96 | — | — | 1.7 |
| 883 | 1.5 | 0.84 | — | — | 0.83 |
| 884 | 4.6 | 2.4 | — | — | 2.2 |
| 885 | 3.0 | 1.2 | — | — | 2.4 |
| 886 | 1.3 | 0.49 | 0.0096 | — | 0.60 |
| 887 | 0.42 | 0.47 | — | — | 1.6 |
| 888 | 0.51 | 0.33 | — | — | 1.2 |
| 889 | 1.3 | 0.37 | 0.22 | — | 0.67 |
| 890 | 11 | 8.4 | — | — | 6.6 |
| 891 | 3.1 | 3.0 | — | — | 2.8 |
| 892 | 1.8 | 1.3 | — | — | 5.0 |
| 893 | 0.92 | 0.72 | — | — | 1.7 |
| 894 | 8.6 | 0.68 | — | — | 4.0 |
| 895 | 0.71 | 2.7 | — | — | 1.8 |
| 896 | 0.19 | 0.60 | 0.15 | — | 0.21 |
| 897 | 0.25 | 5.1 | — | — | 13 |
| 898 | 0.34 | 0.70 | — | — | 0.48 |
| 899 | 0.63 | 1.7 | — | — | 0.99 |
| 900 | 2.6 | 0.80 | — | — | — |
| 901 | 0.39 | 1.7 | — | — | — |
| 902 | 0.25 | 2.6 | — | — | 2.2 |
| 903 | 0.63 | 3.5 | 0.14 | — | 0.73 |
| 904 | 0.17 | 1.4 | — | — | 0.52 |
| 905 | 4.6 | 1.2 | — | — | 1.3 |
| 906 | 1.0 | 0.94 | 0.067 | — | 0.81 |
| 907 | 4.4 | 1.5 | 0.070 | — | 0.73 |
| 908 | 0.77 | 3.9 | — | — | 1.4 |
| 909 | 3.4 | 16 | — | — | — |
| 910 | 3.0 | 11 | — | — | 20 |
| 911 | 0.69 | 1.2 | — | — | 0.34 |
| 912 | 2.1 | 0.58 | — | — | — |
| 913 | 2.1 | 5.5 | — | — | — |
| 914 | 1.3 | 1.5 | — | — | 1.9 |
| 915 | 0.74 | 1.3 | 0.10 | — | 0.55 |
| 916 | — | 0.45 | — | — | 1.9 |
| 917 | 6.1 | 0.70 | — | — | 0.85 |
| 918 | 0.052 | 0.38 | 0.13 | — | 0.38 |
| 919 | 0.98 | 5.8 | — | — | 1.4 |
| 920 | 4.9 | 13 | — | — | 1.9 |
| 921 | 23 | 3.1 | — | — | 1.5 |
| 922 | 1.5 | 0.78 | 0.16 | — | 0.43 |
| 923 | 5.5 | 1.9 | — | — | 0.80 |
| 924 | 3.2 | 10 | — | — | 4.0 |
| 925 | 2.5 | 2.8 | 0.091 | — | 0.71 |
| 926 | 2.5 | 4.0 | — | — | 1.2 |
| 927 | 2.6 | 1.6 | 0.30 | — | 0.80 |
| 928 | 2.4 | 1.5 | — | — | 1.7 |
| 929 | 7.7 | 1.1 | — | — | 1.3 |
| 930 | 0.64 | 1.3 | — | — | 1.3 |
| 931 | 0.80 | 2.7 | — | — | — |
| 932 | 0.15 | 1.2 | 0.052 | — | 0.31 |
| 933 | 0.20 | 1.0 | 0.35 | — | 0.55 |
| 934 | 8.6 | 5.4 | — | — | — |
| 935 | 1.9 | 1.8 | — | — | — |
| 936 | 1.0 | 3.3 | — | — | — |
| 937 | 0.34 | 1.1 | — | — | — |
| 938 | 5.9 | 2.8 | — | — | — |
| 939 | 83 | 4.0 | — | — | 2.6 |
| 940 | 25 | 7.2 | — | — | 2.2 |
| 941 | 4.3 | 20 | — | — | 20 |
| 942 | 26 | 2.8 | — | — | 20 |
| 943 | 1.1 | 6.7 | — | — | — |
| 944 | 37 | 41 | — | — | 6.7 |
| 945 | 9.8 | 9.3 | — | — | 1.6 |
| 946 | 0.59 | 0.73 | — | — | 0.68 |
| 947 | 2.0 | 0.27 | — | — | 0.34 |
| 948 | 0.60 | 0.31 | — | — | 0.34 |
| 949 | 6.6 | 1.1 | — | — | 20 |
| 950 | 0.21 | 0.37 | — | — | 3.8 |
| 951 | 3.7 | 9.8 | — | — | 20 |
| 952 | 0.59 | 2.3 | — | 5.9 | 3.0 |
| 953 | 1.1 | 15 | — | 1.7 | — |
| 954 | 0.13 | 6.5 | — | — | 20 |
| 955 | 0.22 | 3.0 | — | — | 20 |
| 956 | 0.78 | 7.5 | — | — | 4.0 |
| 957 | 0.26 | 8.6 | — | — | 1.7 |
| 958 | 0.49 | 28 | — | — | 20 |
| 959 | 2.4 | 5.9 | — | — | 5.4 |
| 960 | 6.7 | 6.6 | — | — | 20 |
| 961 | 1.5 | — | — | — | 20 |
| 962 | 1.5 | >250 | — | — | 20 |
| 963 | 1.4 | 180 | — | — | 20 |
| 964 | 1.9 | 32 | — | — | 13 |
| 965 | 0.96 | 60 | — | — | — |
| 966 | 61 | >250 | — | — | 20 |
| 967 | 2.8 | 51 | — | — | 18 |
| 968 | >250 | >250 | — | — | 20 |
| 969 | 0.76 | 1.2 | — | — | 1.3 |
| 970 | 0.87 | 28 | — | — | 11 |
| 971 | 1.8 | 4.9 | — | — | — |
| 972 | 20 | 15 | — | — | — |
| 973 | >250 | >250 | — | — | — |
| 974 | 1.1 | 7.6 | — | — | 20 |
| 975 | 0.33 | 83 | — | — | 20 |
| 976 | 17 | 6.4 | — | — | 20 |
| 977 | 48 | 1.0 | — | — | 4.9 |
| 978 | 1.3 | 4.9 | — | — | — |
| 979 | 0.91 | 55 | — | — | 20 |
| 980 | 5.7 | 13 | — | — | — |
| 981 | 2.1 | 28 | — | — | 13 |
| 982 | 8.1 | 1.7 | — | — | 20 |
| 983 | 3.5 | 7.2 | — | — | 13 |
| 984 | 1.5 | 0.88 | — | — | — |
| 985 | 2.2 | 3.0 | — | 4.1 | 9.7 |
| 986 | 4.2 | 2.6 | — | 3.7 | 20 |
| 987 | 2.9 | 1.8 | — | — | 7.3 |
| 988 | 2.8 | 5.3 | — | — | 20 |
| 989 | 5.2 | 32 | — | — | 20 |
| 990 | 0.74 | 25 | — | — | 20 |

TABLE A-continued

In vitro DGK Inhibition IC$_{50}$ Activity Values

| x. No. | DGKa LIPGLO IC$_{50}$ (µM) | DGKz LIPGLO IC$_{50}$ (µM) | HuCD8 INFG Normalized EC$_{50}$ (µM) | msCTL INFg IC$_{50}$ (µM) | INFg Whole Blood Normalized Agonist EC$_{50}$ (µM) |
|---|---|---|---|---|---|
| 991 | 0.31 | 0.80 | — | — | 11 |
| 992 | 1.3 | 3.2 | — | — | 5.8 |
| 993 | 1.3 | 3.9 | — | — | 3.8 |
| 994 | 6.4 | 110 | — | — | 20 |
| 995 | 3.2 | 5.6 | — | — | 2.5 |
| 996 | 4.1 | 5.8 | — | — | 20 |
| 997 | 1.1 | 3.3 | — | — | 20 |
| 998 | 21 | >250 | — | — | — |
| 999 | 0.27 | — | — | — | 17 |
| 1000 | 2.7 | 6.2 | — | — | 4.0 |
| 1001 | 1.5 | 4.6 | — | — | 4.7 |
| 1002 | 2.7 | 4.7 | — | — | 5.5 |
| 1003 | 2.8 | 3.9 | — | — | 20 |
| 1004 | 3.9 | 11 | — | — | 3.5 |
| 1005 | 0.87 | 7.7 | — | — | 20 |
| 1006 | 2.6 | 7.0 | — | — | 11 |
| 1007 | 0.42 | 3.9 | — | — | — |
| 1008 | 1.7 | 7.1 | — | — | — |
| 1009 | 1.8 | 6.7 | — | — | 20 |
| 1010 | 1.8 | 1.0 | — | — | 2.0 |
| 1011 | 1.2 | 8.3 | — | — | 20 |
| 1012 | 0.35 | 1.4 | — | — | — |
| 1013 | 7.3 | 47 | — | — | 1.4 |
| 1014 | 1.3 | 1.9 | — | — | 20 |
| 1015 | 1.4 | 8.2 | — | — | 2.7 |
| 1016 | 3.3 | 7.5 | — | — | 3.3 |
| 1017 | 7.2 | 8.4 | — | — | 3.3 |
| 1018 | 81 | 74 | — | — | 20 |
| 1019 | 32 | 5.9 | — | — | 20 |
| 1020 | 32 | 21 | — | — | 20 |
| 1021 | 5.7 | 19 | — | — | 8.9 |
| 1022 | 2.9 | 12 | — | — | 2.5 |
| 1023 | 3.6 | 13 | — | — | 3.5 |
| 1024 | 0.44 | 2.2 | — | — | 1.2 |
| 1025 | 1.2 | 19 | — | — | 2.0 |
| 1026 | 20 | 65 | — | — | 20 |
| 1027 | 29 | 2.2 | — | — | 7.3 |
| 1028 | 1.5 | 7.0 | — | — | 2.8 |
| 1029 | 0.45 | 2.1 | — | — | 3.6 |
| 1030 | 2.2 | 1.1 | — | — | 0.67 |
| 1031 | 0.26 | 0.24 | 0.0013 | — | 0.085 |
| 1032 | 0.31 | 0.28 | — | — | 0.28 |
| 1033 | 0.098 | 0.059 | 0.19 | — | 0.12 |
| 1034 | 0.064 | 0.34 | 0.017 | — | 0.23 |
| 1035 | 0.37 | 1.1 | — | — | 0.29 |
| 1036 | 0.30 | 0.52 | — | — | 0.20 |
| 1037 | 0.049 | 0.28 | 0.014 | — | 0.13 |
| 1038 | 0.077 | 0.85 | 0.021 | — | 0.28 |
| 1039 | 0.11 | 0.087 | — | — | 0.091 |
| 1040 | 0.042 | 0.059 | — | — | 0.057 |
| 1041 | 0.036 | 0.043 | — | — | 0.23 |
| 1042 | 0.17 | 0.063 | — | — | 0.13 |
| 1043 | 0.049 | 0.29 | — | — | 0.39 |
| 1044 | — | 0.070 | — | — | 0.35 |
| 1045 | 0.56 | 0.12 | — | — | 0.17 |
| 1046 | 0.090 | 0.054 | — | — | 0.14 |
| 1047 | 0.21 | 0.27 | — | — | — |
| 1048 | 0.083 | 0.15 | — | — | 0.19 |
| 1049 | 0.015 | 0.042 | — | — | 0.13 |
| 1050 | 0.51 | 0.90 | — | — | 4.4 |
| 1051 | 0.27 | 0.21 | — | — | 0.042 |
| 1052 | 2.5 | 2.0 | — | — | 0.19 |
| 1053 | 0.021 | 0.14 | — | — | 0.21 |
| 1054 | 0.47 | 0.59 | — | — | 2.7 |
| 1055 | 0.017 | 0.016 | — | — | 0.016 |
| 1056 | 0.88 | 0.59 | — | — | 0.58 |
| 1057 | 0.023 | 0.040 | — | — | — |
| 1058 | 0.75 | 0.57 | — | — | — |
| 1059 | 0.0090 | 0.044 | — | — | — |
| 1060 | 0.34 | 0.63 | — | — | 2.5 |
| 1061 | 0.011 | 0.10 | — | — | — |
| 1062 | 0.058 | 0.076 | — | — | 0.11 |
| 1063 | 1.1 | 1.8 | — | — | 0.43 |
| 1064 | 0.080 | 0.039 | — | — | — |
| 1065 | — | 0.031 | — | — | — |
| 1066 | 0.028 | 0.030 | — | — | — |
| 1067 | 0.079 | 0.047 | — | — | 0.011 |
| 1068 | 0.043 | 0.092 | — | — | 0.25 |
| 1069 | 0.060 | 0.91 | — | — | 2.1 |
| 1070 | 0.013 | 0.18 | — | — | 1.1 |
| 1071 | 0.014 | 0.044 | — | — | 0.19 |
| 1072 | 0.10 | 0.75 | — | — | 0.77 |
| 1073 | 0.033 | 0.12 | — | — | 0.21 |
| 1074 | 0.044 | 0.047 | — | — | 0.042 |
| 1075 | 0.011 | 0.027 | — | — | 0.037 |
| 1076 | 0.11 | 1.0 | — | — | 1.7 |
| 1077 | 0.46 | 0.32 | — | — | 0.14 |
| 1078 | 2.7 | 0.11 | — | — | 0.97 |
| 1079 | 0.028 | 0.089 | — | — | 0.65 |
| 1080 | 0.64 | 0.69 | — | — | 0.24 |
| 1081 | 1.5 | 0.68 | — | — | 0.25 |
| 1082 | 5.2 | 1.5 | — | — | 0.58 |
| 1083 | 0.037 | 0.079 | — | — | 0.075 |
| 1084 | 1.7 | 5.0 | — | — | 2.6 |
| 1085 | 0.36 | 0.032 | — | — | 0.16 |
| 1086 | 6.2 | 2.1 | — | — | 2.5 |
| 1087 | 0.072 | 0.086 | — | — | — |
| 1088 | 3.4 | 4.9 | — | — | — |
| 1089 | 0.51 | 0.12 | — | — | — |
| 1090 | 4.1 | 1.8 | — | — | — |
| 1091 | 0.23 | 0.11 | — | — | 0.14 |
| 1092 | 3.7 | 4.0 | — | — | 3.2 |
| 1093 | 0.25 | 0.18 | — | — | 0.13 |
| 1094 | 0.46 | 2.1 | — | — | — |
| 1095 | 0.027 | 0.018 | — | — | — |
| 1096 | 2.2 | 1.4 | — | — | — |
| 1097 | 0.40 | 0.21 | — | — | 0.66 |
| 1098 | 0.57 | 0.30 | — | — | 0.15 |
| 1099 | 1.7 | 1.5 | 0.0025 | — | 0.22 |
| 1100 | 0.39 | 0.37 | 0.0046 | — | 0.12 |
| 1101 | 0.35 | 0.24 | — | — | 0.23 |
| 1102 | 0.64 | 1.4 | 0.031 | — | 0.22 |
| 1103 | 0.25 | 0.27 | 0.021 | — | 0.26 |
| 1104 | 0.25 | 0.90 | 0.056 | — | 0.30 |
| 1105 | 0.15 | 0.44 | 0.20 | — | 0.32 |
| 1106 | 0.27 | 0.12 | — | — | 0.52 |
| 1107 | 0.065 | 0.13 | — | — | 0.077 |
| 1108 | 0.031 | 0.090 | — | — | — |
| 1109 | 0.73 | 0.47 | — | — | 0.92 |
| 1110 | — | 0.16 | — | — | 1.3 |
| 1111 | 0.20 | 0.078 | — | — | 0.31 |
| 1112 | 1.2 | 0.15 | — | — | 0.17 |
| 1113 | 0.62 | 0.31 | — | — | 1.0 |
| 1114 | 0.056 | 0.40 | — | — | 0.10 |
| 1115 | 0.084 | 1.4 | — | — | 0.80 |
| 1116 | 0.031 | 0.013 | — | — | — |
| 1117 | 0.015 | 0.017 | — | — | 0.15 |
| 1118 | 0.40 | 0.58 | — | — | 0.36 |
| 1119 | 1.0 | 0.43 | — | — | 17 |
| 1120 | 0.11 | 0.075 | 0.032 | — | 0.68 |
| 1121 | 1.8 | 2.7 | — | — | — |
| 1122 | 0.71 | 0.84 | — | — | — |
| 1123 | 1.2 | 4.7 | — | — | 2.6 |
| 1124 | 0.88 | 3.1 | — | — | 1.4 |
| 1125 | 0.36 | 1.5 | — | — | 0.17 |
| 1126 | 1.2 | 3.0 | — | — | 0.95 |
| 1127 | 0.68 | 2.4 | — | — | 0.52 |
| 1128 | 0.73 | 0.94 | — | — | 0.55 |
| 1129 | 0.11 | 1.8 | — | — | 0.41 |
| 1130 | 0.17 | 0.43 | — | — | 0.28 |
| 1131 | 0.073 | 0.18 | — | — | 0.43 |
| 1132 | 0.62 | 0.79 | — | — | 1.6 |
| 1133 | 1.6 | 0.13 | — | — | 0.57 |
| 1134 | 0.36 | 0.13 | — | — | 0.34 |

TABLE A-continued

In vitro DGK Inhibition IC$_{50}$ Activity Values

| x. No. | DGKa LIPGLO IC$_{50}$ (μM) | DGKz LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) |
|---|---|---|---|---|---|
| 1135 | 0.018 | 0.36 | 0.022 | — | 0.32 |
| 1136 | 1.1 | 11 | — | — | 2.3 |
| 1137 | 0.026 | 0.045 | — | — | 0.29 |
| 1138 | 0.98 | 1.4 | — | — | 3.7 |
| 1139 | 0.064 | 0.10 | — | — | 1.1 |
| 1140 | 1.6 | 0.99 | — | — | 3.4 |
| 1141 | 0.0083 | 0.37 | — | — | 0.47 |
| 1142 | 0.70 | 1.6 | — | — | 1.2 |
| 1143 | 1.4 | 13 | — | — | 4.0 |
| 1144 | 0.26 | 1.5 | — | — | 0.25 |
| 1145 | 0.31 | 0.86 | — | — | 3.3 |
| 1146 | 0.013 | 0.41 | — | — | 1.2 |
| 1147 | 1.2 | 3.6 | — | — | 9.0 |
| 1148 | 0.038 | 0.16 | — | — | 1.2 |
| 1149 | 0.65 | 3.5 | — | — | 0.51 |
| 1150 | 18 | 18 | — | — | — |
| 1151 | 9.6 | 22 | — | — | — |
| 1152 | 7.4 | 24 | 10 | — | 0.78 |
| 1153 | 6.6 | 32 | — | — | — |
| 1154 | 8.1 | 50 | — | — | 2.4 |
| 1155 | 1.8 | 0.66 | 0.0035 | — | 0.86 |
| 1156 | 2.5 | 0.44 | 0.019 | — | 0.34 |
| 1157 | 4.2 | 0.70 | — | — | 0.27 |
| 1158 | 6.5 | 1.3 | — | — | 0.35 |
| 1159 | 0.36 | 0.13 | — | — | 0.30 |
| 1160 | 1.5 | 1.7 | — | — | 1.1 |
| 1161 | 18 | 0.33 | — | — | 15 |
| 1162 | 0.48 | 0.55 | — | — | — |
| 1163 | 10 | 7.5 | — | — | — |
| 1164 | 18 | 0.67 | 0.017 | — | 0.34 |
| 1165 | 3.4 | 1.1 | — | — | 0.24 |
| 1166 | 1.8 | 0.37 | — | — | 0.35 |
| 1167 | 50 | 6.6 | 0.047 | — | 0.97 |
| 1168 | 83 | 60 | — | — | 20 |
| 1169 | 39 | 6.2 | — | — | 2.3 |
| 1170 | 0.76 | 0.17 | — | — | 0.23 |
| 1171 | 1.5 | 0.35 | — | — | 0.17 |
| 1172 | 22 | 3.2 | — | — | 0.42 |
| 1173 | 10 | 0.98 | — | — | 1.4 |
| 1174 | 11 | 0.43 | — | — | 1.4 |
| 1175 | 21 | 1.0 | — | — | 20 |
| 1176 | 12 | 2.9 | — | — | — |
| 1177 | 10 | 0.62 | — | — | — |
| 1178 | 43 | 0.72 | — | — | 3.1 |
| 1179 | >250 | 0.85 | — | — | 20 |
| 1180 | 7.6 | 1.4 | — | — | — |
| 1181 | 77 | 2.5 | — | — | — |
| 1182 | 34 | 1.2 | — | — | 20 |
| 1183 | >250 | 8.9 | — | — | 9.2 |
| 1184 | 110 | 11 | — | — | — |
| 1185 | 81 | 2.4 | — | — | 4.3 |
| 1186 | >250 | 30 | — | — | — |
| 1187 | 150 | 2.9 | — | — | — |
| 1188 | 0.029 | 0.78 | — | — | — |
| 1189 | 0.81 | 2.6 | — | — | 1.2 |
| 1190 | 2.3 | 5.9 | — | — | 1.2 |
| 1191 | 0.20 | 42 | — | — | 20 |
| 1192 | 2.3 | 130 | — | — | 20 |
| 1193 | 0.20 | 0.68 | — | — | 2.8 |
| 1194 | 0.019 | 0.10 | — | — | 0.19 |
| 1195 | 0.83 | 0.28 | — | — | — |
| 1196 | 1.4 | 0.27 | — | — | — |
| 1197 | 9.5 | 1.6 | — | — | 3.5 |
| 1198 | 0.99 | 1.1 | — | — | 1.7 |
| 1199 | 0.020 | 0.037 | — | — | 0.034 |
| 1200 | 0.25 | 0.053 | — | — | 0.23 |
| 1201 | 13 | 3.4 | — | — | 5.6 |
| 1202 | 2.2 | — | — | — | 1.3 |
| 1203 | 3.0 | 1.6 | — | — | 20 |
| 1204 | 0.12 | 0.47 | — | — | 0.54 |
| 1205 | 1.7 | 2.7 | — | — | 8.0 |
| 1206 | — | — | — | — | 2.1 |
| 1207 | 14 | 1.4 | — | — | 13 |
| 1208 | 1.1 | 0.037 | — | — | 1.0 |
| 1209 | 20 | 1.2 | — | — | 12 |
| 1210 | 9.3 | 0.018 | — | — | 0.88 |
| 1211 | 13 | 0.67 | — | — | 8.3 |
| 1212 | 23 | 0.11 | — | — | 11 |
| 1213 | 56 | 3.6 | — | — | 8.4 |
| 1214 | 0.075 | 0.075 | — | — | 0.22 |
| 1215 | 0.72 | 0.68 | — | — | 7.2 |
| 1216 | 83 | 0.15 | — | — | 1.8 |
| 1217 | 37 | 2.1 | — | — | 4.6 |
| 1218 | 0.067 | 0.069 | — | — | 0.32 |
| 1219 | 0.067 | 0.069 | — | — | 0.32 |
| 1220 | 0.11 | 0.095 | — | — | 0.12 |
| 1221 | 0.85 | 2.7 | — | — | 4.2 |
| 1222 | 0.016 | 0.11 | — | — | 0.52 |
| 1223 | 0.016 | 0.11 | — | — | 0.52 |
| 1224 | 0.041 | 1.4 | — | — | 1.8 |
| 1225 | 0.15 | 1.2 | — | — | 7.7 |
| 1226 | 0.75 | 1.7 | — | — | 8.7 |
| 1227 | 0.051 | 0.11 | — | — | 0.67 |
| 1228 | 5.4 | 3.0 | — | — | — |
| 1229 | 0.30 | 0.16 | — | — | 0.51 |
| 1230 | — | 0.16 | — | — | 0.10 |
| 1231 | 3.8 | 0.11 | — | — | 1.2 |
| 1232 | 33 | 1.4 | — | — | 20 |
| 1233 | 0.29 | 0.10 | — | — | 0.38 |
| 1234 | 2.2 | 1.4 | — | — | 5.4 |
| 1235 | 1.1 | 0.63 | — | — | 3.3 |
| 1236 | 11 | 0.043 | — | — | 1.3 |
| 1237 | 6.1 | 0.58 | — | — | 12 |
| 1238 | 0.20 | 3.2 | — | — | 9.7 |
| 1239 | 26 | 23 | — | — | 20 |
| 1240 | 3.5 | 0.15 | — | — | — |
| 1241 | 3.8 | 0.60 | — | — | — |
| 1242 | 0.20 | 0.019 | — | — | 0.18 |
| 1243 | 2.7 | 0.25 | — | — | 3.8 |
| 1244 | 0.66 | 0.030 | — | — | 0.12 |
| 1245 | 4.1 | 1.4 | — | — | 4.9 |
| 1246 | 11 | 0.10 | — | — | 2.1 |
| 1247 | 24 | 7.4 | — | — | 20 |
| 1249 | 51 | 0.64 | — | — | 17 |
| 1250 | 20 | 1.7 | — | — | 18 |
| 1251 | 1.6 | 0.25 | — | — | 3.9 |
| 1252 | 5.7 | 3.1 | — | — | 7.7 |
| 1253 | 1.9 | 0.34 | — | — | 1.8 |
| 1254 | 1.9 | 0.34 | — | — | 1.8 |
| 1255 | 3.1 | 2.0 | — | — | 2.9 |
| 1256 | 0.68 | 0.18 | — | — | 0.48 |
| 1257 | 7.9 | 1.1 | — | — | 1.7 |
| 1258 | 2.2 | 0.015 | — | — | 2.6 |
| 1259 | 5.6 | 0.67 | — | — | 4.9 |
| 1260 | 54 | 0.086 | — | — | — |
| 1261 | 4.2 | 1.1 | — | — | — |
| 1262 | 5.4 | 1.3 | — | — | — |
| 1263 | 0.95 | 0.15 | — | — | — |
| 1264 | 10 | 3.6 | — | — | — |
| 1265 | 0.049 | 0.048 | — | — | 0.12 |
| 1266 | — | — | — | — | 1.4 |
| 1267 | 3.5 | 0.11 | — | — | 0.73 |
| 1268 | 2.1 | 1.0 | — | — | 5.2 |
| 1269 | 0.12 | 0.47 | — | — | 0.54 |
| 1270 | 1.7 | 2.7 | — | — | 8.0 |
| 1271 | 0.15 | 0.030 | — | — | — |
| 1272 | 5.0 | 0.66 | — | — | — |
| 1273 | 0.18 | 0.36 | — | — | 1.7 |
| 1274 | 0.59 | — | — | — | 3.3 |
| 1275 | 0.14 | 0.26 | — | — | 0.19 |
| 1276 | 0.071 | 0.24 | — | — | 0.49 |
| 1277 | 0.069 | 0.61 | — | — | 1.4 |
| 1278 | 0.22 | 0.40 | — | — | 2.0 |
| 1279 | 1.4 | 1.4 | — | — | — |

TABLE A-continued

In vitro DGK Inhibition IC$_{50}$ Activity Values

| x. No. | DGKa LIPGLO IC$_{50}$ (μM) | DGKz LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) |
|---|---|---|---|---|---|
| 1280 | 1.3 | 8.5 | — | — | 9.9 |
| 1281 | 0.49 | 1.1 | — | — | 1.6 |
| 1282 | 1.4 | 2.1 | — | — | 5.2 |
| 1283 | 4.1 | 7.6 | — | — | 4.0 |
| 1284 | 0.76 | — | — | — | 2.8 |
| 1285 | 0.026 | 0.017 | — | — | 0.092 |
| 1286 | 0.038 | 0.10 | — | — | 0.27 |
| 1287 | 250 | 3.7 | — | — | 8.4 |
| 1288 | 290 | — | — | — | 8.8 |
| 1289 | 51 | 130 | — | — | 20 |
| 1290 | 170 | 43 | — | — | 20 |
| 1291 | 97 | 96 | — | — | 20 |
| 1292 | 8.0 | 4.1 | — | — | 12 |
| 1293 | 100 | 6.1 | — | — | — |
| 1294 | 250 | 220 | — | — | 20 |
| 1295 | 130 | 47 | — | — | — |
| 1296 | 2.4 | 5 | — | — | 20 |
| 1297 | 0.22 | 0.092 | — | — | 2.7 |
| 1298 | 2.6 | 2.7 | — | — | 13 |
| 1299 | 89 | 26 | — | — | 15 |
| 1300 | 14 | 1.8 | — | — | 7.0 |
| 1301 | 91 | 3.6 | — | — | — |
| 1302 | 130 | 6.6 | — | — | 20 |
| 1303 | 65 | 2.9 | — | — | 20 |
| 1304 | 110 | 17 | — | — | — |
| 1305 | 130 | 7.5 | — | — | 20 |
| 1306 | 9.4 | 1.1 | — | — | 2.9 |
| 1307 | 5.6 | 14 | — | — | 20 |
| 1308 | 20 | 2.2 | — | — | 2.1 |
| 1309 | 4.6 | 13 | — | — | 7.9 |
| 1310 | 6.2 | 7.5 | — | — | 3.6 |
| 1311 | 120 | 19 | — | — | 11 |
| 1312 | 0.10 | 0.15 | — | — | 0.33 |
| 1313 | 2.2 | 5.3 | — | — | 4.8 |
| 1314 | 10 | 0.049 | — | — | 0.46 |
| 1315 | 79 | 1.4 | — | — | 20 |
| 1316 | 1.8 | 0.018 | — | — | 4.5 |
| 1317 | 8.0 | 0.97 | — | — | 2.9 |
| 1318 | 0.0062 | 0.034 | — | — | 0.088 |
| 1319 | 0.099 | 0.61 | — | — | — |
| 1320 | 75 | 0.16 | — | — | 7.0 |
| 1321 | 7.5 | 0.31 | — | — | 3.0 |
| 1322 | 130 | 53 | — | — | — |
| 1323 | 130 | 7.1 | — | — | — |
| 1324 | 12 | 0.14 | — | — | 0.69 |
| 1325 | 1.3 | 0.91 | — | — | 1.8 |
| 1326 | 1.2 | 0.47 | — | — | 1.7 |
| 1327 | 0.20 | 0.29 | — | — | 0.18 |
| 1328 | 4.9 | 1.5 | — | — | 3.4 |
| 1329 | 1.5 | 26 | — | — | 3.6 |
| 1330 | 0.044 | 0.38 | — | — | 1.5 |
| 1331 | — | 0.31 | — | — | 0.44 |
| 1332 | 0.53 | 0.61 | — | — | 4.4 |
| 1333 | 0.37 | 0.16 | — | — | 0.31 |
| 1334 | 0.11 | 0.14 | — | — | 0.26 |
| 1336 | 1.8 | 14 | — | — | 11 |
| 1337 | 1.8 | 8.2 | — | — | 2.7 |
| 1338 | 0.069 | 0.029 | — | — | 0.13 |
| 1339 | 0.27 | 0.16 | — | — | 0.10 |
| 1340 | 0.63 | 0.040 | — | — | 0.080 |
| 1341 | 4.4 | 1.4 | — | — | 2.0 |
| 1342 | 0.044 | 0.38 | — | — | 1.5 |
| 1343 | 0.0044 | 0.016 | — | — | 0.051 |
| 1344 | 0.0044 | 0.016 | — | — | 0.051 |
| 1345 | 0.041 | 0.075 | — | — | 0.48 |
| 1346 | 0.052 | 0.45 | — | — | 6.0 |
| 1347 | — | 0.17 | — | — | 0.73 |
| 1348 | 0.11 | 0.015 | — | — | 0.029 |
| 1349 | 5.4 | 2.2 | — | — | 0.58 |
| 1350 | 0.097 | 0.011 | — | — | 0.030 |
| 1351 | 1.1 | 0.78 | — | — | 0.74 |
| 1352 | 0.12 | 0.016 | — | — | 0.028 |
| 1353 | 0.46 | 0.51 | — | — | — |
| 1354 | 1.6 | 0.84 | — | — | 1.2 |
| 1355 | 0.062 | 0.033 | — | — | 0.028 |
| 1356 | 1.9 | 3.4 | — | — | 1.3 |
| 1357 | 0.12 | 0.020 | — | — | — |
| 1358 | 1.7 | 0.68 | — | — | 1.2 |
| 1359 | 0.052 | 0.025 | — | — | 0.044 |
| 1360 | 0.83 | 0.11 | — | — | 0.70 |
| 1361 | 0.011 | 0.011 | — | — | — |
| 1362 | 0.16 | 0.050 | — | — | — |
| 1363 | 0.045 | 0.55 | — | — | 0.43 |
| 1364 | 0.15 | 0.029 | — | — | 0.058 |
| 1365 | 0.48 | 0.48 | — | — | 2.2 |
| 1366 | 0.024 | 0.015 | — | — | 0.011 |
| 1367 | 0.17 | 2.9 | — | — | 1.9 |
| 1368 | 0.33 | 0.034 | — | — | 0.063 |
| 1369 | 1.4 | 0.75 | — | — | 1.3 |
| 1370 | 0.023 | 0.14 | — | — | 0.24 |
| 1371 | 0.021 | 0.058 | — | — | 0.15 |
| 1372 | 0.46 | 1.7 | — | — | 1.4 |
| 1373 | 0.0095 | 0.032 | — | — | 0.095 |
| 1374 | 0.29 | 0.28 | — | — | 2.7 |
| 1375 | 0.19 | 0.89 | — | — | 1.8 |
| 1376 | 0.84 | 17 | — | — | — |
| 1377 | 0.029 | 0.27 | — | — | 2.0 |
| 1378 | 1.4 | 2.8 | — | — | 9.5 |
| 1379 | 0.0088 | 0.16 | — | — | 0.51 |
| 1380 | 0.85 | 0.18 | — | — | 0.47 |
| 1381 | 19 | 2.1 | — | — | 20 |
| 1382 | 0.66 | 0.060 | — | — | — |
| 1383 | 0.97 | 0.48 | — | — | 7.0 |
| 1384 | 9.4 | 0.26 | — | — | 8.0 |
| 1385 | 5.9 | 0.70 | — | — | 5.3 |
| 1386 | 0.14 | 2.2 | — | — | 3.9 |
| 1387 | 2.6 | 12 | — | — | 20 |
| 1388 | 1.1 | 2.8 | — | — | 0.88 |
| 1389 | 0.17 | 0.88 | — | — | 0.92 |
| 1390 | 4.0 | 15 | — | — | 14 |
| 1391 | 0.15 | 2.0 | — | — | 0.70 |
| 1392 | 1.9 | 3.8 | — | — | 14 |
| 1393 | 0.022 | 0.016 | — | — | — |
| 1394 | 0.053 | 0.037 | — | — | 0.45 |
| 1395 | — | 0.070 | — | — | 0.19 |
| 1396 | 0.062 | 0.012 | — | — | 0.026 |
| 1397 | 1.3 | 0.054 | — | — | — |
| 1398 | 5.5 | 1.6 | — | — | — |
| 1399 | 0.16 | 0.45 | — | — | 3.0 |
| 1400 | 0.053 | 0.020 | — | — | 0.12 |
| 1401 | 0.30 | 0.049 | — | — | 0.47 |
| 1402 | 0.30 | 0.10 | — | — | 0.26 |
| 1403 | 1.1 | 0.045 | — | — | 1.9 |
| 1404 | 0.90 | 0.050 | — | — | 0.9 |
| 1405 | 0.96 | 0.057 | — | — | 0.48 |
| 1406 | 2.7 | 0.95 | — | — | 12 |
| 1407 | 7.1 | 0.35 | — | — | 4.4 |
| 1408 | 0.019 | 0.083 | — | — | — |
| 1409 | 9.2 | 0.81 | — | — | 2.3 |
| 1410 | 22 | 0.098 | — | — | 1.8 |
| 1411 | 0.20 | 1.2 | — | — | 2.2 |
| 1412 | 0.29 | 1.7 | — | — | 1.6 |
| 1413 | — | 1.8 | — | — | 1.4 |
| 1414 | 40 | 4.9 | — | — | 10 |
| 1415 | 19 | 1.8 | — | — | 6.9 |
| 1416 | 48 | 52 | — | — | 20 |
| 1417 | 26 | 65 | — | — | 11 |
| 1418 | 67 | 62 | — | — | 20 |
| 1419 | 0.075 | 0.68 | — | — | 1.1 |
| 1420 | 0.82 | 1.7 | — | — | 1.7 |
| 1421 | 2.1 | 0.47 | — | — | 1.5 |
| 1422 | 0.29 | 4.2 | — | — | 6.9 |
| 1423 | 50 | 44 | — | — | 20 |
| 1424 | 3.7 | 14 | — | — | 20 |

TABLE A-continued

In vitro DGK Inhibition IC$_{50}$ Activity Values

| x. No. | DGKa LIPGLO IC$_{50}$ (μM) | DGKz LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) |
|---|---|---|---|---|---|
| 1425 | 5.9 | 4.9 | — | — | 20 |
| 1426 | 33 | 4.0 | — | — | 20 |
| 1427 | 21 | 5.2 | — | — | 20 |
| 1428 | 34 | 53 | — | — | 20 |
| 1429 | 48 | 18 | — | — | 20 |
| 1430 | 21 | 4.7 | — | — | 7.0 |
| 1431 | 59 | 12 | — | — | 13 |
| 1432 | 2.1 | 7.7 | — | — | 20 |
| 1433 | 2.5 | 2.8 | — | — | 13 |
| 1434 | 2.1 | 0.96 | — | — | 21 |
| 1435 | 160 | 250 | — | — | — |
| 1436 | 11 | 5.6 | — | — | — |
| 1437 | 150 | 250 | — | — | — |
| 1438 | 250 | 250 | — | — | — |
| 1439 | 0.20 | 0.65 | — | — | 0.25 |
| 1440 | 1.6 | 1.1 | — | — | 2.1 |
| 1441 | 20 | 4.8 | — | — | 5.4 |
| 1442 | 0.065 | 1.0 | — | — | 0.53 |
| 1443 | 0.056 | 0.24 | — | — | 0.81 |
| 1444 | 10 | 0.48 | — | — | — |
| 1445 | 5.4 | 3.6 | — | — | 5.3 |
| 1446 | 0.26 | 0.23 | — | — | 0.23 |
| 1447 | 0.28 | 0.024 | — | — | 0.050 |
| 1448 | 4.2 | 1.7 | — | — | 1.6 |
| 1449 | 0.61 | 0.35 | — | — | 0.87 |
| 1450 | 22 | 3.6 | — | — | 6.8 |
| 1454 | 1.6 | 45 | — | — | 10 |

Table 1 lists in vitro DGK inhibition IC$_{50}$ activity values measured in the DGKα and DGKζ liposome (LIPGLO) assays.

The compounds of the present invention possess activity as an inhibitor(s) of one or both of the DGKα and DGKζ enzymes, and therefore, may be used in the treatment of diseases associated with the inhibition of DGKα and DGKζ activity.

```
Nucleotide sequence encoding hDGKα-(M1-S735)-Ct-TVMV-His:
                                               (SEQ ID NO: 1)
   1 ATGGCCAAGG AGAGGGGCCT AATAAGCCCC AGTGATTTTG CCCAGCTGCA

51 AAAATACATG GAATACTCCA CCAAAAAGGT CAGTGATGTC CTAAAGCTCT

101 TCGAGGATGG CGAGATGGCT AAATATGTCC AAGGAGATGC CATTGGGTAC

151 GAGGGATTCC AGCAATTCCT GAAAATCTAT CTCGAAGTGG ATAATGTTCC

201 CAGACACCTA AGCCTGGCAC TGTTTCAATC CTTTGAGACT GGTCACTGCT

251 TAAATGAGAC AAATGTGACA AAAGATGTGG TGTGTCTCAA TGATGTTTCC

301 TGCTACTTTT CCCTTCTGGA GGGTGGTCGG CCAGAAGACA AGTTAGAATT

351 CACCTTCAAG CTGTACGACA CGGACAGAAA TGGGATCCTG GACAGCTCAG

401 AAGTGGACAA AATTATCCTA CAGATGATGC GAGTGGCTGA ATACCTGGAT

451 TGGGATGTGT CTGAGCTGAG GCCGATTCTT CAGGAGATGA TGAAAGAGAT

501 TGACTATGAT GGCAGTGGCT CTGTCTCTCA AGCTGAGTGG GTCCGGGCTG

551 GGGCCACCAC CGTGCCACTG CTAGTGCTGC TGGGTCTGGA GATGACTCTG

601 AAGGACGACG GACAGCACAT GTGGAGGCCC AAGAGGTTCC CCAGACCAGT

651 CTACTGCAAT CTGTGCGAGT CAAGCATTGG TCTTGGCAAA CAGGGACTGA

701 GCTGTAACCT CTGTAAGTAC ACTGTTCACG ACCAGTGTGC CATGAAAGCC

751 CTGCCTTGTG AAGTCAGCAC CTATGCCAAG TCTCGGAAGG ACATTGGTGT

801 CCAATCACAT GTGTGGGTGC GAGGAGGCTG TGAGTCCGGG CGCTGCGACC

851 GCTGTCAGAA AAAGATCCGG ATCTACCACA GTCTGACCGG GCTGCATTGT

901 GTATGGTGCC ACCTAGAGAT CCACGATGAC TGCCTGCAAG CGGTGGGCCA

951 TGAGTGTGAC TGTGGGCTGC TCCGGGATCA CATCCTGCCT CCATCTTCCA

1001 TCTATCCCAG TGTCCTGGCC TCTGGACCGG ATCGTAAAAA TAGCAAAACA

1051 AGCCAGAAGA CCATGGATGA TTTAAATTTG AGCACCTCTG AGGCTCTGCG

1101 GATTGACCCT GTTCCTAACA CCCACCCACT TCTCGTCTTT GTCAATCCTA

1151 AGAGTGGCGG GAAGCAGGGG CAGAGGGTGC TCTGGAAGTT CCAGTATATA
```

```
1201 TTAAACCCTC GACAGGTGTT CAACCTCCTA AAGGATGGTC CTGAGATAGG

1251 GCTCCGATTA TTCAAGGATG TTCCTGATAG CCGGATTTTG GTGTGTGGTG

1301 GAGACGGCAC AGTAGGCTGG ATTCTAGAGA CCATTGACAA AGCTAACTTG

1351 CCAGTTTTGC CTCCTGTTGC TGTGTTGCCC CTGGGTACTG GAAATGATCT

1401 GGCTCGATGC CTAAGATGGG GAGGAGGTTA TGAAGGACAG AATCTGGCAA

1451 AGATCCTCAA GGATTTAGAG ATGAGTAAAG TGGTACATAT GGATCGATGG

1501 TCTGTGGAGG TGATACCTCA ACAAACTGAA GAAAAAGTG ACCCAGTCCC

1551 CTTTCAAATC ATCAATAACT ACTTCTCTAT TGGCGTGGAT GCCTCTATTG

1601 CTCATCGATT CCACATCATG CGAGAGAAAT ATCCGGAGAA GTTCAACAGC

1651 AGAATGAAGA ACAAGCTATG GTACTTCGAA TTTGCCACAT CTGAATCCAT

1701 CTTCTCAACA TGCAAAAAGC TGGAGGAGTC TTTGACAGTT GAGATCTGTG

1751 GGAAACCGCT GGATCTGAGC AACCTGTCCC TAGAAGGCAT CGCAGTGCTA

1801 AACATCCCTA GCATGCATGG TGGCTCCAAC CTCTGGGGTG ATACCAGGAG

1851 ACCCCATGGG GATATCTATG GGATCAACCA GGCCTTAGGT GCTACAGCTA

1901 AAGTCATCAC CGACCCTGAT ATCCTGAAAA CCTGTGTACC AGACCTAAGT

1951 GACAAGAGAC TGGAAGTGGT TGGGCTGGAG GGTGCAATTG AGATGGGCCA

2001 AATCTATACC AAGCTCAAGA ATGCTGGACG TCGGCTGGCC AAGTGCTCTG

2051 AGATCACCTT CCACACCACA AAACCCTTC CCATGCAAAT TGACGGAGAA

2101 CCCTGGATGC AGACGCCCTG TACAATCAAG ATCACCCACA GAACCAGAT

2151 GCCCATGCTC ATGGGCCCAC CCCCCCGCTC ACCAATTTC TTTGGCTTCT

2201 TGAGCGGATC CTCGGAGACA GTGCGGTTTC AGGGACACCA CCACCATCAC

2251 CACTGA

Amino acid sequence of hDGKα-(M1-S735)-Ct-TVMV-His:
                                                         (SEQ ID NO: 2)
0001 MAKERGLISP SDFAQLQKYM EYSTKKVSDV LKLFEDGEMA KYVQGDAIGY EGFQQFLKIY 0060

0061 LEVDNVPRHL SLALFQSFET GHCLNETNVT KDVVCLNDVS CYFSLLEGGR PEDKLEFTFK 0120

0121 LYDTDRNGIL DSSEVDKIIL QMMRVAEYLD WDVSELRPIL QEMMKEIDYD GSGSVSQAEW 0180

0181 VRAGATTVPL LVLLGLEMTL KDDGQHMWRP KRFPRPVYCN LCESSIGLGK QGLSCNLCKY 0240

0241 TVHDQCAMKA LPCEVSTYAK SRKDIGVQSH VWVRGGCESG RCDRCQKKIR IYHSLTGLHC 0300

0301 VWCHLEIHDD CLQAVGHECD CGLLRDHILP PSSIYPSVLA SGPDRKNSKT SQKTMDDLNL 0360

0361 STSEALRIDP VPNTHPLLVF VNPKSGGKQG QRVLWKFQYI LNPRQVFNLL KDGPEIGLRL 0420

0421 FKDVPDSRIL VCGGDGTVGW ILETIDKANL PVLPPVAVLP LGTGNDLARC LRWGGGYEGQ 0480

0481 NLAKILKDLE MSKVVHMDRW SVEVIPQQTE EKSDPVPFQI INNYFSIGVD ASIAHRFHIM 0540

0541 REKYPEKFNS RMKNKLWYFE FATSESIFST CKKLEESLTV EICGKPLDLS NLSLEGIAVL 0600

0601 NIPSMHGGSN LWGDTRRPHG DIYGINQALG ATAKVITDPD ILKTCVPDLS DKRLEVVGLE 0660

0661 GAIEMGQIYT KLKNAGRRLA KCSEITFHTT KTLPMQIDGE PWMQTPCTIK ITHKNQMPML 0720

0721 MGPPPRSTNF FGFLSGSSET VRFQGHHHHH H                              0751
```

Nucleotide sequence encoding hDGKζ-(M1-A928)-transcript variant-2
Ct-TVMV-His:

(SEQ ID NO: 3)

```
   1 ATGGAGCCGC GGGACGGTAG CCCCGAGGCC CGGAGCAGCG ACTCCGAGTC
  51 GGCTTCCGCC TCGTCCAGCG GCTCCGAGCC CGACGCCGGT CCCGAGCCGG
 101 ACAAGGCGCC GCGGCGACTC AACAAGCGGC GCTTCCCGGG GCTGCGGCTC
 151 TTCGGGCACA GGAAAGCCAT CACGAAGTCG GGCCTCCAGC ACCTGGCCCC
 201 CCCTCCGCCC ACCCCTGGGG CCCCGTGCAG CGAGTCAGAG CGGCAGATCC
 251 GGAGTACAGT GGACTGGAGC GAGTCAGCGA CATATGGGGA GCACATCTGG
 301 TTCGAGACCA ACGTGTCCGG GGACTTCTGC TACGTTGGGG AGCAGTACTG
 351 TGTAGCCAGG ATGCTGCAGA AGTCAGTGTC TCGAAGAAAG TGCGCAGCCT
 401 GCAAGATTGT GGTGCACACG CCCTGCATCG AGCAGCTGGA GAAGATAAAT
 451 TTCCGCTGTA AGCCGTCCTT CCGTGAATCA GGCTCCAGGA ATGTCCGCGA
 501 GCCAACCTTT GTACGGCACC ACTGGGTACA CAGACGACGC CAGGACGGCA
 551 AGTGTCGGCA CTGTGGGAAG GGATTCCAGC AGAAGTTCAC CTTCCACAGC
 601 AAGGAGATTG TGGCCATCAG CTGCTCGTGG TGCAAGCAGG CATACCACAG
 651 CAAGGTGTCC TGCTTCATGC TGCAGCAGAT CGAGGAGCCG TGCTCGCTGG
 701 GGGTCCACGC AGCCGTGGTC ATCCCGCCCA CCTGGATCCT CCGCGCCCGG
 751 AGGCCCCAGA ATACTCTGAA AGCAAGCAAG AAGAAGAAGA GGGCATCCTT
 801 CAAGAGGAAG TCCAGCAAGA AAGGGCCTGA GGAGGGCCGC TGGAGACCCT
 851 TCATCATCAG GCCCACCCCC TCCCCGCTCA TGAAGCCCCT GCTGGTGTTT
 901 GTGAACCCCA AGAGTGGGGG CAACCAGGGT GCAAAGATCA TCCAGTCTTT
 951 CCTCTGGTAT CTCAATCCCC GACAAGTCTT CGACCTGAGC CAGGGAGGGC
1001 CCAAGGAGGC GCTGGAGATG TACCGCAAAG TGCACAACCT GCGGATCCTG
1051 GCGTGCGGGG GCGACGGCAC GGTGGGCTGG ATCCTCTCCA CCCTGGACCA
1101 GCTACGCCTG AAGCCGCCAC CCCTGTTGC CATCCTGCCC CTGGGTACTG
1151 GCAACGACTT GGCCCGAACC CTCAACTGGG GTGGGGGCTA CACAGATGAG
1201 CCTGTGTCCA AGATCCTCTC CCACGTGGAG GAGGGGAACG TGGTACAGCT
1251 GGACCGCTGG GACCTCCACG CTGAGCCCAA CCCCGAGGCA GGGCCTGAGG
1301 ACCGAGATGA AGGCGCCACC GACCGGTTGC CCCTGGATGT CTTCAACAAC
1351 TACTTCAGCC TGGGCTTTGA CGCCCACGTC ACCCTGGAGT TCCACGAGTC
1401 TCGAGAGGCC AACCCAGAGA AATTCAACAG CCGCTTTCGG AATAAGATGT
1451 TCTACGCCGG ACAGCTTTC TCTGACTTCC TGATGGGCAG CTCCAAGGAC
1501 CTGGCCAAGC ACATCCGAGT GGTGTGTGAT GGAATGGACT TGACTCCCAA
1551 GATCCAGGAC CTGAAACCCC AGTGTGTTGT TTTCCTGAAC ATCCCCAGGT
1601 ACTGTGCGGG CACCATGCCC TGGGGCCACC CTGGGGAGCA CCACGACTTT
1651 GAGCCCCAGC GGCATGACGA CGGCTACCTC GAGGTCATTG GCTTCACCAT
1701 GACGTCGTTG GCCGCGCTGC AGGTGGGCGG ACACGGCGAG CGGCTGACGC
1751 AGTGTCGCGA GGTGGTGCTC ACCACATCCA AGGCCATCCC GGTGCAGGTG
1801 GATGGCGAGC CCTGCAAGCT GCAGCCTCA CGCATCCGCA TCGCCCTGCG
1851 CAACCAGGCC ACCATGGTGC AGAAGGCCAA GCGGCGGAGC GCCGCCCCCC
1901 TGCACAGCGA CCAGCAGCCG GTGCCAGAGC AGTTGCGCAT CCAGGTGAGT
```

-continued

```
1951 CGCGTCAGCA TGCACGACTA TGAGGCCCTG CACTACGACA AGGAGCAGCT

2001 CAAGGAGGCC TCTGTGCCGC TGGGCACTGT GGTGGTCCCA GGAGACAGTG

2051 ACCTAGAGCT CTGCCGTGCC CACATTGAGA GACTCCAGCA GGAGCCCGAT

2101 GGTGCTGGAG CCAAGTCCCC GACATGCCAG AAACTGTCCC CCAAGTGGTG

2151 CTTCCTGGAC GCCACCACTG CCAGCCGCTT CTACAGGATC GACCGAGCCC

2201 AGGAGCACCT CAACTATGTG ACTGAGATCG CACAGGATGA GATTTATATC

2251 CTGGACCCTG AGCTGCTGGG GGCATCGGCC CGGCCTGACC TCCCAACCCC

2301 CACTTCCCCT CTCCCCACCT CACCCTGCTC ACCCACGCCC CGGTCACTGC

2351 AAGGGGATGC TGCACCCCCT CAAGGTGAAG AGCTGATTGA GGCTGCCAAG

2401 AGGAACGACT TCTGTAAGCT CCAGGAGCTG CACCGAGCTG GGGGCGACCT

2451 CATGCACCGA GACGAGCAGA GTCGCACGCT CCTGCACCAC GCAGTCAGCA

2501 CTGGCAGCAA GGATGTGGTC CGCTACCTGC TGGACCACGC CCCCCCAGAG

2551 ATCCTTGATG CGGTGGAGGA AAACGGGGAG ACCTGTTTGC ACCAAGCAGC

2601 GGCCCTGGGC CAGCGCACCA TCTGCCACTA CATCGTGGAG GCCGGGGCCT

2651 CGCTCATGAA GACAGACCAG CAGGGCGACA CTCCCCGGCA GCGGGCTGAG

2701 AAGGCTCAGG ACACCGAGCT GGCCGCCTAC CTGGAGAACC GGCAGCACTA

2751 CCAGATGATC CAGCGGGAGG ACCAGGAGAC GGCTGTGGGA TCCTCGGAGA

2801 CAGTGCGGTT TCAGGGACAC CACCACCATC ACCACTGA
```

Amino acid sequence of hDGKζ-(M1-A928)-transcript variant-2 Ct-TVMV-His:
(SEQ ID NO: 4)

```
0001 MEPRDGSPEA RSSDSESASA SSSGSERDAG PEPDKAPRRL NKRRFPGLRL FGHRKAITKS 0060

0061 GLQHLAPPPP TPGAPCSESE RQIRSTVDWS ESATYGEHIW FETNVSGDFC YVGEQYCVAR 0120

0121 MLQKSVSRRK CAACKIVVHT PCIEQLEKIN FRCKPSFRES GSRNVREPTF VRHHWVHRRR 0180

0181 QDGKCRHCGK GFQQKFTFHS KEIVAISCSW CKQAYHSKVS CFMLQQIEEP CSLGVHAAVV 0240

0241 IPPTWILRAR RPQNTLKASK KKKRASFKRK SSKKGPEEGR WRPFIIRPTP SPLMKPLLVF 0300

0301 VNPKSGGNQG AKIIQSFLWY LNPRQVFDLS QGGPKEALEM YRKVHNLRIL ACGGDGTVGW 0360

0361 ILSTLDQLRL KPPPPVAILP LGTGNDLART LNWGGGYTDE PVSKILSHVE EGNVVQLDRW 0420

0421 DLHAEPNPEA GPEDRDEGAT DRLPLDVFNN YFSLGFDAHV TLEFHESREA NPEKFNSRFR 0480

0481 NKMFYAGTAF SDFLMGSSKD LAKHIRVVCD GMDLTPKIQD LKPQCVVFLN IPRYCAGTMP 0540

0541 WGHPGEHHDF EPQRHDDGYL EVIGFTMTSL AALQVGGHGE RLTQCREVVL TTSKAIPVQV 0600

0601 DGEPCKLAAS RIRIALRNQA TMVQKAKRRS AAPLHSDQQP VPEQLRIQVS RVSMHDYEAL 0660

0661 HYDKEQLKEA SVPLGTVVVP GDSDLELCRA HIERLQQEPD GAGAKSPTCQ KLSPKWCFLD 0720

0721 ATTASRFYRI DRAQEHLNYV TEIAQDEIYI LDPELLGASA RPDLPTPTSP LPTSPCSPTP 0780

0781 RSLQGDAAPP QGEELIEAAK RNDFCKLQEL HRAGGDLMHR DEQSRTLLHH AVSTGSKDVV 0840

0841 RYLLDHAPPE ILDAVEENGE TCLHQAAALG QRTICHYIVE AGASLMKTDQ QGDTPRQRAE 0900

0901 KAQDTELAAY LENRQHYQMI QREDQETAVG SSETVRFQGH HHHH          0945
```

What is claimed is:

1. A compound having the structure:

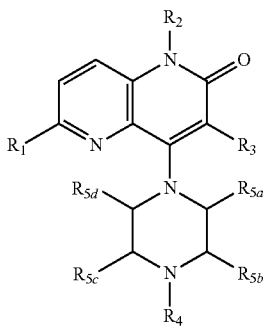

or a pharmaceutically acceptable salt thereof, wherein:
$R_1$ is H, Cl, Br, —CN, or —OCH$_3$;
$R_2$ is —CH$_3$;
$R_3$ is H, F, Cl, Br, —CN, —CH$_3$, cyclopropyl, or —NO$_2$;
$R_4$ is —CH$_2$R$_{4a}$, —CH$_2$CH$_2$R$_{4a}$, or —CHR$_{4a}$R$_{4b}$;
$R_{4a}$ is phenyl, pyridinyl, pyrimidinyl, pyrazinyl, pyridazinyl, pyrazolyl, imidazolyl, isoxazolyl, isothiazolyl, oxazolyl, oxadiazolyl, tetrazolyl, thiadiazolyl, thiazolyl, triazolyl, thiophenyl, tetrahydropyranyl, dihydrobenzo[b][1,4]dioxinyl, dihydrobenzo[b][1,4]dioxepinyl, dihydrobenzofuranyl, benzo[d]isoxazolyl, benzoxazinyl, benzoxazinonyl, indazolyl, indolyl, benzo[d][1,3]dioxolyl, pyrazolo[1,5-a]pyridinyl, dioxidotetrahydrothiopyranyl, quinolinyl, or naphthyridinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —CH$_2$OH, —CH$_2$OCH$_3$, —OCH$_3$, —OCH$_2$CH$_3$, —OCH(CH$_3$)$_2$, —OC(CH$_3$)$_3$, —OCH$_2$C(CH$_3$)$_2$OH, —OCH$_2$CH$_2$OCH$_3$, —OCHF$_2$, —OCF$_3$, —OCH$_2$CH$_2$N(CH$_3$)$_2$, —C(O)CH$_3$, —C(O)C(CH$_3$)$_3$, —C(O)OH, —C(O)OCH$_3$, —C(O)OC(CH$_3$)$_3$, —N(CH$_3$)$_2$, —P(O)(CH$_3$)$_2$, —S(O)$_2$CH$_3$, —OCH$_2$(cyclopropyl), —OCH$_2$CH$_2$(cyclopropyl), —OCH$_2$CH$_2$ (morpholinyl), cyclopropyl, cyanocyclopropyl, methylazetidinyl, acetylazetidinyl, (tert-butoxycarbonyl) azetidinyl, triazolyl, tetrahydropyranyl, morpholinyl, phenyl, fluorophenyl, cyanophenyl, thiophenyl, fluorophenyl, and methylpiperidinyl;

$R_{4b}$ is:

(i) —CH$_3$, —CH$_2$CH$_3$, —CH$_2$CH$_2$CH$_3$, —C(CH$_3$)$_3$, —CH$_2$F, —CF$_3$, —CH$_2$OH, —C(CH$_3$)$_2$OH, —CH$_2$OCH$_3$, —CH$_2$OCHF$_2$, —CF$_2$CH$_2$OH, —CF$_2$CH$_2$OCH$_3$, —CH$_2$SCH$_3$, cyclopropyl, —CH$_2$(cyclohexyl), or —CH$_2$(cyclopropyl-oxadiazolyl); or (ii) phenyl, pyridinyl, pyrimidinyl, pyrazinyl, pyridazinyl, pyrazolyl, imidazolyl, isoxazolyl, isothiazolyl, oxazolyl, oxadiazolyl, tetrazolyl, thiadiazolyl, thiazolyl, triazolyl, thiophenyl, tetrahydropyranyl, dihydrobenzo[b][1,4]dioxinyl, dihydrobenzo[b][1,4]dioxepinyl, dihydrobenzofuranyl, benzo[d]isoxazolyl, benzoxazinyl, benzoxazinonyl, indazolyl, indolyl, benzo[d][1,3]dioxolyl, pyrazolo[1,5-a]pyridinyl, dioxidotetrahydrothiopyranyl, quinolinyl, or naphthyridinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —CH$_2$OH, —CH$_2$OCH$_3$, —OCH$_3$, —OCH$_2$CH$_3$, —OCH(CH$_3$)$_2$, —OC(CH$_3$)$_3$, —OCH$_2$C(CH$_3$)$_2$OH, —OCH$_2$CH$_2$OCH$_3$, —OCHF$_2$, —OCF$_3$, —OCH$_2$CH$_2$N(CH$_3$)$_2$, —C(O)CH$_3$, —C(O)C(CH$_3$)$_3$, —C(O)OH, —C(O)OCH$_3$, —C(O)OC(CH$_3$)$_3$, —N(CH$_3$)$_2$, —P(O)(CH$_3$)$_2$, —S(O)$_2$CH$_3$, —OCH$_2$(cyclopropyl), —OCH$_2$CH$_2$(cyclopropyl), —OCH$_2$CH$_2$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, phenyl, fluorophenyl, cyanophenyl, thiophenyl, fluorophenyl, and methylpiperidinyl; and (i) $R_{5a}$ is —CN, —CH$_3$, —CH$_2$CH$_3$, —CH(CH$_3$)$_2$, —CH$_2$F, —CH$_2$OH, —C(O)OH, —C(O)OCH$_3$, —C(O)NH$_2$, cyclopropyl, —C(O)NH(cyclopropyl), or phenyl, and $R_{5b}$, $R_{5c}$, and $R_{5d}$ are each H; or (ii) $R_{5b}$ is —CN, —CH$_3$, —CH$_2$CH$_3$, —CH(CH$_3$)$_2$, —CH$_2$F, —C(CH$_3$)$_2$F, —CF(CH$_3$)CH(CH$_3$)$_2$, —CH$_2$OH, —C(CH$_3$)$_2$OH, —CH$_2$OCH$_3$, —C(O)OH, —C(O)OCH$_3$, —C(O)C(CH$_3$)$_2$, —C(O)OCH$_3$, —C(O)OC(CH$_3$)$_2$, —C(O)NH$_2$, —C(CH$_3$)(OH)CH(CH$_3$)$_2$, —C(O)NH(cyclopropyl), —C(O)O(cyclopropyl), or methyloxadiazolyl, and $R_{5a}$, $R_{5c}$, and $R_{5d}$ are each H.

2. The compound according to claim 1 or a pharmaceutically acceptable salt thereof, wherein $R_{5a}$ is —CN, —CH$_3$, —CH$_2$CH$_3$, —CH(CH$_3$)$_2$, —CH$_2$F, —CH$_2$OH, —C(O)OH, —C(O)OCH$_3$, —C(O)NH$_2$, cyclopropyl, —C(O)NH(cyclopropyl), or phenyl, and $R_{5b}$, $R_{5c}$, and $R_{5d}$ are each H.

3. The compound according to claim 1 or a pharmaceutically acceptable salt thereof, wherein $R_{5b}$ is —CN, —CH$_3$, —CH$_2$CH$_3$, —CH(CH$_3$)$_2$, —CH$_2$F, —C(CH$_3$)$_2$F, —CF(CH$_3$)CH(CH$_3$)$_2$, —CH$_2$OH, —C(CH$_3$)$_2$OH, —CH$_2$OCH$_3$, —C(O)OH, —C(O)OCH$_3$, —C(O)C(CH$_3$)$_2$, —C(O)OCH$_3$, —C(O)OC(CH$_3$)$_2$, —C(O)NH$_2$, —C(CH$_3$)(OH)CH(CH$_3$)$_2$, —C(O)NH(cyclopropyl), —C(O)O(cyclopropyl), or methyloxadiazolyl, and $R_{5a}$, $R_{5c}$, and $R_{5d}$ are each H.

4. The compound according to claim 1 or a pharmaceutically acceptable salt thereof, wherein:
$R_{5a}$ is —CH$_3$ or —CH$_2$CH$_3$;
$R_{5b}$ is H;
$R_{5c}$ is H; and
$R_{5d}$ is H.

5. The compound according to claim 1 or a pharmaceutically acceptable salt thereof, wherein:
$R_{5a}$ is H;
$R_{5b}$ is —CH$_3$ or —CH$_2$CH$_3$;
$R_{5c}$ is H; and
$R_{5d}$ is H.

6. The compound according to claim 1 or a pharmaceutically acceptable salt thereof, wherein $R_1$ is —CN.

7. The compound according to claim 1 or a pharmaceutically acceptable salt thereof, wherein $R_3$ is H.

8. The compound according to claim 1 or a pharmaceutically acceptable salt thereof, wherein $R_1$ is —CN; and $R_3$ is H.

9. The compound according to claim 1 or a pharmaceutically acceptable salt thereof, wherein $R_4$ is —CH$_2$R$_{4a}$.

10. The compound according to claim 1 or a pharmaceutically acceptable salt thereof, wherein $R_4$ is —CHR$_{4a}$R$_{4b}$.

11. A pharmaceutical composition comprising a compound according to claim 1 or a pharmaceutically-acceptable salt thereof; and a pharmaceutically acceptable carrier.

* * * * *

SEQUENCE LISTING

<160> NUMBER OF SEQ ID NOS: 4

<210> SEQ ID NO 1
<211> LENGTH: 2256
<212> TYPE: DNA
<213> ORGANISM: Homo sapiens

<400> SEQUENCE: 1

| | | | | | |
|---|---|---|---|---|---|
| atggccaagg | agagggggcct | aataagcccc | agtgattttg | cccagctgca | aaaatacatg | 60 |
| gaatactcca | ccaaaaaggt | cagtgatgtc | ctaaagctct | tcgaggatgg | cgagatggct | 120 |
| aaatatgtcc | aaggagatgc | cattgggtac | gagggattcc | agcaattcct | gaaaatctat | 180 |
| ctcgaagtgg | ataatgttcc | cagacaccta | agcctggcac | tgtttcaatc | ctttgagact | 240 |
| ggtcactgct | taaatgagac | aaatgtgaca | aaagatgtgt | tgtgtctcaa | tgatgtttcc | 300 |
| tgctactttt | cccttctgga | gggtggtcgg | ccagaagaca | agttagaatt | caccttcaag | 360 |
| ctgtacgaca | cggacagaaa | tgggatcctg | acagctcag | aagtggacaa | aattatccta | 420 |
| cagatgatgc | gagtggctga | atacctggat | tgggatgtgt | ctgagctgag | gccgattctt | 480 |
| caggagatga | tgaaagagat | tgactatgat | ggcagtggct | ctgtctctca | agctgagtgg | 540 |
| gtccgggctg | gggccaccac | cgtgccactg | ctagtgctgc | tgggtctgga | gatgactctg | 600 |
| aaggacgacg | gacagcacat | gtggaggccc | aagaggttcc | ccagaccagt | ctactgcaat | 660 |
| ctgtgcgagt | caagcattgg | tcttggcaaa | cagggactga | gctgtaacct | ctgtaagtac | 720 |
| actgttcacg | accagtgtgc | catgaaagcc | ctgccttgtg | aagtcagcac | ctatgccaag | 780 |
| tctcggaagg | acattggtgt | ccaatcacat | gtgtgggtgc | gaggaggctg | tgagtccggg | 840 |
| cgctgcgacc | gctgtcagaa | aaagatccgg | atctaccaca | gtctgaccgg | gctgcattgt | 900 |
| gtatggtgcc | acctagagat | ccacgatgac | tgcctgcaag | cggtgggcca | tgagtgtgac | 960 |
| tgtgggctgc | tccgggatca | catcctgcct | ccatcttcca | tctatcccag | tgtcctggcc | 1020 |
| tctggaccgg | atcgtaaaaa | tagcaaaaca | agccagaaga | ccatggatga | tttaaatttg | 1080 |
| agcacctctg | aggctctgcg | gattgaccct | gttcctaaca | cccacccact | tctcgtctt | 1140 |
| gtcaatccta | agagtggcgg | gaagcagggg | cagagggtgc | tctggaagtt | ccagtatata | 1200 |
| ttaaaccctc | gacaggtgtt | caacctccta | aaggatggtc | ctgagatagg | gctccgatta | 1260 |
| ttcaaggatg | ttcctgatag | ccggattttg | gtgtgtggtg | gagacggcac | agtaggctgg | 1320 |
| attctagaga | ccattgacaa | agctaacttg | ccagttttgc | ctcctgttgc | tgtgttgccc | 1380 |
| ctgggtactg | gaaatgatct | ggctcgatgc | ctaagatggg | gaggaggtta | tgaaggacag | 1440 |
| aatctggcaa | agatcctcaa | ggatttagag | atgagtaaag | tggtacatat | ggatcgatgg | 1500 |
| tctgtggagg | tgataccttca | acaaactgaa | gaaaaagtg | acccagtccc | ctttcaaatc | 1560 |
| atcaataact | acttctctat | tggcgtggat | gcctctattg | ctcatcgatt | ccacatcatg | 1620 |
| cgagagaaat | atccggagaa | gttcaacagc | agaatgaaga | acaagctatg | gtacttcgaa | 1680 |
| tttgccacat | ctgaatccat | cttctcaaca | tgcaaaaagc | tggaggagtc | tttgacagtt | 1740 |
| gagatctgtg | ggaaaccgct | ggatctgagc | aacctgtccc | tagaaggcat | cgcagtgcta | 1800 |
| aacatcccta | gcatgcatgg | tggctccaac | ctctggggtg | ataccaggag | accccatggg | 1860 |
| gatatctatg | ggatcaacca | ggcccttaggt | gctacagcta | aagtcatcac | cgaccctgat | 1920 |
| atcctgaaaa | cctgtgtacc | agacctaagt | gacaagagac | tggaagtggt | tgggctggag | 1980 |
| ggtgcaattg | agatgggcca | aatctatacc | aagctcaaga | atgctggacg | tcggctggcc | 2040 |
| aagtgctctg | agatcacctt | ccacaccaca | aaaacccttc | ccatgcaaat | tgacggagaa | 2100 |

-continued

```
ccctggatgc agacgccctg tacaatcaag atcacccaca agaaccagat gcccatgctc    2160
atgggcccac ccccccgctc caccaatttc tttggcttct tgagcggatc ctcggagaca    2220
gtgcggtttc aggacacca ccaccatcac cactga                               2256
```

<210> SEQ ID NO 2
<211> LENGTH: 751
<212> TYPE: PRT
<213> ORGANISM: Homo sapiens

<400> SEQUENCE: 2

| Met | Ala | Lys | Glu | Arg | Gly | Leu | Ile | Ser | Pro | Ser | Asp | Phe | Ala | Gln | Leu |
|---|---|---|---|---|---|---|---|---|---|---|---|---|---|---|---|
| 1 |  |  |  | 5 |  |  |  |  | 10 |  |  |  |  | 15 |  |

Gln Lys Tyr Met Glu Tyr Ser Thr Lys Lys Val Ser Asp Val Leu Lys
              20                  25                  30

Leu Phe Glu Asp Gly Glu Met Ala Lys Tyr Val Gln Gly Asp Ala Ile
          35                  40                  45

Gly Tyr Glu Gly Phe Gln Gln Phe Leu Lys Ile Tyr Leu Glu Val Asp
     50                   55                  60

Asn Val Pro Arg His Leu Ser Leu Ala Leu Phe Gln Ser Phe Glu Thr
65                  70                  75                  80

Gly His Cys Leu Asn Glu Thr Asn Val Thr Lys Asp Val Val Cys Leu
                 85                  90                  95

Asn Asp Val Ser Cys Tyr Phe Ser Leu Leu Glu Gly Gly Arg Pro Glu
            100                 105                 110

Asp Lys Leu Glu Phe Thr Phe Lys Leu Tyr Asp Thr Asp Arg Asn Gly
        115                 120                 125

Ile Leu Asp Ser Ser Glu Val Asp Lys Ile Ile Leu Gln Met Met Arg
    130                 135                 140

Val Ala Glu Tyr Leu Asp Trp Asp Val Ser Glu Leu Arg Pro Ile Leu
145                 150                 155                 160

Gln Glu Met Met Lys Glu Ile Asp Tyr Asp Gly Ser Gly Ser Val Ser
                165                 170                 175

Gln Ala Glu Trp Val Arg Ala Gly Ala Thr Thr Val Pro Leu Leu Val
            180                 185                 190

Leu Leu Gly Leu Glu Met Thr Leu Lys Asp Asp Gly Gln His Met Trp
        195                 200                 205

Arg Pro Lys Arg Phe Pro Arg Pro Val Tyr Cys Asn Leu Cys Glu Ser
    210                 215                 220

Ser Ile Gly Leu Gly Lys Gln Gly Leu Ser Cys Asn Leu Cys Lys Tyr
225                 230                 235                 240

Thr Val His Asp Gln Cys Ala Met Lys Ala Leu Pro Cys Glu Val Ser
                245                 250                 255

Thr Tyr Ala Lys Ser Arg Lys Asp Ile Gly Val Gln Ser His Val Trp
            260                 265                 270

Val Arg Gly Gly Cys Glu Ser Gly Arg Cys Asp Arg Cys Gln Lys Lys
        275                 280                 285

Ile Arg Ile Tyr His Ser Leu Thr Gly Leu His Cys Val Trp Cys His
    290                 295                 300

Leu Glu Ile His Asp Asp Cys Leu Gln Ala Val Gly His Glu Cys Asp
305                 310                 315                 320

Cys Gly Leu Leu Arg Asp His Ile Leu Pro Pro Ser Ser Ile Tyr Pro
                325                 330                 335

Ser Val Leu Ala Ser Gly Pro Asp Arg Lys Asn Ser Lys Thr Ser Gln

```
            340                 345                 350
Lys Thr Met Asp Asp Leu Asn Leu Ser Thr Ser Glu Ala Leu Arg Ile
            355                 360                 365
Asp Pro Val Pro Asn Thr His Pro Leu Leu Val Phe Val Asn Pro Lys
370                 375                 380
Ser Gly Gly Lys Gln Gly Gln Arg Val Leu Trp Lys Phe Gln Tyr Ile
385                 390                 395                 400
Leu Asn Pro Arg Gln Val Phe Asn Leu Leu Lys Asp Gly Pro Glu Ile
                405                 410                 415
Gly Leu Arg Leu Phe Lys Asp Val Pro Asp Ser Arg Ile Leu Val Cys
            420                 425                 430
Gly Gly Asp Gly Thr Val Gly Trp Ile Leu Glu Thr Ile Asp Lys Ala
            435                 440                 445
Asn Leu Pro Val Leu Pro Pro Val Ala Val Leu Pro Leu Gly Thr Gly
            450                 455                 460
Asn Asp Leu Ala Arg Cys Leu Arg Trp Gly Gly Gly Tyr Glu Gly Gln
465                 470                 475                 480
Asn Leu Ala Lys Ile Leu Lys Asp Leu Glu Met Ser Lys Val Val His
                485                 490                 495
Met Asp Arg Trp Ser Val Glu Val Ile Pro Gln Gln Thr Glu Glu Lys
            500                 505                 510
Ser Asp Pro Val Pro Phe Gln Ile Ile Asn Asn Tyr Phe Ser Ile Gly
            515                 520                 525
Val Asp Ala Ser Ile Ala His Arg Phe His Ile Met Arg Glu Lys Tyr
530                 535                 540
Pro Glu Lys Phe Asn Ser Arg Met Lys Asn Lys Leu Trp Tyr Phe Glu
545                 550                 555                 560
Phe Ala Thr Ser Glu Ser Ile Phe Ser Thr Cys Lys Lys Leu Glu Glu
                565                 570                 575
Ser Leu Thr Val Glu Ile Cys Gly Lys Pro Leu Asp Leu Ser Asn Leu
            580                 585                 590
Ser Leu Glu Gly Ile Ala Val Leu Asn Ile Pro Ser Met His Gly Gly
            595                 600                 605
Ser Asn Leu Trp Gly Asp Thr Arg Arg Pro His Gly Asp Ile Tyr Gly
            610                 615                 620
Ile Asn Gln Ala Leu Gly Ala Thr Ala Lys Val Ile Thr Asp Pro Asp
625                 630                 635                 640
Ile Leu Lys Thr Cys Val Pro Asp Leu Ser Asp Lys Arg Leu Glu Val
                645                 650                 655
Val Gly Leu Glu Gly Ala Ile Glu Met Gly Gln Ile Tyr Thr Lys Leu
            660                 665                 670
Lys Asn Ala Gly Arg Arg Leu Ala Lys Cys Ser Glu Ile Thr Phe His
            675                 680                 685
Thr Thr Lys Thr Leu Pro Met Gln Ile Asp Gly Glu Pro Trp Met Gln
            690                 695                 700
Thr Pro Cys Thr Ile Lys Ile Thr His Lys Asn Gln Met Pro Met Leu
705                 710                 715                 720
Met Gly Pro Pro Arg Ser Thr Asn Phe Phe Gly Phe Leu Ser Gly
                725                 730                 735
Ser Ser Glu Thr Val Arg Phe Gln Gly His His His His His
            740                 745                 750

<210> SEQ ID NO 3
```

```
<211> LENGTH: 2838
<212> TYPE: DNA
<213> ORGANISM: Homo sapiens

<400> SEQUENCE: 3
atggagccgc gggacggtag ccccgaggcc cggagcagcg actccgagtc ggcttccgcc      60
tcgtccagcg gctccgagcg cgacgccggt cccgagccgg acaaggcgcc gcggcgactc     120
aacaagcggc gcttcccggg gctgcggctc ttcgggcaca ggaaagccat cacgaagtcg     180
ggcctccagc acctggcccc ccctccgccc accctgggg ccccgtgcag cgagtcagag     240
cggcagatcc ggagtacagt ggactggagc gagtcagcga catatgggga gcacatctgg     300
ttcgagacca acgtgtccgg ggacttctgc tacgttgggg agcagtactg tgtagccagg     360
atgctgcaga agtcagtgtc tcgaagaaag tgcgcagcct gcaagattgt ggtgcacacg     420
ccctgcatcg agcagctgga gaagataaat ttccgctgta agccgtcctt ccgtgaatca     480
ggctccagga atgtccgcga gccaaccttt gtacggcacc actgggtaca gacgacgc     540
caggacggca agtgtcggca ctgtgggaag ggattccagc agaagttcac cttccacagc     600
aaggagattg tggccatcag ctgctcgtgg tgcaagcagg cataccacag caaggtgtcc     660
tgcttcatgc tgcagcagat cgaggagccg tgctcgctgg gggtccacgc agccgtggtc     720
atcccgccca cctggatcct ccgcgcccgg aggccccaga atactctgaa agcaagcaag     780
aagaagaaga gggcatcctt caagaggaag tccagcaaga aagggcctga ggagggccgc     840
tggagaccct tcatcatcag gcccaccccc tccccgctca tgaagcccct gctggtgttt     900
gtgaacccca agagtggggg caaccagggt gcaaagatca tccagtcttt cctctggtat     960
ctcaatcccc gacaagtctt cgacctgagc cagggagggc ccaaggaggc gctggagatg    1020
taccgcaaag tgcacaacct gcggatcctg gcgtgcgggg gcgacggcac ggtgggctgg    1080
atcctctcca ccctggacca gctacgcctg aagccgccac ccctgttgc catcctgccc    1140
ctgggtactg gcaacgactt ggcccgaacc ctcaactggg gtggggcta cacagatgag    1200
cctgtgtcca agatcctctc ccacgtggag gaggggaacg tggtacagct ggaccgctgg    1260
gacctccacg ctgagcccaa ccccgaggca gggcctgagg accgagatga aggcgccacc    1320
gaccggttgc ccctggatgt cttcaacaac tacttcagcc tgggctttga cgcccacgtc    1380
accctggagt tccacgagtc tcgagaggcc aacccagaga aattcaacag ccgctttcgg    1440
aataagatgt tctacgccgg gacagctttc tctgacttcc tgatgggcag ctccaaggac    1500
ctggccaagc acatccgagt ggtgtgtgat ggaatggact tgactcccaa gatccaggac    1560
ctgaaaccc agtgtgttgt tttcctgaac atccccaggt actgtgcggg caccatgccc    1620
tggggccacc ctgggggagca ccacgacttt gagccccagc ggcatgacga cggctacctc    1680
gaggtcattg gcttcaccat gacgtcgttg gccgcgctgc aggtgggcgg acacggcgag    1740
cggctgacgc agtgtcgcga ggtggtgctc accacatcca aggccatccc ggtgcaggtg    1800
gatggcgagc cctgcaagct tgcagcctca cgcatccgca tcgccctgcg caaccaggcc    1860
accatggtgc agaaggccaa gcggcggagc gccgccccc tgcacagcga ccagcagccg    1920
gtgccagagc agttgcgcat ccaggtgagt cgcgtcagca tgcacgacta tgaggccctg    1980
cactacgaca aggagcagct caaggaggcc tctgtgccgc tgggcactgt ggtggtccca    2040
ggagacagtg acctagagct ctgccgtgcc cacattgaga gactccagca ggagcccgat    2100
ggtgctggag ccagtccccc gacatgccag aaactgtccc ccagtggtg cttcctggac    2160
gccaccactg ccagccgctt ctacaggatc gaccgagccc aggagcaccct caactatgtg    2220
```

-continued

```
actgagatcg cacaggatga gatttatatc ctggaccctg agctgctggg ggcatcggcc    2280
cggcctgacc tcccaacccc cacttcccct ctccccacct caccctgctc acccacgccc    2340
cggtcactgc aagggatgc tgcacccct caaggtgaag agctgattga ggctgccaag      2400
aggaacgact tctgtaagct ccaggagctg caccgagctg ggggcgacct catgcaccga    2460
gacgagcaga gtcgcacgct cctgcaccac gcagtcagca ctggcagcaa ggatgtggtc    2520
cgctacctgc tggaccacgc ccccccagag atccttgatg cggtggagga aaacggggag    2580
acctgtttgc accaagcagc ggccctgggc cagcgcacca tctgccacta catcgtggag    2640 gccgggcct cgctcatgaa gacagaccag cagggcgaca ctccccggca gcgggctgag     2700
aaggctcagg acaccgagct ggccgcctac ctggagaacc ggcagcacta ccagatgatc    2760
cagcgggagg accaggagac ggctgtggga tcctcggaga cagtgcggtt tcagggacac    2820
caccaccatc accactga                                                  2838
```

<210> SEQ ID NO 4
<211> LENGTH: 945
<212> TYPE: PRT
<213> ORGANISM: Homo sapiens

<400> SEQUENCE: 4

```
Met Glu Pro Arg Asp Gly Ser Pro Glu Ala Arg Ser Ser Asp Ser Glu
1               5                   10                  15

Ser Ala Ser Ala Ser Ser Ser Gly Ser Glu Arg Asp Ala Gly Pro Glu
                20                  25                  30

Pro Asp Lys Ala Pro Arg Arg Leu Asn Lys Arg Phe Pro Gly Leu
            35                  40                  45

Arg Leu Phe Gly His Arg Lys Ala Ile Thr Lys Ser Gly Leu Gln His
    50                  55                  60

Leu Ala Pro Pro Pro Thr Pro Gly Ala Pro Cys Ser Glu Ser Glu
65                  70                  75                  80

Arg Gln Ile Arg Ser Thr Val Asp Trp Ser Glu Ser Ala Thr Tyr Gly
                85                  90                  95

Glu His Ile Trp Phe Glu Thr Asn Val Ser Gly Asp Phe Cys Tyr Val
            100                 105                 110

Gly Glu Gln Tyr Cys Val Ala Arg Met Leu Gln Lys Ser Val Ser Arg
        115                 120                 125

Arg Lys Cys Ala Ala Cys Lys Ile Val Val His Thr Pro Cys Ile Glu
    130                 135                 140

Gln Leu Glu Lys Ile Asn Phe Arg Cys Lys Pro Ser Phe Arg Glu Ser
145                 150                 155                 160

Gly Ser Arg Asn Val Arg Glu Pro Thr Phe Val Arg His His Trp Val
                165                 170                 175

His Arg Arg Arg Gln Asp Gly Lys Cys Arg His Cys Gly Lys Gly Phe
            180                 185                 190

Gln Gln Lys Phe Thr Phe His Ser Lys Glu Ile Val Ala Ile Ser Cys
        195                 200                 205

Ser Trp Cys Lys Gln Ala Tyr His Ser Lys Val Ser Cys Phe Met Leu
    210                 215                 220

Gln Gln Ile Glu Glu Pro Cys Ser Leu Gly Val His Ala Ala Val Val
225                 230                 235                 240

Ile Pro Pro Thr Trp Ile Leu Arg Ala Arg Arg Pro Gln Asn Thr Leu
                245                 250                 255
```

```
Lys Ala Ser Lys Lys Lys Arg Ala Ser Phe Lys Arg Lys Ser Ser
            260                 265                 270

Lys Lys Gly Pro Glu Glu Gly Arg Trp Arg Pro Phe Ile Ile Arg Pro
        275                 280                 285

Thr Pro Ser Pro Leu Met Lys Pro Leu Leu Val Phe Val Asn Pro Lys
        290                 295                 300

Ser Gly Gly Asn Gln Gly Ala Lys Ile Ile Gln Ser Phe Leu Trp Tyr
305                 310                 315                 320

Leu Asn Pro Arg Gln Val Phe Asp Leu Ser Gln Gly Gly Pro Lys Glu
            325                 330                 335

Ala Leu Glu Met Tyr Arg Lys Val His Asn Leu Arg Ile Leu Ala Cys
            340                 345                 350

Gly Gly Asp Gly Thr Val Gly Trp Ile Leu Ser Thr Leu Asp Gln Leu
            355                 360                 365

Arg Leu Lys Pro Pro Pro Val Ala Ile Leu Pro Leu Gly Thr Gly
            370                 375                 380

Asn Asp Leu Ala Arg Thr Leu Asn Trp Gly Gly Gly Tyr Thr Asp Glu
385                 390                 395                 400

Pro Val Ser Lys Ile Leu Ser His Val Glu Glu Gly Asn Val Val Gln
            405                 410                 415

Leu Asp Arg Trp Asp Leu His Ala Glu Pro Asn Pro Glu Ala Gly Pro
            420                 425                 430

Glu Asp Arg Asp Glu Gly Ala Thr Asp Arg Leu Pro Leu Asp Val Phe
            435                 440                 445

Asn Asn Tyr Phe Ser Leu Gly Phe Asp Ala His Val Thr Leu Glu Phe
450                 455                 460

His Glu Ser Arg Glu Ala Asn Pro Glu Lys Phe Asn Ser Arg Phe Arg
465                 470                 475                 480

Asn Lys Met Phe Tyr Ala Gly Thr Ala Phe Ser Asp Phe Leu Met Gly
            485                 490                 495

Ser Ser Lys Asp Leu Ala Lys His Ile Arg Val Val Cys Asp Gly Met
            500                 505                 510

Asp Leu Thr Pro Lys Ile Gln Asp Leu Lys Pro Gln Cys Val Val Phe
            515                 520                 525

Leu Asn Ile Pro Arg Tyr Cys Ala Gly Thr Met Pro Trp Gly His Pro
530                 535                 540

Gly Glu His His Asp Phe Glu Pro Gln Arg His Asp Asp Gly Tyr Leu
545                 550                 555                 560

Glu Val Ile Gly Phe Thr Met Thr Ser Leu Ala Ala Leu Gln Val Gly
            565                 570                 575

Gly His Gly Glu Arg Leu Thr Gln Cys Arg Glu Val Val Leu Thr Thr
            580                 585                 590

Ser Lys Ala Ile Pro Val Gln Val Asp Gly Glu Pro Cys Lys Leu Ala
            595                 600                 605

Ala Ser Arg Ile Arg Ile Ala Leu Arg Asn Gln Ala Thr Met Val Gln
            610                 615                 620

Lys Ala Lys Arg Arg Ser Ala Ala Pro Leu His Ser Asp Gln Pro
625                 630                 635                 640

Val Pro Glu Gln Leu Arg Ile Gln Val Ser Arg Val Ser Met His Asp
            645                 650                 655

Tyr Glu Ala Leu His Tyr Asp Lys Glu Gln Leu Lys Glu Ala Ser Val
            660                 665                 670

Pro Leu Gly Thr Val Val Val Pro Gly Asp Ser Asp Leu Glu Leu Cys
```

```
                 675                 680                 685
Arg Ala His Ile Glu Arg Leu Gln Gln Glu Pro Asp Gly Ala Gly Ala
    690                 695                 700
Lys Ser Pro Thr Cys Gln Lys Leu Ser Pro Lys Trp Cys Phe Leu Asp
705                 710                 715                 720
Ala Thr Thr Ala Ser Arg Phe Tyr Arg Ile Asp Arg Ala Gln Glu His
                725                 730                 735
Leu Asn Tyr Val Thr Glu Ile Ala Gln Asp Glu Ile Tyr Ile Leu Asp
            740                 745                 750
Pro Glu Leu Leu Gly Ala Ser Ala Arg Pro Asp Leu Pro Thr Pro Thr
        755                 760                 765
Ser Pro Leu Pro Thr Ser Pro Cys Ser Pro Thr Pro Arg Ser Leu Gln
    770                 775                 780
Gly Asp Ala Ala Pro Pro Gln Gly Glu Glu Leu Ile Glu Ala Ala Lys
785                 790                 795                 800
Arg Asn Asp Phe Cys Lys Leu Gln Glu Leu His Arg Ala Gly Gly Asp
                805                 810                 815
Leu Met His Arg Asp Glu Gln Ser Arg Thr Leu Leu His His Ala Val
            820                 825                 830
Ser Thr Gly Ser Lys Asp Val Val Arg Tyr Leu Leu Asp His Ala Pro
        835                 840                 845
Pro Glu Ile Leu Asp Ala Val Glu Glu Asn Gly Glu Thr Cys Leu His
    850                 855                 860
Gln Ala Ala Leu Gly Gln Arg Thr Ile Cys His Tyr Ile Val Glu
865                 870                 875                 880
Ala Gly Ala Ser Leu Met Lys Thr Asp Gln Gln Gly Asp Thr Pro Arg
                885                 890                 895
Gln Arg Ala Glu Lys Ala Gln Asp Thr Glu Leu Ala Ala Tyr Leu Glu
            900                 905                 910
Asn Arg Gln His Tyr Gln Met Ile Gln Arg Glu Asp Gln Glu Thr Ala
        915                 920                 925
Val Gly Ser Ser Glu Thr Val Arg Phe Gln Gly His His His His
    930                 935                 940
His
945
```